(12) United States Patent
Duncan

(10) Patent No.: US 12,421,216 B2
(45) Date of Patent: Sep. 23, 2025

(54) VORUCICLIB POLYMORPHS AND METHODS OF MAKING AND USING THEREOF

(71) Applicant: MEI PHARMA, INC., San Diego, CA (US)

(72) Inventor: David Frank Duncan, San Diego, CA (US)

(73) Assignee: MEI PHARMA, INC., San Diego, CA (US)

( * ) Notice: Subject to any disclaimer, the term of this patent is extended or adjusted under 35 U.S.C. 154(b) by 838 days.

(21) Appl. No.: 17/602,935

(22) PCT Filed: Apr. 11, 2020

(86) PCT No.: PCT/US2020/027847
§ 371 (c)(1),
(2) Date: Oct. 11, 2021

(87) PCT Pub. No.: WO2020/210760
PCT Pub. Date: Oct. 15, 2020

(65) Prior Publication Data
US 2023/0167096 A1    Jun. 1, 2023

Related U.S. Application Data

(60) Provisional application No. 62/832,637, filed on Apr. 11, 2019.

(51) Int. Cl.
*C07D 405/04*     (2006.01)

(52) U.S. Cl.
CPC ........ *C07D 405/04* (2013.01); *C07B 2200/13* (2013.01)

(58) Field of Classification Search
CPC .......................... C07D 405/04; C07B 2200/13
See application file for complete search history.

(56) References Cited

U.S. PATENT DOCUMENTS

| | | | |
|---|---|---|---|
| 8,563,596 B2 | 10/2013 | Sivakumar et al. | |
| 2010/0179210 A1 | 7/2010 | Sivakumar et al. | |
| 2013/0237582 A1 | 9/2013 | Rathos et al. | |
| 2016/0136132 A1 | 5/2016 | Agarwal et al. | |

FOREIGN PATENT DOCUMENTS

| | | |
|---|---|---|
| CA | 3103604 C | 10/2017 |
| EA | 014641 B1 | 12/2010 |
| JP | 2003519698 A | 6/2003 |
| JP | 2009541294 A | 11/2009 |
| JP | 2013542979 A | 11/2013 |
| KR | 20090023705 A | 3/2009 |
| RU | 22334746 C2 | 9/2008 |
| RU | 2418786 C2 | 5/2011 |
| WO | 01/51919 A2 | 7/2001 |

OTHER PUBLICATIONS

First Office Action issued in Chinese Patent Application No. 202080042371.X, dated Jan. 6, 2024, 23 pages.
Examination Report issued in Indian Patent Application No. 20117049166, dated Jan. 16, 2024, 7 pages.
English translation of an Office Action issued in corresponding Russian Application No. 2021131138, dated Jul. 29, 2024, 9 pages.
English translation of an Office Action issued in corresponding Chinese Application No. 202080042371, dated Jan. 6, 2024, 7 pages.
English translation of an Office Action issued in corresponding Israeli Application No. 286993, dated Jun. 20, 2024, 6 pages.
English translation of an Office Action issued in corresponding Mexican Application No. 2021/012248, dated Jun. 25, 2024, 4 pages.
Jaakko Aaltonen, et al., "Solid form screening—A review", European Journal of Pharmaceutics and Biopharmaceutics, 2009, vol. 71(1), 23-37.
"Polymorphism in pharmaceutical solids" [Edited by H.G. Brittain, Marcel Dekker, D.J.W. Grant (chapter 1) p. 1-10 and J.K. Guillory (chapter 5) p. 183-226; ISBN: 0-8247-0237-9]—Dec. 31, 1999.
Rolf Hilfiker "Relevance of Solid-State Properties for Pharmaceutical Products", 2006, pp. 1-19.
Darío Braga, "Crystal Polymorphism and Multiple Crystal Forms", 2009, pp. 25-50.
Second Office Action issued in corresponding Chinese Application No. 202080042371, dated Aug. 3, 2024, 7 pages, with English translation.
Office Action for Russian Patent Application No. 2021131138 dated Sep. 18, 2023, 21 pages.
Decision of Rejection for Japanese Patent Application No. 2021-559726 mailed Aug. 23, 2023, 6 pages.
International Search Report mailed Jun. 16, 2020 for International Patent Application No. PCT/US2020/027847.
Written Opinion mailed Jun. 16, 2020 for International Patent Application No. PCT/US2020/027847.
Notification of Reason for Rejection in JP Appl. No. 2021-559726, mailed Nov. 24, 2022, 8 pages.
Berge, S. M., et al., "Pharmaceutical Salts," Journal of Pharmaceutical Sciences, 1977, 66(1):1-19.
Kawaguchi, Y. et al., "Drug and crystal polymorphism," Journal of Human Environmental Engineering, 2002, 4(2):310-317.
Takata, "API form screening and selection in drug discovery stage," Pharm. Stage, 2007, 6(10):20-25.
Yamano, "Approach to Crystal Polymorph in Process Research of New Drug," Journal of Synthetic Organic Chemistry, 2007, 65(9):69-75.
Extended European Search Report in EP Appl. No. 20787296.1, mailed Dec. 12, 2022, 5 pages.

(Continued)

*Primary Examiner* — Kamal A Saeed
(74) *Attorney, Agent, or Firm* — Morgan, Lewis & Bockius LLP

(57) ABSTRACT

The disclosure relates to crystalline solid forms of voruciclib, including voruciclib free base and various voruciclib salts, pharmaceutical compositions containing voruciclib crystalline solid forms, and methods for treating conditions or disorders by administering pharmaceutical compositions including voruciclib crystalline solid forms.

17 Claims, 160 Drawing Sheets

(56) References Cited

OTHER PUBLICATIONS

Office Action issued in Russian Patent Application No. 2021131138, dated Feb. 16, 2024, 29 pages.
Richard J.Bastin et al., "Salt selection and Optimisation Procedures for Pharmaceutical New Chemical Entities," Organic Process Research & Development, 2000, vol. 4, p. 427-435.
Mino R. Caira, "Crystalline Polymorphism of Organic Compounds," Topics in Current Chemistry, 1998, vol. 198, pp. 163-208.
Sarma B. et al., "Solid formation of pharmaceuticals: Polymorphs, salt and cocrystals," Korean J. Chem. Eng., 2011, 28(2), p. 315-322.
Narayan Variankaval et al., "From form to function: Crystallization of active pharmaceutical ingredients," AIChE, 2008, vol. 54(7), p. 1682-1688.
Office Action issued in Canadian Patent Application No. 3,136,599, dated Mar. 1, 2024, 4 pages.
Byrn et al., "Pharmaceutical solids—A strategic approach to regulatory considerations," Pharm. Res., 1995, 12(7), pp. 945-954.
English translation of the hearing notice issued in corresponding Indian Application No. 202117049166, dated Nov. 6, 2024, 3 pages.
International Preliminary Report on Patentability mailed Oct. 21, 2021, in connection with International Application No. PCT/US2020/027847 (10 pages).
Office Action issued in corresponding Australian Application No. 2020271908, dated Nov. 13, 2025, 3 pages.
Office Action issued in corresponding European Application No. 20787296.1, dated Jan. 27, 2025, 4 pages.
English translation of the Office Action issued in corresponding Indian Application No. 202117049166, dated Apr. 4, 2025, 3 pages.
English translation of the Office Action issued in corresponding Mexican Application No. MX/a/2021/012248, dated Nov. 26, 2024, 4 pages.
English translation of the Office Action issued in corresponding Russian Application No. 2021131138, dated Mar. 28, 2025, 11 pages.
Barbara Rodriguez-Spong et al.: "General principles of pharmaceutical solidpolymorphism: a supramolecular perspective", Advanced Drug Delivery Reviews, 2004, 56, p. 241-274.
Office Action issued in corresponding Russian Application No. 2021131138, 23 pages, with English translation.
Office Action issued in corresponding Japanese Application No. 2023-217619, 8 pages, dated Jun. 27, 2025, with English translation.
Kawaguchi, et al., Drug and crystal polymorphism, 2002, vol. 4, No. 2, p. 310-317 (machine translation).
Establishment of Specifications and Test Methods for New Drugs, 2001, May 1, Notice No. 58 of the Pharmaceutical Affairs Bureau (machine translation).
Takada Noriyuki, "API form screening and selection in drug discovery stage", Pharm Stage, vol. 6, No. 10, 2007, Jan. 15, p. 20-25 (machine translation).
Mitsuhisa Yamano, "Approach to Crystal Polymorph in Process Research of New Drug", 2007, 65(9), p. 907-913 (machine translation).
Berge, et al., "Pharmaceutical Salts", Journal of Pharmaceutical Sciences, 1977, vol. 66, No. 1, p. 1-19.
Kono, et al. "Current Analysis of Salt Selection", 2013, 73(3), p. 176-182 (machine translation).
Office Action issued in corresponding Korean Patent Application No. 10-2021-7036116, dated Mar. 5, 2025, 9 pages, with English translation.

pKa = 6.46

| Polymorphic/Form | Stable | Solvent |
|---|---|---|
| 1 | Yes | Various |
| 2 | Yes | MeOH/Acetone, THF/Water, DMA, Anisole, p-Xylene, Heptane, Hexanes, Dioxane/Water, DMSO/TBME, MeOH/p-Xylene |
| 3 | No | Alcohols (long-chain) and Alcohol mixtures |
| 4 | No | Anisole, Chloroform, Cumene, Dichloromethane, Ether, Ethyl formate, p-Xylene, TBME, THF, Toluene |
| 5 | No | 2-MethylTHF, Dioxane |
| 6 | Yes | Water (forms 4 and 5 converted to Form 6 after AAC) |
| 7 | Yes | 1,2-Dimethoxyethane |
| 8 | Yes | Alcohols (short chain) and Alcohol mixtures |
| 9 | No | DMF |
| 10 | No | DMF |
| 11 | No | DMA |
| 12 | Yes | Acetone/Water, Acetonitrile/Water |
| 13 | Yes | Ethanol (Form 3 converts to Form 13 after AAC) |
| 14 | Yes | Acetone/Water, Acetonitrile/Water |
| 15 | No | DMF/Dioxane, Methanol |
| 16 | No | DMSO or DMSO mixtures |
| 17 | No | TFE/Heptane |
| 18 | Yes | DMF/Isopropyl acetate |
| 19 | Yes | Methanol/Diisopropyl ether 20/80 |
| 20 | Yes | DMF, DMA |

Fig. 287

| Attributes | Target Product Attribute |
|---|---|
| Gelling | No |
| Water Solubility | >5mg/mL |
| Number of Polymorphs/hydrates/solvates | <5 total |
| Anhydrous and Solvent Free | Yes |
| Stable Polymorphs | ≥1 |
| Stability (under Accelerated Aging Conditions) | Yes |
| Hygroscopic | No |
| Cl (salt) stoichiometry | 1:1 |
| Crystalline Material | Yes |
| Manufacturable | Yes |

Fig. 288

| Acid Counter Ion (CI) | Form | Crystallinity | Stability |
|---|---|---|---|
| 1,2-Ethanedisulfonic | Edy1 | Medium | No => Edy1+Edy2_Ic |
|  | Edy2_Ic | Poor | Yes |
|  | Edy1+Edy2 | Mixture | No => Edy2_Ic |
| 1,5-Naphthalenedisulfonic | Nds1a | Good | Yes |
|  | Nds1b | Good | No => Nds2 |
|  | Nds2 | Good | Sometimes => Nds5 |
|  | Nds3 (brown) | Poor | Yes |
|  | Nds4 | Medium | Yes |
| 3-Hydroxy-2-naphthoic | Xin1 | Medium | Yes |
| Benzenesulfonic | Bes1 | Medium | No => Am or dissociation |
| Benzoic | Ben1 | Good | No => Ben3 |
|  | Ben2 | Medium | Yes |
| Citric | Am | - | - |
| Dibenzoyl-L-tartaric | DTr1 | Good | Yes |
|  | DTr1+DTr2 | Mixture | Yes |
| Ethanesulfonic | E | Good | Yes |
| Fumaric | Fum1 | Medium | Yes |
|  | Fum2a | Poor | No |
|  | Fum2b | Poor | Yes |
|  | Fum2c | Poor | Yes |
| Gentisic | Gen1 | Good | Yes |
|  | Gen2 | Poor | Yes |
| Gluconic | Am | - | - |
| D-Glucuronic | Glr1 | Medium | No => Am |
| L-(+)-Glutamic | B, C, Glm0 | - | - |
| Glutaric | Glt1 | Medium | No => dark brown |
|  | Glt2 | Poor | No => dark brown |
|  | Glt3 | Poor | Yes |

| Acid Counter Ion (CI) | Form | Crystallinity | Stability |
|---|---|---|---|
| Hydrobromic | HBr1 | Good | No => HBr2 |
| Maleic | Mae1 | Good | Yes |
|  | Mae1+Mae2 | Mixture | No => Mae1 |
| L-(-)-Malic | Mal1 | Poor | Yes |
| Malonic | Mao1 | Good | Yes |
|  | Mao2 | Poor | No => Mao1+Mao2 |
| Naphthalene-2-sulfonic | Nsu1 | Poor | No => Am |
|  | Nsu2 | Medium | No => Am |
|  | Nsu3 | Poor | Yes |
| Oxalic | Oxa1 | Good | Yes |
| Phosphoric | Pho1 | Good | Yes |
|  | Pho2 | Poor | Yes |
| Succinic | Suc1 | Medium | No => Suc1+Suc2 |
|  | Suc2 | Medium | Yes |
|  | Suc1+Suc3 | Mixture | Yes |
| Sulfuric | Sul1 | Good | Yes |
|  | Sul2 | Medium | Yes |
|  | Sul3 | Medium | Yes |
|  | Sul4 | Poor | Yes |
| L-(+)-Tartaric | Tar1+Tar2 | Mixture | Yes |
|  | Tar1+Tar3 | Mixture | Yes |
|  | Tar2 | Poor | Yes |
|  | Tar3 | Medium | Yes |
| p-Toluenesulfonic | Tos1 | Medium | No => Tos1+Tos3 |
|  | Tos2 | Good | Yes |
| None | A | Good | Yes |
|  | C | Medium | Yes |

Fig. 289

| Salt | # Polymorphs | Residual Solvent (%) | Gelling | Water solubility (mg/mL) |
|---|---|---|---|---|
| ME-522 Free Base | >2 | 0.3 | Yes | <0.01 |
| ME-522 HCl | >2 | 0.2 | Yes | Gel |
| Malonate | 2 | 0.2 | No | >5 |
| Oxalate | 1 | Hemi-hydrate | No | >5 |
| Phosphate | 2 | 1.9 | No | >5 |
| Dibenzoyl-L-tartaric[1] | 2 | 0.9 | No | 0.03 |
| Ethanesulfonic | 1 | 4.6 | No | ND |
| Napadisylate | >2 | 1.1 | No | 0.02 |
| Gentisic | 2 | 9.2 | No | ND |
| Napadisylate | >2 | 1.1 | No | 0.02 |
| Maleic | 2 | 3.4 | No | ND |
| Sulfuric | >2 | 2.4 | No | ND |
| p-Toluenesulfonic | 2 | 4.6 | No | ND |

[1]Not included on the list of Pharmaceutically Acceptable Salts

Fig. 290

| Attributes | Target Product Attribute | Salt Options | | | |
|---|---|---|---|---|---|
| | | #1 (HCl) | #2 (Oxa) | #3 (Phos) | #4 (Mao) |
| Gelling | No | | | | |
| Water Solubility | >5 mg/mL | | | | |
| No of Polymorphs/hydrates/solvates | <5 total | No | No | No | |
| Anhydrous and Solvent Free | Yes | | | | |
| Stable polymorphs | ≥1 | | | | |
| Stability (Accelerated Aging Conditions) | Yes | | | | |
| Hygroscopic | No | | | | |
| Cl (salt) stoichiometry | 1:1 | | | | |
| Crystalline Material | Yes | | Yes | Yes | |
| Manufacturable | Yes | | Yes | Yes | |

| Pretreatment | Salt | Tmax | Cmax/Dose | AUC/Dose |
|---|---|---|---|---|
| Famotidine | HCl | 114 | 84 | 52 |
| Famotidine | Malonate | 35 | 45 | 37 |
| none | HCl | 87 | 42 | NA |
| none | Malonate | 87 | 22 | NA |
| Pentagastrin | HCl | 0 | 37 | 20 |
| Pentagastrin | Malonate | 0 | 26 | 14 |
| Combined | HCl | 93 | 52 | 62 |
| Combined | Malonate | 65 | 33[1] | 24[2] |

[1] Statistically significant by F-Test Two-Sample for Variances, p = 0.007
[2] Statistically significant by F-Test Two-Sample for Variances, p = 0.0009

Fig. 293

| Pretreatment | Mean Cmax/D ratio | Mean AUClast/D ratio |
|---|---|---|
| Famotidine | 0.97 | 0.96 |
| Pentagastrin | 0.88 | 0.85 |
| None | 0.41 | |

Fig. 294

| | |
|---|---|
| Sensor Type | Photon-counting, Xe-based MIKROGAP™ detector (US Patent 6,340,819.) Window size: 140 mm in diameter |
| | Number of pixels     Pixel size |
| | 2048 × 2048     68 µm × 68 µm |
| | 1024 × 1024     136 µm × 136 µm |
| | 512 × 512     272 µm × 272 µm |
| Simultaneous 2θ coverage of a single frame at different sample-to-detector distances | Detector distance     2θ range |
| | 5 cm     83° |
| | 10 cm     56° |
| | 15 cm     42° |
| | 20 cm     33° |
| | 25 cm     27° |
| | 30 cm     23° |
| Detection Quantum Efficiency | 80% for Cu Kα (8.04 keV), residual 20% absorbed by the Be-window |
| Energy Range | 3–15 keV (Cr, Fe, Co and Cu radiation) |
| Energy Resolution | 20% for Cu Kα (8.04 keV) |
| Global Counting Rate | Maximum: 1.0 Mcps |
| | Linear (10% deviation from linearity): 0.5 Mcps |
| Local Counting Rate | Maximum per a point-like reflection: 250 Kcps |
| | Linear (10% deviation from linearity): 150 Kcps |
| Background | < 5 cps per whole area (< 0.0005 cps/mm²) |
| Maximum Dynamic Range | $10^5 \times \sqrt{t}$ (t = collection time in seconds) |
| Radiation Hardness | $10^{11}$ X-ray photons/mm² ($10^{15}$ photons in total) |
| Maintenance | not required |
| Detector Guarantee | Bruker Detector Guarantee: no defective/dead areas |

Fig. 297

| Detector Specifications | |
|---|---|
| Suitable systems | All D8 SUPER SPEED SOLUTIONS systems, all D8 systems and the D4 ENDEAVOR |
| Active area | 14.4 mm x 16 mm; (in and perpendicular to the scattering plane) |
| Max 2-theta range simultaneously covered | 4° at 401 mm measurement circle diameter |
| Usable wavelength range | From Cr-Kα up to Cu-Kα, factory-set default for Cu-Kα |
| Maximum global count rate | > 100,000,000 cps |
| Maximum local count rate (per strip) | 850,000 cps |
| Energy resolution | 25% with 55Fe radiation at 5.9 keV |
| Efficiency | > 96% (Cu-radiation) |
| Spatial resolution (pitch) | 75 µm, 192 individual readout channels |
| Voltage of power supply | 100–240 V AC |
| Frequency of power supply | 50/60 Hz |
| Power rating | 100 VA |
| Detector (overall dimensions and weight) | 200 mm D x 120 mm W x 120 mm H, 2.5 kg |
| Controller (overall dimensions and weight) | 420 mm D x 485 mm W x 90 mm H, 8.5 kg |
| Length of cables between the detector and 19" controller chassis unit | 4 m |
| Disconnect device | IEC 320 connector/plug on power supply cord |
| Software | DIFFRAC$^{plus}$ Measurement package version 2.4 or higher, for 0-D mode version 2.6 or higher |
| Included in delivery | LynxEye detector; front-end read-out and supply electronics; mounting and optics assembly, including Kβ-filter, 2.5° Soller slit, 3 mm and 8 mm plug-in slits |

Fig. 298

VORUCICLIB POLYMORPHS AND METHODS OF MAKING AND USING THEREOF

CROSS-REFERENCE TO RELATED APPLICATIONS

This application is a U.S. National Stage Patent Application of International PCT Patent Application No. PCT/US2020/027847, filed on Apr. 11, 2020, which claims priority to U.S. Provisional Patent Application No. 62/832,637, filed on Apr. 11, 2019, each of which is hereby incorporated by reference in its entirety.

FIELD

The disclosure provides novel polymorphs of CDK inhibitor voruciclib, and methods of making and using thereof.

BACKGROUND

Certain chemical compounds, including various drugs, may exist in polymorphic forms. Polymorphic forms generally refer to different crystalline forms with different physical properties, but may also include solvation or hydration products, and amorphous forms (International Conference on Harmonization of Technical Requirements for Registration of Pharmaceuticals for Human Use, ICH Harmonized Tripartite Guideline, Specifications: Test Procedures and Acceptance Criteria for New Drug Substances and New Drug Products: Chemical Substances, Q6A, version dated 6 Oct. 1999). Differences in polymorph forms may affect the quality and performance of drugs, including drug performance, bioavailability, stability, etc. Various physicochemical measurements and techniques may be used to explore and identify polymorphs, including melting point determination, infra red spectroscopy (IR), X-ray diffraction, thermal analysis (DSC, TGA, etc.), Raman spectroscopy, optical microscopy, and NMR.

SUMMARY

The disclosure provides polymorphs, for example crystal forms, of voruciclib. In some embodiments, the polymorphs include free base voruciclib. In some embodiments, the polymorphs include voruciclib salts including a counterion corresponding to an acid selected from 1,5-naphthalenedisulfonic acid, 1-hydroxy-2-naphthoic acid, benzenesulfonic acid, benzoic acid, dibenzoyl-L-tartaric acid, ethanesulfonic acid, gentisic acid, hydrobromic acid, hydrochloric acid, maleic acid, malonic acid, oxalic acid, ortho-phosphoric acid, sulfuric acid, p-toluenesulfonic acid, and the like.

In one embodiment, the disclosure provides a crystal form of voruciclib characterized by an X-ray powder diffraction pattern including one or more peaks selected from 7.30°±0.2°, 13.58°±0.2°, 14.06°±0.2°, 15.18°±0.2°, 15.66°±0.2°, 17.50°±0.2°, 18.94°±0.2°, 19.54°±0.2°, 22.22°±0.2°, 23.38°±0.2°, 24.10°±0.2°, 24.98°±0.2°, 25.94°±0.2°, 27.26°±0.2°, 28.50°±0.2°, and 32.82°±0.2° 2θ. In some embodiments, the crystal form includes voruciclib malonate.

In one embodiment, the disclosure provides a crystal form of voruciclib characterized by an X-ray powder diffraction pattern including one or more peaks selected from 5.06°±0.2°, 6.42°±0.2°, 9.34°±0.2°, 10.14°±0.2°, 12.30°±0.2°, 13.66°±0.2°, 14.14°±0.2°, 15.82°±0.2°, 17.02°±0.2°, 19.74°±0.2°, 20.38°±0.2°, 21.82°±0.2°, 22.66°±0.2°, 24.62°±0.2°, 25.78°±0.2°, 26.58°±0.2°, 28.66°±0.2°, and 29.98°±0.2° 2θ. In some embodiments, the crystal form includes voruciclib dibenzoyl-tartrate.

In one embodiment, the disclosure provides a crystal form of voruciclib characterized by an X-ray powder diffraction pattern including one or more peaks selected from 4.94°±0.2°, 6.78°±0.2°, 9.34°±0.2°, 10.94°±0.2°, 12.70°±0.2°, 13.38°±0.2°, 14.90°±0.2°, 15.66°±0.2°, 17.54°±0.2°, 18.82°±0.2°, 22.02°±0.2°, 23.98°±0.2°, 24.78°±0.2°, 25.30°±0.2°, 26.66°±0.2°, and 29.98°±0.2° 2θ. In some embodiments, the crystal form includes voruciclib phosphate.

In one embodiment, the disclosure provides a crystal form of voruciclib characterized by an X-ray powder diffraction pattern including one or more peaks selected from 6.86°±0.2°, 12.66°±0.2°, 13.58°±0.2°, 14.74°±0.2°, 15.98°±0.2°, 19.38°±0.2°, 23.94°±0.2°, 24.78°±0.2°, and 25.94°±0.2° 2θ. In some embodiments, the crystal form includes voruciclib oxalate.

In one embodiment, the disclosure provides a crystal form of voruciclib characterized by an X-ray powder diffraction pattern including one or more peaks selected from 9.02°±0.2°, 10.50°±0.2°, 11.06°±0.2°, 12.30°±0.2°, 12.82°±0.2°, 13.90°±0.2°, 14.82°±0.2°, 15.30°±0.2°, 15.94°±0.2°, 17.26°±0.2°, 19.34°±0.2°, 20.62°±0.2°, 22.18°±0.2°, 22.86°±0.2°, 24.58°±0.2°, 25.42°±0.2°, 25.86°±0.2°, 27.38°±0.2°, and 28.66°±0.2° 2θ. In some embodiments, the crystal form includes voruciclib napadisylate.

In one embodiment, the disclosure provides a crystalline anhydrate crystal form of voruciclib. In one embodiment, the disclosure provides a crystalline hydrate crystal form of voruciclib.

In one embodiment, the disclosure provides a composition including a voruciclib crystal form described herein, and a pharmaceutically acceptable excipient.

In one embodiment, the disclosure provides a method of treating a disease in a patient, the method including administering to the patient a therapeutically effective amount of a composition including a voruciclib crystal form described herein, wherein the disease is selected from the group consisting of chronic lymphocytic leukemia, non-Hodgkin's lymphoma, diffuse large B-cell lymphoma, mantle cell lymphoma, follicular lymphoma, B-cell lymphoproliferative disease, B cell acute lymphoblastic leukemia, Waldenström's macroglobulinemia, Burkitt's leukemia, Hodgkin's disease, multiple myeloma, acute myeloid leukemia, juvenile myelomonocytic leukemia, hairy cell leukemia, mast cell leukemia, mastocytosis, myeloproliferative disorders (MPDs), myeloproliferative neoplasms, polycythemia vera (PV), essential thrombocythemia (ET), primary myelofibrosis (PMF), myelodysplastic syndrome, chronic myelogenous leukemia (BCR-ABL1-positive), chronic neutrophilic leukemia, chronic eosinophilic leukemia, primary central nervous system (CNS) lymphoma, primary multifocal lymphoma of peripheral nervous system (PNS), thymus cancer, brain cancer, glioblastoma, lung cancer, squamous cell cancer, skin cancer (e.g., melanoma), eye cancer, retinoblastoma, intraocular melanoma, oral cavity and oropharyngeal cancers, bladder cancer, gastric cancer, stomach cancer, pancreatic cancer, breast cancer, cervical cancer, head and neck cancer, renal cancer, kidney cancer, liver cancer, ovarian cancer, prostate cancer, colorectal cancer, bone cancer (e.g., metastatic bone cancer), esophageal cancer, testicular cancer, gynecological cancer, thyroid cancer, epidermoid cancer, AIDS-related cancer (e.g., lymphoma), viral-induced cervical carcinoma (human papillomavirus), nasopharyngeal carcinoma (Epstein-Barr virus), Kaposi's sarcoma, primary effusion lymphoma (Kaposi's sarcoma herpesvirus), hepatocellular carcinoma (hepatitis B and hepatitis C viruses), T-cell leukemias (Human T-cell leukemia virus-1), benign hyperplasia of the skin, restenosis, benign prostatic hypertrophy, tumor angiogenesis, chronic inflammatory disease, rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, ulcerative colitis, atopic dermatitis, pouchitis, spondylarthritis, uveitis, Behcet's disease, polymyalgia rheumatica, giant-cell arteritis, sarcoidosis, Kawasaki disease, juvenile idiopathic arthritis, hidratenitis suppurativa, Sjögren's syndrome, psoriatic arthritis, juvenile rheumatoid arthritis, ankylosing spondylitis, Crohn's disease, lupus, and lupus nephritis.

In one embodiment, the disclosure provides a method of treating a hyperproliferative disease in a patient, the method comprising administering to the patient a therapeutically effective amount of a composition including a voruciclib crystal form described herein, wherein the hyperproliferative disease is selected from the group consisting of acute lymphoblastic leukemia, acute myeloid leukemia, chronic lymphocytic leukemia, non-Hodgkin's lymphoma, diffuse large B-cell lymphoma, mantle cell lymphoma, follicular lymphoma, B-cell lymphoproliferative disease, B cell acute lymphoblastic leukemia, and Waldenström's macroglobulinemia.

In one embodiment, the disclosure provides a method of treating a blood cancer in a patient, the method comprising administering to the patient a therapeutically effective amount of a composition including a voruciclib crystal form described herein. In some embodiments, the blood cancer is selected from the group consisting of acute myeloid leukemia (AML), chronic myeloid leukemia (CML), acute lymphocytic lymphoma (ALL), and chronic lymphocytic leukemia (CLL).

In one embodiment, the disclosure provides a composition for treating blood cancer in a patient, the composition including a voruciclib crystal form described herein, and a pharmaceutically acceptable excipient. In some embodiments, the blood cancer is selected from the group consisting of acute myeloid leukemia (AML), chronic myeloid leukemia (CML), acute lymphocytic lymphoma (ALL), and chronic lymphocytic leukemia (CLL).

In one embodiment, the disclosure provides a crystal form of voruciclib HCl, or a crystal form of voruciclib free base, each characterized by an X-ray diffraction pattern substantially in agreement with the X-ray diffraction patterns of FIG. 1.

In one embodiment, the disclosure provides a crystal form of voruciclib HCl characterized by an X-ray diffraction pattern substantially in agreement with one or more X-ray diffraction patterns of FIG. 2.

In one embodiment, the disclosure provides a crystal form of voruciclib HCl characterized by an X-ray diffraction pattern substantially in agreement with the X-ray diffraction pattern of FIG. 4.

In one embodiment, the disclosure provides a crystal form of voruciclib HCl characterized by an X-ray diffraction pattern substantially in agreement with one or more X-ray diffraction patterns of FIG. 8.

In one embodiment, the disclosure provides a crystal form of voruciclib HCl characterized by an X-ray diffraction pattern substantially in agreement with one or more X-ray diffraction patterns of FIG. 11.

In one embodiment, the disclosure provides a crystal form of voruciclib HCl characterized by an X-ray diffraction pattern substantially in agreement with one or more X-ray diffraction patterns of FIGS. 12A and 12B.

In one embodiment, the disclosure provides a crystal form of voruciclib HCl characterized by an X-ray diffraction pattern substantially in agreement with one or more X-ray diffraction patterns of FIG. 14.

In one embodiment, the disclosure provides a crystal form of voruciclib HCl characterized by an X-ray diffraction pattern substantially in agreement with one or more X-ray diffraction patterns of FIG. 18.

In one embodiment, the disclosure provides a crystal form of voruciclib HCl characterized by an X-ray diffraction pattern substantially in agreement with one or more X-ray diffraction patterns of FIG. 22.

In one embodiment, the disclosure provides a crystal form of voruciclib HCl characterized by an X-ray diffraction pattern substantially in agreement with one or more X-ray diffraction patterns of FIG. 26.

In one embodiment, the disclosure provides a crystal form of voruciclib HCl characterized by an X-ray diffraction pattern substantially in agreement with one or more X-ray diffraction patterns of FIG. 29.

In one embodiment, the disclosure provides a crystal form of voruciclib HCl characterized by an X-ray diffraction pattern substantially in agreement with one or more X-ray diffraction patterns of FIG. 32.

In one embodiment, the disclosure provides a crystal form of voruciclib HCl characterized by an X-ray diffraction pattern substantially in agreement with one or more X-ray diffraction patterns of FIG. 36.

In one embodiment, the disclosure provides a crystal form of voruciclib HCl characterized by an X-ray diffraction pattern substantially in agreement with one or more X-ray diffraction patterns of FIG. 40.

In one embodiment, the disclosure provides a crystal form of voruciclib HCl characterized by an X-ray diffraction pattern substantially in agreement with one or more X-ray diffraction patterns of FIG. 45.

In one embodiment, the disclosure provides a crystal form of voruciclib HCl characterized by an X-ray diffraction pattern substantially in agreement with one or more X-ray diffraction patterns of FIG. 49.

In one embodiment, the disclosure provides a crystal form of voruciclib HCl characterized by an X-ray diffraction pattern substantially in agreement with one or more X-ray diffraction patterns of FIG. 53.

In one embodiment, the disclosure provides a crystal form of voruciclib HCl characterized by an X-ray diffraction pattern substantially in agreement with one or more X-ray diffraction patterns of FIG. 57.

In one embodiment, the disclosure provides a crystal form of voruciclib HCl characterized by an X-ray diffraction pattern substantially in agreement with one or more X-ray diffraction patterns of FIG. 61.

In one embodiment, the disclosure provides a crystal form of voruciclib HCl characterized by an X-ray diffraction pattern substantially in agreement with one or more X-ray diffraction patterns of FIG. 65.

In one embodiment, the disclosure provides a crystal form of voruciclib HCl characterized by an X-ray diffraction pattern substantially in agreement with one or more X-ray diffraction patterns of FIG. 69.

In one embodiment, the disclosure provides a crystal form of voruciclib HCl characterized by an X-ray diffraction pattern substantially in agreement with one or more X-ray diffraction patterns of FIG. 73.

In one embodiment, the disclosure provides a crystal form of voruciclib HCl characterized by an X-ray diffraction pattern substantially in agreement with one or more X-ray diffraction patterns of FIG. 77.

In one embodiment, the disclosure provides a crystal form of voruciclib HCl characterized by an X-ray diffraction pattern substantially in agreement with one or more X-ray diffraction patterns of FIG. 81.

In one embodiment, the disclosure provides a crystal form of voruciclib HCl characterized by an X-ray diffraction pattern substantially in agreement with one or more X-ray diffraction patterns of FIG. 82.

In one embodiment, the disclosure provides a crystal form of voruciclib free base characterized by an X-ray diffraction pattern substantially in agreement with the X-ray diffraction patterns of FIGS. 85 and 142.

In one embodiment, the disclosure provides a crystal form of voruciclib free base characterized by a $^1$H-NMR spectra substantially in agreement with the $^1$H-NMR spectra of FIG. 89.

In one embodiment, the disclosure provides a crystal form of voruciclib malonate characterized by an X-ray diffraction pattern substantially in agreement with one or more X-ray diffraction patterns of FIGS. 90 and 91.

In one embodiment, the disclosure provides a crystal form of voruciclib malonate characterized by a $^1$H-NMR spectra substantially in agreement with the $^1$H-NMR spectra of FIG. 94 (Mao1).

In one embodiment, the disclosure provides a crystal form of voruciclib dibenzoyl-L-tartrate characterized by an X-ray diffraction pattern substantially in agreement with one or more X-ray diffraction patterns of FIGS. 96 and 97.

In one embodiment, the disclosure provides a crystal form of voruciclib dibenzoyl-L-tartrate characterized by a $^1$H-NMR spectra substantially in agreement with the $^1$H-NMR spectra of FIG. 100 (DiTr1).

In one embodiment, the disclosure provides a crystal form of voruciclib phosphate characterized by an X-ray diffraction pattern substantially in agreement with one or more X-ray diffraction patterns of FIGS. 102 and 103.

In one embodiment, the disclosure provides a crystal form of voruciclib phosphate characterized by a $^1$H-NMR spectra substantially in agreement with the $^1$H-NMR spectra of FIG. 106 (Pho1).

In one embodiment, the disclosure provides a crystal form of voruciclib oxalate characterized by an X-ray diffraction pattern substantially in agreement with one or more X-ray diffraction patterns of FIG. 108.

In one embodiment, the disclosure provides a crystal form of voruciclib oxalate characterized by a $^1$H-NMR spectra substantially in agreement with the $^1$H-NMR spectra of FIG. 111 (Oxa).

In one embodiment, the disclosure provides a crystal form of voruciclib napadisylate characterized by an X-ray diffraction pattern substantially in agreement with one or more X-ray diffraction patterns of FIGS. 113 and 114.

In one embodiment, the disclosure provides a crystal form of voruciclib napadisylate characterized by a $^1$H-NMR spectra substantially in agreement with the $^1$H-NMR spectra of FIG. 117 (Nds1a).

In one embodiment, the disclosure provides a crystal form of voruciclib esylate characterized by an X-ray diffraction pattern substantially in agreement with one or more X-ray diffraction patterns of FIG. 118.

In one embodiment, the disclosure provides a crystal form of voruciclib esylate characterized by a $^1$H-NMR spectra substantially in agreement with the $^1$H-NMR spectra of FIG. 120 (Esy1).

In one embodiment, the disclosure provides a crystal form of voruciclib 1-hydroxy-2-naphthoate characterized by an X-ray diffraction pattern substantially in agreement with one or more X-ray diffraction patterns of FIG. 121.

In one embodiment, the disclosure provides a crystal form of voruciclib benzoate characterized by an X-ray diffraction pattern substantially in agreement with one or more X-ray diffraction patterns of FIGS. 123 and 124.

In one embodiment, the disclosure provides a crystal form of voruciclib besylate characterized by an X-ray diffraction pattern substantially in agreement with one or more X-ray diffraction patterns of FIG. 126.

In one embodiment, the disclosure provides a crystal form of voruciclib gentisate characterized by an X-ray diffraction pattern substantially in agreement with one or more X-ray diffraction patterns of FIGS. 128 and 129.

In one embodiment, the disclosure provides a crystal form of voruciclib hydrobromide characterized by an X-ray diffraction pattern substantially in agreement with one or more X-ray diffraction patterns of FIG. 131.

In one embodiment, the disclosure provides a crystal form of voruciclib maleate characterized by an X-ray diffraction pattern substantially in agreement with one or more X-ray diffraction patterns of FIGS. 133 and 134.

In one embodiment, the disclosure provides a crystal form of voruciclib sulfate characterized by an X-ray diffraction pattern substantially in agreement with one or more X-ray diffraction patterns of FIGS. 136 and 137.

In one embodiment, the disclosure provides a crystal form of voruciclib toluenesulfonate characterized by an X-ray diffraction pattern substantially in agreement with one or more X-ray diffraction patterns of FIGS. 139 and 140.

BRIEF DESCRIPTION OF THE DRAWINGS

The foregoing summary, as well as the following detailed description of the invention, will be better understood when read in conjunction with the appended drawings.

FIG. 12A: Form 1 starting material, Form 2 obtained from thermocycling in 1,4-dioxane (Exp. ID TCP15), Form 3 obtained from thermocycling in IPA (Exp. ID TCP13), Form 4 obtained from solvent equilibration in THF at RT (Exp. ID SLP30), Form 5 obtained from thermocycling in 1,4-dioxane (Exp. ID TCP8), Form 6 (poor crystalline) obtained from solvent equilibration in water at 50° C. (Exp. ID SLP65), Form 7 obtained from thermocycling in 1,2-dimethoxyethane (Exp. ID TCP5), Form 8 obtained from evaporative crystallization from acetone (Exp. ID ECP34), Form 9 obtained from ambient dried solids from the cooling crystallization in DMF (Exp. ID PSM60), Form 10 obtained from vacuum dried solids from the cooling crystallization in DMF (Exp. ID PSM60); FIG. 12B: Form 11 obtained from ambient dried solids from the cooling crystallization in DMA (Exp. ID PSM59), Form 12 obtained after evaporation of the mother liquor from thermocycling in acetonitrile/water 90/10 (v/v) (Exp. ID TCP20 ML), Form 13 obtained from the cooling crystallization in ethanol (Exp. ID PSM52), Form 14 obtained from thermocycling in acetonitrile/water 90/10 (v/v) (Exp. ID TCP20), Form 15 obtained from the vapor diffusion into solution from DMF/1,4-dioxane (Exp. ID VDL8), Form 16 obtained from evaporative crystallization from DMSO (Exp. ID ECP18), Form 17 obtained from the anti-solvent addition with TFE/heptane, Form 18 obtained from the ambient dried solids from anti-solvent addition with DMF/isopropyl acetate, Form 19 obtained from evaporative crystallization from methanol/diisopropyl ether 20/80 and Form 20 obtained after conversion of Form 10 after AAC.

FIG. 120 illustrates the ¹H-NMR spectrum of Esy1/Form D obtained from ethanesulfonic acid and THF (Exp. ID SSm16, bottom) compared to the starting material (top).

FIG. 121 illustrates the XRPD patterns of Xin1 obtained from THF (Exp. ID SSm19) before and after AAC; the starting material and 1-hydroxy-2-naphthoic acid are shown as references.

Figure 122:
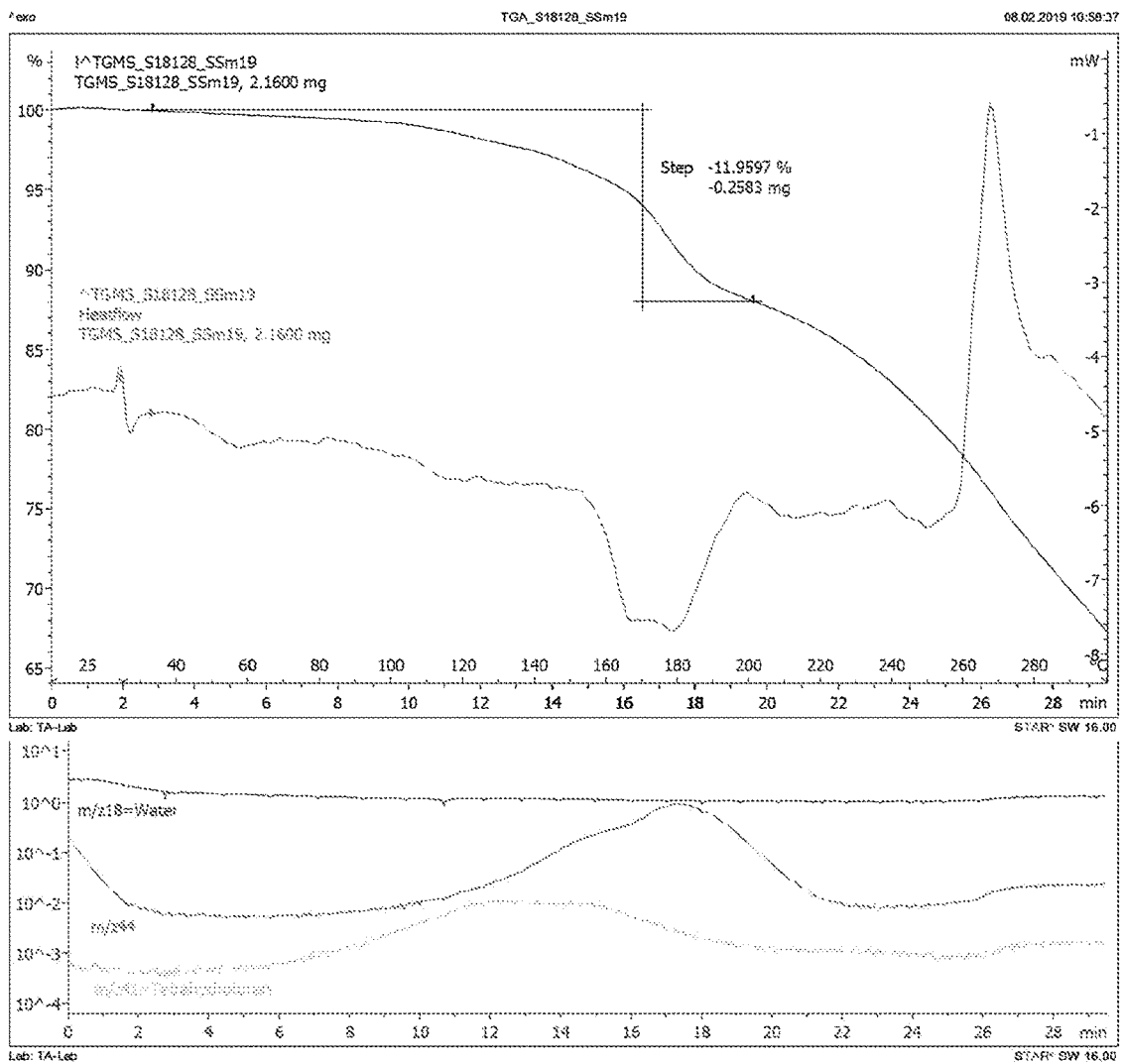

FIG. 122 illustrates the TGMS analysis (heating rate 10° C./min) of Xin1 obtained with 1-hydroxy-2-naphthoic acid and THF (Exp. ID SSm19); a mass loss of 12% is observed between 25-200° C., related to solvent loss and the start of decomposition.

Figure 123:
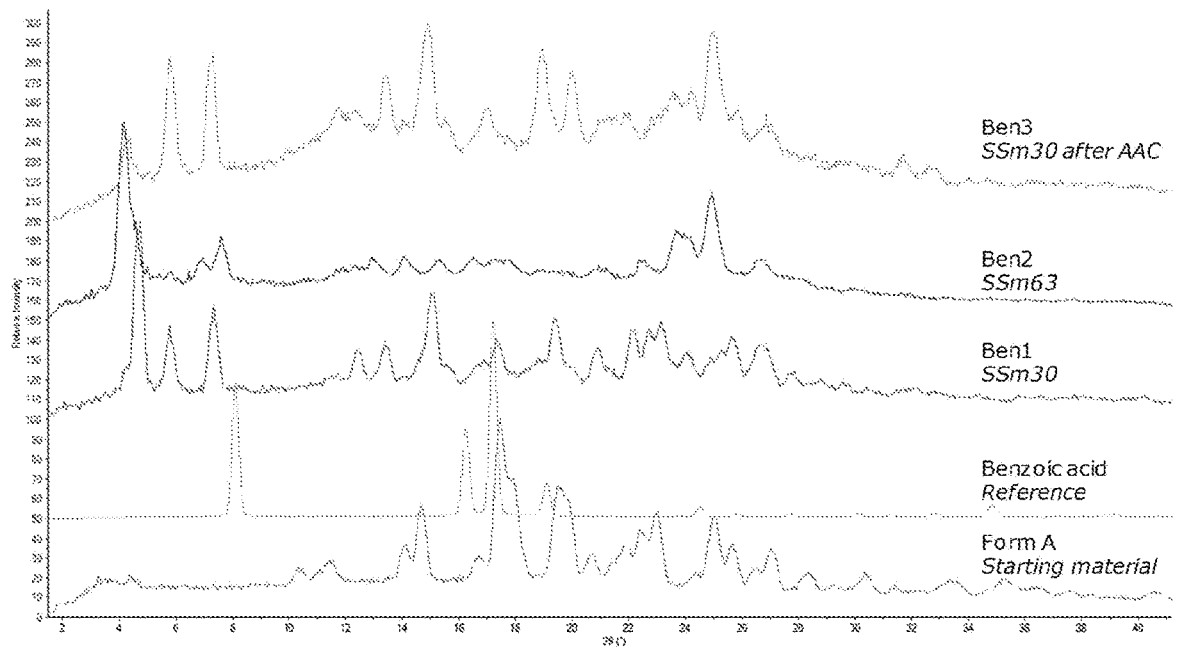

FIG. 123 illustrates the XRPD patterns of (from bottom to top): Form A starting material, benzoic acid reference, Ben2 obtained from acetone (Exp. ID SSm63) and Mao2 obtained from THF (Exp. ID SSm20).

Figure 124:
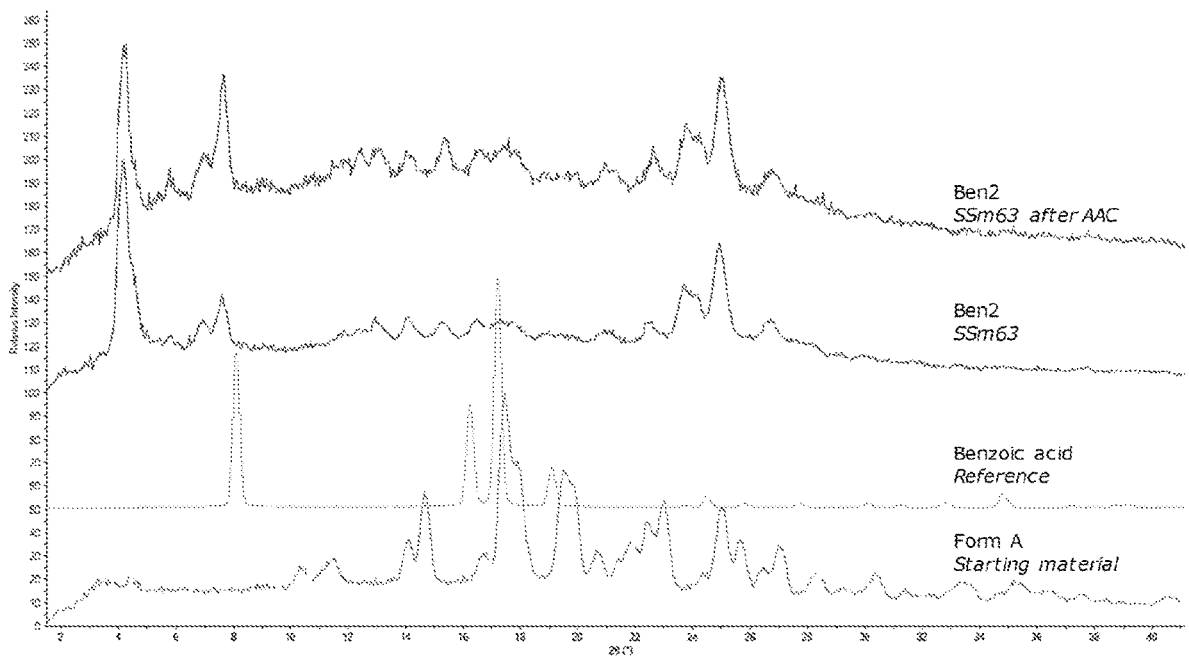

FIG. 124 illustrates the XRPD patterns of Ben2 (Exp. ID SSm63) before and after AAC; the starting material and benzoic acid are shown as references.

Figure 125:
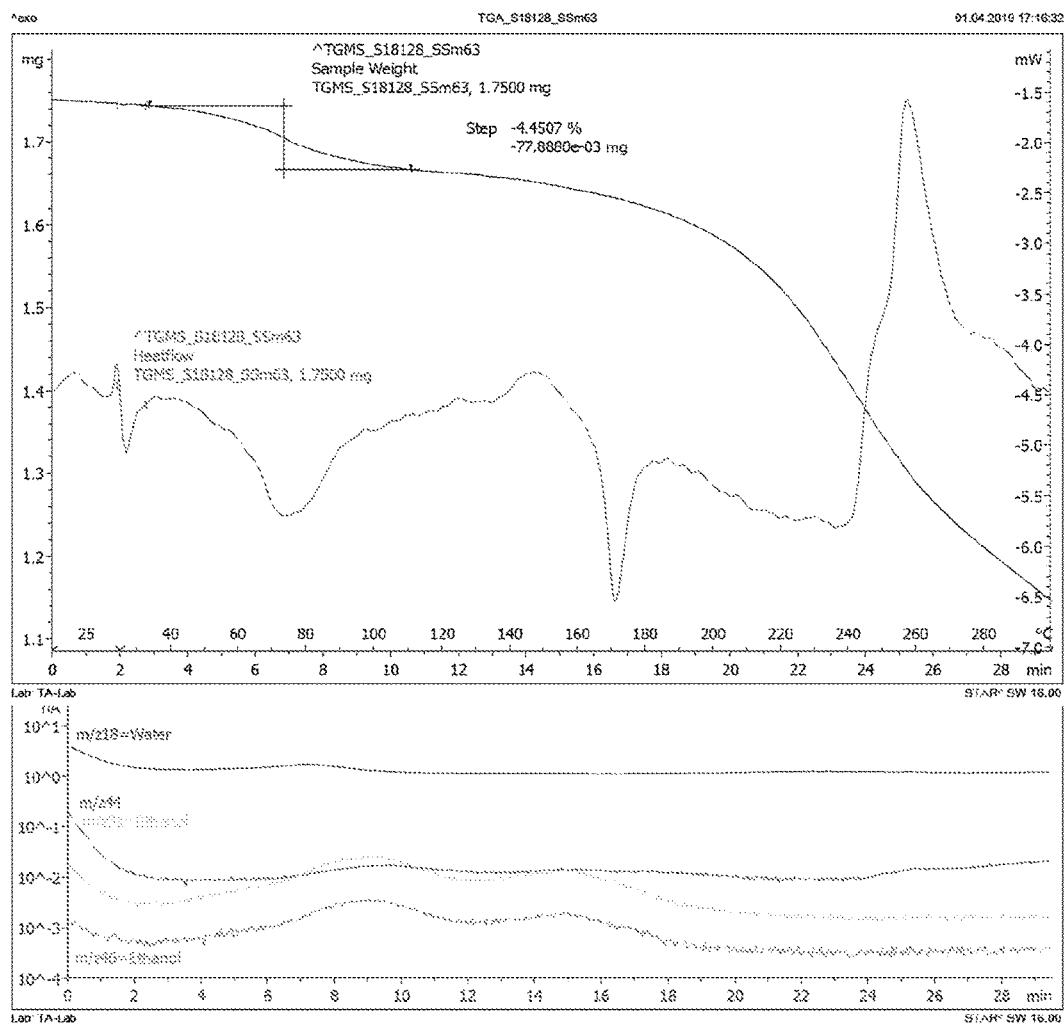

FIG. 125 illustrates the TGMS analysis (heating rate 10° C./min) of Ben2 obtained with benzoic acid and ethanol (Exp. ID SSm63).

Figure 126:
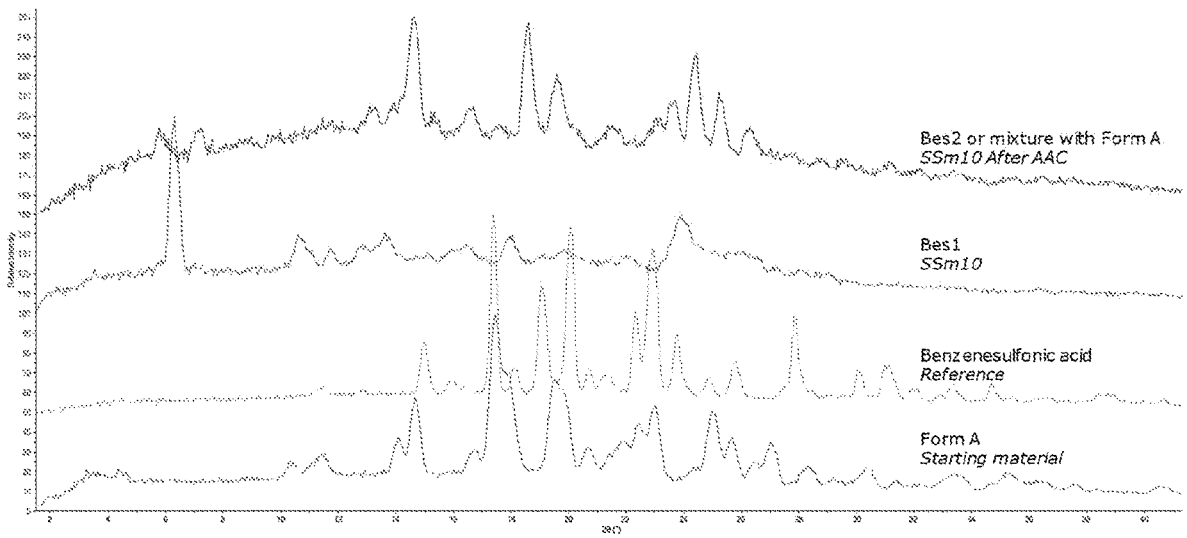

FIG. 126 illustrates the XRPD patterns of the solids obtained from THF (Exp. ID SSm10) before and after AAC; the starting material and benzenesulfonic acid are shown as references.

Figure 127:
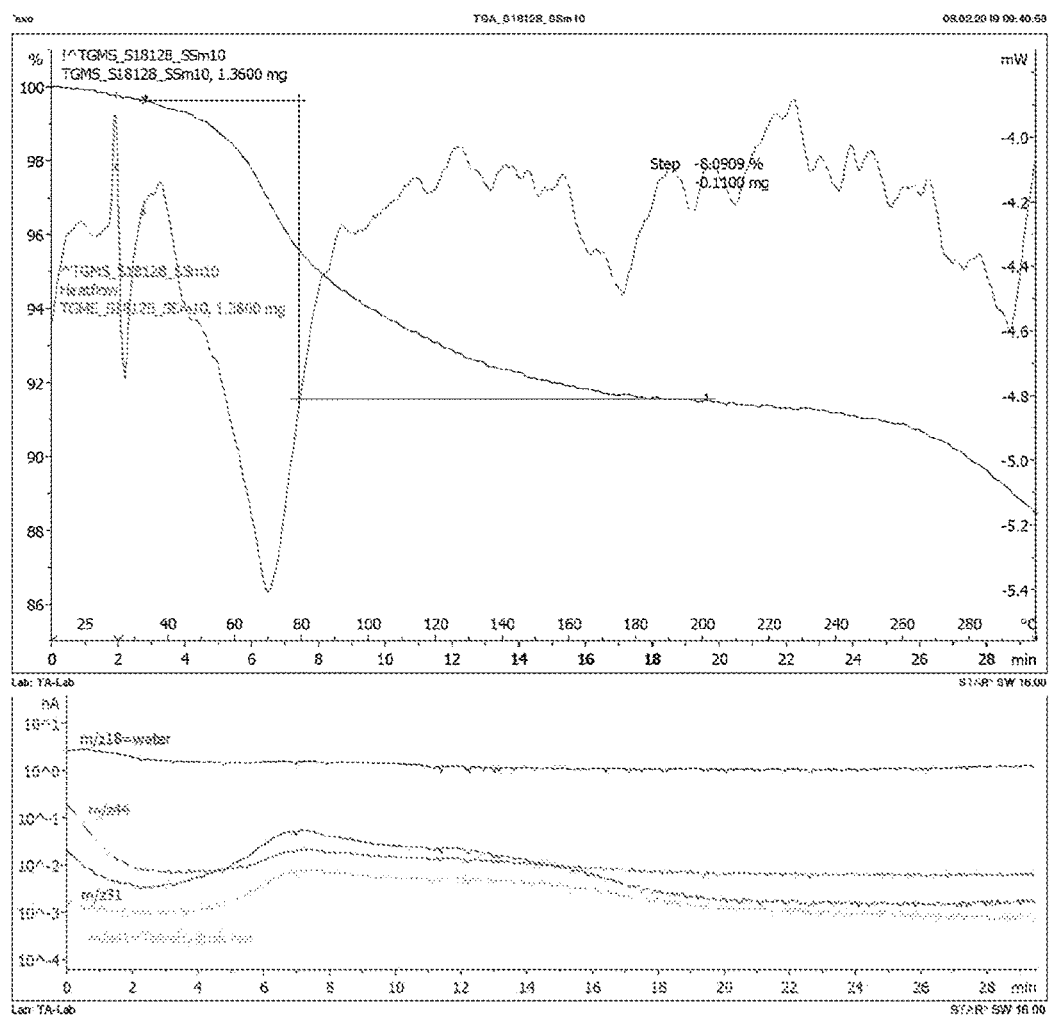

FIG. 127 illustrates the TGMS analysis (heating rate 10° C./min) of Bes1 obtained with benzenesulfonic acid and THF (Exp. ID SSm10); a mass loss of 8.1% between 25-180° C. is observed due to loss of THF, followed by decomposition around 230° C.

Figure 128:
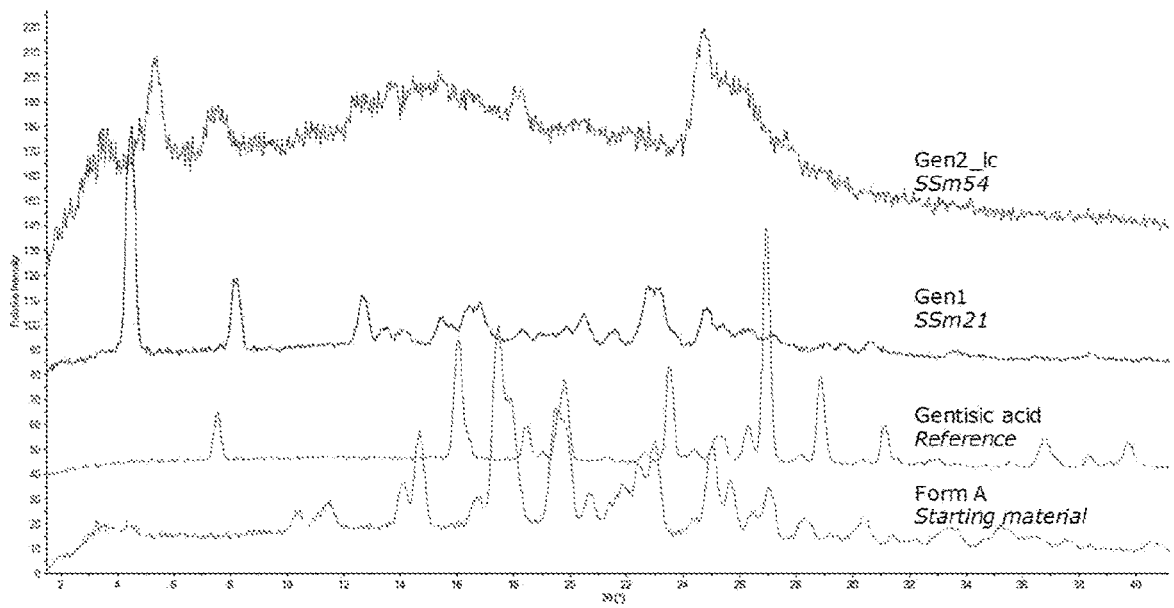

FIG. 128 illustrates the XRPD patterns of (from bottom to top): Form A starting material, gentisic acid reference, Gen1 obtained from THF (Exp. ID SSm21) and Gen2_1c obtained from ethanol (solid phase) (Exp. ID SSm54).

Figure 129:
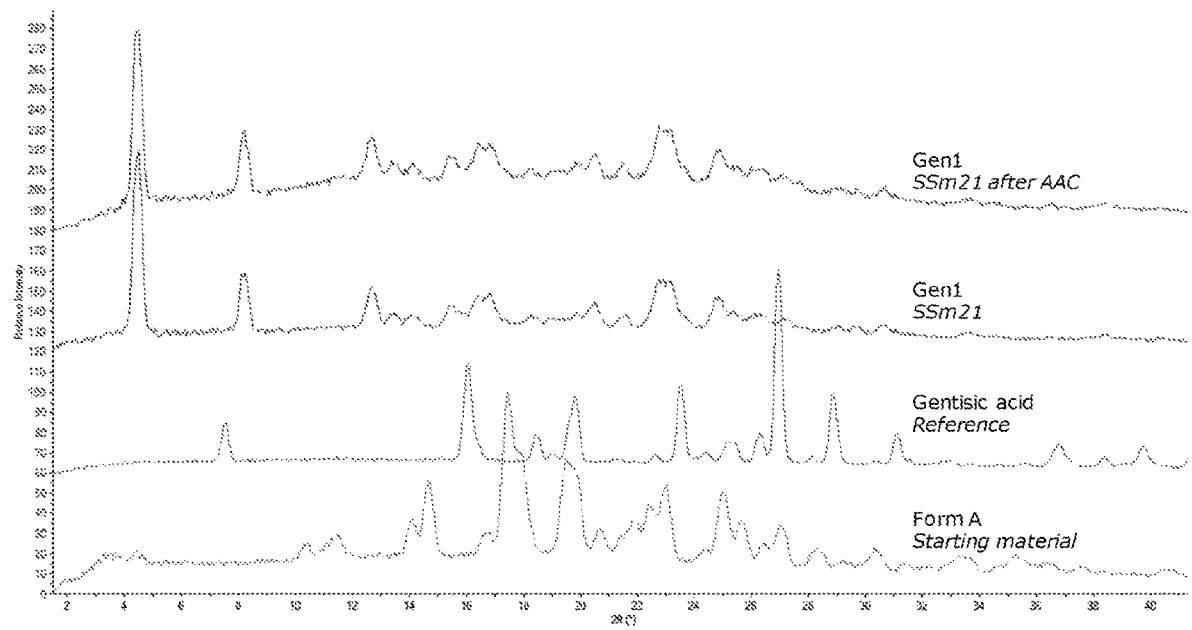

FIG. 129 illustrates the XRPD patterns of Gen1 (Exp. ID SSm21) before and after AAC; the starting material and gentisic acid are shown as references.

Figure 130:
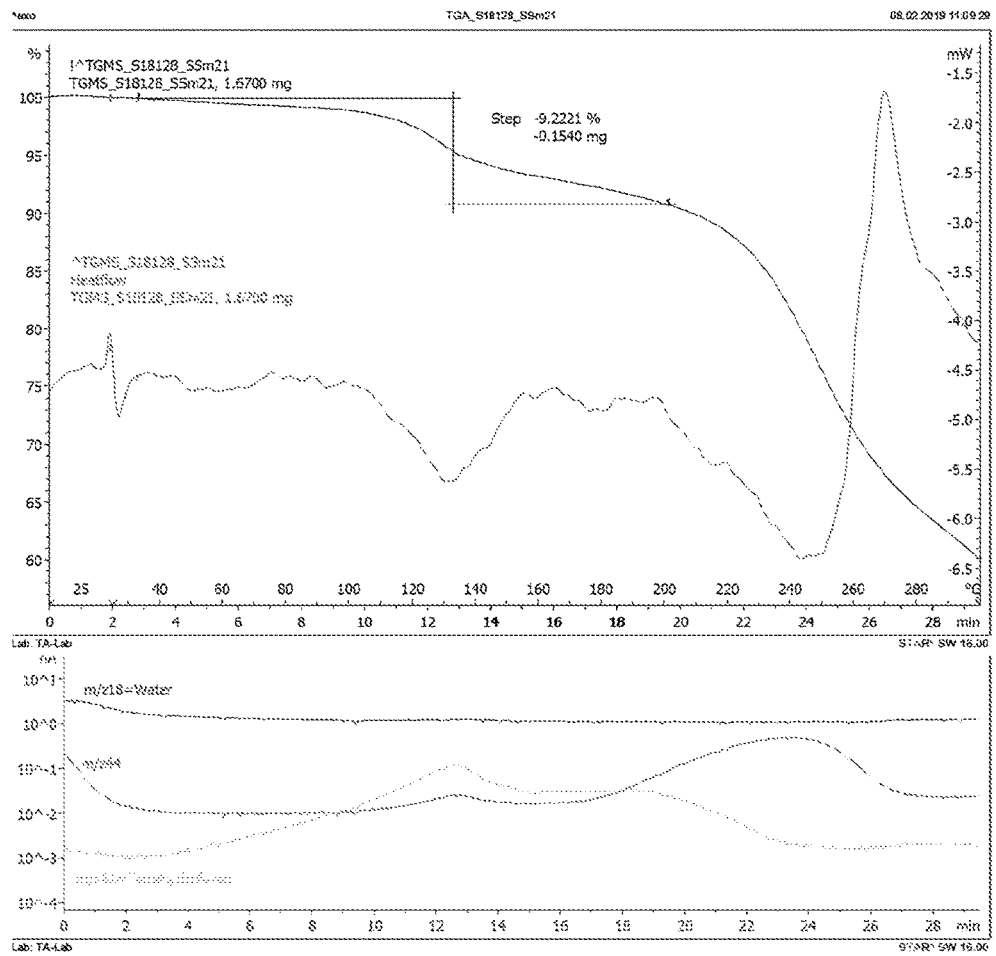

FIG. 130 illustrates the TGMS analysis (heating rate 10° C./min) of Gen1 obtained with gentisic acid and THF (Exp. ID SSm21); a mass loss of 9.2% is observed between 25-200° C., followed by thermal decomposition.

Figure 131:
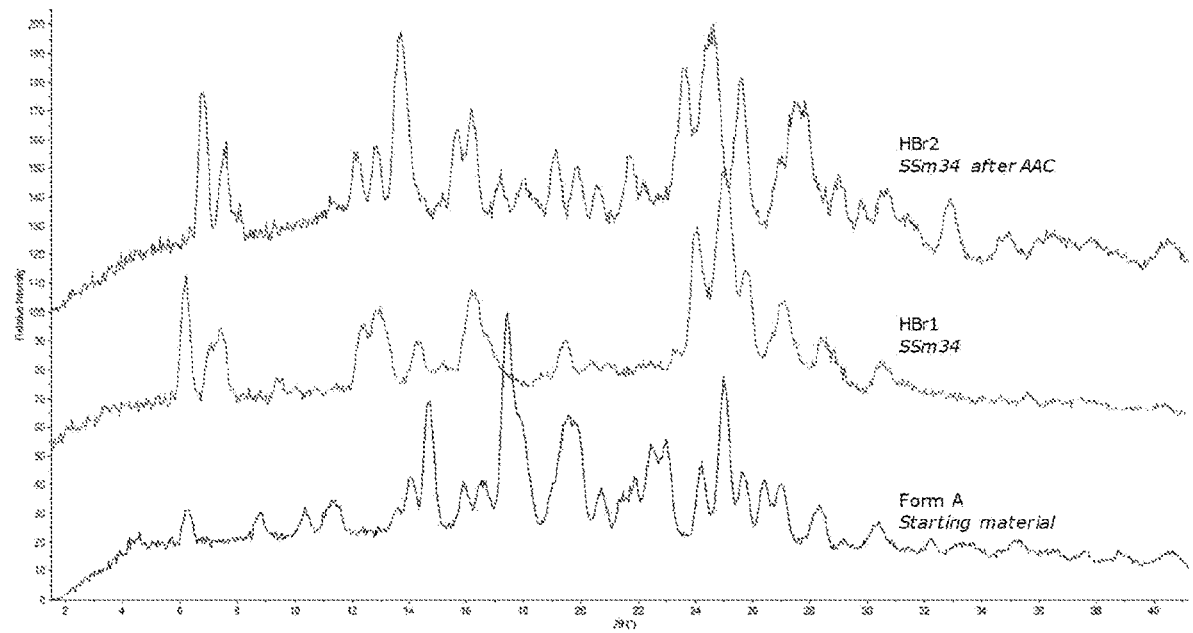

FIG. 131 illustrates the XRPD patterns of HBr1 (Exp. ID SSm34) before and after AAC; the starting material and hydrobromic acid are shown as references.

Figure 132:
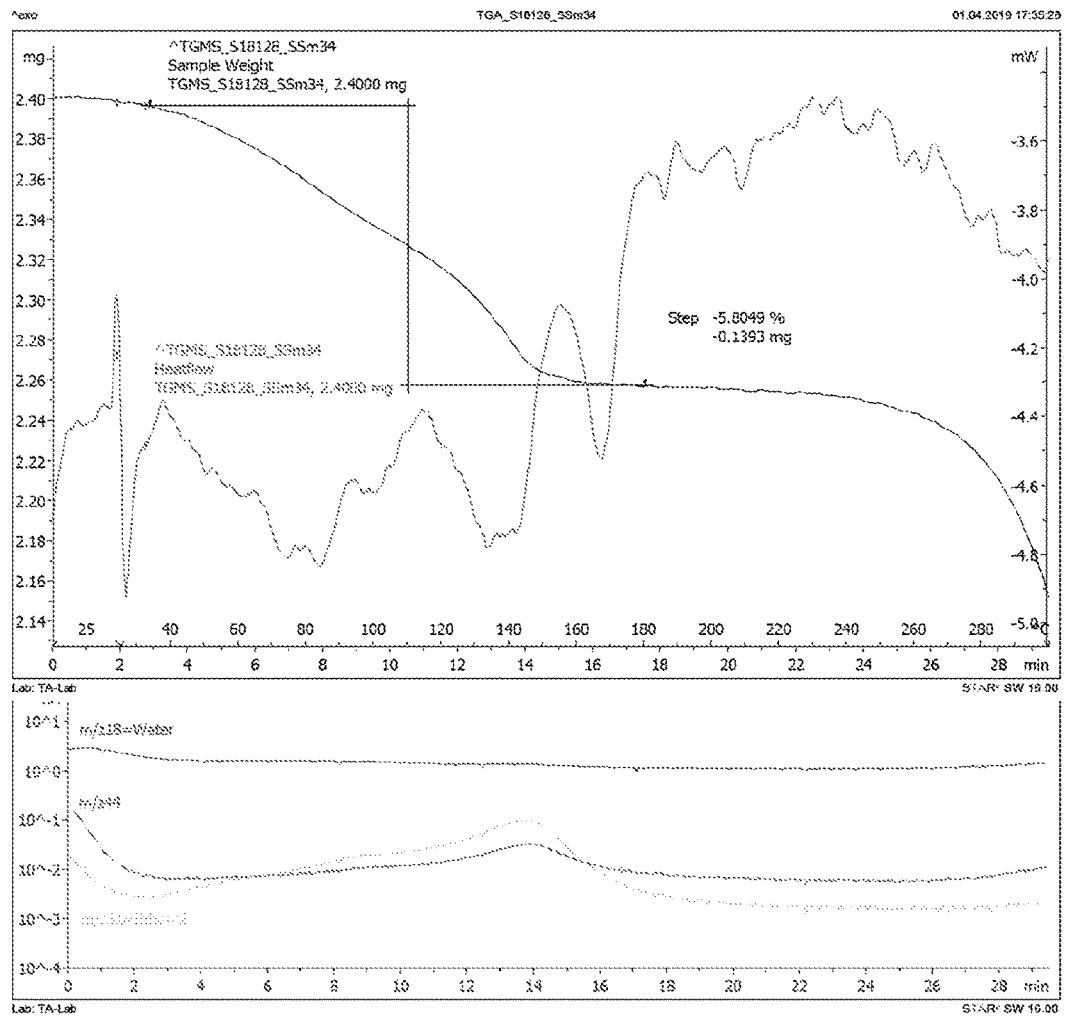

FIG. 132 illustrates the TGMS analysis (heating rate 10° C./min) of HBr1 obtained with hydrobromic acid and ethanol (Exp. ID SSm34); a mass loss of 5.9% is observed, accompanied by several endothermic events in the heat flow signal; the thermal decomposition is observed around 240° C.

Figure 133:
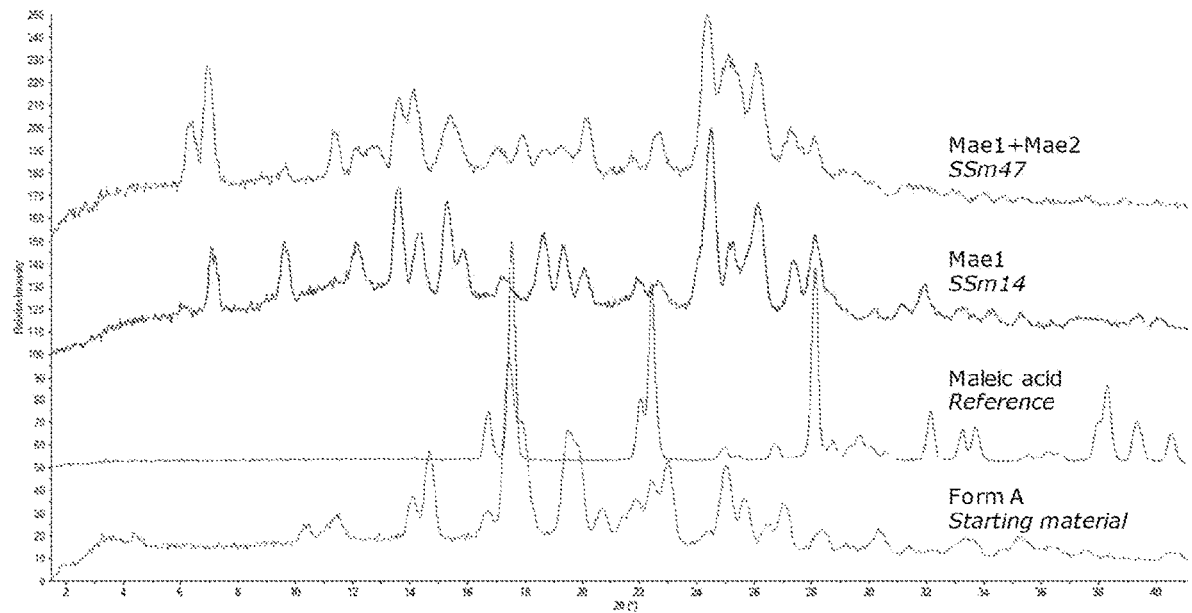

FIG. 133 illustrates the XRPD patterns of (from bottom to top): Form A starting material, maleic acid reference, Mae1 obtained from THF (Exp. ID SSm14) and Mae2 obtained from THF (Exp. ID SSm47).

Figure 134:
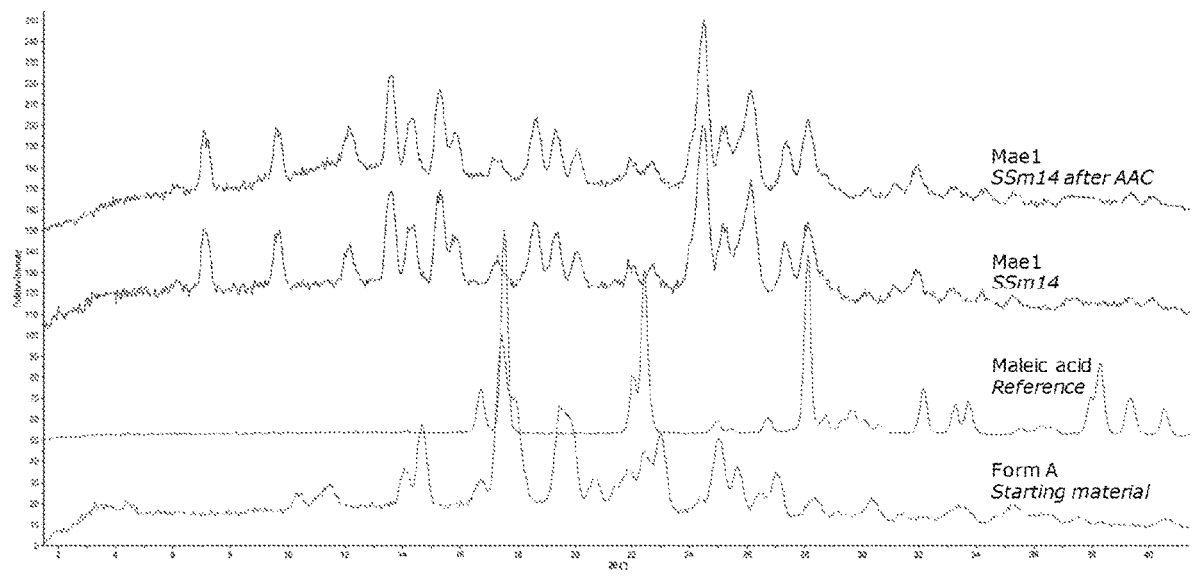

FIG. 134 illustrates the XRPD patterns of Mae1 (Exp. ID SSm14) before and after AAC; the starting material and maleic acid are shown as references.

Figure 135:
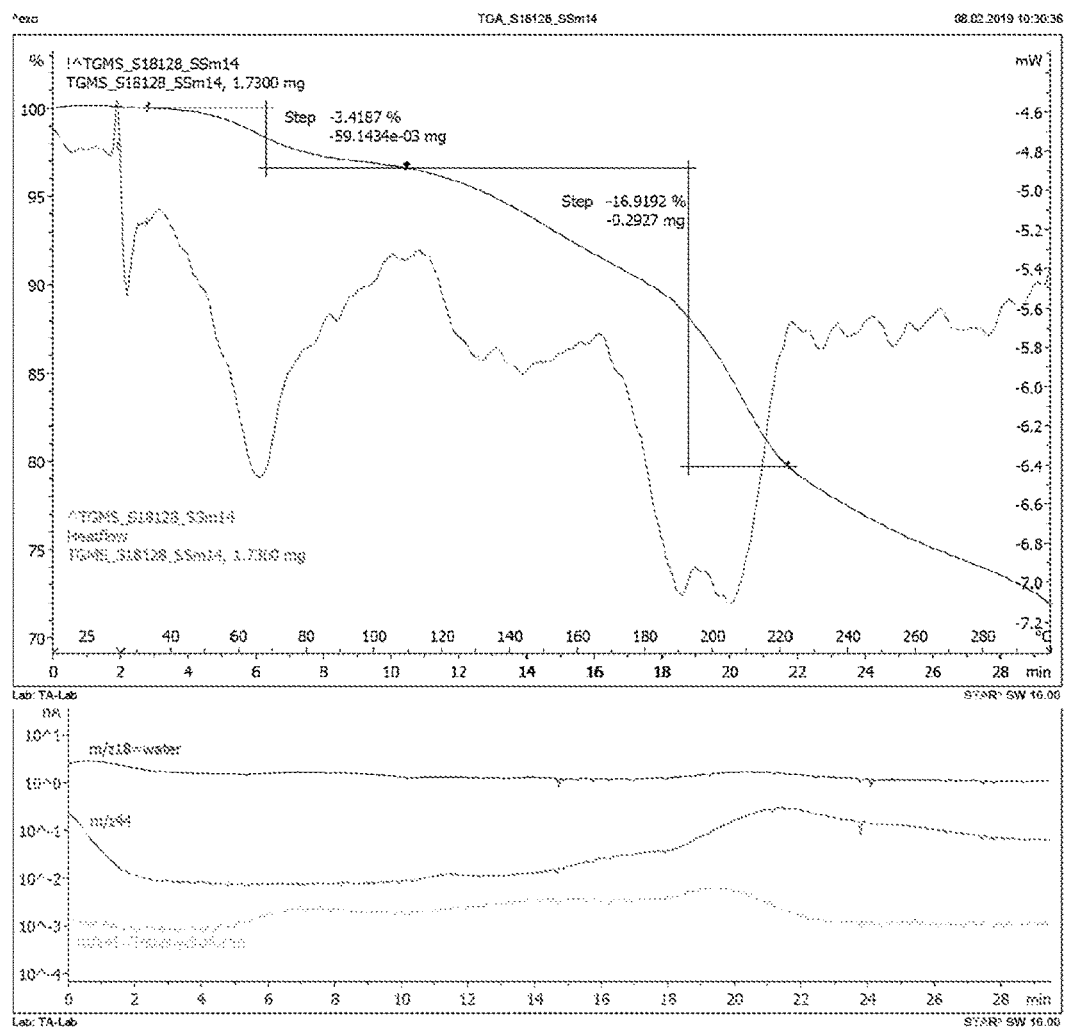

FIG. 135 illustrates the TGMS analysis (heating rate 10° C./min) of Mae1 obtained with maleic acid and THF (Exp. ID SSm14); a mass loss of 3.4% is observed between 25-110° C. due to solvent/water loss, followed by decomposition.

Figure 136:
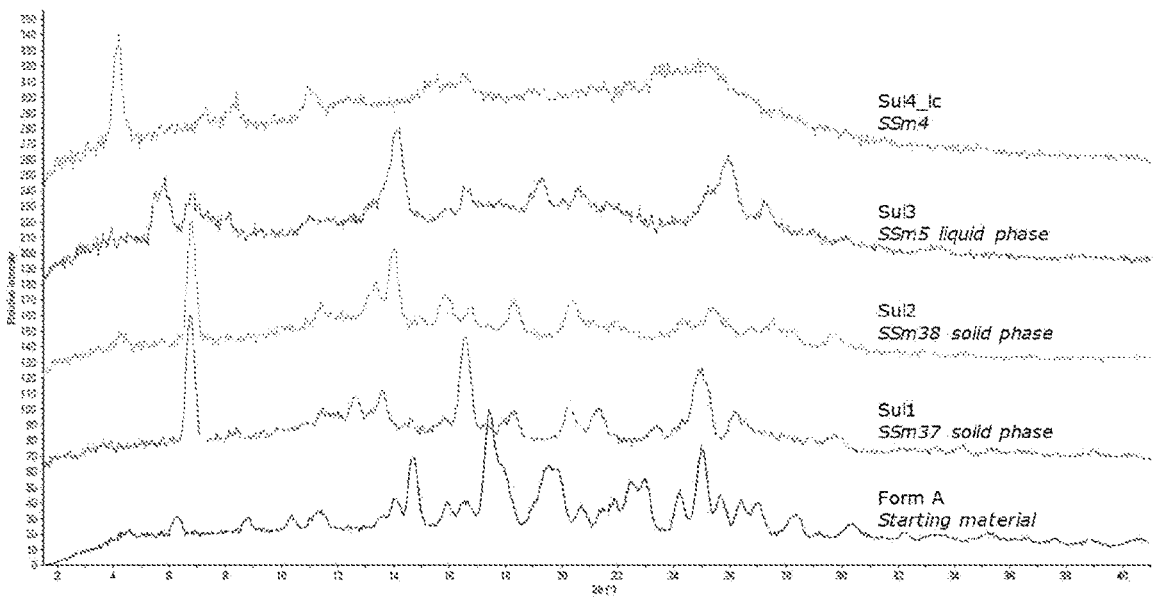

FIG. 136 illustrates the XRPD patterns of (from bottom to top): Form A starting material, Sul1 obtained from ethanol and 1 molar eq. sulfuric acid (Exp. ID SSm37), Sul2 obtained from ethanol and 0.5 mol eq. sulfuric acid (Exp. ID SSm38, solid phase), Sul3 obtained from the mother liquor of the experiment in THF and 0.5 molar eq. sulfuric acid (Exp. ID SSm5, liquid phase) and Sul4 obtained from THF with 1 molar eq. sulfuric acid (SSm4).

Figure 137:
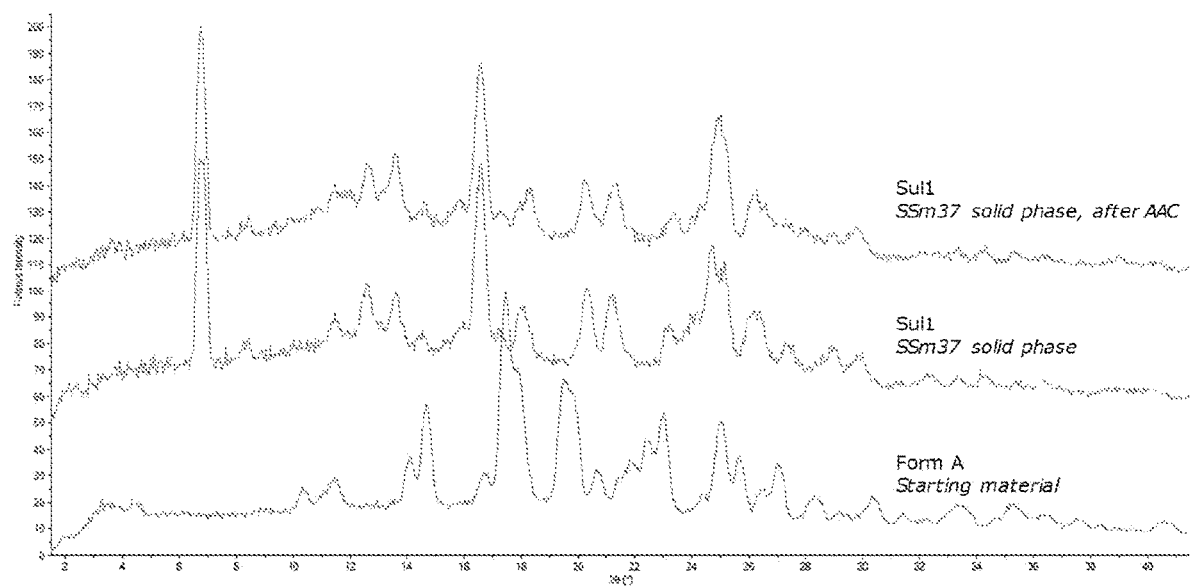

FIG. 137 illustrates the XRPD patterns of Sul1 (Exp. ID SSm37) before and after AAC; the starting material is shown as references.

Figure 138:
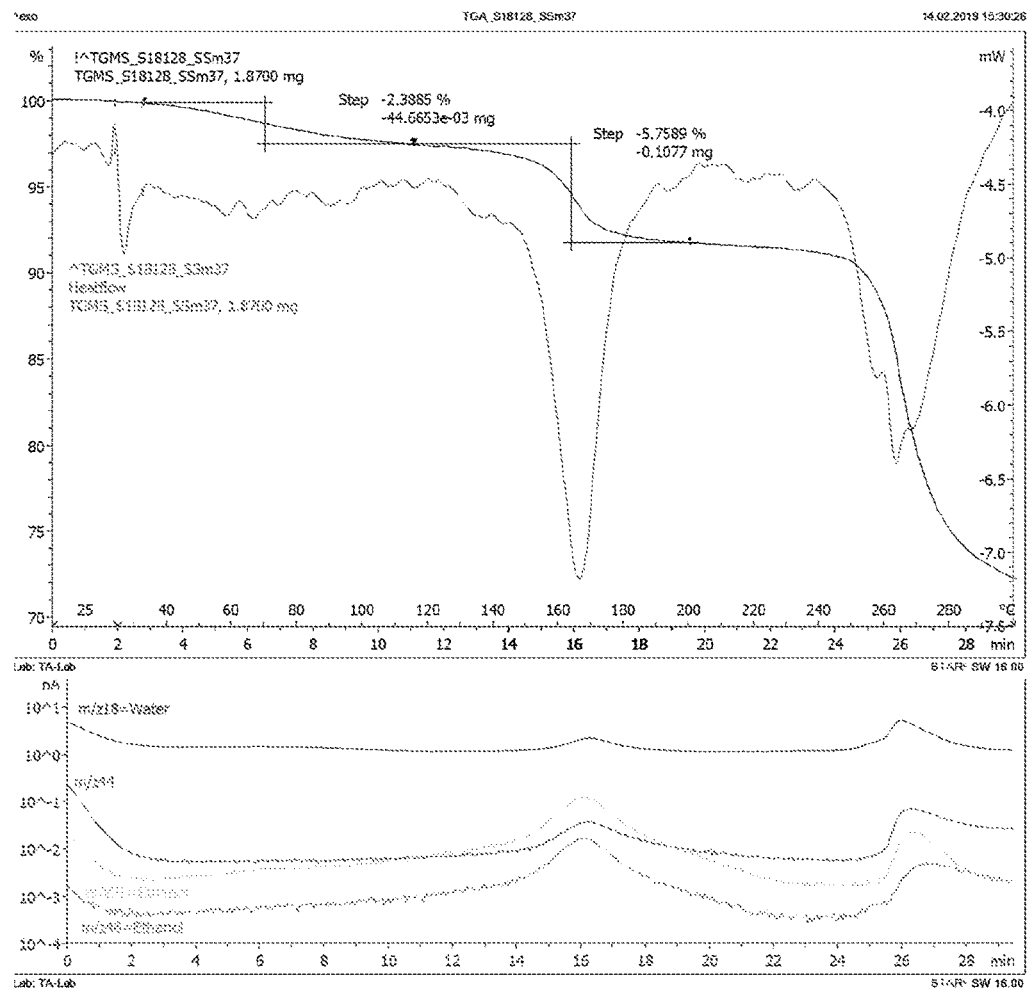

FIG. 138 illustrates the TGMS analysis (heating rate 10° C./min) of Sul1 obtained with 1 molar equivalent sulfuric acid in ethanol (Exp. ID SSm37); a mass loss of 2.4% is observed between 25-120° C. and 5.8% between 120-200° C. followed by decomposition above 240° C.

Figure 139:
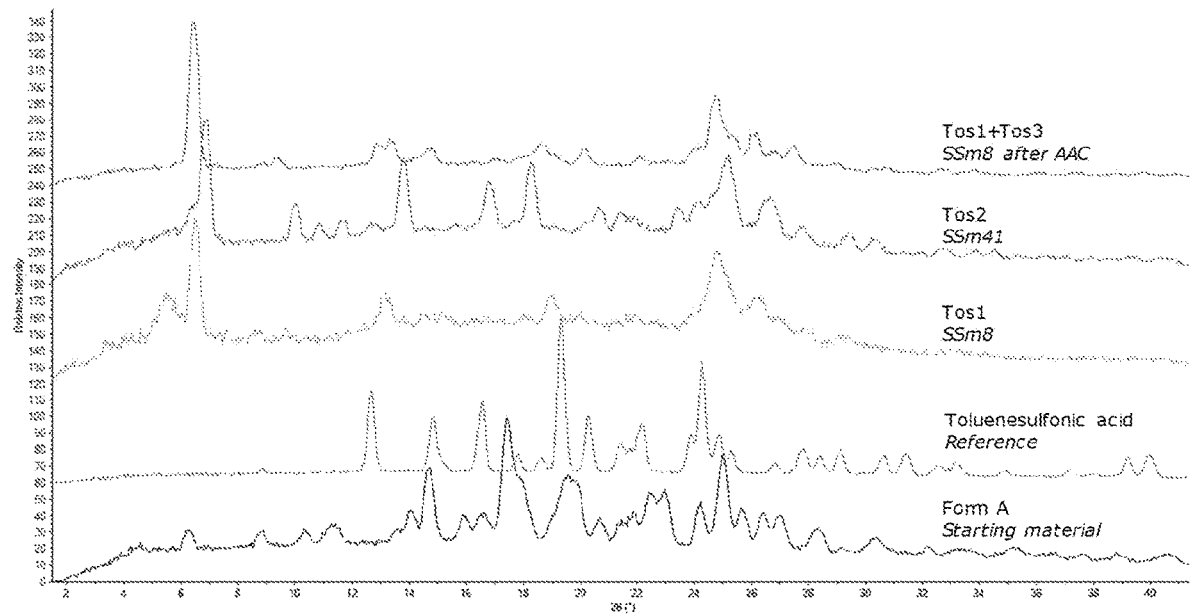

FIG. 139 illustrates the XRPD patterns of (from bottom to top): Form A starting material, p-toluenesulfonic acid reference, Tos1 obtained from THF (Exp. ID SSm8), Tos2 obtained from ethanol (Exp. ID SSm41) and Tos1+Tos3 obtained by conversion of Tos1 during exposure to AAC (Exp. ID SSm8 after AAC).

Figure 140:
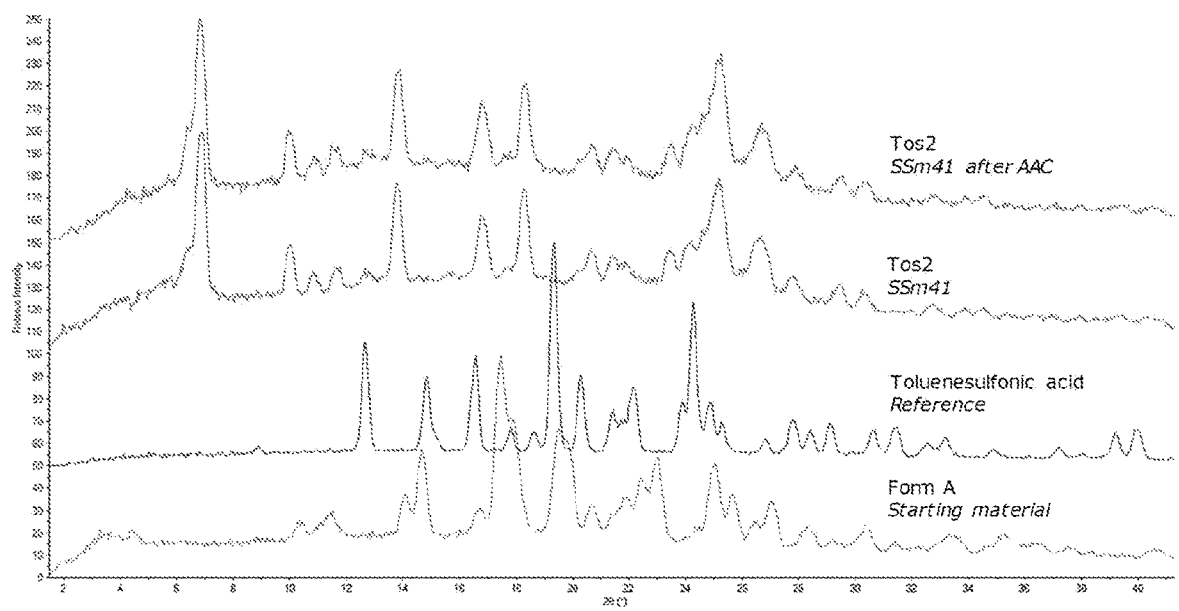

FIG. 140 illustrates the XRPD patterns of Tos2 (Exp. ID SSm41) before and after AAC; the starting material and p-toluenesulfonic acid are shown as references.

Figure 141:
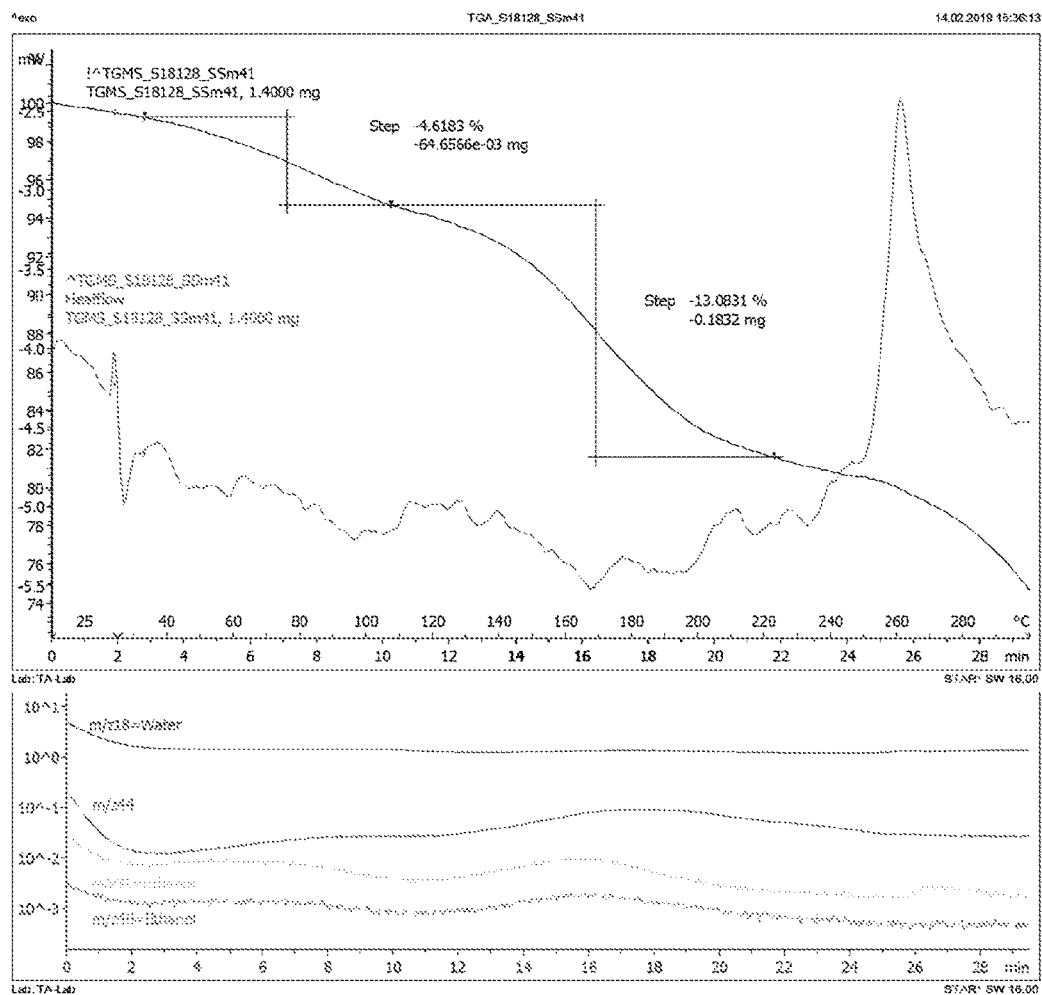

FIG. 141 illustrates the TGMS analysis (heating rate 10° C./min) of Tos2 obtained with p-toluenesulfonic acid and ethanol (Exp. ID SSm41); a mass loss of 4.6%, due to ethanol, is observed between 25-110° C., followed by decomposition.

Figure 142:
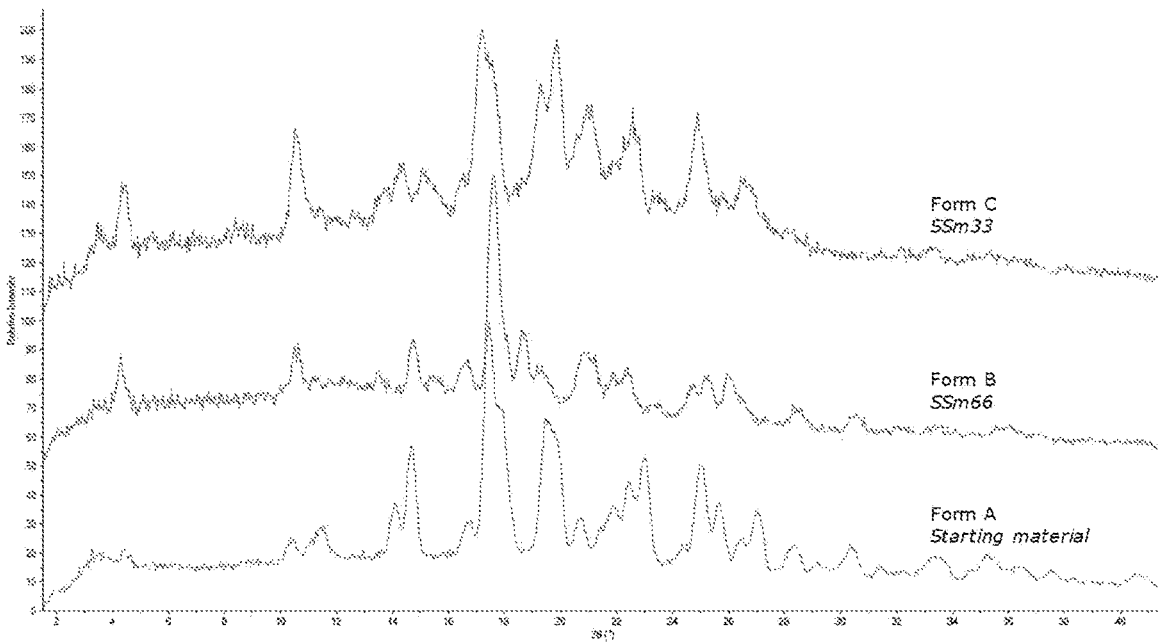

FIG. 142 illustrates XRPD patterns of (from bottom to top): Form A starting material, Form B obtained from ethanol (Exp. ID SSm66) and Form C obtained from THF (Exp. ID SSm33).

Figure 143:
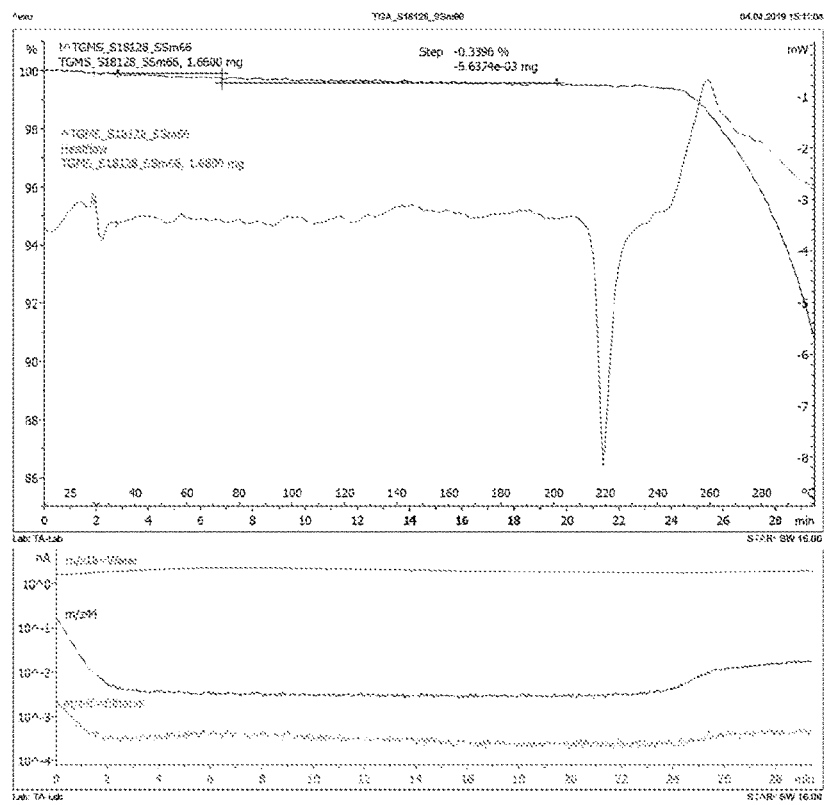

FIG. 143 illustrates the TGMS analysis (heating rate 10° C./min) of Form B obtained from the control sample in ethanol (Exp. ID SSm66); a small mass loss of 0.3% was observed prior to melting, due to residual solvent.

Figure 144:
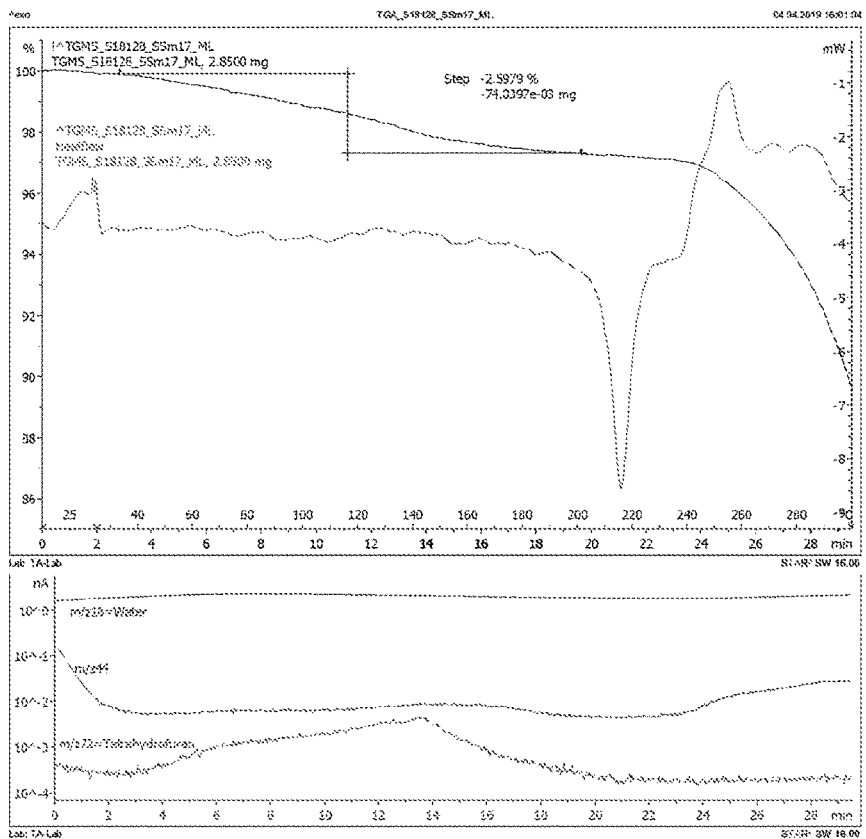

FIG. 144 illustrates the TGMS analysis (heating rate 10° C./min) of Form C obtained from the mother liquor of the experiment with glutamic acid in THF (Exp. ID SSm17 liquid phase); a mass loss of 2.6%, due to THF, is observed between 25-200° C., followed by decomposition.

Figure 145:
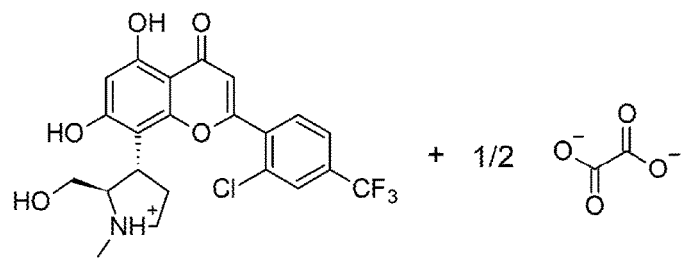

FIG. 145 illustrates the molecular structure of the hemi-oxalate salt of ME-522. The molecular weight of the free base is 469.8 g/mol.

Figure 146:
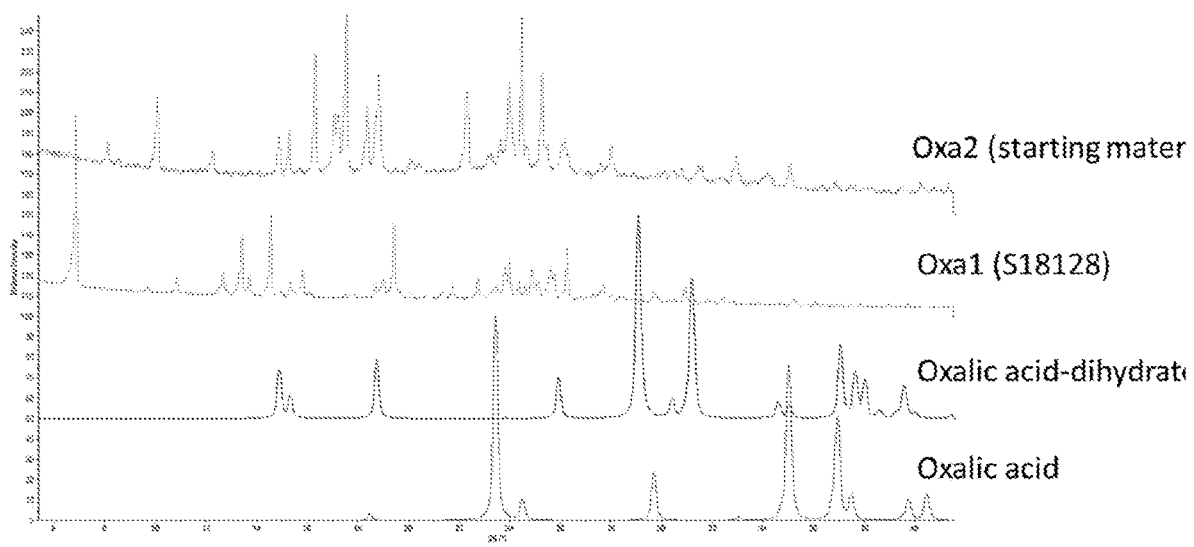

FIG. 146 illustrates the overlay of HT-XRPD patterns, with from bottom to top: oxalic acid, oxalic acid-dihydrate, Oxa1 (from project S18128) and Oxa2 (starting material).

Figure 147:
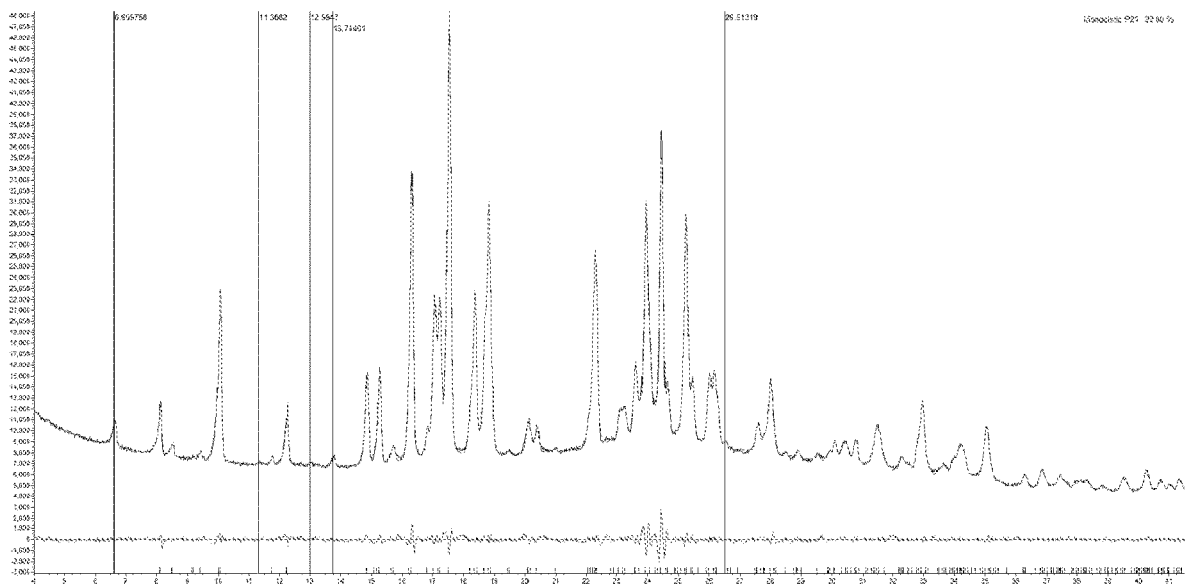

FIG. 147 illustrates the graphical representation of Rietveld analysis on Oxa2 (starting material). The black line represents collected data, the red line is the calculated powder pattern and the grey line is the difference between them. The blue sticks at the bottom show the peak positions of the fitted cell. The vertical lines indicate the diffraction peaks associated to non-indexed crystalline impurities.

Figure 148:
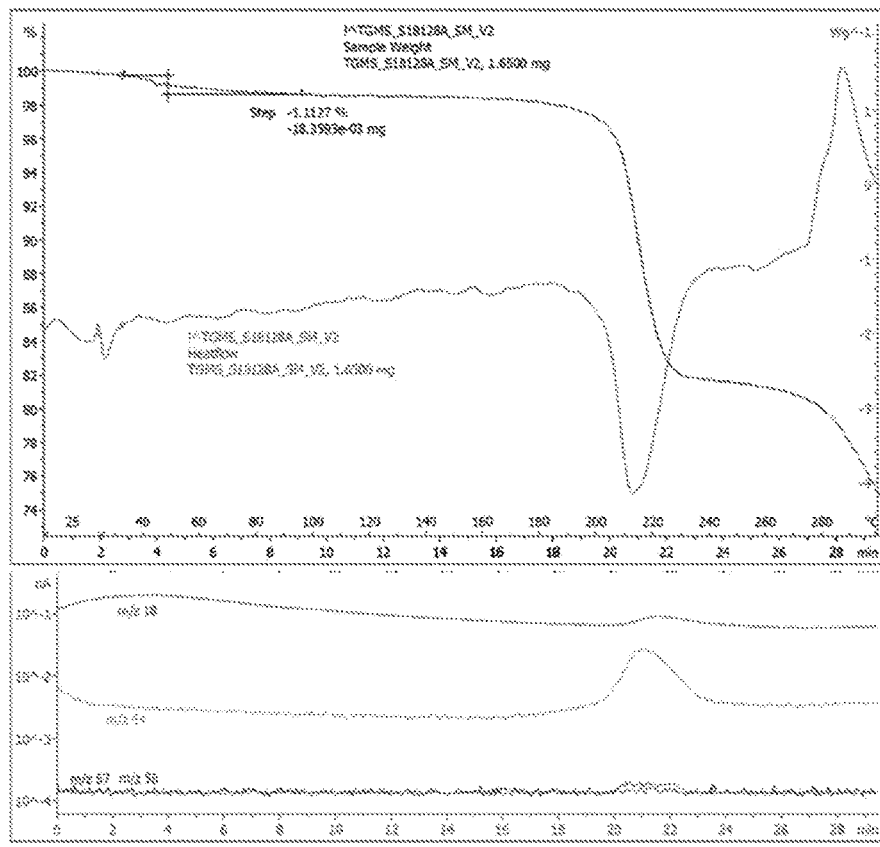

FIG. 148 illustrates the TGMS thermogram (heating rate 10° C./min) of Oxa2 (starting material). A mass loss of 1.1% was recorded between 40 and 100° C.

Figure 149:
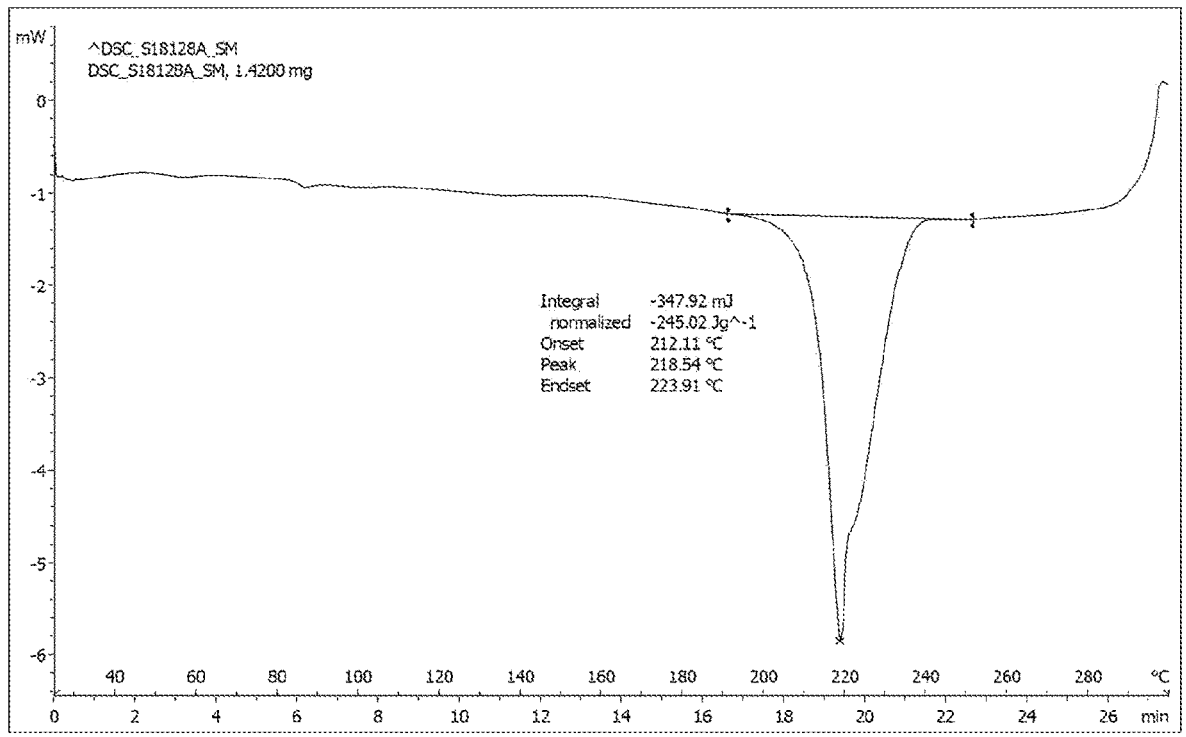

FIG. 149 illustrates the DSC trace (heating rate 10° C./min) of Oxa2 (starting material). A single broad endothermic event was observed at $T_{peak}$ 218.5° C.

Figure 150:
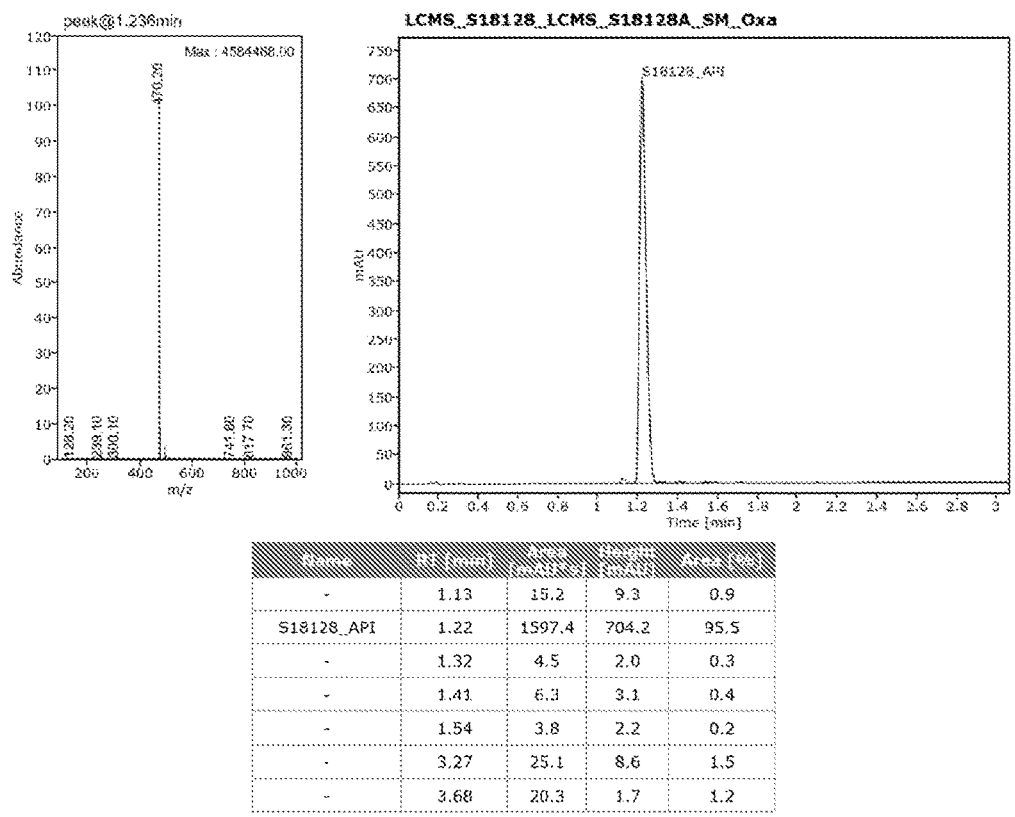

FIG. 150 illustrates the UPLC-MS analysis of Oxa2 (starting material). The peak corresponding to the API had a retention time of 1.2 min and the positive ion spectrum showed an ion with m/z of 470.2 $[M+H]^+$, in agreement with the API molecular mass of 469.8 g/mol. The table shows the retention times, peak areas and heights of the API and unidentified impurities.

Figure 151:
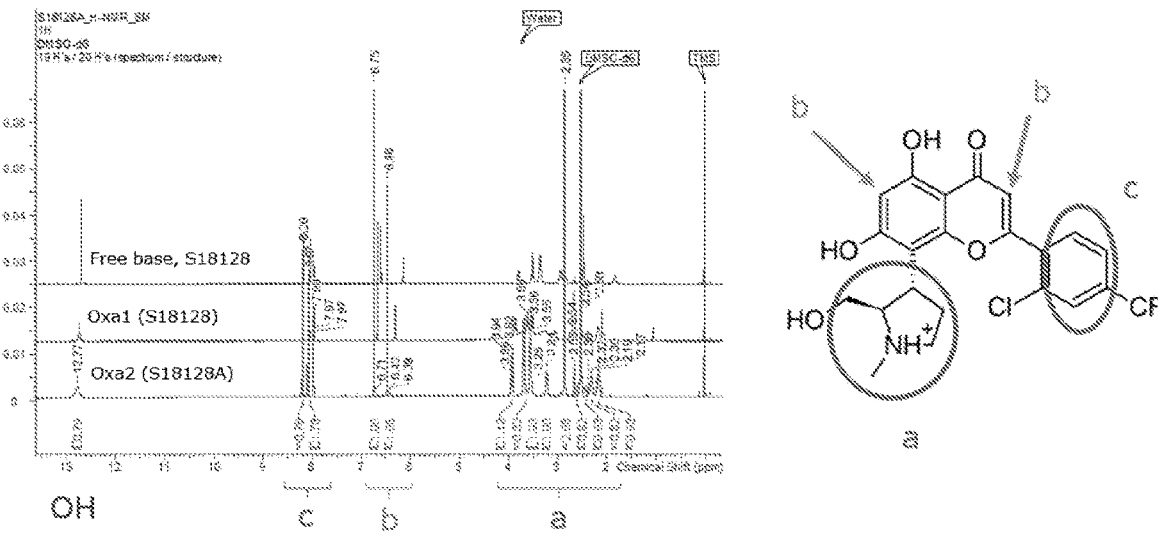

FIG. 151 illustrates the $^1$H-NMR spectra of Oxa2 (SM, bottom), Oxa1 (from S18128, Exp. ID: SSm12, middle) and the free base (from S18128, top) measured in DMSO-$d_6$ (bottom). The letters at the bottom of the spectrum correspond to the hydrogens in the molecular structure of the API.

Figure 152:
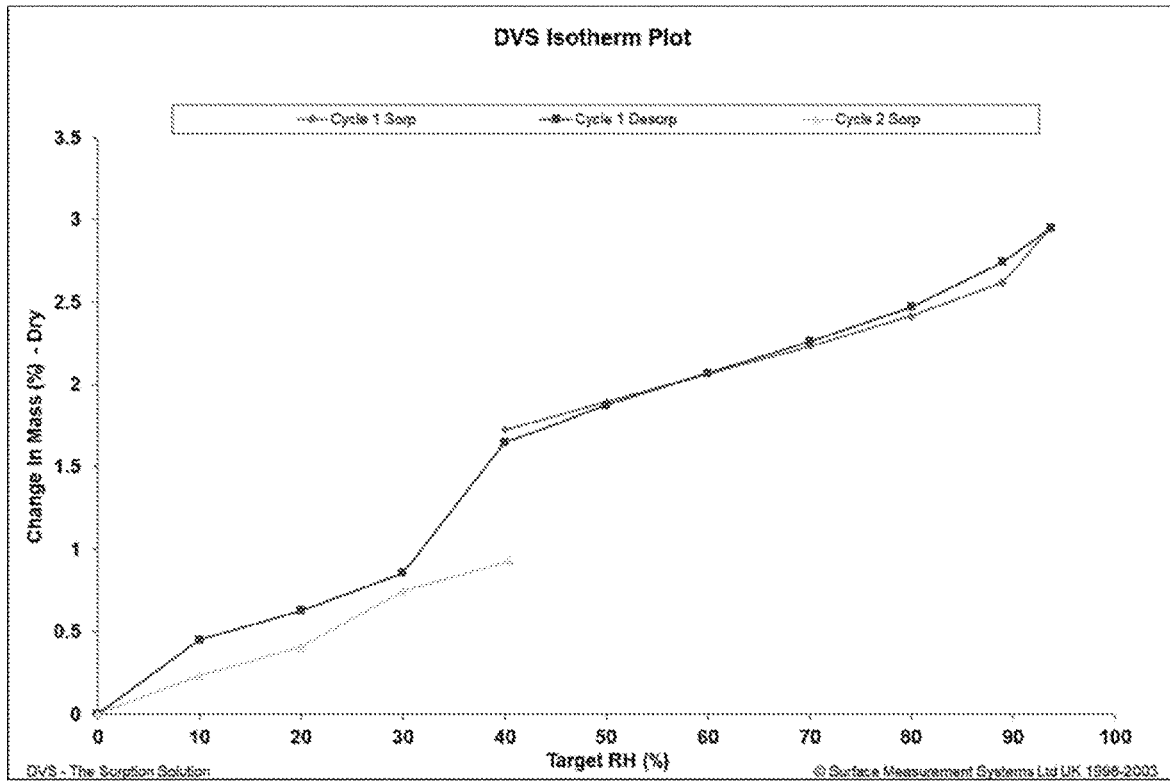

FIG. 152 illustrates the DVS isotherm plot of Oxa2 (starting material) in which the change in mass is plotted as a function of the RH. Initially, a sorption profile was applied from 40% RH to 95% (red diamond), followed by a desorption profile from 95% RH to 0% RH (blue square). Finally, the RH was set to the start value of 40% (green triangle).

Figure 153:
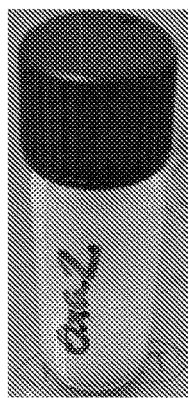

FIG. 153 illustrates the picture of the suspension obtained after a small aliquot of water was added to Oxa2 (starting material).

Figure 154:
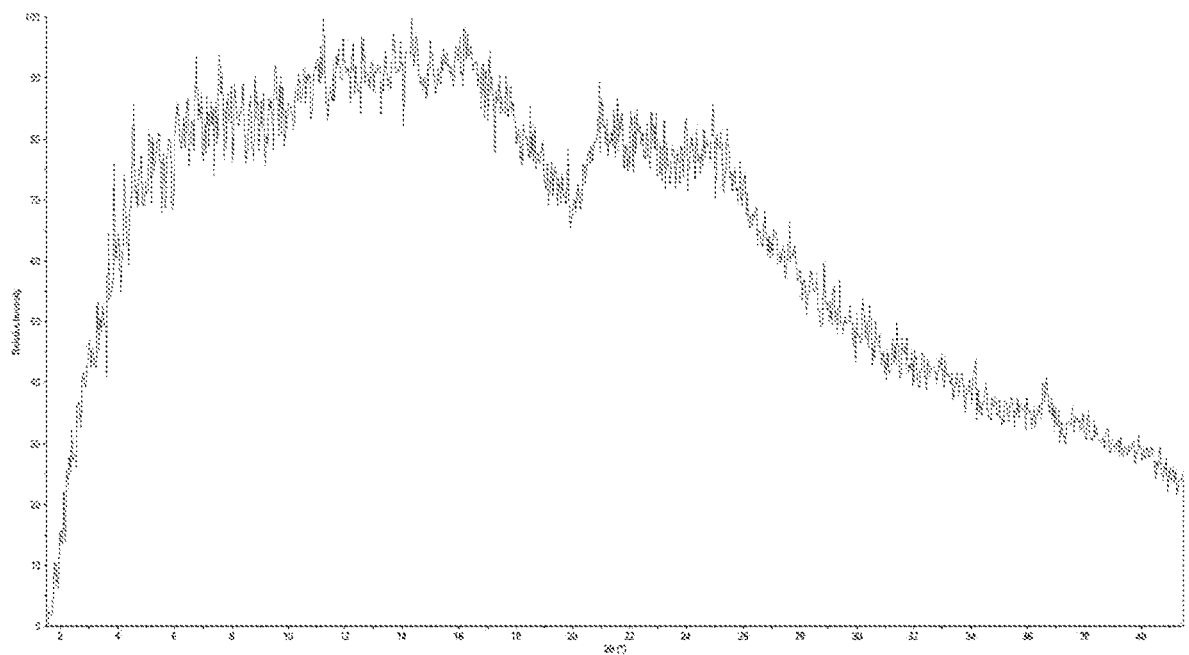

FIG. 154 illustrates the HT-XRPD pattern of ME-522 oxalate salt (Exp. ID: QSA8) prepared by freeze-drying the starting material in acetone/water (50/50, v/v).

Figure 155:
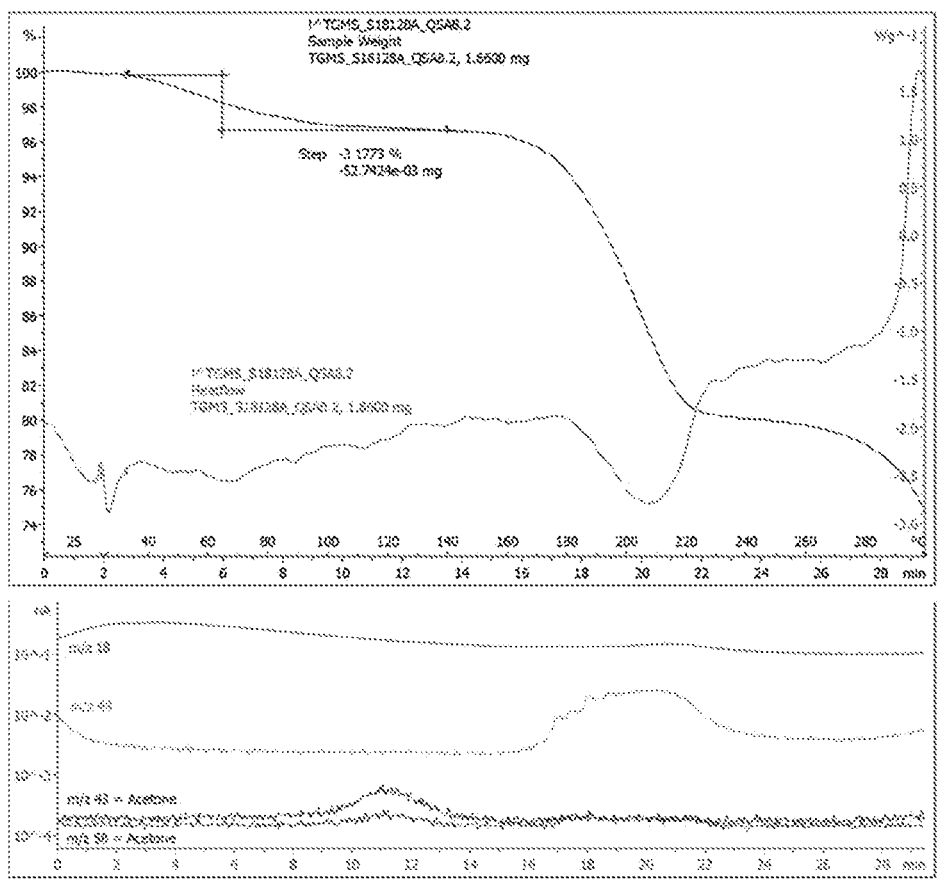

FIG. 155 illustrates the TGMS thermogram (heating rate 10° C./min) of the amorphous oxalate salt obtained after freeze-drying (Exp. ID: QSA8). A mass loss of 3.2% was recorded between 40 and 140° C.

Figure 156:
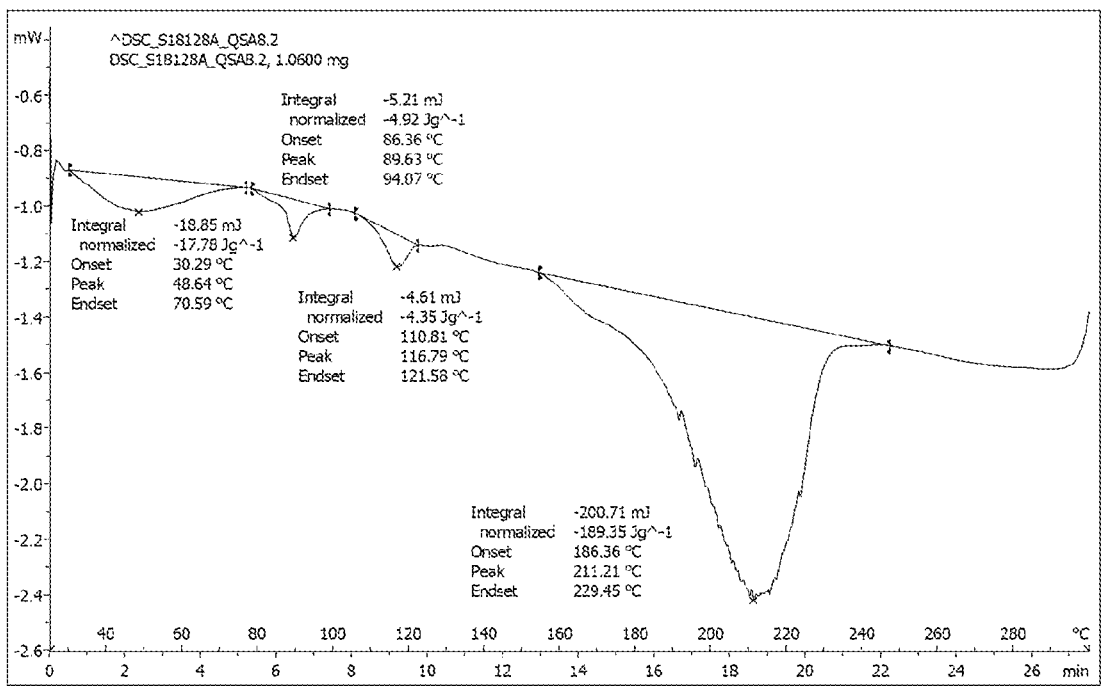

FIG. 156 illustrates the DSC trace (heating rate 10° C./min) of the amorphous oxalate salt obtained after freeze-drying (Exp. ID: QSA8). Three endothermic events were detected between 25-140° C. in addition to a broad endothermic event between 185-230° C.

Figure 157:
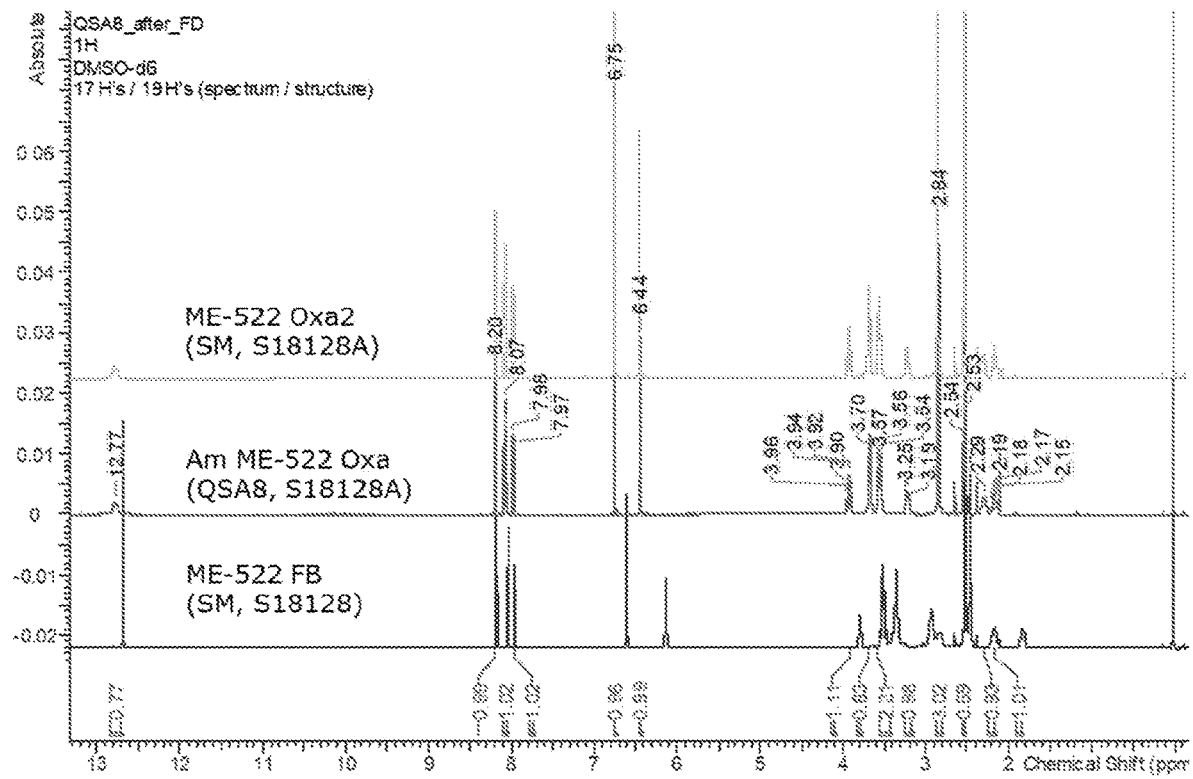

FIG. 157 illustrates the $^1$H-NMR spectra of the ME-522 free base (SM from project S128128, bottom), amorphous ME-522 oxalate salt (Exp. ID: QSA8, middle) and ME-522 Oxa2 (SM from the current project S18128A, top) measured in DMSO-$d_6$.

Figure 158:
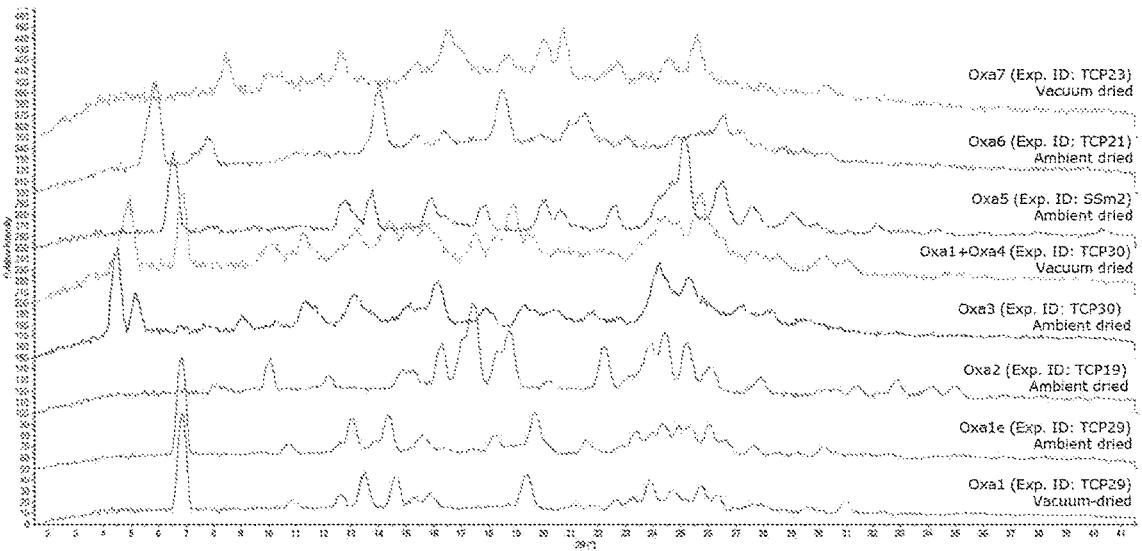

FIG. 158 illustrates the HT-XRPD diffractograms of the forms observed during the polymorph screen performed on ME-522 oxalate salt (from bottom to top): Oxa1, Oxa1e, Oxa2, Oxa3, Oxa1+Oxa4, Oxa5, Oxa6 and Oxa7.

Figure 159:
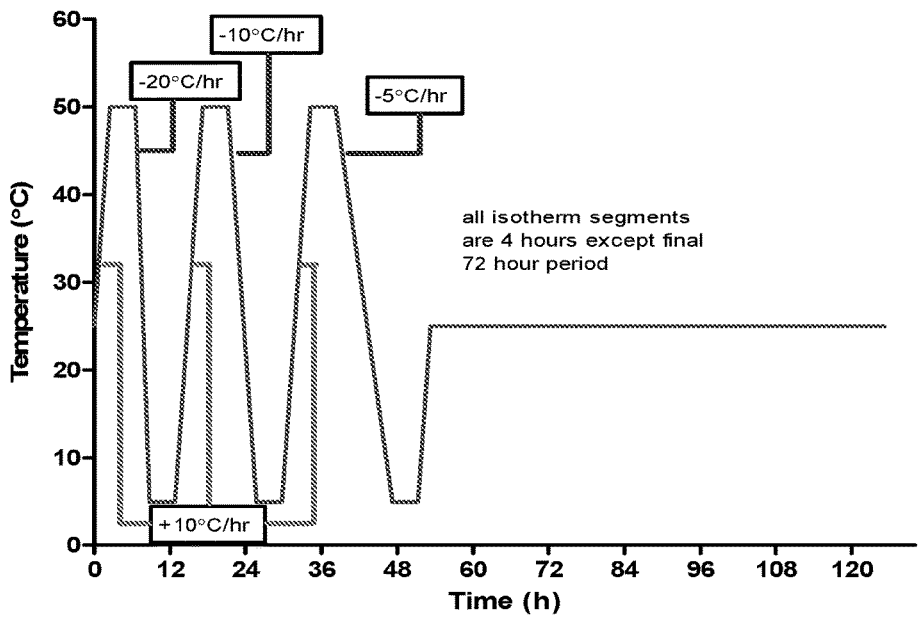

FIG. 159 illustrates the temperature profile of the thermocycling experiments.

Figure 160:
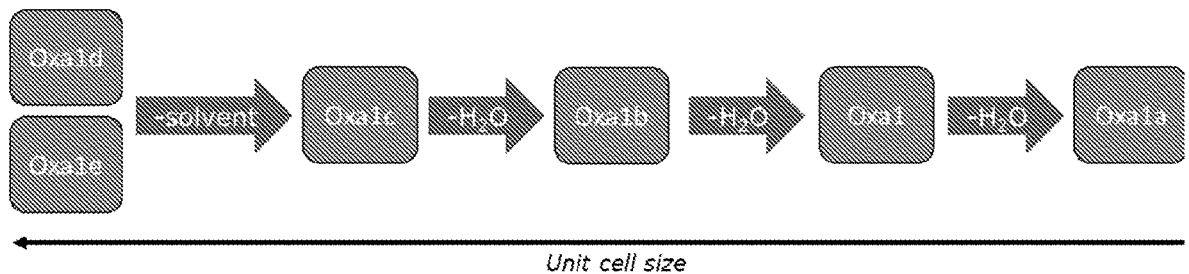

FIG. 160 illustrates the schematic overview of the Oxa1 forms and how these forms are associated to each other. All Oxa1 form are hemi-oxalate/hemihydrates. Oxa1d and Oxa1e have non-stoichiometric solvent and water present in the structures. From left to right, the unit cell size becomes smaller upon removal of solvent and water. The most dried form obtained (i.e. Oxa1a) still contained approximately 0.24 eq. of non-stochiometric water per molecule of API.

Figure 161:
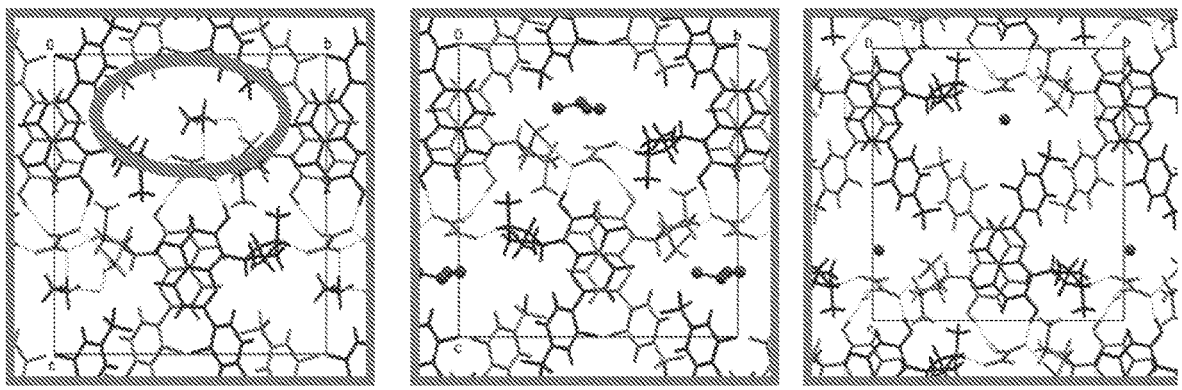

FIG. 161 illustrates the crystal packing and H-bonds scheme viewed along the [100] direction of Oxa1d (left, Oxa1c (middle) and Oxa1a (right), as determined by single crystal X-ray diffraction. Molecules a and b (classified in FIG. 175) are shown in green and blue, respectively. The oxalate dianions are shown in red, in orange are highlighted the stochiometric water molecules (0.5 per 1 API cation). The cavity which can accommodate solvent/water molecules is highlighted in the left image for Oxa1d. In Oxa1d, ethanol was present in the cavities. In Oxa1c and Oxa1a, water was present in the cavities (as indicated by the purple spheres). From left to right, the size of the unit cell decreases.

Figure 162:
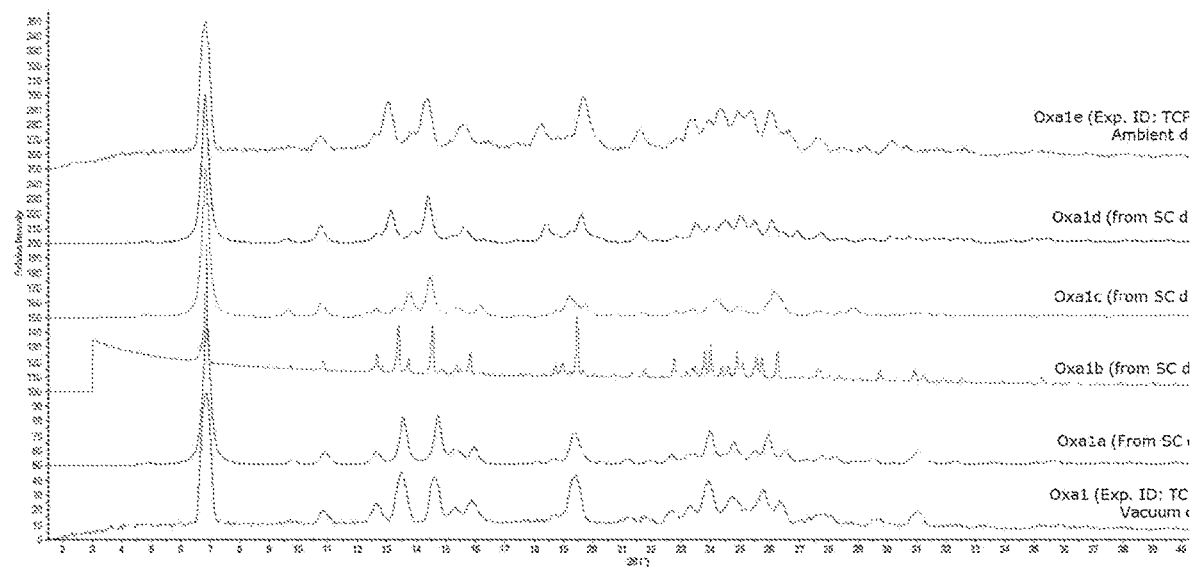

FIG. 162 illustrates the overlay of HT-XRPD patterns of the Oxa1 forms, with from bottom to top: Oxa1, Oxa1a, Oxa1b, Oxa1c, Oxa1d and Oxa1e.

Figure 163:
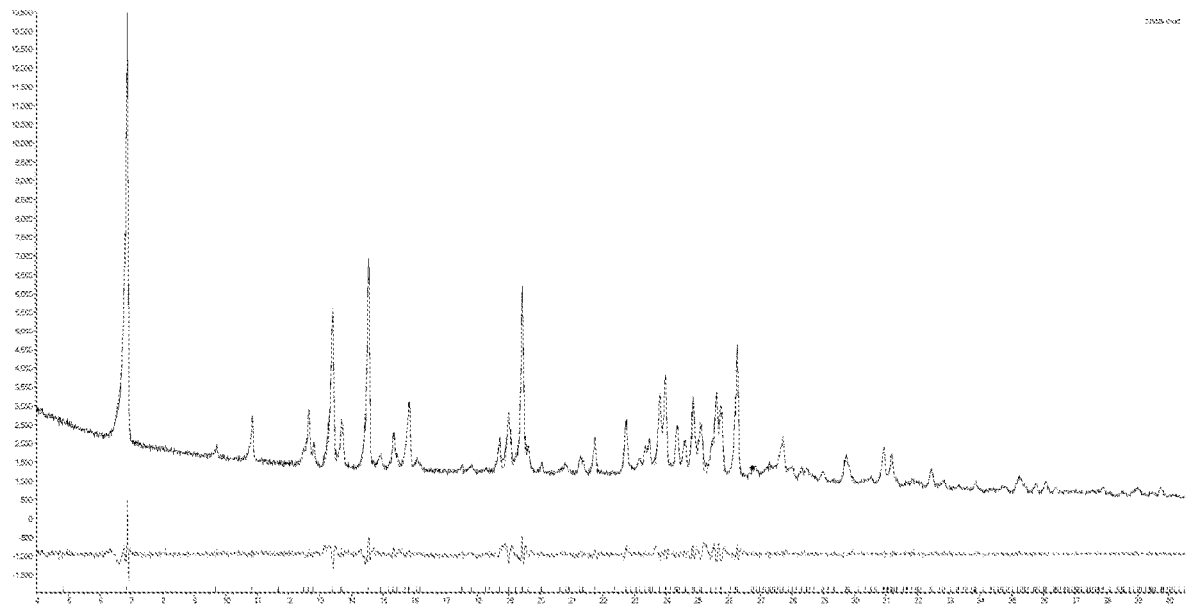

FIG. 163 illustrates the graphical representation of Rietveld analysis on Oxa1 (Exp. ID: SSm12, project S18128). The black line represents collected data, the red is the calculated powder pattern and the grey line is the difference between them. The blue sticks at the bottom show the peak positions of the fitted cell.

Figure 164:
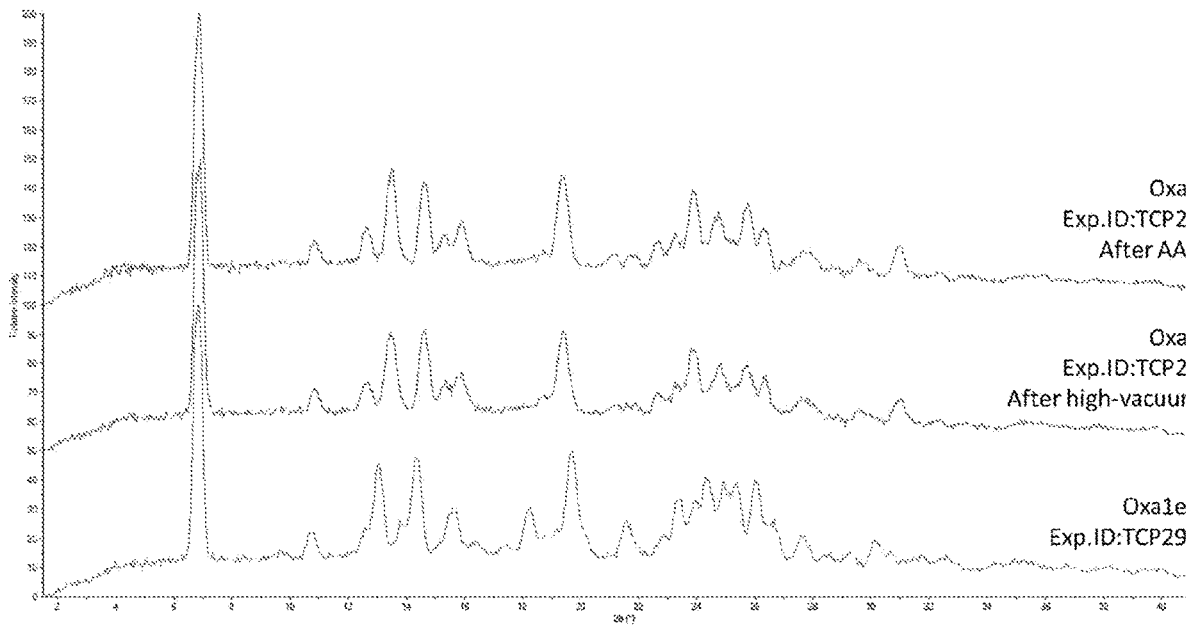

FIG. 164 illustrates the overlay of HT-XRPD patterns of the materials obtained in Exp. ID: TCP29, with from bottom to top: Oxa1e (ambient dried), Oxa1 (vacuum dried) and Oxa1 (after 2 days at 40° C./75% RH).

Figure 165:
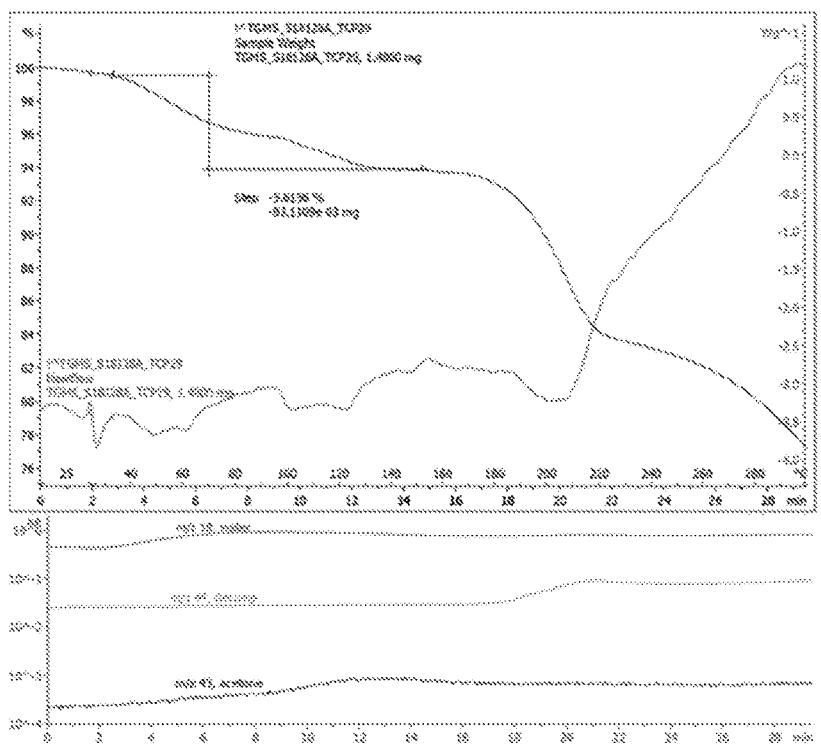

FIG. 165 illustrates the TGMS thermogram (heating rate 10° C./min) of Oxa1 (Exp. ID: TCP29). A mass loss of 5.6% was recorded between 40 and 140° C.

Figure 166:
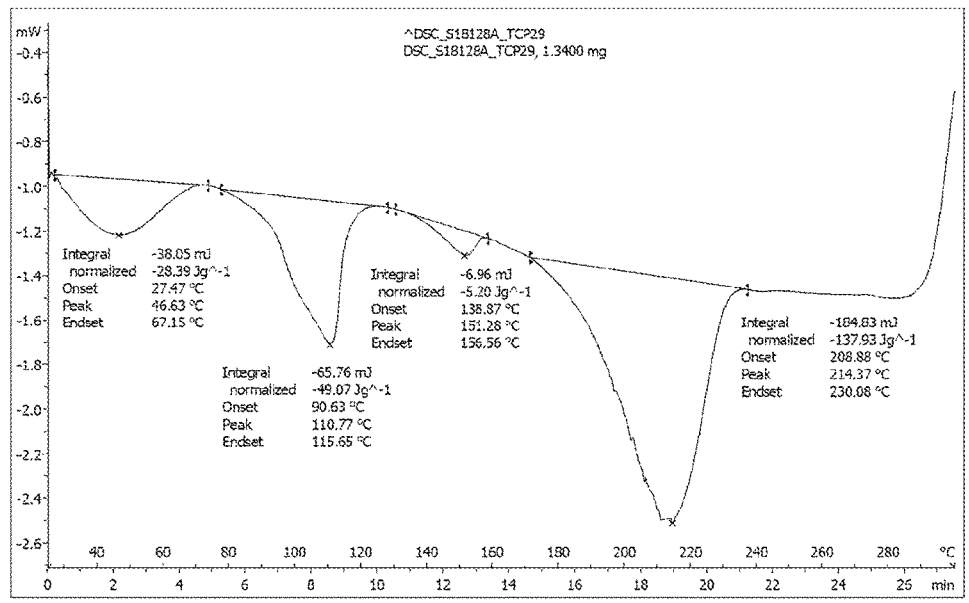

FIG. 166 illustrates the DSC trace (heating rate 10° C./min) of Oxa1 (Exp. ID: TCP29). Three endothermic events between 25-160° C. are most likely associated to water/solvent loss. The broad endothermic event between 209-230° C. is related to thermal decomposition of the salt.

Figure 167:
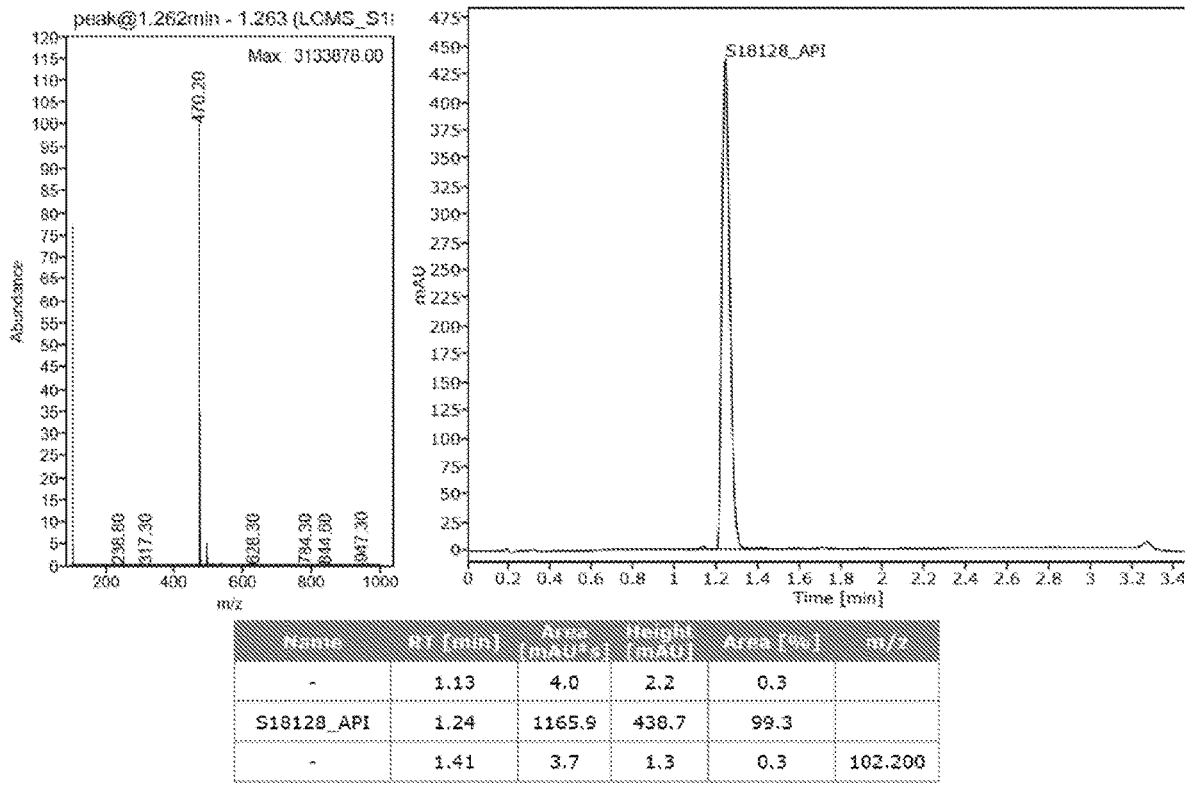

FIG. 167 illustrates the UPLC-MS analysis of Oxa1 (Exp. ID: TCP29). The peak corresponding to the API had a retention time of 1.2 min and the positive ion spectrum showed an ion with m/z of 470.2 $[M+H]^+$, in agreement with the API molecular mass of 469.8 g/mol. The table shows the retention times, peak areas and heights of the API and unidentified impurities.

Figures 168, 169:
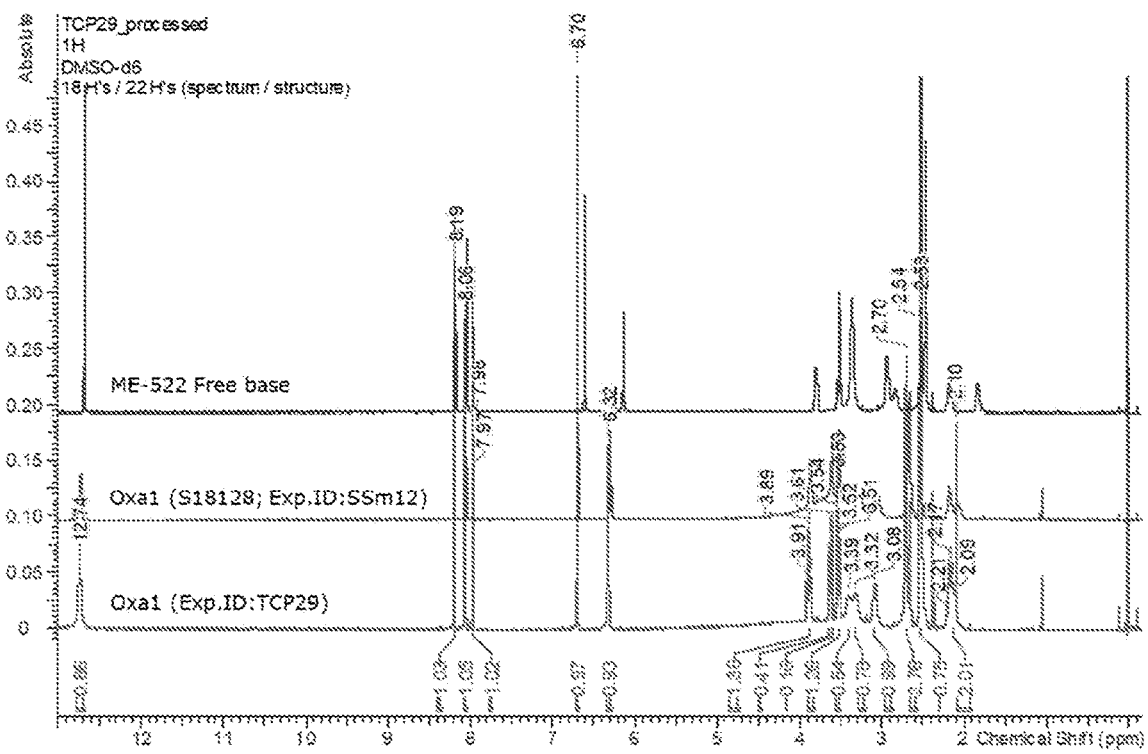

FIG. 168 illustrates the $^1$H-NMR spectra of Oxa1 (Exp. ID: TCP29, bottom), Oxa1 (Exp. ID: SSm12 from S18128, middle) and the ME-522 free base (from S18128, top) measured in DMSO-$d_6$ (bottom).

FIG. 169 illustrates the crystal packing and H-bonds scheme along the [100] direction in Oxa1a. Molecules a and b (classified in FIG. 175) are shown in green and blue, respectively. The oxalate dianions are shown in red, in orange are highlighted the stochiometric water molecules (0.5 per 1 API cation), whereas the symmetrically independent (non-stoichiometric) water molecules are depicted as purple circles.

Figure 170:
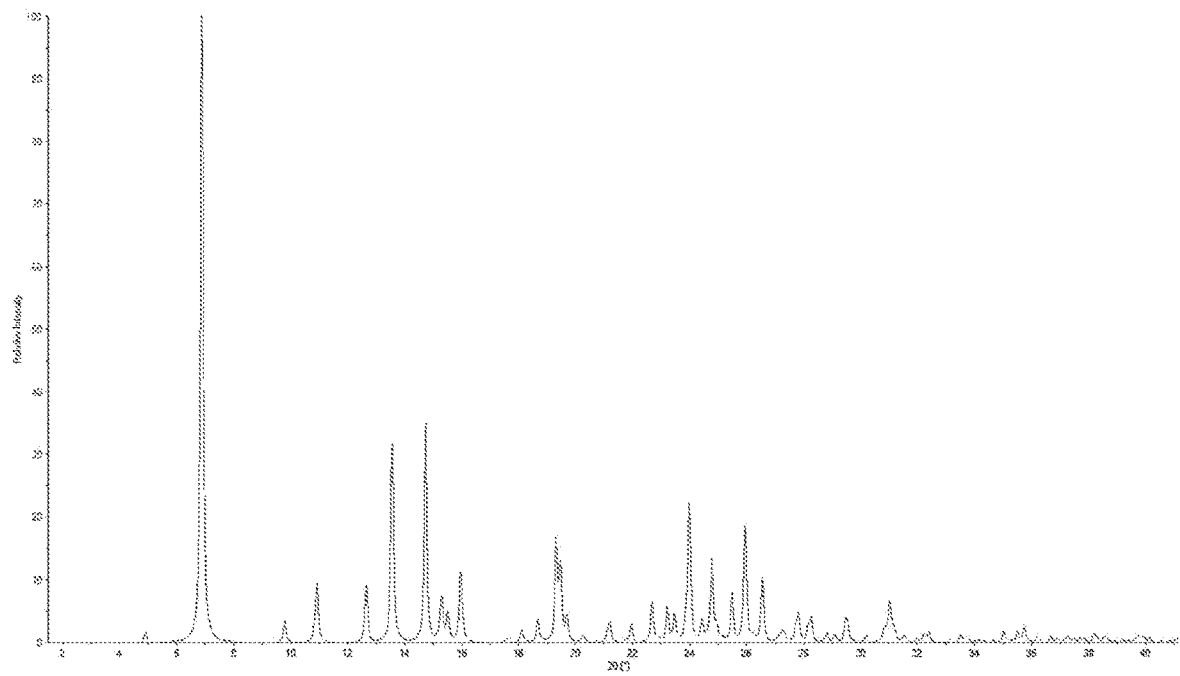

FIG. 170 illustrates the X-ray powder pattern of Oxa1a simulated from the single crystal data.

Figure 171:
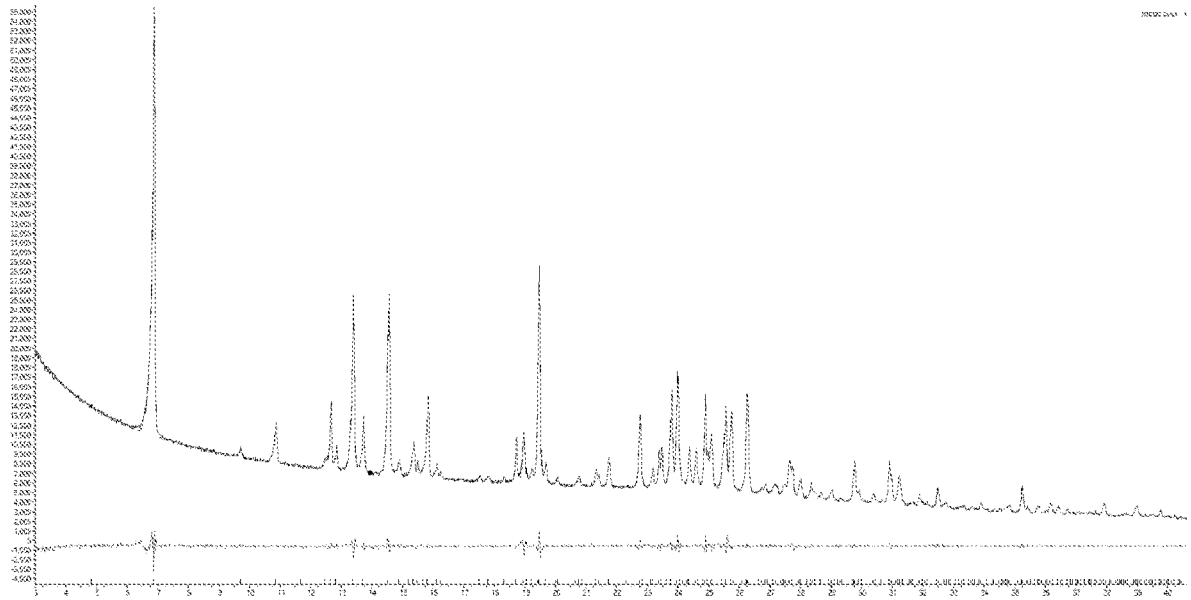

FIG. 171 illustrates the graphical representation of Rietveld analysis on Oxa1b. The black line represents the collected data, the red line is the calculated XRPD pattern and the grey line is the difference between them. The blue sticks at the bottom show the peak positions of the fitted cell.

Figure 172:
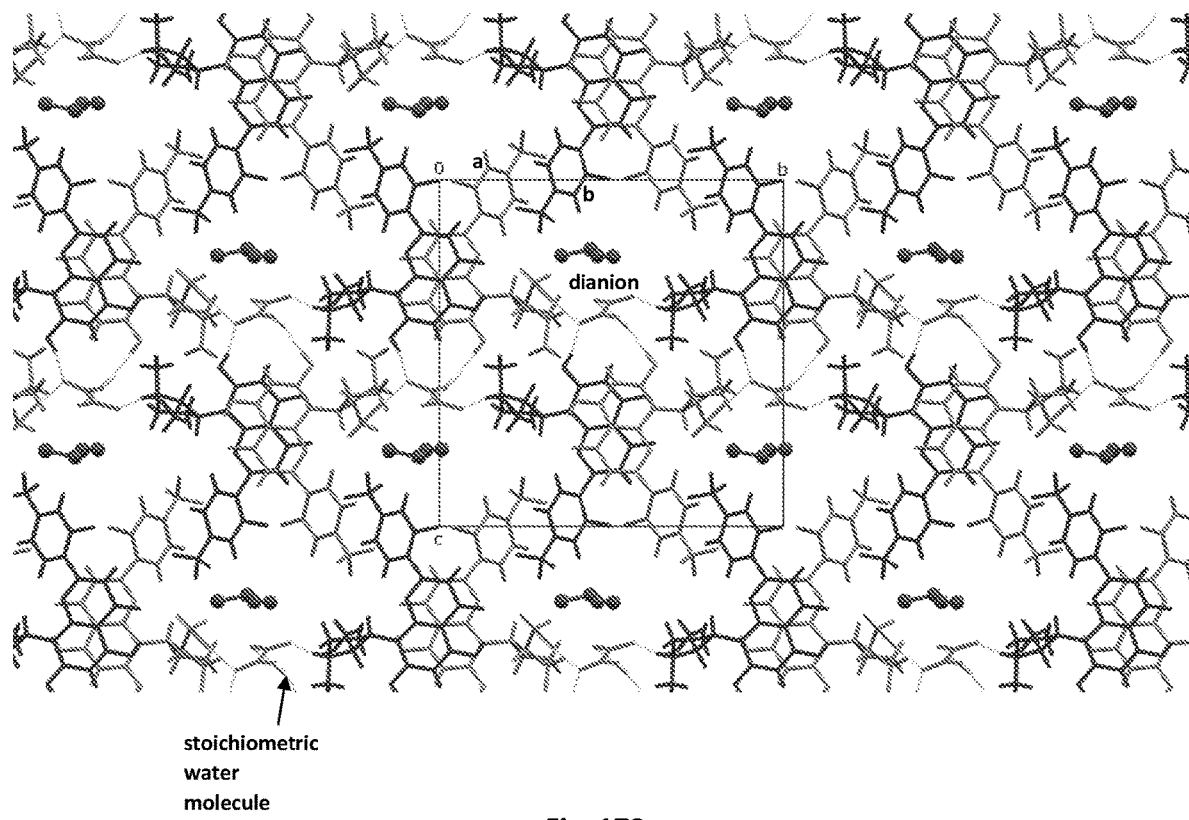

FIG. 172 illustrates the crystal packing and H-Bonds scheme along the [100] direction in Oxa1c. Molecules a and b (classified in FIG. 175) are shown in green and blue, respectively. The oxalate dianions are shown in red, in orange are highlighted the stochiometric water molecules (0.5 per 1 API cation), purple circles represent symmetrically independent (non-stoichiometric) water molecules.

Figure 173:
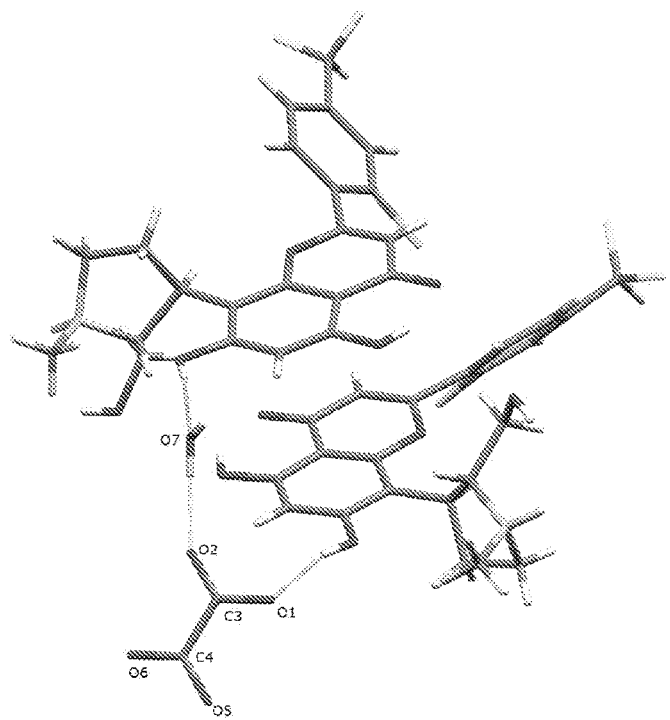

FIG. 173 illustrates the asymmetric unit of Oxa1c: two ME-522 cations were found together with an oxalate anion and a water molecule. Interstitial water molecules were also identified but omitted for clarity. For clarity, the atom numbering scheme is shown only for the oxalate anion and water molecule. The blue dashed lines show intermolecular hydrogen bonding between dianion, cations and water.

Figure 174:
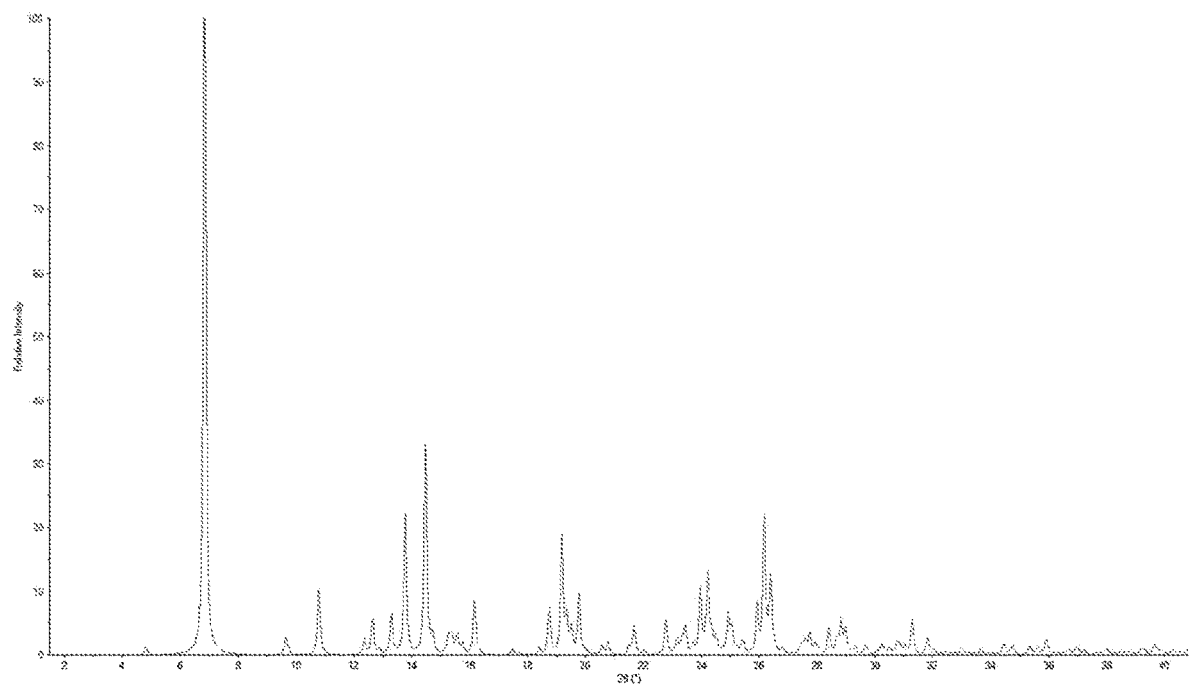

FIG. 174 illustrates the X-ray powder pattern of Oxa1c simulated from the single crystal data.

Figure 175:
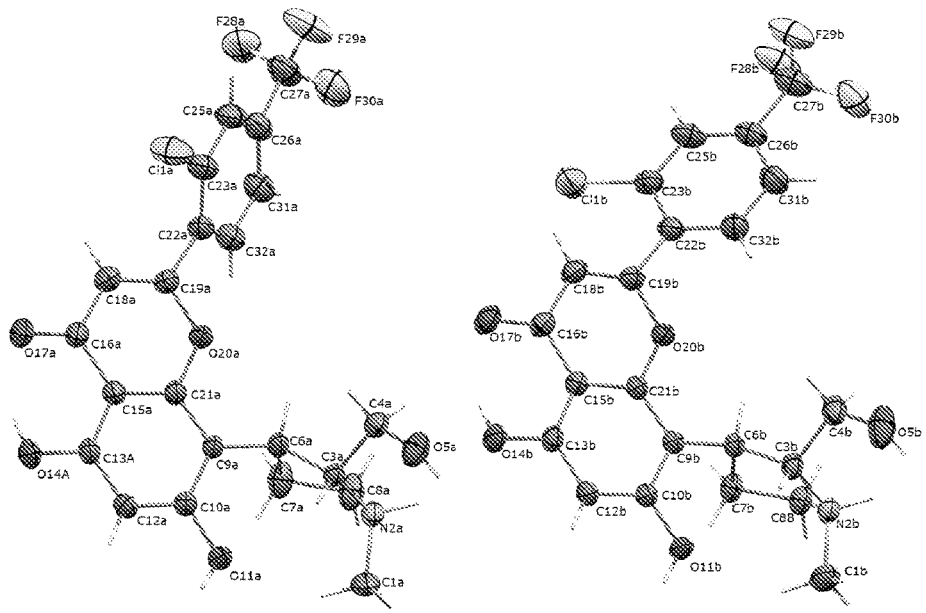

FIG. 175 illustrates the molecular structure and atom numbering scheme for two symmetrically independent cations found in Oxa1d. The left image shows cation denominated as a in the cif file while the right image shows cation b.

Figure 176:
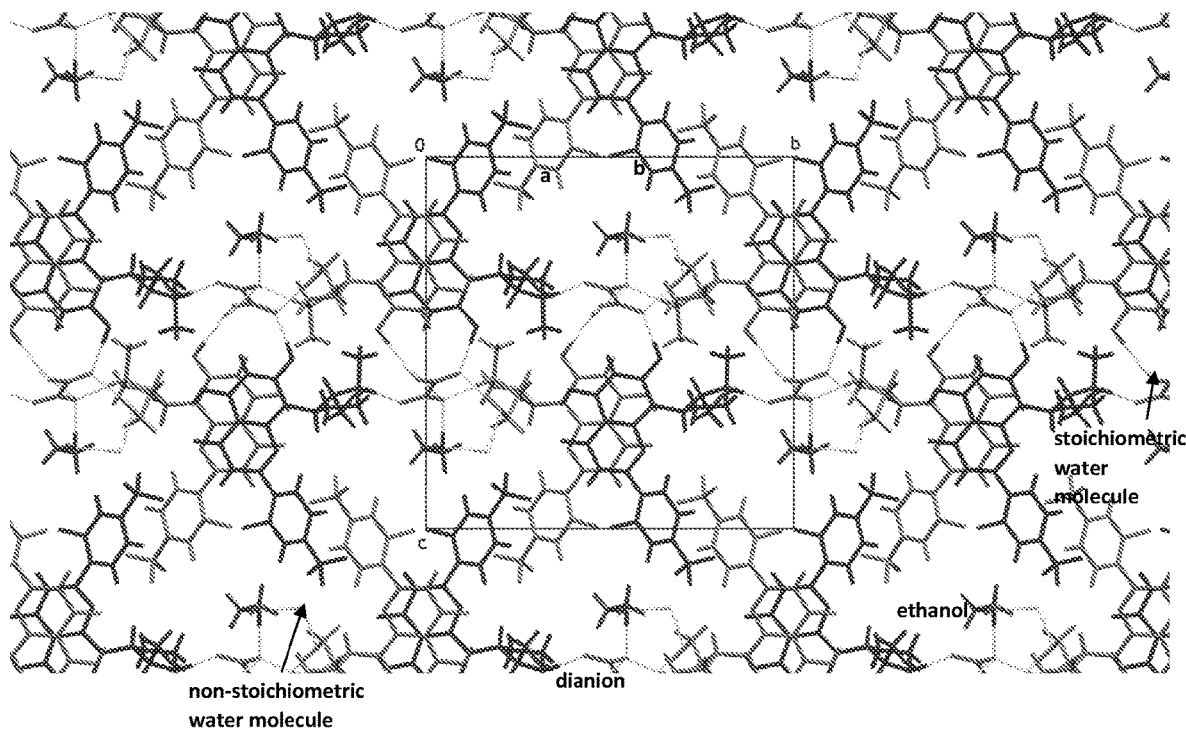

FIG. 176 illustrates the crystal packing and hydrogen bonds scheme along the [100] direction in Oxa1d. Molecules a and b (classified in FIG. 175) are shown in green and blue, respectively. The oxalate dianions are shown in red, in orange are highlighted the stochiometric water molecules (0.5 per 1 API cation), pink represents symmetrically independent (non-stoichiometric) water molecules and ethanol molecules are represented in purple.

Figure 177:
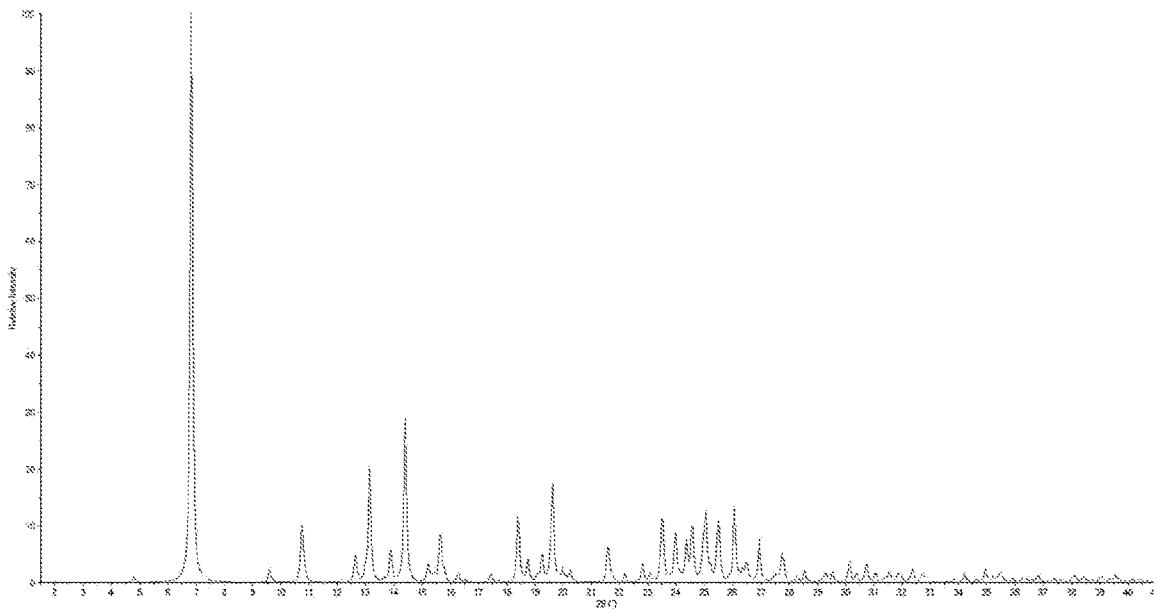

FIG. 177 illustrates the X-ray powder pattern of Oxa1d simulated from the single crystal data.

Figure 178:
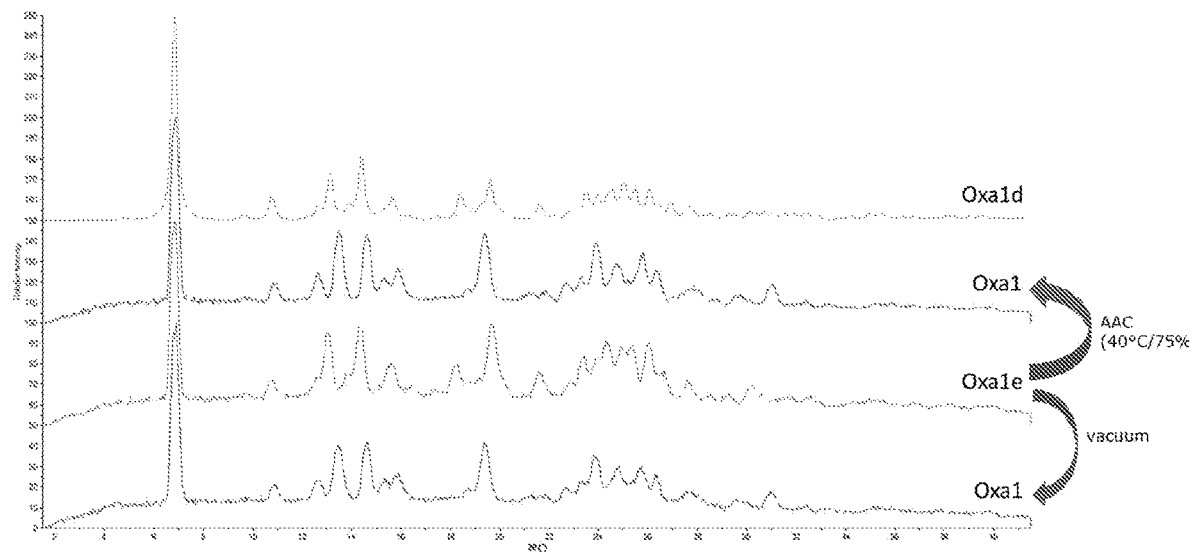

FIG. 178 illustrates the overlay of HT-XRPD patterns of the materials obtained in Exp. ID: TCP29, with from bottom to top: Oxa1 (vacuum dried), Oxa1e (ambient dried), Oxa1 (after 2 days at 40° C./75% RH) and Oxa1d generated from single crystal data).

Figure 179:
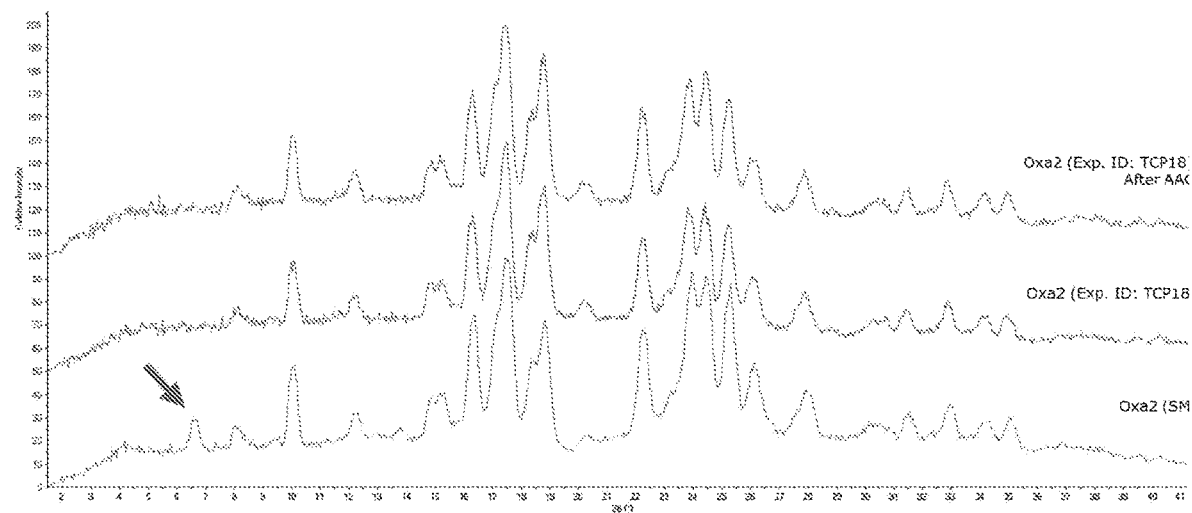

FIG. 179 illustrates the overlay of HT-XRPD patterns of Oxa2 obtained from the starting material (bottom), Oxa2 obtained from 2-propanol (Exp. ID: TCP18, middle) and Oxa2 obtained from 2-propanol after exposure to AAC (Exp. ID: TCP18, top). In the starting material, an extra diffraction peak was identified at about 6.6° 2θ, as indicated by the arrow.

Figure 180:
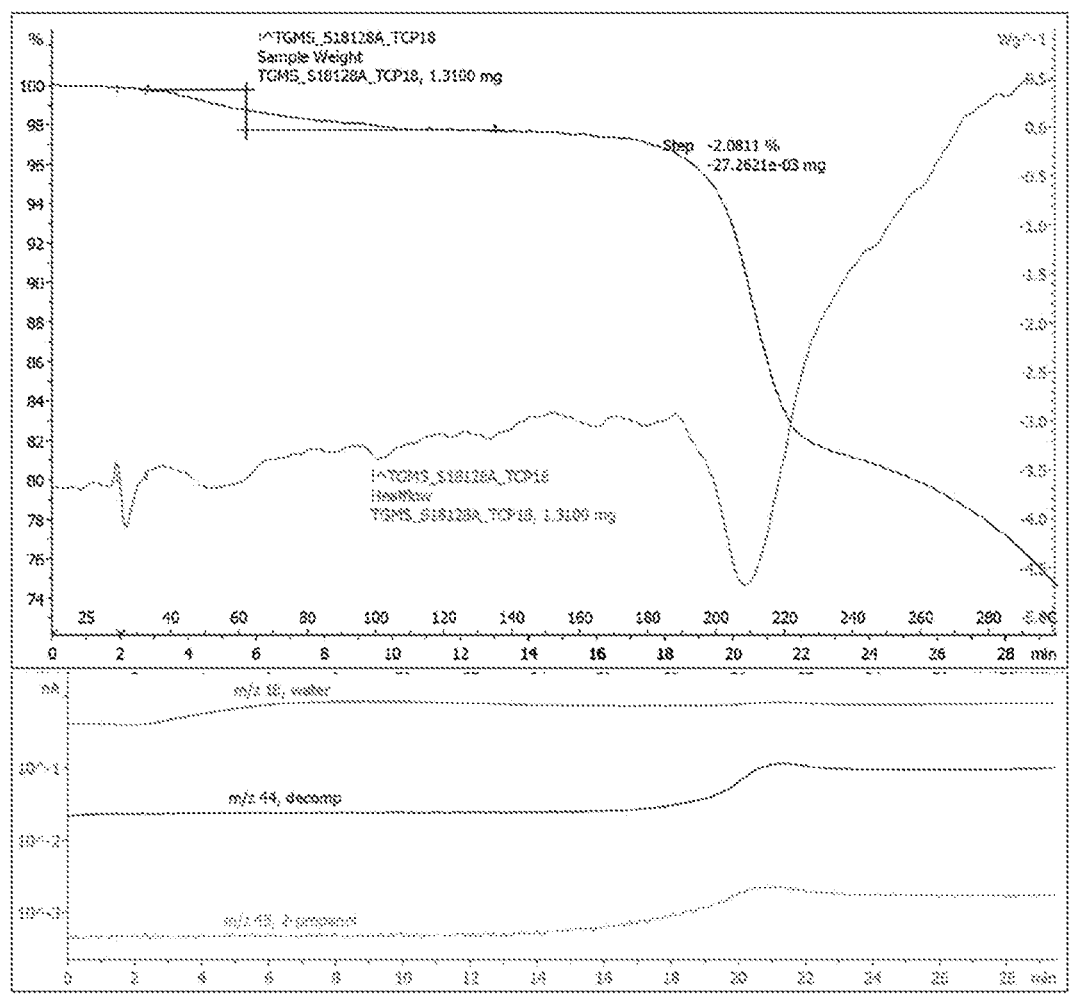

FIG. 180 illustrates the TGMS thermogram (heating rate 10° C./min) of Oxa2 (Exp. ID: TCP18). A mass loss of 2.1% was recorded between 40 and 140° C.

Figure 181:
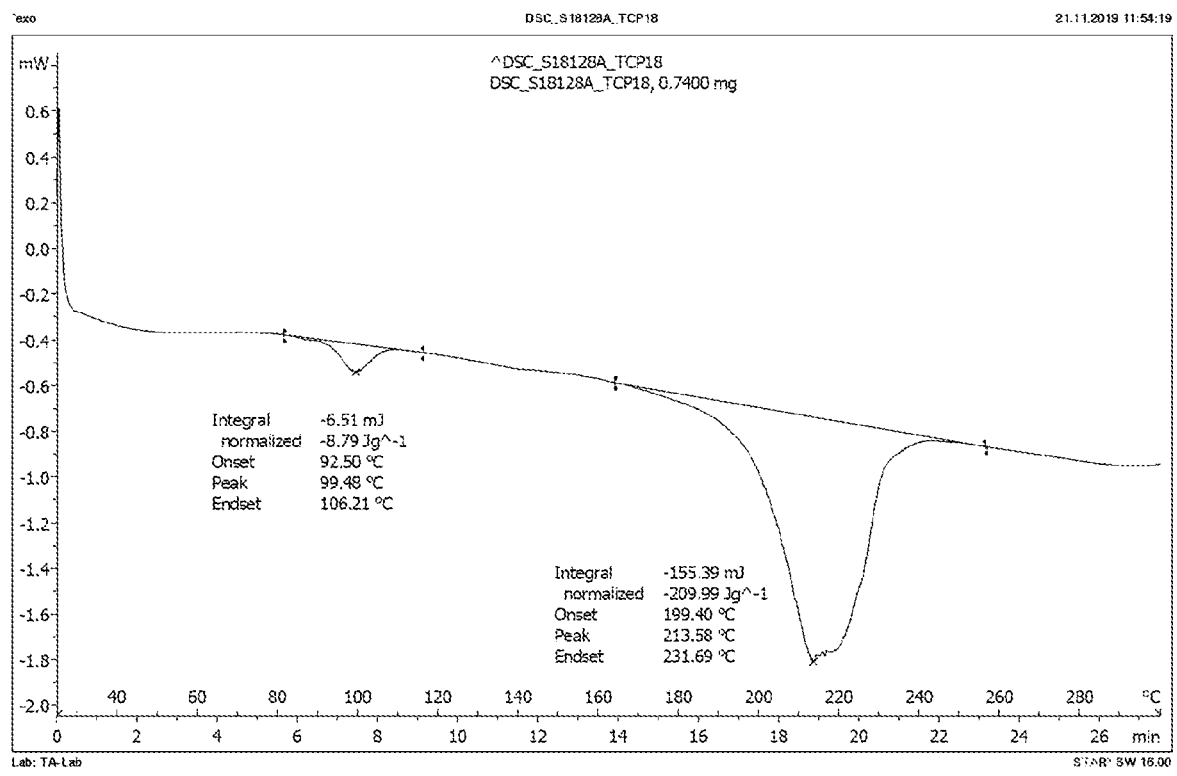

FIG. 181 illustrates the DSC trace (heating rate 10° C./min) of Oxa2 (Exp. ID: TCP18). A small endothermic event at $T_{peak}$ 99° C. was followed by a broad endothermic at $T_{peak}$ 214° C.

Figure 182:
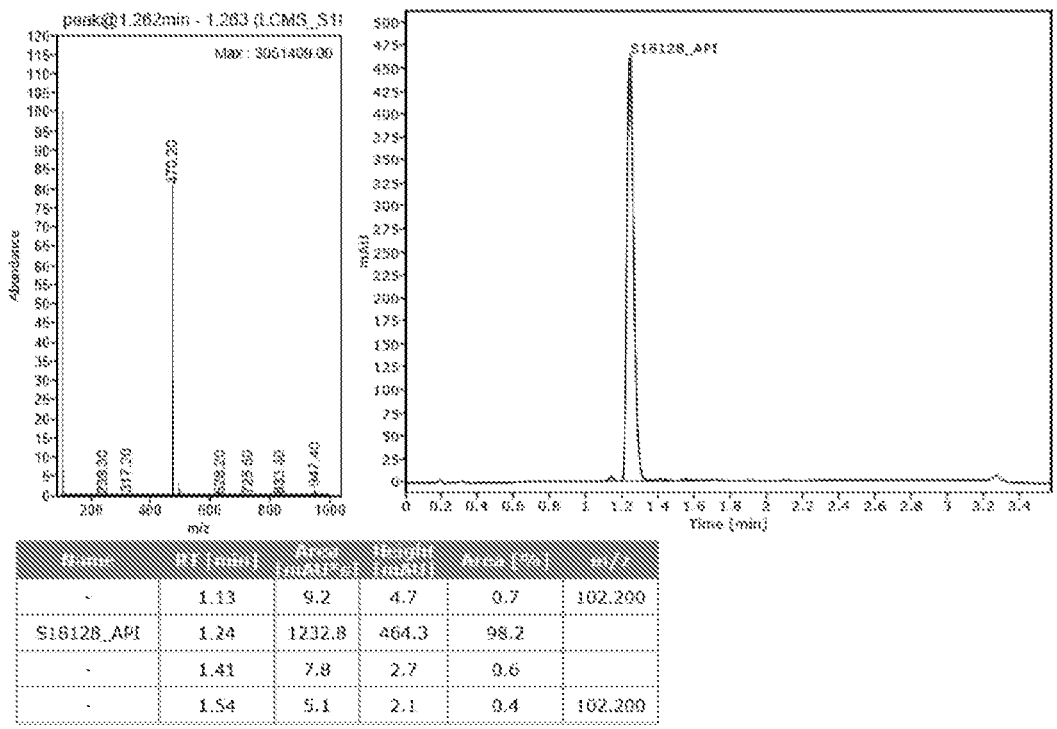

FIG. 182 illustrates the UPLC-MS analysis of Oxa2 (Exp. ID: TCP18). The peak corresponding to the API had a retention time of 1.2 min and the positive ion spectrum showed an ion with m/z of 470.2 $[M+H]^+$, in agreement with the API molecular mass of 470.2 g/mol. The table shows the retention times, peak area's and heights of the API and unidentified impurities.

Figure 183:
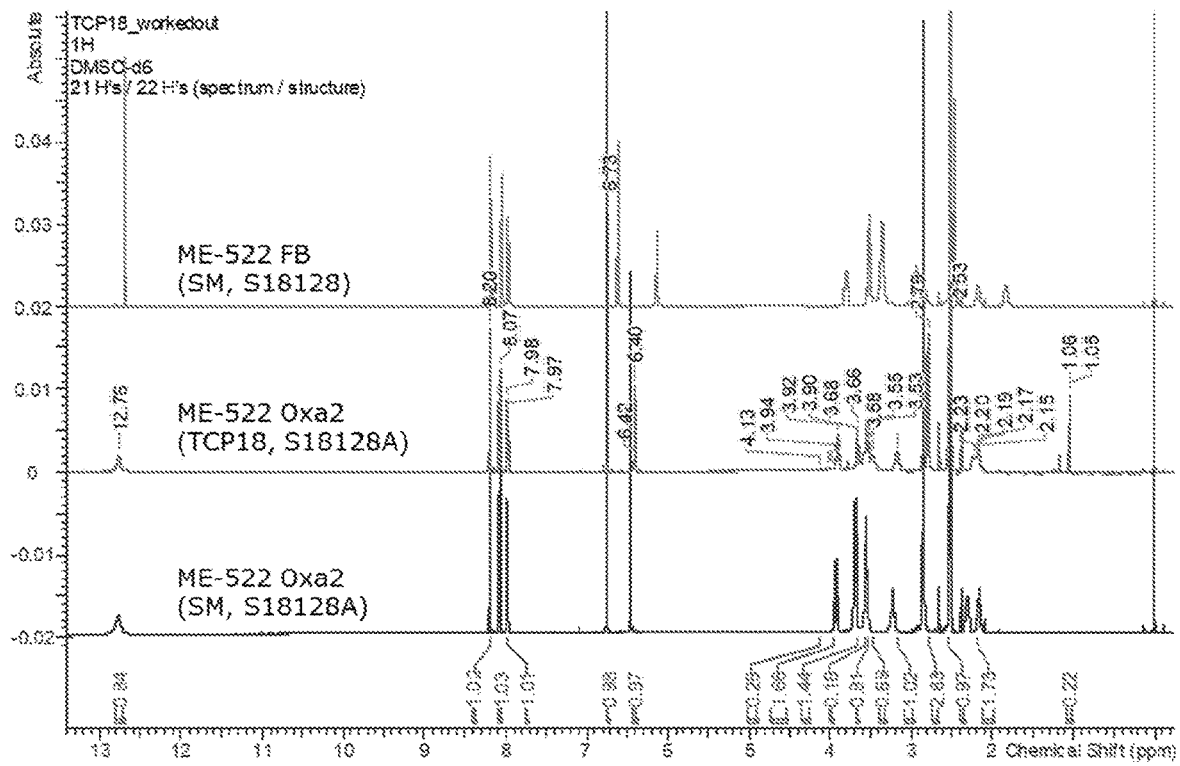

FIG. 183 illustrates the $^1$H-NMR spectra of the free base (SM of S18128, bottom), Oxa2 (Exp. ID: TCP18, middle) and Oxa2 (SM, S18128A) measured in DMSO-$d_6$. The integration values and peak values apply to Oxa2 (Exp. ID: TCP18, middle). The doublet signal at 1.05 ppm corresponds to the $CH_3$ groups of 2-propanol.

Figure 184:
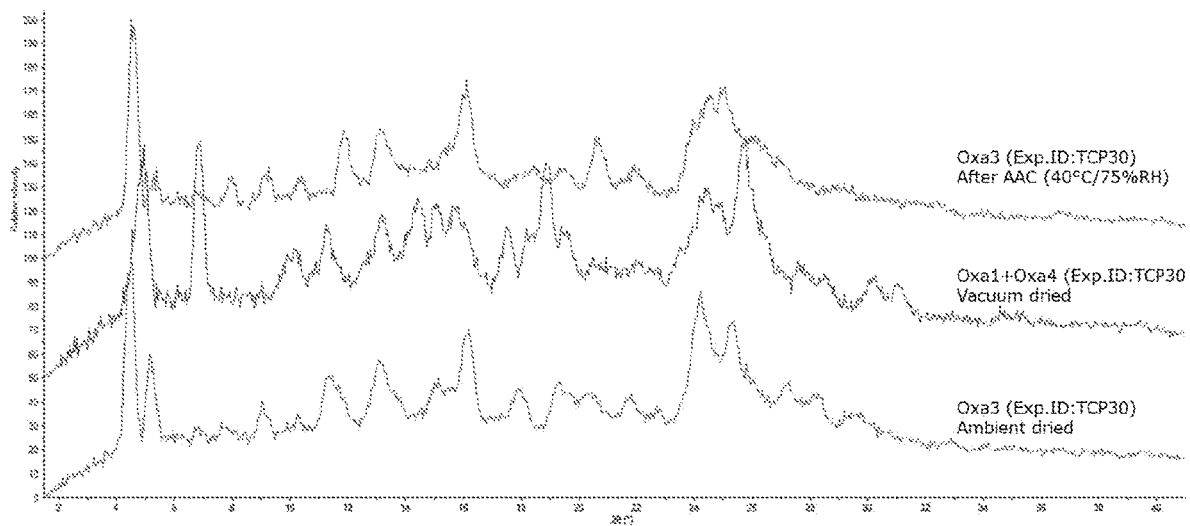

FIG. 184 illustrates the overlay of HT-XRPD patterns from the solids obtained from 2-propanol/water (90/10, Exp. ID: TCP30). From bottom to top: Oxa3a (ambient dried), Oxa1+Oxa4 (vacuum dried) and Oxa3b (after AAC).

Figure 185:
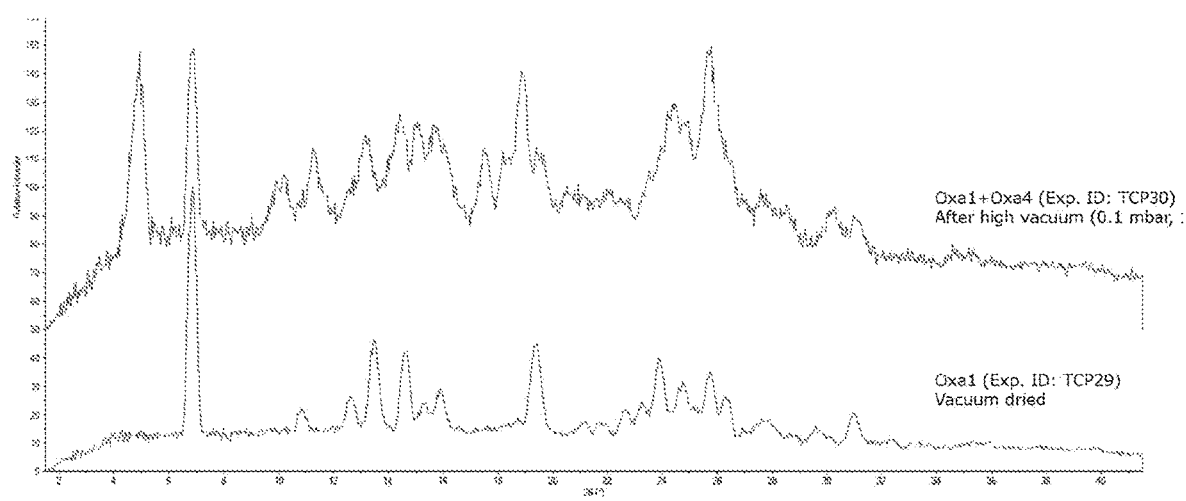

FIG. 185 illustrates the overlay of HT-XRPD patterns of Oxa1 (Exp. ID: TCP29, bottom) and Oxa1+Oxa4 (Exp. ID: TCP30, top).

Figure 186:
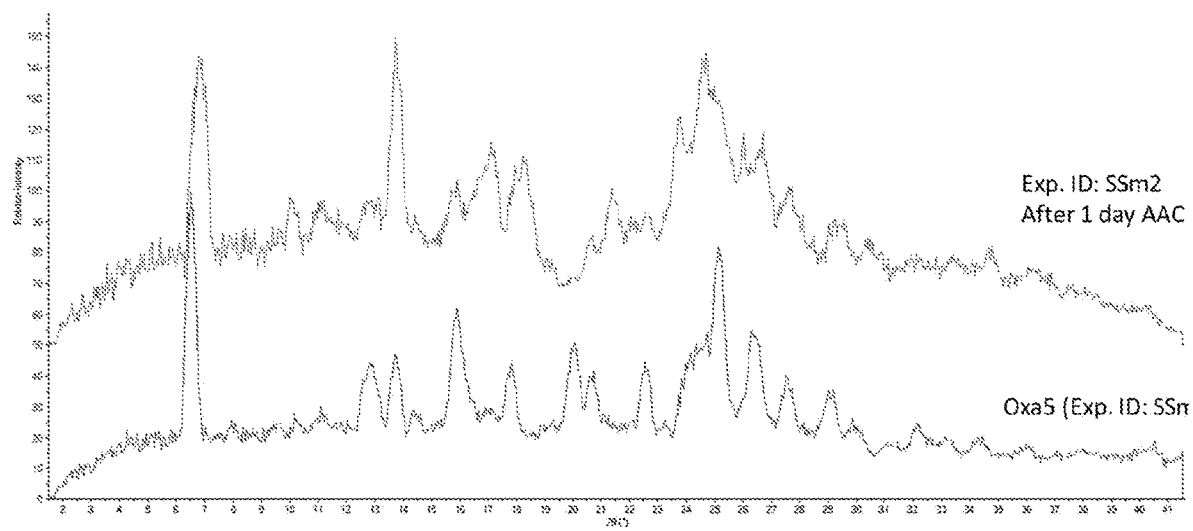

FIG. 186 illustrates the overlay of HT-XRPD patterns of Oxa5 (Exp. ID: SSm2, bottom) and the same material after 1-day exposure to AAC (top).

Figure 187:
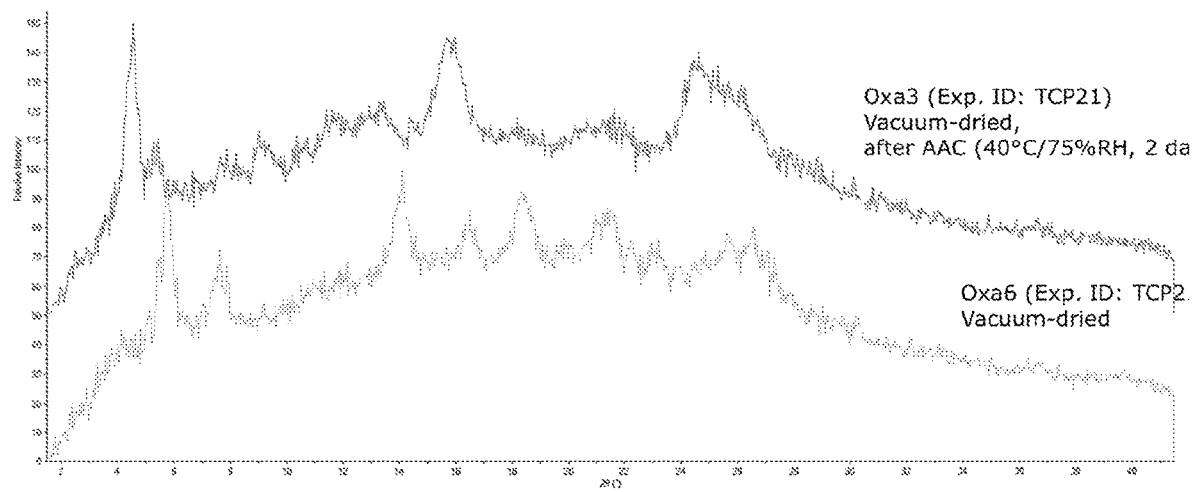

FIG. 187 illustrates the overlay of HT-XRPD patterns of the material obtained from chloroform (Exp. ID: TCP21). The bottom pattern shows Oxa6 (vacuum dried) and the top pattern is of Oxa3 (vacuum dried, after AAC).

Figure 188:
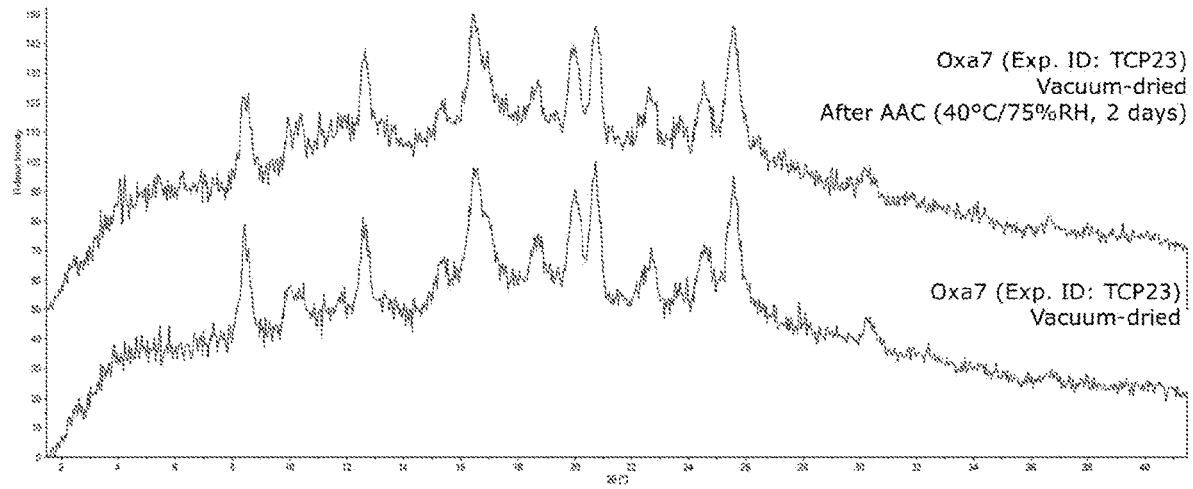

FIG. 188 illustrates the overlay of HT-XRPD patterns of Oxa7 obtained from the thermocycling experiment in ethanol (Exp. ID: TCP23). The bottom pattern shows the vacuum-dried sample whereas the top pattern is of the same sample after it was subjected to AAC (40° C./75% RH, 2 days).

Figure 189:
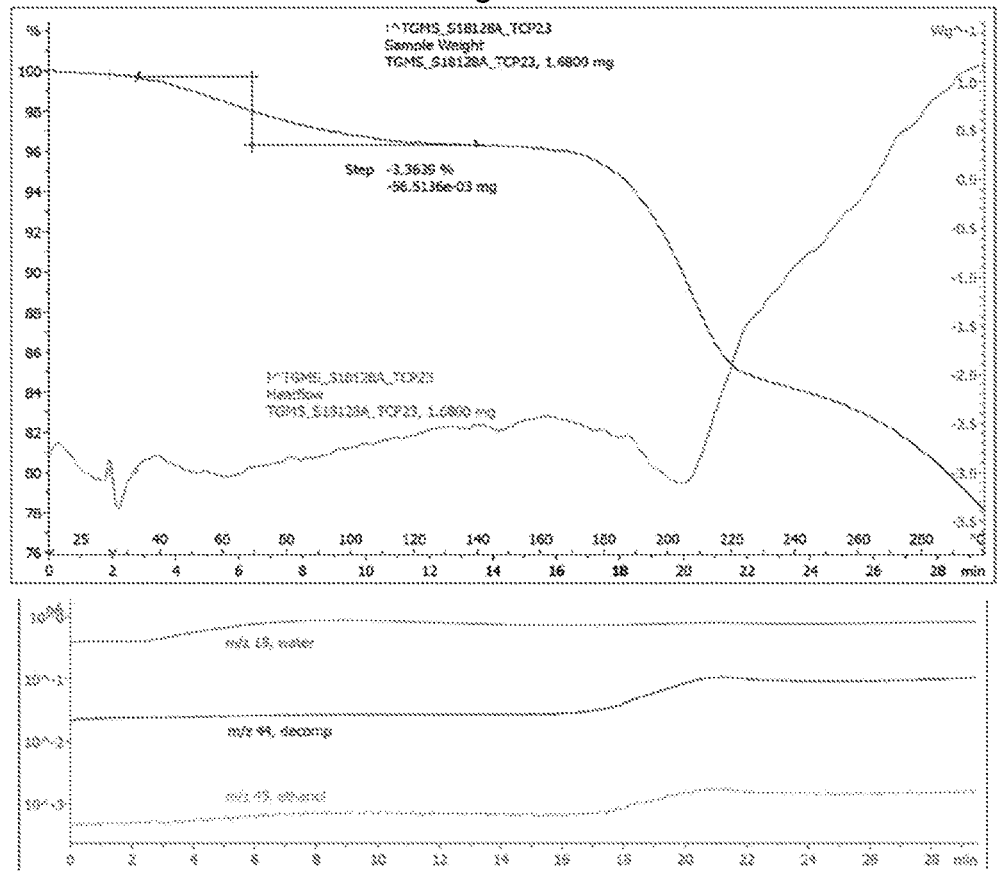

FIG. 189 illustrates the TGMS thermogram (heating rate 10° C./min) of Oxa7 (Exp. ID: TCP23). A mass loss of 3.4% was recorded between 40-140° C.

Figure 190:
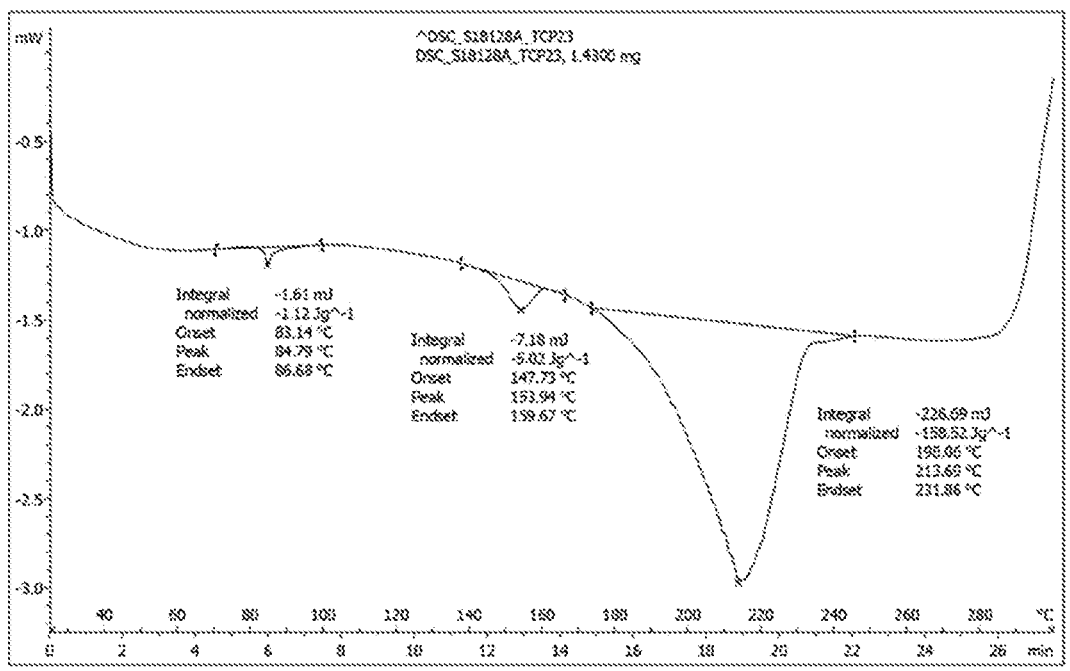

FIG. 190 illustrates the DSC trace (heating rate 10° C./min) of Oxa7 (Exp. ID: TCP23). Two small endothermic events at 85° C. and 154° C. were followed by a broad endothermic event at $T_{peak}$ 214° C.

Figure 191:
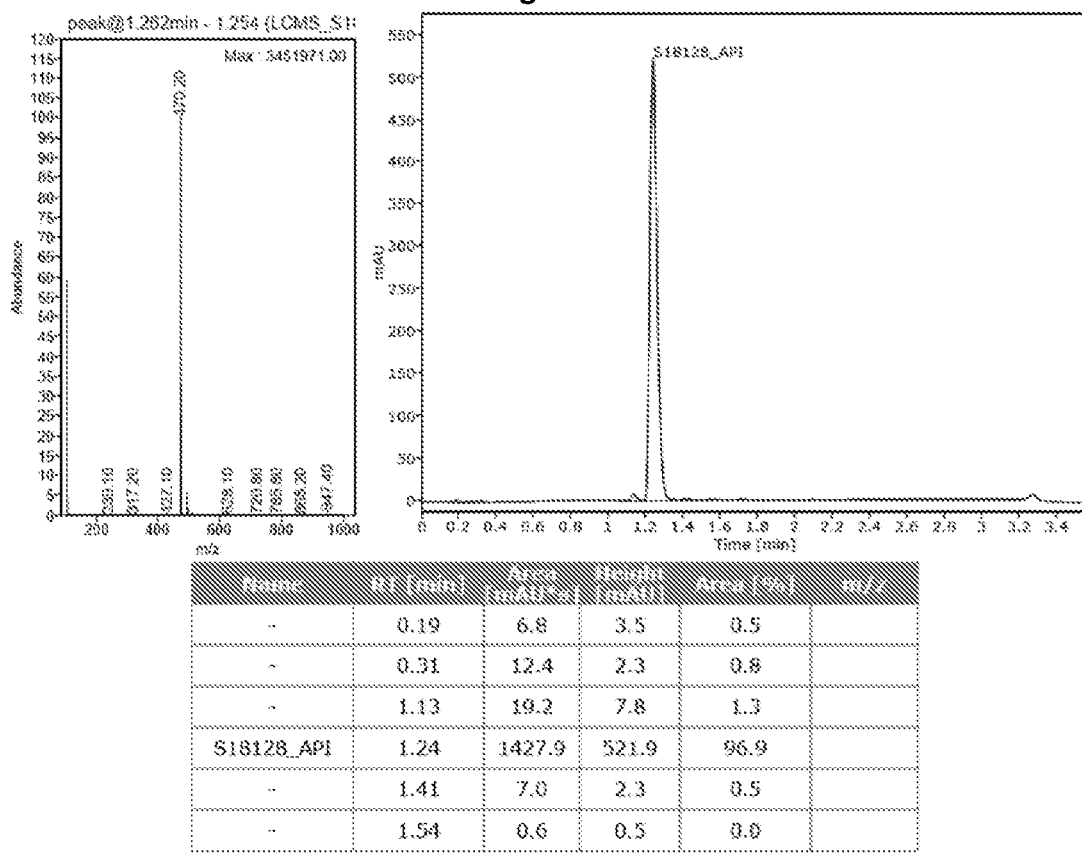

FIG. 191 illustrates the UPLC-MS analysis of Oxa7 (Exp. ID: TCP23). The peak corresponding to the API had a retention time of 1.2 min and the positive ion spectrum showed an ion with m/z of 470.2 [M+H]$^+$, in agreement with the API molecular mass of 470.2 g/mol. The table shows the retention times, peak area's and heights of the API and unidentified impurities.

Figure 192:
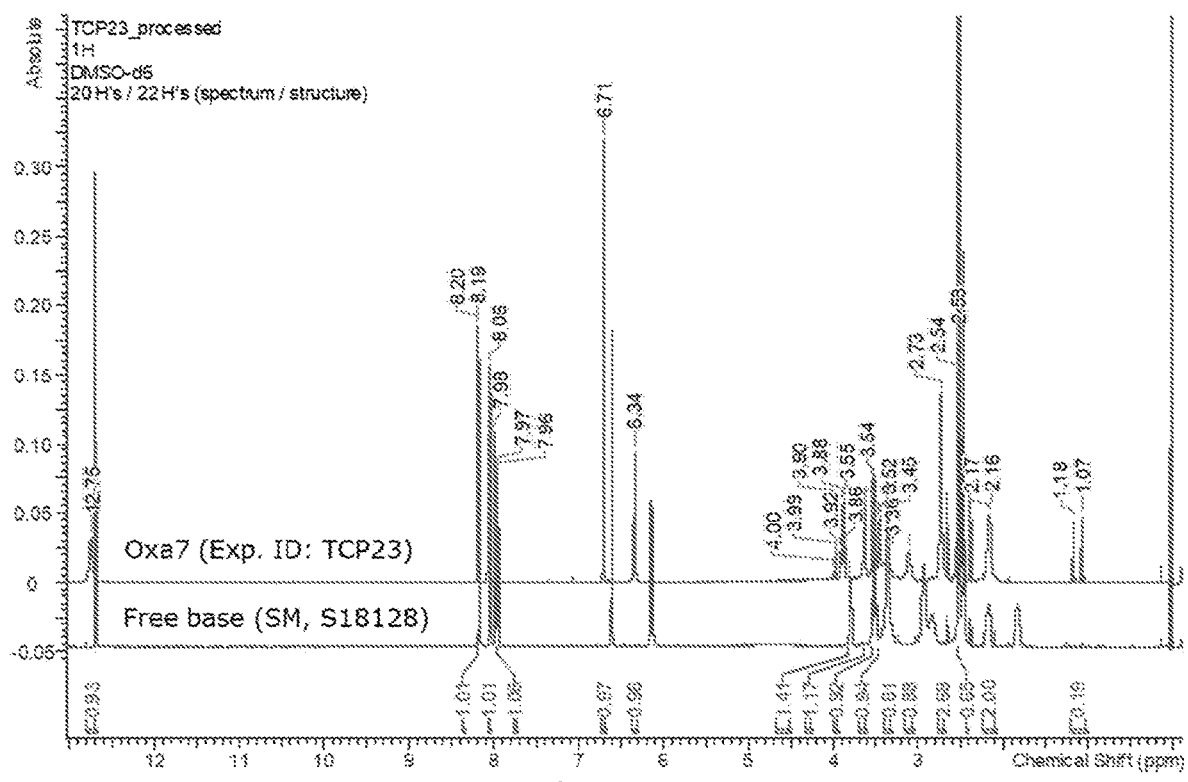

FIG. 192 illustrates the $^1$H-NMR spectra of the freebase (SM of S18128, bottom) and Oxa7 (Exp. ID: TCP23, top) measured in DMSO-d$_6$ (bottom). The triplet signals at 1.1 and 1.2 ppm as well as the quartet signals at 3.5 and 4.0 ppm correspond to the CH$_3$ and CH$_2$ groups of ethanol, respectively.

Figure 193:
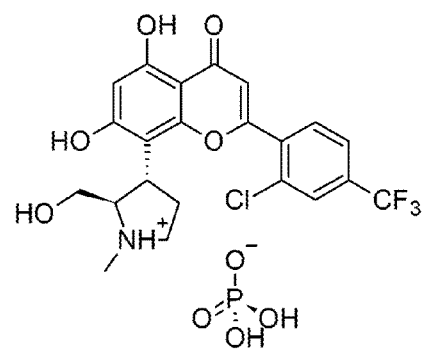

FIG. 193 illustrates the molecular structure of the monophosphate salt of ME-522. The molecular weight of the free base is 469.8 g/mol.

Figure 194:
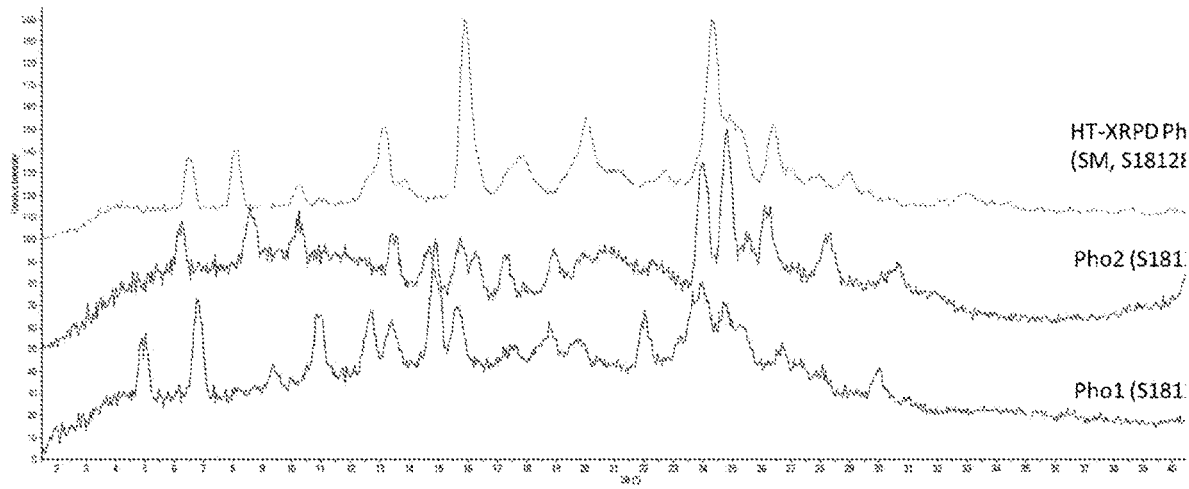

FIG. 194 illustrates the overlay of HT-XRPD patterns of Pho1 (project S18128, bottom), Pho2 (project S18128, middle) and Pho3 (starting material, current project S18128B, top).

Figure 195:
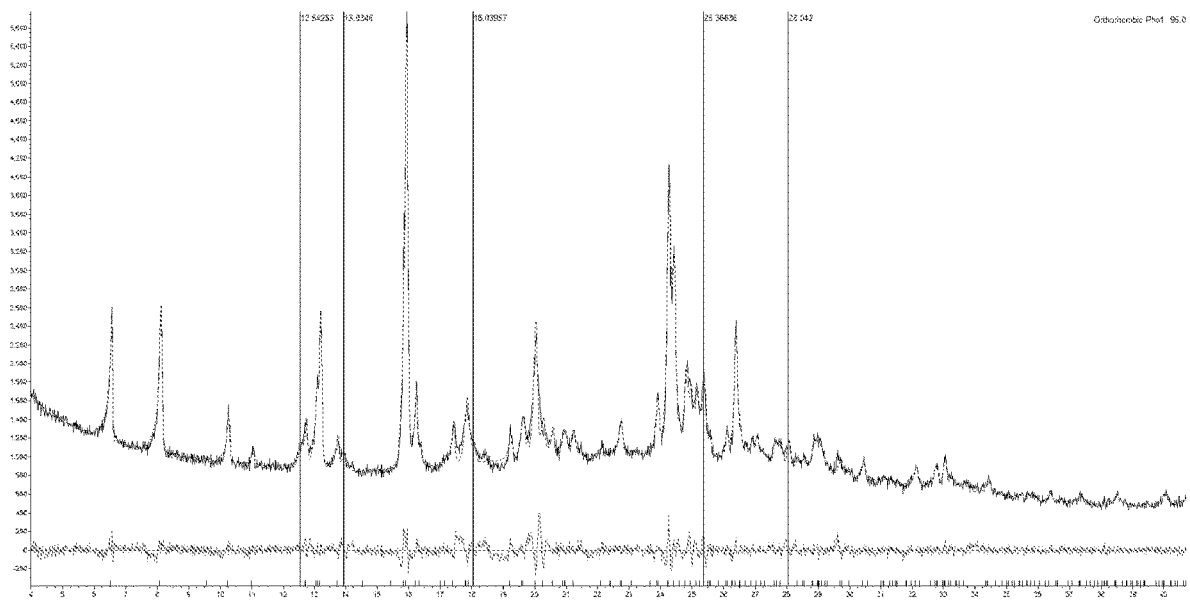

FIG. 195 illustrates the graphical representation of Rietveld analysis on Pho3 (starting material). The black line represents collected data, the red line is the calculated powder pattern and the grey line is the difference between them. The blue sticks at the bottom show the peak positions of the fitted cell. The vertical lines indicate the diffraction peaks associated to non-indexed crystalline impurities.

Figure 196:
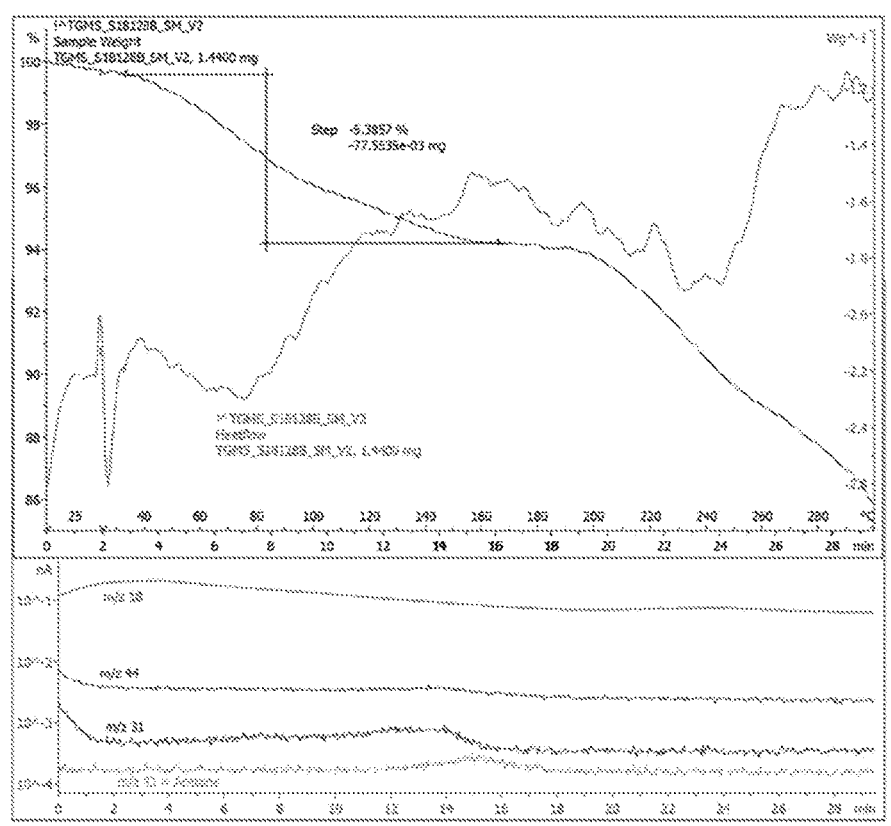

FIG. 196 illustrates the TGMS thermogram (heating rate 10° C./min) of Pho3 (starting material). A mass loss of 5.4% was recorded between 40 and 160° C.

Figure 197:
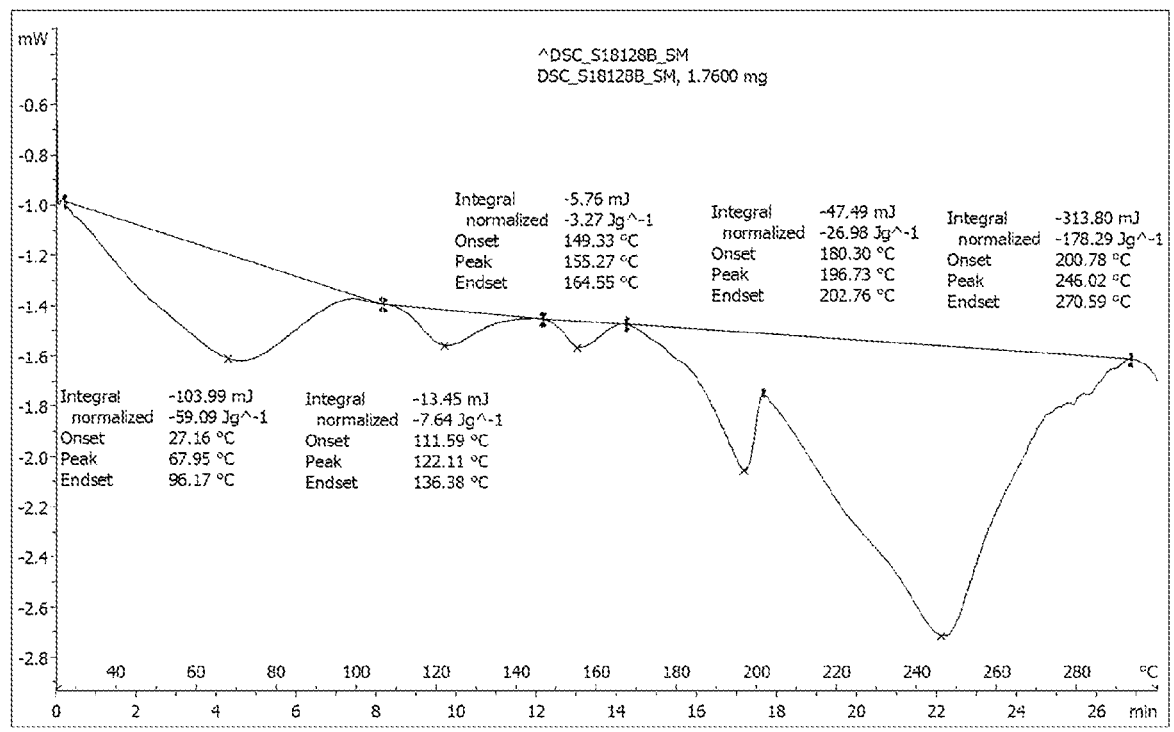

FIG. 197 illustrates the DSC trace (heating rate 10° C./min) of Pho3 (starting material). Several endothermic events were observed before 200° C. in addition to a broad endothermic event at $T_{peak}$ 246° C.

Figure 198A:
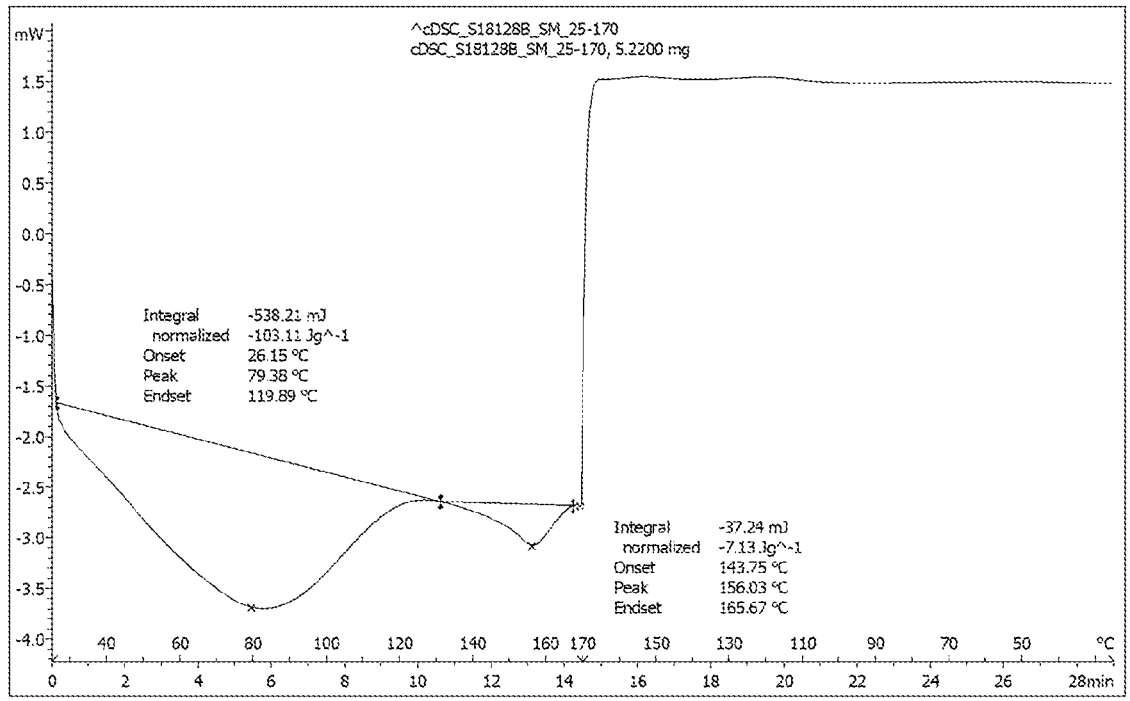
Figure 198B:
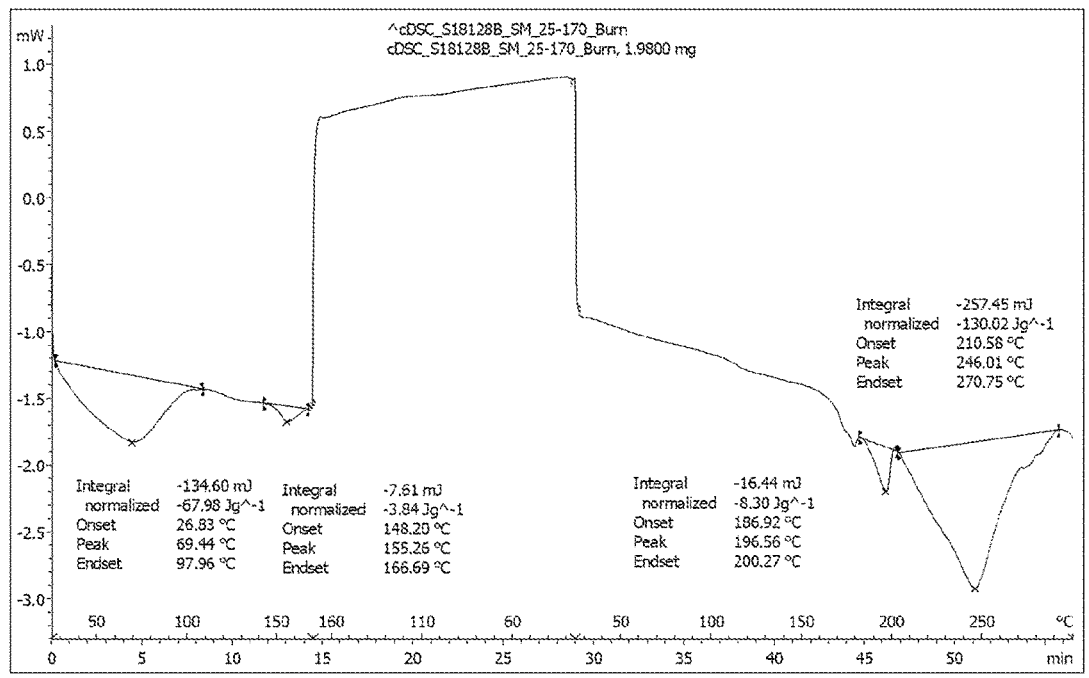

FIG. 198A and FIG. 198B illustrate cDSC traces (heating rate 10° C./min) of Pho3 (starting material). In the first experiment (FIG. 198A), the material was heated to 170° C. and cooled to room temperature. After the material was analyzed by HT-XRPD, the compound was again heated to 170° C., cooled to room temperature and finally heated to 300° C. (FIG. 198B).

Figure 199:
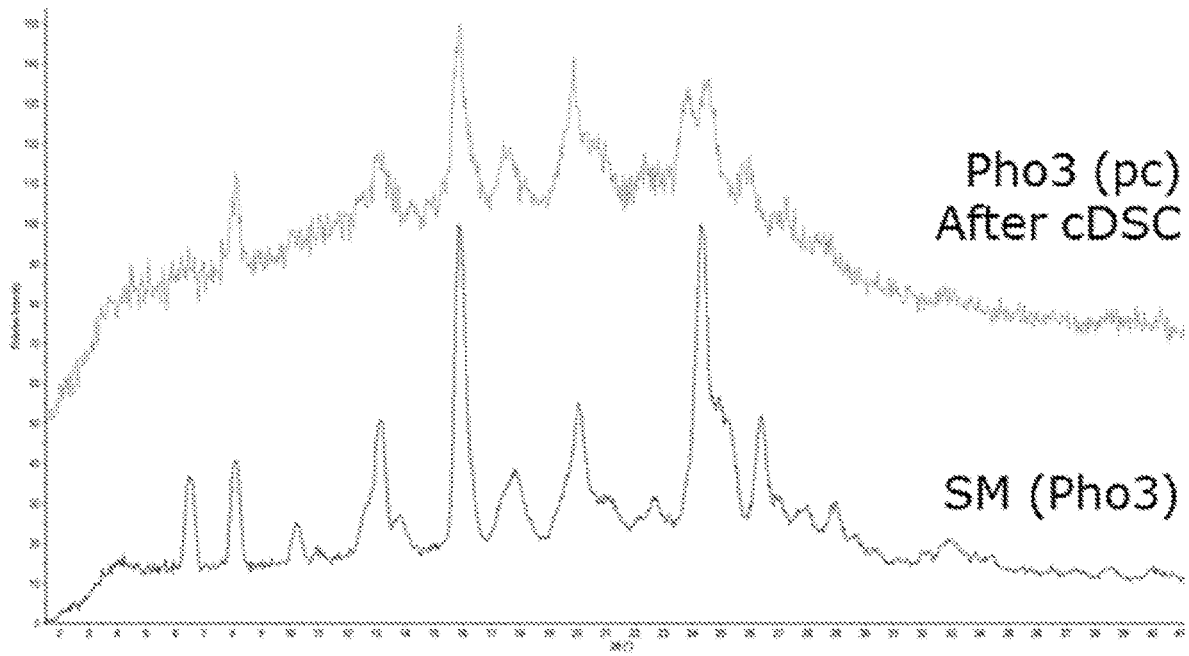

FIG. 199 illustrates the overlay of HT-XRPD patterns of received Pho3 and of the poorly crystalline (pc) material obtained after cDSC.

Figure 200:
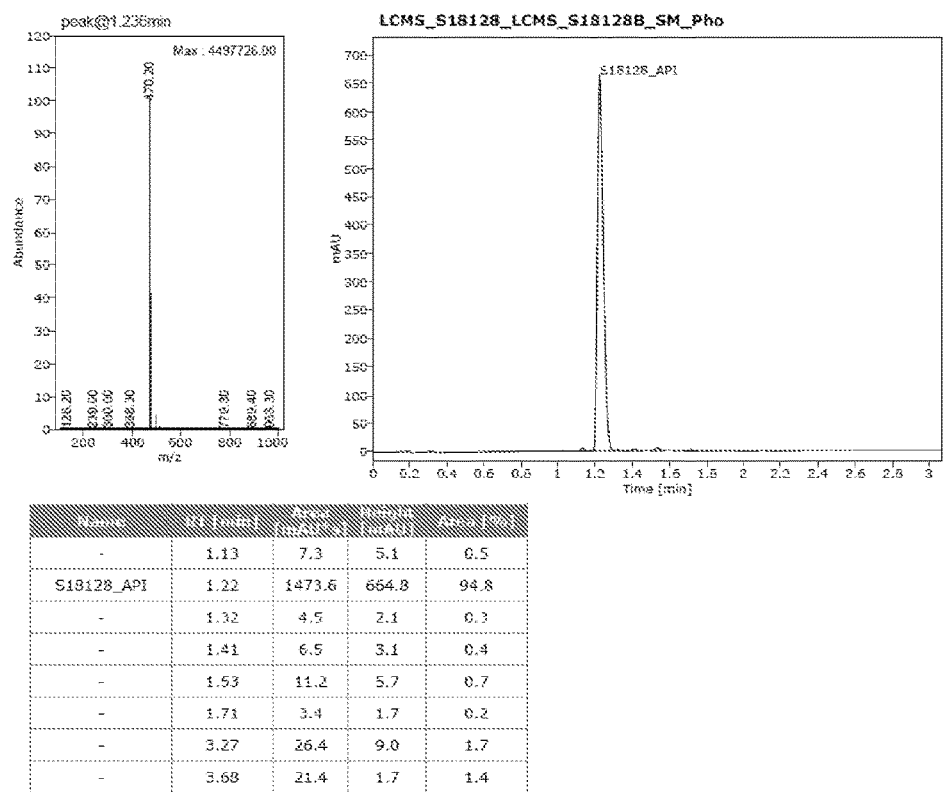

FIG. 200 illustrates the UPLC-MS analysis of Pho3 (starting material). The peak corresponding to the API had a retention time of 1.2 min and the positive ion spectrum showed an ion with m/z of 470.2 [M+H]$^+$, in agreement with the free base molecular mass of 469.8 g/mol. The table shows the retention times, peak areas and heights of the API and unidentified impurities.

Figure 201:
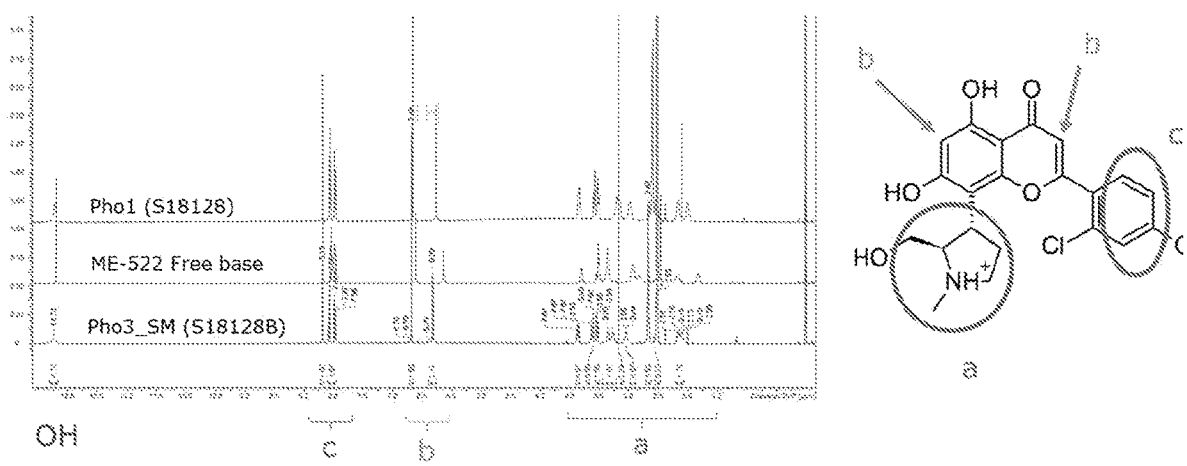

FIG. 201 illustrates the $^1$H-NMR spectra of Pho3 (SM, bottom), ME-522 free base (from S18128, middle) and Pho1 (from S18128, top) measured in DMSO-d$_6$. The letters at the bottom of the spectrum correspond to the hydrogen atoms in the molecular structure of the API.

Figure 202:
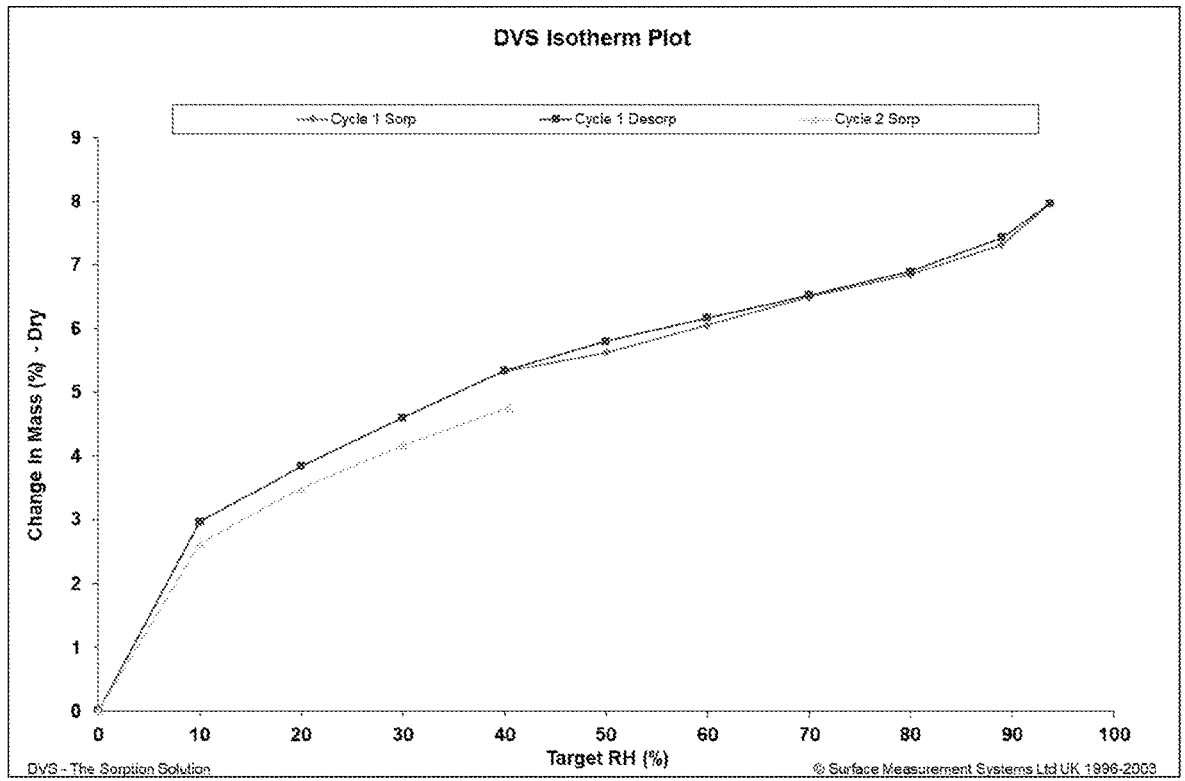

FIG. 202 illustrates the DVS isotherm plot of Pho3 (starting material) in which the change in mass is plotted as a function of the RH. Initially, a sorption profile was applied from 40% to 95% RH (red diamond), followed by a desorption profile from 95% to 0% RH (blue square). Finally, the RH was set to the starting value of 40% (green triangle).

Figure 203:
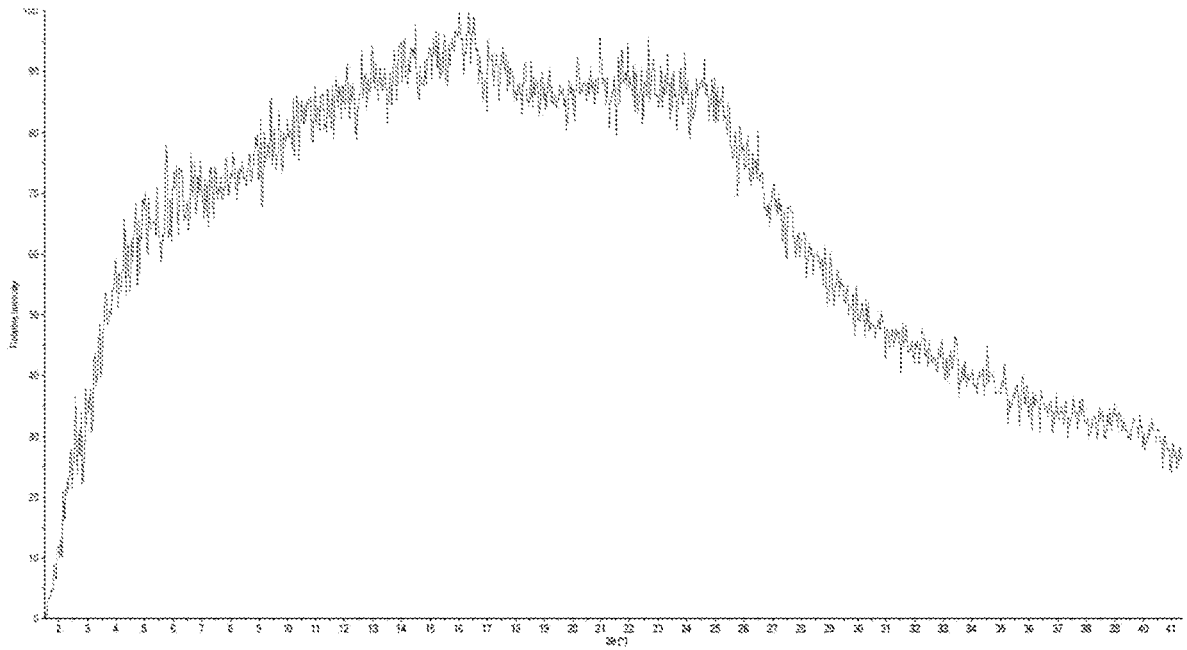

FIG. 203 illustrates the HT-XRPD pattern of ME-522 phosphate salt (Exp. ID: QSA8) prepared by freeze-drying the starting material in acetone/water (50/50, v/v).

Figure 204:
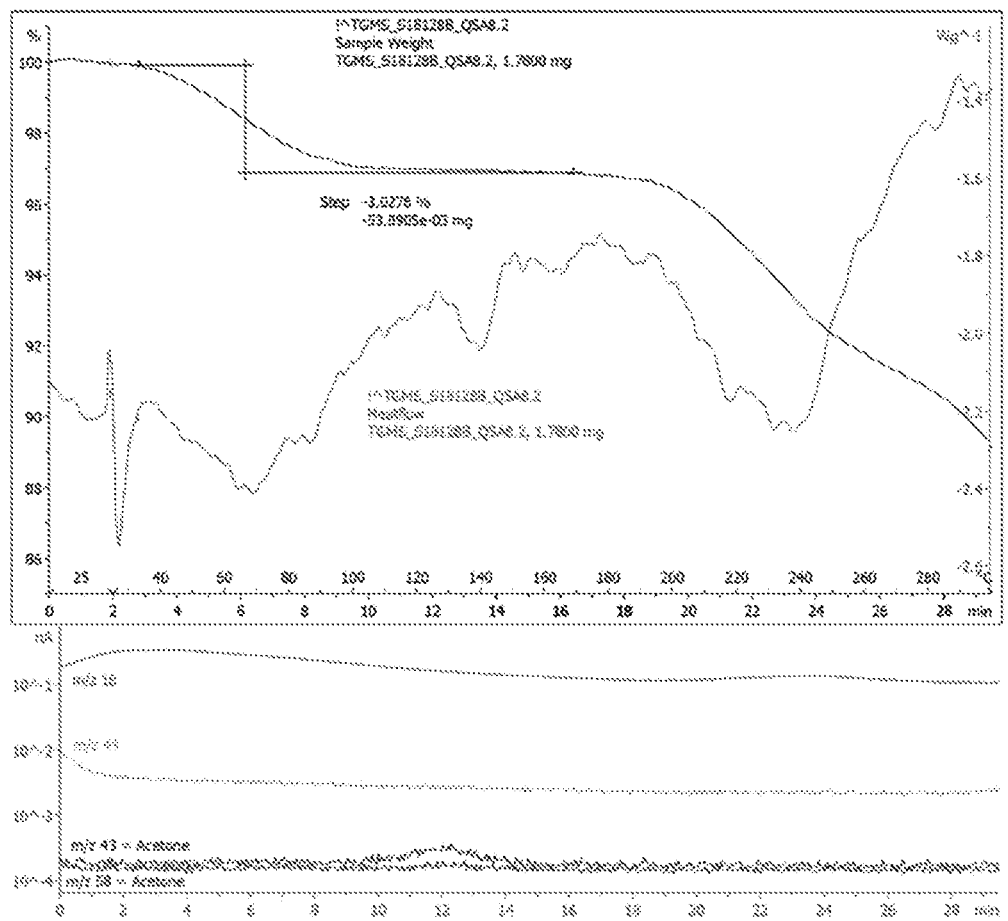

FIG. 204 illustrates the TGMS thermogram (heating rate 10° C./min) of the amorphous phosphate salt obtained by freeze-drying (Exp. ID: QSA8). A mass loss of 3.0% was recorded between 40-160° C.

Figure 205:
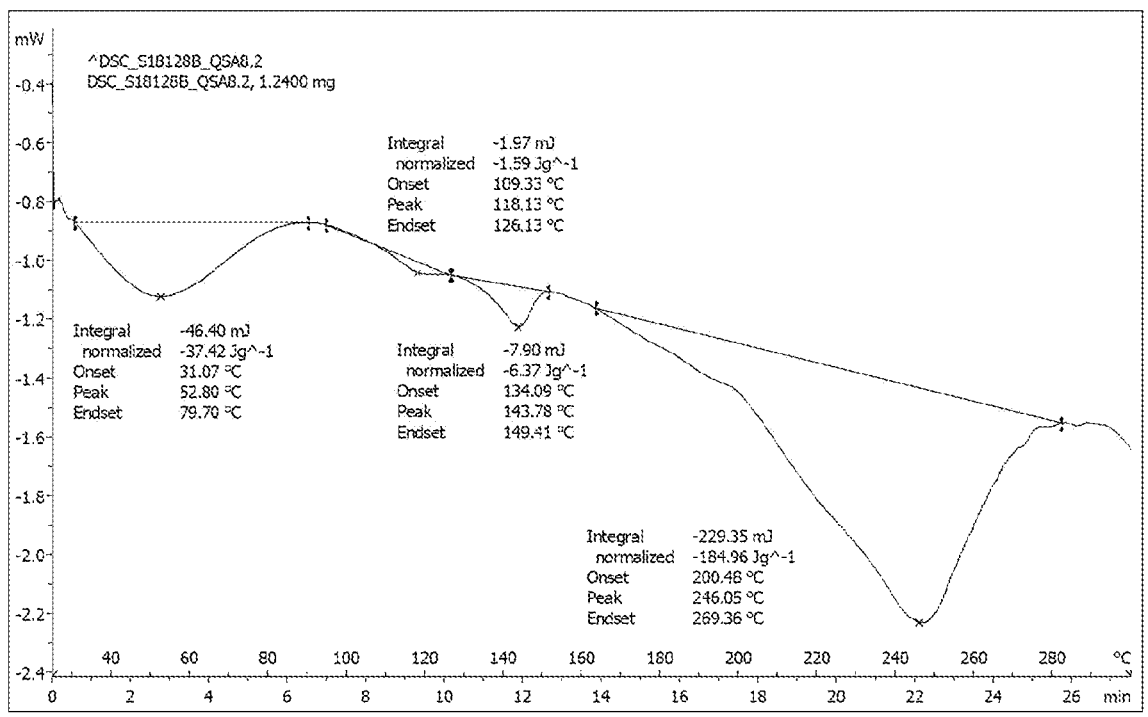

FIG. 205 illustrates the DSC trace (heating rate 10° C./min) of the amorphous phosphate salt obtained by freeze-drying (Exp. ID: QSA8). Three endothermic events were detected between 25 and 150° C. in addition to a broad endothermic event between 200 and 270° C.

Figure 206:
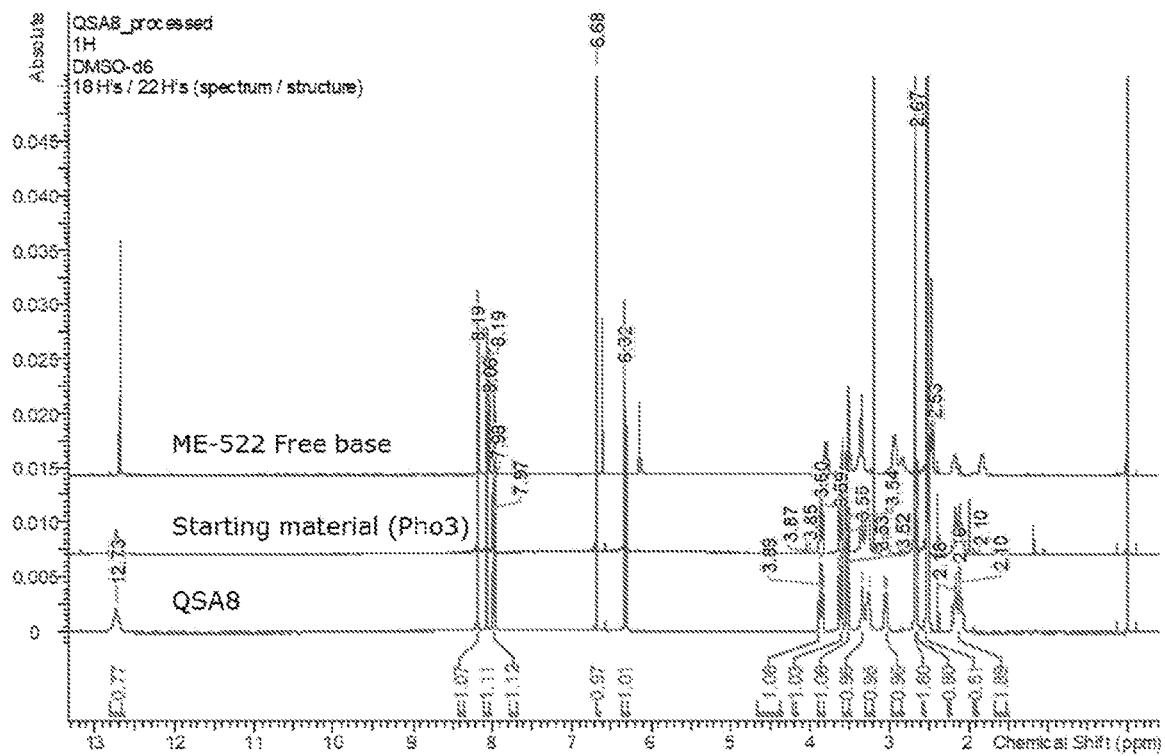

FIG. 206 illustrates the $^1$H-NMR spectra of the amorphous ME-522 phosphate salt (Exp. ID: QSA8, bottom), ME-522 Pho3 (SM, middle) and the ME-522 free base (SM from project S128128, top) measured in DMSO-d$_6$.

Figure 207:
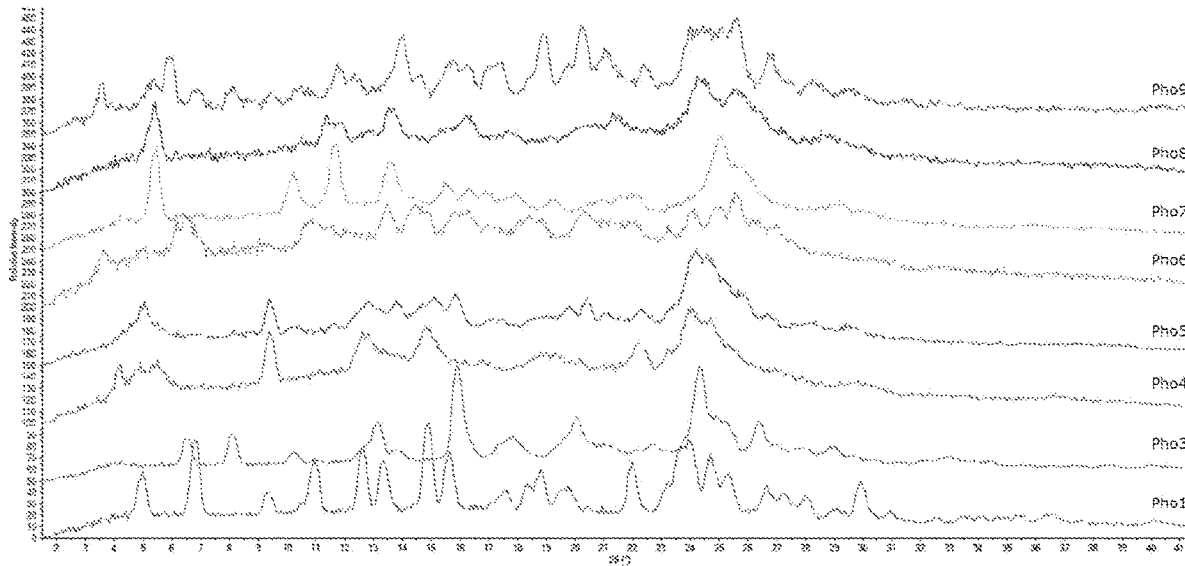

FIG. 207 illustrates the HT-XRPD diffractograms of the forms observed in the present study on the ME-522 phosphate salt. From bottom to top: Pho1, Pho3, Pho4, Pho5, Pho6, Pho7, Pho8 and Pho9.

Figure 208:
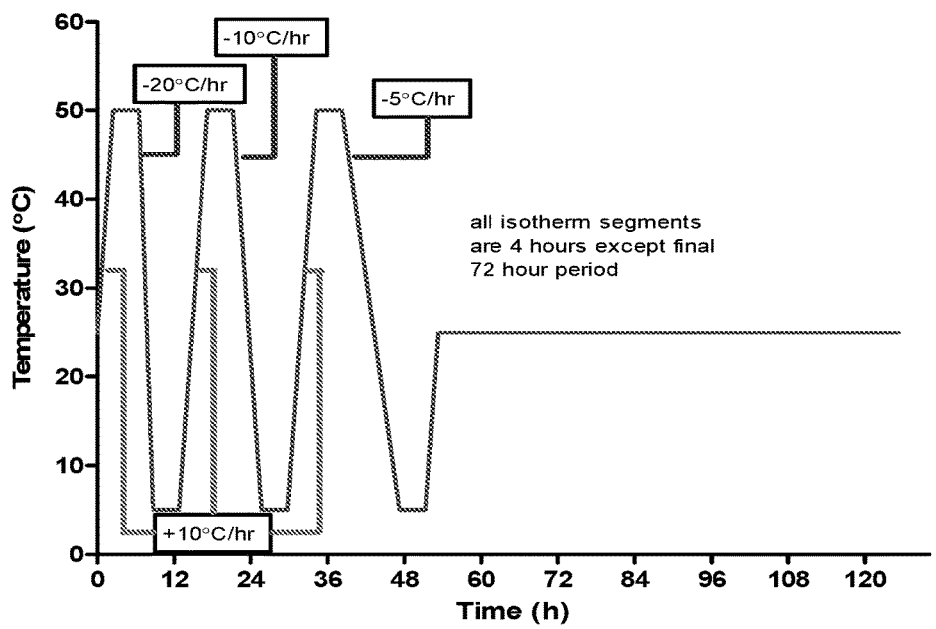

FIG. 208 illustrates the temperature profile of the thermocycling experiments.

Figure 209:
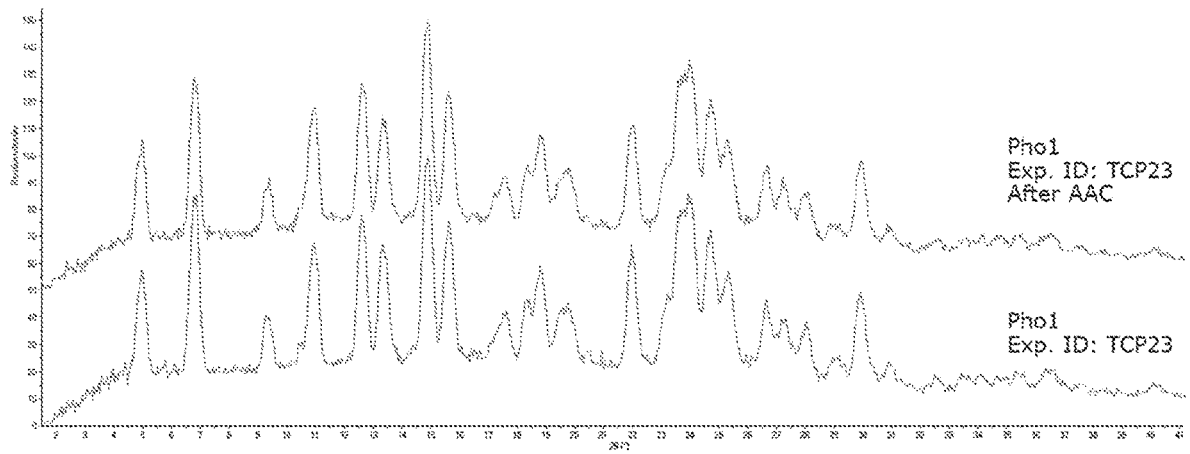

FIG. 209 illustrates the overlay of HT-XRPD patterns of Pho1 (Exp. ID: TCP23, vacuum-dried) and Pho1 (Exp. ID: TCP23, vacuum-dried after AAC).

Figure 210:
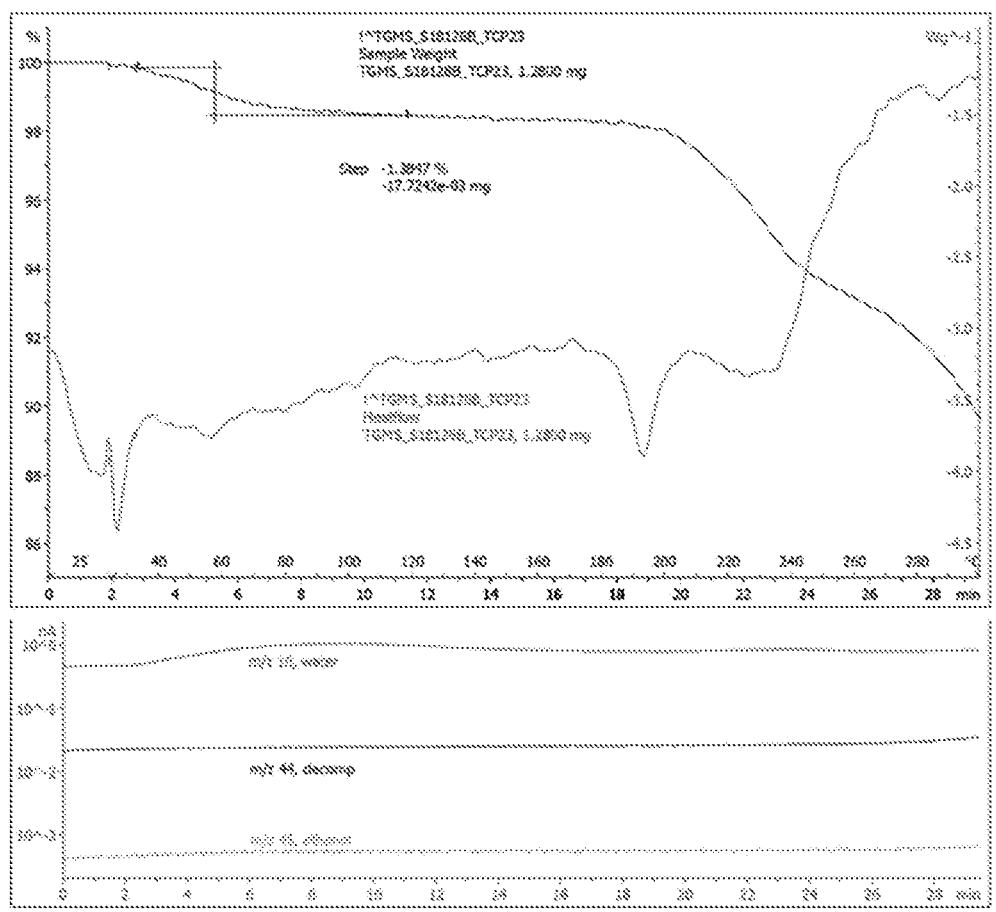

FIG. 210 illustrates the TGMS thermogram (heating rate 10° C./min) of Pho1 (Exp. ID: TCP23). A mass loss of 1.4% was recorded between 40 and 120° C.

Figure 211:
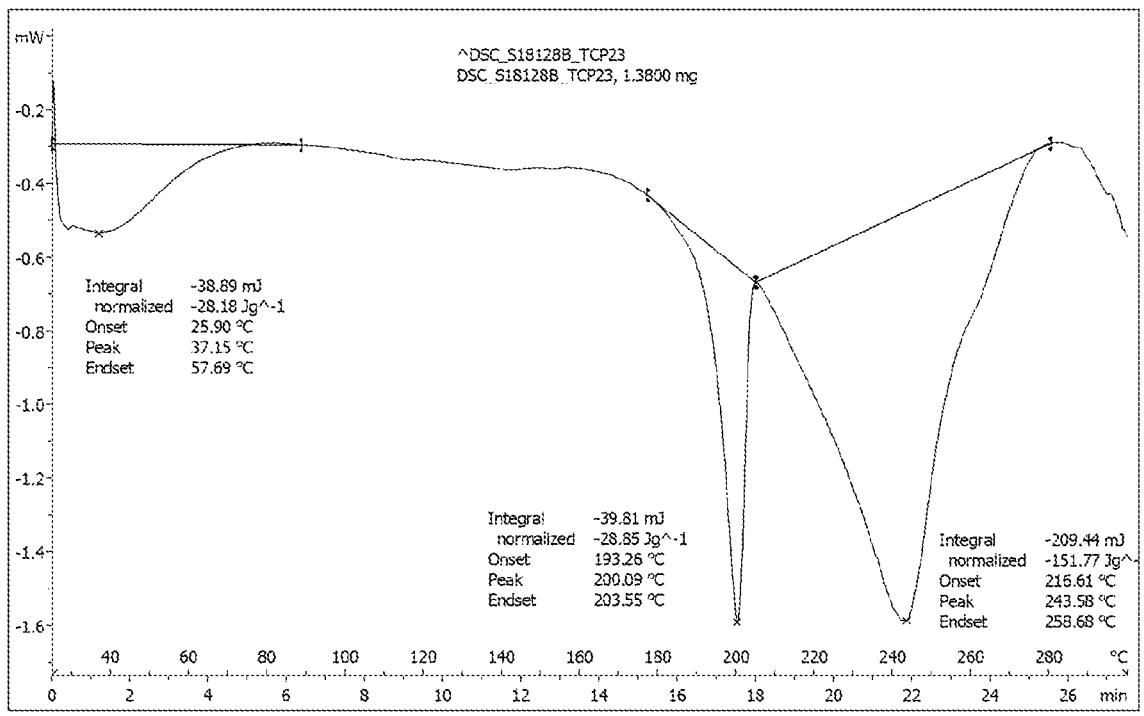

FIG. 211 illustrates the DSC trace (heating rate 10° C./min) of Pho1 (Exp. ID: TCP23). A broad endothermic event was observed before 80° C. in addition to a sharp endotherm at 200° C. and a broad endotherm between 217-259° C.

Figure 212A:
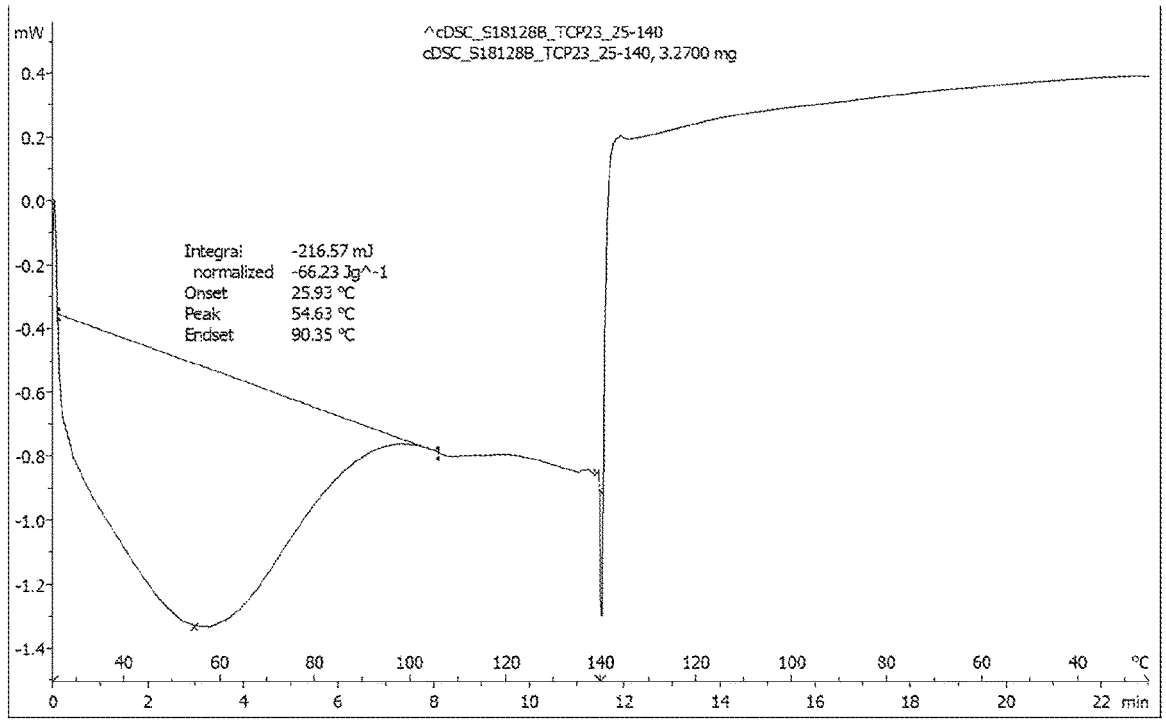
Figure 212B:
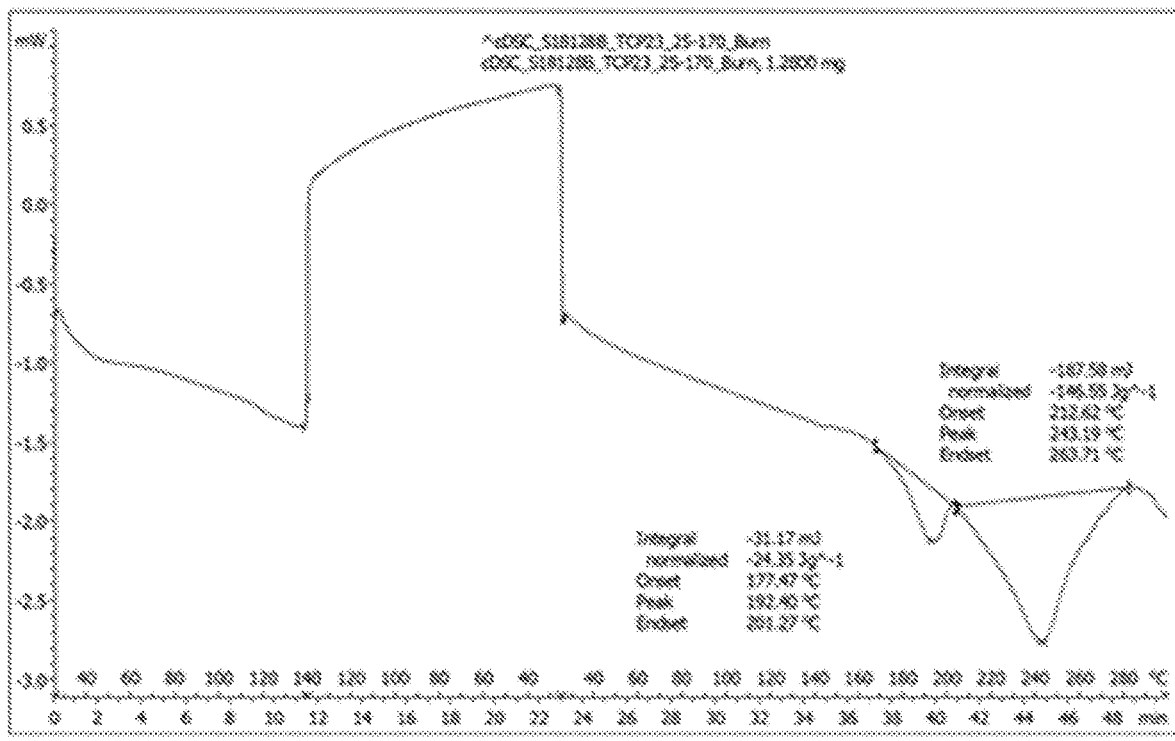

FIG. 212A and FIG. 212B illustrate the cDSC traces (heating rate 10° C./min) of Pho1 (Exp. ID: TCP23). In the first experiment (FIG. 212A), the material was heated up to 140° C. and cooled down to room temperature. After the material was analyzed by HT-XRPD, the compound obtained from the first cDSC cycle was again heated to 140° C., cooled to room temperature and finally heated to 300° C. in a second cDSC cycle (FIG. 212B).

Figure 213:
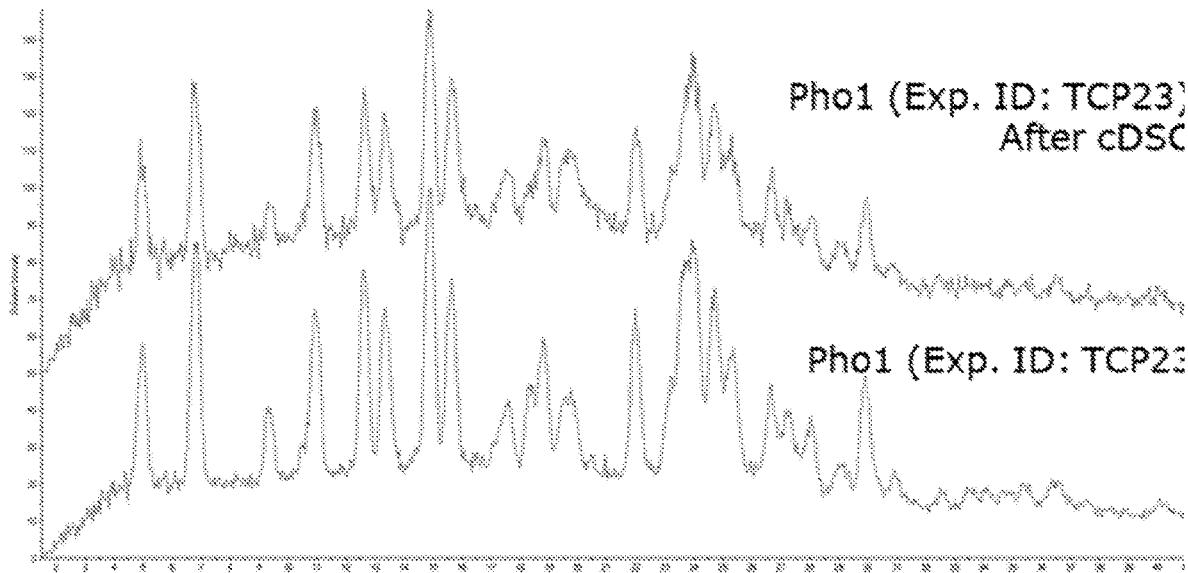

FIG. 213 illustrates the overlay of HT-XRPD patterns of Pho1 (Exp. ID: TCP23) before and after cDSC.

Figure 214:
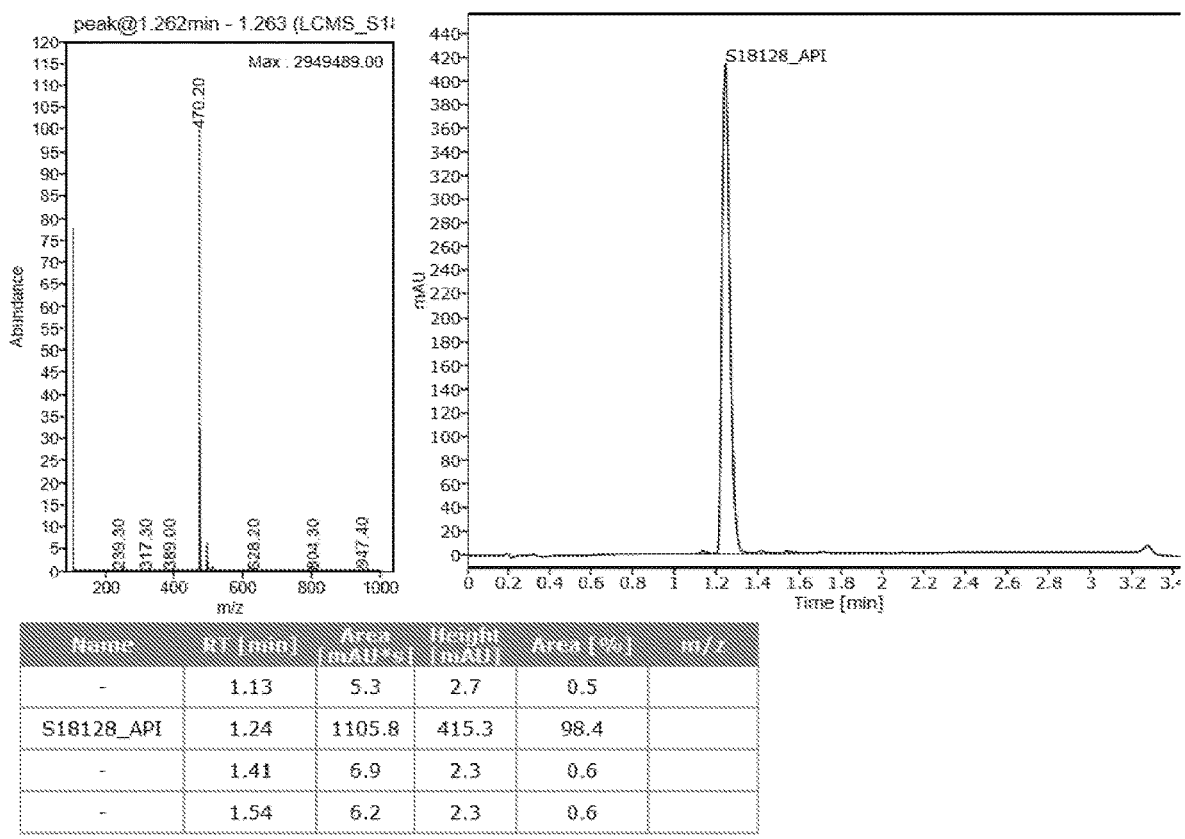

FIG. 214 illustrates the UPLC-MS analysis of Pho1 (Exp. ID: TCP23). The peak corresponding to the API had a retention time of 1.2 min and the positive ion spectrum showed an ion with m/z of 470.2 [M+H]$^+$, in agreement with the API molecular mass of 469.8 g/mol. The table shows the retention times, peak areas and heights of the API and unidentified impurities.

Figure 215:
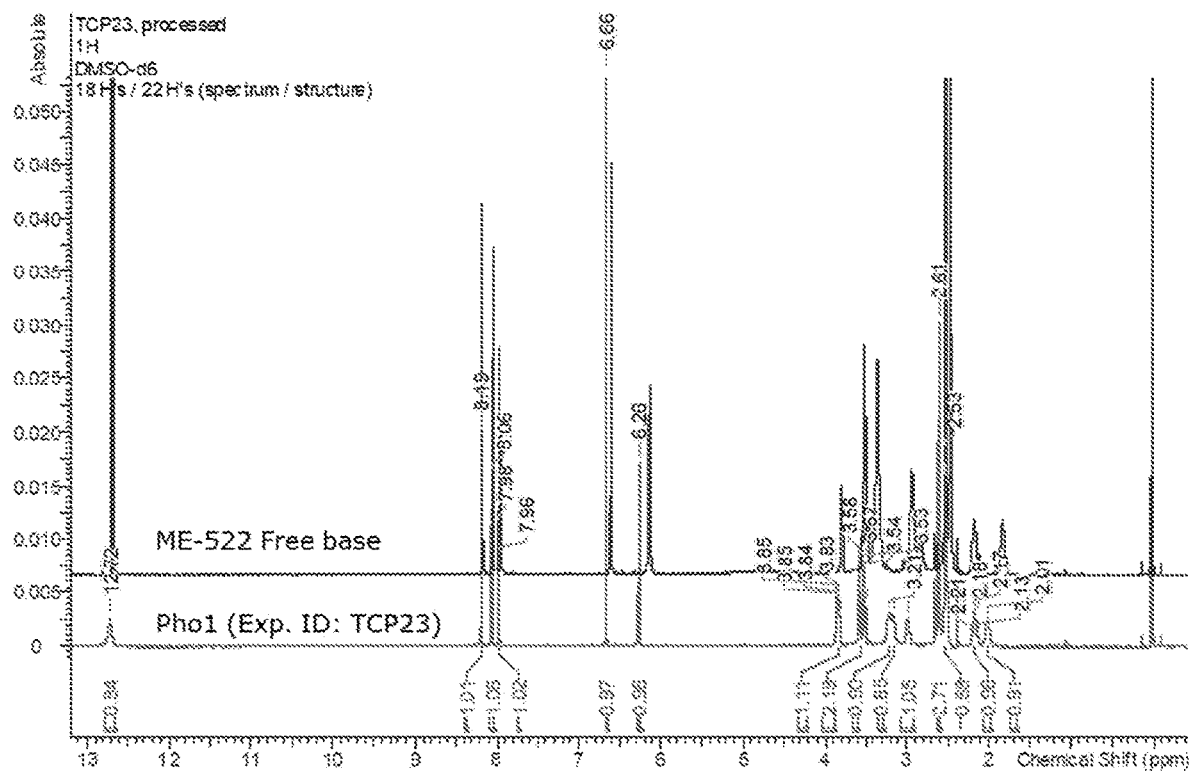

FIG. 215 illustrates the $^1$H-NMR spectra of Pho1 (Exp. ID: TCP23, bottom) and ME-522 free base (from S18128, top) measured in DMSO-d$_6$.

Figure 216:
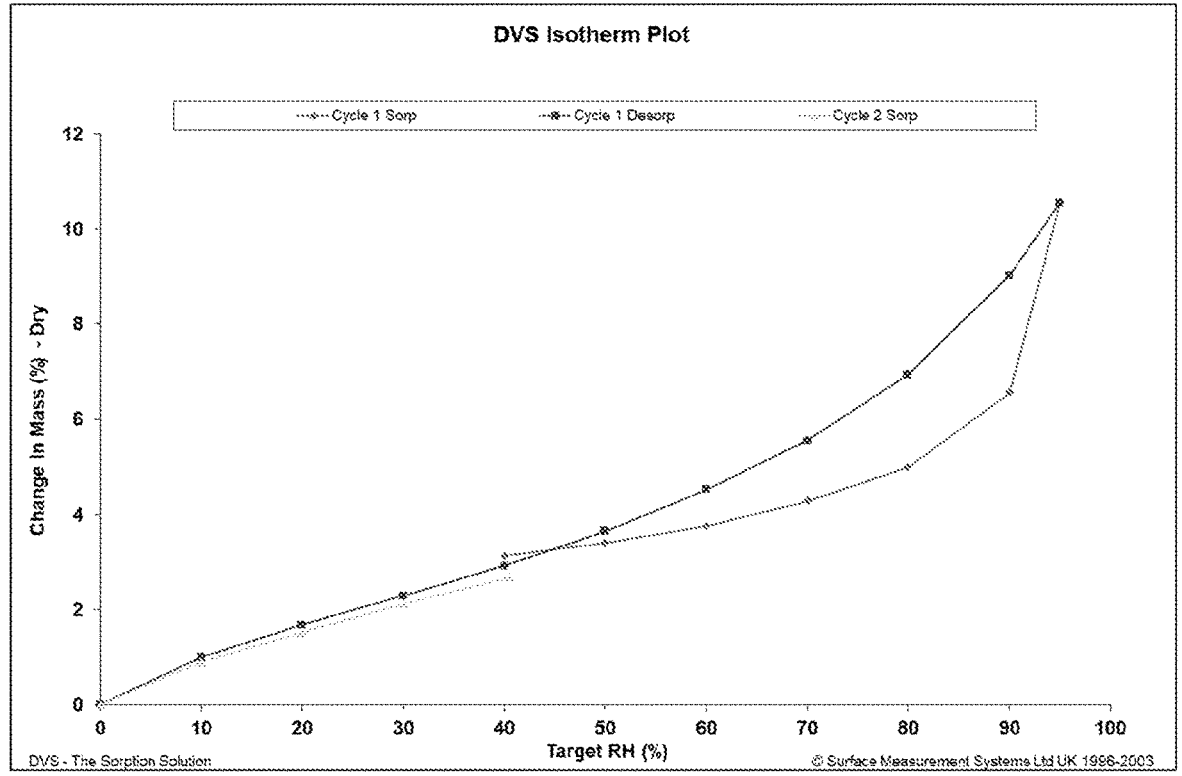

FIG. 216 illustrates the DVS isotherm plot of Pho1 (Exp. ID: TCP23) in which the change in mass is plotted as a function of the RH. Initially, a sorption profile was applied from 40% to 95% RH (red diamond), followed by a desorption profile from 95% RH to 0% RH (blue square). Finally, the RH was set to the start value of 40% (green triangle).

Figure 217:
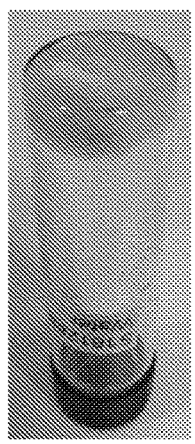

FIG. 217 illustrates the photograph of the material obtained after a small amount of water was added to a solid sample of Pho1 (Exp. ID: TCP23).

Figure 218:
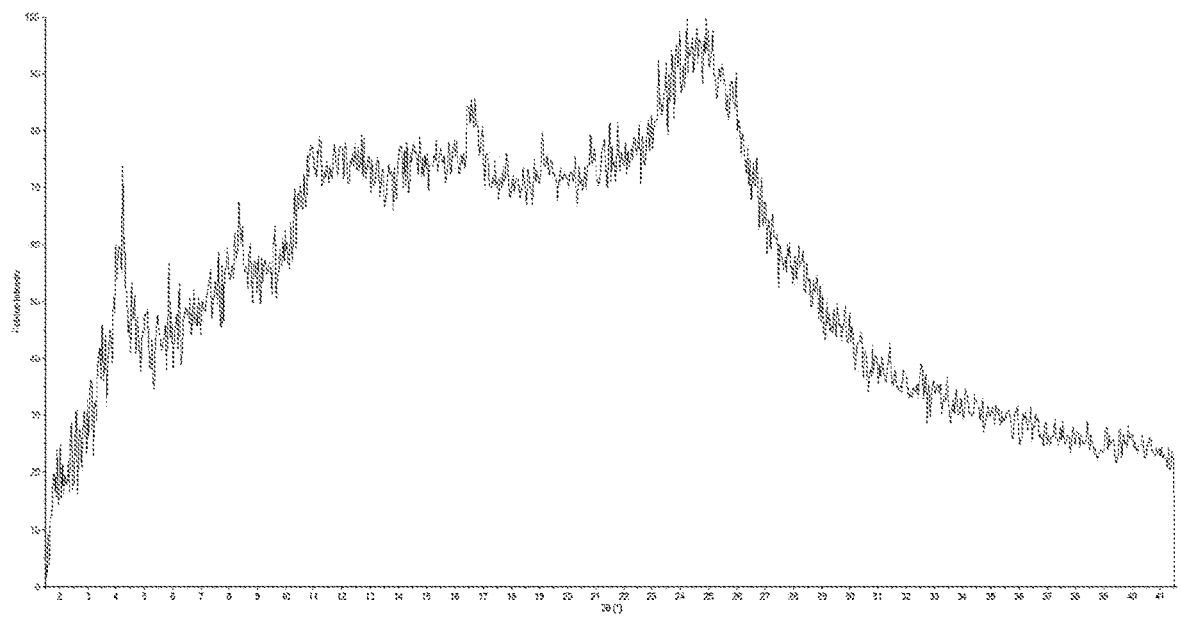

FIG. 218 illustrates the HT-XRPD pattern of Pho2 (Exp. ID: SSm15 from project S18128).

Figure 219:
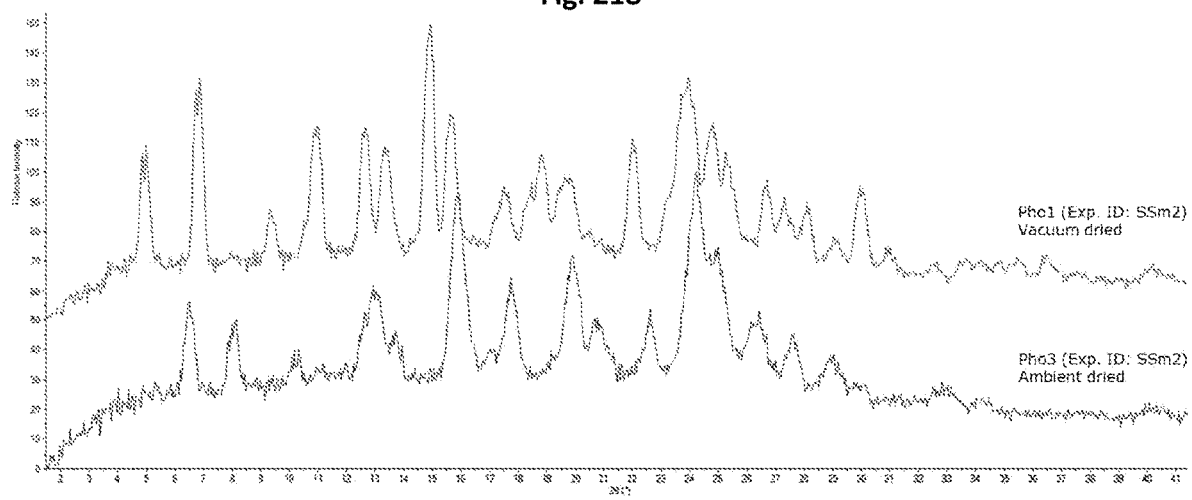

FIG. 219 illustrates the overlay of HT-XRPD patterns from the solids obtained through cooling crystallization from ethanol (Exp. ID: SSm2). From bottom to top: Pho3 (ambient-dried) and Pho1 (vacuum-dried).

Figure 220:
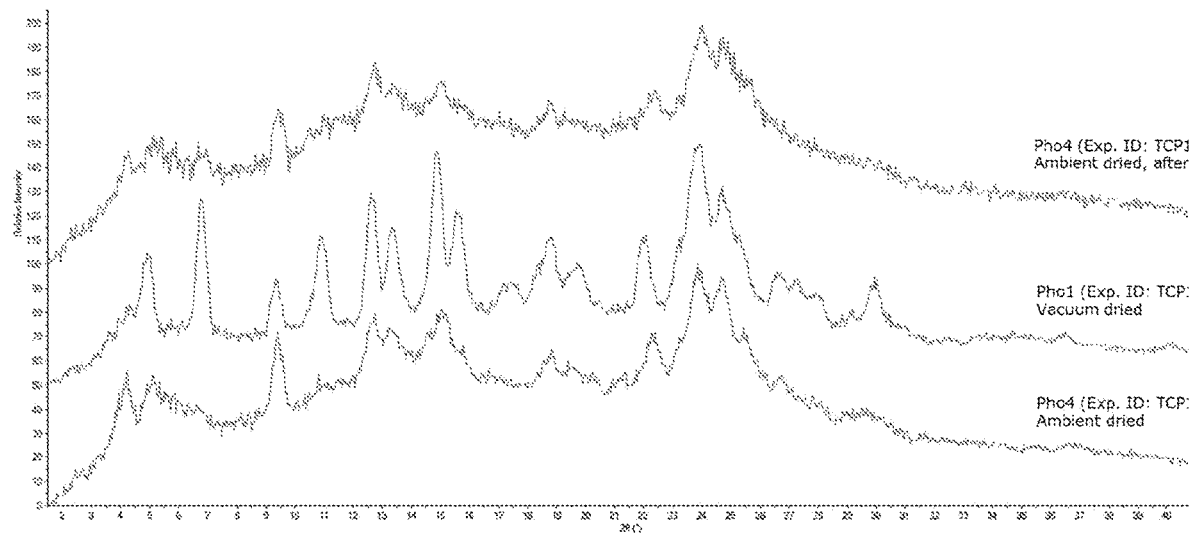

FIG. 220 illustrates the overlay of HT-XRPD patterns of the materials obtained through thermocycling in 1,2-dimetoxyethane (Exp. ID: TCP16). From bottom to top: Pho4 (ambient-dried), Pho1 (vacuum-dried) and Pho4 (ambient-dried, after AAC).

Figure 221:
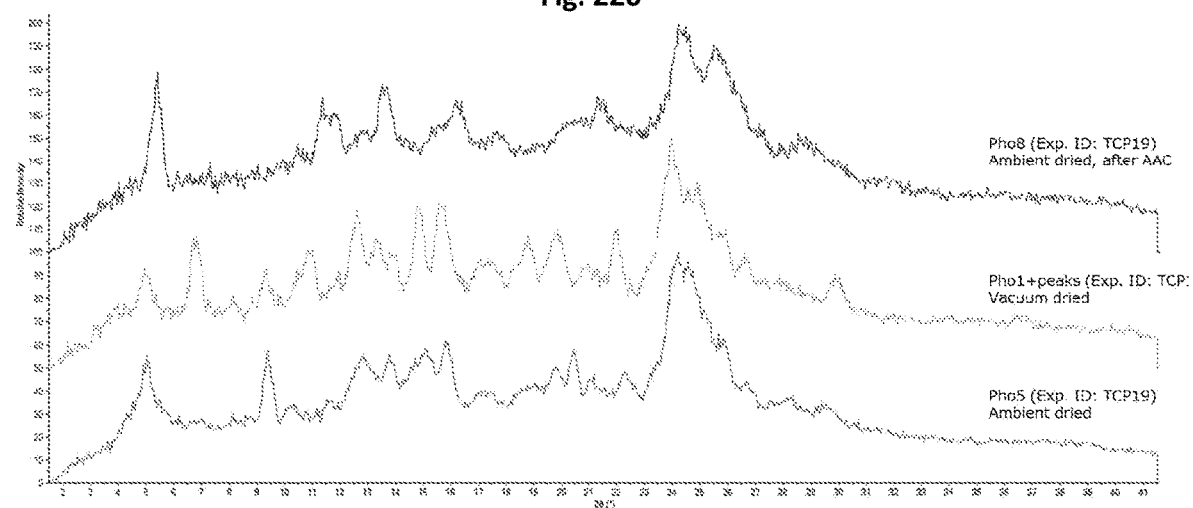

FIG. 221 illustrates the overlay of HT-XRPD patterns of the materials obtained through thermocycling in acetone (Exp. ID: TCP19). From bottom to top: Pho5 (ambient-dried), Pho1+peaks (vacuum-dried) and Pho8 (ambient-dried, after AAC).

Figure 222:
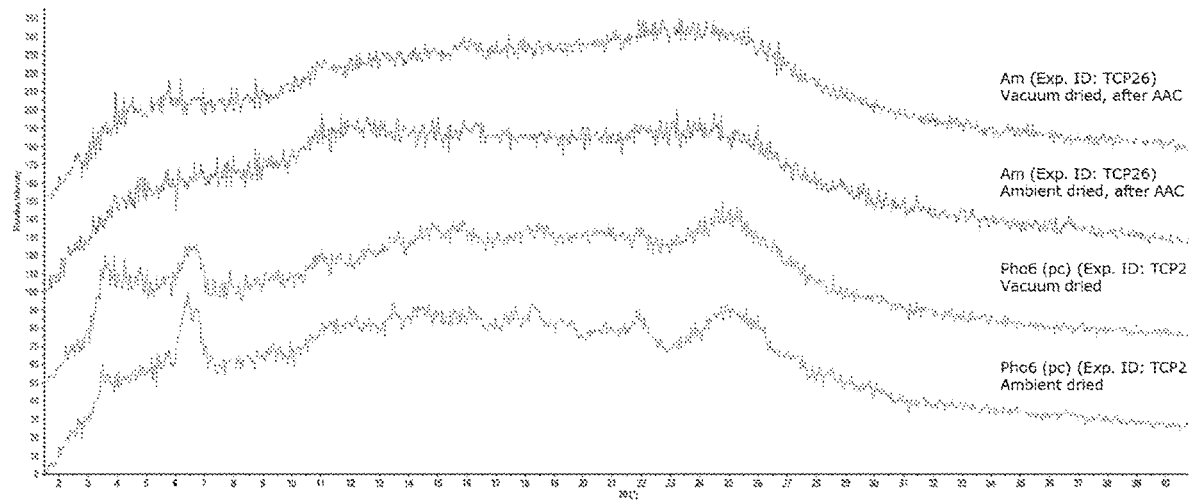

FIG. 222 illustrates the overlay of HT-XRPD patterns of the poorly crystalline (pc) material obtained from TBME (Exp. ID: TCP26). From bottom to top: Pho6 (ambient-dried), Pho6 (vacuum-dried), amorphous material (ambient-dried, after AAC) and amorphous material (vacuum-dried, after AAC).

Figure 223:
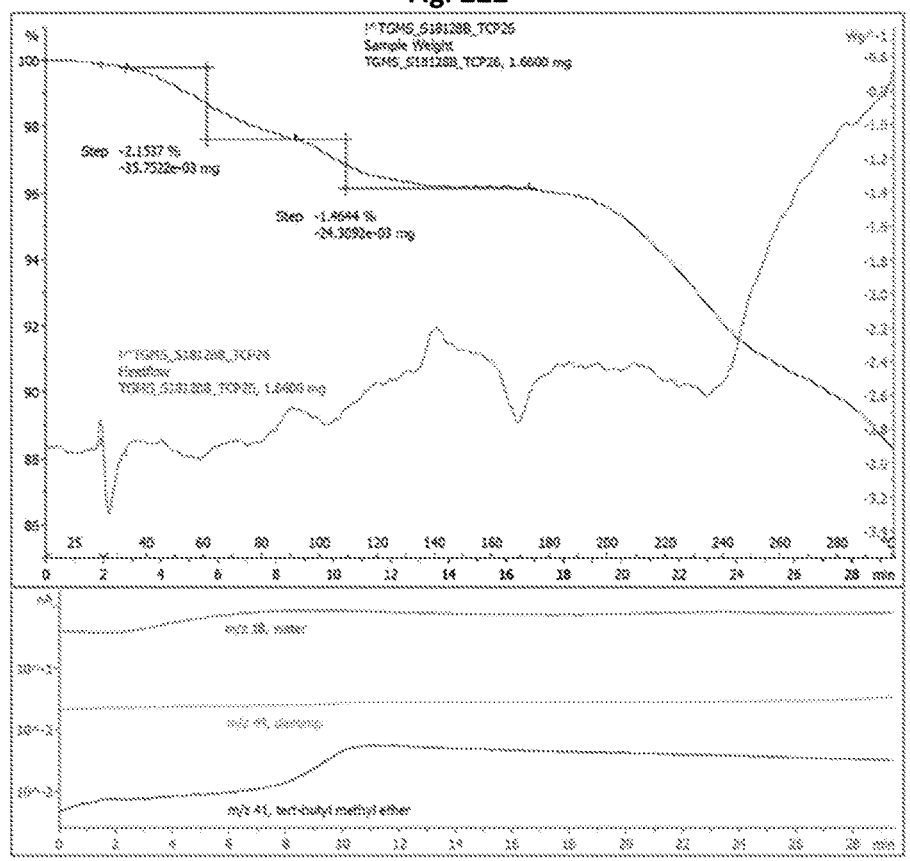

FIG. 223 illustrates the TGMS thermogram (heating rate 10° C./min) of Pho6 (Exp. ID: TCP26). A total mass loss of 3.6% was recorded between 30-180° C.

Figure 224:
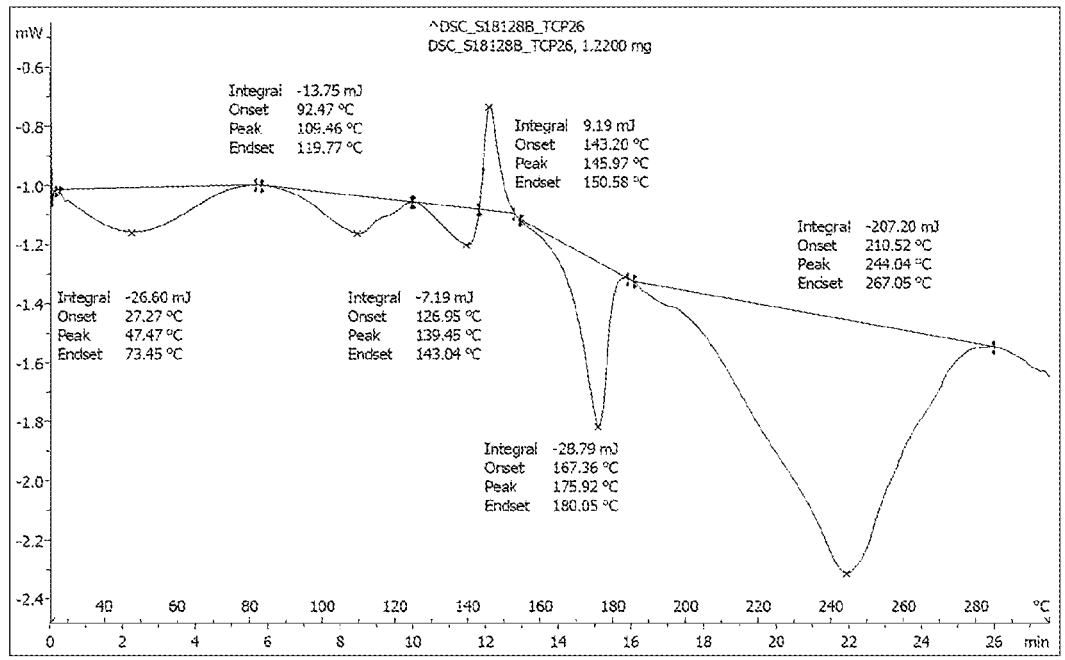

FIG. 224 illustrates the DSC trace (heating rate 10° C./min) of Pho6 (Exp. ID: TCP26). Upon heating, three endothermic events up to 143° C. were followed by an exothermic event at 146° C. Subsequently, an endotherm at 176° C. was followed by a broad endotherm between 211-267° C.

Figure 225:
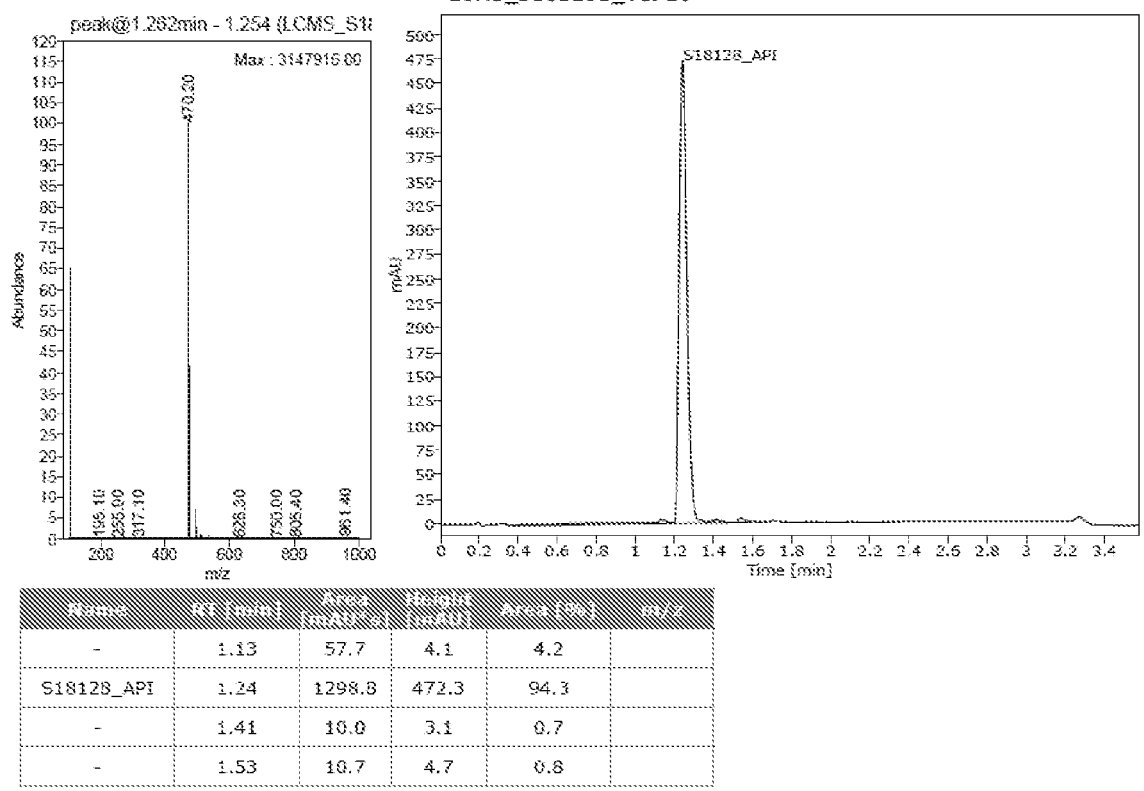

FIG. 225 illustrates the UPLC-MS analysis of Pho6 (Exp. ID: TCP26). The peak corresponding to the API had a retention time of 1.2 min and the positive ion spectrum showed an ion with m/z of 470.2 [M+H]$^+$, in agreement with the free base molecular mass of 469.8 g/mol. The table shows the retention times, peak areas and heights of the API and unidentified impurities.

Figure 226:
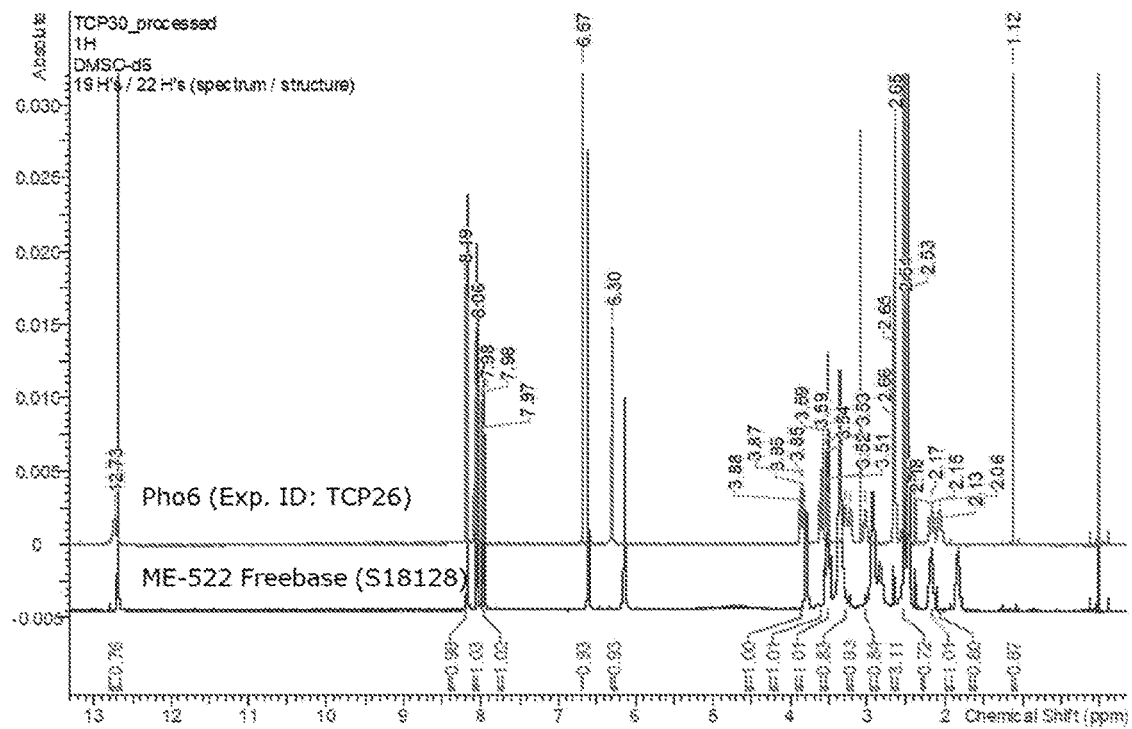

FIG. 226 illustrates the $^1$H-NMR spectra of the free base (SM of S18128, bottom) and Pho6 (Exp. ID: TCP26, top) measured in DMSO-d$_6$. The singlet signal at 1.12 ppm represents the protons of the three CH$_3$ group of TBME.

Figure 227:
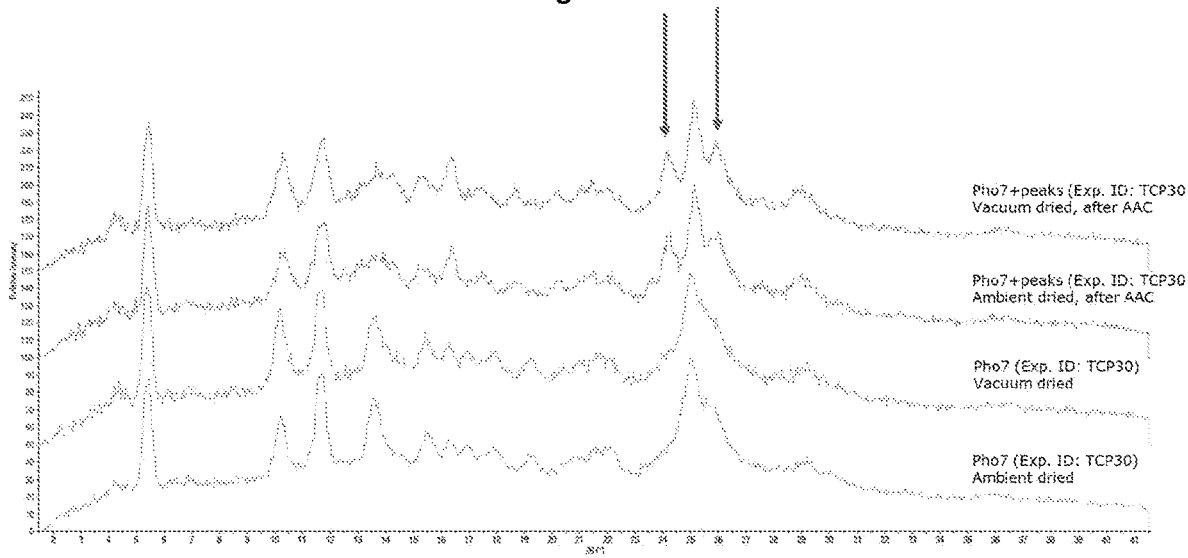

FIG. 227 illustrates the overlay of HT-XRPD patterns of Pho7 obtained from the thermocycling experiment in 2-propanol/water (90/10, v/v; Exp. ID: TCP30). From bottom to top, the XRPD patterns represent the ambient-dried sample, the vacuum-dried material, the ambient-dried sample after exposure to AAC (40° C./75% RH, 2 days) and the vacuum-dried material after exposure to AAC (40° C./75% RH, 2 days). The additional diffraction peaks are indicated with arrows.

Figure 228:
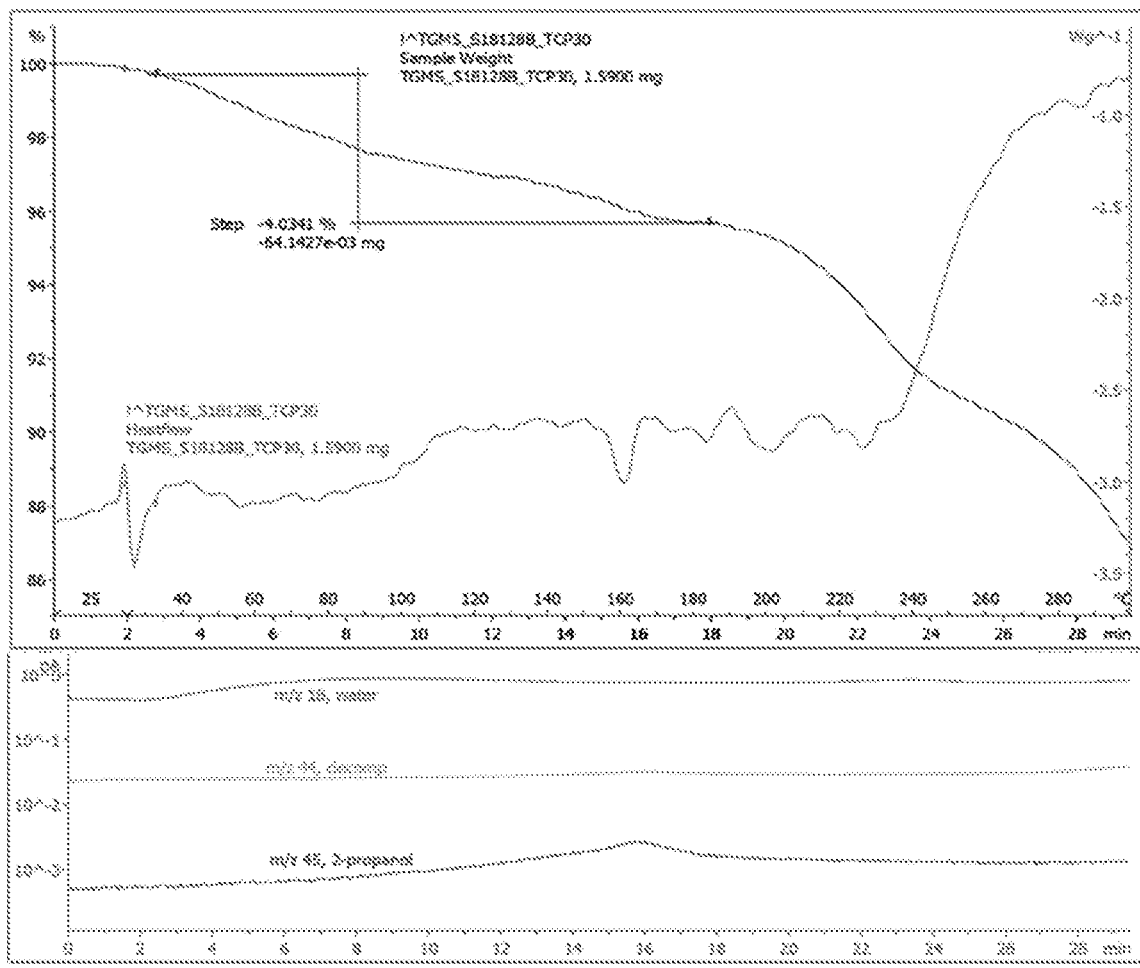

FIG. 228 illustrates the TGMS thermogram (heating rate 10° C./min) of Pho7 (Exp. ID: TCP30). A mass loss of 4.0% was recorded between 25-180° C.

Figure 229:
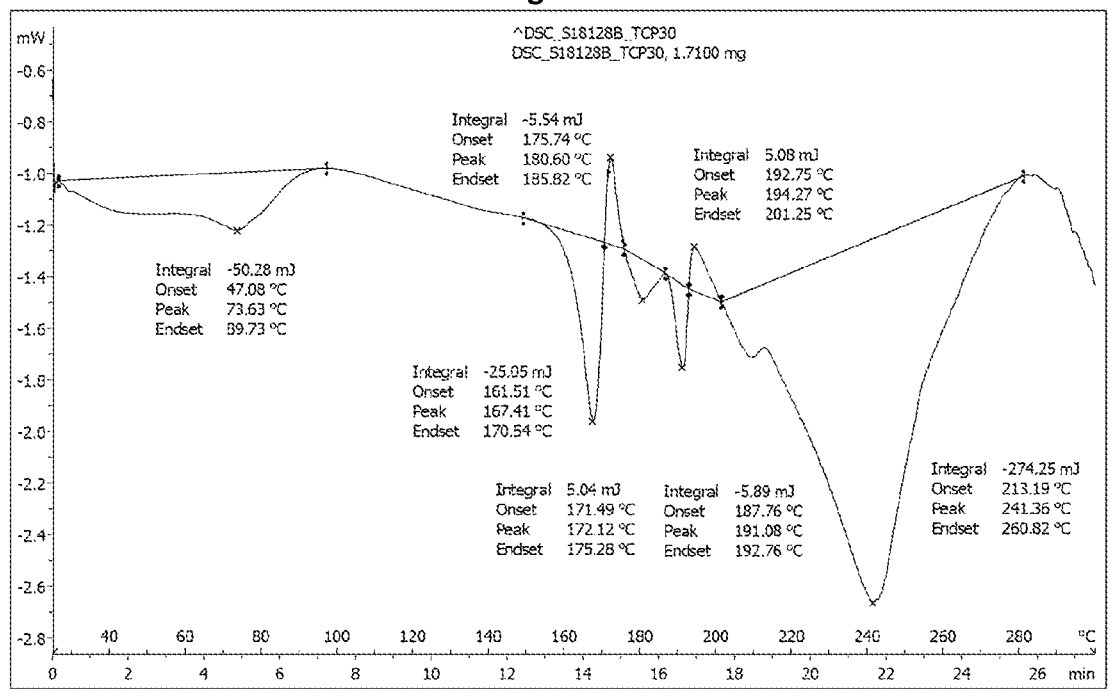

FIG. 229 illustrates the DSC trace (heating rate 10° C./min) of Pho7 (Exp. ID: TCP30). Several endo- and exothermic events were detected before 200° C. which were followed by a broad endothermic event between 213-261° C.

Figure 230:
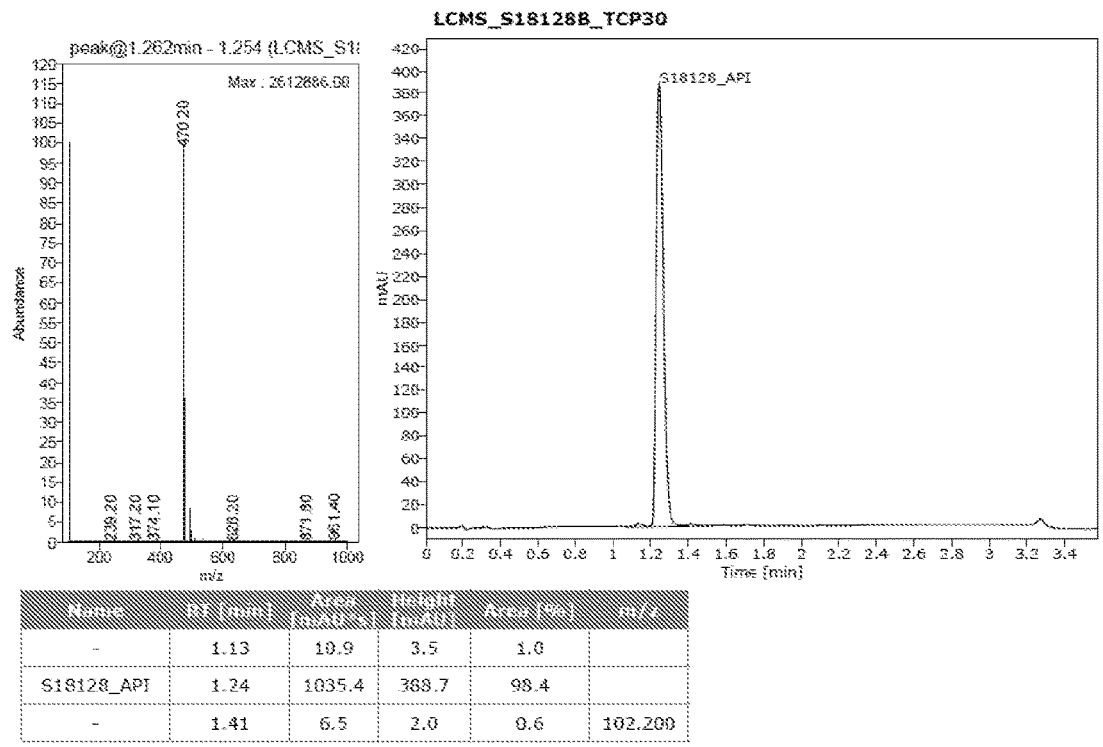

FIG. 230 illustrates the UPLC-MS analysis of Pho7 (Exp. ID: TCP30). The peak corresponding to the API had a retention time of 1.2 min and the positive ion spectrum showed an ion with m/z of 470.2 [M+H]$^+$, in agreement with the free base molecular mass of 469.8 g/mol. The table shows the retention times, peak areas and heights of the API and unidentified impurities.

Figure 231:
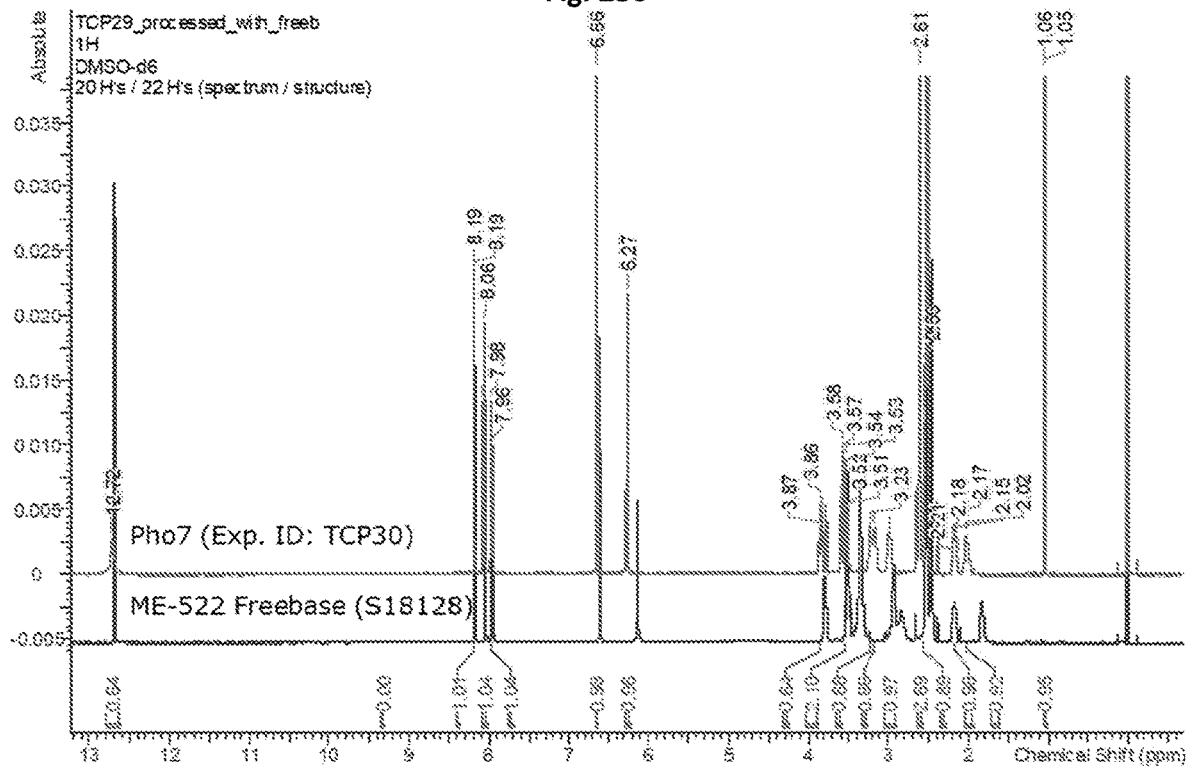

FIG. 231 illustrates the $^1$H-NMR spectra of the free base (SM of S18128, bottom) and Pho7 (Exp. ID: TCP30, top) measured in DMSO-d$_6$. The doublet signal at 1.06 ppm represents the protons of the two CH$_3$ group of 2-propanol.

Figure 232:
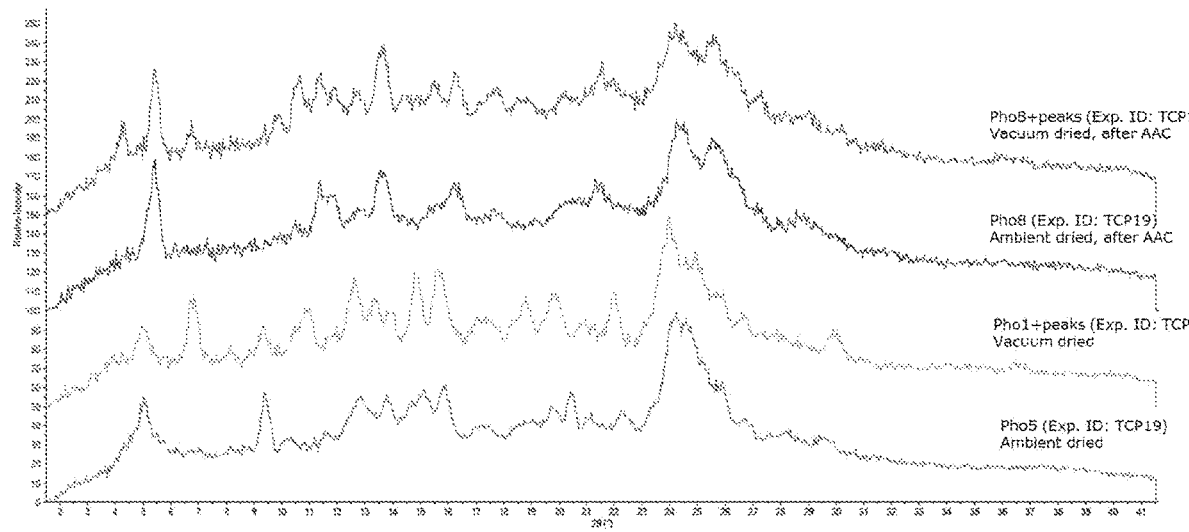

FIG. 232 illustrates the overlay of HT-XRPD patterns of the materials obtained from the thermocycling experiment in acetone (Exp. ID: TCP19). From bottom to top: Pho5 (ambient-dried), Pho1+peaks (vacuum-dried), Pho8 (ambient-dried, after AAC) and Pho8+peaks (vacuum-dried after AAC).

Figure 233:
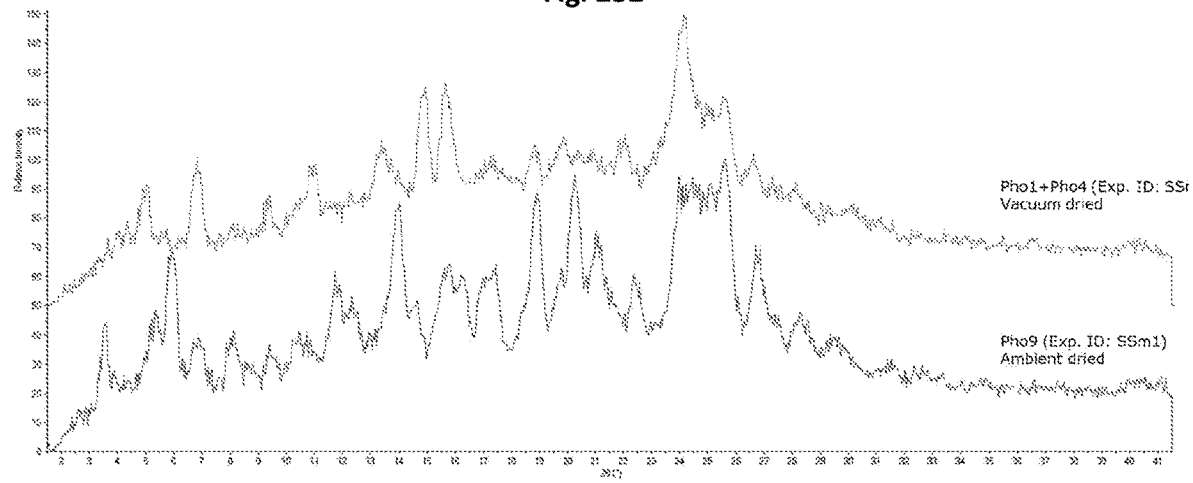

FIG. 233 illustrates the overlay of HT-XRPD patterns of Pho9 (ambient-dried) and Pho1+Pho4 (vacuum-dried) obtained through the cooling crystallization experiment from THF (Exp. ID: SSm1).

Figure 234:
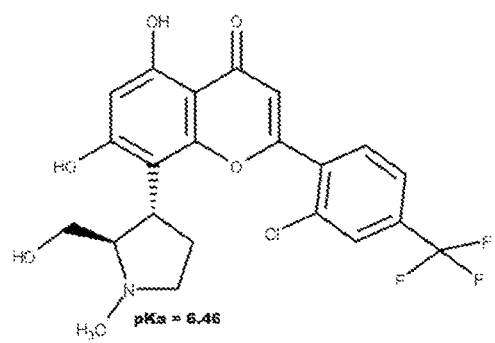

FIG. 234 illustrates the molecular structure of ME-522 free base (MW 469.8 g/mol).

Figure 235:
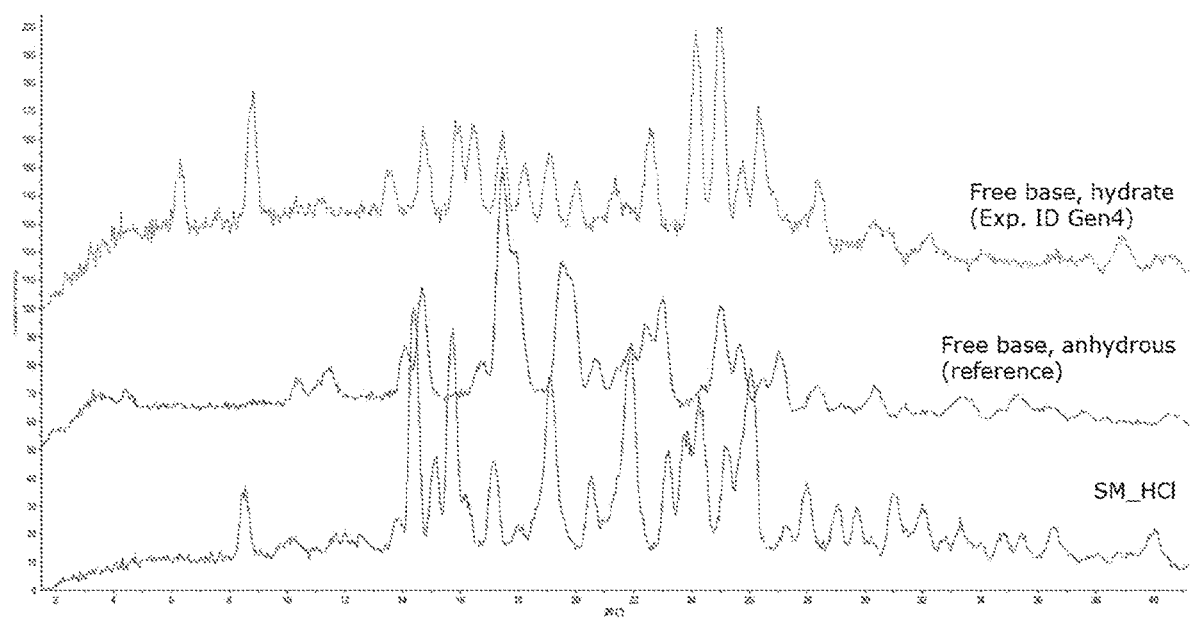

FIG. 235 illustrates the overlay of HT-XRPD patterns of ME-522 hydrochloride salt (starting material received for this study), ME-522 free base received for the salt formation experiments performed on S18128 and ME-522 free base obtained from the conversion of the HCl salt to the free base (Exp. ID GEN4).

Figure 236A:
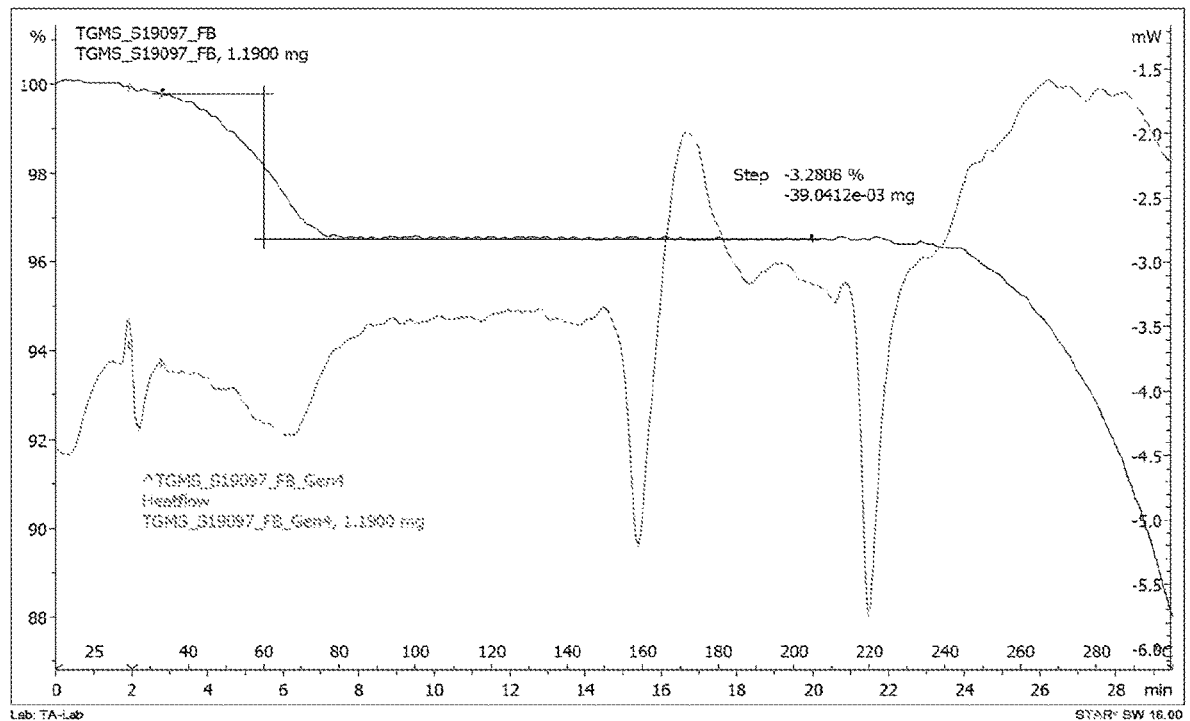
Figure 236B:
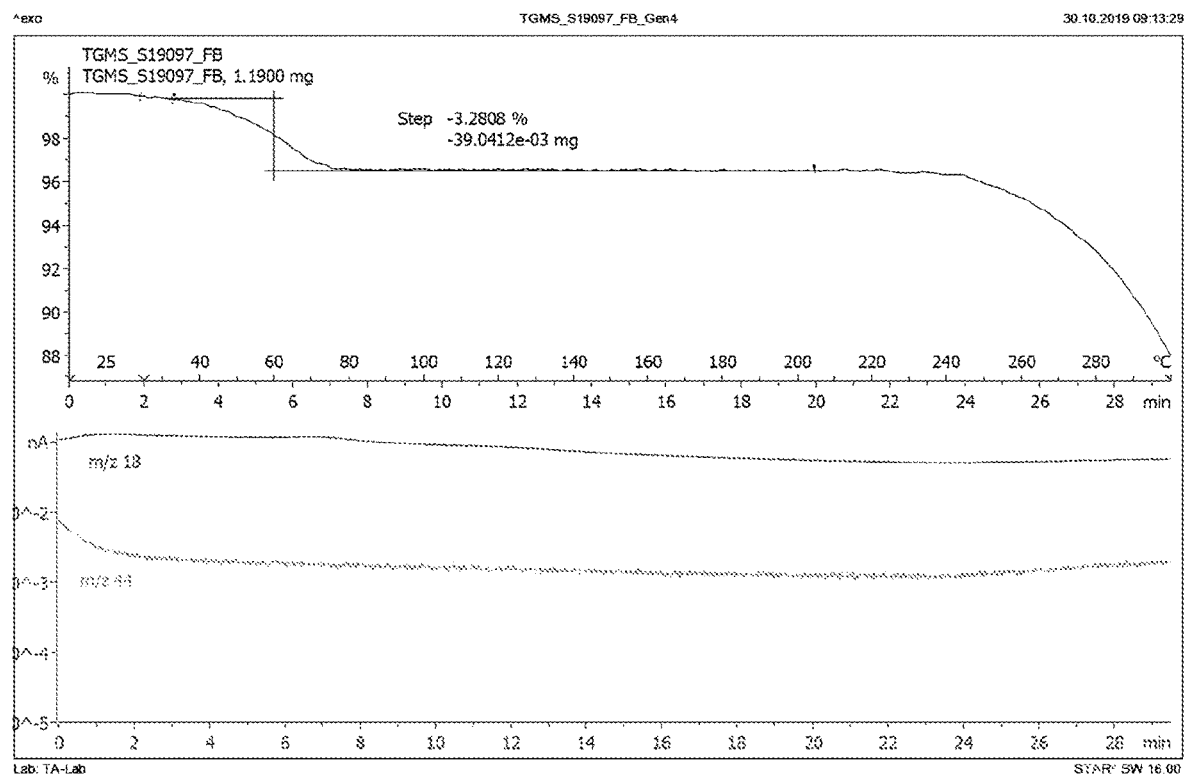

FIG. 236A and FIG. 236B illustrate TGA (FIG. 236A) and TGMS (FIG. 236B) analysis (heating rate of 10° C./min) of the recovered free base from the HCl conversion (Exp. ID GEN4). A mass loss of 3.3% was observed prior to the thermal decomposition (observed above 240° C.).

Figure 237:
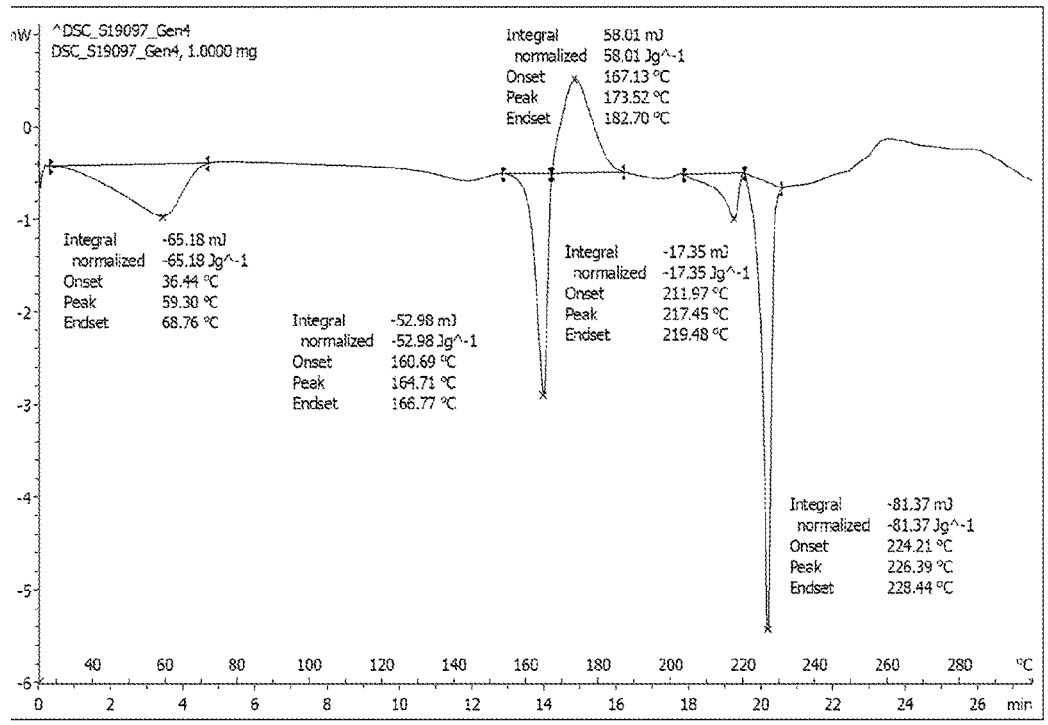

FIG. 237 illustrates the DSC curve (heating rate 10° C./min) of the free base obtained after the conversion from the HCl salt (Exp. ID GEN4). One broad endothermic event was recorded between 25-70° C. due to water loss. The exo/endothermic events recorded between 160 and 182° C. could be due to a recrystallisation event. Subsequently, a small endothermic event at 217° C. was observed followed by a sharp endothermic event at 226° C.

Figure 238:
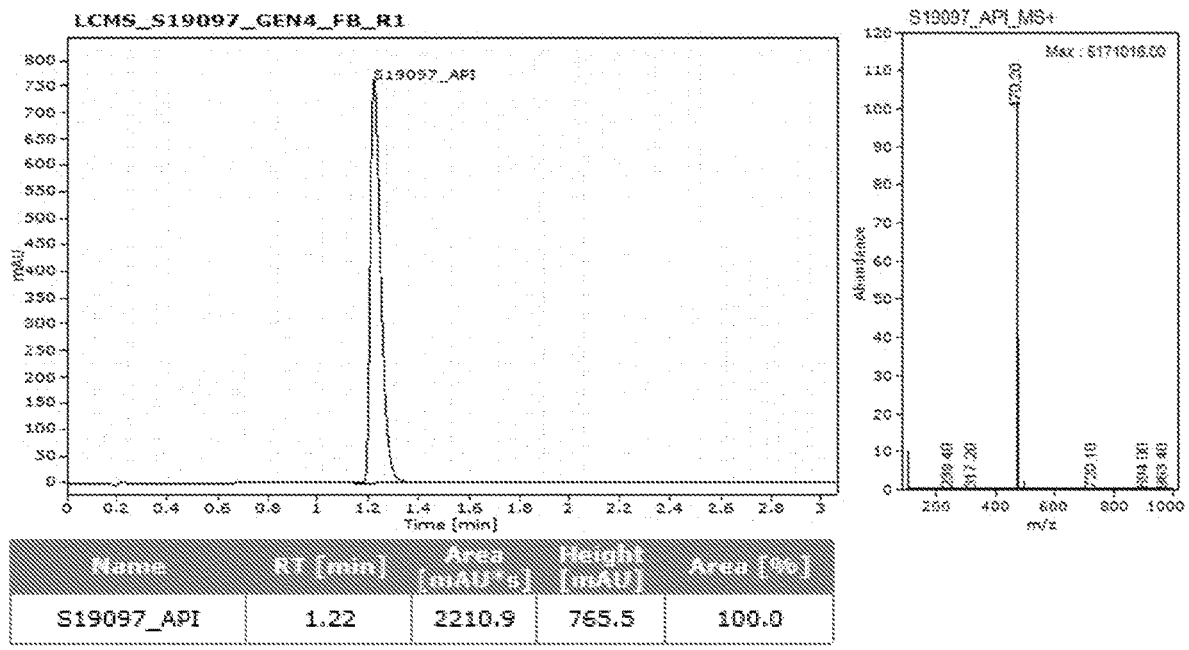

FIG. 238 illustrates the UPLC-MS chromatogram of the free base obtained after the conversion from the HCl salt (Exp. ID GEN4). The API peak appeared at 1.2 minutes with a chemical purity of 100% (area %). The molecular peak of 470.2 m/z in the mass spectrum could correspond to the positively charged species [M+H]$^+$ (API MW: 469 g/mol).

Figure 239:
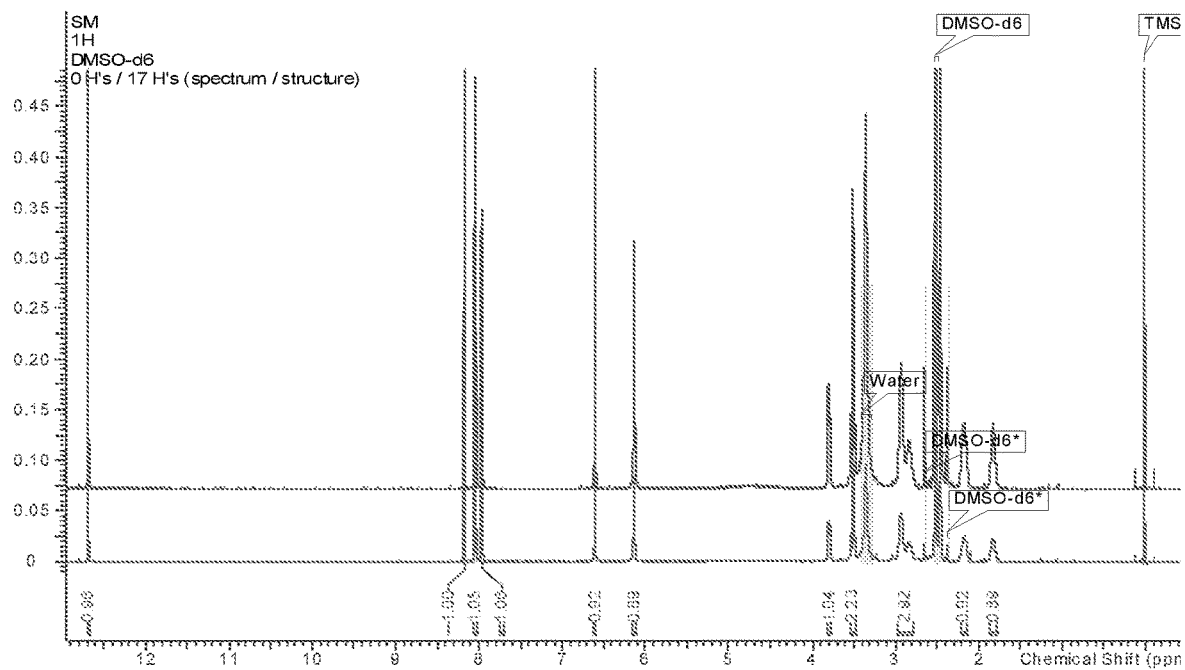

FIG. 239 illustrates the overlay of $^1$H-NMR spectra (500 MHz, DMSO-d$_6$) of ME-522 free base received for previous project (green line) and ME-522 free base produced in this study (Exp. ID GEN4, red line).

Figure 240:
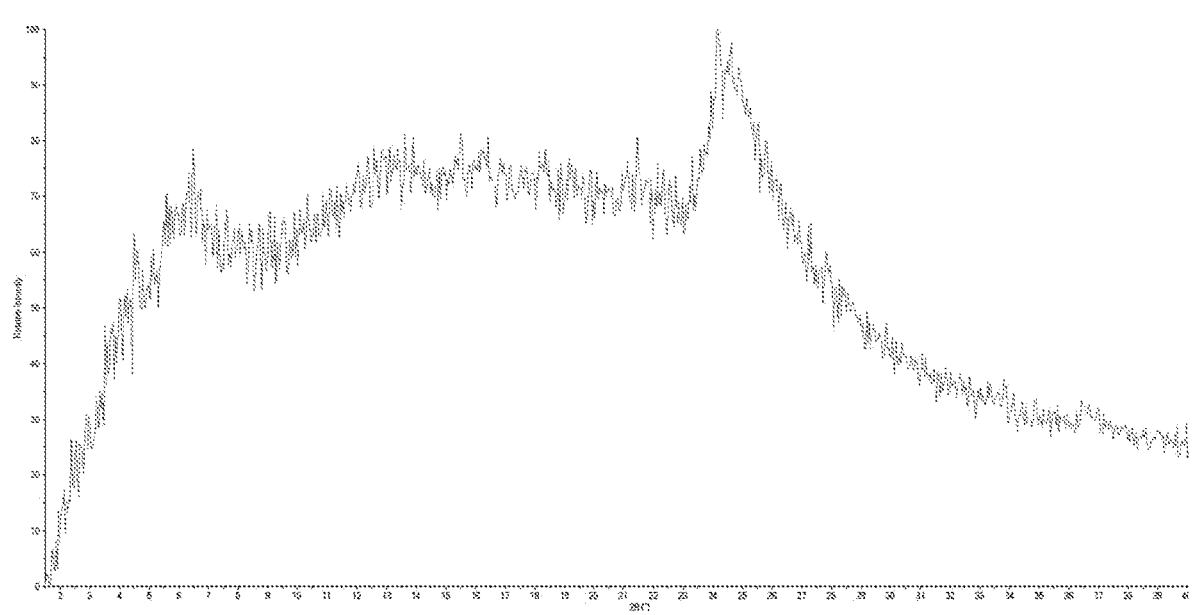

FIG. 240 illustrates the HT-XRPD pattern of ME-522 malonate salt (Exp. ID GEN8) prepared by freeze-drying a free base solution containing one equivalent of malonic acid in THF/water/acetone (32.5/32.5/35, v/v/v).

Figure 241A:
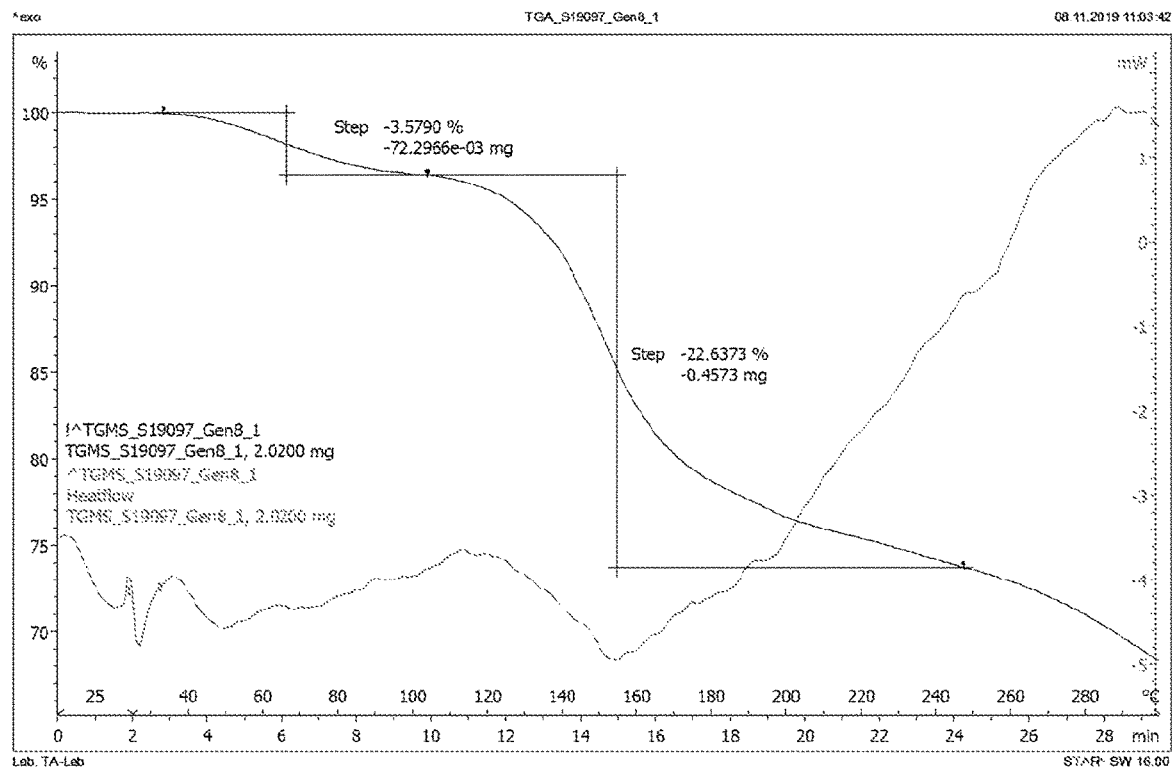
Figure 241B:
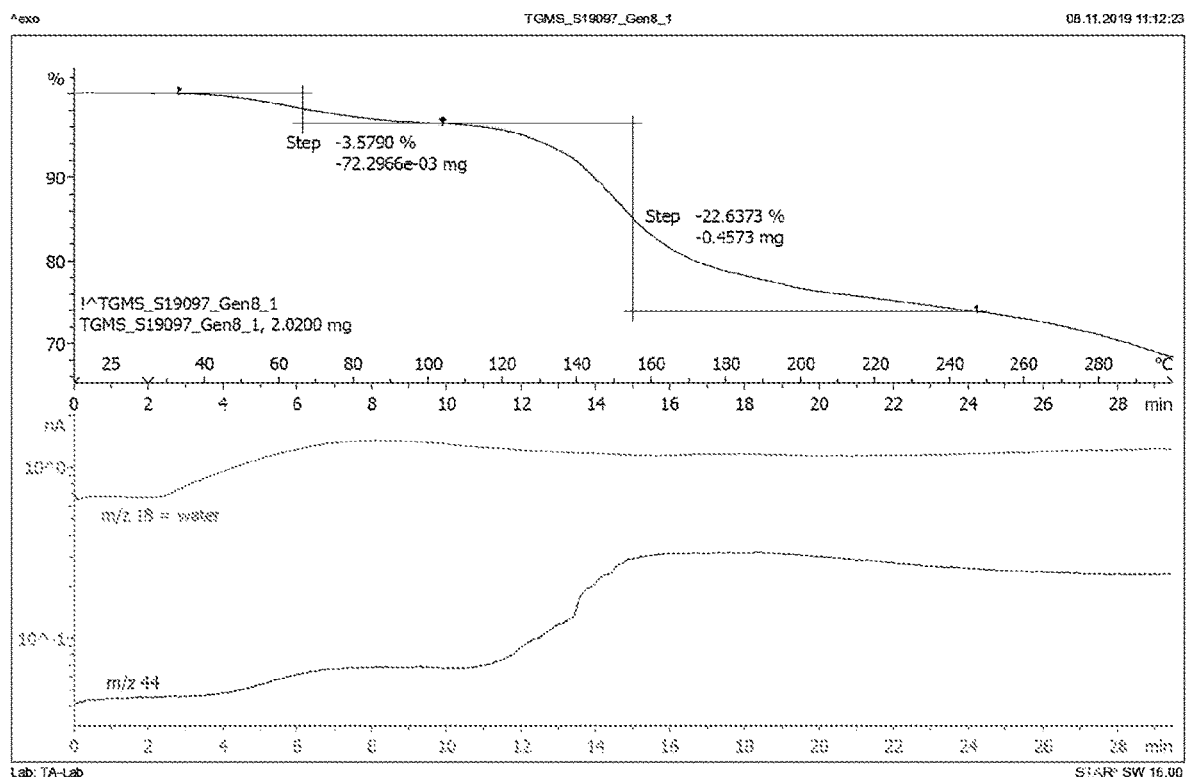

FIG. 241A and FIG. 241B illustrate the TGA (FIG. 241A) and TGMS (FIG. 241B) analysis (heating rate of 10° C./min) of the amorphous malonate salt obtained after freeze-drying (Exp. ID GEN8). A mass loss of 3.6% was observed prior to the thermal decomposition (observed above 120° C.).

Figure 242:
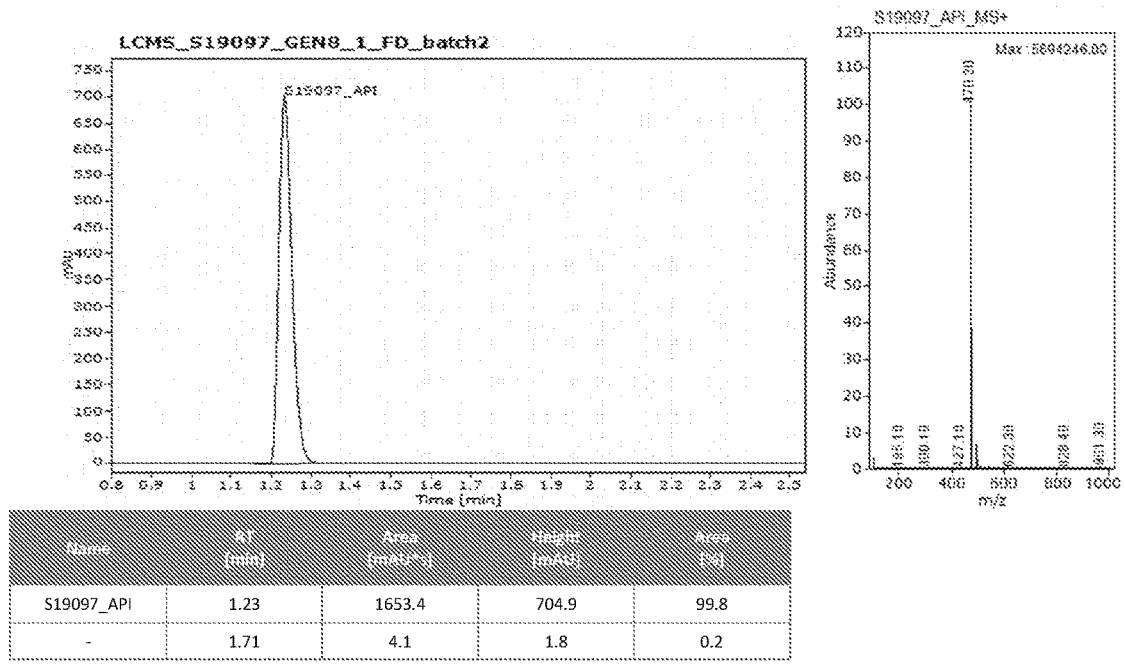

FIG. 242 illustrates the UPLC-MS chromatogram of the malonate salt obtained after freeze-drying (Exp. ID GEN8). The API peak appeared at 1.2 minutes with a chemical purity of 99.8% (area %). The molecular peak of 470.2 m/z in the mass spectrum could correspond to the positively charged species [M+H]$^+$ (API MW: 469 g/mol).

Figure 243:
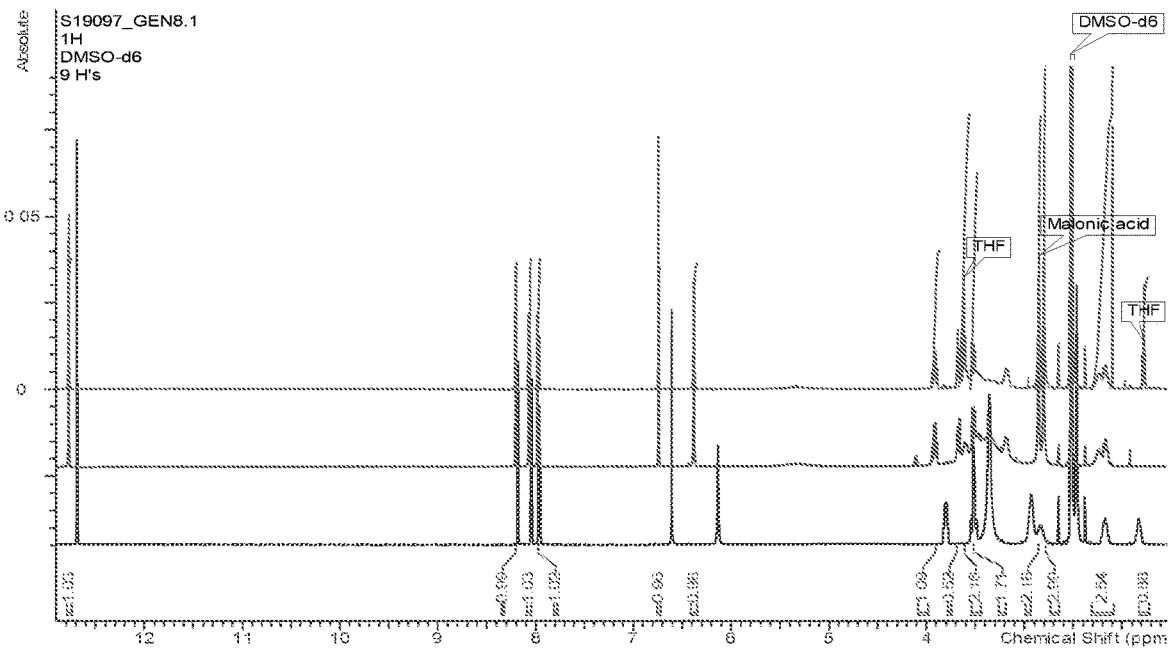

FIG. 243 illustrates the overlay of $^1$H-NMR spectra (500 MHz, DMSO-$d_6$) of ME-522 free base obtained earlier in this study (Exp. ID GEN4, green line), ME-522 malonate salt (Mao1) found in previous study (S18128, Exp. SSm53) and ME-522 malonate salt obtained by freeze-drying (Exp. ID GEN8, red line). The chemical shift observed at 2.85 ppm corresponds to the malonic acid. Additional resonance shifts were observed corresponding to residual THF (at 3.60 and 1.76 ppm).

Figure 244:
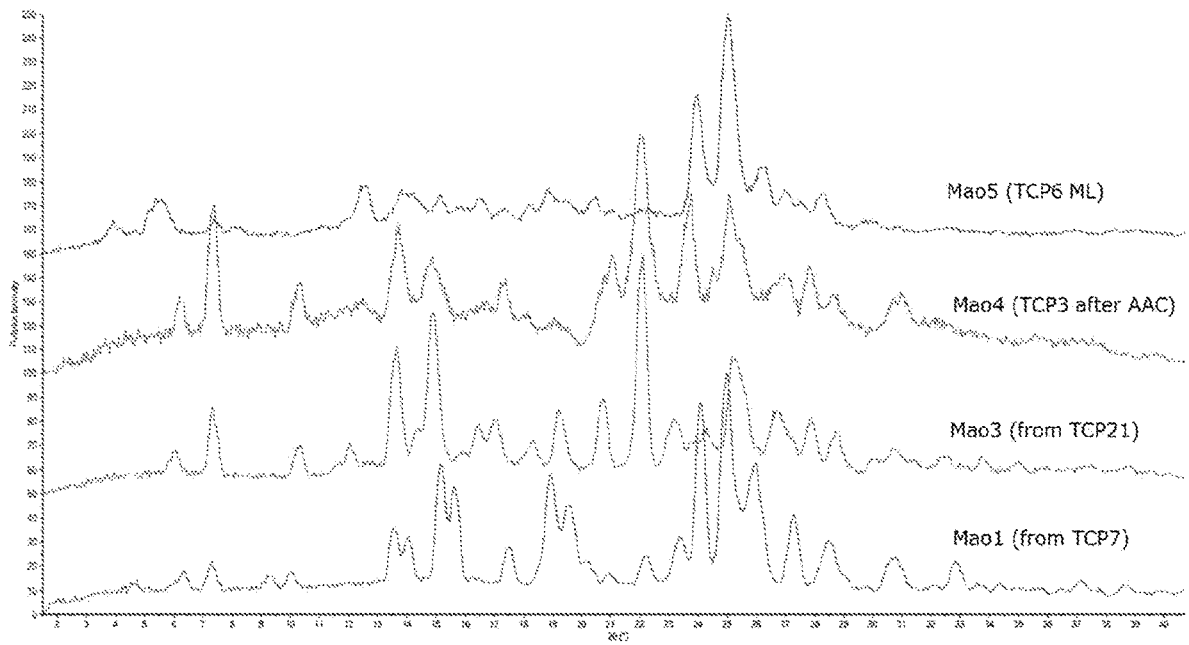

FIG. 244 illustrates the HT-XRPD diffractograms of the forms observed in the polymorph screen performed on ME-522 malonate salt (from bottom to top): Mao1, Mao3, Mao4 and Mao5.

Figure 245:
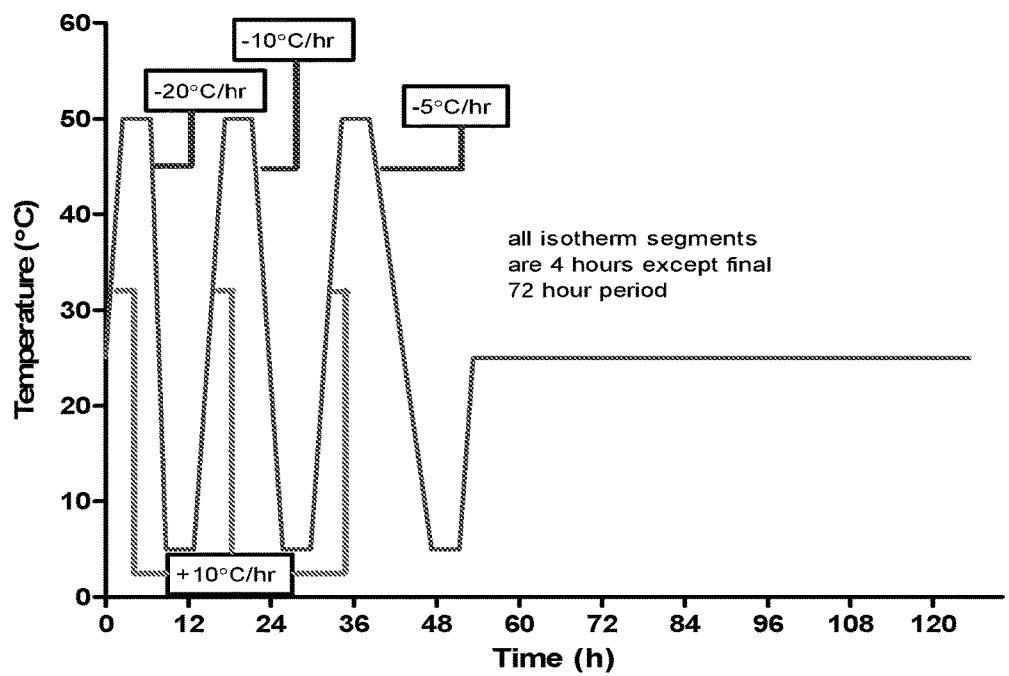

FIG. 245 illustrates the experimental conditions for the thermocycling experiments. Slurries of ME-522 malonate salt were prepared in neat solvents and solvent mixtures and placed in the Crystal16™ reactor to undergo a thermal profile as described in FIG. 245. After the temperature profile the precipitated solids were dried at ambient conditions and under vacuum and analyzed before and after exposure to AAC (40° C./75% RH, 2 days) by HT-XRPD. The mother liquors were used for solubility determination. Subsequently, the solutions were dried under vacuum and the obtained dried solids were analyzed by XRPD.

Figure 246:
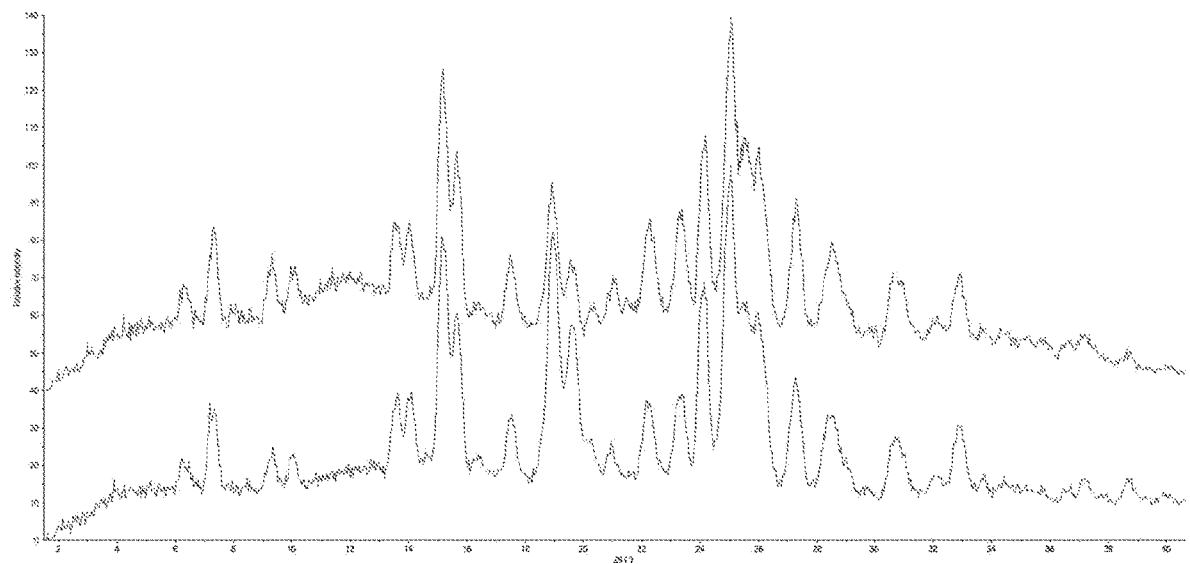

FIG. 246 illustrates the XRPD patterns of Mao1 obtained in the thermocycling experiment performed in THF (Exp. ID TCP7) before (bottom pattern) and after (top pattern) exposure to AAC.

Figure 247:
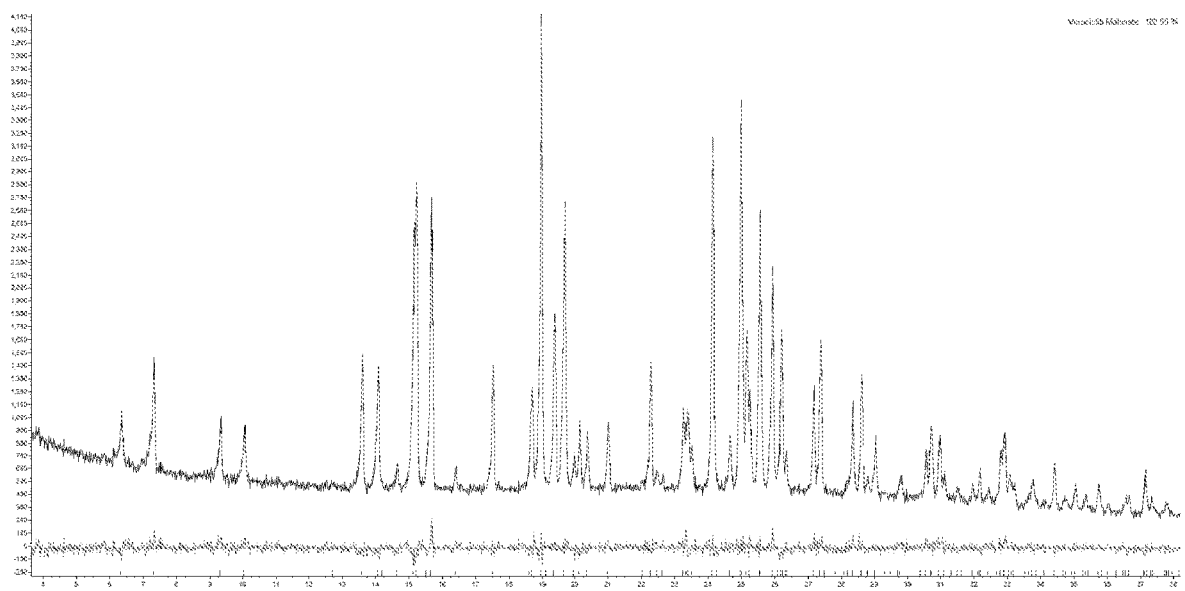

FIG. 247 illustrates the graphical representation of the Rietveld analyze (Rietveld, 1969) for ME-522 Mao1 obtained in the thermocycling experiment performed in THF (Exp. ID TCP7). The black line represents the obtained powder pattern, the red line the calculated one and the grey line is the difference between them. The blue sticks at the bottom show the peak positions for the fitted cell (the cell parameters as well as atom positions were taken from the single crystal data reported in study S18128).

Figure 248A:
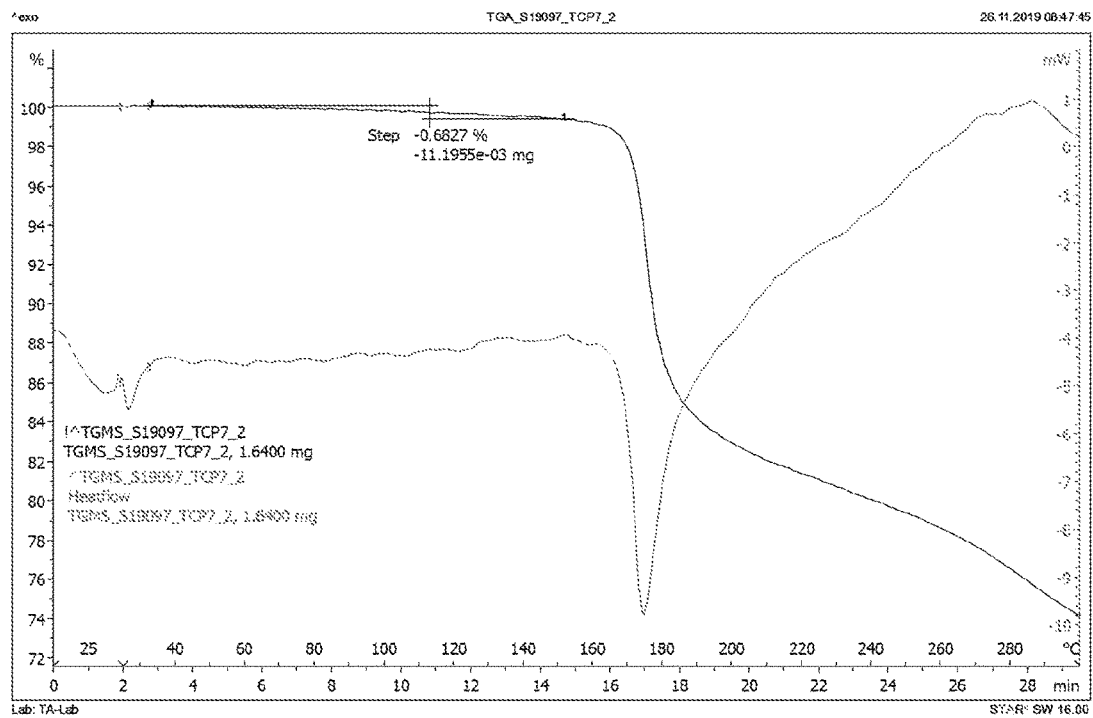
Figure 248B:
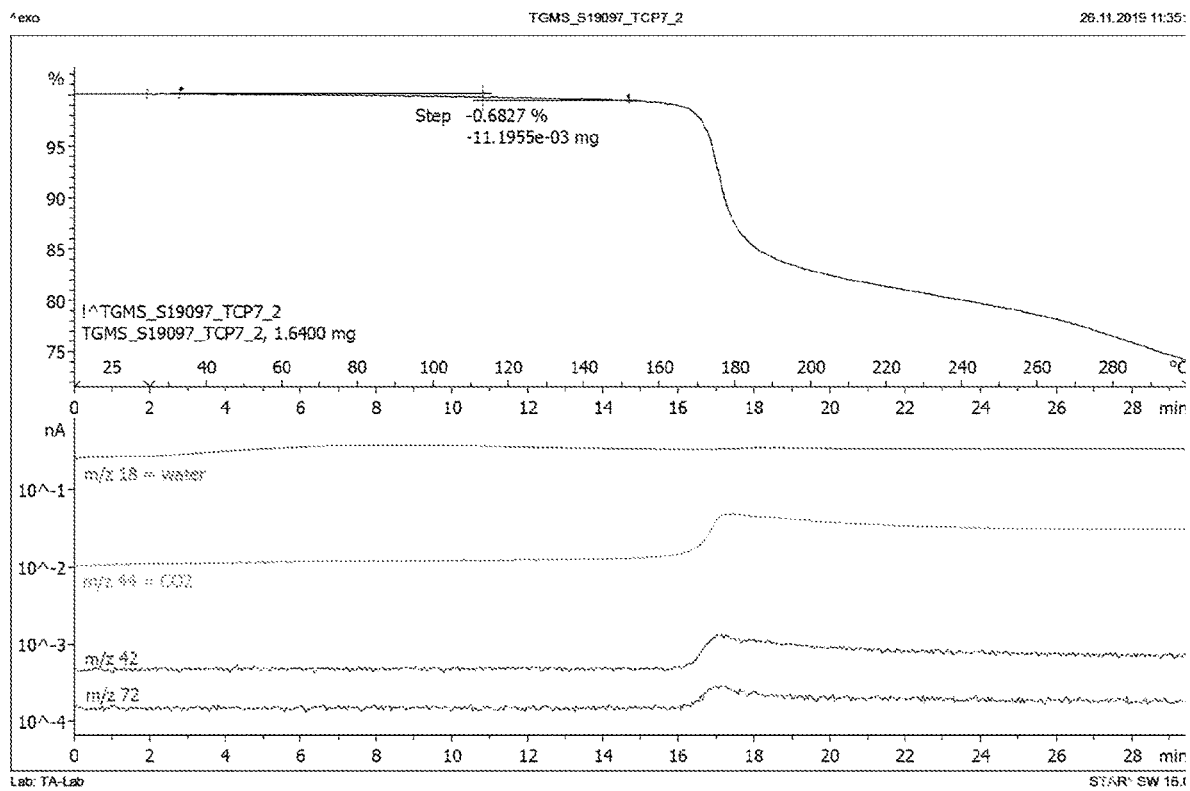

FIG. 248A and FIG. 248B illustrate the TGA (FIG. 248A) and TGMS (FIG. 248B) analysis (heating rate of 10° C./min) of Mao1 obtained in the thermocycling experiment performed in THF (Exp. ID TCP7). A mass loss of 0.7% is observed prior to melting/decomposition starting around 160° C. This mass loos could be attributed to residual water based on the MS signal.

Figure 249:
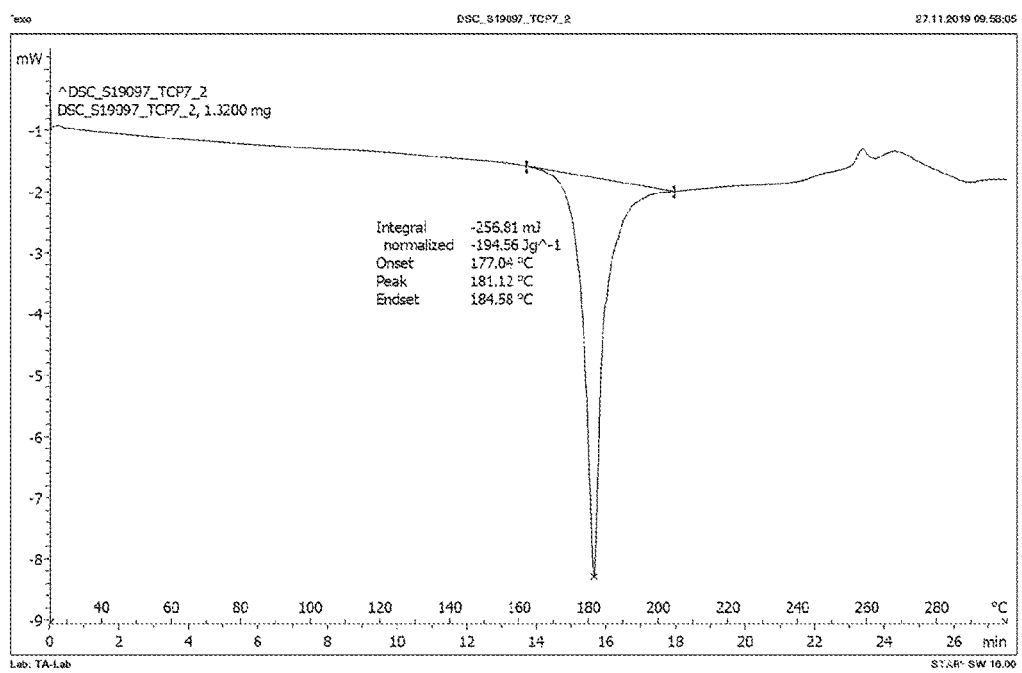

FIG. 249 illustrates the DSC analysis (heating rate 10° C./min) of Mao1 obtained in the thermocycling experiment performed in THF (Exp. ID TCP7). An endothermic event was observed with peak temperature at 181.1° C., due to melting/thermal decomposition.

Figure 250:
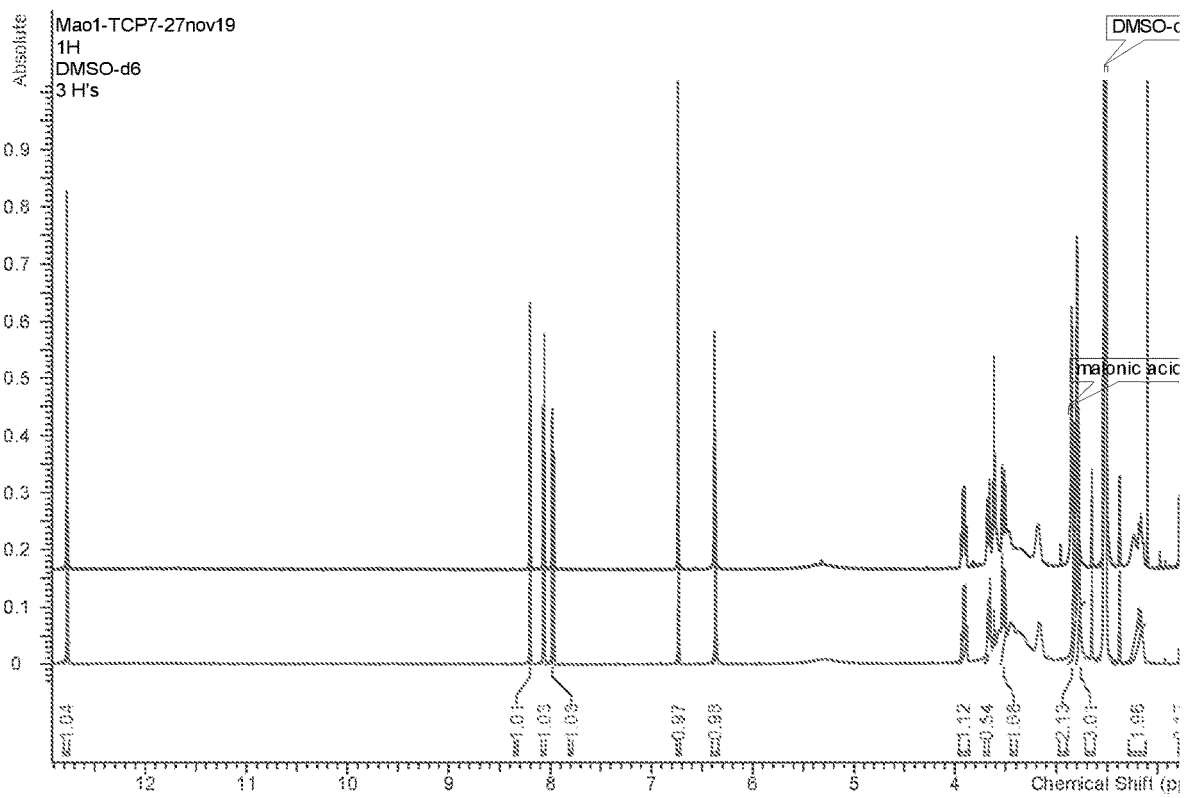

FIG. 250 illustrates the $^1$H-NMR spectrum of Mao1 obtained in the thermocycling experiment performed in THF (Exp. ID TCP7, bottom) compared to the amorphous malonate salt (Exp. ID GEN8, top).

Figure 251:
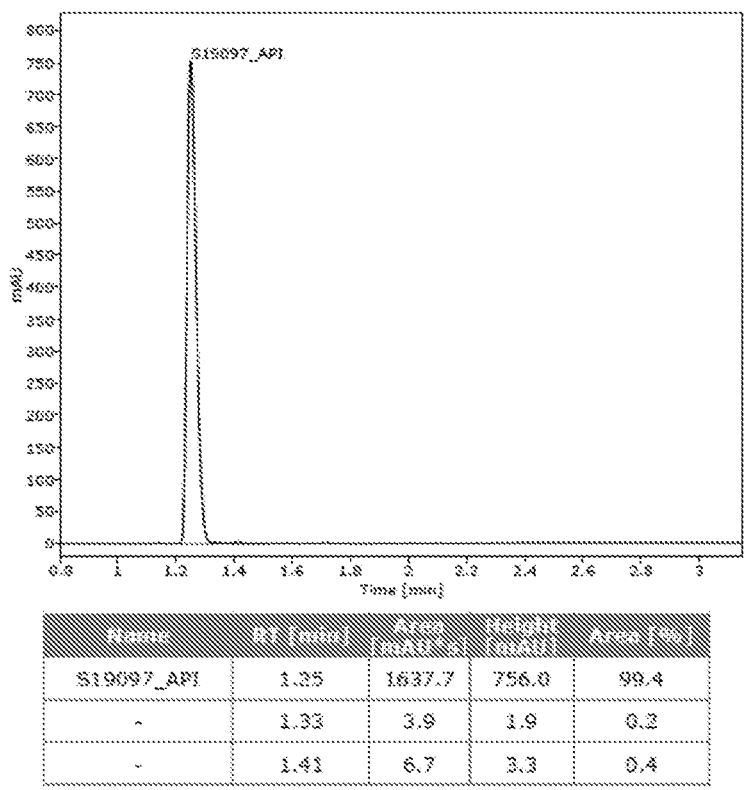

FIG. 251 illustrates the UPLC chromatogram of Mao1 obtained in the thermocycling experiment performed in THF (Exp. ID TCP7). The API chemical purity was 99.4% (area %).

Figure 252A:
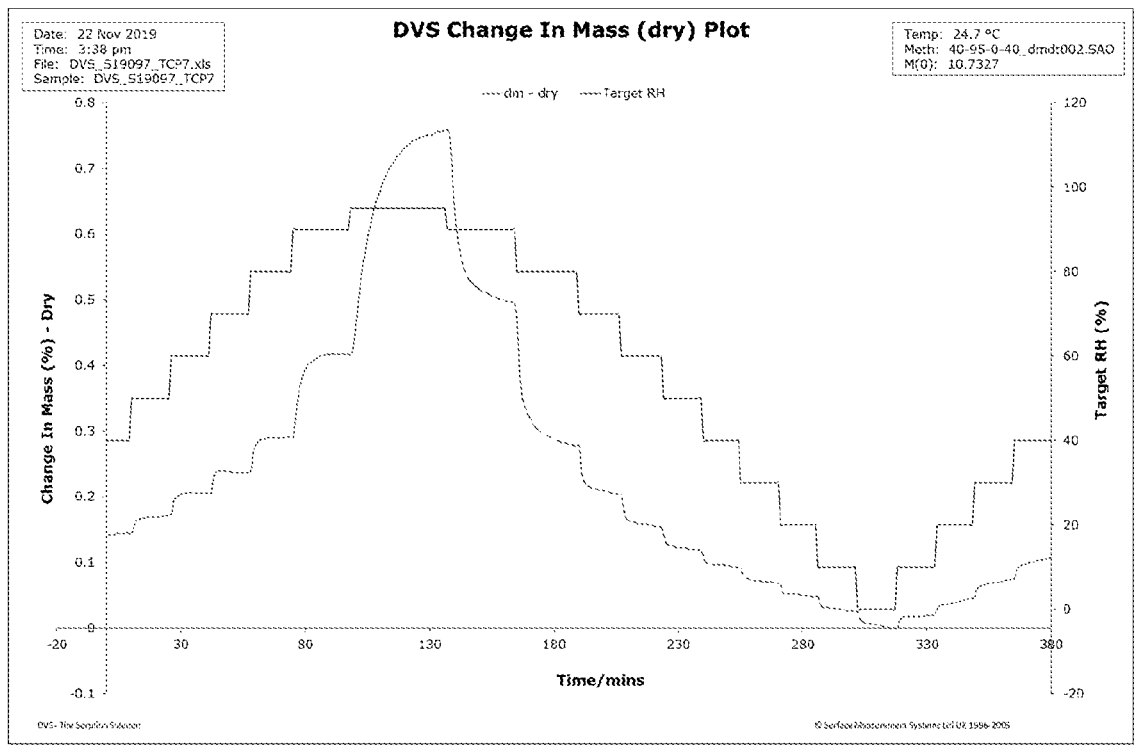
Figure 252B:
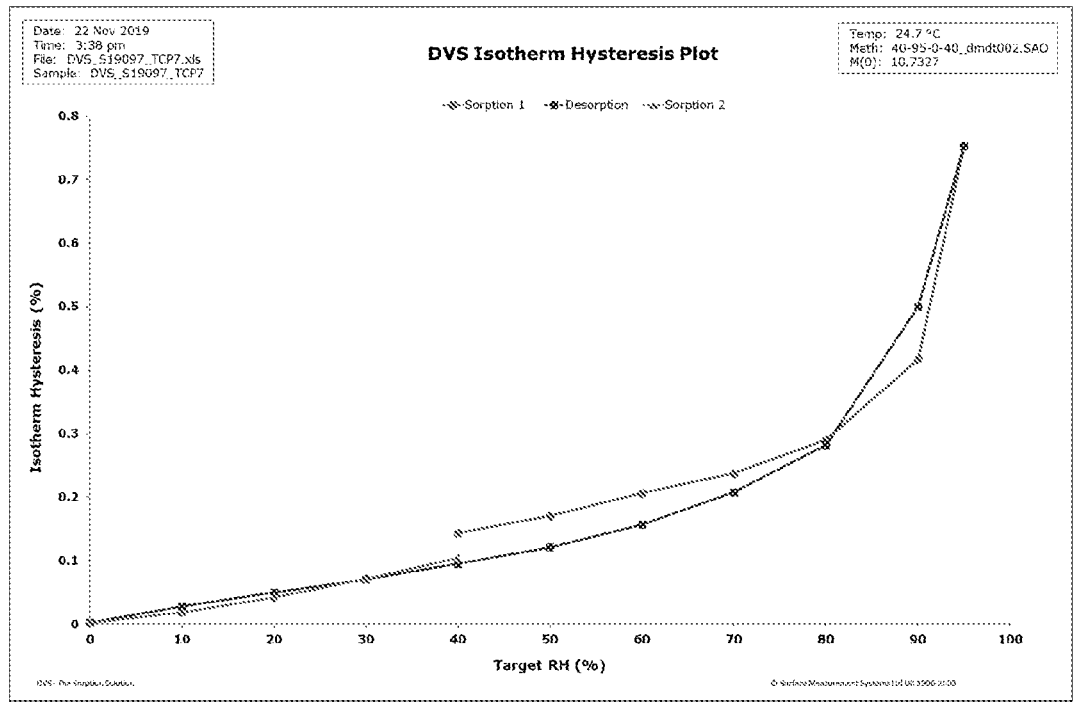

FIG. 252A and FIG. 252B illustrate the change in mass (FIG. 252A) and isotherm plot (FIG. 252B) resulting from the DVS analysis performed on Mao1 obtained in the thermocycling experiment performed in THF (Exp. ID TCP7). The DVS analysis consisted of one sorption cycle from 40-95% RH, one desorption cycle from 95-0% RH and sorption cycle from 0-40% RH. Weight equilibration per step was set at dm/dt<0.0002 for a minimum of 1 hour or maximum of 6 hours.

Figure 253:
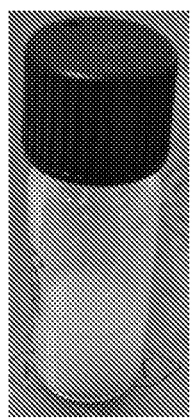

FIG. 253 illustrates the photograph of the suspension obtained after a small aliquot of water was added to solids of Mao1.

Figure 254:
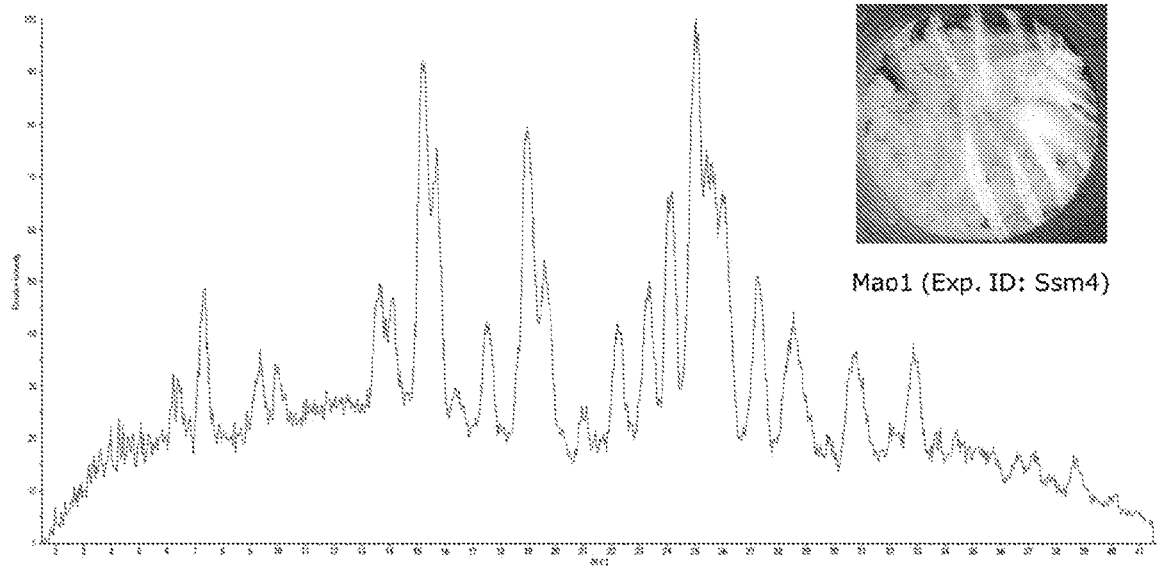

FIG. 254 illustrates the HT-XRPD pattern of Mao1 obtained from the scale-up experiment (Exp. ID: Ssm4) and an image of the material used for the XRPD analysis.

Figure 255:
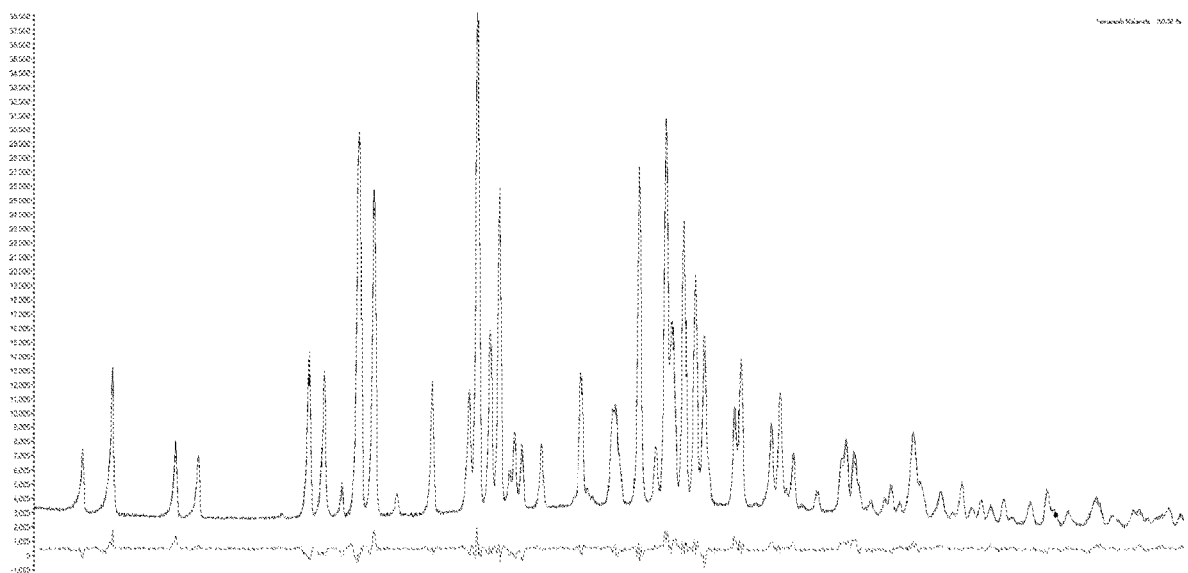

FIG. 255 illustrates the graphical representation of the Rietveld analyze (Rietveld, 1969) for ME-522 Mao1 obtained in the scale-up cooling crystallization experiment in THF (Exp. ID Ssm4). The black line represents the obtained powder pattern, the red line the calculated one and the grey line is the difference between them. The blue sticks at the bottom show the peak positions for the fitted cell (the cell parameters as well as atom positions were taken from the single crystal data reported in study S18128).

Figure 256A:
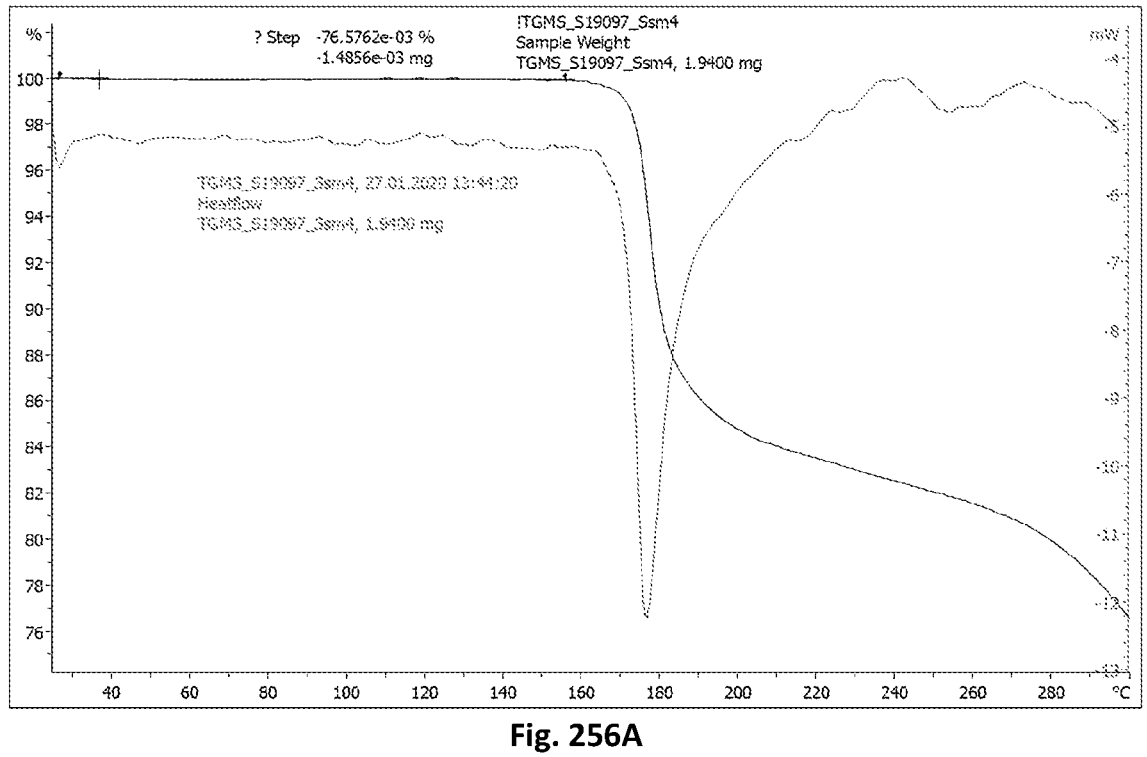
Figure 256B:
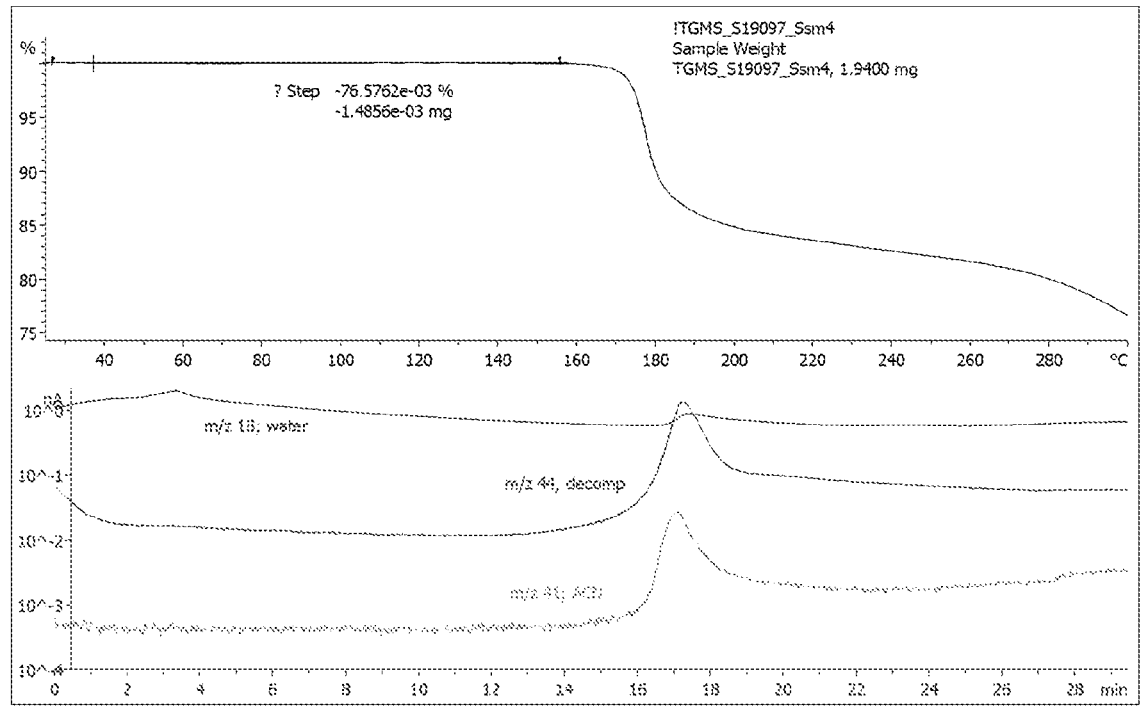

FIG. 256A and FIG. 256B illustrate the TGA (FIG. 256A) and TGMS (FIG. 256B) analysis (heating rate of 10° C./min) of Mao1 obtained in the scale-up cooling crystallization experiment in THF (Exp. ID Ssm4). A mass loss of 0.08% was observed prior to melting/decomposition starting around 160° C.

Figure 257:
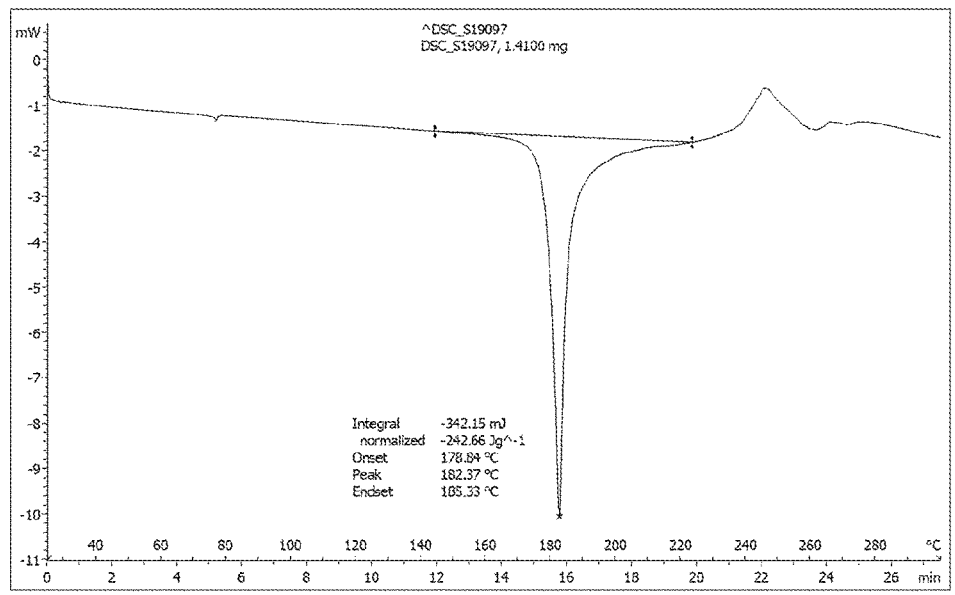

FIG. 257 illustrates the DSC analysis (heating rate 10° C./min) of Mao1 obtained in the scale-up cooling crystallization experiments performed in THF (Exp. ID Ssm4). An endothermic event was observed with peak temperature at 182.4° C., due to melting/thermal decomposition.

Figure 258:
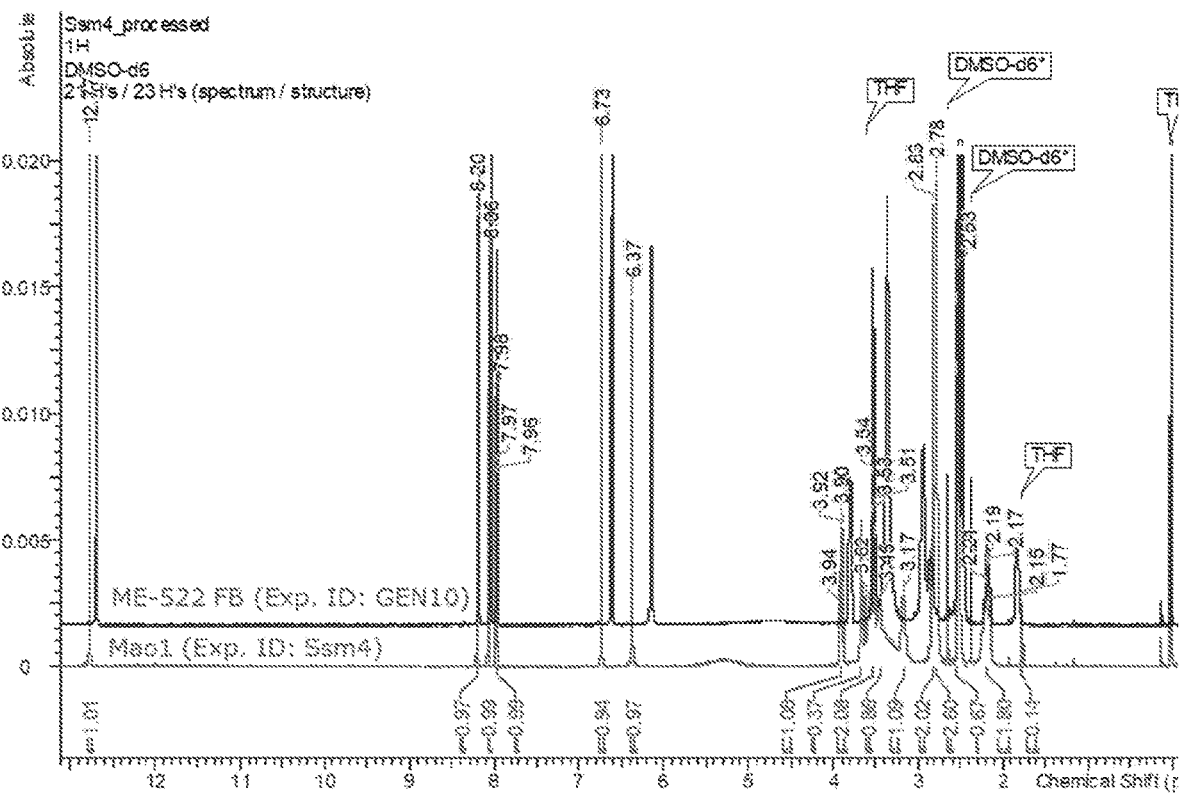

FIG. 258 illustrates the overlay of $^1$H-NMR spectra (500 MHz, DMSO-$d_6$) of ME-522 free base obtained from the freebasing scale-up experiment (Exp. ID: GEN10, top) and of Mao1 obtained from the cooling crystallization experiment from THF (Exp. ID: Ssm4).

Figure 259:
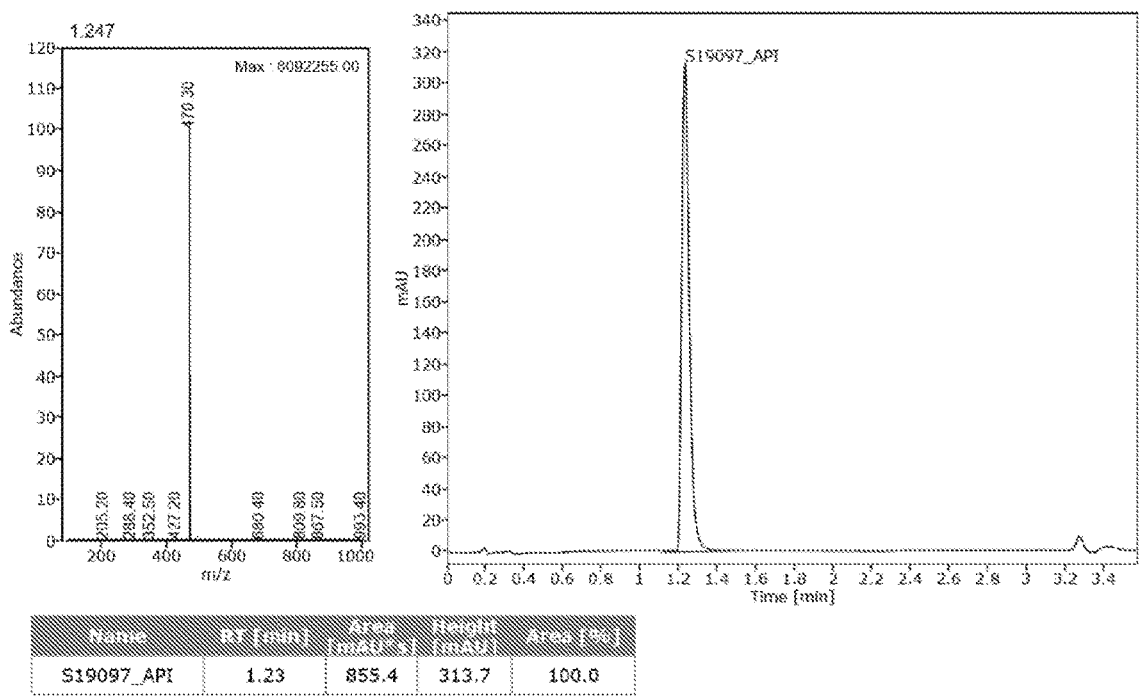

FIG. 259 illustrates the UPLC chromatogram of Mao1 obtained in the scale-up cooling crystallization experiment performed in THF (Exp. ID Ssm4). The API chemical purity was 100% (area %). The mass associated to the main peak was 470.3 m/z, corresponding to the positively charged species [M+H]$^+$.

Figure 260:
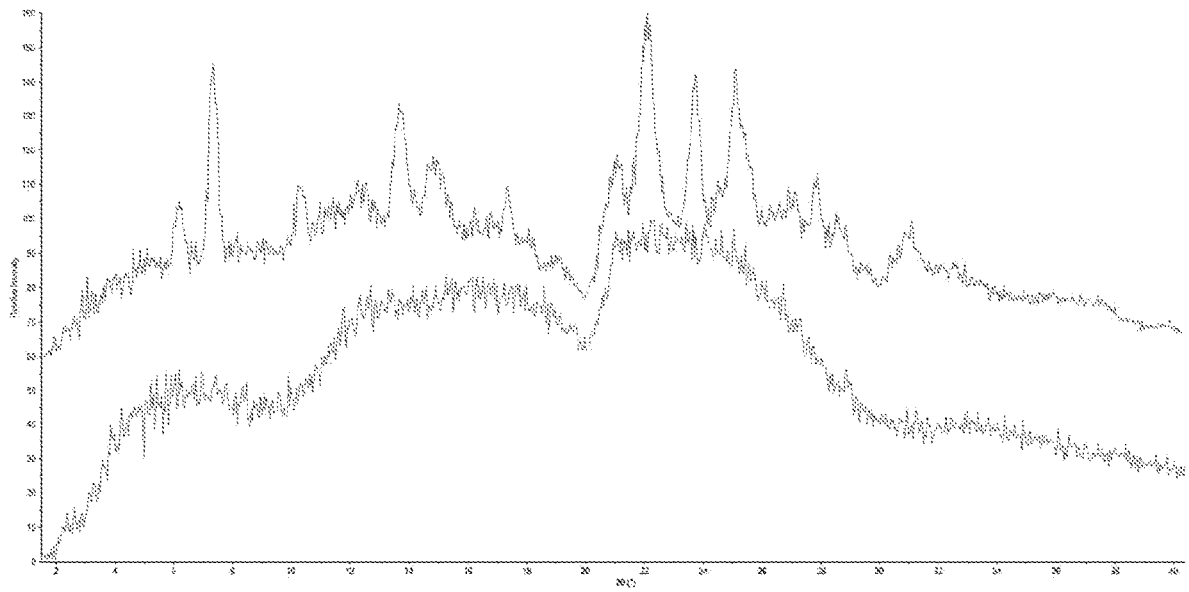

FIG. 260 illustrates the overlay of HT-XRPD patterns of the amorphous solid obtained after the thermocycling experiment performed in cyclohexane (Exp. ID TCP3) and Mao4 upon exposure (top pattern) to AAC the amorphous solid obtained in TCP3.

Figure 261A:
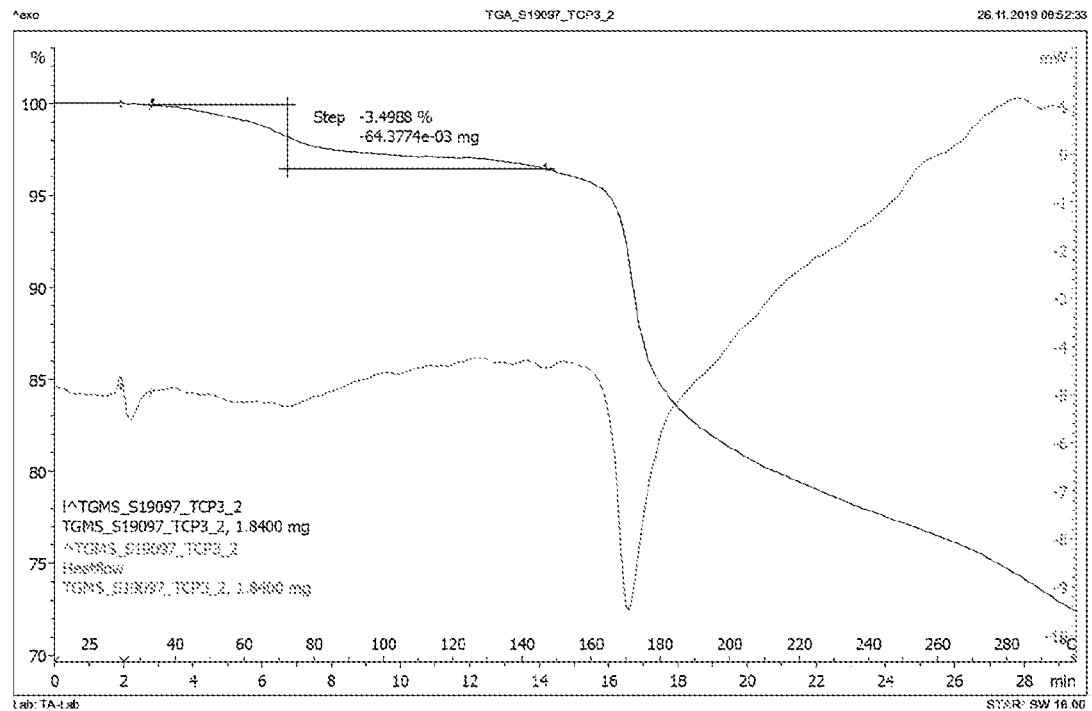
Figure 261B:
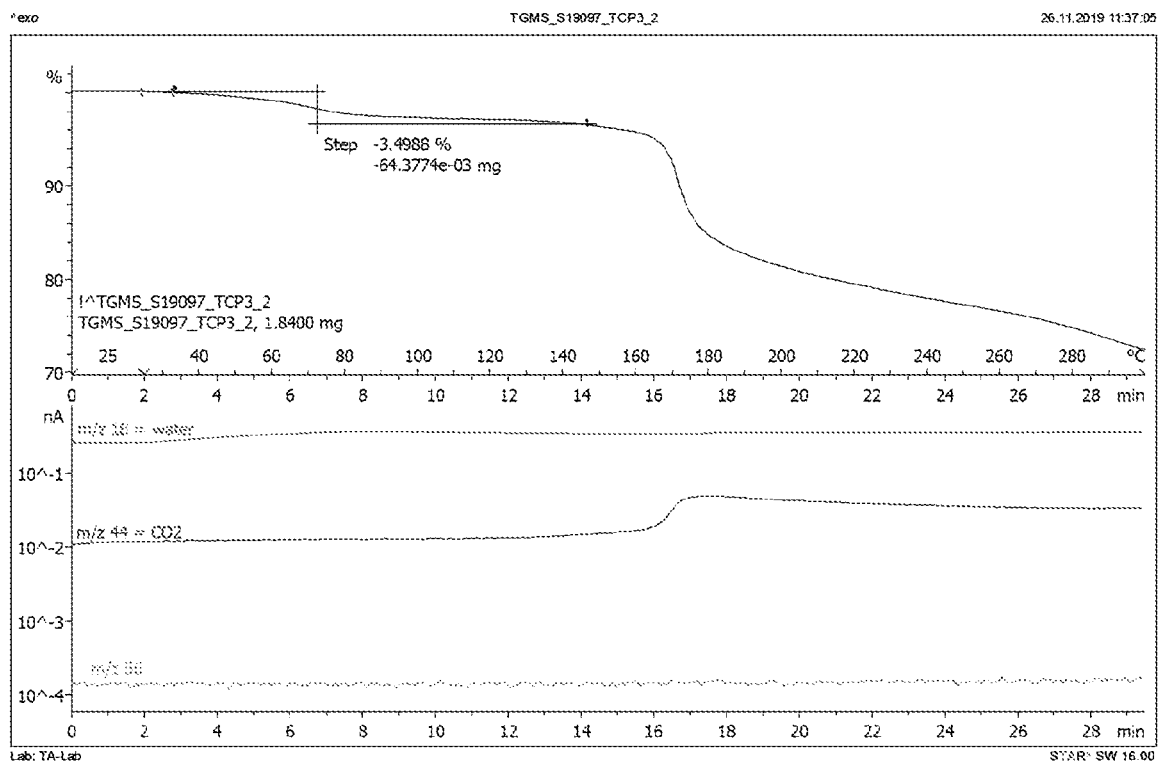

FIG. 261A and FIG. 261B illustrate the TGA (FIG. 261A) and TGMS (FIG. 261B) analysis (heating rate of 10° C./min) of Mao4 obtained upon exposure to AAC the amorphous solid obtained in TCP3 (from cyclohexane). A mass loss of 3.5% was observed in the temperature range 40-150° C., due to water (API:Maionic acid:Water 1:1:1.1).

Figure 262:
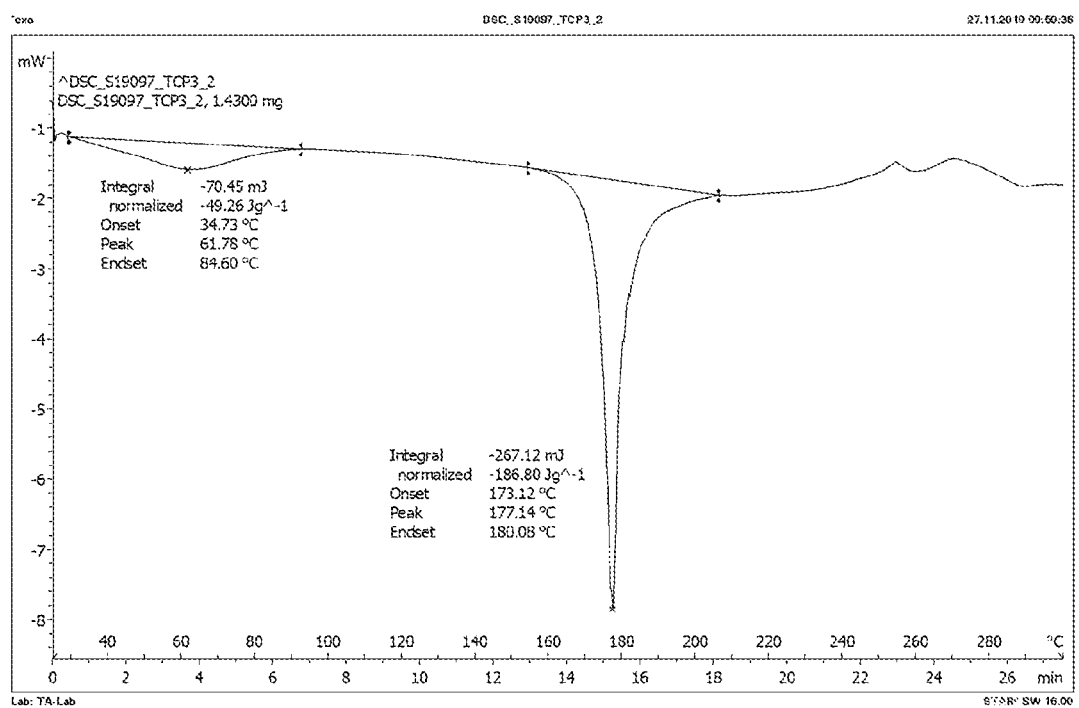

FIG. 262 illustrates the DSC analysis (heating rate 10° C./min) of Mao4 obtained upon exposure to AAC the amorphous solid obtained in TCP3 (from cyclohexane). A broad endothermic event was observed between 25-100° C. attributed to the water loss followed by an endothermic event peak temperature at 177.1° C., due to melting/thermal decomposition.

Figure 263:
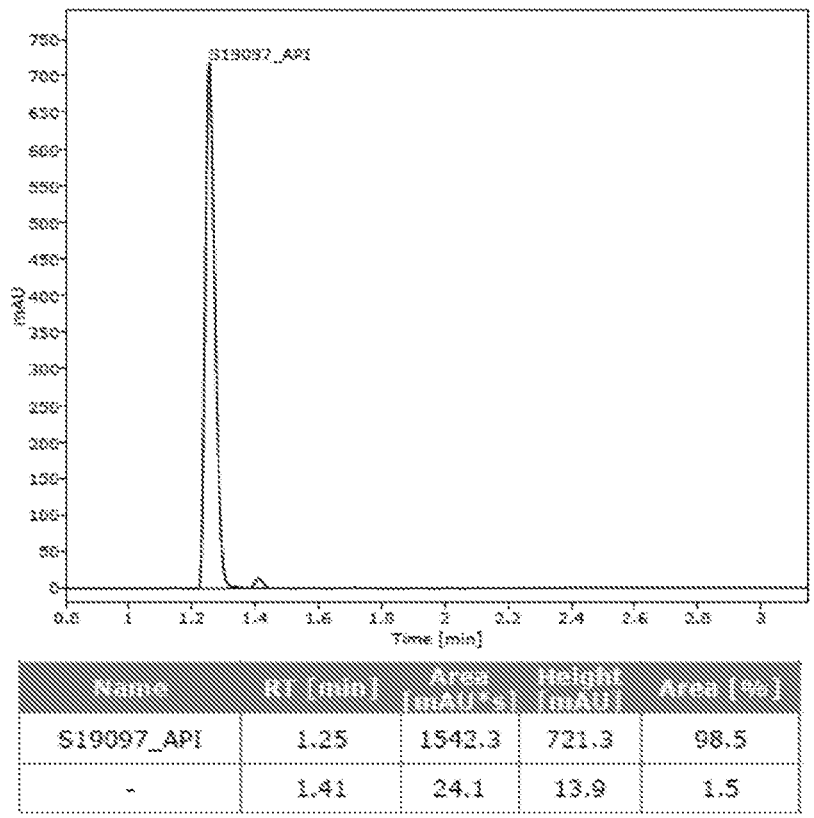

FIG. 263 illustrates the UPLC-MS chromatogram of Mao4 obtained upon exposure to AAC the amorphous solid obtained in TCP3 (from cyclohexane). The API chemical purity was 98.5% (area %).

Figure 264:
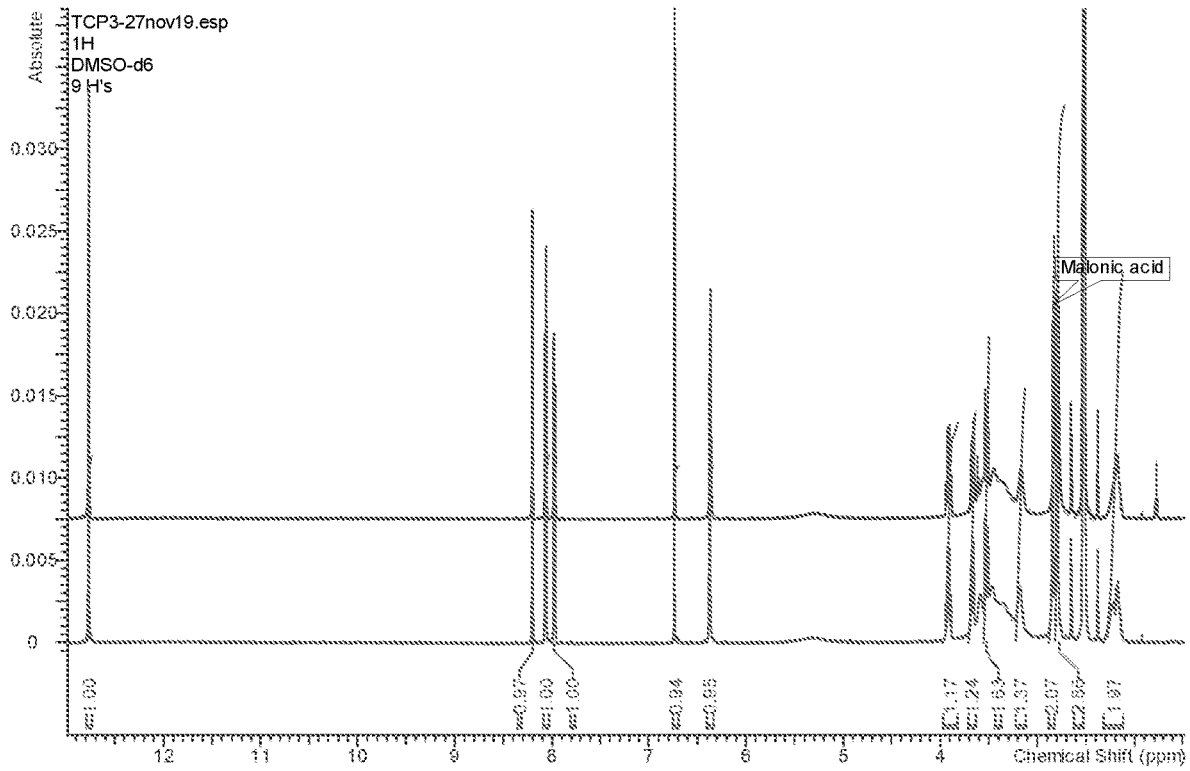

FIG. 264 illustrates the $^1$H-NMR spectrum of Mao4 obtained upon exposure to AAC the amorphous solid obtained in TCP3 (from cyclohexane, Exp. ID TCP3, bottom) compared to Mao1 from Exp. ID TCP7 (top).

Figure 265A:
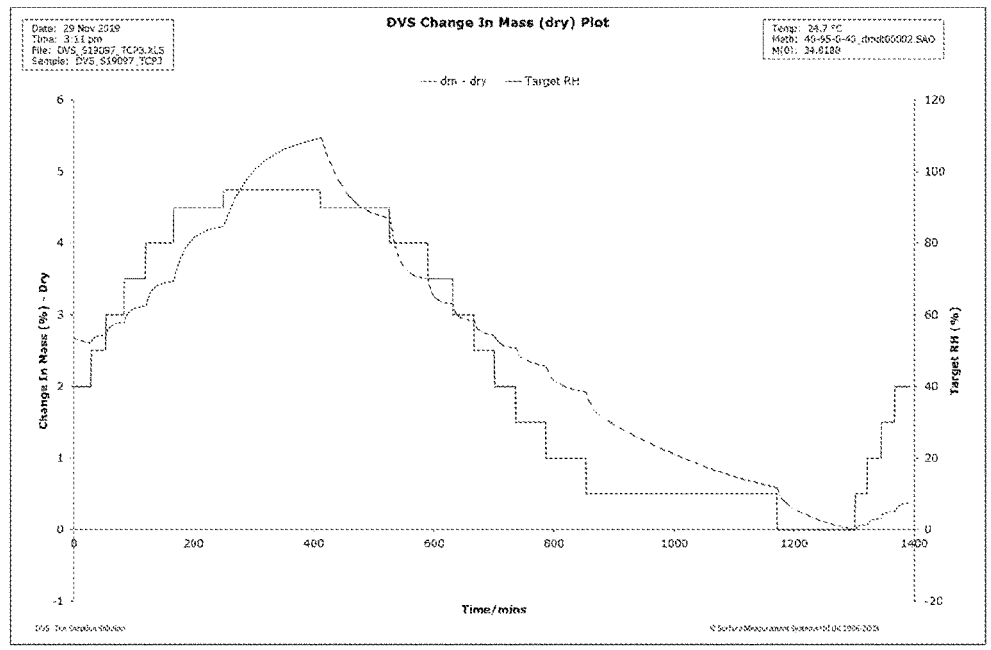
Figure 265B:
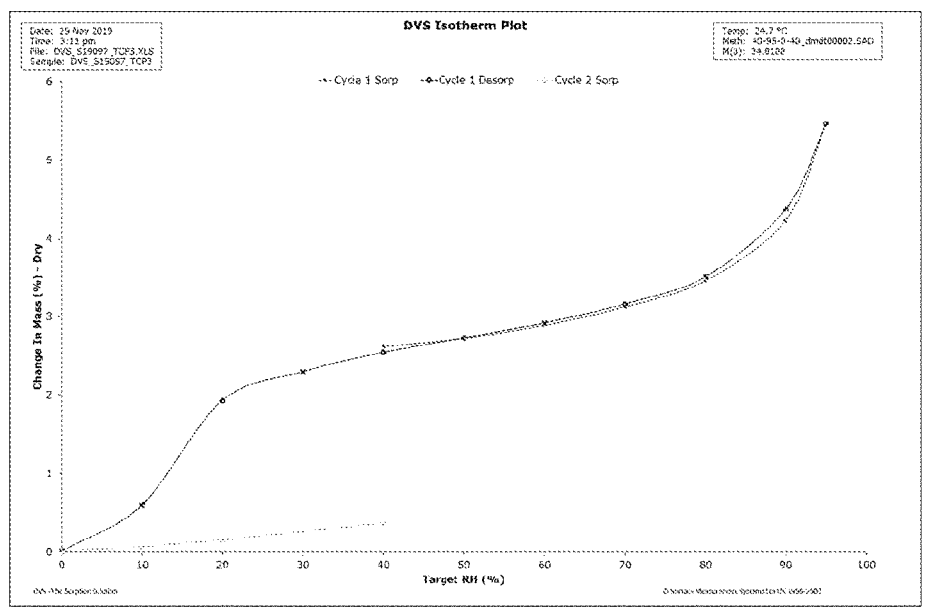

FIG. 265A and FIG. 265B illustrate the change in mass (FIG. 265A) and isotherm plot (FIG. 265B) resulting from the DVS analysis performed on Mao4 obtained upon exposure to AAC the amorphous solid obtained in TCP3 (from cyclohexane). The DVS analysis consisted of one sorption cycle from 40-95% RH, one desorption cycle from 95-0% RH and sorption cycle from 0-40% RH. The sample was incubated at each relative humidity value for 1 hour.

Figure 266:
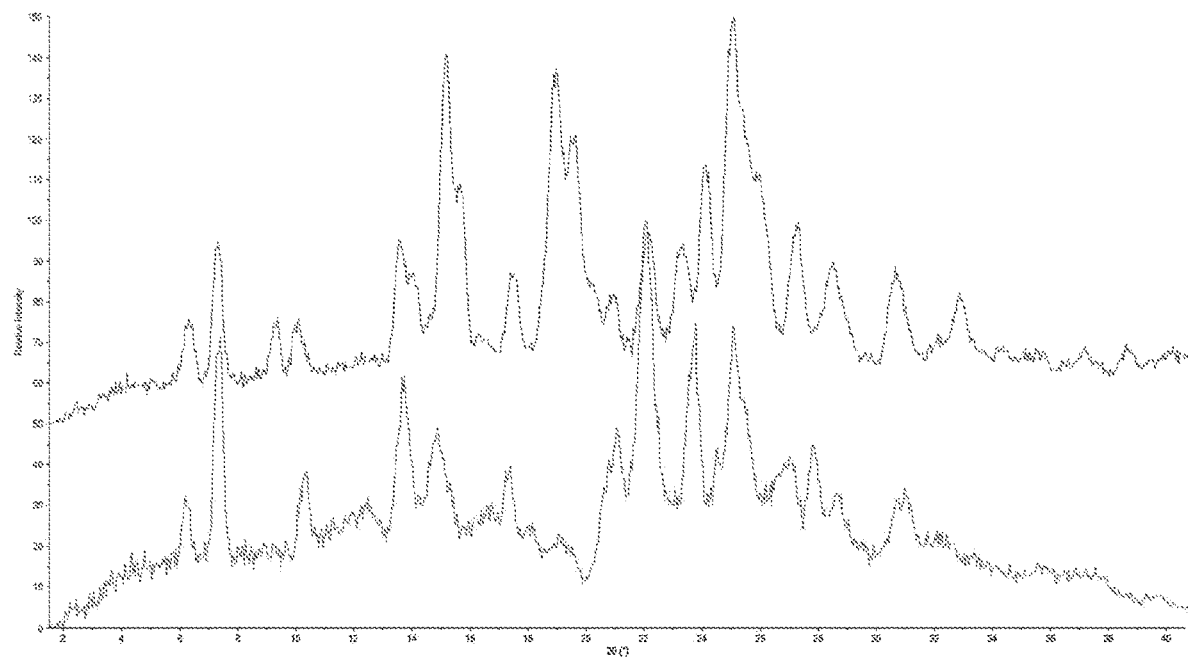

FIG. 266 illustrates the HT-XRPD patterns of Mao4 (Exp. ID TCP3, after AAC) and Mao1 recovered after DVS (top pattern) measurement.

Figure 267:
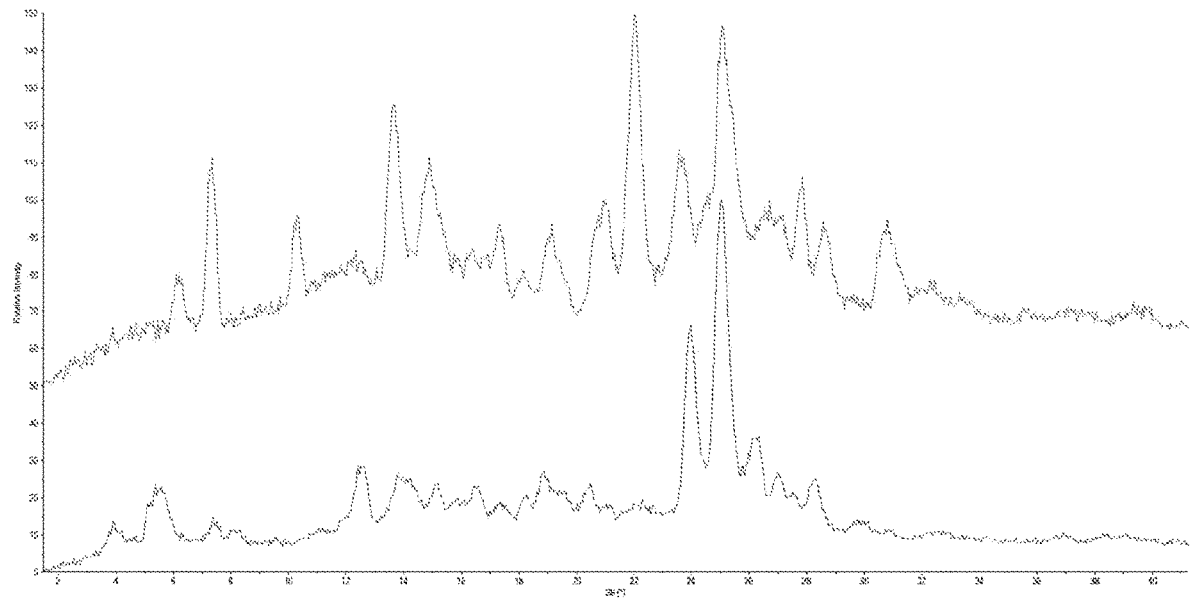

FIG. 267 illustrates the overlay of HT-XRPD patterns of Mao5 obtained after evaporative crystallization of the mother liquor recovered from the thermocycling experiment performed in methanol (Exp. ID TCP6_ML) and Mao4 obtained after (top pattern) exposure to AAC.

Figure 268A:
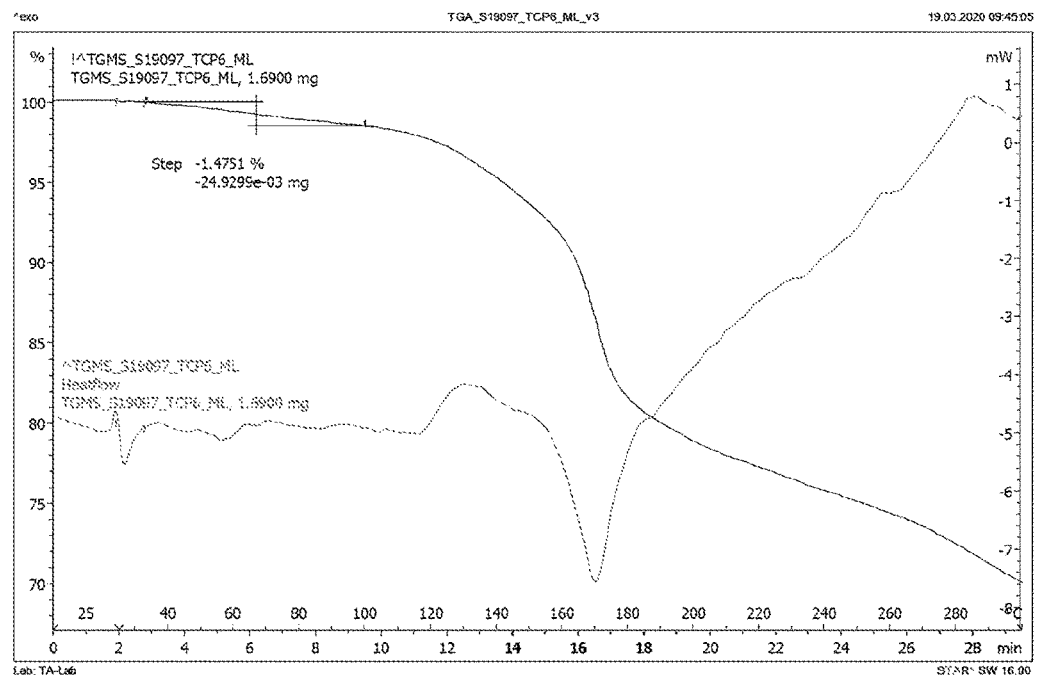
Figure 268B:
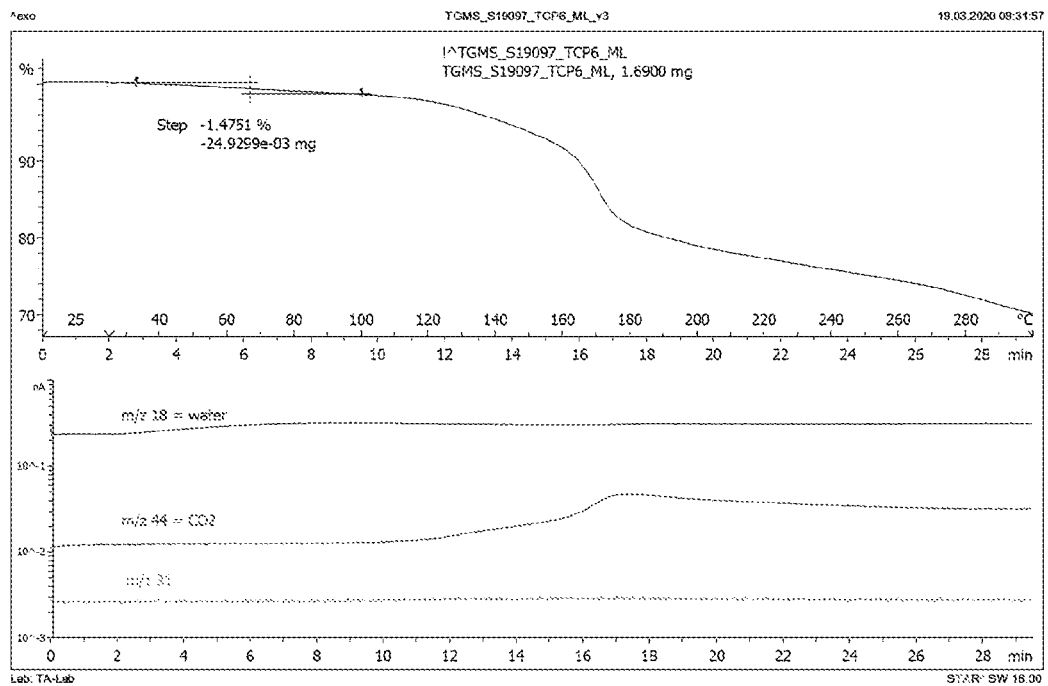

FIG. 268A and FIG. 268B illustrates the TGA (FIG. 268A) and TGMS (FIG. 268B) analysis (heating rate of 10° C./min) of Mao5 obtained after evaporative crystallization of the mother liquor recovered from the thermocycling experiment performed in methanol (Exp. ID TCP6_ML). A mass loss of 1.5% was observed in the temperature range 40-100° C., due to water (1.5% of water corresponds to 0.5 molecule of water per malonate salt).

Figure 269:
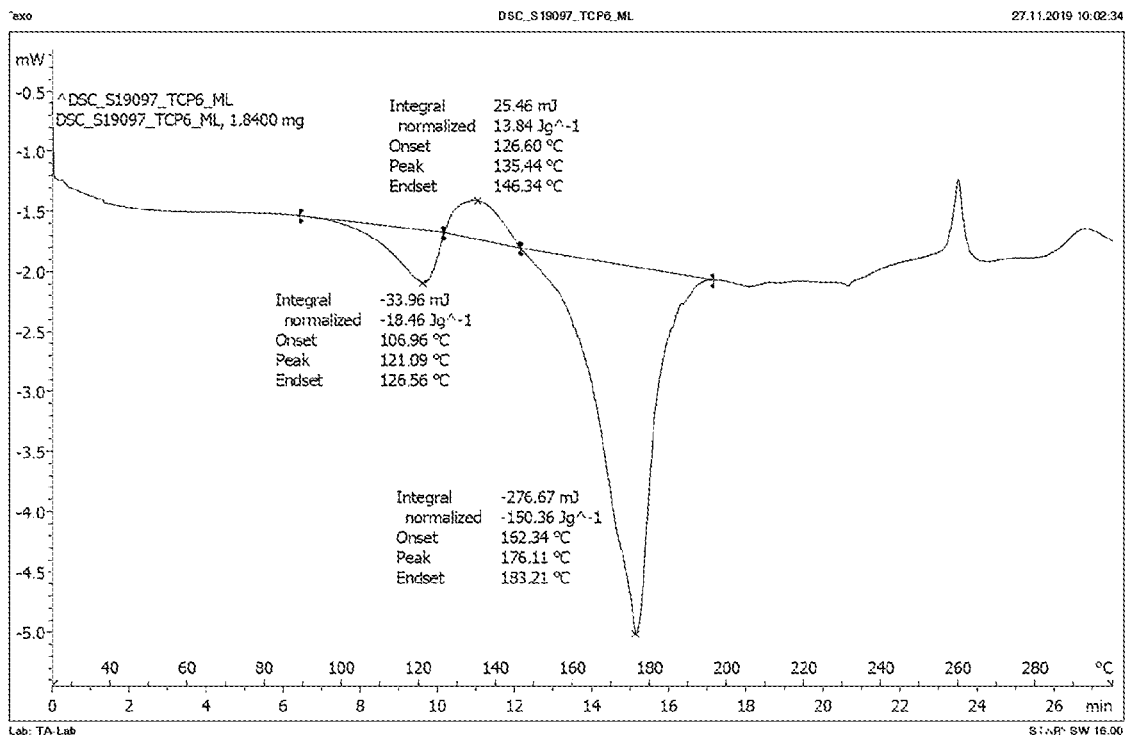

FIG. 269 illustrates the DSC analysis (heating rate 10° C./min) of Mao5 obtained after evaporative crystallization of the mother liquor recovered from the thermocycling experiment performed in methanol (Exp. ID TCP6_ML). A broad endothermic event was observed between 90-130° C. attributed to the water loss followed by an exothermic event at 135.4° C., due probably to recrystallization. An endothermic event was recorded at 176.1° C.

Figure 270:
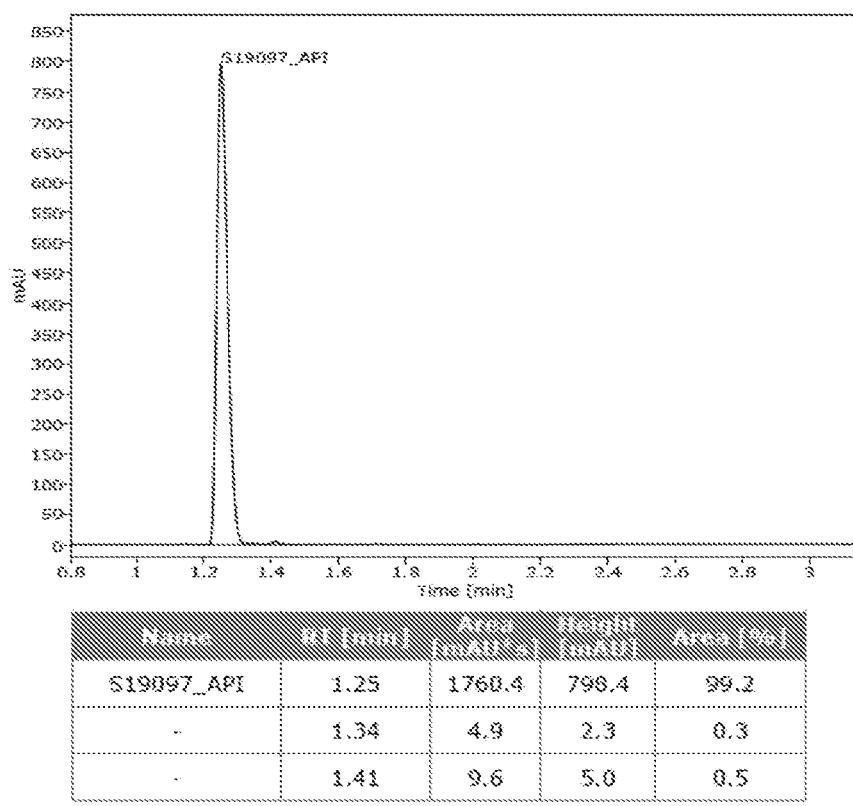

FIG. 270 illustrates the UPLC-MS chromatogram of Mao5 obtained after evaporative crystallization of the mother liquor recovered from the thermocycling experiment performed in methanol (Exp. ID TCP6_ML). The API chemical purity was 99.2% (area %).

Figure 271:
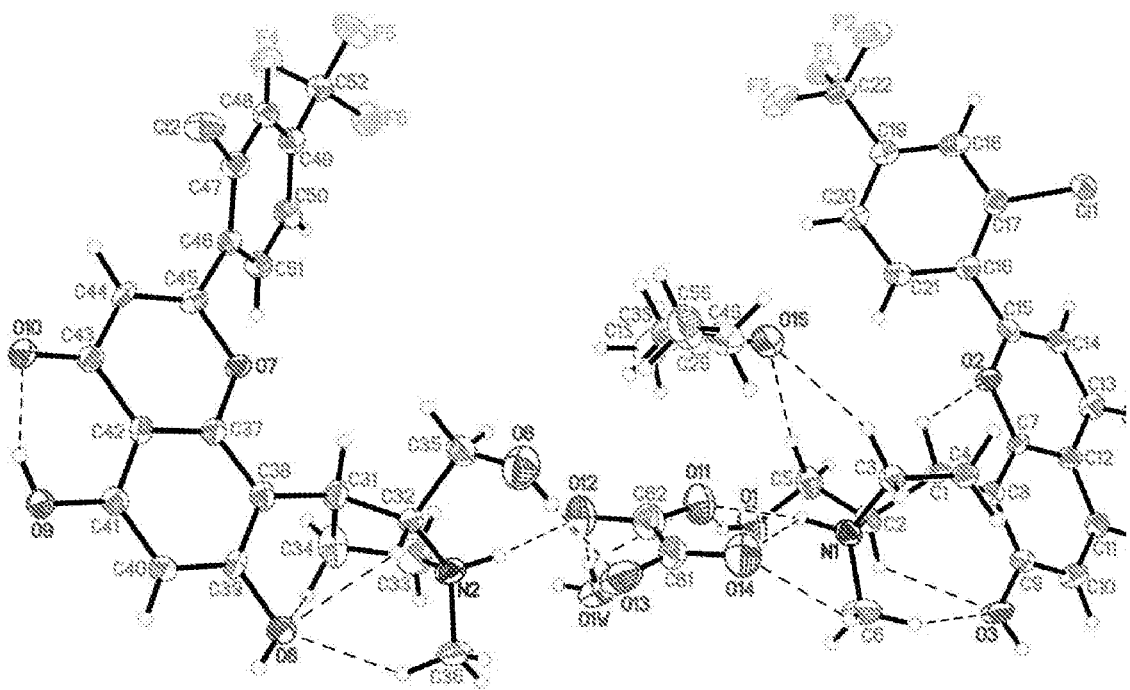

FIG. 271 illustrates the thermal ellipsoid representation at the 50% probability level for contents of the asymmetric unit in the structure of Voruciclib oxalate with atomic labeling scheme. Hydrogen bonds drawn as thin dashed lines. The molecules are shown in their correct relative orientation as they occur in the structure.

Figure 272:
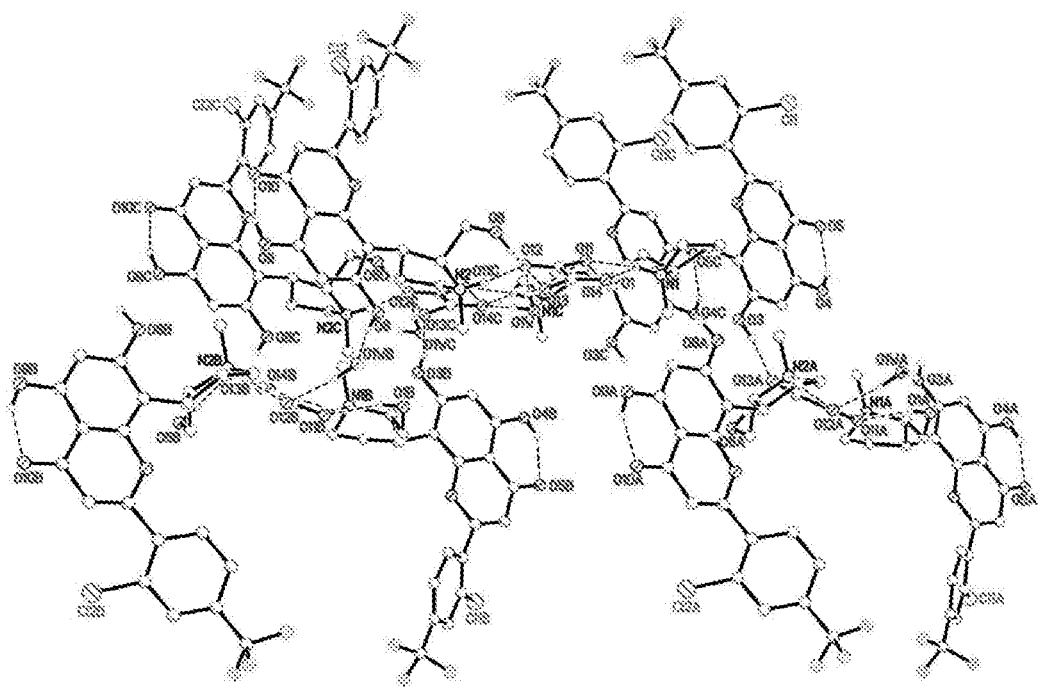

FIG. 272 illustrates the hydrogen bonding in the structure of Voruciclib oxalate. The O3-H3 . . . O13i, O8-H8 . . . O1Wii, and O1W-H1WA . . . O14iii interactions crosslink the building blocks shown in FIG. 271. Atoms with the letter A in their atom label are generated by symmetry operation i: −x+2, y−0.5, −z+1, letter B indicates symmetry operation ii: −x+1, y+0.5, −z+1, and letter C corresponds to symmetry operation iii: x−1, y, z. The view is the same as in FIG. 271. Hydrogen atoms bound to carbon and 2-pentanone omitted for clarity. Hydrogen bonds are drawn as thin dashed lines.

Figure 273:
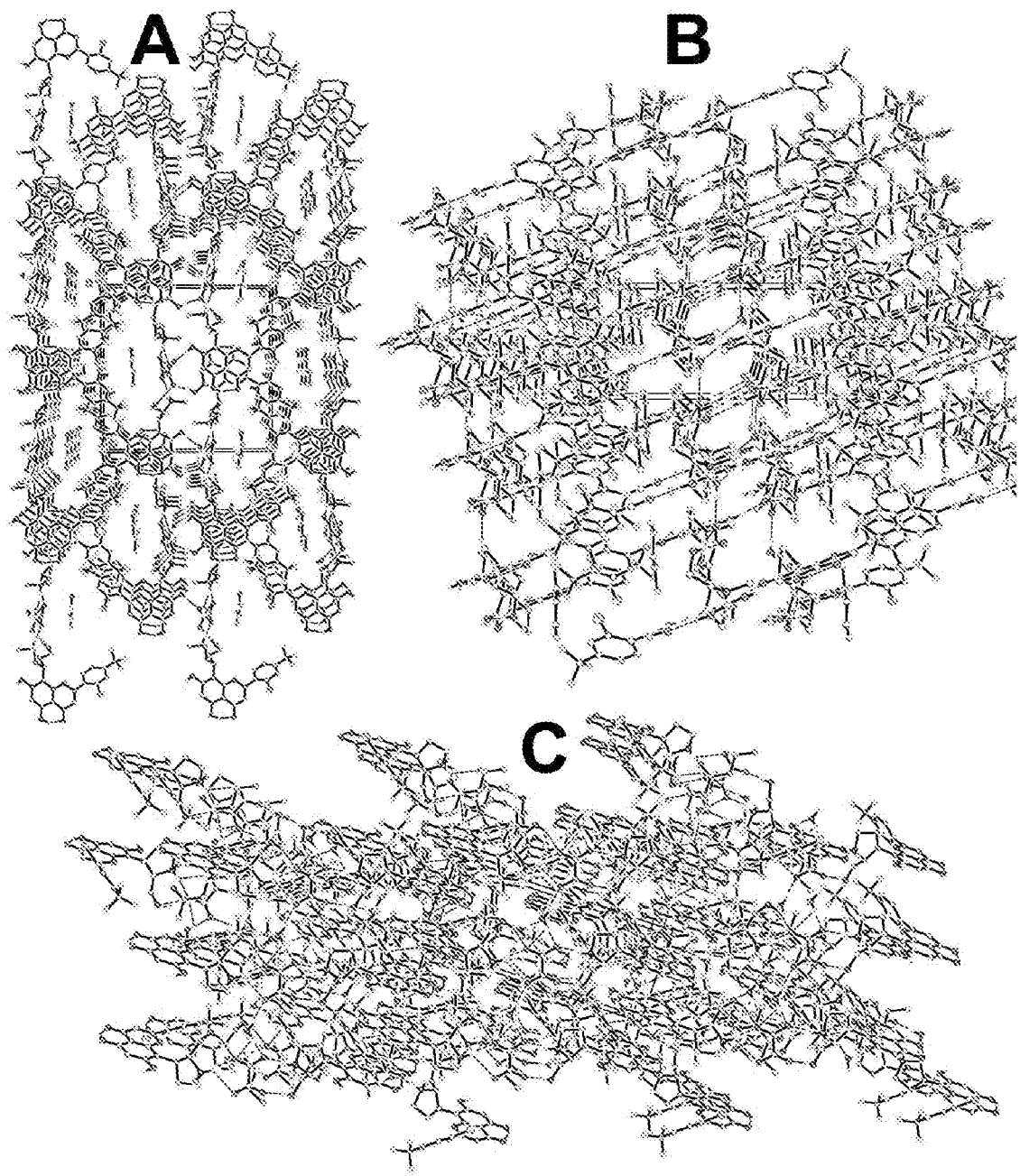

FIG. 273 illustrates the packing plots of the structure of Voruciclib oxalate in projections along the crystallographic a-, b- and c-axes (Panels A, B and C, respectively). Hydrogen bonds are drawn as thin dashed lines. Panel A shows the solvent channels, which extend along the crystallographic a-axis. Hydrogen atoms bound to carbon omitted for clarity.

Figure 274:
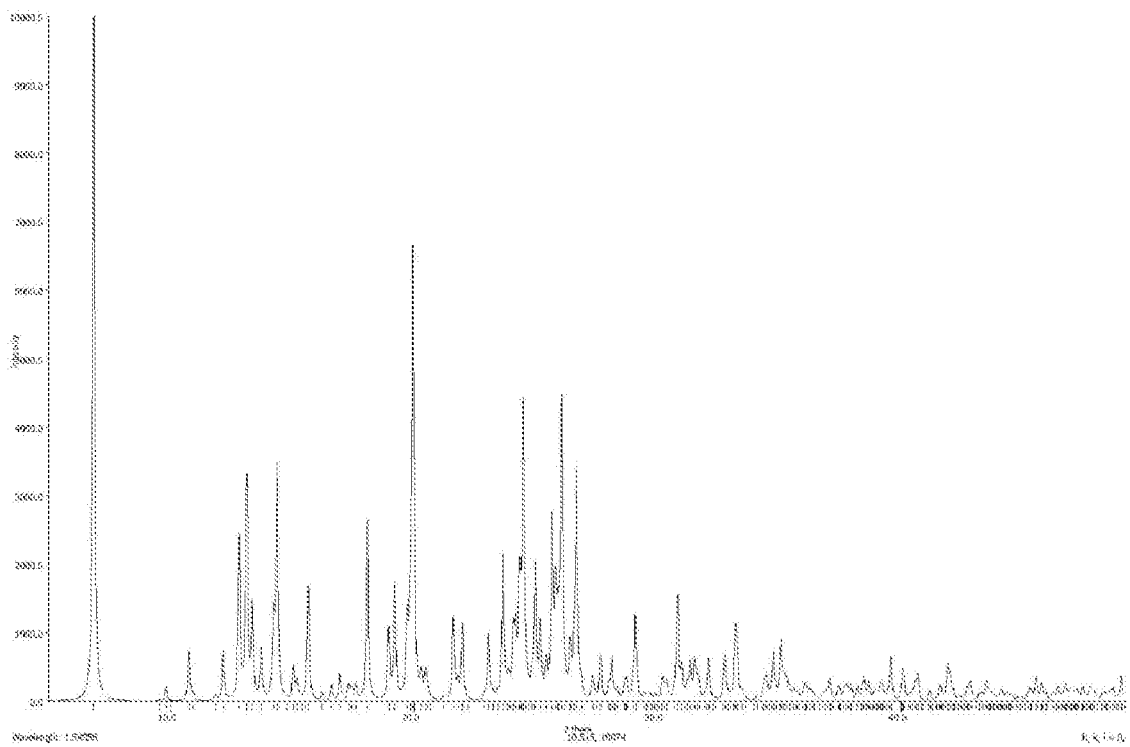

FIG. 274 illustrates the simulated powder diffractogram for the structure of Voruciclib oxalate.

Figure 275:
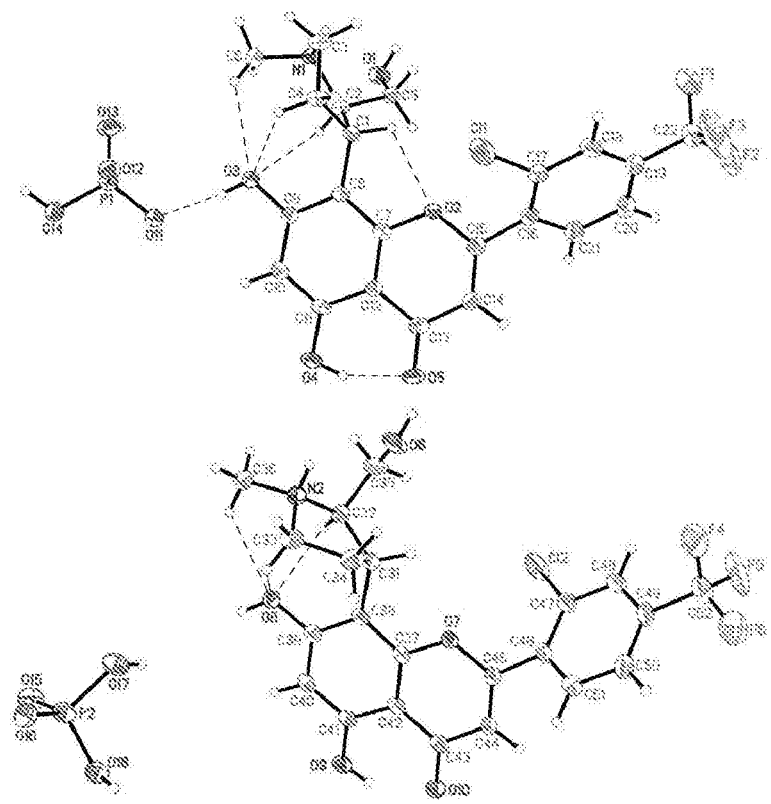
Figure 276:
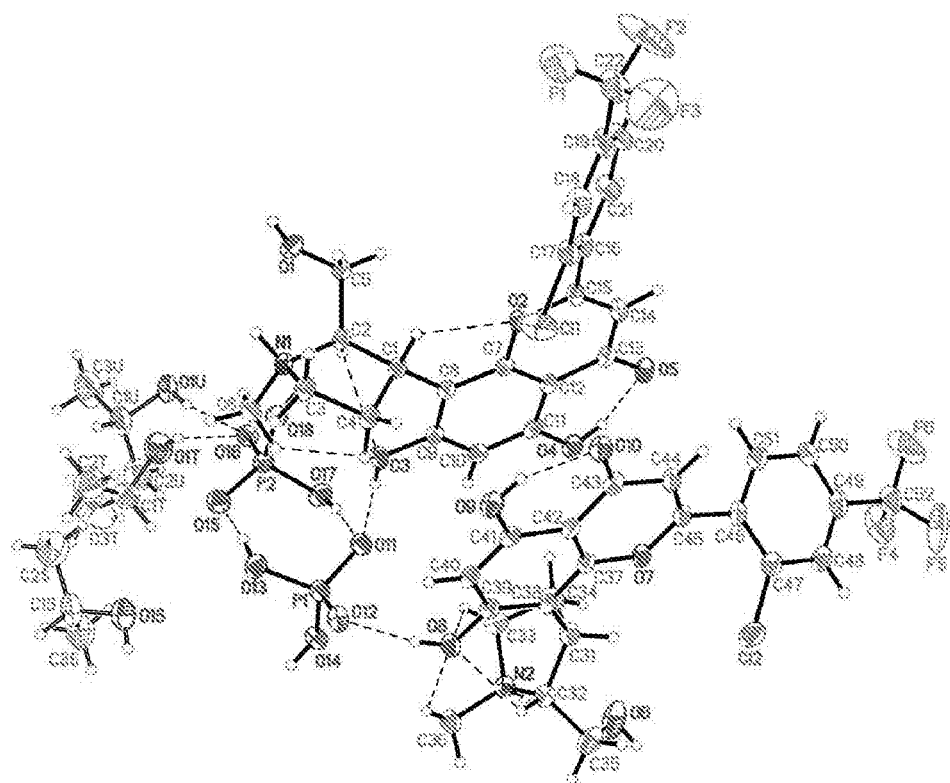

FIG. 275 illustrates the thermal ellipsoid representation at the 50% probability level for the two crystallographically independent molecules of Voruciclib phosphate with atomic labeling scheme. Hydrogen bonds drawn as thin dashed lines, solvent molecules omitted for clarity. The molecules are not shown in their correct relative orientations but were oriented to maximize clarity. FIG. 276 shows the full content of the asymmetric unit with the two target molecules, the two phosphate counter ions and the solvent, all in their correct relative orientation.

FIG. 276 illustrates the contents of the asymmetric unit in the structure of Voruciclib phosphate with atomic labeling scheme. The individual moieties are all in their correct relative orientation as they occur in the crystal structure. Hydrogen bonds drawn as thin dashed lines, the three half occupied solvent molecules are drawn with open lines.

Figure 277:
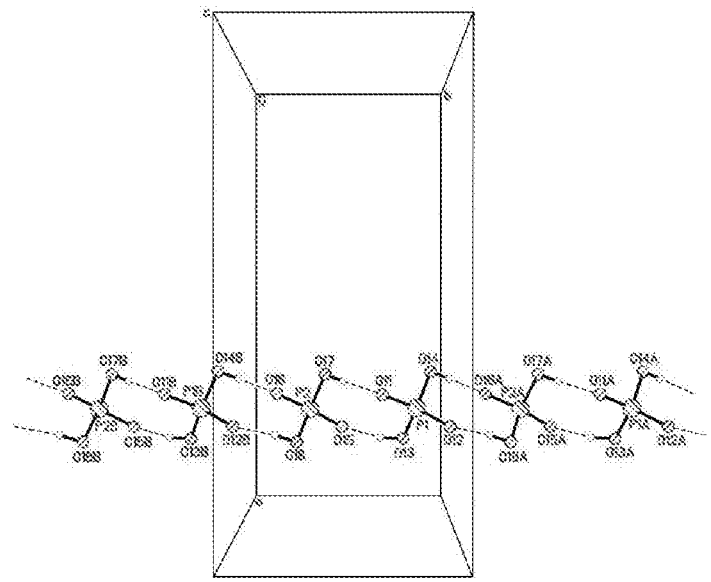

FIG. 277 illustrates the O13-H13 . . . O15, O17-H17 . . . O11, O14-H14 . . . O16i and O18-H18 . . . O12ii hydrogen bonds link the phosphate ions into infinite chains extending along the crystallographic b-axis. Atoms with the letter A in their atom label are generated by symmetry operation i: x, y+1, z and letter B indicates symmetry operation ii: x, y−1, z. Hydrogen bonds are drawn as thin dashed lines.

Figure 278:
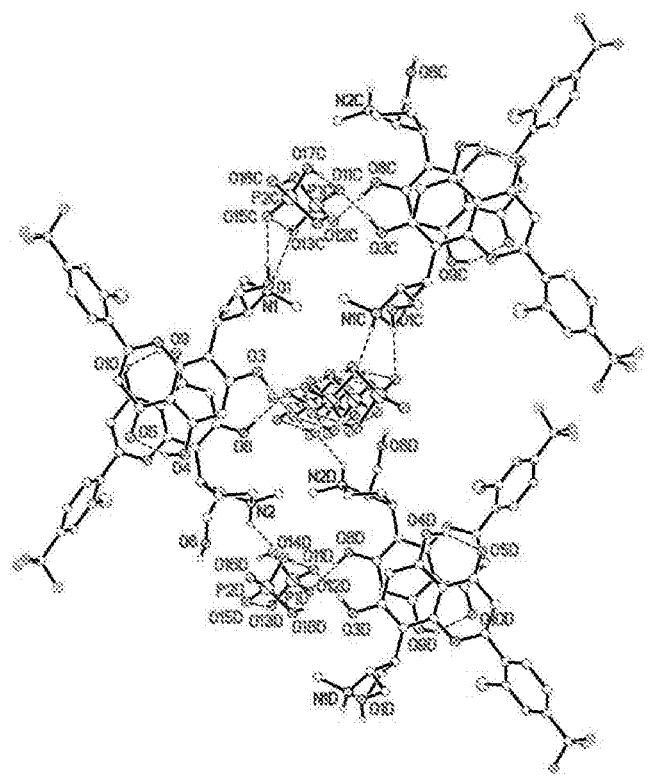

FIG. 278 illustrates the hydrogen bonds O3-H3 . . . O11, O8-H8 . . . O12, O9-H9 . . . O10, O1-H1A . . . O15iii, N1-H1 . . . O13iii, and N2-H2 . . . O17iv connect the Voruciclib molecules to the phosphate chain shown in FIG. 277. Depicted is a projection along the phosphate chains, perpendicular to the view in FIG. 277. Atoms with the letter A in their atom label are generated by symmetry operation i: x, y+1, z, letter B indicates symmetry operation ii: x, y−1, z, letter C symmetry operation iii: −x+2, y−0.5, −z+1, and D symmetry operation iv: −x+2, y−0.5, −z+1. Hydrogen bonds are drawn as thin dashed lines, hydrogen atoms not involved in classical hydrogen bonds and solvent molecules omitted for clarity.

Figure 279:
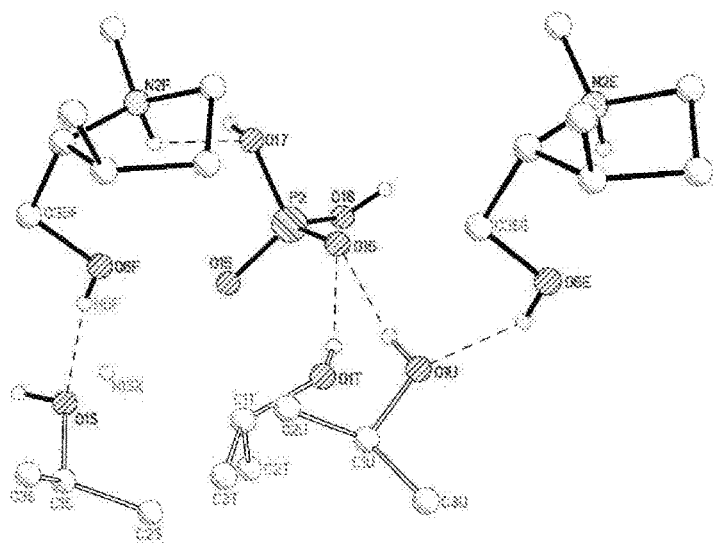

FIG. 279 illustrates the integration of the solvent molecules into the supramolecular framework via the O1T-H1T . . . O16, O1U-H1U . . . O16, O6-H6 . . . O1Siv and O6-H6 . . . O1Uv hydrogen bonds. Hypothetical hydrogen position H1SX would allow for an O1S-H1S . . . O15 hydrogen bond, however this position clashes with a symmetry equivalent of the hydrogen atom on H6 (shown here as H6F). Atoms with the letter E in their atom label are generated by symmetry operation −x+1, y−1.5, −z+1 and letter F indicates symmetry operation −x+1, y−0.5, −z+1. Hydrogen bonds are drawn as thin dashed lines.

Figure 280:
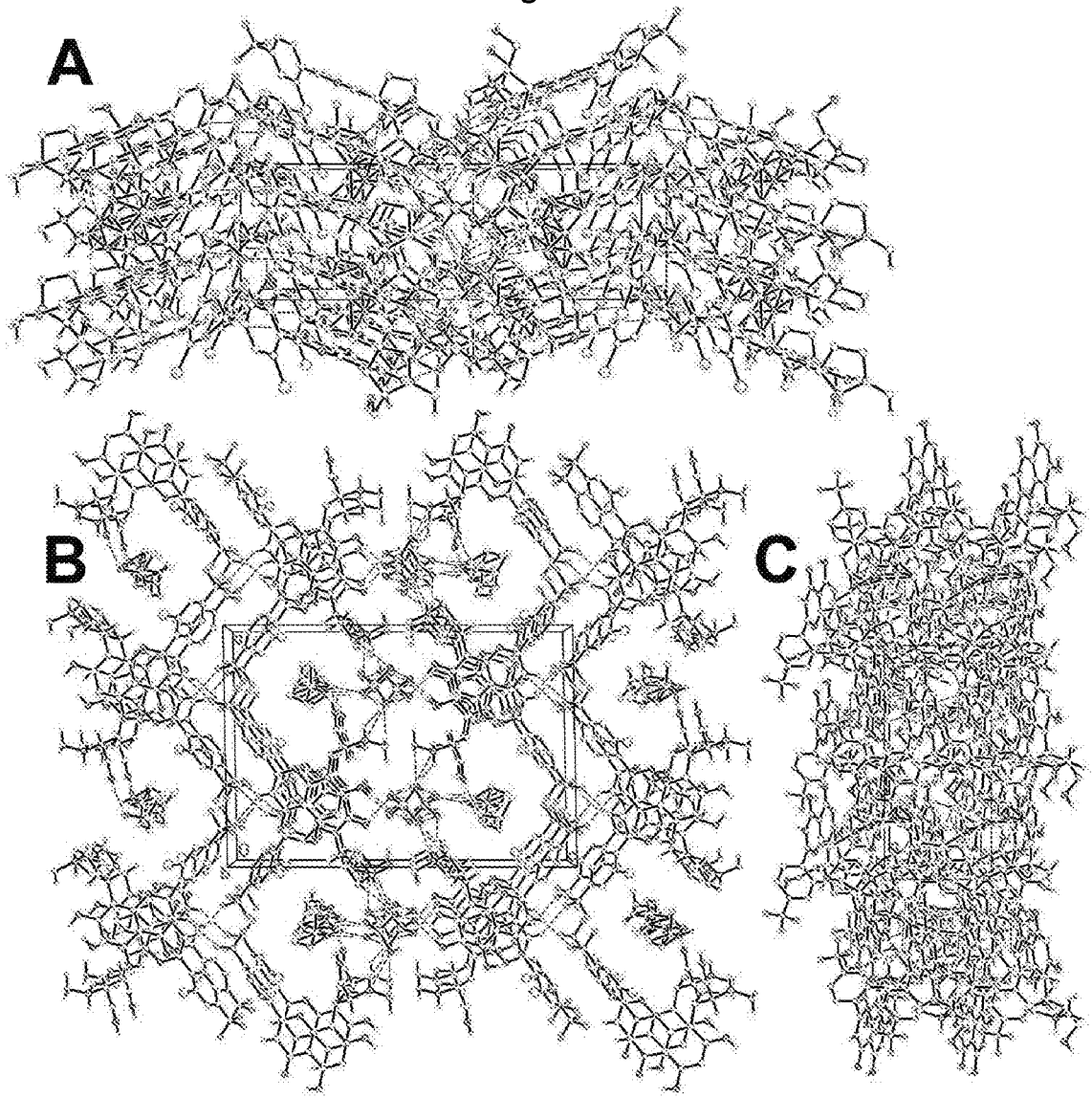

FIG. 280 illustrates the packing plots of the structure of Voruciclib phosphate isopropyl alcohol solvate in projections along the crystallographic a-, b- and c-axes (Panels A, B and C, respectively). To better illustrate the role of the solvent molecules, solvent carbon atoms are drawn in orange. Hydrogen bonds are drawn as thin dashed lines. Panels A and B show how the solvent channels extend parallel to the phosphate chains. Hydrogen atoms not involved in hydrogen bonds omitted for clarity.

Figure 281:
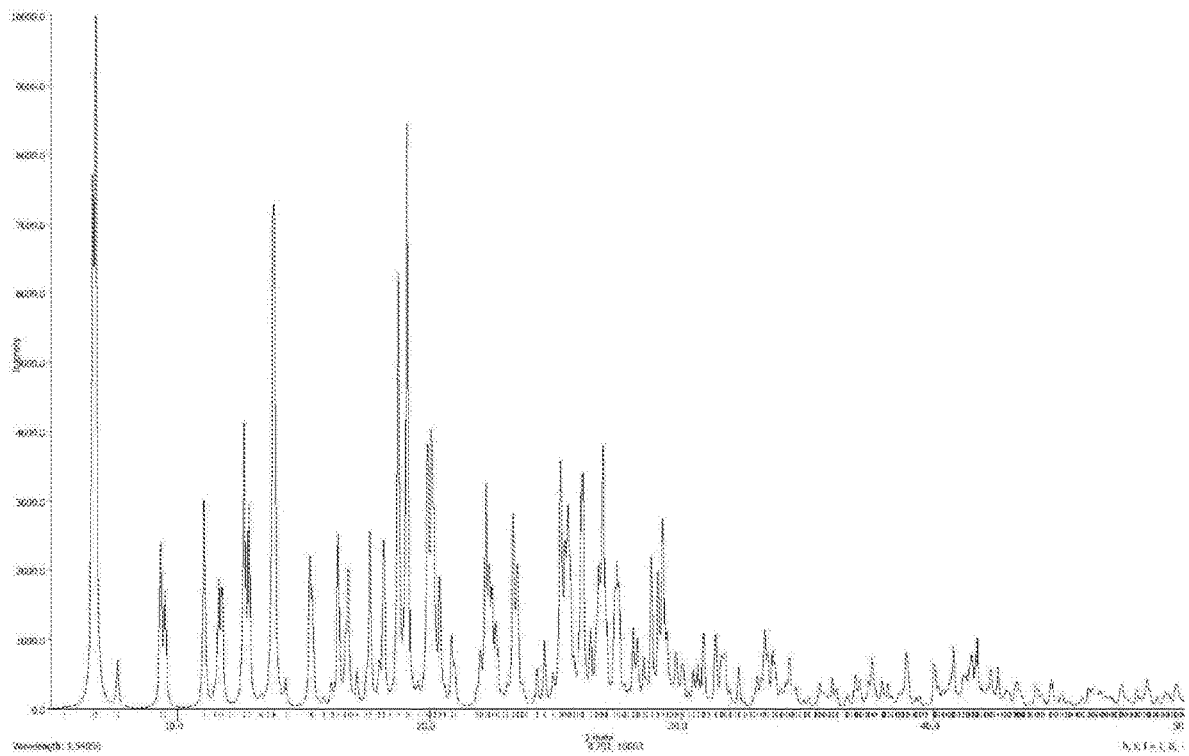

FIG. 281 illustrates the simulated powder diffractogram for the structure of Voruciclib phosphate isopropyl alcohol solvate.

Figure 282:
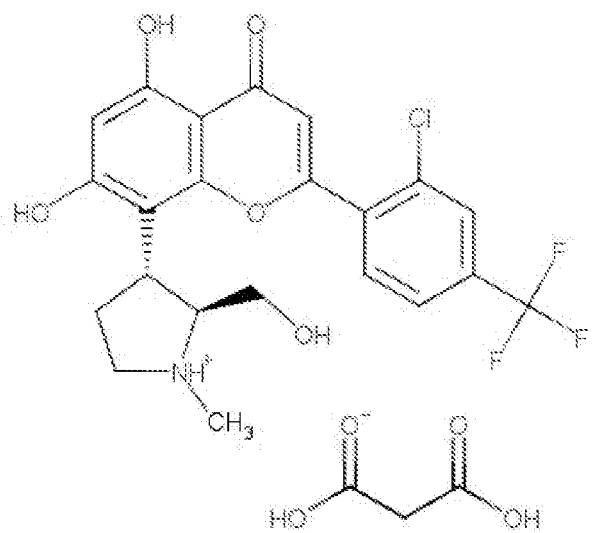

FIG. 282 illustrates the molecular structure of Voruciclib Malonate salt.

Figure 283:
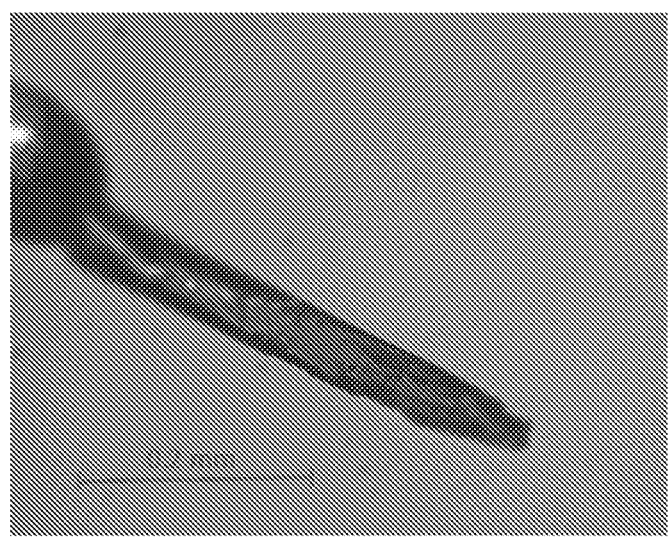

FIG. 283 illustrates the microphotograph under polarized light (with magnification 10×) of Voruciclib Malonate crystal.

Figure 284:
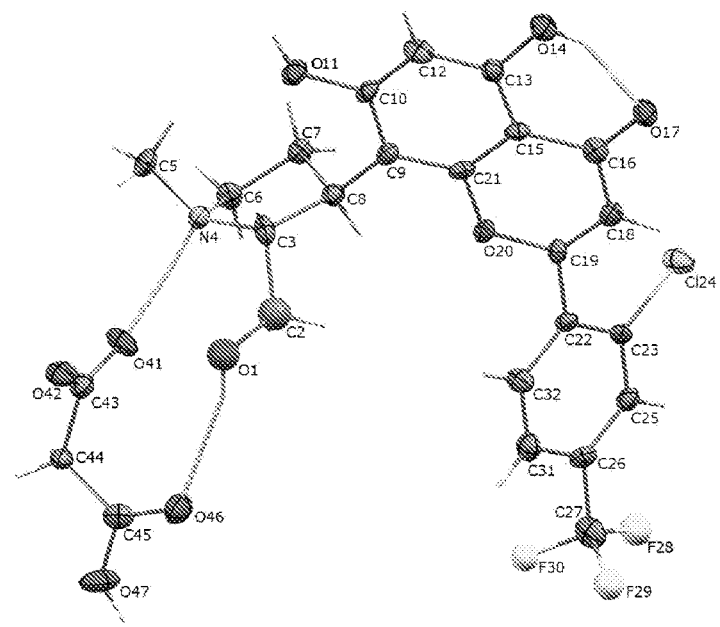

FIG. 284 illustrates the molecular structure and atom numbering scheme for cation-anion pair of Voruciclib Malonate.

Figure 285:
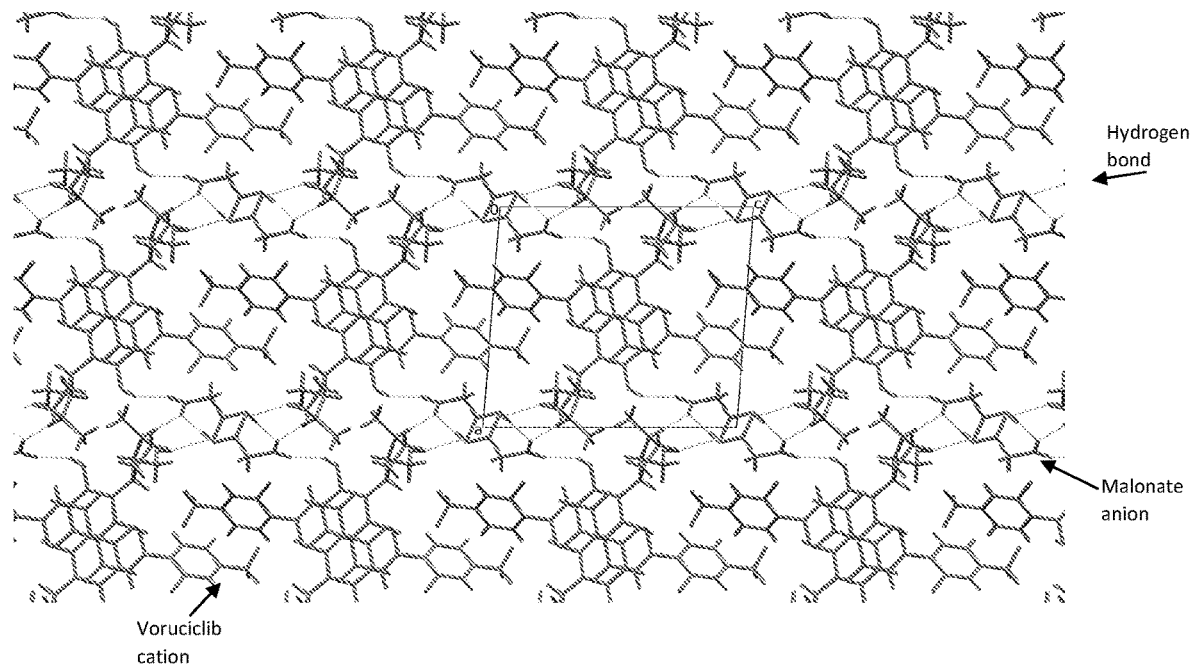

FIG. 285 illustrates the crystal packing and hydrogen bonds scheme along [0 1 0] direction for Voruciclib Malonate. The Voruciclib cations are presented in green color, while the malonate anions are red. The light blue lines represent the hydrogen bonds.

Figure 286:
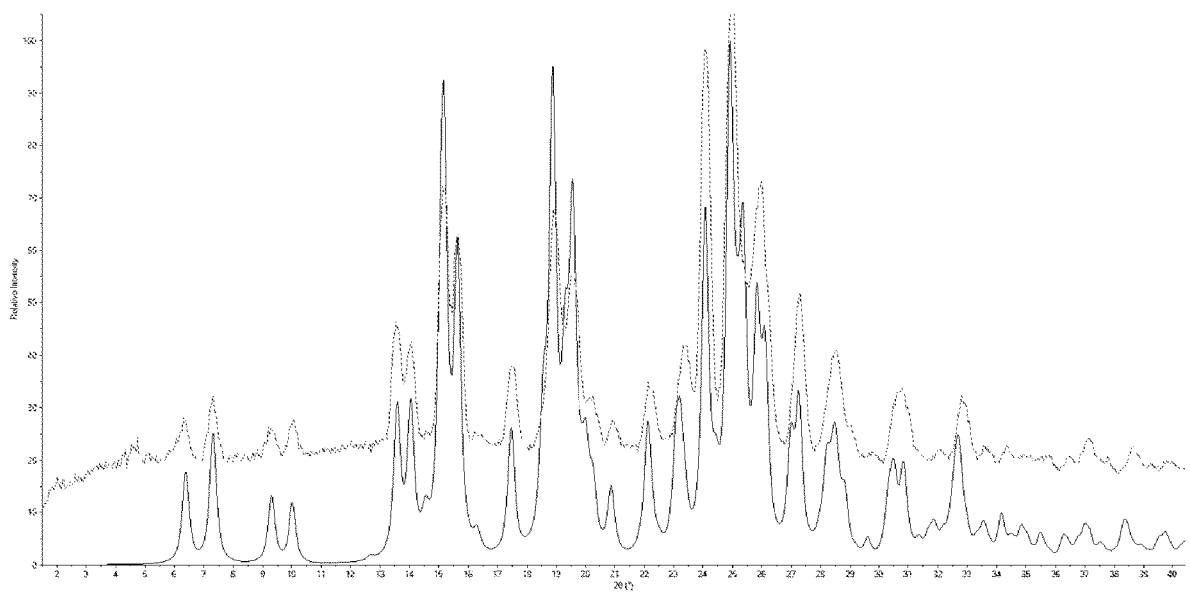

FIG. 286 illustrates the comparison of simulated powder pattern with FWHM=0.28° based on single crystal data (black) with the HT-XRPD pattern obtained for malonate salt Exp. ID SSm53 (red).

FIG. 287 illustrates a table depicting the stability of polymorphs in various solvents identified in a solid state characterization of Voruciclib HCl.

FIG. 288 illustrates non-limiting examples of target product attributes of Voruciclib (ME-522).

FIG. 289 illustrates the results of an initial salt screen, comparing the form, crystallinity, and stability of various acid counterions.

FIG. 290 illustrates the results of a secondary salt screen, comparing the number of polymorphs, percent residual solvent, gelling, and water solubility (mg/mL).

Figures 291, 292:
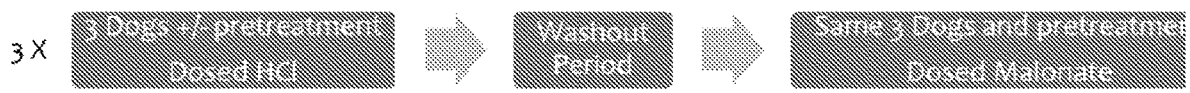

FIG. 291 illustrates the properties of the HCl, malonate, oxalate, and phosphate salts of Voruciclib related to product attributes shown in FIG. 288.

FIG. 292 illustrates the crossover design of the dog PK study comparing the HCl and malonate salts of Voruciclib.

FIG. 293 illustrates the analysis of variability for each pretreatment group and dosed salt form combination of the crossover dog PK study comparing the HCl and malonate Voruciclib salts.

FIG. 294 illustrates the ratio of malonate/HCl calculated for each dog and PK parameter.

Figure 295:
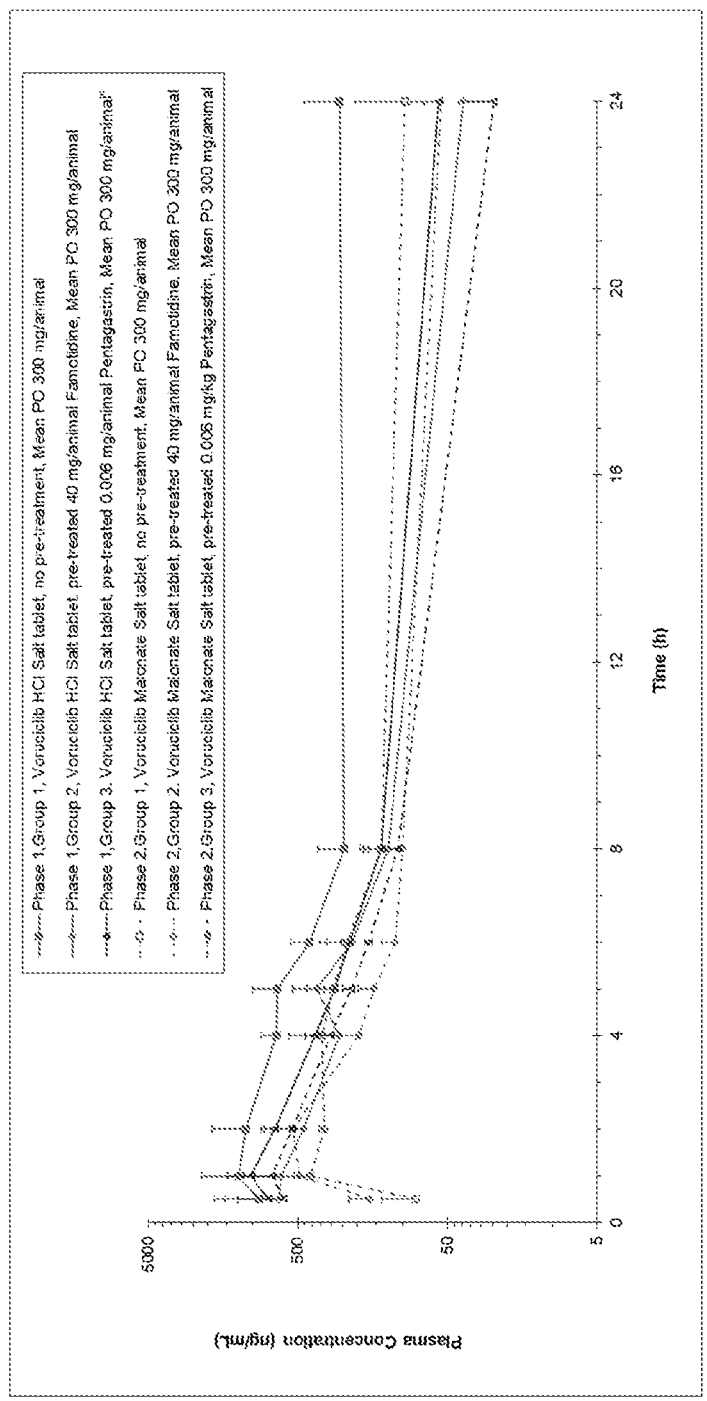
Figure 296A:
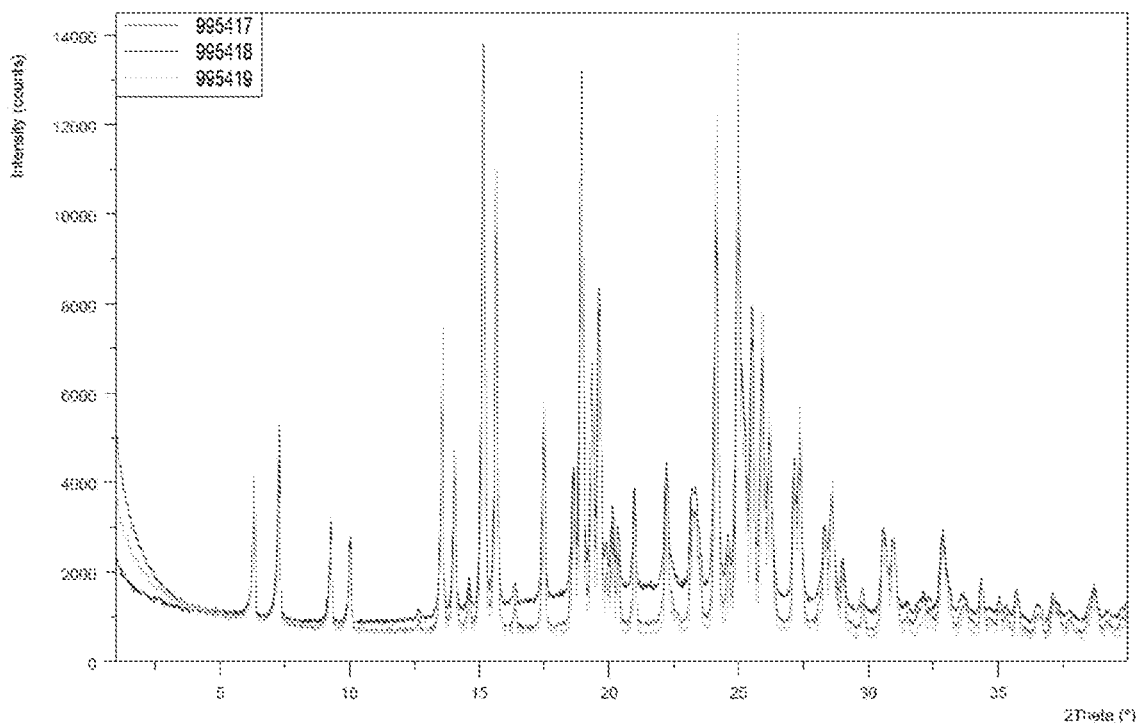
Figure 296B:
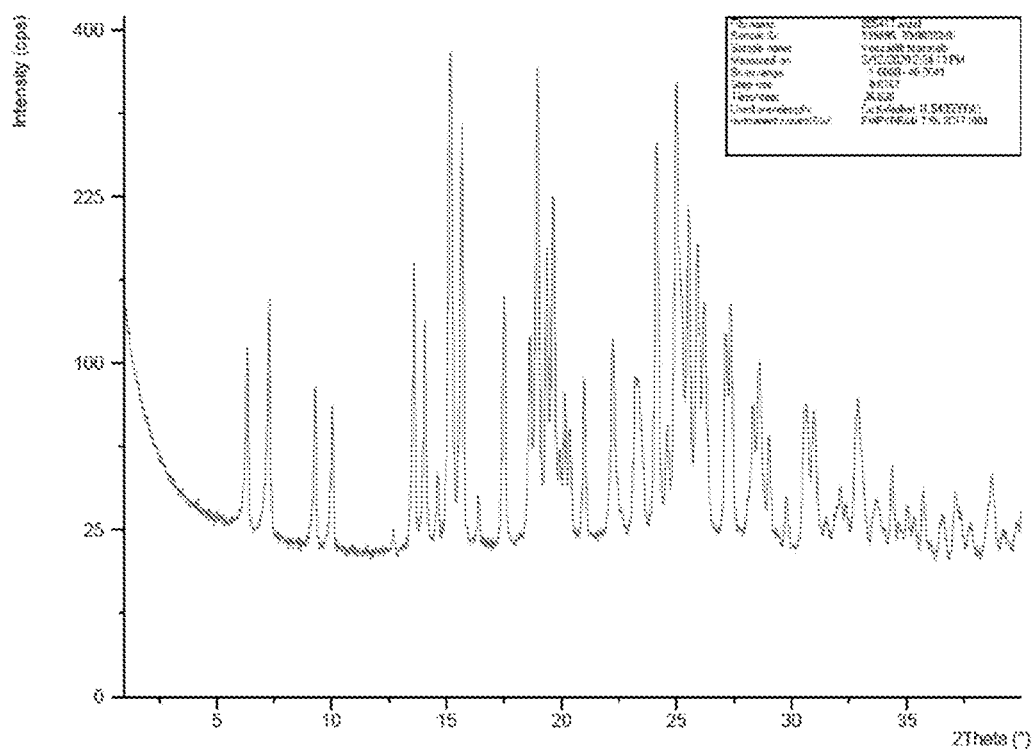
Figure 296C:
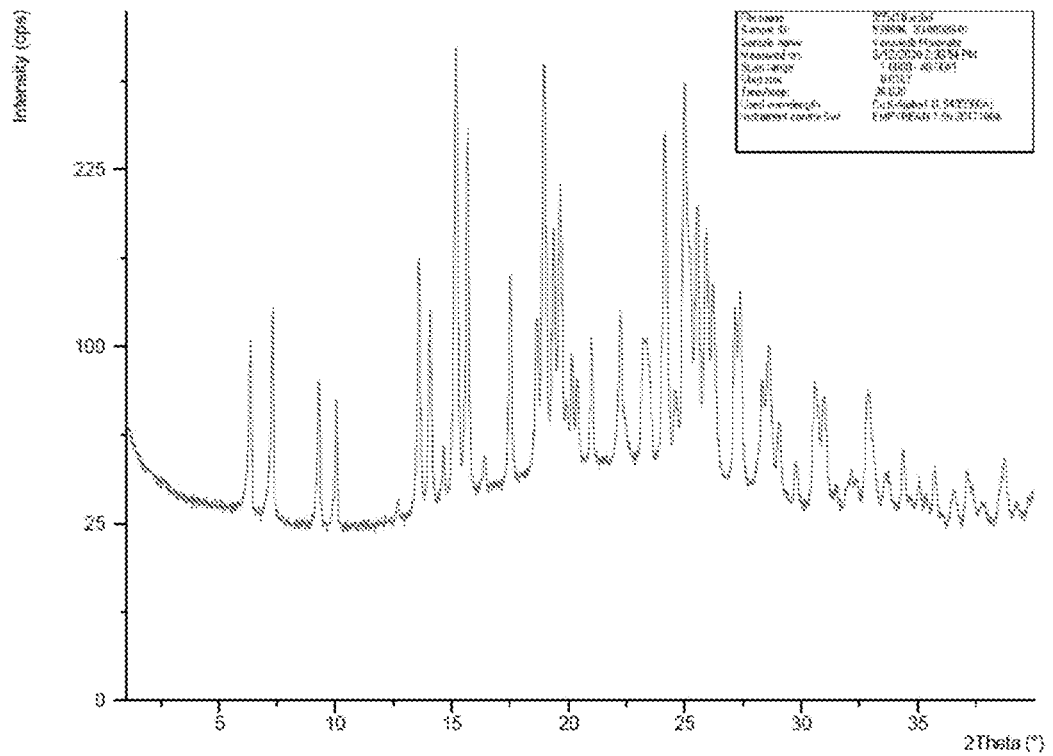
Figure 296D:
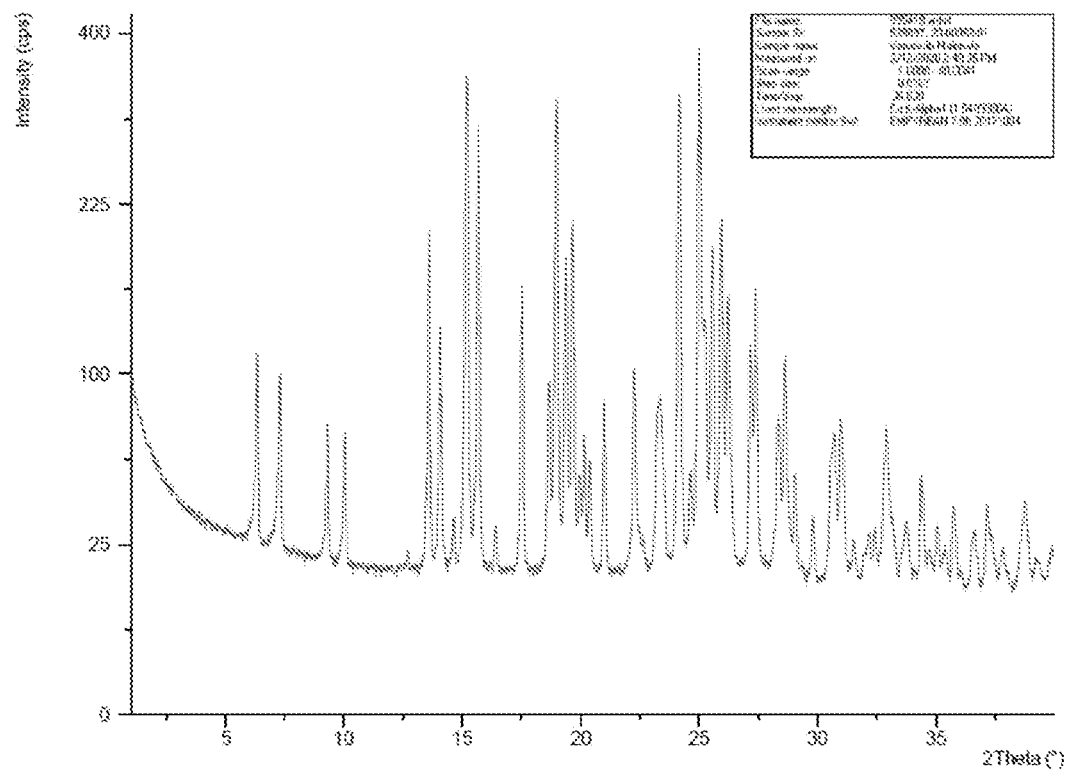

FIG. 295 illustrates the Voruciclib plasma concentration vs. time following a single dose crossover oral administration to male beagle dogs.

FIGS. 296A-D illustrate the XRPD patterns of voruciclib malonate lots 20-00022-01, 20-00026-01, and 20-00062-01.

FIG. 297 illustrates the technical specifications for the VÅNTEC-500 Area Detector.

FIG. 298 illustrates the technical specifications for the Lynxeye detector.

DETAILED DESCRIPTION

While preferred embodiments of the invention are shown and described herein, such embodiments are provided by way of example only and are not intended to otherwise limit the scope of the invention. Various alternatives to the described embodiments of the invention may be employed in practicing the invention.

Definitions

Unless defined otherwise, all technical and scientific terms used herein have the same meaning as is commonly understood by one of skill in the art to which this invention belongs. All patents and publications referred to herein are incorporated by reference in their entireties.

The term "solid form" may refer to a crystalline solid form or phase, including a crystalline free base and a crystalline salt.

The terms "co-administration," "co-administering," "administered in combination with," and "administering in combination with" as used herein, encompass administration of two or more agents to a subject so that both agents and/or their metabolites are present in the subject at the same time. Co-administration includes simultaneous administration in separate compositions, administration at different times in separate compositions, or administration in a composition in which two or more agents are present.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., CDK inhibition). The specific dose will vary depending on the particular compounds chosen, the dosing regimen to be followed, whether the compound is administered in combination with other compounds, timing of administration, the tissue to which it is administered, and the physical delivery system in which the compound is carried.

The terms "QD," "qd," or "q.d." mean quaque die, once a day, or once daily. The terms "BID," "bid," or "b.i.d." mean bis in die, twice a day, or twice daily. The terms "TID," "tid," or "t.i.d." mean ter in die, three times a day, or three times daily. The terms "QID," "qid," or "q.i.d." mean quater in die, four times a day, or four times daily.

A "therapeutic effect" as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable salt" refers to salts derived from a variety of organic and inorganic counter ions, including fumarate, maleate, phosphate, L-tartrate, esylate, besylate, hydrobromide, hydrochloride, citrate, gentisate, oxalate, sulfate counter ions, and the like. Pharmaceutically acceptable acid addition salts can be formed with inorganic acids and organic acids.

"Pharmaceutically acceptable carrier" or "pharmaceutically acceptable excipient" is intended to include any and all solvents, dispersion media, coatings, antibacterial and antifungal agents, isotonic and absorption delaying agents. Except insofar as any conventional media or agent is incompatible with the active ingredient, its use in the therapeutic compositions of the invention is contemplated. Supplementary active ingredients can also be incorporated into the described compositions.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "extragranular" refers to substances that are outside of a granule, e.g., a substance added to granules (multiparticle compacts formed by a granulation process) and physically mixed with granules, but not contained within the granules.

The term "intragranular" refers to substances that are within a granule (a multiparticle compact formed by a granulation process). Granules may be formed by processes such as wet granulation (i.e., prepared using moisture or steam, thermal, melt, freeze, foam, and other processes) or dry granulation.

The term "acidulant" refers to a substance that increases acidity.

The terms "transmission" or "transmission mode," when used in conjunction with powder X-ray diffraction, refers to the transmission (also known as Debye-Scherrer) sampling mode. The terms "reflection" or "reflection mode," when used in conjunction with powder X-ray diffraction, refers to the reflection (also known as Bragg-Brentano) sampling mode.

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}$C- or $^{14}$C-enriched carbons, are within the scope of this invention.

When ranges are used herein to describe, for example, physical or chemical properties such as molecular weight or chemical formulae, all combinations and subcombinations of ranges and specific embodiments therein are intended to be included. Use of the term "about" or "approximately" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)-isomer and 20% (R)-isomer, the enantiomeric purity of the compound with respect to the (S)-isomeric form is 80%. The enantiomeric purity of a compound can be determined in a number of ways, including but not limited to chromatography using a chiral support, polarimetric measurement of the rotation of polarized light, nuclear magnetic resonance spectroscopy using chiral shift reagents which include but are not limited to lanthanide containing chiral complexes or Pirkle's reagents, or derivatization of a compounds using a chiral compound such as Mosher's acid followed by chromatography or nuclear magnetic resonance spectroscopy.

In preferred embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., *Enantiomers, Racemates and Resolutions*, Wiley Interscience, New York, 1981; Eliel, *Stereochemistry of Carbon Compounds*, McGraw-Hill, NY, 1962; and Eliel and Wilen, *Stereochemistry of Organic Compounds*, Wiley-Interscience, New York, 1994.

The terms "enantiomerically enriched" and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, or such as at least 80% by weight. In some embodiments, the enrichment can be significantly greater than 80% by weight, providing a "substantially enantiomerically enriched" or a "substantially non-racemic" preparation, which refers to preparations of compositions which have at least 85% by weight of one enantiomer relative to other enantiomer, such as at least 90% by weight, or such as at least 95% by weight. The terms "enantiomerically pure" or "substantially enantiomerically pure" refers to a composition that comprises at least 98% of a single enantiomer and less than 2% of the opposite enantiomer.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. The formation of solid forms in different tautomerization states is known as "desmotropy" and such forms are known as "desmotropes."

Compositions of the invention also include crystalline forms of Formula (1), including, for example, polymorphs, pseudopolymorphs, solvates, hydrates, unsolvated polymorphs (including anhydrates), and conformational polymorphs, as well as mixtures thereof. "Crystalline form", "form," and "polymorph" are intended to include all crystalline forms of the compound, including, for example, polymorphs, pseudopolymorphs, solvates, hydrates, unsolvated polymorphs (including anhydrates), and conformational polymorphs, as well as mixtures thereof, unless a particular crystalline form is referred to.

"Solvate" refers to a crystalline phase of a compound in physical association with one or more molecules of a solvent. The crystalline phase of a compound in physical association with one or more molecules of water is referred to as a "hydrate."

"Amorphous form" refers to a form of a compound, or a salt or molecular complex of a compound, that lacks long range crystalline order.

Voruciclib

Voruciclib is a CDK inhibitor described for example in U.S. Pat. Nos. 7,271,193, 7,915,301, 8,304,449, 7,884,127, and 8,563,596, incorporated herein by reference in their entireties.

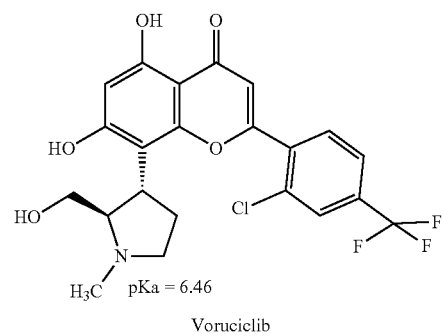 [SMILES: CN1CC[C@@H](c2c(O)cc(O)c3c(=O)cc(-c4ccc(C(F)(F)F)cc4Cl)oc23)[C@@H]1CO]

Voruciclib

In some embodiments, voruciclib refers to (+)-trans-2-(2-chloro-4-trifluoromethylphenyl)-5,7-dihydroxy-8-(2-hydroxymethyl-1-methylpyrrolidin-3-yl)-chromen-4-one. In some embodiments, voruciclib refers to 2-(2-chloro-4-trifluoromethylphenyl)-5,7-dihydroxy-8-((2R,3S)-2-hydroxymethyl-1-methylpyrrolidin-3-yl)-4H-chromen-4-one.

Crystalline Forms

In an embodiment, the disclosure provides a crystalline solid form of voruciclib. In an embodiment, the disclosure provides a crystalline solid form of voruciclib free base. In an embodiment, the disclosure provides a crystalline solid form of a voruciclib salt. The disclosure provides polymorphs, for example crystal forms, of voruciclib. In some embodiments, the polymorphs include free base voruciclib. In some embodiments, the polymorphs include voruciclib salts including a counterion corresponding to an acid selected from 1,5-naphthalenedisulfonic acid, 1-hydroxy-2-naphthoic acid, benzenesulfonic acid, benzoic acid, dibenzoyl-L-tartaric acid, ethanesulfonic acid, gentisic acid, hydrobromic acid, hydrochloric acid, maleic acid, malonic acid, oxalic acid, ortho-phosphoric acid, sulfuric acid, p-toluenesulfonic acid, and the like.

Any crystalline form described herein can be characterized by X-ray diffraction. In some embodiments, X-ray diffraction refers to X-ray powder diffraction. In some embodiments, X-ray diffraction may be measured using transmission mode or reflection mode. In an embodiment, the X-ray diffraction pattern of any embodiments herein is measured in transmission mode. In an embodiment, the X-ray diffraction pattern of any embodiments herein is measured in reflection mode. It is known in the art that an X-ray powder diffraction pattern may be obtained which has one or more measurement errors depending on measurement conditions (such as equipment, sample preparation, or instrument used). In particular, it is generally known that intensities in an X-ray powder diffraction pattern may vary depending on measurement conditions and sample preparation. For example, persons skilled in the art of X-ray powder diffraction will realize that the relative intensities of peaks may vary according to the orientation of the sample under test and based on the type and settings of the instrument used. The skilled person will also realize that the position of reflections can be affected by the precise height at which the sample sits in the diffractometer, the sample's surface planarity, and the zero calibration of the diffractometer. Hence a person skilled in the art will appreciate that the diffraction pattern data presented herein is not to be construed as absolute and any crystalline form that provides a power diffraction pattern substantially the same as those disclosed herein fall within the scope of the present disclosure. For further information, see Jenkins and Snyder, *Introduction to X-Ray Powder Diffractometry*, John Wiley & Sons, 1996.

Different crystalline form may provide surprising advantages compared to non-crystalline forms, including improved thermodynamic stability, faster dissolution rate, improved performance in the stomach and gastric environment (including the avoidance of, or reduced, precipitation from solution upon a change to higher pH), improved exposure in mammals, and superior processability for formulation of drug into finished products suitable for patients.

In one embodiment, the disclosure provides a crystal form of voruciclib malonate, and/or a polymorph crystal form of voruciclib malonate (Mao1), characterized by an X-ray powder diffraction pattern including one or more peaks selected from:

| No | 2θ (°) | D (Å) | I (%) |
|---|---|---|---|
| 1 | 6.36 | 13.88 | 11 |
| 2 | 7.31 | 12.08 | 28 |
| 3 | 9.34 | 9.46 | 15 |
| 4 | 10.05 | 8.79 | 12 |
| 5 | 13.59 | 6.51 | 31 |
| 6 | 14.08 | 6.28 | 29 |
| 7 | 15.21 | 5.82 | 76 |
| 8 | 15.67 | 5.65 | 65 |
| 9 | 17.53 | 5.06 | 27 |
| 10 | 18.70 | 4.74 | 23 |
| 11 | 18.98 | 4.67 | 100 |
| 12 | 19.38 | 4.58 | 36 |
| 13 | 19.67 | 4.51 | 63 |
| 14 | 20.16 | 4.40 | 14 |
| 15 | 20.39 | 4.35 | 12 |
| 16 | 21.01 | 4.23 | 13 |
| 17 | 22.27 | 3.99 | 26 |
| 18 | 23.35 | 3.81 | 19 |
| 19 | 24.15 | 3.68 | 66 |
| 20 | 24.67 | 3.61 | 11 |
| 21 | 25.00 | 3.56 | 77 |
| 22 | 25.18 | 3.53 | 37 |
| 23 | 25.57 | 3.48 | 57 |
| 24 | 25.93 | 3.43 | 45 |
| 25 | 26.21 | 3.40 | 31 |
| 26 | 27.19 | 3.28 | 20 |
| 27 | 27.38 | 3.25 | 29 |

In some embodiments, each peak independently may include a variation of ±0.1°, ±0.2°, or ±0.3°.

In one embodiment, the disclosure provides a crystal form of voruciclib oxalate, and/or a polymorph crystal form of voruciclib oxalate (Oxa1), characterized by an X-ray powder diffraction pattern including one or more peaks selected from:

| No | 2θ (°) | D (Å) | I (%) |
|---|---|---|---|
| 1 | 6.86 | 12.88 | 100 |
| 2 | 9.70 | 9.11 | 3 |
| 3 | 10.84 | 8.15 | 11 |
| 4 | 12.50 | 7.08 | 4 |
| 5 | 12.66 | 6.99 | 13 |
| 6 | 12.81 | 6.90 | 6 |
| 7 | 13.41 | 6.60 | 35 |
| 8 | 13.71 | 6.46 | 11 |
| 9 | 14.54 | 6.09 | 49 |
| 10 | 15.35 | 5.77 | 9 |
| 11 | 15.83 | 5.59 | 16 |
| 12 | 18.70 | 4.74 | 8 |
| 13 | 19.00 | 4.67 | 12 |
| 14 | 19.43 | 4.57 | 44 |
| 15 | 19.62 | 4.52 | 6 |
| 16 | 21.75 | 4.08 | 9 |
| 17 | 22.75 | 3.91 | 13 |
| 18 | 23.35 | 3.81 | 7 |
| 19 | 23.47 | 3.79 | 8 |
| 20 | 23.81 | 3.73 | 18 |
| 21 | 23.98 | 3.71 | 23 |
| 22 | 24.36 | 3.65 | 11 |
| 23 | 24.60 | 3.62 | 8 |
| 24 | 24.86 | 3.58 | 18 |
| 25 | 25.11 | 3.54 | 12 |
| 26 | 25.60 | 3.48 | 19 |
| 27 | 25.75 | 3.46 | 15 |
| 28 | 26.25 | 3.39 | 31 |

In some embodiments, each peak independently may include a variation of ±0.1°, ±0.2°, or ±0.3°.

In one embodiment, the disclosure provides a crystal form of voruciclib phosphate, and/or a polymorph crystal form of voruciclib phosphate (Pho1), characterized by an X-ray powder diffraction pattern including one or more peaks selected from:

| No | 2θ (°) | d (Å) | I (%) |
|---|---|---|---|
| 1 | 4.93 | 17.92 | 31 |
| 2 | 6.79 | 13.01 | 61 |
| 3 | 9.35 | 9.45 | 22 |
| 4 | 10.58 | 8.35 | 12 |
| 5 | 10.91 | 8.10 | 52 |
| 6 | 12.64 | 7.00 | 37 |
| 7 | 13.35 | 6.63 | 23 |
| 8 | 13.58 | 6.51 | 7 |
| 9 | 14.81 | 5.98 | 100 |
| 10 | 15.60 | 5.68 | 28 |
| 11 | 17.18 | 5.16 | 14 |
| 12 | 17.52 | 5.06 | 15 |
| 13 | 18.32 | 4.84 | 14 |
| 14 | 18.78 | 4.72 | 25 |
| 15 | 19.34 | 4.59 | 10 |
| 16 | 19.64 | 4.52 | 13 |
| 17 | 19.78 | 4.49 | 23 |
| 18 | 22.02 | 4.03 | 28 |
| 19 | 23.20 | 3.83 | 16 |
| 20 | 23.67 | 3.76 | 36 |
| 21 | 24.00 | 3.70 | 45 |
| 22 | 24.71 | 3.60 | 35 |
| 23 | 25.21 | 3.53 | 20 |
| 24 | 25.39 | 3.51 | 19 |
| 25 | 26.55 | 3.35 | 23 |
| 26 | 27.22 | 3.27 | 13 |
| 27 | 28.07 | 3.18 | 11 |
| 28 | 29.90 | 2.99 | 15 |

In some embodiments, each peak independently may include a variation of ±0.1°, ±0.2°, or ±0.3°.

In one embodiment, the disclosure provides a crystal form of voruciclib characterized by an X-ray powder diffraction pattern including one or more peaks selected from 7.30°±0.2°, 13.58°±0.2°, 14.06°±0.2°, 15.18°±0.2°, 15.66°±0.2°, 17.50°±0.2°, 18.94°±0.2°, 19.54°±0.2°, 22.22°±0.2°, 23.38°±0.2°, 24.10°±0.2°, 24.98°±0.2°, 25.94°±0.2°, 27.26°±0.2°, 28.50°±0.2°, and 32.82°±0.2° 2θ. In some embodiments, the X-ray diffraction pattern includes at least one peak, at least two peaks, at least three peaks, at least four peaks, at least five peaks, or the like, selected from the above group of peaks. In some embodiments, the crystal form includes voruciclib malonate. In some embodiments, the crystal form includes hydrated voruciclib malonate. In some embodiments, the crystal form includes anhydrous voruciclib malonate.

In one embodiment, the disclosure provides a crystal form of voruciclib characterized by an X-ray powder diffraction pattern including one or more peaks selected from 5.06°±0.2°, 6.42°±0.2°, 9.34°±0.2°, 10.14°±0.2°, 12.30°±0.2°, 13.66°±0.2°, 14.14°±0.2°, 15.82°±0.2°, 17.02°±0.2°, 19.74°±0.2°, 20.38°±0.2°, 21.82°±0.2°, 22.66°±0.2°, 24.62°±0.2°, 25.78°±0.2°, 26.58°±0.2°, 28.66°±0.2°, and 29.98°±0.2° 2θ. In some embodiments, the X-ray diffraction pattern includes at least one peak, at least two peaks, at least three peaks, at least four peaks, at least five peaks, or the like, selected from the above group of peaks. In some embodiments, the crystal form includes voruciclib dibenzoyl-tartrate. In some embodiments, the crystal form includes hydrated voruciclib dibenzoyl-tartrate. In some embodiments, the crystal form includes anhydrous voruciclib dibenzoyl-tartrate.

In one embodiment, the disclosure provides a crystal form of voruciclib characterized by an X-ray powder diffraction pattern including one or more peaks selected from 4.94°±0.2°, 6.78°±0.2°, 9.34°±0.2°, 10.94°±0.2°, 12.70°±0.2°, 13.38°±0.2°, 14.90°±0.2°, 15.66°±0.2°, 17.54°±0.2°, 18.82°±0.2°, 22.02°±0.2°, 23.98°±0.2°, 24.78°±0.2°, 25.30°±0.2°, 26.66°±0.2°, and 29.98°±0.2° 2θ. In some embodiments, the X-ray diffraction pattern includes at least one peak, at least two peaks, at least three peaks, at least four peaks, at least five peaks, or the like, selected from the above group of peaks. In some embodiments, the crystal form includes voruciclib phosphate. In some embodiments, the crystal form includes hydrated voruciclib phosphate. In some embodiments, the crystal form includes anhydrous voruciclib phosphate.

In one embodiment, the disclosure provides a crystal form of voruciclib characterized by an X-ray powder diffraction pattern including one or more peaks selected from 6.86°±0.2°, 12.66°±0.2°, 13.58°±0.2°, 14.74°±0.2°, 15.98°±0.2°, 19.38°±0.2°, 23.94°±0.2°, 24.78°±0.2°, and 25.94°±0.2° 2θ. In some embodiments, the X-ray diffraction pattern includes at least one peak, at least two peaks, at least three peaks, at least four peaks, at least five peaks, or the like, selected from the above group of peaks. In some embodiments, the crystal form includes voruciclib oxalate. In some embodiments, the crystal form includes hydrated voruciclib oxalate. In some embodiments, the crystal form includes anhydrous voruciclib oxalate.

In one embodiment, the disclosure provides a crystal form of voruciclib characterized by an X-ray powder diffraction pattern including one or more peaks selected from 9.02°±0.2°, 10.50°±0.2°, 11.06°±0.2°, 12.30°±0.2°, 12.82°±0.2°, 13.90°±0.2°, 14.82°±0.2°, 15.30°±0.2°, 15.94°±0.2°, 17.26°±0.2°, 19.34°±0.2°, 20.62°±0.2°, 22.18°±0.2°, 22.86°±0.2°, 24.58°±0.2°, 25.42°±0.2°, 25.86°±0.2°, 27.38°±0.2°, and 28.66°±0.2° 2θ. In some embodiments, the X-ray diffraction pattern includes at least one peak, at least two peaks, at least three peaks, at least four peaks, at least five peaks, or the like, selected from the above group of peaks. In some embodiments, the crystal form includes voruciclib napadisylate. In some embodiments, the crystal form includes hydrated voruciclib napadisylate. In some embodiments, the crystal form includes anhydrous voruciclib napadisylate.

Pharmaceutical Compositions

In an embodiment, the invention provides a pharmaceutical composition comprising a crystalline form of the voruciclib free base. In an embodiment, the invention provides a pharmaceutical composition comprising a crystalline form of a voruciclib salt. The pharmaceutical compositions are typically formulated to provide a therapeutically effective amount of a solid form of voruciclib as the active ingredient, or a pharmaceutically acceptable salt, ester, prodrug, solvate, hydrate or derivative thereof. Where desired, the pharmaceutical compositions contains a pharmaceutically acceptable salt thereof, and one or more pharmaceutically acceptable excipients, carriers, including inert solid diluents and fillers, diluents, permeation enhancers, solubilizers, or adjuvants. The pharmaceutical compositions may also contain an acidulant, as described herein.

In some embodiments, the concentration of a solid form of voruciclib, including any voruciclib free base polymorph described herein, or any voruciclib salt polymorph described herein, provided in the pharmaceutical compositions of the invention, is independently less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, or 0.001% w/w, w/v, or v/v, relative to the total mass or volume of the pharmaceutical composition. In an embodiment, the solid form of voruciclib is selected from voruciclib malonate, voruciclib dibenzoyl-tartrate, voruciclib phosphate, voruciclib oxalate, and voruciclib napadisylate, each as described herein.

In some embodiments, the concentration of a solid form of voruciclib, including any voruciclib free base polymorph described herein, or any voruciclib salt polymorph described herein, provided in the pharmaceutical compositions of the invention is independently greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, or 0.001% w/w, w/v, or v/v, relative to the total mass or volume of the pharmaceutical composition. In an embodiment, the solid form of voruciclib is selected from voruciclib malonate, voruciclib dibenzoyl-tartrate, voruciclib phosphate, voruciclib oxalate, and voruciclib napadisylate, each as described herein.

In some embodiments, the concentration of a solid form of voruciclib, including any voruciclib free base polymorph described herein, or any voruciclib salt polymorph described herein, is independently in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12% or approximately 1% to approximately 10% w/w, w/v or v/v, relative to the total mass or volume of the pharmaceutical composition. In an embodiment, the solid form of voruciclib is selected from voruciclib malonate, voruciclib dibenzoyl-tartrate, voruciclib phosphate, voruciclib oxalate, and voruciclib napadisylate, each as described herein.

In some embodiments, the concentration of voruciclib, including any voruciclib free base polymorph described herein, or any voruciclib salt polymorph described herein, is independently in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v, or v/v, relative to the total mass or volume of the pharmaceutical composition. In an embodiment, the solid form of voruciclib is selected from voruciclib malonate, voruciclib dibenzoyl-tartrate, voruciclib phosphate, voruciclib oxalate, and voruciclib napadisylate, each as described herein.

In some embodiments, the amount of voruciclib, including any voruciclib free base polymorph described herein, or any voruciclib salt polymorph described herein, is independently equal to or less than 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g or 0.0001 g. In an embodiment, the solid form of In some embodiments, the amount of a solid form of voruciclib, including any voruciclib free base polymorph described herein, or any voruciclib salt polymorph described herein, is independently more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, or 3 g. In an embodiment, the solid form of voruciclib is selected from voruciclib malonate, voruciclib dibenzoyl-tartrate, voruciclib phosphate, voruciclib oxalate, and voruciclib napadisylate, each as described herein.

Each of the solid forms of voruciclib, including any voruciclib free base polymorph described herein, or any voruciclib salt polymorph described herein, is effective over a wide dosage range. For example, in the treatment of adult humans, dosages independently range from 0.01 to 1000 mg, from 0.5 to 100 mg, from 1 to 50 mg per day, from 2 to 40 mg per day, and from 5 to 25 mg per day are examples of dosages that may be used. The exact dosage will depend upon the route of administration, the form in which the compound is administered, the gender and age of the subject to be treated, the body weight of the subject to be treated, and the preference and experience of the attending physician. In an embodiment, the solid form of voruciclib is selected from voruciclib malonate, voruciclib dibenzoyl-tartrate, voruciclib phosphate, voruciclib oxalate, and voruciclib napadisylate, each as described herein.

In selected embodiments, the invention provides a pharmaceutical composition for oral administration containing voruciclib, including any voruciclib free base polymorph described herein, or any voruciclib salt polymorph described herein, and a pharmaceutical excipient suitable for oral administration. In an embodiment, the solid form of voruciclib is selected from voruciclib malonate, voruciclib dibenzoyl-tartrate, voruciclib phosphate, voruciclib oxalate, and voruciclib napadisylate, each as described herein.

In selected embodiments, the invention provides a solid pharmaceutical composition for oral administration containing: (i) an effective amount of voruciclib, including any voruciclib free base polymorph described herein, or any voruciclib salt polymorph described herein, and (ii) a pharmaceutical excipient suitable for oral administration. In selected embodiments, the composition further contains (iii) an effective amount of another active pharmaceutical ingredient. In an embodiment, the solid form of voruciclib is selected from voruciclib malonate, voruciclib dibenzoyl-tartrate, voruciclib phosphate, voruciclib oxalate, and voruciclib napadisylate, each as described herein.

In selected embodiments, the pharmaceutical composition may be a liquid pharmaceutical composition suitable for oral consumption. Pharmaceutical compositions of the invention suitable for oral administration can be presented as discrete dosage forms, such as capsules, sachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil emulsion. Pharmaceutical compositions of the invention also include powder for reconstitution, powders for oral consumptions, bottles (such as powder or liquid in bottle), orally dissolving films, lozenges, pastes, tubes, gums, and packs. Such dosage forms can be prepared by any of the methods of pharmacy, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The invention further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

Each of the solid forms of voruciclib, including any voruciclib free base polymorph described herein, or any voruciclib salt polymorph described herein, can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, sodium cross carmelose, magnesium stearate, diluents, granulating agents, lubricants, glidants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium stearyl fumarate, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, silicified microcrystalline cellulose, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

An empirical parameter used to characterize the relative hydrophilicity and hydrophobicity of non-ionic amphiphilic compounds is the hydrophilic-lipophilic balance ("HLB" value). A suitable hydrophilic surfactant may generally have an HLB value of at least 10, while suitable lipophilic surfactants may generally have an HLB value of or less than about 10. Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyllactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acyllactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10-oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols, glycerol fatty acid esters, acetylated glycerol fatty acid esters, lower alcohol fatty acids esters, propylene glycol fatty acid esters, sorbitan fatty acid esters, polyethylene glycol sorbitan fatty acid esters, sterols and sterol derivatives, polyoxyethylated sterols and sterol derivatives, polyethylene glycol alkyl ethers, sugar ethers, sugar esters, lactic acid derivatives of mono- and di-glycerides, and hydrophobic transesterification products of a polyol with at least one member of the group consisting of glycerides, vegetable oils, hydrogenated vegetable oils, fatty acids and sterols, oil-soluble vitamins/vitamin derivatives, and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In an embodiment, the composition may include a solubilizer to ensure good solubilization and/or dissolution of the compound of the present invention and to minimize precipitation of the compound of the present invention. This can be especially important for compositions for non-oral use— e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, xylitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, .epsilon.-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1%, or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the pharmaceutical composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals and alkaline earth metals. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, and uric acid.

Dosages and Dosing Regimens

The amounts of the solid form of voruciclib, including any voruciclib free base polymorph described herein, or any voruciclib salt polymorph described herein, administered will be dependent on the mammal being treated, the severity of the disorder or condition, the rate of administration, the disposition of the compounds and the discretion of the prescribing physician. However, an effective dosage is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect, for example by dividing such larger doses into several small doses for administration throughout the day.

In selected embodiments, a solid form of voruciclib, including any voruciclib free base polymorph described herein, or any voruciclib salt polymorph described herein, is administered in a single dose. Typically, such administration will be by injection, for example by intravenous injection, in order to introduce the active pharmaceutical ingredients quickly. However, other routes may be used as appropriate. A single dose of a solid form of voruciclib, including any voruciclib free base polymorph described herein, or any voruciclib salt polymorph described herein, may also be used for treatment of an acute condition.

In selected embodiments, a solid form of voruciclib, including any voruciclib free base polymorph described herein, or any voruciclib salt polymorph described herein, is administered in multiple doses. Dosing may be about once, twice, three times, four times, five times, six times, or more than six times per day. Dosing may be about once a month, once every two weeks, once a week, or once every other day. In other embodiments, a solid form of voruciclib, including any voruciclib free base polymorph described herein, or any voruciclib salt polymorph described herein, is administered about once per day to about 6 times per day. In another embodiment the administration of the solid forms of voruciclib, including any voruciclib free base polymorph described herein, or any voruciclib salt polymorph described herein, continues for less than about 7 days. In yet another embodiment the administration continues for more than about 6, 10, 14, 28 days, two months, six months, or one year. In some cases, continuous dosing is achieved and maintained as long as necessary. In an embodiment, the solid form of voruciclib is selected from voruciclib malonate, voruciclib dibenzoyl-tartrate, voruciclib phosphate, voruciclib oxalate, and voruciclib napadisylate, each as described herein.

Administration of the active pharmaceutical ingredients of the invention may continue as long as necessary. In selected embodiments, a solid form of voruciclib, including any voruciclib free base polymorph described herein, or any voruciclib salt polymorph described herein, is administered for more than 1, 2, 3, 4, 5, 6, 7, 14, or 28 days. In some embodiments, the solid forms of voruciclib, including any voruciclib free base polymorph described herein, or any voruciclib salt polymorph described herein, are administered for less than 28, 14, 7, 6, 5, 4, 3, 2, or 1 day. In selected embodiments, a solid form of voruciclib, including any voruciclib free base polymorph described herein, or any voruciclib salt polymorph described herein, is administered chronically on an ongoing basis—e.g., for the treatment of chronic effects. In an embodiment, the solid form of voruciclib, in any of the foregoing embodiments is selected from voruciclib malonate, voruciclib dibenzoyl-tartrate, voruciclib phosphate, voruciclib oxalate, and voruciclib napadisylate, each as described herein.

In some embodiments, an effective dosage of voruciclib, including any voruciclib free base polymorph described herein, or any voruciclib salt polymorph described herein, is in the range of about 1 mg to about 500 mg, about 10 mg to about 300 mg, about 20 mg to about 250 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg. In some embodiments, an effective dosage of a solid form of voruciclib, including any voruciclib free base polymorph described herein, or any voruciclib salt polymorph described herein, is about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg. In some embodiments, an effective dosage of a solid form of voruciclib, including any voruciclib free base polymorph described herein, or any voruciclib salt polymorph described herein, is 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, or 500 mg. In an embodiment, the solid form of voruciclib in any of the foregoing embodiments is selected from voruciclib malonate, voruciclib dibenzoyl-tartrate, voruciclib phosphate, voruciclib oxalate, and voruciclib napadisylate, each as described herein.

In some embodiments, an effective dosage of voruciclib, including any voruciclib free base polymorph described herein, or any voruciclib salt polymorph described herein, is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg. In some embodiments, an effective dosage of a solid form of voruciclib, including any voruciclib free base polymorph described herein, or any voruciclib salt polymorph described herein, is about 0.35 mg/kg, about 0.7 mg/kg, about 1 mg/kg, about 1.4 mg/kg, about 1.8 mg/kg, about 2.1 mg/kg, about 2.5 mg/kg, about 2.85 mg/kg, about 3.2 mg/kg, or about 3.6 mg/kg. In an embodiment, the solid form of voruciclib in any of the foregoing embodiments is selected from voruciclib malonate, voruciclib dibenzoyl-tartrate, voruciclib phosphate, voruciclib oxalate, and voruciclib napadisylate, each as described herein.

In some embodiments, a solid form of voruciclib, including any voruciclib free base polymorph described herein, or any voruciclib salt polymorph described herein, is administered at a dosage of 10 to 400 mg once daily (QD), including a dosage of 5 mg, 10 mg, 12.5 mg, 25 mg, 50 mg, 75 mg, 100 mg, 150 mg, 175 mg, 200 mg, 225 mg, 250 mg, 275 mg, 300 mg, 325 mg, 350 mg, 375 mg, 400 mg, 425 mg, 450 mg, 475 mg, and 500 mg once daily (QD). In an embodiment, the solid form of voruciclib in any of the foregoing embodiments is selected from voruciclib malonate, voruciclib dibenzoyl-tartrate, voruciclib phosphate, voruciclib oxalate, and voruciclib napadisylate, each as described herein.

In some embodiments, a solid form of voruciclib, including any voruciclib free base polymorph described herein, or any voruciclib salt polymorph described herein, is administered at a dosage of 10 to 400 mg BID, including a dosage of 5 mg, 10 mg, 12.5 mg, 25 mg, 50 mg, 75 mg, 100 mg, 150 mg, 175 mg, 200 mg, 225 mg, 250 mg, 275 mg, 300 mg, 325 mg, 350 mg, 375 mg, 400 mg, 425 mg, 450 mg, 475 mg, and 500 mg BID. In an embodiment, the solid form of voruciclib in any of the foregoing embodiments is selected from voruciclib malonate, voruciclib dibenzoyl-tartrate, voruciclib phosphate, voruciclib oxalate, and voruciclib napadisylate, each as described herein.

In some embodiments, a solid form of voruciclib, including any voruciclib free base polymorph described herein, or any voruciclib salt polymorph described herein, is administered at a dosage of 10 to 400 mg TID, including a dosage of 5 mg, 10 mg, 12.5 mg, 25 mg, 50 mg, 75 mg, 100 mg, 150 mg, 175 mg, 200 mg, 225 mg, 250 mg, 275 mg, 300 mg, 325 mg, 350 mg, 375 mg, 400 mg, 425 mg, 450 mg, 475 mg, and 500 mg TID. In an embodiment, the solid form of voruciclib in any of the foregoing embodiments is selected from voruciclib malonate, voruciclib dibenzoyl-tartrate, voruciclib phosphate, voruciclib oxalate, and voruciclib napadisylate, each as described herein.

An effective amount of a solid form of voruciclib, including any voruciclib free base polymorph described herein, or any voruciclib salt polymorph described herein, may be administered in either single or multiple doses by any of the accepted modes of administration of active pharmaceutical ingredients having similar utilities, including rectal, buccal, intranasal and transdermal routes, by intra-arterial injection, intravenously, intraperitoneally, parenterally, intramuscularly, subcutaneously, orally, topically, or as an inhalant.

Pharmaceutical Compositions for Overcoming the Effects of Acid Reducing Agents

The compositions and methods described herein can be used to overcome the effects of acid reducing agents. Acid-reducing agents can greatly limit the exposure of weakly acidic drugs in mammals. Smelick, et al., *Mol. Pharmaceutics* 2013, 10, 4055-4062. Acid reducing agents include proton pump inhibitors, such as omeprazole, esomeprazole, lansoprazole, dexlansoprazole, pantoprazole, rabeprazole, and ilaprazole; H2 receptor antagonists, such as cimetidine, ranitidine, and famotidine; and antacids such as bicarbonates, carbonates, and hydroxides of aluminum, calcium, magnesium, potassium, and sodium, as well as mixtures of antacids with agents targeting mechanisms of gastric secretion. Overcoming the effects of acid reducing agents is a significant issue in the treatment of patients with cancer, inflammatory diseases, immune diseases, and autoimmune diseases, since these patients are commonly co-administered acid reducing agents for gastric irritation that often accompanies their conditions, because acid reducing agents are some of the most commonly prescribed medications in North America and Western Europe. Most recently approved oral cancer therapeutics have pH-dependent solubility and thus a potential drug-drug interaction with regards to acid reducing agents. In cancer patients, it is estimated that 20-33% of all patients are using some form of acid-reducing agent. In particular cancers, such as pancreatic cancer or gastrointestinal cancers, acid reducing agent use is as high as 60-80% of patients. Smelick, et al., *Mol. Pharmaceutics* 2013, 10, 4055-4062.

In an embodiment, a pharmaceutical composition comprises voruciclib, including any voruciclib free base polymorph described herein, or any voruciclib salt polymorph described herein, and an acidulant. In an embodiment, a pharmaceutical composition comprises voruciclib, including any voruciclib free base polymorph described herein, or any voruciclib salt polymorph described herein, and an acidulant selected from the group consisting of fumaric acid, tartaric acid, ascorbic acid, alginic acid, sodium alginate, potassium alginate, and Carbopol 971P (carboxypolymethylene). In an embodiment, a pharmaceutical composition comprises voruciclib, including any voruciclib free base polymorph described herein, or any voruciclib salt polymorph described herein, and an acidulant selected from the group consisting of fumaric acid, succinic acid, D-tartaric acid, L-tartaric acid, racemic tartaric acid, ascorbic acid, isoascorbic acid (also known as erythorbic acid and D-araboascorbic acid), alginic acid, Protacid F 120 NM, Protacid AR 1112 (also known as Kelacid NF), Carbomer 941 (polyacrylic acid), and Carbopol 971P (carboxypolymethylene). In an embodiment, the solid form of voruciclib in any of the foregoing embodiments is selected from voruciclib malonate, voruciclib dibenzoyl-tartrate, voruciclib phosphate, voruciclib oxalate, and voruciclib napadisylate, each as described herein. In an embodiment, the acidulant is extragranular. In an embodiment, the acidulant is intragranular.

Alginic acid is a polysaccharide copolymer, $\beta$-D-mannuronic acid (M) and $\alpha$-L-guluronic acid (G) linked by 1-4 glycosidic bonds. In an embodiment, a pharmaceutical composition comprises voruciclib, including any voruciclib free base polymorph described herein, or any voruciclib salt polymorph described herein, and an acidulant that is an alginic acid or salt thereof, wherein the alginic acid or salt thereof exhibits an M/G ratio selected from the group consisting of between 0.1 and 0.5, between 0.2 and 0.6, between 0.3 and 0.7, between 0.4 and 0.8, between 0.5 and 0.9, between 0.6 and 1.0, between 0.7 and 1.1, between 0.8 and 1.2, between 0.9 and 1.3, between 1.0 and 1.4, between 1.1 and 1.5, between 1.2 and 1.6, between 1.3 and 1.7, between 1.4 and 1.8, between 1.5 and 1.9, between 1.6 and 2.0, between 1.7 and 2.1, between 1.8 and 2.2, between 1.9 and 2.3, between 2.0 and 2.4, and between 2.1 and 2.5. In an embodiment, a pharmaceutical composition comprises voruciclib, including any voruciclib free base polymorph described herein, or any voruciclib salt polymorph described herein, and an acidulant that is an alginic acid or salt thereof, wherein the alginic acid or salt thereof exhibits an M/G ratio selected from the group consisting of less than 0.5, less than 1.0, less than 1.5, less than 2.0, and less than 2.5. In an embodiment, a pharmaceutical composition comprises voruciclib, including any voruciclib free base polymorph described herein, or any voruciclib salt polymorph described herein, and an acidulant that is an alginic acid or salt thereof, wherein the alginic acid or salt thereof exhibits an M/G ratio selected from the group consisting of greater than 0.5, greater than 1.0, greater than 1.5, greater than 2.0, and greater than 2.5. In an embodiment, a pharmaceutical composition comprises voruciclib, including any voruciclib free base polymorph described herein, or any voruciclib salt polymorph described herein, and an acidulant that is an alginic acid or salt thereof, wherein the alginic acid or salt thereof exhibits an M/G ratio selected from the group consisting of 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, and 2.5. In an embodiment, the solid form of voruciclib in any of the foregoing embodiments is selected from voruciclib malonate, voruciclib dibenzoyl-tartrate, voruciclib phosphate, voruciclib oxalate, and voruciclib napadisylate, each as described herein.

M/G ratio, as well as the fraction of M and G groups, the fractions of MM and GG "diads," the fractions of "triads" (e.g., MGG), and the fractions of larger sequences of M and G groups, may be determined by methods known to those of ordinary skill in the art, including nuclear magnetic resonance (NMR) spectroscopy (with or without digestion) and mass spectrometry. Larsen, et al., *Carbohydr. Res.*, 2003, 338, 2325-2336.

In an embodiment, a pharmaceutical composition comprises voruciclib, including any voruciclib free base polymorph described herein, or any voruciclib salt polymorph described herein, and an acidulant in a concentration (% mass) selected from the group consisting of between 1% and 5%, between 5% and 10%, between 10% and 15%, between 15% and 20%, between 20% and 25%, between 25% and 30%, and between 30% and 35%. In an embodiment, a pharmaceutical composition comprises voruciclib, including any voruciclib free base polymorph described herein, or any voruciclib salt polymorph described herein, and an acidulant in a concentration (% mass) selected from the group consisting of between 1% and 5%, between 5% and 10%, between 10% and 15%, between 15% and 20%, between 20% and 25%, between 25% and 30%, and between 30% and 35%, wherein the acidulant is selected from the group consisting of fumaric acid, succinic acid, D-tartaric acid, L-tartaric acid, racemic tartaric acid, ascorbic acid, isoascorbic acid (also known as erythorbic acid and D-araboascorbic acid), alginic acid, sodium alginate, potassium alginate, Protacid F 120 NM, Protacid AR 1112 (also known as Kelacid NF), and Carbopol 971P (carboxypolymethylene). In an embodiment, the solid form of voruciclib in any of the foregoing embodiments is selected from voruciclib malonate, voruciclib dibenzoyl-tartrate, voruciclib phosphate, voruciclib oxalate, and voruciclib napadisylate, each as described herein.

In an embodiment, a pharmaceutical composition comprises voruciclib, including any voruciclib free base polymorph described herein, or any voruciclib salt polymorph described herein, and an acidulant in a concentration (% mass) selected from the group consisting of less than 1%, less than 5%, less than 10%, less than 15%, less than 20%, less than 25%, less than 30%, and less than 35%. In an embodiment, a pharmaceutical composition comprises voruciclib, including any voruciclib free base polymorph described herein, or any voruciclib salt polymorph described herein, and an acidulant in a concentration (% mass) selected from the group consisting of less than 1%, less than 5%, less than 10%, less than 15%, less than 20%, less than 25%, less than 30%, and less than 35%, wherein the acidulant is selected from the group consisting of fumaric acid, succinic acid, D-tartaric acid, L-tartaric acid, racemic tartaric acid, ascorbic acid, isoascorbic acid (also known as erythorbic acid and D-araboascorbic acid), alginic acid, sodium alginate, potassium alginate, Protacid F 120 NM, Protacid AR 1112 (also known as Kelacid NF), and Carbopol 971P (carboxypolymethylene). In an embodiment, the solid form of voruciclib in any of the foregoing embodiments is selected from voruciclib malonate, voruciclib dibenzoyl-tartrate, voruciclib phosphate, voruciclib oxalate, and voruciclib napadisylate, each as described herein.

In an embodiment, a pharmaceutical composition comprises voruciclib, including any voruciclib free base polymorph described herein, or any voruciclib salt polymorph described herein, and an acidulant in a concentration (% mass) selected from the group consisting of greater than 1%, greater than 5%, greater than 10%, greater than 15%, greater than 20%, greater than 25%, greater than 30%, and greater than 35%. In an embodiment, a pharmaceutical composition comprises voruciclib, including any voruciclib free base polymorph described herein, or any voruciclib salt polymorph described herein, and an acidulant in a concentration (% mass) selected from the group consisting of greater than 1%, greater than 5%, greater than 10%, greater than 15%, greater than 20%, greater than 25%, greater than 30%, and greater than 35%, wherein the acidulant is selected from the group consisting of fumaric acid, succinic acid, D-tartaric acid, L-tartaric acid, racemic tartaric acid, ascorbic acid, isoascorbic acid (also known as erythorbic acid and D-araboascorbic acid), alginic acid, sodium alginate, potassium alginate, Protacid F 120 NM, Protacid AR 1112 (also known as Kelacid NF), and Carbopol 971P (carboxypolymethylene). In an embodiment, the solid form of voruciclib in any of the foregoing embodiments is selected from voruciclib malonate, voruciclib dibenzoyl-tartrate, voruciclib phosphate, voruciclib oxalate, and voruciclib napadisylate, each as described herein.

In an embodiment, a pharmaceutical composition comprises voruciclib, including any voruciclib free base polymorph described herein, or any voruciclib salt polymorph described herein, and an acidulant in a concentration (% mass) selected from the group consisting of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, and about 40%. In an embodiment, a pharmaceutical composition comprises voruciclib, including any voruciclib free base polymorph described herein, or any voruciclib salt polymorph described herein, and an acidulant in a concentration (% mass) selected from the group consisting of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, and about 40%, wherein the acidulant is selected from the group consisting of fumaric acid, succinic acid, D-tartaric acid, L-tartaric acid, racemic tartaric acid, ascorbic acid, isoascorbic acid (also known as erythorbic acid and D-araboascorbic acid), alginic acid, sodium alginate, potassium alginate, Protacid F 120 NM, Protacid AR 1112 (also known as Kelacid NF), and Carbopol 971P (carboxypolymethylene). In an embodiment, the solid form of voruciclib in any of the foregoing embodiments is selected from voruciclib malonate, voruciclib dibenzoyl-tartrate, voruciclib phosphate, voruciclib oxalate, and voruciclib napadisylate, each as described herein.

In an embodiment, a pharmaceutical composition comprises voruciclib, including any voruciclib free base polymorph described herein, or any voruciclib salt polymorph described herein, and an extragranular acidulant, wherein the extragranular acidulant is selected from the group consisting of fumaric acid, succinic acid, D-tartaric acid, L-tartaric acid, racemic tartaric acid, ascorbic acid, isoascorbic acid (also known as erythorbic acid and D-araboascorbic acid), alginic acid, sodium alginate, potassium alginate, Protacid F 120 NM, Protacid AR 1112 (also known as Kelacid NF), and Carbopol 971P (carboxypolymethylene), and combinations thereof. In an embodiment, a pharmaceutical composition comprises voruciclib, including any voruciclib free base polymorph described herein, or any voruciclib salt polymorph described herein, and an extragranular acidulant, wherein the extragranular acidulant is fumaric acid at a concentration of between about 15% to about 33% by weight. In an embodiment, a pharmaceutical composition comprises voruciclib, including any voruciclib free base polymorph described herein, or any voruciclib salt polymorph described herein, and an extragranular acidulant, wherein the extragranular acidulant is alginic acid or a salt thereof (such as sodium alginate or potassium alginate) at a concentration of between about 5% to about 33% by weight. In an embodiment, a pharmaceutical composition comprises voruciclib, including any voruciclib free base polymorph described herein, or any voruciclib salt polymorph described herein, and an extragranular acidulant, wherein the extragranular acidulant is L-tartaric acid at a concentration of between about 25% to about 33% by weight. In an embodiment, a pharmaceutical composition comprises voruciclib, including any voruciclib free base polymorph described herein, or any voruciclib salt polymorph described herein, and an extragranular acidulant, wherein the extragranular acidulant is ascorbic acid at a concentration of between about 20% to about 50% by weight and Carbopol 971P (carboxypolymethylene) at a concentration of between about 2.5% to about 10% by weight. In an embodiment, a pharmaceutical composition comprises voruciclib, including any voruciclib free base polymorph described herein, or any voruciclib salt polymorph described herein, and an extragranular acidulant, wherein the extragranular acidulant is fumaric acid at a concentration of between about 5% to about 15% by weight and alginic acid or a salt thereof at a concentration of about 15% to about 33% by weight. In an embodiment, a pharmaceutical composition comprises voruciclib, including any voruciclib free base polymorph described herein, or any voruciclib salt polymorph described herein, and an extragranular acidulant, wherein the extragranular acidulant is L-tartaric acid at a concentration of between about 5% to 15% by weight and alginic acid at a concentration of between about 15% to about 33% by weight.

In an embodiment, a pharmaceutical composition comprises voruciclib, including any voruciclib free base polymorph described herein, or any voruciclib salt polymorph described herein, and an acidulant, wherein the acidulant is selected from the group consisting of fumaric acid, maleic acid, phosphoric acid, L-tartaric acid, citric acid, gentisic acid, oxalic acid, and sulfuric acid. In an embodiment, a pharmaceutical composition comprises voruciclib, including any voruciclib free base polymorph described herein, or any voruciclib salt polymorph described herein, and an acidulant, wherein the acidulant is selected from the group consisting of fumaric acid, maleic acid, phosphoric acid, L-tartaric acid, citric acid, gentisic acid, oxalic acid, and sulfuric acid, and wherein the acidulant is a salt counterion included in any crystalline form described herein.

In an embodiment, in addition to an acidulant, a pharmaceutical composition includes an excipient to prolong the exposure of voruciclib, including any voruciclib free base polymorph described herein, or any voruciclib salt polymorph described herein, to the acidic microenvironment. In an embodiment, this excipient is a polymer of natural, synthetic or semisynthetic origins. The polymer may contain acidic, anionic, or non-ionic monomers, oligomers or polymers or a mixture of acidic, anionic and non-ionic monomers or copolymers. In one version the excipient is selected from the group consisting of hydroxypropylmethylcellulose, low substituted hydroxypropylcellulose, hydroxypropylcellulose, tocopherol polyethyleneoxide succinate (D-α-tocopherol polyethylene glycol succinate, TPGS, or vitamin E TPGS), methylcellulose, carboxymethylcellulose, sodium carboxymethylcellulose, methylacrylate, ethylacrylate, copolymers of methyl and ethyl acrylate, hydroxypropylmethylcellulose acetate succinate, gelatin, maize starch, pea starch, modified maize starch, potato starch, modified potato starch, sodium starch glycolate, croscarmellose, crospovidone, copovidone, polyethylene glycol, polypropylene glycol, polyethylene and polypropylene glycol copolymers, polyvinylalcohol, polyvinylalcohol and polyethylene oxide copolymers. Copolymers of the foregoing polymers, where applicable, may also be used. Copolymers may be block, branched or terminal copolymers. In an embodiment, the polymer exhibits swelling, binding, or gelling properties that inhibit the disintegration, dissolution, and erosion of the pharmaceutical composition in order to prolong dissolution or to increase total dissolution. In an embodiment, the inclusion of the polymer increases dissolution rate and extent of dissolution over the use of an acidulant alone. The swelling, binding or gelling properties are pH-dependent in one embodiment, wherein the polymer swells, binds, or gels at one pH or range of pH in a different manner than at another pH. In one embodiment this may decrease dissolution at a lower pH than at a higher pH or vice versa. In another embodiment this leads to similar dissolution of voruciclib, including any voruciclib free base polymorph described herein, or any voruciclib salt polymorph described herein, in acidic, neutral or basic pH. This leads to similar plasma exposure independent of stomach pH.

The dissolution profile of a formulation containing one or more swelling, gelling, or binding excipients may exhibit a zero, first, or second differential rate order at one or more pH value or a mixture of different rate orders at different pH values. In an embodiment, a pharmaceutical composition will provide a constant level of drug into the gastrointestinal tract of a mammal by dissolution. Where voruciclib, including any voruciclib free base polymorph described herein, or any voruciclib salt polymorph described herein, is absorbed, this leads to a sustained plasma level of drug over a period, delays the tmax, and reduces the cmax of an equivalent dose of an immediate release formulation voruciclib, including any voruciclib free base polymorph described herein, or any voruciclib salt polymorph described herein. In another embodiment this leads to similar exposure in a mammal regardless of stomach pH.

Methods of Treating Solid Tumor Cancers, Hematological Malignancies, Inflammatory Diseases, Autoimmune Disorders, Immune Disorders, and Other Diseases The pharmaceutical compositions described herein can be used in a method for treating diseases. In preferred embodiments, they are for use in treating hyperproliferative disorders. They may also be used in treating other disorders as described herein and in the following paragraphs.

In some embodiments, the invention provides a method of treating a hyperproliferative disorder in a mammal that comprises administering to the mammal a therapeutically effective amount of a crystalline solid form of voruciclib, including any voruciclib free base polymorph described herein, or any voruciclib salt polymorph described herein, or a pharmaceutical composition comprising a crystalline solid form of voruciclib, including any voruciclib free base polymorph described herein, or any voruciclib salt polymorph described herein, as described herein. In preferred embodiments, the mammal is a human. In some embodiments, the hyperproliferative disorder is cancer. In preferred embodiments, the cancer is selected from the group consisting of chronic lymphocytic leukemia, non-Hodgkin's lymphoma, diffuse large B-cell lymphoma, mantle cell lymphoma, follicular lymphoma, and Waldenström's macroglobulinemia. In preferred embodiments, the cancer is selected from the group consisting of non-Hodgkin's lymphomas (such as diffuse large B-cell lymphoma), acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, bone (e.g., metastatic bone), esophageal, testicular, gynecological, thyroid, CNS, PNS, AIDS-related (e.g., lymphoma and Kaposi's sarcoma), viral-induced cancers such as cervical carcinoma (human papillomavirus), B-cell lymphoproliferative disease and nasopharyngeal carcinoma (Epstein-Barr virus), Kaposi's sarcoma and primary effusion lymphomas (Kaposi's sarcoma herpesvirus), hepatocellular carcinoma (hepatitis B and hepatitis C viruses), and T-cell leukemias (Human T-cell leukemia virus-1), B cell acute lymphoblastic leukemia, Burkitt's leukemia, juvenile myelomonocytic leukemia, hairy cell leukemia, Hodgkin's disease, multiple myeloma, mast cell leukemia, and mastocytosis. In selected embodiments, the method relates to the treatment of a non-cancerous hyperproliferative disorder such as benign hyperplasia of the skin (e.g., psoriasis), restenosis, or prostate conditions (e.g., benign prostatic hypertrophy (BPH)). In some embodiments, the hyperproliferative disorder is an inflammatory, immune, or autoimmune disorder. In some embodiments, the hyperproliferative disorder is selected from the group consisting of tumor angiogenesis, chronic inflammatory disease, rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma and melanoma, ulcerative colitis, atopic dermatitis, pouchitis, spondylarthritis, uveitis, Behcet's disease, polymyalgia rheumatica, giant-cell arteritis, sarcoidosis, Kawasaki disease, juvenile idiopathic arthritis, hidratenitis suppurativa, Sjögren's syndrome, psoriatic arthritis, juvenile rheumatoid arthritis, ankylosing spondylitis, Crohn's disease, lupus, and lupus nephritis. In an embodiment, the solid form of voruciclib, including any voruciclib free base polymorph described herein, or any voruciclib salt polymorph described herein, in any of the foregoing embodiments is selected from voruciclib malonate, voruciclib dibenzoyl-tartrate, voruciclib phosphate, voruciclib oxalate, and voruciclib napadisylate, each as described herein.

In an embodiment, the method of any of the foregoing embodiments further includes the step of administering an acid reducing agent to the mammal. In an embodiment, the acid reducing agent is selected from the group consisting of proton pump inhibitors, such as omeprazole, esomeprazole, lansoprazole, dexlansoprazole, pantoprazole, rabeprazole, and ilaprazole; $H_2$ receptor antagonists, such as cimetidine, ranitidine, and famotidine; and antacids such as bicarbonates, carbonates, and hydroxides of aluminum, calcium, magnesium, potassium, and sodium.

In some embodiments, the invention provides pharmaceutical compositions of a solid form of voruciclib, including any voruciclib free base polymorph described herein, or any voruciclib salt polymorph described herein, for use in the treatment of cancers such as thymus cancer, brain cancer (e.g., glioma), lung cancer, squamous cell cancer, skin cancer (e.g., melanona), eye cancer, retinoblastoma cancer, intraocular melanoma cancer, oral cavity cancer, oropharyngeal cancer, bladder cancer, gastric cancer, stomach cancer, pancreatic cancer, bladder cancer, breast cancer, cervical cancer, head and neck cancer, renal cancer, kidney cancer, liver cancer, ovarian cancer, prostate cancer, colorectal cancer, colon cancer, esophageal cancer, testicular cancer, gynecological cancer, ovarian cancer, thyroid cancer, CNS cancer, PNS cancer, AIDS-related cancer (e.g., lymphoma and Kaposi's sarcoma), viral-induced cancer, and epidermoid cancer. In some embodiments, the invention provides pharmaceutical compositions of a solid form of voruciclib, including any voruciclib free base polymorph described herein, or any voruciclib salt polymorph described herein, for the treatment of a non-cancerous hyperproliferative disorder such as benign hyperplasia of the skin (e.g., psoriasis), restenosis, or prostate (e.g., benign prostatic hypertrophy (BPH)). In some embodiments, the invention provides pharmaceutical compositions of a solid form of voruciclib, including any voruciclib free base polymorph described herein, or any voruciclib salt polymorph described herein, for use in the treatment of disorders such as myeloproliferative disorders (MPDs), myeloproliferative neoplasms, polycythemia vera (PV), essential thrombocythemia (ET), primary myelofibrosis (PMF), myelodysplastic syndrome, chronic myelogenous leukemia (BCR-ABL 1-positive), chronic neutrophilic leukemia, chronic eosinophilic leukemia, or mastocytosis. The invention also provides compositions for use in treating a disease related to vasculogenesis or angiogenesis in a mammal which can manifest as tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, and hemangioma. In an embodiment, the solid form of voruciclib in any of the foregoing embodiments is selected from voruciclib malonate, voruciclib dibenzoyl-tartrate, voruciclib phosphate, voruciclib oxalate, and voruciclib napadisylate, each as described herein.

In some embodiments, the invention provides a method of treating a solid tumor cancer with a composition including a solid form of voruciclib, including any voruciclib free base polymorph described herein, or any voruciclib salt polymorph described herein. In some embodiments, the invention provides a method of treating pancreatic cancer, breast cancer, ovarian cancer, melanoma, lung cancer, squamous cell carcinoma including head and neck cancer, or a blood cancer. In an embodiment, the invention provides a method for treating pancreatic cancer, breast cancer, ovarian cancer, melanoma, lung cancer, head and neck cancer, colorectal cancer, or a blood cancer using a combination of a solid form of voruciclib, including any voruciclib free base polymorph described herein, or any voruciclib salt polymorph described herein, and a second agent selected from the group consisting of bendamustine, venetoclax, vemurafenib, abraxane, enasidenib, pomalidomide, lenalidomide, azacitidine, decitabine, a hypomethylating agent, gemcitabine, albumin-bound paclitaxel, rituximab, obinutuzumab, ofatumumab, pembrolizumab, nivolumab, durvalumab, avelumab, atezolizumab, bortezomib, marizomib, ixazomib, disulfiram, epigallocatechin-3-gallate, salinosporamide A, carfilzomib, ONX 0912, CEP-18770, MLN9708, epoxomicin, or MG13. In an embodiment, the invention provides a method for treating pancreatic cancer, breast cancer, ovarian cancer, melanoma, lung cancer, head and neck cancer, colorectal cancer, or a blood cancer using a combination of a CDK inhibitor and bendamustine, venetoclax, vemurafenib, abraxane, enasidenib, pomalidomide, lenalidomide, azacitidine, decitabine, a hypomethylating agent, gemcitabine, albumin-bound paclitaxel, rituximab, obinutuzumab, ofatumumab, pembrolizumab, nivolumab, durvalumab, avelumab, atezolizumab, For certain methods described herein, the proteasome inhibitor is selected from bortezomib, marizomib, ixazomib, disulfiram, epigallocatechin-3-gallate, salinosporamide A, carfilzomib, ONX 0912, CEP-18770, MLN9708, epoxomicin, or MG13, wherein the CDK inhibitor is a solid form of voruciclib, including any voruciclib free base polymorph described herein, or any voruciclib salt polymorph described herein. In an embodiment, the solid form of voruciclib in any of the foregoing embodiments is selected from voruciclib malonate, voruciclib dibenzoyl-tartrate, voruciclib phosphate, voruciclib oxalate, and voruciclib napadisylate, each as described herein.

In some embodiments, the invention provides a method of treating a solid tumor cancer with a composition including a solid form of voruciclib, including any voruciclib free base polymorph described herein, or any voruciclib salt polymorph described herein. In some embodiments, the invention provides a method of treating pancreatic cancer, breast cancer, ovarian cancer, melanoma, lung cancer, squamous cell carcinoma including head and neck cancer. In an embodiment, the invention provides a method for treating pancreatic cancer, breast cancer, ovarian cancer, melanoma, lung cancer, head and neck cancer, and colorectal cancer using a solid form of voruciclib, including any voruciclib free base polymorph described herein, or any voruciclib salt polymorph described herein. In an embodiment, the solid form of voruciclib in any of the foregoing embodiments is selected from voruciclib malonate, voruciclib dibenzoyl-tartrate, voruciclib phosphate, voruciclib oxalate, and voruciclib napadisylate, each as described herein.

In some embodiments, the invention relates to a method of treating an inflammatory, immune, or autoimmune disorder in a mammal with a composition including a solid form of voruciclib, including any voruciclib free base polymorph described herein, or any voruciclib salt polymorph described herein. In selected embodiments, the invention also relates to a method of treating a disease with a composition including a solid form of voruciclib, including any voruciclib free base polymorph described herein, or any voruciclib salt polymorph described herein, wherein the disease is selected from the group consisting of tumor angiogenesis, chronic inflammatory disease, rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma and melanoma, ulcerative colitis, atopic dermatitis, pouchitis, spondylarthritis, uveitis, Behcet's disease, polymyalgia rheumatica, giant-cell arteritis, sarcoidosis, Kawasaki disease, juvenile idiopathic arthritis, hidratenitis suppurativa, Sjögren's syndrome, psoriatic arthritis, juvenile rheumatoid arthritis, ankylosing spondylitis, Crohn's Disease, lupus, and lupus nephritis. In an embodiment, the solid form of voruciclib in any of the foregoing embodiments is selected from voruciclib malonate, voruciclib dibenzoyl-tartrate, voruciclib phosphate, voruciclib oxalate, and voruciclib napadisylate, each as described herein.

In some embodiments, the invention relates to a method of treating a hyperproliferative disorder in a mammal with a composition including a solid form of voruciclib, including any voruciclib free base polymorph described herein, or any voruciclib salt polymorph described herein, wherein the hyperproliferative disorder is a B cell hematological malignancy selected from the group consisting of chronic lymphocytic leukemia (CLL), small lymphocytic leukemia (SLL), non-Hodgkin's lymphoma (NHL), diffuse large B cell lymphoma (DLBCL), follicular lymphoma (FL), mantle cell lymphoma (MCL), Hodgkin's lymphoma, B cell acute lymphoblastic leukemia (B-ALL), Burkitt's lymphoma, Waldenström's macroglobulinemia (WM), Burkitt's lymphoma, multiple myeloma, myelodysplastic syndromes, or myelofibrosis. In some embodiments, the invention relates to a method of treating a hyperproliferative disorder in a mammal with a composition including a solid form of voruciclib, including any voruciclib free base polymorph described herein, or any voruciclib salt polymorph described herein, wherein the hyperproliferative disorder is selected from the group consisting of chronic myelocytic leukemia, acute myeloid leukemia, DLBCL (including activated B-cell (ABC) and germinal center B-cell (GCB) subtypes), follicle center lymphoma, Hodgkin's disease, multiple myeloma, indolent non-Hodgkin's lymphoma, and mature B-cell ALL. In an embodiment, the solid form of voruciclib in any of the foregoing embodiments is selected from voruciclib malonate, voruciclib dibenzoyl-tartrate, voruciclib phosphate, voruciclib oxalate, and voruciclib napadisylate, each as described herein.

In some embodiments, the hyperproliferative disorder is a subtype of CLL. A number of subtypes of CLL have been characterized. CLL is often classified for immunoglobulin heavy-chain variable-region ($IgV_H$) mutational status in leukemic cells. R. N. Damle, et al., *Blood* 1999, 94, 1840-47; T. J. Hamblin, et al., *Blood* 1999, 94, 1848-54. Patients with $IgV_H$ mutations generally survive longer than patients without $IgV_H$ mutations. ZAP70 expression (positive or negative) is also used to characterize CLL. L. Z. Rassenti, et al., *N. Engl. J. Med.* 2004, 351, 893-901. The methylation of ZAP-70 at CpG3 is also used to characterize CLL, for example by pyrosequencing. R. Claus, et al., *J. Clin. Oncol.* 2012, 30, 2483-91; J. A. Woyach, et al., *Blood* 2014, 123, 1810-17. CLL is also classified by stage of disease under the Binet or Rai criteria. J. L. Binet, et al., *Cancer* 1977, 40, 855-64; K. R. Rai, T. Han, *Hematol. Oncol. Clin. North Am.* 1990, 4, 447-56. Other common mutations, such as 11q deletion, 13q deletion, and 17p deletion can be assessed using well-known techniques such as fluorescence in situ hybridization (FISH). In an embodiment, the invention relates to a method of treating a CLL in a human, wherein the CLL is selected from the group consisting of $IgV_H$ mutation negative CLL, ZAP-70 positive CLL, ZAP-70 methylated at CpG3 CLL, CD38 positive CLL, chronic lymphocytic leukemia characterized by a 17p13.1 (17p) deletion, and CLL characterized by a 11q22.3 (11q) deletion.

In some embodiments, the hyperproliferative disorder is a CLL wherein the CLL has undergone a Richter's transformation. Methods of assessing Richter's transformation, which is also known as Richter's syndrome, are described in Jain and O'Brien, *Oncology*, 2012, 26, 1146-52. Richter's transformation is a subtype of CLL that is observed in 5-10% of patients. It involves the development of aggressive lymphoma from CLL and has a generally poor prognosis.

In some embodiments, the hyperproliferative disorder is a CLL or SLL in a patient, wherein the patient is sensitive to lymphocytosis. In an embodiment, the invention relates to a method of treating CLL or SLL in a patient, wherein the patient exhibits lymphocytosis caused by a disorder selected from the group consisting of a viral infection, a bacterial infection, a protozoal infection, or a post-splenectomy state. In an embodiment, the viral infection in any of the foregoing embodiments is selected from the group consisting of infectious mononucleosis, hepatitis, and cytomegalovirus. In an embodiment, the bacterial infection in any of the foregoing embodiments is selected from the group consisting of pertussis, tuberculosis, and brucellosis.

In some embodiments, the hyperproliferative disorder is a blood cancer. In certain embodiments, the blood cancer is leukemia, such as acute myeloid leukemia (AML), chronic myeloid leukemia (CML), acute lymphocytic lymphoma (ALL), and chronic lymphocytic leukemia (CLL). In certain embodiments, the blood cancer is a non-Hodgkin lymphoma, such as B-cell or T-cell lymphoma. B-cell lymphomas include diffuse large B-cell lymphoma (DLBCL), primary mediastinal B-cell lymphoma, intravascular large B-cell lymphoma, follicular lymphoma, small lymphocytic lymphomia (SLL), mantle cell lymphoma, marginal zone B-cell lymphomas, extranodal marginal zone B-cell lymphomas, nodal marginal zone B-cell lymphoma, splenic marginal zone B-cell lymphoma, Burkitt lymphoma, lymphoplasmacytic lymphoma, and primary central nervous system lymphoma. T-cell lymphomas include precursor T-lymphoblastic lymphoma, peripheral T-cell lymphomas, cutaneous T-cell lymphomas, adult T-cell lymphoma with subtypes: smoldering chronic, acute, and lymphoma, angio-immunoblastic T-cell lymphoma, extranodal natural killer/T-cell lymphoma, nasal type, enteropathy-associated intestinal T-cell lymphoma (EATL) with subtypes I and II, and anaplastic large cell lymphoma (ALCL).

EXAMPLES

Example 1: Polymorph Screen—Voruciclib HCl

The aim of this study was to explore the polymorphic landscape of voruciclib HCl and to identify the most suitable form for further development. For this purpose, an extensive polymorph screen was performed, using several crystallization methods and a variety of solvents and solvent mixtures. The amorphous phase of voruciclib was used as starting material for the screening experiments to allow unbiased crystallization to occur.

Different crystallization methods were used with a variety of solvents and solvent mixtures. The API was highly soluble in solvents with high dielectric constant and hydrogen acceptor propensities (DMF, DMSO, DMA and alcohols), in all the other solvents tested, the API was poorly soluble. Some of the polymorph screening experiments were started with an amorphous phase as starting material to allow unbiased crystallization to occur.

Without wishing to be bound by any particular theory, it is believed that although only one anhydrous and non-solvated crystalline phase was obtained directly from the several crystallization experiments (Form 1), the API showed a very complex pseudo polymorphic behavior and 20 new solid forms were identified. The crystallization of the different forms not only depends on the solvent used, but also on the crystallization method. For that reason, and without wishing to be bound by any particular theory, it is believed that even more solvated forms might exist when using different crystallization conditions. Some of the solvated forms are non-stoichiometric and can be obtained from different solvents (isostructural pseudo polymorphs).

Without wishing to be bound by any particular theory, it is believed that Form 1 is the unique stable non-solvated and anhydrous form identified herein, suggesting that Form 1 is a thermodynamically stable form. The experiments exploring the mixtures of the current process solvents (methanol, 2-propanol and diisopropyl ether) showed that the solid phase that precipitate from these solvent mixtures is Form 1, except upon evaporation of solutions where solvated forms are obtained.

Twenty (20) unique solid forms of voruciclib HCl were identified, of which Form 1 was a non-solvated and anhydrous form (identical to the starting material, with a melting point around 260° C.). All other forms appeared to be solvated forms. Upon desolvation, these forms seemed to convert to Form 1 (based on the melting event observed at 260° C. in the DSC traces) or became amorphous.

Experiments performed with the current process solvents (methanol, 2-propanol, diisopropyl ether) resulted in the crystallization of Form 1 by slurry conversion or cooling crystallization, but when solutions were evaporated, solvated forms were recovered.

From the analytical characterization performed on several batches of voruciclib HCl, a small crystalline phase impurity was identified by XRPD, possibly attributed to a solvate form.

Although only one anhydrous and non-solvated crystalline phase was crystallized in this study (Form 1), voruciclib showed a very complex pseudo-polymorphic behavior. The crystallization of the different forms not only depends on the solvent used, but also on the crystallization method. Many solvated forms are non-stoichiometric and can be obtained from different solvents (isostructural pseudo polymorphs).

The experiments exploring the mixtures of the current process solvents (methanol, 2-propanol and diisopropyl ether) showed that the solid phase crystallized from these solvent mixtures is Form 1, but from evaporation of solutions, solvated forms are obtained. Hence, during the manufacturing of voruciclib HCl there is always the risk of the formation of (traces of) a solvated form. The origin of the phase impurity found in some of the batches that were analyzed could be attributed to the evaporation of the crystallization solvent during the crystallization process, filtration or the final drying stage.

Abbreviations: AAC: Accelerated Aging Conditions (40° C. and 75% RH); Am: Amorphous; API: Active Pharmaceutical Ingredient; AS: Experiment ID for anti-solvent addition experiments; DSC: Differential Scanning Calorimetry; ECP: Experiment ID for the evaporative experiments; HPLC: High-Performance Liquid Chromatography; HR-XRPD: High Resolution X-Ray Powder Diffraction; HT-XRPD: High Throughput X-Ray Powder Diffraction; LCMS: Liquid Chromatography Mass spectroscopy; MS: Mass Spectroscopy; PSM: Experiment ID for the cooling crystallization experiments; QSA: Experiment ID for the solubility determination experiments; RH: Relative Humidity; RT: Room Temperature; SLP: Experiment ID for solvent equilibration experiments; SM: Starting Material; TCP: Experiment ID for the thermocycling experiments; TGA: Thermogravimetric Analysis; TGMS: Thermogravimetric Analysis coupled with Mass Spectroscopy; VDL: Experiment ID for the vapor diffusion experiments; ACN: Acetonitrile; DMA: N,N-Dimethylacetamide; DMF: N,N-Dimethylformamide; DMSO: Dimethyl sulfoxide; IPA: 2-Propanol; MeOH: Methanol; TBME: tert-Butyl methyl ether; TFE: 2,2,2-Trifluoroethanol; THF: Tetrahydrofuran.

Figure 1:
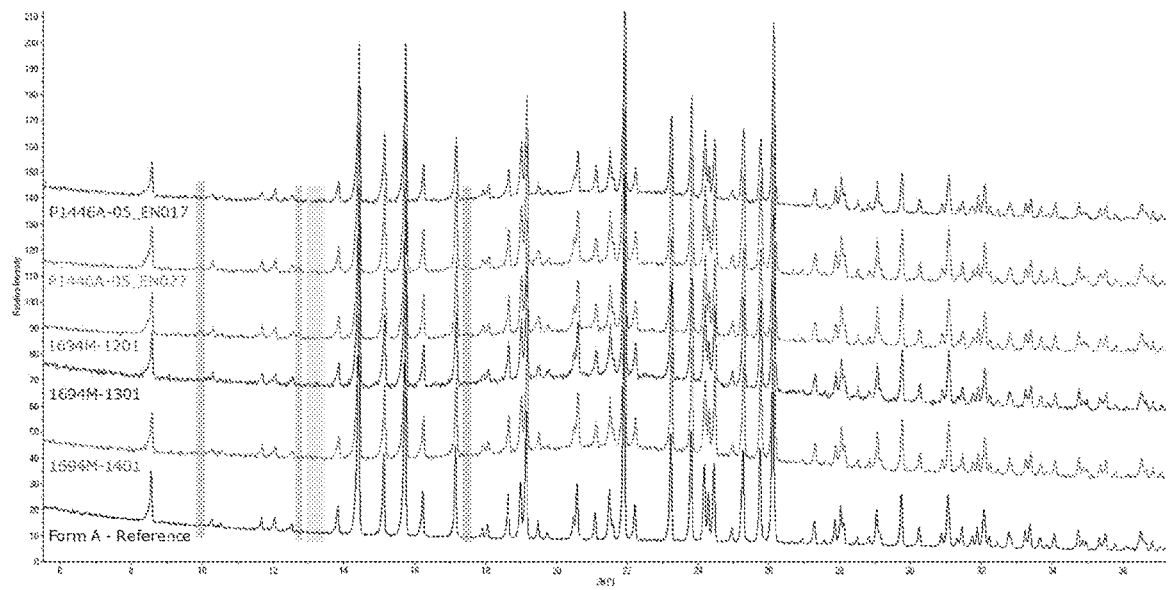
FIG. 1 illustrates a comparison of HR Powder Diffraction Patterns of five different batches of voruciclib HCl with the powder pattern of Form 1 recorded in a previous study. From bottom to top: Form 1—reference, #1694M-1401, #1694M-1301, #1694M-1201, #P1446A-05_EN027 and #P1446A-05_EN017. The orange areas highlight the diffraction peaks that could be attributed to crystalline impurities in batches 1694M-1201 and P1446A-05_EN027, while the grey area highlights a crystalline phase detected only in batch 1694M-1301.

Five batches of voruciclib HCl were used for analytical characterization which included HR-XRPD (with indexing), DSC, TGMS and LCMS. The crystalline phases were quantified from the recorded powder patterns by Rietveld analysis using the single crystal data of voruciclib HCl Form 1 obtained in a previous study. The overlay of the XRPD patterns is shown in FIG. 1 and the final Rietveld parameters are shown in Table 1. All the batches were comprised of Form 1. Batches 1694M-1401 and P1446A-05_EN017 were pure Form 1 (no other crystalline phases were detected). Batches 1694M-1301, 1694M-1201 and P1446A-05_EN027 contained about 1-2% of crystalline impurities.

TABLE 1

Final Rietveld parameters for the five batches of voruciclib HCl; the purity of the samples was determined (BDL: below detection limit)

| Batch | Rexp | Rw | Rwp | Gof | Form 1 (%) | Other (%) |
|---|---|---|---|---|---|---|
| 1694M-1401 | 2.39 | 2.99 | 2.28 | 1.25 | 100 | BDL |
| 1694M-1301 | 2.46 | 2.97 | 2.31 | 1.21 | 99 | ~1 |
| 1694M-1201 | 2.30 | 3.47 | 2.70 | 1.51 | 98 | ~2 |
| P1446A-05_EN017 | 2.38 | 2.91 | 2.25 | 1.23 | 100 | BDL |
| P1446A-05_EN027 | 2.28 | 3.18 | 2.46 | 1.40 | 99 | ~1 |

Figure 2:
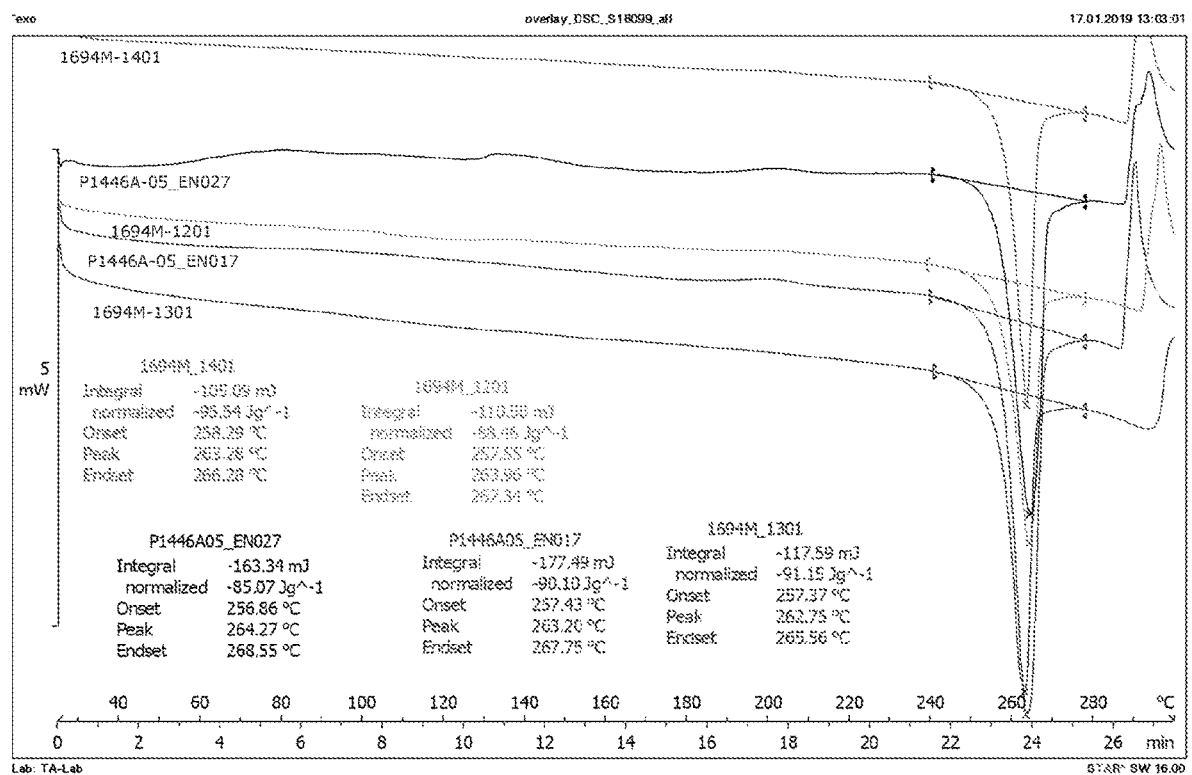
FIG. 2 illustrates DSC traces of five batches of voruciclib HCl (heating rate 10° C./min). The endothermic event, related to melting/decomposition was observed around 263° C. Batch 1694M-1401 (red), P1446A-05_EN027 (black), 1694M-1201 (green), P1446A-05_EN017 (purple) and 1694M-1301 (blue).
Figure 3:
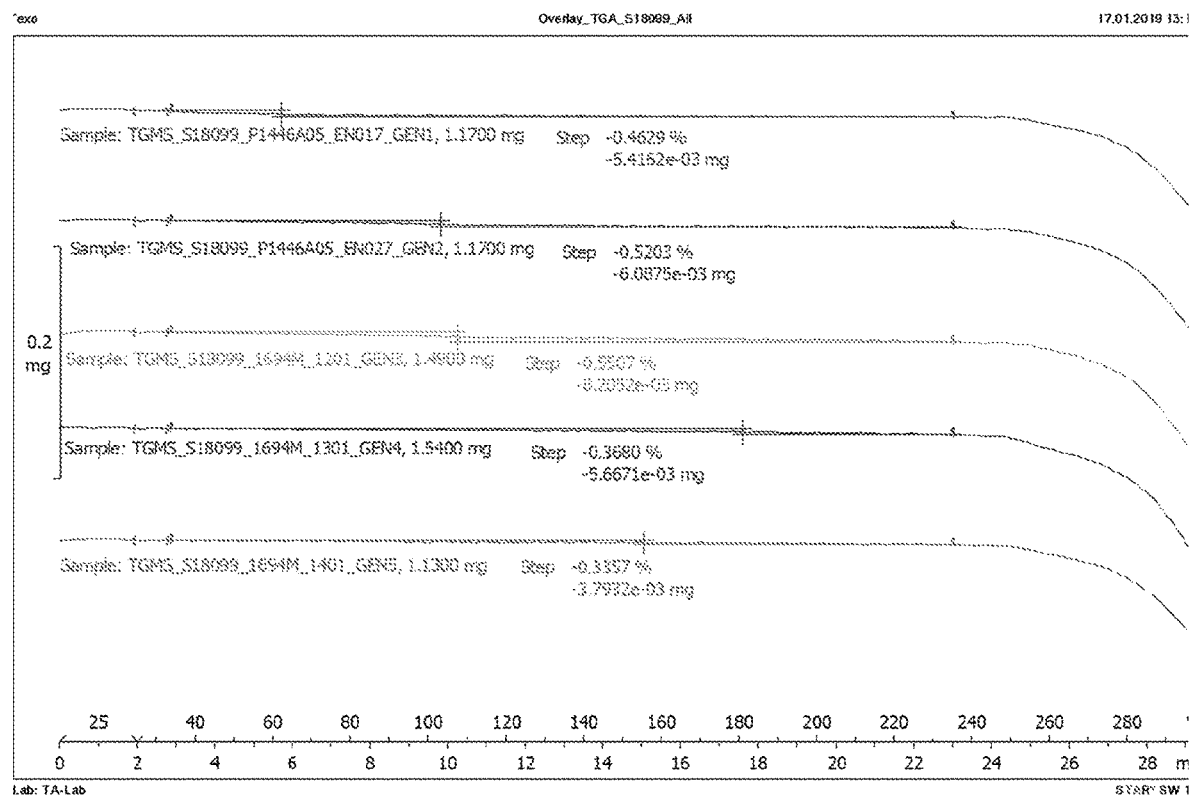
FIG. 3 illustrates the TGA analysis of five batches of voruciclib HCl (heating rate 10° C./min). The mass loss prior to decomposition varied between 0.3-0.6%. Decomposition started around 250° C. Batch P1446A-05_EN017 (brown), P1446A-05_EN027 (purple), 1694M-1201 (green), 1694M-1301 (blue) and 1694M-1401 (red).

The DSC traces showed that all five batches showed an endothermic event with an onset temperature at 257-258° C. and a peak temperature around 263-264° C. (FIG. 2). The TGA analysis of the batches revealed that the residual solvent/moisture content varied between 0.3-0.5% (FIG. 3). The decomposition started around 250° C.

The chemical purity of the API was assessed by HPLC analysis. The results are summarized in Table 2. Based on HPLC assay, the chemical purity was comparable for all the batches. The HPLC chromatogram of batch P1446A-05_EN017 showed a small shoulder in the main peak resulting in area % of 98.9%. The other batches showed one peak, resulting in area % of 100%.

TABLE 2

HPLC results of the five batches. The purity was determined by area % as well as by assay (recovery).

| API Batch ID | Mass (mg) | Area (mAu*s) | Recovery (%) | Purity (area %) |
|---|---|---|---|---|
| P1446A-05_EN017 | 2.28 | 3008.4 | 101.5 | 98.9 |
| P1446A-05_EN027 | 2.00 | 2639.9 | 101.6 | 100 |
| 1694M-1201 | 2.04 | 2677.0 | 101.0 | 100 |
| 1694M-1301 | 1.97 | 2581.6 | 100.7 | 100 |
| 1694M-1401 | 2.03 | 2664.6 | 100.8 | 100 |

The characterization of the five batches revealed that no significant differences were observed in neither thermal behavior nor chemical purity, although by XRPD three of the batches showed below 2% of crystalline impurities.

Batch 1694M-1301 of voruciclib HCl (approximately 39 grams) was used as starting material for the polymorph screen. The high throughput XRPD (HT-XRPD) is shown in FIG. for reference purposes.

Figure 5:
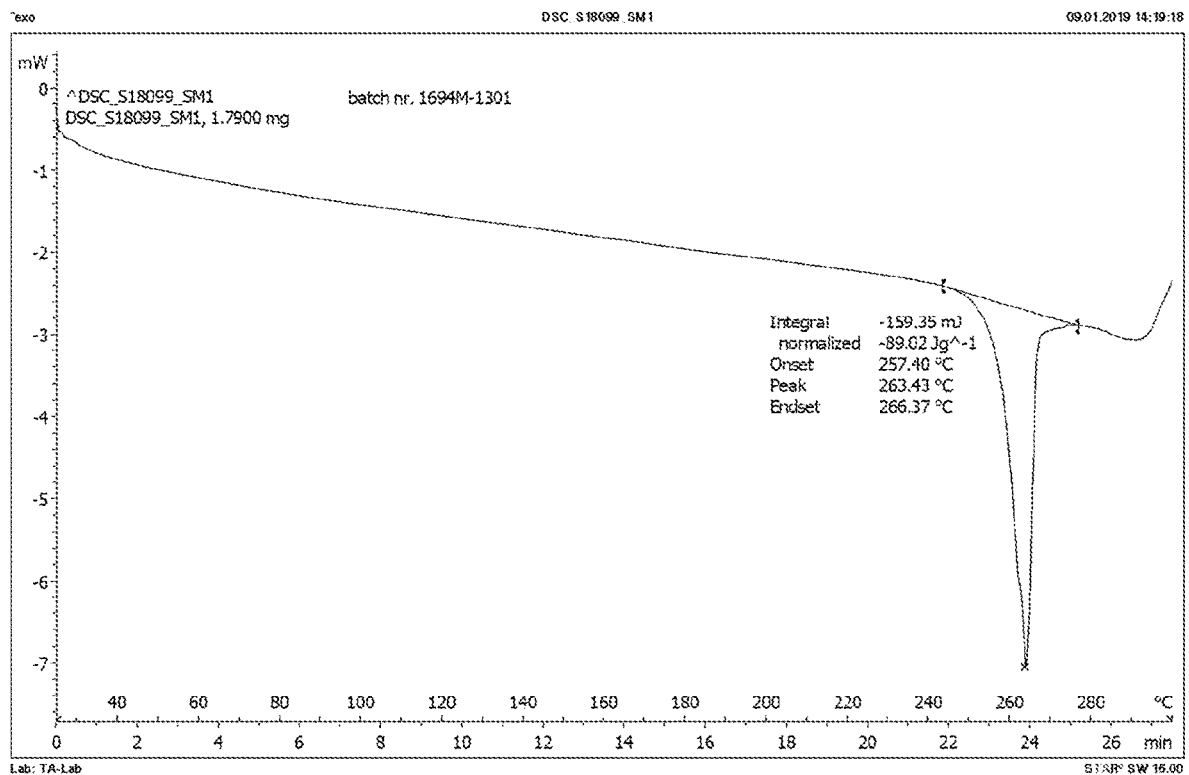
FIG. 5 illustrates the DSC trace of voruciclib HCl, batch 1694M-1301, starting material (heating rate 10° C./min). The endothermic event at Tpeak 263.4° C. could be attributed to the melting/decomposition of the compound.
Figure 6:
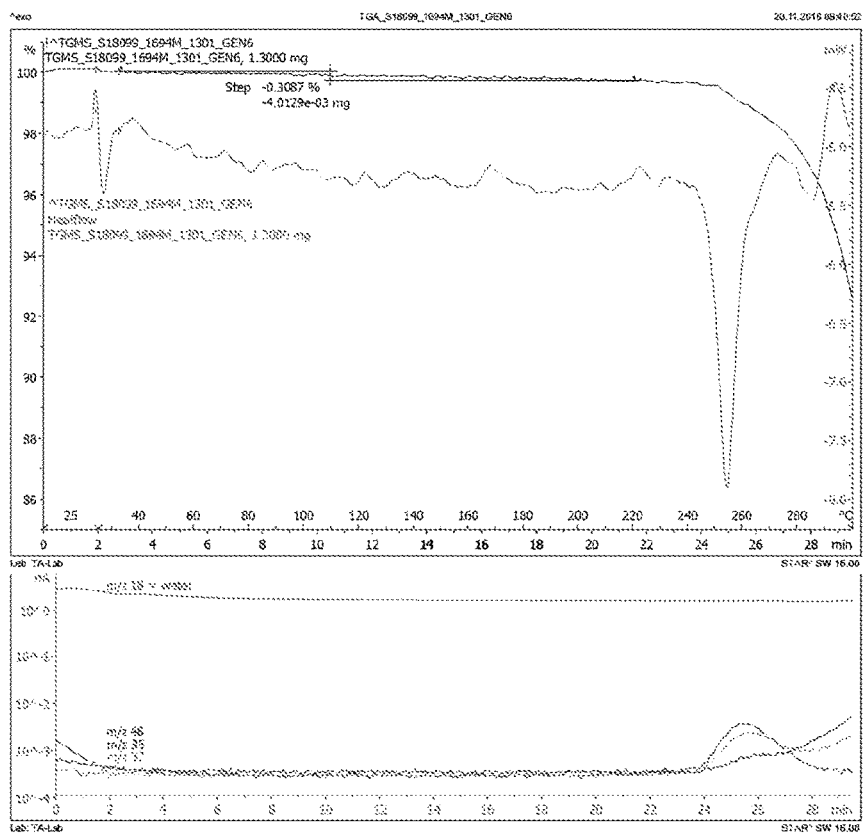
FIG. 6 illustrates the TGMS analysis of voruciclib HCl, batch 1694M-1301, starting material (heating rate 10° C./min). A mass loss of 0.3% was observed prior to decomposition. Decomposition started around 250° C., accompanied by an endothermic event in the heat flow signal.
Figure 7A:
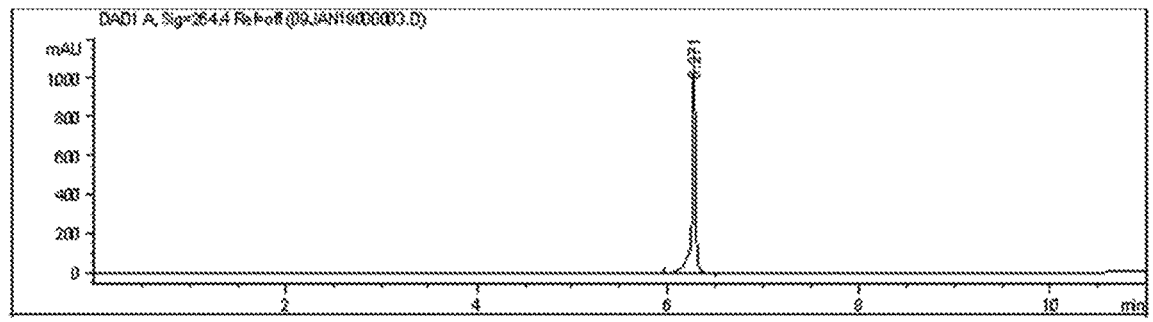
FIG. 7 illustrates the LCMS analysis of voruciclib HCL, batch 1694M-1301, starting material. The peak corresponding to the API had a retention time of 6.3 min (FIG. 7A), and the positive mass spectrum showed ions with m/z of 470.1 $(M+H)^+$ (FIG. 7B).
Figure 7B:
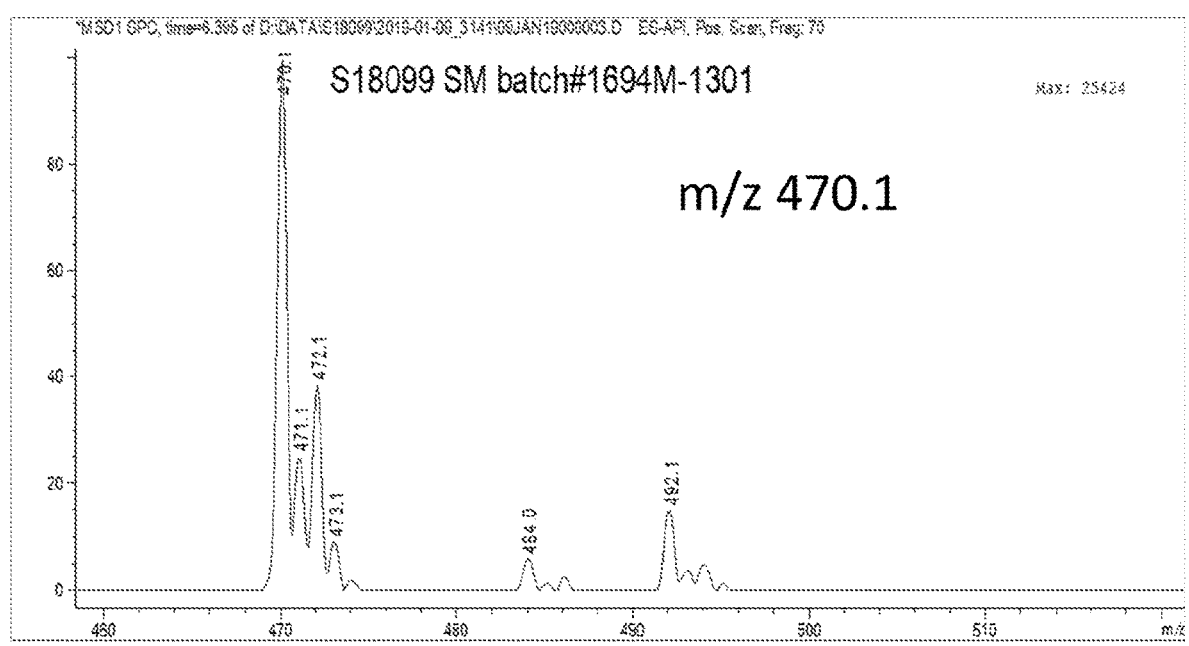

The DSC analysis showed an endothermic event with an onset temperature of 257° C. and Tpeak at 263° C. (FIG. 5). The TGMS analysis showed a mass loss of 0.3%, due to residual solvent or moisture, prior to decomposition (FIG. 6). The decomposition started around 250° C. and was accompanied by an endothermic event in the heat flow signal.

The results of the thermal analyses indicated that the starting material (Form 1) is an anhydrous crystalline phase of voruciclib HCl.

The chemical purity of the API was assessed by LCMS analysis. The result indicated the purity of the solids was 100% (area %). The positive ion spectrum showed an ion with m/z of 470.1 corresponding to ion $(M+H)^+$ and agreed with the molecular mass of the free base of 469.8 g/mol.

Figure 8:
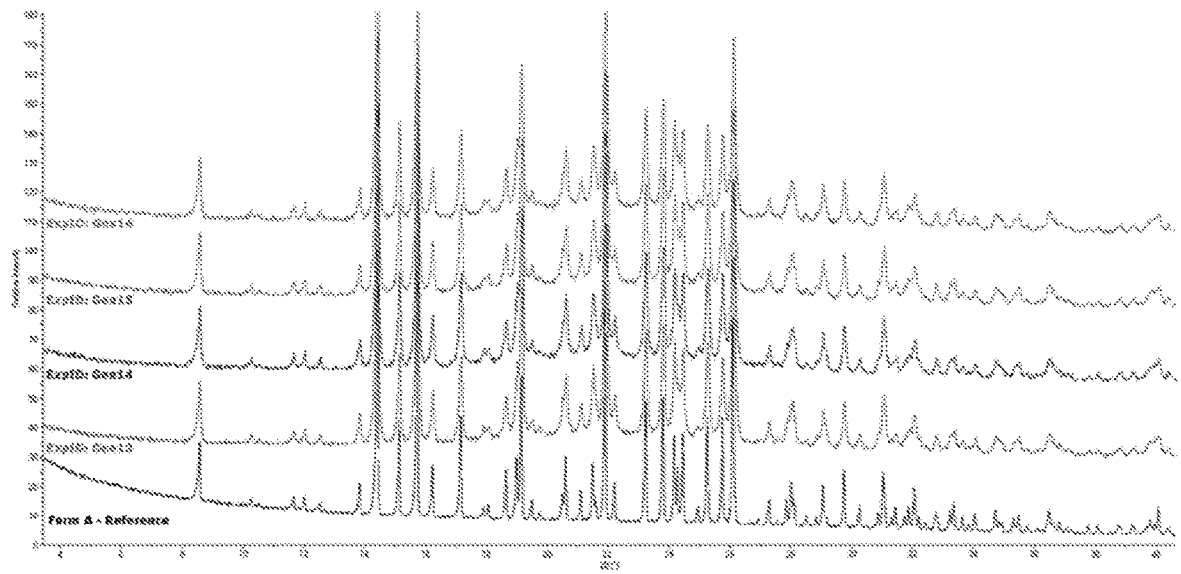
FIG. 8 illustrates a comparison of HR XRPD of voruciclib HCl Form 1 used in high pressure study. From bottom to top: Form 1—reference, Exp. ID Gen13 (10 tons, 1 min, RT), Exp. ID Gen14 (10 tons 10 min, RT), Exp. ID Gen15 (10 tons, 1 min, 80° C.) and Exp. ID Gen16 (10 tons, 10 min, 80° C.).

The physical stability of Form 1 under pressure was evaluated. Four experiments were performed. About 100 mg of API was pressed in a tablet press (10 tons, 13 mm diameter die) for 1 minute at RT, 10 minutes at RT, 1 minute at 80° C. and 10 minutes at 80° C. Afterwards the samples were analyzed by HR-XRPD. The overlay of the XRPD patterns is shown in FIG. 8. All samples had remained Form 1 and there were no clear differences between the crystallinity and physical appearance of the solids, indicating that Form 1 is stable under pressure at RT and elevated temperatures.

Figure 9:
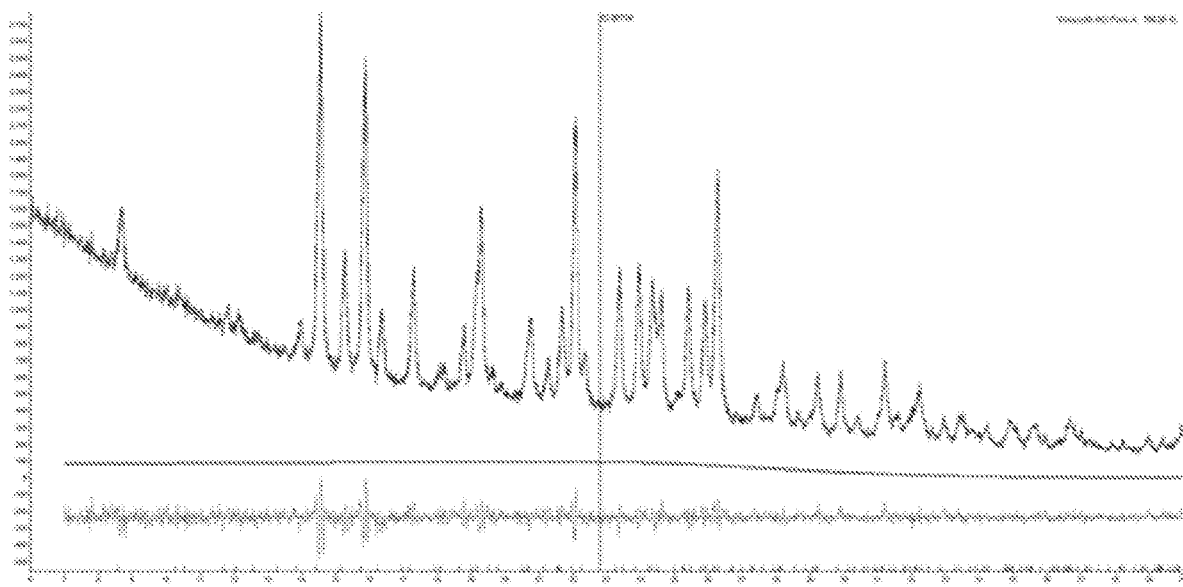
FIG. 9 illustrates the Rietveld analysis of a sample manually ground with a mortar and pestle for ~5 min, including the calculation of the amorphous part based on the background line. The black line represents the obtained powder pattern, the red is calculated and the grey line is the difference between them. The blue stick at the bottom show the peak positions of the fitted cell. The purple line represents the calculated amorphous part of the sample (10±2%).
Figure 10:
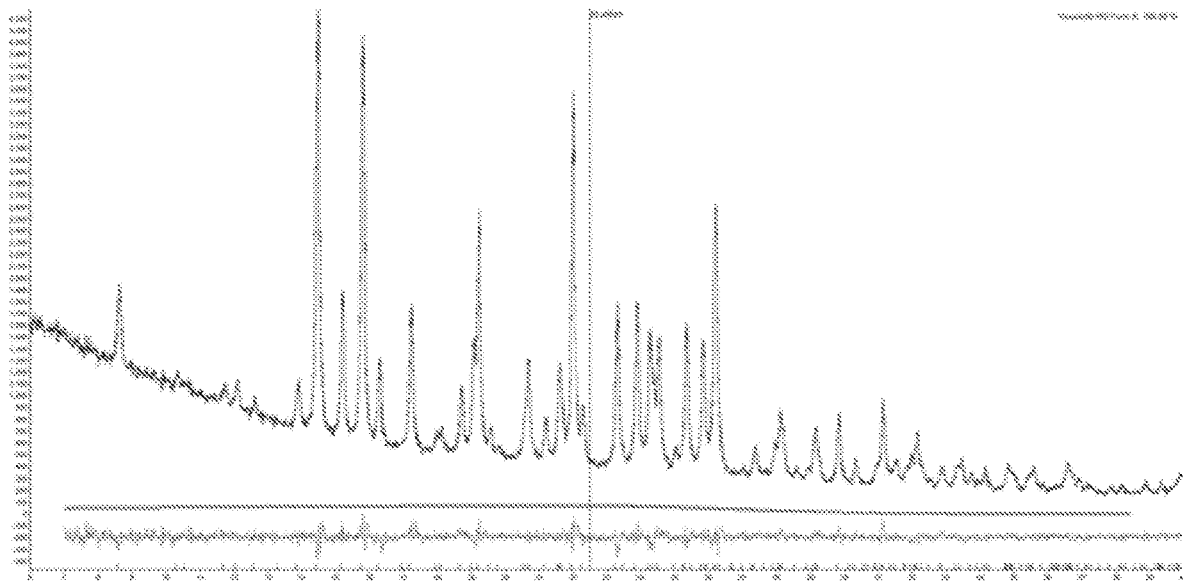
FIG. 10 illustrates the Rietveld analysis of the sample ground using a Retch grinder for 5 min at 30 Hz, including the calculation of the amorphous part based on the background line. The black line represents the obtained powder pattern, the red is calculated and the grey line is the difference between them. The blue stick at the bottom show the peak positions of the fitted cell. The purple line represents the calculated amorphous part of the sample (7±2%).

The physical stability of Form 1 was evaluated during milling processes. One sample was ground using a Retch grinder using 1 mm diameter stainless steel balls for 5 min at 30 Hz and a second sample was ground manually with a mortar and pestle for about 5 minutes. Afterwards the samples were analyzed by HR-XRPD and the amount of amorphous content was calculated (assuming the starting material was 100% crystalline). The result of the manually ground sample is shown in FIG. 9 and contained about 10% of amorphous content. The result of the mechanically ground sample is shown in FIG. 10 and contained about 7% of amorphous phase. No other crystalline phases were observed.

Preferably polymorph screening experiments are initiated with an amorphous phase to promote unbiased crystallization. Therefore, attempts were made to produce amorphous voruciclib HCl. Solutions of the API were prepared in methanol/water 90/10, THF/water 90/10 and 1,4-dioxane/water 90/10. The solutions were freeze dried and the obtained solids were analyzed by HT-XRPD. The experimental details are reported in § 6.2.1, page 20.

Figure 11:
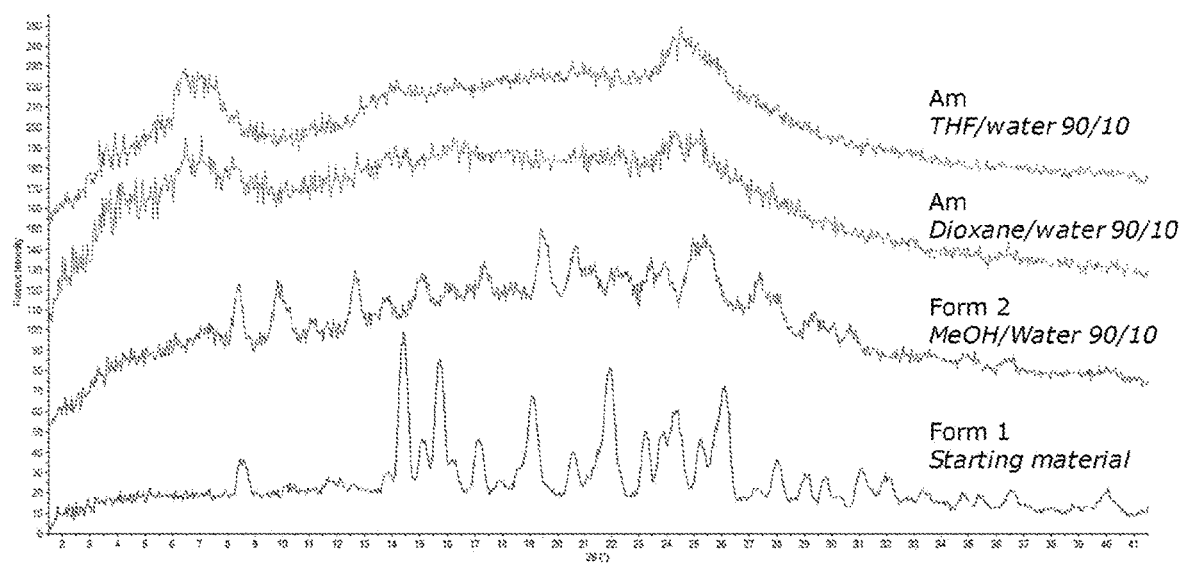
FIG. 11 illustrates an overlay of XRPD of the solids obtained by freeze drying compared to the starting material. From bottom to top: Form 1, starting material; Form 2 obtained from MeOH/water (90/10 v/v), Am obtained from 1,4-dioxane/water (90/10 v/v) and Am obtained from THF/water (90/10 v/v).

The XRPD diffractograms of the solids obtained by freeze drying are shown in FIG. 11. From 1,4-dioxane/water (90/10 v/v) and THF/water (90/10 v/v) amorphous solids were recovered. From methanol/water (90/10 v/v) a crystalline solid was recovered different than the starting material, designated Form 2.

The amorphous materials were analyzed by TGMS. Both amorphous solids contained about 4% of solvent. Since 1,4-dioxane/water is a better solvent mixture for freeze drying, this solvent system was selected to produce amorphous material for the screen.

Solubility Study

The thermodynamic solubilities were determined by the shake-flask method. Suspensions of the amorphous API were prepared in 33 solvents. Subsequently, the solids were equilibrated at RT under continuous stirring for 24 hours. After equilibration a small aliquot of the mother liquor was filtered and analyzed by HPLC. The concentration of solute was determined against a calibration curve of the API.

The solubility values are ranked in Table 3 according to US pharmacopeia's classification (USP29). The API was freely soluble in DMA, DMF and DMSO with solubilities above 400 mg/mL. The API was soluble in alcohols. In short chain alcohols the solubility was higher than in long chain alcohols, i.e. in methanol the solubility was 230 mg/mL versus 10 mg/mL in 2-butanol. In all the other solvents the solubility was less than 10 mg/mL. These results suggest that the API is more soluble in solvents with a high dielectric constant and hydrogen acceptor propensities. A gel was formed in water.

TABLE 3

Solubility results of voruciclib HCl at RT. Suspensions were prepared with the amorphous API and after 24 hours an aliquot of the mother liquors was filtered. The concentration of solute was determined by HPLC analysis. In DMA, DMSO and DMF no suspensions were obtained and the concentration mentioned is that of the solution obtained after the first aliquot addition. The solubility is ranked according to US Pharmacopeia (USP29).

| Solvent | Solubility (mg/mL) | Solibility classification |
|---|---|---|
| N,N-Dimethylacetamide | >400 | Freely soluble |
| Dimethyl sulfoxide | >400 | |
| N,N-Dimethylformamide | >400 | |
| Methanol | 230 | |
| Ethanol | 62 | Soluble |
| 1-Propanol | 34 | |
| 2-Propanol | 19 | Sparingly soluble |
| 2-Butanol | 10 | |
| Tetrahydrofuran | 9.6 | Slightly soluble |
| Acetone | 3.5 | |
| Chloroform | 3.1 | |
| 1,2-Dimethoxyethane | 1.6 | |
| 2-Methyltetrahydrofuran | 1.6 | |
| Ethyl formate | 1.6 | |
| Methyl ethyl ketone | 1.1 | |
| Acetonitrile | 0.9 | Very slightly soluble |
| Ethyl acetate | 0.8 | |
| Methyl isobutyl ketone | 0.7 | |
| Dichloromethane | 0.5 | |
| Isopropyl acetate | 0.5 | |
| 1,4-Dioxane | 0.4 | |
| Diethyl ether | 0.2 | |
| tert-Butyl methyl ether | 0.1 | |
| Toluene | 0.1 | |
| Anisole | <0.1 | Practically insoluble |
| p-Xylene | <0.1 | |
| Diisopropyl ether | <0.1 | |
| Cumene | <0.1 | |
| Cyclohexane | <0.1 | |
| n-Hexane | <0.1 | |
| n-Heptane | <0.1 | |
| Hexanes | <0.1 | |

Polymorph Screen

The polymorph screen was performed by combining different crystallization techniques with a variety of solvents and solvent mixtures.

Solvent equilibration experiments were performed at two temperatures; 2 weeks at RT and 1 week at 50° C. Suspensions were prepared with the amorphous API and upon completion of the equilibration time the solids were separated from the mother liquors. One part of the solids was dried overnight at ambient conditions and analyzed by HT-XRPD, and a second part of the solids was dried overnight at 50° C. under vacuum (10 mbar).

Evaporative crystallization experiments from neat solvents were set up with the filtered mother liquors recovered from the solvent equilibration experiments at RT and from saturated solutions from solvent mixtures. The mother liquors were slowly evaporated at ambient conditions, followed by further drying under vacuum at 50° C.

Cooling crystallization experiments from neat solvents were set up with the filtered mother liquors recovered from the solvent equilibration experiments performed at 50° C. and from saturated solutions from solvent mixtures. The mother liquors were slowly cooled to 5° C. and aged for 72 hours. The precipitated solids were separated from the liquid phases and dried under vacuum (10 mbar) at 50° C. overnight.

Crystallization by thermocycling experiments were performed in solvent mixtures and in solvent/water mixtures. Suspensions were prepared with the amorphous API and subjected to a temperature profile, which included three heating and cooling cycles between 5-50° C.

Anti-solvent addition experiments were performed according to the reversed anti-solvent addition method, meaning that a small volume of (saturated) API solution was quickly added to 20 mL of anti-solvent.

Vapor diffusion into solution experiments were performed using (close to) saturated solutions of the API in solvents where the solubility was high in a small vial. The open vials were placed in larger vials containing 2 mL of anti-solvent. The vials were stored at RT for 2 weeks after which the precipitated solids were separated from the liquids.

Vapor diffusion onto solids were performed using the amorphous API. The amorphous solid was exposed to the vapors of five different solvents for two weeks at room temperature. An open 1.5 mL HPLC vial containing the amorphous API was placed in a larger container containing 2 mL of solvent.

All obtained solids were analyzed by HT-XRPD. Subsequently, all solids were exposed to accelerated aging conditions (40° C./75% RH, AAC) for two days and then reanalyzed by HT-XRPD.

Several novel XRPD diffractograms were obtained from the different crystallization conditions. A list of the forms and the crystallization conditions where the new forms were found is shown in Table 4 while a summary of the different forms is presented below:

Form 1, identical to the starting material was found from various solvents and crystallization methods. Form 1 was stable upon exposure to AAC.

Form 2 was a stable form obtained from different type of solvents and almost all crystallization methods, except from the vapor diffusion methods.

Form 3 was mostly observed from experiments performed in long chain alcohols and alcohol mixtures. In most cases, Form 3 was unstable upon exposure to AAC and conversion to Form 13 was observed. Form 13 was obtained only once by direct crystallization from evaporative crystallization in ethanol.

Form 4 and Form 5 were mostly observed from solvent equilibration and thermocycling experiments in neat solvents and converted to Form 6, a poorly crystalline form, after AAC. Form 6 was also obtained by drying the gel formed in water.

Form 7 was obtained from solvent equilibration experiments at RT and thermocycling in 1,2-dimethoxyethane. This form was stable upon exposure to AAC.

Form 8 was mostly recovered from crystallization experiments performed with short chain alcohol and alcohol mixtures. Form 8 remained stable during AAC.

Form 9 was only crystallized from DMF and was physically unstable. Several solid form conversions were observed. The vacuum dried solids from the cooling crystallization experiment performed in DMF was identified as Form 10. Form 10 converted to Form 20 after exposure to AAC. Form 20 was not found directly from the crystallization experiments.

Form 11 was an unstable form found from experiments performed in DMA.

Form 12 and Form 14 were found from thermocycling experiments using acetone/water and acetonitrile/water. Although both forms were stable upon exposure to AAC, Form 12 was identified in the solids dried under ambient conditions and converted to Form 14 when dried under vacuum at 50° C.

Form 15 was obtained from vapor diffusion into solution from DMF/1,4-dioxane and from cooling crystallization from methanol. This form converted to Form 2 after AAC.

Form 16 was always obtained when the crystallization experiment contained DMSO and converted to different forms after AAC.

Form 17 was an unstable form that converted to Form 13 after AAC and was obtained from the anti-solvent addition experiment with TFE/heptane.

Form 18 was obtained from the anti-solvent experiment using DMF/isopropyl acetate and remained stable upon exposure to AAC.

Form 19 was obtained from the evaporative crystallization experiment in methanol/diisopropyl ether (20/80) and was stable during AAC.

A cycling DSC experiment was performed on Form 7 to investigate if a solvent free form could be obtained. The solid was heated to 155° C., just after the solvent loss, and prior to the first endothermic event. The XRPD of the solids obtained after heating to 155° C. was the same as the solids before the experiment. TGMS analysis on the dried solids showed a mass loss of 2.3% of water. Most likely the solid absorbed water as soon as the sample was removed from the DSC crucible. These results suggest that Form 7 could be a 1,2-dimethoxyethane solvate and/or a hydrated form.

Forms 2, 3, 4, 5, 8, 11, 12, 13, 14, 15 and 17 appeared to be solvated forms obtained from different crystallization solvents; hence, they are most likely isostructural solvates (similar crystal structure is obtained with different solvents and solvent content). The results of the thermal analyses

TABLE 4

List of the forms of voruciclib HCl identified in the screen with the crystallization conditions where they were found. The physical stability of the forms was evaluated after exposure to accelerated aging conditions (AAC, 40° C./75% RH) for 2 days.

| Form | Stable after AAC | Method* | Solvent |
|---|---|---|---|
| 1 | Yes | All | Various |
| 2 | Yes | SLP, PSM, ECP, TCP, AS | MeOH/Acetone, THF/Water, DMA, Anisole, p-Xylene, Heptane, Hexanes, Dioxane/Water, DMSO/TBME, MeOH/p-Xylene |
| 3 | No, converts to 13 | SLP, PSM, ECP, TCP, AS | Alcohols (long-chain) and Alcohol mixtures |
| 4 | No, converts to 6 | SLP, TCP, AS | Anisole, Chloroform, Cumene, Dichloromethane, Ether, Ethyl formate, p-Xylene, TBME, THF, Toluene |
| 5 | No, converts to 6 | SLP, TCP | 2-MethylTHF, Dioxane |
| 6 | Yes | SLP/ECP | Water (forms 4 and 5 converted to Form 6 after AAC) |
| 7 | Yes | SLP-RT, TCP | 1,2-Dimethoxyethane |
| 8 | Yes | SLP, ECP, PSM | Alcohols (short-chain) and Alcohol mixtures |
| 9 | No, converts to 20 | SLP, PSM | DMF |
| 10 | No, converts to 20 | PSM | DMF |
| 11 | No, converts to 2 | PSM, ECP | DMA |
| 12 | Yes | TCP, ECP | Acetone/Water, Acetonitrile/Water |
| 13 | Yes | PSM | Ethanol (Form 3 converts to Form 13 after AAC) |
| 14 | Yes | TCP | Acetone/Water, Acetonitrile/Water |
| 15 | No, converts to 2 | VDL, PSM | DMF/Dioxane, Methanol |
| 16 | No, converts to different forms | PSM, ECP, AS, VDL | DMSO or DMSO mixtures |
| 17 | No, converts to 13 | AS | TFE/Heptane |
| 18 | Yes | AS | DMF/Isopropyl acetate |
| 19 | Yes | ECP | Methanol/Diisopropyl ether 20/80 |

Figure 12A:
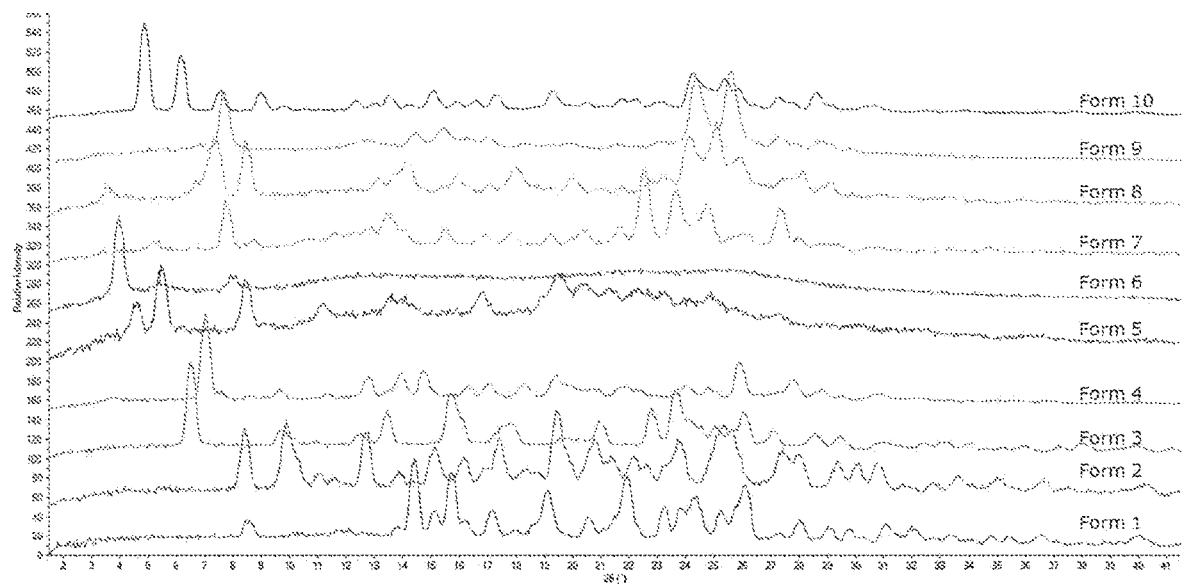
FIGS. 12A and 12B illustrate HT-XRPD of the unique forms identified during the screen (from bottom to top)
Figure 12B:
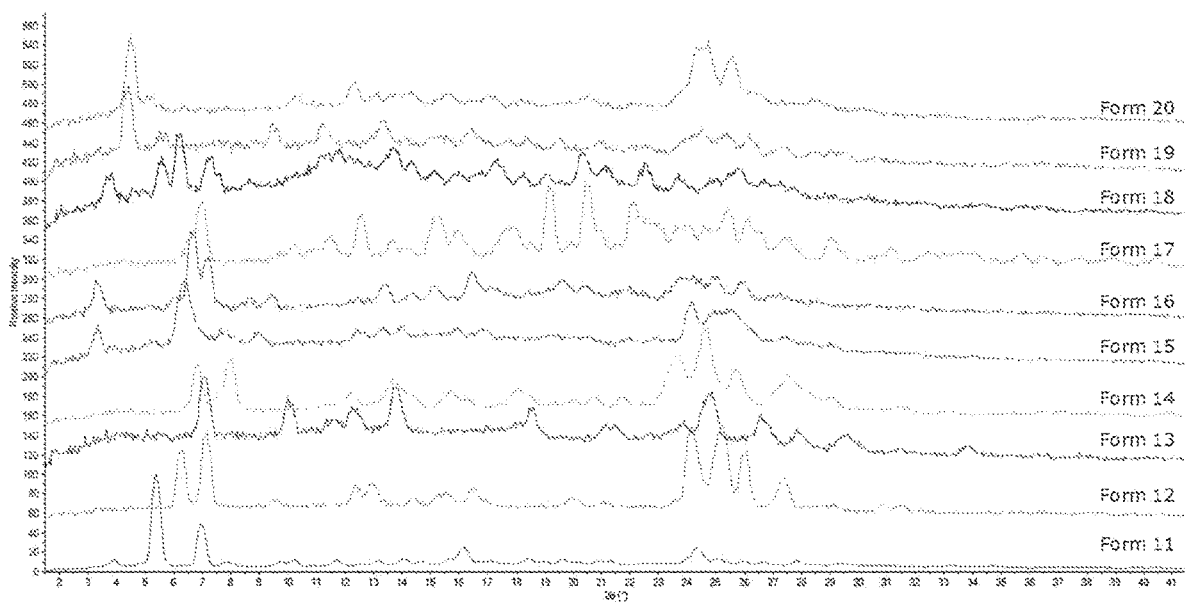

*Methods: SLP = solvent equilibration, PSM = cooling, ECP = evaporative, TCP = thermocycling, AS = anti-solvent, VDL = vapor diffusion The unique XRPD diffractograms observed during this study are shown in FIGS. 12A and 12B.

The new solid forms were further analyzed by DSC, TGMS and HPLC for confirmation of the compound's integrity and nature of the form. For each form one sample was selected for further analysis. The analytical results are reported in detail herein, and summarized in Table 5.

Form 1, identical to the crystalline starting material, appeared to be the only non-solvated and anhydrous form obtained directly from the crystallization experiments. All other forms contained solvent and/or water.

Forms 7, 10, 16 and 19 were obtained from specific solvents, but the mass losses observed from the TGMS analyses indicated that these forms were non-stoichiometric solvates. The thermal events observed by DSC analysis indicated that each of these forms could convert to Form 1 upon heating (based on the melting event observed around 260° C.).

indicated that Forms 3 and 8 will become amorphous upon desolvation, while the other solvated forms could convert to Form 1 (based on the melting event observed around 260° C.).

Forms 3 and 8 were mostly obtained from alcohols. Form 3 converted in many cases to Form 13, suggesting that Form 13 might be a hydrated form or a mixed solvate/hydrate.

Form 4 was obtained from several solvents. The cycling DSC experiment performed on Form 4 showed a similar behavior to that observed for Form 7. The XRPD pattern of the heated solids was slightly different to that of Form 4 (designated Form 4b). The TGMS analysis on the solid recovered after the cycling DSC showed a mass loss of about 2%, suggesting that the solid immediately adsorbed water as soon as it is at ambient conditions.

Forms 12 and 14 were obtained from acetone/water and acetonitrile/water mixtures. Form 12 converted to Form 14 upon drying under vacuum. Additional cycling DSC experiments were performed on Forms 12 and 14 by heating a solid sample to 155° C. (just after the solvent loss). The powder patterns of the recovered solids were similar to Form 14. TGMS analysis on the solid obtained after the cycling DSC experiment contained about 1.9% of water, suggesting that Form 14 could be a solvate and/or hydrated form.

Form 6 was a poor crystalline form and contained about 0.5 molar equivalent of water. After dehydration, the solid became amorphous.

Forms 9 and 18 were only identified in the ambient dried solids and converted to other forms upon drying under vacuum. Without wishing to be bound by any particular theory, it is believed that these forms are most likely metastable solvated forms.

analysis only and 39 g of batch 1694M-1301 was utilized for the polymorph screen. Other chemicals were obtained from Fisher Scientific, Sigma Aldrich or VWR. Chemicals used were at least of research grade and the HPLC mobile phases were of HPLC grade.

Attempts to produce amorphous solids were performed. The API was weighed into standard HPLC vials and aliquots of solvent were added until the API was dissolved. The solutions were frozen in liquid nitrogen and placed under deep vacuum using a freeze dryer (Alpha 2-4 LD, Christ). The solids were additionally dried under vacuum (10 mbar) at 50° C. for 24 h. The obtained solids were analyzed by HT-XRPD. The experimental conditions and results are shown in Table 6. The amorphous materials were further analyzed by TGMS to determine the solvent content.

TABLE 5

Summary of the analytical characterization performed on the novel forms of voruciclib HCl. Form 1 was a non-solvated and anhydrous form. All other forms were (isostructural) solvated (or hydrated) forms that either converted (eventually) to Form 1 or became amorphous after solvent removal.

| Form | Mass loss (%) | DSC events | Nature |
|---|---|---|---|
| Non-solvated form ||||
| 1 | 0.2 | 259 (m) | Anhydrous, non-solvated |
| Solvates that convert to Form 1 upon desolvation ||||
| 10 | 20.8 | 84 (endo), 256 (m) | Non-stoichiometric DMF solvate |
| 16 | 16.6 | 50 (br endo), 102 (endo), 200 (small endo), 258 (m) | Non-stoichiometric DMSO solvate |
| 19 | 4.5 | 70 (br endo), 200 (exo), 250 (m) [SDTA] | Non-stoichiometric isopropyl ether solvate |
| Isostructural solvates that convert to Form 1 upon desolvation ||||
| 2 | 5.4 | 145 (br endo), 165 (small endo), 260 (m) | Non-stoichiometric isostructural solvate |
| 4 | 4.3 | 50, 108, 158 (3xsmall endo), 217 (exo), 260 (m) | Non-stoichiometric isostructural solvate/hydrate |
| 5 | 9.4 | 60, 110 (2xbr endo) | Non-stoichiometric isostructural solvate |
| 7 | 2.0 | 172 (endo), 216 (exo), 262 (m) | Non-stoichiometric 1,2-dimethoxyethane solvate or hydrate |
| 11 | 9.1 | 85 (endo), 257 (m) | Non-stoichiometric isostructural solvate |
| 12 | 5.9 | 70 (br endo), 255 (m) | Non-stoichiometric isostructural solvate |
| 13 | 6.3 | 55, 107 (2x br endo), 164 (br double endo), 258 (m) | Possibly a (di)hydrate or mixed solvate/hydrate |
| 14 | 2.5 | 172 (endo), 258 (m) | Non-stoichiometric isostructural solvate/hydrate |
| 15 | 13.2 | 77 (endo), 256 (m) | Isostructural solvate |
| 17 | 16.9 | 97 (endo), 135, 153 (double endo), 257 (m) | Non-stoichiometric solvate |
| Solvates/hydrate that become amorphous upon desolvation/dehydration ||||
| 3 | 13.2 | 103.3 (endo) | Non-stoichiometric isostructural solvate |
| 6 pc | 2.1 | 151 (small endo) | Poor crystalline hemi-hydrate |
| 8 | 5.3 | 80 (br endo), 147 (small endo) | Non-stoichiometric isostructural solvate |
| Physically unstable forms, no thermal analysis could be performed ||||
| 9 | | | Most likely DMF solvate; converts to Form 10 upon drying under vacuum and to Form 20 during AAC |
| 18 | | | Most likely solvate; becomes amorphous upon drying under vacuum |

(m: melting; br endo: broad endothermic event; exo: exothermic event)

Materials and Methods

Six batches of voruciclib HCl were provided. Batches P1446A-05_EN017, P1446A-05_EN027, 1694M-1201, 1694M-1301, 1694M-1401 of 250 mg each were used for The amorphous batch with experiment ID Gen12 was used as starting material for the screening experiments. The solution was divided over 1.8 mL glass vials and then freeze dried, resulting in about 40 mg of amorphous API per vial.

TABLE 6

Experimental conditions and results of the attempts to produce amorphous solids. Solutions were prepared with voruciclib HCl. The solutions were freeze dried overnight and the resulting solids were analyzed by HT-XRPD.

| Exp. ID | Solvent (v/v) | Mass (mg) | Volume (μL) | Conc. (mg/mL) | Dissolved | XRPD Form | Mass loss (%) |
|---|---|---|---|---|---|---|---|
| GEN 7 | Methanol/Water (90/10) | 40.6 | 300 | 135.4 | Yes | 2 | — |
| GEN 8 | Ethanol/Water (90/10) | 41.2 | 500 | 82.5 | No | — | — |
| GEN 9 | 1,4-Dioxane/Water (90/10) | 41.5 | 300 | 138.3 | Yes | Am | 3.7 |
| GEN 10 | Acetonitrile/Water (90/10) | 41.0 | 500 | 82.5 | No | — | — |
| GEN 11 | Tetrahydrofuran/Water (90/10) | 40.2 | 200 | 200.9 | Yes | Am | 7 |
| GEN 12 | 1,4-Dioxane/Water (90/10) | 3802.3 | 28500 | 133.4 | Yes | Am | 3.7 |

Solubility Determination

The solubility was determined in 33 solvents. To the amorphous solid in 1.8 mL glass vial a volume of solvent was added in small steps until a thin suspension was obtained (Table 7). The suspensions were left to equilibrate with continuous stirring at RT. After 24 hours a small aliquot of mother liquor was taken and filtered using 0.2 μM PTFE syringe filters. The concentration of solute was determined by HPLC analysis. The calibration line was prepared from two independent stock solutions in acetonitrile/water 25/75 (v/v).

The remainder of the suspensions were used for the solvent equilibration experiments at RT for two weeks.

TABLE 7

Experimental conditions of the thermodynamic solubility determination by the shake-flask method. Suspensions were prepared and equilibrated at RT. After 24 hours a small aliquot of the mother liquor was filtered, and the concentration of solute was determined by HPLC analysis.

| Exp. ID | Mass (mg) | Solvent | Volume (μL) | Dissolved | Solubility (mg/mL) |
|---|---|---|---|---|---|
| QSA1 | 40 | 1,2-Dimethoxyethane | 800 | No | 1.6 |
| QSA2 | 40 | 1,4-Dioxane | 700 | No | 0.4 |
| QSA3 | 40 | 1-Propanol | 700 | No | 34.5 |
| QSA4 | 40 | 2-Butanol | 500 | No | 10.2 |
| QSA5 | 40 | 2-Methyltetrahydrofuran | 600 | No | 1.6 |
| QSA6 | 40 | 2-Propanol | 700 | No | 18.8 |
| QSA7 | 40 | Methylisobutyl ketone | 600 | No | 0.7 |
| QSA8 | 40 | Acetone | 600 | No | 3.5 |
| QSA9 | 40 | Acetonitrile | 600 | No | 0.9 |
| QSA10 | 40 | Anisole | 600 | No | <0.1 |
| QSA11 | 40 | Chloroform | 600 | No | 3.1 |
| QSA12 | 40 | Cumene | 700 | No | <0.1 |
| QSA13 | 40 | Cyclohexane | 1000 | No | <0.1 |
| QSA14 | 40 | Dichloromethane | 800 | No | 0.5 |
| QSA15 | 40 | Diethyl ether | 900 | No | 0.2 |
| QSA16 | 40 | Diisopropyl ether | 700 | No | <0.1 |
| QSA17 | 40 | n-Hexane | 1000 | No | <0.1 |
| QSA18 | 40 | DMSO | 100 | Yes | >400 |
| QSA19 | 40 | Ethanol | 500 | No | 62.0 |
| QSA20 | 40 | Ethyl acetate | 600 | No | 0.8 |
| QSA21 | 40 | Ethyl formate | 700 | No | 1.6 |
| QSA22 | 40 | Isopropyl acetate | 900 | No | 0.5 |
| QSA23 | 40 | Methanol | 150 | No | 229.5 |
| QSA24 | 40 | Methyl ethyl ketone | 800 | No | 1.1 |
| QSA25 | 40 | n-Heptane | 1000 | No | <0.1 |
| QSA26 | 40 | N,N-Dimethylacetamide | 100 | Yes | >400 |
| QSA27 | 40 | N,N-Dimethylformamide | 100 | Yes | >400 |
| QSA28 | 40 | p-Xylene | 900 | No | <0.1 |
| QSA29 | 40 | tert-Butyl methyl ether | 900 | No | 0.1 |
| QSA30 | 40 | Tetrahydrofuran | 900 | No | 9.6 |
| QSA31 | 40 | Toluene | 800 | No | 0.1 |
| QSA32 | 40 | Water | 800 | No | Not determined |
| QSA33 | 40 | Hexanes | 1000 | No | <0.1 |

Equilibration Experiments at RT and at 50° C.

The solvent equilibration experiments were performed in 33 solvents. To the vials containing about 40 mg of amorphous API solvent was added in small steps, until a thin suspension was obtained. The suspensions were left to equilibrate with continuous stirring for 2 weeks at RT (Table 8) and 1 week at 50° C. (Table 9).

After the equilibration time, the solids were separated by centrifugation. A part of the solids was collected and harvested on a 96 well plate and dried at ambient conditions overnight. The remaining solids were dried under vacuum (50° C. and 10 mbar) overnight and then harvested on a 96 well plate. All solids were analyzed by HT-XRPD. Subsequently, all solids were exposed to accelerated aging conditions for two days (AAC, 40° C./75% RH) and re-analyzed by HT-XRPD.

TABLE 8

Experimental conditions and XRPD results for the solvent equilibration experiments performed on voruciclib HCl at RT. Suspensions of amorphous voruciclib HCl were prepared in the solvents listed and stirred at RT for 2 weeks. After the equilibration time, the solids were analyzed by HT-XRPD after drying at ambient conditions (Ambient) and after drying under vacuum (Vacuum). All solids were exposed to AAC for 2 days and re-analyzed by XRPD.

| Exp. ID | Mass (mg) | Solvent | Volume (µL) | Conc. (mg/mL) | Ambient | AAC | Vacuum | AAC |
|---|---|---|---|---|---|---|---|---|
| SLP1 | 40 | 1,2-Dimethoxyethane | 800 | 50.0 | 7 | 7 | 7 | 7 |
| SLP2 | 40 | 1,4-Dioxane | 700 | 57.1 | 5 | Am | Am | 6 pc |
| SLP3 | 40 | 1-Propanol | 700 | 57.1 | 1 | 1 | 1 | 1 |
| SLP4 | 40 | 2-Butanol | 500 | 80.0 | 3 | 3 + 13 | 3 | 3 + 13 |
| SLP5 | 40 | 2-Methyltetrahydrofuran | 600 | 66.7 | 5 | 6 pc | 5 | 6 pc |
| SLP6 | 40 | 2-Propanol | 700 | 57.1 | 3 + 8 | 13 + 8 | 8 pc | 8 |
| SLP7 | 40 | Methyl isobutyl ketone | 600 | 66.7 | 1 | 1 | 1 | 1 |
| SLP8 | 40 | Acetone | 600 | 66.7 | 1 | 1 | 1 | 1 |
| SLP9 | 40 | Acetonitrile | 600 | 66.7 | 1 | 1 | 1 | 1 |
| SLP10 | 40 | Anisole | 600 | 66.7 | 2 + 4 | 2 | 4 | 6 pc |
| SLP11 | 40 | Chloroform | 600 | 66.7 | 4a | 6 pc | 4 | 6 pc |
| SLP12 | 40 | Cumene | 700 | 57.1 | 4 | 2 + 4 + 6 pc | 4 | 4 + 6 pc |
| SLP13 | 40 | Cyclohexane | 1000 | 40.0 | Am | 6 pc | Am | 6 pc |
| SLP14 | 40 | Dichloromethane | 800 | 50.0 | 4 | 6 pc | 4 | 6 pc |
| SLP15 | 40 | Diethyl ether | 900 | 44.4 | 4 | 6 pc | 4a | 6 pc |
| SLP16 | 40 | Diisopropyl ether | 700 | 57.1 | 1 + 2 | 1 + 2 | 1 + 2 | 1 + 2 |
| SLP17 | 40 | n-Hexane | 1000 | 40.0 | Am | 6 pc | Am | 6 pc |
| SLP18 | 40 | DMSO | 100 | 400.0 | — | — | — | — |
| SLP19 | 40 | Ethanol | 500 | 80.0 | 1 | 1 | 1 | 1 |
| SLP20 | 40 | Ethyl acetate | 600 | 66.7 | 1 | 1 | 1 | 1 |
| SLP21 | 40 | Ethyl formate | 700 | 57.1 | 4 | 6 pc | 4 | 6 pc |
| SLP22 | 40 | Isopropyl acetate | 900 | 44.4 | 1 | 1 | 1 | 1 |
| SLP23 | 40 | Methanol | 150 | 266.7 | 1 | 1 | 1 | 1 |
| SLP24 | 40 | Methyl ethyl ketone | 800 | 50.0 | 1 | 1 | 1 | 1 |
| SLP25 | 40 | n-Heptane | 1000 | 40.0 | Am | 6 pc | Am | 6 pc |
| SLP26 | 40 | N,N-Dimethylacetamide | 100 | 400.0 | — | — | — | — |
| SLP27 | 40 | N,N-Dimethylformamide | 100 | 400.0 | 9 + 11 | 2 + 20 | 4 + 9 | 6 pc |
| SLP28 | 40 | p-Xylene | 900 | 44.4 | 2 + 4 | 2 | 4 | 4 + 6 pc |
| SLP29 | 40 | tert-Butyl methyl ether | 900 | 44.4 | 4a | 6 pc | 4 | 6 pc |
| SLP30 | 40 | Tetrahydrofuran | 900 | 44.4 | 4a | 6 pc | 4 | 6 pc |
| SLP31 | 40 | Toluene | 800 | 50.0 | 4 | 6 pc | 4 | 6 pc |
| SLP32 | 40 | Water | 800 | 50.0 | — | — | — | — |
| SLP33 | 40 | Hexanes | 1000 | 40.0 | Am | 6 pc | Am | 6 pc |

TABLE 9

Experimental conditions and XRPD results for the solvent equilibration experiments performed on voruciclib HCl at 50° C. Suspensions of voruciclib HCl were prepared in the solvents listed and stirred at 50° C. for 1 week. After the equilibration time, the solids were analyzed by HT-XRPD after drying at ambient conditions (Ambient) and after drying under vacuum (Vacuum). All solids were exposed to AAC for 2 days and re-analyzed by XRPD.

| Exp. ID | Mass (mg) | Solvent | Volume (µL) | Conc. (mg/mL) | Ambient | AAC | Vacuum | AAC |
|---|---|---|---|---|---|---|---|---|
| SLP34 | 40 | 1,2-Dimethoxyethane | 800 | 50.0 | 1 | 1 | 1 | 1 |
| SLP35 | 40 | 1,4-Dioxane | 800 | 50.0 | 5 | 6 pc | 5 | 6 pc |
| SLP36 | 40 | 1-Propanol | 400 | 100.0 | 1 | 1 | 1 | 1 |
| SLP37 | 40 | 2-Butanol | 400 | 100.0 | 3 | 3 + 13 | 3 | 3 + 13 |
| SLP38 | 40 | 2-Methyltetrahydrofuran | 400 | 100.0 | 1 | 1 | 1 | 1 |
| SLP39 | 40 | 2-Propanol | 400 | 100.0 | 1 | 1 | 1 | 1 |
| SLP40 | 40 | Methyl isobutyl ketone | 400 | 100.0 | 1 | 1 | 1 | 1 |
| SLP41 | 40 | Acetone | 400 | 100.0 | 1 | 1 | 1 | 1 |
| SLP42 | 40 | Acetonitrile | 400 | 100.0 | 1 | 1 | 1 | 1 |
| SLP43 | 40 | Anisole | 400 | 100.0 | 4 | 6 pc | 4 | 4 + 6 pc |
| SLP44 | 40 | Chloroform | 500 | 80.0 | 4a | 2 + 4 + 6 pc | 4 + trace 2 | 2 + 6 pc |
| SLP45 | 40 | Cumene | 600 | 66.7 | 1 | 1 | 1 | 1 + 2 |
| SLP46 | 40 | Cyclohexane | 500 | 80.0 | Am | 6 pc | Am | 6 pc |
| SLP47 | 40 | Dichloromethane | 500 | 80.0 | 1 + 2 | 1 + 2 | 1 + 2 | 1 + 2 |
| SLP48 | 40 | Diethyl ether | 800 | 50.0 | 1 | 1 | 1 | 1 |
| SLP49 | 40 | Diisopropyl ether | 700 | 57.1 | 1 + 2 | 1 + 2 | 1 + 2 | 1 + 2 |

TABLE 9-continued

Experimental conditions and XRPD results for the solvent equilibration experiments performed on voruciclib HCl at 50° C. Suspensions of voruciclib HCl were prepared in the solvents listed and stirred at 50° C. for 1 week. After the equilibration time, the solids were analyzed by HT-XRPD after drying at ambient conditions (Ambient) and after drying under vacuum (Vacuum). All solids were exposed to AAC for 2 days and re-analyzed by XRPD.

| Exp. ID | Mass (mg) | Solvent | Volume (µL) | Conc. (mg/mL) | Ambient | AAC | Vacuum | AAC |
|---|---|---|---|---|---|---|---|---|
| SLP50 | 40 | n-Hexane | 500 | 80.0 | 1 + 2 + 4 | 1 + 2 | 1 + 2 + 4 | 2 + 6 pc |
| SLP51 | 40 | DMSO | 100 | 400.0 | — | — | — | — |
| SLP52 | 40 | Ethanol | 200 | 200.0 | 1 | 1 | 1 | 1 |
| SLP53 | 40 | Ethyl acetate | 700 | 57.1 | 1 | 1 | 1 | 1 |
| SLP54 | 40 | Ethyl formate | 500 | 80.0 | 1 + peak7 | 1 | 1 + peak7 | 1 |
| SLP55 | 40 | Isopropyl acetate | 700 | 57.1 | 1 | 1 | 1 | 1 |
| SLP56 | 40 | Methanol | 100 | 400.0 | 1 | 1 | 1 | 1 |
| SLP57 | 40 | Methyl ethyl ketone | 300 | 133.3 | 1 | 1 | 1 | 1 |
| SLP58 | 40 | n-Heptane | 1000 | 40.0 | 2 | 2 | 2 | 2 |
| SLP59 | 40 | N,N-Dimethylacetamide | 100 | 400.0 | — | — | — | — |
| SLP60 | 40 | N,N-Dimethylformamide | 100 | 400.0 | — | — | — | — |
| SLP61 | 40 | p-Xylene | 900 | 44.4 | 2 + 4 | 2 + 4 | 4 | 4 |
| SLP62 | 40 | tert-Butyl methyl ether | 700 | 57.1 | 1 | 1 | 1 | 1 |
| SLP63 | 40 | Tetrahydrofuran | 500 | 80.0 | 1 | 1 | 1 | 1 |

Evaporative Crystallization Experiments

For the evaporative crystallization experiments from neat solvents the mother liquors recovered from the solvent equilibration experiments at RT were used. For the evaporative crystallization experiments from solvent mixtures new suspensions were prepared.

The mother liquors were filtered using 0.2 µm PTFE syringe filters. The solutions were transferred to vials (without caps) and left at ambient conditions to allow the solvents to evaporate slowly at ambient conditions for 3 days, followed by vacuum at 50° C. until all solvent was evaporated. The obtained solids were analyzed by HT-XRPD. Subsequently, the solids were exposed to accelerated aging conditions (40°/75% RH) for 2 days and re-analyzed by HT-XRPD.

TABLE 10

Experimental conditions and XRPD results for the evaporative crystallization experiments. Solutions were placed at ambient conditions to allow slow evaporation of the solvent. The solids that were recovered were analyzed by HT-XRPD. In case no solids were obtained, this is noted with "—".

| Exp. ID | Solvent or Solvent mixture (v/v) | Volume (µL) | Form | AAC |
|---|---|---|---|---|
| ECP1 | 1,2-Dimethoxyethane | 800 | — | — |
| ECP2 | 1,4-Dioxane | 700 | — | — |
| ECP3 | 1-Propanol | 700 | 3 + 9 + 11 | Am |
| ECP4 | 2-Butanol | 500 | 3 | 3 |
| ECP5 | 2-Methyltetrahydrofuran | 600 | — | — |
| ECP6 | 2-Propanol | 700 | 8 | — |
| ECP7 | Methyl isobutyl ketone | 600 | — | — |
| ECP8 | Acetone | 600 | — | — |
| ECP9 | Acetonitrile | 600 | — | — |
| ECP10 | Anisole | 600 | — | — |
| ECP11 | Chloroform | 600 | — | — |
| ECP12 | Cumene | 700 | — | — |
| ECP13 | Cyclohexane | 1000 | — | — |
| ECP14 | Dichloromethane | 800 | — | — |
| ECP15 | Diethyl ether | 900 | — | — |
| ECP16 | Diisopropyl ether | 700 | — | — |
| ECP17 | n-Hexane | 1000 | — | — |
| ECP18 | DMSO | 100 | 16 | 1 + 2 |
| ECP19 | Ethanol | 500 | 8 pc | 8 pc |
| ECP20 | Ethyl acetate | 600 | — | — |
| ECP21 | Ethyl formate | 700 | — | — |
| ECP22 | Isopropyl acetate | 900 | — | — |
| ECP23 | Methanol | 150 | 8 pc | 8 pc |
| ECP24 | Methyl ethyl ketone | 800 | — | — |
| ECP25 | n-Heptane | 1000 | — | — |
| ECP26 | N,N-Dimethylacetamide | 100 | 1 + 3 + 12 | 1 + 2 + peak 4.5° |
| ECP27 | N,N-Dimethylformamide | 100 | 10 + peak3.2° | 2 + 20 |
| ECP28 | p-Xylene | 900 | — | — |
| ECP29 | tert-Butyl methyl ether | 900 | — | — |

TABLE 10-continued

Experimental conditions and XRPD results for the evaporative crystallization experiments. Solutions were placed at ambient conditions to allow slow evaporation of the solvent. The solids that were recovered were analyzed by HT-XRPD. In case no solids were obtained, this is noted with "—".

| Exp. ID | Solvent or Solvent mixture (v/v) | Volume (µL) | Form | AAC |
|---|---|---|---|---|
| ECP30 | Tetrahydrofuran | 900 | 1 | 1 |
| ECP31 | Toluene | 800 | — | — |
| ECP32 | Water | 800 | 6 pc | 6 pc |
| ECP33 | Hexanes | 1000 | — | — |
| ECP34 | Methanol/Acetone (75/25) | 400 | 8 | 8 |
| ECP35 | Ethanol/Chloroform (75/25) | 700 | 3 | 3 + 13 |
| ECP36 | 1-Propanol/1,2-Dimethoxyethane (75/25) | 700 | 3a | 3 + 13 |
| ECP37 | 2-Propanol/Ethyl formate (75/25) | 1100 | 3 | 3 |
| ECP38 | 2-Butanol/Acetonitrile (75/25) | 1100 | 3 | 3 |
| ECP39 | Methanol/Diethyl ether (75/25) | 600 | 14 pc | 14 pc |
| ECP40 | Ethanol/Toluene (75/25) | 1100 | 3 + 13 | 3 + 13 |
| ECP41 | 1-Propanol/Ethyl acetate (75/25) | 1000 | 3a | 3a |
| ECP42 | TFE/Heptane (75/25) | 1000 | 3a | 3a |
| ECP43 | TFE/2-Methyltetrahydrofuran (75/25) | 1300 | 3a | 3a |
| ECP44 | Methanol/2-Propanol (75/25) | 600 | 3 | 3 |
| ECP45 | Methanol/Diisopropyl ether (20/80) | 1200 | 19 | 19 |
| ECP46 | Diisopropyl ether/2-Propanol (90/10) | 1200 | — | — |
| ECP47 | 50/50 mixture of IPA/MeOH (25/75) and MeOH/Diisopropyl ether (20/80) | 1000 | 3 | 3 + 13 |

Cooling Crystallization Experiments

Cooling crystallization experiments from neat solvents were performed using the mother liquors recovered from the solvent equilibration experiments at 50° C. For the cooling crystallization experiments from solvent mixtures new suspensions were prepared.

The mother liquors were filtered at 50° C. using 0.2 µm PTFE syringe filters. The solutions were transferred to standard HPLC vials and the solutions were slowly cooled in Crystal16™ reactors. The solutions were cooled to 5° C. with 1° C./h and aged for 72 hours at 5° C. The solids that had precipitated were separated by centrifugation and dried under vacuum (50° C./10 mbar) overnight and analyzed by HT-XRPD.

The mother liquors and the solutions in which no precipitation had occurred were placed at ambient conditions to allow the solvents to evaporate followed by vacuum. The recovered solids were analyzed by HT-XRPD.

Subsequently, all solids were exposed to AAC for 2 days and re-analyzed by HT-XRPD.

TABLE 11

Experimental conditions and XRPD results for the cooling crystallization experiments. Saturated solutions obtained at 50° C. were cooled with 1° C./h to 5° C. and aged for 72 hours. Solids that had precipitated were analyzed by HT-XRPD after drying under vacuum (Solid). The mother liquors and solutions in which no precipitation occurred were evaporated, and the solids obtained analyzed by HT-XRPD (ML). All solids were exposed to AAC for 2 days and re-analyzed by XRPD. In case no solids were obtained, this is noted with "—".

| Exp ID | Solvent or solvent mixture (v/v) | Volume (mL) | Solid Form | Solid AAC | Liquid Form | Liquid AAC |
|---|---|---|---|---|---|---|
| PSM34 | 1,2-Dimethoxyethane | 800 | — | — | — | — |
| PSM35 | 1,4-Dioxane | 800 | — | — | — | — |
| PSM36 | 1-Propanol | 400 | — | — | Am | Am |
| PSM37 | 2-Butanol | 400 | — | — | 3 | 3 |
| PSM38 | 2-Methyltetrahydrofuran | 400 | — | — | — | — |
| PSM39 | 2-Propanol | 400 | — | — | Am | Am |
| PSM40 | Methyl isobutyl ketone | 400 | — | — | — | — |
| PSM41 | Acetone | 400 | — | — | — | — |
| PSM42 | Acetonitrile | 400 | — | — | — | — |
| PSM43 | Anisole | 400 | — | — | — | — |
| PSM44 | Chloroform | 500 | — | — | — | — |
| PSM45 | Cumene | 600 | — | — | — | — |
| PSM46 | Cyclohexane | 500 | — | — | — | — |
| PSM47 | Dichloromethane | 500 | — | — | — | — |
| PSM48 | Diethyl ether | 800 | — | — | — | — |
| PSM49 | Diisopropyl ether | 700 | — | — | — | — |
| PSM50 | n-Hexane | 500 | — | — | — | — |

TABLE 11-continued

Experimental conditions and XRPD results for the cooling crystallization experiments. Saturated solutions obtained at 50° C. were cooled with 1° C./h to 5° C. and aged for 72 hours. Solids that had precipitated were analyzed by HT-XRPD after drying under vacuum (Solid). The mother liquors and solutions in which no precipitation occurred were evaporated, and the solids obtained analyzed by HT-XRPD (ML). All solids were exposed to AAC for 2 days and re-analyzed by XRPD. In case no solids were obtained, this is noted with "—".

| Exp ID | Solvent or solvent mixture (v/v) | Volume (mL) | Solid Form | AAC | Liquid Form | AAC |
|---|---|---|---|---|---|---|
| PSM51 | DMSO | 100 | — | — | 16 | 16 |
| PSM52 | Ethanol | 200 | — | — | 13 | 13 |
| PSM53 | Ethyl acetate | 700 | — | — | — | — |
| PSM54 | Ethyl formate | 500 | — | — | 1 | — |
| PSM55 | Isopropyl acetate | 700 | — | — | — | — |
| PSM56 | Methanol | 100 | 15 | 2 + 8? | — | — |
| PSM57 | Methyl ethyl ketone | 300 | — | — | — | — |
| PSM58 | n-Heptane | 1000 | — | — | — | — |
| PSM59 | N,N-Dimethylacetamide | 100 | — | — | Am | 2 + 20 |
| PSM60 | N,N-Dimethylformamide | 100 | 10 | 20 | — | — |
| PSM61 | p-Xylene | 900 | — | — | — | — |
| PSM62 | tert-Butyl methyl ether | 700 | — | — | — | — |
| PSM63 | Tetrahydrofuran | 500 | — | — | Am | Am |
| PSM64 | Toluene | 400 | — | — | — | — |
| PSM65 | Water** | 400 | — | — | — | — |
| PSM66 | Hexanes | 1000 | — | — | — | — |
| PSM1 | Methanol/Acetone (50/50) | 700 | 2 | 2 | — | — |
| PSM2 | Ethanol/Chloroform (50/50) | 500 | 3 + 13 | 1 + 13 | — | — |
| PSM3 | DMSO/1,2-Dimethoxyethane (10/90) | 900 | 16 | 13 + 16 | — | — |
| PSM4 | 2-Propanol/Ethyl formate (75/25) | 900 | 3 | 3 + 13 | — | — |
| PSM5 | Dioxane/Water (90/10) | 400 | 8 + 13 | 8 + 13 | — | — |
| PSM6 | THF/Water (90/10) | 200 | 2 + 4 | 2 | — | — |
| PSM7 | Ethanol/Toluene (50/50) | 900 | 9 + 13 | 9 + 13 | — | — |
| PSM8 | 1-Propanol/Ethyl acetate (75/25) | 1100 | 3 + 3a | 3a | — | — |
| PSM9 | TFE/Ethyl acetate (50/50) | 800 | 3 | 3 + 13 | — | — |
| PSM10 | TFE/2-Methyltetrahydrofuran (50/50) | 1100 | 3a | 3 + 13 | — | — |
| PSM11 | 1-Propanol/Heptane (75/25) | 800 | 3a | 3 + 13 | — | — |
| PSM12 | Methanol/2-Propanol (75/25) | 600 | 1 | 1 + 8 | 3 | 3 + 13 |
| PSM13 | Methanol/Diisopropyl ether (20/80) | 1100 | — | — | 19 | 19 |
| PSM14 | Diisopropyl ether/2-Propanol (90/10) | 1100 | — | — | — | — |
| PSM15 | 50/50 mixture of IPA/MeOH (25/75) and MeOH/Diisopropyl ether (20/80) | 800 | — | — | 3 | 3 + 13 |

Thermocycling

The polymorphic behavior of the selected salts was evaluated by thermocycling in 6 solvents. To the vials containing the (amorphous) salts, aliquots of solvent were added until a suspension was obtained. The experimental details are shown in Table 12.

Figure 13:
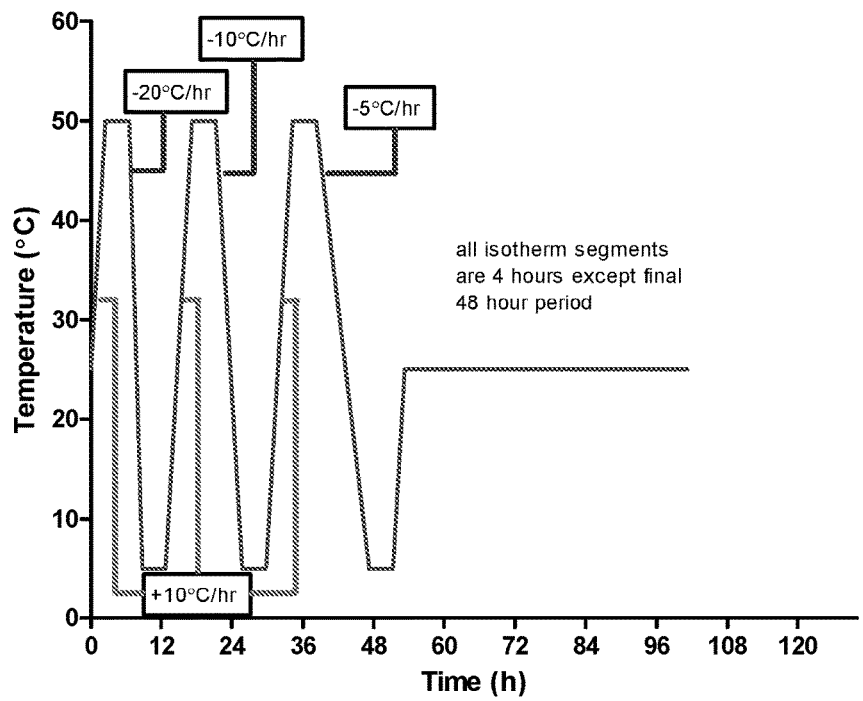
FIG. 13 illustrates temperature profiles for the thermocycling experiments.

The vials were subjected to a temperature profile including 3 thermocycles between 5-50° C. and aged at RT for 2 days, see FIG. 13. After the temperature profile the samples were dried under vacuum (10 mbar) at RT for 24 hours. The samples were harvested and analyzed by HT-XRPD. Subsequently the solids were exposed to accelerated aging conditions (AAC, 40° C./75% RH) for two days and reanalyzed by HT-XRPD.

TABLE 12

Experimental conditions and XRPD results of the thermocycling experiments on the voruciclib salts. Suspensions of the amorphous API were subjected to a temperature profile, including three heating and cooling cycles (FIG. 13). After the aging time, the solids were analyzed by HT-XRPD after drying at ambient conditions (Ambient) and after drying under vacuum (Vacuum). The solvents from the liquid phases were evaporated and recovered solids were analyzed. All solids were exposed to AAC for 2 days and re-analyzed by XRPD. In case no solids were obtained, this is noted with "—". "tr" means "traces".

| Exp. ID | Mass (mg) | Solvent or Solvent Mixture (v/v) | Volume (µL) | Solid Ambient | AAC | Vacuum | AAC | Liquid Form | AAC |
|---|---|---|---|---|---|---|---|---|---|
| TCP1 | 40 | 1-Propanol | 500 | 1 + 3 | 1 + 4 | 1 | 1 | 3a | 3 + 6 pc + 13 |
| TCP2 | 40 | Tetrahydrofuran | 1000 | 4 | 1 + 4 | 4a | 6 pc | 4 | 6 pc |

TABLE 12-continued

Experimental conditions and XRPD results of the thermocycling experiments on the voruciclib salts. Suspensions of the amorphous API were subjected to a temperature profile, including three heating and cooling cycles (FIG. 13). After the aging time, the solids were analyzed by HT-XRPD after drying at ambient conditions (Ambient) and after drying under vacuum (Vacuum). The solvents from the liquid phases were evaporated and recovered solids were analyzed. All solids were exposed to AAC for 2 days and re-analyzed by XRPD. In case no solids were obtained, this is noted with "—". "tr" means "traces".

| Exp. ID | Mass (mg) | Solvent or Solvent Mixture (v/v) | Volume (μL) | Solid Ambient | AAC | Vacuum | AAC | Liquid Form | AAC |
|---|---|---|---|---|---|---|---|---|---|
| TCP3 | 40 | Acetone | 1000 | 1 | 1 | 1 | 1 | — | — |
| TCP4 | 40 | Chloroform | 1000 | 4a | 6 pc | 4a | 6 pc | 4 | 6 pc |
| TCP5 | 40 | 1,2-Dimethoxyethane | 1000 | 7 | 7 | 7 | 7 | — | — |
| TCP6 | 40 | Ethyl formate | 1000 | 4a | 6 pc | 4a | 1 + 6 pc | — | — |
| TCP7 | 40 | Acetonitrile | 1000 | 1 | 1 | 1 | 1 | — | — |
| TCP8 | 40 | 1,4-Dioxane | 1000 | 4a + 5 | 4 + 6 pc | 5 | 6 pc | — | — |
| TCP9 | 40 | p-Xylene | 1000 | 4 | 4 | 4 | 4 | — | — |
| TCP10 | 40 | n-Hexane | 1000 | Am | 6 pc | Am | 6 pc | — | — |
| TCP11 | 40 | IPA/H$_2$O (99/1) | 1000 | 3 | 3 + 13 | 3 | 3 + 13 | — | — |
| TCP12 | 40 | IPA/H$_2$O (97/3) | 1000 | 3 | 3 + 13 | 3 | 3 + 13 | — | — |
| TCP13 | 40 | IPA/H$_2$O (95/5) | 1000 | 3 | 3 + 13 | 3 | 3 + 13 | — | — |
| TCP14 | 40 | 1,4-Dioxane/H$_2$O (99/1) | 1000 | 5 + 8 | 6 pc | 5 | 6 pc | — | — |
| TCP15 | 40 | 1,4-Dioxane/H$_2$O (95/5) | 900 | 2 | 2 | 2 | 2 | — | — |
| TCP16 | 40 | Acetone/H$_2$O (99/1) | 700 | 1 + peaks | 1 | 1 | 1 | 12 pc | 12 pc |
| TCP17 | 40 | Acetone/H$_2$O (95/5) | 1000 | 12 | 12 | 14 | 14 | 12 | 12 |
| TCP18 | 40 | Acetone/H$_2$O (90/10) | 900 | 12 | 12 | 6 pc + 9 | 14 | 12 + tr 3 | 12 + tr 3 |
| TCP19 | 40 | Acetonitrile/H$_2$O (97/3) | 1000 | 12 | 12 | 14 | 7 + 14 | 12 | 12 |
| TCP20 | 40 | Acetonitrile/H$_2$O (90/10) | 1000 | 12 | 12 | 14 | 14 | 12 | 12 |
| TCP21 | 19 | Methanol/IPA (75/25) | 100 | 1 | 1 | 1 | 1 | 8 pc | 8 |
| TCP22 | 36 | MeOH/Diisopropyl ether (20/80) | 300 | — | — | 1 | 1 | — | — |
| TCP23 | 24 | Diisopropyl ether/IPA (90/10) | 1100 | 1 | 1 | 1 | 1 | — | — |
| TCP24 | 23 | 50/50 mixture of IPA/MeOH (25/75) and MeOH/Diisopropyl ether (20/80) | 800 | — | — | — | — | 8 pc | 8 |

Anti-Solvent

Anti-solvent addition experiments were performed according to the reversed anti-solvent addition method. Highly concentrated solutions of voruciclib HCl were prepared in solvents in which the API is good soluble. The solutions were added at once to 20 mL of anti-solvent (in which the API is not soluble), while vigorously stirring. The precipitated solids were separated by centrifugation and one part of the solids was harvested and dried under ambient conditions. The other part of the solids was dried under vacuum (10 mbar) at 50° C. for 24 hours. Subsequently the solids were exposed to accelerated aging conditions (AAC, 40° C./75% RH) for two days and reanalyzed by HT-XRPD.

Vapor Diffusion Into Solution (Close to) saturated solutions of voruciclib HCl were prepared by dissolving approximately 50 mg of API in a solvent in a 1.5 mL or 8 mL glass vial. In ethanol and THF the API did not dissolve completely, hence these suspensions were filtered to obtain saturated solutions. The solutions in small vials were placed in larger vials containing 2 mL of anti-solvent (see Table 14). The vials were stored at RT for 2 weeks after which the precipitated solids were carefully collected from the liquids and analyzed by HT-XRPD. In case no solids precipitated the solvents were evaporated under ambient conditions, followed by evaporation under vacuum (10 mbar/50° C.) and the recovered solids were

TABLE 13

Experimental conditions and XRPD results for the anti-solvent experiments. Solutions in solvent/water mixtures were added to 20 mL of THF. No precipitation occurred, also not during aging at 5° C. for 72 hours. "tr" means "traces".

| Exp ID | Solvent | m (mg) | V (μL) | Anti-solvent | Ambient | AAC | Vacuum | AAC |
|---|---|---|---|---|---|---|---|---|
| AS1 | DMSO | 51.2 | 110 | TBME | 16 pc | 2 | 16 | 2 |
| AS2 | DMF | 50.2 | 120 | Toluene | 4 | Am | 4a | Am |
| AS3 | TFE | 51.5 | 130 | Heptane | 17 | 13 | 17 | 13 |
| AS4 | Methanol | 49.5 | 215 | p-Xylene | 2 | 2 | 2 | 2 |
| AS5 | IPA | 50.3 | 2500 | 2,2,4-Trimethylpentane | 3 + tr 13 | 13 | 3 + tr 13 | 13 |
| AS6 | IPA | 49.9 | 2500 | Cyclohexane | 3 + tr 13 | 13 | 3 + tr 13 | 13 |
| AS7 | DMF | 52.1 | 130 | Isopropyl acetate | 18 | 18 | Am | 6 pc |
| AS8 | TFE | 49.8 | 125 | Pentane | 3a | 13 | 3 pc | 13 |
| AS9 | Methanol | 52.1 | 230 | Diethyl ether | 1 | 1 | 1 | 1 |
| AS10 | DMSO | 53.6 | 130 | Water | Am | — | pc | pc | analyzed by XRPD. Subsequently, all solids were exposed to AAC (40° C./75% RH) and re-analyzed by XRPD.

TABLE 14

Experimental conditions and XRPD results of the vapor diffusion into solution experiments. Close to saturated solutions were prepared in solvents and the solutions were exposed to the vapors of an anti-solvent. After 2 weeks equilibration at RT the solids were analyzed by XRPD (Solid). In case no precipitation occurred the solvents were evaporated and the recovered solids analyzed by XRPD (Liquid). All solids were exposed to AAC and reanalyzed by XRPD.

| Exp ID | Solvent (solution) | Mass (mg) | Volume (μL) | Anti-solvent (vapor) | Solid | AAC | Liquid | AAC |
|---|---|---|---|---|---|---|---|---|
| VDL6 | DMA | 50.6 | 100 | Acetonitrile | 1 | 1 | — | — |
| VDL7 | DMSO | 50.7 | 100 | TBME | — | — | 16 | 1 + 12 |
| VDL8 | DMF | 51.1 | 200 | 1,4-Dioxane | — | — | 15 | 2 + traces 1 |
| VDL9 | Ethanol | 50.6 | 850 | Acetone | — | — | 3 + 9 + 11 | 1 + peak7 |
| VDL10 | THF | 50.4 | 4900 | Pentane | Am | Am | — | — |

Vapor Diffusion Onto Solid

The vapor diffusion onto solid experiments were performed using the amorphous voruciclib HCl as starting material. Small vials containing about 20 mg of the amorphous API were placed in larger vials containing 2 mL of solvent (see Table 15). The vials were stored at RT for 2 weeks after which the solids were analyzed by HT-XRPD. In solvent was trapped in the small vial, the solvent was evaporated under vacuum (10 mbar/50° C.) and the recovered solids were analyzed by XRPD. Subsequently, all solids were exposed to AAC (40° C./75% RH) and re-analyzed by XRPD.

TABLE 15

Experimental conditions and XRPD results of the vapor diffusion onto solid experiments. Amorphous API was exposed to the vapors of a solvent. After 2 weeks equilibration at RT the solids were analyzed by XRPD (Solid). In one sample solvent was trapped in the small vial and the solvent was evaporated (Liquid). All solids were exposed to AAC and reanalyzed by XRPD.

| Exp ID | Mass (mg) | Anti-solvent (vapor) | Solid | AAC | Liquid | AAC |
|---|---|---|---|---|---|---|
| VDL1 | 20.0 | Heptane | Am | Am | — | — |
| VDL2 | 21.1 | Ethyl acetate | 1 | 1 | — | — |
| VDL3 | 20.4 | 2-Propanol | 3 + trace 8 | 3 + trace 8 | 8 | 8 |
| VDL4 | 21.5 | Methyl ethyl ketone | 1 + 3 | 1 + 3 + 8 | — | — |
| VDL5 | 20.7 | Chloroform | 2 + 4a + 6 pc | 2 + 4 | — | — |

X-Ray Powder Diffraction

XRPD patterns were obtained using the Crystallics T2 high-throughput XRPD set-up. The plates were mounted on a Bruker D8 Discover General Area Detector Diffraction System (GADDS) equipped with a VÅNTEC-500 gas area detector corrected for intensity and geometric variations (product sheet XRD 37, DOC-S88-EXS037V3, FIG. 297). The calibration of the measurement accuracy (peaks position) was performed using NIST SRM1976 standard (Corundum).

Data collection was carried out at room temperature using monochromatic CuK$_\alpha$ radiation in the 2θ region between 1.5° and 41.5°, which is the most distinctive part of the XRPD pattern. The diffraction pattern of each well was collected in two 2θ ranges (1.5°≤2θ≤21.5° for the first frame, and 19.5°≤2θ≤41.5° for the second) with an exposure time of 45 s for each frame. No background subtraction or curve smoothing was applied to the XRPD patterns.

The carrier material used during XRPD analysis was transparent to X-rays and contributed only slightly to the background.

TGA/SDTA and TGMS Analysis

Mass loss due to solvent or water loss from the crystals was determined by TGMS analysis. Monitoring the sample weight, during heating in a TGA/DSC 3+ STARe system (Mettler-Toledo GmbH, Switzerland), resulted in a weight vs. temperature curve. The TGA/DSC 3+ was calibrated for temperature with indium and aluminum. Samples (circa 2 mg) were weighed into 100 μL aluminum crucibles and sealed. The seals were pin-holed and the crucibles heated in the TGA from 25 to 300° C. at a heating rate of 10° C./min. Dry N$_2$ gas was used for purging.

The gases evolved from the TGA samples were analyzed by an Omnistar GSD 301 T2 mass spectrometer (Pfeiffer Vacuum GmbH, Germany). This MS is a quadrupole mass spectrometer, which analyses masses in the range of 0-200 amu.

DSC Analysis

Melting properties were obtained from DSC thermograms, recorded with a heat flux DSC3+ STARe system (Mettler-Toledo GmbH, Switzerland). The DSC3+ was calibrated for temperature and enthalpy with a small piece of indium (m.p.=156.6° C.; δH$_f$=28.45 J/g) and zinc (m.p.=419.6° C.; δH$_f$=107.5 J/g). Samples (circa 2 mg) were sealed in standard 40 μL aluminum pans, pin-holed and heated in the DSC from 25° C. to 300° C., at a heating rate of 10° C./min. Dry N$_2$ gas, at a flow rate of 50 mL/min was used to purge the DSC equipment during measurement.

LCMS Analytical Methods

Method name: S18099_01; HPLC System: Agilent 1200; Detector 1: DAD set at 264 nm; Detector 2: HP1100 LC/MSD in Positive Scan mode.

HPLC Conditions: Autosampler temp: 15° C.; Column: Waters Sunfire C18 (100×4.6 mm; 3.5 μm); Column temp: 35° C.; Flow cell: 10 mm path; Gradient: Table 16; Mobile phase A: 0.1% TFA in water; Mobile phase B: 0.1% TFA in acetonitrile; Flow: 1.0 ml/min.

TABLE 16

| | HPLC mobile phase gradient | |
|---|---|---|
| Time [min] | Mobile phase A | Mobile phase B |
| 0 | 90% | 10% |
| 9 | 10% | 90% |
| 10 | 5% | 95% |
| 11 | 5% | 95% |

Sample: Concentration: ca. 1 mg/ml; Solvent: Water: Acetonitrile:TFA (50:50:0.1 v/v/v); Injection volume: 5 µL.

The compound integrity is expressed as a peak-area percentage, calculated from the area of each peak in the chromatogram, except the 'injection peak', and the total peak-area, as follows:

$$\text{peak} - \text{area } \% = \frac{\text{peak} - \text{area}}{\text{total} - \text{area}} * 100\%$$

The peak-area percentage of the compound of interest is employed as an indication of the purity of the component in the sample.

Form 1

Figure 14:
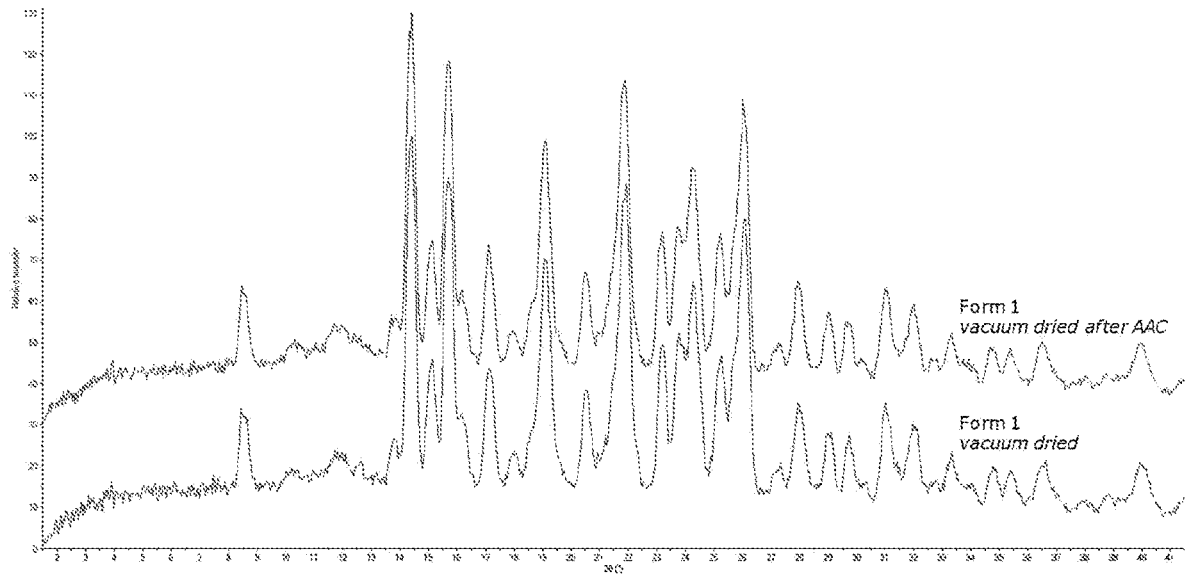
FIG. 14 illustrates an overlay of HT-XRPD patterns of the material obtained from the solvent equilibration experiment in ethanol (Exp. ID SLP19) before and after exposure to AAC.
Figure 15:
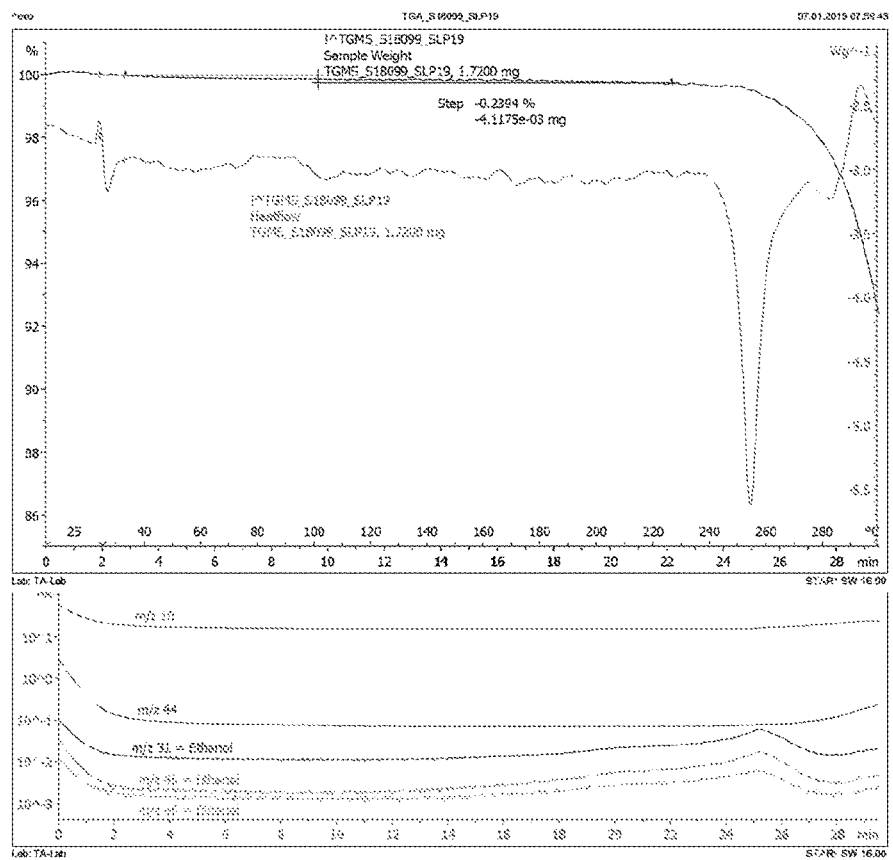
FIG. 15 illustrates the TGMS analysis (heating rate 10° C./min) of Form 1 (Exp. ID SLP19). The mass loss of 0.2% is most likely related to residual solvent or moisture.
Figure 16:
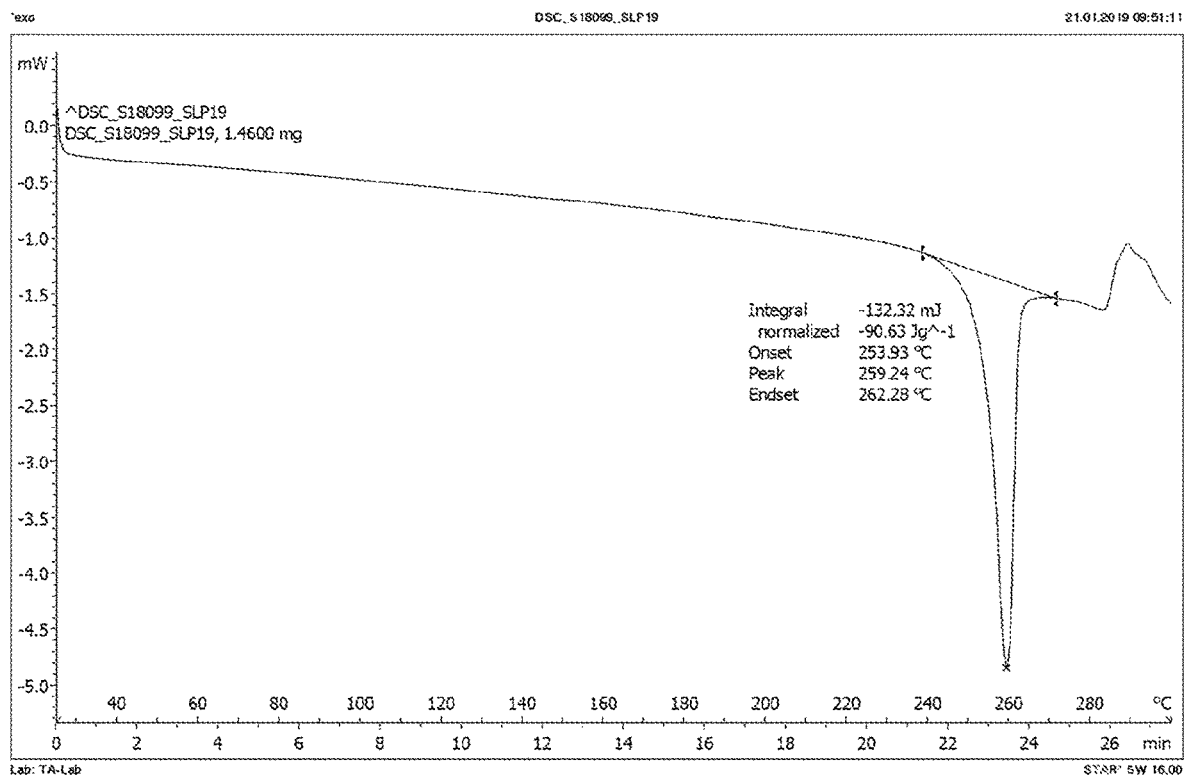
FIG. 16 illustrates the DSC analysis (heating rate 10° C./min) of Form 1 (Exp. ID SLP19). An endothermic event was observed, most likely related to melting and decomposition.
Figure 17:
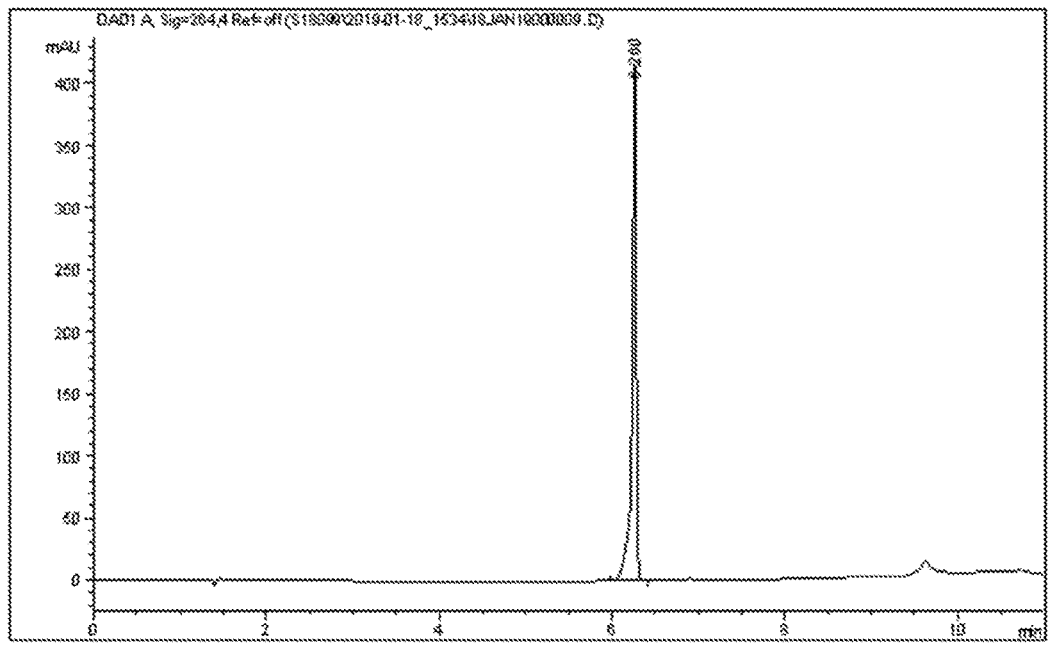
FIG. 17 illustrates an HPLC chromatogram of Form 1 (Exp. ID SLP19). The API peak appeared at 6.3 minutes with a chemical purity of 100% (area percentage).

From the solvent equilibration experiment performed in ethanol, Form 1 was obtained and used for the characterization (Exp. ID SLP19), to compare with the starting material. Form 1 was physically stable upon exposure to AAC (40° C./75% RH) for 2 days. The HT-XRPD patterns of the material of Exp. ID SLP19 before and after exposure to AAC are shown in FIG. 14. The TGMS analysis of Form 1 (FIG. 15) showed a mass loss of 0.2% in the temperature range of 25-220° C. Without wishing to be bound by any particular theory, it is believed that the mass loss was most likely related to residual solvent or moisture. From the heat flow curve, a single endothermic event was observed around 260° C., which without wishing to be bound by any particular theory, it is believed that is related to melting and decomposition. In the DSC curve of Form 1 (FIG. 16), a single endothermic event was recorded at 259° C., which without wishing to be bound by any particular theory, it is believed to most likely be related to melting and decomposition of Form 1. The HPLC chromatogram of Form 1, shown in FIG. 17, revealed the presence of the API with a chemical purity of 100% (area percentage).

Form 2

Figure 18:
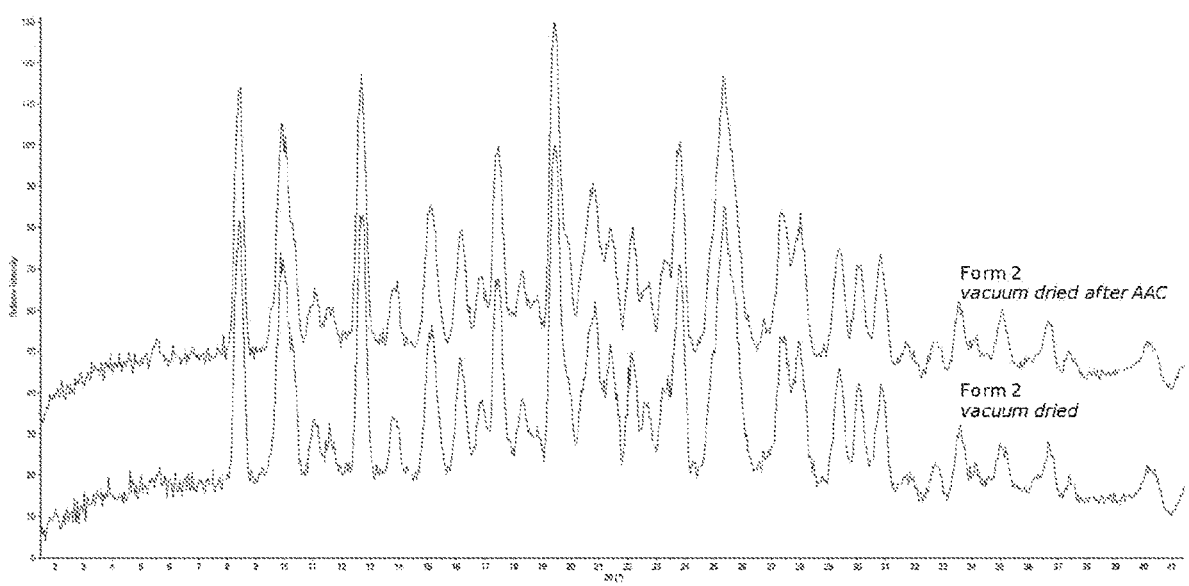
FIG. 18 illustrates an overlay of HT-XRPD patterns of the material obtained from the thermocycling experiment in 1,4-dioxane/water 95/5 (Exp. ID TCP2) before and after exposure to AAC.
Figure 19:
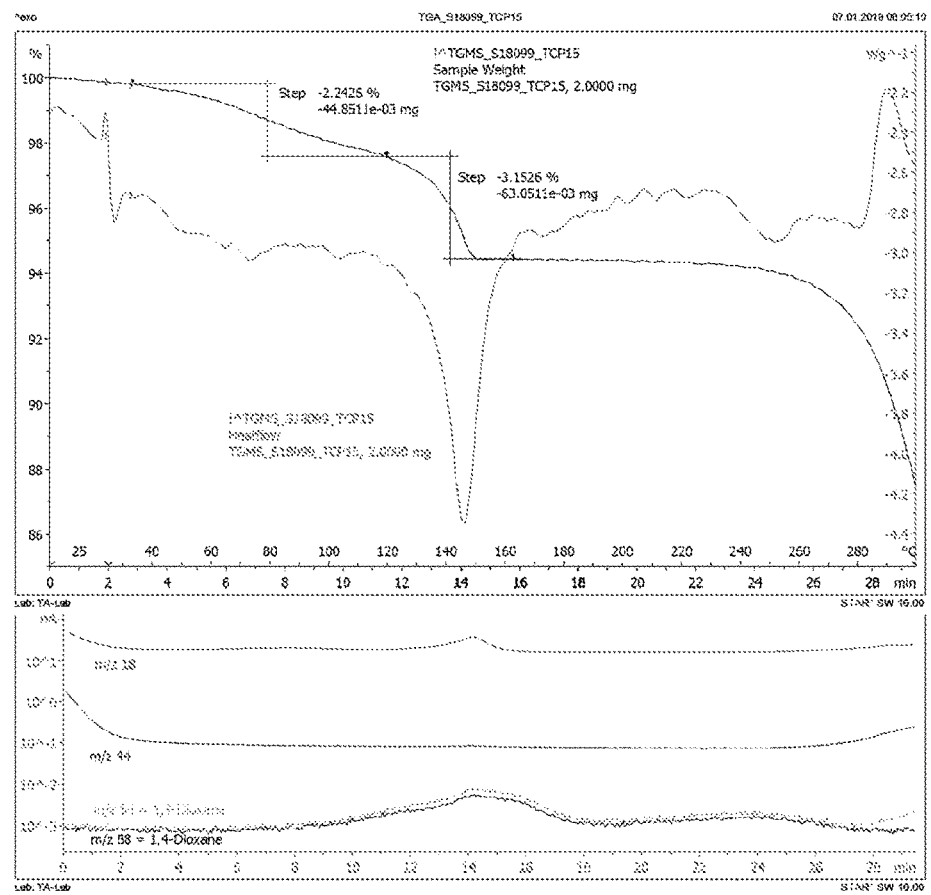
FIG. 19 illustrates a TGMS analysis (heating rate 10° C./min) of Form 2 (Exp. ID TCP15). The total mass loss of 5.4% is related to solvent loss (equal to 0.3 molecules of dioxane).
Figure 20:
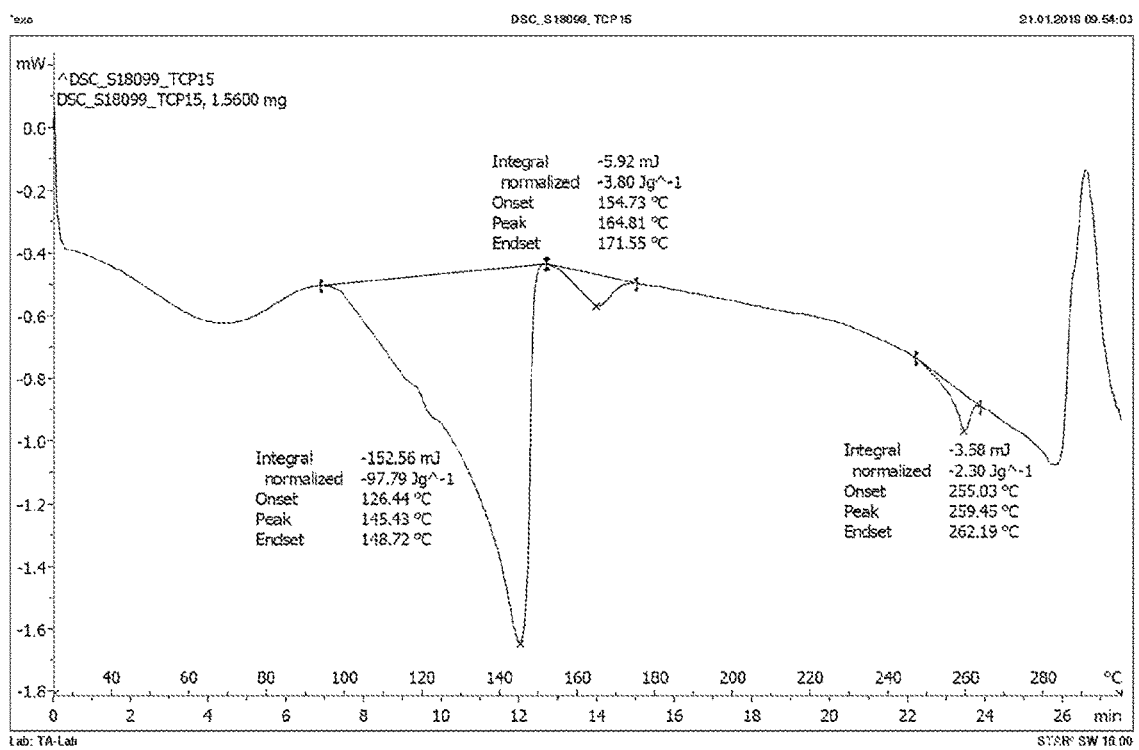
FIG. 20 illustrates a DSC analysis (heating rate 10° C./min) of Form 2 (Exp. ID TCP15). Two broad endothermic events were observed, related to solvent loss. The small endothermic event at 165° C. was possibly the transition to Form 1 as the small endothermic event observed at 259° C. coincides with the melting of Form 1.
Figure 21:
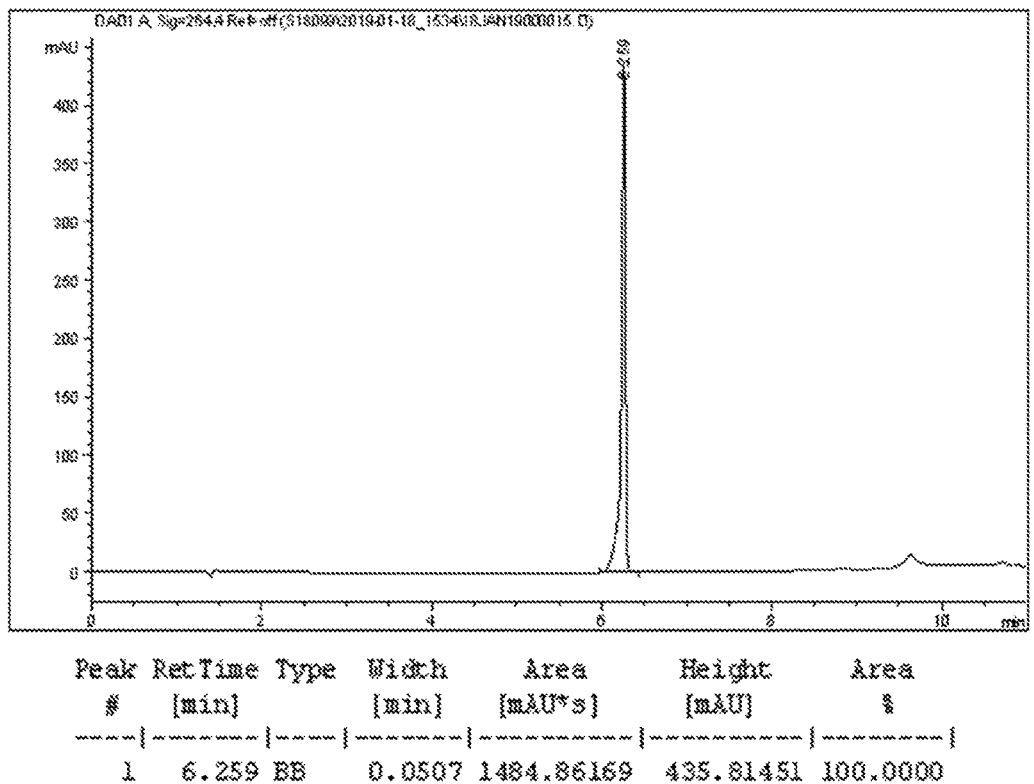
FIG. 21 illustrates an HPLC chromatogram of Form 2 (Exp. ID TCP5). The API peak appeared at 6.3 minutes with a chemical purity of 100% (area percentage).

From the thermocycling experiment performed in 1,4-dioxane/water 95/5 (v/v) Form 2 was obtained and used for the characterization (Exp. ID TCP2). Form 2 was physically stable upon exposure to AAC (40° C./75% RH) for 2 days. The HT-XRPD patterns of the material of Exp. ID TCP2 before and after exposure to AAC are shown in FIG. 18. The TGMS analysis of Form 2 (FIG. 19) showed a total mass loss of 5.4% in the temperature range of 25-150° C. This mass loss is equal to 0.3 molar equivalent 1,4-dioxane. Form 2 was found from different type of solvents and, without wishing to be bound by any particular theory, it is believed that is a non-stoichiometric isostructural solvate. In the DSC curve of Form 2 (FIG. 20), two broad endothermic events were recorded between 25-150° C., related to mass loss. Without wishing to be bound by any particular theory, it is believed that the small endothermic event at 165° C. was possibly the transition to Form 1 as a small endothermic event was observed at 259° C. (coinciding with the melt of Form 1). The HPLC chromatogram of Form 2, shown in FIG. 21, revealed the presence of the API with a chemical purity of 100% (area percentage).

Form 3

Figure 22:
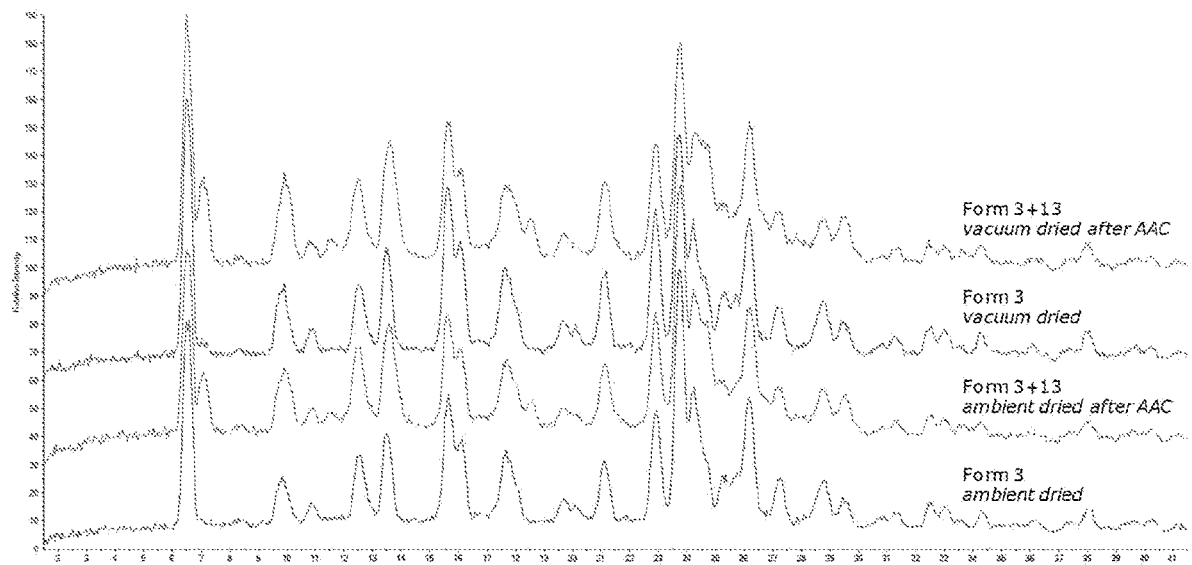
FIG. 22 illustrates an overlay of HT-XRPD patterns of the material obtained from the thermocycling experiment in IPA/water 95/5 (Exp. ID TCP13) dried at ambient conditions and under vacuum, before and after exposure to AAC.
Figure 23:
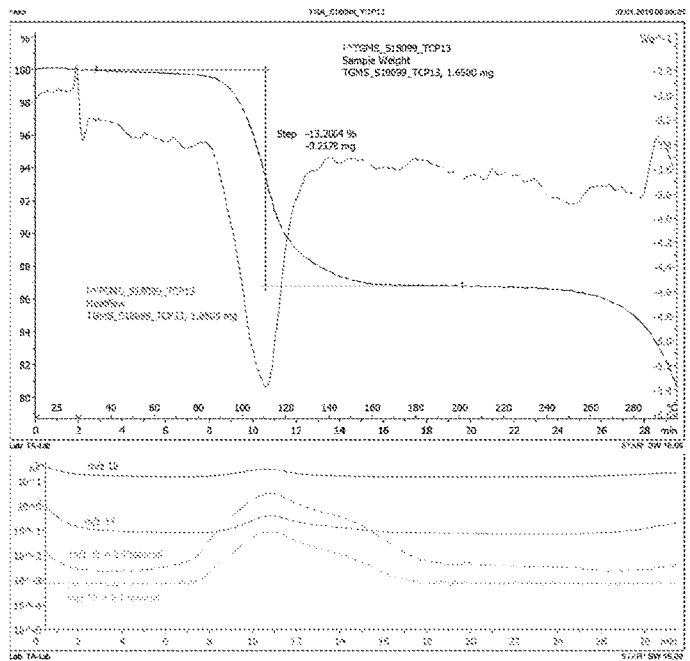
FIG. 23 illustrates a TGMS analysis (heating rate 10° C./min) of Form 3 (Exp. ID TCP13). The mass loss of 13.2% is related to solvent loss.
Figure 24:
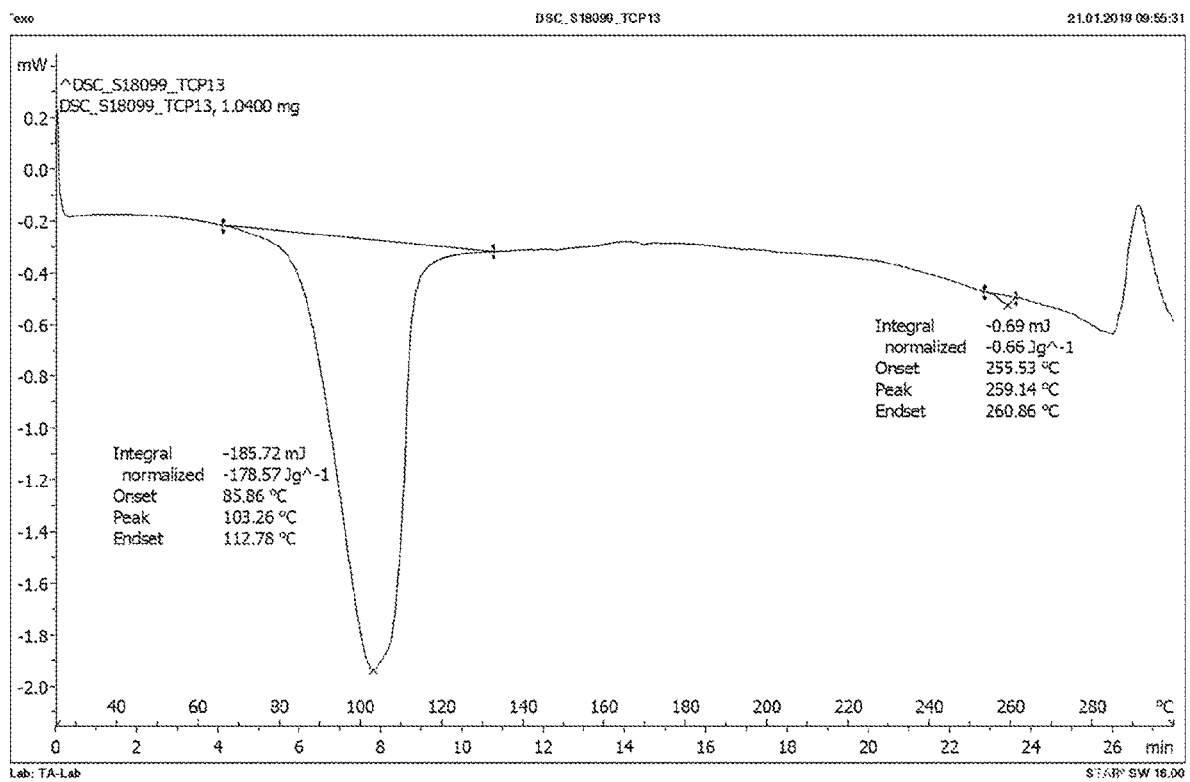
FIG. 24 illustrates a DSC analysis (heating rate 10° C./min) of Form 3 (Exp. ID TCP13). A broad endothermic event was observed, most likely related with solvent loss. A very small endotherm at 259° C. was observed, although most likely the bulk material had become amorphous after the solvent loss.
Figure 25:
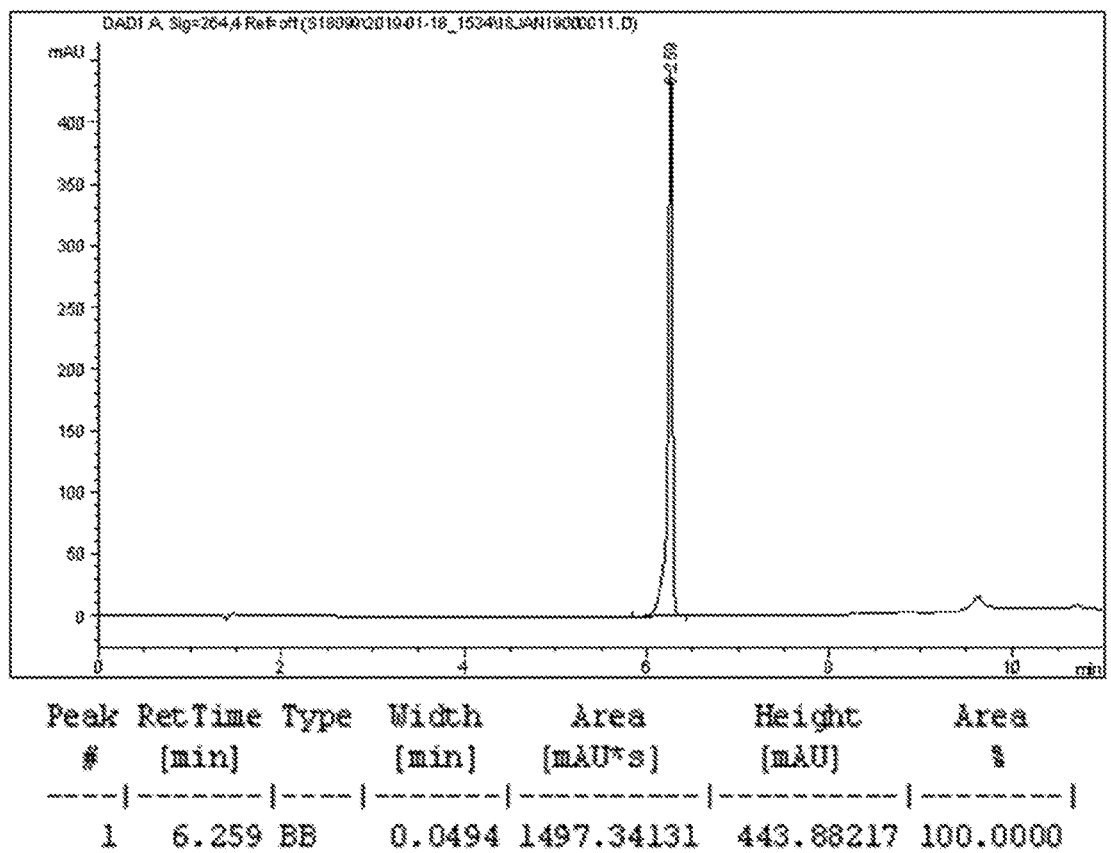
FIG. 25 illustrates an HPLC chromatogram of Form 3 (Exp. ID TCP13). The API peak appeared at 6.3 minutes with a chemical purity of 100% (area percentage).

From the thermocycling experiment performed in 2-propanol/water 95/5 (v/v) Form 3 was obtained and used for the characterization (Exp. ID TCP2). Form 3 was obtained from the ambient dried and vacuum dried solids, but was physically unstable upon exposure to AAC (40° C./75% RH) for 2 days and turned into a mixture of Form 3+13. The HT-XRPD patterns of the ambient dried and vacuum dried solids of Exp. ID TCP13 before and after exposure to AAC are shown in FIG. 22. The TGMS analysis of Form 3 (FIG. 23) showed a mass loss of 13.2% in the temperature range of 80-160° C., which without wishing to be bound by any particular theory, it is believed to be due to loss of IPA (1.3 equivalents IPA), accompanied by a large endothermic event in the heat flow signal (Tpeak 103° C.). No melting event was observed after the mass loss, suggesting, without wishing to be bound by any particular theory, that the material became amorphous after the solvent loss. Without wishing to be bound by any particular theory, it is believed that Form 3 was found from different alcohols and is therefore a non-stoichiometric isostructural solvate. In the DSC curve of Form 3 (FIG. 24), a broad endothermic event was recorded at 103° C., which without wishing to be bound by any particular theory, it is believed to be related to loss of IPA. A very small endothermic event was observed at 259° C., coinciding with the melt of Form 1, although the bulk material was most likely amorphous after the solvent loss. The HPLC chromatogram of Form 3, shown in FIG. 25, revealed the presence of the API with a chemical purity of 100% (area percentage).

Form 4

Figure 26:
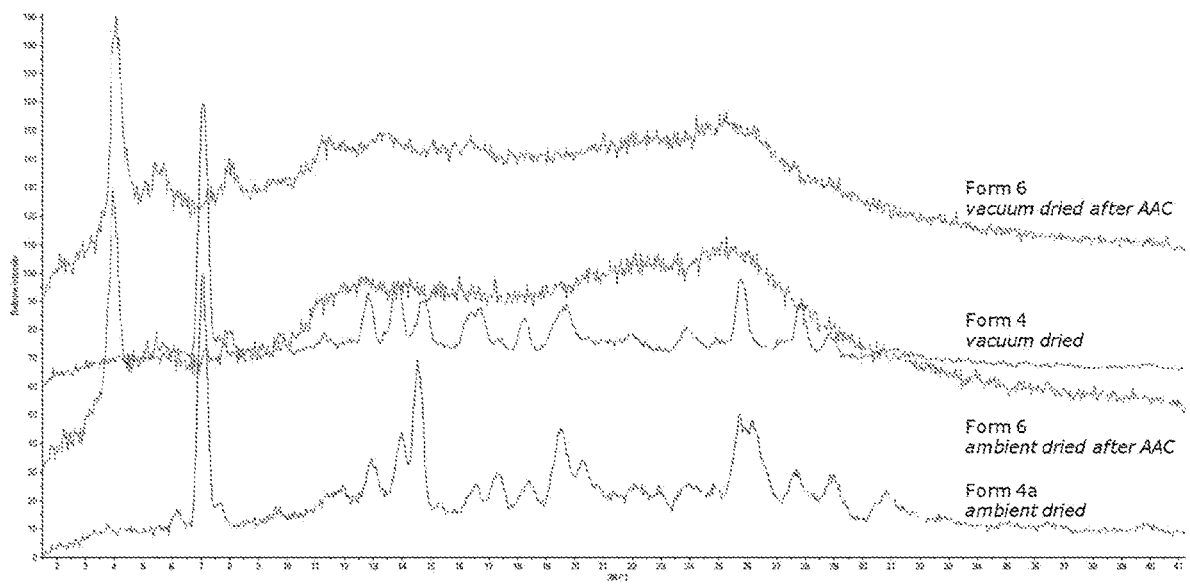
FIG. 26 illustrates an overlay of HT-XRPD patterns of the material obtained from the solvent equilibration experiment in THF (Exp. ID SLP30) dried ambient (purple) and under vacuum (blue) and after exposure to AAC (green).
Figure 27:
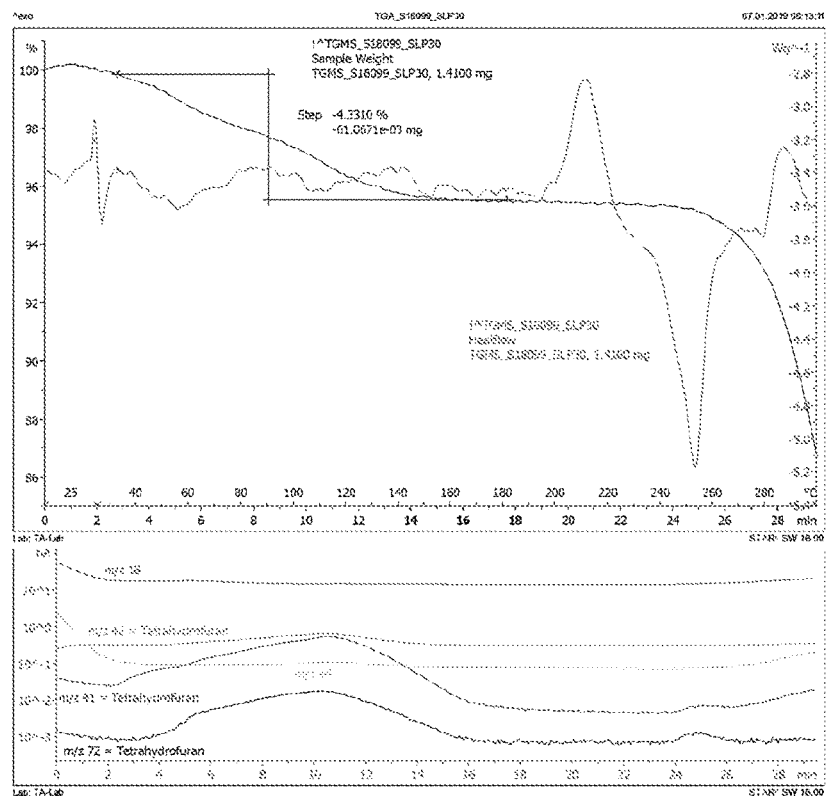
FIG. 27 illustrates the TGMS analysis (heating rate 10° C./min) of Form 4 (Exp. ID SLP30). The mass loss of 4.3% is related to the solvent loss. The following exothermic and endothermic events were respectively attributed to recrystallization and melting/decomposition.
Figure 28:
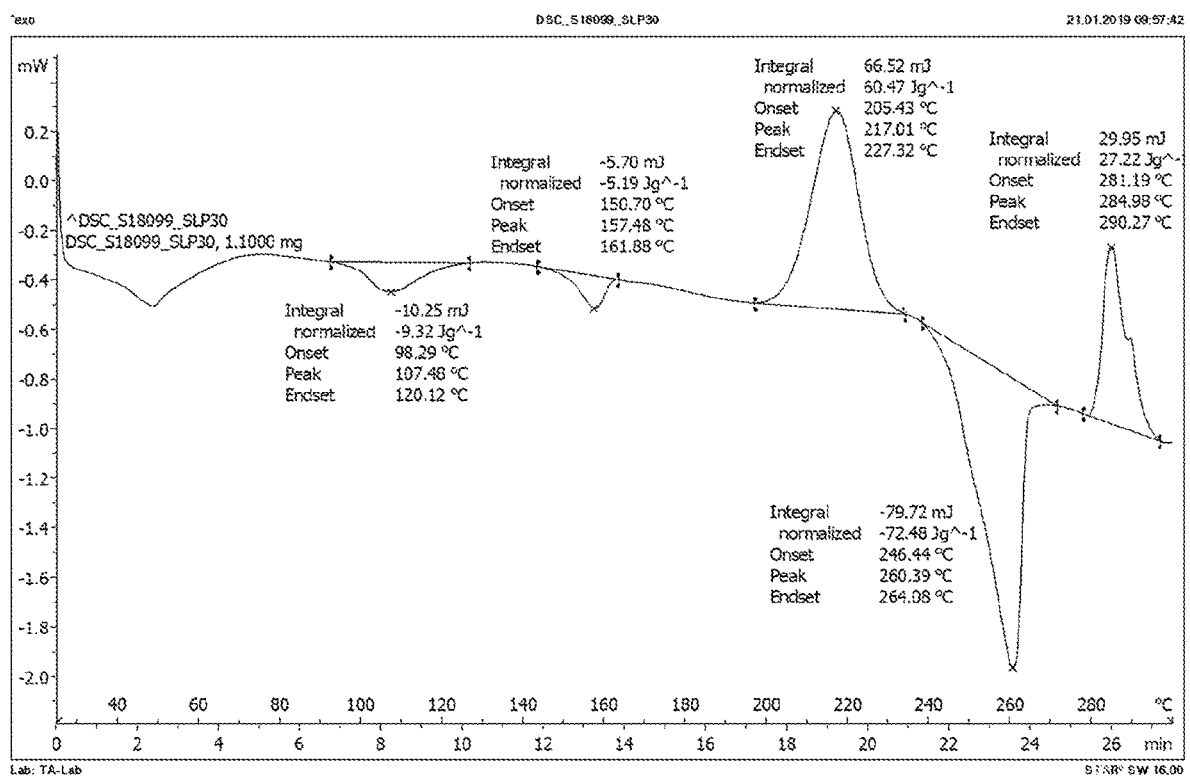
FIG. 28 illustrates the DSC analysis (heating rate 10° C./min) of Form 4 (Exp. ID SLP30). Three broad endothermic events were observed, related with solvent loss. Following, an exothermic recrystallization event at 217° C., an endothermic melting (at 260° C.) and decomposition event.
Figure 29:
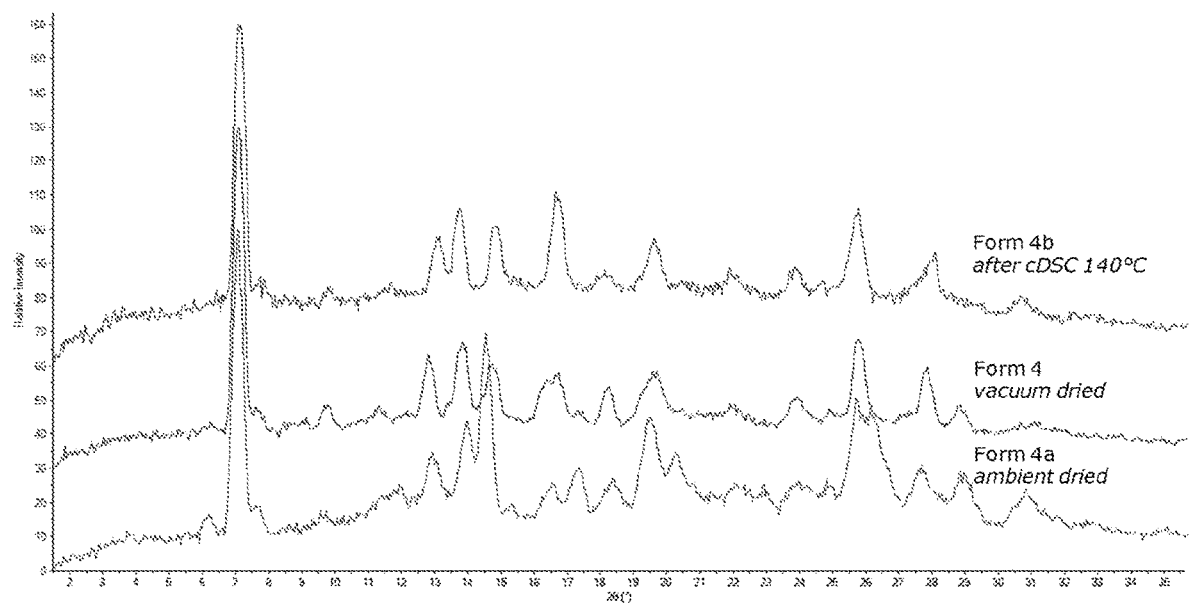
FIG. 29 illustrates an overlay of XRPD of solid phases obtained from Exp. ID SLP30 (from bottom to top): Form 4a (ambient dried solids), Form 4 (vacuum dried solids) and Form 4b obtained after cycling DSC experiment to 140° C.
Figure 30:
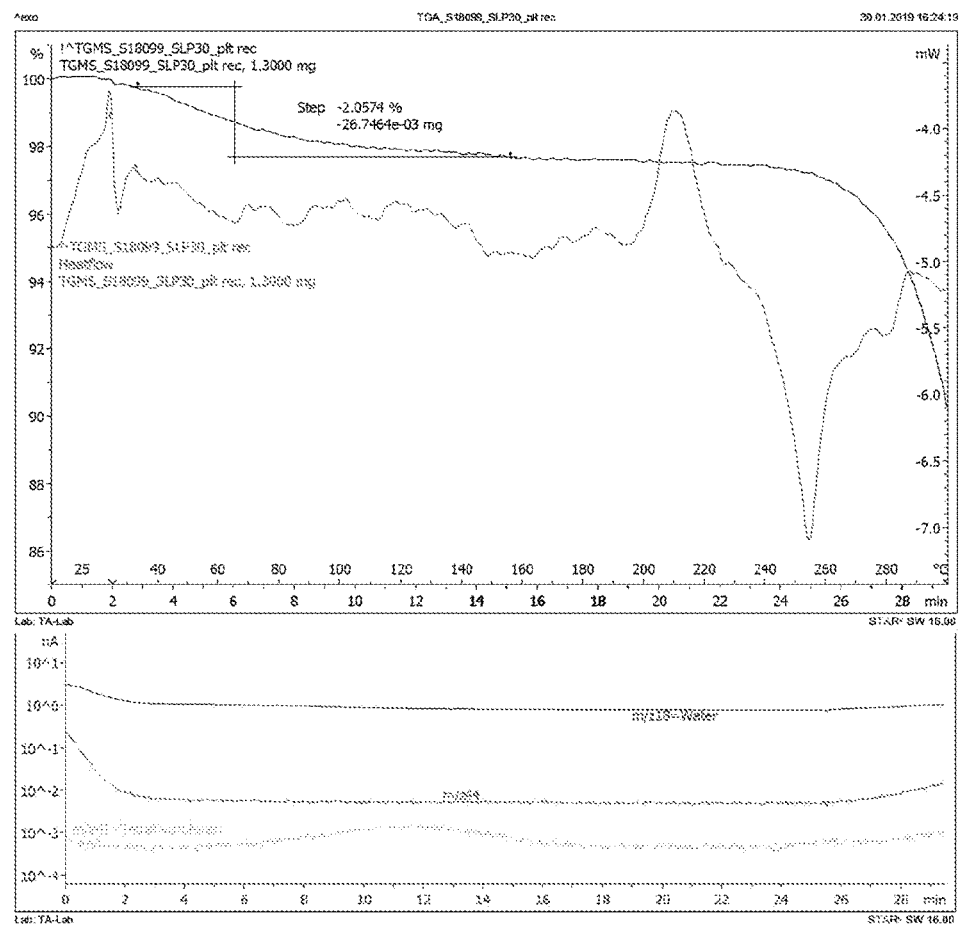
FIG. 30 illustrates the TGMS analysis on the solids obtained after the cycling DSC experiment to 155° C. on Form 4.
Figure 31:
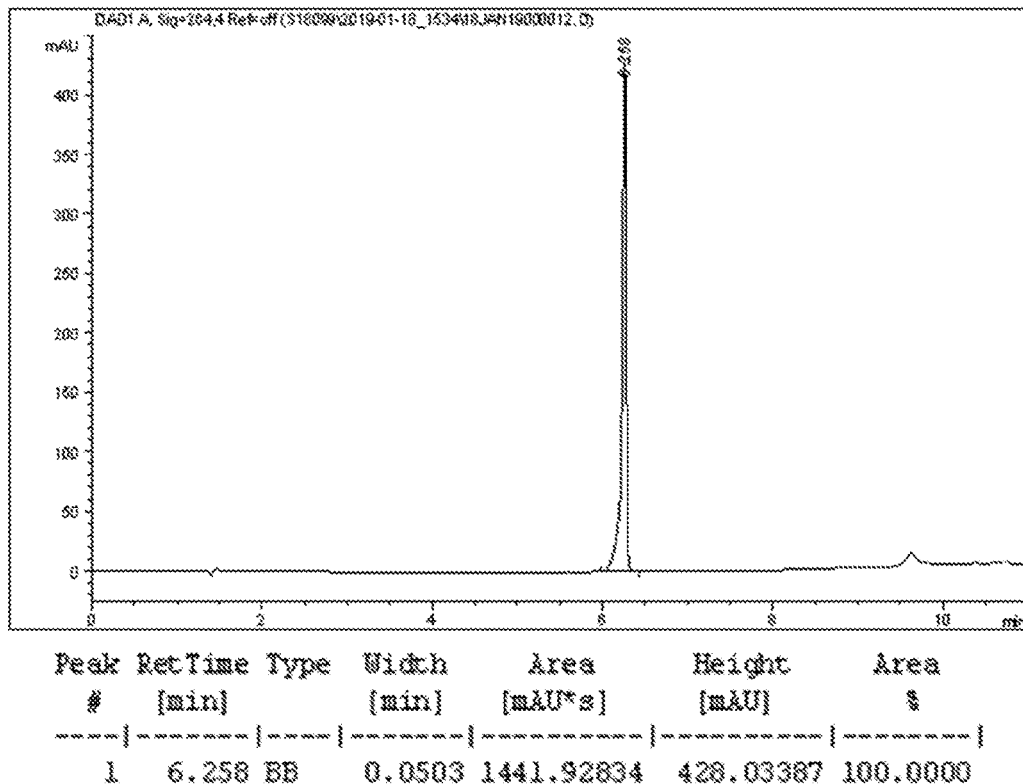
FIG. 31 illustrates an HPLC chromatogram of Form 4 (Exp. ID SLP30). The API peak appeared at 6.3 minutes with a chemical purity of 100% (area percentage).

From the solvent equilibration experiment performed in tetrahydrofuran Form 4 was obtained and used for the characterization (Exp. ID SLP30). The pattern of the solid dried under ambient conditions (Form 4a) was slightly different than the pattern of the solids dried under vacuum (Form 4). Form 4(a) was physically unstable upon exposure to AAC (40° C./75% RH) for 2 days and converted to Form 6. The HT-XRPD patterns of the solids of Exp. ID SLP30 before and after exposure to AAC are shown in FIG. 26. The TGMS analysis of Form 4 (FIG. 27) showed a mass loss of 4.3% in the temperature range of 25-160° C. Without wishing to be bound by any particular theory, it is believed that the mass loss was most likely related to loss of THF (0.3 equivalent THF). After the mass loss an exothermic recrystallization event was observed around 220° C., followed by a melting and decomposition around 260° C. (melt of Form 1). Without wishing to be bound by any particular theory, it is believed that Form 4 was obtained from different solvents and therefore is a non-stoichiometric isostructural solvate. In the DSC curve of Form 4 (FIG. 28), three endothermic events were recorded, of which the first two occur during the solvent loss. The small endothermic event at 157° C. is observed at a temperature directly after the solvent loss. An exothermic recrystallization event was observed at 217° C., followed by a melting at 260° C. (melt of Form 1) and decomposition. A cycling DSC experiment was performed in which the solids of Form 4 were heated to 140° C. (after solvent removal). The solids were recovered and analyzed by XRPD and TGMS, which showed a similar pattern (Form 4b) and 2% of water content. The HPLC chromatogram of Form 4, shown in FIG. 31, revealed the presence of the API with a chemical purity of 100% (area percentage).

Form 5

Figure 32:
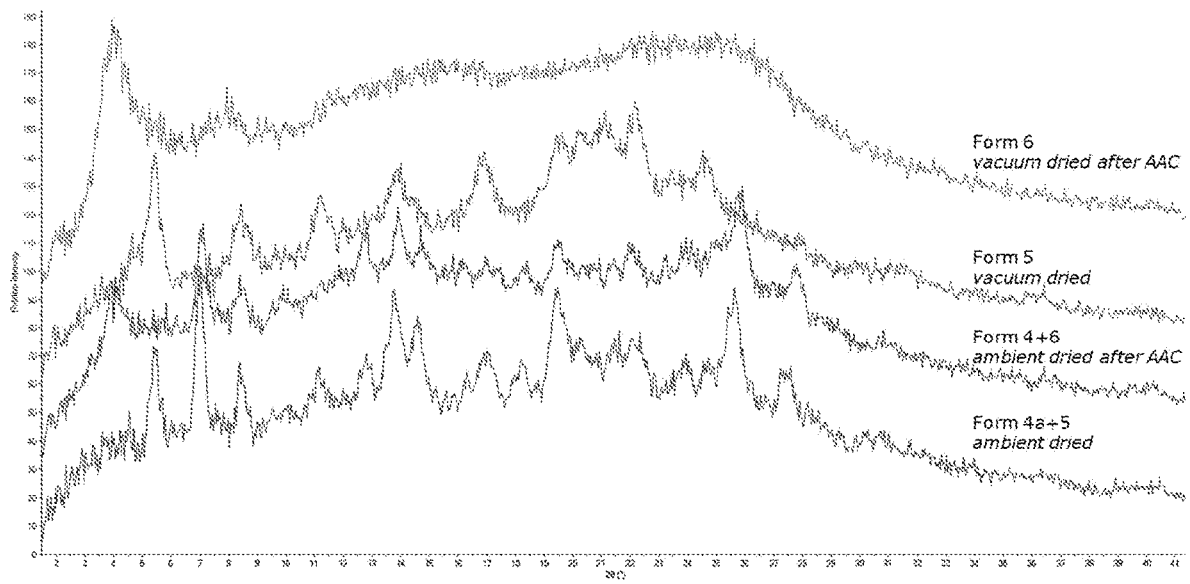
FIG. 32 illustrates an overlay of HT-XRPD patterns of the material obtained from the thermocycling experiment in 1,4-dioxane (Exp. ID TCP8) dried ambient and under vacuum, before and after exposure to AAC.
Figure 33:
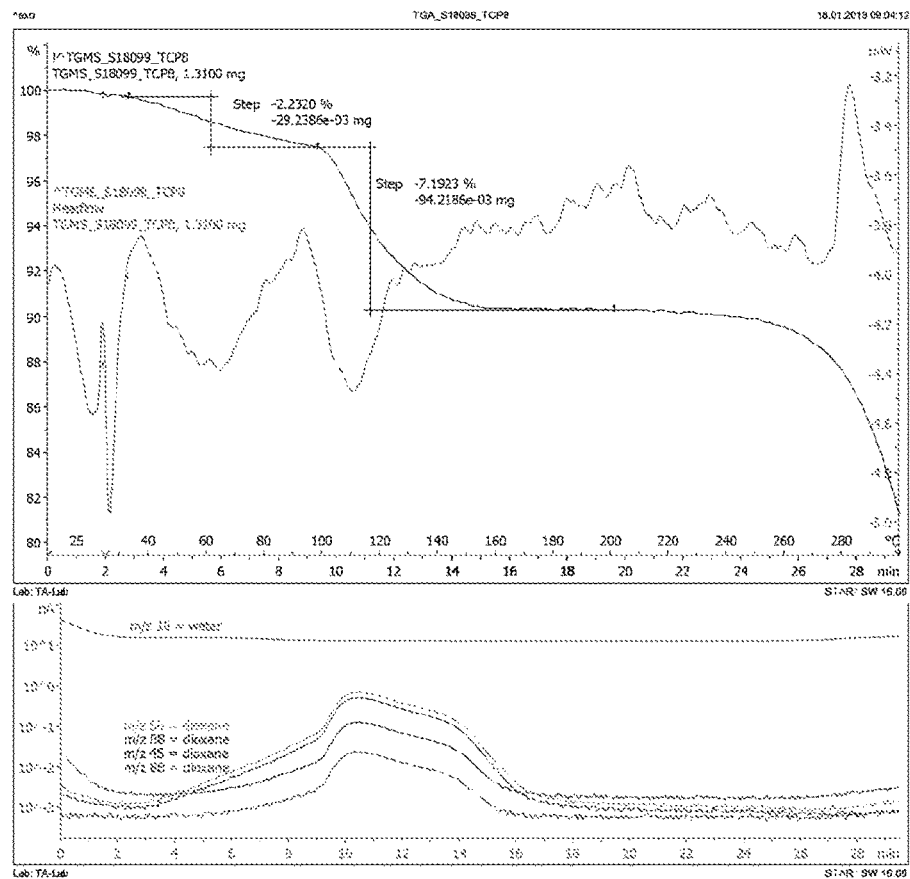
FIG. 33 illustrates the TGMS analysis (heating rate 10° C./min) of Form 5 (Exp. ID TCP8). The total mass loss of 9.4% is related to solvent loss.
Figure 34:
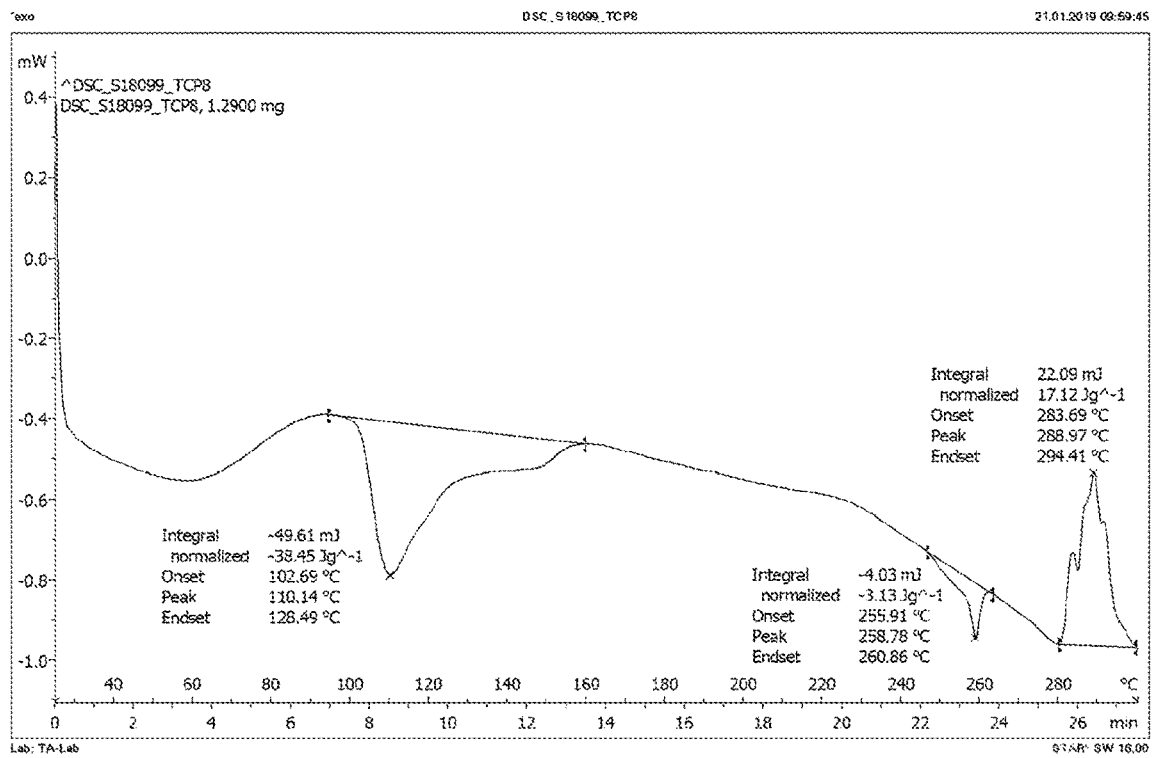
FIG. 34 illustrates the DSC analysis (heating rate 10° C./min) of Form 5 (Exp. ID TCP8). A broad endothermic event was observed, most likely related with solvent loss, followed by a small endotherm at 259° C. and decomposition events.
Figure 35:
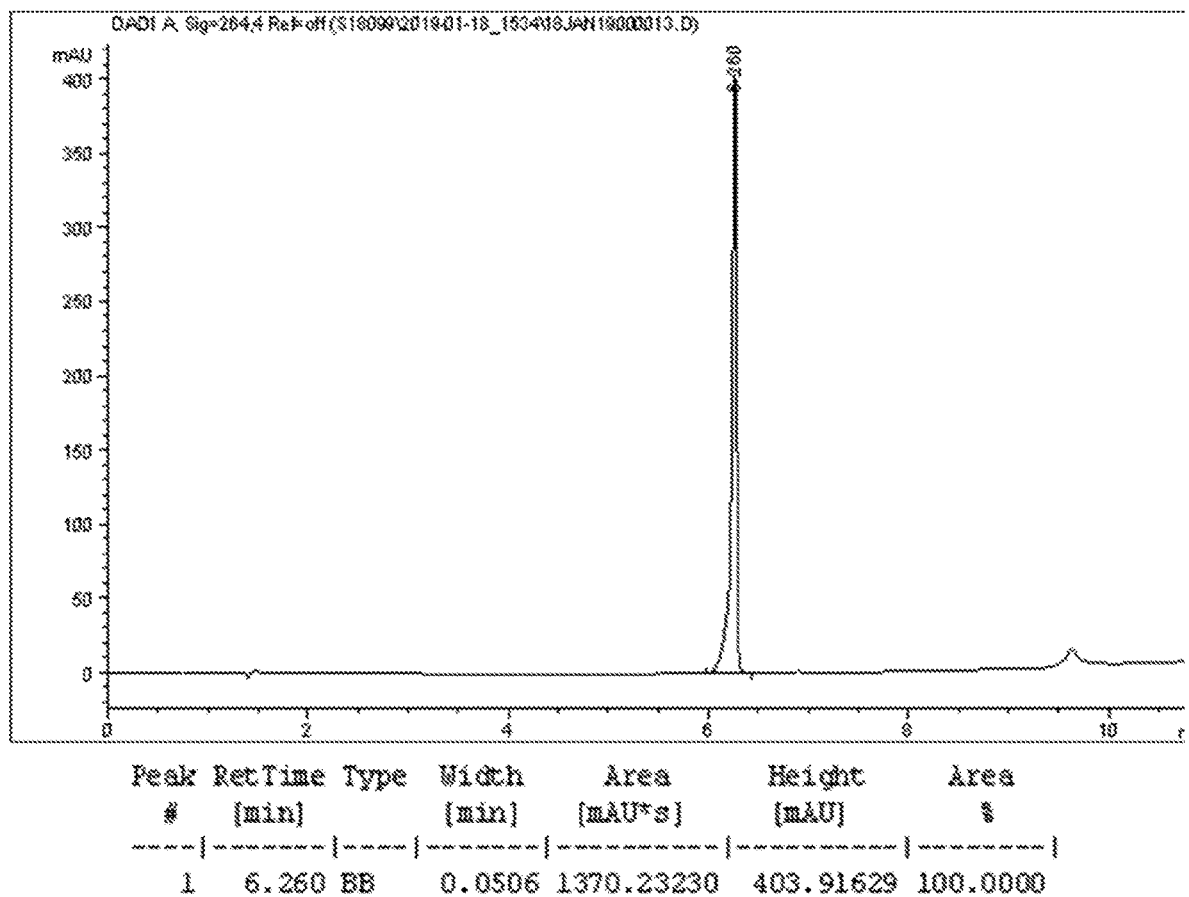
FIG. 35 illustrates an HPLC chromatogram of Form 5 (Exp. ID TCP8). The API peak appeared at 6.3 minutes with a chemical purity of 100% (area percentage).

From the thermocycling experiment performed in 1,4-dioxane Form 5 was obtained and used for the characterization (Exp. ID TCP8). The ambient dried solids of Exp. ID TCP8 was a physical mixture of Forms 4a and 5. The vacuum dried solids were Form 5. Form 5 was physically unstable upon exposure to AAC (40° C./75% RH) for 2 days and turned into Form 6. The HT-XRPD patterns of the solids of Exp. ID TCP8 before and after exposure to AAC are shown in FIG. 32. Without wishing to be bound by any particular theory, it is believed that the TGMS analysis of Form 5 (FIG. 33) showed a total mass loss of 9.4% in the temperature range of 25-160° C., due to loss of 1,4-dioxane (0.6 molar equivalent 1,4-dioxane). The mass loss occurred in 2 steps, accompanied by two endothermic events. Without wishing to be bound by any particular theory, it is believed that the material most likely became amorphous after the solvent loss. Without wishing to be bound by any particular theory, it is believed that Form 5 was obtained from samples with dioxane and 2-methylTHF and is therefore most likely an isostructural solvate. In the DSC curve of Form 5 (FIG. 34), a broad endothermic event was recorded at 110° C., most likely related to solvent loss. A very small endothermic event was observed at 259° C., coinciding with the melt of Form 1, but most likely the bulk of the solid had become amorphous after the solvent removal. The HPLC chromatogram of Form 5, shown in FIG. 35, revealed the presence of the API with a chemical purity of 100% (area percentage).

Form 6

Figure 36:
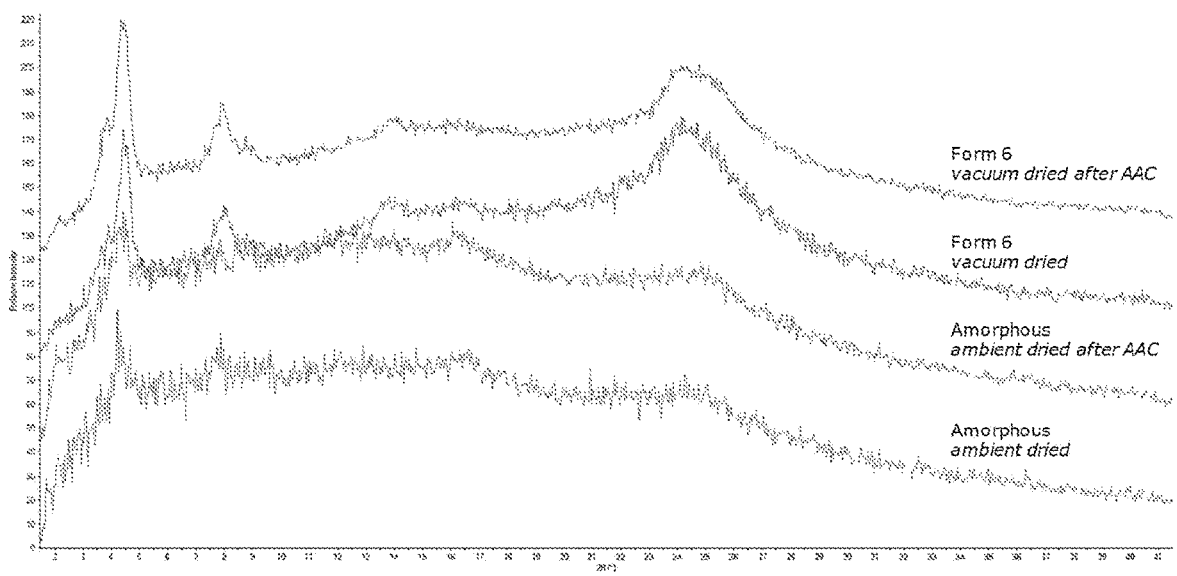
FIG. 36 illustrates an overlay of HT-XRPD patterns of the material obtained from the solvent equilibration experiment in water (Exp. ID SLP65) dried ambient and under vacuum, before and after exposure to AAC.
Figure 37:
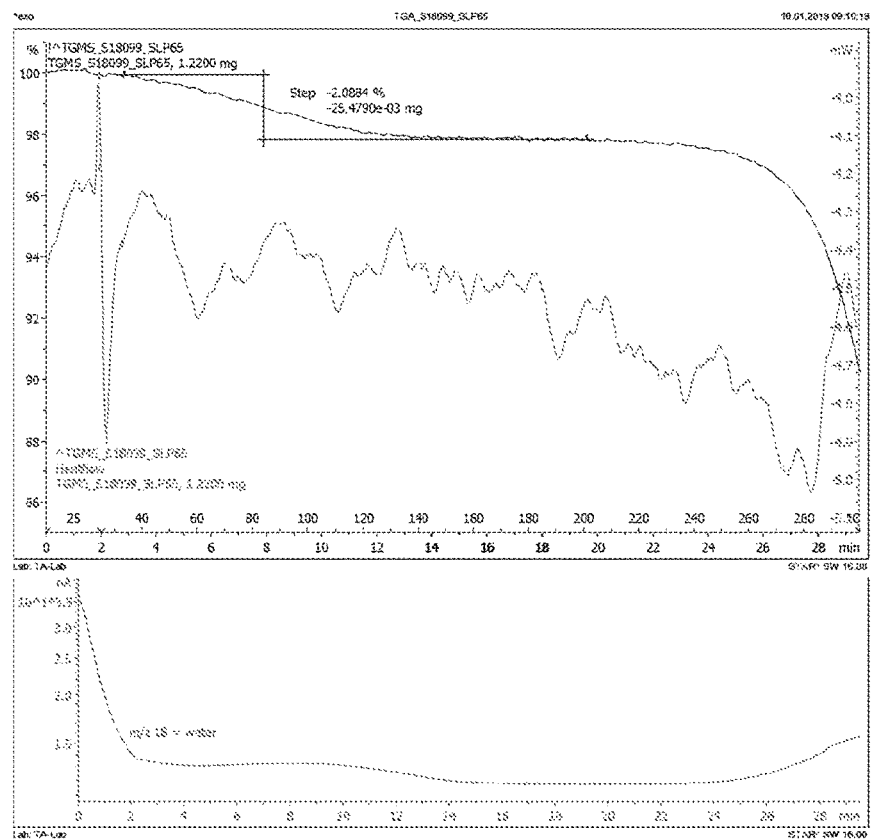
FIG. 37 illustrates the TGMS analysis (heating rate 10° C./min) of Form 6 (Exp. ID SLP65). The mass loss of 2.1% is related to loss of water.
Figure 38:
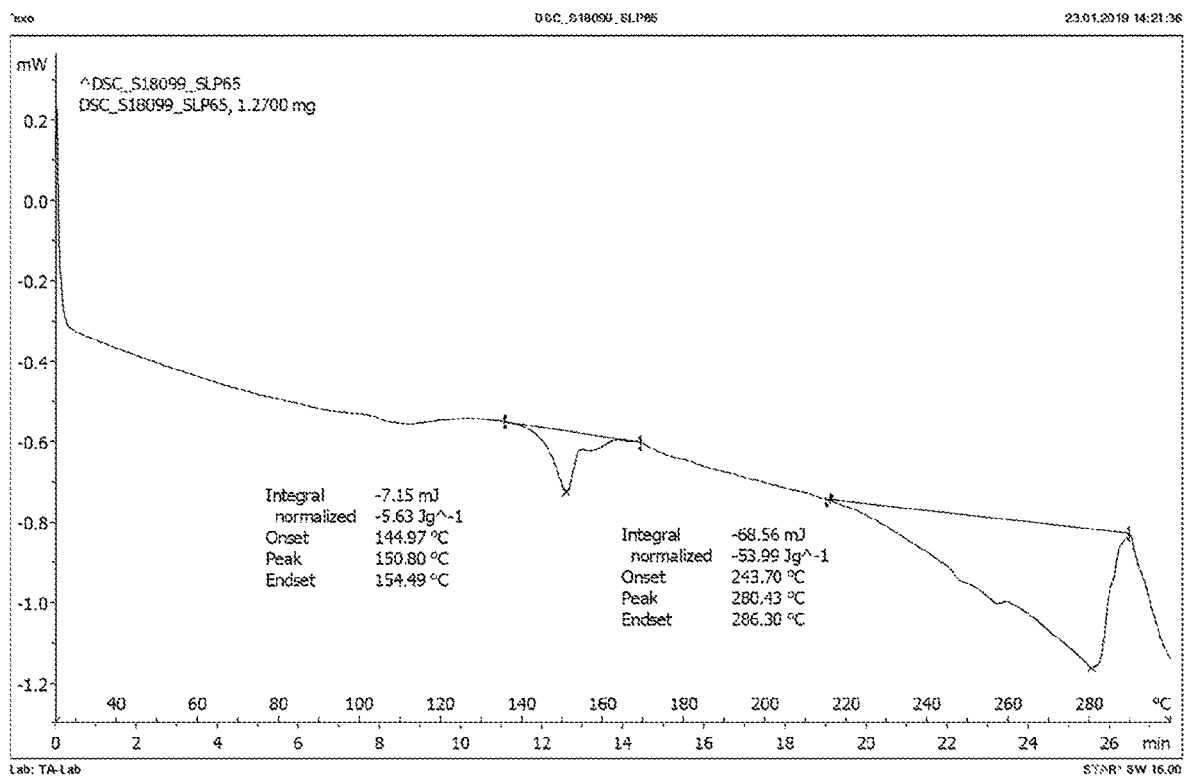
FIG. 38 illustrates the DSC analysis (heating rate 10° C./min) of Form 6 (Exp. ID SLP65). A broad endothermic event was observed at 151° C., related to loss of water. The thermal events above 220° C. are related to decomposition processes.
Figure 39:
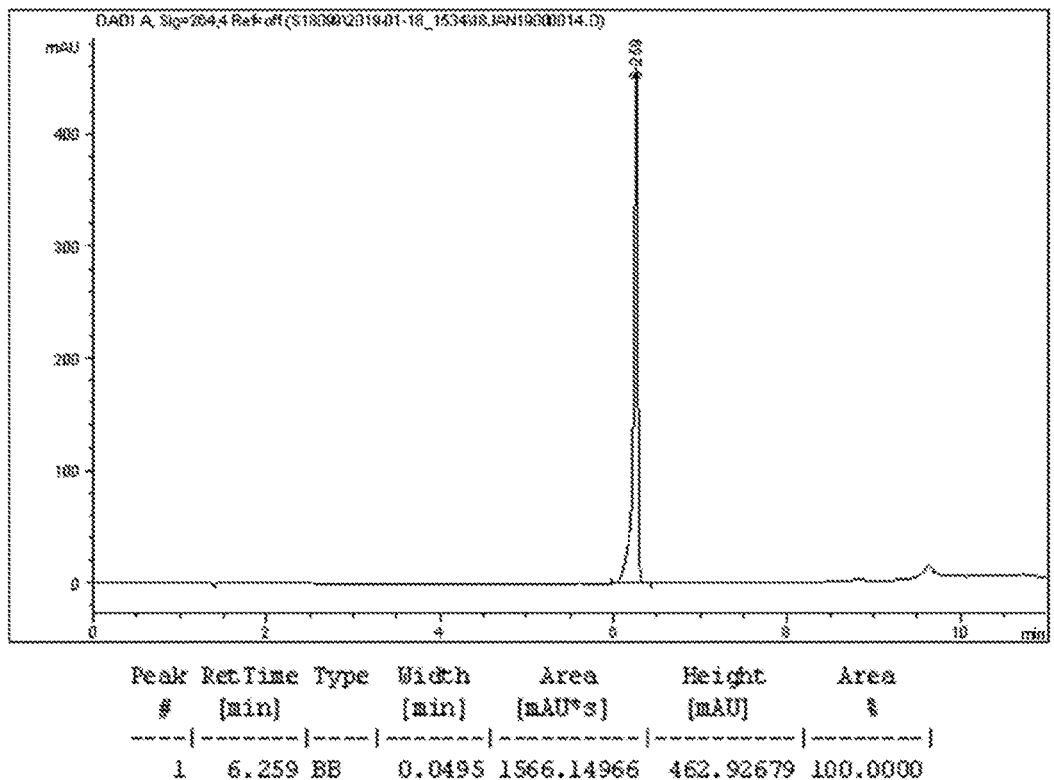
FIG. 39 illustrates an HPLC chromatogram of Form 6 (Exp. ID SLP65). The API peak appeared at 6.3 minutes with a chemical purity of 100% (area percentage).

From the solvent equilibration experiment at 50° C. performed in water Form 6 was obtained and used for the characterization (Exp. ID SLP65). Form 6 was a poorly crystalline material and was physically stable upon exposure to AAC (40° C./75% RH) for 2 days. The HT-XRPD patterns of the material of Exp. ID SLP65 before and after exposure to AAC are shown in FIG. 36. The TGMS analysis of Form 6 (FIG. 37) showed a mass loss of 2.1% in the temperature range of 25-160° C. Without wishing to be bound by any particular theory, it is believed that the mass loss was most likely related to water loss (0.6 molar equivalent water), and the material became amorphous after the water loss upon heating. Form 6 was obtained from samples in water and after exposure to AAC. Without wishing to be bound by any particular theory, it is believed that Form 6 is possibly a hemi-hydrate. In the DSC curve of Form 6 (FIG. 38), a broad endothermic event was recorded at 151° C., related to loss of water. The thermal events observed above 220° C. are related to decomposition processes. The HPLC chromatogram of Form 6, shown in FIG. 39, revealed the presence of the API with a chemical purity of 100% (area percentage).

Form 7

Figure 40:
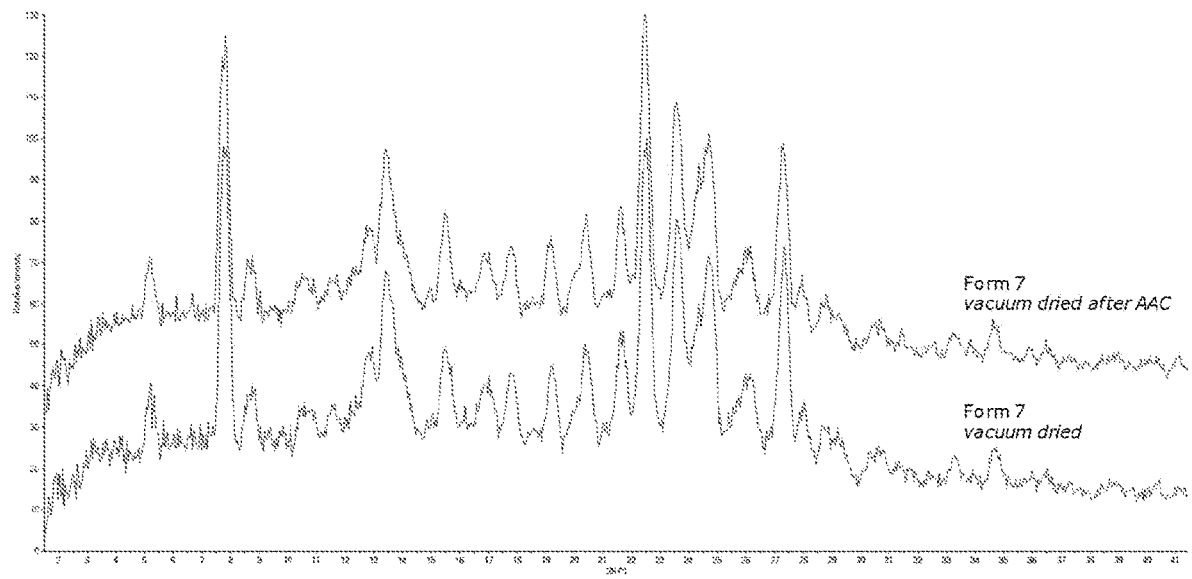
FIG. 40 illustrates an overlay of HT-XRPD patterns of the material obtained from the thermocycling experiment in 1,2-dimethoxyethane (Exp. ID TCP5) before and after exposure to AAC.
Figure 41:
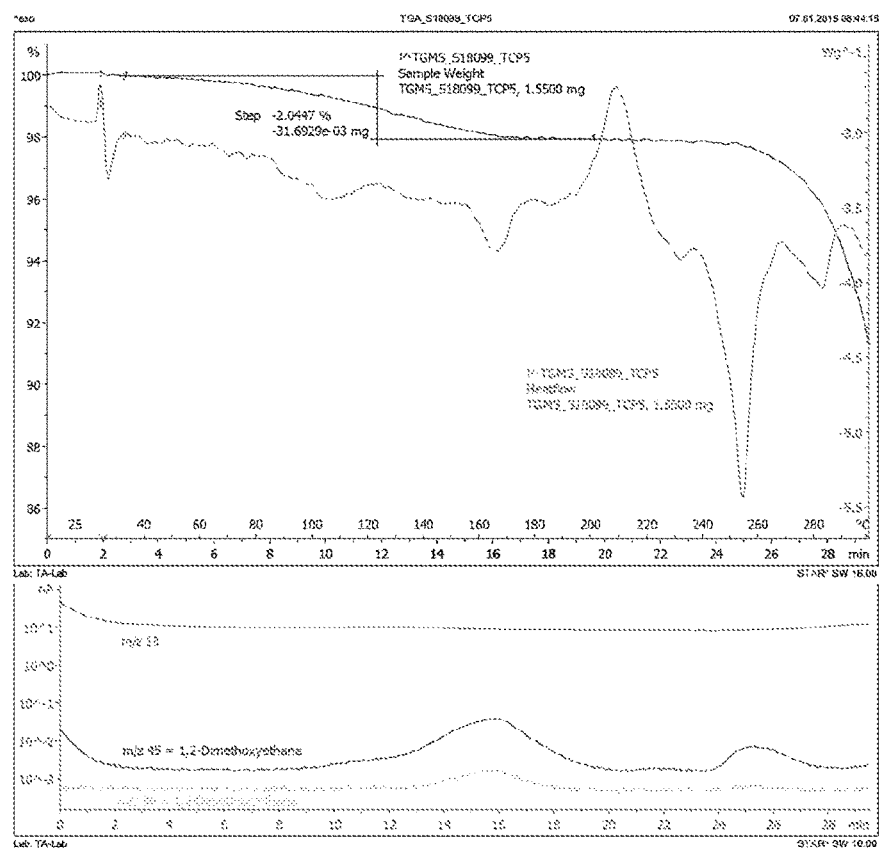
FIG. 41 illustrates the TGMS analysis (heating rate 10° C./min) of Form 7 (Exp. ID TCP5). The mass loss of 2.0% is most likely related to solvent loss and/or water.
Figure 42:
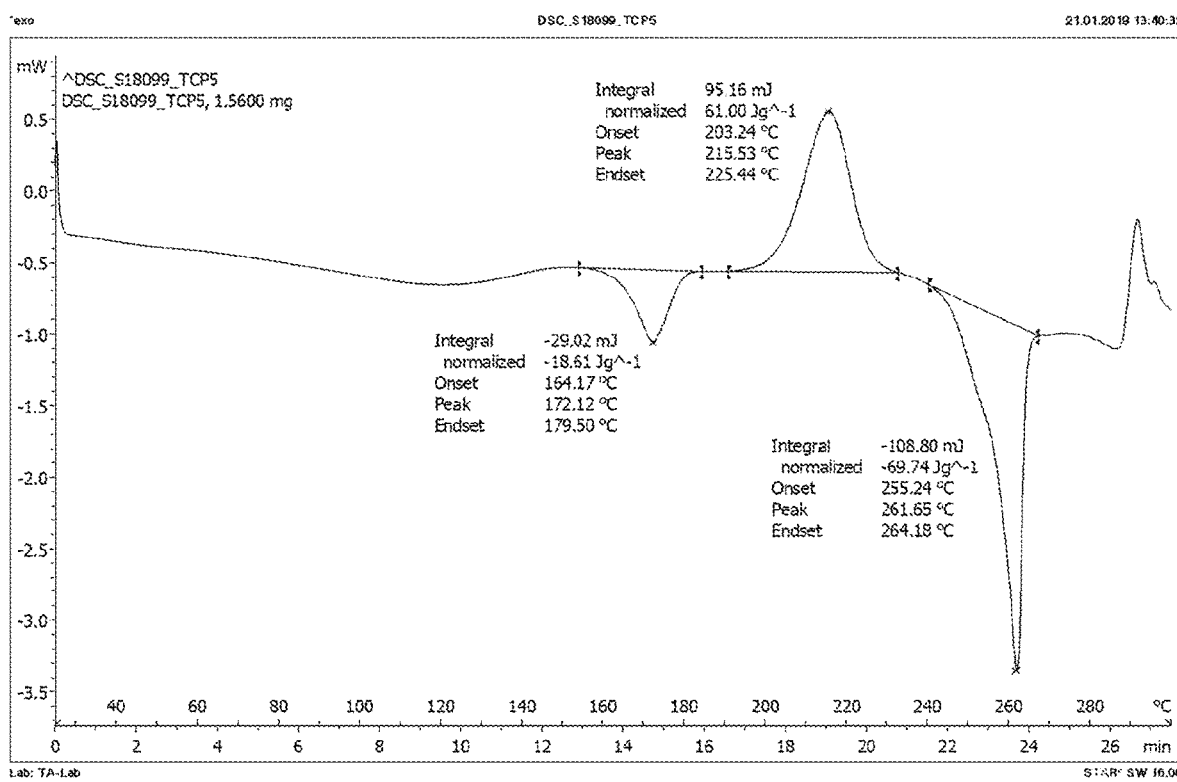
FIG. 42 illustrates the DSC analysis (heating rate 10° C./min) of Form 7 (Exp. ID TCP5). An endothermic event was observed, most likely related with solvent loss, followed by an exothermic recrystallization event and melting and decomposition of Form 1.
Figure 43:
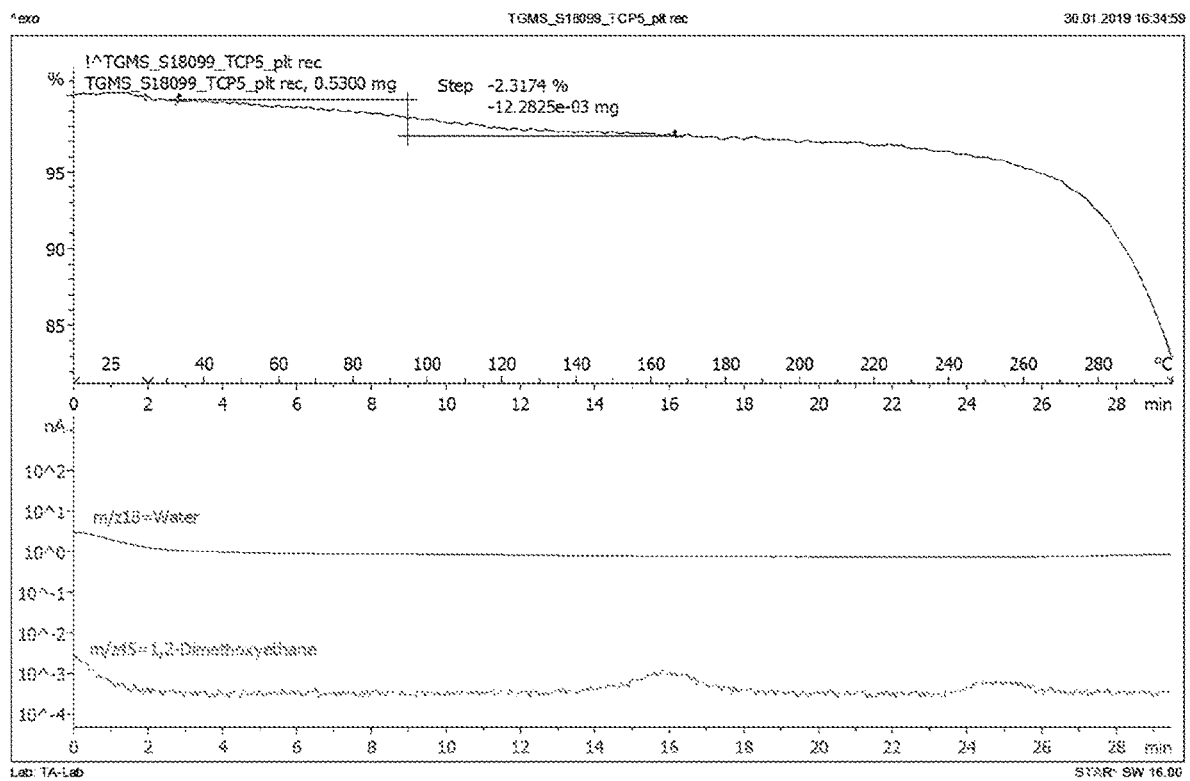
FIG. 43 illustrates the TGMS analysis (heating rate 10° C./min) of Form 7 after cycling DSC to 155° C. The mass loss of 2.3% is most likely related to loss of water.
Figure 44:
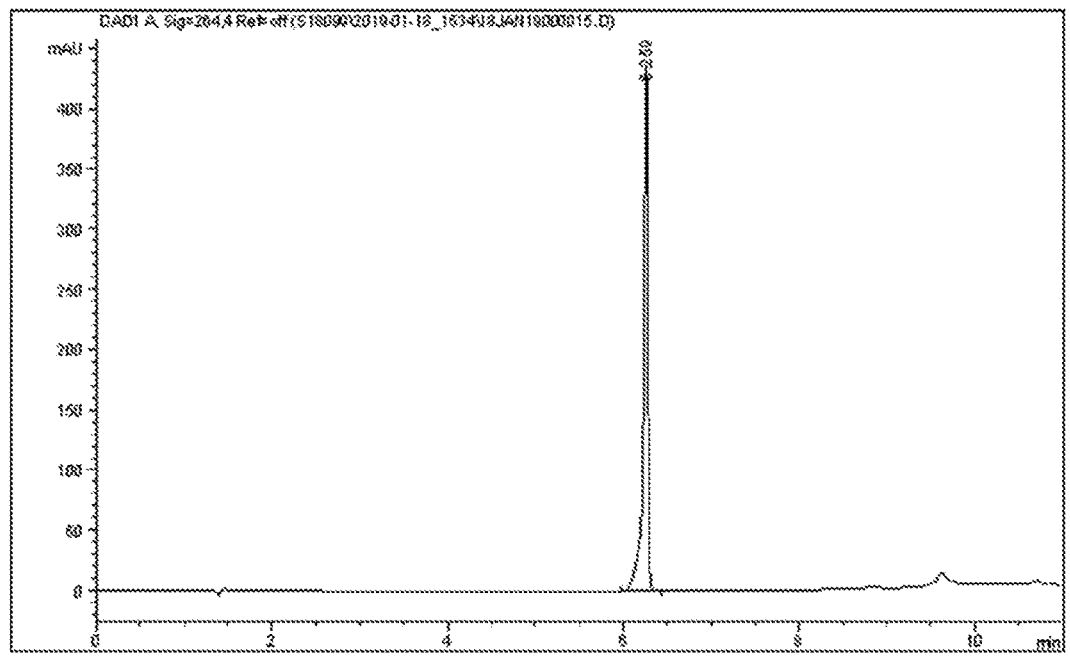
FIG. 44 illustrates an HPLC chromatogram of Form 7 (Exp. ID TCP5). The API peak appeared at 6.3 minutes with a chemical purity of 100% (area percentage).

From the thermocycling experiment performed in 1,2-dimethoxyethane Form 7 was obtained and used for the characterization (Exp. ID TCP5). Both ambient and vacuum dried solids from Exp. ID TCP5 were Form 7. Form 7 was physically stable upon exposure to AAC (40° C./75% RH) for 2 days. The HT-XRPD patterns of the solid of Exp. ID TCP5 before and after exposure to AAC are shown in FIG. 40. The TGMS analysis of Form 7 (FIG. 41) showed a mass loss of 2.0% in the temperature range of 25-170° C. Without wishing to be bound by any particular theory, it is believed that the mass loss was most likely related to loss of 1,2-dimethoxyethane and possibly water (the mass loss would be equal to 0.1 molar equivalent 1,2-dimethoxyethane). Without wishing to be bound by any particular theory, it is believed that the material recrystallized to Form 1 after the solvent loss. Without wishing to be bound by any particular theory, it is believed that Form 7 was only observed in samples with 1,2-dimethoxyethane and therefore is most likely a non-stoichiometric dimethoxyethane solvate or mixed dimethoxyethane solvate/hydrate. In the DSC curve of Form 7 (FIG. 42), a weak broad endotherm was observed between 25-160° C., due to solvent loss. An endothermic event was recorded at 172° C. and an exothermic recrystallization event at 216° C., followed by an endothermic event at 262° C. (melt of Form 1). Without wishing to be bound by any particular theory, it is believed that most likely Form 7 converts to Form 1 upon heating. A cycling DSC experiment was performed on the solid of Form 7 to see if a (stable) non-solvated form was obtained after the solvent loss. The solids recovered after the cycling DSC experiment to 155° C. were analyzed by XRPD and TGMS. The XRPD pattern was the same and from the TGMS analysis 2.3% mass loss was observed (without wishing to be bound by any particular theory, it is believed that it was most likely adsorbed water) (FIG. 43). The HPLC chromatogram of Form 7, shown in FIG. 44, revealed the presence of the API with a chemical purity of 100% (area percentage).

Form 8

Figure 45:
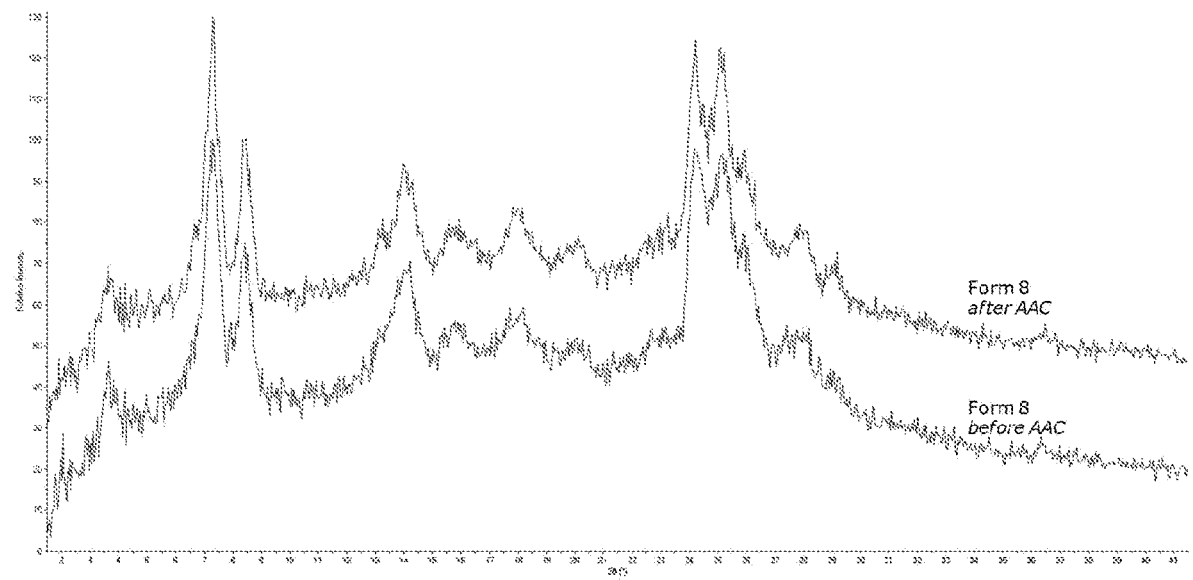
FIG. 45 illustrates an overlay of HT-XRPD patterns of the material obtained from the evaporative experiment in methanol/acetone 75/25 (Exp. ID ECP34) before and after exposure to AAC.
Figure 46:
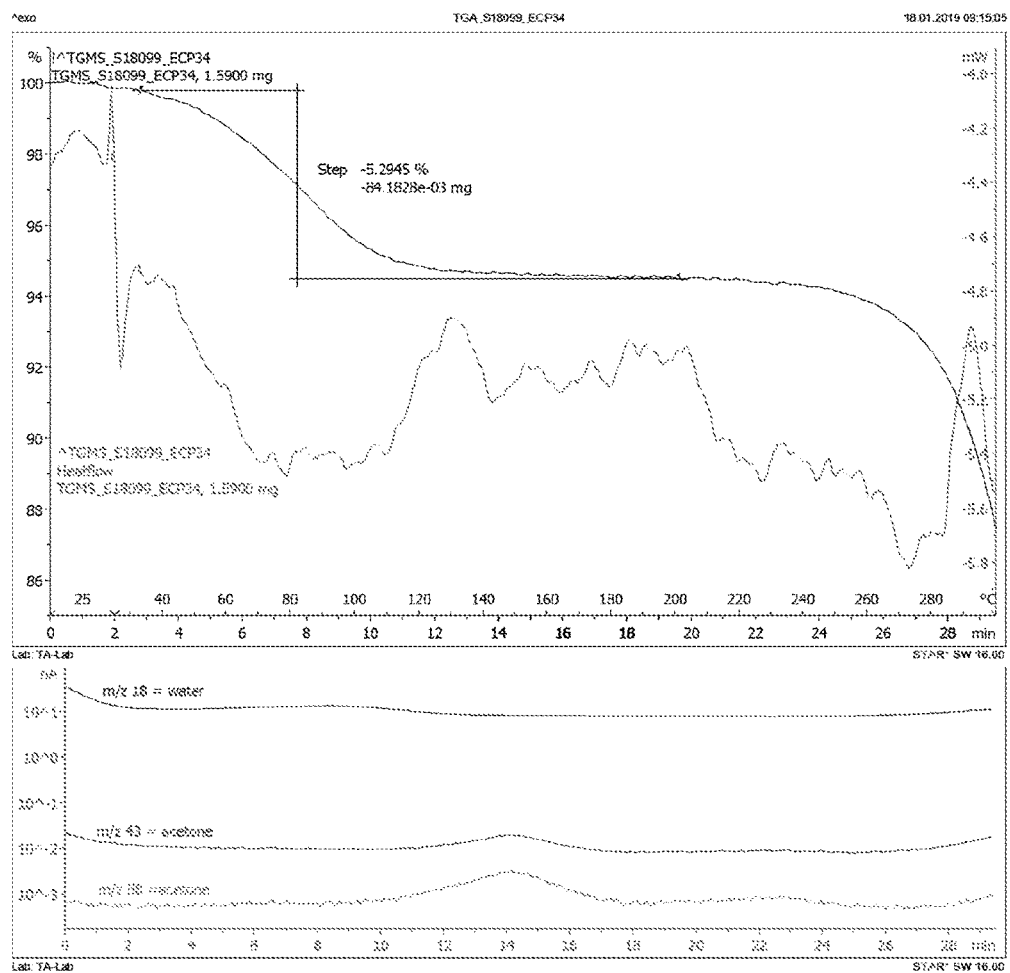
FIG. 46 illustrates the TGMS analysis (heating rate 10° C./min) of Form 8 (Exp. ID ECP34). The mass loss of 5.3% is most likely related to solvent loss and/or water.
Figure 47:
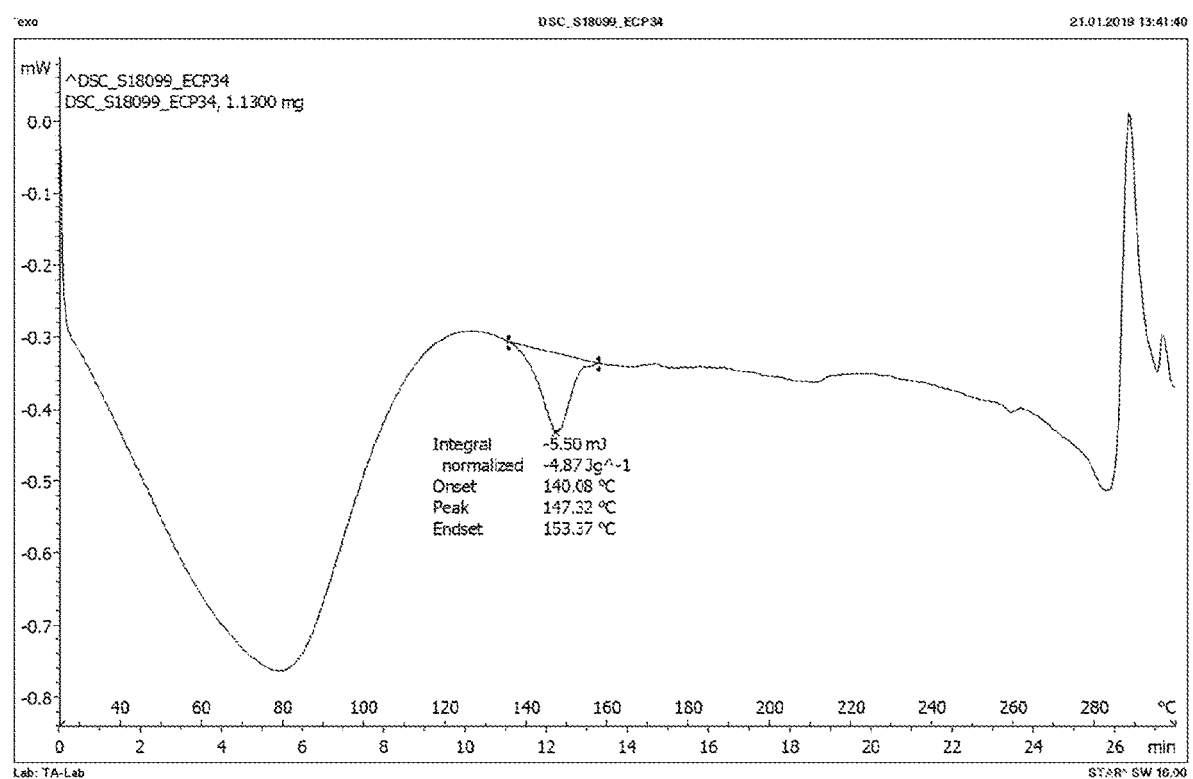
FIG. 47 illustrates the DSC analysis (heating rate 10° C./min) of Form 8 (Exp. ID ECP34). A broad endothermic event was observed, most likely related with solvent loss, followed by a small endothermic event possibly related to melting.
Figure 48:
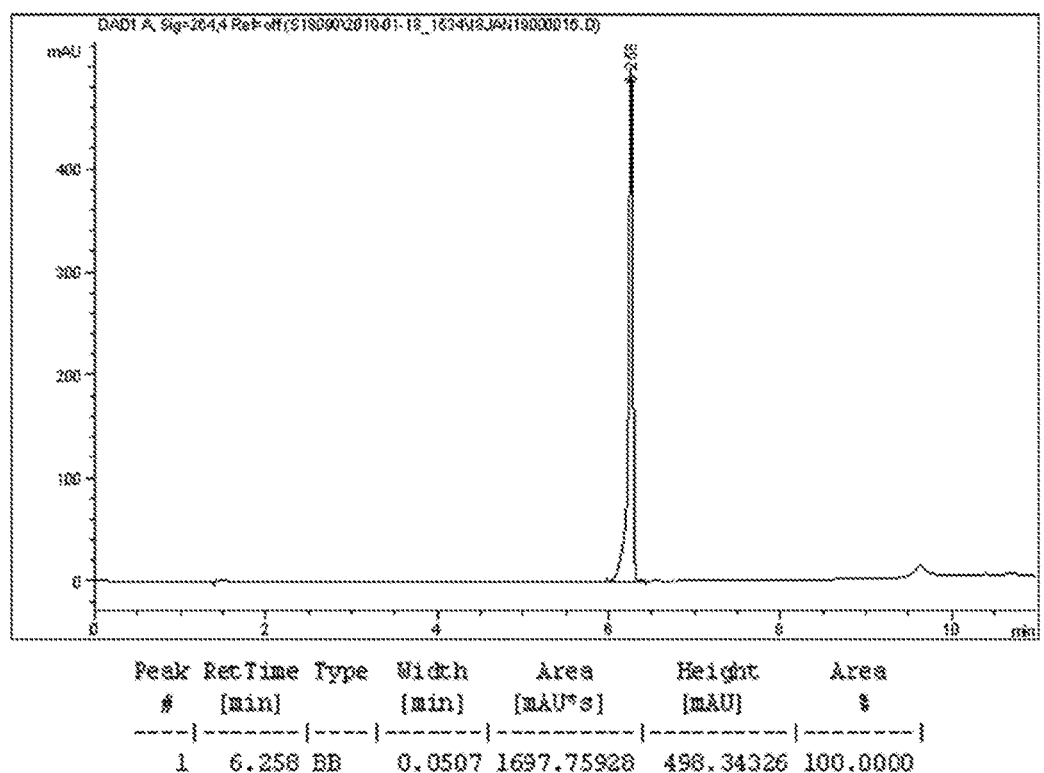
FIG. 48 illustrates an HPLC chromatogram of Form 8 (Exp. ID ECP34). The API peak appeared at 6.3 minutes with a chemical purity of 100% (area percentage).

From the evaporative experiment performed in methanol/acetone 75/25 (v/v) Form 8 was obtained and used for the characterization (Exp. ID ECP34). Form 8 was physically stable upon exposure to AAC (40° C./75% RH) for 2 days. The HT-XRPD patterns of the material of Exp. ID ECP34 before and after exposure to AAC are shown in FIG. 45. The TGMS analysis of Form 8 (FIG. 46) showed a mass loss of 5.3% in the temperature range of 25-130° C. The mass loss was related to loss of water and/or acetone (0.5 equivalent acetone or 1.5 equivalents water). From the heat flow curve, a broad endothermic event was observed coinciding with the mass loss. Without wishing to be bound by any particular theory, it is believed that Form 8 was observed in samples from different solvents and is therefore most likely a non-stoichiometric isostructural solvate/hydrate. In the DSC curve of Form 8 (FIG. 47), a broad endothermic event was recorded, most likely related to solvent loss followed by a small endothermic event observed at 147° C., possibly attributed to melting. The HPLC chromatogram of Form 8, shown in FIG. 48, revealed the presence of the API with a chemical purity of 100% (area percentage).

Form 10 (and Form 9)

Figure 49:
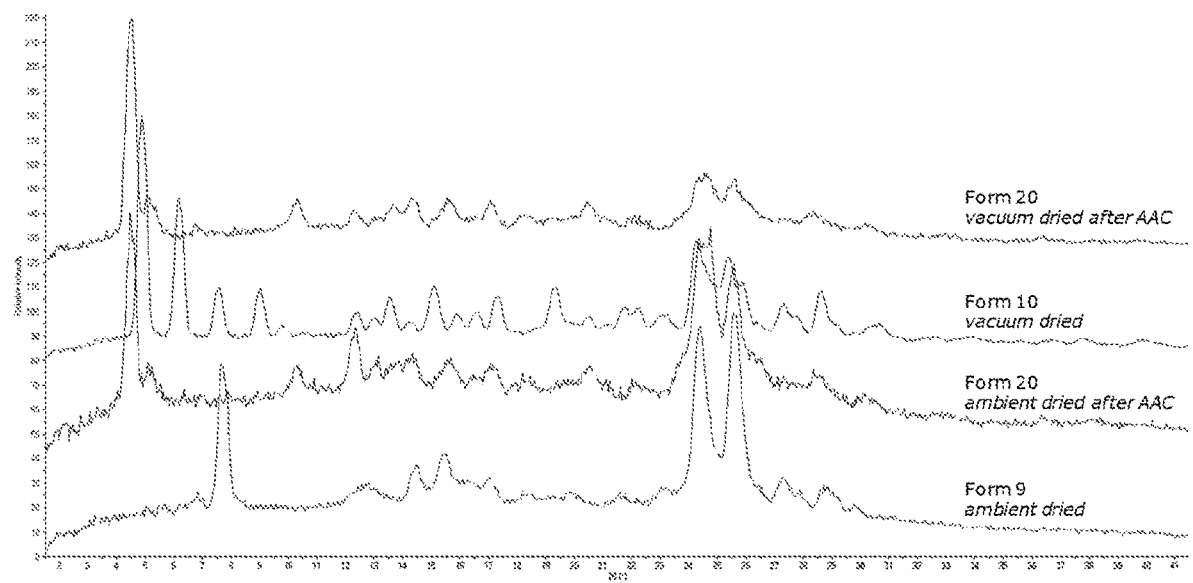
FIG. 49 illustrates an overlay of HT-XRPD patterns of the solid obtained from the cooling crystallization experiment in N,N-dimethylformamide (Exp. ID PSM60) dried ambient and under vacuum, before and after exposure to AAC.
Figure 50:
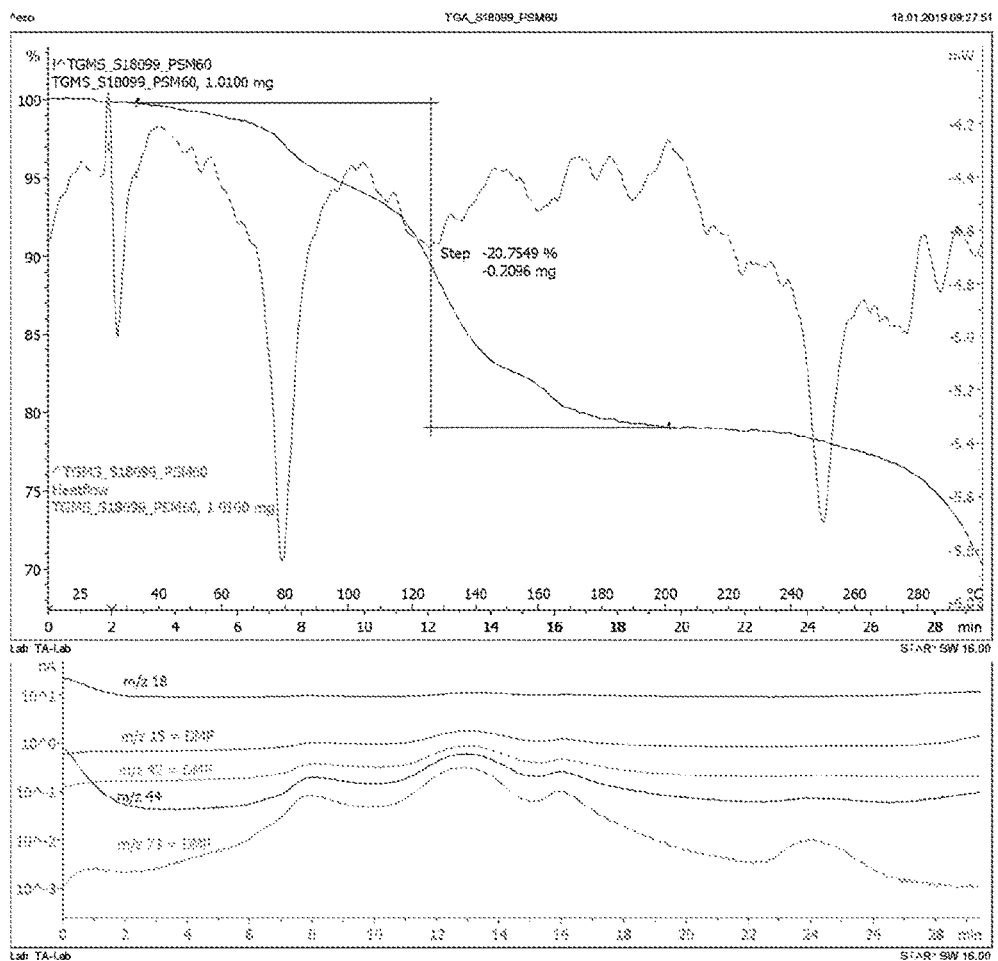
FIG. 50 illustrates the TGMS analysis (heating rate 10° C./min) of Form 10 (Exp. ID PSM60). The mass loss of 20.8% is related to solvent loss.
Figure 51:
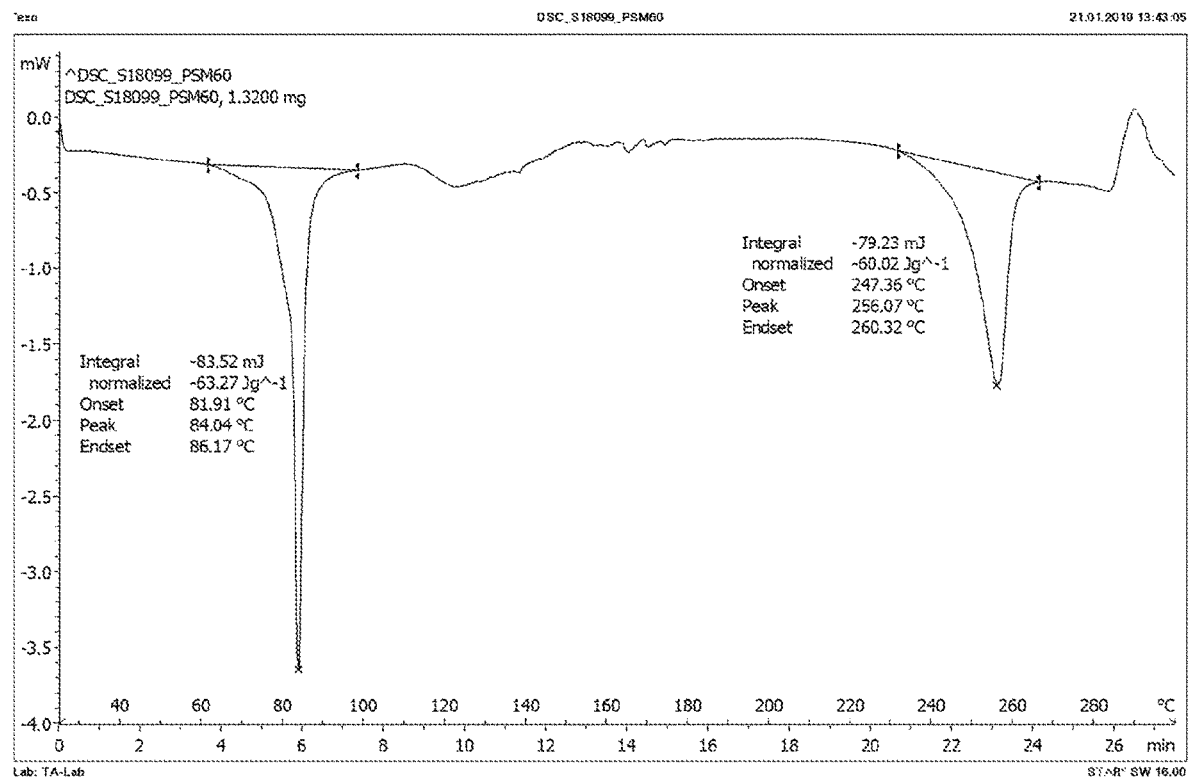
FIG. 51 illustrates the DSC analysis (heating rate 10° C./min) of Form 10 (Exp. ID PSM60). An endothermic event was observed, most likely related to solvent loss, followed by a second endothermic event, associated with the melt of Form 1.
Figure 52:
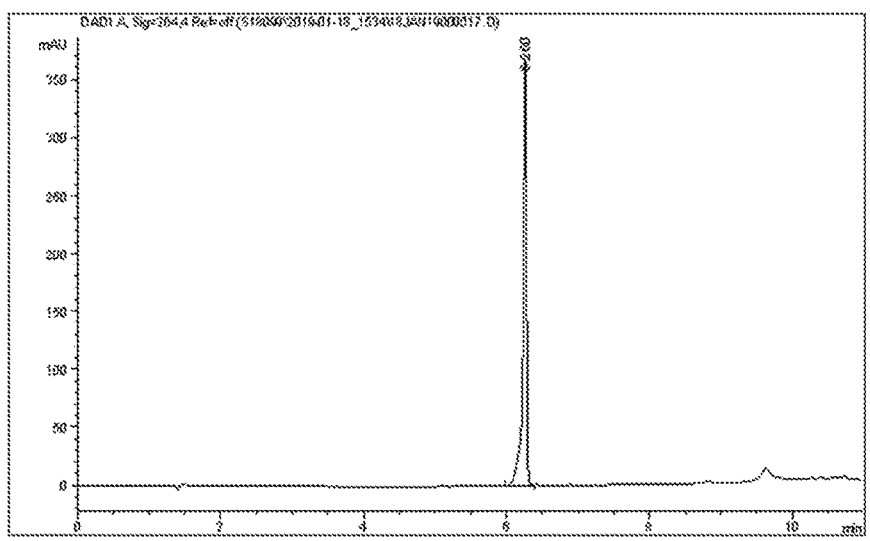
FIG. 52 illustrates an HPLC chromatogram of Form 10 (Exp. ID PSM60). The API peak appeared at 6.3 minutes with a chemical purity of 100% (area percentage).

From the cooling crystallization experiment performed in N,N-dimethylformamide Form 10 was obtained (upon drying under vacuum) and used for the characterization (Exp. ID PSM60). The ambient dried solid was Form 9 and the solid dried under vacuum was Form 10. Both Form 9 and Form 10 were physically unstable upon exposure to AAC (40° C./75% RH) for 2 days and turned into Form 20. The HT-XRPD patterns of the solids of Exp. ID PSM60 before and after exposure to AAC are shown in FIG. 49. The TGMS analysis of Form 10 (FIG. 50) showed a mass loss of 20.8% in the temperature range of 25-200° C. The mass loss was most likely related to loss of DMF (1.8 molar equivalents DMF). From the heat flow curve, an endothermic event was observed around 80° C., due to mass loss and a second endothermic event was observed around 250° C. (most likely melting of Form 1). Form 10 was observed in samples from DMF and is therefore a non-stoichiometric DMF solvate. In the DSC curve of Form 10 (FIG. 51), an endothermic event was recorded at 84° C., most likely related to solvent loss. A second endothermic event was observed at 256° C., most likely associated with the melting of Form 1. The HPLC chromatogram of Form 10, shown in FIG. 52, revealed the presence of the API with a chemical purity of 100% (area percentage).

Form 11

Figure 53:
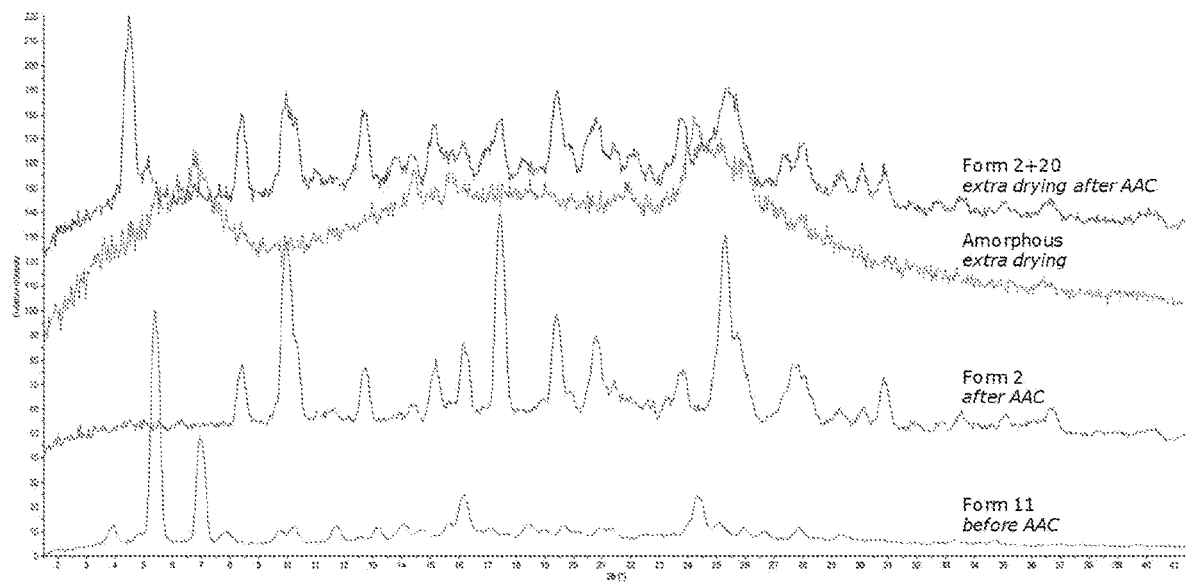
FIG. 53 illustrates an overlay of HT-XRPD patterns of the material obtained from the cooling crystallization experiment in N,N-dimethylacetamide (Exp. ID PSM59) before and after exposure to AAC.
Figure 54:
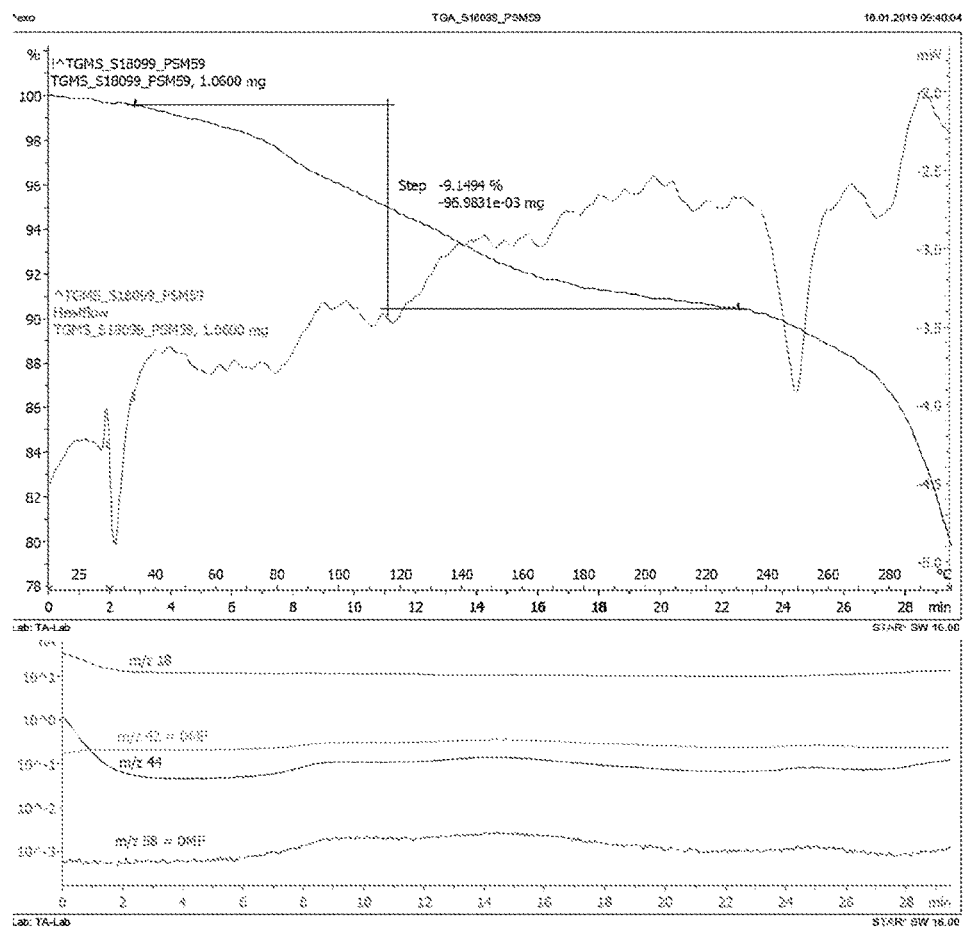
FIG. 54 illustrates the TGMS analysis (heating rate 10° C./min) of Form 11 (Exp. ID PSM59). The mass loss of 9.1% is most likely related to solvent loss.
Figure 55:
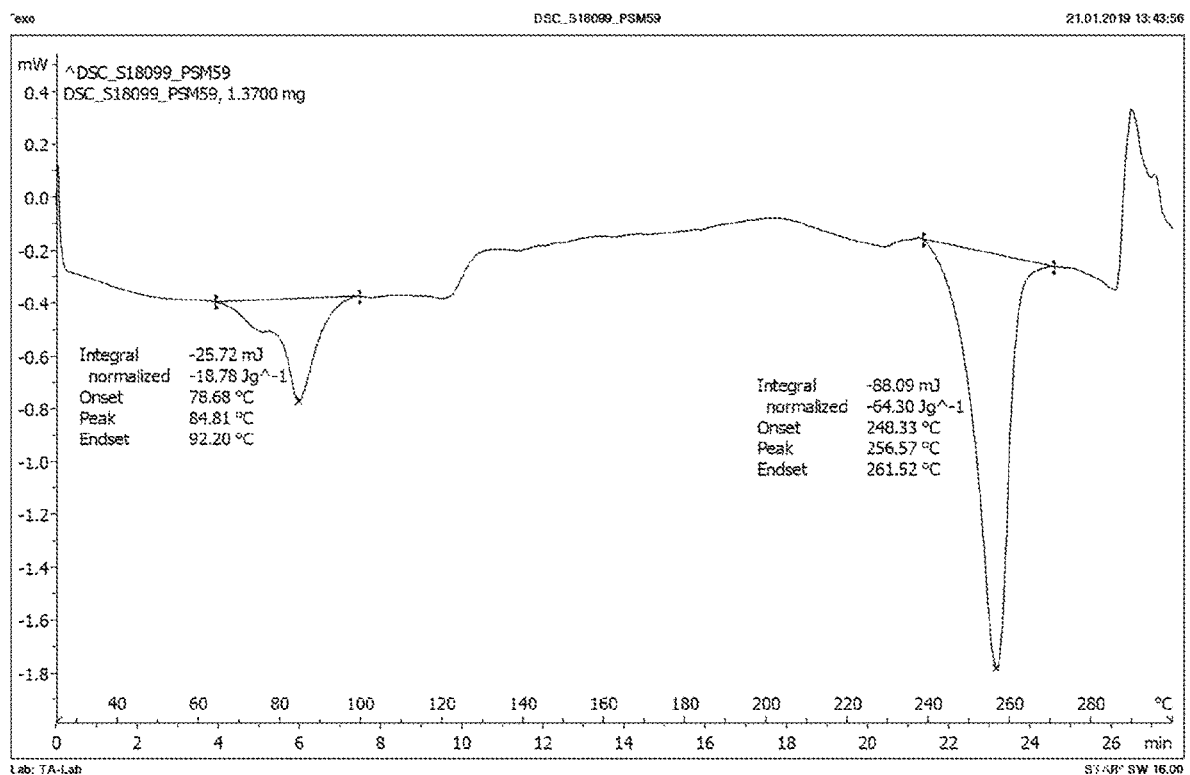
FIG. 55 illustrates the DSC analysis (heating rate 10° C./min) of Form 11 (Exp. ID PSM59). Two endothermic events were observed, most likely related with solvent loss and melting of Form 1, respectively.
Figure 56:
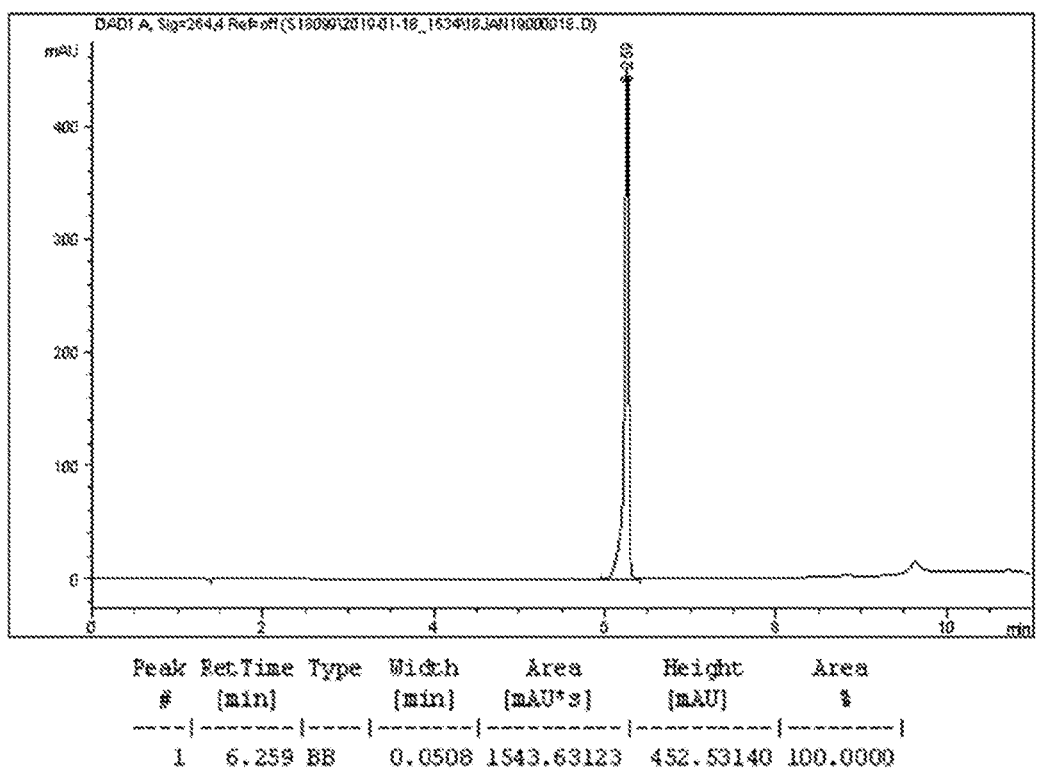
FIG. 56 illustrates an HPLC chromatogram of Form 11 (Exp. ID PSM59). The API peak appeared at 6.3 minutes with a chemical purity of 100% (area percentage).

From the cooling crystallization experiment performed in N,N-dimethylacetamide Form 11 was obtained and used for the characterization (Exp. ID PSM59). Form 11 was physically unstable upon exposure to AAC (40° C./75% RH) for 2 days and turned into Form 2. Upon extra drying under vacuum and at 50° C. for 72 hours the solid became amorphous. The HT-XRPD patterns of the material of Exp. ID PSM59 before and after exposure to AAC are shown in FIG. 53. The TGMS analysis of Form 11 (FIG. 54) showed a mass loss of 9.1% in the temperature range of 25-230° C. The mass loss was most likely related to loss of DMA (0.6 molar equivalent DMA). From the heat flow curve, a broad endothermic event was observed coinciding with the mass loss. A second endothermic event was observed around 250° C. (most likely melting of Form 1). Form 11 was observed in samples from DMA but sometimes also in mixtures with other forms from other solvents and is therefore most likely a non-stoichiometric isostructural solvate. In the DSC curve of Form 11 (FIG. 55), an endothermic event was recorded at 85° C., most likely due to solvent loss. A second endothermic event was observed at 257° C., attributed to melting of Form 1. The HPLC chromatogram of Form 11, shown in FIG. 56, revealed the presence of the API with a chemical purity of 100% (area percentage).

Form 12

Figure 57:
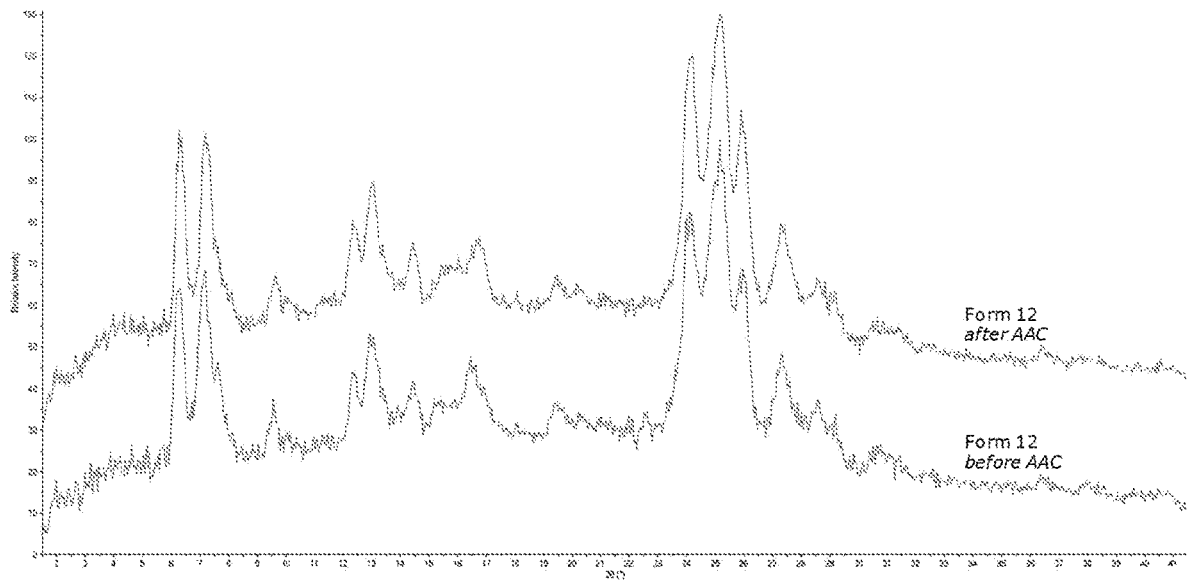
FIG. 57 illustrates an overlay of HT-XRPD patterns of the material obtained from the mother liquor of the thermocycling experiment in ACN/water 90/10 (Exp. ID TCP20_ML) before and after exposure to AAC.
Figure 58:
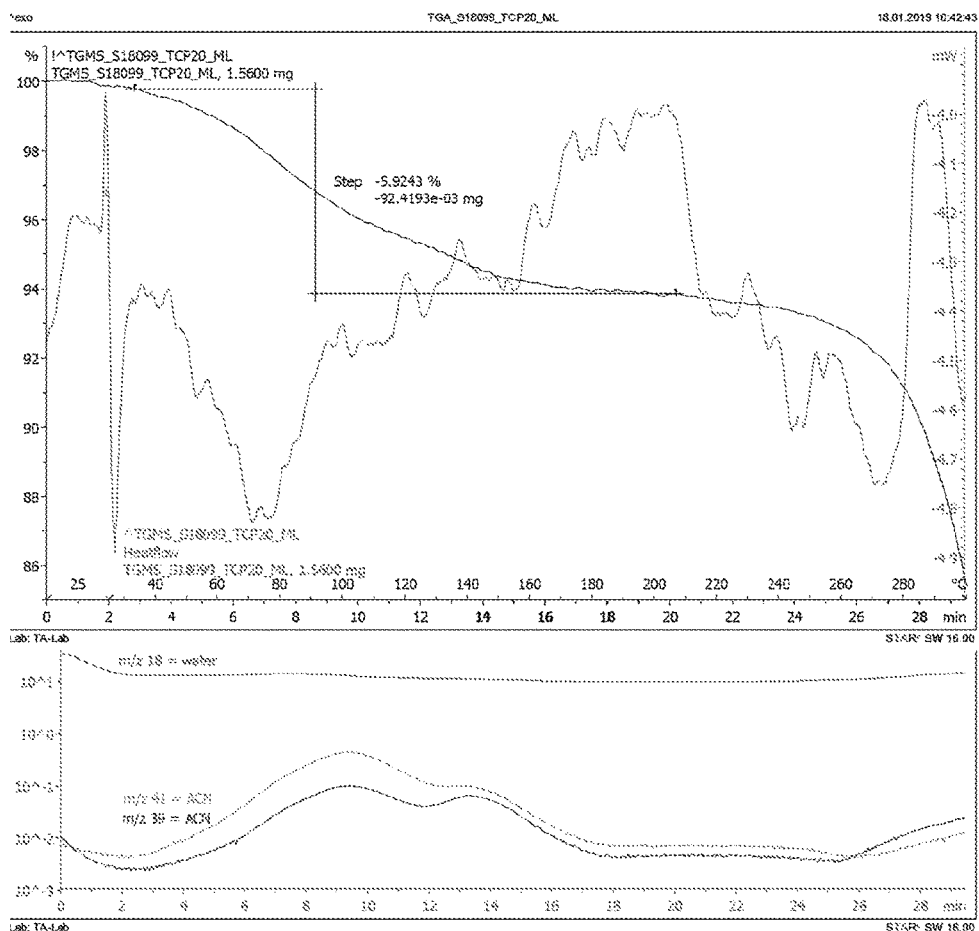
FIG. 58 illustrates the TGMS analysis (heating rate 10° C./min) of Form 12 (Exp. ID TCP20_ML). The mass loss of 5.9% is related to solvent loss.
Figure 59:
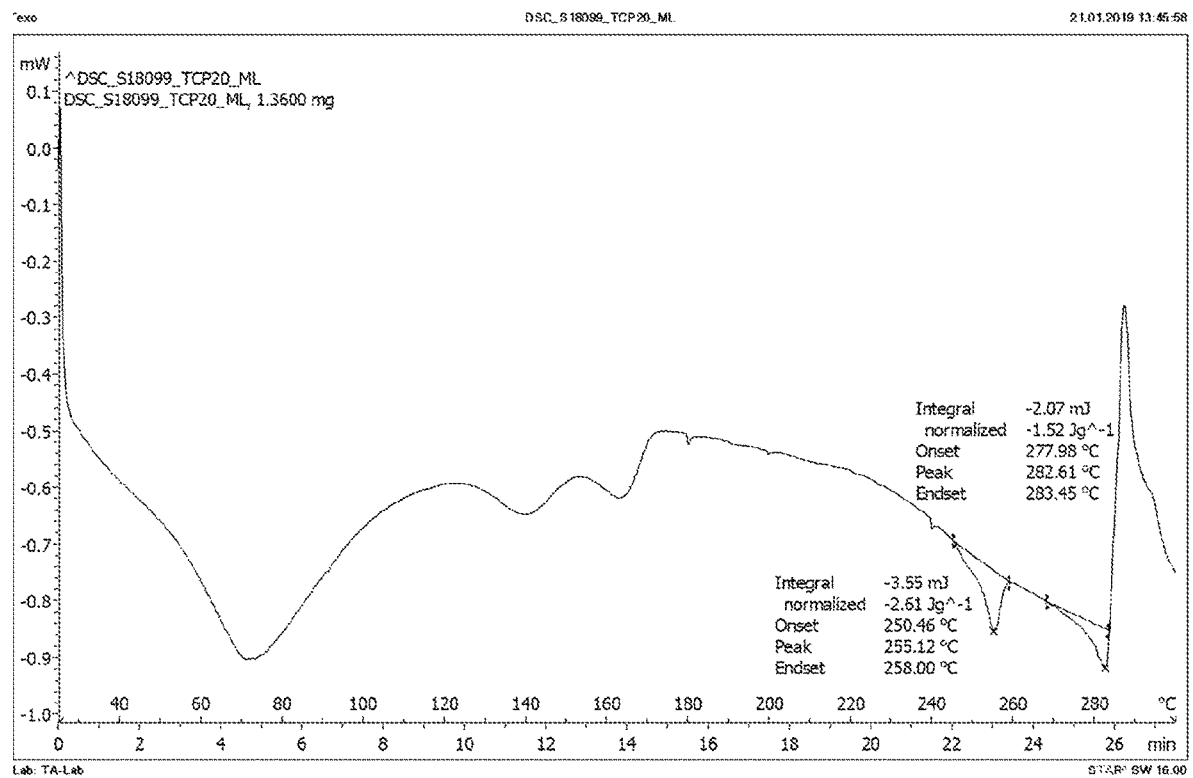
FIG. 59 illustrates the DSC analysis (heating rate 10° C./min) of Form 12 (Exp. ID TCP20_ML). Endothermic events observed between 25-180° C. are most likely related to solvent loss, while the small endothermic event observed at 255° C. might be related to the melting of Form 1.
Figure 60:
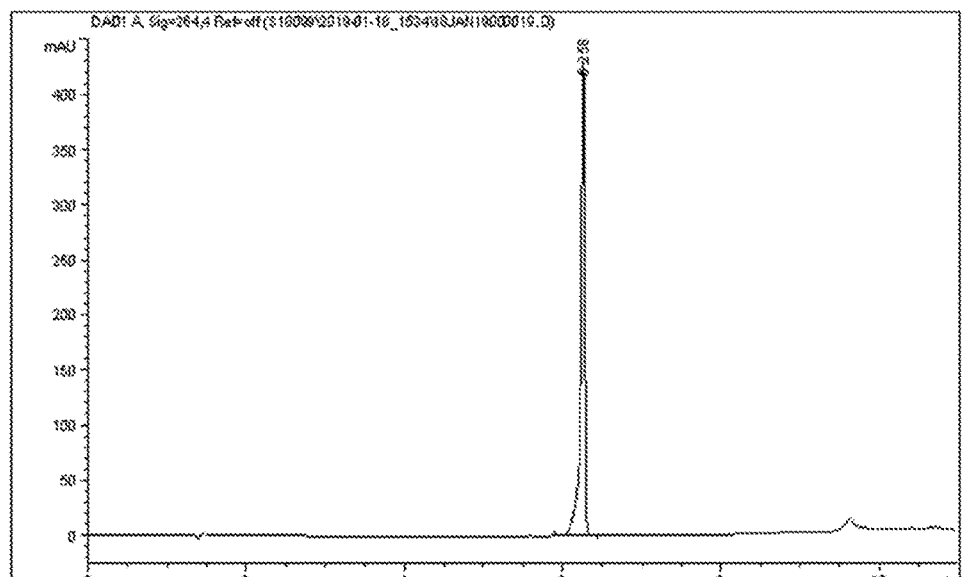
FIG. 60 illustrates an HPLC chromatogram of Form 12 (Exp. ID TCP20_ML). The API peak appeared at 6.3 minutes with a chemical purity of 100% (area percentage).

After evaporation of the mother liquor of the thermocycling experiment performed with acetonitrile/water 90/10 (v/v) Form 12 was obtained and used for the characterization (Exp. ID TCP20_ML). Form 12 was physically stable upon exposure to AAC (40° C./75% RH) for 2 days. The HT-XRPD patterns of the material of Exp. ID TCP20_ML before and after exposure to AAC are shown in FIG. 57. The TGMS analysis of Form 12 (FIG. 58) showed a mass loss of 5.9% in the temperature range of 25-200° C. The mass loss was most likely related to loss of acetonitrile (0.8 molar equivalent acetonitrile). From the heat flow curve, a broad endothermic event was observed attributed to the mass loss. Decomposition started around 220° C. Without wishing to be bound by any particular theory, it is believed that Form 12 was observed in (gently dried) samples from acetonitrile/water and acetone/water and is therefore most likely a non-stoichiometric isostructural solvate. In the DSC curve of Form 12 (FIG. 59), endothermic events were recorded between 25-180° C., related to solvent loss and a small endothermic event was observed at 255° C., possibly attributed to melting of Form 1. The HPLC chromatogram of Form 12, shown in FIG. 60, revealed the presence of the API with a chemical purity of 100% (area percentage).

Form 13

Figure 61:
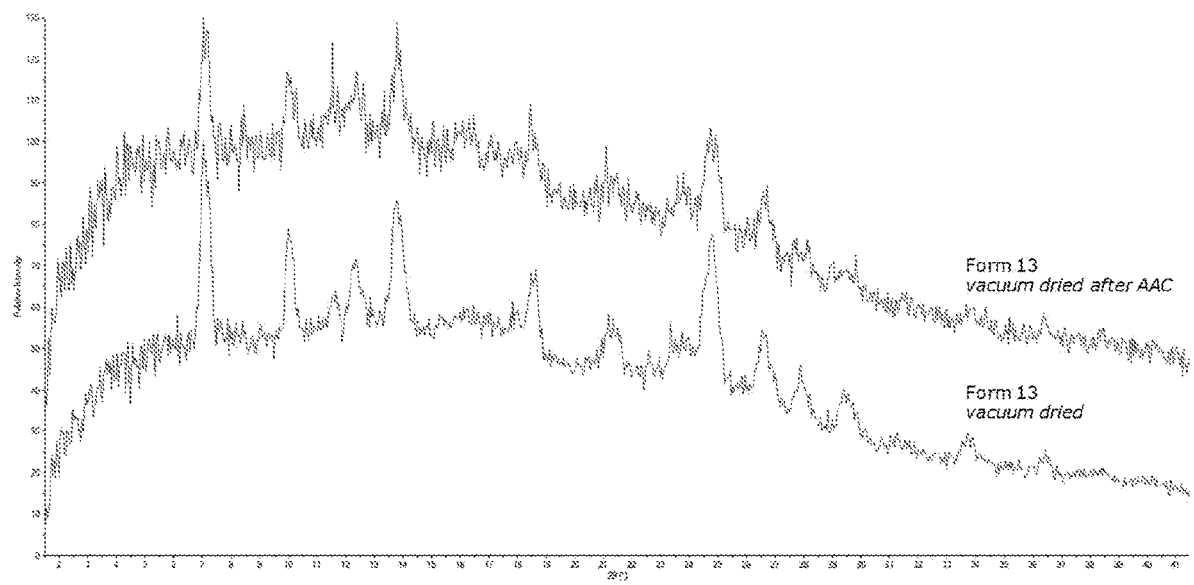
FIG. 61 illustrates an overlay of HT-XRPD patterns of the material obtained from the cooling-evaporative crystallization experiment in ethanol (Exp. ID PSM52) before and after exposure to AAC.
Figure 62:
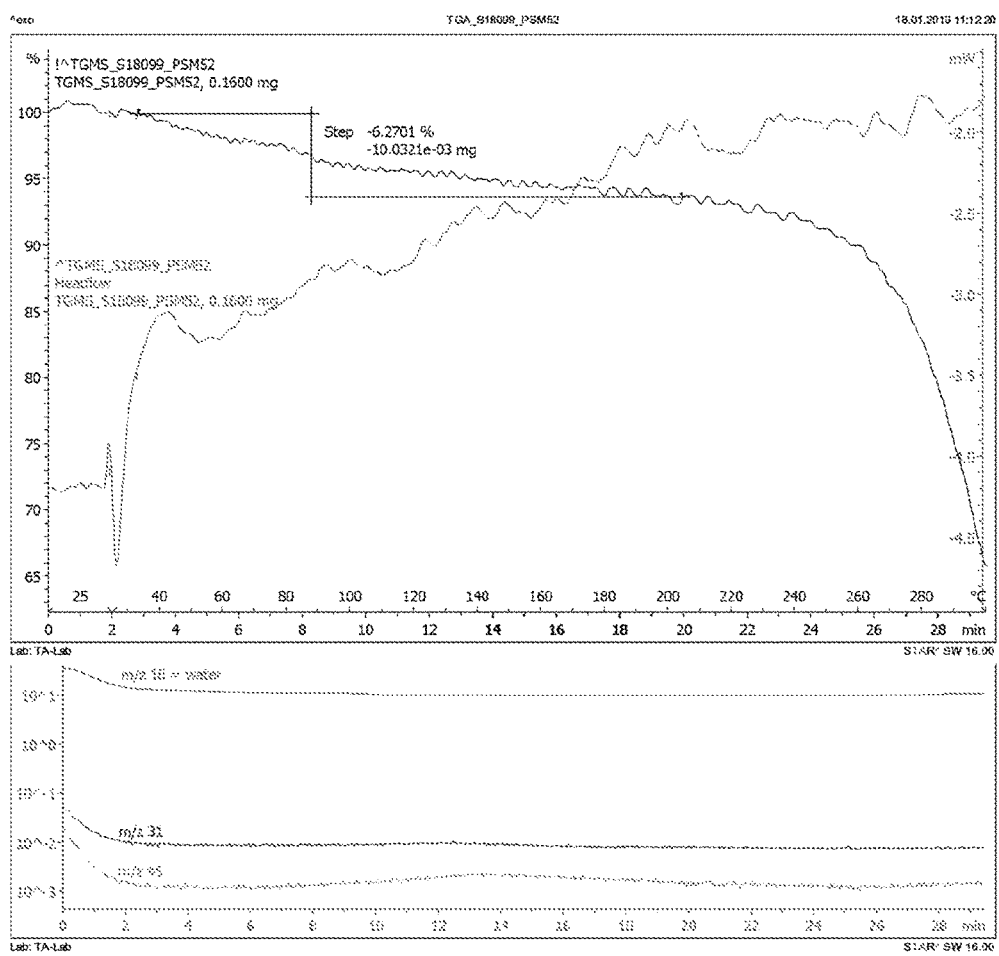
FIG. 62 illustrates the TGMS analysis (heating rate 10° C./min) of Form 13 (Exp. ID PSM52). The mass loss of 6.3% is most likely related to solvent loss or water.
Figure 63:
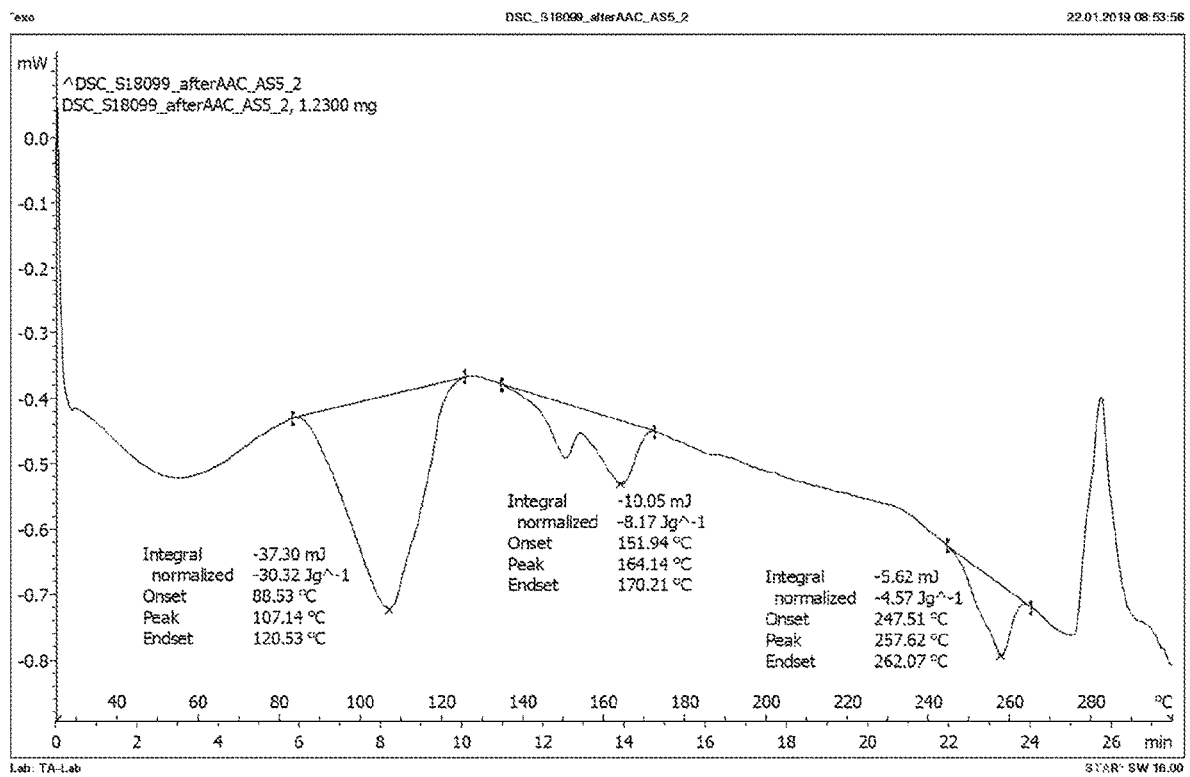
FIG. 63 illustrates the DSC analysis (heating rate 10° C./min) of Form 13 (Exp. ID AS5 after AAC). Several broad endothermic events were observed, most likely related with solvent loss, followed by a small endothermic event, related to melting of Form 1.
Figure 64:
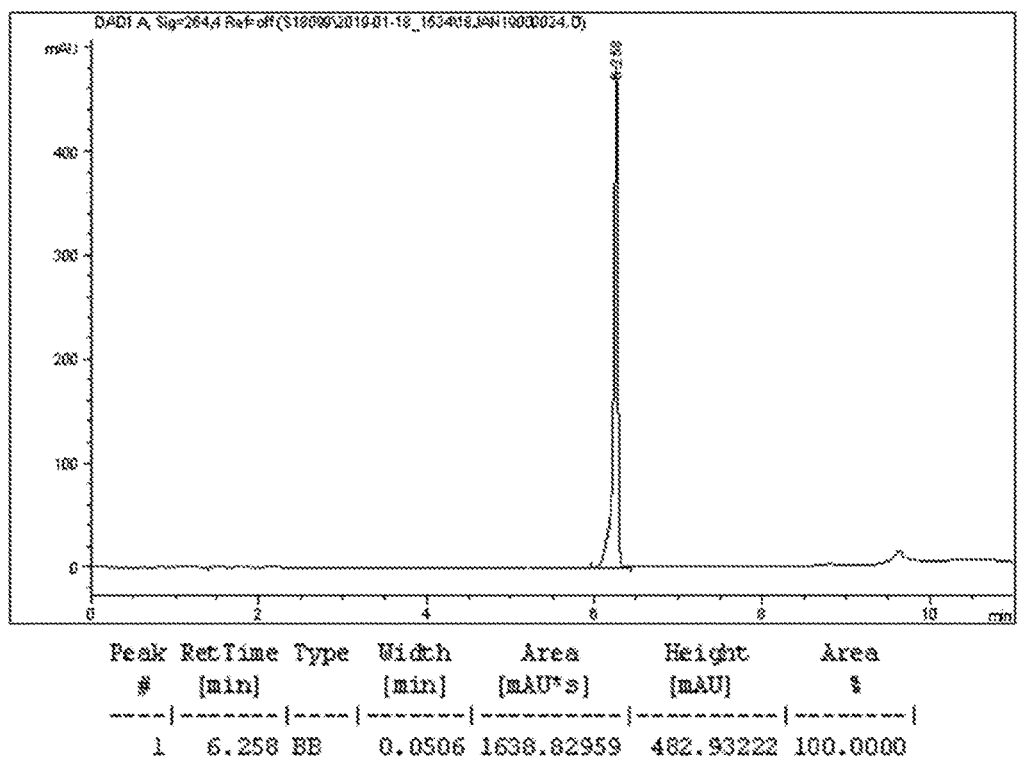
FIG. 64 illustrates an HPLC chromatogram of Form 13 (Exp. ID PSM52). The API peak appeared at 6.3 minutes with a chemical purity of 100% (area percentage).

From the cooling-evaporative crystallization experiment performed in ethanol Form 13 was obtained and used for the characterization (Exp. ID PSM52). Form 13 was physically stable upon exposure to AAC (40° C./75% RH) for 2 days. The HT-XRPD patterns of the material of Exp. ID PSM52 before and after exposure to AAC are shown in FIG. 61. The TGMS analysis of Form 13 (FIG. 62) showed a mass loss of 6.3% in the temperature range of 25-220° C. Due to the low amount of sample available, it is unclear which solvent came off during the mass loss (6.3% equals 1.9 equivalent water). In the DSC curve of Form 13 (FIG. 63), several broad endothermic events were recorded (in the temperature range 25-170° C.) related to mass loss and finally a small endothermic event was observed at 258° C. (due to melting of Form 1). The HPLC chromatogram of Form 13, shown in FIG. 64, revealed the presence of the API with a chemical purity of 100% (area percentage).

Form 14

Figure 65:
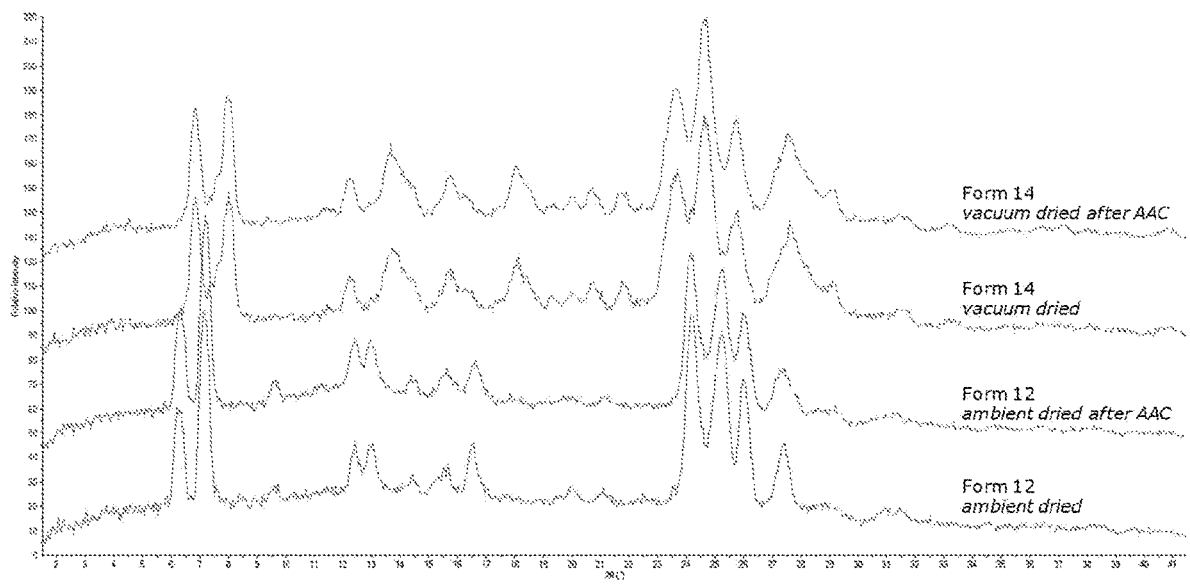
FIG. 65 illustrates an overlay of HT-XRPD patterns of the solid obtained from the thermocycling experiment in ACN/water 90/10 (Exp. ID TCP20) dried ambient and under vacuum, before and after exposure to AAC.
Figure 66:
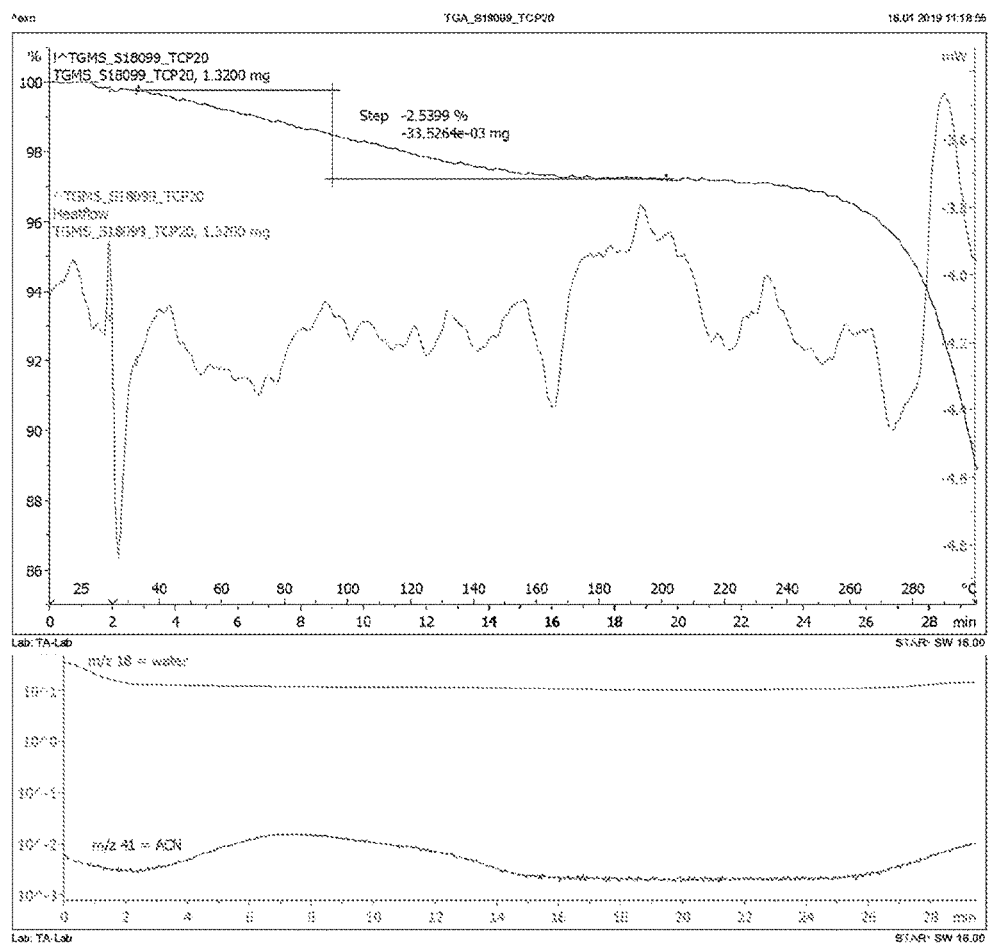
FIG. 66 illustrates the TGMS analysis (heating rate 10° C./min) of Form 14 (Exp. ID TCP20). The mass loss of 2.5% is most likely related to solvent loss.
Figure 67:
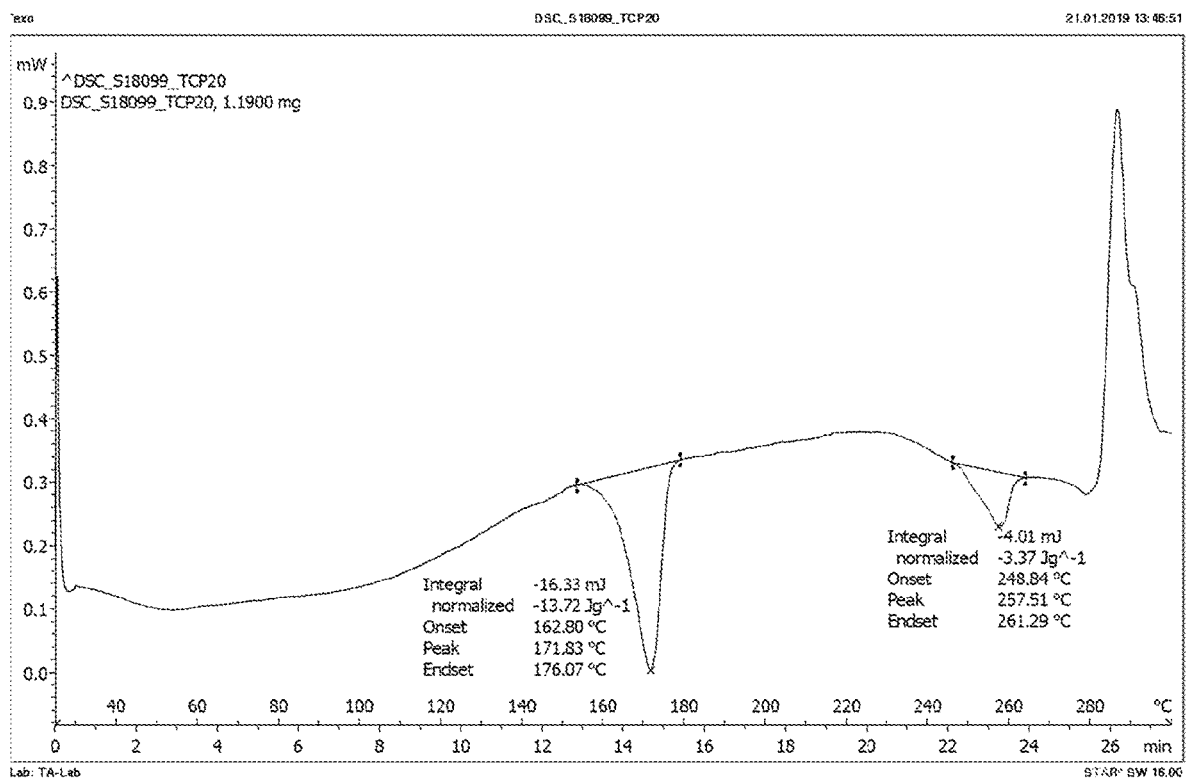
FIG. 67 illustrates the DSC analysis (heating rate 10° C./min) of Form 14 (Exp. ID TCP20). Two endothermic events were observed.
Figure 68:
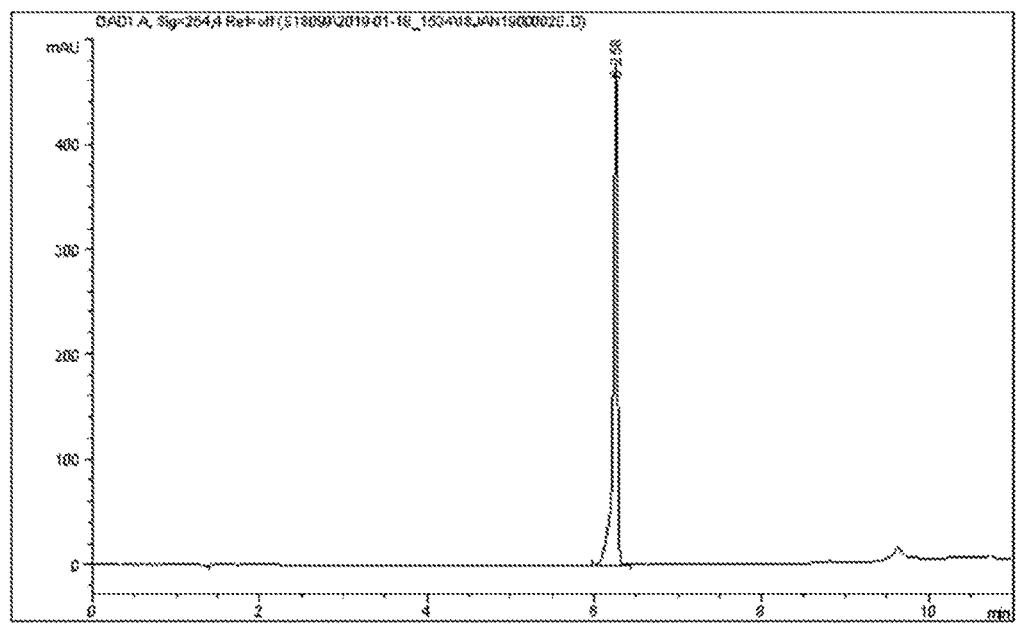
FIG. 68 illustrates an HPLC chromatogram of Form 14 (Exp. ID TCP20). The API peak appeared at 6.3 minutes with a chemical purity of 100% (area percentage).

From the thermocycling experiment performed in acetonitrile/water 90/10 (v/v) Form 14 was obtained in the vacuum dried solid and used for the characterization (Exp. ID TCP20). The ambient dried solid was Form 12 and the solid dried under vacuum was Form 14. Form 14 was physically stable upon exposure to AAC (40° C./75% RH) for 2 days. The HT-XRPD patterns of the solid of Exp. ID TCP20 before and after exposure to AAC are shown in FIG. 65. The TGMS analysis of Form 14 (FIG. 66) showed a gradual mass loss of 2.5% in the temperature range of 25-170° C. This mass loss is equal to 0.3 molar equivalent acetonitrile. From the heat flow curve, an endothermic event was observed at 165° C., just after the mass loss. An endothermic event observed around 250° C. is most likely related to melting of Form 1. Form 14 was observed in harshly dried samples from acetonitrile/water and acetone/water and is therefore most likely a non-stoichiometric isostructural solvate. In the DSC curve of Form 14 (FIG. 67), an endothermic event was recorded at 172° C. and a small endothermic event was observed at 258° C. (due to melting of Form 1). Without wishing to be bound by any particular theory, it is believed that most likely Form 14 converts to Form 1 after the solvent loss. The HPLC chromatogram of Form 14, shown in FIG. 68, revealed the presence of the API with a chemical purity of 100% (area percentage).

Form 15

Figure 69:
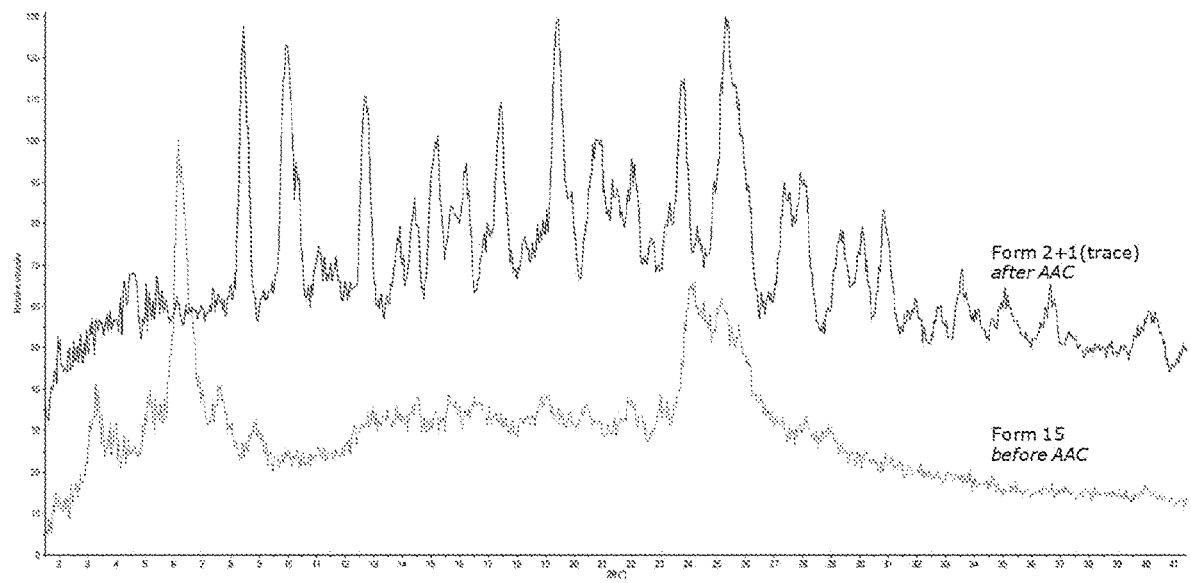
FIG. 69 illustrates an overlay of HT-XRPD patterns of the material obtained from the vapor diffusion into liquid experiment in N,N-dimethylformamide/1,4-dioxane (Exp. ID VDL8) before and after exposure to AAC.
Figure 70:
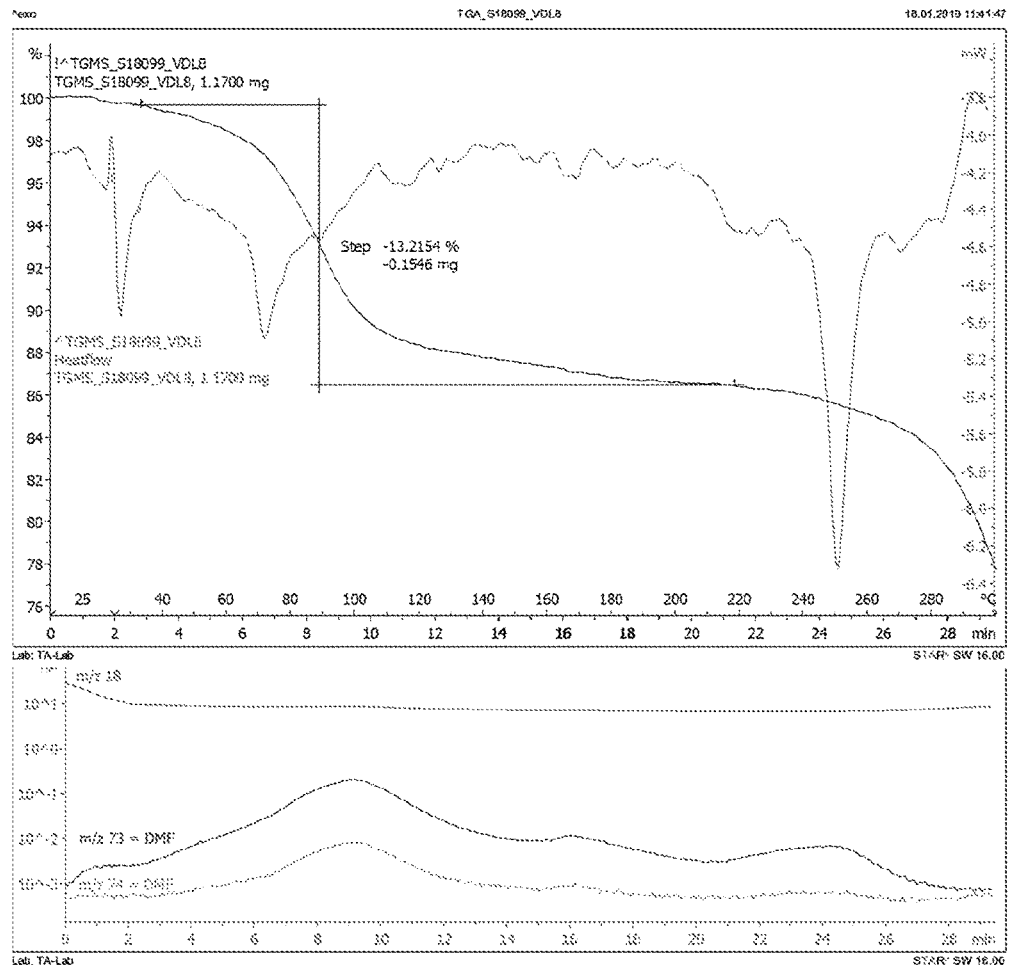
FIG. 70 illustrates the TGMS analysis (heating rate 10° C./min) of Form 15 (Exp. ID VDL8). The mass loss of 13.2% is related to solvent loss.
Figure 71:
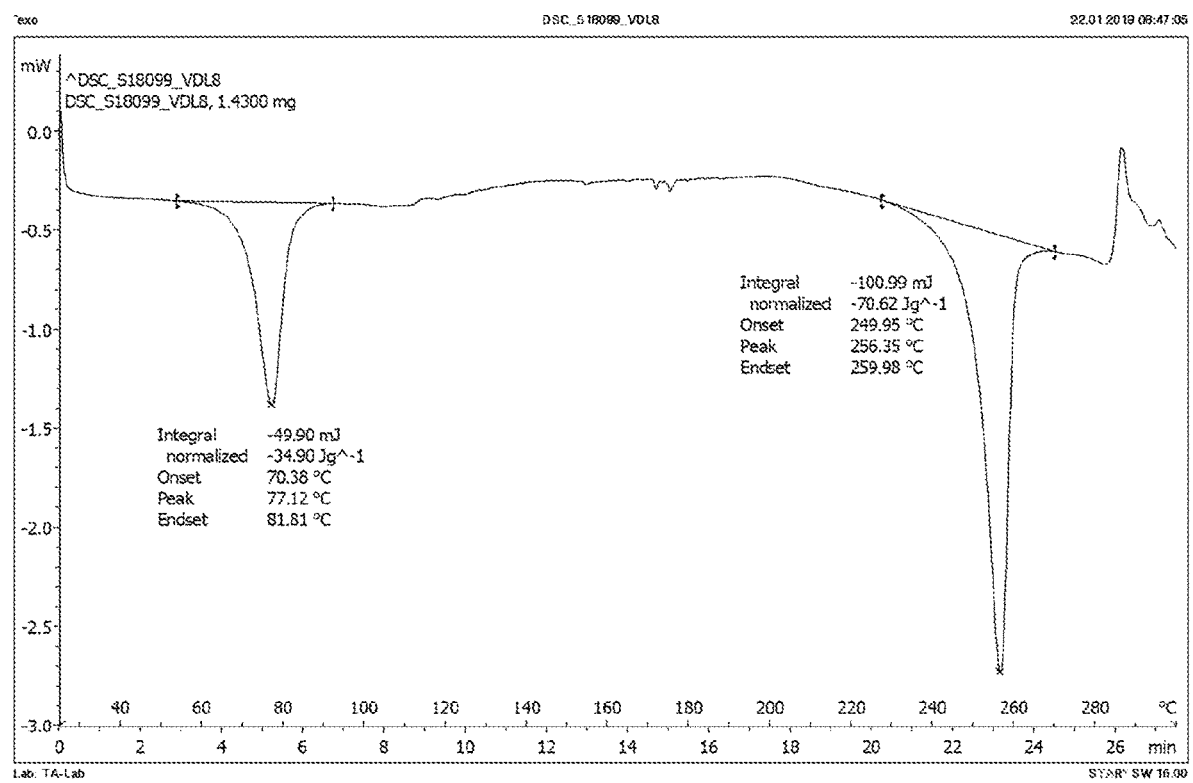
FIG. 71 illustrates the DSC analysis (heating rate 10° C./min) of Form 15 (Exp. ID VDL8). Two endothermic events were observed, most likely related with solvent loss and melting of Form 1, respectively.
Figure 72:
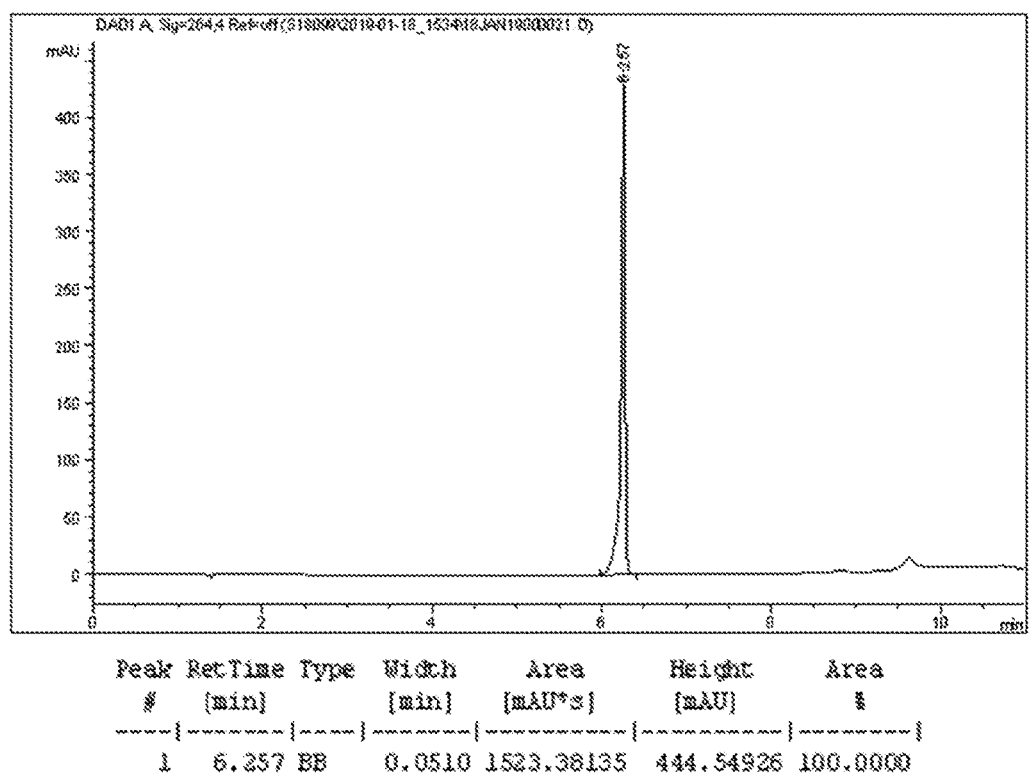
FIG. 72 illustrates an HPLC chromatogram of Form 15 (Exp. ID VDL8). The API peak appeared at 6.3 minutes with a chemical purity of 100% (area percentage).

From the vapor diffusion into liquid experiment performed in N,N-dimethylformamide/1,4-dioxane Form 15 was obtained and used for the characterization (Exp. ID VDL8). Form 15 was physically unstable upon exposure to AAC (40° C./75% RH) for 2 days and turned into a mixture of Forms 2 and 1. The HT-XRPD patterns of the solid of Exp. ID VDL8 before and after exposure to AAC are shown in FIG. 69. The TGMS analysis of Form 15 (FIG. 70) showed a mass loss of 13.2% in the temperature range of 25-220° C. The mass loss was most likely related to DMF loss (1 molar equivalent DMF). From the heat flow curve, an endothermic event was observed coinciding with the mass loss (70° C.), followed by another endothermic event around 250° C. (melting of Form 1). Form 15 was mostly obtained from experiments using DMF but sometimes Form 15 was observed in mixture with other forms from other solvents and is therefore most likely an isostructural solvate. In the DSC curve of Form 15 (FIG. 71), an endothermic event was recorded at 77° C., most likely related to solvent loss. The final endotherm at 256° C. corresponds to the melting of Form 1. The HPLC chromatogram of Form 15, shown in FIG. 72, revealed the presence of the API with a chemical purity of 100% (area percentage).

Form 16

Figure 73:
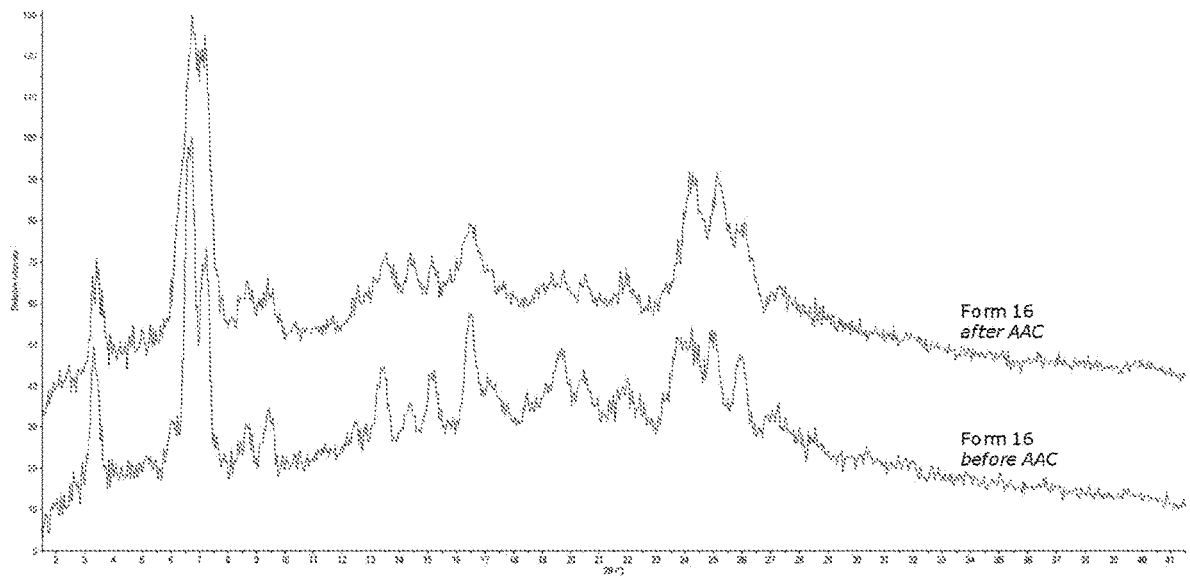
FIG. 73 illustrates an overlay of HT-XRPD patterns of the material obtained from the evaporative experiment in DMSO (Exp. ID ECP18) before and after exposure to AAC.
Figure 74:
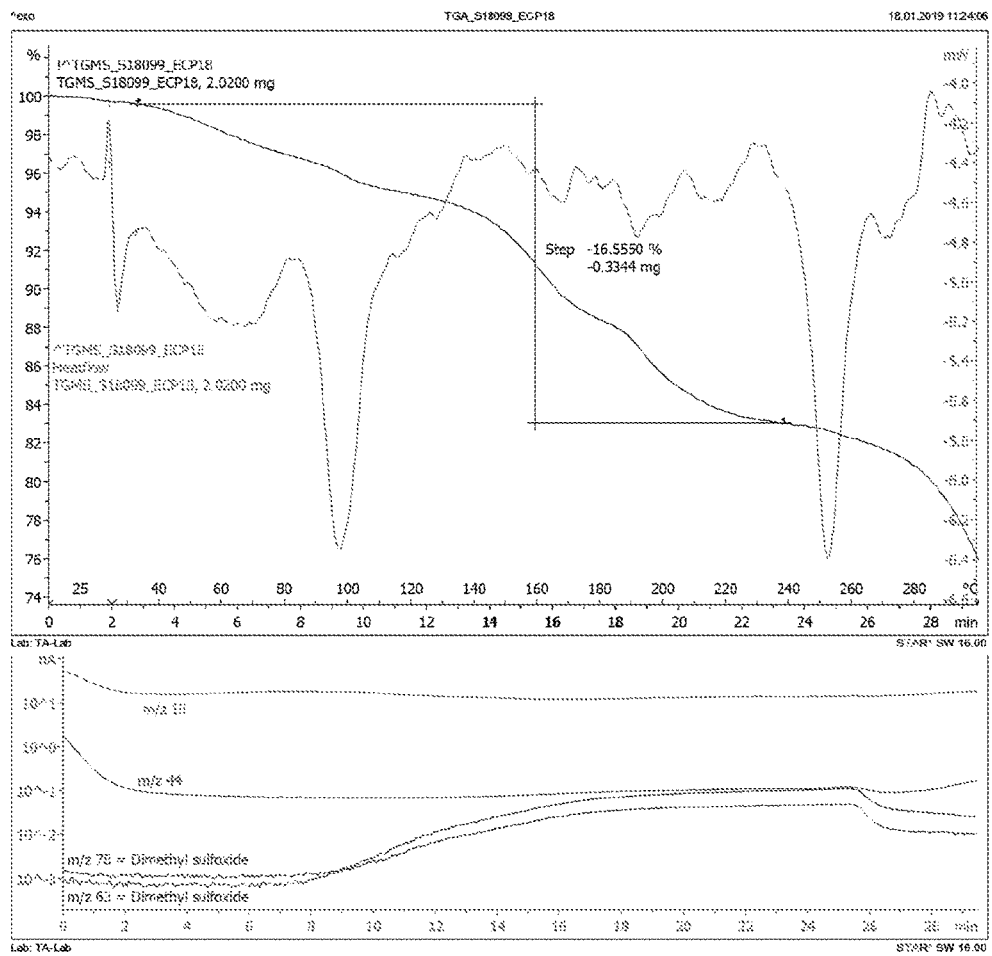
FIG. 74 illustrates the TGMS analysis (heating rate 10° C./min) of Form 16 (Exp. ID ECP18). The mass loss of 16.6% is related to solvent loss.
Figure 75:
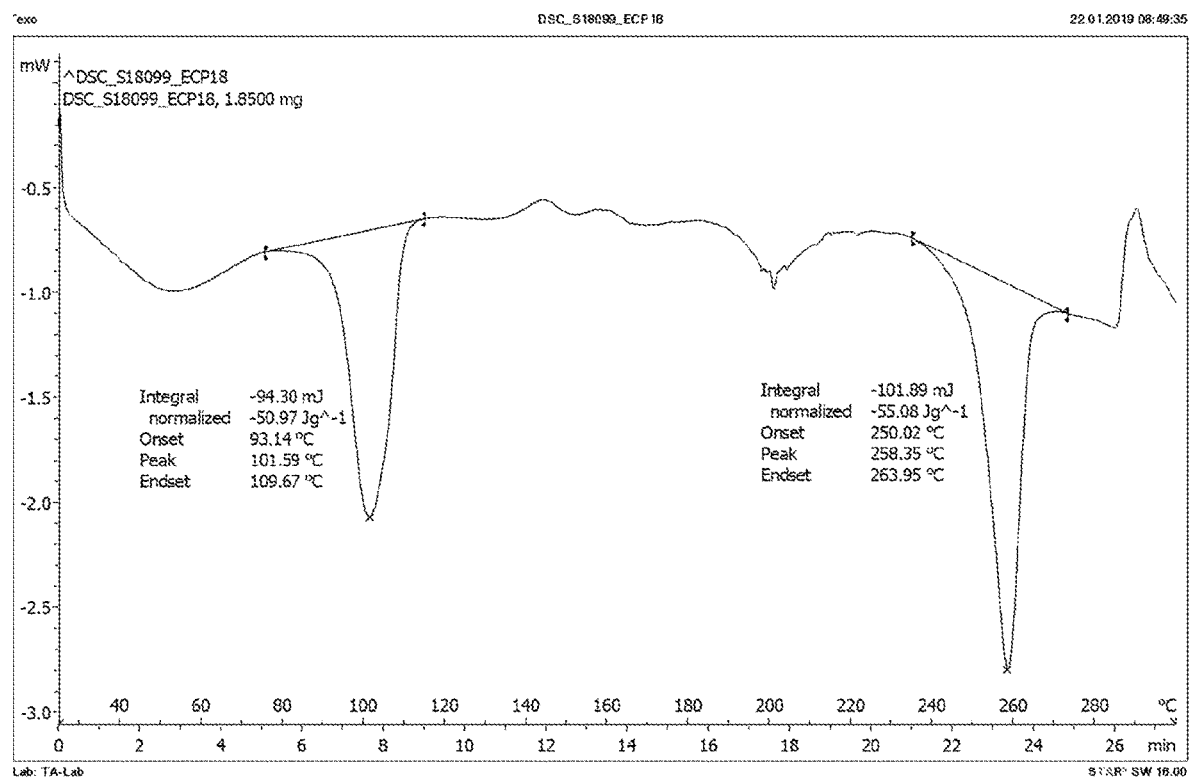
FIG. 75 illustrates the DSC analysis (heating rate 10° C./min) of Form 16 (Exp. ID ECP18). Two endothermic events were observed, most likely related with solvent loss and melting of Form 1, respectively.
Figure 76:
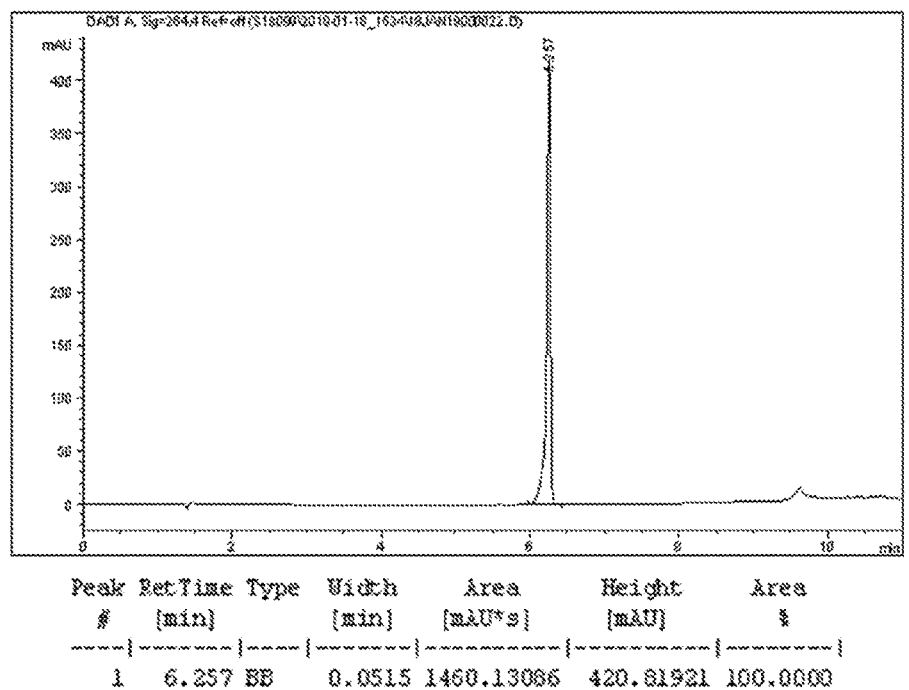
FIG. 76 illustrates an HPLC chromatogram of Form 16 (Exp. ID ECP18). The API peak appeared at 6.3 minutes with a chemical purity of 100% (area percentage).

From the evaporative experiment performed in dimethyl sulfoxide Form 16 was obtained and used for the characterization (Exp. ID ECP18). Form 16 was physically stable upon exposure to AAC (40° C./75% RH) for 2 days. The HT-XRPD patterns of the material of Exp. ID ECP18 before and after exposure to AAC are shown in FIG. 73. The TGMS analysis of Form 16 (FIG. 74) showed a mass loss of 16.6% in the temperature range of 25-240° C. The mass loss was most likely related to loss of DMSO (1.3 equivalents DMSO). From the heat flow curve, a broad endothermic event was observed coinciding with the mass loss. A final endothermic event was observed around 250° C. most likely related to the melting of Form 1. Without wishing to be bound by any particular theory, it is believed that Form 16 was found in samples containing DMSO and is therefore a non-stoichiometric DMSO solvate. In the DSC curve of Form 16 (FIG. 75), an endothermic event was recorded at 102° C., most likely related to solvent loss. The final endotherm at 256° C. corresponds to the melting of Form 1. The HPLC chromatogram of Form 16, shown in FIG. 76, revealed the presence of the API with a chemical purity of 100% (area percentage).

Form 17

Figure 77:
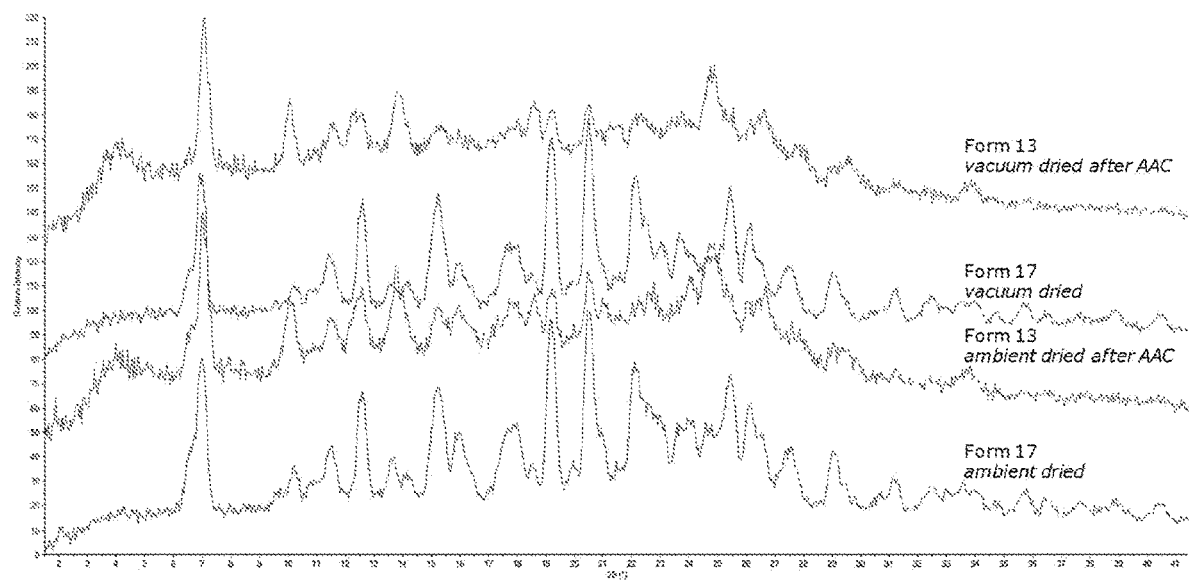
FIG. 77 illustrates an overlay of HT-XRPD patterns of the material obtained from the anti-solvent experiment in TFE/heptane (Exp. ID AS3) dried ambient and under vacuum, before and after exposure to AAC.
Figure 78:
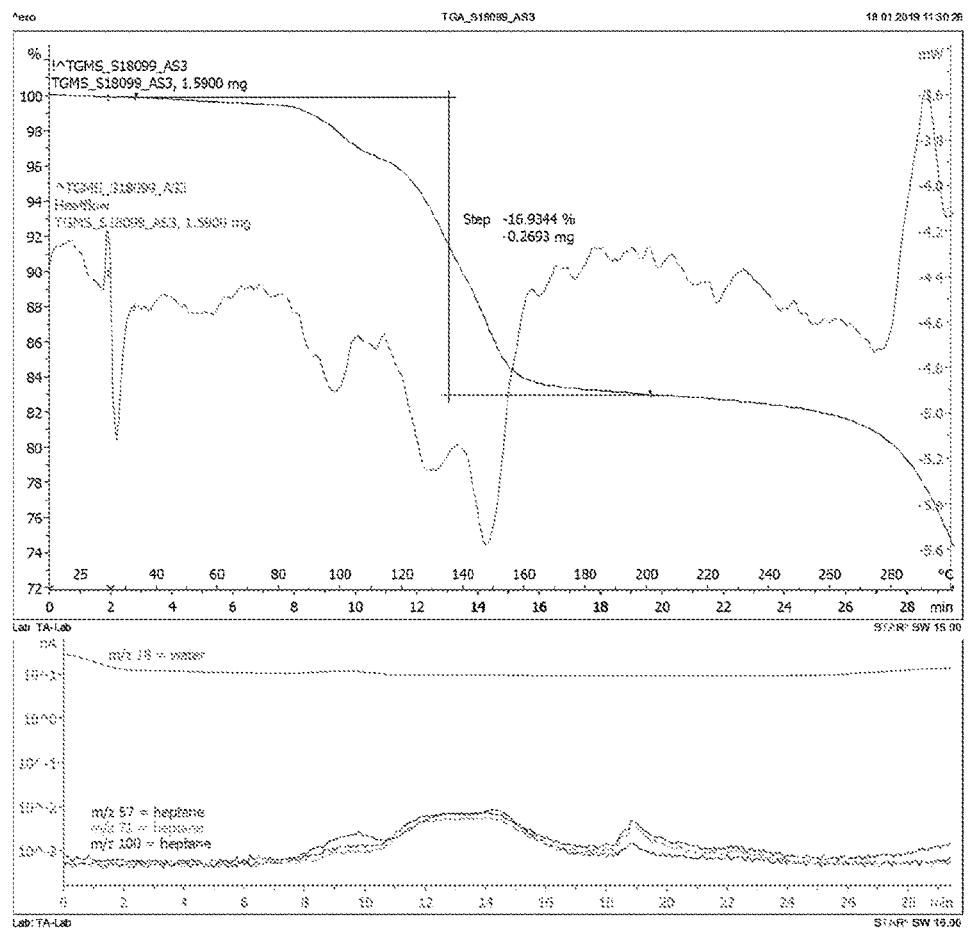
FIG. 78 illustrates the TGMS analysis (heating rate 10° C./min) of Form 17 (Exp. ID AS3). The mass loss of 16.9% is related to solvent loss.
Figure 79:
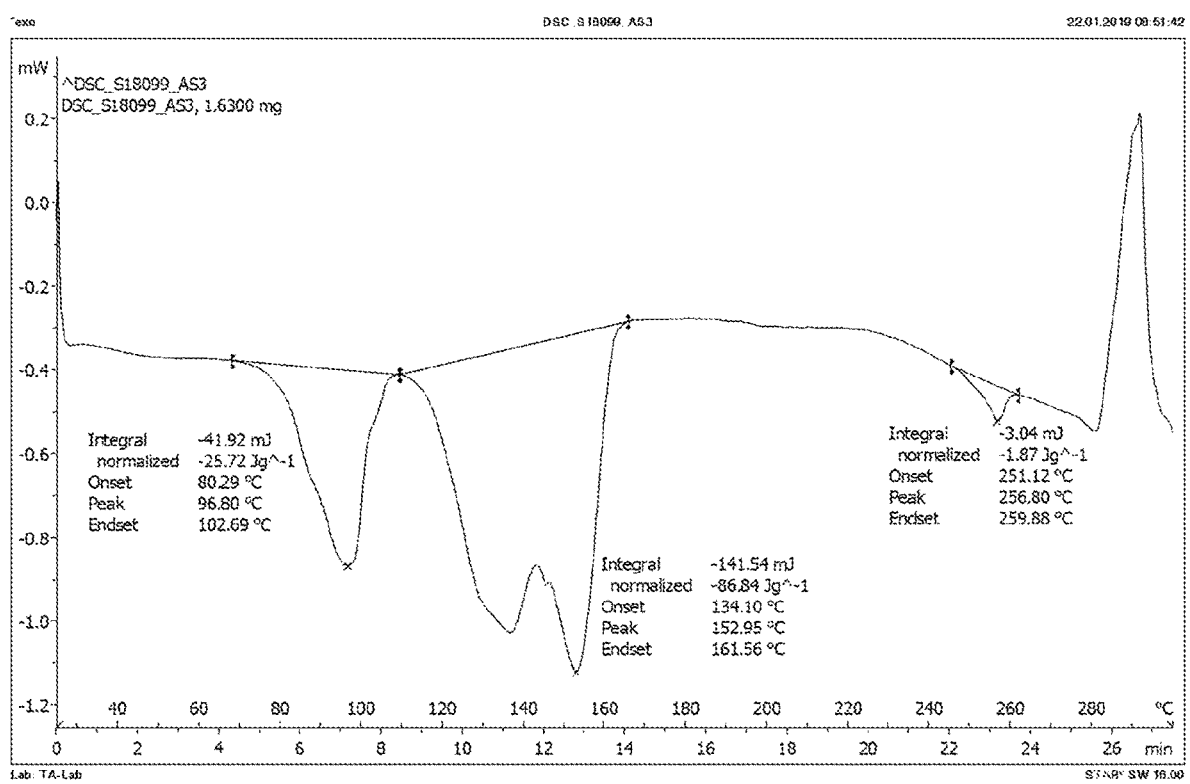
FIG. 79 illustrates the DSC analysis (heating rate 10° C./min) of Form 17 (Exp. ID AS3). Three endothermic events were observed, most likely related with solvent loss. The final endotherm at 257° C. was related to the melting of Form 1.
Figure 80:
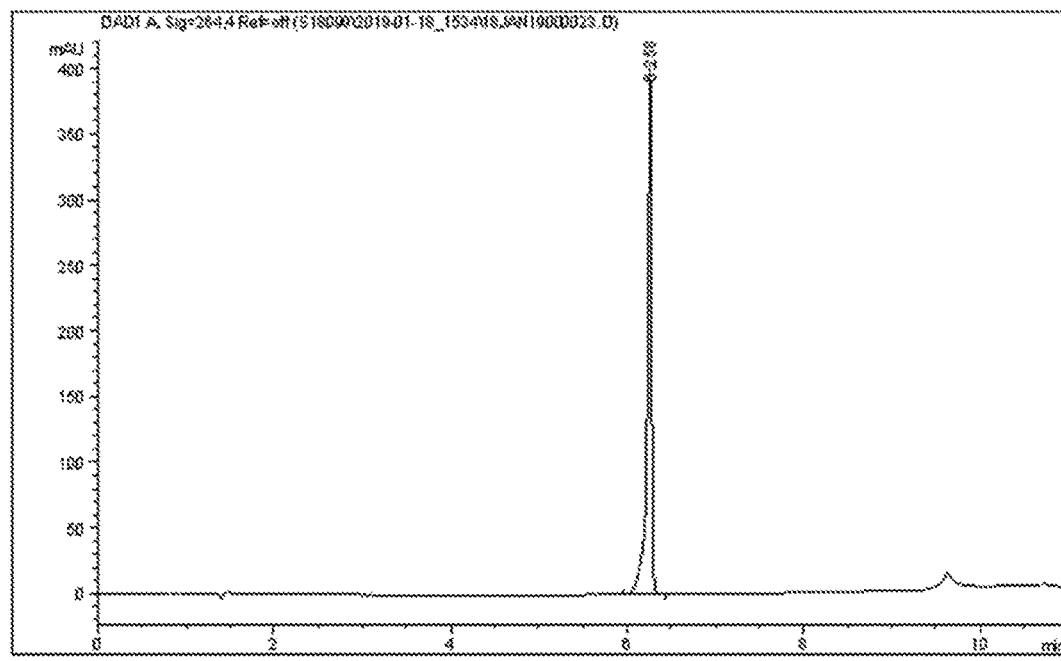
FIG. 80 illustrates an HPLC chromatogram of Form 17 (Exp. ID AS3). The API peak appeared at 6.3 minutes with a chemical purity of 100% (area percentage).

From the anti-solvent experiment performed in 2,2,2-trifluoroethanol/heptane Form 17 was obtained and used for the characterization (Exp. ID AS3). Both ambient dried and vacuum dried solids were Form 17. Form 17 was physically unstable upon exposure to AAC (40° C./75% RH) for 2 days and turned into Form 13. The HT-XRPD patterns of the solid of Exp. ID AS3 before and after exposure to AAC are shown in FIG. 77. The TGMS analysis of Form 17 (FIG. 78) showed a mass loss of 16.9% in the temperature range of 25-200° C. Without wishing to be bound by any particular theory, it is believed that the mass loss was most likely related to solvent loss, released in a step-wise manner (16.9% equals 1 molar equivalent heptane or TFE). From the heat flow curve, three endothermic events were observed coinciding with the mass loss. Without wishing to be bound by any particular theory, it is believed that Form 17 is most likely a stoichiometric TFE or heptane solvate. In the DSC curve of Form 17 (FIG. 79), three endothermic events were recorded at 97, 135 and 153° C., most likely related to solvent loss. A small endothermic event was observed at 257° C., due to melting of Form 1. The HPLC chromatogram of Form 17, shown in FIG. 80, revealed the presence of the API with a chemical purity of 100% (area percentage).

Form 18

Figure 81:
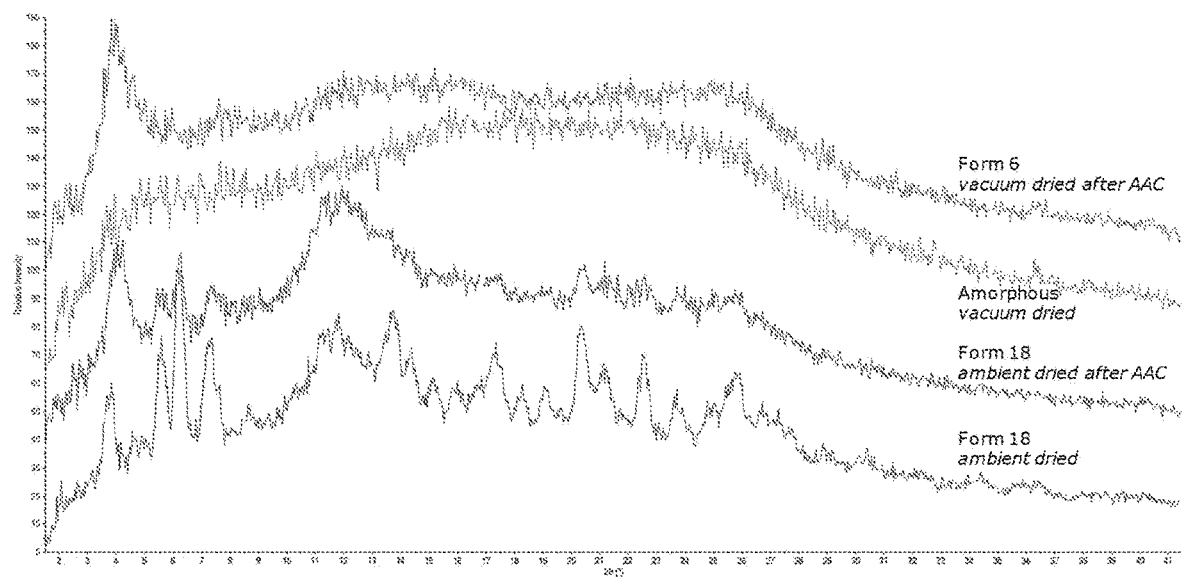
FIG. 81 illustrates an overlay of HT-XRPD patterns of the solid obtained from the anti-solvent experiment in DMF/isopropylacetate (Exp. ID AS7) dried ambient and under vacuum, before and after exposure to AAC.

From the anti-solvent experiment performed in N,N-dimethylformamide/isopropyl acetate (Exp. ID AS7) Form 18 was obtained in the ambient dried solid. During drying under vacuum the solid became amorphous. Form 18 became less crystalline during exposure to AAC (40° C./75% RH) for 2 days. The HT-XRPD patterns of the material of Exp. ID AS7 before and after exposure to AAC are shown in FIG. 81.

Form 19

Figure 82:
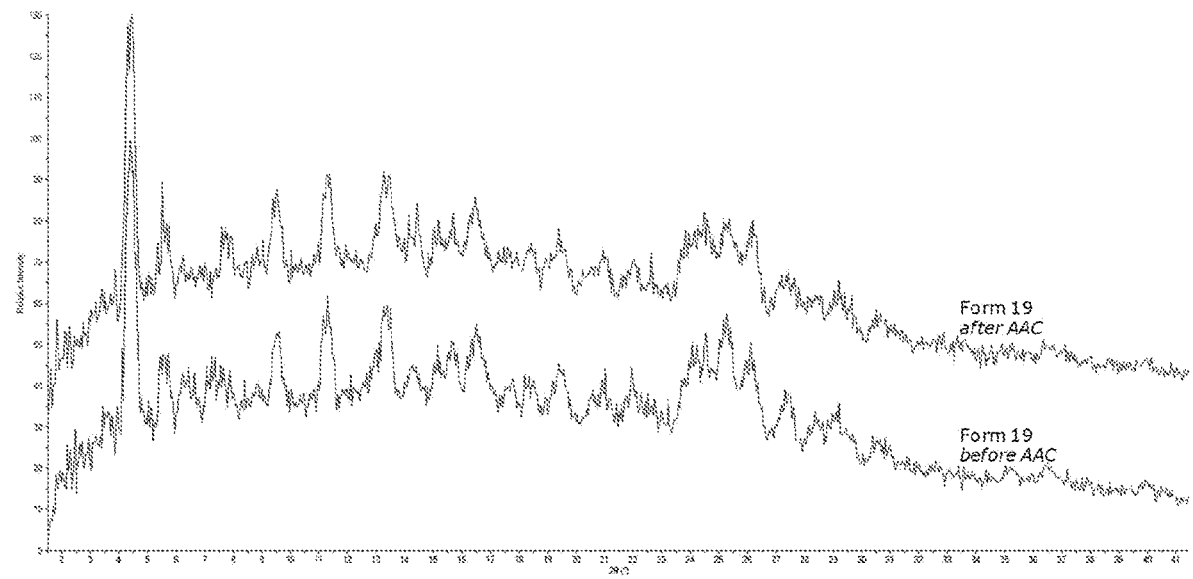
FIG. 82 illustrates an overlay of HT-XRPD patterns of the material obtained from the evaporative experiment in methanol/diisopropyl ether 20/80 (Exp. ID ECP45/PSM13) before and after exposure to AAC.
Figure 83:
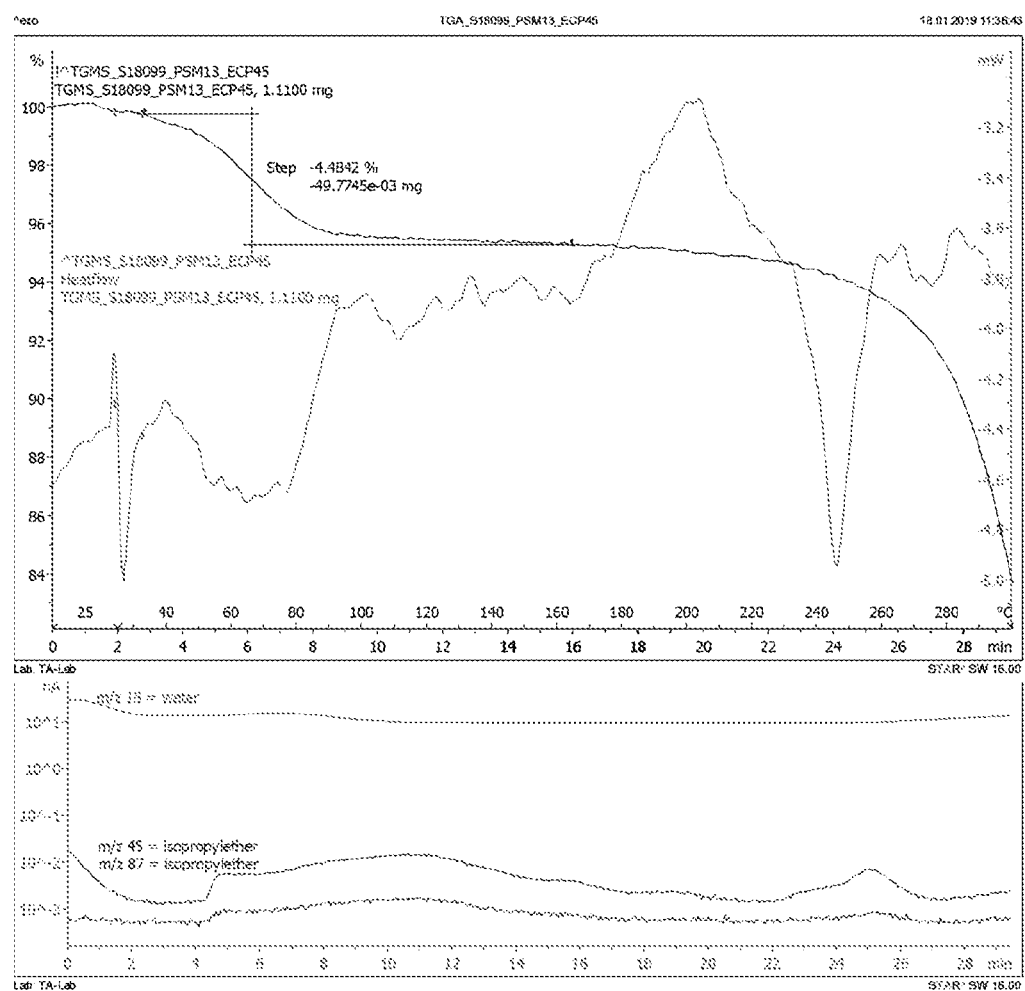
FIG. 83 illustrates the TGMS analysis (heating rate 10° C./min) of Form 19 (Exp. ID ECP45/PSM13). The mass loss of 4.5% is most likely related to solvent loss, followed by an exothermic recrystallization event and an endothermic melting event of Form 1.

From the evaporative experiment performed in methanol/diisopropyl ether 20/80 (v/v) Form 19 was obtained and used for the characterization (Exp. ID ECP45/PSM13). Form 19 was physically stable upon exposure to AAC (40° C./75% RH) for 2 days. The HT-XRPD patterns of the material of Exp. ID ECP45/PSM13 before and after exposure to AAC are shown in FIG. 82. The TGMS analysis of Form 19 (FIG. 83) showed a mass loss of 4.5% in the temperature range of 25-120° C. The mass loss was most likely related to diisopropyl ether (0.23 molar equivalent diisopropyl ether). From the heat flow curve, a broad endothermic event was observed coinciding with the mass loss. After the solvent loss an exothermic recrystallization event is observed to Form 1, followed by the melting of Form 1 (endotherm around 250° C.). Without wishing to be bound by any particular theory, it is believed that Form 19 is most likely a non-stoichiometric solvate.

Example 2: Polymorph Screen—Voruciclib Salts

The aim of the study was to identify an alternative salt of voruciclib with better and/or different physico-chemical properties than voruciclib HCl. Without wishing to be bound by any particular theory, it is believed that the HCl salt has a complex pseudo polymorphic behavior and is prone to gelling in aqueous media. The salt screen presented in this study included 25 acidic counterions and was performed according to the saturated solution method in THF, ethanol and acetone.

General abbreviations: AAC: Accelerated Aging Conditions (40° C. and 75% RH); Am: Amorphous; API: Active Pharmaceutical Ingredient; CI: Counterion; DSC: Differential Scanning Calorimetry; HPLC: High-Performance Liquid Chromatography; HR-XRPD: High Resolution X-Ray Powder Diffraction; HT-XRPD: High Throughput X-Ray Powder Diffraction; LCMS: Liquid Chromatography Mass spectroscopy; MS: Mass Spectroscopy; RH: Relative Humidity; RT: Room Temperature; SM: Starting Material; SSm: Experiment ID for the salt screen experiments; TGA: Thermogravimetric Analysis; TGMS: Thermogravimetric Analysis coupled with Mass Spectroscopy; EtOH: Ethanol; THF: Tetrahydrofuran.

Starting Material Characterization

Figure 84:
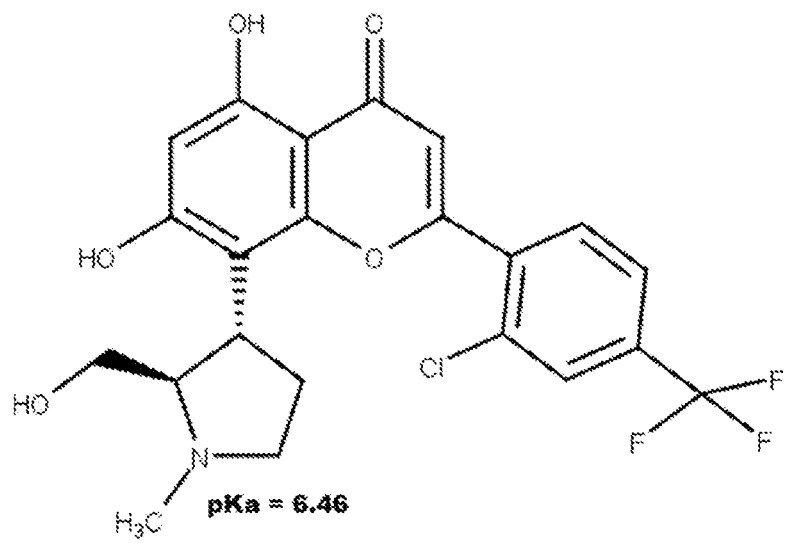
FIG. 84 illustrates the molecular structure of voruciclib (free base); the free base has a basic site with a $pK_a$ of 6.46.
Figure 85:
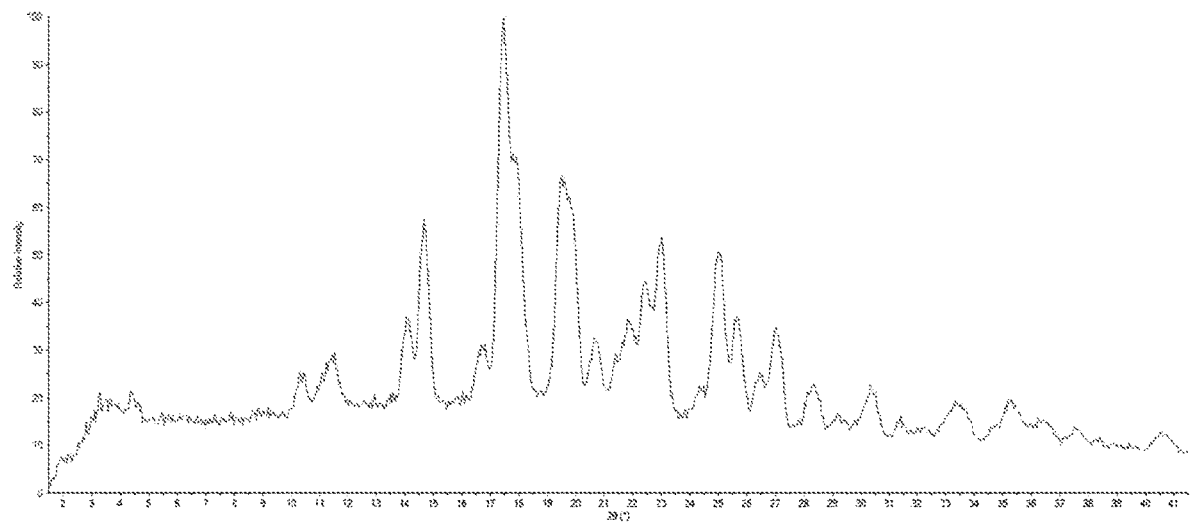
FIG. 85 illustrates the high throughput XRPD of voruciclib free base, starting material, Form A.
Figure 86:
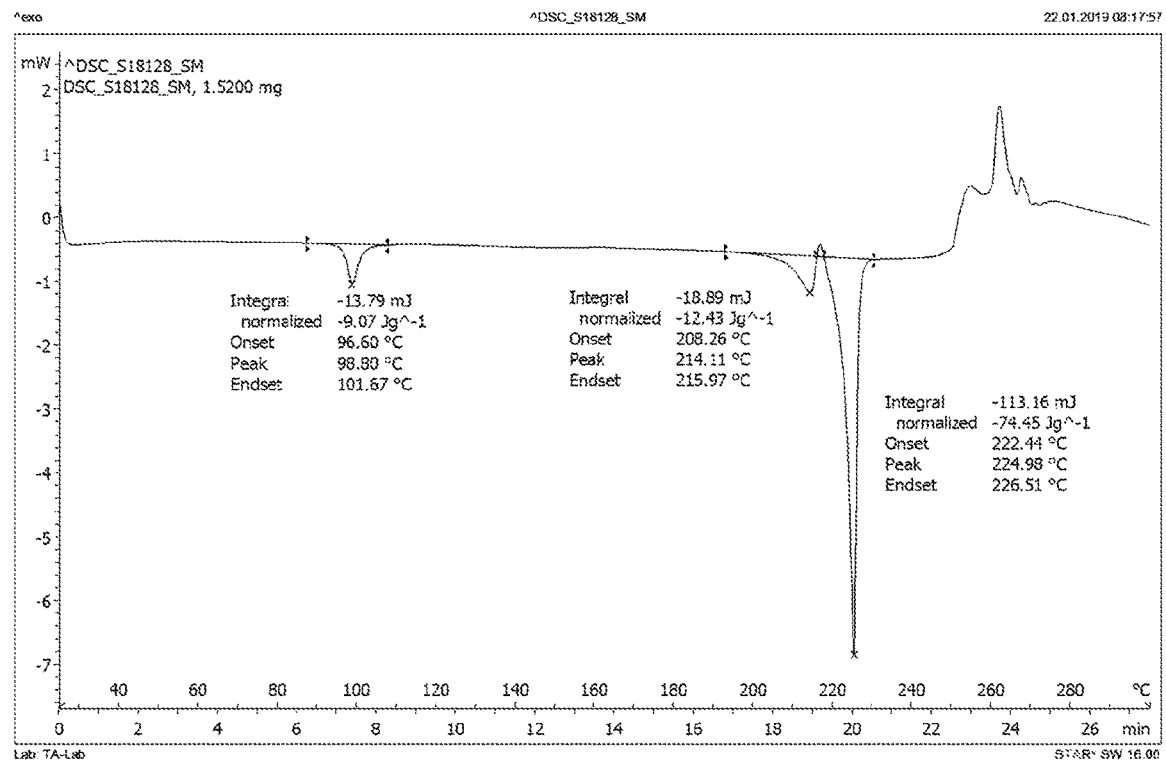
FIG. 86 illustrates the DSC trace of voruciclib free base, starting material (heating rate 10° C./min); a small endothermic event is observed at 99° C., followed by a small endothermic event at 214° C. and a final melting at 225° C.
Figure 87:
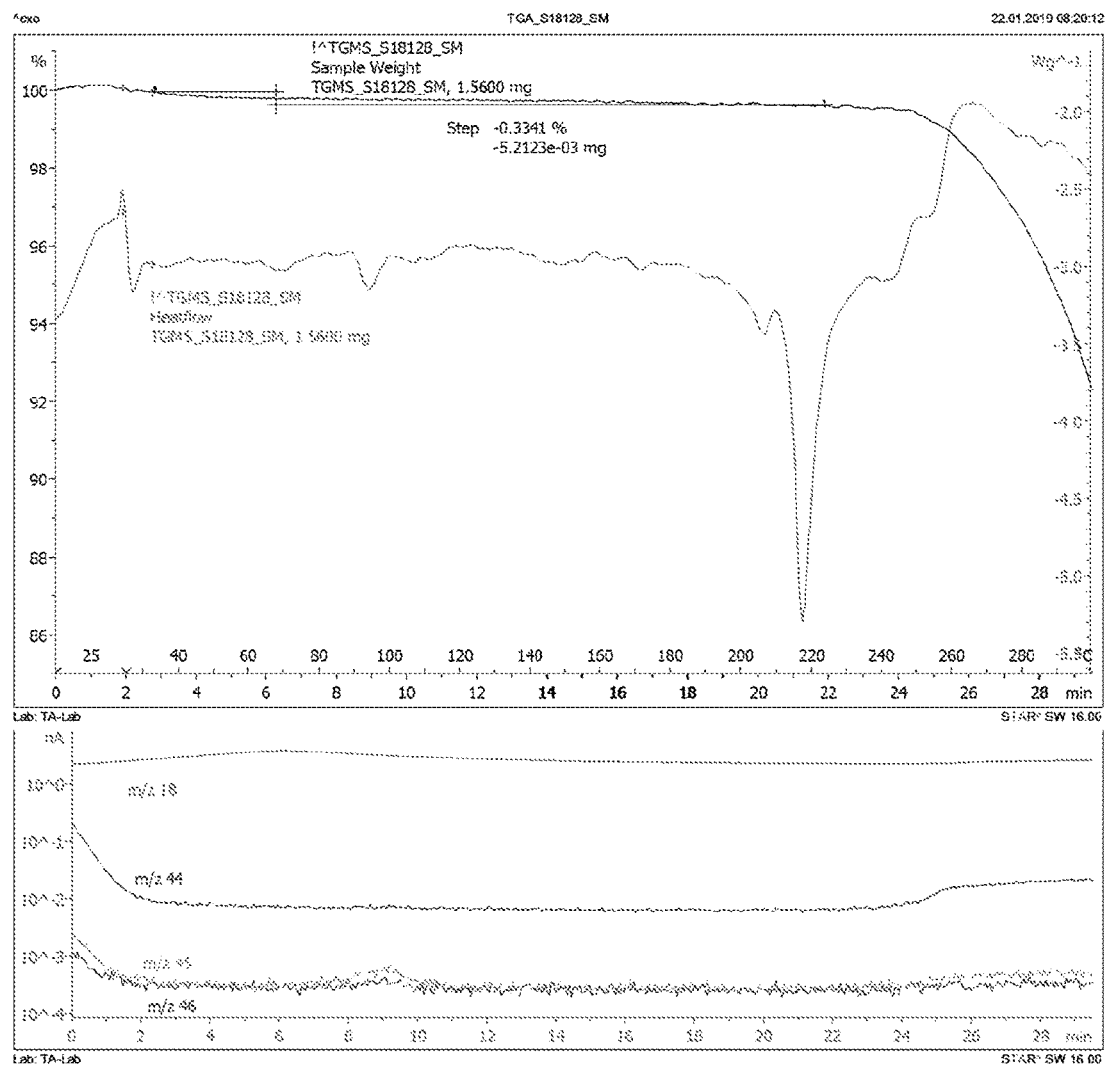
FIG. 87 illustrates the TGMS data of voruciclib free base, starting material (heating rate 10° C./min); a mass loss of 0.3% was observed prior to decomposition; decomposition started around 240° C.; the mass loss is most likely related to residual solvent/moisture and the start of decomposition was confirmed by the MS data; the heat flow signal showed an endothermic event due to melting around 220° C.
Figure 88:
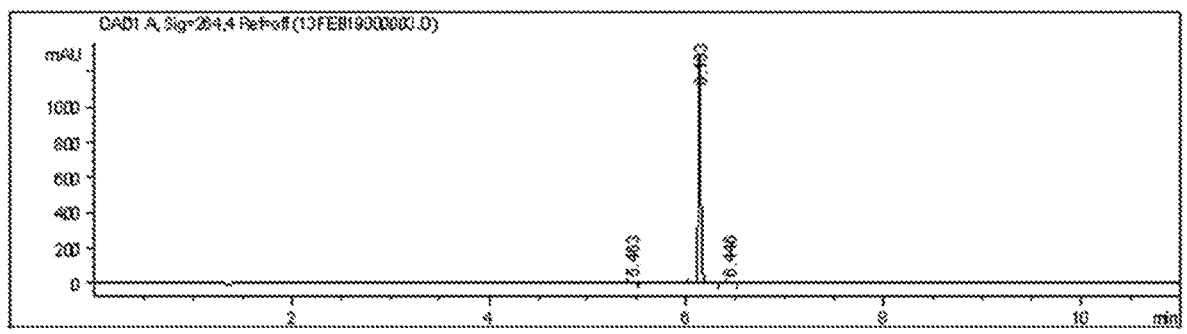
FIG. 88 illustrates the HPLC analysis of voruciclib free base, starting material; the peak corresponding to the free base had a retention time of 6.1 min and showed a chemical purity of 99.3% (area %).
Figure 89:
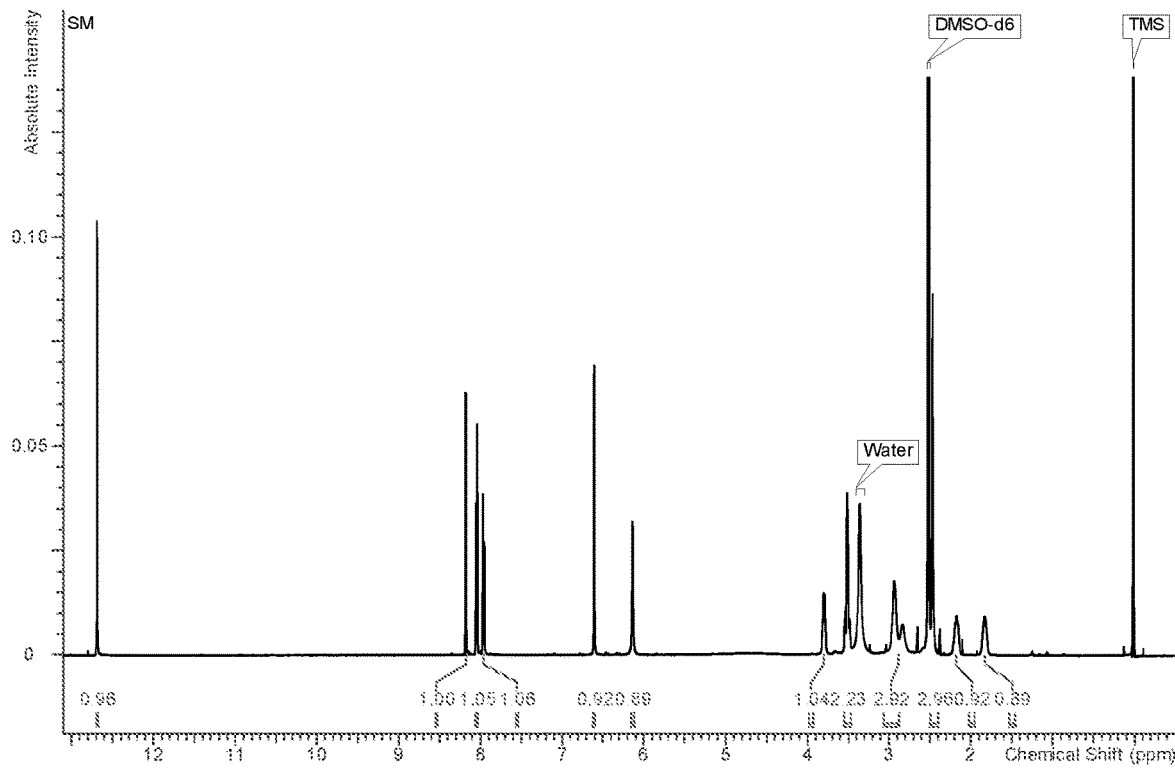
FIG. 89 illustrates the $^1$H-NMR spectrum of voruciclib free base, starting material.

Approximately 5 grams of voruciclib free base (FIG. 84) were employed, available as a light yellow powder. For reference purposes the starting material was analyzed by XRPD, DSC, TGMS, LCMS and $^1$H-NMR. The High Throughput XRPD (HT-XRPD) analysis confirmed the crystalline nature of the starting material (FIG. 85). The crystalline starting material was designated Form A. The DSC analysis (FIG. 86) showed a small endothermic event at 99° C., followed by a second small endothermic event at 214° C. and a final melting at 225° C. Without wishing to be bound by any particular theory, it is believed that the small endothermic events suggest that more than one polymorph of the free base may exist. The TGMS analysis (FIG. 87) showed a mass loss of 0.3% prior to decomposition around 240° C. This mass loss is related to water and possibly residual solvent (released during the small thermal event at 100° C.). The heat flow signal was similar to the DSC trace and showed a sharp endothermic event at 215° C. before thermal decomposition which could be attributed to the melting of voruciclib free base. The chemical purity of the free base was assessed by HPLC analysis (FIG. 88). The result indicated the purity of the solids was 99.3% (area %). The $^1$H-NMR spectrum was recorded for reference purposes and is shown in FIG. 89. The peak at 2.47 ppm (protons of CH3-group connected to the basic N-atom) shows the strongest resonance shift in case of salt formation. The results of the characterization indicated that the starting material is a non-solvated and anhydrous solid form.

Solvent Selection

The approximate solubility of the free base was assessed in several organic solvents (Table 17) by the solvent addition method. To about 5 mg of free base, aliquots of solvent were added until complete dissolution was observed or until a concentration below 1 mg/mL was reached. Aliquots of 100 μL were used up to 2 mL, followed by aliquots of 1 mL up to 8 mL. The free base was soluble in THF and sparingly soluble in methanol, ethanol and acetone. In other solvents, the solubility of the free base was below 10 mg/mL while in water voruciclib was practically insoluble. Based on the solubility results, in some embodiments the crystallization solvents selected for salt formation were THF, ethanol and acetone.

TABLE 17

| Approximate solubility assessment of ME-522 in 10 solvents at RT. | |
|---|---|
| Solvent | Solubility (mg/mL) |
| Methanol | 17 < S < 26 |
| Chloroform | ~5 |

TABLE 17-continued

Approximate solubility assessment
of ME-522 in 10 solvents at RT.

| Solvent | Solubility (mg/mL) |
|---|---|
| Ethanol | 14 < S < 18 |
| Acetonitrile | ~5 |
| Tetrahydrofuran | 30 < S < 60 |
| Acetone | 10 < S < 13 |
| 1,4-Dioxane | ~1 |
| 2-Propanol | ~8 |
| Ethyl acetate | ~1 |
| Water | <1 |

Counterions

The acidic counterions used for the salt screen are listed in Table 18. The abbreviation of the counterions was used for the nomenclature of potential salt forms. Counterions were used with 1 molar equivalent and the acids with two ionization sites were also used with 0.5 molar equivalent.

TABLE 18

List of acidic counterions used for the salt screen on voruciclib.

| # | Acid counterions | ICH class | $pka_1$ | $pka_2$ | Abbreviation |
|---|---|---|---|---|---|
| 1 | Hydrobromic | 3 | <−6 | — | HBr |
| 2 | Naphthalene-1,5-disulfonic | 2 | −3.4 | −2.6 | Nds |
| 3 | Sulfuric | 1 | −3 | 1.9 | Sul |
| 4 | Ethane-1,2-disulfonic | 2 | −2.1 | −1.5 | Edy |
| 5 | p-Toluenesulfonic | 2 | −1.3 | — | Tos |
| 6 | Naphthalene-2-sulfonic | 2 | 0.2 | — | Nsa |
| 7 | Benzenesulfonic | 2 | 0.7 | — | Bes |
| 8 | Oxalic | 2 | 1.3 | 4.3 | Oxa |
| 9 | Dibenzoyl-L-tartaric | 2 | 1.9 | — | DiTr |
| 10 | Maleic | 1 | 1.9 | 6.2 | Mae |
| 11 | Phosphoric | 1 | 2.0 | 7.1 | Pho |
| 12 | Ethanesulfonic | 2 | 2.1 | — | Esy |
| 13 | Glutamic | 1 | 2.2 | 4.3 | Glm |
| 14 | 1-Hydroxy-2-naphthoic | 2 | 2.7 | 13.5 | Xin |
| 15 | Malonic | 2 | 2.8 | 5.7 | Mao |
| 16 | Gentisic | 2 | 2.9 | — | Gen |
| 17 | (+)-L-Tartaric | 1 | 3.0 | 4.4 | Tar |
| 18 | Fumaric | 1 | 3.0 | 4.4 | Fum |
| 19 | D-Glucuronic | 1 | 3.2 | — | Glr |
| 20 | Citric | 1 | 3.1 | 4.8 | Cit |
| 21 | (−)-L-Malic | 1 | 3.5 | 5.1 | Mal |
| 22 | D-Gluconic | 1 | 3.8 | — | Glc |
| 23 | Benzoic | 2 | 4.2 | — | Ben |
| 24 | Succinic | 1 | 4.2 | 5.6 | Suc |
| 25 | Glutaric | 1 | 4.3 | 5.3 | Glt |

Temperature Profile

To select the temperature profile for the salt screening experiments the thermal stability of the free base in solution was tested. Solutions of the free base were prepared in THF, ethanol and acetone and were divided over 3 vials. The vials were placed at RT for 24 hours and at 50° C. and 80° C. for 1 hour. The solutions were analyzed by HPLC. No significant differences in the chemical purity were observed compared to the starting material. Hence, the free base was considered thermally stable in solution.

Salt Screen

The salt screen was performed using the saturated solution method. Saturated solutions of the free base were prepared at 50° C. in THF, ethanol and acetone. Aliquots of aqueous counterion solutions were added resulting in a stoichiometric ratio of free base:counterion of 1:1.1 or 1:0.55.

The vials were incubated at 50° C. for 1 hour and then slowly cooled to 5° C. followed by aging at 5° C. for 72 hours. If solids had precipitated, the solids were separated and dried under vacuum at 50° C. All liquid phases were evaporated at ambient conditions and obtained solids subsequently dried under vacuum until dry. All obtained solids were analyzed by XRPD. Subsequently the solids were exposed to accelerated aging conditions (40° C./75% RH, AAC) for 2 days to evaluate their physical stability. The nomenclature uses the abbreviation of the counterions followed by '0' in case the pure counterion is observed, or a number in case a novel XRPD pattern is obtained. For example, the recovery of neat glutamic acid is named Glm0, unique XRPD patterns obtained from experiments with 1,2-ethanedisulfonic acid are named Edy1 and Edy2. XRPD patterns with very small differences are grouped under one number and differentiated by a letter, for instance Nds1a and Nds1b. In case the free base was recovered, the solids were classified as Form B or C (because they were different than the starting material Form A).

The results of the salt screen are summarized in Table 19. Hints of salt formation were observed with almost all 25 counterions used (counterions are listed in alphabetical order). Only from the experiments performed with glutamic acid, mixtures of free base and counterion were recovered. With citric and gluconic acid, only amorphous or poor crystalline solids were recovered.

With hydrobromic, benzenesulfonic, oxalic and 1-hydroxy-2-naphthoic acid only one crystalline salt form was obtained. With all the other counterions, more than one solid form was identified, even though only 3 crystallization solvents were tested. Most solids were physically stable during the exposure to stress conditions.

TABLE 19

Summary of the results of the salt screen on voruciclib. The potential salt forms are listed per counterion and free base:counterion ratio from which the specific form was obtained.

| Acid counterion | Eq. CI | Form | Crystallinity | Stable during AAC |
|---|---|---|---|---|
| 1,2-Ethanedisulfonic | 0.5 | Edy1 | Medium | No => Edy1 + Edy2_lc |
|  |  | Edy2_lc | Poor | Yes |
|  | 1, 0.5 | Edy1 + Edy2 | Mixture | No => Edy2_lc |
| 1,5-Naphthalene-disulfonic | 1, 0.5 | Nds1a | Good | Yes |
|  | 1 | Nds1b | Good | No => Nds2 |
|  | 1, 0.5 | Nds2 | Good | Sometimes => Nds5 |
|  | 1 | Nds3 (brown) | Poor | Yes |
|  | 0.5 | Nds4 | Medium | Yes |
| 1-Hydroxy-2-naphthoic | 1 | Xin1 | Medium | Yes |
| Benzenesulfonic | 1 | Bes1 | Medium | No => Am or dissociation |
| Benzoic | 1 | Ben1 | Good | No => Ben3 |
|  |  | Ben2 | Medium | Yes |
| Citric | 1 | Am | — | — |
| Dibenzoyl-L-tartaric | 1 | DiTr1 | Good | Yes |
|  |  | DiTr1 + DiTr2 | Mixture | Yes |
| Ethanesulfonic | 1 | D | Good | Yes |
| Fumaric | 1 | Fum1 | Medium | Yes |
|  | 0.5 | Fum2a | Poor | No |
|  | 0.5 | Fum2b | Poor | Yes |
|  | 1 | Fum2c | Poor | Yes |
| Gentisic | 1 | Gen1 | Good | Yes |
|  |  | Gen2 | Poor | Yes |
| Gluconic | 1 | Am | — | — |
| D-Glucuronic | 1 | Glr1 | Medium | No => Am |
| L(+)-Glutamic | 1, 0.5 | B, C, Glm0 | — | — |

TABLE 19-continued

Summary of the results of the salt screen on voruciclib. The potential salt forms are listed per counterion and free base:counterion ratio from which the specific form was obtained.

| Acid counterion | Eq. CI | Form | Crystal-linity | Stable during AAC |
|---|---|---|---|---|
| Glutaric | 1 | Glt1 | Medium | No => dark brown |
|  |  | Glt2 | Poor | No => dark brown |
|  |  | Glt3 | Poor | Yes |
| Hydrobromic | 1 | HBr1 | Good | No => HBr2 |
| Maleic | 1 | Mae1 | Good | Yes |
|  |  | Mae1 + Mae2 | Mixture | No => Mae1 |
| L-(−)-Malic | 1 | Mal1 | Poor | Yes |
| Malonic | 1 | Mao1 | Good | Yes |
|  |  | Mao2 | Poor | No => Mao1 + Mao2 |
| Naphthalene-2-sulfonic | 1 | Nsu1 | Poor | No => Am |
|  |  | Nsu2 | Medium | No => Am |
|  |  | Nus3 | Poor | Yes |
| Oxalic | 1, 0.5 | Oxa1 | Good | Yes |
| ortho-Phosphoric | 1 | Pho1 | Good | Yes |
|  |  | Pho2 | Poor | Yes |
| Succinic | 1 | Suc1 | Medium | No => Suc1 + Suc2 |
|  |  | Suc2 | Medium | Yes |
|  |  | Suc1 + Suc3 | Mixture | Yes |
| Sulfuric | 1, 0.5 | Sul1 | Good | Yes |
|  | 0.5 | Sul2 | Medium | Yes |
|  | 0.5 | Sul3 | Medium | Yes |
|  | 1 | Sul4 | Poor | Yes |
| L(+)-Tartaric | 0.5 | Tar1 + Tar2 | Mixture | Yes |
|  | 0.5 | Tar1 + Tar3 | Mixture | Yes |
|  | 1 | Tar2 | Poor | Yes |
|  | 1 | Tar3 | Medium | Yes |
| p-Toluenesulfonic | 1.1 | Tos1 | Medium | No => Tos1 + Tos3 |
|  |  | Tos2 | Good | Yes |
| None | — | B | Good | Yes |
|  |  | C | Medium | Yes |

Malonic Acid

The malonate salt Mao1 was obtained by evaporation from ethanol and was physically stable upon exposure to AAC. From THF and acetone, a poor crystalline solid (Mao2) was obtained, that partly converted to Mao1 during AAC, suggesting, without wishing to be bound by any particular theory, that Mao1 is a more stable salt form than Mao2. Mao1 was further analyzed by DSC, TGMS, HPLC and $^1$H-NMR and the results are described herein. HPLC and $^1$H-NMR confirmed the compound's integrity and from the NMR spectrum salt formation was confirmed with a stoichiometric ratio of free base:malonic acid of 1:1. The thermal analysis revealed that the salt contained about 0.2% of residual solvent. Decomposition started around 140° C., while an endothermic melting/decomposition event was observed in the DSC trace at 180° C. Moreover, the solubility of the salt was determined in water and in 0.2 M phosphate buffer pH 6 at 37° C. upon incubation for 4 hours. In water, Mao1 forms a very fine suspension and the determined solubility was 4.4 mg/mL and the solids recovered were still identical to Mao1. In the phosphate buffer solution dissociation of the salt occurred and the solubility was 0.07 mg/mL. Although the salt seemed to oil out at first, a yellow suspension was obtained after about 20 min and there was no gelling or increase in viscosity observed.

Dibenzoyl-L-Tartaric Acid

The salt formation with benzoyl tartaric acid in ethanol led to precipitation of DiTr1, while in THF and acetone a mixture of DiTr1 and DiTr2 had formed. The solids were physically stable under AAC. Without wishing to be bound by any particular theory, it is believed that DiTr2 was only observed in mixture with DiTr1. DiTr1 was further characterized and the analytical results are reported herein. The solid contained 0.9% of residual solvent and decomposed above 180° C. HPLC and NMR spectroscopy confirmed the compound's integrity, salt formation and a stoichiometry of free base:DiTr of 2:1; therefore, DiTr1 is a hemi-dibenzoyl tartrate salt. The solubility of the salt was determined in water and phosphate buffer pH 6. In both media the solubility was about 0.03-0.04 mg/mL. The salt had a poor wettability, it was poorly mixing with the water phase, and after 4 hours incubation DiTr1 was recovered. In both media the color of the solids did not change, and the suspensions remained pale yellow.

Ortho-Phosphoric Acid

With phosphoric acid a crystalline salt form was obtained from acetone. The experiment performed in THF resulted in the formation of a poor crystalline solid (Pho2) and from ethanol a free base form (Form D) was collected. All solid phases were physically stable under AAC for 2 days. The crystalline salt Pho1 was further analyzed and the characterization is described herein. From the TGMS analysis a mass loss of 1.9% was observed between 25-160° C., most likely due to residual solvent or moisture and the thermal decomposition started around 200° C. From the DSC trace, a melting event was observed at 202° C., immediately followed by decomposition. The compound's integrity was confirmed by HPLC and NMR analysis. The $^1$H-NMR spectrum confirmed salt formation and from the HPLC data the stoichiometric ratio was calculated as 1:1. The solubility of the phosphate salt was determined in water and 0.2 M phosphate buffer pH 6 at 37° C. after 4 hours. About 5 mg of solid was used to prepare the suspension and after the addition of the first aliquot of 200 μL of water, an oil was formed. More water was added up to a volume of 800 μL and only after mixing the oil with a spatula, a clear solution was obtained (pH 3.7). Hence the exact solubility was not determined, and the actual solubility is higher than 5 mg/mL. Although an oil had formed, due to the high solubility, no gelling was observed. In the phosphate buffer the solubility was about 0.03 mg/mL and the XRPD of the solids recovered afterwards indicated that salt had dissociated in the buffer solution.

Oxalic Acid

With oxalic acid only one crystalline form was found, Oxa1. This form was obtained from experiments using 0.5 or 1 molar equivalents. Oxa1 was physically stable under short term stress conditions. The solid obtained from the experiment with half molar equivalent oxalic acid in THF was used for the characterization and is described herein. The HPLC analysis confirmed the compound's integrity and the free base:oxalic acid stoichiometry of 1:0.5 was determined, suggesting, without wishing to be bound by any particular theory, that Oxa1 is a hemi-oxalate salt. From the thermal analysis and $^1$H-NMR spectrum it was observed that the solid contained water. The TGMS analysis showed a mass loss of 3.2% in 2 steps. Therefore, without wishing to be bound by any particular theory, it is believed that the hemi-oxalate salt is either a mono-hydrate or hemi-hydrate (containing residual solvent/moisture). The solubility of Oxa1 was determined in 0.2 M phosphate buffer pH 6 at 37° C. after 4 hours and was 0.03 mg/mL. The salt had dissociated in the buffer. The attempt to determine the solubility in water failed, as after filtration of the sample, still very fine particles could be observed. The residual solids of the suspension were identical to Oxa1. In both media the suspensions were bright yellow.

1,5-Naphthalendisulfonic Acid

With 1,5-naphthalenedisulfonic acid several forms were observed, suggesting that the salt exhibits polymorphic/pseudo polymorphic behavior. However, Nds1a was mostly obtained by precipitation, while by evaporation Nds2 was obtained. Nds1a was stable during exposure to AAC for 2 days. Nds1b had the same pattern as Nds1a, but the peak positions were slightly shifted, and hence was designated Nds1b. Nds1b converted to Nds2 during exposure to accelerated aging conditions. Nds1a obtained from the salt formation experiment with 1 molar equivalent of 1,5-naphthalenedisulfonic acid in ethanol was selected for further characterization. The thermal analysis revealed that the solid contained 1.1% of residual solvent/moisture and the melting and decomposition of the salt started around 250° C. From the $^1$H-NMR spectrum the stoichiometric ratio determined for free base:Nds was 1:0.5. Therefore, without wishing to be bound by any particular theory, it seems that Nds1a is a non-solvated and anhydrous hemi-napadisylate salt. The solubility of Nds1a in water and 0.2 M phosphate buffer at 37° C. after 4 hours was 0.02 mg/mL in both media. The suspension in water was white (pH 3.4), while the suspension at pH 6 was yellow. The salt was stable in both media as the residual solids were identical to Nds1a.

Solvated Salts

Other crystalline salts (physically stable and/or with limited polymorphic behavior) were characterized by thermal analysis. Those salts were identified with the following acids (in alphabetical order): 1-Hydroxy-2-naphthoate salt, Xin1; Benzoate salt, Ben2; Besylate salt, Bes1; Esylate salt, Esy1/Form D; Gentisate salt, Gen1; Hydrobromide salt, HBr1; Maleate salt, Mae1; Sulfate salt, Sul1; Toluenesulfonate salt, Tos2. All these salt forms contained significant amounts of solvent and the melting or thermal decomposition was immediately observed after solvent loss (Table 20). Without wishing to be bound by any particular theory, it is believed that this behavior may indicate that in some embodiments these solids are only stable as solvate and do not convert to crystalline non-solvated salt forms upon desolvation.

TABLE 20

Characterization of solvated salts of voruciclib

| Salt | Mass loss (temperature range) | Solvent | Decomposition (° C.) |
| --- | --- | --- | --- |
| Xin1 | 12.0% (25-200° C.) | THF and/or water | 160 |
| Ben2 | 4.1% (25-100° C.) | Ethanol and/or water | 170 |
| Bes1 | 8.1% (25-180° C.) | THF | 230 |
| Esy1/Form D | 4.6% (25-160° C.) | Water | 240 |
| Gen1 | 9.2% (25-200° C.) | THF | 180 |
| HBr1 | 5.9% (25-180° C.) | Ethanol | 240 |
| Mae1 | 3.4% (25-110° C.) | THF and/or water | 110 |
| Sul1 | 2.4% (25-120° C.), 5.8% (120-200° C.) | Ethanol | 240 |
| Tos2 | 4.6% (25-110° C.) | Ethanol | 110 |

Polymorphic Forms of Free Base

The control samples (without counterion) resulted in the recovery of different forms than the starting material. From ethanol and acetone the same form was obtained, designated Form B and the solid obtained from THF was designated Form C. Form B appeared to be a non-solvated form with a melting around 220° C. The small endothermic events in the heat flow that were observed with Form A (at 100° C. and at 214° C.) were not present, suggesting that Form B is the more stable form than Form A. Form C appeared to be a solvated form with a melting at 220° C., coinciding with the melting of Form B.

Solubility Assessment

The solubility assessment was performed according to the aliquot addition method and visually assessed. About 5 mg of free base was weighed into 8 mL glass vials. Aliquots of 100 µL were added up to 2 mL, followed by aliquots of 1 mL up to 8 mL. The experimental conditions are described in Table 21. Additionally, the suspension in water was heated at 60° C. for 30 minutes but did not dissolve.

TABLE 21

Approximate solubility assessment of voruciclib in 10 solvents.

| Exp. ID | Solvent | Mass (mg) | Volume (mL) | Solubility at RT (mg/mL) |
| --- | --- | --- | --- | --- |
| SAS1 | Methanol | 5.1 | 0.3 | 17 < S < 26 |
| SAS2 | Chloroform | 5.0 | 1.0 | ~5 |
| SAS3 | Ethanol | 5.5 | 0.4 | 14 < S < 18 |
| SAS4 | Acetonitrile | 6.1 | 1.2 | ~5 |
| SAS5 | Tetrahydrofuran | 5.9 | 0.2 | 30 < S < 60 |
| SAS6 | Acetone | 5.0 | 0.5 | 10 < S < 13 |
| SAS7 | 1,4-Dioxane | 5.1 | 6.0 | ~1 |
| SAS8 | 2-Propanol | 5.5 | 0.7 | ~8 |
| SAS9 | Ethyl acetate | 5.3 | 6.0 | ~1 |
| SAS10 | Water | 5.3 | 8.0 | <1 |

Thermal Stability

Solutions of voruciclib (0.2 mg/mL) were prepared in tetrahydrofuran, ethanol and acetone. The solutions were divided over 3 vials. The vials were placed at RT for 24 hours and at 50° C. and 80° C. for one hour. Afterwards the solutions were measured by HPLC analysis. The experimental conditions and results are shown in Table 22.

TABLE 22

Experimental details and results of the thermal stability tests.

| Solvent | Mass API (mg) | Volume (mL) | Area (mAu*s) | | |
| --- | --- | --- | --- | --- | --- |
| | | | 25° C., 1 h | 50° C., 1 h | 80° C., 1 h |
| Tetrahydrofuran | 0.2 | 1.0 | 1697.99 | 1713.96 | 1701.15 |
| Ethanol | 0.3 | 1.5 | 1633.32 | 1625.98 | 1625.83 |
| Acetone | 0.3 | 1.5 | 1562.10 | 1566.22 | 1566.56 |

Salt Screen

The salt screen was performed using the saturated solution method. Saturated solutions of the free base were prepared at 50° C. in tetrahydrofuran, ethanol and acetone (Table 23). The stock solutions were divided over 33 glass vials (1.8 mL). L(+)-glutamic acid was added as solid while fumaric acid and 1-hydroxy-2-naphthoic acid were added from 0.3 M and 0.4 M ethanol solutions, respectively. All the other counterions were added as 1 M aqueous solution, resulting in a stoichiometric ratio of free base:counterion of 1:1.1 or 1:0.55. The experimental conditions and results are listed in Table 24.

The experiments were heated at 50° C. followed by cooled from 50° C. to 5° C. and aging at 5° C. for 72 hours. After the aging time, if solids had precipitated, the solids were separated and dried under vacuum at 50° C. The liquid phases were evaporated at ambient conditions for 2 days and under vacuum at 50° C. for 24 hours. All obtained solids were analyzed by HT-XRPD. Subsequently, the solids were exposed to accelerated aging conditions (40° C./75% RH, AAC) for 2 days and reanalyzed by HT-XRPD.

The XRPD nomenclature uses the abbreviation of the counterions followed by '0' in case the pure counterion is observed, or a number in case a novel XRPD pattern is obtained. For example, the recovery of neat glutamic acid is named Glm0, unique XRPD patterns obtained from experiments with 1,2-ethanedisulfonic acid are named Edy1, Edy2. XRPD patterns with very small differences are grouped under one number and differentiated by a letter, for instance Nds1a and Nds1b. In case the free base was recovered, the solids were classified as Form B, C, D or E (because they were different than the starting material Form A).

TABLE 23

Experimental details of the stock solutions of free base.

| Solvent | Mass API (mg) | Volume (mL) | Dissolved |
|---|---|---|---|
| Tetrahydrofuran | 1100.1 | 18.3 | Dissolved at 50° C. |
| Ethanol | 1100.8 | 36.6 | Dissolved at 50° C. |
| Acetone | 1100.6 | 36.6 | Dissolved at 50° C. |

TABLE 24

Experimental conditions and XRPD results of the salt screen on voruciclib. Salt screen experiments were performed with a 1:1.1 or 1:0.55 ratio of free base:CI. The counterions were added as 1M aqueous solution except glutamic acid was added as solid and fumaric acid and 1-hydroxy-2-naphthoic acid were added respectively as 0.3M and 0.4M ethanol solutions. The solid phase represents the solids that had precipitated. The liquid phase represents solids obtained after evaporation of the solvents from the mother liquors and samples in which no precipitation had occurred. "lc" refers to poor crystalline solids, "ly" refers to low yield and "Am" means "amorphous". A, B and C are (pseudo)polymorphic forms of voruciclib free base.

| Exp. ID | Mass API (mg) | Solvent | Volume (mL) | Counterion | Mass CI (mg) | Solids after T profile |
|---|---|---|---|---|---|---|
| SSm1 | 30 | Tetrahydrofuran | 500 | Hydrobromic acid | 12.1 | No |
| SSm2 | 30 | Tetrahydrofuran | 500 | 1,5-Naphthalenedisulfonic acid | 25.3 | No |
| SSm3 | 30 | Tetrahydrofuran | 500 | 1,5-Naphthalenedisulfonic acid | 12.6 | Yes |
| SSm4 | 30 | Tetrahydrofuran | 500 | Sulfuric acid | 7.3 | No |
| SSm5 | 30 | Tetrahydrofuran | 500 | Sulfuric acid | 3.6 | Yes |
| SSm6 | 30 | Tetrahydrofuran | 500 | 1,2-Ethanedisulfonic acid | 16.0 | No |
| SSm7 | 30 | Tetrahydrofuran | 500 | 1,2-Ethanedisulfonic acid | 8.0 | No |
| SSm8 | 30 | Tetrahydrofuran | 500 | p-Toluenesulfonic acid | 13.4 | No |
| SSm9 | 30 | Tetrahydrofuran | 500 | Naphthalene-2-sulfonic acid | 14.7 | No |
| SSm10 | 30 | Tetrahydrofuran | 500 | Benzenesulfonic acid | 11.1 | No |
| SSm11 | 30 | Tetrahydrofuran | 500 | Oxalic acid | 6.4 | No |
| SSm12 | 30 | Tetrahydrofuran | 500 | Oxalic acid | 3.2 | Yes |
| SSm13 | 30 | Tetrahydrofuran | 500 | Dibenzoyl-L-tartaric acid | 25.3 | Yes |
| SSm14 | 30 | Tetrahydrofuran | 500 | Maleic acid | 8.2 | No |
| SSm15 | 30 | Tetrahydrofuran | 500 | ortho-Phosphoric acid | 8.0 | No |
| SSm16 | 30 | Tetrahydrofuran | 500 | Ethanesulfonic acid | 8.1 | Yes |
| SSm17 | 30 | Tetrahydrofuran | 500 | L(+)-Glutamic acid | 10.4 | Yes |
| SSm18 | 30 | Tetrahydrofuran | 500 | L(+)-Glutamic acid | 5.2 | Yes |
| SSm19 | 30 | Tetrahydrofuran | 500 | 1-Hydroxy-2-naphthoic acid | 13.4 | No |
| SSm20 | 30 | Tetrahydrofuran | 500 | Malonic acid | 7.3 | No |
| SSm21 | 30 | Tetrahydrofuran | 500 | Gentisic acid | 10.9 | No |
| SSm22 | 30 | Tetrahydrofuran | 500 | L(+)-Tartaric acid | 10.6 | Yes |
| SSm23 | 30 | Tetrahydrofuran | 500 | L(+)-Tartaric acid | 5.3 | Yes |
| SSm24 | 30 | Tetrahydrofuran | 500 | Fumaric acid | 8.1 | Yes |
| SSm25 | 30 | Tetrahydrofuran | 500 | Fumaric acid | 4.1 | Yes |
| SSm26 | 30 | Tetrahydrofuran | 500 | D-Glucuronic acid | 13.6 | No |
| SSm27 | 30 | Tetrahydrofuran | 500 | Citric acid | 14.8 | No |
| SSm28 | 30 | Tetrahydrofuran | 500 | L-(−)-Malic acid | 9.5 | No |
| SSm29 | 30 | Tetrahydrofuran | 500 | Gluconic acid | 28.2 | Yes |
| SSm30 | 30 | Tetrahydrofuran | 500 | Benzoic acid | 8.5 | No |
| SSm31 | 30 | Tetrahydrofuran | 500 | Succinic acid | 8.4 | Yes |
| SSm32 | 30 | Tetrahydrofuran | 500 | Glutaric acid | 9.0 | No |
| SSm33 | 30 | Tetrahydrofuran | 500 | None | — | Yes |
| SSm34 | 30 | Ethanol | 1000 | Hydrobromic acid | 12.1 | No |
| SSm35 | 30 | Ethanol | 1000 | 1,5-Naphthalenedisulfonic acid | 25.3 | Yes |

TABLE 24-continued

Experimental conditions and XRPD results of the salt screen on voruciclib. Salt screen experiments were performed with a 1:1.1 or 1:0.55 ratio of free base:CI. The counterions were added as 1M aqueous solution except glutamic acid was added as solid and fumaric acid and 1-hydroxy-2-naphthoic acid were added respectively as 0.3M and 0.4M ethanol solutions. The solid phase represents the solids that had precipitated. The liquid phase represents solids obtained after evaporation of the solvents from the mother liquors and samples in which no precipitation had occurred. "lc" refers to poor crystalline solids, "ly" refers to low yield and "Am" means "amorphous". A, B and C are (pseudo)polymorphic forms of voruciclib free base.

| | | | | | | |
|---|---|---|---|---|---|---|
| SSm36 | 30 | Ethanol | 1000 | 1,5-Naphthalenedisulfonic acid | 12.6 | Yes |
| SSm37 | 30 | Ethanol | 1000 | Sulfuric acid | 7.3 | Yes |
| SSm38 | 30 | Ethanol | 1000 | Sulfuric acid | 3.6 | Yes |
| SSm39 | 30 | Ethanol | 1000 | 1,2-Ethanedisulfonic acid | 16.0 | No |
| SSm40 | 30 | Ethanol | 1000 | 1,2-Ethanedisulfonic acid | 8.0 | Yes |
| SSm41 | 30 | Ethanol | 1000 | p-Toluenesulfonic acid | 13.4 | No |
| SSm42 | 30 | Ethanol | 1000 | Naphthalene-2-sulfonic acid | 14.7 | No |
| SSm43 | 30 | Ethanol | 1000 | Benzenesulfonic acid | 11.1 | No |
| SSm44 | 30 | Ethanol | 1000 | Oxalic acid | 6.4 | Yes |
| SSm45 | 30 | Ethanol | 1000 | Oxalic acid | 3.2 | Yes |
| SSm46 | 30 | Ethanol | 1000 | Dibenzoyl-L-tartaric acid | 25.3 | Yes |
| SSm47 | 30 | Ethanol | 1000 | Maleic acid | 8.2 | No |
| SSm48 | 30 | Ethanol | 1000 | ortho-Phosphoric acid | 8.0 | Yes |
| SSm49 | 30 | Ethanol | 1000 | Ethanesulfonic acid | 8.1 | Yes |
| SSm50 | 30 | Ethanol | 1000 | L(+)-Glutamic acid | 10.4 | Yes |
| SSm51 | 30 | Ethanol | 1000 | L(+)-Glutamic acid | 5.2 | Yes |
| SSm52 | 30 | Ethanol | 1000 | 1-Hydroxy-2-naphthoic acid | 13.4 | Yes |
| SSm53 | 30 | Ethanol | 1000 | Malonic acid | 7.3 | No |
| SSm54 | 30 | Ethanol | 1000 | Gentisic acid | 10.9 | Yes |
| SSm55 | 30 | Ethanol | 1000 | L(+)-Tartaric acid | 10.6 | Yes |
| SSm56 | 30 | Ethanol | 1000 | L(+)-Tartaric acid | 5.3 | Yes |
| SSm57 | 30 | Ethanol | 1000 | Fumaric acid | 8.1 | Yes |
| SSm58 | 30 | Ethanol | 1000 | Fumaric acid | 4.1 | Yes |
| SSm59 | 30 | Ethanol | 1000 | D-Glucuronic acid | 13.6 | Yes |
| SSm60 | 30 | Ethanol | 1000 | Citric acid | 14.8 | Yes |
| SSm61 | 30 | Ethanol | 1000 | L-(−)-Malic acid | 9.5 | Yes |
| SSm62 | 30 | Ethanol | 1000 | Gluconic acid | 28.2 | Yes |
| SSm63 | 30 | Ethanol | 1000 | Benzoic acid | 8.5 | No |
| SSm64 | 30 | Ethanol | 1000 | Succinic acid | 8.4 | No |
| SSm65 | 30 | Ethanol | 1000 | Glutaric acid | 9.0 | Yes |
| SSm66 | 30 | Ethanol | 1000 | None | — | Yes |
| SSm67 | 30 | Acetone | 1000 | Hydrobromic acid | 12.1 | No |
| SSm68 | 30 | Acetone | 1000 | 1,5-Naphthalenedisulfonic acid | 25.3 | Yes |
| SSm69 | 30 | Acetone | 1000 | 1,5-Naphthalenedisulfonic acid | 12.6 | Yes |
| SSm70 | 30 | Acetone | 1000 | Sulfuric acid | 7.3 | Yes |
| SSm71 | 30 | Acetone | 1000 | Sulfuric acid | 3.6 | Yes |
| SSm72 | 30 | Acetone | 1000 | 1,2-Ethanedisulfonic acid | 16.0 | Yes |
| SSm73 | 30 | Acetone | 1000 | 1,2-Ethanedisulfonic acid | 8.0 | Yes |
| SSm74 | 30 | Acetone | 1000 | p-Toluenesulfonic acid | 13.4 | Yes |
| SSm75 | 30 | Acetone | 1000 | Naphthalene-2-sulfonic acid | 14.7 | No |
| SSm76 | 30 | Acetone | 1000 | Benzenesulfonic acid | 11.1 | No |
| SSm77 | 30 | Acetone | 1000 | Oxalic acid | 6.4 | Yes |
| SSm78 | 30 | Acetone | 1000 | Oxalic acid | 3.2 | Yes |
| SSm79 | 30 | Acetone | 1000 | Dibenzoyl-L-tartaric acid | 25.3 | Yes |
| SSm80 | 30 | Acetone | 1000 | Maleic acid | 8.2 | No |
| SSm81 | 30 | Acetone | 1000 | ortho-Phosphoric acid | 8.0 | Yes |
| SSm82 | 30 | Acetone | 1000 | Ethanesulfonic acid | 8.1 | Yes |
| SSm83 | 30 | Acetone | 1000 | L(+)-Glutamic acid | 10.4 | Yes |
| SSm84 | 30 | Acetone | 1000 | L(+)-Glutamic acid | 5.2 | Yes |
| SSm85 | 30 | Acetone | 1000 | 1-Hydroxy-2-naphthoic acid | 13.4 | No |
| SSm86 | 30 | Acetone | 1000 | Malonic acid | 7.3 | No |
| SSm87 | 30 | Acetone | 1000 | Gentisic acid | 10.9 | Yes |
| SSm88 | 30 | Acetone | 1000 | L(+)-Tartaric acid | 10.6 | Yes |
| SSm89 | 30 | Acetone | 1000 | L(+)-Tartaric acid | 5.3 | Yes |
| SSm90 | 30 | Acetone | 1000 | Fumaric acid | 8.1 | Yes |

TABLE 24-continued

Experimental conditions and XRPD results of the salt screen on voruciclib. Salt screen experiments were performed with a 1:1.1 or 1:0.55 ratio of free base:CI. The counterions were added as 1M aqueous solution except glutamic acid was added as solid and fumaric acid and 1-hydroxy-2-naphthoic acid were added respectively as 0.3M and 0.4M ethanol solutions. The solid phase represents the solids that had precipitated. The liquid phase represents solids obtained after evaporation of the solvents from the mother liquors and samples in which no precipitation had occurred. "lc" refers to poor crystalline solids, "ly" refers to low yield and "Am" means "amorphous". A, B and C are (pseudo)polymorphic forms of voruciclib free base.

| | | | | | | |
|---|---|---|---|---|---|---|
| SSm91 | 30 | Acetone | 1000 | Fumaric acid | 4.1 | Yes |
| SSm92 | 30 | Acetone | 1000 | D-Glucuronic acid | 13.6 | Yes |
| SSm93 | 30 | Acetone | 1000 | Citric acid | 14.8 | No |
| SSm94 | 30 | Acetone | 1000 | L-(−)-Malic acid | 9.5 | Yes |
| SSm95 | 30 | Acetone | 1000 | Gluconic acid | 28.2 | No |
| SSm96 | 30 | Acetone | 1000 | Benzoic acid | 8.5 | No |
| SSm97 | 30 | Acetone | 1000 | Succinic acid | 8.4 | Yes |
| SSm98 | 30 | Acetone | 1000 | Glutaric acid | 9.0 | No |
| SSm99 | 30 | Acetone | 1000 | None | — | Yes |

| Exp. ID | Solid phase | | Liquid phase | |
|---|---|---|---|---|
| | | AAC | | AAC |
| SSm1 | — | — | Am | Am |
| SSm2 | — | — | Nds3_lc | Nds3_lc brown |
| SSm3 | Nds4_lc | Nds4_lc | Am | Am |
| SSm4 | — | — | Sul4_lc | Sul4_lc |
| SSm5 | Sul2 | Sul2 | Sul3 | Sul3 |
| SSm6 | — | — | E_lc | E_lc |
| SSm7 | — | — | Edy2_lc | Edy2_lc |
| SSm8 | — | — | Tos1 | Tos1 + Tos3 |
| SSm9 | — | — | Nsu1_lc | Nsu1_lc |
| SSm10 | — | — | Bes1 | Bes2 or dissociation |
| SSm11 | — | — | Am | Am |
| SSm12 | Oxa1 | Oxa1 | Am | Am |
| SSm13 | DiTr1 + DiTr2 | DiTr1 + DiTr2 | Oil | Oil |
| SSm14 | — | — | Mae1 | Mae1 |
| SSm15 | — | — | Pho2_lc | Pho2_lc |
| SSm16 | D | D | D | D |
| SSm17 | Glm0 | Glm0 | C | C |
| SSm18 | Glm0 | Glm0 | C | C |
| SSm19 | — | — | Xin1 | Xin1 |
| SSm20 | — | — | Mao2_lc | Mao1 + Mao2 |
| SSm21 | — | — | Gen1 | Gen1 |
| SSm22 | Am | Am | Tar3 | Tar3 |
| SSm23 | Tar1 + Tar3 | Tar1 + Tar3 | Tar1 + Tar2_lc | Tar1 + Tar2_lc |
| SSm24 | Am | Am | Fum0_lc | Fum1_lc_Fum0 |
| SSm25 | Am | Am | Fum2a_lc | Fum2a_lc |
| SSm26 | — | — | E_lc | E_lc |
| SSm27 | — | — | E_lc | E_lc |
| SSm28 | — | — | Mal1_lc | Mal1_lc |
| SSm29 | Oil | Am | — | — |
| SSm30 | — | — | Ben1 | Ben3 |
| SSm31 | Suc2_lc | Suc2_lc | Suc1 | Suc1 + Suc2 |
| SSm32 | — | — | Glt2_lc brown | Dark brown |
| SSm33 | C | C | — | — |
| SSm34 | — | — | HBr1 | HBr2 |
| SSm35 | Nds1a | Nds1a | Nds2 | Nds2 |
| SSm36 | Nds1a | Nds1a | Nds2 | Nds2 |
| SSm37 | Sul1 | Sul1 | Sul1 | Sul1 |
| SSm38 | Sul2 | Sul2 | Sul1 | Sul1 |
| SSm39 | — | — | E_lc | E_lc |
| SSm40 | Am | Am | Edy1 + Edy2 | Edy2_lc |
| SSm41 | — | — | Tos1 | Tos2 |
| SSm42 | — | — | Nsu2 | Nsu2_lc |
| SSm43 | — | — | Bes1 | Bes1_lc |
| SSm44 | Oxa1 | Oxa1 | D | D |
| SSm45 | Oxa1 | Oxa1 | Oxa1 ly | Oxa1 ly |
| SSm46 | DiTr1 | DiTr1 | Am | Am |
| SSm47 | — | — | Mae1 + Mae2 | Mae1 |

TABLE 24-continued

Experimental conditions and XRPD results of the salt screen on voruciclib. Salt screen experiments were performed with a 1:1.1 or 1:0.55 ratio of free base:CI. The counterions were added as 1M aqueous solution except glutamic acid was added as solid and fumaric acid and 1-hydroxy-2-naphthoic acid were added respectively as 0.3M and 0.4M ethanol solutions. The solid phase represents the solids that had precipitated. The liquid phase represents solids obtained after evaporation of the solvents from the mother liquors and samples in which no precipitation had occurred. "lc" refers to poor crystalline solids, "ly" refers to low yield and "Am" means "amorphous". A, B and C are (pseudo)polymorphic forms of voruciclib free base.

| | | | | |
|---|---|---|---|---|
| SSm48 | D | D | — | — |
| SSm49 | D | D | D | D |
| SSm50 | B + Glm0 | B + Glm0 | B + ep7.5 | B + ep7.5 |
| SSm51 | B + trace Glm0 | B | B + ep7.5 | B + ep7.5 |
| SSm52 | Xin1_lc | Xin1_lc | Xin1 | Xin1 |
| SSm53 | — | — | Mao1 | Mao1 |
| SSm54 | Gen2_lc | Gen2_lc | Gen2_lc | Gen2_lc |
| SSm55 | Tar2_lc | Tar2_lc | — | — |
| SSm56 | Tar1 + Tar2_lc | Tar1 + Tar2_lc | Am | Am |
| SSm57 | Fum2c_lc | Fum2c_lc | Fum0 | Fum0_lc |
| SSm58 | Fum2b_lc | Fum2b | Fum2a_lc | Fum2b_lc |
| SSm59 | Glr1 | Am | — | — |
| SSm60 | Am | E_lc | Am | Oil |
| SSm61 | Am peak at 24.5 | Am peak at 24.5 | Mal1_lc | Mal1_lc |
| SSm62 | Am | Am | Am | Am |
| SSm63 | — | — | Ben2 | Ben2 |
| SSm64 | — | — | Suc1 + Suc3 | Suc1 + Suc3 |
| SSm65 | Glt3_lc | Glt3_lc | Glt3_lc | Dark brown |
| SSm66 | B | B | B | B |
| SSm67 | — | — | HBr1_lc | HBr_lc |
| SSm68 | Nds1b | Nds2 | Nds2 | Nds5 |
| SSm69 | Nds1a | Nds1a | Nds2 | Nds2 |
| SSm70 | Sul1_lc | Sul1 + Sul4_lc | Sul1 + Sul4_lc | Sul1 + Sul4_lc |
| SSm71 | Sul2 | Sul2 | Am | Am |
| SSm72 | Edy1 + Edy2_lc | Edy2_lc | E_lc | E_lc |
| SSm73 | Edy1 | Edy1 + Edy2_lc | E_lc | E_lc |
| SSm74 | Tos1_lc | Tos1_lc | Am | Tos1_lc brown |
| SSm75 | — | — | Nsu3_lc | Nsu3_lc |
| SSm76 | — | — | Bes1_lc | Bes2 or dissociation |
| SSm77 | Oxa1 | Oxa1 | Oxa0 + Am | Oxa0 + Am |
| SSm78 | Oxa1 | Oxa1 | — | — |
| SSm79 | DiTr1 + DiTr2 | DiTr1 + DiTr2 | Am | Am |
| SSm80 | — | — | Mae1 | Mae1 |
| SSm81 | Pho1 | Pho1 | — | — |
| SSm82 | D | D | — | — |
| SSm83 | B | B + Glm0 | B | B |
| SSm84 | B | B + Glm0 | B | C |
| SSm85 | — | — | Xin1 | Xin1 |
| SSm86 | — | — | Mao2_lc | Mao1 + Mao2 |
| SSm87 | Gen2_lc | Gen2_lc | Gen1 | Gen1_lc |
| SSm88 | Tar2_lc | Tar2_lc | — | — |
| SSm89 | Tar1 + Tar2_lc | Tar1 + Tar2_lc | — | — |
| SSm90 | Fum1 | Fum1 | Am | Am |
| SSm91 | Am | Am | Am | Am |
| SSm92 | Am | E_lc | Am | Am |
| SSm93 | — | — | E_lc | E_lc |
| SSm94 | Am peak at 24.5 | Am peak at 24.5 | Mal1_lc | Mal1_lc |
| SSm95 | — | — | Am | Am |
| SSm96 | — | — | Ben2 | Ben2 |
| SSm97 | Suc2 | Suc2 | C + Suc1 | B + Suc1 |
| SSm98 | — | — | Glt1 brown | Dark brown |
| SSm99 | B | B | B | B |

Solubility of Salts

The solubility of five salt candidates was determined in 0.2 M phosphate buffer pH 6 and in water. Two sets of solubility experiments were performed. In one set of solubility experiments about 1 mg of the salt was weighed in 1.8 mL glass vials and 1 mL of medium was added at once. In the second set of solubility experiments about 5 mg of the salt was weighed in a standard 1.8 mL HPLC vial. Subsequently, aliquots of 200 µL of aqueous medium were added up to a maximum of 1 mL, while making observations regarding the dissolution behavior of the salts. The vials were left to equilibrate at 37° C. with continuous stirring (see Table 25 for details). After 4 hours the solids were separated from the liquid by centrifugation and the liquid phase was further filtrated through a 0.2 µM PTFE filter to remove any particulate matter. The concentration of solute was determined by HPLC-DAD analysis. A calibration curve was made from two independent stock solutions of voruciclib prepared in acetonitrile/water. The pH was recorded at the end of the equilibration time.

TABLE 25

Experimental conditions and results of the solubility determination of the salts in 0.2M phosphate buffer pH 6 and water. The solubility was determined at 37° C. after 4 hours, by HPLC analysis.

| Exp. ID | Salt | Medium | Mass (mg) | Volume (mL) | pH (4 h) | Solubility (mg/mL) | Form (4 h) | Observations |
|---|---|---|---|---|---|---|---|---|
| QSA1 | Nds1a | Water | 1.1 | 1.0 | 4.3 | 0.03 | — | White hazy suspension |
| QSA2 | DiTr1 | Water | 1.1 | 1.0 | 4.0 | 0.04 | — | White hazy suspension |
| QSA3 | Mao1 | Water | 1.1 | 1.0 | 4.1 | Dissolved (0.9) | — | Clear solution |
| QSA4 | Pho1 | Water | 1.1 | 1.0 | 4.6 | Dissolved (0.9) | — | Clear solution |
| QSA5 | Oxa1 | Water | 1.1 | 1.0 | 4.4 | hazy | Free base | Yellow suspension |
| QSA6 | Nds1a | Water | 5.1 | 1.0 | 3.4 | 0.02 | Nds1a | Light yellow suspension |
| QSA7 | DiTr1 | Water | 5.0 | 1.0 | 3.5 | 0.03 | DiTr1 | Poor wettability, light yellow |
| QSA8 | Mao1 | Water | 5.1 | 1.0 | 3.5 | 4.44 | Mao1 | Light yellow suspension |
| QSA9 | Pho1 | Water | 5.1 | 0.8 | 3.7 | Dissolved (5.2) | — | Initially oil, then clear solution |
| QSA10 | Oxa1 | Water | 4.9 | 1.0 | 4.3 | hazy | Oxa1 | Yellow suspension |
| QSA11 | Nds1a | Buffer pH 6 | 1.1 | 1.0 | 6.0 | 0.02 | Free base | Bright yellow suspension |
| QSA12 | DiTr1 | Buffer pH 6 | 1.0 | 1.0 | 6.0 | 0.03 | DiTr1 | Light yellow suspension |
| QSA13 | Mao1 | Buffer pH 6 | 1.0 | 1.0 | 6.2 | 0.02 | Free base | Seems oily at first, bright yellow suspension at end |
| QSA14 | Pho1 | Buffer pH 6 | 1.1 | 1.0 | 6.0 | hazy | Free base | Bright yellow suspension |
| QSA15 | Oxa1 | Buffer pH 6 | 1.0 | 1.0 | 6.0 | 0.02 | Am | Bright yellow suspension |
| QSA16 | Nds1a | Buffer pH 6 | 5.1 | 1.0 | 5.9 | 0.02 | Nds1a | Yellow suspension |
| QSA17 | DiTr1 | Buffer pH 6 | 5.0 | 1.0 | 6.3 | 0.04 | DiTr1 | Light yellow suspension |
| QSA18 | Mao1 | Buffer pH 6 | 5.0 | 1.0 | 5.8 | 0.07 | Free base | Suspension containing big particles |
| QSA19 | Pho1 | Buffer pH 6 | 5.0 | 1.0 | 5.8 | 0.03 | Free base | Bright yellow suspension |
| QSA20 | Oxa1 | Buffer pH 6 | 4.8 | 1.0 | 5.8 | 0.03 | Free base | Bright yellow suspension |

X-Ray Powder Diffraction

XRPD patterns were obtained using the Crystallics T2 high-throughput XRPD set-up. The plates were mounted on a Bruker D8 Discover General Area Detector Diffraction System (GADDS) equipped with a VÅNTEC-500 gas area detector corrected for intensity and geometric variations (product sheet XRD 37, DOC-S88-EXS037V3, FIG. 297). The calibration of the measurement accuracy (peaks position) was performed using NIST SRM1976 standard (Corundum). Data collection was carried out at room temperature using monochromatic CuK$_\alpha$ radiation in the 2θ region between 1.5° and 41.5°, which is the most distinctive part of the XRPD pattern. The diffraction pattern of each well was collected in two 2θ ranges (1.5°≤2θ≤21.5° for the first frame, and 19.5°≤2θ≤41.5° for the second) with an exposure time of 45 s for each frame. No background subtraction or curve smoothing was applied to the XRPD patterns.

TGA/SDTA and TGMS Analysis

Mass loss due to solvent or water loss from the crystals was determined by TGA/SDTA. Monitoring the sample weight, during heating in a TGA/DSC 3+ STARe system (Mettler-Toledo GmbH, Switzerland), resulted in a weight vs. temperature curve. The TGA/DSC 3+ was calibrated for temperature with indium and aluminum. Samples (circa 2 mg) were weighed into 100 μL aluminum crucibles and sealed. The seals were pin-holed, and the crucibles heated in the TGA from 25 to 300° C. at a heating rate of 10° C./min. Dry $N_2$ gas was used for purging.

The gasses evolved from the TGA samples were analyzed by an Omnistar GSD 301 T2 mass spectrometer (Pfeiffer Vacuum GmbH, Germany). This MS is a quadrupole mass spectrometer, which analyses masses in the range of 0-200 amu.

DSC Analysis

Melting properties were obtained from DSC thermograms, recorded with a heat flux DSC3+ STARe system (Mettler-Toledo GmbH, Switzerland). The DSC3+ was calibrated for temperature and enthalpy with a small piece of indium (m.p.=156.6° C.; δH$_f$=28.45 J/g) and zinc (m.p.=419.6° C.; δH$_f$=107.5 J/g). Samples (circa 2 mg) were sealed in standard 40 µL aluminum pans, pin-holed and heated in the DSC from 25° C. to 300° C., at a heating rate of 10° C./min. Dry $N_2$ gas, at a flow rate of 50 mL/min was used to purge the DSC equipment during measurement.

Proton-NMR $^1$H-NMR spectroscopy in DMSO-d$^6$ was used for compound integrity characterization and to determine the stoichiometry of the salt. The spectra were recorded at room temperature (32 scans) on a 500 MHz instrument (Bruker BioSpin GmbH) using standard pulse sequences. The data was processed with ACD Labs software Spectrus Processor 2016.2.2 (Advanced Chemistry Development Inc. Canada).

LCMS Analytical Methods

Method name: S18099_01; HPLC System: Agilent 1200; Detector 1: DAD set at 264 nm; Detector 2: HP1100 LC/MSD in Positive Scan mode. HPLC Conditions: Autosampler temp: 15° C.; Column: Waters Sunfire C18 (100×4.6 mm; 3.5 µm); Column temp: 35° C.; Flow cell: 10 mm path; Gradient: Table 26; Mobile phase A: 0.1% TFA in water; Mobile phase B: 0.1% TFA in acetonitrile; Flow: 1.0 ml/min.

TABLE 26

HPLC mobile phase gradient

| Time [min] | Mobile phase A | Mobile phase B |
|---|---|---|
| 0 | 90% | 10% |
| 9 | 10% | 90% |
| 10 | 5% | 95% |
| 11 | 5% | 95% |

Sample: Concentration: ca. 0.5 mg/ml; Solvent: Water: Acetonitrile:TFA (50:50:0.1 v/v/v); Injection volume: 5 µL.

The compound integrity is expressed as a peak-area percentage, calculated from the area of each peak in the chromatogram, except the 'injection peak', and the total peak-area, as follows:

$$\text{peak} - \text{area }\% = \frac{\text{peak} - \text{area}}{\text{total} - \text{area}} * 100\%$$

The peak-area percentage of the compound of interest is employed as an indication of the purity of the component in the sample. Calculation of the stoichiometry of free base: CI in the salts was based on the area (free base recovery) versus sample weight. The weight of the sample was corrected for the mass loss observed by TGMS analysis.

Malonate Salt, Mao1

Figure 90:
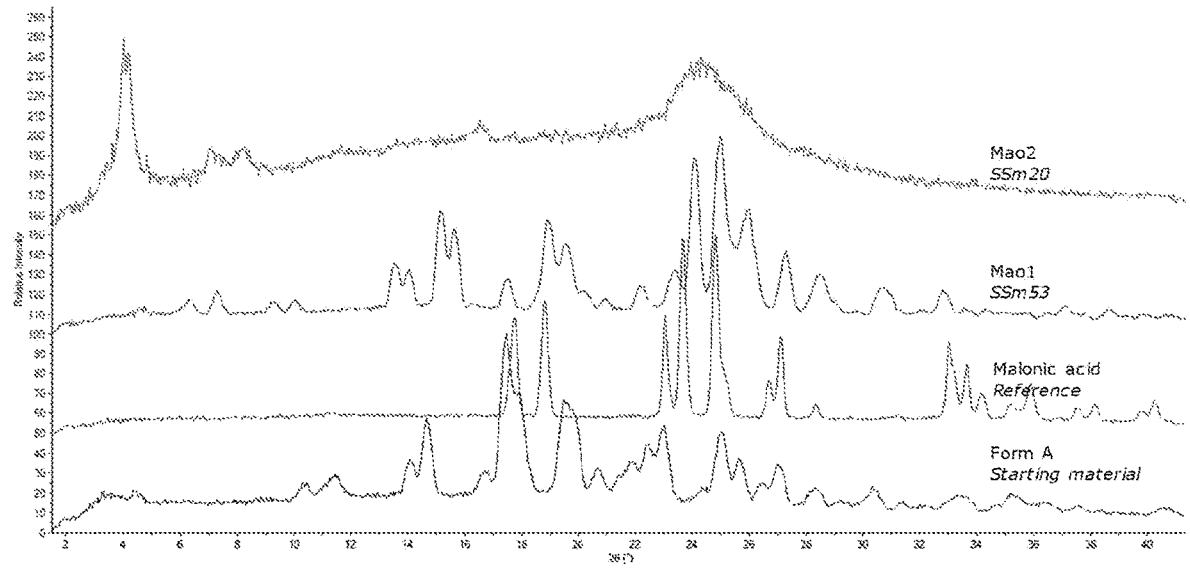
FIG. 90 illustrates the XRPD patterns of (from bottom to top): Form A starting material, malonic acid reference, Mao1 obtained from ethanol (Exp. ID SSm53) and Mao2 obtained from THF (Exp. ID SSm20).
Figure 91:
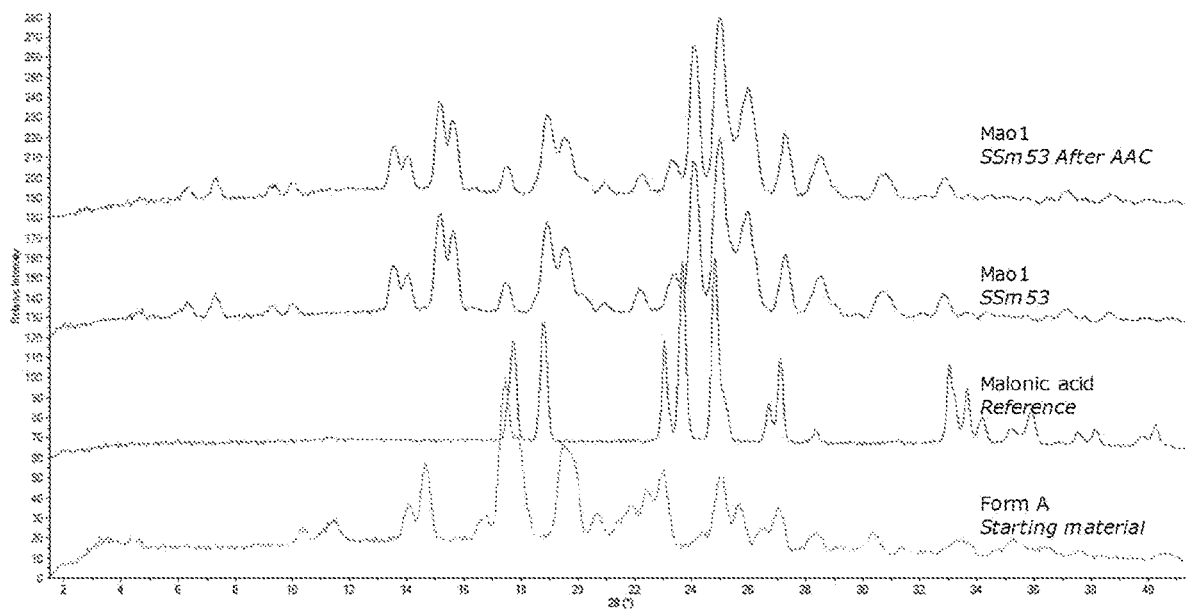
FIG. 91 illustrates the XRPD patterns of Mao1 (Exp. ID SSm53) before and after AAC; the starting material and malonic acid are shown as references.

With malonic acid 2 different XRPD patterns were obtained. From the experiment in ethanol the crystalline salt Mao1 was obtained. From acetone and THF poor crystalline solids were recovered, Mao2. The XRPD patterns of the two forms are shown in FIG. 90. Based on crystallinity and physical stability, Mao1 was selected for further characterization. In FIG. 91 the powder patterns of Mao1 before and after exposure to AAC for two days are presented. The peak list of Mao1 is shown in Table 27. The stable crystalline malonate salt Mao1 (Exp. ID SSm53) was further characterized by DSC, TGMS, HPLC and 1H-NMR analysis.

TABLE 27

Peak list of XRPD of Mao1.

| Peak ID | Angle (2θ) | d-Spacing | Intensity |
|---|---|---|---|
| 1 | 7.30 | 12.10 | 10.97 |
| 2 | 13.58 | 6.51 | 23.49 |
| 3 | 14.06 | 6.29 | 18.99 |
| 4 | 15.18 | 5.83 | 49.23 |
| 5 | 15.66 | 5.65 | 39.60 |
| 6 | 17.50 | 5.06 | 15.62 |
| 7 | 18.94 | 4.68 | 44.63 |
| 8 | 19.54 | 4.54 | 33.07 |
| 9 | 22.22 | 4.00 | 11.64 |
| 10 | 23.38 | 3.80 | 18.97 |
| 11 | 24.10 | 3.69 | 75.50 |
| 12 | 24.98 | 3.56 | 85.99 |
| 13 | 25.94 | 3.43 | 49.70 |
| 14 | 27.26 | 3.27 | 28.18 |
| 15 | 28.50 | 3.13 | 19.10 |
| 16 | 32.82 | 2.73 | 14.09 |

Figure 92:
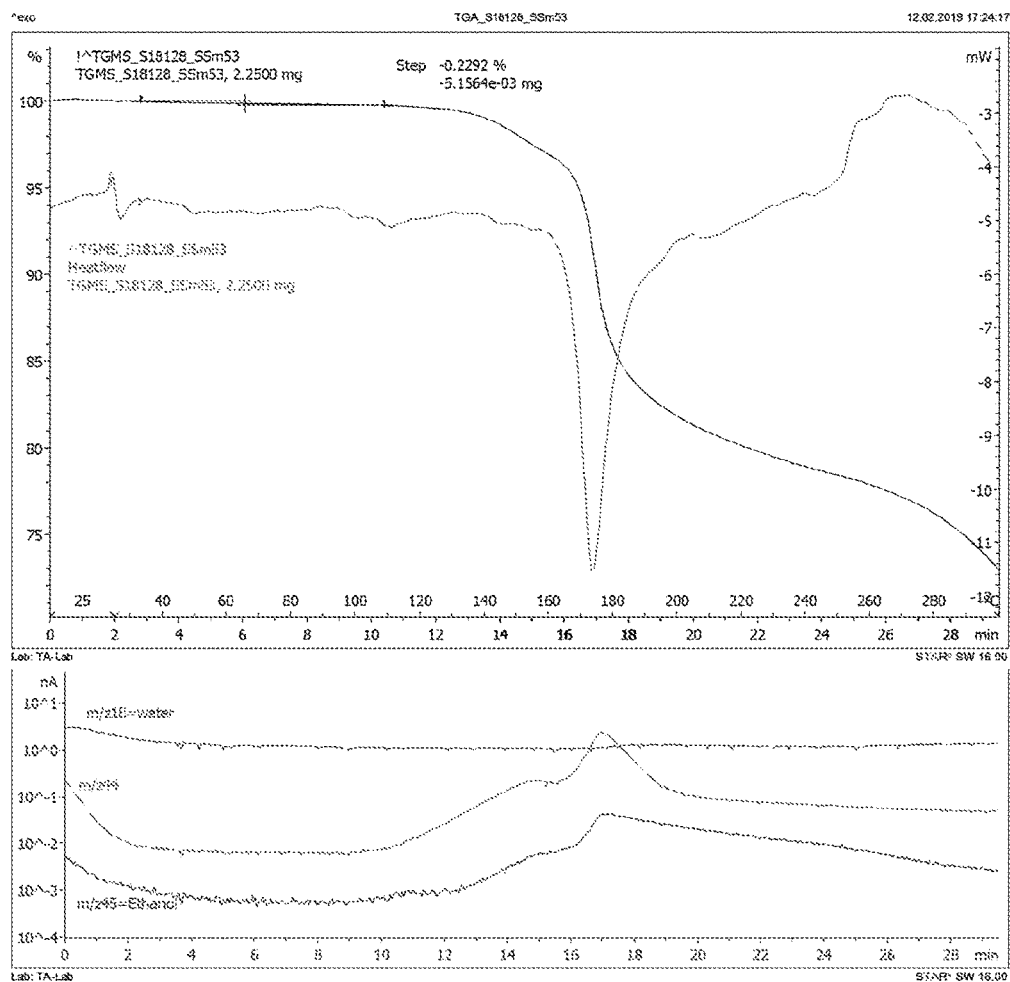
FIG. 92 illustrates the TGMS analysis (heating rate 10° C./min) of Mao1 obtained with malonic acid and ethanol (Exp. ID SSm53); a mass loss of 0.2% is observed prior to melting/decomposition starting around 140° C.
Figure 93:
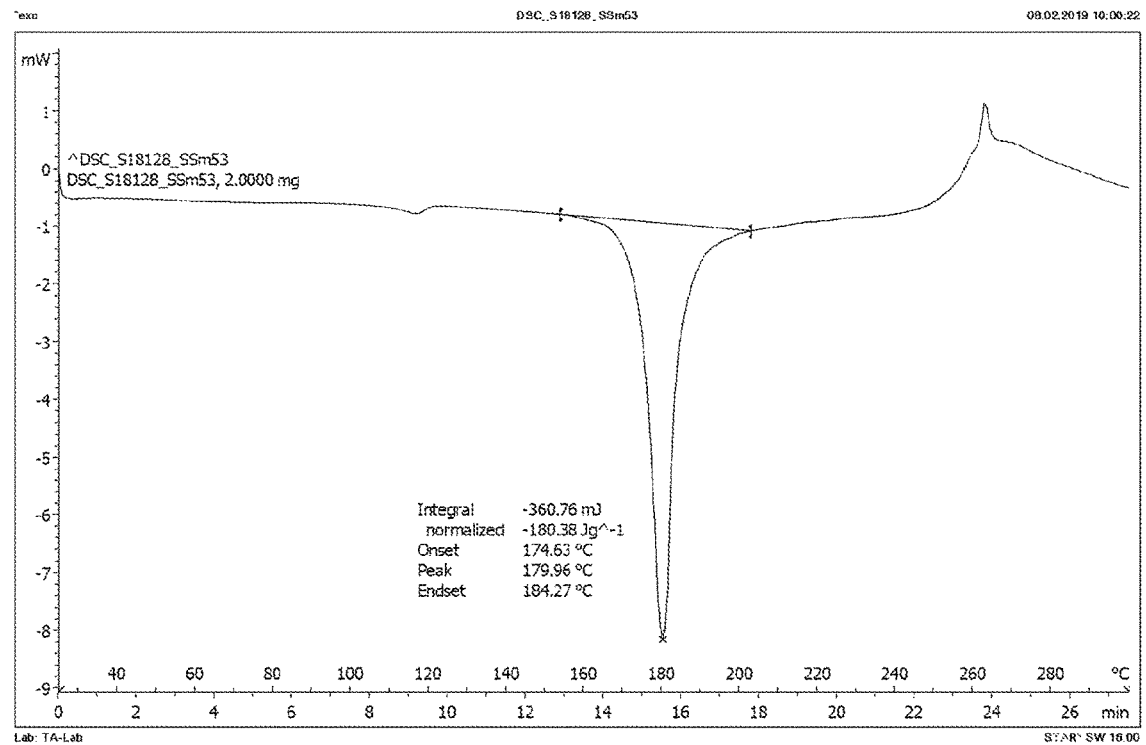
FIG. 93 illustrates the DSC analysis (heating rate 10° C./min) of Mao1 obtained with malonic acid and ethanol (Exp. ID SSm53); an endothermic event was observed with peak temperature at 180° C., due to melting/decomposition.
Figure 94:
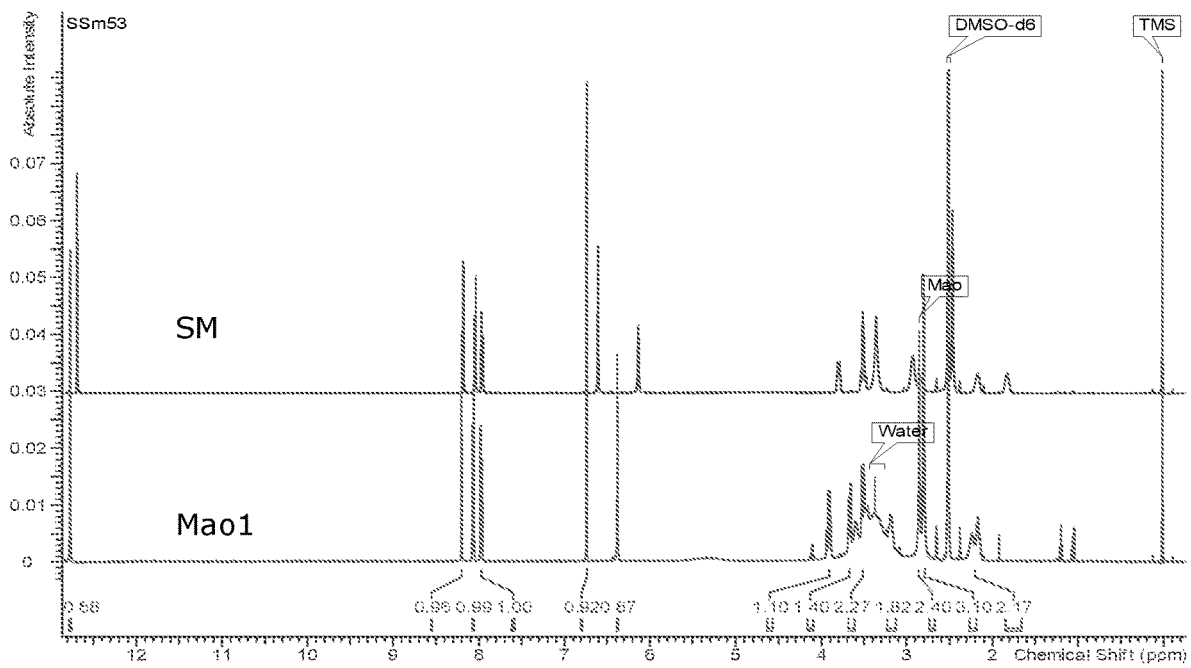
FIG. 94 illustrates the $^1$H-NMR spectrum of Mao1 obtained from malonic acid and ethanol (Exp. ID SSm53, bottom) compared to the starting material (top).
Figure 95:
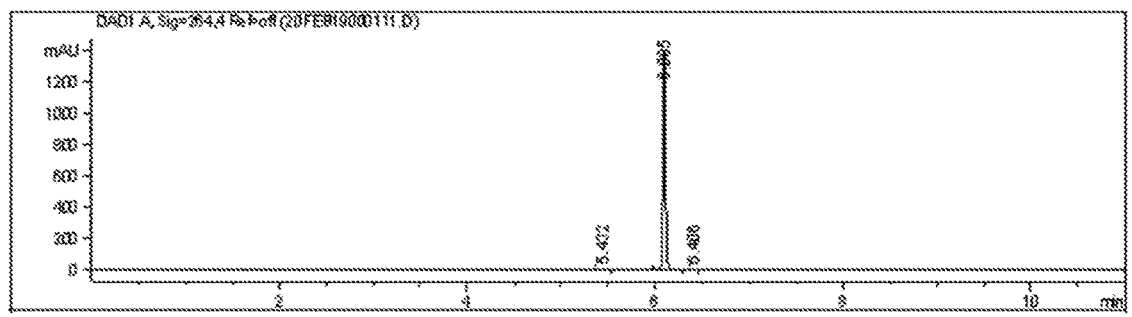
FIG. 95 illustrates the HPLC chromatogram of Mao1 obtained from malonic acid and ethanol (Exp. ID SSm53).

Without wishing to be bound by any particular theory, it is believed that the TGMS analysis (FIG. 92) of Mao1 indicated that this form was a non-solvated anhydrous form as the mass loss was only 0.2% prior to the start of decomposition. Decomposition started around 140° C. The DSC trace (FIG. 93) of Mao1 showed an endothermic event with peak temperature at 180° C., due to melting/decomposition. The proton NMR spectrum (FIG. 94) obtained for Mao1 confirmed salt formation as the proton resonances of the salt were shifted compared to those of the starting material. The free base:malonic acid stoichiometry determined was 1:1. The HPLC chromatogram (FIG. 95) obtained for Mao1 confirmed the compound's integrity with a chemical purity of 99.3% (area %).

Dibenzoyl-Tartrate Salt, DiTr1

Figure 96:
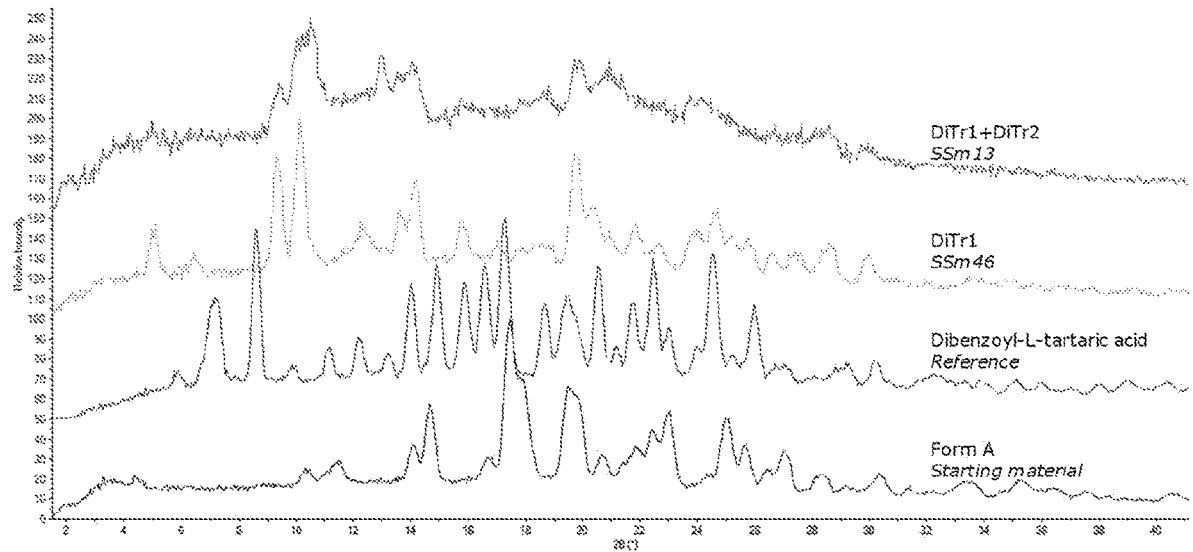
FIG. 96 illustrates the XRPD patterns of (from bottom to top): Form A starting material, dibenzoyl-L-tartaric acid reference, DiTr1 obtained from ethanol (Exp. ID SSm46) and mixture DiTr1+DiTr2 obtained from THF (Exp. ID SSm13).
Figure 97:
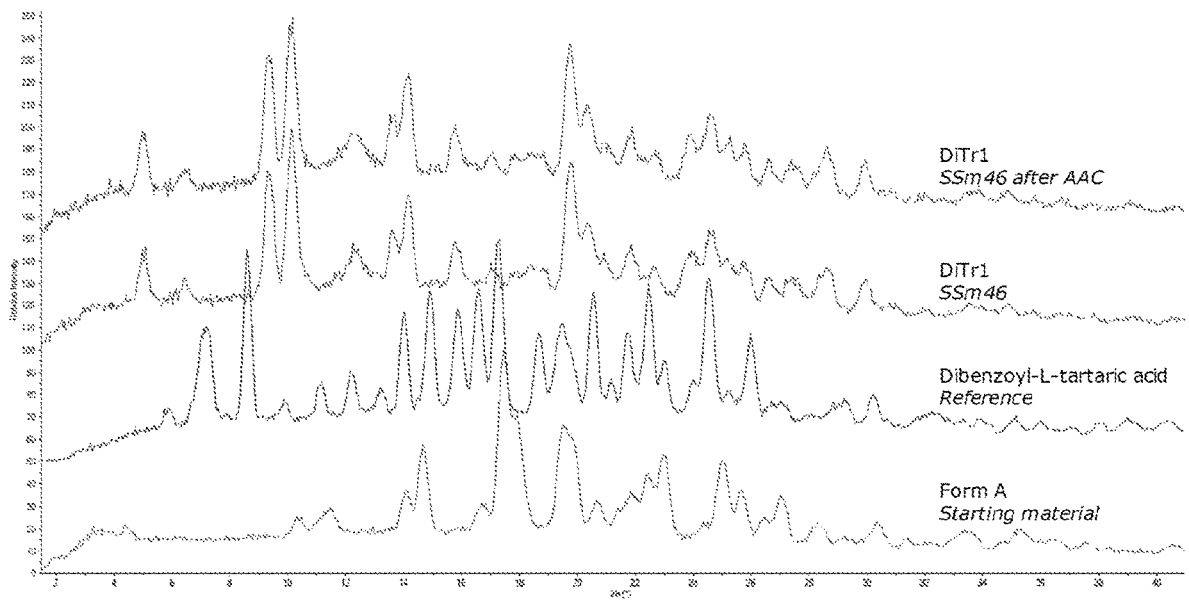
FIG. 97 illustrates the XRPD patterns of DiTr1 (Exp. ID SSm46) before and after AAC; the starting material and dibenzoyl-L-tartaric acid are shown as references.

With dibenzoyl-L-tartaric acid, two different XRPD patterns were observed. The solid crystallized from ethanol, led to the identification of DiTr1. From acetone and THF, mixtures of DiTr1 and DiTr2 were recovered. The XRPD patterns of the two forms are shown in FIG. 96. DiTr1 was selected for further characterization and it was physically stable upon exposure to AAC for two days (FIG. 97). The peak list of DiTr1 is shown in Table 28. The pure form DiTr1 (Exp. ID SSm46) was further characterized by DSC, TGMS, HPLC and $^1$H-NMR analysis.

TABLE 28

Peak list of XRPD of DiTr1.

| Peak ID | Angle (2θ) | d-Spacing | Intensity |
|---|---|---|---|
| 1 | 5.06 | 17.44 | 24.43 |
| 2 | 6.42 | 13.75 | 9.60 |
| 3 | 9.34 | 9.46 | 55.48 |
| 4 | 10.14 | 8.71 | 69.81 |
| 5 | 12.30 | 7.19 | 17.51 |
| 6 | 13.66 | 6.47 | 24.46 |
| 7 | 14.14 | 6.26 | 40.05 |
| 8 | 15.82 | 5.60 | 18.80 |
| 9 | 17.02 | 5.20 | 8.06 |
| 10 | 19.74 | 4.49 | 55.96 |
| 11 | 20.38 | 4.35 | 28.74 |
| 12 | 21.82 | 4.07 | 19.17 |
| 13 | 22.66 | 3.92 | 11.14 |
| 14 | 24.62 | 3.61 | 29.48 |
| 15 | 25.78 | 3.45 | 16.36 |
| 16 | 26.58 | 3.35 | 11.44 |
| 17 | 28.66 | 3.11 | 18.50 |
| 18 | 29.98 | 2.98 | 14.56 |

Figure 98:
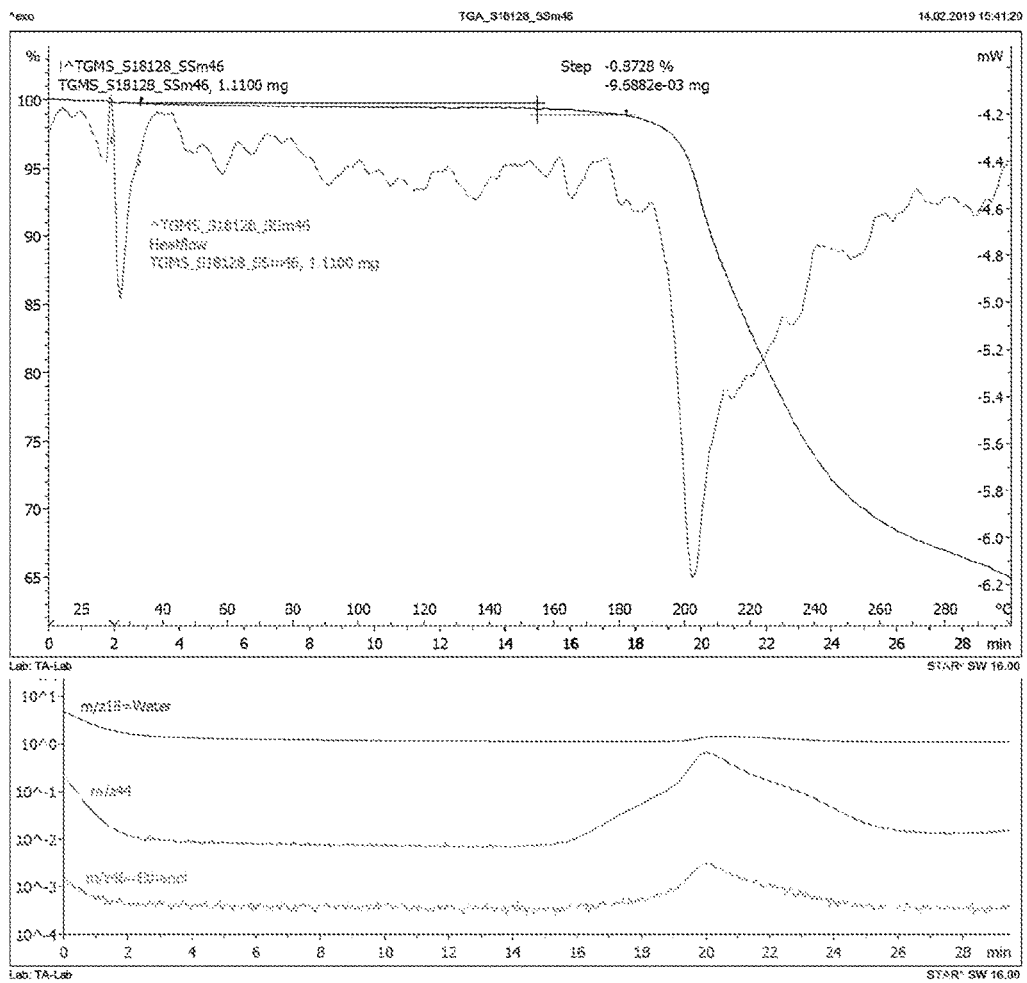
FIG. 98 illustrates the TGMS analysis (heating rate 10° C./min) of DiTr1 obtained from dibenzoyl-L-tartaric acid in ethanol (Exp. ID SSm46); a mass loss of 0.9% is observed prior to melting/decomposition starting around 180° C.
Figure 99:
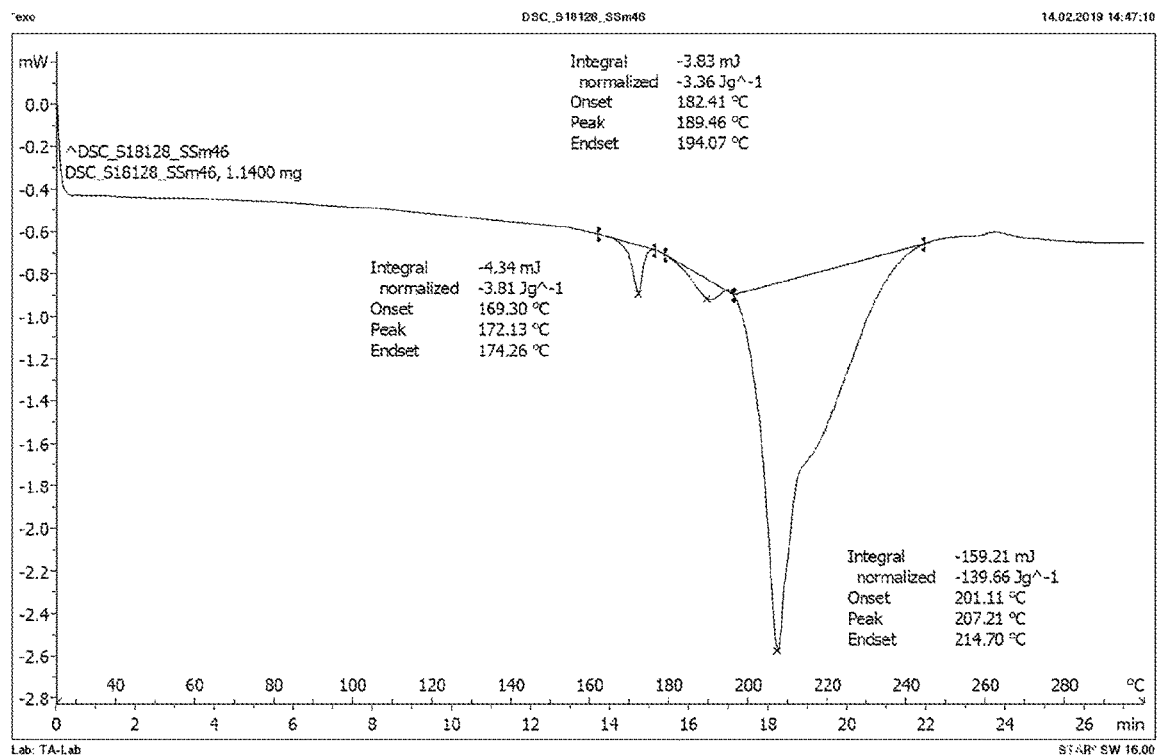
FIG. 99 illustrates the DSC analysis (heating rate 10° C./min) of DiTr1 obtained from dibenzoyl-L-tartaric acid in ethanol (Exp. ID SSm46); a small endothermic event was observed at 172° C., prior to the decomposition processes with peak temperature of 207° C.
Figure 100:
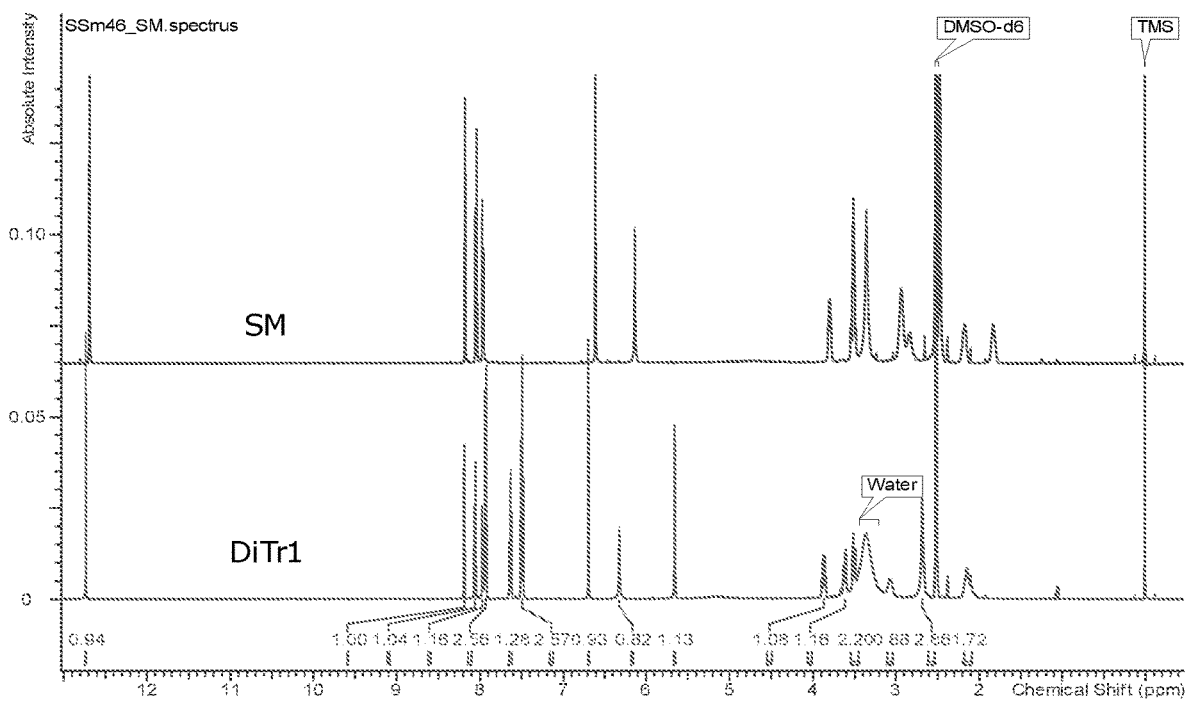
FIG. 100 illustrates the ¹H-NMR spectrum of DiTr1 obtained from dibenzoyl-L-tartaric acid and ethanol (Exp. ID SSm46, bottom) compared to the starting material (top).
Figure 101:
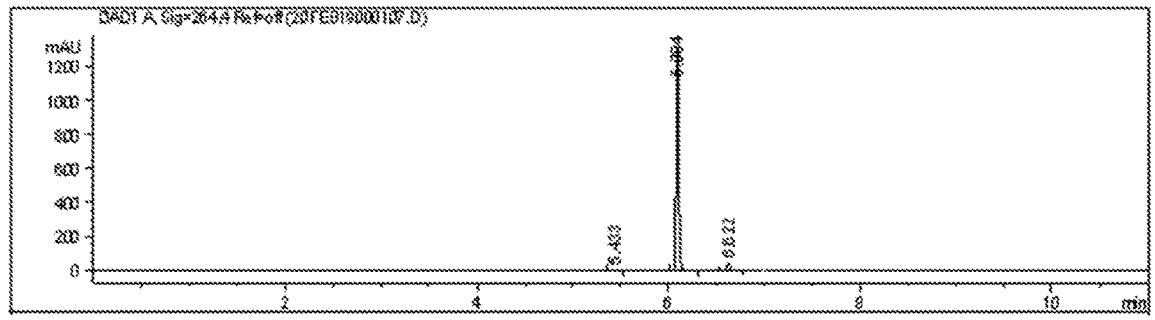
FIG. 101 illustrates the HPLC chromatogram of DiTr1 obtained from dibenzoyl-L-tartaric acid and ethanol (Exp. ID SSm46).

Without wishing to be bound by any particular theory, it is believed that the TGMS analysis (FIG. 98) indicated that DiTr1 was a non-solvated anhydrous form with a residual solvent/water content of 0.9%. This mass loss was observed prior to the start of the thermal decomposition (around 180° C.). The DSC trace (FIG. 99) of DiTr1 showed a small endothermic event at 172° C., prior to the decomposition processes with peak temperature of 207° C. The proton NMR spectrum (FIG. 100) of DiTr1 confirmed salt formation as the proton resonances of the salt were shifted compared to those of the starting material. The stoichiometry determined for free base:dibenzoyl-L-tartaric acid was 1:0.5. The HPLC chromatogram (FIG. 101) obtained for DiTr1 confirmed the compound's integrity with a chemical purity of 95.7% (area %).

Phosphate Salt, Pho1

Figure 102:
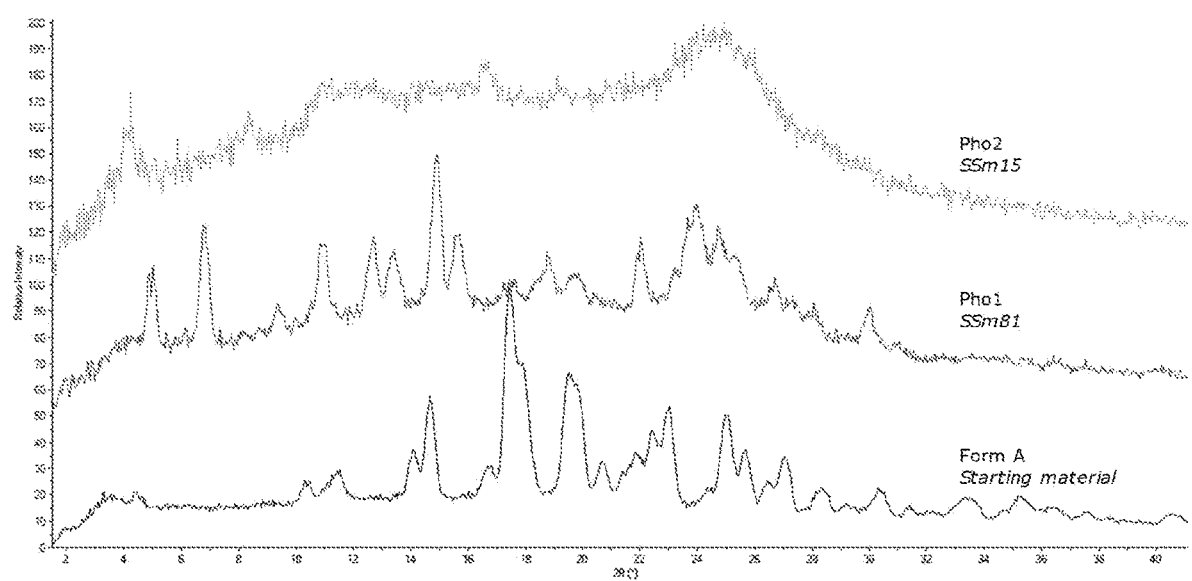
FIG. 102 illustrates the XRPD patterns of (from bottom to top): Form A starting material, Pho1 obtained from acetone (Exp. ID SSm81) and poor crystalline Pho2 obtained from THF (Exp. ID SSm15).
Figure 103:
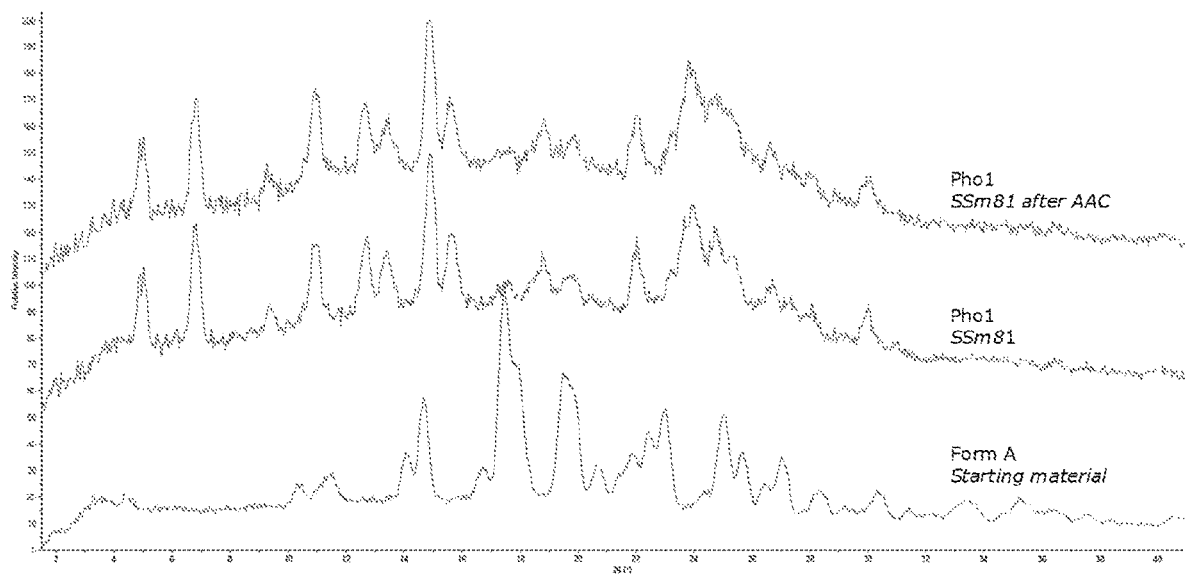
FIG. 103 illustrates the XRPD patterns of Pho1 (Exp. ID SSm81) before and after AAC; the starting material and phosphoric acid are shown as references.

With phosphoric acid, two different XRPD patterns were observed. From the experiment performed in acetone the crystalline salt Pho1 was obtained. From THF, a poor crystalline solid was recovered, Pho2. The XRPD patterns of the two forms are shown in FIG. 102. Pho1 was obtained with high crystallinity and it was physically stable upon exposure to AAC for two days (FIG. 103). The peak list is shown in Table 29. The stable crystalline phosphate salt Pho1 (Exp. ID SSm81) was further characterized by DSC, TGMS, HPLC and 1H-NMR analysis.

TABLE 29

Peak list of XRPD of Pho1.

| Peak ID | Angle (2θ) | d-Spacing | Intensity |
|---|---|---|---|
| 1 | 4.94 | 17.87 | 30.40 |
| 2 | 6.78 | 13.02 | 45.04 |
| 3 | 9.34 | 9.46 | 10.19 |
| 4 | 10.94 | 8.08 | 31.93 |
| 5 | 12.70 | 6.96 | 28.03 |
| 6 | 13.38 | 6.61 | 22.23 |
| 7 | 14.90 | 5.94 | 55.90 |
| 8 | 15.66 | 5.65 | 27.65 |
| 9 | 17.54 | 5.05 | 8.82 |
| 10 | 18.82 | 4.71 | 17.04 |
| 11 | 22.02 | 4.03 | 23.49 |
| 12 | 23.98 | 3.71 | 39.67 |
| 13 | 24.78 | 3.59 | 31.46 |
| 14 | 25.30 | 3.52 | 23.89 |
| 15 | 26.66 | 3.34 | 15.25 |
| 16 | 29.98 | 2.98 | 14.07 |

Figure 104:
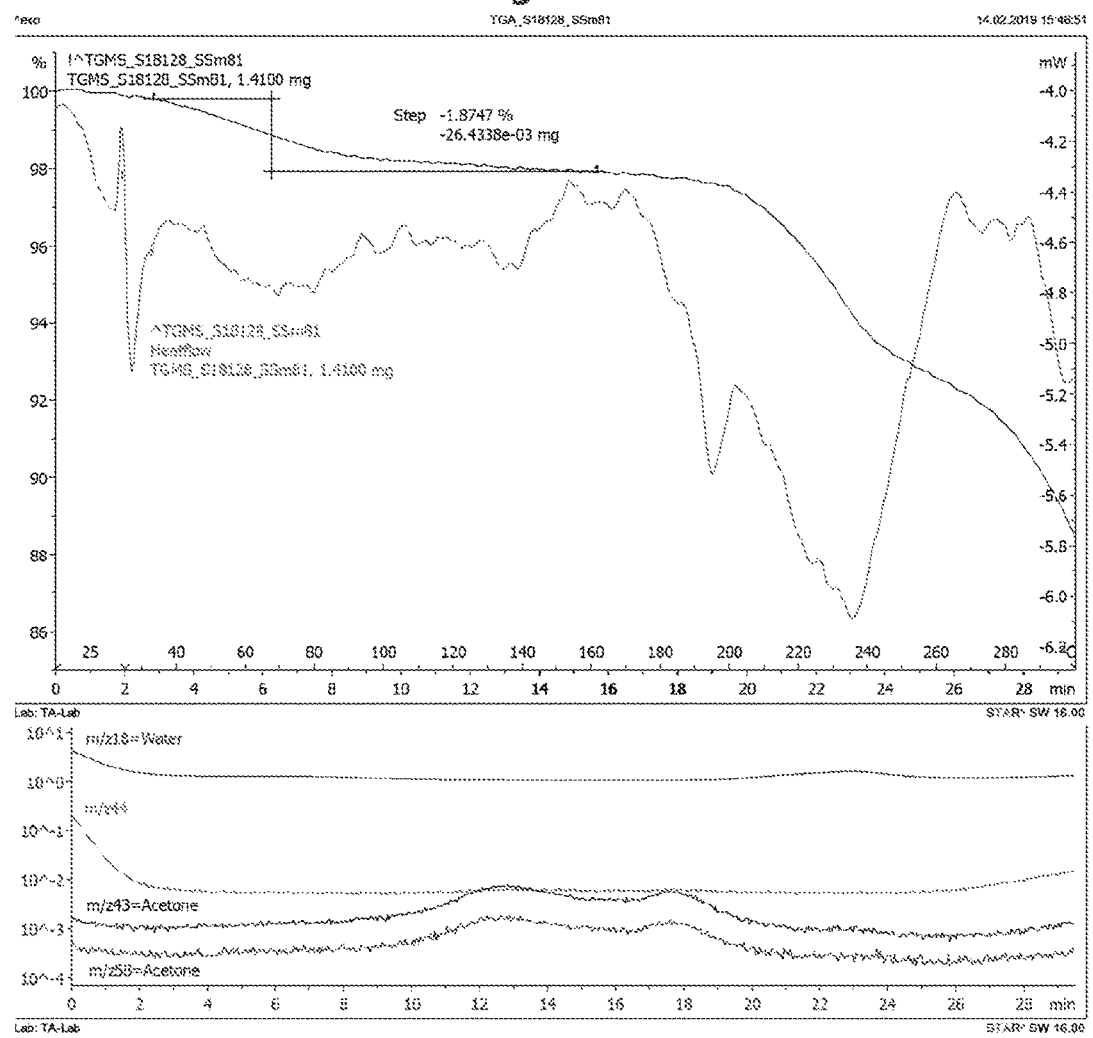
FIG. 104 illustrates the TGMS analysis (heating rate 10° C./min) of Pho1 obtained with phosphoric acid in acetone (Exp. ID SSm81); a mass loss of 1.9% is observed between 25-160° C., prior to melting; the thermal decomposition started around 200° C.
Figure 105:
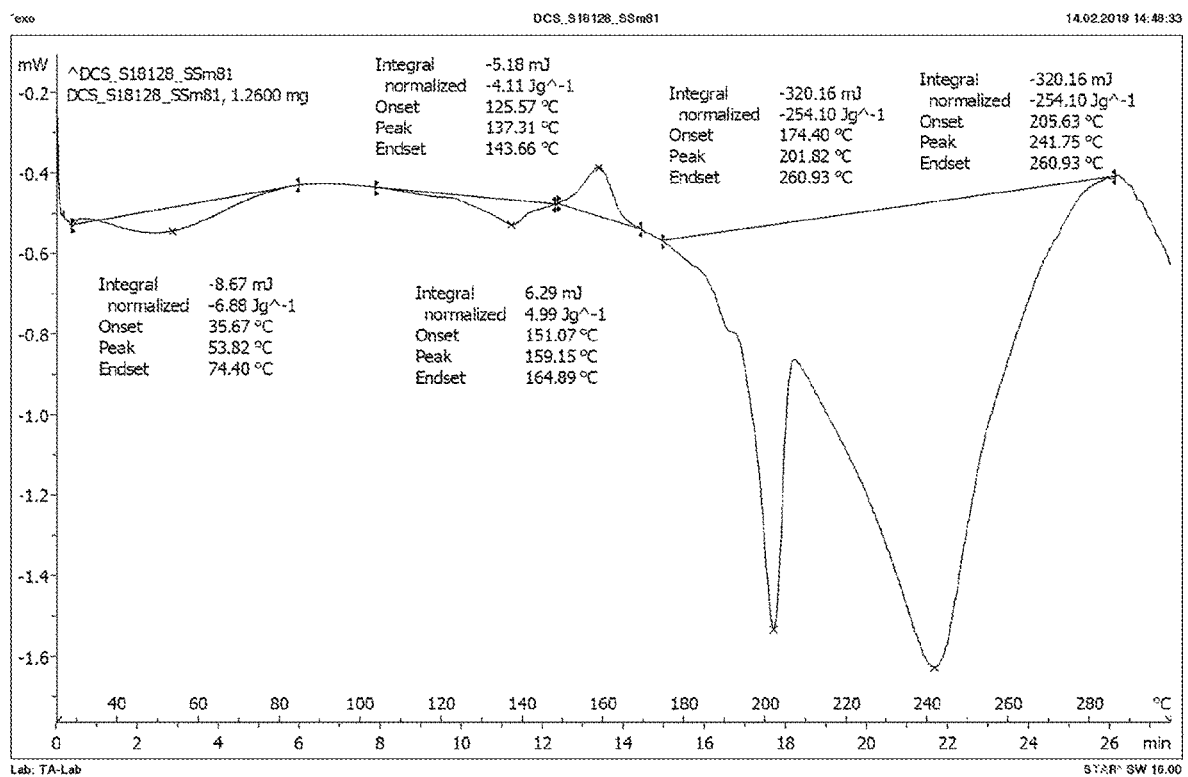
FIG. 105 illustrates the DSC analysis (heating rate 10° C./min) of Pho1 obtained with phosphoric acid in acetone (Exp. ID SSm81).
Figure 106:
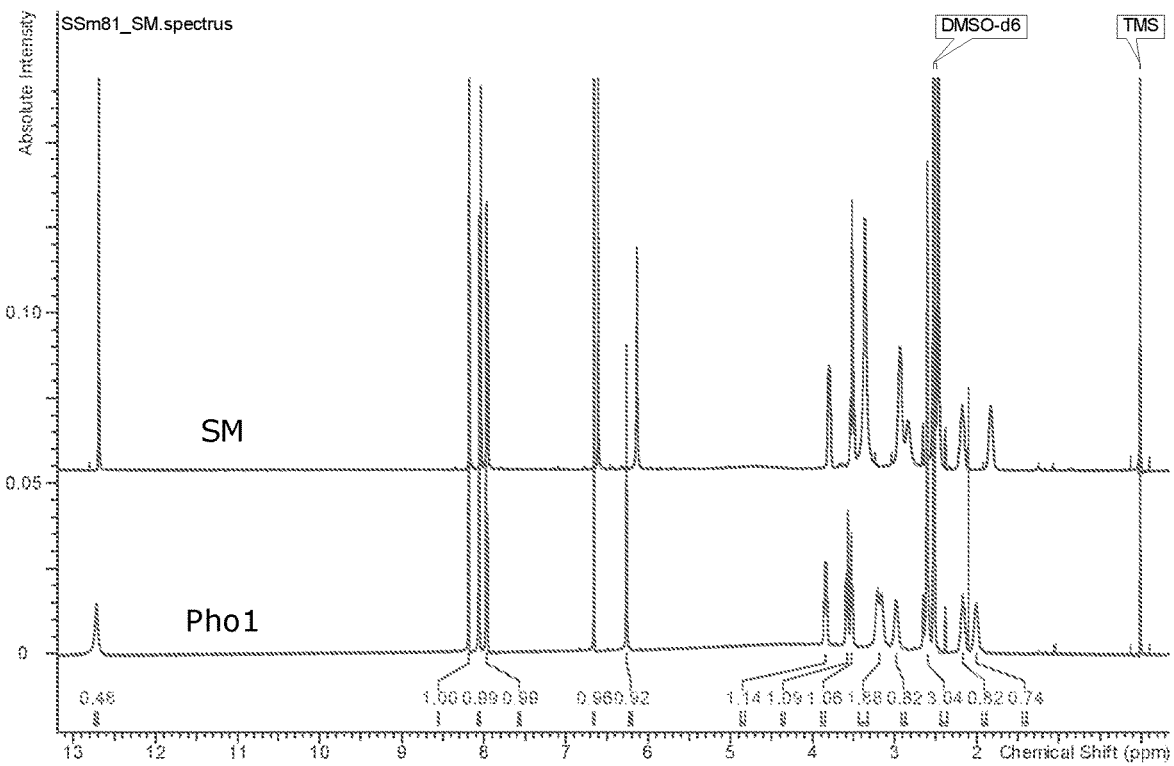
FIG. 106 illustrates the ¹H-NMR spectrum of Pho1 obtained from phosphoric acid and acetone (Exp. ID SSm81, bottom) compared to the starting material (top).
Figure 107:
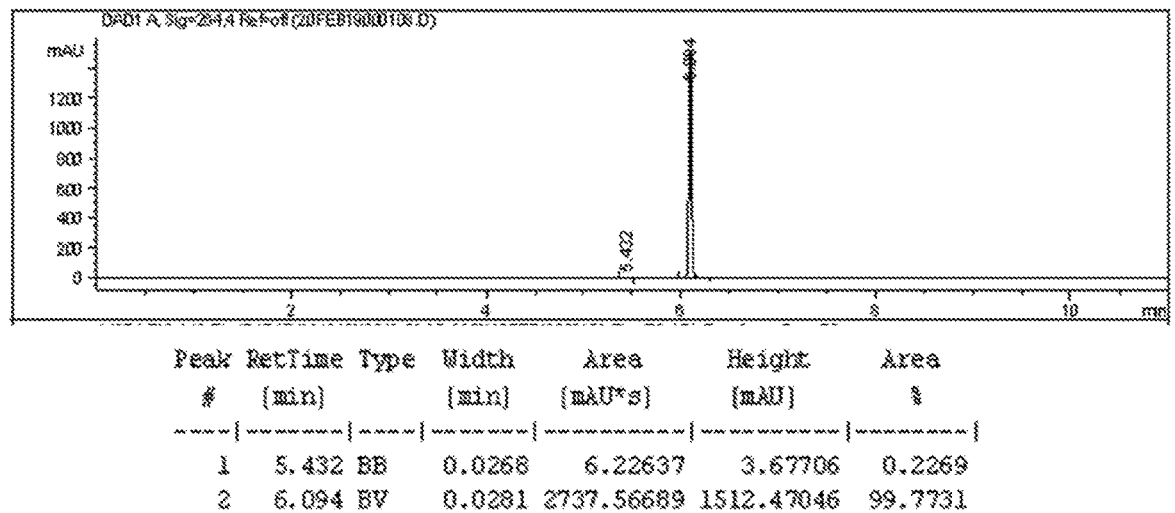
FIG. 107 illustrates the HPLC chromatogram of Pho1 obtained from phosphoric acid and acetone (Exp. ID SSm81).

The TGMS analysis (FIG. 104) of Pho1 showed a mass loss of 1.9% most likely related to water. The mass loss was observed between 25-160° C. prior to melting. The thermal decomposition was observed above 200° C. The DSC trace (FIG. 105) of Pho1 showed a series of small thermal events (related to water/solvent loss) prior to melting at 202° C., followed by decomposition. The proton NMR spectrum (FIG. 106) obtained for Pho1 confirmed salt formation as the proton resonances of the salt were shifted compared to those of the starting material. The HPLC chromatogram (FIG. 107) obtained for Pho1 confirmed the compound's integrity with a chemical purity of 99.8% (area %). The stoichiometry of the salt was determined based on area of the main chromatographic peak (attributed to the free base) and it was free base:phosphoric acid 1:1.

Oxalate Salt, Oxa1

Figure 108:
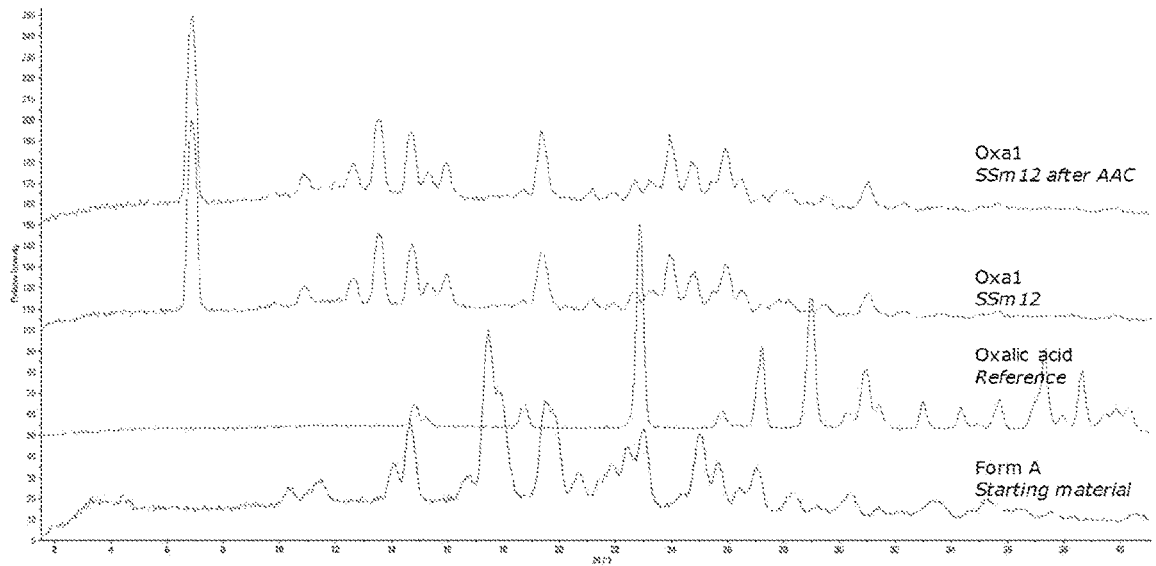
FIG. 108 illustrates the XRPD patterns of Oxa1 (Exp. ID SSm12) before and after AAC; the starting material and oxalic acid are shown as references.

With oxalic acid only one potential salt was identified, Oxa1. This form was identified independently on the molar equivalent of oxalic acid used in the experiments. Oxa1 was physically stable upon exposure to AAC for two days. The XRPD of Oxa1 is shown in FIG. 108 and the peak list is shown in Table 30. The solid obtained with half molar equivalent of oxalic acid from THF (Exp. ID SSm12) was further characterized by DSC, TGMS, HPLC and 1H-NMR analysis.

TABLE 30

Peak list of XRPD of Oxa1.

| Peak ID | Angle (2θ) | d-Spacing | Intensity |
|---|---|---|---|
| 1 | 6.86 | 12.87 | 100 |
| 2 | 12.66 | 6.98 | 24.49 |
| 3 | 13.58 | 6.51 | 44.55 |
| 4 | 14.74 | 6.00 | 40.82 |
| 5 | 15.98 | 5.54 | 26.86 |
| 6 | 19.38 | 4.57 | 37.91 |
| 7 | 23.94 | 3.71 | 36.71 |
| 8 | 24.78 | 3.59 | 26.63 |
| 9 | 25.94 | 3.43 | 31.37 |

Figure 109:
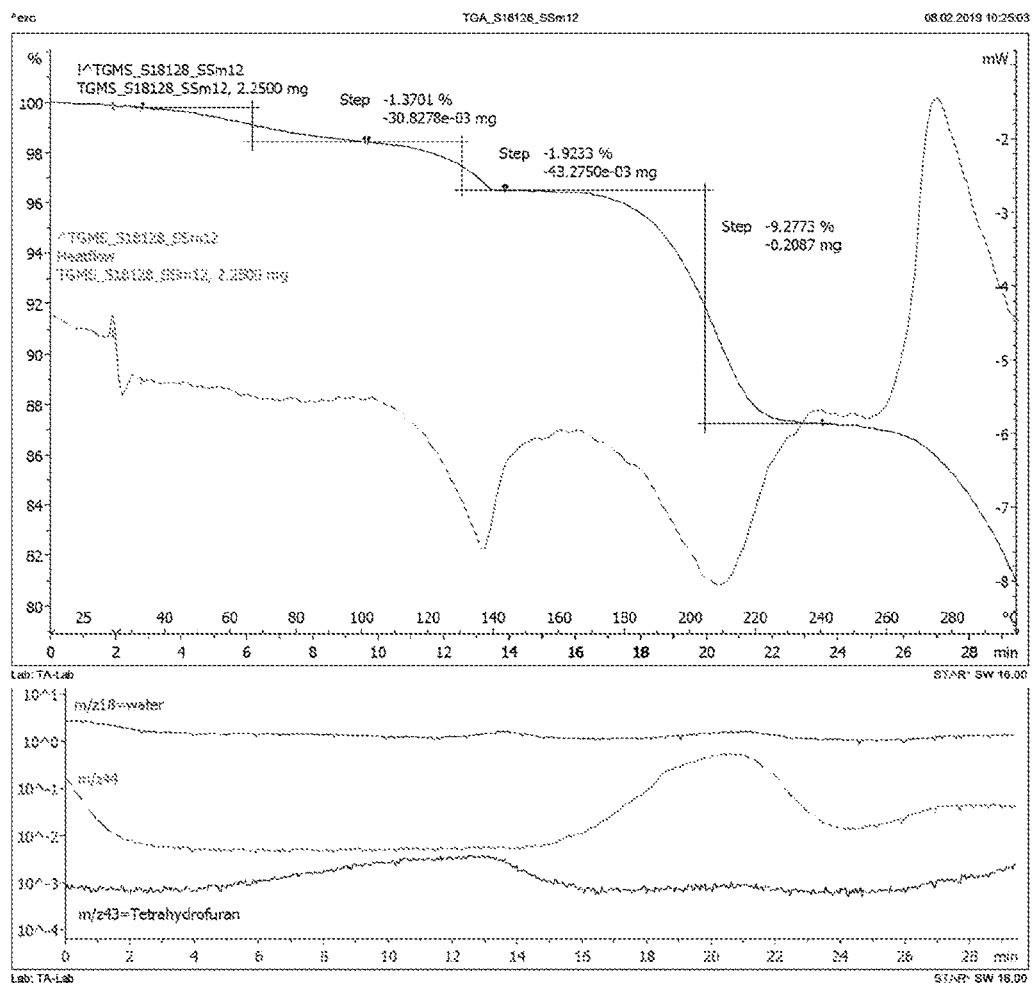
FIG. 109 illustrates the TGMS analysis (heating rate 10° C./min) of Oxa1 obtained with oxalic acid in THF (Exp. ID SSm12); a mass loss is observed of 1.4% between 25-100° C. and a second mass loss of 1.9% between 100-150° C.; the mass loss above 160° C. is related to decomposition of the salt.
Figure 110:
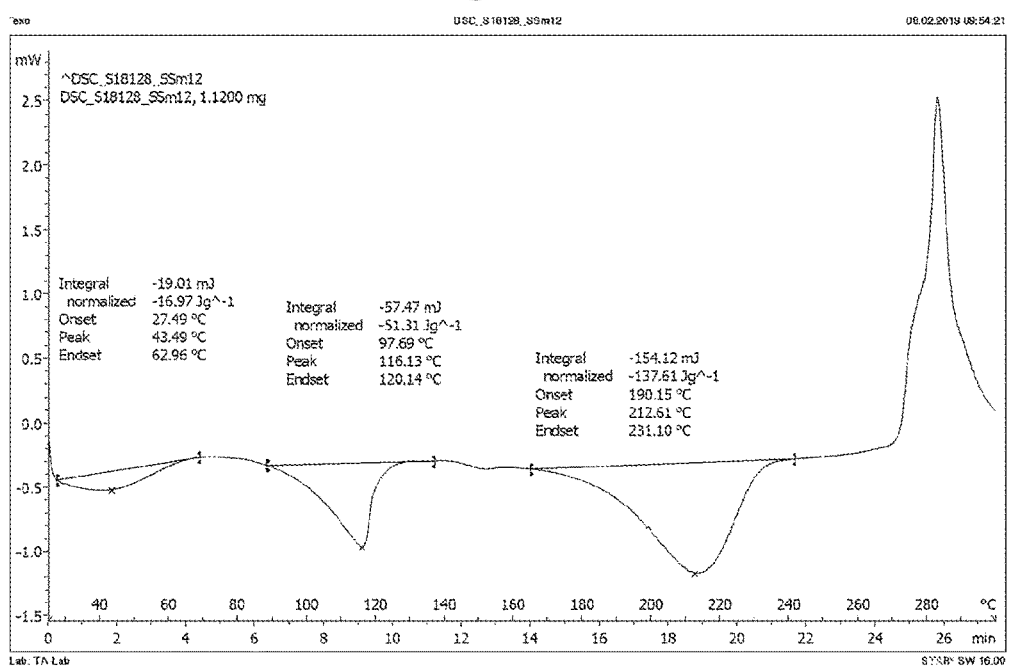
FIG. 110 illustrates the DSC analysis (heating rate 10° C./min) of Oxa1 obtained with oxalic acid in THF (Exp. ID SSm12); the first two endothermic events are due to solvent/water loss, while the broad endothermic event around 213° C. is related to decomposition of the salt.
Figure 111:
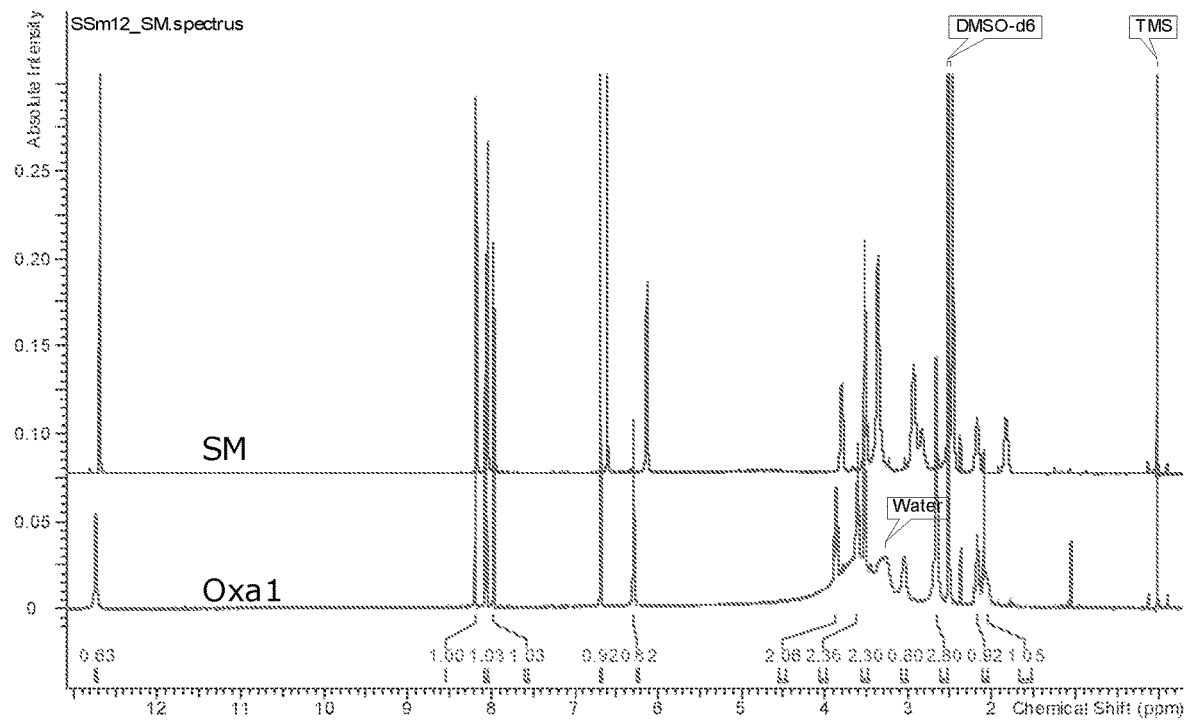
FIG. 111 illustrates the ¹H-NMR spectrum of Oxa1 obtained from oxalic acid and THF (Exp. ID SSm12, bottom) compared to the starting material (top).
Figure 112:
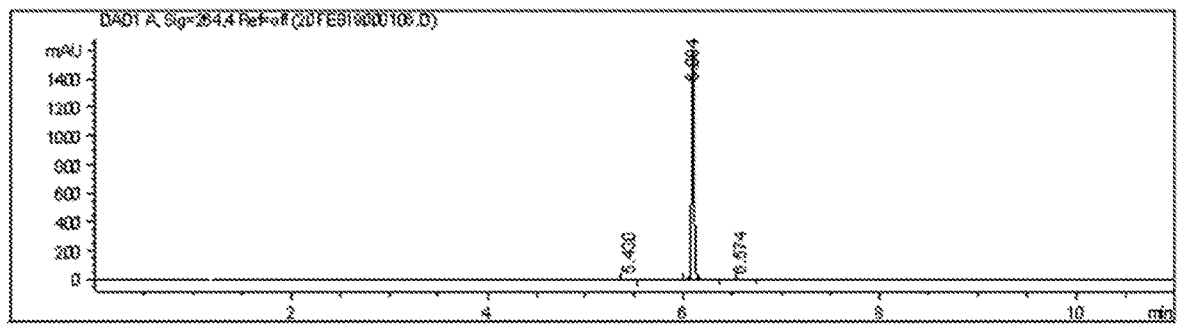
FIG. 112 illustrates the HPLC chromatogram of Oxa1 obtained from oxalic acid and THF (Exp. ID SSm12).

The TGMS analysis (FIG. 109) of Oxa1 showed a mass loss of 1.4% between 25-100° C. and a second mass loss of 1.9% between 100-150° C. The mass loss above 160° C. is related to decomposition of the salt. The total mass loss of 3.3% corresponds to about 1 molar equivalent of water. Therefore the salt is either a monohydrate or a hemi-hydrate with residual solvent/water. The DSC trace (FIG. 110) of Oxa1 showed two endothermic events between 25-130° C. related to solvent or water loss and the broad endothermic event with peak temperature at 213° C. was attributed to the thermal decomposition of the salt. The proton NMR spectrum (FIG. 111) obtained for Oxa1 confirmed salt formation as the proton resonances of the salt were shifted compared to those of the starting material. The HPLC chromatogram (FIG. 112) obtained for Oxa1 confirmed the compound's integrity with a chemical purity of 99.6% (area %). Calculation of the salt stoichiometry was based on the area of the main chromatographic peak attributed to the free base. The free base:oxalic acid stoichiometry was 1:0.5.

Napadisylate Salt, Nds1a

Figure 113:
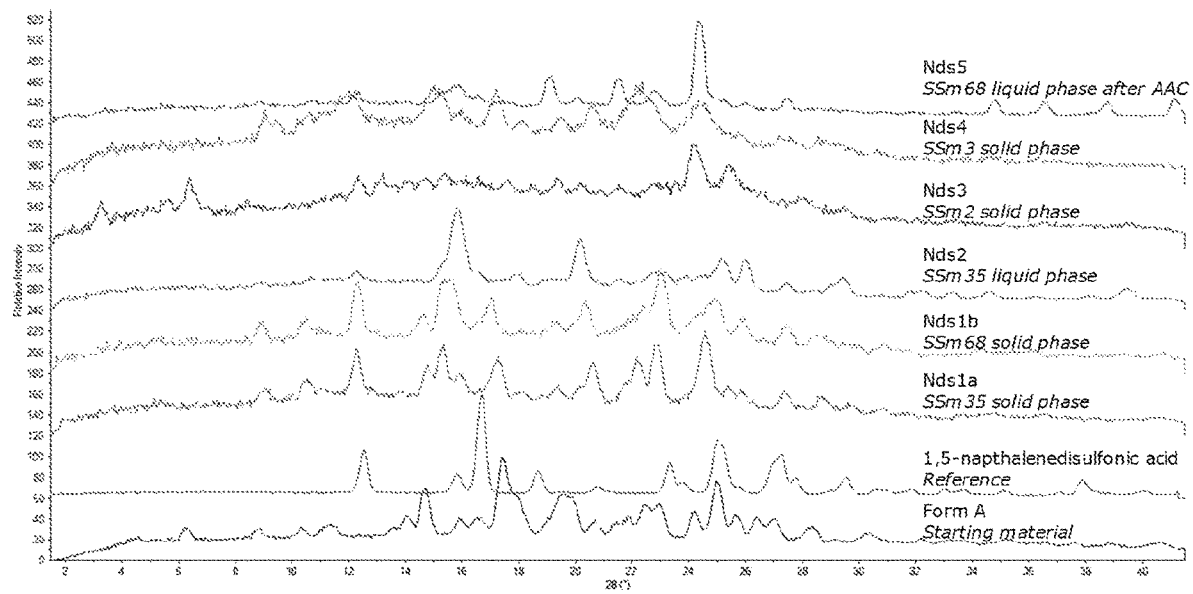
FIG. 113 illustrates the XRPD patterns of (from bottom to top): Form A starting material, 1,5-napthalenedisulfonic acid reference, Nds1a obtained from ethanol, solid phase (Exp. ID SSm35), Nds1b obtained from acetone, solid phase (Exp. ID SSm68), Nds2 obtained from ethanol, liquid phase (Exp. ID SSm35), Nds3 obtained from THF (Exp. ID SSm2), Nds4 obtained from THF, solid phase (Exp. ID SSm3) and Nds5 obtained by conversion of Nds2 after AAC (SSm68 liquid phase after AAC).
Figure 114:
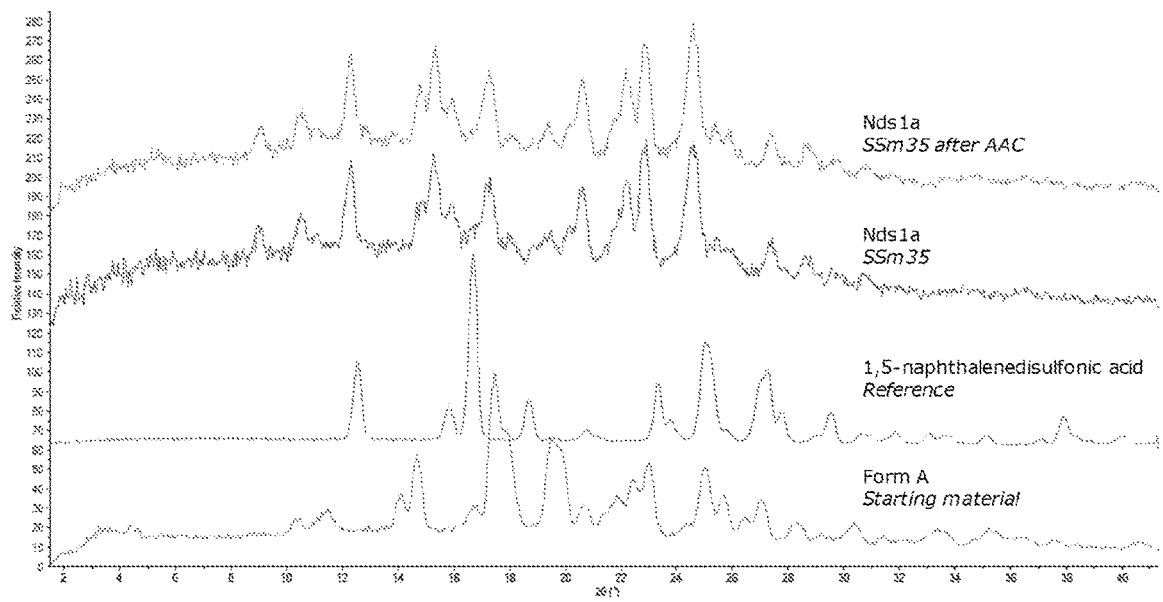
FIG. 114 illustrates the XRPD patterns of Nds1a (Exp. ID SSm35) before and after AAC; the starting material and 1,5-napthalenedisulfonic acid are shown as references.

With 1,5-napthalenedisulfonic acid several different XRPD patterns were obtained. From the experiment in ethanol the crystalline salt Nds1a had precipitated, while after evaporation of the mother liquor Nds2 was obtained. From acetone and THF other forms were obtained. The different XRPD patterns obtained from the experiments with 1,5-naphthalenedisulfonic acid are shown in FIG. 113. Nds1a was highly crystalline and physically stable upon exposure to AAC for two days (FIG. 114). For that reason, Nds1a (Exp. ID SSm35) was further characterized by DSC, TGMS, HPLC and 1H-NMR analysis. The XRPD is shown in FIG. 114 and the peak list is shown in Table 31.

TABLE 31

Peak list of XRPD of Nds1a.

| Peak ID | Angle (2θ) | d-Spacing | Intensity |
|---|---|---|---|
| 1 | 9.02 | 9.79 | 45.30 |
| 2 | 10.50 | 8.42 | 51.58 |
| 3 | 11.06 | 7.99 | 45.06 |
| 4 | 12.30 | 7.19 | 83.54 |
| 5 | 12.82 | 6.90 | 46.39 |
| 6 | 13.90 | 6.36 | 42.01 |
| 7 | 14.82 | 5.97 | 63.93 |
| 8 | 15.30 | 5.78 | 84.42 |
| 9 | 15.94 | 5.55 | 60.95 |
| 10 | 17.26 | 5.13 | 74.96 |

TABLE 31-continued

Peak list of XRPD of Nds1a.

| Peak ID | Angle (2θ) | d-Spacing | Intensity |
|---|---|---|---|
| 11 | 19.34 | 4.58 | 45.30 |
| 12 | 20.62 | 4.30 | 71.25 |
| 13 | 22.18 | 4.00 | 75.41 |
| 14 | 22.86 | 3.89 | 86.24 |
| 15 | 24.58 | 3.62 | 100 |
| 16 | 25.42 | 3.50 | 44.96 |
| 17 | 25.86 | 3.44 | 41.64 |
| 18 | 27.38 | 3.25 | 43.27 |
| 19 | 28.66 | 3.11 | 35.08 |

Figure 115:
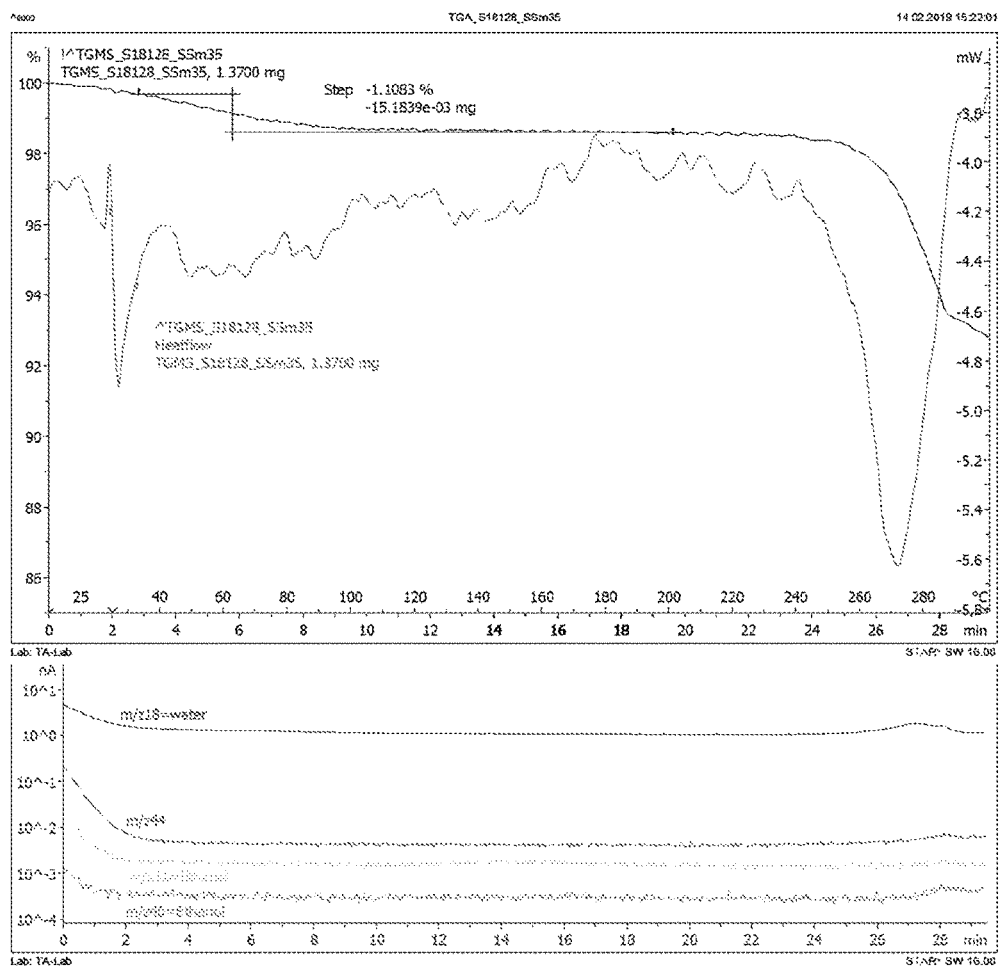
FIG. 115 illustrates the TGMS analysis (heating rate 10° C./min) of Nds1a obtained with 1,5-napthalenedisulfonic acid in ethanol (Exp. ID SSm35); a mass loss of 1.1% is observed between 25-100° C. due to residual solvent/water; decomposition started around 250° C.
Figure 116:
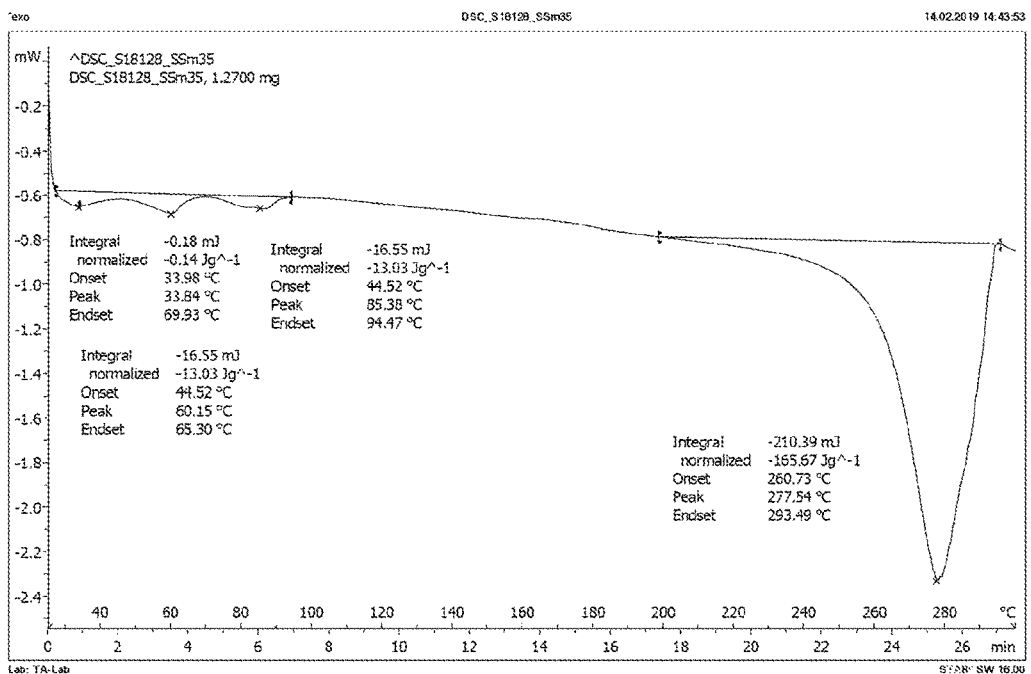
FIG. 116 illustrates the DSC analysis (heating rate 10° C./min) of Nds1a obtained with 1,5-napthalenedisulfonic acid in ethanol (Exp. ID SSm35); a series of small broad endothermic events were observed between 25-100° C., related to the residual solvent loss
Figure 117:
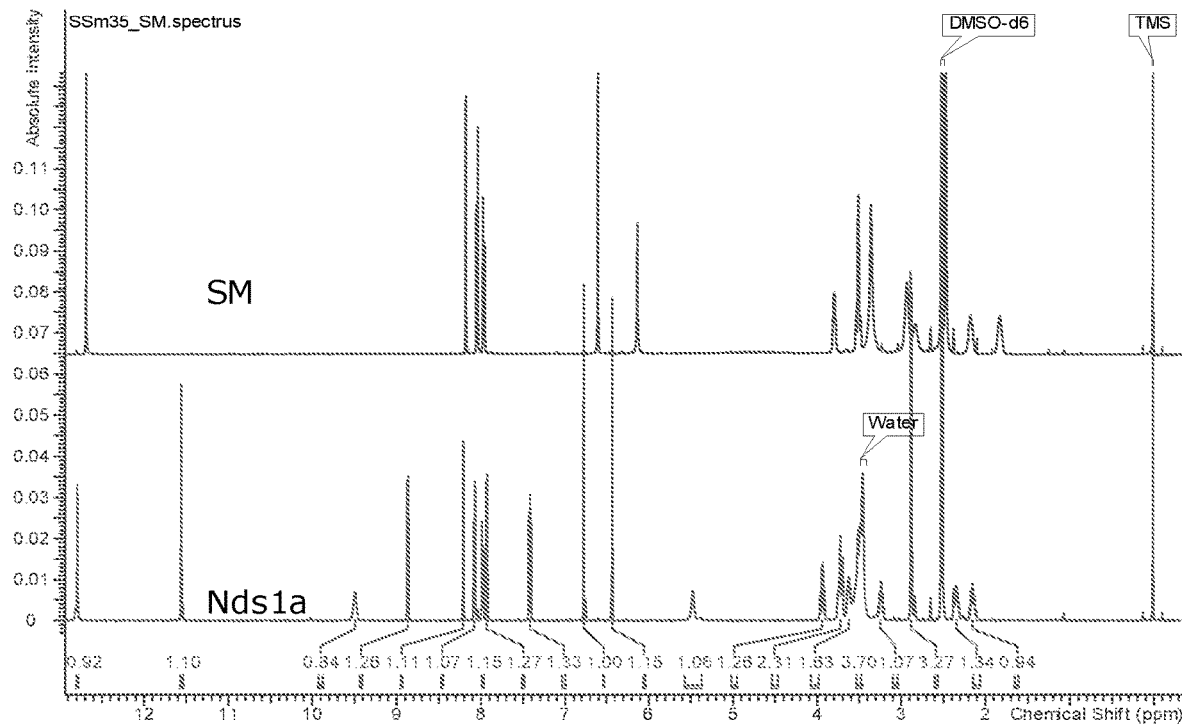
FIG. 117 illustrates the ¹H-NMR spectrum of Nds1a obtained from 1,5-napthalenedisulfonic acid and ethanol (Exp. ID SSm35, bottom) compared to the starting material (top).

Without wishing to be bound by any particular theory, it is believed that the TGMS analysis (FIG. 115) indicated that Nds1 was a non-solvated anhydrous form with a residual solvent content of 1.1% between 25-100° C. Decomposition started around 250° C. The DSC trace (FIG. 116) of Nds1a showed a series of small endothermic events between 25-100° C. due to residual solvent loss. The endothermic event with peak temperature at 280° C. was due to melting/decomposition. The proton NMR spectrum (FIG. 117) obtained for Nds1a confirmed salt formation as the proton resonances of the salt were shifted compared to those of the starting material. The free base: 1,5-napthalenedisulfonic acid stoichiometry determined for Nds1a was 1:0.5.

Form D/Esylate Salt, Esy1

Figure 118:
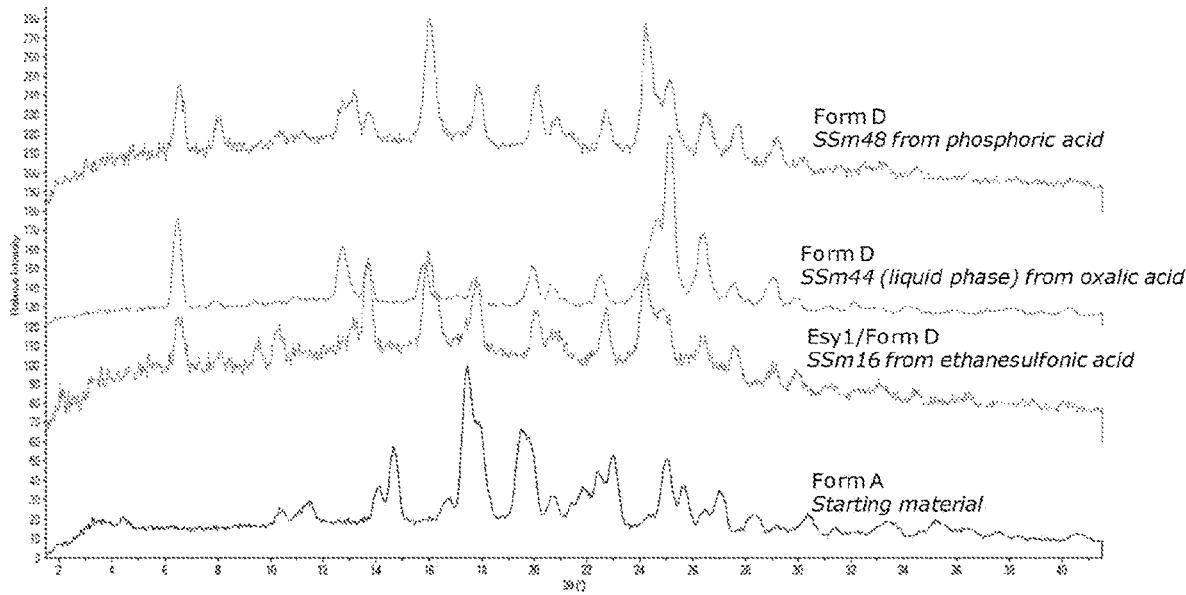
FIG. 118 illustrates the XRPD patterns of (from bottom to top): Form A starting material, Esy1 or Form D obtained from ethanesulfonic acid in THF (Exp. ID SSm16), Form D obtained from oxalic acid after evaporation of ethanol (Exp. ID SSm44 liquid phase) and Form D obtained with phosphoric acid in ethanol (Exp. ID SSm48).
Figure 119:
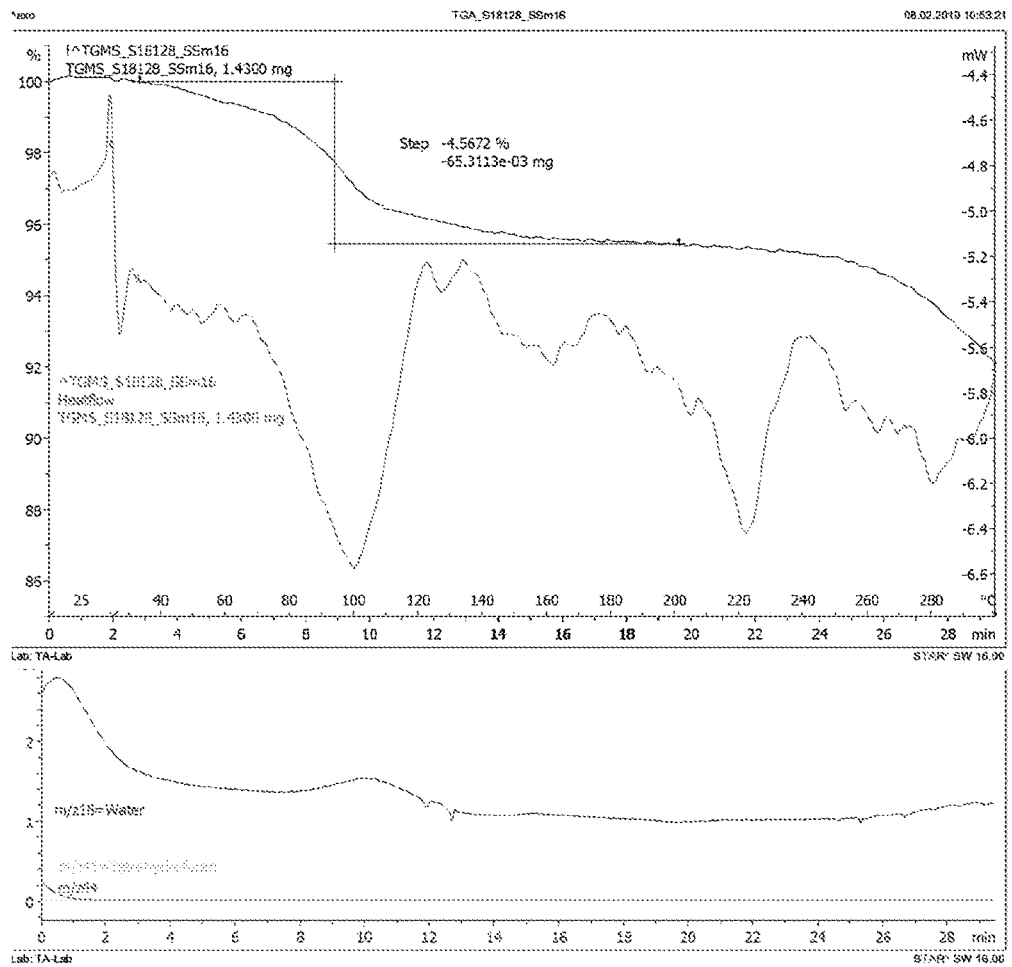
FIG. 119 illustrates the TGMS analysis (heating rate 10° C./min) of Esy1/Form D obtained with ethanesulfonic acid in THF (Exp. ID SSm16); a mass loss of 4.6% is observed between 25-200° C. due to solvent or water; decomposition started around 250° C.
Figure 120:
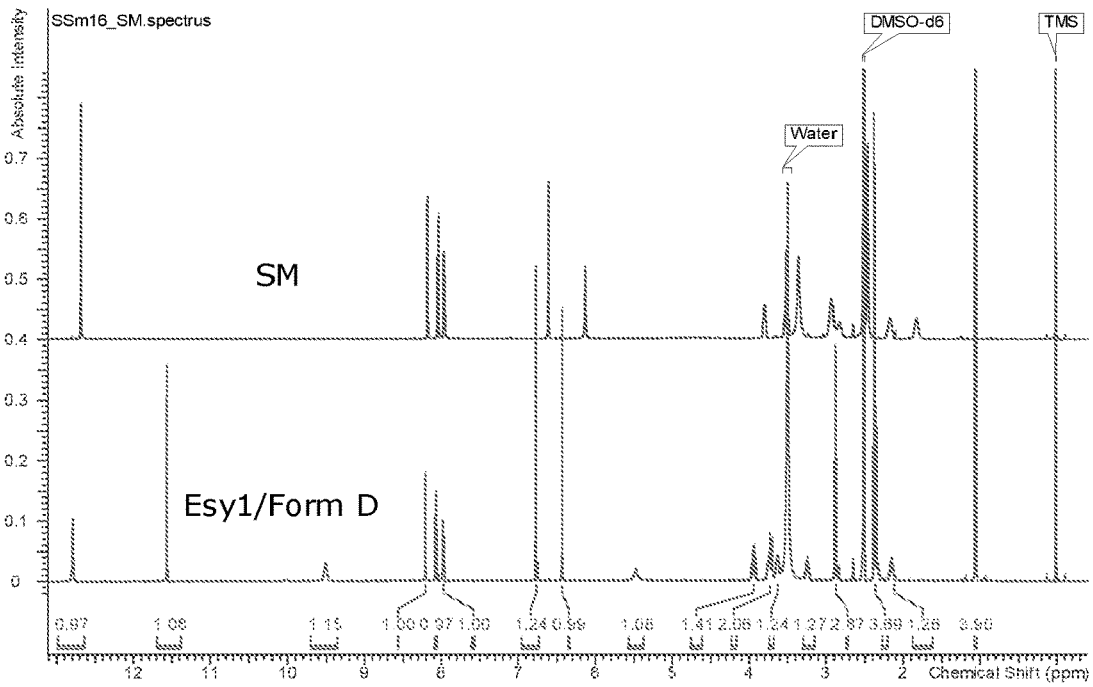

With ethanesulfonic acid Esy1 or Form D was obtained. Without wishing to be bound by any particular theory, it is believed that the same XRPD pattern was observed from experiments with phosphoric acid and oxalic acid, for that reason, it could be attributed to solid form of the free base, rather than a salt. The XRPD patterns obtained from the experiments with ethanesulfonic acid, phosphoric acid and oxalic acid are shown in FIG. 118. In all cases a very similar powder pattern was obtained with small shifts in some diffraction peaks. Without wishing to be bound by any particular theory, it is believed that the TGMS analysis (FIG. 119) of Esy1 or Form D obtained from ethanesulfonic acid in THF indicated that the form was most likely a solvated or hydrated form. A mass loss of 4.6% was observed between 25-200° C., followed by decomposition starting around 250° C. The proton NMR spectrum (FIG. 120) obtained for Esy1/Form D suggests salt formation as the proton resonances were shifted compared to the starting material. The free base:ethanesulfonic acid stoichiometry could not be determined.

1-Hydroxy-2-Naphthoate Salt, Xin1

Figure 121:
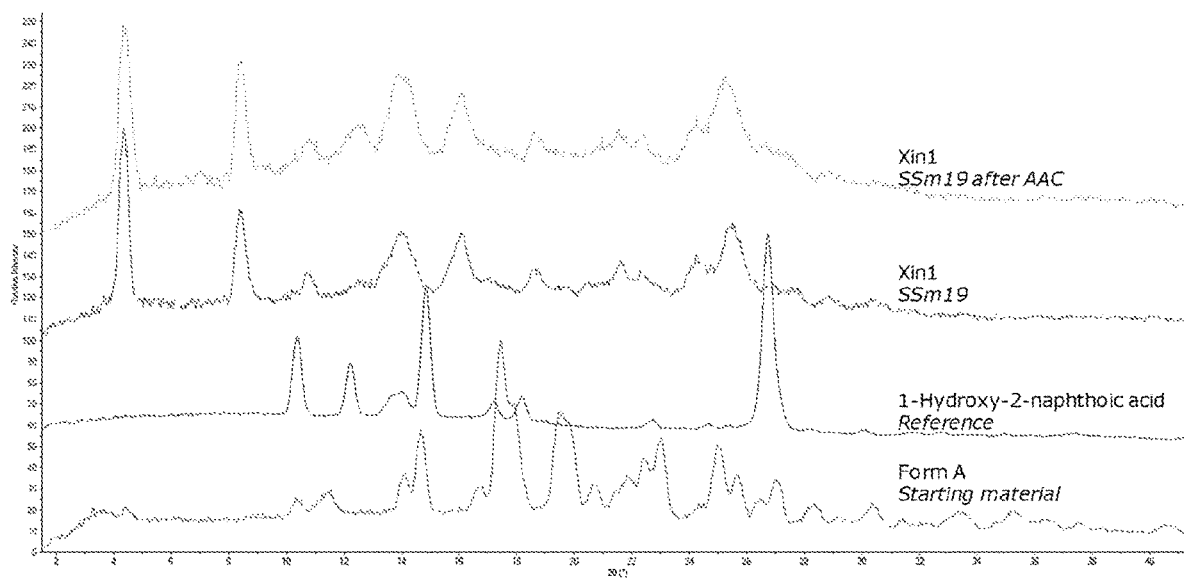

With 1-hydroxy-2-naphthoic acid the same XRPD pattern was obtained from all three solvents, Xin1. Xin1 was physically stable during exposure to AAC and in FIG. 121 the powder patterns of Xin1 before and after exposure to AAC for two days are presented. The stable crystalline malonate salt Xin1 (Exp. ID SSm19) was further analyzed by TGMS. The TGMS analysis (FIG. 122) of Xin1 showed a gradual mass loss of 12% between 25-200° C. The mass loss is related to loss of THF followed by decomposition. The endothermic event in the heat flow signal between 160-180° C. most likely indicates the dissociation/decomposition of the salt.

Benzoate Salt, Ben2

With benzoic acid three different XRPD patterns were obtained. From THF Ben1 was obtained and from ethanol and acetone Ben2 was obtained. Ben1 was physically unstable during exposure to AAC for two days and converted to Ben3. The XRPD patterns of the different forms have some similarities and are shown in FIG. 123. In FIG. 124 the powder patterns of Ben2 obtained from ethanol (Exp. ID SSm63) before and after exposure to AAC for two days are presented. The benzoate salt Ben2 obtained from ethanol (Exp. ID SSm63) was further analyzed by TGMS. The TGMS analysis (FIG. 125) showed a mass loss of 4.5% between 25-100° C., followed by decomposition. The mass loss is most likely due to ethanol and water. The heat flow showed an endothermic event around 170° C. that could be due to melting/decomposition events.

Besylate Salt, Bes1

With benzenesulfonic acid one salt was obtained from each solvent, Bes1. Bes1 was physically unstable during exposure to AAC and became less crystalline and most likely dissociation of the salt took place. In FIG. 126 the powder patterns of Bes1, obtained from THF (Exp. ID SSm10), before and after exposure to AAC for two days are presented. The besylate salt Bes1 obtained from THF was further analyzed by TGMS. The TGMS analysis (FIG. 127) of Bes1 showed an immediate mass loss of 8.1% (25-180° C.), followed by decomposition around 230° C. The besylate salt is most likely a solvated form and is not stable as a non-solvated form.

Gentisate Salt, Gen1

With gentisic acid 2 different XRPD patterns were obtained. From the experiment in THF the crystalline salt Gen1 was obtained after evaporation of the solvent. From acetone and ethanol poor crystalline solids had precipitated, Gen2_1c. The XRPD patterns of the two forms are shown in FIG. 128. Based on crystallinity and physical stability, Gen1 was selected for further characterization. In FIG. 129 the powder patterns of Gen1 before and after exposure to AAC for two days are presented. The solid obtained from THF (Exp. ID SSm21) was further characterized by TGMS analysis. The TGMS analysis (FIG. 130) of Gen1 showed a mass loss of 9.2% between 25-200° C. The mass loss is related to solvent loss and thermal decomposition. The endothermic event observed in the heat flow signal around 130° C. might be related to the solvent loss.

Hydrobromide Salt, HBr1

With hydrobromic acid in ethanol the crystalline salt HBr1 was obtained. From acetone and THF poor crystalline/amorphous solids were recovered. The crystalline solid HBr1 was physically unstable during exposure to accelerated aging conditions and converted to HBr2. In FIG. 131 the powder patterns of the solid before and after exposure to AAC for two days are presented. The hydrobromide salt HBr1 (Exp. ID SSm34) was further characterized by TGMS analysis. The TGMS analysis (FIG. 132) of HBr1 showed a mass loss of 5.9% due to loss of ethanol. The heat flow signal recorded several endothermic events related to the mass loss and the endothermic event at 170° C. is most likely related to the melting. Decomposition started around 240° C. The result suggest that the HBr1 is a solvated salt and is unstable as non-solvated form.

Maleate Salt, Mae1

With maleic acid two different XRPD patterns were obtained. From the experiment in THF and acetone a pure salt phase Mae1 was obtained. From ethanol a mixture of Mae1 and Mae2 was obtained. The XRPD patterns of the two forms are shown in FIG. 133. Mae1 was physically stable during AAC, while the mixture of Mae1 and Mae2 converted to Mae1. In FIG. 134 the powder patterns of Mae1 before and after exposure to AAC for two days are presented. The stable crystalline salt Mae1 (Exp. ID SSm14) was further analyzed by TGMS. The TGMS analysis (FIG.

135) of Mae1 showed a mass loss of 3.4% between 25-110° C. most likely due to loss of THF and/or water, followed by decomposition.

Sulfate Salt, Sul1

Experiments with sulfuric acid were performed with half molar and one molar equivalent. In total four different XRPD patterns were observed. Sul1 and Sul4 were mostly observed in the experiments using 1 molar equivalent and Sul2 was only observed in experiments using half molar equivalent sulfuric acid. However after evaporation of the mother liquors of the experiments that resulted in Sul2 in the solid phase resulted in either Sul1 or Sul3. The unique XRPD patterns obtained from experiments with sulfuric acid are shown in FIG. 136. Based on crystallinity and physical stability, Sul1 was selected for further characterization. In FIG. 137 the powder patterns of Sul1 before and after exposure to AAC for two days are presented. The stable crystalline salt Sul1 (Exp. ID SSm37) was further characterized by TGMS analysis. The TGMS analysis (FIG. 138) of Sul1 showed a mass loss of 2.4% between 25-120° C. and 5.8% between 120-200° C., suggesting that the salt is a solvated form. Decomposition is observed above 240° C.

Toluenesulfonate Salt, Tos2

With p-toluenesulfonic acid two different XRPD patterns were obtained from the experiments and after AAC the appearance of a third form was observed. From the experiment in ethanol the crystalline salt Tos2 was obtained. From acetone and THF poor crystalline solids were recovered, Tos1. The XRPD patterns of the observed forms with toluenesulfonic acid are shown in FIG. 139. In FIG. 140 the powder patterns of Tos2 before and after exposure to AAC for two days are presented. The stable crystalline toluenesulfonate salt Tos2 (Exp. ID SSm41) was further characterized by TGMS. The TGMS analysis (FIG. 141) of Tos2 showed a mass loss of 4.6%, due to loss of ethanol, between 25-110° C. and was immediately followed by degradation.

Free Base Forms

The control samples resulted in the formation of Form B in ethanol and acetone and Form C in THF. The novel polymorphic forms of the free base were physically stable during exposure to AAC for two days. The XRPD patterns of the free base are shown in FIG. 142. Forms B and C were analyzed by TGMS. The TGMS analysis of Form B is shown in FIG. 143 and indicated that Form B is a non-solvated and anhydrous form with a melting around 220° C. Decomposition occurred above 250° C. The TGMS analysis of Form C is shown in FIG. 144 and indicates that Form C is most likely a solvated form. A mass loss of 2.6% is observed prior to melting around 220° C. Decomposition is observed around 250° C.

Summary of Several Voruciclib Salts

The results of the physico-chemical characterization and solubility study on five salt candidates compared to the free base and HCl salt of voruciclib are summarized in Table 32. Without wishing to be bound by any particular theory, it is believed that salts had improved solubility compared to the free base and HCl salt and none of the salt candidates formed gels in the aqueous media.

TABLE 32

Ranking of salt candidates of voruciclib based on physico-chemical properties and solubility behavior in water and 0.2M phosphate buffer (pH 6).

| Salt | Form | No of polymorphs | Residual solvent (%) | Decomposition (° C.) | Solubility water (mg/mL) | Solubility pH 6 (mg/mL) |
|---|---|---|---|---|---|---|
| Voruciclib Free base | A | >2 | 0.3 | 240 | <0.01 | 0.01 |
| Voruciclib HCl salt | HCl1 | >2 | 0.2 | 250 | Gel | 0.01 |
| Hemi-dibenzoyl-L-tartrate | DiTr1 | 2 | 0.9 | 180 | 0.03 | 0.04 |
| Malonate | Mao1 | 2 | 0.2 | 140/160 | 4.4 | 0.07 |
| Phosphate | Pho1 | 2 | 1.9 | 190 | >5.2 | 0.03 |
| Hemi-napadisylate | Nds1a | >2 | 1.1 | 250 | 0.02 | 0.02 |
| Hemi-oxalate | Oxa1 | 1 | Hemi-hydrate | 160 | — | 0.03 |

All these selected salt forming acids are included in the list of Pharmaceutical Salts (Handbook of Pharmaceutical Salts: properties, selection and use; P. Heinrich Stahl, Camille G. Wermuth; Wiley-VCH), except for dibenzoyl tartaric acid. Malonic, phosphoric, oxalic and 1,5-naphthalene disulfonic acids are used in commercially available products in the US, Europe and Japan.

Example 3: Voruciclib Oxalate

Previous studies performed on the HCl salt showed that the material exhibited complex pseudo-polymorphic behavior and a tendency to form a gel in aqueous media. For that reason, a previous salt screen evaluated the isolation of alternative salts of voruciclib with better physico-chemical properties than the HCl salt. A solid form screen on the oxalate salt to assess its polymorphic behavior was performed. For this aim, a polymorph screen was designed involving thermocycling experiments in 15 solvents as well as cooling crystallization experiments.

The received material was a voruciclib oxalate salt which was classified as Oxa2. The starting material was an anhydrous salt with a purity of 96% and an API:CI ratio of 1:1. The polymorph screen experiments were started with amorphous voruciclib oxalate salt to enable unbiased crystallization. In total, 7 oxalate forms were identified in the present study. Most oxalate forms from the polymorph screen were unstable upon drying under vacuum or upon exposure to short-term stress conditions, except for Oxa1, Oxa2 and Oxa7. Oxa1 was characterized as a hemi-oxalate/hemihydrate salt having cavities in its structure which could accommodate solvent or water molecules. The crystal structure of several Oxa1 forms was determined by single crystal analysis. The unit cell dimensions were slightly different and also the amounts of solvent or water was variable for such structures. Oxa7 was characterized as a hemi-oxalate hydrate. Crystals of Oxa7 could not be obtained through cooling crystallization. Oxa2 (anhydrous salt) was most often found in the polymorph screen and was selected as the most promising oxalate form. Therefore, additional analytical data was obtained for Oxa2. The solubility of Oxa2 in water at room temperature was low (<0.1 mg/ml) and the material was moderately hygroscopic. Upon the addition of water, Oxa2 became a suspension and no gel formation was observed. Crystals of Oxa2 could not be obtained through cooling crystallization.

Within the investigated experimental conditions, Oxa2 appeared to be the most favored crystalline form of the oxalate salts. However, Oxa2 was moderately hygroscopic, showed poor aqueous solubility and cooling crystallization of Oxa2 was not feasible. In addition, the polymorph screen yielded both hemi- and mono-oxalate forms which could pose a problem for producing the oxalate salt with the desired stoichiometry of counterion. Based on the parallel polymorph screens performed on the phosphate and malonate salts of voruciclib. Mao1 was identified as a non-hygroscopic anhydrous form which exhibited limited polymorphism. The form could be reproduced through cooling crystallization in high yield.

Abbreviations

AAC Accelerated Aging Conditions (40° C. and 75% RH for 2 days)
Am Amorphous
API Active Pharmaceutical Ingredient
DSC Differential Scanning Calorimetry
DVS Dynamic Vapor Sorption
H-bond Hydrogen bond
$^1$H-NMR Proton Nuclear Magnetic Resonance
HR-XRPD High Resolution X-Ray Powder Diffraction
HT-XRPD High Throughput X-Ray Powder Diffraction
Lc Low crystallinity
LCMS Liquid Chromatography Mass spectroscopy
MS Mass Spectroscopy
ML Mother Liquor (liquid phases)
MW Molecular Weight
Pc Poorly Crystalline
QSA Experiment ID for the freeze-drying experiments
RF Response Factor
RH Relative Humidity
RT Room Temperature
SAS Experiment ID for the solubility determination experiments
SM Starting Material
SSR Solid State Research
TCP Experiment ID for the thermocycling experiments
TGA Thermogravimetric Analysis
TGMS Thermogravimetric Analysis coupled with Mass Spectroscopy
TMS Tetramethylsilane
UPLC Ultra-Performance Liquid Chromatography
Wt % Weight percentage
DME 1,2-Dimethoxyethane
DMSO-$d_6$ Deuterated dimethyl sulfoxide
EtOH Ethanol
IPA 2-Propanol
Mao Malonate salt
MeOH Methanol
Oxa Oxalate salt
TBME tert-Butyl methyl ether
TFE 2,2,2-Trifluoroethanol
THF Tetrahydrofuran The polymorphic behavior of the oxalate salt (FIG. 145) has been evaluated in a solid form screen. A thermocycling screen involving 15 solvents to identify novel crystalline phases of voruciclib oxalate salt and to select the best form for further investigations was designed. This study consisted of the following project steps: Starting material characterization; Generation of amorphous oxalate salt; Thermodynamic solid form screen in 15 solvents; Analytical characterization of novel solid forms.

29.13 grams of voruciclib oxalate salt were provided (batch ID: 19-09333-01) as a crystalline powder (starting material). The High Throughput-XRPD (HT-XRPD) patterns of the starting material, Oxa1, oxalic acid-dihydrate and oxalic acid are shown in FIG. 146. Based on the XRPD pattern comparisons, the starting material contained no traces of oxalic acid or oxalic acid-dihydrate. The material obtained in the salt screen was classified as Oxa1 and was different by XPRD as compared to the received starting material in the present study. The starting material in the present study was classified as Oxa2.

An HR-XRPD analysis was performed on the starting material (Oxa2). Rietveld analysis (FIG. 147) revealed that the starting material was a crystalline phase with approximately 1% of unidentified impurities.

The TGMS analysis in FIG. 148 shows that between 40-100° C. approximately 1.1% of water was released, corresponding to approximately 0.3 molecules of water per molecule of API. Between 180-240° C., the material underwent thermal decomposition as indicated by a significant mass loss. The DSC analysis of the starting material is shown in FIG. 149. A single broad endothermic event was observed at 218° C. The chemical purity of the API was assessed by LCMS analysis (FIG. 150). The result indicated that the API purity was 95.5% (area %). The positive ion spectrum showed ions with m/z of 470 corresponding to the positively charged species [M+H]$^+$ and agreed with the molecular mass of the free base (i.e. 470 g/mol). Based on the LCMS assay analysis, the ratio of API:oxalate is 1:1. FIG. 151 shows the $^1$H-NMR spectrum and molecular structure of Oxa2 (starting material). Overall, 17 of the 20 hydrogen atoms of the molecule could be assigned to the peaks in the spectrum. The remaining three undetected hydrogens correspond to two OH and NH groups of the API. The 11 aliphatic hydrogens of the pyrrolidine group appeared between 2-4 ppm (group a). The two aromatic hydrogens on the benzopyran ring appeared between 6-7 ppm (group b) whereas the three aromatic hydrogens of the halogenated aromatic ring appeared further downfield at 8 ppm (group c). The hydrogen at 12.8 ppm (d) most likely belongs to one of the alcohol groups. Compared to both the free base and the Oxa1 spectrum, only the NMR peaks of the pyrrolidine (a) and benzopyran (b) group of the starting material were shifted further downfield. A Dynamic Vapor Sorption (DVS) measurement was performed on Oxa2 (starting material). As shown in FIG. 152, the material gradually took up water with increasing relative humidity (RH). At 25° C./80% RH, the water uptake was approximately 2.4%, which makes the material moderately hygroscopic (European Pharmacopoeia Hygroscopicity classification. Water uptake percentage at 25° C./80% RH is: Change in mass <0.2%—Non-hygroscopic; Change in mass <2% & >0.2%—Slightly hygroscopic; Change in mass <15% & 2%—Moderately hygroscopic; Change in mass >15%—Very hygroscopic).

After DVS analysis, Oxa2 was recovered as indicated by XRPD. The solubility of Oxa2 (starting material) in water at room temperature was determined by the qualitative solubility determination. Oxa2 (starting material) was practically insoluble in water at room temperature, as the aqueous solubility <0.1 mg/ml, according to the USP classification.

Upon the addition of water to Oxa2 (starting material), the material became a uniform suspension. No indication of gel-formation was observed.

Generally, it is preferred to start a polymorph screen with amorphous material to avoid biased crystallization. Amorphous material was produced by lyophilization of Oxa2 (starting material) from different water/organic solvent mixtures. The conditions selected to generate amorphous material for the polymorph screen involved lyophilization of the starting material from acetone/water (50/50, v/v). After freeze-drying, the material was analyzed by HT-XRPD to confirm that the resulting material was amorphous (FIG. 154). Based on the TGMS analysis of the amorphous material, the residual solvent content was 3.2% (FIG. 155). The DSC trace in FIG. 156 shows three endothermic events between 25-140° C. which may be associated to solvent removal. The broad endothermic event between 185-230° C. is the result of thermal decomposition of the oxalate salt. $^1$H-NMR analysis confirmed that the chemical identity of the oxalate salt was retained after lyophilization (FIG. 157). The chemical shifts of the amorphous material corresponded with the starting material oxalate salt (Oxa2) but were shifted with respect to the free base sample.

Amorphous voruciclib oxalate salt, generated by freeze-drying, was used to start the thermocycling experiments. Suspensions were prepared in the selected solvent systems at RT. Subsequently, the mixtures were subjected to a temperature profile. After the temperature profile, the solids were separated from the solutions by centrifugation and were dried at ambient conditions and under deep vacuum before being harvested and analyzed by HT-XRPD. The liquid phases were also dried under deep vacuum before being harvested and analyzed by HT-XRPD. All solids were exposed to AAC (40° C./75% RH, 2 days).

In total, seven salt forms were identified in the polymorph screen performed on the oxalate salt, which were designated Oxa1, Oxa1e, Oxa2, Oxa3, Oxa4, Oxa6 and Oxa7. Oxa1, Oxa2 and Oxa7 were physically stable upon exposure to both vacuum drying (5 mbar, 18 h) and AAC (40° C./75% RH, 2 days) and were selected for further characterization. The results are summarized in Table 33.

Oxa1 was the salt form identified in the previous screen (S18128) and existed as a hemi-oxalate/hemi-hydrate form with cavities in its structure which could accommodate solvents and/or water. In the case of Oxa1e, the structure most likely contained acetone and water. Oxa2 was most often obtained in the polymorph screen and was also the form obtained as the starting material. Analysis of Oxa2 obtained from 2-propanol (Exp. ID: TCP18) confirmed that the material has an API:CI ratio of 1:1. Oxa2 was physically stable upon exposure to AAC.

Oxa3 was obtained from 2-propanol/water (90/10, v/v) but converted into a mixture of Oxa1+Oxa4 upon drying under high vacuum (5 mbar, 18 h). In some experiments, the amorphous materials converted into Oxa3 upon exposure to AAC (40° C./75% RH, 2 days). The solid obtained in Exp. ID: TCP21 in combination with chloroform was initially Oxa6 but converted into Oxa3 upon exposure to AAC (40° C./75% RH, 2 days).

Oxa4 was obtained as a mixture with Oxa1 in the thermocycling experiment (Exp. ID: TCP30) involving 2-propanol/water (90/10, v/v), after the material was dried under vacuum (5 mbar, 18 h).

Oxa6 was obtained in the thermocycling experiment involving chloroform (Exp. ID: TCP21). Oxa6 was physically unstable as it converted into Oxa3 upon exposure to AAC (40° C./75% RH, 2 days).

Oxa7 was obtained in the thermocycling experiment involving ethanol (Exp. ID: TCP23). Oxa7 was physically stable upon exposure to both AAC (40° C./75% RH, 2 days) and vacuum conditions (5 mbar, 18 h).

TABLE 33

Results of the thermocycling experiments performed on the oxalate salt. "—" indicated that no solids were recovered after evaporation of the solutions. "Am" stands for amorphous, "peaks" indicate that diffraction peaks were detected in addition to Oxa2 and poorly crystalline samples are denoted with "pc". Highlighted in green are the samples that were selected for further analytical characterization.

| Exp. ID | Solvent | Concentration (mg/mL) | Solid forms | | | | | |
|---|---|---|---|---|---|---|---|---|
| | | | Ambient | Vacuum | ML | Ambient AAC | Vacuum AAC | ML AAC |
| TCP16 | DME | 67 | Oxa1 + Oxa2 | Oxa1 + Oxa2 | Oxa2 | Oxa1 + Oxa2 | Oxa1 + Oxa2 | Oxa2 |
| TCP17 | 1,4-Dioxane | 67 | Oxa2 + peaks | Oxa2 + peaks | — | Oxa2 + peaks | Oxa2 + peaks | — |
| TCP18 | 2-Propanol | 33 | Oxa2 | Oxa2 | Am | Oxa2 | Oxa2 | Oxa3 (pc) |
| TCP19 | Acetone | 67 | Oxa2 | Oxa2 | — | Oxa2 | Oxa2 | — |
| TCP20 | Acetonitrile | 33 | Oxa2 | Oxa2 | — | Oxa2 | Oxa2 | — |
| TCP21 | Chloroform | 67 | Oxa6 | Oxa6 | — | Oxa3 | Oxa3 | — |
| TCP22 | Cyclohexane | 22 | Am | Am | — | Oxa3 (pc) | Oxa3 (pc) | — |
| TCP23 | Ethanol | 67 | Oxa7 | Oxa7 | — | Oxa7 | Oxa7 | — |
| TCP24 | Ethyl acetate | 22 | Oxa2 | Oxa2 | Oxa2 | Oxa2 | Oxa2 | Oxa2 |
| TCP25 | Ethyl formate | 22 | Oxa2 | Oxa2 | — | Oxa2 | Oxa2 | — |
| TCP26 | TBME | 67 | Am | Am | Am | Am | Am | Oxa3 |
| TCP27 | Tetrahydrofuran | 67 | Oxa2 | Oxa2 | — | Oxa2 | Oxa2 | — |
| TCP28 | Toluene | 67 | Am | Am | — | Am | Oxa3 (pc) | — |
| TCP29 | Acetone/water 90/10 | 67 | Oxa1e | Oxa1 | — | Oxa1 | Oxa1 | — |
| TCP30 | IPA/water 90/10 | 67 | Oxa3 | Oxa1 + Oxa4 | — | Oxa3 | Oxa1 + Oxa3 | — |

Solid State Characterization

An overlay of the powder diffraction patterns of the solid forms identified in this study is presented in FIG. 158. The various similar Oxa1 forms (i.e. Oxa1a-Oxa1e) are shown in FIG. 162.

Additional analytical data including DSC, TGMS, UPLC and $^1$H-NMR were obtained for the three physically stable solid forms (Oxa1, Oxa2 and Oxa7). A summary of the results is presented below and in Table 34.

The thermal analyses performed on the oxalate salt forms indicated that Oxa2 is the only anhydrous oxalate salt form. Oxa1 is a hemi-oxalate/hemihydrate containing non-stochiometric water in its cavities whereas Oxa1e was identified as a similar form to Oxa1 but with non-stochiometric amounts of ethanol in the structure. Oxa7 appeared to be a hemi-oxalate form with a water content of 3.4%.

The UPLC analyses confirmed that all oxalate salt forms were obtained with good chemical purities (>96%, UPLC area %). The lowest chemical purity was determined for the Oxa2 starting material (95.5%).

The $^1$H-NMR spectra for the different oxalate salt forms showed significant shifts in the resonances with respect to the free base which confirmed that salt formation occurred. All the spectra were compared to the free base used in the previous project (SM, S18128) and with the received oxalate starting material (Oxa2).

which exhibits structural cavities that can accommodate water and/or process solvents. As a result, Oxa1 can adopt different configurations leading to several different forms (designated as Oxa1a-Oxa1e).

Oxa7 was only obtained from ethanol and was characterized as a hemi-oxalate salt with 3.4% of residual water. However, cooling crystallization of the oxalate salt from ethanol led to the crystallization of Oxa5.

Oxa2 was the crystalline phase found most often in the present screen which is the only anhydrous crystalline phase characterized in this study and which was received as starting material.

However, Oxa2 was moderately hygroscopic and was practically insoluble in water at room temperature (solubility <0.1 mg/ml). Cooling crystallization attempts to obtain Oxa2 from THF, ethanol and acetone resulted in Oxa1 and Oxa5 instead. Furthermore, the polymorph screen yielded both hemi- and mono-oxalate forms which could pose a

TABLE 34

Summary of the analytical characterization performed on the oxalate salt forms of voruciclib found in this study which remained physically stable upon high vacuum (5 mbar) and AAC (40° C., 75% RH). The thermal analyses were performed by DSC, the chemical purity and API:CI ratio was determined by UPLC assay. The solvent content was determined by TGMS (for water) and by $^1$H-NMR for organic solvents. The notations "br", "m" and "d" stand, respectively, for broad endotherm corresponding to water loss, melting or decomposition events.

| Solid form | Exp. ID | Crystallization solvent | Solvent Content (wt %) | Thermal events by DSC | UPLC Purity (area %) | API:CI ratio |
|---|---|---|---|---|---|---|
| Oxa1 | TCP29 | Acetone/water (90/10) | 5.5% water | 46.6 (br), 110.8 (br), 151.3 (m), 180-240 (d) | 99.3 | 1:0.5 |
| Oxa2 | SM | — | 1.1% water | 219 (d) | 95.5 | 1:1 |
| Oxa2 | TCP18 | 2-Propanol | 1.7% water + 0.4% 2-propanol | 219 (d) | 98.2 | 1:1 |
| Oxa7 | TCP23 | Ethanol | 3.0% water + 0.4% ethanol | 25-120 (br), 153.9 (m), 180-240 (d) | 96.9 | 1:0.5 |

Cooling Crystallization Experiments

Based on the solid-state characterization, Oxa2 appeared to be the most promising oxalate form. Therefore, additional cooling crystallization experiments were performed to attempt the controlled crystallization of Oxa2. These experiments were started by mixing voruciclib free base solutions (from batch 1694ER1201) prepared in three different crystallization solvents and 1.3 eq. of 1M aqueous oxalic acid solutions (API:CI ratio of 1:1.3) at 50° C. Subsequently, a cooling profile was applied until a temperature of 40° C. was reached upon seed crystals of Oxa2 were added. Subsequently, the solutions were cooled to 5° C.

In all cooling crystallization experiments, the seed crystals dissolved after addition to the solutions. From THF, no salts precipitated upon cooling. From ethanol, a new salt form was isolated in 72% yield, which was designated as Oxa5. Oxa5 was unstable upon exposure to AAC (40° C./75% RH). From acetone, Oxa1 was obtained in 40% yield.

The polymorph screen on voruciclib malonate salt was started with the amorphous phase to favor unbiased crystallization of novel forms. In total, seven polymorphic forms were identified in the present study from which Oxa1, Oxa2 and Oxa7 were determined to be physically stable upon both vacuum drying and AAC (40° C./75% RH, 2 days).

Oxa1 was obtained in the previous salt screen (S18128) and was herein identified as a hemi-oxalate/hemihydrate problem for producing the salt with a controlled API:counterion stoichiometric ratio.

Preparation of Amorphous Voruciclib Oxalate Salt

Preferably a polymorph screen is initiated with an amorphous phase to promote unbiased crystallization. The generation of amorphous material was attempted through lyophilization of the Oxa2 (starting material) from different organic/water mixtures (Table 35). In the most polar protic solvents tested (i.e. water, MeOH/water and EtOH/water), the material did not dissolve at room temperature with a concentration of 20 mg/mL and these conditions were therefore not suitable for freeze-drying. An amorphous phase was obtained after freeze-drying in the experiments in which the material completely dissolved. The material obtained through lyophilization from acetone/water (50/50) resulted in an amorphous phase with the least amount of residual solvent of 4.3% which could further be reduced by subjecting the material to high vacuum (5 mbar) for 18 h at RT (Exp. ID QSA3). These conditions were used to generate amorphous materials for the polymorph screen. An API solution was prepared in acetone/water 50/50 (Exp. ID: QSA8) and liquid-dosed over 18 vials. The solutions were frozen in liquid nitrogen and placed under deep vacuum using a freeze dryer (Alpha 2-4 LD, Christ). Solvents were removed by freeze-drying. A sample (Exp. ID: QSA8) of amorphous material was taken from the polymorph screen as a reference and analyzed by HT-XRPD, TGMS and $^1$H-NMR.

TABLE 35

Conditions and results of the experiments to produce amorphous solids. Solutions were prepared with voruciclib oxalate. The solutions were freeze-dried overnight and the resulting solids were analyzed by HT-XRPD and by TGMS to determine the solvent content. The solid materials were subjected to high vacuum (5 mbar) for 18 h and reanalyzed by TGMS. Samples that were not analyzed are indicated by "—", amorphous materials are denoted as "Am" and samples which exhibited low crystallinity are indicated with "Lc".

| Exp. ID | API [mg] | Solvent (v/v) | Solvent [ml] | Concentration [mg/ml] | Dissolved? | Material after freeze-drying | Solvent content by TGMS [%] Ambient | Vacuum |
|---|---|---|---|---|---|---|---|---|
| QSA1 | 20.7 | t-Butanol/water (50/50) | 1 | 21 | Yes | Am | 5.5 | 3.2 |
| QSA2 | 23.8 | THF/water (50/50) | 1 | 24 | Yes | Lc | — | — |
| QSA3 | 20.3 | Acetone/water (50/50) | 1 | 20 | Yes | Am | 4.3 | 2.7 |
| QSA4 | 19.8 | EtOH/water (50/50) | 1 | 20 | No | — | — | — |
| QSA5 | 23.6 | MeOH/water (50/50) | 1 | 24 | No | — | — | — |
| QSA6 | 21.9 | TFE/water (50/50) | 1 | 22 | Yes | Lc | — | — |
| QSA7 | 19.1 | Water | 1 | 19 | No | — | — | — |
| QSA8 | 511.0 | Acetone/water (50/50) | 10 | 51 | Yes | Am | 4.2 | 3.2 |

Qualitative Solubility Determination

The aqueous solubility of Oxa2 (starting material) was assessed by the qualitative solubility determination approach. To 5.4 mg of Oxa2, water was added in steps of 50 μl until the material was dissolved (Exp. ID: SAS1). Visual inspection by the naked eye was used to decide whether complete dissolution occurred.

After the addition of 7.5 ml water, Oxa2 was not dissolved in water at room temperature. The suspension was heated to 50° C. upon which complete dissolution occurred, as indicated by a clear solution.

Thermocycling Experiments

Suspensions of amorphous voruciclib oxalate salt were prepared in the selected solvent systems. About 33 mg of API were mixed with 15 solvent systems at room temperature (see Table 36 for details). Subsequently, the mixtures were placed in the Crystal16™ apparatus and were subjected to the temperature profile as displayed in FIG. 159.

After the temperature profile, the solids were separated from the liquids by centrifugation and the solid phase was dried at ambient conditions and under deep vacuum (5 mbar) before being harvested and analyzed by HT-XRPD. The liquid phases were dried under deep vacuum (5 mbar) and the recovered solids were analyzed by HT-XRPD. All solids were then exposed to accelerated aging conditions (40° C./75% RH, 2 days) followed by HT-XRPD re-analysis.

TABLE 36

Experimental conditions for the thermocycling experiments. Slurries of amorphous voruciclib oxalate were prepared in neat solvents and solvent mixtures and placed in the Crystal16 ™ reactor to undergo a thermal profile as described in FIG. 159. After the temperature profile, the solids were ambient-dried and vacuum-dried and analyzed before and after exposure to AAC by HT-XRPD. The solutions were dried under vacuum and the obtained dried solids were analyzed by XRPD.

| Exp ID | Mass SM (mg) | Solvent | Solvent volume (μL) | Concentration (mg/mL) | Dissolved at initial temperature | Solids after Tprofile |
|---|---|---|---|---|---|---|
| TCP16 | 33.3 | 1,2-Dimethoxyethane | 500 | 67 | No | Yes |
| TCP17 | 33.3 | 1,4-Dioxane | 500 | 67 | No | Yes |
| TCP18 | 33.3 | 2-Propanol | 1000 | 33 | No | Yes |
| TCP19 | 33.3 | Acetone | 500 | 67 | No | Yes |
| TCP20 | 33.3 | Acetonitrile | 100 | 33 | No | Yes |
| TCP21 | 33.3 | Chloroform | 500 | 67 | No | Yes |
| TCP22 | 33.3 | Cyclohexane | 1500 | 22 | No | Yes |
| TCP23 | 33.3 | Ethanol | 500 | 67 | No | Yes |
| TCP24 | 33.3 | Ethyl acetate | 1500 | 22 | No | Yes |
| TCP25 | 33.3 | Ethyl formate | 1500 | 22 | No | Yes |
| TCP26 | 33.3 | t-Butyl methyl ether | 500 | 67 | No | Yes |
| TCP27 | 33.3 | Tetrahydrofuran | 500 | 67 | No | Yes |
| TCP28 | 33.3 | Toluene | 500 | 67 | No | Yes |
| TCP29 | 33.3 | Acetone/water (90/10) | 500 | 67 | No | Yes |
| TCP30 | 33.3 | 2-Propanol/water (90/10) | 500 | 67 | No | Yes |

Cooling Crystallization Experiments

Additional crystallization attempts were performed to prepare the selected oxalate salt form Oxa2 by cooling crystallization and to evaluate the yield of such experiment. The three experiments performed consisted of preparing a saturated solution of the free base (received for project S18128, batch 1694ER1201) in ethanol, THF and acetone at 50° C. Suspensions of ME-522 were incubated at 50° C. for 3 hours and afterwards were filtrated. To the 1-ml saturated solutions, 1.3 equivalent of oxalic acid was added as a 1M aqueous stock solution. The experimental conditions are described in table 37.

After addition of the counterion, the solutions were subjected to a temperature profile in a Crystal16™ apparatus. After 30 min at 50° C., the temperature of the solutions was lowered with a cooling rate of 10° C./h. At 40° C., seed crystals of Oxa2 were added and cooling continued at a rate of 10° C./h until the temperature of 5° C. was reached. Aging for 18 hours at the final temperature (5° C.) was finally applied.

After the temperature profile the solids were separated from the solution by centrifugation and were dried at ambient conditions and under deep vacuum (5 mbar) before being harvested and analyzed by HT-XRPD. The solids were also subjected to AAC (40° C./75% RH, 1 day) and reanalyzed by HT-XRPD. The mother liquors were evaporated to assess the yield based on the weight of the solids.

TABLE 37

Experimental conditions and results for the additional cooling crystallization experiments performed on voruciclib free base to produce the oxalate salt.

| Exp ID | Mass SM (mg) | Solvent | Yield (%) | Ambient | Vacuum | Stability AAC |
|---|---|---|---|---|---|---|
| SSm1 | 107 | Tetrahydrofuran | — | — | — | — |
| SSm2 | 40 | Ethanol | 72 | Oxa5 | Oxa5 | Unstable |
| SSm3 | 44 | Acetone | 40 | Oxa1 | Oxa1 | Stable |

Analytical Methods
High Throughput X-Ray Powder Diffraction

XRPD patterns were obtained using the Crystallics T2 high-throughput XRPD set-up. The plates were mounted on a Bruker D8 Discover General Area Detector Diffraction System (GADDS) equipped with a VÅNTEC-500 gas area detector corrected for intensity and geometric variations (product sheet XRD 37, DOC-S88-EXS037V3, FIG. 297). The calibration of the measurement accuracy (peaks position) was performed using NIST SRM1976 standard (Corundum).

Data collection was carried out at room temperature using monochromatic Cu Kα radiation in the 2θ region between 1.5° and 41.5°, which is the most distinctive part of the XRPD pattern. The diffraction pattern of each well was collected in two 2θ ranges (1.5°≤2θ≤21.5° for the first frame, and 19.5°≤2θ≤41.5° for the second) with an exposure time of 90 s for each frame. No background subtraction or curve smoothing was applied to the XRPD patterns. The carrier material used during XRPD analysis was transparent to X-rays and contributed only slightly to the background.

High Resolution X-Ray Powder Diffraction

The HR-XRPD data were collected on D8 Advance diffractometer using Cu $K_{\alpha 1}$ radiation (1.54056 Å) with germanium monochromator at RT. Diffraction data were collected in the 2θ range 1.5-41.5° 2θ. Detector scan on solid state LynxEye detector was performed using 0.016° per step with 4 sec/step scan speed (DOC-M88-EXX95 V2—11.2007, FIG. 298). The samples were measured in 8 mm long glass capillary with 0.4 mm outer diameter.

Calculations

For Rietveld calculations the cell parameters, crystal system as well as atom positions were taken from the single crystal file (cif). The results for Oxa1, Oxa1b and Oxa2 are shown in Table 38. During the refinement the following parameters were refined:

cell constants;
background;
instrument geometry;
zero shift;
absorption

Neither atom positions nor thermal motion parameters were refined during whole process. The following criteria of fit were used:

$Y_{o,m}$ and $Y_{c,m}$ are the observed and calculated data, respectively at data point m,
M the number of data points,
P the number of parameters,
$w_m$ the weighting given to data point m which for counting statistics is given by $w_m = 1/\sigma(Y_{o,m})^2$ where $\sigma(Y_{o,m})$ is the error in $Y_{o,m}$, $$R_{exp} = \sqrt{\frac{M-P}{\sum w_m Y_{o,m}^2}} ;$$

$$R_{wp} = \sqrt{\frac{\sum w_m (Y_{o,m} - Y_{c,m})^2}{\sum w_m Y_{o,m}^2}} ;$$

$$R_p = \sqrt{\frac{\sum |Y_{o,m} - Y_{c,m}|}{\sum Y_{o,m}}}$$

$$GOF = chi^2 = \frac{R_{wp}}{R_{exp}} = \sqrt{\frac{\sum w_m (Y_{o,m} - Y_{c,m})^2}{M-P}}$$

TABLE 38

Crystal data obtained from HR-XRPD for Oxa1, Oxa1b and Oxa2 (SM).

| Polymorph | Oxa1 | Oxa1b | Oxa2 (SM) |
|---|---|---|---|
| Empirical formula | [($C_{22}H_{20}ClF_3NO_5^+$)•0.5 ($C_2O_4^{2-}$)•0.5 ($H_2O$)] | [($C_{22}H_{20}ClF_3NO_5^+$)•0.5 ($C_2O_4^{2-}$)•0.5 ($H_2O$)] | [($C_{22}H_{20}ClF_3NO_5^+$)•0.5 ($C_2O_4^{2-}$)] |
| Formula weight | 523.82 | 523.82 | 514.82 |

TABLE 38-continued

Crystal data obtained from HR-XRPD for Oxa1, Oxa1b and Oxa2 (SM).

| Polymorph | Oxa1 | Oxa1b | Oxa2 (SM) |
|---|---|---|---|
| T [K] | 296 | 296 | 296 |
| λ [Å] | 1.54056 | 1.54056 | 1.54056 |
| Crystal system | Monoclinic | Monoclinic | Monoclinic |
| Space group | $P2_1$ | $P2_1$ | $P2_1$ |
| Unit cell dimensions | | | |
| a [Å] | 7.5833 (3) | 7.5856 (3) | 10.8807 (3) |
| b [Å] | 18.2579 (9) | 18.2445 (5) | 21.8501 (6) |
| c [Å] | 18.2861 (9) | 18.2986 (5) | 11.7752 (4) |
| β [°] | 92.021 (4) | 92.306 (2) | 117.8523 (12) |
| V [Å$^3$] | 2530.2 (3) | 2530.4 (3) | 2475.18 (12) |
| Z (Z') | 4 (2) | 4 (2) | 4 (2) |
| Dc [g/cm$^3$] | 1.375 | 1.375 | 1.387 |
| Measurement parameters | | | |
| Cap. size [mm$^2$] | 0.5 × 8 | 0.5 × 8 | 0.5 × 8 |
| 2θ Step size [°] | 0.015 | 0.015 | 0.015 |
| No of steps | 2561 | 2628 | 2561 |
| Time per step [s] | 6 | 20 | 10 |
| 2θ range [°] | 4-41.5 | 3-41.5 | 4-41.5 |
| Rexp | 2.58 | 1.18 | 1.05 |
| Rwp | 3.56 | 2.10 | 2.11 |
| Rp | 2.72 | 1.55 | 1.53 |
| GOF | 1.38 | 1.77 | 2.02 |
| RBrag | 0.16 | 0.11 | 0.07 |
| Impurities [%] | Below detection limits | Below detection limits | ~1% (unidentified) |

Single Crystal Diffraction

Single crystal measurements were performed on a Nonius Kappa-CCD diffractometer. The data were collected at 296K. The structures were solved using direct methods by SHELXT-2014/7 (Sheldrick, G. M., 2008). The structures were refined by least square full matrix refinement using SHELXL-2014/7 (Sheldrick, G. M., 2008).

TABLE 39

Crystal data obtained from single crystal X-ray diffraction for Oxa1a, Oxa1d and Oxa1c. Interstitial solvent/water molecules that exist in the cavities of the structure are indicated in italic in the empirical formula.

| Polymorph | Oxa1a | Oxa1d | Oxa1c |
|---|---|---|---|
| Empirical formula | [(C$_{22}$H$_{20}$ClF$_3$NO$_5^+$)•0.5 (C$_2$O$_4^{2-}$)•0.5 (H$_2$O)•*0.24 (H$_2$O)*] | [(C$_{22}$H$_{20}$ClF$_3$NO$_5^+$)•0.5 (C$_2$O$_4^{2-}$)•0.5 (H$_2$O)•*0.36* (*C$_2$H$_5$OH*)•*0.25 (H$_2$O)*] | [(C$_{22}$H$_{20}$ClF$_3$NO$_5^+$)•0.5 (C$_2$O$_4^{2-}$)•0.5 (H$_2$O)•*0.9 (H$_2$O)*] |
| Formula weight | 1055.31 | 1089.31 | 1074.91 |
| T [K] | 296 (2) | 296 (2) | 296 (2) |
| λ [Å] | 0.71073 | 0.71073 | 0.71073 |
| Crystal system | Monoclinic | Monoclinic | Monoclinic |
| Space group | $P2_1$ | $P2_1$ | $P2_1$ |
| Unit cell dimensions | | | |
| a [Å] | 7.5925 (6) | 7.6104 (6) | 7.5714 (4) |
| b [Å] | 18.1942 (15) | 18.1627 (12) | 18.3024 (9) |
| c [Å] | 18.3755 (14) | 18.5099 (14) | 18.0252 (9) |
| β [°] | 93.289 (5) | 95.1448 (19) | 90.034 (3) |
| V [Å$^3$] | 2534.2 (3) | 2548.2 (3) | 2497.8 (2) |
| Z | 2 | 2 | 2 |
| Dc [g/cm$^3$] | 1.409 | 1.420 | 1.403 |
| Additional Data | | | |
| μ [mm$^{-1}$] | 0.221 | 0.220 | 0.221 |
| F(000) | 1088 | 1127 | 1107 |
| Crystal size | 0.15 × 0.08 × 0.06 | 0.40 × 0.30 × 0.10 | 0.26 × 0.12 × 0.10 |
| θ range for data collection [°] | 2.7 → 26.4 | 2.5 → 27.4 | 2.7 → 26.4. |
| Reflections collected | 33528 | 38649 | 14151 |

TABLE 39-continued

Crystal data obtained from single crystal X-ray diffraction for Oxa1a, Oxa1d and Oxa1c. Interstitial solvent/water molecules that exist in the cavities of the structure are indicated in italic in the empirical formula.

| Polymorph | Oxa1a | Oxa1d | Oxa1c |
|---|---|---|---|
| Independent reflections | 10203 [$R_{int}$ = 0.0889] | 11523 [$R_{int}$ = 0.0605] | 9177 [Rint = 0.0742] |
| Completeness [%] | 99.8 | 99.8 | 99.5 |
| Absorption correction | Integration | Integration | Integration |
| Max. and min. transmission | 0.991 and 0.967 | 0.985 and 0.942 | 0.990 and 0.972 |
| Data/restraints/parameters | 10203/1/683 | 11523/1/661 | 9177/1/634 |
| Goodness-of-fit on $F^2$ | 1.025 | 1.025 | 0.979 |
| Final R indices [I > 2σ(I)] | R1 = 0.0641 wR2 = 0.1260 | R1 = 0.0573 wR2 = 0.1497 | R1 = 0.0839 wR2 = 0.1622 |
| R indices (all data) | R1 = 0.1437 wR2 = 0.1583 | R1 = 0.0862 wR2 = 0.1711 | R1 = 0.2377 wR2 = 0.2199 |
| Absolute structure parameter | 0.06 (6) | −0.08 (4) | −0.04 (11) |
| Extinction coefficient | n/a | 0.012 (2) | n/a |
| Largest diff peak and hole [e/Å$^3$] | 0.288 and −0.221 | 0.425 and −0.253 | 0.273 and −0.265 |
| Cavity volume [Å$^3$] | 190.6 [7.6%] | 85.1 [3.3%] | 119.6 [4.7%] |

Thermal Analysis

TGA/SDTA and TGMS Analysis

Mass loss due to solvent or water loss from the crystals was determined by TGA/heat flow. Monitoring the sample weight, during heating in a TGA/DSC 3+ STARe system (Mettler Toledo GmbH, Switzerland), resulted in a weight vs. temperature curve. The TGA/DSC 3+ was calibrated for temperature with indium and aluminum. Samples (circa 2 mg) were weighed into 100 μL aluminum crucibles and sealed. The seals were pin-holed and the crucibles heated in the TGA from 25 to 300° C. at a heating rate of 10° C./min unless stated otherwise. Dry $N_2$ gas was used for purging.

The gases evolved from the TGA samples were analyzed by an Omnistar GSD 301 T2 mass spectrometer (Pfeiffer Vacuum GmbH, Germany). This MS is a quadrupole mass spectrometer, which analyses masses in the range of 0-200 amu.

DSC Analysis

Melting properties were obtained from DSC thermograms, recorded with a heat flux DSC3+ STARe system (Mettler-Toledo GmbH, Switzerland). The DSC3+ was calibrated for temperature and enthalpy with a small piece of indium (m.p.=156.6° C.; δHf=28.45 J/g) and zinc (m.p.=419.6° C.; δHf=107.5 J/g). Samples (circa 2 mg) were sealed in standard 40 μL aluminum pans, pin-holed and heated in the DSC from 25° C. to 300° C., at a heating rate of 10° C./min unless stated otherwise. Dry $N_2$ gas, at a flow rate of 50 mL/min was used to purge the DSC equipment during measurement.

Proton-NMR $^1$H-NMR spectroscopy in DMSO-$d_6$ was used for compound integrity characterization. The spectra were recorded at room temperature (32 scans) on a 500 MHz instrument (Bruker BioSpin GmbH) using standard pulse sequences. The data was processed with ACD Labs software Spectrus Processor 2016.2.2 (Advanced Chemistry Development Inc. Canada).

DVS Analysis

Differences in hygroscopicity (moisture uptake) of the various forms of a solid material provided a measure of their relative stability at increasing relative humidity. Moisture sorption isotherms of small samples were obtained using a DVS-1 system from Surface Measurement Systems (London, UK); this instrument is suitable for use with a few milligrams of sample, with an accuracy of 0.1 μg. The relative humidity was varied during sorption-desorption-sorption (45-95-0-45% RH) at a constant temperature of 25° C. Weight equilibration per step was set at dm/dt <0.0002 for a minimum of 1 hour or maximum of 6 hours. Afterwards the sample was measured by HT-XRPD.

The hygroscopicity was classified according to the European Pharmacopoeia Hygroscopicity classification. Water uptake percentage at 25° C./80% RH (24 h) is:

Change in mass <0.2%—Non-hygroscopic
Change in mass >0.2% & <2%—Slightly hygroscopic
Change in mass >2% & <15%—Moderately hygroscopic
Change in mass >15%—Very hygroscopic UPLC Analysis Method Name: S18128A_01_LCMS

| | |
|---|---|
| Instrument | Agilent 1290 series with diode array UV detector and MSD XT single quad mass detector |
| Mobile phase A | 0.1% Formic acid in water |
| Mobile phase B | 0.1% Formic acid in acetonitrile |
| Column | Agilent Eclipse Plus C18 HD (50 × 2.1 mm; 1.8 μm) |
| Detection: | UV at 264 nm, bandwidth 4 nm, UV spectrum 200 to 400 nm. MS in positive scan mode 100-1000 m/z, 500 ms scan time |
| Flow: | 0.8 mL/min. |
| Run time | 4 minutes |
| Injection volume | 1.0 μL |
| Column temp. | 35° C. |
| Autosampler temp. | Ambient |

-continued

| Gradient: | Time [min.] | Eluent A [%] | Eluent B [%] |
|---|---|---|---|
| | 0 | 90 | 10 |
| | 0.25 | 90 | 10 |
| | 2 | 2 | 98 |
| | 2.95 | 2 | 98 |
| | 3 | 90 | 10 |
| | 4 | 90 | 10 |

The compound integrity is expressed as a peak-area percentage, calculated from the area of each peak in the chromatogram, except the 'injection peak', and the total peak-area, as follows:

$$\text{peak area (\%)} = \frac{\text{peak area}}{\text{total area of all peaks}} \cdot 100\%$$

The peak area percentage of the compound of interest is employed as an indication of the purity of the component in the sample.

UPLC Assay

For the UPLC assay, a solution of voruciclib free base (from project S18128) was measured as a reference and the peak area was assigned to 100% recovery after taking into account the amount of solvent determined by TGMS. Samples of the salts were measured in the same way and the % recovery was calculated again by taking into account the amount of solvent. With all measured salts, <100% recovery could be assigned to the API and the remaining % recovered could be assigned to the counterion from which the ratio API:counterion could be determined (Table 40).

TABLE 40

Assay results for the oxalate salts.

| Sample Name | Area [mV*s] | Weight (mg) | Volume (ml) | TGMS (%) | Purity (%) | RF | Recovery (%) | Ratio API:CI |
|---|---|---|---|---|---|---|---|---|
| S18128_Ref-SOL1_R1 | 2014.3 | 30.03 | 50 | 0.33 | 99.67 | 33.65 | — | — |
| S18128_Ref-SOL2_R2 | 2021.0 | 30.03 | 50 | 0.33 | 99.67 | 33.76 | — | — |
| S18128_Ref-SOL2_R2 | 2011.8 | 30.03 | 50 | 0.33 | 99.67 | 33.6 | — | — |
| Average | 2015.7 | | | | | 33.67 | — | — |
| RSD | 0.23 | | | | | | | — |
| LCMS_S18128A_Ref-SOL2 | 1971.0 | 29.13 | 50 | 0.33 | 99.67 | 33.94 | — | — |
| LCMS_S18128A_SM_Oxa (Oxa2) | 1597.4 | 29.76 | 50 | 1.11 | 98.89 | 27.14 | 81.4 | 1:1.2 |
| LCMS_S18128A_TCP18 (Oxa2) | 1232.8 | 2.32 | 5 | 2.08 | 97.92 | 27.13 | 80.6 | 1:1.2 |
| LCMS_S18128A_TCP21 (Oxa6) | 1303.6 | 5.01 | 40 | 7.98 | 92.02 | 28.28 | 84.0 | 1:1.0 |
| TCMS_S18128A_TCP23 (Oxa7) | 4427.9 | 4.97 | 40 | 3.36 | 96.64 | 29.73 | 88.3 | 1:0.7 |

Characterization of Novel Forms

Oxa1 Series

The Oxa1 series was characterized as the hemi-oxalate/hemihydrate crystal structure which contains cavities that could accommodate solvent molecules and/or water, based on single crystal X-ray diffraction. FIG. 160 shows a schematic overview of how the different Oxa1 forms are related to each other.

The crystal structures viewed along the [100] direction of Oxa1a, Oxa1c and Oxa1d are shown in FIG. 161. In Oxa1d, ethanol and water were present in the cavities of the structure whereas in Oxa1c and Oxa1d only water was present.

The unit cell dimensions of Oxa1a, Oxa1c and Oxa1d were determined from the single crystal structure data before and after drying whereas the unit cell dimensions of Oxa1 and Oxa1b were obtained from the HR-XRPD data (Table 41). Upon the removal of solvent and water under ambient conditions, the unit cell volume (V) of the Oxa1 structures became smaller. Furthermore, the unit cell dimensions a and b and the interaxial angle β became smaller, whereas the unit cell dimension b became larger upon removal of interstitial solvent/water. An overlay of the XRPD patterns of the Oxa1 forms is shown in FIG. 162.

TABLE 41

Unit cell dimensions (a, b and c), interaxial angle β
and the unit cell volume V of Oxa1d, Oxa1c, Oxa1b, Oxa1
and Oxa1a. From left to right, the unit cell becomes smaller.

| Unit cell parameter | Oxa1d | Oxa1c | Oxa1b | Oxa1 | Oxa1a |
|---|---|---|---|---|---|
| a [Å] | 7.6104 | 7.5925 | 7.585582 | 7.583326 | 7.5714 |
| b [Å] | 18.1627 | 18.1942 | 18.24446 | 18.2579 | 18.3024 |
| c [Å] | 18.5099 | 18.3755 | 18.29857 | 18.28607 | 18.0252 |
| β [°] | 95.1448 | 93.289 | 92.3062 | 92.021 | 90.034 |
| V [Å$^3$] | 2548.2 | 2534.2 | 2530.377 | 2530.23 | 2497.8 |

Oxa1

Oxa1 was obtained as the only oxalate form in the salt screen on voruciclib (project S18128). From that screen, Oxa1 could be obtained through cooling crystallization from THF, ethanol and acetone using API:CI ratios of both 1:0.55 and 1:1.1.

A High Resolution XRPD (HR-XRPD) analysis was performed on Oxa1 (Exp. ID: SSm12, project S18128). Rietveld analysis (FIG. 163) revealed that Oxa1 was a pure crystalline phase which existed as a hemi-oxalate/hemihydrate form. Based on the single crystal analyses of similar solid forms, it was assumed that the crystal structure of Oxa1 contains cavities which could accommodate solvent and water molecules. From HR-XRPD analyses it was unclear how much interstitial water was present in the structure. However, since the crystal structure was larger than Oxa1a but smaller than Oxa1c, it can be assumed that Oxa1 contains between 0.24-0.9 eq. of interstitial water per molecule of API.

In the present screen, Oxa1 was obtained as a pure phase from acetone/water (Exp. ID: TCP29) upon drying under deep vacuum (5 mbar, 18 h). The ambient-dried material was classified as Oxa1e which most likely has the same structure as Oxa1 but with residual acetone and water in its cavities. After high-vacuum, most of the interstitial solvents were removed from the solids and Oxa1 was obtained based on HT-XRPD (FIG. 164). Oxa1 remained stable upon exposure to AAC (40° C./75% RH) for 2 days.

The thermal analytical data of Oxa1 (Exp. ID: TCP29) corresponds to the data of Oxa1 from project S18128. The TGMS data of Oxa1 (Exp. ID: TCP29) is shown in FIG. 165 and revealed a total mass loss of 5.6% between 40-140° C. Approximately 1.7% of mass loss can be attributed to stochiometric water as Oxa1 is classified as a hemihydrate. The remaining 3.9% mass loss may be attributed to interstitial water and acetone which may be present in the cavities of the structure. Thermal decomposition started at about 180° C.

The DSC trace (FIG. 166) of Oxa1 (Exp. ID:TCP29) showed three endothermic events between 25-160° C. which are most likely associated to solvent/water loss. Thermal decomposition of the salt was characterized by the broad endothermic event between 209-230° C.

The chemical purity of Oxa1 was assessed by LCMS analysis (FIG. 167). The result indicated that the API purity was 99.3% (area %) and therefore higher than the starting material (i.e. 95.5%). The positive ion spectrum showed ions with m/z of 470 corresponding to the positively charged species [M+H]$^+$ and agreed with the molecular mass of the free base (i.e. 470 g/mol).

FIG. 170 shows the $^1$H-NMR spectrum of Oxa1 (Exp. ID: TCP29) in comparison to Oxa1 from S18128 (Exp. ID: SSm12) and the voruciclib free base. The $^1$H-NMR spectrum of Oxa1 obtained in the present screen corresponds to the Oxa1 spectrum measured in project S18128. The $^1$H-NMR spectrum obtained of Oxa1 confirmed salt formation as the proton resonances of the salt were shifted compared to those of the free base.

Oxa1a

Oxa1a was obtained by incubating a single crystal of Oxa1d at ambient conditions. The crystal structure of Oxa1a was the same as Oxa1d but without ethanol in its cavities (FIG. 169). Oxa1a was determined to be a hemi-oxalate/hemihydrate with approximately 0.24 eq. of non-stochiometric interstitial water molecules, based on single crystal analysis. Among the Oxa1 forms found in this study, form Oxa1a exhibited the smallest unit cell dimensions. The simulated powder pattern of Oxa1a is shown in FIG. 170.

Oxa1b

Oxa1b was obtained by further exposing a single crystal of Oxa1c to ambient conditions. The crystal structure of Oxa1b can be considered the same as Oxa1d (initial structure) but without ethanol in its cavities. Oxa1b appeared to be the same form as Oxa1c but with less non-stochiometric water than Oxa1b as Oxa1b was estimated to be a hemi-oxalate/hemihydrate with approximately 0.24-0.9 eq. of interstitial water per molecule of API. Rietveld analysis (FIG. 171) revealed that Oxa1b was a crystalline phase without any measurable impurities. Oxa1b was an intermediate form which upon further drying converted via Oxa1 into Oxa1a.

Oxa1c

Oxa1c was obtained by incubating a single crystal of Oxa1d (ethanol solvate) at ambient conditions. The crystal structure of Oxa1c was the same as Oxa1d but without ethanol in its cavities. Oxa1a was determined to be a hemi-oxalate/hemi-hydrate with approximately 1.7 eq. of interstitial water molecules per molecule of API in its cavity, based on single crystal analysis (FIG. 172). A depiction of the asymmetric unit cell of Oxa1c is shown in FIG. 173. Upon further drying at room temperature, Oxa1c converted via intermediates Oxa1b and Oxa1 into Oxa1a. The calculated powder pattern of Oxa1a is shown in FIG. 174.

Oxa1d

Oxa1d was obtained as a single crystal through recrystallization of Oxa2 (starting material) from ethanol by cooling from a refluxing solution. Based on the single crystal data analysis, Oxa1d was obtained as a hemi-oxalate/hemihydrate structure with 0.36 eq. of interstitial ethanol and 0.25 eq. of interstitial water molecules per molecule of API in its cavities. The molecular structures of the two symmetry-independent molecules in Oxa1d are shown in FIG. 175. The crystal packing motif in the [100] direction of Oxa1d is shown in FIG. 176. The calculated powder pattern of Oxa1d is shown in FIG. 177.

Oxa1e

Oxa1e (Exp. ID: TCP29) was obtained from acetone/water (90/10) and its powder pattern is similar to the powder pattern measured from the ethanol solvate (Oxa1d, FIG. 178). Most likely, Oxa1e existed as a hemi-oxalate/hemihydrate with acetone present in the cavities of the structure. Oxa1e converted into Oxa1 upon drying under high-vacuum and after exposure to AAC (40° C./75% RH, 2 days).

Oxa2

The starting material was characterized as Oxa2 and was the form most frequently obtained in the polymorph screen. FIG. 179 shows an overlay of HT-XRPD patterns of the Oxa2 materials obtained as the starting material and from the crystallization from 2-propanol (Exp. ID: TCP18). The Oxa2 form of the starting material contained an additional diffraction peak associated to a crystalline impurity whereas this impurity was not detected in Oxa2 obtained from the polymorph screen. Oxa2 was stable upon exposure to AAC (40° C./75% RH) and after drying under high vacuum (5 mbar).

The TGMS analysis in FIG. 180 shows that between 40-140° C. approximately 2.1% of water was released, corresponding to 0.6 molecules of water per molecule of API. Water was most likely present as an unbound non-stochiometric species since it was gradually removed upon heating. Between 180-240° C., the material underwent thermal decomposition as indicated by a significant mass loss.

The DSC analysis of Oxa2 (Exp. ID: TCP18) is shown in FIG. 181. A small endothermic event was observed at 99° C. A broad endothermic event between 199-232° C. may be associated to thermal decomposition of the salt.

The chemical purity of Oxa2 (Exp. ID: TCP18) was assessed by LCMS analysis (FIG. 182). The result indicated that the API purity was 98.2% (area %), an increase with respect to the starting material (95.5%). The positive ion spectrum showed ions with m/z of 470 corresponding to the positively charged species [M+H]$^+$ and agreed with the molecular mass of the free base (i.e. 470 g/mol). Based on the LCMS assay analysis, the ratio of API:oxalate in Oxa2 is most likely 1:0.5, which confirms the assay results obtained for the starting material (Oxa2).

FIG. 183 shows the $^1$H-NMR spectrum of Oxa2 (Exp. ID: TCP18) in comparison to the free base (starting material, project S18128) and Oxa2 (starting material, project S18128A). Compared to the free base, the NMR peaks of Oxa2 were shifted downfield which confirms that Oxa2 was isolated as a salt. The $^1$H-NMR spectrum of Oxa2 (Exp. ID: TCP18) was virtually the same as Oxa2 obtained as the starting material. According to the 2-propanol signal at 1.05 ppm, the API: 2-propanol ratio was 1:0.04 in the solid phase corresponding to approximately 0.4% of the mass loss observed by TGMS (FIG. 180).

Oxa3

The ambient-dried solids that were isolated from 2-propanol/water (90/10, Exp. ID: TCP30) were classified as Oxa3. The material was stable upon exposure to AAC (40° C./75% RH, 2 days) but upon exposure to high vacuum (5 mbar, 18 h), Oxa3 converted into Oxa1+Oxa4.

In some experiments, amorphous materials converted into Oxa3 upon exposure to AAC (40° C./75% RH, 2 days). Furthermore, the material obtained from chloroform (Exp. ID: TCP21) was initially obtained as Oxa6 but converted into Oxa3 upon exposure to AAC (40° C./75% RH, 2 days).

Oxa4

In the present screen, Oxa4 could only be obtained as a mixture with Oxa1 (FIG. 185). The Oxa1+Oxa4 mixture was obtained after the Oxa3 material from 2-propanol/water (90/10, Exp. ID: TCP30) was exposed to high vacuum (5 mbar, 18 h).

Oxa5

Cooling crystallization of the free base from ethanol (Exp. ID: SSm2) in combination with a 1M aqueous solution of oxalic acid (API:CI ratio of 1:1.3) led to the crystallization of Oxa5 (FIG. 186). As indicated by HT-XRPD, Oxa5 was different from the ethanol solvate Oxa1d and different from Oxa7 (Exp. ID: TCP23) which was obtained in the polymorph screen from ethanol. Oxa5 was exposed to short-term stress conditions (40° C./75% RH, 1 day) and the material was reanalyzed by XRPD. After only 1 day at 40° C./75% RH, the material converted into a different form. Given the instability of Oxa5, this material was not investigated further.

Oxa6

Oxa6 was the salt form obtained from chloroform (Exp. ID: TCP21). As indicated by the HT-XRPD patterns (FIG. 187), Oxa6 converted into Oxa3 upon exposure to AAC (40° C./75% RH, 2 days).

Oxa7

Oxa7 was the salt form obtained through thermocycling the amorphous voruciclib oxalate salt in ethanol (Exp. ID: TCP23). Oxa7 remained physically stable upon drying under high-vacuum and upon exposure to AAC (40° C./75% RH, 2 days). The vacuum dried Oxa7 sample (Exp. ID: TCP23) was used for further analytical characterization of this form.

The TGMS analysis in FIG. 189 shows that between 40-140° C. approximately 3.4% of water was released, corresponding to approximately 1.1 molecules of water per molecule of API. Between 180-240° C., the material underwent thermal decomposition as indicated by a significant mass loss.

The DSC analysis of the Oxa7 is shown in FIG. 190. Two endothermic events were observed at 85° C. and 154° C. A broad endothermic event between 198-232° C. can be associated to thermal decomposition of the salt.

The chemical purity of Oxa7 was assessed by LCMS analysis (FIG. 191). The result indicated that the API purity was 96.9% (area %), a slight increase with respect to the starting material (95.5%). The positive ion spectrum showed ions with m/z of 470 corresponding to the positively charged species [M+H]$^+$ and agreed with the molecular mass of the free base (i.e. 470 g/mol). Based on the LCMS assay analysis, the ratio of API:oxalate was most likely 1:0.5.

FIG. 192 shows the $^1$H-NMR spectrum of Oxa7 in comparison to the free base (starting material, project S18128). Compared to the free base, the NMR peaks of Oxa7 were shifted downfield which confirmed that Oxa7 was isolated as a salt. According to the ethanol signal at 1.07 and 1.18 ppm, the API:ethanol ratio in Oxa7 was approximately 1:0.06 corresponding to approximately 0.4% of residual solvent detected by TGMS (FIG. 189).

Example 4: Voruciclib Phosphate

The received material was an voruciclib phosphate salt that was classified as Pho3. Pho3 was a hydrate with a purity of 95%. The polymorph screen experiments were started with amorphous voruciclib phosphate salt to enable unbiased crystallization. In total, 9 phosphate forms were identified in the present study. Pho1 was the only form that was physically stable against both AAC (40° C./75% RH, 2 days) and deep vacuum (5 mbar, 18 h).

In the polymorph screen, Pho1 was most frequently obtained. Moreover, in this study Pho1 was identified as the only anhydrous form which could be obtained through cooling crystallization. However, Pho1 was moderately hygroscopic and became a gel upon addition of water. The solubility of Pho1 in water at room temperature was approximately 8 mg/ml.

Abbreviations

AAC Accelerated Aging Conditions (40° C. and 75% RH for 2 days)
Am Amorphous
API Active Pharmaceutical Ingredient
cDSC Cycling Differential Scanning Calorimetry
DSC Differential Scanning Calorimetry
DVS Dynamic Vapor Sorption
$^1$H-NMR Proton Nuclear Magnetic Resonance
HR-XRPD High Resolution X-Ray Powder Diffraction
HT-XRPD High Throughput X-Ray Powder Diffraction
LCMS Liquid Chromatography Mass spectroscopy
MS Mass Spectroscopy
ML Mother Liquor (liquid phases)
MW Molecular Weight
Pc Poorly Crystalline
QSA Experiment ID for the freeze-drying experiments
RF Response Factor
RH Relative Humidity
RT Room Temperature
SAS Experiment ID for the solubility determination experiments
SM Starting Material
SSm Experiment ID for the salt formation experiments
SSR Solid State Research
TCP Experiment ID for the thermocycling experiments
TGA Thermogravimetric Analysis
TGMS Thermogravimetric Analysis coupled with Mass Spectroscopy
TMS Tetramethylsilane
UPLC Ultra-Performance Liquid Chromatography
DME 1,2-Dimethoxyethane
DMSO-$d_6$ Deuterated dimethyl sulfoxide
EtOH Ethanol
IPA 2-Propanol
Mao Malonate salt
MeOH Methanol
Pho Phosphate salt
t-BuOH tert-Butanol
TBME tert-Butyl methyl ether
TFE 2,2,2-Trifluoroethanol
THF Tetrahydrofuran Previous research showed that the HCl salt exhibited complex pseudo-polymorphic behavior and that the material had a tendency of forming a gel in aqueous media. In a follow up study, a salt screen (project S18128) was performed on ME-522 which led to the selection of the malonate, oxalate and phosphate salts as suitable candidates for further development. In this study, the polymorphic behavior of the phosphate salt (FIG. 193) has been evaluated in a solid form screen. A thermocycling screen involving 15 solvents to identify novel crystalline phases of voruciclib phosphate salt and to select the best form for further investigations was designed.

This study consisted of the following project steps: Starting material characterization; Generation of amorphous phosphate salt; Thermodynamic solid form screen in 15 solvents; Analytical characterization of novel solid forms.

28.89 grams of voruciclib phosphate salt were provided (batch ID: 19-09334-01) as a crystalline powder (starting material). The High Throughput-XRPD (HT-XRPD) patterns of Pho1 and Pho2 from project S18128 and the starting material of the current project are shown in FIG. 194. The materials obtained in the salt screen (S18128) were classified as Pho1 and Pho2 and are different by XRPD as compared to the received starting material in the present study. Therefore, the starting material of the present study was classified as Pho3. Pho3 remained stable upon exposure to AAC (40° C./75% RH, 2 days).

A HR-XRPD analysis was performed on the starting material (Pho3). Rietveld analysis (FIG. 195) revealed that the starting material was a crystalline phase with approximately 5% of unidentified impurities.

The TGMS analysis in FIG. 196 shows that between 40-160° C. approximately 5.4% of water was released, corresponding to 1.8 molecules of water per molecule of API. From 200° C. onwards, the material underwent thermal decomposition as indicated by a significant mass loss.

The DSC analysis of the starting material (Pho3) is shown in FIG. 197. Three endothermic events were recorded between 30-165° C. which may be associated to the release of water and possibly other process solvents. The endothermic event at 197° C. could be associated to the melting of Pho3 whereas the broad endothermic event at 246° C. represents thermal decomposition.

A cycling DSC (cDSC) was performed on the starting material (Pho3) to determine whether Pho3 was stable upon the removal of water. A sample of the starting material was heated to 170° C. (FIG. 198A) and cooled back to room temperature for analysis by HT-XRPD. As indicated by the HT-XRPD results (FIG. 199), the material recovered after cDSC was determined to be a poorly crystalline phase of Pho3. This suggests that the water in Pho3 was present as unbound non-stochiometric water.

The material after the cDSC program was subjected to another cDSC program (FIG. 198B) and during heating again showed two endothermic events related to water loss. This indicates that after drying through cDSC, Pho3 takes up water under ambient conditions.

The chemical purity of the API was assessed by LCMS analysis. The result indicated that the API purity was 94.8% (area %). The positive ion spectrum showed ions with m/z of 470 corresponding to the positively charged species [M+H]$^+$ and agreed with the molecular mass of the free base (i.e. 469.8 g/mol). From the LCMS assay analysis, the ratio of API:phosphate in Pho3 was estimated to be 1:1.6.

FIG. 201 shows the $^1$H-NMR spectrum and molecular structure of Pho3 (starting material). Overall, 17 of the 20 hydrogen atoms of the molecule could be assigned to the peaks in the spectrum. The remaining three undetected hydrogens correspond to two OH— and the NH groups of the API. The 11 aliphatic hydrogens of the pyrrolidine group appeared between 2-4 ppm (group a). The two aromatic hydrogen atoms on the benzopyran ring appeared between 6 and 7 ppm (group b), whereas the three aromatic hydrogens of the halogenated aromatic ring appeared further downfield around 8 ppm (group c). The hydrogen at 12.7 ppm (d) most likely belongs to one of the hydroxyl groups. Compared to both the free base and the Pho1 spectrum, only the NMR peaks of the pyrrolidine (a) and benzopyran (b) group of the starting material were shifted further downfield.

A Dynamic Vapor Sorption (DVS) measurement was performed on Pho3 (starting material). As shown in FIG. 202, the material gradually took up water with increasing relative humidity (RH). At 25° C./80% RH, the water uptake was approximately 6.9%, which led to the classification of Pho3 being moderately hygroscopic (European Pharmacopoeia Hygroscopicity classification. Water uptake percentage at 25° C./80% RH is: Change in mass <0.2%—Non-hygroscopic; Change in mass <2% & >0.2%—Slightly hygroscopic; Change in mass <15% & 2%—Moderately hygroscopic; Change in mass >15%—Very hygroscopic). After DVS analysis, Pho3 was recovered as indicated by XRPD.

Generally, it is preferred to start a polymorph screen with amorphous material to avoid biased crystallization. Amorphous material was produced by lyophilization of Pho3 (starting material) from different water/organic solvent mixtures.

Amorphous voruciclib phosphate salt for the polymorph screen was produced by lyophilization of the starting material from acetone/water (50/50). After freeze-drying, the material was analyzed by HT-XRPD to confirm that the resulting material was amorphous (FIG. 203). Based on the TGMS analysis (FIG. 204) of the amorphous material, the residual solvent content was 3.0%.

The DSC trace in FIG. 205 shows three endothermic events between 25-150° C. which may be associated to solvent removal. The broad endothermic event between 200 and 270° C. corresponds to thermal decomposition of the phosphate salt.

$^1$H-NMR analysis confirmed that the chemical integrity of the salt was retained after lyophilization (FIG. 206). The chemical shifts of the amorphous material corresponded with the starting material phosphate salt (Pho3) but were shifted with respect to the free base.

Amorphous voruciclib phosphate salt, generated by freeze-drying, was used to start the thermocycling experiments. Suspensions were prepared in the selected solvent systems at RT. Subsequently, the mixtures were subjected to a temperature profile. Upon completion of the temperature profile, the solids were separated from the solutions by centrifugation and were dried under ambient conditions and under deep vacuum before being harvested and analyzed by HT-XRPD. The liquid phases were also dried under deep vacuum before being harvested and analyzed by HT-XRPD. All solids were exposed to AAC (40° C./75% RH, 2 days).

In total, six salt forms were identified in the polymorph screen performed on the phosphate salt, which were designated Pho1, Pho4, Pho5, Pho6, Pho7 and Pho8. The results are summarized in Table 42.

Pho1 was the prevalent salt form in the polymorph screen which was also the form identified in the previous screen (S18128). In some experiments, Pho1 was obtained as a mixture and in some of those experiments (e.g. Exp. ID: TCP19), the mixtures were unstable upon exposure to AAC (40° C./75% RH, 2 days). However, pure Pho1 was the only form that was stable after both vacuum drying (5 mbar, 18 h) and AAC (40° C./75% RH, 2 days).

Pho4 was obtained through thermocycling experiments in 1,2-dimethoxyethane and THF and as a mixture with Pho1 through thermocycling experiments in 1,4-dioxane, 2-propanol and acetone/water (90/10, v/v). Upon exposure to deep vacuum (5 mbar, 18 h), Pho4 converted into Pho1.

Pho5 was the ambient-dried solid material obtained from the thermocycling experiment in acetone. Pho5 was unstable upon exposure to AAC (40° C./75% RH, 2 days) and deep vacuum (5 mbar, 18 h) as it converted into Pho8 and Pho1+peaks, respectively.

Pho6 was obtained as a poorly crystalline solid material from several thermocycling experiments, including from solvents chloroform, ethyl acetate, ethyl formate and t-butyl methyl ether (TBME). Pho6 remained stable after exposure to deep vacuum (5 mbar, 18 h) but became amorphous upon exposure to AAC (40° C./75% RH, 2 days).

Pho7 was the salt form obtained through thermocycling the amorphous voruciclib phosphate salt in 2-propanol/water (90/10, v/v; Exp. ID: TCP30). Pho7 remained physically stable upon drying under high-vacuum but additional diffraction peaks were observed in the material after it was exposed to AAC (40° C./75% RH, 2 days).

Pho8 was obtained as a poorly crystalline phase after the ambient-dried materials obtained from thermocycling experiments in acetone and acetonitrile were exposed to AAC (40° C./75% RH, 2 days). The corresponding vacuum-dried solids transformed into Pho8+peaks after exposure to AAC (40° C./75% RH, 2 days).

TABLE 42

Results of the thermocycling experiments performed on the voruciclib phosphate salt. "—" indicated that no solids were recovered after evaporation of the solutions. "Am" stands for amorphous, "peaks" indicate that a few diffraction peaks were detected in addition to the salt form and poorly crystalline samples are denoted with "pc". AAC stands for accelerated aging conditions (40° C./75% RH, 2 days). Highlighted in green are the samples selected for further analytical characterization.

| | | Solid forms | | | | | |
|---|---|---|---|---|---|---|---|
| Exp. ID | Solvent | Ambient | Vacuum | ML | Ambient (AAC) | Vacuum (AAC) | ML (AAC) |
| TCP16 | DME | Pho4 (pc) | Pho1 | Pho4 (pc) | Pho1 | — | — |
| TCP17 | 1,4-Dioxane | Pho1 + Pho4 (pc) | Pho1 | Pho1 + Pho4 (pc) | Pho1 | — | — |
| TCP18 | 2-Propanol | Pho1 + Pho4 (pc) | Pho1 + Pho4 (pc) | Pho1 + Pho4 (pc) | Pho1 + Pho4 (pc) | — | — |
| TCP19 | Acetone | Pho5 (pc) | Pho1 + peaks | Pho8 (pc) | Pho8 + peaks (pc) | — | — |
| TCP20 | Acetonitrile | Pho1 + peaks | Pho1 + peaks | Pho8 (pc) | Pho8 + peaks (pc) | — | — |

TABLE 42-continued

Results of the thermocycling experiments performed on the voruciclib phosphate salt. "—" indicated that no solids were recovered after evaporation of the solutions. "Am" stands for amorphous, "peaks" indicate that a few diffraction peaks were detected in addition to the salt form and poorly crystalline samples are denoted with "pc". AAC stands for accelerated aging conditions (40° C./75% RH, 2 days). Highlighted in green are the samples selected for further analytical characterization.

| | | Solid forms | | | | | |
|---|---|---|---|---|---|---|---|
| Exp. ID | Solvent | Ambient | Vacuum | ML | Ambient (AAC) | Vacuum (AAC) | ML (AAC) |
| TCP21 | Chloroform | Pho6 (pc) | Pho6 (pc) | Am | Am | Am | Am |
| TCP22 | Cyclohexane | Am | Am | Am | Am | — | — |
| TCP23 | Ethanol | Pho1 | Pho1 | Pho1 | — | — | |
| TCP24 | Ethyl acetate | Pho6 (pc) + peaks | Pho6 (pc) + peaks | Am | Am | — | — |
| TCP25 | Ethyl formate | Pho6 (pc) | Pho1 + peaks (pc) | Am | Am | Am | Am |
| TCP26 | TBME | Pho6 (pc) | Pho6 (pc) | Am | Am | — | — |
| TCP27 | Tetrahydrofuran | Pho4 (pc) | Pho1 | Pho4 (pc) | Pho1 | — | — |
| TCP28 | Toluene | Am | Am | Am | Am | — | — |
| TCP29 | Acetone/water (90/10) | Pho1 + Pho4 (pc) | Pho1 | Pho1 | Pho1 | — | — |
| TCP30 | IPA/water (90/10) | Pho7 | Pho7 | Pho7 + peaks | Pho7 + peaks | Am | Am |

Cooling Crystallization Experiments

From the polymorph screen on the voruciclib phosphate salt it was found that Pho1 was the most promising candidate among the phosphate salt forms. Cooling crystallization experiments were performed to attempt the controlled crystallization of Pho1. These experiments were started by mixing Voruciclib free base solutions (from batch 1694ER1201) prepared in three different crystallization solvents and 1.1 eq. of neat phosphoric acid at 50° C. The mixtures were subsequently cooled to 5° C. and the solids were isolated and analyzed by XRPD. The crystallization solvents were selected based on the solubility of the free base as determined in project S18128.

Upon addition of the counterion, the material immediately precipitated, resulting in a highly dense suspension in all three experiments. Due to the high density, it was not possible to properly stir the suspensions during cooling. From the small amount of liquid phase recovered after the experiments, the yield was determined to be high (81-98%).

From THF, a new phosphate form was identified which was classified as Pho9. Upon drying under deep vacuum (5 mbar, 18 h), Pho9 converted into a mixture of Pho1+Pho4. From ethanol, Pho3 was recovered which converted into Pho1 upon deep vacuum (5 mbar, 18 h). From acetone, Pho1 was obtained which remained stable upon drying under deep vacuum (5 mbar, 18 h).

Solid State Characterization

An overlay of the powder diffraction patterns of the solid forms identified in this study is presented in FIG. 207. Additional analytical data including DSC, TGMS, UPLC and $^1$H-NMR was obtained for Pho1, Pho6 and Pho7 as these forms were obtained as pure phases after vacuum drying (5 mbar, 18 h). The API:CI ratio of these forms was estimated by the UPLC assay method and ranged between 1.1-1.6. The $^1$H-NMR spectra for the different phosphate salt forms showed significant shifts in the resonances with respect to the free base which confirmed that salt formation occurred. The analytical data of each form is presented herein, while a summary of the results is presented below and in Table 43.

Pho1 was identified as an anhydrous form with a high purity (98.4%) and about 1.4% residual water. The material melted at 200° C. and underwent thermal decomposition at 210° C. Due to its practically anhydrous nature and physical stability against both AAC and deep vacuum, Pho1 was selected as the most promising phosphate salt form of voruciclib and therefore additional analytical data was obtained on the material. Pho1 was stable against variable humidity conditions (between 0-95% RH) and was classified as moderately hygroscopic. The material became a gel upon addition of water and the solubility in water at room temperature was approximately 8 mg/ml.

The starting material Pho3 was not obtained in the polymorph screen. Pho3 was physically stable against AAC (40° C./75% RH, 2 days) but unstable upon exposure to deep vacuum (5 mbar, 18 h), as evidenced by the cooling crystallization experiment from ethanol (Exp. ID: SSm2).

Both Pho4 and Pho5 were physically unstable upon drying under vacuum. Pho6 and Pho7 were identified as hydrates which contained residual process solvents, and which were unstable upon exposure to AAC (40° C./75% RH, 2 days). Pho8 could be only obtained after AAC (40° C./75% RH, 2 days), whereas Pho9 was physically unstable upon exposure to AAC (40° C./75% RH, 2 days) and could be only obtained through cooling crystallization from THF.

TABLE 43

Summary of the analytical characterization performed on selected phosphate salt forms of voruciclib found in this study. The thermal analyses were performed by DSC. The chemical purity and the ratio API:CI were determined by UPLC. The solvent content was determined by TGMS (for water) and by $^1$H-NMR for organic solvents. The notations "br", "m", "ex" and "d" stand for broad endotherm corresponding to water loss, melting, exotherm and decomposition events, respectively.

| Solid form | Crystallization solvent | Solvent content | Thermal events by DSC [° C.] | Chemical Purity [area %] | Ratio API:CI |
|---|---|---|---|---|---|
| Pho1 | Ethanol | 1.4% water | 25-80 (br), 200 (m), 210 (d) | 98.4 | 1.4 |
| Pho3 | — | 5.4% water | 27-96 (br), 112-136 (br), 149-165 (br), 197 (m), 200 (d) | 94.8 | 1.6 |
| Pho6 | TBME | 2.2% water + 1.5% TBME | 27-73 (br), 109-120 (br), 127-143 (br), 147 (ex), 176 (m), 211 (d) | 94.3 | 1.6 |
| Pho7 | IPA/water (90/10) | 2.3% water + 1.7% IPA | 25-90 (br), 167 (m), 172 (ex), 180 (br), 191 (d) | 98.4 | 1.1 |

The polymorph screen on voruciclib phosphate salt was started with the amorphous phase to favor unbiased crystallization of novel forms. In total, nine polymorphic forms were identified in the present study from which Pho1 was the only form that was physically stable against both AAC (40° C./75% RH, 2 days) and deep vacuum (5 mbar, 18 h). In the polymorph screen, Pho1 was most frequently obtained. Moreover, Pho1 could be an anhydrous form containing residual water adsorbed on the surface. Pho1 could be obtained through cooling crystallization from ethanol (after drying under vacuum) and from acetone. Based on these considerations, it was decided that Pho1 was the best phosphate salt form of voruciclib within the investigated experimental conditions. However, additional data on the selected Pho1 form showed that the material was moderately hygroscopic. Upon the addition of water, Pho1 became a gel. The solubility of Pho1 in water at room temperature was approximately 8 mg/ml.

28.89 grams of ME-522 (batch ID: 19-09334-01) were provided as a crystalline powder. The free base used for the cooling crystallization experiments was taken from project S18128, batch 1694ER1201. Other chemicals were purchased from Sigma Aldrich, Fisher Scientific or VWR. Chemicals were at least of research grade and the solvents used for the UPLC analyses were of UPLC grade.

Preferably a polymorph screen is initiated with an amorphous phase to promote unbiased crystallization. It was attempted to generate amorphous material through lyophilization of the Pho3 (starting material) from different organic/water mixtures (Table 44).

In the most polar protic solvents tested (i.e. water, MeOH/water and EtOH/water), the material did not dissolve at room temperature with a concentration of 20 mg/mL and these conditions were therefore not suitable for freeze-drying.

An amorphous phase was obtained by freeze-drying the solutions obtained in t-BuOH/water, THF/water, acetone/water and TFE/water 50/50% (v/v). The residual solvent content in the amorphous solids was initially estimated by TGMS. The solvent content was further reduced by drying under vacuum (5 mbar/RT, 18 h). The amorphous sample with the lowest residual solvent content was recovered from acetone/water 50/50% (Exp. ID QSA3). These conditions in combination with a concentration of 21 mg/ml were used to generate amorphous materials for the polymorph screen.

An API solution was prepared in acetone/water 50/50 (Exp. ID: QSA8) and liquid-dosed over 18 vials. The solutions were frozen in liquid nitrogen and placed under deep vacuum using a freeze dryer (Alpha 2-4 LD, Christ). Solvents were removed by freeze-drying. A sample of amorphous material was taken from the polymorph screen (Exp. ID: QSA8) as a reference and analyzed by HT-XRPD, TGMS and $^1$H-NMR.

TABLE 44

Conditions and results of the experiments to produce amorphous solids. Solutions were prepared with voruciclib Pho starting material. The solutions were freeze-dried overnight and the resulting solids were analyzed by HT-XRPD to determine the crystallinity and by TGMS to determine the residual solvent content. The solid materials were subjected to high vacuum (5 mbar) for 18 h and reanalyzed by TGMS. Samples that were not analyzed are indicated by "—".

| Exp. ID | SM Mass [mg] | Solvent system | Solvent [ml] | Concentration [mg/ml] | Dissolved? | XRPD | Mass loss [%] | Mass loss [%]* |
|---|---|---|---|---|---|---|---|---|
| QSA1 | 20.9 | t-BuOH/water (50/50) | 1.0 | 21 | Yes | Am | 5.2 | 2.5 |
| QSA2 | 23.0 | THF/water (50/50) | 1.0 | 23 | Yes | Am | 5.0 | 2.6 |

TABLE 44-continued

Conditions and results of the experiments to produce amorphous solids. Solutions were prepared with voruciclib Pho starting material. The solutions were freeze-dried overnight and the resulting solids were analyzed by HT-XRPD to determine the crystallinity and by TGMS to determine the residual solvent content. The solid materials were subjected to high vacuum (5 mbar) for 18 h and reanalyzed by TGMS. Samples that were not analyzed are indicated by "—".

| Exp. ID | SM Mass [mg] | Solvent system | Solvent [ml] | Concentration [mg/ml] | Dissolved? | XRPD | Mass loss [%] | Mass loss [%]* |
|---|---|---|---|---|---|---|---|---|
| QSA3 | 19.2 | Acetone/water (50/50) | 1.5 | 13 | Yes | Am | 4.4 | 2.9 |
| QSA4 | 21.7 | EtOH/water (50/50) | 1.0 | 22 | No | — | — | — |
| QSA5 | 19.9 | MeOH/water (50/50) | 1.0 | 20 | No | — | — | — |
| QSA6 | 20.2 | TFE/water (50/50) | 1.0 | 20 | Yes | Am | 10.1 | 6.6 |
| QSA7 | 21.2 | Water | 1.0 | 21 | No | — | — | — |
| QSA8 | 515.5 | Acetone/water (50/50) | 2.5 | 21 | Yes | Am | 4.0 | 3.0 |

The aqueous solubility of Pho1 (Exp. ID: TCP23) was assessed by the qualitative solubility determination approach. To 5.6 mg of Pho1, water was added in steps of 50 μl until the material was dissolved (Exp. ID: SAS2). Visual inspection by the naked eye was used to decide whether complete dissolution occurred. After the addition of 700 μl water, Pho1 was not dissolved in water at room temperature whereas after a subsequent addition of 200 μl water (900 μl in total), the material completely dissolved.

About 33 mg of amorphous voruciclib phosphate salt were mixed with 15 solvent systems at room temperature (see Table 45 for details). Subsequently, the mixtures were placed in the Crystal16™ apparatus and were subjected to the temperature profile as displayed in FIG. 208.

After the temperature profile, the solids were separated from the liquids by centrifugation and the solid phase was dried under ambient conditions and under deep vacuum (5 mbar, 18 h) before being harvested and analyzed by HT-XRPD. The liquid phases were dried under deep vacuum (5 mbar, 18 h) and the recovered solids were analyzed by HT-XRPD. All solids were then exposed to accelerated aging conditions (40° C./75% RH, 2 days) followed by HT-XRPD re-analysis.

TABLE 45

Experimental conditions for the thermocycling experiments. Slurries of amorphous voruciclib Phosphate (33.3 mg) were prepared in neat solvents and solvent mixtures and placed in the Crystal16 ™ reactor to undergo a thermal profile as described in FIG. 208. After the temperature profile, the solids were ambient-dried and vacuum-dried and analyzed before and after exposure to AAC (40° C./75% RH, 2 days) by HT-XRPD. The solutions were dried under vacuum and the obtained dried solids were analyzed by XRPD.

| Exp ID | Solvent | Solvent volume [μL] | Concentration [mg/ml] | Dissolved at initial temperature | Solids after Tprofile |
|---|---|---|---|---|---|
| TCP16 | 1,2-Dimethoxyethane | 1500 | 22.2 | No | Yes |
| TCP17 | 1,4-Dioxane | 1500 | 22.2 | No | Yes |
| TCP18 | 2-Propanol | 1000 | 33.3 | No | Yes |
| TCP19 | Acetone | 1500 | 22.2 | No | Yes |
| TCP20 | Acetonitrile | 1500 | 22.2 | No | Yes |
| TCP21 | Chloroform | 1500 | 22.2 | No | Yes |
| TCP22 | Cyclohexane | 1000 | 33.3 | No | Yes |
| TCP23 | Ethanol | 1000 | 33.3 | No | Yes |
| TCP24 | Ethyl acetate | 1500 | 22.2 | No | Yes |
| TCP25 | Ethyl formate | 1500 | 22.2 | No | Yes |
| TCP26 | t-Butyl methyl ether | 1000 | 33.3 | No | Yes |
| TCP27 | Tetrahydrofuran | 1500 | 22.2 | No | Yes |
| TCP28 | Toluene | 1000 | 33.3 | No | Yes |
| TCP29 | Acetone/water (90/10) | 1500 | 22.2 | No | Yes |
| TCP30 | 2-Propanol/water (90/10) | 1500 | 22.2 | No | Yes |

Additional crystallization experiments were performed to prepare the selected phosphate salt form Pho1 by cooling crystallization and to evaluate the yield of such experiment. The three experiments performed consisted of preparing a saturated solution of the free base (received for project S18128, batch 1694ER1201) in ethanol, THF and acetone at 50° C. Suspensions of voruciclib were incubated at 50° C. for 3 hours before being filtrated. To the 1 ml saturated solutions, 1.1 equivalent of neat phosphoric acid was added. The experimental conditions are described in Table 46.

After addition of the counterion, the solutions were subjected to a temperature profile in a Crystal16™ apparatus. After 30 min at 50° C., the temperature of the solutions was lowered with a cooling rate of 10° C./h until 5° C. Aging for 18 hours at the final temperature (5° C.) was finally applied.

Upon completion of the temperature profile, the solids were separated from the solution by centrifugation and were dried at ambient conditions and under deep vacuum (5 mbar) before being harvested and analyzed by HT-XRPD. The mother liquors were evaporated to assess the yield based on the weight of the solids.

TABLE 46

Experimental conditions and results for the cooling crystallization experiments performed on Voruciclib free base (SM) to produce the phosphate salt. The solids were analyzed after drying under ambient- and vacuum conditions. Poorly crystalline phases are denoted with "pc".

| Exp ID | SM [mg] | Solvent | Yield [%] | Ambient | Vacuum |
|---|---|---|---|---|---|
| SSm1 | 107 | Tetrahydrofuran | 81 | Pho9 | Pho1 + Pho4 (pc) |
| SSm2 | 40 | Ethanol | 95 | Pho3 | Pho1 |
| SSm3 | 44 | Acetone | 98 | Pho1 (pc) | Pho1 |

XRPD patterns were obtained using the Crystallics T2 high-throughput XRPD set-up. The plates were mounted on a Bruker D8 Discover General Area Detector Diffraction System (GADDS) equipped with a VÅNTEC-500 gas area detector corrected for intensity and geometric variations (product sheet XRD 37, DOC-S88-EXS037V3, FIG. 297). The calibration of the measurement accuracy (peaks position) was performed using NIST SRM1976 standard (Corundum).

Data collection was carried out at room temperature using monochromatic Cu $K_\alpha$ radiation in the $2\theta$ region between 1.5° and 41.5°, which is the most distinctive part of the XRPD pattern. The diffraction pattern of each well was collected in two $2\theta$ ranges ($1.5° \leq 2\theta \leq 21.5°$ for the first frame, and $19.5° \leq 2\theta \leq 41.5°$ for the second) with an exposure time of 90 s for each frame. No background subtraction or curve smoothing was applied to the XRPD patterns. The carrier material used during XRPD analysis was transparent to X-rays and contributed only slightly to the background.

The HR-XRPD data were collected on D8 Advance diffractometer using Cu $K_{\alpha 1}$ radiation (1.54056 Å) with germanium monochromator at RT. Diffraction data were collected in the $2\theta$ range 1.5-41.5° $2\theta$. Detector scan on solid state LynxEye detector was performed using 0.016° per step with 4 sec/step scan speed (DOC-M88-EXX95 V2—11.2007, FIG. 298). The samples were measured in 8 mm long glass capillary with 0.4 mm outer diameter.

The results for Pho1 (S18128) and Pho3 (SM, S18128B) are shown in Table 47. During the refinement the following parameters were refined:

cell constants;

background;

instrument geometry;

zero shift;

absorption

Neither atom positions nor thermal motion parameters were refined during whole process. The following criteria of fit were used:

$Y_{o,m}$ and $Y_{c,m}$ are the observed and calculated data, respectively at data point m, M the number of data points, P the number of parameters, $w_m$ the weighting given to data point m which for counting statistics is given by $w_m = 1/\sigma(Y_{o,m})^2$ where $\sigma(Y_{o,m})$ is the error in $Y_{o,m}$, $$R_{exp} = \sqrt{\frac{M-P}{\sum w_m Y_{o,m}^2}};$$

$$R_{wp} = \sqrt{\frac{\sum w_m (Y_{o,m} - Y_{c,m})^2}{\sum w_m Y_{o,m}^2}};$$

$$R_p = \sqrt{\frac{\sum |Y_{o,m} - Y_{c,m}|}{\sum Y_{o,m}}}$$

$$GOF = chi^2 = \frac{R_{wp}}{R_{exp}} = \sqrt{\frac{\sum w_m (Y_{o,m} - Y_{c,m})^2}{M-P}}$$

TABLE 47

Crystal data obtained from HR-XRPD for Pho1 (S18128) and Pho3 (SM, S18128B).

| Polymorph | Pho1 | Pho3 |
|---|---|---|
| Empirical formula | $C_{22}H_{20}ClF_3NO_5^+ \cdot H_2PO_4^-$ | $C_{22}H_{20}ClF_3NO_5^+ \cdot H_2PO_4^-$ |
| Formula weight | 514.82 | 514.82 |
| T [K] | 296 | 296 |
| λ [Å] | 1.54056 | 1.54056 |
| Crystal system | Orthorhombic | Orthorhombic |
| Space group | $P2_12_12_1$ | $P2_12_12_1$ |
| a [Å] | 7.3398 (7) | 7.7136 (8) |
| b [Å] | 17.289 (3) | 18.954 (3) |
| c [Å] | 21.875 (3) | 35.935 (5) |
| V [Å$^3$] | 2775.8 (6) | 5254.0 (11) |
| Z (Z') | 4 (1) | 8 (2) |
| Dc [g/cm$^3$] | 1.366 | 1.444 |
| Cap. size [mm$^2$] | 0.5 × 8 | 0.5 × 8 |
| 2θ Step size [°] | 0.015 | 0.015 |
| No of steps | 2561 | 2561 |
| Time per step [s] | 5 | 6 |
| 2θ range [°] | 4-41.5 | 4-41.5 |
| Rexp | 3.00 | 1.24 |
| Rwp | 4.77 | 1.56 |
| Rp | 3.63 | 1.22 |
| GOF | 1.59 | 1.26 |

TABLE 47-continued

Crystal data obtained from HR-XRPD for
Pho1 (S18128) and Pho3 (SM, S18128B).

| Polymorph | Pho1 | Pho3 |
|---|---|---|
| RBrag | 0.23 | 0.07 |
| Impurities, other forms [%] | ~5% (unidentified) | Below detection limits |

Mass loss due to solvent or water loss from the crystals was determined by TGA/heat flow. Monitoring the sample weight, during heating in a TGA/DSC 3+ STARe system (Mettler Toledo GmbH, Switzerland), resulted in a weight vs. temperature curve. The TGA/DSC 3+ was calibrated for temperature with indium and aluminum. Samples (circa 2 mg) were weighed into 100 µL aluminum crucibles and sealed. The seals were pin-holed and the crucibles heated in the TGA from 25 to 300° C. at a heating rate of 10° C./min unless stated otherwise. Dry $N_2$ gas was used for purging.

The gases evolved from the TGA samples were analyzed by an Omnistar GSD 301 T2 mass spectrometer (Pfeiffer Vacuum GmbH, Germany). This MS is a quadrupole mass spectrometer, which analyses masses in the range of 0-200 amu.

Melting properties were obtained from DSC thermograms, recorded with a heat flux DSC3+ STARe system (Mettler-Toledo GmbH, Switzerland). The DSC3+ was calibrated for temperature and enthalpy with a small piece of indium (m.p.=156.6° C.; δHf=28.45 J/g) and zinc (m.p.=419.6° C.; δHf=107.5 J/g). Samples (circa 2 mg) were sealed in standard 40 µL aluminum pans, pin-holed and heated in the DSC from 25° C. to 300° C., at a heating rate of 10° C./min unless stated otherwise. Dry $N_2$ gas, at a flow rate of 50 mL/min was used to purge the DSC equipment during measurement.

$^1$H-NMR spectroscopy in DMSO-$d_6$ was used for compound integrity characterization. The spectra were recorded at room temperature (32 scans) on a 500 MHz instrument (Bruker BioSpin GmbH) using standard pulse sequences. The data was processed with ACD Labs software Spectrus Processor 2016.2.2 (Advanced Chemistry Development Inc. Canada).

Differences in hygroscopicity (moisture uptake) of the various forms of a solid material provided a measure of their relative stability at increasing relative humidity. Moisture sorption isotherms of small samples were obtained using a DVS-1 system from Surface Measurement Systems (London, UK); this instrument is suitable for use with a few milligrams of sample, with an accuracy of 0.1 µg. The relative humidity was varied during sorption-desorption-sorption (40-95-0-40% RH) at a constant temperature of 25° C. Weight equilibration per step was set at dm/dt <0.0002 for a minimum of 1 hour or maximum of 6 hours. Afterwards the sample was measured by HT-XRPD.

The hygroscopicity was classified according to the European Pharmacopoeia Hygroscopicity classification. Water uptake percentage at 25° C./80% RH (24 h) is: Change in mass <0.2%—Non-hygroscopic; Change in mass >0.2% & <2%—Slightly hygroscopic; Change in mass >2% & <15%—Moderately hygroscopic; Change in mass >15%—Very hygroscopic.

UPLC Analysis

Method Name: S18128B_01_LCMS

| | |
|---|---|
| Instrument | Agilent 1290 series with diode array UV detector and MSD XT single quad mass detector |
| Mobile phase A | 0.1% Formic acid in water |
| Mobile phase B | 0.1% Formic acid in acetonitrile |
| Column | Agilent Eclipse Plus C18 HD (50 × 2.1 mm; 1.8 µm) |
| Detection: | UV at 264 nm, bandwidth 4 nm, UV spectrum 200 to 400 nm. MS in positive scan mode 100-1000 m/z, 500 ms scan time |
| Flow: | 0.8 mL/min. |
| Runtime | 4 minutes |
| Injection volume | 1.0 µL |
| Column temp. | 35° C. |
| Autosampler temp. | Ambient |

| Gradient: | Time [min.] | Eluent A [%] | Eluent B [%] |
|---|---|---|---|
| | 0 | 90 | 10 |
| | 0.25 | 90 | 10 |
| | 2 | 2 | 98 |
| | 2.95 | 2 | 98 |
| | 3 | 90 | 10 |
| | 4 | 90 | 10 |

The compound integrity is expressed as a peak-area percentage, calculated from the area of each peak in the chromatogram, except the 'injection peak', and the total peak-area, as follows:

$$\text{peak area (\%)} = \frac{\text{peak area}}{\text{total area of all peaks}} \cdot 100\%$$

The peak area percentage of the compound of interest is employed as an indication of the purity of the component in the sample.

For the UPLC assay, a solution of Voruciclib free base (from project S18128) was measured as a reference and the peak area was assigned to 100% recovery after taking into account the amount of solvent determined by TGMS. Samples of the salts were measured in the same way and the % recovery was calculated again by taking into account the amount of solvent. With all measured salts, <100% recovery could be assigned to the API and the remaining % recovered could be assigned to the counterion from which the ratio API:counterion could be determined (Table 48).

TABLE 48

Assay results for the phosphate salts.

| Sample Name | Area [mV*s] | Weight [mg] | Volume [ml] | TGMS [%] | Purity [%] | RF | Recovery [%] | Ratio API:CI |
|---|---|---|---|---|---|---|---|---|
| S18128_Ref-SOL1_R1 | 2014.3 | 30.03 | 50 | 0.33 | 99.67 | 33.65 | — | — |
| S18128_Ref-SOL2_R2 | 2021.0 | 30.03 | 50 | 0.33 | 99.67 | 33.76 | — | — |
| S18128_Ref-SOL2_R2 | 2011.8 | 30.03 | 50 | 0.33 | 99.67 | 33.61 | — | — |
| Average | 2015.7 | | | | | 33.67 | — | — |
| RSD | 0.23 | | | | | | | |
| LCMS_S18128_Ref-SOL2 | 1971.0 | 29.13 | 50 | 0.33 | 99.67 | 33.94 | — | — |
| LCMS_S18128B_SM_Pho (Pho3) | 1473.6 | 31.13 | 50 | 5.39 | 94.61 | 25.02 | 75.1 | 1:1.6 |
| LCMS_S18128B_TCP23 (Pho1) | 1105.8 | 4.27 | 10 | 1.38 | 98.62 | 26.26 | 78.0 | 1:1.4 |
| LCMS_S18128B_TCP26 (Pho6) | 1298.8 | 5.35 | 10 | 3.54 | 96.46 | 25.17 | 74.7 | 1:1.6 |
| LCMS_S18128B_TCP30 (Pho7) | 1035.4 | 3.91 | 10 | 4.03 | 95.97 | 27.59 | 81.9 | 1:1.1 |

Pho1 was the prevalent form obtained in the polymorph screen. Vacuum-dried Pho1 obtained from the thermocycling experiment involving ethanol (Exp. ID: TCP23) was used for analytical characterization. Upon exposure to either deep vacuum (5 mbar) or AAC (40° C./75% RH, 2 days), Pho1 remained stable as indicated by the XRPD patterns (FIG. 209).

The TGMS analysis of Pho1 in FIG. 210 shows that between 40-120° C. approximately 1.4% of water was released, corresponding to 0.4 molecules of water per molecule of API. The endothermic event at about 190° C. most likely corresponds to the melting of Pho1. From 200° C. onwards, the material underwent thermal decomposition as indicated by a significant mass loss.

The DSC analysis of the starting material (Pho1) is shown in FIG. 211. The broad endothermic event between 25-80° C. may be associated to the release of water. The sharp endothermic event at 200° C. could be associated to the melting of Pho1, whereas the broad endothermic event between 217-269° C. represents thermal decomposition.

A cycling DSC (cDSC) was performed on Pho1 (Exp. ID: TCP23) to determine if Pho1 would remain stable after the removal of water. A sample of Pho1 was heated to 140° C. (FIG. 212A) and cooled back to room temperature for analysis by HT-XRPD. As indicated by the HT-XRPD results (FIG. 213), Pho1 was recovered after cDSC which suggests that the water in Pho1 could be present as unbound non-stochiometric water or adsorbed on the surface of the solid particles.

The chemical purity of Pho1 was assessed by LCMS analysis (FIG. 214). The result indicated that the API purity was 98.4% (area %). The positive ion spectrum showed ions with m/z of 470 corresponding to the positively charged species [M+H]$^+$ and agreed with the molecular mass of the free base (i.e. 469.8 g/mol). From the LCMS assay analysis, the ratio of API:phosphate of Pho1 was estimated to be 1:1.4.

FIG. 215 shows the $^1$H-NMR spectrum of Pho1 in comparison to the free base (starting material, project S18128). Compared to the free base, the NMR peaks of Pho1 were shifted downfield which indicated that Pho1 was isolated as a salt.

A Dynamic Vapor Sorption (DVS) measurement was performed on Pho1 (Exp. ID: TCP23). As shown in FIG. 216, the material gradually took up water with increasing relative humidity (RH). At 25° C./80% RH, the water uptake was approximately 5.0%, which makes the material moderately hygroscopic (European Pharmacopoeia Hygroscopicity classification. Water uptake percentage at 25° C./80% RH is: Change in mass <0.2%—Non-hygroscopic; Change in mass <2% & >0.2%—Slightly hygroscopic; Change in mass <15% & 2%—Moderately hygroscopic; Change in mass >15%—Very hygroscopic). After DVS analysis, Pho1 was recovered as indicated by XRPD.

The solubility of Pho1 (Exp. ID: TCP23) in water at room temperature was determined by the qualitative solubility determination. The solubility of Pho1 in water was approximately 6-8 mg/ml. Upon addition of water to the solid material, Pho1 became a gel-like material (FIG. 217).

Pho2 was obtained as a poorly crystalline phase from THF in project S18128 but was not obtained in the present study. The XRPD pattern of Pho2 is shown in FIG. 218.

Pho3 was the material received but was not obtained in the thermocycling experiments. The cooling crystallization experiment of the Voruciclib free base with neat phosphoric acid from ethanol yielded Pho3 after drying under ambient conditions (FIG. 219). However, Pho3 converted into Pho1 after the material was dried under deep vacuum (5 mbar, 18 h).

Pho4 was obtained through thermocycling experiments in 1,2-dimethoxyethane and THF and as a mixture with Pho1 through thermocycling experiments in 1,4-dioxane, 2-propanol and acetone/water (90/10, v/v). The XRPD patterns of the materials obtained through the thermocycling experiment in 1,2-dimethoxyethane (Exp. ID: TCP16) are shown in FIG. 220. The ambient-dried material was obtained as Pho4 which remained stable upon exposure to AAC (40° C./75% RH, 2 days). Pho4 was dried under deep vacuum (5 mbar, 18 h) upon which the material converted into Pho1.

Pho5 was the ambient-dried solid material obtained from the thermocycling experiment in acetone (Exp. ID: TCP19). Pho5 was unstable upon exposure to AAC (40° C./75% RH, 2 days) and deep vacuum (5 mbar, 18 h) as it converted into Pho8 and Pho1+peaks, respectively (FIG. 221).

Pho6 was obtained as a poorly crystalline solid material from several thermocycling experiments, including from solvents chloroform, ethyl acetate, ethyl formate and t-butyl methyl ether (TBME). FIG. 222 shows an overlay of the HT-XRPD patterns of the materials obtained from the thermocycling experiment in TBME (Exp. ID: TCP26). Pho6 remained stable after exposure to deep vacuum (5 mbar, 18 h) but became amorphous upon exposure to AAC (40° C./75% RH, 2 days).

The TGMS analysis of Pho6 in FIG. 223 shows that between 30-180° C. approximately 2.2% of water and 1.5% of TBME was released. The amount of TBME in Pho6 was confirmed by $^1$H-NMR analysis (FIG. 226). From 180° C. onwards, Pho6 underwent thermal decomposition as indicated by a significant mass loss.

The DSC analysis of Pho6 is shown in FIG. 224. Three endothermic events before 143° C. were detected which were associated to the removal of water and TBME. The exothermic event at 146° C. may denote a recrystallization event whereas the endothermic event at 176° C. may be associated to the melting of the salt. Thermal decomposition of the material was characterized by the broad endothermic event between 211-267° C.

The chemical purity of Pho6 was assessed by LCMS analysis. The result indicated that the API purity was 94.3% (area %). The positive ion spectrum showed ions with m/z of 470 corresponding to the positively charged species [M+H]$^+$ and agreed with the molecular mass of the free base (i.e. 469.8 g/mol). From the LCMS assay analysis, the ratio of API:phosphate of Pho6 was estimated to be 1:1.6.

FIG. 231 shows the $^1$H-NMR spectrum of Pho6 in comparison to the free base (starting material, project S18128). Compared to the free base, the NMR peaks of Pho6 were shifted downfield which confirmed that Pho6 was isolated as a salt. Based on the TBME signal at 1.12 ppm, the ratio of Pho6:TBME was estimated to be 1:0.1 which corresponds to approximately 1.4%, in accordance with the TGMS results (FIG. 223).

Pho7 was the salt form obtained through thermocycling the amorphous voruciclib phosphate salt in 2-propanol/water (90/10, v/v; Exp. ID: TCP30). As shown in FIG. 227, Pho7 remained physically stable upon drying under high vacuum, but additional diffraction peaks were observed in the material after exposure to AAC (40° C./75% RH, 2 days). The vacuum-dried Pho7 sample (Exp. ID: TCP30) was used for further analytical characterization of this form.

The TGMS analysis in FIG. 228 shows that between 25-180° C. approximately 4.0% of water and 2-propanol was released. From 200° C. onwards, the material underwent thermal decomposition as indicated by a significant mass loss.

The DSC analysis of the Pho7 is shown in FIG. 229. Several endo- and exothermic events were detected before 200° C., whereas significant thermal decomposition was characterized by the broad endothermic event between 213-261° C.

The chemical purity of Pho7 was assessed by LCMS analysis. The result indicated that the API purity was 98.4% (area %). The positive ion spectrum showed ions with m/z of 470 corresponding to the positively charged species [M+H]$^+$ and agreed with the molecular mass of the free base (i.e. 469.8 g/mol). From the LCMS assay analysis, the ratio of API:phosphate of Pho7 was estimated to be 1:1.1.

FIG. 231 shows the $^1$H-NMR spectrum of Pho7 in comparison to the free base (starting material, project S18128). Compared to the free base, the NMR peaks of Pho7 were shifted downfield which confirmed that Pho7 was isolated as a salt. According to the 2-propanol signal at 1.06 ppm, the ratio of Pho7:2-propanol was 1:0.15. Therefore, approximately 1.7% of 2-propanol was present in the solid phase.

Pho8 (FIG. 232) was obtained as a poorly crystalline phase after the ambient-dried materials obtained from thermocycling experiments in acetone and acetonitrile were exposed to AAC (40° C./75% RH, 2 days). The corresponding vacuum-dried solids were classified as Pho1+peaks and transformed into Pho8+peaks after exposure to AAC (40° C./75% RH, 2 days). No additional analytical data was obtained on Pho8 due to the difficulty of producing the pure material.

Pho9 was obtained as the ambient-dried material through cooling crystallization using the Voruciclib free base dissolved in THF in combination with neat phosphoric acid (Exp. ID: SSm1). Upon drying under deep vacuum (5 mbar, 18 h), Pho9 converted into a mixture of Pho1+Pho4 (FIG. 233).

Example 5: Voruciclib Malonate

A polymorph screen was designed involving 24 solvents. The selected malonate salt was produced at a 20 g scale. The received material was voruciclib chloride salt which was used to produce the free base. The malonate salt was prepared by freeze-drying a free base solution containing one equimolar amount of malonic acid. The polymorph screen experiments were started with amorphous voruciclib malonate salt to favor unbiased crystallization. Mao1 was the most abundantly found phase which was the anhydrous solid form identified in previous salt screen. Mao1 was non-hygroscopic and had a solubility of approximately 13 mg/ml in water. Upon the addition of a small aliquot of water, Mao1 became a suspension and gel formation was not observed. A large-scale cooling crystallization experiment successfully yielded Mao1 in high yield and high purity. Three other phases, designated Mao3, Mao4 and Mao5 were identified in the study from very few crystallization conditions. The three novel crystalline phases appeared to be hydrates. All these phases were physically unstable and converted to Mao1 upon drying under vacuum or exposure to stress conditions.

Abbreviations

AAC Accelerated Aging Conditions (40° C./75% RH)
Am Amorphous
API Active Pharmaceutical Ingredient
DSC Differential Scanning Calorimetry
GEN Experimental ID for the free base conversion experiments
$^1$H NMR Proton Nuclear Magnetic Resonance
HR-XRPD High Resolution X-Ray Powder Diffraction
HT-XRPD High Throughput X-Ray Powder Diffraction
ML Mother liquor (liquid phases)
MS Mass Spectroscopy
RF Response Factor
RH Relative Humidity
RT Room Temperature
SM Starting Material
TCP Experimental ID for the thermocycling experiments
TGA Thermogravimetric Analysis
TGMS Thermogravimetric Analysis coupled with Mass Spectroscopy
UPLC Ultra-Performance Liquid Chromatography
AcN Acetonitrile
DCM Dichloromethane
EtOH Ethanol
HCl Hydrochloride salt
IPA 2-propanol
Mao Malonate salt
MEK Methyl ethyl ketone
MTBE Methyl tert-butyl ether
THF Tetrahydrofuran In this study, the polymorphic behavior of the malonate salt has been evaluated in a solid form screen. A thermocycling screen combining 24 solvents to identify novel crystalline phases of voruciclib malonate salt and to select the thermodynamically stable form for further investigations was designed. This study consisted of the following project steps: Free base conversion from ME-522 hydrochloride salt; Preparation of malonate salt; Thermodynamic solid form screen in 24 solvents; Scale-up and characterization of selected voruciclib malonate salt form; Analytical characterization of novel solid forms.

95 g of ME-522 HCl salt (batch 1201) were provided. The Voruciclib free base was prepared from the ME-522 hydrochloride salt. Approximately 3.4 grams of ME-522 (mono HCl salt) were suspended in 400 ml of water (pH ~4.3). The pH was adjusted to pH=11 by addition of 2M sodium hydroxide solution. The color of the solution became yellow and precipitation occurred after 30 min. The precipitated solid was filtered and washed with water until the pH of the filtrate was 8.5. The material was dried overnight at 50° C. and 5 mbar. The obtained solid was analyzed by High Throughput XRPD (HT-XRPD), DSC, TGMS, UPLC and $^1$H-NMR.

The HT-XRPD analysis of the obtained free base showed a different powder pattern to the free base received for previous study (S18128). The powder patterns are presented in FIG. 235.

The TGA/TGMS analysis of the recovered free base (FIG. 236) showed a mass loss of 3.3% between 30-100° C. attributed to water, based on the MS signal (3.3% of water corresponds to 0.9 molecules of water per molecule of API). The heat flow signal showed a broad endotherm attributed to the loss of water followed by a melting/recrystallization event between 160-180° C. and a final melting at 220° C. The thermal decomposition was observed at temperatures above 240° C.

In the DSC curve (FIG. 237) a broad endothermic event was observed between 30-70° C. which could be attributed to water loss. Subsequently, a sharp melting event was detected at 164.7° C. followed by an exothermic event. These events could correspond to a recrystallization event. Next, a small endothermic event at 217° C. was observed followed by a sharp endothermic event at 226° C.

The UPLC chromatogram of the Voruciclib free base (FIG. 238) showed the API peak at 1.2 minutes with a chemical purity of 100% (area %). In the MS spectrum, a fragment with 470 m/z was detected, that could correspond to the species $[M+H]^+$ (Free base MW: 469 g/mol).

The assay of the compound solutions showed Response Factor (RF) comparable to that of the reference solutions, with recovery around 100%. This result suggests that the free base conversion was completed. The assay results are presented in Table 55.

The $^1$H-NMR spectrum (FIG. 239) of the generated free base (Exp. ID GEN4) showed the API chemical shifts overlapping with those of the reference anhydrous free base (received for previous project S18128) confirming that the free base conversion was successful.

The malonate salt was prepared by freeze-drying a solution of Voruciclib free base prepared in THF/water/Acetone (32.5/32.5/35, v/v/v) containing 1 molar equivalent of malonic acid. The obtained solid was analyzed by HT-XRPD confirming its amorphous nature (FIG. 240). The amorphous material was further analyzed by TGMS, UPLC and $^1$H-NMR to confirm the nature of the obtained malonate salt.

The TGA/TGMS analysis of the amorphous malonate salt (FIG. 241) showed a mass loss of 3.6% between 30-100° C. which could be attributed mainly to water and THF, based on the MS signal. The heat flow signal showed a broad endotherm attributed to the loss of water followed by a second broad endotherm which could be attributed to the thermal decomposition of the salt.

The UPLC chromatogram of the voruciclib malonate salt obtained by freeze-drying (FIG. 242) showed the API peak at 1.2 minutes with a chemical purity of 99.8% (area %). In the MS spectrum, a fragment with 470 m/z was detected, that could correspond to the species $[M+H]^+$ (Free base MW: 469 g/mol).

The assay of the compound solutions showed Response Factor (RF) comparable to that of the reference solutions, with recovery around 77%. This result suggests an API: malonic acid ratio of 1:1. The assay result is presented in Table 56.

The $^1$H-NMR spectrum (FIG. 243) obtained for the amorphous malonate salt confirmed salt formation as the proton resonances of the salt were shifted compared to those of the free base. The API:malonic acid stoichiometry determined was 1:1. Additional resonance shifts were observed in the NMR spectrum of GEN8 which could be attributed to residual THF (at 3.60 and 1.76 ppm). The API:THF ratio was 1:0.4.

Amorphous voruciclib malonate salt, generated by freeze-drying, was used to start the thermocycling experiments. Suspensions were prepared in the selected solvent systems at RT and were subjected to three thermocycles between 50 and 5° C., followed by aging at 25° C. for 3 days. Upon completion of the aging time, the solids were separated from the liquids by centrifugation and they were dried at ambient conditions and under deep vacuum (5 mbar) before being harvested and analyzed by HT-XRPD.

Moreover, after the thermocycling experiments, an aliquot of the mother liquor was taken and analyzed by UPLC to determine the API solubility. After that, the solutions were evaporated under vacuum (5 mbar) and the dry solids were analyzed by HT-XRPD. The solids were then exposed to accelerated aging conditions (2 days at 40° C./75% RH) followed by HT-XRPD re-analysis. Suspensions of amorphous voruciclib malonate salt were prepared in 24 solvents. After the temperature profile, an aliquot of mother liquor was taken, filtered and analyzed by UPLC to determine the API solubility. The results of the quantitative determination are reported in Table 49.

Voruciclib malonate salt was: freely soluble in acetone/water (90/10, v/v) and IPA/water (90/10, v/v) (solubility 100-1000 mg/mL); soluble in methanol (solubility 33-100 mg/mL); sparingly soluble in THF, water and EtOH (solubility 10-33 mg/mL); slightly soluble in IPA, acetone, AcN, MEK and 1,2-dimethoxyethane (solubility 1-10 mg/mL); very slightly soluble in 1,4-dioxane, chloroform, ethyl formate, DCM, ethyl acetate and isopropyl acetate (solubility 0.1-1 mg/mL), and practically insoluble in toluene, anisole, MTBE, diethyl ether, pentane, cyclohexane and n-heptane (solubility <0.1 mg/mL). Voruciclib malonate was more soluble in polar protic solvents, whereas the solubility decreased in low polar and apolar solvents.

TABLE 49

Results of the quantitative solubility determination performed on voruciclib malonate after the thermocycling experiments. The solubility classification is indicated according to the US Pharmacopoeia.

| Solvent | Solubility (mg/mL) |
| --- | --- |
| Acetone/water (90/10) | 245 |
| 2-Propanol/water (90/10) | 130 |
| Methanol | 65.7 |
| Tetrahydrofuran | 14.2 |
| Water | 13.6 |
| Ethanol | 13.6 |
| 2-Propanol | 5.1 |
| Acetone | 5.0 |
| Acetonitrile | 3.0 |
| Methyl ethyl ketone | 2.9 |
| 1,2-Dimethoxyethane | 2.3 |
| 1,4-Dioxane | 0.9 |
| Chloroform | 0.5 |
| Ethyl formate | 0.4 |
| Dichloromethane | 0.3 |
| Ethyl acetate | 0.3 |
| Isopropyl acetate | 0.1 |
| Toluene | <0.04 |
| Anisole | <0.04 |
| tert-Butyl methyl ether | <0.04 |
| Diethyl ether | <0.04 |
| Pentane | <0.05 |
| n-Heptane | <0.06 |
| Cyclohexane | <0.07 |

Four crystal forms were identified in the polymorph screen performed on the malonate salt designated Mao1, Mao3, Mao4 and Mao5. Mao1 was the salt form identified in previous salt screen (S18128), while Mao3, Mao4 and Mao5 were novel crystalline phases found in this study. Mao1 was the unique crystalline salt form which was physically stable upon exposure to stress conditions (AAC, 40° C./75% RH, 2 days). The results are summarized in Table 50.

Mao1 was the solid form crystallized from most of the solvent systems tested in this study, except from cyclohexane, pentane and n-heptane where an amorphous solid was recovered. It is likely that in those non-polar solvents, the amorphous starting material did not crystallize due to its poor solubility in such apolar solvents.

Mao3 was found in the ambient-dried solids recovered from the crystallization experiments performed in water or in organic solvent/water mixtures. Upon drying under vacuum and upon exposure to AAC, Mao3 converted to Mao1.

The powder pattern of Mao4 was detected after exposure to AAC of the amorphous solids obtained from cyclohexane, pentane and n-heptane. Since Mao4 was obtained after 2 days exposure to AAC, the physical stability of this form is unknown upon long-term stress conditions. On the other hand, Mao5 was obtained only from evaporation of the methanol mother liquor. Mao5 was physically unstable upon exposure to AAC since it converted to Mao4.

TABLE 50

Results of the thermocycling experiments performed on the malonate salt. The "—" indicated that no solid was recovered after evaporation of the solutions. The abbreviation "Am" stands for amorphous. Highlighted in green are the solid samples that were selected for further analytical characterization.

| | | | Solid forms | | | | | |
| --- | --- | --- | --- | --- | --- | --- | --- | --- |
| Exp. ID | Solvent | Concentration (mg/mL) | Ambient-dried solids | Vacuum-dried solids | Evap. ML | Ambient-dried solid (AAC) | Vacuum-dried solids (AAC) | Evap. ML (AAC) |
| TCP1 | Acetonitrile | 132.9 | Mao1 | Mao1 | — | Mao1 | Mao1 | — |
| TCP2 | Chloroform | 310.0 | Mao1 | Mao1 | — | Mao1 | Mao1 | — |
| TCP3 | Cyclohexane | 93.0 | Am | Am | — | Mao4 | Mao4 | — |
| TCP4 | Dichloromethane | 186.0 | Mao1 | Mao1 | — | Mao1 | Mao1 | — |
| TCP5 | 1,4-Dioxane | 186.0 | Mao1 | Mao1 | — | Mao1 | Mao1 | — |
| TCP6 | Methanol | 186.0 | Mao1 | Mao1 | Mao5 | Mao1 | Mao1 | Mao4 |
| TCP7 | Tetrahydrofuran | 93.0 | Mao1 | Mao1 | — | Mao1 | Mao1 | — |
| TCP8 | Toluene | 93.0 | Mao1 | Mao1 | — | Mao1 | Mao1 | — |
| TCP9 | 1,2-Dimethoxyethane | 155.0 | Mao1 | Mao1 | — | Mao1 | Mao1 | — |
| TCP10 | Acetone | 232.5 | Mao1 | Mao1 | — | Mao1 | Mao1 | — |
| TCP11 | Anisole | 103.3 | Mao1 | Mao1 | — | Mao1 | Mao1 | — |
| TCP12 | MTBE | 93.0 | Mao1 | Mao1 | — | Mao1 | Mao1 | — |
| TCP13 | Ethanol | 132.9 | Mao1 | Mao1 | Am | Mao1 | Mao1 | Mao4 |
| TCP14 | Ethyl acetate | 132.9 | Mao1 | Mao1 | — | Mao1 | Mao1 | — |
| TCP15 | Ethyl ether | 93.0 | Mao1 | Mao1 | — | Mao1 | Mao1 | — |
| TCP16 | Ethyl formate | 186.0 | Mao1 | Mao1 | — | Mao1 | Mao1 | — |
| TCP17 | Methyl ethyl ketone | 116.3 | Mao1 | Mao1 | — | Mao1 | Mao1 | — |
| TCP18 | Pentane | 93.0 | Am | Am | — | Mao4 | Mao4 | — |
| TCP19 | 2-Propanol | 116.3 | Mao1 | Mao1 | — | Mao1 | Mao1 | — |
| TCP20 | Heptane | 93.0 | Am | Am | — | Mao4 | Mao4 | — |
| TCP21 | Water | 93.0 | Mao3 | Mao1 | Mao1 | Mao1 | Mao1 | Mao1 |
| TCP22 | Isopropyl acetate | 93.0 | Mao1 | Mao1 | — | Mao1 | Mao1 | — |
| TCP23 | Acetone/water 90/10 | 232.5 | Mao3 | Mao1 | Mao1 | Mao1 | Mao1 | Mao1 |
| TCP24 | IPA/water 90/10 | 310.0 | Mao3 | Mao1 | Mao4 | Mao1 | Mao1 | Mao4 |

Additional cooling crystallization experiments were performed to attempt the precipitation of the malonate salt. These experiments were started by mixing a Voruciclib free base solution (from batch 1694ER1201) prepared in three different crystallization solvents and an equimolar amount of malonic acid at 50° C. An additional cooling crystallization was started with a Voruciclib free base obtained through conversion from the voruciclib phosphate salt (batch ID: 19-09334-01) from project S18128B. After mixing of the free base with the counterion, a cooling profile was applied till reaching 5° C. From all these experiments, the malonate salt Mao1 was precipitated upon cooling and in all cases with a yield >70%. The best yield was recovered from the experiment performed in THF (~95%) with batch 1694ER1201.

A scale-up cooling crystallization experiment was performed to obtain Mao1 on a larger scale. For that, 25 grams of ME-522 HCl was converted into the Voruciclib free base. Subsequently, 20 grams of the Voruciclib free base was converted into Mao1 by unseeded cooling crystallization from THF. This way, Mao1 was recovered in high yield (95%) and high purity (100%, area % by LCMS).

An overlay of the powder diffraction patterns of the solid forms identified in this study is presented in FIG. 244. The three solid forms, Mao1, Mao4 and Mao5 were further analyzed by DSC, TGMS, UPLC and $^1$H-NMR. The analytical data is presented herein, with a summary of the results presented below and in Table 51.

The thermal analyses performed on the malonate salt forms, indicated that Mao1 was the unique anhydrous and non-solvated malonate salt form. Mao4 seemed to be a monohydrate in which the water is gradually lost before the thermal decomposition of the salt. On the other hand, Mao5 showed a water content of 1.5% which seemed to be released gradually between 25 and 100° C. (corresponding to some residual water). Further significant mass loss occurred between 100-180° C. which according to the mass signal is most likely due to thermal decomposition.

The UPLC analysis confirmed that all malonate salt forms were obtained with good chemical purities (>99.2%, area %). In all the UPLC chromatograms a small impurity was observed at 1.4 min (no mass spectrum was recorded in positive mode). The lowest chemical purity was determined for Mao4 (98.5%).

The $^1$H-NMR spectra for the different malonate salt forms showed significant shifts in the resonances which confirmed the structure rearrangement as a result of salt formation due to proton transfer. All the spectra were compared to the initial amorphous malonate salt and to Mao1 obtained in previous project. A stoichiometric ratio API:CI of 1:1 was estimated for all three phases.

The hygroscopicity of Mao1 and Mao4 was evaluated by DVS measurements. Mao1 is non-hygroscopic with a water uptake of 0.15% at 80% RH. Furthermore, Mao4 appeared to be slightly hygroscopic with a water uptake of 0.9% at 80% RH. The water uptake for this salt was irreversible, and conversion to Mao1 occurred during the DVS analysis.

TABLE 51

Summary of the analytical characterization performed on the malonate salt forms of voruciclib found in this study. The thermal analyses were performed by DSC and TGMS, the chemical purity was determined by UPLC while the salt stoichiometry by $^1$H-NMR. The notation "N.D." stands for not determined. The notations "br", "ex" and "d" stand, respectively, for broad endotherm corresponding to water loss, exothermic or decomposition events.

| Solid form | Physically stable | Crystallization solvent | Solvent content by TGMS | Thermal events by DSC | | API:CI ratio from $^1$H-NMR |
|---|---|---|---|---|---|---|
| Mao1 | Yes | THF | 0.7% water | 181.1 (d) | 99.4 | 1:1 |
| Mao4 | N.D. | Cyclohexane | 3.5% water | 25-90 (br), 177.1 (d) | 98.5 | 1:1 |
| Mao5 | No | Methanol | 1.5% water | 121.1 (br), 135.4 (ex), 176.1 (d) | 99.2 | 1:1 |

The polymorph screen on voruciclib malonate salt was started with the amorphous phase to favor unbiased crystallization of novel forms. Mao1 was the most abundantly crystalline phase found in the screen which is the anhydrous crystalline phase found in previous salt screen. Three other phases, designated Mao3, Mao4 and Mao5 were identified in the study from very few crystallization conditions.

Characterization of Mao4 and Mao5 suggested that such phases could be hydrates which are crystallized when amorphous malonate salts are exposed to short-term stress conditions (AAC) or after evaporative crystallization. Mao3 could also be a hydrate, since it was identified in the ambient-dried solids recovered from water and from the mixtures IPA/water and acetone/water. All the novel identified phases were physically unstable since upon drying under vacuum or exposure to stress conditions, conversion to Mao1 occurred. Therefore, such forms do not pose any risk in the development of Mao1. The crystallization of Mao1 was also investigated by cooling a solution of Voruciclib free base containing 1 molar equivalent of malonic acid. The outcome of these experiment suggests that Mao1 can be easily produced by cooling crystallization. The successful scale-up cooling crystallization experiment of Mao1 at a larger 20 g scale confirmed that the process can be carried out at a larger scale. The crystallization conditions can be fine-tuned to design a robust crystallization process that will deliver Mao1 with a good yield and chemical purity.

All chemicals were obtained from Fisher Scientific or Sigma Aldrich. Chemicals used are of research grade and at least 99% pure. The starting material used in the present study, ME-522, Voruciclib HCl salt (95 grams of batch 1201) was provided.

For the polymorph screen, the conversion of the ME-522 HCl salt to the free base was performed as follows: 3.4 grams of ME-522 HCl salt were dissolved in 400 mL of water (resulting in pH 4.3); The pH of the water solution was adjusted to 11 (using 2M NaOH); The color of the solution became yellow and precipitation was observed after 30 min. The solids were filtered and washed with water until the pH of the filtrate was 8.5. The material was dried overnight at 50° C. and 5 mbar. Theoretical yield was 92%. The same procedure was used to prepare the free base from the voruciclib phosphate salt (project S18128B, batch ID: 19-09334-01) but starting with 304.9 mg instead.

Preferably a polymorph screen is initiated with an amorphous phase to promote unbiased crystallization. Thus, to produce amorphous material a solution of the free base was prepared in THF/water/acetone (32.5/32.5/35, v/v/v). To the API solution, 1 molar equivalent of malonic acid was added. The obtained salt solution was liquid does in UPLC vials such that about 90 mg of API were in each vial. The solutions were frozen in liquid nitrogen and placed under deep vacuum using a freeze dryer (Alpha 2-4 LD, Christ). The obtained solids were analyzed by HT-XRPD. The amorphous material was further analyzed by TGMS, UPLC and $^1$H-NMR to confirm the nature of the obtained malonate salt.

Amorphous material was recovered after freeze-drying. The amorphous material showed a mass loss of 3.2% due to water. The chemical purity was comparable to the initial material and the $^1$H-NMR confirmed the API:malonic acid stoichiometric ratio of 1:1.

Suspensions of amorphous voruciclib malonate salt were prepared in the selected solvent systems. About 90 mg of API were mixed with 24 solvent systems at room temperature (see Table 52 for details). Subsequently, the mixtures were placed in the Crystal16™ to undergo the temperature profile as displayed in FIG. 245.

After the temperature profile the solids were separated from the solution by centrifugation and they were dried at ambient conditions and under deep vacuum before being harvested and analyzed by HT-XRPD.

A small aliquot of mother liquor was taken and filtered using 0.2 μM PTFE syringe filters. The concentration of solute was determined by UPLC analysis. After that, the solutions were evaporated under vacuum (5 mbar) and the dry solids were analyzed by HT-XRPD. The solids were then exposed to accelerated aging conditions (2 days at 40° C./75% RH) followed by HT-XRPD re-analysis.

TABLE 52

Experimental conditions for the thermocycling experiments. Slurries of voruciclib malonate salt were prepared in neat solvents and solvent mixtures and placed in the Crystal16™ reactor to undergo a thermal profile as described in FIG. 245. After the temperature profile the precipitated solids were dried at ambient conditions and under vacuum and analyzed before and after exposure to AAC (40° C./75% RH, 2 days) by HT-XRPD. The mother liquors were used for solubility determination. Subsequently, the solutions were dried under vacuum and the obtained dried solids were analyzed by XRPD.

| Exp ID | Mass SM (mg) | Solvent | Solvent volume (μL) | Concentration (mg/mL) | Dissolved at initial temperature | Solids after Tprofile |
|---|---|---|---|---|---|---|
| TCP1 | 93.0 | Acetonitrile | 700 | 132.9 | No | Yes |
| TCP2 | 93.0 | Chloroform | 300 | 310 | No | Yes |
| TCP3 | 93.0 | Cyclohexane | 1000 | 93 | No | Yes |
| TCP4 | 93.0 | Dichloromethane | 500 | 186 | No | Yes |
| TCP5 | 93.0 | 1,4-Dioxane | 500 | 186 | No | Yes |
| TCP6 | 93.0 | Methanol | 500 | 186 | No | Yes |
| TCP7 | 93.0 | Tetrahydrofuran | 1000 | 93 | No | Yes |
| TCP8 | 93.0 | Toluene | 1000 | 93 | No | Yes |
| TCP9 | 93.0 | 1,2-Dimethoxyethane | 600 | 155 | No | Yes |
| TCP10 | 93.0 | Acetone | 400 | 232.5 | No | Yes |
| TCP11 | 93.0 | Anisole | 900 | 103.3 | No | Yes |
| TCP12 | 93.0 | tert-Butyl methyl ether | 1000 | 93 | No | Yes |
| TCP13 | 93.0 | Ethanol | 700 | 132.9 | No | Yes |
| TCP14 | 93.0 | Ethyl acetate | 700 | 132.9 | No | Yes |
| TCP15 | 93.0 | Diethyl ether | 1000 | 93 | No | Yes |
| TCP16 | 93.0 | Ethyl formate | 500 | 186 | No | Yes |
| TCP17 | 93.0 | Methyl ethyl ketone | 800 | 116.3 | No | Yes |
| TCP18 | 93.0 | Pentane | 1000 | 93 | No | Yes |
| TCP19 | 93.0 | 2-Propanol | 800 | 116.3 | No | Yes |
| TCP20 | 93.0 | n-Heptane | 1000 | 93 | No | Yes |
| TCP21 | 93.0 | Water | 1000 | 93 | No | Yes |
| TCP22 | 93.0 | Isopropyl acetate | 1000 | 93 | No | Yes |
| TCP23 | 93.0 | Acetone/water (90/10) | 400 | 232.5 | No | Yes |
| TCP24 | 93.0 | 2-Propanol/water (90/10) | 300 | 310 | No | Yes |

Additional crystallization attempts were performed to prepare the malonate salt form Mao1 by cooling crystallization and to evaluate the yield of such an experiment. Three experiments (Exp. ID: SSm1-3) were initiated with the free base received for project S18128, batch 1694ER1201. A fourth experiment (Exp. ID: SSm5) was started with a free base obtained through conversion from the S18128B phosphate salt.

Saturated free base solutions were prepared in ethanol, THF and acetone at 50° C. For that, very light suspensions of Voruciclib free base were incubated at 50° C. for 3 hours before being filtrated. To the saturated solutions, a stoichiometric amount of malonic acid was added from 1M stock solutions of malonic acid prepared in ethanol, THF and acetone. The experimental conditions are described in Table 53.

After the acid addition the solutions were subjected to a temperature profile in Crystal16 which consisted of holding the samples at 50° C. for 30 min. In the experiments performed in THF and acetone, precipitation was observed at elevated temperatures; since no precipitation was observed in ethanol, seeds of Mao1 were added and crystallization immediately occurred. Subsequently, a cooling profile to 5° C. was applied with a cooling rate of 10° C./h. Aging for 18 hours at the final temperature (5° C.) was applied. After the temperature profile the solids were separated from the solution by centrifugation and they were dried at ambient conditions and under deep vacuum before being harvested and analyzed by HT-XRPD. The mother liquors were evaporated to determine the amount of solids in the mother liquor and with that, the yield of the crystallization experiment.

TABLE 53

Experimental conditions for the additional cooling crystallization experiments performed on Voruciclib free base to produce the malonate salt. To Voruciclib free base solutions prepared in THF, ethanol and acetone, a stoichiometric amount of malonic acid was added from 1M stock solutions. Subsequently, a cooling profile was applied to 5° C. After the temperature profile the solids were isolated from the solution. Solids were analyzed by XRPD and the solutions were evaporated to assess the yield based on the weight of the solids. The freebase used in SSm1-3 were taken from project S18128 (starting material) whereas the freebase used in SSm5 was obtained through free-base conversion from the phosphate salt from project S18128B (starting material).

| Exp ID | SM (mg) | Solvent | Solvent volume (mL) | API:Malonic acid Ratio | Solvent Malonic acid stock solution | Yield (%) | Ambient-dried solid | Vacuum-dried solid |
|---|---|---|---|---|---|---|---|---|
| SSm1 | 107 | THF | 1.0 | 1:1.1 | THF | 96% | Mao1 | Mao1 |
| SSm2 | 40 | Ethanol | 1.0 | 1:1.1 | Ethanol | 70% | Mao1 | Mao1 |
| SSm3 | 44 | Acetone | 1.0 | 1:1.1 | Acetone | 85% | Mao1 | Mao1 |
| SSm5 | 102 | THF | 0.9 | 1:1.1 | THF | 71% | Mao1 | — |

For the scale-up of Mao1, 25 grams of ME-522 HCl salt was initially converted into the free base by suspending the material in 170 mL water (Exp. ID: GEN10). The pH of the solution was adjusted to 11 using 2M NaOH, resulting in a color change to yellow. The pH was regularly measured until it was stable. The suspension was filtered over a Büchner filter and the solids were washed on the filter with water until the pH of the filtrate was 8.5. The solids were dried at 50° C. under deep vacuum (5 mbar) for 15 hours and conversion into the free base was confirmed by HT-XRPD and $^1$H-NMR.

For the conversion of the free base into Mao1, 20.2 grams of Voruciclib free base (obtained from Exp. ID: GEN10) were dissolved in 130 mL THF (Exp. ID: SSm4). The solution was heated to 50° C. and malonic acid was added in an API:CI ratio of 1:1.1. Malonic acid was added as a solution in THF (4.19 grams of malonic acid in 10 mL THF).

After stirring for approximately 10 min at 50° C., precipitation occurred. After stirring for another 20 minutes at 50° C., the suspension was cooled to room temperature and the solids were isolated from the liquid phase by filtration. The solids were subsequently dried at 50° C. under reduced pressure (200 mbar) for 17 h. The scale-up experiment yielded 23.5 grams of Mao1 (95 mol % yield). The analytical data confirms that Mao1 was obtained.

XRPD patterns were obtained using the Crystallics T2 high-throughput XRPD set-up. The plates were mounted on a Bruker D8 Discover General Area Detector Diffraction System (GADDS) equipped with a VÅNTEC-500 gas area detector corrected for intensity and geometric variations (product sheet XRD 37, DOC-S88-EXS037V3, FIG. 297). The calibration of the measurement accuracy (peaks position) was performed using NIST SRM1976 standard (Corundum).

Data collection was carried out at room temperature using monochromatic Cu Kα radiation in the 2θ region between 1.5° and 41.5°, which is the most distinctive part of the XRPD pattern. The diffraction pattern of each well was collected in two 2θ ranges (1.5°≤2θ≤21.5° for the first frame, and 19.5°≤2θ≤41.5° for the second) with an exposure time of 90 s for each frame. No background subtraction or curve smoothing was applied to the XRPD patterns. The carrier material used during XRPD analysis was transparent to X-rays and contributed only slightly to the background.

The HR-XRPD data were collected on D8 Advance diffractometer using Cu K$_{\alpha1}$ radiation (1.54056 Å) with germanium monochromator at RT. Diffraction data were collected in the 2θ range 3-41.5° 2θ. Detector scan on solid state LynxEye detector was performed using 0.016° per step with 2 sec/step scan speed (DOC-M88-EXX95 V2—11.2007, FIG. 298). The samples were measured in 8 mm long glass capillary with 0.3 mm outer diameter.

For Rietveld calculation the cell parameters, crystal system as well as atom positions were taken from the single crystal file (cif). During the refinement the following parameters were refined:

cell constants;

background;

instrument geometry;

zero shift;

absorption

Neither atom positions nor thermal motion parameters were refined during whole process. The following criteria of fit were used:

$Y_{o,m}$ and $Y_{c,m}$ are the observed and calculated data, respectively at data point m, M the number of data points, P the number of parameters, $w_m$ the weighting given to data point m which for counting statistics is given by $w_m = 1/\sigma(Y_{o,m})^2$ where $\sigma(Y_{o,m})$ is the error in $Y_{o,m}$, $$R_{exp} = \sqrt{\frac{M-P}{\sum w_m Y_{o,m}^2}};$$

$$R_{wp} = \sqrt{\frac{\sum w_m (Y_{o,m} - Y_{c,m})^2}{\sum w_m Y_{o,m}^2}};$$

$$R_p = \sqrt{\frac{\sum |Y_{o,m} - Y_{c,m}|}{\sum Y_{o,m}}}$$

$$GOF = chi^2 = \frac{R_{wp}}{R_{exp}} = \sqrt{\frac{\sum w_m (Y_{o,m} - Y_{c,m})^2}{M - P}}$$

TABLE 54

Final Rietveld parameters for refinement of Mao1 (Exp. ID TCP7 & SSm4).

| Exp. ID | TCP7.2 | SSm4 |
|---|---|---|
| 2θ range (°) | 2 - 41.5 | 2 - 41.5 |
| $R_{exp}$ | 4.13 | 2.23 |
| $R_{wp}$ | 5.02 | 3.72 |
| $R_p$ | 3.90 | 2.91 |
| GOF | 1.22 | 1.67 |
| $R_{Brag}$ | 2.00 | 2.33 |
| Impurities, other forms [%] | Below detection limits | Below detection limits |

Mass loss due to solvent or water loss from the crystals was determined by TGA/heat flow. Monitoring the sample weight, during heating in a TGA/DSC 3+ STARe system (Mettler-Toledo GmbH, Switzerland), resulted in a weight vs. temperature curve. The TGA/DSC 3+ was calibrated for temperature with samples of indium and aluminum. Samples (circa 2 mg) were weighed into 100 µL aluminum crucibles and sealed. The seals were pin-holed, and the crucibles heated in the TGA from 25 to 300° C. at a heating rate of 10° C. min$^{-1}$. Dry $N_2$ gas was used for purging.

The gases coming from the TGA samples were analyzed by a mass spectrometer Omnistar GSD 301 T2 (Pfeiffer Vacuum GmbH, Germany). The latter is a quadrupole mass spectrometer, which analyzes masses in the temperature range of 0-200 amu.

Melting properties were obtained from DSC thermograms, recorded with a heat flux DSC3+ STARe system (Mettler-Toledo GmbH, Switzerland). The DSC3+ was calibrated for temperature and enthalpy with a small piece of indium (m.p.=156.6° C.; δHf=28.45 J/g) and zinc (m.p.=419.6° C.; δHf=107.5 J/g). Samples (circa 2 mg) were sealed in standard 40 µL aluminum pans, pin-holed and heated in the DSC from 25° C. to 300° C., at a heating rate of 10° C./min. Dry $N_2$ gas, at a flow rate of 50 mL/min was used to purge the DSC equipment during measurement.

$^1$H-NMR spectroscopy in DMSO-$d_6$ was used for compound integrity characterization and to determine the stoichiometry of the salt. The spectra were recorded at room temperature (32 scans) on a 500 MHz instrument (Bruker BioSpin GmbH) using standard pulse sequences. The data was processed with ACD Labs software Spectrus Processor 2016.2.2 (Advanced Chemistry Development Inc. Canada).

Differences in hygroscopicity (moisture uptake) of the various forms of a solid material provided a measure of their relative stability at increasing relative humidity. Moisture sorption isotherms of small samples were obtained using a DVS-1 system from Surface Measurement Systems (London, UK); this instrument is suitable for use with as little as a few milligrams of sample, with an accuracy of 0.1 µg. The relative humidity was varied during sorption-desorption-sorption (45-95-0-45% RH) at a constant temperature of 25° C. Weight equilibration per step was set at dm/dt <0.0002 for a minimum of 1 hour or maximum of 6 hours. Afterwards the sample was measured by HT-XRPD.

The hygroscopicity was classified according to the European Pharmacopoeia Hygroscopicity classification. Water uptake percentage at 25° C./80% RH (24 h) is: Change in mass <0.2%—Non-hygroscopic; Change in mass >0.2% & <2%—Slightly hygroscopic; Change in mass >2% & <15%—Moderately hygroscopic; Change in mass >15%—Very hygroscopic.

UPLC Method
Method Name: S19097_01_LCMS

| Instrument | Agilent 1290 series with diode array UV detector and MSD XT single quad mass detector | | |
|---|---|---|---|
| Mobile phase A | 0.1% Formic acid in water | | |
| Mobile phase B | 0.1% Formic acid in acetonitrile | | |
| Column | Agilent Eclipse Plus C18 HD (50 × 2.1 mm; 1.8 µm) | | |
| Detection: | UV at 264 nm, bandwidth 4 nm, UV spectrum 200 to 400 nm. MS in positive scan mode 100-1000 m/z, 500 ms scan time | | |
| Flow: | 0.8 mL/min. | | |
| Run time | 4 minutes | | |
| Injection volume | 1.0 µL | | |
| Column temp. | 35° C. | | |
| Autosampler temp. | Ambient | | |
| Gradient: | Time [min.] | Eluent A [%] | Eluent B [%] |
| | 0 | 90 | 10 |
| | 0.25 | 90 | 10 |
| | 2 | 2 | 98 |
| | 2.95 | 2 | 98 |
| | 3 | 90 | 10 |
| | 4 | 90 | 10 |

The compound integrity is expressed as a peak-area percentage, calculated from the area of each peak in the chromatogram, except the 'injection peak', and the total peak-area, as follows:

$$\text{peak area (\%)} = \frac{\text{peak area}}{\text{total area of all peaks}} \cdot 100\%$$

The peak area percentage of the compound of interest is employed as an indication of the purity of the component in the sample.

TABLE 55

Assay results for the free base recovered from the HCl salt (Exp. ID GEN4).

| Sample Name | Area (mV*s) | Weight (mg) | Volume (ml) | TGMS (%) | Purity (%) | RF | Recovery (%) |
|---|---|---|---|---|---|---|---|
| LCMS_S19097_Ref-SOL1_R1 | 2329.74 | 10.29 | 15.0 | 1.11 | 98.89 | 34.3 | |
| LCMS_S19097_Ref-SOL1_R2 | 12363.21 | 10.29 | 15.0 | 1.11 | 98.89 | 34.8 | |
| LCMS_S19097_Ref-SOL1_R3 | 2366.31 | 10.29 | 15.0 | 1.11 | 98.89 | 34.9 | |
| Average | 2353.1 | | | | | 34.7 | |
| RSD | 0.86 | | | | | | |
| LCMS_S19097_Ref-SOL2 | 2352.7 | 10.31 | 15.0 | 1.11 | 98.89 | 34.6 | |
| LCMS_S19097_GEN4_FB_R1 | 2210.9 | 10.0 | 15.0 | 3.3 | 96.7 | 34.5 | 99.3 |
| LCMS_S19097_GEN4_FB_R2 | 2491.6 | 10.9 | 15.0 | 3.3 | 96.7 | 35.3 | 101.8 |

TABLE 56

Assay results for the malonate salt obtained after freeze-drying (Exp. ID GEN8).

| Sample Name | Area (mV*s) | Weight (mg) | Volume (ml) | TGMS (%) | Purity (%) | RF | Recovery (%) |
|---|---|---|---|---|---|---|---|
| LCMS_S19097_Ref-SOL1_R1 | 2308.54 | 10.29 | 15.0 | 1.11 | 98.89 | 34.0 | — |
| LCMS_S19097_Ref-SOL1_R2 | 2329.84 | 10.29 | 15.0 | 1.11 | 98.89 | 34.3 | — |
| LCMS_S19097_Ref-SOL1_R3 | 2348.64 | 10.29 | 15.0 | 1.11 | 98.89 | 34.6 | — |
| Average | 2329.0 | | | | | 34.3 | — |
| RSD | 0.86 | | | | | | |
| LCMS_S19097_Ref-SOL2 | 2339.6 | 10.31 | 15.0 | 1.11 | 98.89 | 34.4 | — |
| LCMS_S19097_GEN8_1_FD_batch2 | 1653.4 | 9.7 | 15.0 | 3.6 | 96.4 | 26.4 | 77.0 |

Mao1 was selected as the best salt form of voruciclib based on the present salt screen and the salt screens involving the oxalate and phosphate counterions (project S18128A and S18128B). A sample of Mao1 obtained from the polymorph screen (Exp. ID: TCP7) was used to fully characterize the form. In addition, analytical data was obtained for the batch of Mao1 obtained from the scale-up experiment (Exp. ID: SSm4).

Mao1 was the most occurred solid form identified in this study. In all cases a solid with good crystallinity was recovered. Mao1 was obtained in the ambient-dried solids and was physically stable upon drying under vacuum and upon exposure to AAC. The experiment selected for analytical characterization was the solid recovered from the thermocycling experiment performed in THF (Exp. ID TCP7). The XRPD patterns of Mao1 before and after AAC are shown in FIG. 246.

High Resolution XRPD was also recorded for Mao1 (Exp. ID TCP7). In FIG. 247, the graphical representation of Rietveld analysis is presented, while in Table 54 the final parameters are presented. The cell parameters were taken from the single crystal data of voruciclib malonate salt obtained in study S18128. The obtained solid of Mao1 (from Exp. ID TCP7) comprises only one phase and no crystalline impurity were detected.

The TGMS analysis (FIG. 248) of Mao1 indicated that this form was a non-solvated anhydrous form as the mass loss was only 0.7% prior to the start of decomposition.

Decomposition started around 140° C.

The DSC trace (FIG. 249) of Mao1 showed an endothermic event with peak temperature at 181.1° C., due to melting/decomposition.

The proton NMR spectrum (FIG. 250) obtained for Mao1 was overlapping the spectrum of the amorphous malonate salt. The determined API:malonic acid stoichiometric ratio was 1:1.

The UPLC chromatogram (FIG. 251) obtained for Mao1 confirmed the compound's integrity with a chemical purity of 99.4% (area %).

The hygroscopicity of Mao1 was determined by DVS. The powder was exposed to a RH profile consisting of sorption/desorption/sorption cycles (40-95-0-40% RH) performed at 25° C. The change in mass and isotherm plot are shown in FIG. 252A, 252B. The water vapor uptake gained during the sorption half-cycle was 0.75%. The DVS analysis showed a water uptake of 0.15% at 80% RH, suggesting that this material is non-hygroscopic (based on the European Pharmacopeia Hygroscopicity classification). No solid form conversion was observed after the DVS analysis, since Mao1 was still identified by HT-XRPD in the recovered solid.

The solubility of Mao1 in water was determined by adding small aliquots of water to the material until it was dissolved. This way, it was estimated that the solubility of Mao1 in water was approximately 13 mg/ml. After the addition of a small amount of water to Mao1, a suspension was obtained and no gel-formation was observed (FIG. 253).

The HT-XRPD pattern of Mao1 obtained from the scale-up experiment is shown in FIG. 254.

High Resolution XRPD was recorded for Mao1 (Exp. ID Ssm4). In FIG. 255, the graphical representation of Rietveld analysis is presented, while in Table 54 the final parameters are presented. The cell parameters were taken from the single crystal data of voruciclib malonate salt obtained in study S18128. The obtained solid of Mao1 (from Exp. ID TCP7) comprises only one phase and no crystalline impurities were detected.

The TGMS analysis (FIG. 256) of Mao1 indicated that this form was a non-solvated anhydrous form as the mass loss was only 0.08% prior to the start of decomposition.

Decomposition started around 160° C.

The DSC trace (FIG. 257) of Mao1 showed an endothermic event with peak temperature at 182.4° C., due to melting/decomposition.

The $^1$H-NMR spectrum of Mao1 obtained from the scale-up experiment (Exp. ID Ssm4) is shown in FIG. 258 in comparison to the starting material free base (Exp. ID GEN10). The downfield shift of the signals of the Mao1 salt in comparison to the free base confirmed that the obtained material is a salt. A trace of THF (1 wt %) was estimated to be present based on the NMR signal. The determined API:malonic acid stoichiometric ratio was 1:1.

The UPLC chromatogram (FIG. 259) obtained for Mao1 confirmed the compound integrity with a chemical purity of 100% (area %). The mass associated to the main peak was 470.3 [M+H]$^+$, in agreement with the molecular weight of the free base (i.e. 469.8 g/mol).

In few solvents, where the malonate salt was practically insoluble (such as cyclohexane, pentane and heptane), an amorphous solid was recovered after the thermocycling experiments. Upon exposure to short-term stress conditions (AAC, 40° C./75% RH, 2 days), the amorphous solid crystallized to Mao4. The experiment selected for analytical characterization was the solid recovered from cyclohexane (Exp. ID TCP3) after exposure to 2 days at 40° C./75% RH. The HT-XRPD diffractogram of Mao4 is shown in FIG. 260.

The TGMS analysis of Mao4 (FIG. 261) showed a mass loss of 3.5% in the range 40-150° C., due to water (1.1 water molecules per salt molecule). Thermal decomposition started above 160° C.

The DSC trace (FIG. 262) of Mao4 showed a broad endothermic event between 25-100° C. attributed to the water loss followed by a sharp endothermic event at 177.1° C. which corresponds to the melting/thermal decomposition of the salt.

The UPLC-MS analysis (FIG. 263) showed that the API had a chemical purity of 98.5% (area %).

The proton NMR spectrum (FIG. 264) obtained for Mao4 confirmed that this form was a malonate salt since the spectrum of Mao4 was overlapping the spectrum of Mao1. The API:malonic acid stoichiometric ratio was 1:1.

The hygroscopicity of Mao4 was determined by DVS. The powder was exposed to a RH profile consisting of sorption/desorption/sorption cycles (40-95-0-40% RH) performed at 25° C. The change in mass and isotherm plot are shown in FIG. 265. In the first sorption half-cycle, the water uptake gained was 2.8% at 95% RH. The change in mass plot (FIG. 265A) showed that the water sorption had not reached equilibrium during sorption at 90-95% RH. During the desorption cycle, from 95 to 0% RH, water was released. In the last sorption half-cycle, the change in mass was 0.37% (in the range 0→40% RH).

The water uptake was irreversible, suggesting that a form change occurred. Mao1 was identified by HT-XRPD in the recovered solid (FIG. 266).

The DVS analysis showed a change in mass at 80% RH of 0.9% suggesting that Mao4 was slightly hygroscopic (based on the European Pharmacopeia Hygroscopicity classification).

In one single evaporative crystallization experiment from methanol, a new powder pattern, designated Mao5, was identified (Exp. ID TCP6_ML). Upon exposure to short-term stress conditions (AAC, 40° C./75% RH, 2 days), Mao5 converted to Mao4. The HT-XRPD diffractogram of Mao5 is shown in FIG. 267.

The TGMS analysis of Mao5 (FIG. 268) showed a mass loss of 1.5% in the range 40-100° C., due to water (0.5 water molecules per salt molecule). Based on the MS signal, it is likely that the gradual mass loss between 25-100° C. corresponds to residual water, whereas the second weight loss step between 100-180° C. could be attributed to thermal decomposition.

The DSC trace (FIG. 269) of Mao5 showed a broad endothermic event between 90-130° C. attributed to the water loss followed by an exothermic event which could correspond to a recrystallization event to the anhydrous Mao1.

The UPLC-MS analysis (FIG. 270) showed that the API had a chemical purity of 99.2% (area %).

Example 6: Voruciclib Oxalate Crystal Structure

The structure of Voruciclib Oxalate (assigned sample code SFY_242) was determined at 100K in the monoclinic chiral space group P2$_1$ with two molecules of Voruciclib, one oxalate ion, one molecule of 2-pentanone and one water molecule in the asymmetric unit. The data contain significant anomalous signal and the absolute configuration could be determined based on resonant scattering: The molecule contains two chiral carbon atoms; they have the configuration C1: S, C2: R for the first and C31: S, C32: R for the second crystallographically independent molecule (for atom labeling scheme refer to FIG. 1). The final residual values of the refinements are R1=0.0525 (I>2σ(I)) and wR2=0.1297 (all reflections).

Several samples of crystals of Voruciclib oxalate were used. The vials labeled 113-1, 113-2 and 113-5 contained crystals of free oxalic acid, and vial 113-7 was not examined. The vial labeled simply with the number 5 contained crystals of the target compound in 2-pentanone and the specimen chosen for data collection was a plate with the dimensions 0.010×0.040×0.050 mm$^3$. The crystal was mounted on a MiTeGen™ mount with mineral oil (STP Oil Treatment). First diffraction patterns showed the crystal to be of adequate quality without signs of non-merohedral twinning.

Diffraction data (φ- and ω-scans) were collected at 100K on a Bruker-AXS X8 Kappa diffractometer coupled to a Bruker Photon2 CPAD detector using Cu K$_\alpha$ radiation (λ=1.54178 Å) from an IμS microsource. Data reduction was carried out with the program SAINT and semi-empirical absorption correction based on equivalents was performed with the program SADABS. A summary of crystal properties and data/refinement statistics is given in Table 57.

The structure was solved with dual-space methods using the program SHELXT and refined against F$^2$ on all data with SHELXL using established refinement techniques. All non-hydrogen atoms were refined anisotropically. All hydrogen atoms bound to carbon were placed in geometrically calculated positions and refined using a riding model while constraining their U$_{iso}$ to 1.2 times the U$_{eq}$ of the atoms to which they bind (1.5 times for methyl and OH groups). Hydrogen atoms connected to nitrogen or oxygen were taken from the difference Fourier synthesis and those hydrogen atoms were subsequently refined semi-freely with the help of distance restraints on the N—H and O—H distances (target values 0.91(2) Å for N—H and 0.84(2) Å for O—H). No additional restraints were applied. It should be mentioned that some hydrogen positions could be located more easily than others and in some cases alternative hydrogen sites appeared possible (although not necessarily likely). The set of hydrogen positions chosen is sensible and all N—H and O—H hydrogen atoms are involved in meaningful hydrogen bonds; however it is possible that the crystal represents a mixture of protonation patterns. This does not diminish the accuracy of the non-hydrogen atom positions, nor does it decrease the confidence in the determination of the absolute configuration of the chiral atoms.

The structure of Voruciclib oxalate (assigned sample code SFY_242) was determined at 100K in the monoclinic chiral space group P2$_1$ with two molecules of Voruciclib, one oxalate ion, one molecule of 2-pentanone and one water molecule in the asymmetric unit. FIG. 271 shows the contents of the asymmetric unit with atomic labeling scheme.

The structure shows 12 classical and 15 non-classical hydrogen bonds. Nine of the classical and nine of the non-classical ones occur within the asymmetric unit and are shown in FIG. 271. The two independent molecules of Voruciclib are linked together by the oxalate ion, and the water molecule also connects to the oxalate. The 2-pentanone phosphate is loosely linked to one of the two Voruciclib molecules through two non-classical hydrogen bonds. This leaves only three classical hydrogen bond donors available for crosslinking, namely O3-H3, O8-H8, and O1W-H1WA. As shown in FIG. 272, the corresponding hydrogen bonds, O3-H3 . . . O13$^i$, O8-H8 . . . O1W$^{ii}$, and O1W-H1WA . . . O14$^{iii}$, crosslink the arrangement shown in FIG. 271 into the three-dimensional framework that can be seen in the packing plots below (FIG. 273). Symmetry operators i: −x+2, y−0.5, −z+1; −x+1, y+0.5, −z+1; iii: x−1, y, z. All hydrogen bonds are listed in Table 58.

The packing plot (FIG. 273) shows channels extending along the crystallographic a-axis that host the 2-pentanone molecules. Considering that the 2-pentanone is only loosely connected to the rest of the structure, it is conceivable that other solvent molecules of similar size could also be incorporated. FIG. 274 shows the simulated powder pattern.

The molecule at hand is chiral and the absolute structure could be determined based on resonant scattering data: The Flack-x parameters as calculated by the Parsons method refined to 0.043(13). Analysis of the anomalous signal using the method introduced by Hooft & Spek calculates the probability of the absolute structure to be correct to 1, the probability of the structure to be a racemic twin to 0 and the probability of the absolute structure to be incorrect to 0. The Hoof method also affords an absolute structure parameter, the Hoof-y, which is directly comparable to the Flack-x. The Hooft-y was calculated to 0.039(14). Therefore, it can be determined with high confidence that the chiral atoms have the configuration N1: S, C1: S, C2: R for the first and N2: S, C31: S, C32: R for the second crystallographically independent molecule (both independent molecules have the same absolute configuration).

TABLE 57

Crystal data and structure refinement for Voruciclib oxalate

| | |
|---|---|
| Identification code | sfy241 |
| Identification code | sfy242 |
| Empirical formula | $C_{25.50}H_{26}ClF_3NO_8$ |
| Moiety formula | $C_{22}H_{20}ClF_3NO_5$, $0.5(C_5H_{10}O)$, $0.5(C_2O)$, $0.5(H_2O)$ |
| Formula weight | 566.92 |
| Temperature | 100(2) K |
| Wavelength | 1.54178 Å |
| Crystal system | Monoclinic |
| Space group | P2$_1$ |
| Unit cell dimensions | a = 7.5306(6) Å   α = 90°. |
| | b = 17.9889(14) Å   β = 97.653(6)°. |
| | c = 18.6224(14) Å   γ = 90°. |
| Volume | 2500.3(3) Å$^3$ |
| Z | 4 |
| Density (calculated) | 1.506 Mg/m$^3$ |
| Absorption coefficient | 2.024 mm$^{-1}$ |
| F(000) | 1176 |
| Crystal size | 0.050 × 0.040 × 0.010 mm$^3$ |
| Theta range for data collection | 2.394 to 68.237°. |
| Index ranges | −9 <= h <= 8, −21 <= k <= 21, −22 <= l <= 21 |
| Reflections collected | 35591 |
| Independent reflections | 9089 [R$_{int}$ = 0.0876] |
| Completeness to theta = 67.679° | 99.9% |
| Absorption correction | Semi-empirical from equivalents |
| Max. and min. transmission | 0.7531 and 0.6562 |
| Refinement method | Full-matrix least-squares on F$^2$ |
| Data/restraints/parameters | 9089/18/726 |
| Goodness-of-fit on F$^2$ | 1.005 |
| Final R indices [I > 2σ(I)] | R1 = 0.0525, wR2 = 0.1161 |
| R indices (all data) | R1 = 0.0818, wR2 = 0.1297 |
| Absolute structure parameter | 0.043(13) |
| Largest diff. peak and hole | 0.381 and −0.267 e.Å$^{-3}$ |

TABLE 58

Hydrogen bond parameters for Voruciclib oxalate [Å and °].

| D—H...A | d(D—H) | d(H...A) | d(D...A) | <(DHA) |
|---|---|---|---|---|
| O(1)—H(1A)...O(11) | 0.86(3) | 1.96(4) | 2.729(7) | 148(4) |
| O(3)—H(3)...O(13)#1 | 0.82(3) | 1.77(4) | 2.573(7) | 166(5) |
| O(4)—H(4)...O(5) | 0.84(3) | 1.87(4) | 2.612(6) | 146(4) |
| N(1)—H(1)...O(11) | 0.92(3) | 1.85(3) | 2.753(7) | 167(6) |
| N(1)—H(1)...O(14) | 0.92(3) | 2.49(6) | 3.023(8) | 117(5) |
| C(1)—H(1B)...O(2) | 1.00 | 2.26 | 2.776(7) | 110.6 |
| C(2)—H(2B)...O(3) | 1.00 | 2.36 | 2.971(8) | 118.2 |
| C(3)—H(3B)...O(1S) | 0.99 | 2.60 | 3.498(9) | 150.3 |
| C(5)—H(5A)...O(1S) | 0.99 | 2.46 | 3.440(9) | 168.6 |
| C(6)—H(6A)...O(3) | 0.98 | 2.54 | 3.299(9) | 134.3 |
| C(6)—H(6C)...O(14) | 0.98 | 2.40 | 3.034(10) | 122.2 |
| C(10)—H(10)...O(14)#1 | 0.95 | 2.53 | 3.457(9) | 163.7 |
| O(6)—H(6)...O(13) | 0.88(3) | 1.84(3) | 2.716(7) | 172(6) |
| O(8)—H(8)...O(1W)#2 | 0.84(3) | 1.85(3) | 2.669(7) | 164(8) |
| O(9)—H(9)...O(10) | 0.86(3) | 1.79(4) | 2.570(6) | 149(4) |
| N(2)—H(2)...O(12) | 0.92(3) | 1.83(3) | 2.738(7) | 166(7) |

TABLE 58-continued

Hydrogen bond parameters for Voruciclib oxalate [Å and °].

| D—H...A | d(D— | d(H... | d(D...A) | <(DHA) |
|---|---|---|---|---|
| C(32)—H(32)...O(8) | 1.00 | 2.35 | 2.936(7) | 116.7 |
| C(34)—H(34A)...O(8) | 0.99 | 2.57 | 3.133(9) | 116.2 |
| C(34)—H(34B)...O(6)#3 | 0.99 | 2.38 | 3.284(10) | 151.0 |
| C(35)—H(35B)...O(5)#4 | 0.99 | 2.41 | 3.211(8) | 137.4 |
| C(36)—H(36A)...O(8) | 0.98 | 2.51 | 3.250(9) | 132.3 |
| C(36)—H(36C)...O(9)#5 | 0.98 | 2.48 | 3.236(8) | 134.1 |
| C(40)—H(40)...O(1W)#2 | 0.95 | 2.60 | 3.279(8) | 128.9 |
| C(48)—H(48)...O(1S)#6 | 0.95 | 2.27 | 3.213(8) | 172.3 |
| O(1W)— | 0.90(3 | 2.57(8) | 3.083(8) | 117(7) |
| O(1W)— | 0.90(3 | 1.88(3) | 2.761(8) | 168(8) |
| O(1W)— | 0.89(3 | 1.82(4) | 2.675(8) | 161(8) |

Symmetry transformations used to generate equivalent atoms:
1 −x+2,y−1/2,−z+1; #2 −x+1,y+1/2,−z+1; #3 x−1,y,z;
4 x,y+1,z; #5 −x+1,y−1/2,−z+1; #6 −x+1,y+1/2,−z Example 7: Voruciclib Phosphate Crystal Structure The structure of Voruciclib phosphate (assigned sample code SFY_241) was determined at 100K in the in the monoclinic chiral space group $P2_1$ with two molecules of Voruciclib, two phosphate ions and 1.5 molecules of isopropyl alcohol in the asymmetric unit. This corresponds to 0.75 solvent molecules per molecule of Voruciclib, placing this between hemi- and monosolvate. The data contain significant anomalous signal and the absolute configuration could be determined based on resonant scattering: The molecule contains two chiral carbon atoms; they have the configuration C1: S, C2: R for the first and C31: S, C32: R for the second crystallographically independent molecule (for atom labeling scheme refer to FIG. 1). The final residual values of the refinements are R1=0.0326 (I>2(5(I)) and wR2=0.0845 (all reflections).

Several samples of crystals of Voruciclib were submitted. Crystals from vial 114_20, containing the phosphate salt of Voruciclib in isopropyl alcohol, appeared to be of the best quality and the specimen chosen for data collection was blade with the dimensions 0.008×0.025×0.270 mm³. The crystal was mounted on a MiTeGen™ mount with mineral oil (STP Oil Treatment). First diffraction patterns showed the crystal to be of good quality without signs of non-merohedral twinning.

Diffraction data ((f- and w-scans) were collected at 100K on a Bruker-AXS X8 Kappa diffractometer coupled to a Bruker Photon2 CPAD detector using Cu $K_\alpha$ radiation ($\lambda$=1.54178 Å) from an IµS microsource. Data reduction was carried out with the program SAINT and semi-empirical absorption correction based on equivalents was performed with the program SADABS. A summary of crystal properties and data/refinement statistics is given in Table 59.

The structure was solved with dual-space methods using the program SHELXT and refined against $F^2$ on all data with SHELXL using established refinement techniques. All non-hydrogen atoms were refined anisotropically. All hydrogen atoms bound to carbon were placed in geometrically calculated positions and refined using a riding model while constraining their $U_{iso}$ to 1.2 times the $U_{eq}$ of the atoms to which they bind (1.5 times for methyl and OH groups). Except for the disordered solvent, coordinates for the hydrogen atoms connected to nitrogen or oxygen were taken from the difference Fourier synthesis and those hydrogen atoms were subsequently refined semi-freely with the help of distance restraints on the N—H and O—H distances (target values 0.91(2) Å for N—H and 0.84(2) Å for O—H). The 1.5 molecules of isopropyl alcohol in the asymmetric unit were found to be distributed over three sites, each corresponding to one half molecule. The three hydroxyl hydrogen atoms on the half occupied solvent molecules were placed to allow for the best hydrogen bonding pattern and then refined using a riding model. The $CF_3$ groups show slightly more than average motion, however no reasonable disorder model could be established. Similarity restraints on 1-2 and 1-3 distances and displacement parameters as well as rigid bond restraints for anisotropic displacement parameters were applied to solvent atoms and to the atoms of the $CF_3$ groups.

The structure of Voruciclib phosphate isopropyl alcohol solvate (assigned sample code SFY_241) was determined at 100K in the monoclinic chiral space group $P2_1$ with two molecules of Voruciclib, two phosphate ions—one per target molecule—and 1.5 molecules of isopropyl alcohol in the asymmetric unit. This corresponds to 0.75 solvent molecules per molecule of Voruciclib, placing this structure between hemi- and monosolvate. FIGS. 275 and 276 show the two independent molecules with atomic labeling scheme.

Figure 4:
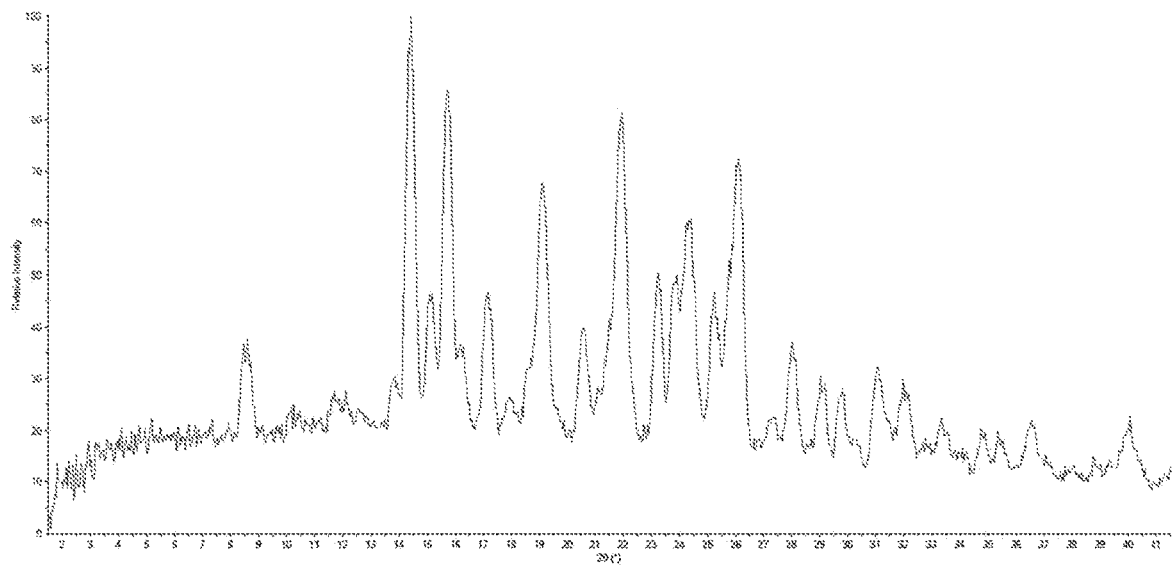
FIG. 4 illustrates the high throughput XRPD of voruciclib HCl, batch 1694M-1301, starting material for the screen, Form 1.

The supramolecular arrangement of the structure of Voruciclib phosphate is dominated by hydrogen bonds. Together with the two PO—H . . . OP bonds shown in FIGS. 275 and 276 (namely O13-H13 . . . O15 and O17-H17 . . . O11), hydrogen bonds O14-H14 . . . O16$^i$ and O18-H18 . . . O12$^{ii}$ link the phosphate ions into infinite chains extending along the crystallographic b-axis (FIG. 277). The two Voruciclib molecules attach themselves to this phosphate chain through hydrogen bonds O3-H3 . . . O11, O8-H8 . . . O12, O9-H9 . . . O10, O1-H1A . . . O15$^{iii}$, N1-H1 . . . O13$^{iii}$, and N2-H2 . . . O17$^{iv}$ as shown in FIG. 278 4. This gives rise to a tight three-dimensional framework as can also be seen in the packing plots (FIG. 280). The solvent molecules fairly evenly fill channels extending along the crystallographic b-direction (in parallel with the phosphate chain). Two of the three disordered solvent molecules hydrogen bond to one of the phosphate ions via interactions O1T-H1T . . . O16 and O1U-H1U . . . O16. For the third solvent hydroxyl group, no suitable hydrogen bond could be established, although there is one possible hydrogen position that would allow for an O1S—H1S . . . O15 hydrogen bond. This position, however, clashes with the hydrogen atom on O6 and was, therefore, not adopted. The hydroxyl group O6-H6 hydrogen bonds to two of the solvent oxygen atoms via the O6-H6 . . . O1S$^{iv}$ and O6-H6 . . . O1U$^{V}$ interactions (FIG. 279). In addition, there is a number of non-classical C—H . . . O and C—H . . . F hydrogen bonds. Symmetry operators is x, y+1, z; ii: x, y−1, z; iii: −x+2, y−0.5, −z+1; iv: −x+2, y−0.5, −z+1; v: −x+2, y+1.5, −z+1. All hydrogen bonds are listed in Table 60.

FIG. 280 shows packing plots of the structure of Voruciclib phosphate and FIG. 281 the simulated powder pattern.

The molecule at hand is chiral and the absolute structure could be determined based on resonant scattering data: The Flack-x parameters as calculated by the Parsons method refined to 0.002(5). Analysis of the anomalous signal using the method introduced by Hooft & Spek calculates the probability of the absolute structure to be correct to 1, the probability of the structure to be a racemic twin to 0 and the probability of the absolute structure to be incorrect to 0. The Hoof method also affords an absolute structure parameter, the Hoof-y, which is directly comparable to the Flack-x. The Hooft-y was calculated to 0.005(6). Therefore, it can be determined with high confidence that the chiral atoms have the configuration N1: S, C1: S, C2: R for the first and N2: S, C31: S, C32: R for the second crystallographically independent molecule (both independent molecules have the same absolute configuration).

TABLE 59

Crystal data and structure refinement for Voracidib phosphate

| | |
|---|---|
| Identification code | sfy241 |
| Empirical formula | $C_{24.25} H_{28} Cl F_3 N O_{9.75} P$ |
| Moiety formula | $C_{22} H_{20} Cl F_3 N O_5, H_2 O_4 P, 0.75(C_3 H_8 O)$ |
| Formula weight | 612.89 |
| Temperature | 100(2) K |
| Wavelength | 1.54178 Å |
| Crystal system | Monoclinic |
| Space group | $P2_1$ |
| Unit cell dimensions | a = 15.9810(5) Å         α = 90°. |
| | b = 7.3336(2) Å           β = 91.087(2)°. |
| | c = 23.1123(7) Å         θ = 90°. |
| Volume | 2708.23(14) Å$^3$ |
| Z | 4 |
| Density (calculated) | 1.503 Mg/m$^3$ |
| Absorption coefficient | 2.503 mm$^{-1}$ |
| F(000) | 1270 |
| Crystal size | 0.270 × 0.025 × 0.008 mm$^3$ |
| Theta range for data collection | 1.912 to 68.230°. |
| Index ranges | −19 <= h <= 19, −8 <= k <= 8, −27 <= l = 27 |
| Reflections collected | 72788 |
| Independent reflections | 9882 [$R_{int}$ = 0.0656] |
| Completeness to theta = 67.679° | 99.9% |
| Absorption correction | Semi-empirical from equivalents |
| Max. and min. transmission | 0.7531 and 0.6266 |
| Refinement method | Full-matrix least-squares on F$^2$ |
| Data/restraints/parameters | 9882/238/813 |
| Goodness-of-fit on F$^2$ | 1.062 |
| Final R indices [I > 2(5(I)] | R1 = 0.0327, wR2 = 0.0826 |
| R indices (all data) | R1 = 0.0360, wR2 = 0.0845 |
| Absolute structure parameter | 0.002(5) |
| Largest diff. peak and hole | 0.440 and −0.300 e.Å$^{-3}$ |

TABLE 60

Hydrogen bond parameters for Voruciclib phosphate [A and °].

| D—H...A | d(D... | d(H... | d(D... | <(DHA) |
|---|---|---|---|---|
| O(1)—H(1A)...O(15)#1 | 0.84(3 | 1.93(3) | 2.761(3 | 168(5) |
| O(3)—H(3)...O(11) | 0.86(2 | 1.80(3) | 2.650(3 | 170(4) |
| O(4)—H(4)...O(5) | 0.85(2 | 1.78(3) | 2.577(3 | 155(4) |
| N(1)—H(1)...O(13)#1 | 0.90(2 | 1.97(3) | 2.839(4 | 162(4) |
| C(1)—H(1B)...O(2) | 1.00 | 2.29 | 2.795(4 | 110.2 |
| C(2)—H(2A)...O(3) | 1.00 | 2.50 | 3.002(4 | 110.4 |
| C(3)—H(3A)...O(18)#2 | 0.99 | 2.56 | 3.418(4 | 144.9 |
| C(4)—H(4A)...O(3) | 0.99 | 2.45 | 3.038(4 | 117.9 |
| C(6)—H(6A)...O(3) | 0.98 | 2.51 | 3.204(4 | 127.9 |
| C(14)—H(14A)...F(5)#3 | 0.95 | 2.50 | 3.317(4 | 144.4 |
| O(13)—H(13)...O(15) | 0.86(3 | 1.67(3) | 2.509(4 | 166(5) |
| O(14)—H(14)...O(16)#4 | 0.88(3 | 1.70(3) | 2.577(3 | 176(4) |
| O(6)—H(6)...O(1S˜a)#5 | 0.83(3 | 2.00(3) | 2.818(6 | 165(6) |
| O(6)—H(6)...O(1U˜c)#6 | 0.83(3 | 2.14(4) | 2.910(6 | 153(6) |
| O(8)—H(8)...O(12) | 0.83(2 | 1.79(3) | 2.601(3 | 167(5) |
| O(9)—H(9)...O(10) | 0.83(2 | 1.83(3) | 2.577(3 | 149(4) |
| N(2)—H(2)...O(17)#5 | 0.90(2 | 2.21(3) | 2.871(4 | 130(3) |
| C(32)—H(32)...O(8) | 1.00 | 2.26 | 2.806(4 | 113.3 |
| C(33)—H(33A)...O(8) | 0.99 | 2.48 | 3.078(4 | 118.8 |
| C(36)—H(36A)...O(8) | 0.98 | 2.46 | 3.166(4 | 129.1 |
| C(36)— | 0.98 | 2.54 | 3.344(4 | 139.2 |
| C(44)—H(44)...F(3)#7 | 0.95 | 2.53 | 3.276(4 | 135.7 |
| O(17)—H(17)...O(11) | 0.86(3 | 1.69(3) | 2.544(3 | 172(5) |
| O(18)—H(18)...O(12)#8 | 0.90(3 | 1.65(3) | 2.548(3 | 175(5) |
| O(1T˜b)— | | 0.84 | 1.86 | 2.618(7 | 149.1 |
| O(1U˜c)— | | 0.84 | 1.97 | 2.790(6 | 166.8 |

Symmetry transformations used to generate equivalent atoms: #1 −x+2,y−1/2,−z+1; #2 −x+2,y+1/2,−z+1; #3 −x+1, y−1/2,−z+2; #4 x,y+1,z; #5 −x+1,y+1/2,−z+1; #6 −x+1,y+ 3/2,−z+1; #7 −x+2,y+1/2,−z+2; #8 x,y−1,z Example 8: Voruciclib Malonate Crystal Structure During the salt screen on Voruciclib in project S18128 a malonate salt was identified (FIG. 282). At the time, the crystals were too small for single crystal structure determination. In the current study, attempts to grow the crystals by recrystallization from ethanol resulted in crystals suitable for the structure analysis.

Voruciclib malonate was recrystallized from EtOH by cooling crystallization. The crystals that were obtained had a needle-like morphology. A crystal with a size of approximately 0.39×0.07×0.06 mm was selected for single crystal diffraction, without cutting (FIG. 283).

Single crystal diffraction data was collected on the diffractometer available at Ardena using molybdenum radiation. The malonate salt had crystallized in a monoclinic space group $P2_1$, and confirmed the ratio of Voruciclib and malonic acid of 1:1. The final crystallographic data and structural refinement parameters are presented in Table 61.

TABLE 61

Crystal data and structure refinement for Voruciclib malonate

| Identification code | Voruciclib malonate |
|---|---|
| Polymorph | 1 |
| Empirical formula | $C_{25}H_{20}ClF_3NO_5^+ \cdot C_3H_3O_4^-$ |
| Formula weight | 573.89 |
| T [K] | 296(2) |
| λ [Å] | 0.71073 |
| Crystal system | Monoclinic |
| Space group | $P2_1$ |
| Unit cell dimensions | |
| a [Å] | 12.289(9) |
| b [Å] | 7.417(5) |
| c [Å] | 14.105(9) |
| β [°] | 94.366(9) |
| V [Å$^3$] | 1281.9(15) |
| Z | 2 |
| $D_c$ [g/cm$^3$] | 1.487 |
| μ [mm$^{-1}$] | 0.226 |
| F(000) | 592 |
| Crystal size [mm$^3$] | 0.39 × 0.07 × 0.06 |

TABLE 61-continued

Crystal data and structure refinement for Voruciclib malonate

| Identification code | Voruciclib malonate |
|---|---|
| θ range for data collection [°] | 2.90 → 22.59°. |
| Reflections collected | 4575 |
| Independent reflections | 2792 [$R_{int}$ = 0.0728] |
| Completeness to θ = 25.242° [%] | 93.3 |
| Absorption correction | Integration |
| Max. and min. transmission | 0.992 and 0.976 |
| Data/restraints/parameters | 2792/11/350 |
| Goodness-of-fit on $F^2$ | 1.010 |
| Final R indices [I > 2σ(I)] | R1 = 0.0681, wR2 = 0.1568 |
| R indices (all data) | R1 = 0.1249, wR2 = 0.1870 |
| Absolute structure parameter | 0.12(14) |
| Absolute configuration | R R |
| Extinction coefficient | n/a |
| Largest diff. peak and hole [e/Å$^3$] | 0.323 and −0.264 |

The crystals of Voruciclib malonate comprised of Voruciclib cations and malonate monoanions in ratio 1:1. The hydrogen bonds between the Voruciclib cation and malonate anion, together with the atom labeling, is shown in FIG. 284. The charged carboxylic group of the malonate anion (O41) serves as an acceptor of a hydrogen atom from the charged Voruciclib amine group (N4). The neutral carboxylic group of the malonate ion (O46) acts a hydrogen acceptor of the Voruciclib alcohol group (O1).

FIG. 285 shows the crystal packing and hydrogen bond scheme along the b axis, while Table 62 shows the detailed description of hydrogen bonds. The crystal structure of Voruciclib malonate is a tunnel-like structure where Voruciclib cations form tunnels in which the malonate anions are located. These tunnels run along the direction [0 1 0] with anions laying around screw axis $2_1$ and are connected through hydrogen bonds to other malonate anions as well as to the Voruciclib cations.

TABLE 62

Hydrogen bonds found in the crystal structure of Voruciclib malonate.

| D—H...A | D—HA[Å] | H...A [Å] | D...A [Å] | D—H...A [°] |
|---|---|---|---|---|
| O(1)—H(1A)...O(46) | 0.83 | 2.55 | 3.34(4) | 161 |
| O(1B)—H(1B)...O(42) | 0.86 | 2.36 | 3.05(2) | 138 |
| N(4)—H(4)...O(41) | 0.98 | 1.77 | 2.732(12) | 168 |
| O(11)—H(11)...O(42)$^i$ | 0.85 | 1.91 | 2.686(11) | 152 |
| O(14)—H(14A)...O(17) | 0.82 | 1.87 | 2.600(14) | 148 |
| O(47)—H(47)...O(41)$^{ii}$ | 0.87 | 1.74 | 2.609(14) | 179 |

Symmetry transformations: (i) 2−x, y−0.5, 1−z; (ii) 2−x, y+0.5, −z

Due to low amount of material available, a HR-XRPD experiment and Rietveld analysis (Rietveld, 1969) using the model obtained in the single crystal diffraction could not be performed. Nevertheless, the simulated powder pattern from the single crystal data was the same as the diffraction pattern obtained from the HT-XRPD experiment (FIG. 286).

Voruciclib malonate obtained from experiment SSm53 (project S18128) was used to grow the single crystals.

The remaining material obtained in experiment SSm53 was suspended in 200 μL of EtOH in a 1.8 mL vial. The suspension was heated up to the boiling point of EtOH and kept at this temperature for about 1 min until all material was dissolved. The vial was left at RT. After several days the needle-like crystals appeared.

The single crystal measurements were performed on Nonius Kappa-CCD. The data were collected at 296 K. The full sphere data were collected up to θ=22.6° resulting with 4575 reflections. Data reduction was performed using HKL Scalepack (Otwinowski & Minor 1997) and cell parameters were obtained using Denzo and Scalepak (Otwinowski & Minor, 1997) from 11508 reflections within θ range 1 to 27.5°. The structure was solved using direct methods by SHELXT-2014/7 (Sheldrick, G. M., 2015a). The structure was refined by least square full matrix refinement using SHELXL-2014/7 (Sheldrick, G. M., 2015b). All H atoms were incorporated from the geometry and not refined. Several static disorders were detected (alcohol and trifluoromethyl groups). Both disorders were refined with isotropical thermal parameters, due to low angle of collected data as well as low number of reflections.

Example 9: Voruciclib (ME-522) Salt Selection

This example discloses a study to select the salt form of voruciclib. The initial drug substance exhibited a gelling problem, where the drug substance was gelling when exposed to water, as well as a manufacturing problem, where different forms of Voruciclib HCl were isolated at different manufacturing sites using the same manufacturing process.

The solid state of Voruciclib HCl was characterized in various solvents. Of the 20 different forms identified, 11 were found to be stable forms (forms 1, 2, 6-7, 12-14, and 18-20). FIG. 287 shows the results of the study.

Attributes of voruciclib were also examined. In a non-limiting example, FIG. 288 shows examples of target product attributes of Voruciclib. In one embodiment, the Voruciclib product has one or more of the following properties: does not exhibit gelling, water solubility of greater than 5 mg/mL; less than 5 total number of polymorphs/hydrates/solvates; is anhydrous and solvent-free; has one or more stable polymorphs; exhibits stability (under accelerated aging conditions); is not hygroscopic; has 1:1 Cl (salt) stoichiometry; is a crystalline material; and is manufacturable.

An initial salt screen was performed. FIG. 289 shows the results of the screen. Using various acid counterions, the salts were examined for form, crystallinity, and stability. 11 salts having good crystallinity and stability were initially chosen for subsequent analysis.

A secondary salt screen was performed. Three salts (malonate, oxalate, and phosphate) were chosen for subsequent development based on having 2 or fewer polymorphs, no gelling, low residual solvent percent, and greater than 5 mg/mL of water solubility. FIG. 290 shows the results of the screen.

The properties of the HCl, malonate, oxalate, and phosphate salts of Voruciclib related to the product attributes shown in FIG. 288 were examined. FIG. 291 shows the results of the analysis.

A. Voruciclib Oxalate: properties of Voruciclib Oxalate include: Oxa2 was the most common and stable mono-oxalate observed, and was stable under vacuum conditions; Oxa1, Oxa2, Oxa6, and Oxa7 were stable when exposed to advanced aging conditions (40° C./75% RH); and gelling was not observed when the forms when exposed to water. However, several solid forms of the mono-salt, hemi-salt, or mixtures of both were found; several oxalate salt single crystal structures were identified which were all attributed to hemi-oxalates salts (Oxa1, Oxa3 and Oxa4); and several unstable forms converted to Oxa8 upon exposure to advanced aging conditions. Moreover, based on single crystal data, Voruciclib oxalate salt crystals have voids/cavities in the structure which can be filled by water or solvent molecules. The non-stoichiometric water/solvent present in the structure was found to be difficult to control and most likely can very depending on the relative humidity of the environment.

B. Voruciclib Phosphate: properties of Voruciclib Phosphate included: the initial salt screen found only two forms: Pho1 and Pho2; the material manufactured at the plant was determined to be a new form: Pho3; Pho1 was the only stable form from when exposed to advance aging conditions (40° C./75% RH); gelling was not observed when exposed to water; and Pho1 had a solubility of >5 mg/mL. Further, after an exhaustive polymorph screen several additional forms were found: Pho1, Pho3, Pho4, Pho5, Pho6, Pho7, Pho8 and Pho9, and Pho1 was found to be moderately hygroscopic and became a gel when exposed to water.

C. Voruciclib Malonate: properties of Voruciclib Malonate included: Mao1 was the most common form, is an anhydrous solid, was non-hygroscopic, and had a solubility of approximately 13 mg/mL; gelling was not observed when exposed to water; Mao3 and Mao5 were physically unstable and converted to Mao1 upon drying under vacuum or when exposed to advance aging conditions (40° C./75% RH); Mao4 was only formed directly from amorphous material when exposed to hydrocarbon solvents (cyclohexane, pentane and heptane); and Mao1 can be manufactured/purified by cooling crystallization in high yield and high purity. However, three additional forms were identified: Mao3, Mao4 and Mao5—all of which appear to be hydrates. Based on these manufacturability, polymorphic, and hygroscopic properties, the malonate salt was selected for further development.

The Voruciclib HCl and malonate salts were compared in a dog PK study (see also Example 10). Each salt form was formulated into tablets with identical formulations. 9 dogs were divided into three group of 3 dogs/group. Each group received one of the following different pre-treatments:
1. No pretreatment (natural gastric pH—could be acidic or alkaline)
2. Famotidine (causes alkaline gastric pH)
3. Pentagastrin (causes acidic gastric pH)

The study used a crossover design. Each group of dogs first received pretreatment and was dosed with the Voruciclib HCl salt. After a washout period, the same group of dogs received the same pretreatment and was dosed with the Voruciclib malonate salt. The results were then analyzed for variability. FIG. 293 shows this analysis of variability. The analysis of variability for each group showed malonate to afford more consistent exposure. These results were statistically significant when all three groups together were analyzed together (see the "combined" pretreatment rows in FIG. 293); the malonate salt was found to have a lower T max, C max/dose, and AUClast/dose than HCl. FIG. 294 shows the ratio of malonate to HCl for each dog and PK parameter was calculated.

Example 10: Evaluation of Voruciclib Salts Absorption in Male Beagle Dogs

This example discloses a study evaluating the absorption of Voruciclib salts in male beagle dogs. The objective of the study was evaluate the variability of absorption of voruciclib (ME-522) hydrochloride and malonate salts across a variety of gastrointestinal pH conditions.

Materials and Methods

Voruciclib hydrochloride and malonate salts were formulated into 300 mg tablets with identical composition, as summarized in Table 62.

TABLE 62

Composition of voruciclib tablets.

| Component | Percentage |
| --- | --- |
| Voruciclib Salt | 37.5 |
| Microcrystalline cellulose (MCC PH102) | 23 |
| Tablettose 100 | 33.5 |
| Croscarmellose sodium | 5 |
| Magnesium stearate | 1 |

Dog Pharmacokinetic study: 9 male Beagle dogs were divided into 3 treatment group (Groups 1-3) of 3 dogs per group, in this two-phase study. Animals were ranked by body weight and assigned to treatment groups using a computerized randomization assignment. All dogs were administered one oral tablet of 300 mg Voruciclib HCl salt in Phase 1 and Voruciclib Malonate salt in Phase 2, with a seven-day washout period between phases. During each phase, oral Famotidine (40 mg/dog) was administered to Group 2 one hour prior to Voruciclib administration and intramuscular (IM) Pentagastrin (0.006 mg/kg) was administered to Group 3 approximately 30 minutes prior to Voruciclib administration.

Clinical observations were recorded at least once daily, approximately 1 hour post-Voruciclib dose on dosing days. Body weight measurements were recorded for randomization, prior to dose administration (Day 1 and 8), and on the last day of the washout period following Phase 1 (Day 7). Plasma samples were collected during each phase from all groups prior to dose administration (Phase 2 only) and also at 0.5, 1, 2, 4, 5, 6, 8, and 24 hours post-dose for analysis of plasma concentrations of Voruciclib.

Pharmacokinetic Analysis: Pharmacokinetic (PK) analyses were performed on the individual plasma concentration versus time data for Voruciclib using Phoenix WinNonlin non-compartmental analysis. To evaluate drug absorption, the PK parameter C max (maximum plasma concentration) was measured.

For each dog, the actual administered dose of voruciclib free base was calculated on a mg/kg basis, using the dog body weight data. The dose-normalized C max/Dose PK parameter was then calculated for each dog.

Statistical Analysis: The C max for each dog and treatment is tabulated in Table 63. Body weights, voruciclib free base administered per dose and calculation of the dose-normalized C max/Dose is summarized in Table 64.

TABLE 63

Cmax for each dog and treatment

| Pretreatment | Salt | Dog ID | Cmax (ng/ml) |
|---|---|---|---|
| Famotidine | HCl | 2M001 | 525 |
| Famotidine | HCl | 2M002 | 1650 |
| Famotidine | HCl | 2M003 | 333 |
| Famotidine | Malonate | 2M001 | 465 |
| Famotidine | Malonate | 2M002 | 875 |
| Famotidine | Malonate | 2M003 | 391 |
| none | HCl | 1M001 | 739 |
| none | HCl | 1M002 | 1500 |
| none | HCl | 1M003 | 2040 |
| none | Malonate | 1M001 | 341 |
| none | Malonate | 1M002 | 544 |
| none | Malonate | 1M003 | 587 |
| Pentagastrin | HCl | 3M001 | 1520 |
| Pentagastrin | HCl | 3M002 | 897 |
| Pentagastrin | HCl | 3M003 | 695 |
| Pentagastrin | Malonate | 3M001 | 663 |
| Pentagastrin | Malonate | 3M002 | 1010 |
| Pentagastrin | Malonate | 3M003 | 578 |

TABLE 64

Body weights, voruciclib free base administered per dose and calculation of the dose-normalized Cmax/Dose

| Pretreatment | Salt | Dog ID | Dose Free Base (mg) | BW (Kg) | Dose (mg/Kg) | Cmax/Dose |
|---|---|---|---|---|---|---|
| Famotidine | HCl | 2M001 | 104 | 9.1 | 11 | 46 |
| Famotidine | HCl | 2M002 | 104 | 8.5 | 12 | 134 |
| Famotidine | HCl | 2M003 | 104 | 8.1 | 13 | 26 |
| Famotidine | Malonate | 2M001 | 92 | 8.8 | 10 | 44 |
| Famotidine | Malonate | 2M002 | 92 | 8.4 | 11 | 80 |
| Famotidine | Malonate | 2M003 | 92 | 8.1 | 11 | 34 |
| none | HCl | 1M001 | 104 | 9.5 | 11 | 67 |
| none | HCl | 1M002 | 104 | 8.7 | 12 | 125 |
| none | HCl | 1M003 | 104 | 8.5 | 12 | 166 |
| none | Malonate | 1M001 | 92 | 9.3 | 10 | 34 |
| none | Malonate | 1M002 | 92 | 8.6 | 11 | 51 |
| none | Malonate | 1M003 | 92 | 8.3 | 11 | 53 |
| Pentagastrin | HCl | 3M001 | 104 | 8.1 | 13 | 118 |
| Pentagastrin | HCl | 3M002 | 104 | 8.3 | 13 | 71 |
| Pentagastrin | HCl | 3M003 | 104 | 9 | 12 | 60 |
| Pentagastrin | Malonate | 3M001 | 92 | 8 | 12 | 58 |
| Pentagastrin | Malonate | 3M002 | 92 | 7.9 | 12 | 87 |
| Pentagastrin | Malonate | 3M003 | 92 | 9 | 10 | 56 |

Statistical Analysis: The % CV's for each salt and pre-treatment (3 dogs per analysis) are presented in Table 65. The % CV's for each salt across all pre-treatments (9 dogs per analysis) are presented in Table 66. The F-Test Two-Sample for Variances indicated that the difference in C max/Dose between the malonate and hydrochloride salts, across all pre-treatments (9 dogs) was statistically significant (p=0.007).

TABLE 65

% CV for each salt and pretreatment

| Pretreatment | Salt | N | % CV Cmax/D |
|---|---|---|---|
| Famotidine | HCl | 3 | 84 |
| Famotidine | Malonate | 3 | 45 |
| none | HCl | 3 | 42 |
| none | Malonate | 3 | 22 |
| Pentagastrin | HCl | 3 | 37 |
| Pentagastrin | Malonate | 3 | 26 |

TABLE 66

% CV for each salt across all pre-treatments, and p-value for the statistical comparison of the 2 salts via the F-Test Two-Sample for Variances

| Salt | N | % CV Cmax/D | p-value |
|---|---|---|---|
| HCl | 9 | 52 | 0.007 |
| Malonate | 9 | 33 | |

Based on these results, it was found that variability of absorption of voruciclib malonate, across a variety of gastrointestinal pH conditions, is lower than the hydrochloride salt.

The Voruciclib plasma concentration for each subject per group was measured by HPLC. Table 67 shows the bioanalysis methods. Table 68 shows the Voruciclib plasma concentration (ng/mL) for each subject per group measured at various time intervals. The results are also graphically depicted in FIG. 295.

TABLE 67

Bioanalysis Methods

| System Components | | |
|---|---|---|
| Module | Manufacturer | Model |
| LC | Shimadzu | Prominence |
| Autosampler | Shimadzu | SIL 30AC MP |
| MS Detection | AB Sciex | API 4000 Q Trap_5 |

| HPLC Method | |
|---|---|
| Column | Phenomenex Kinetex C18 (2.1 x 50 mm, 2.6 μm) |
| Elution | Gradient, 0.4 mL/min |
| | Mobile Phase A: 0.1% Formic Acid in Water |
| | Mobile Phase B: 0.1% Formic Acid in Acetonitrile |

TABLE 67-continued

Bioanalysis Methods

MS Detection and Calibration for Voruciclib in Dog Plasma

Peak Name: Tolbutamide
Use as Internal Standard
Q1/Q3 Masses: 271.00/155.00 Da
Peak Name: Voruciclib
Internal Standard: Tolbutamide
Q1/Q3 Masses: 470.20/427.30 Da

| Fit | Linear | Weighting | 1/x |
|---|---|---|---|
| Intercept | −0.000339 | | |
| Slope | 0.00143 | | |
| Correlation coefficient | 0.9998 | | |
| Use Area | | | |

TABLE 68

Voruciclib plasma concentration (ng/mL) at various time intervals

| Analyte | Route | Test Article (Tablet) | Phase | Dose (mg/animal) | Pre-Treatment | Group | Time (hr) | Plasma Concentration (ng/mL) by Subject | | | Mean | SD | N |
|---|---|---|---|---|---|---|---|---|---|---|---|---|---|
| | | | | | | | | 1M001 | 1M002 | 1M003 | | | |
| Voruciclib | PO | Voruciclib HCl Salt | 1 | 300 | none | 1 | 0.5 | 32.6 | 826 | 1850 | 903 | 911 | 3 |
| | | | | | | | 1 | 167 | 1500 | 2040 | 1240 | 960 | 3 |
| | | | | | | | 2 | 383 | 1100 | 1880 | 1120 | 750 | 3 |
| | | | | | | | 4 | 739 | 502 | 854 | 698 | 179 | 3 |
| | | | | | | | 5 | 545 | 466 | 1040 | 684 | 311 | 3 |
| | | | | | | | 6 | 395 | 288 | 572 | 418 | 143 | 3 |
| | | | | | | | 8 | 222 | 141 | 375 | 246 | 119 | 3 |
| | | | | | | | 24 | 476 | 133 | 181 | 263 | 186 | 3 |
| | | | | | | | | 2M001 | 2M002 | 2M003 | Mean | SD | N |
| | | | | | Famotidine 40 mg/dog | 2 | 0.5 | 224 | 1650 | 129 | 668 | 852 | 3 |
| | | | | | | | 1 | 525 | 1190 | 231 | 649 | 491 | 3 |
| | | | | | | | 2 | 358 | 802 | 213 | 458 | 307 | 3 |
| | | | | | | | 4 | 215 | 427 | 154 | 265 | 143 | 3 |
| | | | | | | | 5 | 236 | 560 | 333 | 376 | 166 | 3 |
| | | | | | | | 6 | 154 | 336 | 165 | 218 | 102 | 3 |
| | | | | | | | 8 | 95.0 | 176 | 101 | 124 | 45 | 3 |
| | | | | | | | 24 | 40.5 | 41.1 | 36.4 | 39.3 | 2.6 | 3 |
| | | | | | | | | 3M001 | 3M002 | 3M003 | Mean | SD | N |
| | | | | | Pentagastrin 0.006 mg/kg | 3 | 0.5 | 1290 | 703 | 360 | 784 | 470 | 3 |
| | | | | | | | 1 | 1520 | 897 | 695 | 1040 | 430 | 3 |
| | | | | | | | 2 | 902 | 605 | 640 | 716 | 162 | 3 |
| | | | | | | | 4 | 420 | 315 | 416 | 384 | 60 | 3 |
| | | | | | | | 5 | 287 | 235 | 333 | 285 | 49 | 3 |
| | | | | | | | 6 | 231 | 186 | 254 | 224 | 35 | 3 |
| | | | | | | | 8 | 152 | 90.9 | 174 | 139 | 43 | 3 |
| | | | | | | | 24 | 71.0 | 43.9 | 57.8 | 57.6 | 13.6 | 3 |
| | | | | | | | | 1M001 | 1M002 | 1M003 | Mean | SD | N |
| | | Voruciclib Malonate Salt | 2 | 300 | none | 1 | 0 | BLQ | BLQ | BLQ | BLQ | — | 0 |
| | | | | | | | 0.5 | 125 | 100 | 18.5 | 81.2 | 55.7 | 3 |
| | | | | | | | 1 | 341 | 544 | 356 | 414 | 113 | 3 |
| | | | | | | | 2 | 300 | 350 | 350 | 333 | 29 | 3 |
| | | | | | | | 4 | 141 | 303 | 587 | 344 | 226 | 3 |
| | | | | | | | 5 | 164 | 256 | 446 | 289 | 144 | 3 |
| | | | | | | | 6 | 127 | 209 | 365 | 234 | 121 | 3 |
| | | | | | | | 8 | 81.9 | 146 | 188 | 139 | 53 | 3 |
| | | | | | | | 24 | 29.6 | 35.1 | 225 | 96.6 | 111.3 | 3 |
| | | | | | | | | 2M001 | 2M002 | 2M003 | Mean | SD | N |
| | | | | | Famotidine 40 mg/dog | 2 | 0 | BLQ | BLQ | BLQ | BLQ | — | 0 |
| | | | | | | | 0.5 | 234 | 152 | 109 | 165 | 64 | 3 |
| | | | | | | | 1 | 465 | 710 | 299 | 491 | 207 | 3 |
| | | | | | | | 2 | 349 | 875 | 391 | 538 | 292 | 3 |
| | | | | | | | 4 | 149 | 274 | 160 | 194 | 69 | 3 |

TABLE 68-continued

| | | | | Vorucicl | ib plasma con | centration (ng/mL) at various time intervals | | | | | |
|---|---|---|---|---|---|---|---|---|---|---|---|
| Analyte | Route | Test Article (Tablet) | Phase | Dose (mg/animal) | Pre-Treatment | Group | Time (hr) | Plasma Concentration (ng/mL) by Subject | | | |
| | | | | | | | 5 | 111 | 196 | 157 | 155 | 43 | 3 |
| | | | | | | | 6 | 83.2 | 135 | 114 | 111 | 26 | 3 |
| | | | | | | | 8 | 56.8 | 119 | 124 | 100 | 37 | 3 |
| | | | | | | | 24 | 23.7 | 89.6 | 52.2 | 55.2 | 33.1 | 3 |
| | | | | | | | | 3M001 | 3M002 | 3M003 | Mean | SD | N |
| | | | | | Pentagastrin 0.006 mg/kg | 3 | 0 | BLQ | BLQ | BLQ | BLQ | — | 0 |
| | | | | | | | 0.5 | 614 | 874 | 374 | 621 | 250 | 3 |
| | | | | | | | 1 | 663 | 1010 | 578 | 750 | 229 | 3 |
| | | | | | | | 2 | 533 | 539 | 571 | 548 | 20 | 3 |
| | | | | | | | 4 | 247 | 299 | 353 | 300 | 53 | 3 |
| | | | | | | | 5 | 183 | 236 | 239 | 219 | 32 | 3 |
| | | | | | | | 6 | 164 | 166 | 178 | 169 | 8 | 3 |
| | | | | | | | 8 | 96.3 | 94.4 | 133 | 108 | 22 | 3 |
| | | | | | | | 24 | 7.04 | 36.1 | 30.4 | 24.5 | 15.4 | 3 |

BLQ—Below the Limit of Quantitation (1 ng/mL)

Example 11: Voruciclib Malonate Salt Formation

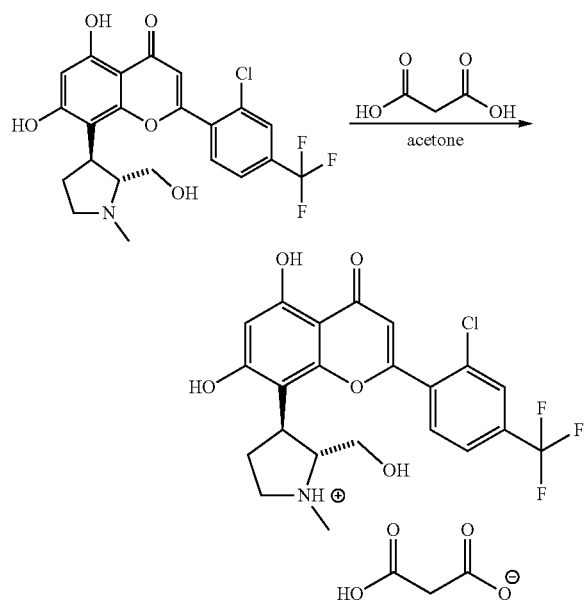

2-(2-chloro-4-(trifluoromethyl)phenyl)-5,7-dihydroxy-8-((2S,3R)-2-(hydroxymethyl)-1-methylpyrrolidin-3-yl)-4H-chromen-4-one malonate salt (ME-522 malonate):

Voruciclib free base (Int-5A) and acetone (5 volumes) were charged into a reaction flask to give a heterogenous reaction mixture. The reaction mixture was heated at 50±5° C. and stirred until all of the solids dissolved to give a homogenous reaction solution. While maintaining a temperature of 50±5° C. malonic acid (1.1 eq) was added to the reaction solution (slight exotherm) and agitated for 1 hour. The reaction mixture was slowly cool from 50° C. to 25° C. over 4.5 hours and held at 25±5° C. for not less than 16 hours. The crude product was collected by vacuum filtration and the wet-cake was wash with 1 volume of acetone. The resulting solids were dried at 40° C. under vacuum to afford the title compound as a yellow solid with a purity of 96%.

A second crop of material was generated by concentrating the mother liquor and recrystallizing the resulting crude solids from acetone using the same procedure as above. Both lots resulted in form Mao1.

Voruciclib Malonate sample information and XRPD results are summarized in Table 1. The XRPD patterns of lots 20-00022-01, 20-00026-01, and 20-00062-01 exhibit sharp peaks indicating the samples are primarily composed of crystalline materials (see Data section). The sample patterns are similar to each other in terms of peak positions (FIG. 1) suggesting they are composed of the same material(s). The pattern of Lot 20-00026-01 shows diffused scattering in the range of approximately 10-30° 2θ suggesting that this lot is more disordered or possibly contains an amorphous component.

TABLE 1

Voruciclib Malonate Sample Information and Results

| Sample ID | LIMS No. | Results | File |
|---|---|---|---|
| Lot 20-00022-01 MEI-026 | 539895 | Crystalline | 995417 |
| Lot 20-00026-01 MEI-026 | 539896 | Crystalline with disorder | 995418 |
| Lot 20-00062-01 MEI-026 | 539897 | Crystalline | 995419 |

The XRPD patterns were collected with a PANalytical Empyrean diffractometer using an incident beam of Cu radiation produced using an Optix long, fine-focus source. An elliptically graded multilayer mirror was used to focus Cu Kα X-rays through the specimens and onto the detector. Prior to the analyses, a silicon specimen (NIST SRM 640e) was analyzed to verify the observed position of the Si 111 peak is consistent with the NIST-certified position. A specimen of each sample was sandwiched between 3-μm-thick films and analyzed in transmission geometry. A beam-stop, short anti-scatter extension, and an anti-scatter knife edge were used to minimize the background generated by air. Soller slits for the incident and diffracted beams were used to minimize broadening from axial divergence. The diffraction patterns were collected using a scanning position-sensitive detector (X'Celerator) located 240 mm from the specimens and Data Collector software v. 5.5. Data Viewer v. 1.8 was used to create the XRPD images in the Data section of this report. Data acquisition parameters are displayed on the images in the Data section of this report. Data Viewer version 1.8 was used to create FIG. 1.

REFERENCES

Bruker A X S. (2017). Topas version 6.0, Bruker-AXS, Karlsruhe

Coelho, A. A. (2000). Whole-profile structure solution from powder diffraction data using simulated annealing. J. Appl. Cryst., 33, 899-908.

Coelho, A. A. (2003). Indexing of powder diffraction patterns by iterative use of singular value decomposition. J. Appl. Cryst., 36, 86-95.

Coelho, A. A. & Kern, A. (2005). Discussion of the indexing algorithms within TOPAS. CPD Newsletter, 32, 43-45.

Pawley, G. S. (1981). Unit-cell refinement from powder diffraction scans. J. Appl. Cryst., 14, 357-361.

Rietveld, H. (1969). A profile refinement method for nuclear and magnetic structures. J. Appl. Cryst., 2, 65-71

Toraya, H. (2000). Estimation of statistical uncertainties in quantitative phase analysis using the Rietveld method and the whole-powder-pattern decomposition method. J. Appl. Cryst., 33, 1324-1328.

Toraya, H., & Tsusaka, S. (1995). Quantitative phase analysis using the whole-powder-pattern decomposition method. I. Solution from knowledge of chemical compositions. J. Appl. Cryst., 28, 392-399.

Bruker (2011). SAINT, Bruker-AXS Inc., Madison, Wisconsin, USA.

Krause, L., Herbst-Irmer, R., Sheldrick, G. M. & Stalke, D., J. Appl. Cryst. 2015, 48, 3-10.

Sheldrick, G. M., Acta Cryst. 2015, A71, 3-8.

Sheldrick, G. M., Acta Cryst. 2015, C71, 3-8.

Müller, P., Crystallography Reviews 2009, 15, 57-83.

Parsons, S. & Flack, H. D., Acta Cryst. 2004, A60, s61.

Hooft, R. W. W., Strayer, L. H. Spek, A. L., J. Appl. Cryst. 2008, 41, 96-103.

Hooft, R. W. W. (1998). COLLECT. Nonius BV, Delft, The Netherlands.

Kitajgorodskij, A. I. (1973). Molecular Crystals and Molecules. New York: Academic Press.

Mackay, S., Gilmore, C. J., Edwards, C., Stewart, N. & Shankland, K. (1999). MaXus Computer Program for the Solution and Refinement of Crystal Structures. Bruker Nonius, The Netherlands, MacScience, Japan & The University of Glasgow.

Macrae, C. F., Bruno, I. J., Chisholm, J. A., Edgington, P. R., McCabe, P., Pidcock, E., Rodriguez-Monge, L., Taylor, R., van de Streek, J. & Wood, P. A. (2008). J. Appl. Cryst. 41, 466

Otwinowski, Z. and Minor, W, (1997). In Methods in Enzymology, 276, edited by C. W. Carter, Jr. & R. M. Sweet pp. 307-326, New York, Academic Press.

Rietveld, H. (1969). A profile refinement method for nuclear and magnetic structures. J. Appl. Cryst., 2, 65-71

Sheldrick, G. M. (2015a). Acta Cryst. A71, 3-8.

Sheldrick, G. M. (2015b). Acta Cryst. C71, 3-8.

Spek, A. L. (2009). Acta Cryst. D65, 148-155.

Topas version 4.2 Bruker AXS, 2008

| | | | | | Form | | | | | | |
|---|---|---|---|---|---|---|---|---|---|---|---|
| | A = SM | B | C | D | E_lc | Ben1 | Ben2 | Ben3 | Bes1 | Bes2 | DiTr1 |
| | | | | | ExperimentID | | | | | | |
| Counter ion | SM — | SSm66 _none | SSm33 _none | SSm82 Ethanesulfonic acid | SSm6 1,2-Ethanedisulfonic acid | SSm30 Benzoic acid | SSm96 Benzoic acid | SSm30 Benzoic acid | SSm10 Benzene-sulfonic acid | SSm76 Benzene-sulfonic acid | SSm46 Dibenzoyl-L-tartaric acid |
| 1.5 | 6101 | 1986 | 2737 | 1443 | 972 | 2304 | 2041 | 916 | 4017 | 532 | 2868 |
| 1.54 | 3623 | 1001 | 2401 | 4025 | 2219 | 1422 | 2996 | 545 | 4230 | 298 | 3084 |
| 1.58 | 6259 | 4917 | 3921 | 2622 | 6306 | 2657 | 5697 | 1079 | 4497 | 1242 | 3740 |
| 1.62 | 8313 | 2438 | 3895 | 5076 | 5787 | 4848 | 4463 | 935 | 8980 | 2887 | 3113 |
| 1.66 | 6800 | 4667 | 5309 | 4971 | 9717 | 4123 | 5193 | 762 | 9528 | 2260 | 4670 |
| 1.7 | 8586 | 5863 | 5353 | 4882 | 6910 | 4638 | 6643 | 1702 | 12517 | 1952 | 7260 |
| 1.74 | 8933 | 6878 | 11583 | 5443 | 8496 | 4221 | 9243 | 3553 | 12567 | 340 | 6037 |
| 1.78 | 14881 | 7838 | 7190 | 4591 | 7489 | 6018 | 5300 | 2113 | 12165 | 2406 | 3673 |
| 1.82 | 13941 | 9152 | 11629 | 6450 | 14326 | 8042 | 6148 | 1304 | 16937 | 2378 | 8066 |
| 1.86 | 17328 | 10187 | 10418 | 8633 | 14226 | 8403 | 7235 | 1804 | 17048 | 1557 | 7761 |
| 1.9 | 17592 | 8497 | 8911 | 9969 | 11474 | 9019 | 7450 | 2382 | 19823 | 1219 | 8360 |
| 1.94 | 18982 | 9125 | 9567 | 8700 | 15824 | 8394 | 8431 | 1363 | 22291 | 2012 | 7664 |
| 1.98 | 17944 | 11056 | 8438 | 8999 | 11355 | 9168 | 7204 | 4046 | 21164 | 2353 | 8306 |
| 2.02 | 16567 | 13200 | 8606 | 5213 | 14134 | 8385 | 10219 | 3166 | 17939 | 3568 | 9314 |
| 2.06 | 18375 | 12982 | 12508 | 9920 | 11115 | 13340 | 8618 | 4787 | 21842 | 4617 | 8298 |
| 2.1 | 18481 | 10343 | 11878 | 7718 | 12279 | 11738 | 8925 | 2912 | 21073 | 4941 | 11257 |
| 2.14 | 16126 | 11392 | 9453 | 6867 | 14099 | 7416 | 6533 | 6027 | 22912 | 5192 | 11622 |
| 2.18 | 20636 | 13193 | 10026 | 8942 | 14631 | 10596 | 9409 | 5422 | 19123 | 3089 | 12626 |
| 2.22 | 20307 | 11889 | 8749 | 9845 | 16479 | 10220 | 9740 | 5489 | 26704 | 7314 | 13343 |
| 2.26 | 21375 | 9913 | 15437 | 9589 | 18956 | 10803 | 9876 | 7600 | 22023 | 6991 | 9129 |
| 2.3 | 16567 | 10014 | 12411 | 6551 | 16175 | 9940 | 8921 | 5747 | 26886 | 6514 | 12607 |
| 2.34 | 19804 | 10419 | 10104 | 7050 | 15033 | 10417 | 13947 | 5225 | 20686 | 7943 | 9016 |
| 2.38 | 19683 | 14806 | 10442 | 9186 | 15785 | 11100 | 10589 | 4796 | 20936 | 6821 | 10582 |
| 2.42 | 20262 | 10929 | 11305 | 9238 | 15129 | 10009 | 9766 | 6875 | 19330 | 6644 | 11229 |
| 2.46 | 20655 | 12351 | 10895 | 11919 | 17060 | 10848 | 9961 | 7127 | 26442 | 6469 | 14274 |
| 2.5 | 24041 | 14425 | 8348 | 6585 | 14940 | 11521 | 9550 | 6624 | 23164 | 5815 | 13203 |
| 2.54 | 27125 | 14031 | 10133 | 11216 | 18527 | 11145 | 8577 | 8759 | 18080 | 7052 | 9767 |
| 2.58 | 24355 | 13223 | 12131 | 10631 | 13016 | 7514 | 8842 | 8697 | 25930 | 7403 | 11373 |
| 2.62 | 27625 | 14363 | 11072 | 11924 | 15666 | 8101 | 9190 | 7417 | 25623 | 8147 | 10846 |
| 2.66 | 26367 | 14656 | 15134 | 6998 | 17637 | 13435 | 14061 | 8389 | 23083 | 6813 | 14242 |
| 2.7 | 30889 | 15340 | 12352 | 9891 | 18027 | 11351 | 11899 | 7906 | 24302 | 10495 | 13050 |
| 2.74 | 27925 | 16932 | 13144 | 10769 | 17762 | 13682 | 11083 | 8188 | 27527 | 9983 | 13619 |
| 2.78 | 32013 | 14623 | 12102 | 11492 | 16812 | 10971 | 11649 | 8690 | 24851 | 7461 | 13764 |

-continued

| | | | | | | | | | | | |
|---|---|---|---|---|---|---|---|---|---|---|---|
| 2.82 | 38096 | 17373 | 13326 | 12073 | 20454 | 13336 | 12348 | 10639 | 23467 | 10382 | 12582 |
| 2.86 | 31778 | 15451 | 13345 | 9945 | 22192 | 13633 | 14775 | 9947 | 24851 | 11753 | 16884 |
| 2.9 | 31785 | 18694 | 12399 | 12983 | 22628 | 14166 | 13808 | 13082 | 25167 | 7804 | 15718 |
| 2.94 | 35480 | 15595 | 12564 | 10441 | 22171 | 14848 | 14751 | 8775 | 22224 | 8467 | 18594 |
| 2.98 | 40624 | 15162 | 14591 | 10616 | 19138 | 11854 | 15687 | 8829 | 28368 | 9847 | 18517 |
| 3.02 | 40297 | 16695 | 14558 | 11786 | 20429 | 13012 | 21168 | 9856 | 28087 | 8410 | 16285 |
| 3.06 | 38921 | 13892 | 13307 | 11320 | 23420 | 12206 | 20651 | 10705 | 29503 | 9226 | 18321 |
| 3.1 | 44599 | 17041 | 18096 | 11404 | 26056 | 14394 | 16848 | 12202 | 32285 | 9180 | 19055 |
| 3.14 | 38027 | 18603 | 16870 | 12101 | 27289 | 13895 | 17306 | 12784 | 26590 | 10326 | 17397 |
| 3.18 | 43580 | 20217 | 19321 | 9955 | 28765 | 19001 | 17463 | 11419 | 29550 | 11490 | 16727 |
| 3.22 | 43523 | 20007 | 18635 | 10419 | 31151 | 14755 | 20664 | 11465 | 32382 | 12189 | 20122 |
| 3.26 | 53897 | 16341 | 20291 | 14343 | 30535 | 16409 | 17234 | 11786 | 34724 | 9628 | 20215 |
| 3.3 | 53434 | 20918 | 18949 | 14628 | 29505 | 13487 | 18486 | 16008 | 32019 | 9836 | 19929 |
| 3.34 | 43452 | 23471 | 17850 | 14417 | 36437 | 16021 | 18501 | 14076 | 34305 | 9314 | 18059 |
| 3.38 | 45731 | 19951 | 19353 | 13481 | 41904 | 17746 | 20697 | 13006 | 33357 | 10834 | 18528 |
| 3.42 | 48561 | 19917 | 22629 | 14457 | 45731 | 17078 | 23082 | 13181 | 33901 | 11000 | 18833 |
| 3.46 | 48522 | 21165 | 26258 | 12218 | 54652 | 17944 | 23559 | 15702 | 39257 | 11043 | 20399 |
| 3.5 | 49471 | 23019 | 22937 | 12426 | 58970 | 20070 | 22216 | 16366 | 39506 | 14702 | 20022 |
| 3.54 | 51343 | 19941 | 21105 | 11857 | 78642 | 21243 | 23706 | 16131 | 44101 | 13220 | 19883 |
| 3.58 | 43714 | 20246 | 25288 | 11647 | 91133 | 20441 | 22052 | 15814 | 40810 | 14927 | 19415 |
| 3.62 | 50087 | 21008 | 21986 | 17179 | 115272 | 17967 | 23677 | 15211 | 38034 | 15329 | 18995 |
| 3.66 | 50880 | 19938 | 20000 | 12518 | 127637 | 16570 | 26005 | 16177 | 38817 | 16414 | 17321 |
| 3.7 | 46727 | 20694 | 23008 | 15353 | 133068 | 17884 | 26826 | 17009 | 35406 | 18306 | 19650 |
| 3.74 | 47340 | 23765 | 22835 | 13869 | 142011 | 19094 | 24602 | 20941 | 36260 | 16614 | 20331 |
| 3.78 | 47067 | 21308 | 21668 | 15327 | 152366 | 21137 | 29046 | 17043 | 35016 | 15598 | 19805 |
| 3.82 | 47382 | 18232 | 19528 | 14067 | 142203 | 19989 | 34336 | 21359 | 37247 | 15306 | 18277 |
| 3.86 | 47470 | 20304 | 20832 | 10481 | 133659 | 21237 | 42435 | 20763 | 32637 | 18700 | 21257 |
| 3.9 | 45191 | 19264 | 18953 | 12911 | 128255 | 24958 | 57907 | 21156 | 38069 | 19261 | 17242 |
| 3.94 | 48062 | 20744 | 18933 | 14285 | 111303 | 23047 | 70082 | 21952 | 33239 | 19175 | 21106 |
| 3.98 | 44675 | 25816 | 21106 | 15719 | 94025 | 24225 | 95942 | 24546 | 39915 | 18512 | 18832 |
| 4.02 | 43775 | 23152 | 23084 | 15510 | 71520 | 21550 | 110181 | 26136 | 38990 | 20988 | 20162 |
| 4.06 | 43250 | 22604 | 19643 | 16276 | 48761 | 28840 | 115483 | 27366 | 36436 | 16772 | 19645 |
| 4.1 | 42236 | 26592 | 19492 | 14782 | 45904 | 28140 | 134490 | 33366 | 33417 | 16981 | 17888 |
| 4.14 | 44621 | 28096 | 24412 | 14734 | 35226 | 36032 | 153047 | 39414 | 37775 | 19611 | 19591 |
| 4.18 | 43327 | 30659 | 27233 | 16405 | 33107 | 34507 | 156627 | 45954 | 37238 | 17589 | 19590 |
| 4.22 | 45891 | 34722 | 29342 | 16311 | 35985 | 40080 | 160470 | 48500 | 41472 | 23428 | 20085 |
| 4.26 | 44805 | 35163 | 30234 | 13983 | 32462 | 38187 | 140984 | 47032 | 39622 | 23233 | 20510 |
| 4.3 | 45642 | 39256 | 34354 | 11495 | 31717 | 38230 | 138229 | 47654 | 38998 | 22217 | 19502 |
| 4.34 | 54286 | 34507 | 36968 | 16713 | 33732 | 42063 | 126947 | 47546 | 39988 | 21757 | 22091 |
| 4.38 | 54204 | 31975 | 33835 | 14058 | 29659 | 40463 | 113408 | 50781 | 33674 | 20225 | 21461 |
| 4.42 | 54212 | 31311 | 35976 | 17028 | 31642 | 50013 | 101208 | 40672 | 33532 | 22154 | 24807 |
| 4.46 | 51377 | 28706 | 35725 | 19082 | 25779 | 64213 | 89131 | 36733 | 40536 | 20894 | 20680 |
| 4.5 | 51076 | 26954 | 35969 | 13451 | 34015 | 91611 | 83412 | 34204 | 41991 | 20332 | 21112 |
| 4.54 | 45669 | 27254 | 30429 | 13200 | 30487 | 117762 | 68438 | 31154 | 37681 | 22238 | 22661 |
| 4.58 | 47344 | 26604 | 26805 | 15085 | 30530 | 126666 | 68765 | 31744 | 41643 | 23620 | 22168 |
| 4.62 | 49800 | 22903 | 26262 | 13656 | 27618 | 138346 | 56027 | 33466 | 42860 | 20275 | 22856 |
| 4.66 | 48342 | 22827 | 25465 | 14042 | 33349 | 142831 | 54721 | 26906 | 42840 | 22783 | 22699 |
| 4.7 | 42170 | 19328 | 19695 | 15021 | 33423 | 140657 | 51747 | 27164 | 36510 | 24292 | 21743 |
| 4.74 | 46602 | 22536 | 18712 | 14496 | 30610 | 150083 | 47116 | 28502 | 35130 | 21577 | 24273 |
| 4.78 | 37802 | 24502 | 21356 | 13862 | 31251 | 136782 | 44462 | 26841 | 41273 | 23939 | 27861 |
| 4.82 | 40612 | 21574 | 19248 | 13311 | 34445 | 117983 | 38403 | 25270 | 37473 | 23576 | 31679 |
| 4.86 | 39785 | 17358 | 18744 | 14107 | 28303 | 94290 | 36652 | 28158 | 36330 | 19065 | 34282 |
| 4.9 | 38804 | 20812 | 22825 | 16753 | 32538 | 69234 | 31937 | 26521 | 36304 | 21789 | 34902 |
| 4.94 | 38381 | 19027 | 16974 | 17811 | 29228 | 51561 | 32105 | 28768 | 36656 | 23475 | 40787 |
| 4.98 | 38191 | 22402 | 20223 | 15497 | 31760 | 32515 | 31827 | 26653 | 38965 | 20823 | 44456 |
| 5.02 | 39539 | 22241 | 20972 | 16921 | 31754 | 27477 | 30946 | 30481 | 38297 | 23570 | 39614 |
| 5.06 | 40043 | 21765 | 19793 | 14818 | 32042 | 27242 | 28560 | 28976 | 39730 | 23809 | 43039 |
| 5.1 | 39028 | 25216 | 20126 | 16914 | 31813 | 29976 | 31221 | 29304 | 43659 | 21233 | 46717 |
| 5.14 | 39752 | 23422 | 22048 | 18668 | 29195 | 26914 | 28815 | 26501 | 44333 | 20502 | 37375 |
| 5.18 | 41169 | 21644 | 20366 | 16823 | 30357 | 25627 | 29195 | 23073 | 37056 | 26323 | 33770 |
| 5.22 | 37487 | 20066 | 18553 | 15615 | 26587 | 21389 | 27867 | 26839 | 39605 | 23002 | 32911 |
| 5.26 | 36529 | 22939 | 23061 | 15589 | 33089 | 21739 | 28198 | 27737 | 44363 | 22347 | 25876 |
| 5.3 | 36916 | 19476 | 21191 | 14626 | 29307 | 26437 | 27525 | 27497 | 40538 | 20902 | 26979 |
| 5.34 | 38425 | 22659 | 22465 | 16367 | 30012 | 24604 | 28220 | 30081 | 43129 | 23671 | 23904 |
| 5.38 | 40419 | 23301 | 22728 | 16933 | 30303 | 24824 | 31356 | 27919 | 42294 | 22384 | 25804 |
| 5.42 | 41168 | 22089 | 23999 | 16754 | 29642 | 25227 | 31045 | 32074 | 47625 | 23258 | 23194 |
| 5.46 | 43110 | 23318 | 23344 | 17882 | 28674 | 29844 | 32940 | 31404 | 43726 | 25877 | 23619 |
| 5.5 | 42220 | 25265 | 20626 | 16398 | 29474 | 29391 | 32906 | 32537 | 45305 | 26672 | 22752 |
| 5.54 | 35795 | 23294 | 21387 | 20025 | 31030 | 31186 | 38276 | 41716 | 37719 | 24913 | 22581 |
| 5.58 | 40928 | 19701 | 22606 | 19161 | 33803 | 36740 | 45006 | 49778 | 43705 | 23989 | 21111 |
| 5.62 | 38527 | 23310 | 19565 | 18347 | 32187 | 46000 | 46342 | 61218 | 42863 | 28859 | 20231 |
| 5.66 | 40205 | 21116 | 18907 | 16984 | 30998 | 54301 | 54845 | 73658 | 46356 | 31067 | 19096 |
| 5.7 | 42266 | 21553 | 20594 | 16787 | 31136 | 57967 | 54861 | 83709 | 49817 | 31377 | 22661 |
| 5.74 | 38588 | 21112 | 19860 | 16311 | 28076 | 65094 | 62054 | 91185 | 49960 | 34768 | 23575 |
| 5.78 | 40868 | 24348 | 21346 | 15287 | 34590 | 71083 | 68729 | 96994 | 52437 | 33310 | 21448 |
| 5.82 | 37649 | 24688 | 20370 | 15044 | 32218 | 60014 | 70098 | 93596 | 48828 | 33307 | 22970 |
| 5.86 | 41520 | 20239 | 18047 | 16531 | 30511 | 56945 | 58953 | 87605 | 52973 | 32163 | 20809 |
| 5.9 | 38550 | 20799 | 20937 | 14636 | 30036 | 55957 | 55812 | 85337 | 50249 | 34495 | 25086 |
| 5.94 | 38909 | 21853 | 21522 | 15804 | 32195 | 49243 | 52782 | 72858 | 49734 | 37002 | 25816 |

-continued

| | | | | | | | | | | | |
|---|---|---|---|---|---|---|---|---|---|---|---|
| 5.98 | 37673 | 23794 | 19437 | 15846 | 32091 | 40552 | 46371 | 67630 | 53537 | 30462 | 23681 |
| 6.02 | 39178 | 20649 | 18892 | 19343 | 31411 | 36091 | 37692 | 60619 | 65962 | 31003 | 19327 |
| 6.06 | 40112 | 21557 | 23486 | 16290 | 33511 | 29437 | 42583 | 52381 | 76091 | 24235 | 24829 |
| 6.1 | 42496 | 27663 | 20885 | 17903 | 32333 | 29235 | 34458 | 40413 | 105282 | 28874 | 26023 |
| 6.14 | 39459 | 21790 | 21697 | 17223 | 32826 | 25649 | 30823 | 39700 | 128961 | 27461 | 27441 |
| 6.18 | 40992 | 23359 | 23878 | 19644 | 34832 | 26635 | 31945 | 34834 | 159007 | 24959 | 23579 |
| 6.22 | 41819 | 20501 | 19974 | 22091 | 32937 | 22348 | 28853 | 32581 | 180021 | 25529 | 22381 |
| 6.26 | 41197 | 21757 | 20457 | 22525 | 31552 | 24226 | 27300 | 33495 | 185180 | 27924 | 26907 |
| 6.3 | 41562 | 23381 | 20944 | 25005 | 37932 | 23888 | 28909 | 35141 | 197593 | 23638 | 27169 |
| 6.34 | 41425 | 25234 | 20036 | 31061 | 37793 | 22673 | 29151 | 33606 | 178928 | 24442 | 26992 |
| 6.38 | 37353 | 21710 | 20021 | 36879 | 36338 | 23317 | 29853 | 30463 | 168173 | 25831 | 29942 |
| 6.42 | 41086 | 21842 | 23013 | 40021 | 35160 | 21027 | 27365 | 28596 | 158183 | 26558 | 32506 |
| 6.46 | 40574 | 22788 | 18913 | 44653 | 37926 | 20024 | 29470 | 27622 | 136110 | 26422 | 30586 |
| 6.5 | 37861 | 21744 | 19774 | 47738 | 41381 | 19445 | 28480 | 30529 | 114351 | 25907 | 30774 |
| 6.54 | 38209 | 20721 | 19441 | 47568 | 41297 | 22749 | 26386 | 29155 | 95115 | 26858 | 27079 |
| 6.58 | 38434 | 19748 | 20008 | 45548 | 41910 | 19274 | 30291 | 28415 | 70984 | 24853 | 27583 |
| 6.62 | 37301 | 24488 | 21342 | 39799 | 40346 | 21506 | 30119 | 29624 | 57278 | 25515 | 26221 |
| 6.66 | 39132 | 21954 | 18234 | 40911 | 38049 | 22188 | 31386 | 29351 | 50223 | 25084 | 25973 |
| 6.7 | 41146 | 21983 | 22268 | 29856 | 38973 | 20836 | 36182 | 31200 | 42688 | 27413 | 25460 |
| 6.74 | 37940 | 23147 | 17873 | 24719 | 42926 | 21734 | 40083 | 31259 | 46360 | 27402 | 23415 |
| 6.78 | 38268 | 22187 | 21472 | 21674 | 35643 | 20929 | 38797 | 29988 | 42461 | 27596 | 22864 |
| 6.82 | 39241 | 24097 | 19863 | 17954 | 36810 | 23333 | 44680 | 32527 | 38784 | 24920 | 23480 |
| 6.86 | 36836 | 23941 | 23172 | 15994 | 39214 | 21071 | 40227 | 33616 | 47395 | 24871 | 22122 |
| 6.9 | 39354 | 21632 | 24048 | 17601 | 36848 | 27013 | 42866 | 34306 | 44781 | 30952 | 21209 |
| 6.94 | 38958 | 21167 | 19604 | 17222 | 34603 | 20085 | 46223 | 36979 | 46577 | 33374 | 21272 |
| 6.98 | 34854 | 22506 | 21240 | 15495 | 36269 | 24929 | 45771 | 45713 | 50319 | 35254 | 20621 |
| 7.02 | 39174 | 25102 | 22209 | 17155 | 37008 | 28541 | 49568 | 55734 | 50147 | 34080 | 21642 |
| 7.06 | 38802 | 23075 | 22574 | 17805 | 38717 | 36414 | 48459 | 65133 | 44632 | 35668 | 23970 |
| 7.1 | 36463 | 24294 | 20134 | 18593 | 37375 | 43177 | 46296 | 80059 | 45081 | 38202 | 22521 |
| 7.14 | 39702 | 22007 | 23401 | 17189 | 36819 | 54248 | 42099 | 89226 | 46156 | 33897 | 21763 |
| 7.18 | 38961 | 22899 | 22410 | 19347 | 37730 | 63552 | 48554 | 92764 | 43713 | 35512 | 23973 |
| 7.22 | 37250 | 19913 | 20112 | 16796 | 36132 | 73618 | 45422 | 94193 | 45281 | 35131 | 22050 |
| 7.26 | 38844 | 24284 | 20588 | 15492 | 34031 | 73351 | 44006 | 94146 | 47822 | 34123 | 21703 |
| 7.3 | 42572 | 24174 | 20471 | 18093 | 39577 | 84376 | 45148 | 99360 | 45526 | 30243 | 23799 |
| 7.34 | 41296 | 24091 | 22474 | 15904 | 40028 | 87033 | 48089 | 92618 | 45054 | 33519 | 24682 |
| 7.38 | 38124 | 22720 | 19115 | 17111 | 36938 | 73486 | 49559 | 74757 | 38489 | 24033 | 19315 |
| 7.42 | 38559 | 26300 | 20613 | 17329 | 38940 | 73136 | 56449 | 71713 | 40989 | 25923 | 20871 |
| 7.46 | 36151 | 24359 | 19928 | 16086 | 41305 | 64084 | 56794 | 52217 | 41336 | 23473 | 24019 |
| 7.5 | 36921 | 21617 | 19556 | 16415 | 40035 | 53332 | 65824 | 46847 | 42192 | 25912 | 23428 |
| 7.54 | 40615 | 24759 | 20387 | 16992 | 43957 | 45554 | 69706 | 36248 | 42754 | 26808 | 25007 |
| 7.58 | 38387 | 22226 | 22280 | 19036 | 46017 | 38171 | 76726 | 33908 | 44008 | 29818 | 21097 |
| 7.62 | 40258 | 22310 | 22407 | 17569 | 47700 | 29091 | 81195 | 35246 | 41772 | 26768 | 23236 |
| 7.66 | 38967 | 24951 | 21929 | 15818 | 41370 | 24438 | 75177 | 33787 | 37379 | 24314 | 21809 |
| 7.7 | 38192 | 21628 | 19436 | 16402 | 41113 | 23470 | 67347 | 31670 | 43693 | 24813 | 23587 |
| 7.74 | 39276 | 21910 | 19876 | 17634 | 42604 | 24666 | 70467 | 31718 | 43522 | 24931 | 20433 |
| 7.78 | 38102 | 20857 | 20574 | 17762 | 42908 | 23782 | 61826 | 29359 | 38183 | 25256 | 22107 |
| 7.82 | 39182 | 25871 | 22319 | 18689 | 41609 | 21188 | 58391 | 30786 | 41160 | 26978 | 23308 |
| 7.86 | 43332 | 22730 | 21102 | 22060 | 44167 | 25074 | 52483 | 35243 | 43904 | 28950 | 23955 |
| 7.9 | 38939 | 25551 | 20395 | 19972 | 40031 | 21904 | 45391 | 30268 | 40851 | 26289 | 22717 |
| 7.94 | 41901 | 23890 | 20478 | 19790 | 38139 | 24025 | 37195 | 33022 | 46074 | 28052 | 24927 |
| 7.98 | 36460 | 21454 | 21143 | 21738 | 43093 | 23136 | 29453 | 31012 | 40549 | 24639 | 21589 |
| 8.02 | 39600 | 23198 | 23097 | 22117 | 41427 | 21046 | 30877 | 30207 | 41344 | 23901 | 24059 |
| 8.06 | 40054 | 21625 | 21144 | 22732 | 39299 | 19282 | 29000 | 34952 | 41650 | 25437 | 21995 |
| 8.1 | 39973 | 25187 | 24534 | 23690 | 39006 | 21739 | 29832 | 31216 | 44046 | 28161 | 25104 |
| 8.14 | 41273 | 21293 | 23326 | 22208 | 38521 | 22039 | 33583 | 32799 | 46152 | 28739 | 24964 |
| 8.18 | 37616 | 21176 | 23900 | 22889 | 36922 | 24058 | 26629 | 31434 | 42127 | 30417 | 23897 |
| 8.22 | 39488 | 23168 | 20125 | 21062 | 35934 | 25726 | 26488 | 32261 | 44689 | 28126 | 24032 |
| 8.26 | 40643 | 23759 | 22186 | 19395 | 38834 | 23467 | 27411 | 31347 | 39100 | 25898 | 24662 |
| 8.3 | 36068 | 22904 | 23176 | 16488 | 36199 | 23028 | 28722 | 31105 | 40934 | 28704 | 23550 |
| 8.34 | 40510 | 22699 | 23532 | 17597 | 38114 | 22880 | 28964 | 33210 | 43101 | 28399 | 25228 |
| 8.38 | 39753 | 25638 | 27291 | 17596 | 41287 | 25303 | 25417 | 33539 | 41584 | 30868 | 23910 |
| 8.42 | 39635 | 26054 | 25694 | 18229 | 38853 | 22200 | 25431 | 32279 | 42688 | 27061 | 22965 |
| 8.46 | 41311 | 22643 | 24177 | 16725 | 39448 | 23814 | 27110 | 35125 | 41580 | 31226 | 24308 |
| 8.5 | 39296 | 24105 | 21655 | 16005 | 35669 | 20904 | 24090 | 29903 | 40550 | 27571 | 20588 |
| 8.54 | 38151 | 20658 | 24633 | 15987 | 38952 | 22839 | 26816 | 32257 | 38624 | 30201 | 21530 |
| 8.58 | 41647 | 22461 | 25087 | 17410 | 39601 | 22329 | 24695 | 31232 | 39738 | 30051 | 24731 |
| 8.62 | 43667 | 22839 | 23701 | 16248 | 39517 | 20630 | 22423 | 30149 | 42216 | 30228 | 25182 |
| 8.66 | 43410 | 21473 | 26362 | 15996 | 39821 | 21545 | 25771 | 29975 | 40368 | 33616 | 26770 |
| 8.7 | 42209 | 24316 | 23687 | 16699 | 39731 | 20658 | 23916 | 31647 | 41478 | 31588 | 22258 |
| 8.74 | 42989 | 25755 | 21501 | 18553 | 38668 | 21798 | 22787 | 33854 | 42823 | 29872 | 21984 |
| 8.78 | 39194 | 23623 | 23625 | 17808 | 39629 | 19412 | 23994 | 31187 | 41011 | 31432 | 24130 |
| 8.82 | 46010 | 25863 | 25981 | 17637 | 37692 | 20760 | 27908 | 33638 | 44038 | 34362 | 24248 |
| 8.86 | 43393 | 26392 | 21736 | 16109 | 41100 | 21438 | 24972 | 32506 | 45872 | 32202 | 24853 |
| 8.9 | 43599 | 22558 | 21871 | 17587 | 38580 | 19968 | 25386 | 32784 | 43192 | 31662 | 26313 |
| 8.94 | 39893 | 24727 | 20350 | 16914 | 39264 | 19654 | 26629 | 32324 | 40545 | 29129 | 28997 |
| 8.98 | 42820 | 24543 | 22734 | 18455 | 37169 | 21214 | 24146 | 31925 | 45418 | 29089 | 28115 |
| 9.02 | 44968 | 23612 | 25728 | 17883 | 41069 | 22779 | 25242 | 35907 | 46080 | 31362 | 31499 |
| 9.06 | 41475 | 21518 | 22610 | 17132 | 39808 | 25747 | 27132 | 32665 | 45066 | 31979 | 34988 |
| 9.1 | 41193 | 21959 | 21855 | 16768 | 37790 | 22771 | 26863 | 30592 | 46471 | 28366 | 36836 |

| | | | | | | | | | | | |
|---|---|---|---|---|---|---|---|---|---|---|---|
| 9.14 | 41893 | 24915 | 20102 | 14729 | 39819 | 19801 | 23490 | 33578 | 44400 | 29932 | 46489 |
| 9.18 | 45969 | 25884 | 22039 | 17360 | 39433 | 20756 | 26650 | 33081 | 38471 | 30521 | 57638 |
| 9.22 | 40008 | 25275 | 21743 | 18419 | 38394 | 23975 | 24460 | 34801 | 41801 | 29681 | 70407 |
| 9.26 | 44064 | 23899 | 20104 | 18740 | 41965 | 20325 | 25915 | 36299 | 44368 | 31136 | 74326 |
| 9.3 | 41847 | 24544 | 22162 | 23151 | 41662 | 22378 | 26099 | 36537 | 45415 | 29568 | 80097 |
| 9.34 | 42626 | 25468 | 22032 | 22288 | 42872 | 22840 | 25830 | 35422 | 45866 | 33798 | 77301 |
| 9.38 | 43576 | 26230 | 23102 | 21665 | 42289 | 26192 | 23340 | 35809 | 44424 | 34262 | 77977 |
| 9.42 | 41611 | 24533 | 21381 | 24336 | 42217 | 23053 | 24424 | 32679 | 43648 | 30681 | 72942 |
| 9.46 | 41601 | 23341 | 23259 | 24465 | 41107 | 24012 | 25301 | 33086 | 40793 | 32611 | 68291 |
| 9.5 | 41972 | 24646 | 19690 | 24591 | 46221 | 22114 | 25218 | 33940 | 43103 | 30225 | 65405 |
| 9.54 | 40569 | 26128 | 21903 | 25840 | 41030 | 24526 | 23587 | 35319 | 45840 | 32081 | 51994 |
| 9.58 | 40937 | 24886 | 22690 | 24256 | 44435 | 23895 | 22335 | 35240 | 45388 | 32382 | 43280 |
| 9.62 | 41873 | 24158 | 23332 | 24413 | 44740 | 20551 | 22886 | 34966 | 40928 | 30363 | 40799 |
| 9.66 | 41946 | 25054 | 22091 | 26063 | 45612 | 24277 | 22773 | 35140 | 41406 | 33666 | 35734 |
| 9.7 | 44857 | 23481 | 21472 | 23439 | 45825 | 24443 | 21983 | 38997 | 42736 | 35967 | 32678 |
| 9.74 | 42940 | 24258 | 22762 | 22410 | 45734 | 24838 | 24669 | 38565 | 46396 | 32761 | 29780 |
| 9.78 | 40670 | 21551 | 22804 | 20459 | 50405 | 23440 | 23804 | 35560 | 44367 | 34481 | 35778 |
| 9.82 | 40595 | 24422 | 22981 | 20941 | 47664 | 21258 | 21917 | 38912 | 44685 | 33011 | 41586 |
| 9.86 | 40260 | 25398 | 21565 | 18167 | 49527 | 23034 | 23412 | 43069 | 43094 | 35864 | 46130 |
| 9.9 | 43882 | 25305 | 23096 | 17289 | 49103 | 20836 | 23486 | 40756 | 45801 | 35270 | 51975 |
| 9.94 | 45555 | 25424 | 21109 | 20963 | 51367 | 22177 | 24284 | 44383 | 46349 | 32092 | 62602 |
| 9.98 | 45484 | 28662 | 21286 | 22415 | 51979 | 25203 | 21750 | 43427 | 45189 | 32612 | 70549 |
| 10.02 | 45649 | 26911 | 24676 | 22930 | 53374 | 24164 | 21518 | 39737 | 44501 | 32771 | 78121 |
| 10.06 | 45665 | 25850 | 22617 | 25692 | 52410 | 22347 | 24912 | 42009 | 45251 | 34857 | 84746 |
| 10.1 | 46607 | 27378 | 24635 | 28900 | 54629 | 23773 | 22404 | 41741 | 46781 | 33583 | 92604 |
| 10.14 | 52266 | 28075 | 24416 | 31631 | 52784 | 23072 | 23614 | 39445 | 50679 | 32693 | 99102 |
| 10.18 | 55409 | 29102 | 25789 | 34178 | 49714 | 23807 | 24917 | 40748 | 46986 | 38438 | 95451 |
| 10.22 | 55968 | 28485 | 29171 | 35564 | 51621 | 22077 | 21735 | 40848 | 46094 | 33041 | 90031 |
| 10.26 | 57190 | 28936 | 27875 | 37509 | 52589 | 24325 | 23727 | 41908 | 50163 | 32295 | 79601 |
| 10.3 | 64874 | 28119 | 32791 | 38532 | 48714 | 25192 | 25055 | 41589 | 46419 | 33451 | 74479 |
| 10.34 | 64978 | 31599 | 38685 | 39463 | 47127 | 25526 | 24637 | 41529 | 51405 | 36309 | 62605 |
| 10.38 | 59400 | 33114 | 41339 | 35580 | 44539 | 24323 | 23946 | 44735 | 55242 | 35572 | 56281 |
| 10.42 | 60452 | 38623 | 43138 | 34776 | 46994 | 25765 | 25951 | 43333 | 59658 | 34092 | 46992 |
| 10.46 | 64285 | 39495 | 46115 | 28362 | 46139 | 25934 | 25366 | 44588 | 58545 | 35250 | 40933 |
| 10.5 | 62693 | 41947 | 51247 | 21695 | 45863 | 23809 | 23456 | 41476 | 67265 | 36851 | 39192 |
| 10.54 | 55501 | 39332 | 50376 | 21564 | 45659 | 24884 | 25838 | 47133 | 70775 | 35880 | 37816 |
| 10.58 | 54182 | 36718 | 49565 | 20860 | 45230 | 25342 | 26242 | 45859 | 74330 | 33794 | 37269 |
| 10.62 | 52622 | 42849 | 46478 | 18557 | 46671 | 24072 | 24350 | 45869 | 78906 | 36903 | 33014 |
| 10.66 | 50403 | 41256 | 48074 | 20865 | 45307 | 22749 | 24709 | 45499 | 73885 | 36263 | 33239 |
| 10.7 | 50011 | 36748 | 44072 | 21311 | 41749 | 26082 | 25970 | 44494 | 74650 | 37536 | 34306 |
| 10.74 | 48643 | 37248 | 40746 | 20429 | 47438 | 25346 | 25568 | 48360 | 75314 | 40194 | 32400 |
| 10.78 | 49395 | 31512 | 37965 | 19966 | 47507 | 27977 | 25165 | 45759 | 70232 | 38605 | 31169 |
| 10.82 | 51407 | 29297 | 38269 | 20638 | 44634 | 25572 | 26650 | 49219 | 73726 | 36070 | 30134 |
| 10.86 | 52239 | 30930 | 33150 | 22111 | 46302 | 25594 | 26961 | 46935 | 69877 | 37303 | 29699 |
| 10.9 | 55729 | 29022 | 32198 | 22532 | 46797 | 27285 | 25563 | 49042 | 63350 | 39937 | 30587 |
| 10.94 | 57679 | 28983 | 32689 | 22011 | 43586 | 26410 | 28765 | 47667 | 63644 | 38448 | 30113 |
| 10.98 | 54874 | 27454 | 31287 | 22439 | 44159 | 26167 | 25542 | 52115 | 62974 | 35970 | 28308 |
| 11.02 | 57515 | 26629 | 31188 | 21194 | 46832 | 27080 | 31035 | 50852 | 61687 | 38144 | 28585 |
| 11.06 | 60718 | 29193 | 30160 | 25810 | 48917 | 26768 | 26706 | 47656 | 59217 | 38565 | 26046 |
| 11.1 | 63982 | 29690 | 28658 | 25479 | 46386 | 28299 | 28026 | 49539 | 62969 | 40110 | 26843 |
| 11.14 | 61561 | 32233 | 30455 | 20448 | 47079 | 27366 | 29761 | 52334 | 57661 | 39704 | 28716 |
| 11.18 | 58759 | 29752 | 28410 | 20708 | 47822 | 25241 | 28008 | 52236 | 54100 | 43750 | 28643 |
| 11.22 | 64487 | 31582 | 27276 | 22030 | 50944 | 28429 | 30143 | 53268 | 52519 | 43067 | 28964 |
| 11.26 | 70636 | 29606 | 28102 | 20676 | 51608 | 31155 | 31442 | 53901 | 51377 | 43124 | 30057 |
| 11.3 | 65970 | 30754 | 29831 | 22293 | 52079 | 29358 | 31513 | 54686 | 47113 | 42594 | 28064 |
| 11.34 | 70540 | 31233 | 27488 | 20280 | 50275 | 30465 | 30191 | 53401 | 49641 | 38890 | 30603 |
| 11.38 | 71237 | 29404 | 30262 | 20650 | 50569 | 31090 | 28343 | 54088 | 47580 | 41803 | 29376 |
| 11.42 | 72210 | 28647 | 28890 | 20007 | 51143 | 31219 | 35044 | 54866 | 48488 | 42900 | 28285 |
| 11.46 | 74863 | 28391 | 29716 | 18986 | 51716 | 32663 | 35011 | 56055 | 48674 | 41913 | 31104 |
| 11.5 | 69894 | 27214 | 29332 | 19225 | 50637 | 32704 | 35538 | 60421 | 50602 | 42329 | 28342 |
| 11.54 | 75232 | 27866 | 28224 | 20860 | 50669 | 33686 | 35674 | 61124 | 52675 | 43978 | 30006 |
| 11.58 | 68854 | 29541 | 27079 | 22013 | 53604 | 31147 | 34032 | 60985 | 57150 | 44439 | 30548 |
| 11.62 | 66094 | 27878 | 23850 | 19628 | 52727 | 31969 | 34015 | 61278 | 57736 | 41370 | 34783 |
| 11.66 | 61664 | 28199 | 27358 | 20891 | 53364 | 32652 | 37966 | 65599 | 59395 | 44861 | 31622 |
| 11.7 | 58012 | 30821 | 27828 | 19976 | 50430 | 34774 | 37650 | 65900 | 63864 | 44702 | 33989 |
| 11.74 | 59358 | 31114 | 27578 | 20372 | 48263 | 34200 | 35080 | 67351 | 67491 | 45970 | 34479 |
| 11.78 | 52206 | 30579 | 25855 | 19349 | 49536 | 33061 | 38518 | 67875 | 63509 | 42185 | 35469 |
| 11.82 | 54599 | 30402 | 27296 | 19966 | 47729 | 29316 | 37354 | 66541 | 60175 | 45679 | 31319 |
| 11.86 | 50922 | 27931 | 25860 | 22834 | 48603 | 30128 | 34897 | 62280 | 60563 | 45396 | 30953 |
| 11.9 | 51853 | 28635 | 27710 | 21636 | 50981 | 31488 | 34517 | 61124 | 58808 | 42072 | 33592 |
| 11.94 | 48369 | 28995 | 26534 | 21400 | 50534 | 29572 | 37475 | 63699 | 53334 | 43124 | 33248 |
| 11.98 | 50195 | 29134 | 27935 | 21115 | 48833 | 30647 | 38905 | 64027 | 52088 | 41545 | 34365 |
| 12.02 | 46821 | 29259 | 25858 | 20522 | 48888 | 30899 | 36735 | 58088 | 53325 | 44501 | 38470 |
| 12.06 | 49883 | 29153 | 26788 | 22246 | 48473 | 29825 | 37376 | 64706 | 49437 | 42508 | 38870 |
| 12.1 | 48737 | 29055 | 27691 | 19992 | 48662 | 32587 | 35956 | 59930 | 49887 | 43031 | 38134 |
| 12.14 | 47953 | 28359 | 25841 | 20808 | 47151 | 31620 | 37083 | 59229 | 48125 | 40784 | 41689 |
| 12.18 | 47391 | 31906 | 25568 | 20163 | 50575 | 35470 | 38162 | 61447 | 49810 | 42684 | 38372 |
| 12.22 | 47769 | 28931 | 26385 | 20444 | 49293 | 38195 | 39354 | 62831 | 50542 | 44298 | 41139 |
| 12.26 | 46934 | 31633 | 27060 | 18805 | 49060 | 42160 | 43075 | 64744 | 52070 | 44237 | 47935 |

-continued

| | | | | | | | | | | | |
|---|---|---|---|---|---|---|---|---|---|---|---|
| 12.3 | 46638 | 28964 | 26308 | 21464 | 47934 | 44171 | 43764 | 64354 | 48292 | 44376 | 44533 |
| 12.34 | 47790 | 28788 | 25415 | 20654 | 47984 | 49306 | 44105 | 65887 | 50539 | 44130 | 42490 |
| 12.38 | 45349 | 30414 | 25259 | 22871 | 51323 | 51667 | 44647 | 64605 | 49837 | 42688 | 43526 |
| 12.42 | 47127 | 27680 | 24170 | 23313 | 47899 | 52584 | 42527 | 64439 | 51750 | 41986 | 45097 |
| 12.46 | 46304 | 27125 | 26256 | 25825 | 49330 | 53303 | 45551 | 62552 | 51455 | 43040 | 41918 |
| 12.5 | 47662 | 30551 | 26941 | 26300 | 48660 | 51783 | 45932 | 64441 | 51392 | 44916 | 40644 |
| 12.54 | 47945 | 28548 | 28903 | 27651 | 48432 | 46953 | 42998 | 61984 | 56482 | 45221 | 41891 |
| 12.58 | 50692 | 28570 | 29668 | 31500 | 50374 | 45427 | 40305 | 60886 | 54537 | 46256 | 39030 |
| 12.62 | 48288 | 28828 | 27197 | 32089 | 47442 | 42114 | 37228 | 60027 | 59498 | 42574 | 35429 |
| 12.66 | 47877 | 28229 | 27073 | 29248 | 45376 | 36341 | 35168 | 57226 | 62495 | 44936 | 38553 |
| 12.7 | 48127 | 29526 | 27296 | 27398 | 49255 | 35181 | 39523 | 56444 | 65485 | 46163 | 37044 |
| 12.74 | 46027 | 28727 | 28465 | 28640 | 50520 | 33438 | 37428 | 55262 | 66182 | 47064 | 38191 |
| 12.78 | 49330 | 26931 | 29035 | 29619 | 51455 | 30649 | 38232 | 56371 | 66246 | 46402 | 33700 |
| 12.82 | 49782 | 27501 | 26177 | 27590 | 47652 | 30883 | 40035 | 58458 | 67940 | 47690 | 35401 |
| 12.86 | 45086 | 28581 | 27426 | 28725 | 49102 | 30537 | 41154 | 53938 | 68446 | 50987 | 32320 |
| 12.9 | 48689 | 26940 | 27042 | 27849 | 46028 | 30555 | 42705 | 53623 | 64261 | 51363 | 32554 |
| 12.94 | 53051 | 27153 | 25241 | 32946 | 46654 | 32035 | 43470 | 54060 | 68204 | 53950 | 35502 |
| 12.98 | 48043 | 28352 | 27292 | 35346 | 48162 | 33019 | 41696 | 58115 | 62646 | 55007 | 34494 |
| 13.02 | 45704 | 26943 | 26970 | 38757 | 54372 | 34362 | 45130 | 54402 | 62287 | 59124 | 34276 |
| 13.06 | 46515 | 29312 | 24874 | 36930 | 50346 | 35208 | 44780 | 55349 | 64239 | 63226 | 34632 |
| 13.1 | 48570 | 26747 | 24125 | 38022 | 49926 | 35191 | 47737 | 56760 | 62249 | 59352 | 34674 |
| 13.14 | 47719 | 29511 | 25774 | 40321 | 51088 | 38164 | 44677 | 58533 | 61223 | 63271 | 34820 |
| 13.18 | 47757 | 27440 | 27906 | 38107 | 51348 | 38646 | 42605 | 60597 | 63141 | 59222 | 34660 |
| 13.22 | 48101 | 29308 | 28177 | 35992 | 52643 | 43546 | 42368 | 64525 | 62008 | 62986 | 33010 |
| 13.26 | 44752 | 27014 | 28165 | 32774 | 50675 | 46484 | 40717 | 70296 | 66573 | 61676 | 32173 |
| 13.3 | 46187 | 26869 | 25964 | 31729 | 50495 | 51774 | 39960 | 79999 | 65133 | 61381 | 32001 |
| 13.34 | 46299 | 29634 | 30229 | 30989 | 52972 | 51568 | 37712 | 83919 | 66982 | 60957 | 32039 |
| 13.38 | 51225 | 29779 | 32978 | 35147 | 52959 | 58386 | 38690 | 85443 | 67865 | 56376 | 33985 |
| 13.42 | 50878 | 32888 | 29415 | 40424 | 51194 | 55527 | 41047 | 85044 | 66666 | 52887 | 38057 |
| 13.46 | 48069 | 33099 | 31842 | 51592 | 51884 | 54468 | 39389 | 87034 | 67527 | 54760 | 40802 |
| 13.5 | 52950 | 33847 | 33318 | 64546 | 51271 | 55189 | 35869 | 83603 | 72329 | 48890 | 42553 |
| 13.54 | 47672 | 32335 | 31258 | 74265 | 49980 | 51344 | 34718 | 79269 | 72831 | 47307 | 50383 |
| 13.58 | 53925 | 30942 | 33675 | 87426 | 52289 | 44100 | 34804 | 76486 | 76051 | 49991 | 52741 |
| 13.62 | 51353 | 29334 | 33566 | 84673 | 54600 | 43042 | 34431 | 70619 | 80040 | 51989 | 53528 |
| 13.66 | 49682 | 31270 | 34052 | 90401 | 50852 | 37220 | 35854 | 65575 | 76899 | 49976 | 50768 |
| 13.7 | 53460 | 30218 | 36029 | 91671 | 51563 | 33504 | 34712 | 57612 | 72241 | 50648 | 49858 |
| 13.74 | 51118 | 27590 | 35240 | 82729 | 53819 | 31225 | 35326 | 56204 | 74793 | 55890 | 49368 |
| 13.78 | 53004 | 25890 | 34388 | 74993 | 51356 | 28558 | 32899 | 54980 | 76964 | 56730 | 47814 |
| 13.82 | 61170 | 29582 | 33201 | 63995 | 52350 | 29767 | 34387 | 53892 | 71961 | 60793 | 44509 |
| 13.86 | 66141 | 30199 | 35918 | 51013 | 51835 | 28984 | 37619 | 50417 | 71277 | 59285 | 43067 |
| 13.9 | 75265 | 27493 | 34271 | 40049 | 54818 | 31948 | 38208 | 54179 | 66712 | 61936 | 47751 |
| 13.94 | 80937 | 27168 | 31712 | 32402 | 52146 | 30556 | 39776 | 56577 | 66107 | 62328 | 47669 |
| 13.98 | 85366 | 26841 | 32168 | 24224 | 48921 | 31071 | 45090 | 54718 | 60822 | 63646 | 50783 |
| 14.02 | 87634 | 26071 | 35120 | 23429 | 54002 | 32705 | 43185 | 60329 | 57212 | 61899 | 59152 |
| 14.06 | 94752 | 25847 | 38252 | 22573 | 51661 | 31713 | 44756 | 58729 | 59721 | 64751 | 62135 |
| 14.1 | 94497 | 26134 | 36295 | 20782 | 56140 | 32112 | 46246 | 60026 | 59526 | 63065 | 64673 |
| 14.14 | 93554 | 28371 | 38699 | 21189 | 54131 | 32971 | 47407 | 55787 | 58381 | 61655 | 68413 |
| 14.18 | 87152 | 26489 | 37172 | 22616 | 50932 | 29074 | 44988 | 58510 | 56954 | 60032 | 68593 |
| 14.22 | 85196 | 26853 | 40668 | 22270 | 55194 | 31112 | 44356 | 57817 | 57075 | 59452 | 66483 |
| 14.26 | 79357 | 28572 | 42219 | 24524 | 51388 | 31304 | 44877 | 54279 | 55105 | 67114 | 62469 |
| 14.3 | 74263 | 25456 | 39235 | 22455 | 53793 | 30972 | 43102 | 52801 | 54801 | 67436 | 57732 |
| 14.34 | 71962 | 25874 | 41209 | 23509 | 54696 | 33417 | 40880 | 53618 | 52293 | 68292 | 47309 |
| 14.38 | 74375 | 26588 | 42348 | 23549 | 55453 | 34521 | 38937 | 54141 | 53747 | 68582 | 42903 |
| 14.42 | 83145 | 29006 | 40039 | 24046 | 56112 | 35843 | 37698 | 61811 | 52345 | 79500 | 38035 |
| 14.46 | 90249 | 28723 | 38300 | 22217 | 57426 | 41058 | 38401 | 61747 | 54191 | 89099 | 32704 |
| 14.5 | 107030 | 29710 | 36416 | 23179 | 53658 | 41825 | 35929 | 69211 | 55104 | 104165 | 29949 |
| 14.54 | 122381 | 33112 | 35727 | 23388 | 55468 | 43246 | 35182 | 71386 | 54648 | 118285 | 29857 |
| 14.58 | 132950 | 38527 | 34993 | 24246 | 58464 | 45623 | 34684 | 78664 | 53047 | 123013 | 28253 |
| 14.62 | 136349 | 40335 | 32712 | 21838 | 58446 | 43588 | 36003 | 80862 | 53791 | 131911 | 28998 |
| 14.66 | 147293 | 42077 | 32787 | 20846 | 58993 | 49843 | 38250 | 88178 | 58332 | 132820 | 29123 |
| 14.7 | 141977 | 43600 | 31699 | 18588 | 60072 | 48957 | 36584 | 94435 | 56142 | 127921 | 30378 |
| 14.74 | 139042 | 44799 | 33022 | 20961 | 59079 | 54809 | 37116 | 103371 | 54474 | 125882 | 29039 |
| 14.78 | 126931 | 42401 | 33885 | 18776 | 59329 | 52844 | 38458 | 109381 | 58529 | 114111 | 30741 |
| 14.82 | 114213 | 41335 | 34256 | 22003 | 61736 | 61688 | 39172 | 112136 | 57386 | 103467 | 30099 |
| 14.86 | 102252 | 39677 | 34527 | 20041 | 62020 | 66767 | 37589 | 115501 | 54640 | 88315 | 28530 |
| 14.9 | 89679 | 38380 | 33826 | 21047 | 61688 | 78522 | 38735 | 117195 | 55253 | 71659 | 28719 |
| 14.94 | 74506 | 35532 | 34983 | 18423 | 63589 | 83130 | 40412 | 115992 | 55826 | 59511 | 31410 |
| 14.98 | 64259 | 32176 | 36684 | 18769 | 64944 | 86538 | 41524 | 109933 | 55847 | 49580 | 29176 |
| 15.02 | 58657 | 29567 | 39179 | 19995 | 64535 | 96788 | 42540 | 108482 | 55549 | 45946 | 29813 |
| 15.06 | 51865 | 29546 | 40622 | 22250 | 62063 | 95853 | 44603 | 95526 | 60468 | 44142 | 29414 |
| 15.1 | 51066 | 29090 | 38416 | 21221 | 62324 | 95564 | 44208 | 88587 | 59750 | 46769 | 29958 |
| 15.14 | 51584 | 27741 | 38345 | 20841 | 66232 | 88970 | 45517 | 76786 | 62630 | 48452 | 30805 |
| 15.18 | 52278 | 29724 | 40324 | 22869 | 67066 | 84099 | 46885 | 71998 | 58891 | 50401 | 31677 |
| 15.22 | 48538 | 28799 | 36140 | 26161 | 66435 | 75702 | 48901 | 64492 | 57286 | 51449 | 28604 |
| 15.26 | 48967 | 26031 | 38060 | 27448 | 65734 | 63839 | 52778 | 58584 | 56261 | 53456 | 27807 |
| 15.3 | 49112 | 29615 | 38063 | 25816 | 64877 | 54976 | 54524 | 57156 | 54744 | 57040 | 28992 |
| 15.34 | 49695 | 32003 | 36562 | 25842 | 64249 | 46350 | 53370 | 55126 | 55474 | 52899 | 28627 |
| 15.38 | 49084 | 29939 | 35907 | 26863 | 64836 | 40958 | 53035 | 56099 | 55461 | 54122 | 31005 |
| 15.42 | 48323 | 29710 | 36356 | 27522 | 66010 | 40837 | 50677 | 57895 | 51599 | 51355 | 30165 |

-continued

| | | | | | | | | | | | |
|---|---|---|---|---|---|---|---|---|---|---|---|
| 15.46 | 44784 | 31964 | 34462 | 24181 | 68558 | 41162 | 51523 | 57868 | 53190 | 49692 | 29532 |
| 15.5 | 47685 | 30588 | 36208 | 24309 | 68294 | 39291 | 48283 | 62150 | 52054 | 47178 | 30670 |
| 15.54 | 49283 | 29729 | 33749 | 23532 | 68092 | 41742 | 46957 | 59729 | 52563 | 46644 | 32499 |
| 15.58 | 46561 | 29404 | 34576 | 26993 | 67406 | 41143 | 42359 | 57778 | 57671 | 41060 | 36329 |
| 15.62 | 48655 | 31758 | 32995 | 28576 | 71520 | 38737 | 40188 | 57188 | 55162 | 40428 | 39639 |
| 15.66 | 49212 | 28946 | 32783 | 35834 | 70013 | 39877 | 37334 | 55942 | 57691 | 41535 | 42439 |
| 15.7 | 48606 | 31107 | 33123 | 42810 | 70057 | 38916 | 39408 | 55624 | 56164 | 42269 | 45619 |
| 15.74 | 49072 | 28205 | 33363 | 47269 | 70118 | 37199 | 35293 | 50678 | 58711 | 38285 | 48235 |
| 15.78 | 51306 | 30308 | 31407 | 56795 | 67827 | 35924 | 32511 | 50303 | 59360 | 37152 | 48304 |
| 15.82 | 50689 | 27975 | 30834 | 65885 | 68919 | 36844 | 32884 | 51564 | 59717 | 38913 | 46425 |
| 15.86 | 51862 | 26478 | 31512 | 69135 | 69793 | 31792 | 31877 | 46585 | 61142 | 39948 | 44856 |
| 15.9 | 48983 | 25604 | 29804 | 72290 | 68908 | 32372 | 31955 | 43772 | 64411 | 37304 | 43500 |
| 15.94 | 46674 | 26663 | 31190 | 74708 | 67490 | 31304 | 36484 | 43879 | 63165 | 38509 | 44636 |
| 15.98 | 50796 | 28005 | 28748 | 74437 | 71015 | 27739 | 31936 | 42601 | 62833 | 39061 | 41843 |
| 16.02 | 54409 | 26985 | 28373 | 72931 | 68120 | 30019 | 32865 | 42302 | 62819 | 37631 | 36942 |
| 16.06 | 49615 | 26886 | 27756 | 67068 | 69815 | 27123 | 32960 | 43116 | 62172 | 39796 | 35446 |
| 16.1 | 48012 | 26930 | 30530 | 67479 | 69912 | 26939 | 36556 | 40892 | 62301 | 39720 | 33810 |
| 16.14 | 53027 | 27930 | 30613 | 58918 | 69459 | 30420 | 34477 | 43713 | 63814 | 40954 | 31411 |
| 16.18 | 51137 | 26265 | 28610 | 54586 | 73435 | 29901 | 35799 | 44030 | 63307 | 39581 | 31859 |
| 16.22 | 50546 | 28603 | 31465 | 50862 | 73795 | 27510 | 38442 | 44202 | 61868 | 40331 | 31796 |
| 16.26 | 49279 | 28814 | 34046 | 49910 | 71462 | 30984 | 39331 | 43937 | 64806 | 41161 | 31707 |
| 16.3 | 50921 | 29358 | 34457 | 49210 | 74680 | 31072 | 40427 | 44660 | 64399 | 42177 | 32029 |
| 16.34 | 57237 | 30891 | 34415 | 47499 | 74688 | 32583 | 42874 | 45710 | 64899 | 43439 | 32024 |
| 16.38 | 55603 | 32601 | 35877 | 46238 | 77276 | 33891 | 43637 | 46043 | 66566 | 45826 | 30326 |
| 16.42 | 59223 | 33138 | 37370 | 40894 | 73495 | 33364 | 47692 | 48951 | 65058 | 49092 | 30762 |
| 16.46 | 64732 | 34417 | 37917 | 37291 | 71978 | 35255 | 49773 | 50076 | 68592 | 55156 | 28792 |
| 16.5 | 67812 | 34256 | 36882 | 33050 | 72699 | 38297 | 47862 | 49035 | 67374 | 56270 | 31081 |
| 16.54 | 69919 | 36195 | 39247 | 30757 | 72757 | 38857 | 50166 | 50789 | 67409 | 62472 | 29666 |
| 16.58 | 75171 | 36956 | 35577 | 27500 | 73130 | 39940 | 49967 | 52224 | 65653 | 59279 | 29241 |
| 16.62 | 73240 | 37487 | 38156 | 22661 | 72244 | 40771 | 48918 | 54253 | 63555 | 61346 | 31511 |
| 16.66 | 78045 | 35863 | 37034 | 22028 | 68382 | 42026 | 47984 | 52120 | 65621 | 60436 | 30507 |
| 16.7 | 79917 | 37695 | 36266 | 24042 | 71104 | 42096 | 48559 | 55242 | 60579 | 59671 | 31419 |
| 16.74 | 77306 | 34148 | 39969 | 23520 | 67609 | 40598 | 46849 | 56387 | 57677 | 58427 | 30094 |
| 16.78 | 76175 | 34813 | 40354 | 22904 | 70905 | 40874 | 48503 | 60427 | 59633 | 55501 | 29984 |
| 16.82 | 80057 | 32612 | 41020 | 22303 | 70349 | 42890 | 48183 | 60743 | 56787 | 50283 | 29634 |
| 16.86 | 72030 | 32815 | 47912 | 24639 | 70975 | 43971 | 45536 | 64126 | 55352 | 46513 | 33674 |
| 16.9 | 70557 | 28260 | 50856 | 25520 | 67154 | 44750 | 43490 | 66305 | 53936 | 42596 | 33632 |
| 16.94 | 66592 | 29517 | 54231 | 26609 | 65478 | 42879 | 46200 | 66078 | 56780 | 44842 | 34345 |
| 16.98 | 67271 | 26855 | 56720 | 26423 | 67570 | 42567 | 46560 | 66549 | 53390 | 42766 | 35819 |
| 17.02 | 68737 | 27211 | 63808 | 28145 | 74187 | 42313 | 46910 | 67200 | 53872 | 40665 | 39291 |
| 17.06 | 71308 | 28318 | 69941 | 25657 | 70442 | 38712 | 47849 | 66016 | 56118 | 39946 | 35359 |
| 17.1 | 81443 | 28847 | 73426 | 25877 | 70332 | 42385 | 47281 | 64827 | 56750 | 41595 | 35164 |
| 17.14 | 97182 | 27036 | 73650 | 24853 | 68940 | 45987 | 47174 | 62143 | 56266 | 41403 | 36217 |
| 17.18 | 121768 | 28400 | 77138 | 28847 | 68977 | 48919 | 51765 | 58968 | 52174 | 37866 | 34416 |
| 17.22 | 149208 | 31069 | 76976 | 28301 | 71316 | 50262 | 48231 | 55400 | 53872 | 38563 | 32785 |
| 17.26 | 170750 | 34639 | 74323 | 29797 | 71083 | 53977 | 51153 | 53421 | 49837 | 38543 | 33667 |
| 17.3 | 198654 | 39763 | 73905 | 32883 | 72383 | 60470 | 47861 | 53963 | 51736 | 39940 | 30670 |
| 17.34 | 223115 | 47224 | 68866 | 35422 | 67448 | 58689 | 48752 | 52347 | 54056 | 39119 | 27593 |
| 17.38 | 238662 | 55100 | 69773 | 34856 | 70692 | 55614 | 47587 | 50190 | 54160 | 40456 | 27416 |
| 17.42 | 247624 | 73482 | 71380 | 37779 | 70726 | 57018 | 46804 | 50798 | 49927 | 41446 | 27919 |
| 17.46 | 255803 | 80590 | 66825 | 39399 | 72269 | 55306 | 50158 | 51372 | 51648 | 43397 | 30164 |
| 17.5 | 243138 | 90804 | 68525 | 41474 | 72269 | 50760 | 47787 | 50229 | 50596 | 43840 | 28593 |
| 17.54 | 235298 | 97286 | 67597 | 44404 | 72643 | 45959 | 48502 | 50338 | 53021 | 46233 | 28740 |
| 17.58 | 220354 | 102322 | 68895 | 47318 | 72267 | 46684 | 47141 | 48671 | 53501 | 44786 | 29822 |
| 17.62 | 205682 | 101509 | 64645 | 53292 | 71206 | 40089 | 45612 | 48505 | 54104 | 44274 | 30629 |
| 17.66 | 190042 | 101634 | 61975 | 58966 | 73989 | 37087 | 49001 | 47982 | 58967 | 44106 | 33454 |
| 17.7 | 184653 | 96561 | 63471 | 62924 | 71945 | 37299 | 47321 | 51614 | 62300 | 44245 | 34275 |
| 17.74 | 178187 | 88143 | 58538 | 65016 | 69636 | 34044 | 48306 | 50188 | 64801 | 42323 | 33449 |
| 17.78 | 181816 | 80534 | 54307 | 61932 | 72648 | 36525 | 45598 | 48504 | 68659 | 42321 | 32785 |
| 17.82 | 178907 | 70750 | 55002 | 62312 | 69644 | 36941 | 46811 | 48627 | 70780 | 41565 | 35336 |
| 17.86 | 176457 | 63250 | 49605 | 58841 | 70151 | 34870 | 44646 | 47851 | 74323 | 43210 | 35145 |
| 17.9 | 180397 | 56477 | 43392 | 52679 | 71852 | 34467 | 42567 | 46595 | 74063 | 40294 | 33818 |
| 17.94 | 177021 | 51794 | 40678 | 46354 | 72231 | 36000 | 41622 | 47485 | 77837 | 41118 | 35696 |
| 17.98 | 169526 | 50021 | 37392 | 40191 | 68330 | 34308 | 42802 | 44481 | 77002 | 38604 | 32350 |
| 18.02 | 156912 | 46814 | 34741 | 32774 | 72619 | 31529 | 40733 | 42106 | 73378 | 38219 | 32569 |
| 18.06 | 144747 | 44374 | 36041 | 27666 | 69542 | 32540 | 40738 | 44609 | 78188 | 39357 | 32452 |
| 18.1 | 132181 | 46078 | 34965 | 24727 | 70670 | 32409 | 39602 | 44277 | 70778 | 39183 | 34081 |
| 18.14 | 118346 | 41728 | 31339 | 22865 | 69922 | 34981 | 39700 | 45546 | 64498 | 38836 | 34519 |
| 18.18 | 105349 | 38302 | 34301 | 19734 | 70269 | 34052 | 39862 | 44312 | 67055 | 39931 | 33523 |
| 18.22 | 92466 | 34487 | 33617 | 17589 | 73473 | 34648 | 37088 | 48809 | 63556 | 37937 | 34435 |
| 18.26 | 86458 | 32615 | 32934 | 17823 | 70385 | 36623 | 38447 | 44254 | 60968 | 42504 | 35864 |
| 18.3 | 81365 | 30243 | 33385 | 19425 | 71728 | 34571 | 35673 | 47084 | 59183 | 47181 | 37401 |
| 18.34 | 74814 | 32032 | 35794 | 18571 | 72002 | 38118 | 34631 | 47180 | 56008 | 53857 | 37343 |
| 18.38 | 67029 | 31319 | 35127 | 18563 | 72968 | 37123 | 36051 | 48273 | 53560 | 69767 | 38370 |
| 18.42 | 60034 | 35225 | 34511 | 17541 | 71977 | 38092 | 36858 | 46195 | 51980 | 80517 | 38052 |
| 18.46 | 58223 | 35871 | 36922 | 17478 | 72269 | 39740 | 35869 | 49644 | 52415 | 94101 | 36836 |
| 18.5 | 56099 | 39211 | 33055 | 18645 | 72940 | 37252 | 35036 | 50953 | 49982 | 104767 | 35408 |
| 18.54 | 54272 | 40803 | 36411 | 19101 | 74107 | 40140 | 36379 | 55100 | 53768 | 106616 | 36692 |
| 18.58 | 54450 | 44644 | 34688 | 18879 | 74196 | 40491 | 36733 | 57085 | 51521 | 108826 | 36907 |

-continued

| | | | | | | | | | | | |
|---|---|---|---|---|---|---|---|---|---|---|---|
| 18.62 | 51631 | 48015 | 37973 | 18730 | 76916 | 42152 | 36095 | 61404 | 52633 | 107092 | 35822 |
| 18.66 | 52975 | 47162 | 36924 | 18152 | 75727 | 41082 | 37878 | 65032 | 48936 | 102064 | 34757 |
| 18.7 | 54212 | 45018 | 36743 | 17717 | 74949 | 42091 | 35653 | 72509 | 49987 | 94954 | 35217 |
| 18.74 | 54812 | 46385 | 37033 | 18539 | 75731 | 44615 | 38288 | 78163 | 50964 | 83509 | 35868 |
| 18.78 | 53922 | 45448 | 35927 | 17509 | 74851 | 44569 | 39801 | 89096 | 49649 | 77612 | 35907 |
| 18.82 | 55049 | 42488 | 37345 | 17855 | 74847 | 46742 | 38324 | 93486 | 52951 | 65505 | 36634 |
| 18.86 | 52153 | 38725 | 38976 | 16687 | 76801 | 43766 | 40564 | 95834 | 53834 | 59458 | 35035 |
| 18.9 | 52840 | 33239 | 38459 | 17512 | 79174 | 44027 | 38711 | 99926 | 54783 | 53101 | 33929 |
| 18.94 | 54481 | 32403 | 42644 | 17212 | 77158 | 42675 | 39412 | 102190 | 53818 | 50982 | 36139 |
| 18.98 | 57636 | 31255 | 42232 | 17142 | 73621 | 43862 | 39422 | 96081 | 56084 | 47648 | 32963 |
| 19.02 | 56382 | 31216 | 45521 | 16942 | 77423 | 44468 | 36797 | 94778 | 55628 | 46488 | 30449 |
| 19.06 | 60260 | 29742 | 47503 | 18185 | 76607 | 44460 | 37342 | 92815 | 58401 | 48389 | 27217 |
| 19.1 | 65037 | 31642 | 52079 | 17729 | 77655 | 43993 | 39645 | 82652 | 57364 | 45257 | 28919 |
| 19.14 | 68214 | 32498 | 51988 | 18501 | 77039 | 47137 | 39028 | 77537 | 58838 | 45405 | 28717 |
| 19.18 | 78992 | 35705 | 57726 | 17785 | 79190 | 51330 | 39234 | 72514 | 55775 | 43099 | 27995 |
| 19.22 | 89119 | 32679 | 58585 | 19059 | 77003 | 58359 | 36326 | 67528 | 55555 | 42686 | 27070 |
| 19.26 | 107825 | 32328 | 62407 | 19745 | 77412 | 64058 | 35058 | 66273 | 55911 | 43552 | 28423 |
| 19.3 | 122360 | 33294 | 63607 | 17754 | 76787 | 70678 | 36224 | 63668 | 54921 | 47891 | 30002 |
| 19.34 | 134298 | 35149 | 59848 | 18838 | 76626 | 75576 | 38492 | 62645 | 54179 | 53186 | 30920 |
| 19.38 | 150076 | 32004 | 60785 | 19060 | 74951 | 75862 | 39270 | 60023 | 56807 | 56817 | 32257 |
| 19.42 | 158873 | 31863 | 59749 | 18383 | 75373 | 75032 | 36514 | 56623 | 55442 | 59524 | 36572 |
| 19.46 | 169816 | 31105 | 57999 | 16189 | 76168 | 71969 | 38481 | 55842 | 55279 | 61947 | 44235 |
| 19.5 | 169915 | 31964 | 58224 | 19016 | 75512 | 69624 | 37441 | 53582 | 56573 | 64844 | 49178 |
| 19.54 | 164870 | 31270 | 55577 | 18438 | 75499 | 65100 | 38316 | 53376 | 58038 | 70091 | 54646 |
| 19.58 | 168116 | 29409 | 58194 | 17176 | 74738 | 58477 | 38462 | 53022 | 57834 | 70765 | 63803 |
| 19.62 | 165548 | 28528 | 59645 | 17437 | 75233 | 52714 | 36395 | 53502 | 60059 | 71267 | 72245 |
| 19.66 | 161688 | 28318 | 60766 | 18423 | 74455 | 44937 | 37677 | 55479 | 60293 | 67687 | 76342 |
| 19.7 | 157309 | 28226 | 66430 | 22762 | 73719 | 41263 | 39344 | 58359 | 60449 | 70686 | 81364 |
| 19.74 | 159406 | 24387 | 70454 | 24170 | 73890 | 44490 | 39563 | 62043 | 61087 | 65048 | 83138 |
| 19.78 | 158511 | 24808 | 71090 | 26830 | 72724 | 40967 | 38602 | 67285 | 61205 | 64685 | 82880 |
| 19.82 | 153418 | 23983 | 72537 | 32822 | 74526 | 39776 | 40025 | 74877 | 63592 | 58988 | 83281 |
| 19.86 | 152289 | 24696 | 74947 | 39516 | 75633 | 40089 | 41847 | 78912 | 63413 | 54757 | 75570 |
| 19.9 | 147073 | 23884 | 72388 | 40643 | 75932 | 40069 | 42745 | 84532 | 61816 | 52621 | 71898 |
| 19.94 | 138239 | 22897 | 68012 | 45173 | 76267 | 39878 | 41048 | 87820 | 60210 | 50216 | 63237 |
| 19.98 | 132003 | 22028 | 64685 | 49052 | 76163 | 39408 | 41051 | 88950 | 61336 | 49729 | 59594 |
| 20.02 | 118424 | 22842 | 60780 | 48330 | 74817 | 39752 | 40060 | 85769 | 62368 | 47696 | 54874 |
| 20.06 | 105227 | 21754 | 57413 | 44428 | 76459 | 38638 | 40267 | 83487 | 59601 | 49491 | 51363 |
| 20.1 | 90972 | 24473 | 49208 | 46781 | 77109 | 35942 | 39633 | 80672 | 56607 | 46595 | 50596 |
| 20.14 | 79461 | 23858 | 45669 | 43139 | 80489 | 34003 | 37989 | 75114 | 58359 | 45338 | 49596 |
| 20.18 | 68372 | 22884 | 43640 | 39337 | 76571 | 33513 | 37570 | 71544 | 59252 | 44468 | 49435 |
| 20.22 | 63949 | 23576 | 41138 | 35465 | 80512 | 31461 | 36424 | 64618 | 58596 | 43440 | 51954 |
| 20.26 | 58090 | 24311 | 40169 | 30926 | 78697 | 29724 | 36510 | 62435 | 57555 | 44975 | 52892 |
| 20.3 | 57778 | 23651 | 42706 | 28231 | 78484 | 30043 | 34382 | 57024 | 56804 | 45238 | 54380 |
| 20.34 | 57419 | 24673 | 42836 | 25736 | 78677 | 30345 | 33679 | 53395 | 55499 | 43614 | 56490 |
| 20.38 | 59077 | 25837 | 43149 | 25713 | 81764 | 26743 | 34810 | 52050 | 55150 | 41618 | 56578 |
| 20.42 | 61506 | 26564 | 43226 | 24356 | 81672 | 28190 | 34609 | 49645 | 55799 | 41415 | 55984 |
| 20.46 | 66515 | 26597 | 45205 | 25710 | 80655 | 29234 | 35382 | 46958 | 54476 | 41967 | 54409 |
| 20.5 | 70739 | 27670 | 46953 | 27602 | 78883 | 30066 | 34917 | 47513 | 54761 | 38123 | 51623 |
| 20.54 | 70451 | 32207 | 48022 | 27686 | 81098 | 30940 | 37484 | 47034 | 54156 | 40702 | 50220 |
| 20.58 | 75736 | 31958 | 50150 | 29408 | 82170 | 31197 | 35876 | 46363 | 52559 | 36338 | 49252 |
| 20.62 | 80899 | 35905 | 48224 | 31062 | 84339 | 34778 | 36919 | 46518 | 53277 | 37727 | 45762 |
| 20.66 | 83065 | 35690 | 47871 | 33014 | 83395 | 40080 | 38547 | 50497 | 51627 | 35859 | 42227 |
| 20.7 | 80891 | 37814 | 49224 | 33113 | 80875 | 43681 | 39196 | 49914 | 50491 | 34830 | 41816 |
| 20.74 | 81213 | 39614 | 49715 | 32470 | 81290 | 46316 | 40082 | 51712 | 48663 | 33638 | 39884 |
| 20.78 | 79922 | 38927 | 52797 | 32783 | 81182 | 49236 | 39616 | 50146 | 50956 | 35428 | 38222 |
| 20.82 | 76350 | 39401 | 54398 | 31125 | 81464 | 49686 | 41053 | 51018 | 53135 | 35041 | 39466 |
| 20.86 | 71121 | 40461 | 52728 | 29035 | 84674 | 52001 | 42396 | 53432 | 49266 | 33416 | 40994 |
| 20.9 | 68028 | 39204 | 55153 | 29183 | 85702 | 52811 | 40933 | 56227 | 52210 | 33423 | 40489 |
| 20.94 | 64908 | 39285 | 57604 | 28540 | 86857 | 54732 | 43573 | 60360 | 50380 | 38946 | 43940 |
| 20.98 | 58248 | 39778 | 57096 | 26957 | 84911 | 52651 | 44041 | 58346 | 49929 | 39170 | 39267 |
| 21.02 | 56411 | 37034 | 53566 | 27195 | 83444 | 49701 | 40155 | 59476 | 46785 | 37826 | 37994 |
| 21.06 | 55142 | 38370 | 54208 | 27109 | 80808 | 45171 | 44163 | 58570 | 53718 | 36213 | 38874 |
| 21.1 | 55920 | 37728 | 57758 | 23372 | 77334 | 39632 | 44990 | 60978 | 50545 | 40569 | 36036 |
| 21.14 | 55651 | 36451 | 54481 | 25367 | 82800 | 39481 | 46301 | 58210 | 49440 | 43901 | 34955 |
| 21.18 | 54830 | 36329 | 52222 | 22803 | 81458 | 40780 | 42455 | 60259 | 49128 | 41507 | 35146 |
| 21.22 | 59247 | 38857 | 51594 | 22142 | 84488 | 36264 | 43928 | 59935 | 49205 | 40602 | 34678 |
| 21.26 | 59819 | 36110 | 48763 | 22419 | 80682 | 39290 | 41491 | 61627 | 52545 | 42039 | 32258 |
| 21.3 | 66533 | 33974 | 46740 | 24139 | 83196 | 37812 | 46059 | 62491 | 53611 | 44094 | 32007 |
| 21.34 | 67641 | 28452 | 45121 | 22286 | 80504 | 38596 | 43188 | 58914 | 51186 | 45993 | 31503 |
| 21.38 | 73035 | 31098 | 45489 | 20186 | 80771 | 38435 | 39020 | 60717 | 50397 | 41174 | 32004 |
| 21.42 | 74435 | 27421 | 39277 | 20782 | 87334 | 35276 | 42545 | 57284 | 52537 | 42477 | 32921 |
| 21.46 | 70827 | 27829 | 38382 | 18494 | 83243 | 33138 | 38145 | 61386 | 53741 | 44837 | 31668 |
| 21.5 | 70649 | 26922 | 40047 | 16984 | 86842 | 38205 | 41498 | 61126 | 55909 | 43317 | 32443 |
| 21.54 | 71156 | 23796 | 40630 | 16868 | 83824 | 32385 | 39876 | 60308 | 53798 | 44936 | 34313 |
| 21.58 | 76639 | 26426 | 37650 | 18124 | 79555 | 32834 | 40675 | 62217 | 52400 | 48735 | 36485 |
| 21.62 | 77296 | 29192 | 38027 | 18435 | 82842 | 32767 | 38292 | 57208 | 51236 | 45072 | 36227 |
| 21.66 | 81881 | 26854 | 37873 | 18035 | 78026 | 30537 | 35276 | 57559 | 48372 | 46235 | 40382 |
| 21.7 | 78850 | 27048 | 40464 | 16063 | 82018 | 29813 | 36679 | 58311 | 49955 | 45579 | 42166 |
| 21.74 | 85148 | 28724 | 41433 | 16501 | 83290 | 32665 | 37337 | 57446 | 49111 | 45783 | 43584 |

-continued

| | | | | | | | | | | | |
|---|---|---|---|---|---|---|---|---|---|---|---|
| 21.78 | 86031 | 30134 | 38399 | 15557 | 82437 | 31371 | 35240 | 57930 | 53731 | 44365 | 43151 |
| 21.82 | 92852 | 33108 | 42656 | 17803 | 82563 | 36041 | 35119 | 60675 | 54799 | 42523 | 44939 |
| 21.86 | 92699 | 30689 | 41440 | 17033 | 84500 | 36879 | 33867 | 64270 | 56872 | 40984 | 47297 |
| 21.9 | 90302 | 33557 | 41849 | 17292 | 82227 | 40110 | 34822 | 62756 | 57294 | 39147 | 44755 |
| 21.94 | 90851 | 32685 | 41215 | 17296 | 85092 | 47310 | 38615 | 60651 | 57722 | 37627 | 42868 |
| 21.98 | 87172 | 28487 | 42051 | 15004 | 82601 | 51884 | 35516 | 63026 | 53668 | 38270 | 39383 |
| 22.02 | 88544 | 30344 | 42554 | 16055 | 82454 | 57679 | 34995 | 64471 | 58262 | 37218 | 39508 |
| 22.06 | 82124 | 28417 | 40266 | 16948 | 85639 | 65773 | 38294 | 60934 | 57583 | 35095 | 38268 |
| 22.1 | 85169 | 29055 | 40007 | 17464 | 83584 | 67257 | 32423 | 57762 | 55351 | 35580 | 37665 |
| 22.14 | 79592 | 29650 | 43599 | 17737 | 83020 | 68064 | 36757 | 57094 | 56871 | 34793 | 33871 |
| 22.18 | 79957 | 31038 | 42665 | 18293 | 82952 | 66093 | 34471 | 56662 | 55977 | 36242 | 31271 |
| 22.22 | 86456 | 29131 | 42980 | 17995 | 84029 | 68144 | 39520 | 53574 | 53214 | 36262 | 32368 |
| 22.26 | 91054 | 31346 | 49221 | 18969 | 86133 | 61564 | 37979 | 53269 | 50970 | 36871 | 32096 |
| 22.3 | 96649 | 34505 | 44879 | 21330 | 83004 | 59687 | 38640 | 52786 | 54264 | 38461 | 33139 |
| 22.34 | 106381 | 31971 | 45774 | 21690 | 85171 | 52391 | 40026 | 50507 | 52352 | 36296 | 31502 |
| 22.38 | 113149 | 35088 | 47577 | 22677 | 88962 | 47604 | 41177 | 50235 | 48239 | 36296 | 33455 |
| 22.42 | 113834 | 31849 | 46300 | 25974 | 82429 | 47690 | 45215 | 48455 | 47384 | 35149 | 33333 |
| 22.46 | 113222 | 32332 | 49596 | 31356 | 86890 | 47458 | 45124 | 48939 | 45489 | 32984 | 31493 |
| 22.5 | 110512 | 32078 | 51847 | 37202 | 85795 | 47081 | 46928 | 48710 | 50888 | 36197 | 31726 |
| 22.54 | 107094 | 29730 | 52467 | 42195 | 83231 | 55190 | 50749 | 49656 | 49137 | 35076 | 35111 |
| 22.58 | 104131 | 27997 | 56626 | 46353 | 85666 | 56098 | 52699 | 54531 | 48039 | 35645 | 35798 |
| 22.62 | 99081 | 25216 | 48644 | 46779 | 84002 | 60610 | 49856 | 50527 | 46451 | 36021 | 37492 |
| 22.66 | 99278 | 24855 | 51790 | 47065 | 86557 | 66034 | 50994 | 54045 | 46583 | 38556 | 35281 |
| 22.7 | 100645 | 23350 | 47158 | 49870 | 87043 | 68488 | 48569 | 56707 | 47800 | 36451 | 37504 |
| 22.74 | 97665 | 23910 | 47779 | 43500 | 87216 | 65043 | 48320 | 54374 | 41113 | 39177 | 34821 |
| 22.78 | 103866 | 22083 | 49836 | 42696 | 86517 | 67345 | 50224 | 60528 | 49106 | 42306 | 34864 |
| 22.82 | 110432 | 20374 | 46234 | 41605 | 88135 | 62092 | 45590 | 61894 | 45098 | 41210 | 32790 |
| 22.86 | 122479 | 21888 | 40664 | 32746 | 85736 | 63951 | 45301 | 59764 | 42356 | 45403 | 31813 |
| 22.9 | 127979 | 19723 | 39042 | 27949 | 87222 | 59033 | 47916 | 55568 | 45075 | 47519 | 30882 |
| 22.94 | 132703 | 18389 | 36130 | 25328 | 88287 | 60949 | 41979 | 59104 | 42271 | 46596 | 28507 |
| 22.98 | 133409 | 19654 | 33434 | 23711 | 85379 | 63648 | 40063 | 59781 | 44697 | 52760 | 28182 |
| 23.02 | 137727 | 18470 | 32700 | 20665 | 84262 | 65614 | 43664 | 63862 | 44912 | 51468 | 28060 |
| 23.06 | 132392 | 21120 | 30434 | 18824 | 86087 | 69007 | 44671 | 63669 | 46236 | 54477 | 25072 |
| 23.1 | 120794 | 19978 | 29645 | 19776 | 88100 | 69326 | 44064 | 61686 | 42507 | 51859 | 24726 |
| 23.14 | 108128 | 18967 | 28272 | 19298 | 89574 | 74771 | 45804 | 59200 | 46957 | 51828 | 23857 |
| 23.18 | 100220 | 21186 | 30943 | 18704 | 90436 | 71643 | 44276 | 60884 | 47072 | 53673 | 25381 |
| 23.22 | 86017 | 21610 | 30857 | 17109 | 89131 | 66929 | 45768 | 66156 | 51330 | 53128 | 27038 |
| 23.26 | 75721 | 21117 | 33671 | 18095 | 92500 | 67703 | 45059 | 66734 | 51428 | 51707 | 24464 |
| 23.3 | 64401 | 21332 | 34665 | 17840 | 92377 | 61412 | 44833 | 65435 | 53739 | 51267 | 24840 |
| 23.34 | 52295 | 21652 | 31397 | 17060 | 90363 | 57019 | 45212 | 67723 | 53483 | 50179 | 23821 |
| 23.38 | 53737 | 20207 | 32610 | 19703 | 91497 | 53041 | 45054 | 65449 | 55210 | 51992 | 25849 |
| 23.42 | 46738 | 20615 | 34194 | 19081 | 95330 | 48843 | 50317 | 69534 | 58796 | 53390 | 26759 |
| 23.46 | 46023 | 22213 | 33042 | 20958 | 92823 | 44349 | 50821 | 72531 | 64802 | 52831 | 26940 |
| 23.5 | 43124 | 20295 | 30834 | 20830 | 93531 | 42088 | 55180 | 72610 | 66581 | 61962 | 29601 |
| 23.54 | 45417 | 22022 | 33999 | 22719 | 89805 | 41772 | 52468 | 74525 | 68820 | 69818 | 28448 |
| 23.58 | 43904 | 20531 | 31545 | 25800 | 92396 | 43982 | 61677 | 78068 | 72550 | 75763 | 32368 |
| 23.62 | 38654 | 19207 | 32355 | 21865 | 91835 | 41806 | 65729 | 71225 | 74071 | 81598 | 36352 |
| 23.66 | 42452 | 18359 | 31603 | 24149 | 92032 | 40460 | 66601 | 75660 | 77137 | 87428 | 36725 |
| 23.7 | 41495 | 18765 | 30639 | 25404 | 91843 | 40441 | 68756 | 72283 | 80340 | 86815 | 37985 |
| 23.74 | 40257 | 19201 | 32480 | 26938 | 98130 | 38523 | 72037 | 74713 | 88440 | 87208 | 40449 |
| 23.78 | 41794 | 17509 | 28863 | 27406 | 95141 | 42390 | 74340 | 71788 | 91110 | 80562 | 40484 |
| 23.82 | 44489 | 19065 | 30511 | 30619 | 94566 | 40490 | 70736 | 70532 | 93864 | 80468 | 40933 |
| 23.86 | 44523 | 18853 | 29143 | 34037 | 92506 | 43705 | 72921 | 67312 | 95921 | 71496 | 43379 |
| 23.9 | 40304 | 17942 | 30082 | 40493 | 96205 | 44394 | 71105 | 69371 | 94564 | 61630 | 41077 |
| 23.94 | 43097 | 17097 | 29000 | 51332 | 93137 | 48409 | 72093 | 70144 | 98451 | 58116 | 44669 |
| 23.98 | 45706 | 17822 | 28459 | 57924 | 97156 | 50329 | 68580 | 70630 | 93178 | 53067 | 41659 |
| 24.02 | 45589 | 18668 | 28802 | 67139 | 97625 | 48387 | 64166 | 69781 | 91580 | 46713 | 42499 |
| 24.06 | 44646 | 16723 | 28666 | 77366 | 98408 | 51057 | 65208 | 68555 | 89553 | 49551 | 43865 |
| 24.1 | 46274 | 17305 | 29077 | 80788 | 93095 | 48180 | 65935 | 69408 | 86814 | 51231 | 37910 |
| 24.14 | 47195 | 18750 | 29891 | 84144 | 95489 | 49639 | 71151 | 75587 | 88724 | 64959 | 42068 |
| 24.18 | 50467 | 17503 | 30091 | 87540 | 96900 | 44630 | 69510 | 76591 | 85873 | 69488 | 38139 |
| 24.22 | 51626 | 19369 | 32262 | 91012 | 101095 | 47600 | 70244 | 78874 | 81744 | 80608 | 38087 |
| 24.26 | 52297 | 20193 | 30164 | 85090 | 91400 | 42694 | 68978 | 74632 | 79492 | 98432 | 38146 |
| 24.3 | 53613 | 20820 | 30298 | 79840 | 94255 | 40233 | 63298 | 72758 | 71044 | 109891 | 38514 |
| 24.34 | 58623 | 19351 | 30296 | 68728 | 94120 | 37262 | 63036 | 74475 | 69862 | 114351 | 37289 |
| 24.38 | 55936 | 20513 | 30299 | 63127 | 90288 | 36563 | 57888 | 71422 | 69628 | 125246 | 40863 |
| 24.42 | 54378 | 21618 | 32647 | 59493 | 94921 | 36398 | 59980 | 68204 | 67631 | 123911 | 43284 |
| 24.46 | 54194 | 22454 | 31346 | 57303 | 93046 | 35280 | 59806 | 65066 | 69322 | 128320 | 48017 |
| 24.5 | 58465 | 23215 | 36417 | 53137 | 93239 | 33005 | 55300 | 59029 | 67032 | 127065 | 47055 |
| 24.54 | 51443 | 25974 | 36719 | 54386 | 94703 | 31988 | 59328 | 61316 | 66216 | 113626 | 54142 |
| 24.58 | 54588 | 24986 | 36948 | 57231 | 93494 | 34869 | 58579 | 63264 | 66295 | 102484 | 51524 |
| 24.62 | 56742 | 28701 | 40605 | 61182 | 94820 | 33706 | 55774 | 65702 | 65698 | 92735 | 51275 |
| 24.66 | 63351 | 27771 | 39757 | 65481 | 91972 | 37757 | 60524 | 69748 | 64271 | 78000 | 50675 |
| 24.7 | 69210 | 26587 | 45269 | 60277 | 94842 | 39884 | 62841 | 75191 | 63686 | 64500 | 54471 |
| 24.74 | 78757 | 29191 | 45200 | 62148 | 92690 | 40443 | 75487 | 82132 | 64966 | 57588 | 50823 |
| 24.78 | 89161 | 28462 | 48898 | 64678 | 95710 | 40981 | 77440 | 91367 | 63762 | 52857 | 44412 |
| 24.82 | 97827 | 27176 | 50561 | 62711 | 95515 | 41598 | 85948 | 99959 | 61722 | 48775 | 44571 |
| 24.86 | 102844 | 26252 | 52155 | 65945 | 96109 | 43692 | 90759 | 108696 | 61374 | 48338 | 42481 |
| 24.9 | 120562 | 25477 | 55683 | 66404 | 94426 | 47749 | 98879 | 109777 | 58602 | 46830 | 41245 |

-continued

| | | | | | | | | | | | |
|---|---|---|---|---|---|---|---|---|---|---|---|
| 24.94 | 123961 | 25040 | 50690 | 59089 | 95232 | 46101 | 97104 | 112143 | 59906 | 45700 | 37206 |
| 24.98 | 129244 | 26333 | 49871 | 59331 | 96808 | 42156 | 101870 | 112948 | 60097 | 46195 | 37229 |
| 25.02 | 129931 | 25442 | 49820 | 55118 | 93972 | 43833 | 101080 | 108612 | 60765 | 49107 | 38885 |
| 25.06 | 127726 | 27893 | 49219 | 55438 | 93067 | 45555 | 95684 | 108584 | 61909 | 53574 | 38492 |
| 25.1 | 128103 | 30125 | 45165 | 55926 | 91171 | 45100 | 99519 | 110719 | 62369 | 55976 | 39645 |
| 25.14 | 115262 | 31716 | 41510 | 51378 | 94501 | 46369 | 93828 | 97660 | 62276 | 67059 | 39848 |
| 25.18 | 108570 | 30780 | 42486 | 44155 | 90297 | 48838 | 85182 | 94290 | 61250 | 73583 | 42111 |
| 25.22 | 94944 | 29996 | 39748 | 37985 | 90503 | 49400 | 83967 | 84908 | 57526 | 77313 | 38515 |
| 25.26 | 84736 | 32234 | 38471 | 28858 | 92516 | 52454 | 70467 | 84819 | 59075 | 77332 | 38071 |
| 25.3 | 81208 | 30088 | 35164 | 28130 | 90045 | 50349 | 66467 | 76165 | 57106 | 79991 | 38217 |
| 25.34 | 75773 | 30206 | 33686 | 22130 | 86540 | 50491 | 62500 | 73815 | 56100 | 78906 | 35810 |
| 25.38 | 69135 | 30362 | 34848 | 22125 | 86235 | 51754 | 61952 | 73623 | 58749 | 77751 | 37674 |
| 25.42 | 69205 | 28410 | 32611 | 20312 | 86961 | 48053 | 56332 | 67522 | 56807 | 71959 | 35483 |
| 25.46 | 71449 | 26151 | 30790 | 18217 | 81146 | 50341 | 51253 | 66227 | 54483 | 62546 | 33043 |
| 25.5 | 79557 | 24454 | 31223 | 20179 | 86382 | 53391 | 51094 | 63973 | 58918 | 60701 | 35796 |
| 25.54 | 83793 | 22626 | 33130 | 20177 | 82094 | 57285 | 45732 | 59592 | 61968 | 52468 | 34310 |
| 25.58 | 92551 | 20511 | 28189 | 20655 | 87005 | 60032 | 47722 | 61352 | 59051 | 47543 | 33341 |
| 25.62 | 91922 | 22663 | 32743 | 21886 | 83282 | 62698 | 45141 | 63109 | 62181 | 43611 | 35649 |
| 25.66 | 95320 | 22693 | 30340 | 23223 | 81532 | 59338 | 47499 | 60098 | 61519 | 43175 | 38848 |
| 25.7 | 94677 | 22559 | 32874 | 23923 | 77038 | 60489 | 42760 | 63195 | 59654 | 40736 | 39684 |
| 25.74 | 87900 | 22458 | 34081 | 23692 | 84264 | 60284 | 45127 | 61929 | 58706 | 39584 | 35625 |
| 25.78 | 85203 | 22251 | 34154 | 25371 | 79167 | 55386 | 43485 | 65035 | 60164 | 38941 | 39989 |
| 25.82 | 80083 | 25590 | 31755 | 25943 | 80926 | 55317 | 42574 | 64686 | 57527 | 38111 | 38394 |
| 25.86 | 70485 | 28429 | 33133 | 26573 | 81180 | 49634 | 43205 | 66732 | 61091 | 36323 | 35308 |
| 25.9 | 63480 | 29855 | 30935 | 27986 | 77432 | 46447 | 43821 | 63805 | 59757 | 38008 | 36230 |
| 25.94 | 59050 | 32452 | 32029 | 27583 | 77142 | 44518 | 43392 | 62554 | 57048 | 34304 | 35476 |
| 25.98 | 53246 | 32506 | 29735 | 26543 | 74522 | 36915 | 40183 | 61213 | 59379 | 37977 | 34375 |
| 26.02 | 51712 | 32885 | 29643 | 27339 | 76829 | 37001 | 41372 | 54521 | 60499 | 39465 | 30871 |
| 26.06 | 45736 | 30480 | 30870 | 27646 | 73546 | 32682 | 45560 | 51725 | 61215 | 40028 | 27693 |
| 26.1 | 42611 | 30673 | 30497 | 32252 | 72332 | 32288 | 40247 | 53366 | 61830 | 44415 | 27726 |
| 26.14 | 45977 | 29850 | 30388 | 37950 | 72024 | 33397 | 37994 | 49786 | 58353 | 45123 | 25460 |
| 26.18 | 49158 | 28913 | 29077 | 38463 | 72988 | 37765 | 41860 | 53383 | 59370 | 46930 | 23678 |
| 26.22 | 51479 | 27209 | 30747 | 37714 | 70971 | 36160 | 42862 | 47407 | 58134 | 48041 | 22164 |
| 26.26 | 54976 | 25515 | 33726 | 39482 | 68725 | 39403 | 41450 | 46613 | 55950 | 50129 | 22733 |
| 26.3 | 59217 | 24527 | 31954 | 38831 | 70013 | 41535 | 41376 | 49816 | 59085 | 52467 | 22034 |
| 26.34 | 58634 | 23370 | 32951 | 39049 | 70384 | 42501 | 41030 | 48101 | 53491 | 52631 | 25501 |
| 26.38 | 59901 | 25172 | 34847 | 41167 | 67542 | 44023 | 40414 | 49960 | 55742 | 53945 | 25200 |
| 26.42 | 64334 | 21972 | 37734 | 41488 | 68303 | 45125 | 41844 | 49115 | 56850 | 51606 | 27204 |
| 26.46 | 64474 | 24643 | 38148 | 37243 | 69160 | 49795 | 45995 | 51662 | 57950 | 53864 | 29466 |
| 26.5 | 61545 | 24047 | 36605 | 35963 | 65077 | 53575 | 46616 | 50155 | 53399 | 49472 | 32193 |
| 26.54 | 63827 | 22616 | 36602 | 35450 | 65956 | 54990 | 46551 | 54693 | 56854 | 46734 | 31230 |
| 26.58 | 60091 | 22669 | 37899 | 34815 | 65276 | 54575 | 45621 | 52165 | 55449 | 48653 | 32223 |
| 26.62 | 56765 | 20790 | 36044 | 35058 | 63298 | 57612 | 48789 | 52962 | 52904 | 44044 | 32659 |
| 26.66 | 58402 | 20784 | 35265 | 32624 | 59397 | 55449 | 49341 | 52990 | 54272 | 42148 | 31913 |
| 26.7 | 58396 | 19514 | 36108 | 28011 | 63071 | 56387 | 55183 | 55650 | 53889 | 38291 | 31204 |
| 26.74 | 60197 | 19569 | 36415 | 29233 | 65831 | 55175 | 51182 | 55866 | 48713 | 37182 | 29218 |
| 26.78 | 61792 | 18414 | 36362 | 25026 | 62396 | 53457 | 48917 | 55719 | 46751 | 35693 | 27644 |
| 26.82 | 66934 | 18977 | 33861 | 21713 | 63519 | 51959 | 53165 | 58487 | 43903 | 38143 | 26938 |
| 26.86 | 72986 | 18732 | 35466 | 20301 | 60020 | 51290 | 50012 | 63682 | 45722 | 33030 | 28265 |
| 26.9 | 77155 | 16752 | 34153 | 19253 | 58961 | 54329 | 50308 | 55916 | 41148 | 35375 | 25136 |
| 26.94 | 82415 | 15974 | 32824 | 19633 | 59936 | 50859 | 46564 | 52171 | 42629 | 36947 | 25870 |
| 26.98 | 87554 | 15466 | 33542 | 22185 | 60074 | 47462 | 48320 | 56690 | 43133 | 37088 | 24459 |
| 27.02 | 89292 | 17473 | 29170 | 21644 | 60455 | 45354 | 45580 | 59500 | 42068 | 36821 | 25825 |
| 27.06 | 85666 | 14488 | 28599 | 22034 | 57095 | 42801 | 43156 | 55342 | 45435 | 45851 | 26027 |
| 27.1 | 85200 | 15090 | 27764 | 21911 | 57618 | 40978 | 42281 | 52812 | 45851 | 37341 | 24056 |
| 27.14 | 81836 | 14889 | 27456 | 22305 | 56135 | 36597 | 38804 | 51411 | 42278 | 36314 | 27575 |
| 27.18 | 77190 | 16555 | 27295 | 20965 | 57515 | 33648 | 37794 | 49300 | 46239 | 38660 | 32295 |
| 27.22 | 73574 | 16426 | 27476 | 18958 | 57067 | 32375 | 43215 | 48205 | 44884 | 35403 | 29487 |
| 27.26 | 66543 | 15283 | 29310 | 21396 | 57242 | 31741 | 39519 | 50455 | 47465 | 39135 | 31120 |
| 27.3 | 57543 | 17615 | 26094 | 25354 | 60401 | 26567 | 39787 | 46405 | 46628 | 34978 | 30287 |
| 27.34 | 47063 | 16181 | 27689 | 26951 | 59174 | 25097 | 37486 | 45697 | 42870 | 34679 | 30872 |
| 27.38 | 43959 | 15871 | 23940 | 31152 | 56849 | 26422 | 37965 | 41718 | 39352 | 32732 | 31736 |
| 27.42 | 38525 | 15930 | 27163 | 36178 | 59026 | 27242 | 37501 | 41970 | 39858 | 33270 | 33648 |
| 27.46 | 36946 | 16414 | 25598 | 37229 | 56005 | 26559 | 38713 | 39167 | 38548 | 33380 | 31604 |
| 27.5 | 34927 | 16164 | 23751 | 39846 | 59408 | 27641 | 38406 | 38774 | 38040 | 31040 | 28391 |
| 27.54 | 35424 | 15828 | 24402 | 44892 | 58154 | 27877 | 37576 | 39946 | 39251 | 34639 | 31240 |
| 27.58 | 35640 | 15101 | 24810 | 44306 | 58427 | 32190 | 37943 | 42121 | 38748 | 35943 | 32155 |
| 27.62 | 36648 | 15521 | 22476 | 43512 | 55837 | 34249 | 37385 | 43083 | 38317 | 38009 | 31566 |
| 27.66 | 36047 | 15490 | 24922 | 38722 | 55758 | 34770 | 39963 | 38141 | 37752 | 35625 | 30302 |
| 27.7 | 36516 | 14873 | 23354 | 35550 | 56315 | 34323 | 36577 | 41148 | 37888 | 37418 | 26433 |
| 27.74 | 36934 | 14473 | 24400 | 33139 | 54056 | 34427 | 39554 | 41383 | 40567 | 36631 | 27999 |
| 27.78 | 37027 | 15244 | 22516 | 28345 | 56390 | 36652 | 36954 | 39101 | 40252 | 38424 | 23805 |
| 27.82 | 39065 | 16499 | 22330 | 24053 | 55526 | 33379 | 35891 | 41761 | 38310 | 34818 | 24275 |
| 27.86 | 39557 | 14796 | 22660 | 20107 | 58632 | 36034 | 36157 | 42004 | 39145 | 35334 | 24852 |
| 27.9 | 36530 | 14641 | 22685 | 17117 | 52697 | 31047 | 32337 | 40979 | 40506 | 33223 | 23944 |
| 27.94 | 38523 | 14036 | 21276 | 15445 | 54759 | 31945 | 34221 | 37703 | 43485 | 34511 | 22272 |
| 27.98 | 42014 | 14068 | 23610 | 13540 | 54899 | 30394 | 33090 | 39007 | 41364 | 31745 | 23975 |
| 28.02 | 48522 | 15745 | 23915 | 14855 | 54671 | 28546 | 35510 | 35961 | 43841 | 34111 | 24181 |
| 28.06 | 46231 | 16706 | 24585 | 12864 | 50868 | 26310 | 31734 | 36383 | 42114 | 31419 | 23146 |

| | | | | | | | | | | | |
|---|---|---|---|---|---|---|---|---|---|---|---|
| 28.1 | 52123 | 16704 | 24382 | 13392 | 57081 | 28184 | 33850 | 38720 | 43247 | 30603 | 26107 |
| 28.14 | 54051 | 14849 | 23170 | 15564 | 49742 | 25193 | 34098 | 35812 | 41681 | 29944 | 25059 |
| 28.18 | 52511 | 16525 | 23533 | 15510 | 51822 | 25100 | 30399 | 38358 | 40210 | 29848 | 25426 |
| 28.22 | 53638 | 17698 | 23277 | 15807 | 52421 | 26123 | 31683 | 37060 | 40789 | 27669 | 27297 |
| 28.26 | 56241 | 18188 | 23208 | 16053 | 54273 | 26914 | 33715 | 38100 | 40319 | 28461 | 28055 |
| 28.3 | 57640 | 21441 | 23600 | 15129 | 50542 | 26477 | 31482 | 39719 | 39722 | 29796 | 32860 |
| 28.34 | 58288 | 20364 | 24443 | 14772 | 48834 | 28348 | 32119 | 39757 | 38365 | 29098 | 34093 |
| 28.38 | 56804 | 18719 | 23412 | 14750 | 53113 | 27419 | 30414 | 37765 | 39277 | 26997 | 32179 |
| 28.42 | 55377 | 20882 | 20500 | 15212 | 47608 | 25805 | 31280 | 36663 | 36130 | 28815 | 33254 |
| 28.46 | 53122 | 18701 | 22436 | 13791 | 46371 | 27680 | 31139 | 36422 | 36802 | 27890 | 32981 |
| 28.5 | 52445 | 19517 | 21546 | 15317 | 49659 | 26173 | 30416 | 39089 | 35079 | 28968 | 33910 |
| 28.54 | 49376 | 19079 | 22077 | 13365 | 48412 | 27568 | 28650 | 39336 | 39951 | 29903 | 36600 |
| 28.58 | 50935 | 20329 | 21106 | 13751 | 51106 | 27481 | 29280 | 41118 | 42619 | 31112 | 36913 |
| 28.62 | 41480 | 19912 | 21526 | 14147 | 48334 | 27815 | 30843 | 34839 | 38429 | 29523 | 37079 |
| 28.66 | 41870 | 17995 | 20616 | 14150 | 48180 | 26843 | 27059 | 32173 | 39448 | 30165 | 35426 |
| 28.7 | 38494 | 16584 | 20579 | 16090 | 46181 | 28875 | 27285 | 32320 | 40601 | 30059 | 35939 |
| 28.74 | 35097 | 16042 | 19392 | 17407 | 45136 | 28115 | 25982 | 32928 | 36091 | 31458 | 34758 |
| 28.78 | 34161 | 15626 | 23251 | 17705 | 48091 | 30557 | 25738 | 32020 | 39529 | 33588 | 34231 |
| 28.82 | 36132 | 16959 | 22093 | 19715 | 48281 | 28944 | 29468 | 35870 | 40628 | 32050 | 30453 |
| 28.86 | 35461 | 15203 | 19994 | 21359 | 44487 | 28388 | 26589 | 32615 | 37957 | 32434 | 27228 |
| 28.9 | 35142 | 14648 | 18834 | 24381 | 46308 | 26848 | 26679 | 30938 | 38581 | 30850 | 24926 |
| 28.94 | 37008 | 13511 | 17089 | 26643 | 43926 | 27720 | 26992 | 32181 | 39180 | 31270 | 22457 |
| 28.98 | 36895 | 15776 | 19231 | 27362 | 43784 | 27846 | 28116 | 34053 | 41269 | 28220 | 20894 |
| 29.02 | 39587 | 12699 | 19951 | 29307 | 42401 | 25906 | 26566 | 36045 | 40532 | 27455 | 20230 |
| 29.06 | 38421 | 13042 | 19275 | 29140 | 42004 | 25779 | 27222 | 30597 | 39036 | 25848 | 19228 |
| 29.1 | 38378 | 13365 | 18301 | 27959 | 42503 | 23646 | 26664 | 31727 | 38058 | 23923 | 18848 |
| 29.14 | 41720 | 13785 | 17663 | 23992 | 42685 | 25439 | 24771 | 31553 | 37477 | 24385 | 19212 |
| 29.18 | 42742 | 12257 | 21359 | 25093 | 48538 | 26085 | 27090 | 33660 | 38655 | 26545 | 19795 |
| 29.22 | 41326 | 12910 | 19641 | 23589 | 44284 | 22106 | 25965 | 32115 | 35570 | 24318 | 18569 |
| 29.26 | 41366 | 12248 | 18781 | 19643 | 42712 | 23782 | 25242 | 34532 | 35063 | 25665 | 18718 |
| 29.3 | 37669 | 12731 | 18682 | 17801 | 41245 | 21870 | 26582 | 31613 | 32351 | 25346 | 18249 |
| 29.34 | 37473 | 14729 | 18710 | 15970 | 44268 | 23564 | 26995 | 36929 | 33163 | 27914 | 16230 |
| 29.38 | 38484 | 13564 | 17477 | 16180 | 43465 | 22638 | 25453 | 32971 | 34268 | 29550 | 18012 |
| 29.42 | 38849 | 12776 | 19349 | 17789 | 41319 | 23734 | 24048 | 32562 | 32811 | 28182 | 17227 |
| 29.46 | 39009 | 12126 | 18596 | 14358 | 42245 | 26089 | 25480 | 36619 | 33111 | 31431 | 17647 |
| 29.5 | 38406 | 11945 | 19284 | 14682 | 42526 | 27847 | 25597 | 33174 | 32021 | 31009 | 19377 |
| 29.54 | 35899 | 12212 | 18669 | 15084 | 40489 | 27417 | 28300 | 33862 | 34035 | 29316 | 20437 |
| 29.58 | 34899 | 12699 | 18016 | 14312 | 41052 | 27875 | 25485 | 32821 | 30780 | 28984 | 17930 |
| 29.62 | 33480 | 13750 | 18783 | 15070 | 40627 | 26153 | 25964 | 36819 | 32986 | 27347 | 21207 |
| 29.66 | 36771 | 12779 | 17917 | 17123 | 39822 | 26258 | 27189 | 33699 | 32279 | 28863 | 21737 |
| 29.7 | 35709 | 12438 | 18364 | 19127 | 41659 | 25071 | 24827 | 35705 | 32762 | 29171 | 24189 |
| 29.74 | 37177 | 12498 | 17334 | 23094 | 42121 | 26466 | 25202 | 33779 | 30974 | 28716 | 26118 |
| 29.78 | 39096 | 13440 | 17282 | 23651 | 41798 | 26033 | 27166 | 32977 | 32002 | 27105 | 28395 |
| 29.82 | 38167 | 12282 | 18662 | 26682 | 39676 | 24337 | 26243 | 35882 | 31193 | 26555 | 29715 |
| 29.86 | 36031 | 13405 | 18795 | 27247 | 41847 | 22405 | 26502 | 34899 | 31289 | 28421 | 29759 |
| 29.9 | 38936 | 12869 | 18165 | 26441 | 42340 | 20630 | 26821 | 35746 | 32901 | 23269 | 30384 |
| 29.94 | 41050 | 10816 | 18525 | 26390 | 39652 | 19656 | 25772 | 33085 | 31316 | 24034 | 31720 |
| 29.98 | 40785 | 13221 | 16071 | 27783 | 41404 | 21339 | 26823 | 33965 | 31780 | 25766 | 32466 |
| 30.02 | 42848 | 12160 | 18332 | 26773 | 41223 | 21265 | 26615 | 32793 | 30219 | 25635 | 28767 |
| 30.06 | 44064 | 11982 | 16841 | 22455 | 40519 | 19743 | 28621 | 34973 | 29131 | 26934 | 28923 |
| 30.1 | 46615 | 12791 | 17831 | 19807 | 39378 | 22049 | 27739 | 32259 | 30909 | 24753 | 28131 |
| 30.14 | 46337 | 13854 | 18529 | 18328 | 40428 | 20769 | 27596 | 33149 | 30160 | 25203 | 28239 |
| 30.18 | 48137 | 14078 | 16563 | 15738 | 38364 | 19403 | 23121 | 33153 | 28534 | 25645 | 21545 |
| 30.22 | 51419 | 14843 | 16187 | 15518 | 40582 | 23060 | 24780 | 32211 | 29153 | 23948 | 23078 |
| 30.26 | 51623 | 15406 | 18036 | 14554 | 38904 | 19394 | 24919 | 31002 | 27655 | 23399 | 19951 |
| 30.3 | 56393 | 17662 | 17027 | 14185 | 40163 | 22530 | 25009 | 32711 | 28763 | 23682 | 21551 |
| 30.34 | 58997 | 16541 | 17216 | 12979 | 40836 | 22989 | 23363 | 33617 | 29780 | 24034 | 20850 |
| 30.38 | 55093 | 17378 | 18351 | 13249 | 39925 | 24762 | 23466 | 31094 | 27598 | 21696 | 20611 |
| 30.42 | 55582 | 17182 | 16064 | 13659 | 38895 | 22065 | 23216 | 28708 | 29073 | 22323 | 19764 |
| 30.46 | 52898 | 17199 | 18032 | 14321 | 37413 | 22654 | 23338 | 29563 | 28384 | 22512 | 18163 |
| 30.5 | 53014 | 18318 | 18202 | 13199 | 37924 | 22019 | 21657 | 33124 | 27881 | 20789 | 19371 |
| 30.54 | 53727 | 18460 | 16054 | 12634 | 39541 | 21810 | 22512 | 32676 | 29303 | 22275 | 17418 |
| 30.58 | 46111 | 16881 | 17680 | 12129 | 38547 | 21378 | 23245 | 31491 | 26687 | 22036 | 19023 |
| 30.62 | 42854 | 16605 | 16795 | 12249 | 39925 | 21940 | 21997 | 32587 | 27591 | 20870 | 19607 |
| 30.66 | 43089 | 16842 | 16920 | 11766 | 36890 | 20857 | 20884 | 31927 | 28973 | 22664 | 19415 |
| 30.7 | 40134 | 16153 | 16731 | 12978 | 36934 | 19260 | 20642 | 30927 | 28439 | 22710 | 18011 |
| 30.74 | 36385 | 16125 | 18261 | 11981 | 38899 | 20880 | 21521 | 31154 | 28144 | 22422 | 19387 |
| 30.78 | 35001 | 13801 | 18070 | 12007 | 38206 | 19057 | 20661 | 30634 | 28044 | 21490 | 20735 |
| 30.82 | 33238 | 16885 | 17724 | 15114 | 38276 | 21234 | 24095 | 30139 | 30516 | 22146 | 19834 |
| 30.86 | 31663 | 14198 | 18153 | 16367 | 35696 | 21127 | 23494 | 30806 | 28673 | 22204 | 18646 |
| 30.9 | 30889 | 12718 | 17648 | 14891 | 37272 | 18579 | 21921 | 28522 | 30266 | 23012 | 19284 |
| 30.94 | 30833 | 11738 | 17013 | 15739 | 36104 | 18450 | 20638 | 28091 | 29214 | 25045 | 17589 |
| 30.98 | 30368 | 12745 | 15658 | 17587 | 35910 | 19144 | 20731 | 25885 | 28742 | 26738 | 21555 |
| 31.02 | 31361 | 12204 | 17117 | 19034 | 37355 | 18424 | 22927 | 28622 | 28231 | 27253 | 18198 |
| 31.06 | 31281 | 12880 | 16821 | 18666 | 35391 | 19135 | 22117 | 26907 | 28308 | 27385 | 19201 |
| 31.1 | 28741 | 13758 | 16770 | 19798 | 36712 | 19528 | 22430 | 30239 | 29168 | 28121 | 18430 |
| 31.14 | 32241 | 12175 | 15707 | 18290 | 38301 | 17285 | 20451 | 28469 | 27720 | 28025 | 17512 |
| 31.18 | 32609 | 11335 | 17094 | 17915 | 36341 | 17377 | 21809 | 27139 | 27536 | 27625 | 18227 |
| 31.22 | 33935 | 11497 | 17889 | 15809 | 33999 | 18423 | 21135 | 28413 | 29028 | 27654 | 17773 |

-continued

| | | | | | | | | | | | |
|---|---|---|---|---|---|---|---|---|---|---|---|
| 31.26 | 37652 | 12490 | 17057 | 17337 | 35455 | 18092 | 21831 | 29948 | 27214 | 27727 | 16392 |
| 31.3 | 38308 | 11451 | 17804 | 15788 | 33961 | 19818 | 22578 | 28682 | 29762 | 27814 | 15349 |
| 31.34 | 37399 | 11228 | 17853 | 17545 | 34499 | 18623 | 22415 | 26838 | 28586 | 25115 | 16404 |
| 31.38 | 37725 | 11925 | 17027 | 15756 | 33648 | 19481 | 19455 | 30558 | 26401 | 26292 | 15282 |
| 31.42 | 41646 | 12367 | 19328 | 16272 | 36092 | 20358 | 20911 | 29524 | 30612 | 25218 | 17159 |
| 31.46 | 35757 | 12722 | 17250 | 16535 | 35127 | 21970 | 21580 | 32510 | 30574 | 23020 | 16960 |
| 31.5 | 37316 | 11488 | 16866 | 15317 | 34214 | 22357 | 21990 | 31453 | 28944 | 23235 | 15432 |
| 31.54 | 35967 | 13019 | 17026 | 12997 | 33944 | 20630 | 20900 | 37502 | 26671 | 21725 | 14898 |
| 31.58 | 34654 | 12844 | 18101 | 13557 | 35590 | 22444 | 22812 | 35007 | 28151 | 22478 | 16346 |
| 31.62 | 33624 | 13038 | 16117 | 14294 | 36038 | 21646 | 21624 | 35472 | 26862 | 22511 | 15841 |
| 31.66 | 32261 | 12064 | 17579 | 13587 | 32067 | 22306 | 24225 | 35079 | 28860 | 20386 | 15837 |
| 31.7 | 32001 | 12612 | 17005 | 11746 | 33308 | 22354 | 22953 | 40898 | 26527 | 21010 | 16136 |
| 31.74 | 33183 | 11971 | 17067 | 11519 | 36165 | 20984 | 21692 | 37726 | 26646 | 22563 | 16085 |
| 31.78 | 33756 | 10954 | 16977 | 11517 | 33779 | 23412 | 21826 | 34679 | 26616 | 22546 | 16131 |
| 31.82 | 32568 | 12417 | 15787 | 11689 | 32695 | 20273 | 23013 | 36604 | 25700 | 22056 | 17232 |
| 31.86 | 32670 | 12162 | 17460 | 10944 | 34574 | 22906 | 21339 | 34531 | 28532 | 22355 | 16637 |
| 31.9 | 31666 | 13974 | 17103 | 11413 | 35168 | 22099 | 24556 | 31959 | 27855 | 24060 | 16755 |
| 31.94 | 31600 | 13318 | 17454 | 12471 | 35182 | 23153 | 21945 | 31949 | 24797 | 23042 | 18956 |
| 31.98 | 34985 | 13903 | 16942 | 13986 | 32638 | 21861 | 21983 | 29617 | 25240 | 24494 | 18612 |
| 32.02 | 35350 | 13763 | 17795 | 13390 | 32111 | 22169 | 21353 | 30207 | 26599 | 23767 | 17336 |
| 32.06 | 33185 | 14653 | 18168 | 15612 | 32726 | 23381 | 19192 | 28406 | 26900 | 26530 | 17105 |
| 32.1 | 32378 | 13092 | 19104 | 17138 | 33967 | 22913 | 21328 | 28553 | 26744 | 26927 | 17876 |
| 32.14 | 34869 | 13491 | 18392 | 17014 | 34950 | 24209 | 20609 | 25784 | 27029 | 28175 | 17916 |
| 32.18 | 34366 | 12645 | 20123 | 15602 | 33761 | 24041 | 19656 | 28616 | 26766 | 25992 | 17597 |
| 32.22 | 35409 | 12833 | 18976 | 16153 | 33573 | 22918 | 21126 | 26284 | 26737 | 26346 | 15940 |
| 32.26 | 34888 | 13792 | 19089 | 17463 | 34371 | 24361 | 20785 | 25009 | 24769 | 26247 | 16339 |
| 32.3 | 33978 | 12915 | 16833 | 16325 | 32691 | 20370 | 18930 | 26193 | 25316 | 24032 | 14978 |
| 32.34 | 32397 | 12384 | 15672 | 15683 | 35641 | 20520 | 19865 | 25631 | 27086 | 23241 | 14707 |
| 32.38 | 33671 | 11546 | 16679 | 14324 | 33085 | 20028 | 20943 | 26959 | 25936 | 23115 | 15702 |
| 32.42 | 34276 | 13778 | 16945 | 13799 | 33722 | 20642 | 20409 | 30013 | 25933 | 21148 | 15154 |
| 32.46 | 31566 | 12614 | 19505 | 13593 | 31575 | 20368 | 23211 | 30303 | 26864 | 20869 | 15048 |
| 32.5 | 31298 | 11529 | 16812 | 13059 | 32770 | 18744 | 19373 | 28287 | 26121 | 20802 | 16573 |
| 32.54 | 31488 | 11761 | 17750 | 14310 | 30686 | 19674 | 19019 | 32825 | 25992 | 20622 | 15443 |
| 32.58 | 30119 | 13145 | 17204 | 13801 | 32692 | 20003 | 18165 | 30491 | 27535 | 19595 | 15408 |
| 32.62 | 30802 | 12233 | 17657 | 11891 | 33339 | 18633 | 20951 | 32742 | 25909 | 20562 | 15095 |
| 32.66 | 33508 | 11640 | 16675 | 14305 | 33938 | 19124 | 19881 | 32901 | 26135 | 19894 | 15783 |
| 32.7 | 33724 | 11712 | 16669 | 14954 | 32905 | 21568 | 19633 | 32064 | 25852 | 21282 | 14303 |
| 32.74 | 32947 | 11261 | 15947 | 15488 | 31797 | 20845 | 18463 | 30670 | 25700 | 18997 | 15219 |
| 32.78 | 36442 | 11310 | 16478 | 14851 | 31241 | 20102 | 17985 | 31504 | 25868 | 19507 | 16256 |
| 32.82 | 36392 | 11188 | 18167 | 16180 | 32879 | 21418 | 19984 | 31130 | 28651 | 20888 | 17312 |
| 32.86 | 37561 | 12113 | 17001 | 16633 | 32409 | 19306 | 18724 | 31583 | 26870 | 20478 | 15375 |
| 32.9 | 36914 | 11726 | 17211 | 16660 | 31461 | 18713 | 19711 | 31358 | 27849 | 20035 | 16253 |
| 32.94 | 39811 | 11354 | 18736 | 18939 | 32411 | 20706 | 18875 | 28841 | 28095 | 19885 | 15561 |
| 32.98 | 39458 | 12922 | 17577 | 18797 | 31448 | 20828 | 18982 | 28417 | 26886 | 19911 | 17111 |
| 33.02 | 41289 | 13255 | 17235 | 20789 | 32779 | 18848 | 17508 | 28143 | 26256 | 21086 | 15923 |
| 33.06 | 42057 | 12946 | 18563 | 21163 | 29199 | 18996 | 18442 | 25060 | 26580 | 21119 | 15763 |
| 33.1 | 42305 | 14008 | 18918 | 20625 | 31916 | 19601 | 17934 | 26811 | 25223 | 20092 | 16810 |
| 33.14 | 44039 | 12207 | 18367 | 20394 | 32726 | 18687 | 17978 | 23668 | 23787 | 21196 | 17309 |
| 33.18 | 43704 | 13203 | 19634 | 18870 | 33734 | 18670 | 19471 | 24122 | 24537 | 19809 | 17541 |
| 33.22 | 45806 | 11942 | 20294 | 18696 | 32185 | 19790 | 17448 | 23502 | 26068 | 19759 | 17225 |
| 33.26 | 47754 | 12779 | 18423 | 16084 | 32689 | 18201 | 18719 | 21338 | 25134 | 21686 | 16688 |
| 33.3 | 46630 | 14158 | 19447 | 15982 | 34195 | 17085 | 19132 | 23473 | 26307 | 22676 | 17494 |
| 33.34 | 49078 | 14540 | 18812 | 15960 | 31754 | 16809 | 18687 | 22134 | 25574 | 24031 | 18212 |
| 33.38 | 48128 | 12889 | 19331 | 15730 | 32352 | 17933 | 18689 | 23514 | 26038 | 23434 | 18883 |
| 33.42 | 46706 | 13972 | 19529 | 15668 | 33111 | 16854 | 19428 | 22165 | 25645 | 23220 | 20197 |
| 33.46 | 46403 | 13556 | 18609 | 12882 | 32762 | 17931 | 19975 | 22915 | 24881 | 24982 | 18184 |
| 33.5 | 48035 | 13566 | 18287 | 13016 | 32051 | 18018 | 18956 | 20889 | 24672 | 24471 | 21047 |
| 33.54 | 45685 | 13424 | 18385 | 12249 | 32734 | 14902 | 20149 | 22607 | 25255 | 25389 | 19693 |
| 33.58 | 47540 | 13636 | 16611 | 12531 | 33292 | 17078 | 19533 | 21232 | 23309 | 25165 | 20478 |
| 33.62 | 44675 | 14607 | 16306 | 13519 | 31116 | 16013 | 18530 | 22961 | 25688 | 23020 | 20255 |
| 33.66 | 44788 | 12150 | 17141 | 13178 | 33796 | 16339 | 18695 | 21000 | 25388 | 22614 | 20111 |
| 33.7 | 45679 | 11088 | 16667 | 13006 | 32883 | 17360 | 18704 | 23174 | 25499 | 23027 | 19020 |
| 33.74 | 43048 | 11525 | 14911 | 12933 | 32187 | 16544 | 19421 | 22976 | 24382 | 22817 | 18857 |
| 33.78 | 39667 | 12311 | 16437 | 12625 | 33213 | 15851 | 18634 | 22498 | 25208 | 20215 | 19368 |
| 33.82 | 39711 | 13652 | 15498 | 12035 | 33332 | 17001 | 19409 | 23222 | 24954 | 21966 | 17942 |
| 33.86 | 39576 | 11815 | 15772 | 11064 | 33923 | 17175 | 19720 | 23555 | 21210 | 21274 | 18999 |
| 33.9 | 37586 | 11614 | 16841 | 11239 | 33270 | 16590 | 18348 | 25134 | 24470 | 20011 | 19970 |
| 33.94 | 34173 | 11256 | 15740 | 11792 | 34375 | 16741 | 18654 | 24791 | 22957 | 20322 | 19507 |
| 33.98 | 31610 | 11125 | 16184 | 11227 | 31922 | 16696 | 19165 | 24504 | 22270 | 19057 | 19027 |
| 34.02 | 29866 | 12208 | 15582 | 10254 | 33862 | 17843 | 19070 | 26754 | 22854 | 18816 | 17706 |
| 34.06 | 28935 | 12253 | 15198 | 9573 | 30385 | 15950 | 17049 | 24631 | 23835 | 18847 | 18925 |
| 34.1 | 28952 | 13371 | 15696 | 10508 | 33795 | 15974 | 19078 | 23801 | 23686 | 17537 | 17562 |
| 34.14 | 28710 | 10966 | 15731 | 11469 | 30910 | 16714 | 16742 | 24366 | 23910 | 16617 | 17504 |
| 34.18 | 28207 | 11230 | 14896 | 12937 | 33450 | 17326 | 16900 | 24689 | 23498 | 18540 | 17156 |
| 34.22 | 28472 | 10697 | 15299 | 14648 | 35008 | 17214 | 17438 | 23403 | 23541 | 18599 | 17386 |
| 34.26 | 29313 | 11977 | 15860 | 14867 | 30539 | 18998 | 17788 | 22230 | 23222 | 18021 | 17081 |
| 34.3 | 27919 | 11187 | 15443 | 16491 | 32998 | 16619 | 18103 | 23035 | 22754 | 17863 | 17365 |
| 34.34 | 28285 | 10182 | 16552 | 17140 | 32082 | 17870 | 17316 | 22956 | 21882 | 17252 | 17650 |
| 34.38 | 30260 | 10475 | 15318 | 17869 | 31937 | 19117 | 18414 | 22600 | 20807 | 18429 | 16751 |

-continued

| | | | | | | | | | | | |
|---|---|---|---|---|---|---|---|---|---|---|---|
| 34.42 | 29990 | 10373 | 15942 | 17319 | 33164 | 17460 | 18059 | 22442 | 24164 | 17311 | 17901 |
| 34.46 | 31200 | 10735 | 16067 | 17034 | 33447 | 16421 | 19168 | 23121 | 22220 | 18425 | 16571 |
| 34.5 | 30809 | 11408 | 16192 | 16273 | 31790 | 16136 | 18400 | 24642 | 22302 | 17444 | 17977 |
| 34.54 | 35256 | 11117 | 17632 | 15903 | 30835 | 15321 | 18677 | 24142 | 24274 | 19639 | 15872 |
| 34.58 | 34949 | 10845 | 16563 | 13153 | 33337 | 16475 | 19659 | 23276 | 20247 | 17057 | 16555 |
| 34.62 | 34585 | 11675 | 16580 | 13168 | 32227 | 15170 | 19045 | 24156 | 21910 | 18030 | 16709 |
| 34.66 | 36410 | 11220 | 17305 | 11727 | 31387 | 17382 | 19273 | 25996 | 23012 | 18002 | 17485 |
| 34.7 | 35230 | 10757 | 15881 | 11796 | 32552 | 14169 | 19382 | 23764 | 22131 | 17776 | 19135 |
| 34.74 | 35718 | 12065 | 18011 | 10634 | 32286 | 15693 | 17289 | 23622 | 21235 | 18376 | 18287 |
| 34.78 | 36686 | 11903 | 16649 | 10634 | 30466 | 15237 | 18137 | 24862 | 24209 | 17419 | 19289 |
| 34.82 | 34988 | 10736 | 16042 | 9778 | 30471 | 15437 | 19588 | 24378 | 21779 | 18598 | 19619 |
| 34.86 | 34332 | 10744 | 17103 | 9071 | 30165 | 14749 | 19557 | 22328 | 21471 | 17012 | 20332 |
| 34.9 | 36324 | 10901 | 16435 | 10882 | 31664 | 14542 | 18998 | 23460 | 21558 | 17049 | 20280 |
| 34.94 | 38283 | 12162 | 16803 | 9372 | 32701 | 16499 | 19041 | 23096 | 20426 | 16670 | 20396 |
| 34.98 | 40813 | 9853 | 17690 | 8976 | 30005 | 15437 | 19827 | 24057 | 21794 | 17092 | 19713 |
| 35.02 | 41737 | 10451 | 16396 | 8679 | 30709 | 15035 | 18114 | 22808 | 24262 | 18030 | 18147 |
| 35.06 | 44081 | 11410 | 16476 | 9249 | 31220 | 13684 | 17424 | 20942 | 22874 | 17844 | 19086 |
| 35.1 | 47382 | 10439 | 16881 | 9695 | 31728 | 14526 | 17653 | 21239 | 22354 | 17624 | 18968 |
| 35.14 | 43992 | 11067 | 16660 | 9992 | 30331 | 14130 | 18269 | 21858 | 22111 | 18174 | 17278 |
| 35.18 | 50421 | 10824 | 17332 | 9900 | 31427 | 13680 | 18866 | 22726 | 23493 | 19149 | 16936 |
| 35.22 | 49678 | 11138 | 18160 | 10348 | 32102 | 13948 | 18326 | 21256 | 20994 | 20856 | 15171 |
| 35.26 | 48444 | 10623 | 17643 | 11335 | 29867 | 14520 | 17561 | 20837 | 22189 | 19843 | 15979 |
| 35.3 | 50309 | 10146 | 17401 | 11208 | 31141 | 14005 | 16524 | 21863 | 20501 | 18863 | 15485 |
| 35.34 | 47664 | 11211 | 18403 | 12120 | 28386 | 13198 | 17951 | 21041 | 20327 | 18865 | 15007 |
| 35.38 | 45493 | 12098 | 18617 | 12147 | 31201 | 14114 | 15884 | 20302 | 21456 | 21103 | 15118 |
| 35.42 | 47055 | 11535 | 17344 | 10883 | 30270 | 14370 | 17109 | 19566 | 22672 | 21593 | 15541 |
| 35.46 | 45191 | 11867 | 16741 | 11466 | 28784 | 14067 | 17260 | 20698 | 22278 | 20564 | 17380 |
| 35.5 | 44698 | 13480 | 16409 | 10863 | 29172 | 13154 | 16902 | 22646 | 22678 | 18789 | 16619 |
| 35.54 | 43172 | 14450 | 16164 | 11971 | 29081 | 14445 | 17023 | 21389 | 21211 | 20045 | 16093 |
| 35.58 | 43236 | 13318 | 15198 | 12103 | 29063 | 14475 | 17247 | 21270 | 21326 | 19257 | 16151 |
| 35.62 | 41519 | 12803 | 17682 | 10769 | 30568 | 15444 | 16236 | 19547 | 20453 | 19833 | 16256 |
| 35.66 | 40399 | 12906 | 16309 | 11388 | 30743 | 15756 | 18038 | 21286 | 22442 | 18838 | 15827 |
| 35.7 | 38142 | 12911 | 17451 | 11770 | 30144 | 16266 | 15835 | 22408 | 22850 | 18771 | 17234 |
| 35.74 | 38126 | 13068 | 16722 | 10963 | 29869 | 18269 | 17373 | 21777 | 22722 | 16626 | 17788 |
| 35.78 | 36230 | 13486 | 17009 | 10546 | 30587 | 17468 | 17148 | 21563 | 21633 | 17809 | 16868 |
| 35.82 | 37387 | 12827 | 16509 | 12027 | 28960 | 17161 | 18521 | 21974 | 23823 | 19482 | 17323 |
| 35.86 | 36087 | 12761 | 16556 | 12279 | 31223 | 17309 | 16399 | 22335 | 23152 | 16681 | 15182 |
| 35.9 | 35572 | 13485 | 16329 | 11399 | 29631 | 16885 | 16637 | 21157 | 21885 | 17285 | 16154 |
| 35.94 | 36908 | 12723 | 16381 | 12113 | 30454 | 17588 | 17688 | 22274 | 21258 | 16501 | 16577 |
| 35.98 | 37518 | 13338 | 14541 | 11890 | 28407 | 17209 | 18348 | 21545 | 22594 | 17569 | 14638 |
| 36.02 | 36326 | 14155 | 15283 | 12308 | 27646 | 16016 | 17244 | 22521 | 22737 | 16760 | 13709 |
| 36.06 | 34647 | 14388 | 16167 | 13882 | 29746 | 17039 | 17705 | 23627 | 21378 | 17908 | 14316 |
| 36.1 | 36435 | 13665 | 15510 | 12989 | 31012 | 16180 | 16972 | 24676 | 22502 | 17524 | 13979 |
| 36.14 | 37208 | 13599 | 15486 | 11977 | 30029 | 16197 | 17535 | 23691 | 22937 | 18119 | 14790 |
| 36.18 | 34262 | 12614 | 17205 | 11787 | 30852 | 14778 | 18714 | 22282 | 24556 | 17143 | 14488 |
| 36.22 | 40122 | 12957 | 17130 | 12058 | 29395 | 15991 | 18309 | 23988 | 22970 | 17413 | 13662 |
| 36.26 | 38478 | 12478 | 16493 | 12993 | 28358 | 15828 | 19626 | 25084 | 23831 | 17827 | 14691 |
| 36.3 | 38176 | 11899 | 16978 | 13079 | 28463 | 15696 | 18244 | 23217 | 25789 | 18968 | 13793 |
| 36.34 | 37636 | 11664 | 15604 | 12064 | 28942 | 16032 | 19388 | 22370 | 24128 | 17842 | 13585 |
| 36.38 | 39158 | 12509 | 15836 | 11733 | 28561 | 16740 | 19386 | 24481 | 23585 | 19200 | 14015 |
| 36.42 | 38623 | 11528 | 16409 | 14122 | 29034 | 16517 | 19028 | 23380 | 24145 | 19971 | 15927 |
| 36.46 | 37722 | 12583 | 16712 | 13757 | 27274 | 18144 | 18319 | 22871 | 24307 | 17864 | 14423 |
| 36.5 | 38085 | 11980 | 16160 | 13116 | 28960 | 16550 | 17087 | 22403 | 22783 | 19199 | 15767 |
| 36.54 | 37523 | 11539 | 15932 | 12783 | 29291 | 18635 | 16346 | 22543 | 23371 | 18458 | 16647 |
| 36.58 | 38363 | 11911 | 14608 | 11423 | 27373 | 17648 | 17821 | 23835 | 21954 | 17621 | 15879 |
| 36.62 | 35624 | 10902 | 16635 | 12830 | 28892 | 16548 | 18101 | 22876 | 21734 | 18866 | 16027 |
| 36.66 | 35991 | 9839 | 14221 | 12535 | 29124 | 17924 | 17804 | 23161 | 23665 | 19194 | 15669 |
| 36.7 | 35705 | 10983 | 14874 | 11375 | 30618 | 16605 | 18922 | 21038 | 22215 | 18076 | 16815 |
| 36.74 | 33198 | 11148 | 14713 | 11688 | 29163 | 15444 | 17297 | 22250 | 20603 | 18348 | 15696 |
| 36.78 | 31320 | 10395 | 16804 | 12515 | 29514 | 14628 | 16481 | 21799 | 22304 | 18105 | 15550 |
| 36.82 | 32384 | 10059 | 15345 | 11063 | 27662 | 16109 | 16925 | 21478 | 19515 | 18828 | 15392 |
| 36.86 | 32247 | 11679 | 14592 | 11896 | 29014 | 15109 | 16846 | 21406 | 20223 | 19681 | 14713 |
| 36.9 | 29887 | 10917 | 14501 | 12427 | 27904 | 14306 | 17398 | 22823 | 19168 | 20033 | 14476 |
| 36.94 | 31165 | 11444 | 14131 | 11896 | 28259 | 14534 | 15772 | 22545 | 20789 | 20533 | 16791 |
| 36.98 | 28767 | 10656 | 15348 | 12043 | 26489 | 14294 | 16643 | 21837 | 20009 | 20030 | 16058 |
| 37.02 | 26246 | 11112 | 14685 | 10915 | 29236 | 15080 | 17078 | 23211 | 20540 | 19333 | 16090 |
| 37.06 | 27745 | 11017 | 14797 | 11297 | 27759 | 16224 | 17984 | 21315 | 21466 | 19037 | 15096 |
| 37.1 | 29126 | 11743 | 14514 | 10294 | 28964 | 15439 | 16415 | 23089 | 21383 | 19675 | 14686 |
| 37.14 | 29183 | 11252 | 14109 | 10177 | 29262 | 15463 | 15516 | 21780 | 23081 | 18691 | 15635 |
| 37.18 | 30432 | 10705 | 14150 | 9959 | 29294 | 15321 | 15496 | 22126 | 21477 | 18182 | 14747 |
| 37.22 | 28800 | 10670 | 13432 | 11254 | 27719 | 16549 | 18247 | 22053 | 21601 | 19262 | 14275 |
| 37.26 | 30185 | 9750 | 14316 | 10731 | 28011 | 15935 | 16351 | 24793 | 21621 | 20468 | 15465 |
| 37.3 | 30210 | 9831 | 13681 | 10800 | 29813 | 16648 | 15952 | 23501 | 21305 | 20800 | 13150 |
| 37.34 | 30999 | 10404 | 13935 | 10730 | 28383 | 16035 | 17851 | 21932 | 22632 | 20752 | 14527 |
| 37.38 | 31188 | 10090 | 13741 | 10996 | 28113 | 16280 | 16527 | 22713 | 21419 | 19031 | 13751 |
| 37.42 | 31921 | 10180 | 13657 | 11627 | 29405 | 16096 | 17380 | 22162 | 21965 | 19475 | 13988 |
| 37.46 | 34258 | 9768 | 13385 | 12222 | 27984 | 16404 | 16836 | 22143 | 22126 | 18486 | 13823 |
| 37.5 | 35650 | 9498 | 12676 | 12217 | 28242 | 15511 | 17613 | 20711 | 22781 | 18674 | 14196 |
| 37.54 | 34194 | 9222 | 13237 | 12726 | 29118 | 15544 | 17317 | 22048 | 20998 | 19783 | 14778 |

| | | | | | | | | | | |
|---|---|---|---|---|---|---|---|---|---|---|
| 37.58 | 34249 | 9919 | 12952 | 13180 | 30261 | 17720 | 16921 | 22234 | 21519 | 19273 | 14698 |
| 37.62 | 33973 | 7845 | 13743 | 12749 | 30390 | 15401 | 17406 | 22947 | 22549 | 19041 | 15232 |
| 37.66 | 33885 | 8474 | 12975 | 14130 | 31203 | 15121 | 18388 | 21945 | 21599 | 19563 | 15145 |
| 37.7 | 33442 | 8469 | 12619 | 11928 | 28550 | 17693 | 18185 | 21113 | 22461 | 16955 | 14243 |
| 37.74 | 32201 | 9430 | 12246 | 12121 | 28158 | 18651 | 17847 | 21283 | 20926 | 18332 | 14625 |
| 37.78 | 31327 | 8789 | 14116 | 12256 | 28211 | 18044 | 19224 | 22668 | 21395 | 18259 | 14688 |
| 37.82 | 30030 | 10013 | 14233 | 13412 | 27984 | 17697 | 17222 | 22046 | 20401 | 17702 | 16600 |
| 37.86 | 28494 | 9432 | 13237 | 12308 | 29871 | 15339 | 17384 | 21160 | 22851 | 18595 | 14572 |
| 37.9 | 28836 | 8810 | 13606 | 12415 | 28523 | 16405 | 18459 | 22604 | 21911 | 17166 | 13993 |
| 37.94 | 28114 | 9771 | 14141 | 11987 | 29184 | 17137 | 17925 | 22858 | 21160 | 18605 | 13432 |
| 37.98 | 26231 | 8782 | 13871 | 11535 | 28655 | 17868 | 15831 | 21566 | 20119 | 17245 | 13955 |
| 38.02 | 26828 | 9115 | 12802 | 11561 | 28366 | 17423 | 17188 | 22898 | 19278 | 18123 | 12785 |
| 38.06 | 27198 | 8018 | 14093 | 12636 | 28674 | 17781 | 17332 | 22295 | 20600 | 17401 | 12719 |
| 38.1 | 25520 | 8877 | 15255 | 11381 | 27316 | 15556 | 16804 | 23115 | 19594 | 18416 | 12797 |
| 38.14 | 26694 | 9245 | 13358 | 11865 | 29096 | 17548 | 16710 | 20198 | 19923 | 18393 | 12354 |
| 38.18 | 27381 | 8523 | 14150 | 11445 | 30318 | 16928 | 15114 | 22039 | 19712 | 18362 | 13460 |
| 38.22 | 28553 | 7788 | 13796 | 11657 | 26903 | 17327 | 18698 | 20276 | 20344 | 17720 | 12438 |
| 38.26 | 28577 | 8833 | 13177 | 12046 | 26862 | 15784 | 16186 | 21404 | 19024 | 16704 | 12110 |
| 38.3 | 28616 | 7826 | 12636 | 10668 | 28345 | 17150 | 17124 | 21820 | 18806 | 17743 | 11593 |
| 38.34 | 27377 | 9753 | 12910 | 12209 | 29862 | 15824 | 16812 | 20845 | 22066 | 19238 | 12211 |
| 38.38 | 30367 | 8888 | 13197 | 11355 | 28744 | 16866 | 16282 | 21784 | 19850 | 17503 | 13030 |
| 38.42 | 27891 | 9196 | 12593 | 11010 | 28712 | 15623 | 15758 | 21200 | 20804 | 17837 | 13585 |
| 38.46 | 27629 | 8632 | 13980 | 11198 | 29707 | 14457 | 16444 | 21289 | 20341 | 17805 | 12826 |
| 38.5 | 27632 | 9447 | 12903 | 10443 | 29777 | 14208 | 16378 | 20822 | 21289 | 18120 | 12903 |
| 38.54 | 24459 | 8659 | 12554 | 10985 | 27980 | 15012 | 16624 | 20524 | 21172 | 17987 | 13438 |
| 38.58 | 25704 | 9462 | 12844 | 11385 | 27777 | 15813 | 16595 | 21058 | 20920 | 14869 | 12859 |
| 38.62 | 24991 | 9725 | 12861 | 11191 | 28236 | 16312 | 16290 | 22037 | 20322 | 16491 | 14131 |
| 38.66 | 25243 | 9159 | 13019 | 11336 | 28497 | 15071 | 16602 | 21942 | 21540 | 18088 | 12167 |
| 38.7 | 23568 | 9076 | 12320 | 11231 | 27830 | 15651 | 15100 | 21910 | 17216 | 18976 | 13827 |
| 38.74 | 25709 | 9708 | 12765 | 12820 | 25960 | 14286 | 16406 | 20056 | 18375 | 18072 | 13354 |
| 38.78 | 26256 | 8419 | 12903 | 11392 | 29353 | 15776 | 16574 | 24311 | 22334 | 18539 | 13565 |
| 38.82 | 26510 | 8811 | 13279 | 12084 | 27561 | 16198 | 17272 | 22510 | 19850 | 17949 | 12578 |
| 38.86 | 26746 | 9115 | 14098 | 12390 | 29151 | 14676 | 17486 | 23355 | 20920 | 18536 | 12991 |
| 38.9 | 25949 | 9908 | 12434 | 12209 | 27456 | 14053 | 16984 | 22293 | 17486 | 18759 | 13592 |
| 38.94 | 25285 | 9248 | 13206 | 12269 | 27917 | 14532 | 17108 | 23495 | 20327 | 17377 | 14810 |
| 38.98 | 26331 | 9586 | 14251 | 13556 | 27633 | 14979 | 15609 | 22059 | 20165 | 19824 | 13926 |
| 39.02 | 24581 | 10432 | 13402 | 11083 | 26777 | 15093 | 15518 | 20623 | 21522 | 18854 | 13060 |
| 39.06 | 25551 | 9450 | 14494 | 11330 | 28412 | 14441 | 15729 | 21637 | 20693 | 16771 | 13729 |
| 39.1 | 24561 | 9298 | 14205 | 10347 | 27793 | 13784 | 15464 | 21006 | 18119 | 16683 | 15078 |
| 39.14 | 25681 | 8745 | 12208 | 10933 | 27921 | 14296 | 16894 | 22541 | 18897 | 17564 | 14471 |
| 39.18 | 24401 | 8425 | 13205 | 9794 | 26658 | 13321 | 16781 | 21121 | 20096 | 16651 | 15253 |
| 39.22 | 24493 | 8593 | 13631 | 9673 | 27743 | 14137 | 16242 | 20056 | 19667 | 15615 | 14427 |
| 39.26 | 23671 | 8888 | 12816 | 9655 | 28821 | 14177 | 16190 | 19747 | 19906 | 16746 | 15403 |
| 39.3 | 24012 | 8609 | 11597 | 9323 | 27865 | 14930 | 17614 | 21424 | 19792 | 15649 | 13026 |
| 39.34 | 24878 | 8236 | 12942 | 9772 | 28946 | 14278 | 16841 | 19545 | 19070 | 18545 | 13725 |
| 39.38 | 23935 | 9284 | 12963 | 9820 | 28114 | 14688 | 17669 | 20283 | 20862 | 17513 | 15035 |
| 39.42 | 27068 | 7616 | 13956 | 9632 | 27071 | 15979 | 16343 | 20456 | 20638 | 17762 | 14176 |
| 39.46 | 25070 | 8783 | 13399 | 9401 | 30432 | 15334 | 17473 | 19790 | 21329 | 17078 | 13495 |
| 39.5 | 24193 | 6722 | 13012 | 9275 | 27019 | 16035 | 18958 | 20799 | 20695 | 15781 | 12340 |
| 39.54 | 23807 | 8691 | 12947 | 9487 | 28523 | 14128 | 18308 | 19867 | 21126 | 15735 | 13907 |
| 39.58 | 24235 | 8142 | 12389 | 8852 | 28206 | 14434 | 17186 | 20646 | 20617 | 14742 | 12959 |
| 39.62 | 24588 | 8121 | 12314 | 9064 | 27565 | 15733 | 16339 | 19955 | 20099 | 15444 | 13482 |
| 39.66 | 25132 | 8154 | 13144 | 9728 | 28042 | 15535 | 17032 | 20070 | 21370 | 15125 | 12927 |
| 39.7 | 23879 | 8556 | 13324 | 9387 | 29360 | 16760 | 17301 | 19516 | 21863 | 14591 | 12098 |
| 39.74 | 24851 | 8898 | 11992 | 9941 | 28013 | 14496 | 16682 | 21530 | 21472 | 14789 | 11452 |
| 39.78 | 23242 | 8284 | 12631 | 11257 | 28876 | 16330 | 16796 | 20098 | 19854 | 15657 | 13448 |
| 39.82 | 24212 | 9298 | 12288 | 10124 | 26822 | 16002 | 16254 | 19804 | 20135 | 15058 | 12250 |
| 39.86 | 23411 | 9180 | 12790 | 11584 | 28606 | 15516 | 14865 | 21218 | 19822 | 15808 | 11367 |
| 39.9 | 22226 | 8283 | 13922 | 11740 | 27534 | 14935 | 16844 | 20100 | 19018 | 14353 | 11260 |
| 39.94 | 22735 | 8268 | 11712 | 13886 | 27581 | 14271 | 15661 | 20748 | 19131 | 13697 | 12209 |
| 39.98 | 23377 | 9028 | 12504 | 14163 | 27245 | 17201 | 16950 | 19740 | 19240 | 14411 | 11864 |
| 40.02 | 23568 | 8787 | 12344 | 13175 | 29034 | 16926 | 17454 | 21733 | 20293 | 15204 | 10893 |
| 40.06 | 23537 | 8062 | 12835 | 13919 | 26625 | 15879 | 17169 | 20260 | 19204 | 14774 | 11577 |
| 40.1 | 24326 | 8739 | 13218 | 15082 | 28278 | 15551 | 16021 | 19919 | 18050 | 15037 | 11155 |
| 40.14 | 25288 | 7841 | 12735 | 14820 | 28438 | 17774 | 17242 | 20881 | 18400 | 14946 | 11733 |
| 40.18 | 27286 | 7648 | 12218 | 13396 | 27181 | 16683 | 16386 | 19827 | 18598 | 14904 | 12091 |
| 40.22 | 26017 | 9197 | 13653 | 13869 | 27989 | 18118 | 17063 | 19633 | 18055 | 14585 | 13045 |
| 40.26 | 27248 | 8366 | 11685 | 12369 | 28655 | 16300 | 16866 | 21079 | 18497 | 14232 | 13381 |
| 40.3 | 28369 | 8882 | 13332 | 12500 | 27961 | 16452 | 16252 | 21023 | 18838 | 15190 | 12666 |
| 40.34 | 29753 | 7795 | 12400 | 11886 | 25791 | 16095 | 16050 | 19253 | 18543 | 14815 | 12586 |
| 40.38 | 30625 | 8308 | 12328 | 12033 | 26391 | 14889 | 16252 | 19790 | 18375 | 14109 | 12791 |
| 40.42 | 30393 | 9038 | 12386 | 11249 | 26978 | 15245 | 17156 | 20758 | 18897 | 15349 | 12933 |
| 40.46 | 30330 | 7977 | 11657 | 10601 | 26791 | 15027 | 15896 | 19762 | 17892 | 16292 | 13674 |
| 40.5 | 32679 | 8660 | 12523 | 9224 | 26181 | 13990 | 16580 | 19631 | 19340 | 15234 | 15181 |
| 40.54 | 32419 | 8359 | 11800 | 10237 | 26601 | 14038 | 14526 | 20008 | 17834 | 15296 | 13633 |
| 40.58 | 32571 | 9440 | 11599 | 9116 | 27869 | 12615 | 14282 | 18868 | 19030 | 14144 | 12945 |
| 40.62 | 31239 | 7610 | 12305 | 11021 | 27759 | 14595 | 16251 | 19276 | 19695 | 14991 | 13850 |
| 40.66 | 31201 | 8863 | 13155 | 10024 | 26616 | 15000 | 17954 | 17717 | 19919 | 14610 | 14691 |
| 40.7 | 30686 | 9303 | 11021 | 9612 | 25175 | 12309 | 13577 | 17988 | 18932 | 14098 | 12347 |

-continued

| | | | | | | | | | | |
|---|---|---|---|---|---|---|---|---|---|---|
| 40.74 | 31528 | 7678 | 10946 | 9193 | 24943 | 13059 | 14880 | 18485 | 18576 | 14540 | 14087 |
| 40.78 | 31368 | 9063 | 10961 | 9273 | 25939 | 12975 | 15498 | 18752 | 18775 | 15542 | 13978 |
| 40.82 | 29450 | 9543 | 11777 | 8333 | 28673 | 12893 | 14619 | 16919 | 17924 | 14311 | 13169 |
| 40.86 | 30584 | 8775 | 12582 | 9360 | 25337 | 12164 | 14780 | 18887 | 18682 | 14377 | 12947 |
| 40.9 | 29510 | 8467 | 10426 | 8235 | 26146 | 13406 | 14843 | 17597 | 18450 | 13493 | 13710 |
| 40.94 | 27277 | 7887 | 11300 | 9602 | 25688 | 13435 | 13894 | 17938 | 18133 | 13919 | 14567 |
| 40.98 | 26080 | 6988 | 12082 | 7897 | 25195 | 13836 | 14996 | 18492 | 16110 | 12640 | 12997 |
| 41.02 | 26444 | 7713 | 10988 | 8838 | 26135 | 12437 | 14504 | 18474 | 19141 | 12990 | 12608 |
| 41.06 | 25711 | 8906 | 11797 | 9699 | 25554 | 12666 | 15250 | 17742 | 17039 | 13455 | 13605 |
| 41.1 | 24727 | 7552 | 10916 | 9639 | 25705 | 12590 | 14071 | 18995 | 17790 | 13067 | 13413 |
| 41.14 | 24745 | 6910 | 10295 | 9498 | 23565 | 12562 | 13160 | 18028 | 16773 | 13276 | 12778 |
| 41.18 | 22121 | 7575 | 10726 | 9098 | 24333 | 12208 | 15178 | 17646 | 16874 | 12480 | 12060 |
| 41.22 | 23184 | 6613 | 11403 | 9511 | 22906 | 14414 | 13849 | 18123 | 15339 | 13651 | 10803 |
| 41.26 | 22162 | 6124 | 11738 | 9994 | 22101 | 12795 | 13538 | 16775 | 15592 | 13682 | 11957 |
| 41.3 | 21862 | 6996 | 11752 | 10001 | 24874 | 11852 | 13728 | 17843 | 17397 | 13518 | 12800 |
| 41.34 | 21632 | 7358 | 10358 | 8798 | 23389 | 11694 | 12995 | 18169 | 15997 | 12272 | 12069 |
| 41.38 | 21856 | 6946 | 11056 | 9981 | 24105 | 12625 | 13853 | 16426 | 15782 | 12868 | 12128 |
| 41.42 | 22448 | 6668 | 10541 | 9428 | 25069 | 12569 | 14798 | 16411 | 15648 | 11722 | 11166 |
| 41.46 | 21643 | 7139 | 11157 | 11177 | 24458 | 13149 | 14353 | 17954 | 15790 | 14758 | 11565 |
| 41.5 | 23380 | 7272 | 12131 | 9534 | 21794 | 11936 | 13201 | 16207 | 14921 | 13606 | 10757 |

| | Form | | | | | | | | |
|---|---|---|---|---|---|---|---|---|---|
| | DiTr1 + DiTr2 | Edy1 | Edy2_lc | Fum1 | Fum2a_lc | Fum2b | Fum2c_lc | Gen1 | Gen2_lc |
| | | | | ExperimentID | | | | | |
| Counter ion | SSm13 Dibenzoyl-L-tartaric acid | SSm73 1,2-Ethanedisulfonic acid | SSm7 1,2-Ethanedisulfonic acid | SSm90 Fumaric Acid | SSm25 Fumaric Acid | SSm58 Fumaric Acid | SSm57 Fumaric Acid | SSm21 2,5-Dihydroxybenzoic acid | SSm54 2,5-Dihydroxybenzoic acid |
| 1.5 | 3075 | 405 | 1755 | 2458 | 1511 | 1424 | 1625 | 26 | 1279 |
| 1.54 | 2920 | 1532 | 808 | 4204 | 5617 | 812 | 1532 | 1478 | 2605 |
| 1.58 | 2842 | 4575 | 4353 | 4452 | 4816 | 3606 | 2605 | 489 | 3597 |
| 1.62 | 3733 | 4938 | 5312 | 3234 | 4769 | 2592 | 4233 | 744 | 3718 |
| 1.66 | 4667 | 4035 | 2278 | 6186 | 5112 | 4785 | 6507 | 977 | 5182 |
| 1.7 | 6473 | 5485 | 5442 | 8591 | 6003 | 8041 | 6952 | 1992 | 2747 |
| 1.74 | 6406 | 5399 | 4182 | 7103 | 5664 | 5769 | 7647 | 1549 | 5302 |
| 1.78 | 9447 | 6638 | 6770 | 6987 | 7504 | 7339 | 8174 | 2551 | 6300 |
| 1.82 | 11346 | 9422 | 5759 | 11697 | 7372 | 6174 | 9242 | 1241 | 6905 |
| 1.86 | 11015 | 9175 | 5085 | 8461 | 10048 | 11810 | 10670 | 2923 | 8929 |
| 1.9 | 10188 | 11310 | 8342 | 9570 | 11723 | 9280 | 12066 | 4179 | 8906 |
| 1.94 | 11363 | 9005 | 9198 | 9342 | 12489 | 6581 | 10086 | 3267 | 9161 |
| 1.98 | 10154 | 7435 | 10574 | 10893 | 10411 | 6915 | 9087 | 3813 | 10294 |
| 2.02 | 9515 | 10375 | 10311 | 11842 | 9424 | 9555 | 11651 | 6096 | 6793 |
| 2.06 | 13602 | 8825 | 10569 | 11313 | 12418 | 8820 | 13352 | 4810 | 5837 |
| 2.1 | 12905 | 10610 | 9539 | 11969 | 15464 | 11849 | 10546 | 3463 | 13132 |
| 2.14 | 12343 | 13342 | 9797 | 12644 | 12700 | 14322 | 9897 | 4724 | 8099 |
| 2.18 | 10777 | 7790 | 10663 | 9062 | 11983 | 5126 | 13304 | 5683 | 8668 |
| 2.22 | 13122 | 15635 | 10732 | 8220 | 11693 | 8601 | 12926 | 4223 | 8722 |
| 2.26 | 9677 | 13121 | 9567 | 16287 | 10393 | 7039 | 14299 | 3934 | 9410 |
| 2.3 | 11216 | 11061 | 9394 | 13725 | 8886 | 7068 | 8829 | 5544 | 9719 |
| 2.34 | 11285 | 12423 | 9547 | 12597 | 12619 | 9430 | 10905 | 3902 | 9220 |
| 2.38 | 8103 | 7549 | 10230 | 12291 | 11656 | 9926 | 11736 | 5114 | 9670 |
| 2.42 | 9295 | 11341 | 9917 | 8507 | 14514 | 13100 | 12595 | 7657 | 10724 |
| 2.46 | 10437 | 11293 | 10511 | 11742 | 11099 | 10468 | 12105 | 7891 | 12715 |
| 2.5 | 12884 | 16714 | 8351 | 14055 | 11555 | 10925 | 14540 | 9390 | 9670 |
| 2.54 | 12727 | 13176 | 9541 | 13336 | 10148 | 12219 | 9951 | 10321 | 12351 |
| 2.58 | 12264 | 12264 | 7247 | 13745 | 11712 | 10265 | 9486 | 9044 | 12280 |
| 2.62 | 16023 | 10667 | 8404 | 12501 | 11847 | 11930 | 12320 | 9030 | 12693 |
| 2.66 | 10290 | 9540 | 9690 | 16158 | 11841 | 10829 | 12500 | 9457 | 11191 |
| 2.7 | 10898 | 10981 | 9830 | 16743 | 13162 | 10586 | 13602 | 8262 | 10933 |
| 2.74 | 10363 | 13711 | 11134 | 15374 | 12711 | 10118 | 12992 | 9060 | 12147 |
| 2.78 | 10891 | 13681 | 11668 | 13329 | 11795 | 9794 | 13363 | 10652 | 11912 |
| 2.82 | 11808 | 11389 | 14065 | 16094 | 15651 | 9375 | 16736 | 8578 | 13038 |
| 2.86 | 14422 | 13908 | 8953 | 15114 | 14847 | 15295 | 16924 | 9324 | 12926 |
| 2.9 | 15047 | 16316 | 9165 | 18303 | 12859 | 14827 | 14424 | 10593 | 11198 |
| 2.94 | 10533 | 15057 | 11361 | 19832 | 16593 | 13154 | 15959 | 11495 | 11786 |
| 2.98 | 16217 | 11904 | 13202 | 23267 | 14371 | 15127 | 13869 | 12375 | 14153 |
| 3.02 | 13622 | 14469 | 11422 | 19416 | 11941 | 12621 | 15409 | 14264 | 14354 |
| 3.06 | 13326 | 17530 | 13923 | 18052 | 16618 | 13206 | 14302 | 13983 | 15461 |
| 3.1 | 13594 | 12478 | 15751 | 17562 | 15373 | 13500 | 16076 | 12225 | 15342 |
| 3.14 | 15815 | 13498 | 12397 | 17607 | 17826 | 13894 | 14387 | 14042 | 15225 |
| 3.18 | 18317 | 13946 | 12146 | 18730 | 17728 | 15262 | 18728 | 15641 | 15273 |
| 3.22 | 15939 | 13828 | 15522 | 21672 | 15069 | 12832 | 17722 | 16106 | 15031 |
| 3.26 | 20876 | 11633 | 12346 | 27340 | 16986 | 14628 | 19247 | 13917 | 17011 |
| 3.3 | 19389 | 14233 | 17192 | 22697 | 18020 | 13048 | 19712 | 14956 | 17047 |
| 3.34 | 17542 | 13352 | 15573 | 24149 | 19612 | 15572 | 19498 | 13280 | 17182 |

-continued

| | | | | | | | | | |
|---|---|---|---|---|---|---|---|---|---|
| 3.38 | 18416 | 15296 | 16907 | 24685 | 19467 | 16224 | 19862 | 14419 | 20317 |
| 3.42 | 17871 | 17440 | 18538 | 24420 | 18953 | 13971 | 20202 | 14603 | 19667 |
| 3.46 | 17815 | 16151 | 16718 | 24458 | 20047 | 18228 | 25118 | 20058 | 14483 |
| 3.5 | 20337 | 15301 | 17674 | 24340 | 18896 | 17383 | 18490 | 19209 | 19439 |
| 3.54 | 19282 | 17975 | 17870 | 27137 | 23303 | 18941 | 18152 | 20121 | 16091 |
| 3.58 | 18640 | 14803 | 16330 | 27594 | 24143 | 19593 | 19405 | 21305 | 18650 |
| 3.62 | 24316 | 19286 | 20127 | 29062 | 20820 | 19176 | 19077 | 18962 | 18609 |
| 3.66 | 20913 | 16159 | 18783 | 26076 | 18591 | 19196 | 21382 | 15515 | 19899 |
| 3.7 | 22305 | 15772 | 22113 | 22946 | 19592 | 19165 | 20023 | 19890 | 16532 |
| 3.74 | 22332 | 19352 | 24838 | 22944 | 24429 | 16892 | 16847 | 18817 | 20516 |
| 3.78 | 22159 | 17052 | 27036 | 18903 | 23953 | 18491 | 17201 | 18716 | 18513 |
| 3.82 | 21270 | 17315 | 29980 | 19523 | 21762 | 21001 | 18818 | 21524 | 14854 |
| 3.86 | 19402 | 16404 | 35642 | 24652 | 23749 | 20026 | 21223 | 18686 | 17537 |
| 3.9 | 22400 | 19194 | 36302 | 21374 | 24694 | 28572 | 21501 | 28095 | 16392 |
| 3.94 | 21328 | 18869 | 44662 | 23591 | 21809 | 34487 | 17898 | 23319 | 18287 |
| 3.98 | 22160 | 22585 | 47776 | 21911 | 26431 | 47301 | 22721 | 28647 | 18348 |
| 4.02 | 20488 | 17517 | 55778 | 20511 | 22082 | 59801 | 21413 | 23828 | 18079 |
| 4.06 | 22704 | 15153 | 60937 | 21325 | 19969 | 70252 | 21174 | 28804 | 17306 |
| 4.1 | 24595 | 18909 | 54967 | 20736 | 27989 | 78436 | 23855 | 32671 | 20006 |
| 4.14 | 21256 | 21445 | 62602 | 19325 | 23341 | 81480 | 22835 | 33649 | 16930 |
| 4.18 | 25622 | 24091 | 59371 | 22634 | 25909 | 92634 | 22689 | 44980 | 16860 |
| 4.22 | 24863 | 26759 | 60695 | 23679 | 23983 | 90047 | 30517 | 74357 | 24511 |
| 4.26 | 24150 | 24876 | 56772 | 20369 | 26242 | 83302 | 34143 | 96285 | 20707 |
| 4.3 | 23125 | 26772 | 47713 | 19514 | 25882 | 83865 | 40554 | 122116 | 18966 |
| 4.34 | 19876 | 28297 | 44029 | 19614 | 27736 | 71583 | 45619 | 148366 | 19795 |
| 4.38 | 21585 | 30456 | 32759 | 18399 | 30034 | 56649 | 50234 | 174138 | 18625 |
| 4.42 | 21758 | 23679 | 28879 | 20539 | 29157 | 41562 | 54753 | 176149 | 17201 |
| 4.46 | 23607 | 27533 | 30510 | 17430 | 27520 | 35714 | 60039 | 179212 | 19123 |
| 4.5 | 21126 | 27783 | 23733 | 17877 | 39494 | 30756 | 56206 | 177258 | 19937 |
| 4.54 | 19721 | 25028 | 20952 | 19794 | 42968 | 26917 | 60674 | 155903 | 20530 |
| 4.58 | 20936 | 24706 | 20487 | 22124 | 46626 | 25157 | 53271 | 141957 | 18805 |
| 4.62 | 23459 | 26713 | 22771 | 17187 | 50448 | 19836 | 50837 | 118311 | 20717 |
| 4.66 | 24088 | 24795 | 20314 | 19831 | 47332 | 20316 | 44167 | 95780 | 18708 |
| 4.7 | 24151 | 25688 | 19450 | 24132 | 45383 | 19729 | 37277 | 70961 | 21098 |
| 4.74 | 24224 | 28478 | 21138 | 21341 | 54839 | 20608 | 31656 | 48680 | 21692 |
| 4.78 | 22807 | 24139 | 22289 | 21348 | 48951 | 18988 | 29106 | 41174 | 23990 |
| 4.82 | 26207 | 31039 | 21048 | 18146 | 46310 | 15913 | 26350 | 32531 | 18488 |
| 4.86 | 24022 | 32041 | 24146 | 19885 | 43207 | 18305 | 25234 | 27954 | 22273 |
| 4.9 | 24361 | 27961 | 23657 | 22384 | 41230 | 17769 | 23519 | 30358 | 19646 |
| 4.94 | 24742 | 29195 | 22906 | 23161 | 41416 | 16542 | 23079 | 27579 | 23692 |
| 4.98 | 29030 | 27913 | 24121 | 21622 | 41886 | 17441 | 22144 | 28625 | 23411 |
| 5.02 | 24594 | 32453 | 23324 | 21273 | 41320 | 17860 | 26323 | 31381 | 26422 |
| 5.06 | 25709 | 37447 | 20610 | 20995 | 45519 | 19279 | 26305 | 29868 | 23546 |
| 5.1 | 25584 | 43018 | 22112 | 19766 | 46628 | 18180 | 27131 | 30979 | 25597 |
| 5.14 | 24764 | 49357 | 23246 | 21712 | 42855 | 21878 | 28842 | 25260 | 27408 |
| 5.18 | 21793 | 53184 | 19847 | 20996 | 41065 | 16026 | 27580 | 27542 | 27567 |
| 5.22 | 21924 | 53174 | 22180 | 20876 | 39958 | 17009 | 29617 | 27599 | 30652 |
| 5.26 | 21407 | 52903 | 20204 | 21126 | 39949 | 18661 | 29265 | 26225 | 28802 |
| 5.3 | 22882 | 57515 | 19957 | 21212 | 38403 | 19577 | 29630 | 27499 | 27174 |
| 5.34 | 26367 | 52519 | 17002 | 19890 | 41724 | 19883 | 27473 | 25586 | 28259 |
| 5.38 | 26582 | 50894 | 17696 | 19853 | 41115 | 16738 | 32346 | 30255 | 30825 |
| 5.42 | 21828 | 48091 | 18219 | 19736 | 39703 | 20736 | 31253 | 29069 | 33679 |
| 5.46 | 23099 | 43396 | 17405 | 20674 | 40894 | 18196 | 27131 | 31070 | 30949 |
| 5.5 | 24128 | 37085 | 17943 | 22030 | 34928 | 19589 | 26497 | 26341 | 31828 |
| 5.54 | 21315 | 31301 | 19404 | 19319 | 36612 | 18893 | 24840 | 31003 | 29212 |
| 5.58 | 22255 | 26246 | 18685 | 16551 | 36419 | 21766 | 26448 | 29701 | 27049 |
| 5.62 | 18333 | 23844 | 21463 | 21658 | 32379 | 23791 | 24099 | 26594 | 25086 |
| 5.66 | 22876 | 22528 | 19864 | 18808 | 33872 | 22619 | 24449 | 28145 | 25066 |
| 5.7 | 21935 | 21340 | 19116 | 20807 | 34001 | 29075 | 25935 | 26184 | 27162 |
| 5.74 | 24319 | 21169 | 24002 | 21402 | 33305 | 29521 | 24159 | 31354 | 20877 |
| 5.78 | 26039 | 22101 | 19313 | 22819 | 31254 | 25739 | 24894 | 29826 | 21705 |
| 5.82 | 23907 | 19829 | 16772 | 24172 | 33125 | 27552 | 23535 | 27744 | 18410 |
| 5.86 | 21013 | 20497 | 19247 | 20683 | 30028 | 27927 | 21820 | 28135 | 20693 |
| 5.9 | 20419 | 20829 | 18095 | 19852 | 31453 | 28845 | 21958 | 25627 | 19202 |
| 5.94 | 23739 | 20886 | 18433 | 20591 | 27962 | 30299 | 22961 | 27500 | 21862 |
| 5.98 | 21672 | 19810 | 20039 | 17138 | 30966 | 25035 | 21403 | 29611 | 18810 |
| 6.02 | 21207 | 22075 | 18550 | 21176 | 27582 | 24395 | 24605 | 29334 | 22244 |
| 6.06 | 23673 | 20025 | 17639 | 18487 | 32522 | 18984 | 22068 | 29125 | 21917 |
| 6.1 | 24410 | 21667 | 19507 | 22886 | 31049 | 19494 | 22685 | 28027 | 20995 |
| 6.14 | 24212 | 19938 | 19787 | 19414 | 30832 | 20553 | 20213 | 28976 | 20662 |
| 6.18 | 25503 | 21121 | 18828 | 23187 | 30538 | 21044 | 22179 | 28710 | 19366 |
| 6.22 | 23144 | 19311 | 19972 | 22568 | 28805 | 18251 | 23980 | 29724 | 18404 |
| 6.26 | 25182 | 20972 | 18648 | 19970 | 30201 | 18664 | 24353 | 27445 | 17977 |
| 6.3 | 27197 | 19203 | 17634 | 18894 | 29064 | 18909 | 20386 | 27653 | 19516 |
| 6.34 | 23856 | 19949 | 17965 | 21455 | 28760 | 17643 | 19238 | 28707 | 18793 |
| 6.38 | 23688 | 20058 | 17906 | 23085 | 29720 | 17945 | 21720 | 30378 | 18922 |
| 6.42 | 25405 | 20575 | 19361 | 23370 | 27892 | 18445 | 26317 | 28996 | 19254 |
| 6.46 | 25225 | 22550 | 17705 | 23688 | 28569 | 20064 | 21811 | 31868 | 21405 |
| 6.5 | 24768 | 18865 | 18697 | 20919 | 27025 | 22121 | 21467 | 30567 | 17773 |

-continued

| | | | | | | | | | |
|---|---|---|---|---|---|---|---|---|---|
| 6.54 | 24073 | 18342 | 20650 | 23917 | 28602 | 19124 | 22481 | 28092 | 19396 |
| 6.58 | 23019 | 21284 | 19157 | 23152 | 28323 | 19535 | 26222 | 28500 | 20603 |
| 6.62 | 24891 | 22393 | 21707 | 23676 | 25114 | 19085 | 23446 | 29880 | 19277 |
| 6.66 | 24152 | 19878 | 21877 | 24110 | 27222 | 20364 | 24212 | 27154 | 18399 |
| 6.7 | 26822 | 21126 | 19712 | 24133 | 27754 | 22056 | 23085 | 29789 | 19925 |
| 6.74 | 23851 | 21146 | 18983 | 22712 | 25454 | 22082 | 23287 | 28820 | 17991 |
| 6.78 | 23357 | 20751 | 20206 | 22998 | 27456 | 17940 | 23204 | 30285 | 18544 |
| 6.82 | 23434 | 20719 | 22406 | 22262 | 24749 | 18407 | 24917 | 30224 | 19640 |
| 6.86 | 23160 | 20843 | 20583 | 21515 | 23935 | 14640 | 22569 | 27083 | 19180 |
| 6.9 | 24206 | 21241 | 21041 | 20850 | 23161 | 18511 | 25117 | 28662 | 20501 |
| 6.94 | 25168 | 19254 | 20593 | 21807 | 21871 | 19875 | 21039 | 27324 | 22107 |
| 6.98 | 23438 | 18321 | 20317 | 21361 | 23436 | 21706 | 20601 | 29340 | 20450 |
| 7.02 | 24522 | 18627 | 21990 | 21963 | 26309 | 19891 | 22161 | 29274 | 21705 |
| 7.06 | 26584 | 21808 | 23183 | 22403 | 25176 | 19362 | 23640 | 35534 | 25458 |
| 7.1 | 24004 | 20209 | 22052 | 20666 | 23143 | 17437 | 23726 | 30972 | 24300 |
| 7.14 | 24122 | 21876 | 24344 | 22140 | 22957 | 20288 | 20222 | 29736 | 22754 |
| 7.18 | 23060 | 18989 | 24672 | 21423 | 24530 | 18108 | 21452 | 27984 | 26691 |
| 7.22 | 23226 | 18802 | 23692 | 19670 | 24955 | 20690 | 24194 | 28637 | 29291 |
| 7.26 | 23357 | 20578 | 22650 | 22323 | 27226 | 19044 | 22903 | 30073 | 29776 |
| 7.3 | 24236 | 21797 | 25984 | 24024 | 26519 | 18971 | 24842 | 33332 | 26564 |
| 7.34 | 25414 | 21004 | 23633 | 20850 | 25641 | 18833 | 26013 | 31654 | 28107 |
| 7.38 | 20814 | 17661 | 22629 | 20513 | 25351 | 17586 | 20657 | 30051 | 28250 |
| 7.42 | 22522 | 18826 | 23801 | 21134 | 23235 | 18432 | 21487 | 33502 | 28226 |
| 7.46 | 23102 | 20245 | 22846 | 20498 | 23502 | 19804 | 24704 | 28090 | 24440 |
| 7.5 | 23847 | 19337 | 25131 | 20350 | 24827 | 19520 | 24975 | 31499 | 26077 |
| 7.54 | 25060 | 18467 | 21859 | 23541 | 22290 | 18632 | 21720 | 31461 | 26384 |
| 7.58 | 23481 | 18437 | 23138 | 21563 | 24824 | 20607 | 24101 | 30036 | 27560 |
| 7.62 | 26803 | 21749 | 25735 | 23730 | 25024 | 21456 | 24852 | 36650 | 28461 |
| 7.66 | 25865 | 19008 | 21822 | 20907 | 28189 | 21202 | 24329 | 35841 | 27108 |
| 7.7 | 24155 | 18057 | 20463 | 21994 | 25611 | 17312 | 20564 | 32705 | 25868 |
| 7.74 | 23746 | 19445 | 20554 | 20118 | 25430 | 20237 | 21977 | 34360 | 27498 |
| 7.78 | 23235 | 17691 | 20544 | 21551 | 26004 | 20144 | 23493 | 36743 | 24841 |
| 7.82 | 24348 | 19781 | 20375 | 22978 | 25414 | 22266 | 23882 | 35247 | 26044 |
| 7.86 | 24988 | 22744 | 25858 | 23472 | 28360 | 21164 | 26515 | 39520 | 28557 |
| 7.9 | 24214 | 21728 | 21781 | 21783 | 27353 | 23051 | 25208 | 40397 | 25480 |
| 7.94 | 25100 | 23137 | 23443 | 22141 | 28669 | 22696 | 28014 | 46122 | 24879 |
| 7.98 | 22693 | 23602 | 22292 | 23375 | 27470 | 23543 | 24823 | 54043 | 22232 |
| 8.02 | 23883 | 22902 | 22397 | 21491 | 23934 | 26168 | 25232 | 60576 | 22839 |
| 8.06 | 25763 | 23834 | 25449 | 22363 | 27384 | 27065 | 29152 | 70754 | 20216 |
| 8.1 | 26300 | 28151 | 25358 | 22262 | 25030 | 28663 | 25068 | 79776 | 20785 |
| 8.14 | 24581 | 31476 | 24723 | 19992 | 26727 | 31110 | 26885 | 88023 | 21139 |
| 8.18 | 22786 | 33087 | 24781 | 22230 | 26401 | 34315 | 24219 | 88482 | 22235 |
| 8.22 | 25655 | 31791 | 22080 | 22945 | 23795 | 36389 | 23875 | 84886 | 21265 |
| 8.26 | 25190 | 34653 | 24021 | 19554 | 26037 | 39616 | 24053 | 76708 | 21124 |
| 8.3 | 25206 | 35749 | 23607 | 21586 | 23696 | 36264 | 25375 | 73201 | 20344 |
| 8.34 | 25122 | 35074 | 25381 | 19959 | 27753 | 39336 | 23374 | 72915 | 22217 |
| 8.38 | 23673 | 32382 | 25437 | 22123 | 26483 | 37652 | 24280 | 61205 | 22150 |
| 8.42 | 24122 | 32039 | 26120 | 24035 | 27320 | 38535 | 23366 | 53085 | 19228 |
| 8.46 | 23971 | 27766 | 23739 | 23242 | 24316 | 34461 | 25762 | 43658 | 21929 |
| 8.5 | 23355 | 26879 | 23263 | 19969 | 25713 | 29670 | 21911 | 35094 | 20623 |
| 8.54 | 25735 | 22600 | 19470 | 24177 | 28786 | 27219 | 20845 | 34755 | 20198 |
| 8.58 | 24287 | 25423 | 22820 | 22995 | 26354 | 27673 | 27408 | 34247 | 21009 |
| 8.62 | 22203 | 23674 | 24357 | 21287 | 27589 | 24661 | 23806 | 33941 | 22964 |
| 8.66 | 25060 | 23562 | 22727 | 22692 | 26768 | 26186 | 23745 | 32948 | 22633 |
| 8.7 | 25918 | 23857 | 24765 | 21350 | 26442 | 26036 | 24163 | 34788 | 20533 |
| 8.74 | 23782 | 24909 | 20279 | 21669 | 27735 | 25202 | 23346 | 33606 | 20285 |
| 8.78 | 25731 | 25197 | 23925 | 21865 | 25297 | 23077 | 24448 | 36488 | 20154 |
| 8.82 | 28269 | 29618 | 23208 | 21764 | 29917 | 22754 | 27554 | 37295 | 21637 |
| 8.86 | 25323 | 29032 | 21957 | 22597 | 30239 | 24107 | 26980 | 35692 | 22994 |
| 8.9 | 27513 | 26021 | 22519 | 23800 | 27344 | 21417 | 25727 | 35268 | 22201 |
| 8.94 | 24236 | 28371 | 19782 | 19803 | 29137 | 20505 | 27442 | 35219 | 21899 |
| 8.98 | 25258 | 30157 | 21132 | 21575 | 30026 | 22418 | 27521 | 32845 | 23186 |
| 9.02 | 29059 | 28489 | 20767 | 24515 | 32045 | 21482 | 30971 | 30764 | 23825 |
| 9.06 | 29953 | 27364 | 20821 | 22656 | 28969 | 20615 | 30309 | 36249 | 21551 |
| 9.1 | 30974 | 23881 | 20166 | 21970 | 28478 | 21816 | 28767 | 30677 | 20202 |
| 9.14 | 33365 | 25217 | 20631 | 21410 | 27392 | 20388 | 27424 | 33380 | 22281 |
| 9.18 | 32476 | 28532 | 20375 | 22296 | 28167 | 22163 | 28707 | 35763 | 23720 |
| 9.22 | 35178 | 24378 | 22010 | 22724 | 27465 | 22342 | 26574 | 37431 | 24324 |
| 9.26 | 36676 | 22312 | 20859 | 22367 | 26492 | 21462 | 25546 | 35501 | 25175 |
| 9.3 | 36319 | 21300 | 19076 | 23586 | 29200 | 19422 | 26351 | 34173 | 25414 |
| 9.34 | 36814 | 25437 | 20660 | 24649 | 26660 | 21685 | 24724 | 37192 | 23108 |
| 9.38 | 40774 | 22932 | 20233 | 21054 | 30691 | 24360 | 26497 | 38309 | 24651 |
| 9.42 | 38448 | 22667 | 21843 | 23992 | 27624 | 20815 | 25152 | 35022 | 22874 |
| 9.46 | 38819 | 22595 | 21578 | 25117 | 25989 | 21160 | 23919 | 35826 | 21384 |
| 9.5 | 38789 | 22736 | 20857 | 21098 | 29060 | 21289 | 23517 | 36279 | 18470 |
| 9.54 | 35241 | 22689 | 24020 | 26843 | 26549 | 23347 | 24270 | 36320 | 21296 |
| 9.58 | 35603 | 22084 | 22368 | 24866 | 28112 | 24456 | 24409 | 35564 | 24622 |
| 9.62 | 35226 | 23862 | 22618 | 23660 | 27949 | 24816 | 22984 | 36460 | 22445 |
| 9.66 | 33436 | 20705 | 22272 | 24075 | 27794 | 20235 | 23709 | 33692 | 22266 |

-continued

| | | | | | | | | | |
|---|---|---|---|---|---|---|---|---|---|
| 9.7 | 34003 | 23360 | 23394 | 26705 | 27878 | 24727 | 25958 | 35663 | 22954 |
| 9.74 | 35725 | 21490 | 26845 | 24125 | 28222 | 23675 | 23662 | 38910 | 24772 |
| 9.78 | 37575 | 24070 | 23652 | 23160 | 25846 | 23224 | 25042 | 35125 | 21312 |
| 9.82 | 38609 | 24122 | 21640 | 22507 | 23162 | 22302 | 22474 | 37021 | 23062 |
| 9.86 | 44358 | 21365 | 22499 | 24675 | 28903 | 24405 | 26473 | 36276 | 21754 |
| 9.9 | 46087 | 25409 | 24900 | 22571 | 29101 | 22029 | 26395 | 37536 | 20578 |
| 9.94 | 47059 | 23966 | 23565 | 24589 | 28542 | 24835 | 25788 | 37403 | 19880 |
| 9.98 | 48508 | 23309 | 25917 | 24362 | 26505 | 23086 | 25997 | 39382 | 23935 |
| 10.02 | 53199 | 21025 | 26270 | 23933 | 27202 | 21739 | 25306 | 36884 | 22389 |
| 10.06 | 53368 | 23401 | 25621 | 23468 | 31072 | 24770 | 26297 | 39079 | 23114 |
| 10.1 | 52666 | 25348 | 23838 | 25730 | 29186 | 22307 | 23512 | 37884 | 23302 |
| 10.14 | 49601 | 24612 | 23590 | 24128 | 30627 | 24814 | 25742 | 38749 | 24014 |
| 10.18 | 51725 | 24861 | 24252 | 24069 | 29467 | 22788 | 27081 | 39899 | 24082 |
| 10.22 | 54805 | 26679 | 24423 | 24626 | 26637 | 23281 | 26199 | 38165 | 21168 |
| 10.26 | 51970 | 27118 | 25216 | 24937 | 26957 | 27442 | 24443 | 38276 | 23343 |
| 10.3 | 50931 | 27123 | 26112 | 22554 | 28941 | 25954 | 25507 | 39244 | 23787 |
| 10.34 | 53291 | 27636 | 24513 | 25475 | 27598 | 26203 | 28924 | 38213 | 22715 |
| 10.38 | 55344 | 27181 | 24778 | 23192 | 28151 | 23395 | 27587 | 37188 | 26118 |
| 10.42 | 50801 | 27008 | 26007 | 23188 | 27533 | 24043 | 25940 | 43168 | 20982 |
| 10.46 | 53034 | 28100 | 29862 | 23689 | 26121 | 23502 | 27091 | 39626 | 23322 |
| 10.5 | 59299 | 25641 | 28352 | 24114 | 27050 | 25332 | 27106 | 41255 | 22421 |
| 10.54 | 56283 | 27104 | 24681 | 22313 | 26825 | 28293 | 26119 | 40410 | 23836 |
| 10.58 | 56208 | 25572 | 27732 | 22462 | 24644 | 27046 | 25615 | 42322 | 24276 |
| 10.62 | 55073 | 25196 | 29800 | 25471 | 24227 | 26849 | 26568 | 39862 | 26359 |
| 10.66 | 53296 | 25848 | 27420 | 23597 | 27890 | 27031 | 26884 | 40645 | 25709 |
| 10.7 | 52592 | 25873 | 24811 | 22712 | 25286 | 27132 | 29007 | 40984 | 25940 |
| 10.74 | 51407 | 25895 | 27390 | 24743 | 25595 | 28439 | 26830 | 39981 | 27641 |
| 10.78 | 40849 | 25639 | 27728 | 22461 | 25625 | 27276 | 28016 | 43960 | 26367 |
| 10.82 | 42254 | 24691 | 28068 | 26207 | 27512 | 29709 | 28159 | 40463 | 24497 |
| 10.86 | 41187 | 26635 | 30930 | 24518 | 27268 | 33241 | 28417 | 41291 | 24314 |
| 10.9 | 38915 | 26048 | 29609 | 25980 | 26037 | 33439 | 27526 | 43261 | 26607 |
| 10.94 | 38545 | 23809 | 29492 | 24750 | 28683 | 27717 | 27659 | 42673 | 26001 |
| 10.98 | 40731 | 24323 | 27161 | 23086 | 29027 | 31019 | 27443 | 43528 | 26204 |
| 11.02 | 36389 | 21871 | 29699 | 25794 | 27161 | 30192 | 26229 | 45785 | 24618 |
| 11.06 | 35209 | 25048 | 30712 | 25418 | 25924 | 30018 | 29247 | 43919 | 25963 |
| 11.1 | 35232 | 25778 | 28510 | 26069 | 29381 | 31001 | 27000 | 42272 | 25012 |
| 11.14 | 35109 | 25416 | 30908 | 25230 | 28861 | 28137 | 26731 | 45226 | 25439 |
| 11.18 | 35242 | 23566 | 29251 | 24808 | 26866 | 26656 | 27273 | 40482 | 27876 |
| 11.22 | 34786 | 22958 | 27367 | 24256 | 26240 | 29692 | 27617 | 43234 | 23891 |
| 11.26 | 33543 | 23733 | 31326 | 25703 | 29574 | 31345 | 27598 | 47425 | 24720 |
| 11.3 | 36372 | 24566 | 28549 | 26380 | 26929 | 30181 | 26350 | 45415 | 23816 |
| 11.34 | 34361 | 25703 | 29631 | 26604 | 27194 | 30543 | 28662 | 44856 | 28491 |
| 11.38 | 36382 | 25187 | 27294 | 25182 | 28474 | 31923 | 27744 | 47562 | 25585 |
| 11.42 | 35006 | 22536 | 26568 | 26418 | 27233 | 31793 | 28580 | 47007 | 24551 |
| 11.46 | 35798 | 26202 | 28751 | 25420 | 28729 | 31438 | 29365 | 48759 | 27683 |
| 11.5 | 35149 | 22699 | 28921 | 27738 | 25014 | 33194 | 30907 | 45542 | 24852 |
| 11.54 | 34438 | 25690 | 27130 | 29472 | 28202 | 37897 | 31528 | 46426 | 27527 |
| 11.58 | 34942 | 27252 | 30008 | 30889 | 26099 | 40894 | 32493 | 47138 | 25832 |
| 11.62 | 33260 | 26077 | 28952 | 31674 | 28457 | 43657 | 34462 | 46800 | 26810 |
| 11.66 | 36945 | 26725 | 31982 | 27858 | 29438 | 50632 | 32731 | 46667 | 24948 |
| 11.7 | 37919 | 27021 | 30814 | 28056 | 27274 | 52479 | 35717 | 48334 | 27994 |
| 11.74 | 34600 | 24945 | 28966 | 27946 | 28448 | 53051 | 36674 | 49627 | 25490 |
| 11.78 | 34388 | 28779 | 29904 | 28358 | 29669 | 54544 | 37010 | 48382 | 26643 |
| 11.82 | 36526 | 26896 | 27819 | 27583 | 28587 | 53738 | 35827 | 46744 | 26352 |
| 11.86 | 36412 | 28488 | 28914 | 27573 | 30716 | 52763 | 35430 | 45560 | 27583 |
| 11.9 | 34848 | 27561 | 31448 | 29343 | 33679 | 52936 | 35109 | 45418 | 25911 |
| 11.94 | 35715 | 28644 | 31387 | 30095 | 36491 | 46697 | 35166 | 46261 | 28737 |
| 11.98 | 34350 | 32011 | 32782 | 31655 | 31551 | 43090 | 35066 | 46211 | 27321 |
| 12.02 | 34800 | 31177 | 32956 | 34724 | 32377 | 36341 | 33301 | 47334 | 28475 |
| 12.06 | 36952 | 32405 | 32773 | 35181 | 36175 | 38466 | 34707 | 48421 | 28030 |
| 12.1 | 34664 | 31429 | 30196 | 40158 | 32844 | 32740 | 31529 | 43054 | 29495 |
| 12.14 | 35935 | 34616 | 31389 | 42704 | 36487 | 34335 | 30359 | 44688 | 31253 |
| 12.18 | 36929 | 35914 | 32676 | 46116 | 35260 | 30759 | 29487 | 46628 | 27590 |
| 12.22 | 37310 | 33255 | 31683 | 46746 | 34046 | 32941 | 31305 | 50811 | 27613 |
| 12.26 | 35991 | 36438 | 30640 | 48182 | 36611 | 32804 | 31703 | 51535 | 29909 |
| 12.3 | 37745 | 35110 | 31918 | 46202 | 36047 | 31100 | 30401 | 50692 | 31238 |
| 12.34 | 37175 | 35741 | 30168 | 44515 | 32089 | 32030 | 28487 | 53852 | 28259 |
| 12.38 | 36522 | 32448 | 31094 | 44052 | 34135 | 31083 | 30744 | 57542 | 33101 |
| 12.42 | 36813 | 32908 | 30133 | 38325 | 34038 | 34659 | 28512 | 60392 | 30929 |
| 12.46 | 37651 | 31003 | 30373 | 36162 | 30314 | 33072 | 30771 | 61841 | 28498 |
| 12.5 | 38806 | 29347 | 30405 | 32353 | 30605 | 32940 | 30698 | 64775 | 31546 |
| 12.54 | 35123 | 29615 | 28368 | 29986 | 31488 | 33295 | 29001 | 78909 | 30246 |
| 12.58 | 36932 | 30262 | 30078 | 29403 | 32532 | 33473 | 31099 | 78275 | 32218 |
| 12.62 | 38942 | 28013 | 30018 | 28599 | 31511 | 32352 | 32455 | 80321 | 31123 |
| 12.66 | 38610 | 30741 | 30524 | 27691 | 32761 | 32213 | 33942 | 83096 | 30299 |
| 12.7 | 36897 | 32883 | 30329 | 26577 | 31010 | 34317 | 32708 | 85031 | 30347 |
| 12.74 | 36621 | 28871 | 30389 | 25126 | 30614 | 32223 | 32745 | 82837 | 29315 |
| 12.78 | 38365 | 31721 | 33124 | 25342 | 30356 | 30314 | 31023 | 77255 | 30776 |
| 12.82 | 41335 | 30985 | 29996 | 25143 | 30668 | 31042 | 30884 | 73576 | 29911 |

-continued

| | | | | | | | | | |
|---|---|---|---|---|---|---|---|---|---|
| 12.86 | 42654 | 28167 | 29272 | 27607 | 30731 | 28747 | 33620 | 64217 | 31957 |
| 12.9 | 47249 | 29826 | 31298 | 25286 | 29423 | 29704 | 33885 | 63654 | 30691 |
| 12.94 | 48109 | 31806 | 31200 | 26343 | 32472 | 29366 | 34466 | 57643 | 28781 |
| 12.98 | 48675 | 30821 | 31571 | 25882 | 31812 | 31387 | 33637 | 56812 | 29404 |
| 13.02 | 48394 | 32465 | 32984 | 26013 | 34555 | 32737 | 32898 | 54131 | 29000 |
| 13.06 | 47039 | 33363 | 32315 | 25775 | 30730 | 33110 | 34729 | 52682 | 28363 |
| 13.1 | 43553 | 32479 | 35051 | 25252 | 30928 | 34763 | 32550 | 50392 | 29227 |
| 13.14 | 41970 | 30478 | 33406 | 25275 | 35155 | 33413 | 34952 | 51299 | 27960 |
| 13.18 | 41476 | 33011 | 34628 | 25852 | 35643 | 37206 | 32668 | 50738 | 29588 |
| 13.22 | 40118 | 34702 | 35187 | 26271 | 33060 | 36868 | 31716 | 52525 | 27960 |
| 13.26 | 38596 | 33993 | 38899 | 27880 | 37437 | 35490 | 32378 | 54765 | 29562 |
| 13.3 | 38107 | 34828 | 35934 | 29168 | 33902 | 39165 | 32328 | 55549 | 30375 |
| 13.34 | 39007 | 34686 | 39430 | 28153 | 37278 | 35547 | 34522 | 58828 | 29150 |
| 13.38 | 37382 | 34739 | 38332 | 28766 | 40593 | 37406 | 34949 | 61880 | 28757 |
| 13.42 | 38745 | 38419 | 38396 | 28468 | 37986 | 34679 | 35012 | 57244 | 30674 |
| 13.46 | 40477 | 39662 | 38997 | 26727 | 42470 | 30139 | 31859 | 61608 | 30093 |
| 13.5 | 41700 | 40923 | 37115 | 26458 | 39794 | 32444 | 33294 | 59865 | 30249 |
| 13.54 | 43915 | 42116 | 40042 | 29099 | 39096 | 28931 | 33754 | 58318 | 32213 |
| 13.58 | 41436 | 42449 | 37027 | 32942 | 38793 | 26691 | 30937 | 58290 | 32601 |
| 13.62 | 40945 | 42766 | 38336 | 30893 | 39325 | 29281 | 32226 | 54712 | 28619 |
| 13.66 | 43295 | 41075 | 39168 | 33404 | 37625 | 29407 | 32740 | 54641 | 32636 |
| 13.7 | 40080 | 39703 | 38993 | 36425 | 37914 | 29995 | 34321 | 48874 | 31423 |
| 13.74 | 41898 | 39081 | 38592 | 42426 | 37113 | 29462 | 31801 | 51199 | 30311 |
| 13.78 | 40340 | 37318 | 42596 | 47118 | 38033 | 28441 | 31535 | 50581 | 31905 |
| 13.82 | 43706 | 35490 | 39067 | 55227 | 35062 | 29042 | 32947 | 48217 | 30307 |
| 13.86 | 42886 | 34502 | 38428 | 52170 | 35870 | 28668 | 29612 | 54822 | 31002 |
| 13.9 | 43346 | 34759 | 39136 | 57100 | 35387 | 28458 | 30209 | 52386 | 29528 |
| 13.94 | 42527 | 34449 | 37604 | 61608 | 37305 | 29401 | 30952 | 49840 | 29604 |
| 13.98 | 43911 | 31451 | 40464 | 62055 | 37050 | 27256 | 32349 | 56747 | 29669 |
| 14.02 | 46146 | 32185 | 39101 | 58226 | 33446 | 27847 | 30843 | 55113 | 30350 |
| 14.06 | 46795 | 30541 | 38648 | 49322 | 31172 | 26671 | 31701 | 56455 | 29638 |
| 14.1 | 45599 | 31579 | 38439 | 49147 | 32408 | 29903 | 29489 | 59460 | 27391 |
| 14.14 | 42918 | 32750 | 38817 | 45160 | 33196 | 29584 | 29425 | 59992 | 30785 |
| 14.18 | 45142 | 34066 | 38375 | 36754 | 32316 | 29945 | 32334 | 54784 | 29642 |
| 14.22 | 42669 | 35495 | 39115 | 32736 | 32202 | 32359 | 31401 | 55751 | 31142 |
| 14.26 | 41873 | 36694 | 37983 | 28228 | 34711 | 32126 | 31855 | 52933 | 30683 |
| 14.3 | 41569 | 37807 | 39401 | 28989 | 31200 | 33568 | 30533 | 53263 | 30845 |
| 14.34 | 37873 | 37897 | 37368 | 24629 | 33545 | 31559 | 30505 | 49357 | 31431 |
| 14.38 | 37265 | 41259 | 37173 | 26196 | 34204 | 36111 | 29346 | 53500 | 30817 |
| 14.42 | 36483 | 40377 | 36697 | 25518 | 34724 | 35570 | 30697 | 49939 | 34319 |
| 14.46 | 33137 | 36605 | 36947 | 25331 | 35072 | 34421 | 28644 | 48657 | 30161 |
| 14.5 | 33175 | 37897 | 33519 | 27366 | 32623 | 33238 | 30372 | 46418 | 31267 |
| 14.54 | 33359 | 39053 | 33687 | 25781 | 31643 | 32531 | 29642 | 46648 | 33147 |
| 14.58 | 30923 | 35166 | 36331 | 25623 | 31370 | 31124 | 30722 | 46732 | 32803 |
| 14.62 | 28399 | 35409 | 37158 | 24172 | 32689 | 29187 | 30310 | 44825 | 30979 |
| 14.66 | 30120 | 37147 | 37602 | 24223 | 31893 | 29634 | 28659 | 46528 | 31719 |
| 14.7 | 30052 | 34429 | 36757 | 23733 | 32150 | 29879 | 27323 | 42623 | 29664 |
| 14.74 | 28703 | 30479 | 34482 | 24268 | 31425 | 28261 | 30681 | 46725 | 30693 |
| 14.78 | 29759 | 33453 | 37401 | 24606 | 33176 | 25991 | 28552 | 47675 | 33047 |
| 14.82 | 29300 | 33637 | 35428 | 26483 | 31543 | 26135 | 29189 | 46981 | 29191 |
| 14.86 | 28249 | 33792 | 39623 | 26081 | 32472 | 26078 | 30448 | 47646 | 29572 |
| 14.9 | 30022 | 34272 | 37478 | 25966 | 31290 | 25359 | 28982 | 45246 | 30170 |
| 14.94 | 28492 | 32283 | 37697 | 29930 | 32671 | 24704 | 29454 | 47039 | 29212 |
| 14.98 | 28800 | 30650 | 37254 | 31873 | 32007 | 25196 | 30498 | 44279 | 32503 |
| 15.02 | 30688 | 33760 | 38200 | 34337 | 33873 | 24656 | 30125 | 43923 | 31391 |
| 15.06 | 30168 | 34019 | 35775 | 37327 | 33832 | 26410 | 29107 | 46700 | 31948 |
| 15.1 | 29068 | 31822 | 36710 | 39644 | 31747 | 25712 | 30280 | 48539 | 31564 |
| 15.14 | 29135 | 28816 | 36272 | 40912 | 32067 | 25805 | 30971 | 46396 | 33238 |
| 15.18 | 31236 | 33462 | 36557 | 44265 | 32358 | 26256 | 30509 | 49555 | 33629 |
| 15.22 | 32848 | 34419 | 37688 | 46562 | 31800 | 25300 | 31881 | 54973 | 32986 |
| 15.26 | 28967 | 31955 | 38915 | 40859 | 34296 | 27633 | 32347 | 57292 | 35534 |
| 15.3 | 28902 | 34594 | 38286 | 40921 | 33972 | 28214 | 32296 | 63163 | 35119 |
| 15.34 | 29447 | 34617 | 36329 | 40382 | 33259 | 29319 | 33659 | 64449 | 33107 |
| 15.38 | 26785 | 35067 | 36620 | 36584 | 33131 | 30652 | 32981 | 66893 | 33587 |
| 15.42 | 30477 | 35667 | 38320 | 32090 | 35577 | 33000 | 32678 | 67130 | 33107 |
| 15.46 | 30609 | 37177 | 40384 | 31730 | 37000 | 31373 | 32156 | 64049 | 34113 |
| 15.5 | 30682 | 37699 | 38862 | 28852 | 36071 | 34157 | 32091 | 64438 | 30973 |
| 15.54 | 33484 | 39802 | 37532 | 29038 | 35952 | 34090 | 32213 | 64751 | 30590 |
| 15.58 | 32953 | 40064 | 37538 | 29314 | 37979 | 34026 | 32132 | 64436 | 32039 |
| 15.62 | 33112 | 40438 | 44384 | 27247 | 37905 | 32639 | 31512 | 62069 | 33639 |
| 15.66 | 30540 | 40673 | 40641 | 27689 | 38477 | 32764 | 34215 | 58597 | 30047 |
| 15.7 | 33767 | 40084 | 40923 | 26841 | 33756 | 33639 | 34560 | 55592 | 29684 |
| 15.74 | 35538 | 37914 | 39366 | 26610 | 37525 | 31702 | 35688 | 57247 | 30721 |
| 15.78 | 34874 | 39284 | 41346 | 24771 | 37708 | 30763 | 33874 | 55477 | 29276 |
| 15.82 | 34748 | 37718 | 40485 | 25997 | 38860 | 31445 | 32930 | 56292 | 31498 |
| 15.86 | 33226 | 39247 | 41024 | 26233 | 38805 | 30284 | 33362 | 55693 | 30115 |
| 15.9 | 32270 | 37575 | 42059 | 24089 | 37326 | 28526 | 36571 | 54073 | 27631 |
| 15.94 | 34234 | 38814 | 39781 | 23014 | 39728 | 32693 | 34969 | 54981 | 29837 |
| 15.98 | 32999 | 38876 | 42408 | 25273 | 39554 | 29771 | 34907 | 52587 | 30804 |

-continued

| | | | | | | | | | |
|---|---|---|---|---|---|---|---|---|---|
| 16.02 | 31947 | 39708 | 42358 | 26212 | 42704 | 32014 | 34871 | 52892 | 29575 |
| 16.06 | 33462 | 40223 | 43102 | 25613 | 41745 | 31802 | 36477 | 55162 | 31205 |
| 16.1 | 31625 | 40089 | 40022 | 26019 | 42898 | 33852 | 34484 | 57972 | 29183 |
| 16.14 | 34844 | 39322 | 43134 | 25275 | 42295 | 35890 | 35553 | 61890 | 28013 |
| 16.18 | 31513 | 36824 | 42066 | 25120 | 43183 | 36567 | 34795 | 59099 | 31688 |
| 16.22 | 33380 | 40397 | 43809 | 23223 | 42168 | 37786 | 36172 | 60172 | 30960 |
| 16.26 | 32004 | 40280 | 41351 | 25963 | 40896 | 39212 | 33693 | 65921 | 29187 |
| 16.3 | 32240 | 38620 | 45385 | 25932 | 42009 | 34612 | 32922 | 71196 | 30255 |
| 16.34 | 33023 | 36558 | 44021 | 25066 | 39828 | 34582 | 34151 | 72357 | 29825 |
| 16.38 | 31713 | 36680 | 43614 | 24383 | 41892 | 36923 | 33070 | 73878 | 31116 |
| 16.42 | 30772 | 34934 | 43829 | 25392 | 38641 | 36367 | 34423 | 77999 | 31734 |
| 16.46 | 32663 | 36924 | 41426 | 25469 | 40625 | 34248 | 32979 | 77271 | 29130 |
| 16.5 | 33000 | 35388 | 43787 | 26066 | 38629 | 38207 | 32534 | 72366 | 31044 |
| 16.54 | 30138 | 37776 | 42370 | 26880 | 37108 | 37398 | 32827 | 71278 | 31182 |
| 16.58 | 32249 | 38190 | 41382 | 26415 | 34423 | 34972 | 31886 | 74594 | 29090 |
| 16.62 | 32143 | 38674 | 43141 | 30608 | 34930 | 35661 | 31993 | 72663 | 31104 |
| 16.66 | 33142 | 41252 | 43937 | 30607 | 33076 | 34502 | 32814 | 70923 | 27860 |
| 16.7 | 32651 | 39171 | 41021 | 32415 | 34125 | 33224 | 31107 | 72278 | 30413 |
| 16.74 | 32988 | 40239 | 40132 | 34758 | 35558 | 32531 | 30078 | 73909 | 28169 |
| 16.78 | 32443 | 39972 | 41565 | 41599 | 35713 | 33140 | 30614 | 77348 | 29076 |
| 16.82 | 32006 | 39248 | 39427 | 42505 | 33476 | 31485 | 30103 | 77546 | 30138 |
| 16.86 | 32875 | 39093 | 38142 | 47870 | 34528 | 30155 | 30427 | 73720 | 27138 |
| 16.9 | 31653 | 37666 | 38028 | 49102 | 33791 | 30536 | 28304 | 76926 | 27837 |
| 16.94 | 30170 | 36866 | 39757 | 53518 | 33744 | 26882 | 29307 | 70547 | 28209 |
| 16.98 | 33188 | 37889 | 39508 | 57893 | 33279 | 27995 | 29403 | 71241 | 26622 |
| 17.02 | 29598 | 37443 | 40623 | 58292 | 32494 | 30697 | 29008 | 67504 | 28116 |
| 17.06 | 33215 | 36000 | 40203 | 62186 | 32689 | 30056 | 29247 | 64719 | 28517 |
| 17.1 | 31522 | 32954 | 37808 | 61062 | 31616 | 29836 | 29441 | 63558 | 28196 |
| 17.14 | 30829 | 34009 | 39781 | 64388 | 34008 | 30848 | 28540 | 58730 | 26535 |
| 17.18 | 31197 | 31779 | 39185 | 65147 | 31845 | 33837 | 28734 | 55385 | 26371 |
| 17.22 | 32402 | 31418 | 40236 | 60569 | 33400 | 33225 | 26399 | 54864 | 26998 |
| 17.26 | 29582 | 29248 | 40204 | 57721 | 32684 | 33755 | 28638 | 55074 | 27245 |
| 17.3 | 30371 | 28120 | 39695 | 51579 | 33645 | 32681 | 26937 | 54715 | 25907 |
| 17.34 | 33759 | 26605 | 40129 | 47941 | 34939 | 34092 | 26039 | 53322 | 27909 |
| 17.38 | 31668 | 29844 | 40459 | 45700 | 31372 | 32016 | 27853 | 51892 | 28120 |
| 17.42 | 29634 | 30951 | 39952 | 42536 | 32239 | 29996 | 27788 | 49718 | 27627 |
| 17.46 | 31967 | 31145 | 40301 | 37138 | 32624 | 30265 | 29981 | 53478 | 27106 |
| 17.5 | 32208 | 33772 | 39132 | 33120 | 30590 | 28219 | 28256 | 52289 | 27284 |
| 17.54 | 32316 | 36547 | 38894 | 30911 | 30958 | 26210 | 27701 | 49484 | 27564 |
| 17.58 | 31075 | 38766 | 41679 | 28539 | 29927 | 26369 | 25890 | 49911 | 26479 |
| 17.62 | 31973 | 40830 | 40889 | 25268 | 31665 | 24666 | 25971 | 45738 | 27842 |
| 17.66 | 31959 | 42129 | 36935 | 23211 | 31316 | 24365 | 28884 | 48367 | 26950 |
| 17.7 | 31707 | 42084 | 38849 | 24200 | 30047 | 23535 | 25685 | 49342 | 28868 |
| 17.74 | 33402 | 42265 | 40442 | 22845 | 31038 | 23973 | 28089 | 47599 | 27731 |
| 17.78 | 35907 | 42615 | 37717 | 22563 | 30633 | 25149 | 27050 | 46303 | 27674 |
| 17.82 | 33725 | 37868 | 38585 | 23874 | 31422 | 22650 | 27593 | 49959 | 27442 |
| 17.86 | 34234 | 38156 | 39119 | 22185 | 29276 | 23355 | 27721 | 47401 | 27919 |
| 17.9 | 33394 | 37680 | 39563 | 22660 | 29828 | 23929 | 25825 | 47846 | 29225 |
| 17.94 | 35274 | 31247 | 36651 | 23097 | 28712 | 25951 | 27412 | 48840 | 29091 |
| 17.98 | 34003 | 31998 | 38639 | 21284 | 31624 | 24530 | 27728 | 47244 | 29953 |
| 18.02 | 33714 | 32329 | 38307 | 20919 | 29081 | 23602 | 27837 | 49822 | 30424 |
| 18.06 | 33261 | 29995 | 35684 | 23464 | 30077 | 23051 | 29590 | 50026 | 29600 |
| 18.1 | 34717 | 29276 | 40104 | 24530 | 31483 | 25252 | 28922 | 50162 | 31179 |
| 18.14 | 33809 | 29982 | 37274 | 24053 | 29880 | 22664 | 27293 | 52184 | 30919 |
| 18.18 | 33156 | 28485 | 37881 | 23161 | 34770 | 24846 | 28339 | 54164 | 29510 |
| 18.22 | 34238 | 27717 | 40814 | 22612 | 32522 | 25341 | 27192 | 55173 | 31271 |
| 18.26 | 35428 | 28314 | 36874 | 24669 | 33909 | 25364 | 25779 | 52998 | 31512 |
| 18.3 | 34634 | 29656 | 37912 | 24710 | 32015 | 25723 | 26239 | 55225 | 30458 |
| 18.34 | 35982 | 29587 | 40126 | 26653 | 33725 | 27684 | 27492 | 51220 | 29736 |
| 18.38 | 35089 | 28499 | 39205 | 26640 | 34227 | 29324 | 26127 | 51769 | 28808 |
| 18.42 | 35124 | 32242 | 38573 | 26584 | 34072 | 27460 | 27002 | 49394 | 26117 |
| 18.46 | 35338 | 34174 | 39590 | 28220 | 35299 | 30274 | 27006 | 48586 | 27983 |
| 18.5 | 36127 | 32635 | 37977 | 26886 | 34650 | 28124 | 27351 | 51625 | 26218 |
| 18.54 | 35969 | 36985 | 41192 | 26111 | 33835 | 28654 | 25202 | 49320 | 26948 |
| 18.58 | 36791 | 35523 | 40021 | 26562 | 35940 | 28245 | 26202 | 48106 | 26147 |
| 18.62 | 38097 | 36553 | 37143 | 26383 | 34105 | 27257 | 25891 | 47955 | 27184 |
| 18.66 | 36366 | 39062 | 39794 | 26685 | 31851 | 26934 | 24957 | 48510 | 26944 |
| 18.7 | 37109 | 38420 | 40615 | 24237 | 34053 | 26223 | 26799 | 46967 | 25261 |
| 18.74 | 34976 | 39451 | 42304 | 23003 | 33317 | 25719 | 24249 | 45278 | 26790 |
| 18.78 | 39515 | 38094 | 40012 | 22164 | 35532 | 25009 | 27562 | 46965 | 24283 |
| 18.82 | 36760 | 39824 | 40827 | 23278 | 35134 | 25427 | 25842 | 49129 | 25380 |
| 18.86 | 38482 | 39688 | 41485 | 21943 | 31386 | 24863 | 27068 | 50147 | 26874 |
| 18.9 | 36460 | 40077 | 42640 | 22638 | 33452 | 21397 | 27225 | 49095 | 24319 |
| 18.94 | 33116 | 40303 | 39223 | 21398 | 33271 | 21375 | 26967 | 52012 | 26686 |
| 18.98 | 35542 | 36666 | 41265 | 20999 | 35124 | 21337 | 27045 | 52194 | 24573 |
| 19.02 | 32435 | 35823 | 42572 | 22477 | 35666 | 21120 | 26990 | 52084 | 25375 |
| 19.06 | 32284 | 36266 | 43129 | 25215 | 33362 | 21447 | 27928 | 53172 | 23705 |
| 19.1 | 34163 | 37445 | 39986 | 23030 | 30786 | 20949 | 27466 | 51843 | 24120 |
| 19.14 | 30451 | 35296 | 41426 | 23425 | 31086 | 21977 | 27383 | 51588 | 24709 |

-continued

| | | | | | | | | | |
|---|---|---|---|---|---|---|---|---|---|
| 19.18 | 31548 | 34742 | 40799 | 27831 | 32356 | 24843 | 28195 | 53436 | 24932 |
| 19.22 | 34085 | 33225 | 41719 | 26276 | 34430 | 21817 | 26847 | 52373 | 23965 |
| 19.26 | 31912 | 33804 | 42919 | 30023 | 34961 | 22193 | 29039 | 52439 | 24980 |
| 19.3 | 33124 | 32922 | 44059 | 30626 | 36147 | 24473 | 27846 | 51018 | 23738 |
| 19.34 | 32171 | 32773 | 44694 | 32770 | 35973 | 24257 | 29942 | 52216 | 23861 |
| 19.38 | 34441 | 33721 | 44522 | 34931 | 37787 | 23988 | 28674 | 52829 | 24942 |
| 19.42 | 34146 | 33232 | 42309 | 35573 | 39974 | 25647 | 27813 | 52655 | 23878 |
| 19.46 | 34112 | 33580 | 41343 | 35129 | 37544 | 25940 | 29705 | 49638 | 23328 |
| 19.5 | 35457 | 34906 | 40145 | 33078 | 36933 | 26015 | 29149 | 49297 | 23758 |
| 19.54 | 37755 | 35594 | 42118 | 33406 | 36271 | 26889 | 27994 | 50603 | 26179 |
| 19.58 | 40273 | 33584 | 42854 | 32766 | 37206 | 27984 | 28985 | 51609 | 25111 |
| 19.62 | 42133 | 34795 | 41593 | 31514 | 37255 | 27489 | 29055 | 53634 | 24057 |
| 19.66 | 44612 | 33026 | 38992 | 27423 | 35218 | 28529 | 28420 | 56171 | 23698 |
| 19.7 | 47681 | 34456 | 41728 | 28512 | 35224 | 31374 | 30546 | 52840 | 25569 |
| 19.74 | 45553 | 34394 | 40192 | 25770 | 36642 | 29002 | 30265 | 54766 | 23617 |
| 19.78 | 43517 | 34876 | 39771 | 24913 | 36659 | 32884 | 29870 | 55705 | 25168 |
| 19.82 | 46446 | 33646 | 40262 | 23852 | 35365 | 33295 | 29238 | 60119 | 23257 |
| 19.86 | 46907 | 34796 | 40394 | 20650 | 34471 | 35069 | 28431 | 58426 | 25572 |
| 19.9 | 47109 | 34145 | 40790 | 20032 | 36344 | 35833 | 28977 | 59110 | 25295 |
| 19.94 | 45753 | 36290 | 41151 | 21386 | 33451 | 34237 | 32221 | 59551 | 24293 |
| 19.98 | 44066 | 34241 | 40920 | 22262 | 36217 | 34760 | 30693 | 56605 | 25150 |
| 20.02 | 45404 | 34032 | 42146 | 21228 | 35794 | 36308 | 29318 | 58500 | 25457 |
| 20.06 | 42623 | 34192 | 43746 | 20985 | 36140 | 35114 | 30576 | 56243 | 25070 |
| 20.1 | 41746 | 33703 | 42842 | 20754 | 35266 | 34598 | 29711 | 53842 | 25246 |
| 20.14 | 38948 | 33019 | 43399 | 22574 | 36757 | 34540 | 29094 | 55398 | 25923 |
| 20.18 | 39448 | 33178 | 42267 | 20820 | 38399 | 31985 | 29548 | 53886 | 25477 |
| 20.22 | 38080 | 32607 | 43186 | 22573 | 37356 | 29616 | 31156 | 53869 | 26335 |
| 20.26 | 39077 | 33831 | 44310 | 23528 | 33721 | 28370 | 30322 | 56863 | 26194 |
| 20.3 | 37064 | 34650 | 42784 | 22392 | 35279 | 27712 | 30347 | 56746 | 26876 |
| 20.34 | 39144 | 36187 | 45552 | 22457 | 35213 | 27479 | 29992 | 61426 | 25911 |
| 20.38 | 39206 | 36664 | 45553 | 22464 | 35705 | 25782 | 30717 | 64277 | 25509 |
| 20.42 | 39855 | 36054 | 43570 | 23857 | 35165 | 25520 | 30798 | 65791 | 27664 |
| 20.46 | 40339 | 36497 | 43747 | 24622 | 35562 | 25873 | 31348 | 68131 | 26669 |
| 20.5 | 40360 | 35042 | 44104 | 25765 | 34734 | 25490 | 30939 | 67016 | 27794 |
| 20.54 | 40855 | 35653 | 45356 | 26489 | 35654 | 24465 | 30419 | 67465 | 25110 |
| 20.58 | 39531 | 33868 | 44260 | 29446 | 34237 | 23817 | 29439 | 63890 | 26764 |
| 20.62 | 41378 | 33513 | 44410 | 27861 | 35775 | 23243 | 28309 | 63889 | 26314 |
| 20.66 | 40316 | 33508 | 43727 | 30119 | 34675 | 22149 | 29298 | 61505 | 26140 |
| 20.7 | 42426 | 31117 | 42938 | 31598 | 33553 | 22494 | 27948 | 57386 | 25283 |
| 20.74 | 41266 | 31558 | 41164 | 32761 | 34252 | 21339 | 27964 | 55569 | 24982 |
| 20.78 | 41978 | 31506 | 40664 | 33481 | 33538 | 20929 | 27338 | 52069 | 24107 |
| 20.82 | 44513 | 30412 | 42821 | 31770 | 34030 | 21218 | 27453 | 48060 | 23361 |
| 20.86 | 43998 | 30128 | 41732 | 31906 | 32019 | 22437 | 27582 | 46598 | 24591 |
| 20.9 | 40823 | 27855 | 43178 | 31503 | 31376 | 23172 | 29988 | 45850 | 26218 |
| 20.94 | 47289 | 28438 | 45194 | 32328 | 32974 | 21461 | 30129 | 49184 | 25916 |
| 20.98 | 44119 | 28097 | 41232 | 28532 | 30763 | 23087 | 29100 | 47475 | 24884 |
| 21.02 | 40693 | 25448 | 41544 | 31485 | 30307 | 22748 | 27962 | 45174 | 24667 |
| 21.06 | 41844 | 28788 | 46112 | 27754 | 33946 | 23078 | 26858 | 44650 | 23944 |
| 21.1 | 43132 | 28844 | 41960 | 30522 | 30876 | 21211 | 29013 | 48889 | 23202 |
| 21.14 | 38964 | 25456 | 38138 | 32420 | 29172 | 22769 | 26594 | 44985 | 26906 |
| 21.18 | 42209 | 25873 | 39987 | 32261 | 34096 | 22121 | 27525 | 47860 | 23513 |
| 21.22 | 39754 | 25791 | 42783 | 32208 | 33182 | 21721 | 26003 | 49357 | 24178 |
| 21.26 | 38407 | 26888 | 43976 | 32308 | 30924 | 21270 | 26785 | 45507 | 23490 |
| 21.3 | 38516 | 23454 | 43039 | 34585 | 28754 | 22414 | 26658 | 52331 | 21860 |
| 21.34 | 42637 | 26927 | 41494 | 37776 | 31550 | 21801 | 25499 | 53629 | 23977 |
| 21.38 | 41415 | 27676 | 39709 | 37994 | 29869 | 22466 | 25112 | 56093 | 24187 |
| 21.42 | 40039 | 22635 | 40271 | 38832 | 32455 | 22853 | 24383 | 54125 | 22196 |
| 21.46 | 38640 | 25346 | 40998 | 41382 | 29352 | 21305 | 27924 | 59201 | 22719 |
| 21.5 | 38607 | 26717 | 41121 | 43507 | 29438 | 20855 | 27161 | 59055 | 23532 |
| 21.54 | 37444 | 28819 | 37072 | 37198 | 31195 | 22845 | 24771 | 56097 | 23673 |
| 21.58 | 35228 | 25812 | 41435 | 35925 | 32510 | 23381 | 24130 | 55119 | 24327 |
| 21.62 | 36333 | 29206 | 44341 | 34031 | 30506 | 23019 | 27360 | 54962 | 23851 |
| 21.66 | 36423 | 29674 | 39714 | 32812 | 30439 | 22768 | 23043 | 53940 | 23533 |
| 21.7 | 35919 | 28817 | 40715 | 28169 | 28610 | 20951 | 25341 | 49495 | 23724 |
| 21.74 | 36179 | 27748 | 40215 | 31012 | 30482 | 21379 | 24800 | 50121 | 26576 |
| 21.78 | 36916 | 27610 | 41347 | 25139 | 27859 | 22191 | 23633 | 50246 | 22845 |
| 21.82 | 35100 | 29092 | 41384 | 27286 | 27591 | 20685 | 22511 | 46054 | 24173 |
| 21.86 | 33115 | 30653 | 42166 | 26195 | 29789 | 21020 | 24766 | 47521 | 25382 |
| 21.9 | 33189 | 31108 | 40142 | 23693 | 30309 | 21756 | 26010 | 46428 | 23963 |
| 21.94 | 36601 | 31902 | 39924 | 22822 | 29070 | 23145 | 26483 | 46440 | 26084 |
| 21.98 | 33632 | 31362 | 42081 | 22562 | 28788 | 21805 | 25497 | 47540 | 23494 |
| 22.02 | 35648 | 33150 | 40419 | 22823 | 30323 | 20824 | 26812 | 49355 | 25836 |
| 22.06 | 35831 | 30756 | 41067 | 23389 | 29243 | 20959 | 25220 | 45312 | 26961 |
| 22.1 | 35269 | 29395 | 39645 | 22699 | 29656 | 19126 | 23060 | 49322 | 25609 |
| 22.14 | 32959 | 30001 | 41825 | 22838 | 30624 | 22284 | 25705 | 46568 | 25388 |
| 22.18 | 35537 | 28391 | 41118 | 24186 | 27513 | 20623 | 23018 | 50957 | 24709 |
| 22.22 | 34178 | 29597 | 42794 | 21833 | 28079 | 20153 | 24483 | 47595 | 26638 |
| 22.26 | 32989 | 30002 | 42554 | 24556 | 29538 | 21557 | 24390 | 49631 | 24402 |
| 22.3 | 32323 | 25759 | 40655 | 23489 | 30024 | 20695 | 24326 | 52463 | 25090 |

-continued

| | | | | | | | | | |
|---|---|---|---|---|---|---|---|---|---|
| 22.34 | 32932 | 28006 | 40640 | 26437 | 31232 | 19328 | 23700 | 55149 | 26023 |
| 22.38 | 34282 | 29458 | 40504 | 22709 | 29750 | 18725 | 24823 | 57286 | 24806 |
| 22.42 | 31153 | 29571 | 40205 | 25495 | 29811 | 20115 | 26438 | 58270 | 24979 |
| 22.46 | 34739 | 27514 | 41205 | 26288 | 28419 | 20065 | 25136 | 60758 | 24253 |
| 22.5 | 31855 | 27127 | 44397 | 28912 | 28677 | 20141 | 25382 | 63569 | 21741 |
| 22.54 | 33249 | 27030 | 42256 | 30737 | 30489 | 22911 | 28141 | 64390 | 24908 |
| 22.58 | 32140 | 25860 | 40922 | 28325 | 30321 | 22149 | 25540 | 69886 | 23462 |
| 22.62 | 34448 | 26420 | 41069 | 30951 | 31705 | 23407 | 22570 | 77033 | 25174 |
| 22.66 | 35034 | 25725 | 43761 | 29038 | 31335 | 22612 | 23741 | 81031 | 23074 |
| 22.7 | 31637 | 27155 | 44787 | 31087 | 30119 | 22509 | 22212 | 87029 | 20799 |
| 22.74 | 33578 | 28097 | 44212 | 30027 | 28667 | 22529 | 23426 | 86295 | 22781 |
| 22.78 | 33019 | 26374 | 45433 | 28625 | 28875 | 21146 | 24468 | 94194 | 23838 |
| 22.82 | 34692 | 25639 | 41570 | 26432 | 28649 | 22737 | 22684 | 92877 | 22448 |
| 22.86 | 35171 | 26265 | 42160 | 27825 | 26694 | 21909 | 24590 | 92013 | 23885 |
| 22.9 | 30929 | 27021 | 43676 | 29902 | 30302 | 23827 | 25111 | 90629 | 19227 |
| 22.94 | 32623 | 27720 | 43908 | 28923 | 27720 | 19337 | 25890 | 87248 | 21799 |
| 22.98 | 31374 | 26366 | 45182 | 28369 | 29310 | 19091 | 23452 | 89354 | 22305 |
| 23.02 | 32040 | 27055 | 43910 | 31300 | 31198 | 20967 | 25001 | 89879 | 23695 |
| 23.06 | 32205 | 28300 | 47192 | 35821 | 31781 | 20745 | 24045 | 84634 | 21444 |
| 23.1 | 30145 | 27935 | 42738 | 37898 | 29557 | 19908 | 24815 | 86314 | 23857 |
| 23.14 | 27914 | 29456 | 49815 | 46751 | 31484 | 21945 | 24627 | 89972 | 21817 |
| 23.18 | 30375 | 27896 | 48511 | 49527 | 33398 | 20159 | 23265 | 89719 | 21931 |
| 23.22 | 33477 | 30436 | 50784 | 53444 | 33178 | 21514 | 23980 | 85270 | 23041 |
| 23.26 | 29222 | 29174 | 50842 | 51955 | 31820 | 21260 | 27685 | 79823 | 20520 |
| 23.3 | 30731 | 28742 | 52817 | 54783 | 33805 | 19100 | 23916 | 74907 | 20516 |
| 23.34 | 30532 | 28688 | 53751 | 51336 | 30126 | 19492 | 25081 | 75479 | 23694 |
| 23.38 | 30057 | 29602 | 51011 | 51034 | 30276 | 20332 | 25637 | 67035 | 23038 |
| 23.42 | 30303 | 28140 | 51789 | 50324 | 31304 | 19003 | 25549 | 62824 | 21086 |
| 23.46 | 29621 | 27654 | 55272 | 49344 | 30319 | 20788 | 26717 | 62285 | 19784 |
| 23.5 | 31657 | 29550 | 54820 | 44161 | 32971 | 23008 | 26712 | 57947 | 22908 |
| 23.54 | 28403 | 29164 | 53710 | 41561 | 32670 | 21210 | 25016 | 55945 | 21067 |
| 23.58 | 33458 | 32436 | 55505 | 40820 | 31023 | 21524 | 27922 | 55626 | 21034 |
| 23.62 | 33183 | 32518 | 53614 | 35267 | 33304 | 21521 | 27779 | 56855 | 21622 |
| 23.66 | 34697 | 34506 | 56364 | 34700 | 32067 | 21989 | 25591 | 56050 | 22652 |
| 23.7 | 34147 | 35430 | 58698 | 33919 | 31666 | 22271 | 29097 | 53670 | 23225 |
| 23.74 | 36974 | 36364 | 57566 | 35643 | 30044 | 23428 | 30219 | 50277 | 23218 |
| 23.78 | 34863 | 34885 | 59146 | 34975 | 34602 | 22916 | 30717 | 52899 | 23236 |
| 23.82 | 35526 | 37646 | 59419 | 34662 | 31321 | 21316 | 29241 | 48821 | 23978 |
| 23.86 | 34808 | 42992 | 59169 | 39459 | 33360 | 21188 | 29313 | 48092 | 23157 |
| 23.9 | 33637 | 47102 | 58841 | 42274 | 32912 | 23513 | 31999 | 44535 | 22560 |
| 23.94 | 33977 | 54288 | 62894 | 51849 | 36044 | 24028 | 32853 | 45345 | 23405 |
| 23.98 | 33294 | 58816 | 62762 | 59237 | 34871 | 23579 | 36091 | 43168 | 23037 |
| 24.02 | 35756 | 62688 | 64484 | 59927 | 36180 | 23823 | 34859 | 44660 | 24234 |
| 24.06 | 35519 | 62130 | 66892 | 70503 | 35663 | 23895 | 32518 | 42630 | 23170 |
| 24.1 | 34879 | 62825 | 61876 | 75178 | 37626 | 24957 | 34738 | 43362 | 23861 |
| 24.14 | 36225 | 65408 | 65711 | 80772 | 39881 | 27240 | 35521 | 42507 | 25426 |
| 24.18 | 35611 | 65206 | 67916 | 84070 | 38096 | 25743 | 38913 | 41301 | 26285 |
| 24.22 | 34042 | 64169 | 71439 | 89070 | 43906 | 28339 | 38921 | 45782 | 26860 |
| 24.26 | 35521 | 58358 | 72471 | 83961 | 43657 | 30367 | 39180 | 43353 | 28450 |
| 24.3 | 34207 | 54805 | 76567 | 80402 | 45606 | 31374 | 37387 | 46899 | 28196 |
| 24.34 | 34315 | 53296 | 74209 | 77479 | 47709 | 30062 | 37664 | 46667 | 28201 |
| 24.38 | 33598 | 50169 | 78077 | 74048 | 47086 | 33985 | 36499 | 45371 | 30135 |
| 24.42 | 33817 | 48975 | 77869 | 64664 | 47851 | 35074 | 37230 | 44322 | 31321 |
| 24.46 | 35524 | 48108 | 79211 | 66196 | 49357 | 37569 | 38071 | 48822 | 35146 |
| 24.5 | 31133 | 48502 | 76906 | 55661 | 51371 | 37563 | 36526 | 46474 | 37822 |
| 24.54 | 32334 | 49726 | 77951 | 53791 | 53135 | 39684 | 37625 | 53134 | 39249 |
| 24.58 | 32127 | 47786 | 77215 | 48474 | 49323 | 40821 | 36591 | 54269 | 40923 |
| 24.62 | 32451 | 47001 | 73187 | 46464 | 46481 | 38311 | 35362 | 57848 | 44583 |
| 24.66 | 32047 | 43730 | 73345 | 42880 | 49389 | 36961 | 36323 | 64541 | 41630 |
| 24.7 | 32146 | 43210 | 71834 | 43698 | 46185 | 37294 | 34335 | 65636 | 44265 |
| 24.74 | 32120 | 43434 | 69294 | 42484 | 45676 | 37422 | 34342 | 68683 | 44892 |
| 24.78 | 30091 | 40117 | 72150 | 44469 | 47240 | 33921 | 33036 | 71504 | 41367 |
| 24.82 | 29457 | 40100 | 68679 | 44808 | 44688 | 32091 | 33321 | 68903 | 39933 |
| 24.86 | 31651 | 38180 | 67337 | 45201 | 44075 | 27987 | 34299 | 71281 | 42963 |
| 24.9 | 30604 | 40636 | 69724 | 44965 | 41353 | 27542 | 34483 | 72643 | 41389 |
| 24.94 | 30635 | 39558 | 66174 | 46928 | 37864 | 27789 | 33003 | 68921 | 38130 |
| 24.98 | 27755 | 39454 | 63078 | 48685 | 39597 | 26085 | 34752 | 65964 | 38568 |
| 25.02 | 30588 | 40327 | 63885 | 50166 | 38111 | 28420 | 30583 | 62725 | 37968 |
| 25.06 | 29563 | 42261 | 65256 | 49181 | 40267 | 29655 | 34120 | 62160 | 36206 |
| 25.1 | 31505 | 41117 | 66143 | 49601 | 38850 | 32992 | 37646 | 58707 | 35774 |
| 25.14 | 27371 | 40616 | 69155 | 51026 | 39460 | 35427 | 32407 | 56727 | 39857 |
| 25.18 | 30122 | 39424 | 61328 | 50183 | 40161 | 40200 | 32108 | 56572 | 35423 |
| 25.22 | 29166 | 41071 | 67403 | 52255 | 39767 | 45093 | 32615 | 56718 | 35044 |
| 25.26 | 28447 | 42078 | 67621 | 52952 | 42728 | 44726 | 32491 | 55779 | 35357 |
| 25.3 | 28745 | 40001 | 63923 | 50319 | 40199 | 45589 | 34223 | 53605 | 35068 |
| 25.34 | 27636 | 42663 | 65908 | 47026 | 43505 | 46983 | 33343 | 58989 | 36246 |
| 25.38 | 29050 | 42062 | 69169 | 48156 | 42768 | 47008 | 33062 | 52633 | 36364 |
| 25.42 | 28095 | 41351 | 64627 | 48178 | 43610 | 47453 | 35231 | 55319 | 35587 |
| 25.46 | 24471 | 43397 | 59018 | 46544 | 47246 | 44417 | 34969 | 54936 | 33030 |

-continued

| | | | | | | | | | |
|---|---|---|---|---|---|---|---|---|---|
| 25.5 | 25858 | 44083 | 57027 | 44188 | 45087 | 37879 | 33769 | 57033 | 34059 |
| 25.54 | 25878 | 43984 | 57990 | 43019 | 47306 | 37954 | 31592 | 56849 | 33181 |
| 25.58 | 24818 | 45182 | 54555 | 38185 | 44528 | 32049 | 29517 | 54776 | 32889 |
| 25.62 | 28088 | 47974 | 56367 | 35723 | 43898 | 31267 | 32821 | 53440 | 33610 |
| 25.66 | 26115 | 44148 | 57371 | 34171 | 44641 | 26582 | 31620 | 50088 | 34286 |
| 25.7 | 24454 | 45152 | 54370 | 30460 | 45280 | 24466 | 31698 | 48148 | 31392 |
| 25.74 | 26633 | 42635 | 48502 | 25599 | 47594 | 24034 | 31403 | 47747 | 31773 |
| 25.78 | 24476 | 44386 | 49695 | 26535 | 45976 | 22924 | 30885 | 50179 | 31138 |
| 25.82 | 26876 | 42645 | 47767 | 25158 | 41832 | 21563 | 29096 | 50398 | 31455 |
| 25.86 | 25301 | 43298 | 48990 | 25030 | 40528 | 20473 | 27467 | 47333 | 32226 |
| 25.9 | 25201 | 41782 | 47703 | 22973 | 40819 | 20981 | 29202 | 49370 | 32256 |
| 25.94 | 24365 | 39163 | 49388 | 23573 | 40883 | 20792 | 27555 | 52860 | 31879 |
| 25.98 | 23356 | 36694 | 51246 | 25640 | 39756 | 20251 | 27431 | 56029 | 32508 |
| 26.02 | 27189 | 34456 | 49739 | 25139 | 38244 | 19971 | 27356 | 52700 | 32181 |
| 26.06 | 23417 | 36087 | 47362 | 25299 | 38768 | 20540 | 26411 | 54093 | 32578 |
| 26.1 | 24672 | 35093 | 48376 | 27229 | 33894 | 20587 | 27061 | 51927 | 33981 |
| 26.14 | 23029 | 34049 | 50252 | 27444 | 33716 | 19872 | 28592 | 52463 | 32592 |
| 26.18 | 24784 | 34617 | 48743 | 26772 | 33008 | 22320 | 26963 | 53856 | 31707 |
| 26.22 | 22920 | 33986 | 47318 | 25139 | 31952 | 21703 | 24264 | 54705 | 32570 |
| 26.26 | 25179 | 32999 | 44693 | 25465 | 31298 | 21149 | 25072 | 52732 | 33052 |
| 26.3 | 23168 | 35487 | 46166 | 27166 | 33481 | 21483 | 26364 | 53122 | 30298 |
| 26.34 | 23445 | 32314 | 42799 | 25305 | 31406 | 22527 | 28500 | 54847 | 30569 |
| 26.38 | 22329 | 32545 | 40745 | 26492 | 31584 | 23735 | 26616 | 54659 | 27385 |
| 26.42 | 25843 | 30361 | 40544 | 29912 | 31759 | 24309 | 25799 | 52485 | 31924 |
| 26.46 | 23981 | 32315 | 40147 | 27591 | 30817 | 26681 | 26965 | 53103 | 29782 |
| 26.5 | 25352 | 29030 | 39275 | 26954 | 30839 | 27818 | 26207 | 51860 | 30149 |
| 26.54 | 23693 | 30030 | 39942 | 27219 | 30247 | 29395 | 27170 | 51028 | 27986 |
| 26.58 | 25199 | 28086 | 38953 | 25526 | 31400 | 32077 | 26034 | 51030 | 28860 |
| 26.62 | 25769 | 26489 | 39712 | 23109 | 28931 | 29932 | 27041 | 47936 | 25928 |
| 26.66 | 24477 | 28322 | 39033 | 23097 | 32620 | 28666 | 25471 | 43612 | 28255 |
| 26.7 | 27995 | 26492 | 38975 | 23682 | 29360 | 32086 | 29360 | 45401 | 28835 |
| 26.74 | 24843 | 25137 | 36297 | 22162 | 29119 | 29013 | 25840 | 44670 | 24690 |
| 26.78 | 23234 | 24224 | 37923 | 21703 | 29554 | 29607 | 25351 | 45609 | 24803 |
| 26.82 | 24421 | 24006 | 37493 | 22426 | 30089 | 29062 | 25313 | 44484 | 23158 |
| 26.86 | 25081 | 22947 | 34750 | 21958 | 29590 | 27951 | 23405 | 44171 | 22758 |
| 26.9 | 23285 | 26248 | 35396 | 21343 | 27577 | 25975 | 22896 | 44423 | 25718 |
| 26.94 | 21746 | 23378 | 37766 | 21698 | 29046 | 25685 | 24532 | 47859 | 24317 |
| 26.98 | 22933 | 23944 | 38790 | 21211 | 30255 | 26610 | 23618 | 46367 | 26692 |
| 27.02 | 22448 | 24608 | 37868 | 20069 | 28991 | 23491 | 24711 | 49721 | 23286 |
| 27.06 | 23904 | 24909 | 34565 | 21790 | 30595 | 26288 | 23560 | 48327 | 24782 |
| 27.1 | 23217 | 23389 | 34582 | 20897 | 28568 | 23781 | 24226 | 49364 | 24361 |
| 27.14 | 25590 | 24066 | 33612 | 22593 | 28312 | 24943 | 22131 | 45920 | 25439 |
| 27.18 | 22391 | 21954 | 34007 | 20999 | 28456 | 22632 | 23295 | 45694 | 22065 |
| 27.22 | 22590 | 23164 | 33011 | 21781 | 29471 | 25521 | 24119 | 46905 | 23228 |
| 27.26 | 23855 | 23814 | 34022 | 22662 | 27650 | 23024 | 23195 | 48539 | 22444 |
| 27.3 | 25432 | 22730 | 35189 | 25581 | 28082 | 22273 | 24175 | 47056 | 22299 |
| 27.34 | 25517 | 24101 | 31623 | 21917 | 27286 | 21320 | 23458 | 45959 | 24109 |
| 27.38 | 25424 | 22235 | 31939 | 22578 | 26794 | 20613 | 20818 | 44137 | 23403 |
| 27.42 | 25352 | 22013 | 33346 | 26607 | 28010 | 22985 | 21880 | 43836 | 23625 |
| 27.46 | 22459 | 21967 | 31904 | 26459 | 24477 | 21501 | 20733 | 42092 | 21433 |
| 27.5 | 26075 | 24283 | 33228 | 27098 | 25024 | 21305 | 22530 | 41488 | 19790 |
| 27.54 | 23411 | 24697 | 30222 | 27916 | 25986 | 23907 | 20742 | 42782 | 22520 |
| 27.58 | 23865 | 26611 | 32199 | 28331 | 29269 | 21700 | 21579 | 42031 | 22515 |
| 27.62 | 28075 | 26109 | 32055 | 29245 | 26629 | 21726 | 20997 | 40714 | 23310 |
| 27.66 | 21239 | 26078 | 32040 | 32494 | 27813 | 20008 | 22063 | 43026 | 23582 |
| 27.7 | 22569 | 25564 | 32993 | 31238 | 25523 | 19893 | 21907 | 42288 | 21905 |
| 27.74 | 22978 | 25240 | 30075 | 34205 | 25008 | 20526 | 20986 | 40100 | 21874 |
| 27.78 | 21954 | 27551 | 30967 | 37696 | 26966 | 19331 | 21832 | 41624 | 21735 |
| 27.82 | 23727 | 26393 | 31043 | 36740 | 24294 | 20192 | 22219 | 39015 | 22569 |
| 27.86 | 23490 | 29331 | 32403 | 37497 | 27304 | 19491 | 21835 | 38233 | 22117 |
| 27.9 | 22105 | 27856 | 30959 | 38290 | 25990 | 17151 | 21542 | 35248 | 23277 |
| 27.94 | 24786 | 28239 | 28503 | 41060 | 26282 | 17851 | 22302 | 35749 | 22008 |
| 27.98 | 22809 | 24371 | 31578 | 41917 | 23240 | 16325 | 20154 | 37104 | 22656 |
| 28.02 | 25121 | 28403 | 30128 | 39104 | 26889 | 18660 | 19949 | 36420 | 21847 |
| 28.06 | 24046 | 25987 | 29356 | 37372 | 24547 | 18957 | 21286 | 33342 | 20673 |
| 28.1 | 27087 | 27071 | 31893 | 40645 | 25945 | 18551 | 20785 | 33393 | 22294 |
| 28.14 | 27190 | 27200 | 32260 | 38480 | 23643 | 19375 | 19743 | 34100 | 20135 |
| 28.18 | 23826 | 24793 | 30356 | 33457 | 22060 | 16618 | 19881 | 33501 | 19846 |
| 28.22 | 23475 | 23448 | 29292 | 31277 | 22754 | 18612 | 19425 | 36188 | 21298 |
| 28.26 | 24573 | 21452 | 27486 | 29011 | 25487 | 17657 | 20791 | 34653 | 21010 |
| 28.3 | 26918 | 23056 | 29657 | 28809 | 24134 | 18748 | 21471 | 32909 | 17198 |
| 28.34 | 25552 | 22559 | 29575 | 25277 | 22968 | 19804 | 21699 | 33637 | 18547 |
| 28.38 | 23804 | 20793 | 28852 | 24155 | 22791 | 18141 | 20338 | 32184 | 18687 |
| 28.42 | 25752 | 20759 | 26942 | 22689 | 22533 | 19208 | 20839 | 32134 | 18919 |
| 28.46 | 25354 | 19592 | 26338 | 22583 | 23719 | 19652 | 20285 | 31815 | 17589 |
| 28.5 | 25500 | 19676 | 27230 | 22988 | 22210 | 19252 | 19953 | 33671 | 18781 |
| 28.54 | 27129 | 21452 | 28730 | 26288 | 25712 | 19306 | 20183 | 36752 | 20276 |
| 28.58 | 28252 | 21171 | 29566 | 25423 | 22864 | 19960 | 22014 | 33721 | 18993 |
| 28.62 | 25983 | 19761 | 27877 | 25749 | 21927 | 20686 | 21358 | 32493 | 17635 |

| | | | | | | | | | |
|---|---|---|---|---|---|---|---|---|---|
| 28.66 | 23935 | 21077 | 25715 | 25242 | 24850 | 21719 | 20040 | 34805 | 16010 |
| 28.7 | 24097 | 20991 | 25796 | 23255 | 25661 | 21429 | 19857 | 32167 | 17005 |
| 28.74 | 23637 | 21699 | 25084 | 23207 | 22544 | 21328 | 18696 | 33190 | 18166 |
| 28.78 | 24826 | 20445 | 28188 | 25281 | 23622 | 19536 | 21264 | 37197 | 16900 |
| 28.82 | 24678 | 23277 | 28954 | 23316 | 24355 | 22082 | 22444 | 35490 | 17350 |
| 28.86 | 24105 | 22765 | 27876 | 22083 | 22625 | 20102 | 19176 | 37007 | 17840 |
| 28.9 | 20559 | 24182 | 25174 | 21145 | 24145 | 21793 | 18755 | 38243 | 19009 |
| 28.94 | 20540 | 24573 | 22647 | 20123 | 23200 | 19523 | 19057 | 36216 | 16411 |
| 28.98 | 21941 | 25424 | 26291 | 19253 | 24326 | 21784 | 18601 | 38792 | 16648 |
| 29.02 | 17766 | 27279 | 25423 | 19620 | 22926 | 21761 | 19777 | 35857 | 16855 |
| 29.06 | 19847 | 26068 | 24534 | 18949 | 21940 | 21628 | 19002 | 36552 | 17051 |
| 29.1 | 19053 | 24779 | 26147 | 17777 | 22554 | 22171 | 17309 | 38489 | 15966 |
| 29.14 | 18175 | 25730 | 25730 | 18737 | 21964 | 23407 | 18989 | 36598 | 15936 |
| 29.18 | 22356 | 24204 | 26313 | 19594 | 21075 | 24610 | 19283 | 37453 | 17441 |
| 29.22 | 17704 | 20993 | 25997 | 17881 | 21167 | 25103 | 18982 | 34690 | 16487 |
| 29.26 | 17547 | 22477 | 24056 | 18289 | 20986 | 24485 | 17146 | 36256 | 15149 |
| 29.3 | 15870 | 21065 | 24652 | 18629 | 19838 | 22588 | 18857 | 35485 | 15859 |
| 29.34 | 19526 | 19413 | 23543 | 18975 | 21898 | 24254 | 18455 | 32798 | 16444 |
| 29.38 | 19299 | 20003 | 24707 | 18849 | 21634 | 23077 | 18913 | 34920 | 14460 |
| 29.42 | 19548 | 20560 | 21865 | 17701 | 20954 | 21182 | 16802 | 33930 | 16671 |
| 29.46 | 18957 | 18347 | 24098 | 18220 | 20308 | 20528 | 18488 | 30268 | 15426 |
| 29.5 | 19068 | 18067 | 24971 | 17302 | 20509 | 19104 | 17737 | 33468 | 16421 |
| 29.54 | 17414 | 19669 | 24286 | 17382 | 19363 | 18864 | 18444 | 31938 | 14383 |
| 29.58 | 18644 | 17910 | 25003 | 16973 | 21073 | 17265 | 17837 | 33395 | 15741 |
| 29.62 | 20395 | 20539 | 23839 | 15521 | 18834 | 16702 | 17858 | 33125 | 15758 |
| 29.66 | 19561 | 18230 | 22801 | 15472 | 22603 | 18547 | 18740 | 36706 | 14445 |
| 29.7 | 22244 | 17208 | 23538 | 16913 | 20385 | 16198 | 16327 | 35925 | 14702 |
| 29.74 | 20960 | 21442 | 23780 | 16691 | 21462 | 16788 | 17780 | 35919 | 14941 |
| 29.78 | 20024 | 19253 | 24497 | 18100 | 19682 | 15679 | 17142 | 35250 | 15079 |
| 29.82 | 20851 | 18966 | 22654 | 17361 | 20813 | 15236 | 16877 | 34122 | 14477 |
| 29.86 | 20996 | 20364 | 23720 | 18242 | 21089 | 15865 | 16672 | 33612 | 14340 |
| 29.9 | 19830 | 19087 | 23319 | 16211 | 19833 | 15975 | 16404 | 31964 | 15135 |
| 29.94 | 22425 | 19677 | 21928 | 17748 | 19448 | 15749 | 16354 | 31848 | 13551 |
| 29.98 | 19433 | 18850 | 22757 | 19041 | 19400 | 15218 | 15993 | 31591 | 14457 |
| 30.02 | 20511 | 18209 | 22038 | 18393 | 20322 | 13659 | 17741 | 28620 | 15238 |
| 30.06 | 20759 | 19453 | 25952 | 17456 | 18847 | 14880 | 17225 | 31107 | 15464 |
| 30.1 | 19032 | 17915 | 22127 | 16412 | 20160 | 13853 | 16170 | 27733 | 15787 |
| 30.14 | 21730 | 19009 | 21514 | 16597 | 20520 | 12857 | 17035 | 29319 | 14056 |
| 30.18 | 19085 | 18304 | 21882 | 16094 | 20991 | 13831 | 16489 | 28374 | 15761 |
| 30.22 | 19217 | 18947 | 21699 | 14886 | 20272 | 13580 | 18416 | 29373 | 13984 |
| 30.26 | 20079 | 16792 | 21804 | 16079 | 19743 | 13372 | 16972 | 32411 | 13333 |
| 30.3 | 18770 | 17697 | 22349 | 16808 | 18298 | 12787 | 16624 | 31718 | 13565 |
| 30.34 | 17713 | 15302 | 24060 | 17174 | 19139 | 14115 | 16925 | 29786 | 14415 |
| 30.38 | 18035 | 16849 | 21956 | 18647 | 20632 | 13458 | 16863 | 31810 | 14456 |
| 30.42 | 17316 | 16562 | 22188 | 17429 | 18291 | 14125 | 17262 | 31595 | 13399 |
| 30.46 | 17404 | 16410 | 20791 | 21162 | 18227 | 15263 | 16966 | 35017 | 14602 |
| 30.5 | 18547 | 16814 | 21807 | 22557 | 19479 | 14049 | 16144 | 35708 | 13969 |
| 30.54 | 16392 | 16614 | 21621 | 23418 | 18114 | 14169 | 17180 | 34487 | 12633 |
| 30.58 | 18385 | 17636 | 22116 | 24539 | 18862 | 14227 | 15526 | 34969 | 14748 |
| 30.62 | 18520 | 18324 | 21798 | 24165 | 17953 | 14603 | 17192 | 34438 | 13837 |
| 30.66 | 17384 | 17825 | 20490 | 28341 | 16357 | 14450 | 16191 | 38587 | 14430 |
| 30.7 | 18190 | 16831 | 20188 | 25137 | 16640 | 12511 | 17654 | 38892 | 14789 |
| 30.74 | 16967 | 17412 | 21668 | 24605 | 18299 | 13876 | 15095 | 34674 | 14370 |
| 30.78 | 17236 | 17354 | 20917 | 24200 | 17426 | 14111 | 15792 | 34163 | 14489 |
| 30.82 | 17799 | 17446 | 20914 | 25727 | 19282 | 14458 | 15904 | 33349 | 14531 |
| 30.86 | 17376 | 17001 | 21150 | 21888 | 17505 | 13929 | 13591 | 32750 | 13368 |
| 30.9 | 15093 | 17734 | 19675 | 19668 | 17260 | 14415 | 14263 | 30326 | 13029 |
| 30.94 | 16868 | 16580 | 18913 | 17884 | 16984 | 14488 | 14863 | 30462 | 14573 |
| 30.98 | 15403 | 16780 | 20013 | 17306 | 16821 | 14587 | 15406 | 29876 | 14055 |
| 31.02 | 15745 | 18291 | 20627 | 17959 | 17591 | 15074 | 15573 | 32491 | 13321 |
| 31.06 | 17301 | 18388 | 20162 | 15548 | 16831 | 14867 | 15702 | 31004 | 12429 |
| 31.1 | 16686 | 16706 | 19507 | 15309 | 16989 | 15903 | 15943 | 30107 | 14166 |
| 31.14 | 15623 | 18759 | 20839 | 15360 | 17988 | 14761 | 14922 | 29266 | 13497 |
| 31.18 | 16396 | 16170 | 19538 | 14842 | 17241 | 15666 | 13967 | 28583 | 12679 |
| 31.22 | 17498 | 19059 | 19716 | 15051 | 16238 | 14577 | 14959 | 27271 | 13520 |
| 31.26 | 14978 | 17026 | 19462 | 14789 | 16695 | 14206 | 14768 | 28489 | 13678 |
| 31.3 | 16133 | 16647 | 19191 | 15593 | 17196 | 14527 | 15890 | 28210 | 13281 |
| 31.34 | 15393 | 17619 | 18978 | 15945 | 17685 | 15429 | 14279 | 28324 | 13075 |
| 31.38 | 16635 | 16914 | 19929 | 15196 | 17438 | 14748 | 14513 | 28760 | 14365 |
| 31.42 | 16734 | 18283 | 19150 | 16366 | 17735 | 13399 | 13756 | 26812 | 14851 |
| 31.46 | 14504 | 18279 | 18660 | 15621 | 17954 | 14344 | 13898 | 26391 | 13205 |
| 31.5 | 15803 | 16824 | 17656 | 14854 | 16970 | 14694 | 13380 | 26594 | 13983 |
| 31.54 | 14603 | 16771 | 20536 | 14904 | 16567 | 13617 | 13840 | 25563 | 13637 |
| 31.58 | 14648 | 18103 | 20121 | 14746 | 18362 | 12641 | 13948 | 26288 | 13179 |
| 31.62 | 16386 | 16982 | 18015 | 14536 | 17605 | 12671 | 13446 | 27248 | 12855 |
| 31.66 | 15779 | 16842 | 18160 | 16420 | 16688 | 14028 | 14708 | 26614 | 13459 |
| 31.7 | 16501 | 17856 | 18253 | 13175 | 15705 | 13029 | 13557 | 26864 | 14443 |
| 31.74 | 15588 | 18676 | 20594 | 14403 | 16526 | 13721 | 14636 | 26141 | 14783 |
| 31.78 | 16364 | 15339 | 18361 | 14960 | 16221 | 14326 | 14056 | 25807 | 12309 |

-continued

| | | | | | | | | | |
|---|---|---|---|---|---|---|---|---|---|
| 31.82 | 15858 | 16922 | 18602 | 15968 | 15967 | 13607 | 14473 | 25710 | 13215 |
| 31.86 | 16801 | 15761 | 19647 | 14514 | 15604 | 12081 | 13042 | 26044 | 12370 |
| 31.9 | 15731 | 15849 | 18577 | 15711 | 16524 | 14545 | 13839 | 25702 | 15287 |
| 31.94 | 16489 | 15431 | 20842 | 14323 | 16921 | 13248 | 14092 | 25772 | 13215 |
| 31.98 | 16076 | 16979 | 19868 | 14240 | 15678 | 14244 | 13980 | 24818 | 12198 |
| 32.02 | 17153 | 15389 | 20466 | 14483 | 15587 | 14141 | 13397 | 26085 | 13210 |
| 32.06 | 16300 | 14511 | 18756 | 14836 | 17142 | 13827 | 13645 | 25702 | 12093 |
| 32.1 | 16628 | 15304 | 19284 | 13799 | 16497 | 13493 | 13875 | 24253 | 13184 |
| 32.14 | 16109 | 15701 | 20208 | 13956 | 15679 | 12766 | 14471 | 25237 | 13561 |
| 32.18 | 15187 | 14948 | 18456 | 13248 | 15467 | 14015 | 13302 | 24327 | 11675 |
| 32.22 | 15790 | 14067 | 17745 | 12700 | 16234 | 13840 | 14029 | 23103 | 12689 |
| 32.26 | 15745 | 15465 | 17885 | 12994 | 16250 | 16709 | 13967 | 24668 | 13346 |
| 32.3 | 15924 | 14104 | 17355 | 13381 | 16429 | 14622 | 13138 | 24173 | 12636 |
| 32.34 | 15693 | 14390 | 17381 | 13385 | 16148 | 13462 | 13726 | 25319 | 11734 |
| 32.38 | 15319 | 15229 | 17008 | 13324 | 15539 | 13881 | 13575 | 24168 | 12171 |
| 32.42 | 15146 | 15357 | 18412 | 13102 | 18093 | 13839 | 13687 | 24840 | 11777 |
| 32.46 | 15430 | 14584 | 17329 | 13617 | 15101 | 14304 | 14092 | 26545 | 12528 |
| 32.5 | 16122 | 13261 | 17012 | 13614 | 16307 | 13391 | 12929 | 24053 | 12268 |
| 32.54 | 15423 | 15268 | 19116 | 12179 | 14814 | 13952 | 14467 | 24195 | 13239 |
| 32.58 | 15701 | 14731 | 18018 | 11972 | 17506 | 12429 | 13353 | 24467 | 13042 |
| 32.62 | 15764 | 15749 | 18756 | 12773 | 16886 | 12230 | 14322 | 22672 | 12509 |
| 32.66 | 16387 | 16193 | 18216 | 14163 | 17010 | 13917 | 13384 | 23292 | 10993 |
| 32.7 | 15439 | 16393 | 17210 | 11823 | 17144 | 13596 | 14441 | 23829 | 11682 |
| 32.74 | 15236 | 16872 | 17136 | 12761 | 16155 | 12829 | 12843 | 23068 | 13377 |
| 32.78 | 16535 | 15342 | 17269 | 13723 | 16130 | 12159 | 12240 | 22512 | 12181 |
| 32.82 | 16892 | 16665 | 17096 | 12342 | 15746 | 12865 | 13282 | 22174 | 12582 |
| 32.86 | 15460 | 14824 | 18191 | 12111 | 15451 | 12696 | 13475 | 24655 | 11436 |
| 32.9 | 15218 | 16572 | 17869 | 14278 | 15691 | 13045 | 13920 | 24555 | 11922 |
| 32.94 | 14319 | 15048 | 17422 | 12625 | 15573 | 14076 | 14336 | 24644 | 10911 |
| 32.98 | 15519 | 16133 | 18502 | 11664 | 15615 | 12069 | 13249 | 24633 | 10581 |
| 33.02 | 14565 | 14833 | 19638 | 12640 | 16429 | 12850 | 13647 | 24772 | 11767 |
| 33.06 | 16046 | 14522 | 17457 | 12848 | 16969 | 12250 | 14016 | 23994 | 12808 |
| 33.1 | 15084 | 14398 | 17253 | 12770 | 15449 | 11537 | 13061 | 24294 | 12476 |
| 33.14 | 13488 | 14000 | 17886 | 13205 | 15870 | 12336 | 12690 | 24986 | 12930 |
| 33.18 | 14390 | 14851 | 16057 | 12366 | 14981 | 12034 | 13585 | 24432 | 11862 |
| 33.22 | 15512 | 14249 | 18437 | 12513 | 14791 | 13033 | 13425 | 26026 | 11880 |
| 33.26 | 16139 | 13972 | 17301 | 14528 | 15681 | 13139 | 13111 | 24373 | 11753 |
| 33.3 | 14532 | 14653 | 16452 | 14506 | 13931 | 11621 | 13722 | 25011 | 11541 |
| 33.34 | 14550 | 15412 | 18791 | 14251 | 14593 | 10806 | 12969 | 25800 | 13222 |
| 33.38 | 14854 | 13997 | 18798 | 14716 | 14279 | 12297 | 11633 | 26794 | 12300 |
| 33.42 | 15247 | 13740 | 17920 | 14951 | 14963 | 12419 | 13955 | 28407 | 13074 |
| 33.46 | 15814 | 13565 | 16898 | 14293 | 14993 | 12613 | 12773 | 27403 | 12256 |
| 33.5 | 15648 | 13594 | 17448 | 14722 | 15220 | 10577 | 12086 | 25529 | 12018 |
| 33.54 | 15165 | 12649 | 16254 | 16229 | 14305 | 11359 | 12374 | 28322 | 11318 |
| 33.58 | 13727 | 13626 | 16491 | 16354 | 14254 | 12260 | 12974 | 26125 | 11438 |
| 33.62 | 15353 | 13692 | 16400 | 15723 | 12884 | 12562 | 12564 | 26485 | 11068 |
| 33.66 | 15435 | 13817 | 16840 | 14392 | 13999 | 11615 | 13003 | 26862 | 11942 |
| 33.7 | 16065 | 14712 | 17565 | 14753 | 14593 | 11061 | 12100 | 29212 | 11367 |
| 33.74 | 13327 | 13444 | 17775 | 14005 | 15271 | 10411 | 13125 | 26362 | 11209 |
| 33.78 | 14341 | 13511 | 16403 | 14351 | 12848 | 11732 | 12781 | 26691 | 11321 |
| 33.82 | 15281 | 13953 | 16938 | 14582 | 14498 | 12323 | 12571 | 25962 | 10523 |
| 33.86 | 15779 | 13077 | 16279 | 12195 | 13891 | 10465 | 13457 | 26851 | 11873 |
| 33.9 | 15094 | 12235 | 18806 | 13545 | 13635 | 12342 | 11050 | 24461 | 11397 |
| 33.94 | 13820 | 13034 | 17140 | 13005 | 15209 | 11527 | 11889 | 25418 | 10842 |
| 33.98 | 15411 | 12563 | 17493 | 13683 | 13961 | 12059 | 12434 | 24017 | 11512 |
| 34.02 | 15031 | 14810 | 15538 | 14014 | 14577 | 11243 | 12566 | 24293 | 10847 |
| 34.06 | 14035 | 12668 | 16034 | 13798 | 13019 | 10540 | 11714 | 24173 | 11475 |
| 34.1 | 14030 | 13336 | 17848 | 13289 | 14986 | 12008 | 12983 | 22813 | 12099 |
| 34.14 | 14501 | 13402 | 17170 | 13499 | 13777 | 10730 | 11656 | 22003 | 10977 |
| 34.18 | 14178 | 13239 | 15858 | 14088 | 13576 | 11110 | 13132 | 22741 | 11001 |
| 34.22 | 15757 | 14085 | 18429 | 13728 | 14183 | 9837 | 11295 | 23815 | 10229 |
| 34.26 | 12575 | 12877 | 17776 | 13458 | 13856 | 11146 | 12877 | 23902 | 10976 |
| 34.3 | 15988 | 13070 | 17535 | 13253 | 13372 | 11148 | 11283 | 25112 | 11373 |
| 34.34 | 14058 | 13988 | 16412 | 13516 | 14547 | 11235 | 12093 | 24485 | 11961 |
| 34.38 | 13669 | 12246 | 16068 | 13542 | 13519 | 8905 | 10812 | 23479 | 11318 |
| 34.42 | 12339 | 12043 | 16929 | 13920 | 13905 | 9483 | 13706 | 24433 | 12026 |
| 34.46 | 14831 | 13469 | 17301 | 13860 | 15373 | 10650 | 12716 | 24753 | 11950 |
| 34.5 | 13349 | 13133 | 16167 | 13048 | 13794 | 9268 | 11864 | 24565 | 11262 |
| 34.54 | 15490 | 12895 | 16673 | 12138 | 14149 | 11052 | 11861 | 24190 | 10720 |
| 34.58 | 15501 | 12939 | 16962 | 14935 | 13603 | 10681 | 12064 | 24264 | 9914 |
| 34.62 | 14705 | 11470 | 16245 | 13958 | 13754 | 8765 | 11956 | 23267 | 10866 |
| 34.66 | 14018 | 13421 | 16620 | 12835 | 13997 | 9850 | 12083 | 22288 | 11251 |
| 34.7 | 14395 | 14527 | 17641 | 13535 | 14332 | 9729 | 10724 | 24914 | 10697 |
| 34.74 | 15098 | 12564 | 16309 | 14484 | 13580 | 11466 | 12627 | 21327 | 10475 |
| 34.78 | 14050 | 11993 | 14597 | 14175 | 13961 | 10805 | 11301 | 21399 | 11283 |
| 34.82 | 14206 | 13193 | 15089 | 12837 | 13368 | 10807 | 12610 | 22948 | 12192 |
| 34.86 | 14402 | 12777 | 16344 | 13051 | 14201 | 9222 | 12038 | 22282 | 10381 |
| 34.9 | 13998 | 13339 | 15545 | 13433 | 13519 | 9872 | 12498 | 22512 | 11184 |
| 34.94 | 14283 | 12582 | 15903 | 13013 | 13075 | 10433 | 11622 | 21772 | 10397 |

-continued

| | | | | | | | | | |
|---|---|---|---|---|---|---|---|---|---|
| 34.98 | 12671 | 12952 | 15137 | 13175 | 14010 | 10306 | 11651 | 20316 | 11653 |
| 35.02 | 13964 | 11414 | 16096 | 13667 | 13305 | 10463 | 11754 | 20167 | 11331 |
| 35.06 | 14286 | 10996 | 15120 | 14262 | 14147 | 11229 | 10412 | 21560 | 10375 |
| 35.1 | 13409 | 12043 | 15923 | 13730 | 13405 | 9950 | 11518 | 21825 | 11289 |
| 35.14 | 14838 | 12381 | 17240 | 14523 | 15228 | 10591 | 11739 | 21284 | 9569 |
| 35.18 | 14733 | 12775 | 15844 | 12313 | 12974 | 10792 | 11998 | 20962 | 11436 |
| 35.22 | 15346 | 11039 | 16458 | 13460 | 12897 | 10100 | 11838 | 20777 | 10871 |
| 35.26 | 15027 | 13070 | 17136 | 13138 | 13121 | 11552 | 11448 | 18866 | 10379 |
| 35.3 | 13429 | 11919 | 15812 | 10920 | 13424 | 10893 | 12286 | 21257 | 10940 |
| 35.34 | 13934 | 11509 | 17204 | 11324 | 12984 | 10641 | 11519 | 20759 | 11366 |
| 35.38 | 14248 | 12318 | 15705 | 11721 | 14134 | 10837 | 11447 | 18745 | 10154 |
| 35.42 | 15070 | 12019 | 15823 | 13956 | 14723 | 9401 | 10836 | 19244 | 11356 |
| 35.46 | 13692 | 10483 | 15832 | 12407 | 14307 | 11723 | 11699 | 20957 | 11805 |
| 35.5 | 12613 | 11872 | 15347 | 13809 | 13313 | 10733 | 11445 | 20906 | 10103 |
| 35.54 | 14694 | 13025 | 16250 | 12562 | 12695 | 10790 | 12584 | 21365 | 11324 |
| 35.58 | 14013 | 11169 | 15443 | 11612 | 13661 | 11211 | 12250 | 21570 | 10204 |
| 35.62 | 13674 | 11840 | 15037 | 12469 | 13481 | 10687 | 11371 | 22303 | 10665 |
| 35.66 | 13966 | 11937 | 15293 | 13025 | 12804 | 9891 | 11731 | 21022 | 10203 |
| 35.7 | 14055 | 12804 | 15515 | 11218 | 13128 | 11314 | 11368 | 20824 | 9405 |
| 35.74 | 13531 | 11668 | 15515 | 12696 | 13244 | 11834 | 11121 | 20742 | 9317 |
| 35.78 | 12601 | 12653 | 15321 | 13630 | 13853 | 11511 | 11386 | 21113 | 10944 |
| 35.82 | 13912 | 12053 | 14732 | 13290 | 12849 | 11736 | 10701 | 20208 | 11337 |
| 35.86 | 12656 | 12697 | 14914 | 14442 | 13805 | 11639 | 11150 | 19746 | 10134 |
| 35.9 | 12966 | 12573 | 13803 | 13389 | 12347 | 12672 | 11266 | 21404 | 10125 |
| 35.94 | 13211 | 11500 | 16422 | 14159 | 12829 | 11628 | 12359 | 19874 | 10337 |
| 35.98 | 12216 | 13566 | 14399 | 12949 | 11292 | 12022 | 10973 | 20206 | 10633 |
| 36.02 | 12779 | 12950 | 15173 | 15347 | 13412 | 10581 | 10961 | 19833 | 10151 |
| 36.06 | 12558 | 12550 | 15997 | 14810 | 13080 | 11146 | 10641 | 20300 | 12149 |
| 36.1 | 12857 | 11975 | 13667 | 13440 | 13457 | 11855 | 9429 | 18807 | 9739 |
| 36.14 | 12375 | 13120 | 15562 | 13812 | 12633 | 11412 | 11070 | 18702 | 10257 |
| 36.18 | 12942 | 12479 | 14965 | 15103 | 14520 | 11302 | 12094 | 21277 | 9520 |
| 36.22 | 14174 | 13038 | 15371 | 13499 | 14054 | 12220 | 10656 | 19918 | 11345 |
| 36.26 | 13997 | 13843 | 14588 | 13710 | 15310 | 12544 | 11650 | 20633 | 10935 |
| 36.3 | 13276 | 13596 | 13853 | 14775 | 14054 | 12032 | 12315 | 21633 | 10632 |
| 36.34 | 14678 | 13261 | 13539 | 12400 | 13466 | 12505 | 11922 | 22487 | 11248 |
| 36.38 | 13634 | 13364 | 13473 | 15155 | 14526 | 11618 | 12551 | 23320 | 11400 |
| 36.42 | 13617 | 14032 | 14747 | 14694 | 15409 | 12760 | 14112 | 22940 | 12027 |
| 36.46 | 14761 | 13804 | 15421 | 14625 | 16227 | 11447 | 12917 | 21957 | 11081 |
| 36.5 | 12630 | 13532 | 14137 | 14527 | 14263 | 11785 | 13674 | 21886 | 11629 |
| 36.54 | 13068 | 12374 | 15154 | 14044 | 14053 | 10529 | 12502 | 24154 | 11405 |
| 36.58 | 13295 | 12802 | 14674 | 13677 | 13742 | 11386 | 12673 | 23202 | 11713 |
| 36.62 | 13281 | 12429 | 15457 | 14596 | 14979 | 13202 | 12292 | 22085 | 11363 |
| 36.66 | 12701 | 12272 | 16244 | 14888 | 14156 | 10883 | 10893 | 21970 | 10421 |
| 36.7 | 13155 | 12162 | 14915 | 14901 | 14101 | 10284 | 11207 | 20811 | 11232 |
| 36.74 | 13415 | 12147 | 15771 | 15621 | 13207 | 11145 | 11705 | 18373 | 10205 |
| 36.78 | 12576 | 12618 | 14859 | 15243 | 13285 | 10489 | 10300 | 20263 | 9803 |
| 36.82 | 13054 | 12140 | 15059 | 14706 | 13727 | 11618 | 10355 | 20503 | 9358 |
| 36.86 | 12428 | 11828 | 13728 | 14826 | 12111 | 10921 | 11191 | 20241 | 10549 |
| 36.9 | 12154 | 11828 | 14610 | 14928 | 12846 | 11956 | 10920 | 21007 | 10246 |
| 36.94 | 13084 | 10954 | 15167 | 15954 | 12858 | 11673 | 11925 | 21351 | 10240 |
| 36.98 | 12293 | 12550 | 16510 | 14894 | 13978 | 12733 | 10864 | 21694 | 9616 |
| 37.02 | 12730 | 12382 | 15742 | 15942 | 13133 | 10741 | 10780 | 20725 | 9975 |
| 37.06 | 13155 | 12735 | 16889 | 14991 | 14534 | 12020 | 12118 | 21351 | 9894 |
| 37.1 | 12199 | 11457 | 13234 | 16283 | 14229 | 11762 | 11967 | 20773 | 9145 |
| 37.14 | 13484 | 12476 | 15053 | 14491 | 13211 | 13072 | 12216 | 20155 | 9397 |
| 37.18 | 12040 | 13710 | 14838 | 13903 | 13082 | 11241 | 12274 | 20478 | 9548 |
| 37.22 | 11703 | 12334 | 15264 | 13715 | 12508 | 11948 | 11391 | 18724 | 9594 |
| 37.26 | 10999 | 13000 | 14380 | 14069 | 13455 | 11879 | 11234 | 18726 | 10876 |
| 37.3 | 12311 | 12772 | 15180 | 14005 | 12268 | 11965 | 11611 | 19188 | 9350 |
| 37.34 | 11916 | 12947 | 14710 | 14021 | 14258 | 11874 | 11700 | 17865 | 10176 |
| 37.38 | 12094 | 12570 | 14924 | 12541 | 13608 | 12144 | 11240 | 19122 | 10134 |
| 37.42 | 12718 | 12343 | 14591 | 11259 | 13793 | 10947 | 11177 | 19328 | 9525 |
| 37.46 | 12415 | 13083 | 15735 | 13502 | 11534 | 10627 | 11316 | 18661 | 9874 |
| 37.5 | 12338 | 12235 | 15857 | 12711 | 12386 | 10867 | 11624 | 18497 | 10226 |
| 37.54 | 12302 | 13160 | 14359 | 11839 | 13035 | 11196 | 11116 | 21167 | 9583 |
| 37.58 | 12932 | 13628 | 14395 | 11344 | 13882 | 10166 | 11263 | 19863 | 10945 |
| 37.62 | 11370 | 14412 | 13874 | 10255 | 13546 | 10980 | 11743 | 18859 | 11055 |
| 37.66 | 11338 | 13091 | 14653 | 10966 | 12519 | 10433 | 10749 | 20976 | 10559 |
| 37.7 | 12352 | 13630 | 15693 | 9400 | 12743 | 10470 | 10548 | 21438 | 10930 |
| 37.74 | 12730 | 12301 | 14731 | 10094 | 13529 | 11398 | 12101 | 19754 | 9993 |
| 37.78 | 11231 | 13855 | 14341 | 11822 | 12763 | 10568 | 12903 | 20659 | 11208 |
| 37.82 | 12004 | 12874 | 16275 | 11063 | 12739 | 10385 | 12866 | 20962 | 9934 |
| 37.86 | 11270 | 13836 | 15299 | 11085 | 12355 | 9434 | 11721 | 20885 | 10665 |
| 37.9 | 12231 | 11797 | 14631 | 11250 | 12210 | 10015 | 11556 | 21958 | 10285 |
| 37.94 | 12282 | 13573 | 16716 | 10689 | 13589 | 8895 | 10896 | 22095 | 9865 |
| 37.98 | 12425 | 13284 | 14368 | 11102 | 13230 | 8552 | 10871 | 20764 | 10199 |
| 38.02 | 12134 | 12238 | 15023 | 12170 | 13275 | 11359 | 10864 | 22094 | 9729 |
| 38.06 | 12139 | 13174 | 16043 | 12544 | 11704 | 10144 | 10511 | 22041 | 9598 |
| 38.1 | 11676 | 11523 | 15623 | 12232 | 13161 | 9898 | 10338 | 20867 | 9907 |

| | | | | | | | | | |
|---|---|---|---|---|---|---|---|---|---|
| 38.14 | 11992 | 12633 | 14148 | 12667 | 13928 | 10848 | 11574 | 20911 | 9068 |
| 38.18 | 12052 | 12439 | 13811 | 10654 | 12591 | 11613 | 11449 | 23823 | 10419 |
| 38.22 | 11321 | 12573 | 16187 | 11822 | 13907 | 11514 | 11061 | 22963 | 8559 |
| 38.26 | 11750 | 12215 | 15420 | 12149 | 12664 | 10653 | 10396 | 22974 | 9698 |
| 38.3 | 11437 | 12395 | 13250 | 14049 | 11922 | 10861 | 11434 | 23873 | 9764 |
| 38.34 | 12472 | 13017 | 16184 | 11783 | 12222 | 10593 | 11687 | 23567 | 9957 |
| 38.38 | 13348 | 12007 | 15397 | 12700 | 12477 | 10314 | 11273 | 23788 | 10262 |
| 38.42 | 12796 | 13147 | 15477 | 11505 | 12524 | 11324 | 11474 | 23592 | 9668 |
| 38.46 | 11297 | 11997 | 15154 | 12069 | 13199 | 11189 | 11949 | 24350 | 10335 |
| 38.5 | 11353 | 12749 | 13752 | 11850 | 12982 | 9970 | 11506 | 23537 | 9630 |
| 38.54 | 10884 | 13128 | 14223 | 10810 | 12467 | 10995 | 10332 | 22630 | 10040 |
| 38.58 | 10932 | 12919 | 15367 | 11980 | 13906 | 10759 | 10786 | 23102 | 10209 |
| 38.62 | 12074 | 13113 | 15199 | 13016 | 12030 | 8881 | 11080 | 21655 | 9815 |
| 38.66 | 11756 | 11239 | 15202 | 12418 | 12059 | 10582 | 11204 | 19623 | 8821 |
| 38.7 | 11844 | 12817 | 16746 | 13160 | 13220 | 10717 | 11195 | 21085 | 9393 |
| 38.74 | 11096 | 13532 | 14886 | 12888 | 12425 | 10909 | 11069 | 21405 | 9946 |
| 38.78 | 12152 | 11439 | 15731 | 13572 | 12616 | 10223 | 10589 | 21714 | 10820 |
| 38.82 | 11960 | 11938 | 15647 | 11911 | 11866 | 9951 | 10589 | 21849 | 8865 |
| 38.86 | 11894 | 12952 | 13441 | 12814 | 11366 | 11137 | 10657 | 19992 | 9755 |
| 38.9 | 11707 | 13125 | 13366 | 13213 | 11634 | 10415 | 12119 | 19985 | 10957 |
| 38.94 | 11204 | 12574 | 15119 | 12966 | 13351 | 9993 | 11573 | 19281 | 8547 |
| 38.98 | 11002 | 12830 | 14576 | 12823 | 12929 | 11080 | 11137 | 20833 | 9978 |
| 39.02 | 12176 | 10738 | 15038 | 13167 | 11916 | 10229 | 9945 | 20507 | 9959 |
| 39.06 | 12262 | 12070 | 16195 | 12218 | 12685 | 11018 | 10448 | 19322 | 10458 |
| 39.1 | 11607 | 12366 | 15165 | 12845 | 12022 | 10406 | 11264 | 19567 | 10229 |
| 39.14 | 11144 | 12194 | 13563 | 12720 | 11978 | 9745 | 10967 | 19322 | 8880 |
| 39.18 | 12039 | 11600 | 14527 | 12379 | 11592 | 11257 | 10289 | 20626 | 9752 |
| 39.22 | 10746 | 11862 | 14330 | 13405 | 11967 | 11094 | 10817 | 19482 | 10688 |
| 39.26 | 11525 | 12903 | 14927 | 12001 | 11534 | 11039 | 10124 | 19155 | 10144 |
| 39.3 | 11894 | 13394 | 14810 | 11105 | 12513 | 11539 | 10878 | 20712 | 9548 |
| 39.34 | 12582 | 13379 | 13762 | 13466 | 11432 | 11145 | 10158 | 19644 | 9749 |
| 39.38 | 12819 | 13486 | 16331 | 13872 | 12407 | 10526 | 10989 | 19770 | 8207 |
| 39.42 | 11871 | 12928 | 13977 | 14053 | 11717 | 9961 | 10364 | 18962 | 9951 |
| 39.46 | 11678 | 12195 | 15024 | 14062 | 13867 | 9919 | 10453 | 19355 | 9855 |
| 39.5 | 10675 | 12421 | 14000 | 14384 | 14306 | 9797 | 11441 | 17899 | 9270 |
| 39.54 | 10390 | 13266 | 13979 | 13608 | 12407 | 9182 | 11191 | 19097 | 9462 |
| 39.58 | 10792 | 11897 | 14993 | 13647 | 12024 | 9699 | 10102 | 18636 | 9059 |
| 39.62 | 11461 | 13231 | 13591 | 13510 | 11986 | 10754 | 9856 | 19382 | 9849 |
| 39.66 | 10911 | 11708 | 14624 | 13149 | 12345 | 10163 | 10702 | 18429 | 10429 |
| 39.7 | 10366 | 13298 | 13571 | 13005 | 12650 | 10216 | 9423 | 17368 | 9545 |
| 39.74 | 11101 | 10872 | 13053 | 13757 | 10739 | 9640 | 10344 | 18814 | 9385 |
| 39.78 | 10683 | 10685 | 13841 | 11943 | 13097 | 9227 | 10266 | 20625 | 8536 |
| 39.82 | 11339 | 10398 | 13803 | 12915 | 12060 | 9117 | 9804 | 19044 | 10034 |
| 39.86 | 11433 | 11926 | 14338 | 12140 | 12874 | 9615 | 9328 | 17348 | 9259 |
| 39.9 | 12072 | 11279 | 13362 | 11929 | 12836 | 9869 | 10120 | 18983 | 10720 |
| 39.94 | 10967 | 12237 | 14689 | 12440 | 12227 | 10994 | 10798 | 19259 | 8909 |
| 39.98 | 10722 | 11906 | 13669 | 11810 | 12020 | 10091 | 11263 | 19074 | 9874 |
| 40.02 | 10701 | 10837 | 14959 | 11406 | 12118 | 8582 | 10888 | 18782 | 9918 |
| 40.06 | 11694 | 12743 | 15123 | 10184 | 12486 | 10181 | 10872 | 18539 | 9652 |
| 40.1 | 11903 | 11344 | 14918 | 10526 | 11806 | 10197 | 10308 | 19144 | 9638 |
| 40.14 | 11227 | 12275 | 14956 | 11910 | 12561 | 9817 | 10938 | 19120 | 8541 |
| 40.18 | 11859 | 11598 | 14400 | 10948 | 13082 | 9521 | 10019 | 17540 | 9868 |
| 40.22 | 11161 | 12264 | 14811 | 11871 | 12062 | 8968 | 9808 | 19764 | 8129 |
| 40.26 | 12587 | 10758 | 14263 | 9569 | 12818 | 9181 | 11025 | 20554 | 9100 |
| 40.3 | 11192 | 11919 | 14075 | 10136 | 11708 | 8733 | 10739 | 19622 | 8979 |
| 40.34 | 12263 | 11441 | 15058 | 10058 | 11927 | 9804 | 9638 | 20149 | 8851 |
| 40.38 | 12216 | 12664 | 14325 | 9508 | 12038 | 9676 | 10032 | 20033 | 8636 |
| 40.42 | 12078 | 11104 | 13849 | 10795 | 11776 | 9004 | 10067 | 18755 | 8965 |
| 40.46 | 12146 | 12207 | 14413 | 10642 | 11220 | 8535 | 10062 | 19141 | 7629 |
| 40.5 | 11209 | 12136 | 14193 | 9763 | 12410 | 10173 | 9628 | 19413 | 9822 |
| 40.54 | 11642 | 12769 | 13497 | 9849 | 10941 | 9222 | 10560 | 18034 | 8251 |
| 40.58 | 11691 | 11759 | 14181 | 11270 | 12863 | 8210 | 10600 | 19659 | 8260 |
| 40.62 | 11681 | 11757 | 13294 | 10064 | 11286 | 8625 | 9611 | 18382 | 8551 |
| 40.66 | 11102 | 11205 | 13843 | 9863 | 11748 | 9979 | 10070 | 18775 | 9048 |
| 40.7 | 10585 | 11541 | 13102 | 10577 | 11444 | 8130 | 9495 | 17048 | 8570 |
| 40.74 | 10234 | 11784 | 13703 | 9951 | 12656 | 8121 | 9441 | 17556 | 8039 |
| 40.78 | 10727 | 10841 | 12156 | 8699 | 12015 | 9112 | 10405 | 17708 | 8358 |
| 40.82 | 11132 | 10997 | 12887 | 9649 | 11871 | 8836 | 10779 | 18308 | 9493 |
| 40.86 | 11762 | 10664 | 13577 | 10400 | 10506 | 9232 | 10228 | 17950 | 8798 |
| 40.9 | 11420 | 10467 | 13531 | 11303 | 11344 | 8577 | 9400 | 17370 | 7931 |
| 40.94 | 10285 | 11722 | 12982 | 10448 | 12145 | 8449 | 8402 | 18900 | 8442 |
| 40.98 | 12236 | 12347 | 12711 | 11575 | 11786 | 7557 | 10391 | 16938 | 8363 |
| 41.02 | 9849 | 10358 | 13052 | 11618 | 10871 | 8528 | 9937 | 15867 | 7862 |
| 41.06 | 10217 | 10604 | 13062 | 12542 | 11052 | 7743 | 9954 | 17018 | 8761 |
| 41.1 | 10373 | 10950 | 12100 | 11972 | 10083 | 7236 | 10109 | 17198 | 9239 |
| 41.14 | 9997 | 10711 | 11589 | 13411 | 12315 | 8237 | 9421 | 17761 | 8577 |
| 41.18 | 9619 | 11181 | 12243 | 13299 | 11608 | 7639 | 9132 | 16639 | 8960 |
| 41.22 | 11456 | 9647 | 12538 | 13030 | 10076 | 8078 | 8487 | 16155 | 7937 |
| 41.26 | 9574 | 9764 | 10525 | 12723 | 11498 | 8008 | 8142 | 16895 | 7062 |

-continued

| | | | | | | | | | |
|---|---|---|---|---|---|---|---|---|---|
| 41.3 | 9229 | 10372 | 11218 | 12417 | 9849 | 7447 | 9245 | 16183 | 8204 |
| 41.34 | 9572 | 9917 | 12911 | 11704 | 11126 | 9091 | 8442 | 15900 | 7342 |
| 41.38 | 9912 | 9707 | 12061 | 11051 | 10547 | 8040 | 7838 | 15292 | 8210 |
| 41.42 | 10011 | 10097 | 12076 | 12524 | 10216 | 8665 | 7942 | 17898 | 7478 |
| 41.46 | 10877 | 10704 | 10700 | 11026 | 10669 | 9133 | 9198 | 17429 | 7348 |
| 41.5 | 9799 | 10077 | 13368 | 10741 | 10586 | 8352 | 9128 | 16812 | 7982 |

| | | | | Form | | | | | | |
|---|---|---|---|---|---|---|---|---|---|---|
| | Glr1 | Glt1 (brown) | Glt2_lc | Glt3_lc | Glt4 (brown) | Glt5 (brown) | HBr1 | HBr2 | Mae1 | Mae1 + Mae2 | Mal1_lc |
| | | | | | ExperimentID | | | | | | |
| Counter ion | SSm59 D-Glucuronic acid | SSm98 Glutaric acid | SSm32 Glutaric acid | SSm65 Glutaric acid | SSm98 Glutaric acid | SSm65 Glutaric acid | SSm34 Hydrobromic acid | SSm34 Hydrobromic acid | SSm14 Maleic acid | SSm47 Maleic acid | SSm28 L-(−)-Malic acid |
| 1.5 | 4627 | 2519 | 3438 | 1445 | 971 | 1291 | 2510 | 503 | 1547 | 5395 | 624 |
| 1.54 | 4520 | 2646 | 6432 | 2496 | 865 | 1037 | 3483 | 1348 | 725 | 2896 | 2217 |
| 1.58 | 5008 | 2898 | 2498 | 5778 | 939 | 1466 | 8448 | 674 | 2112 | 7125 | 1831 |
| 1.62 | 10218 | 2846 | 2694 | 2700 | 1650 | 1172 | 10742 | 954 | 585 | 9031 | 2415 |
| 1.66 | 8977 | 2540 | 3196 | 5090 | 1864 | 1182 | 7493 | 1073 | 524 | 7854 | 4484 |
| 1.7 | 8628 | 5460 | 6146 | 7558 | 2272 | 455 | 7683 | 1679 | 3145 | 7886 | 5841 |
| 1.74 | 10230 | 3709 | 4710 | 5443 | 2165 | 1593 | 8629 | 463 | 3398 | 10259 | 8432 |
| 1.78 | 15358 | 7593 | 5289 | 6494 | 1685 | 1789 | 12077 | 1193 | 1634 | 14435 | 6924 |
| 1.82 | 18030 | 7244 | 6861 | 11185 | 3595 | 2988 | 14170 | 2466 | 3164 | 12189 | 4011 |
| 1.86 | 18802 | 7157 | 7502 | 11157 | 1601 | 5177 | 7597 | 1934 | 3255 | 16500 | 7288 |
| 1.9 | 20596 | 7272 | 11774 | 10805 | 2897 | 3563 | 12915 | 3337 | 4556 | 14434 | 8741 |
| 1.94 | 16370 | 10736 | 8237 | 8041 | 2255 | 3377 | 12213 | 3194 | 1445 | 16596 | 5880 |
| 1.98 | 19857 | 11627 | 8433 | 14537 | 2340 | 5646 | 16238 | 1533 | 3044 | 13573 | 9701 |
| 2.02 | 20494 | 10119 | 6549 | 15256 | 3893 | 5763 | 18244 | 4020 | 5788 | 18349 | 7193 |
| 2.06 | 21508 | 8761 | 8432 | 17510 | 2841 | 2484 | 16019 | 3370 | 3364 | 18656 | 8532 |
| 2.1 | 16535 | 10230 | 8365 | 13346 | 5689 | 3583 | 18030 | 4057 | 2759 | 22345 | 10349 |
| 2.14 | 22741 | 10445 | 11470 | 12304 | 5952 | 5245 | 16110 | 6628 | 3253 | 22723 | 8115 |
| 2.18 | 21633 | 9936 | 11288 | 12161 | 6378 | 6003 | 16204 | 4525 | 5272 | 22492 | 9997 |
| 2.22 | 22942 | 16637 | 8810 | 11233 | 8162 | 8177 | 22790 | 7173 | 6349 | 18853 | 8295 |
| 2.26 | 22392 | 13640 | 10104 | 10872 | 6583 | 8828 | 15114 | 6768 | 5113 | 23471 | 11780 |
| 2.3 | 19556 | 12187 | 12446 | 10579 | 5554 | 8212 | 18433 | 5284 | 6977 | 16580 | 13023 |
| 2.34 | 22763 | 12313 | 9702 | 11163 | 6078 | 6829 | 18064 | 6118 | 5597 | 23720 | 12887 |
| 2.38 | 20375 | 8977 | 12621 | 12508 | 8880 | 7258 | 15580 | 5823 | 7512 | 21541 | 7063 |
| 2.42 | 19550 | 8119 | 11400 | 12292 | 6007 | 9977 | 17338 | 5868 | 5903 | 21101 | 9355 |
| 2.46 | 23896 | 11492 | 9262 | 14995 | 7878 | 7293 | 15298 | 6227 | 6689 | 17496 | 9903 |
| 2.5 | 24464 | 11229 | 9140 | 13788 | 10053 | 9539 | 17569 | 6004 | 5911 | 23437 | 10084 |
| 2.54 | 18656 | 11983 | 13218 | 15677 | 8621 | 8178 | 17833 | 5691 | 7166 | 23852 | 10825 |
| 2.58 | 21531 | 11154 | 12524 | 11359 | 9904 | 11412 | 19065 | 7380 | 3891 | 21350 | 9674 |
| 2.62 | 27467 | 13485 | 13775 | 13578 | 10631 | 10541 | 20108 | 8934 | 4641 | 24944 | 8624 |
| 2.66 | 22964 | 11154 | 13874 | 14678 | 10394 | 11157 | 19123 | 9125 | 7167 | 28663 | 11429 |
| 2.7 | 24889 | 10334 | 13933 | 13506 | 7611 | 10338 | 16310 | 8820 | 7328 | 27499 | 13861 |
| 2.74 | 21036 | 11975 | 12702 | 14713 | 6815 | 9696 | 22146 | 6957 | 7627 | 24417 | 13825 |
| 2.78 | 17103 | 11801 | 12196 | 16061 | 9730 | 8554 | 25432 | 8358 | 9114 | 21444 | 13605 |
| 2.82 | 27501 | 14894 | 13490 | 14123 | 11027 | 9440 | 20628 | 8692 | 8298 | 21316 | 12970 |
| 2.86 | 25622 | 13528 | 13372 | 13374 | 11433 | 14109 | 21711 | 9107 | 9318 | 24785 | 10789 |
| 2.9 | 24734 | 11387 | 10390 | 13778 | 10063 | 8975 | 21791 | 9623 | 12131 | 25400 | 15214 |
| 2.94 | 25210 | 13327 | 12389 | 16383 | 12789 | 12789 | 21576 | 12693 | 11120 | 21778 | 12846 |
| 2.98 | 30442 | 15085 | 13644 | 18553 | 9904 | 10685 | 20942 | 7896 | 9498 | 27521 | 16514 |
| 3.02 | 29459 | 12671 | 16767 | 17483 | 7857 | 9872 | 18044 | 8265 | 10210 | 29546 | 18025 |
| 3.06 | 33113 | 19505 | 18421 | 15690 | 12114 | 12280 | 23760 | 9429 | 10633 | 26288 | 18467 |
| 3.1 | 30461 | 19081 | 19116 | 19977 | 13563 | 11737 | 20524 | 9581 | 11174 | 23183 | 17129 |
| 3.14 | 34831 | 20120 | 24655 | 23314 | 15508 | 12545 | 21525 | 10379 | 12760 | 32353 | 19444 |
| 3.18 | 35542 | 23297 | 29839 | 18216 | 13992 | 14623 | 23091 | 8572 | 12749 | 31700 | 18974 |
| 3.22 | 32370 | 24075 | 33213 | 18680 | 12613 | 14264 | 25223 | 8740 | 8610 | 38269 | 21045 |
| 3.26 | 35940 | 24010 | 37529 | 19612 | 15603 | 14978 | 30243 | 11511 | 13178 | 30333 | 25784 |
| 3.3 | 43613 | 21074 | 41419 | 19016 | 14664 | 15045 | 25839 | 10895 | 14022 | 31021 | 24598 |
| 3.34 | 43029 | 26782 | 34336 | 22046 | 12871 | 16093 | 30479 | 12888 | 15963 | 32474 | 27090 |
| 3.38 | 43190 | 26268 | 39797 | 20758 | 14800 | 16150 | 29915 | 9520 | 13799 | 31704 | 28899 |
| 3.42 | 53319 | 21981 | 35444 | 22181 | 11519 | 17749 | 30349 | 11164 | 13376 | 38665 | 27194 |
| 3.46 | 58974 | 21664 | 32441 | 18448 | 15287 | 17045 | 29104 | 12405 | 17544 | 32914 | 32023 |
| 3.5 | 69146 | 24484 | 26994 | 19579 | 14243 | 15595 | 29804 | 14776 | 18406 | 34705 | 38733 |
| 3.54 | 62362 | 20150 | 28544 | 21355 | 13475 | 17021 | 26413 | 13704 | 15694 | 33407 | 34756 |
| 3.58 | 67607 | 19836 | 29079 | 17784 | 17620 | 17696 | 27071 | 14931 | 14937 | 35172 | 42079 |
| 3.62 | 68840 | 19814 | 24199 | 24555 | 19756 | 19031 | 30684 | 14949 | 18172 | 33524 | 39109 |
| 3.66 | 62335 | 21880 | 28888 | 22778 | 18649 | 20356 | 31439 | 12832 | 15021 | 32338 | 41617 |
| 3.7 | 54364 | 20978 | 33794 | 21674 | 19604 | 22283 | 31213 | 12659 | 15177 | 34405 | 51189 |
| 3.74 | 57254 | 20445 | 39385 | 18491 | 18685 | 18198 | 30562 | 12037 | 16530 | 33203 | 52620 |
| 3.78 | 46495 | 19180 | 57099 | 22342 | 21232 | 21176 | 28242 | 15301 | 19034 | 38844 | 47773 |

| | | | | | | | | | | |
|---|---|---|---|---|---|---|---|---|---|---|
| 3.82 | 46285 | 22325 | 77354 | 20636 | 17475 | 20483 | 29241 | 15307 | 16878 | 34208 | 49967 |
| 3.86 | 46352 | 22217 | 88615 | 18944 | 15689 | 19518 | 29889 | 16574 | 15531 | 34626 | 53955 |
| 3.9 | 43918 | 18998 | 112471 | 23604 | 16031 | 21243 | 24586 | 13574 | 21967 | 37083 | 58526 |
| 3.94 | 42601 | 23882 | 128080 | 24849 | 18417 | 20514 | 33946 | 19102 | 16724 | 36187 | 61014 |
| 3.98 | 45691 | 21503 | 133799 | 21060 | 21234 | 22255 | 30611 | 15287 | 20554 | 35870 | 61449 |
| 4.02 | 41983 | 23889 | 122399 | 22664 | 20272 | 23274 | 32619 | 14259 | 19594 | 35528 | 68322 |
| 4.06 | 38039 | 27517 | 126619 | 21743 | 18860 | 19663 | 31214 | 14484 | 21297 | 32236 | 66387 |
| 4.1 | 40251 | 30839 | 123268 | 22240 | 22115 | 22612 | 31325 | 18088 | 18266 | 33561 | 65194 |
| 4.14 | 37810 | 37842 | 104374 | 23567 | 19955 | 22054 | 31007 | 16038 | 19732 | 37160 | 66730 |
| 4.18 | 47377 | 43709 | 98298 | 18254 | 20776 | 19766 | 29753 | 15990 | 21492 | 37575 | 65635 |
| 4.22 | 49682 | 52272 | 83137 | 23106 | 22974 | 22442 | 33223 | 16846 | 20349 | 40072 | 65707 |
| 4.26 | 43795 | 58056 | 55902 | 21542 | 19084 | 25992 | 29676 | 19252 | 20278 | 37233 | 62964 |
| 4.3 | 40772 | 59374 | 47734 | 21043 | 19652 | 18631 | 27824 | 16235 | 17897 | 40307 | 53975 |
| 4.34 | 43363 | 65589 | 35792 | 24149 | 20937 | 20555 | 29237 | 17420 | 22167 | 41711 | 47387 |
| 4.38 | 40951 | 61937 | 26703 | 21249 | 21270 | 22574 | 30142 | 16094 | 19723 | 38013 | 37413 |
| 4.42 | 41265 | 63390 | 23385 | 23183 | 19457 | 21974 | 29308 | 19908 | 22903 | 35861 | 38923 |
| 4.46 | 43930 | 59767 | 23089 | 23969 | 23562 | 25533 | 32916 | 19629 | 22681 | 35826 | 36227 |
| 4.5 | 43581 | 54608 | 20047 | 24538 | 24275 | 21888 | 33401 | 20004 | 19225 | 41823 | 34427 |
| 4.54 | 43244 | 48685 | 19838 | 22213 | 23691 | 22831 | 26714 | 19011 | 22581 | 37984 | 30634 |
| 4.58 | 45603 | 38047 | 20358 | 22781 | 26601 | 23513 | 30334 | 17774 | 22214 | 38139 | 29720 |
| 4.62 | 46716 | 33677 | 21115 | 26443 | 23798 | 24391 | 32720 | 20599 | 20492 | 39887 | 27441 |
| 4.66 | 50569 | 28240 | 21122 | 23839 | 26508 | 23801 | 32403 | 16721 | 24449 | 39439 | 26683 |
| 4.7 | 53420 | 24682 | 18834 | 24153 | 25707 | 23419 | 31652 | 16631 | 19989 | 38869 | 26245 |
| 4.74 | 62721 | 23869 | 19828 | 20172 | 20865 | 23719 | 29232 | 19330 | 22228 | 35104 | 22387 |
| 4.78 | 56721 | 23937 | 20719 | 22520 | 22374 | 24206 | 31881 | 17946 | 20435 | 42416 | 26508 |
| 4.82 | 76418 | 20514 | 18763 | 23782 | 24659 | 24425 | 34976 | 19134 | 22438 | 40793 | 23010 |
| 4.86 | 81515 | 20995 | 23893 | 19776 | 21916 | 23254 | 31356 | 19982 | 22991 | 37828 | 27932 |
| 4.9 | 86456 | 23842 | 22603 | 21751 | 22193 | 25875 | 34604 | 19065 | 23392 | 38700 | 27481 |
| 4.94 | 84200 | 20058 | 21932 | 24031 | 22095 | 27704 | 31592 | 18807 | 23043 | 38046 | 29183 |
| 4.98 | 82214 | 23301 | 23029 | 28354 | 24544 | 27074 | 28197 | 18548 | 23211 | 39564 | 30579 |
| 5.02 | 89725 | 22547 | 19186 | 22120 | 26347 | 29897 | 30836 | 22192 | 21254 | 40729 | 27321 |
| 5.06 | 91157 | 23295 | 20763 | 27252 | 25018 | 31574 | 32351 | 18473 | 21860 | 41640 | 28399 |
| 5.1 | 81105 | 24284 | 18316 | 23578 | 25816 | 30963 | 30925 | 21660 | 25413 | 42205 | 28323 |
| 5.14 | 75392 | 27185 | 21266 | 24276 | 24687 | 31726 | 33763 | 19095 | 23531 | 38507 | 26455 |
| 5.18 | 59639 | 24195 | 20575 | 24288 | 21088 | 31469 | 36822 | 20125 | 23138 | 38736 | 27877 |
| 5.22 | 58265 | 22283 | 22003 | 24804 | 22653 | 36017 | 35700 | 20353 | 21113 | 39529 | 26959 |
| 5.26 | 47360 | 24741 | 19642 | 26123 | 23186 | 29648 | 37000 | 19631 | 23356 | 40136 | 25455 |
| 5.3 | 43230 | 21721 | 21846 | 21756 | 22706 | 31726 | 30566 | 24542 | 21365 | 41522 | 23600 |
| 5.34 | 48705 | 24501 | 21391 | 24744 | 23516 | 30005 | 34396 | 19254 | 24921 | 41223 | 25859 |
| 5.38 | 46804 | 23233 | 19736 | 21324 | 26890 | 30611 | 31528 | 21474 | 24643 | 37990 | 24805 |
| 5.42 | 50408 | 24754 | 19396 | 22067 | 25653 | 27329 | 32104 | 22601 | 25075 | 39656 | 21677 |
| 5.46 | 46907 | 24714 | 21450 | 25049 | 24102 | 27190 | 37749 | 19999 | 24035 | 42664 | 25115 |
| 5.5 | 45862 | 26827 | 21040 | 23924 | 23979 | 29613 | 33862 | 19896 | 22047 | 41119 | 23117 |
| 5.54 | 44078 | 27986 | 21731 | 24465 | 24269 | 26837 | 32701 | 20972 | 22673 | 39566 | 24243 |
| 5.58 | 44880 | 25949 | 24743 | 24518 | 25139 | 26434 | 30253 | 24621 | 24730 | 40965 | 21282 |
| 5.62 | 42887 | 29472 | 19678 | 23735 | 24330 | 28300 | 31284 | 21793 | 25517 | 38951 | 22169 |
| 5.66 | 44612 | 28010 | 19754 | 28868 | 23777 | 30990 | 33615 | 18830 | 20208 | 40729 | 24668 |
| 5.7 | 44844 | 25849 | 23313 | 26589 | 25150 | 25509 | 40070 | 20464 | 22650 | 38634 | 18275 |
| 5.74 | 47087 | 32805 | 23548 | 26370 | 27100 | 27843 | 38209 | 22659 | 26556 | 43095 | 24412 |
| 5.78 | 51331 | 29719 | 27801 | 26090 | 28568 | 29359 | 36590 | 21322 | 24914 | 41821 | 23309 |
| 5.82 | 44777 | 27971 | 29471 | 28227 | 26211 | 25582 | 33677 | 21480 | 25093 | 43151 | 20319 |
| 5.86 | 53121 | 27697 | 30135 | 26454 | 25480 | 26257 | 39773 | 22463 | 25094 | 36307 | 20679 |
| 5.9 | 49319 | 26005 | 28051 | 27982 | 27354 | 25441 | 42221 | 21664 | 24427 | 41573 | 20856 |
| 5.94 | 46697 | 21839 | 27481 | 27158 | 28680 | 29189 | 52029 | 22210 | 26794 | 42952 | 22090 |
| 5.98 | 49119 | 26481 | 26751 | 30241 | 28642 | 28736 | 61790 | 20385 | 32006 | 41770 | 21463 |
| 6.02 | 49918 | 25086 | 27117 | 31161 | 32576 | 27070 | 71768 | 21794 | 28012 | 45980 | 21799 |
| 6.06 | 50863 | 27813 | 25808 | 27814 | 31830 | 26238 | 82357 | 20370 | 28764 | 50683 | 21283 |
| 6.1 | 49349 | 26951 | 25562 | 28443 | 33297 | 32578 | 96746 | 25920 | 28617 | 51460 | 21881 |
| 6.14 | 49960 | 22349 | 26549 | 30386 | 38322 | 24930 | 101642 | 22885 | 31215 | 56399 | 21822 |
| 6.18 | 48926 | 23692 | 23135 | 31036 | 36000 | 28114 | 104384 | 21406 | 28645 | 72414 | 21046 |
| 6.22 | 48055 | 23683 | 22914 | 35559 | 38669 | 31022 | 110758 | 22259 | 30101 | 80670 | 25029 |
| 6.26 | 49288 | 24110 | 24307 | 39193 | 38488 | 33774 | 98145 | 23656 | 28086 | 83484 | 23318 |
| 6.3 | 47445 | 22893 | 24174 | 40151 | 35010 | 32988 | 88421 | 24118 | 27707 | 84894 | 22507 |
| 6.34 | 45292 | 25352 | 22106 | 41196 | 34169 | 35957 | 84101 | 27848 | 29001 | 82604 | 20711 |
| 6.38 | 46316 | 25056 | 25501 | 43700 | 29409 | 41103 | 73696 | 26653 | 24938 | 85686 | 21421 |
| 6.42 | 42163 | 27275 | 25232 | 43182 | 30418 | 47884 | 62229 | 26105 | 23211 | 85944 | 22125 |
| 6.46 | 45460 | 27358 | 26562 | 48005 | 27861 | 51879 | 48795 | 24514 | 27729 | 77828 | 20565 |
| 6.5 | 50471 | 25076 | 25645 | 46277 | 27963 | 62663 | 46273 | 24546 | 27053 | 70966 | 20960 |
| 6.54 | 45568 | 26848 | 29917 | 41030 | 25412 | 63389 | 40030 | 32170 | 24945 | 70942 | 23534 |
| 6.58 | 50013 | 34231 | 28253 | 41060 | 29292 | 72555 | 37955 | 39666 | 25066 | 64026 | 22723 |
| 6.62 | 45689 | 33244 | 24949 | 39924 | 27967 | 63155 | 37446 | 45961 | 29578 | 56156 | 22138 |
| 6.66 | 47443 | 39224 | 26943 | 34384 | 23830 | 71119 | 37789 | 56324 | 27257 | 56143 | 22799 |
| 6.7 | 47231 | 39549 | 29614 | 34153 | 26742 | 67906 | 39401 | 60660 | 27057 | 65251 | 23457 |
| 6.74 | 45781 | 42316 | 28419 | 33589 | 29471 | 63486 | 33548 | 71223 | 26848 | 77204 | 24147 |
| 6.78 | 48157 | 39920 | 32634 | 26192 | 26688 | 56413 | 40331 | 69783 | 28891 | 91059 | 22283 |
| 6.82 | 48190 | 37810 | 33723 | 30299 | 25330 | 46365 | 43578 | 71455 | 29713 | 98280 | 23659 |
| 6.86 | 52764 | 35859 | 31837 | 24142 | 27363 | 37936 | 49536 | 69477 | 32152 | 119368 | 21756 |
| 6.9 | 59151 | 37415 | 38119 | 27916 | 28502 | 33083 | 56669 | 65574 | 35678 | 126443 | 25127 |
| 6.94 | 62742 | 33368 | 32929 | 25897 | 24846 | 32620 | 59707 | 58358 | 41412 | 124227 | 23617 |

-continued

| | | | | | | | | | | |
|---|---|---|---|---|---|---|---|---|---|---|
| 6.98 | 64608 | 33258 | 36553 | 27900 | 30058 | 30691 | 65295 | 51526 | 55978 | 124754 | 22730 |
| 7.02 | 72011 | 29343 | 34885 | 29246 | 27735 | 32460 | 67764 | 45183 | 57962 | 120483 | 23226 |
| 7.06 | 68183 | 26153 | 31937 | 26943 | 34581 | 29716 | 64694 | 33525 | 66885 | 115845 | 23960 |
| 7.1 | 68743 | 24925 | 37826 | 25048 | 38880 | 29253 | 69195 | 30264 | 66558 | 101146 | 19047 |
| 7.14 | 62486 | 23539 | 31347 | 29962 | 46847 | 26869 | 65899 | 27074 | 55711 | 91224 | 22105 |
| 7.18 | 65386 | 20768 | 28884 | 28635 | 45831 | 27132 | 63496 | 27922 | 62210 | 75683 | 21397 |
| 7.22 | 61005 | 22114 | 29087 | 22813 | 50226 | 29646 | 68435 | 27705 | 59907 | 61865 | 22138 |
| 7.26 | 60147 | 23174 | 29733 | 24317 | 53794 | 29899 | 69096 | 30777 | 48841 | 58767 | 22966 |
| 7.3 | 59341 | 20891 | 29204 | 25920 | 57642 | 29877 | 69720 | 34150 | 49433 | 57804 | 23262 |
| 7.34 | 60109 | 24766 | 27830 | 24756 | 55345 | 29183 | 72941 | 39894 | 40495 | 50834 | 21846 |
| 7.38 | 55772 | 22691 | 25269 | 25236 | 50531 | 27709 | 78201 | 40379 | 33446 | 43583 | 22697 |
| 7.42 | 54102 | 20462 | 25734 | 27232 | 44470 | 28136 | 78070 | 45527 | 29384 | 43365 | 20612 |
| 7.46 | 52298 | 22835 | 25231 | 24013 | 41011 | 30555 | 76753 | 44626 | 27888 | 45191 | 24173 |
| 7.5 | 46492 | 20111 | 24065 | 24188 | 36728 | 25735 | 73452 | 49080 | 26841 | 46579 | 22805 |
| 7.54 | 47461 | 21552 | 23946 | 25193 | 34131 | 26629 | 71339 | 53353 | 30394 | 42319 | 19346 |
| 7.58 | 49972 | 20956 | 24803 | 25970 | 28895 | 31019 | 69526 | 49999 | 29827 | 43852 | 21142 |
| 7.62 | 49652 | 22125 | 25951 | 23529 | 30939 | 28945 | 65644 | 55883 | 28758 | 43298 | 23390 |
| 7.66 | 43839 | 25504 | 29251 | 25708 | 26185 | 30388 | 55224 | 45239 | 27297 | 40617 | 23908 |
| 7.7 | 48752 | 25186 | 26258 | 23150 | 25949 | 29423 | 47032 | 42661 | 26381 | 39852 | 21768 |
| 7.74 | 46791 | 22175 | 25692 | 25466 | 26659 | 26132 | 43741 | 39784 | 28929 | 42523 | 22569 |
| 7.78 | 45537 | 23258 | 27234 | 25792 | 26593 | 28949 | 40082 | 33522 | 25924 | 41875 | 22207 |
| 7.82 | 46719 | 23621 | 29950 | 22375 | 27615 | 28375 | 41396 | 31763 | 27424 | 40209 | 21953 |
| 7.86 | 50399 | 23929 | 29651 | 26161 | 29209 | 30308 | 40965 | 32568 | 31130 | 41912 | 24861 |
| 7.9 | 45691 | 21712 | 31545 | 28017 | 27890 | 31952 | 38415 | 32791 | 27735 | 41568 | 23088 |
| 7.94 | 46055 | 25478 | 35110 | 26710 | 26919 | 29994 | 38846 | 30587 | 27977 | 41462 | 21271 |
| 7.98 | 47788 | 24318 | 32802 | 25513 | 28427 | 30372 | 32709 | 29151 | 28191 | 42439 | 21356 |
| 8.02 | 45265 | 23604 | 33884 | 26221 | 26569 | 29378 | 36947 | 33217 | 28013 | 40068 | 21998 |
| 8.06 | 45372 | 22880 | 38392 | 23552 | 24097 | 27988 | 32436 | 29910 | 29307 | 39234 | 23844 |
| 8.1 | 48269 | 23482 | 38082 | 27457 | 28848 | 31202 | 34257 | 35251 | 27426 | 42052 | 27481 |
| 8.14 | 47656 | 25856 | 35859 | 27092 | 29156 | 30967 | 38356 | 31400 | 28950 | 44519 | 25167 |
| 8.18 | 50112 | 26031 | 32076 | 25227 | 28315 | 30028 | 37162 | 28186 | 27706 | 43701 | 26077 |
| 8.22 | 47296 | 24309 | 32657 | 27073 | 24867 | 33491 | 38008 | 28440 | 28884 | 38238 | 23846 |
| 8.26 | 46305 | 25126 | 29772 | 25471 | 28528 | 31947 | 34745 | 23016 | 27138 | 41961 | 21522 |
| 8.3 | 49577 | 26665 | 32243 | 25994 | 27124 | 27284 | 34827 | 32663 | 26073 | 44218 | 25007 |
| 8.34 | 54307 | 26883 | 28555 | 26561 | 28082 | 32518 | 37430 | 25103 | 29216 | 43778 | 25457 |
| 8.38 | 60219 | 25376 | 30399 | 27409 | 30944 | 30638 | 35165 | 24224 | 29069 | 42644 | 24965 |
| 8.42 | 70378 | 26934 | 29037 | 28182 | 28678 | 30540 | 41438 | 23900 | 31822 | 43011 | 24849 |
| 8.46 | 68558 | 26755 | 28989 | 26151 | 26304 | 32919 | 37347 | 26573 | 33005 | 44580 | 26459 |
| 8.5 | 80799 | 28295 | 25452 | 25315 | 29290 | 30417 | 34201 | 24188 | 27850 | 40749 | 23519 |
| 8.54 | 79745 | 26796 | 26974 | 25929 | 25210 | 30719 | 35649 | 26295 | 27278 | 40426 | 22307 |
| 8.58 | 85110 | 30129 | 26776 | 25080 | 27290 | 32220 | 34296 | 23834 | 28794 | 43837 | 25515 |
| 8.62 | 84124 | 35127 | 24669 | 26074 | 26914 | 33183 | 38152 | 26736 | 28548 | 45478 | 21927 |
| 8.66 | 84476 | 40133 | 25612 | 26604 | 29951 | 32081 | 33459 | 25892 | 31896 | 43464 | 23817 |
| 8.7 | 90411 | 34144 | 25814 | 25950 | 29130 | 30742 | 35626 | 24089 | 29056 | 43913 | 23517 |
| 8.74 | 80760 | 36352 | 25973 | 24932 | 31455 | 30736 | 37693 | 24748 | 27319 | 44743 | 23787 |
| 8.78 | 80072 | 37600 | 26500 | 24858 | 25285 | 33358 | 36683 | 25677 | 30681 | 47259 | 22627 |
| 8.82 | 74926 | 37413 | 25194 | 28492 | 28397 | 28812 | 40358 | 26923 | 33276 | 49730 | 24469 |
| 8.86 | 73712 | 35977 | 24339 | 25449 | 32254 | 28242 | 35886 | 26085 | 32887 | 44752 | 22655 |
| 8.9 | 67965 | 29852 | 23904 | 24678 | 27322 | 33669 | 34654 | 24476 | 32390 | 46112 | 23516 |
| 8.94 | 59600 | 29930 | 27255 | 25942 | 29491 | 30551 | 36545 | 24038 | 33843 | 46492 | 21157 |
| 8.98 | 60177 | 30110 | 28233 | 25970 | 28340 | 29766 | 33783 | 24997 | 37335 | 47252 | 21682 |
| 9.02 | 58903 | 28213 | 25690 | 28761 | 30401 | 31811 | 37987 | 29358 | 35351 | 47974 | 24231 |
| 9.06 | 59033 | 24699 | 27942 | 27226 | 27505 | 28735 | 31527 | 25033 | 33321 | 43660 | 24424 |
| 9.1 | 55777 | 22574 | 23601 | 27245 | 26855 | 29274 | 32506 | 23490 | 32898 | 40795 | 20849 |
| 9.14 | 54315 | 24209 | 21900 | 28444 | 28730 | 32026 | 38364 | 25892 | 34008 | 41468 | 20566 |
| 9.18 | 52083 | 21978 | 26367 | 23755 | 29041 | 30440 | 34258 | 23012 | 38079 | 48081 | 22727 |
| 9.22 | 50570 | 23022 | 22608 | 24829 | 28215 | 28699 | 39575 | 26355 | 35792 | 45945 | 21646 |
| 9.26 | 51311 | 22539 | 24681 | 27062 | 28387 | 31354 | 39674 | 27215 | 34159 | 45570 | 21284 |
| 9.3 | 50051 | 24223 | 27495 | 28536 | 27729 | 31177 | 41402 | 29632 | 33901 | 44363 | 21417 |
| 9.34 | 52634 | 27183 | 24331 | 26466 | 26612 | 30816 | 47564 | 27510 | 35399 | 45278 | 22504 |
| 9.38 | 50889 | 25305 | 22984 | 27431 | 29994 | 31026 | 48888 | 27453 | 40609 | 49441 | 24237 |
| 9.42 | 49446 | 23446 | 23212 | 24768 | 32885 | 30328 | 48738 | 25265 | 45935 | 44239 | 22540 |
| 9.46 | 48975 | 23908 | 22411 | 25022 | 26392 | 31774 | 44345 | 25119 | 48486 | 49271 | 19884 |
| 9.5 | 50665 | 22021 | 26136 | 26002 | 28869 | 31297 | 43478 | 24782 | 60040 | 49592 | 22952 |
| 9.54 | 49768 | 23405 | 25083 | 25012 | 28851 | 33845 | 46074 | 28318 | 63797 | 51434 | 25344 |
| 9.58 | 44918 | 21921 | 25081 | 26709 | 30314 | 33239 | 47238 | 26347 | 70033 | 52401 | 20716 |
| 9.62 | 49028 | 22880 | 27810 | 26889 | 31807 | 35438 | 39681 | 26881 | 68567 | 53430 | 21986 |
| 9.66 | 49170 | 22229 | 23136 | 28619 | 27938 | 31970 | 40801 | 26568 | 63083 | 56047 | 21552 |
| 9.7 | 49177 | 22781 | 26327 | 29555 | 29739 | 32909 | 40328 | 27312 | 65124 | 53186 | 23614 |
| 9.74 | 47326 | 24006 | 23272 | 26426 | 31190 | 35515 | 38042 | 29209 | 63533 | 48620 | 23801 |
| 9.78 | 48833 | 24606 | 23871 | 26818 | 28550 | 34448 | 38812 | 26703 | 54878 | 46851 | 22970 |
| 9.82 | 46728 | 22860 | 26683 | 26340 | 30624 | 32769 | 39339 | 27184 | 50645 | 47370 | 24507 |
| 9.86 | 47918 | 24604 | 24198 | 29014 | 30504 | 35966 | 38008 | 27907 | 41316 | 45107 | 23824 |
| 9.9 | 49586 | 24918 | 24976 | 26248 | 30707 | 33759 | 38981 | 26081 | 40554 | 43173 | 26622 |
| 9.94 | 50095 | 24893 | 27266 | 25246 | 32744 | 34312 | 40156 | 26068 | 35642 | 43123 | 25182 |
| 9.98 | 49670 | 25514 | 24076 | 25507 | 30832 | 36771 | 41348 | 28687 | 37182 | 43237 | 24675 |
| 10.02 | 50913 | 26940 | 27477 | 26987 | 30812 | 32410 | 42477 | 27511 | 33900 | 42522 | 24389 |
| 10.06 | 48745 | 27923 | 28455 | 28049 | 32019 | 34160 | 42057 | 29483 | 33816 | 43728 | 25556 |
| 10.1 | 48152 | 23440 | 27185 | 26385 | 33950 | 35304 | 39974 | 29156 | 33502 | 43993 | 27053 |

| | | | | | | | | | | |
|---|---|---|---|---|---|---|---|---|---|---|
| 10.14 | 52850 | 24089 | 23975 | 26628 | 33531 | 30881 | 40015 | 29443 | 36473 | 43079 | 26026 |
| 10.18 | 53327 | 26202 | 26566 | 28009 | 33807 | 33080 | 40068 | 29226 | 36931 | 44846 | 25043 |
| 10.22 | 51281 | 27984 | 28327 | 27643 | 32990 | 30897 | 40163 | 26861 | 38438 | 44585 | 24217 |
| 10.26 | 51947 | 26962 | 27788 | 24785 | 34688 | 31856 | 34543 | 27930 | 39160 | 46136 | 24348 |
| 10.3 | 51456 | 26081 | 27643 | 24738 | 33034 | 31831 | 38477 | 30588 | 37198 | 45069 | 25164 |
| 10.34 | 56800 | 27058 | 32129 | 29192 | 33467 | 33258 | 35628 | 30681 | 36907 | 44940 | 25765 |
| 10.38 | 57858 | 28516 | 29248 | 29670 | 31291 | 35679 | 38762 | 28607 | 38282 | 42225 | 25818 |
| 10.42 | 56491 | 26463 | 31768 | 27169 | 34817 | 36691 | 39054 | 27414 | 38488 | 46553 | 24937 |
| 10.46 | 57861 | 27201 | 29912 | 27849 | 32085 | 37530 | 38503 | 27731 | 37102 | 47272 | 27106 |
| 10.5 | 58381 | 29926 | 30773 | 29137 | 30449 | 34975 | 41582 | 30496 | 42628 | 47848 | 24652 |
| 10.54 | 56457 | 27484 | 34186 | 27037 | 28986 | 34355 | 36771 | 30426 | 36856 | 43152 | 27014 |
| 10.58 | 60387 | 26414 | 35826 | 27966 | 29684 | 37782 | 40520 | 30033 | 40134 | 45425 | 25610 |
| 10.62 | 58401 | 27895 | 32779 | 26539 | 30314 | 33362 | 39290 | 28208 | 36958 | 42795 | 27098 |
| 10.66 | 58877 | 28677 | 34272 | 28505 | 30209 | 37718 | 41695 | 30222 | 40749 | 44793 | 24530 |
| 10.7 | 56557 | 27108 | 35783 | 30399 | 31701 | 32958 | 41696 | 30112 | 37446 | 42614 | 25759 |
| 10.74 | 53004 | 26031 | 33311 | 26691 | 31501 | 32751 | 40165 | 31799 | 38731 | 44434 | 25395 |
| 10.78 | 58695 | 26413 | 32998 | 26266 | 29926 | 33743 | 41470 | 28396 | 41313 | 45831 | 26339 |
| 10.82 | 55887 | 25492 | 34550 | 28803 | 31587 | 33975 | 40506 | 31181 | 42648 | 46986 | 26527 |
| 10.86 | 53867 | 24383 | 36123 | 28536 | 34363 | 34747 | 39890 | 30689 | 39879 | 46374 | 25056 |
| 10.9 | 50602 | 25258 | 33096 | 28947 | 32448 | 33626 | 39706 | 31075 | 41012 | 45372 | 26471 |
| 10.94 | 52796 | 23975 | 32848 | 29328 | 31232 | 32203 | 39848 | 32809 | 39333 | 46911 | 25480 |
| 10.98 | 53538 | 24335 | 33285 | 29411 | 28812 | 33771 | 37064 | 30295 | 40665 | 44639 | 25032 |
| 11.02 | 54515 | 24448 | 32899 | 30371 | 32482 | 35230 | 38321 | 32689 | 42771 | 47738 | 27879 |
| 11.06 | 53507 | 26032 | 30676 | 27656 | 32864 | 32997 | 37581 | 33417 | 41315 | 50478 | 28136 |
| 11.1 | 54649 | 26715 | 31298 | 28296 | 31078 | 37497 | 39945 | 30473 | 42311 | 50560 | 26751 |
| 11.14 | 52264 | 25080 | 35419 | 29857 | 30675 | 33624 | 40130 | 33135 | 42600 | 54453 | 26356 |
| 11.18 | 56301 | 26235 | 33923 | 30522 | 29947 | 35866 | 41649 | 33016 | 43674 | 57881 | 28880 |
| 11.22 | 55115 | 28591 | 35333 | 28272 | 31552 | 35212 | 41371 | 37603 | 45954 | 62140 | 26157 |
| 11.26 | 59548 | 27724 | 34151 | 29679 | 29600 | 37436 | 39670 | 34502 | 44416 | 69052 | 26790 |
| 11.3 | 61594 | 27111 | 33972 | 30496 | 32894 | 34409 | 41507 | 35338 | 40892 | 79830 | 27955 |
| 11.34 | 62961 | 28603 | 32505 | 28012 | 32575 | 37030 | 41698 | 35615 | 43372 | 76787 | 28341 |
| 11.38 | 62057 | 27924 | 34883 | 29040 | 29595 | 35976 | 41838 | 35587 | 48741 | 77354 | 27430 |
| 11.42 | 68964 | 26909 | 33458 | 31338 | 33795 | 36017 | 41904 | 35068 | 45633 | 79293 | 28723 |
| 11.46 | 74618 | 27278 | 34132 | 29068 | 34241 | 37539 | 44092 | 34554 | 43875 | 77265 | 29836 |
| 11.5 | 83934 | 26365 | 33653 | 28793 | 34058 | 34020 | 40759 | 33362 | 44166 | 69547 | 29801 |
| 11.54 | 86026 | 26805 | 35293 | 30669 | 35414 | 33413 | 42686 | 34905 | 46589 | 68724 | 26770 |
| 11.58 | 90642 | 26269 | 36132 | 32047 | 35209 | 34628 | 39882 | 33176 | 43889 | 64053 | 28784 |
| 11.62 | 94796 | 26471 | 40398 | 30106 | 33640 | 35549 | 39998 | 32735 | 43980 | 55808 | 28458 |
| 11.66 | 100272 | 26917 | 38847 | 29450 | 32216 | 34905 | 43142 | 34671 | 44167 | 53657 | 26389 |
| 11.7 | 100148 | 28462 | 37352 | 30178 | 34925 | 37220 | 39308 | 32385 | 43235 | 49992 | 28668 |
| 11.74 | 97357 | 26019 | 38264 | 27848 | 32459 | 33667 | 38941 | 34224 | 45857 | 47909 | 29338 |
| 11.78 | 95565 | 25689 | 36594 | 30927 | 35575 | 35791 | 39624 | 33097 | 51473 | 49330 | 26565 |
| 11.82 | 94234 | 23399 | 37415 | 30154 | 36035 | 36673 | 41683 | 33370 | 46188 | 51775 | 30659 |
| 11.86 | 89909 | 26272 | 35609 | 29658 | 34889 | 35381 | 42476 | 35230 | 50514 | 47994 | 28510 |
| 11.9 | 87349 | 27145 | 37856 | 31004 | 33886 | 41008 | 43270 | 36116 | 52373 | 50806 | 27900 |
| 11.94 | 85078 | 26296 | 38961 | 29412 | 36391 | 39534 | 39577 | 39641 | 57636 | 55823 | 29540 |
| 11.98 | 80414 | 26400 | 40168 | 30311 | 34048 | 41977 | 42925 | 41588 | 58328 | 57695 | 31202 |
| 12.02 | 76592 | 27877 | 36922 | 32376 | 34735 | 41205 | 47227 | 46647 | 63746 | 64170 | 31143 |
| 12.06 | 75548 | 27459 | 36180 | 29174 | 32619 | 39875 | 51184 | 51536 | 61559 | 66807 | 31109 |
| 12.1 | 75126 | 28190 | 35096 | 31532 | 34353 | 37201 | 54664 | 52009 | 69690 | 65728 | 30825 |
| 12.14 | 72877 | 27814 | 34848 | 30569 | 37033 | 39195 | 62621 | 48832 | 67668 | 67748 | 29903 |
| 12.18 | 70992 | 28913 | 35559 | 32820 | 36511 | 39199 | 66185 | 52003 | 68143 | 64975 | 29359 |
| 12.22 | 67106 | 27806 | 38537 | 29427 | 39057 | 37693 | 69789 | 49182 | 64876 | 68533 | 29242 |
| 12.26 | 69006 | 28383 | 35489 | 28462 | 40556 | 38148 | 75282 | 48580 | 63778 | 63676 | 30285 |
| 12.3 | 66501 | 29305 | 35503 | 31682 | 44693 | 40781 | 77730 | 48539 | 61135 | 62517 | 29579 |
| 12.34 | 67011 | 28839 | 36092 | 31965 | 41639 | 43524 | 80269 | 43096 | 58156 | 62836 | 29859 |
| 12.38 | 62651 | 28621 | 35625 | 31437 | 43644 | 39469 | 77220 | 40965 | 52480 | 60803 | 31445 |
| 12.42 | 65686 | 30453 | 34052 | 33738 | 44414 | 41684 | 80612 | 39495 | 50399 | 65345 | 30415 |
| 12.46 | 62518 | 28739 | 36003 | 32749 | 45282 | 44750 | 80503 | 37434 | 46705 | 60857 | 30530 |
| 12.5 | 63310 | 29381 | 32771 | 33229 | 44346 | 41433 | 76735 | 36711 | 45774 | 67060 | 32949 |
| 12.54 | 61606 | 27760 | 35667 | 33704 | 40493 | 44128 | 72227 | 35763 | 45911 | 65689 | 32071 |
| 12.58 | 65227 | 30806 | 33818 | 32543 | 41646 | 46324 | 75545 | 38312 | 45764 | 65315 | 33802 |
| 12.62 | 66732 | 30119 | 33162 | 29882 | 37689 | 47113 | 72412 | 39170 | 45583 | 68966 | 33287 |
| 12.66 | 63702 | 29657 | 34020 | 37473 | 35520 | 44387 | 73626 | 42903 | 43346 | 67974 | 36826 |
| 12.7 | 59625 | 30006 | 37116 | 34638 | 35107 | 41481 | 83876 | 45187 | 44891 | 69775 | 36242 |
| 12.74 | 62205 | 29221 | 34230 | 34290 | 34844 | 38802 | 81929 | 49040 | 39838 | 66957 | 37116 |
| 12.78 | 59648 | 30071 | 31779 | 35653 | 34790 | 43715 | 87444 | 53753 | 41321 | 69082 | 37335 |
| 12.82 | 57418 | 30467 | 34228 | 33319 | 37296 | 39066 | 87858 | 52956 | 40555 | 67361 | 40174 |
| 12.86 | 60531 | 28719 | 31423 | 34306 | 36436 | 38084 | 89594 | 54011 | 43436 | 69537 | 43297 |
| 12.9 | 57893 | 31371 | 34720 | 34913 | 40707 | 38631 | 88265 | 52061 | 44539 | 69525 | 39590 |
| 12.94 | 58979 | 31385 | 33101 | 34816 | 45003 | 35961 | 87042 | 51105 | 41259 | 66909 | 43204 |
| 12.98 | 59287 | 31032 | 32477 | 34416 | 45095 | 36856 | 91346 | 50423 | 42127 | 64245 | 42481 |
| 13.02 | 58785 | 32716 | 33004 | 34546 | 47718 | 38936 | 86134 | 44033 | 41839 | 62659 | 44037 |
| 13.06 | 59020 | 34249 | 35586 | 31552 | 49639 | 34089 | 82857 | 41679 | 44675 | 59857 | 43648 |
| 13.1 | 56752 | 33184 | 31971 | 34209 | 50575 | 36062 | 84369 | 39466 | 43464 | 57712 | 43929 |
| 13.14 | 55257 | 34726 | 31874 | 33788 | 52820 | 37001 | 81262 | 36116 | 42812 | 56936 | 43281 |
| 13.18 | 54026 | 35134 | 31442 | 31861 | 50534 | 39806 | 77070 | 36389 | 44182 | 55595 | 45215 |
| 13.22 | 57280 | 34678 | 32829 | 31451 | 48682 | 39390 | 76392 | 37680 | 43641 | 52575 | 43099 |
| 13.26 | 55096 | 32239 | 31913 | 31432 | 46170 | 40700 | 70212 | 36676 | 46004 | 52598 | 43870 |

-continued

| | | | | | | | | | | | |
|---|---|---|---|---|---|---|---|---|---|---|---|
| 13.3 | 56685 | 29510 | 33881 | 31319 | 43157 | 41260 | 69116 | 40581 | 47986 | 55314 | 41532 |
| 13.34 | 53883 | 32285 | 33618 | 32369 | 42214 | 41118 | 64174 | 44358 | 54327 | 68368 | 39803 |
| 13.38 | 58705 | 30878 | 36080 | 32860 | 41253 | 45728 | 62906 | 52365 | 66482 | 75545 | 42039 |
| 13.42 | 57533 | 33160 | 36158 | 32157 | 39908 | 43979 | 54761 | 56334 | 75401 | 82311 | 37039 |
| 13.46 | 54366 | 35929 | 34786 | 33409 | 37994 | 40231 | 52789 | 65289 | 86040 | 92361 | 40345 |
| 13.5 | 54441 | 34952 | 33300 | 35015 | 38294 | 39788 | 50379 | 75125 | 97998 | 95292 | 36834 |
| 13.54 | 55823 | 37170 | 35584 | 32738 | 36924 | 40154 | 47466 | 76915 | 100939 | 101123 | 34615 |
| 13.58 | 57238 | 39470 | 36617 | 32990 | 38932 | 41011 | 47205 | 80498 | 103024 | 100785 | 39329 |
| 13.62 | 55414 | 38250 | 34925 | 32589 | 37972 | 36981 | 45864 | 89835 | 102761 | 104572 | 37335 |
| 13.66 | 56841 | 39389 | 34023 | 33618 | 37429 | 37363 | 44988 | 87676 | 101717 | 99954 | 41606 |
| 13.7 | 58711 | 37976 | 35437 | 33236 | 39762 | 36196 | 44003 | 91091 | 88431 | 97898 | 38896 |
| 13.74 | 58453 | 37727 | 34909 | 31392 | 38111 | 37460 | 44371 | 88035 | 83081 | 91523 | 38717 |
| 13.78 | 60641 | 37669 | 33342 | 31771 | 39253 | 36801 | 47813 | 86043 | 68166 | 90897 | 39377 |
| 13.82 | 57296 | 33259 | 31394 | 30669 | 40343 | 35774 | 48358 | 84413 | 62550 | 87887 | 39530 |
| 13.86 | 63644 | 36682 | 34503 | 31010 | 37374 | 37121 | 44142 | 78216 | 53118 | 86006 | 41774 |
| 13.9 | 61457 | 34112 | 34853 | 30564 | 35437 | 37430 | 46590 | 75286 | 48492 | 84747 | 41361 |
| 13.94 | 59516 | 33601 | 31668 | 28903 | 35520 | 38559 | 50775 | 67303 | 43957 | 91101 | 39824 |
| 13.98 | 63039 | 38006 | 32353 | 30824 | 36029 | 40982 | 53076 | 63249 | 45703 | 93956 | 37606 |
| 14.02 | 63979 | 38042 | 35476 | 30959 | 34837 | 39065 | 52239 | 55512 | 47793 | 100191 | 40467 |
| 14.06 | 64180 | 39341 | 30827 | 31188 | 36376 | 39573 | 57777 | 53369 | 55282 | 105529 | 37433 |
| 14.1 | 63929 | 42087 | 30886 | 29268 | 33901 | 39268 | 60086 | 47819 | 59084 | 108147 | 38515 |
| 14.14 | 64546 | 41327 | 33530 | 30168 | 37191 | 38939 | 60286 | 45550 | 62493 | 110884 | 36552 |
| 14.18 | 67546 | 41380 | 31354 | 31873 | 36496 | 39225 | 66843 | 42204 | 68689 | 102284 | 37908 |
| 14.22 | 69245 | 41438 | 31870 | 30059 | 40282 | 36420 | 68316 | 40912 | 72012 | 99193 | 35382 |
| 14.26 | 75084 | 41698 | 32687 | 30576 | 41117 | 37121 | 71573 | 41210 | 72561 | 95502 | 36618 |
| 14.3 | 78317 | 38251 | 32666 | 29684 | 46649 | 37212 | 68532 | 39759 | 75083 | 92654 | 36084 |
| 14.34 | 84327 | 36899 | 32766 | 29983 | 51595 | 36714 | 70029 | 38171 | 74543 | 88215 | 37036 |
| 14.38 | 86476 | 33947 | 34086 | 29925 | 61964 | 38120 | 69369 | 35658 | 74855 | 78754 | 35681 |
| 14.42 | 87152 | 34513 | 32442 | 30107 | 67661 | 37566 | 68865 | 37671 | 69355 | 72891 | 36408 |
| 14.46 | 94221 | 33420 | 34262 | 31249 | 75726 | 37465 | 66577 | 38326 | 65696 | 61252 | 39387 |
| 14.5 | 91674 | 33378 | 33497 | 30315 | 81225 | 37815 | 62639 | 37396 | 58834 | 60630 | 35204 |
| 14.54 | 90628 | 37649 | 34319 | 31006 | 85511 | 37354 | 57062 | 37156 | 52335 | 56402 | 35712 |
| 14.58 | 85716 | 37058 | 33670 | 31295 | 89311 | 35359 | 56132 | 34943 | 46941 | 56289 | 32817 |
| 14.62 | 86367 | 37302 | 37618 | 34234 | 85880 | 36554 | 51913 | 32443 | 47982 | 51762 | 32224 |
| 14.66 | 82430 | 38496 | 34497 | 32061 | 80416 | 36791 | 52180 | 33623 | 44899 | 52256 | 32762 |
| 14.7 | 77813 | 37248 | 34945 | 33937 | 76911 | 36251 | 50884 | 31513 | 40535 | 50889 | 34608 |
| 14.74 | 75557 | 39974 | 36135 | 32043 | 71344 | 36225 | 50547 | 31014 | 39393 | 50507 | 33519 |
| 14.78 | 72134 | 39688 | 36838 | 31011 | 66262 | 36857 | 49950 | 32674 | 40887 | 56257 | 33378 |
| 14.82 | 73907 | 37785 | 37569 | 31628 | 57729 | 35903 | 52610 | 29512 | 37368 | 56782 | 31698 |
| 14.86 | 74478 | 38031 | 38989 | 35396 | 51276 | 36047 | 50999 | 31980 | 37514 | 55818 | 35835 |
| 14.9 | 70550 | 35453 | 38715 | 33770 | 47800 | 36221 | 50291 | 33607 | 38123 | 56473 | 34341 |
| 14.94 | 71620 | 36752 | 39560 | 32329 | 44151 | 34446 | 52575 | 34391 | 39155 | 61941 | 31727 |
| 14.98 | 72605 | 34009 | 34816 | 34475 | 42843 | 35977 | 53986 | 34428 | 44687 | 62897 | 34516 |
| 15.02 | 72770 | 34310 | 35188 | 33051 | 46521 | 34871 | 53169 | 35713 | 47813 | 66625 | 34683 |
| 15.06 | 74994 | 37642 | 37449 | 32955 | 44172 | 38388 | 54058 | 35328 | 53913 | 67355 | 33536 |
| 15.1 | 75522 | 36112 | 36075 | 33545 | 48001 | 40883 | 55830 | 34347 | 64503 | 73535 | 35281 |
| 15.14 | 76401 | 35356 | 35297 | 33152 | 51806 | 41658 | 55023 | 35886 | 77141 | 78183 | 35726 |
| 15.18 | 73126 | 35608 | 35491 | 36508 | 58120 | 42105 | 57088 | 38501 | 81577 | 81368 | 35307 |
| 15.22 | 73839 | 33448 | 38197 | 33490 | 64689 | 40400 | 58063 | 36197 | 88361 | 80930 | 38516 |
| 15.26 | 78033 | 31480 | 34490 | 33679 | 68229 | 44442 | 54248 | 36231 | 93107 | 84234 | 37806 |
| 15.3 | 76822 | 30572 | 34186 | 33870 | 70689 | 45243 | 56098 | 33743 | 94847 | 83380 | 37966 |
| 15.34 | 76335 | 32295 | 35927 | 32619 | 69310 | 49537 | 51517 | 34448 | 90267 | 89934 | 36938 |
| 15.38 | 77126 | 33092 | 33785 | 33591 | 70637 | 45354 | 54397 | 38390 | 86855 | 90592 | 39855 |
| 15.42 | 75054 | 31535 | 34162 | 32336 | 69816 | 48189 | 53760 | 41602 | 77709 | 91142 | 36081 |
| 15.46 | 74096 | 33557 | 35993 | 33099 | 64579 | 45579 | 53919 | 44860 | 72104 | 88066 | 39856 |
| 15.5 | 73738 | 34313 | 34866 | 35209 | 64126 | 46171 | 52692 | 47716 | 68189 | 85296 | 38773 |
| 15.54 | 73957 | 33877 | 35141 | 31727 | 55463 | 46254 | 53892 | 52669 | 58838 | 81551 | 39683 |
| 15.58 | 77152 | 35601 | 34257 | 31104 | 53050 | 46272 | 53284 | 56021 | 55155 | 83916 | 40254 |
| 15.62 | 70532 | 41658 | 33562 | 31555 | 48959 | 45636 | 51971 | 57661 | 55645 | 81152 | 40869 |
| 15.66 | 71870 | 43732 | 37014 | 32218 | 45514 | 45140 | 53461 | 59340 | 57118 | 79538 | 41544 |
| 15.7 | 73003 | 47758 | 32851 | 30785 | 44864 | 44938 | 51150 | 59829 | 58665 | 76931 | 40899 |
| 15.74 | 71361 | 52098 | 36046 | 32727 | 44111 | 41218 | 57131 | 57447 | 60478 | 73495 | 40349 |
| 15.78 | 72064 | 53320 | 36699 | 32141 | 48061 | 40674 | 60556 | 54403 | 63326 | 70380 | 37418 |
| 15.82 | 74375 | 55779 | 36624 | 33962 | 43940 | 42384 | 65471 | 53128 | 65797 | 68734 | 38802 |
| 15.86 | 73095 | 58238 | 37593 | 32418 | 43194 | 43317 | 70922 | 48676 | 64582 | 65450 | 40165 |
| 15.9 | 73619 | 58815 | 36294 | 33456 | 41794 | 41168 | 75007 | 51465 | 64650 | 61907 | 44170 |
| 15.94 | 72479 | 54552 | 38566 | 32435 | 40341 | 38111 | 75489 | 51229 | 60120 | 62139 | 41959 |
| 15.98 | 73082 | 53128 | 36714 | 31675 | 40647 | 41058 | 82172 | 50603 | 56907 | 58963 | 42148 |
| 16.02 | 72358 | 50444 | 37175 | 31593 | 41400 | 43887 | 85074 | 53470 | 53031 | 57090 | 42117 |
| 16.06 | 73474 | 45856 | 37093 | 33743 | 42499 | 43711 | 93440 | 57404 | 47069 | 53320 | 44523 |
| 16.1 | 72108 | 45396 | 39155 | 30766 | 40305 | 49623 | 94774 | 61035 | 42066 | 56611 | 45729 |
| 16.14 | 72781 | 44730 | 38676 | 30950 | 39047 | 51323 | 100336 | 62502 | 39098 | 54686 | 44469 |
| 16.18 | 75791 | 44772 | 38321 | 33197 | 39902 | 52531 | 101320 | 65917 | 37059 | 52111 | 47740 |
| 16.22 | 73869 | 42725 | 38939 | 31728 | 39992 | 51084 | 97983 | 64404 | 38495 | 48799 | 46130 |
| 16.26 | 73631 | 42425 | 38513 | 30680 | 38372 | 53431 | 99243 | 60176 | 39127 | 52853 | 46773 |
| 16.3 | 68559 | 43965 | 39691 | 33976 | 39844 | 49087 | 99740 | 60848 | 35303 | 54867 | 47364 |
| 16.34 | 69498 | 40388 | 41135 | 35649 | 38551 | 49941 | 96043 | 56478 | 35615 | 51633 | 44599 |
| 16.38 | 72161 | 40254 | 40683 | 32998 | 40901 | 48862 | 96078 | 51733 | 38559 | 55269 | 45126 |
| 16.42 | 71870 | 37383 | 38149 | 32536 | 38704 | 45067 | 95289 | 46835 | 34339 | 54760 | 46503 |

| | | | | | | | | | | |
|---|---|---|---|---|---|---|---|---|---|---|
| 16.46 | 68104 | 38266 | 42934 | 30475 | 40815 | 44358 | 91006 | 41194 | 36251 | 52891 | 50097 |
| 16.5 | 73040 | 36591 | 40879 | 34560 | 38879 | 38986 | 82448 | 39332 | 37528 | 51441 | 45886 |
| 16.54 | 68979 | 35270 | 39523 | 30666 | 40171 | 37313 | 79301 | 35610 | 35705 | 52744 | 48332 |
| 16.58 | 69481 | 35276 | 39536 | 33838 | 38684 | 34674 | 76747 | 33042 | 38598 | 51814 | 48621 |
| 16.62 | 71030 | 37043 | 40404 | 33084 | 38011 | 38327 | 73131 | 32690 | 35934 | 53936 | 49110 |
| 16.66 | 67640 | 34592 | 37936 | 30923 | 37584 | 36057 | 74922 | 32119 | 38231 | 53736 | 48472 |
| 16.7 | 68601 | 35412 | 39304 | 32341 | 38357 | 35496 | 73674 | 33063 | 38453 | 56060 | 47472 |
| 16.74 | 70673 | 35025 | 37217 | 31218 | 40823 | 36812 | 74464 | 31625 | 35997 | 59201 | 49362 |
| 16.78 | 72335 | 36415 | 35531 | 31563 | 41235 | 36475 | 70589 | 31943 | 37031 | 59777 | 48003 |
| 16.82 | 71670 | 38739 | 36486 | 32371 | 40410 | 35634 | 70573 | 32283 | 37107 | 61648 | 46180 |
| 16.86 | 71067 | 39829 | 34734 | 32721 | 41394 | 35234 | 69158 | 35720 | 36582 | 63476 | 47137 |
| 16.9 | 69076 | 39057 | 35605 | 32357 | 40315 | 35496 | 67502 | 30560 | 36666 | 62307 | 47074 |
| 16.94 | 68318 | 44115 | 36664 | 31642 | 40737 | 36713 | 62698 | 35605 | 36259 | 65371 | 45915 |
| 16.98 | 68029 | 44617 | 34767 | 30140 | 41317 | 38333 | 60773 | 36644 | 36908 | 66128 | 42407 |
| 17.02 | 73086 | 48367 | 36001 | 31756 | 40729 | 37848 | 61736 | 40149 | 42080 | 66282 | 43532 |
| 17.06 | 74239 | 45711 | 34164 | 30933 | 38296 | 39479 | 59597 | 38689 | 43081 | 68104 | 42461 |
| 17.1 | 72796 | 46765 | 36299 | 32294 | 40694 | 39846 | 58480 | 41549 | 45226 | 67929 | 41454 |
| 17.14 | 76959 | 46993 | 36772 | 30276 | 38911 | 41401 | 57332 | 41753 | 49000 | 62667 | 40391 |
| 17.18 | 77051 | 46076 | 37939 | 30305 | 37205 | 41063 | 54034 | 41529 | 46474 | 67080 | 38158 |
| 17.22 | 78352 | 45997 | 38116 | 30962 | 38840 | 38316 | 53937 | 46103 | 47810 | 63900 | 36498 |
| 17.26 | 77606 | 43019 | 36407 | 29654 | 37062 | 40122 | 52241 | 41361 | 48149 | 61303 | 37762 |
| 17.3 | 76997 | 40339 | 36444 | 28880 | 37777 | 39471 | 53597 | 39456 | 45741 | 64895 | 34612 |
| 17.34 | 75694 | 38097 | 37400 | 28280 | 37696 | 36363 | 51971 | 37051 | 46112 | 59805 | 36154 |
| 17.38 | 79048 | 36733 | 36818 | 31777 | 35781 | 36214 | 49619 | 37106 | 45139 | 58329 | 34192 |
| 17.42 | 79775 | 34662 | 37014 | 29243 | 37481 | 37528 | 48114 | 37142 | 47121 | 56052 | 36017 |
| 17.46 | 73268 | 37976 | 35495 | 32162 | 36206 | 36783 | 50715 | 35113 | 44746 | 57671 | 35304 |
| 17.5 | 74306 | 38241 | 37182 | 30505 | 36439 | 36878 | 47478 | 34396 | 40728 | 56072 | 34608 |
| 17.54 | 73772 | 39628 | 37067 | 30400 | 39068 | 39016 | 50081 | 31994 | 39969 | 57935 | 34624 |
| 17.58 | 74401 | 39166 | 36698 | 29997 | 39746 | 40114 | 46587 | 33322 | 39305 | 57699 | 35574 |
| 17.62 | 73249 | 37379 | 36709 | 29914 | 40351 | 42016 | 47751 | 33410 | 38943 | 60164 | 34220 |
| 17.66 | 73581 | 41055 | 36438 | 33342 | 42140 | 42854 | 47556 | 33605 | 38754 | 62436 | 32563 |
| 17.7 | 69924 | 39127 | 38732 | 31275 | 41580 | 44184 | 46714 | 35237 | 35324 | 63024 | 33462 |
| 17.74 | 69032 | 41733 | 36562 | 30711 | 41559 | 44588 | 47843 | 37772 | 37331 | 69016 | 34166 |
| 17.78 | 67757 | 44101 | 37026 | 30519 | 41535 | 42133 | 45176 | 38802 | 33826 | 72018 | 34104 |
| 17.82 | 71431 | 47651 | 38554 | 33525 | 41738 | 45129 | 46301 | 37479 | 34548 | 74228 | 34879 |
| 17.86 | 69229 | 50763 | 36259 | 31138 | 40399 | 41518 | 46239 | 39274 | 32897 | 76292 | 31494 |
| 17.9 | 68212 | 47595 | 37120 | 31105 | 40015 | 44291 | 46434 | 40199 | 35089 | 75996 | 32107 |
| 17.94 | 67217 | 51722 | 36967 | 32281 | 40473 | 42910 | 42123 | 42491 | 33474 | 77172 | 32071 |
| 17.98 | 69582 | 49738 | 36739 | 29131 | 39137 | 41321 | 44063 | 42939 | 35473 | 73180 | 33593 |
| 18.02 | 65420 | 49706 | 37336 | 32018 | 38101 | 39794 | 46009 | 43117 | 32945 | 71922 | 32821 |
| 18.06 | 69672 | 51720 | 39612 | 32006 | 35969 | 40443 | 42952 | 43535 | 33320 | 69951 | 33247 |
| 18.1 | 67625 | 49277 | 37327 | 30780 | 38660 | 38372 | 43640 | 38781 | 35716 | 65919 | 34221 |
| 18.14 | 64919 | 49407 | 37325 | 29970 | 37180 | 37838 | 42137 | 38801 | 38564 | 61388 | 35296 |
| 18.18 | 68474 | 45999 | 34921 | 31739 | 38017 | 40356 | 43728 | 39963 | 37159 | 61586 | 34699 |
| 18.22 | 71035 | 42980 | 38306 | 29118 | 37014 | 36696 | 42638 | 37126 | 40346 | 56271 | 32655 |
| 18.26 | 66393 | 41495 | 37815 | 30734 | 38137 | 35503 | 42724 | 38807 | 41952 | 53902 | 33717 |
| 18.3 | 70684 | 39538 | 35508 | 31684 | 41706 | 39244 | 41706 | 36247 | 42890 | 53980 | 35475 |
| 18.34 | 71657 | 40787 | 36300 | 30459 | 48388 | 37569 | 45257 | 37018 | 45235 | 56867 | 35684 |
| 18.38 | 68903 | 42400 | 36552 | 29871 | 52903 | 35021 | 46640 | 37231 | 52316 | 57147 | 34601 |
| 18.42 | 71021 | 39340 | 33941 | 28422 | 64823 | 35588 | 46121 | 35165 | 55355 | 61405 | 36156 |
| 18.46 | 75488 | 41468 | 35727 | 29965 | 79699 | 37068 | 47621 | 36847 | 59937 | 59802 | 35972 |
| 18.5 | 75859 | 42410 | 36933 | 30806 | 96158 | 35555 | 47110 | 37065 | 64036 | 62840 | 33680 |
| 18.54 | 73008 | 41333 | 33730 | 30811 | 112673 | 37147 | 48121 | 33626 | 66912 | 63339 | 33177 |
| 18.58 | 74768 | 41023 | 36686 | 30887 | 127786 | 36634 | 47442 | 34089 | 74039 | 65751 | 34468 |
| 18.62 | 76768 | 40778 | 34531 | 30000 | 139456 | 38551 | 51241 | 34961 | 72537 | 66010 | 33507 |
| 18.66 | 74438 | 39710 | 36686 | 30312 | 147257 | 39469 | 48640 | 33394 | 75238 | 64770 | 34375 |
| 18.7 | 77557 | 37955 | 35386 | 29965 | 146340 | 40050 | 49682 | 32604 | 69513 | 65067 | 32738 |
| 18.74 | 75468 | 38366 | 35692 | 30077 | 146352 | 40773 | 48887 | 30879 | 66646 | 66934 | 33828 |
| 18.78 | 76366 | 37790 | 37738 | 31419 | 138261 | 41742 | 47727 | 34474 | 63386 | 65303 | 35480 |
| 18.82 | 75260 | 37410 | 37631 | 29172 | 124593 | 40215 | 50008 | 35255 | 58900 | 64774 | 34567 |
| 18.86 | 74926 | 34773 | 37181 | 29398 | 111172 | 41353 | 51107 | 36105 | 50160 | 63477 | 35428 |
| 18.9 | 76071 | 37103 | 37710 | 30811 | 99515 | 37885 | 48626 | 38272 | 46138 | 62312 | 35778 |
| 18.94 | 70349 | 35201 | 40535 | 31217 | 83443 | 36349 | 47958 | 42510 | 41489 | 63947 | 34812 |
| 18.98 | 70746 | 36866 | 39188 | 30518 | 72823 | 36975 | 47020 | 47093 | 39457 | 62001 | 37200 |
| 19.02 | 69785 | 35803 | 38456 | 30164 | 62627 | 35851 | 49324 | 48671 | 41767 | 63954 | 37814 |
| 19.06 | 66842 | 35922 | 38883 | 30817 | 58738 | 35187 | 51536 | 50549 | 42473 | 65577 | 38414 |
| 19.1 | 68491 | 38077 | 39271 | 32739 | 55973 | 33955 | 51782 | 51226 | 43600 | 66792 | 37703 |
| 19.14 | 68618 | 37086 | 39317 | 31636 | 51302 | 32687 | 53604 | 53077 | 49320 | 67323 | 40781 |
| 19.18 | 71971 | 38256 | 38535 | 29054 | 47700 | 35693 | 55988 | 51361 | 52946 | 66552 | 38527 |
| 19.22 | 68615 | 37042 | 40204 | 28712 | 47382 | 36022 | 60963 | 48771 | 59119 | 68842 | 40019 |
| 19.26 | 69113 | 36314 | 38938 | 31325 | 47315 | 34731 | 62016 | 46276 | 62050 | 69072 | 40691 |
| 19.3 | 69778 | 34906 | 39790 | 29858 | 44665 | 38429 | 66894 | 43398 | 68076 | 68562 | 39138 |
| 19.34 | 68294 | 35677 | 38590 | 29820 | 44651 | 39079 | 65975 | 41009 | 67993 | 66787 | 38972 |
| 19.38 | 68108 | 35310 | 37557 | 30570 | 43734 | 39360 | 68642 | 35857 | 63551 | 67932 | 39908 |
| 19.42 | 65893 | 37186 | 35410 | 32388 | 41016 | 38580 | 70239 | 33642 | 61416 | 65452 | 39893 |
| 19.46 | 68561 | 38190 | 36754 | 30661 | 40066 | 38305 | 71143 | 33393 | 60618 | 64580 | 40802 |
| 19.5 | 67164 | 39847 | 36598 | 31301 | 39673 | 37896 | 70060 | 30236 | 53092 | 65676 | 37467 |
| 19.54 | 68961 | 36366 | 34452 | 33419 | 38839 | 36458 | 68833 | 34264 | 49710 | 63465 | 39532 |
| 19.58 | 69037 | 40518 | 36109 | 31170 | 39709 | 37167 | 65935 | 36868 | 46513 | 64144 | 39481 |

-continued

| | | | | | | | | | | |
|---|---|---|---|---|---|---|---|---|---|---|
| 19.62 | 72184 | 39703 | 36064 | 30643 | 36852 | 37669 | 62734 | 36715 | 42022 | 59984 | 40846 |
| 19.66 | 71568 | 39960 | 34863 | 33010 | 37200 | 35573 | 60455 | 39382 | 37930 | 60907 | 40051 |
| 19.7 | 72447 | 42834 | 35555 | 33184 | 36366 | 35337 | 55845 | 42488 | 37298 | 59610 | 38701 |
| 19.74 | 73490 | 42901 | 36551 | 32841 | 39058 | 33685 | 53823 | 44217 | 35704 | 63185 | 42207 |
| 19.78 | 75849 | 45802 | 37618 | 33167 | 37544 | 33300 | 54260 | 44726 | 37812 | 62589 | 41396 |
| 19.82 | 76978 | 42324 | 35608 | 30989 | 37200 | 35593 | 52761 | 47284 | 39624 | 63457 | 40226 |
| 19.86 | 81675 | 45295 | 36166 | 31203 | 36821 | 35669 | 52252 | 46395 | 43903 | 65993 | 42131 |
| 19.9 | 80376 | 47189 | 36278 | 31710 | 36914 | 36130 | 49696 | 47542 | 46597 | 64251 | 41980 |
| 19.94 | 81770 | 46809 | 37515 | 31892 | 39191 | 39019 | 50976 | 43723 | 47677 | 69381 | 40915 |
| 19.98 | 84968 | 45712 | 35202 | 31349 | 41117 | 39797 | 51006 | 42475 | 49254 | 76828 | 41515 |
| 20.02 | 86317 | 47527 | 35116 | 32721 | 40767 | 38802 | 52308 | 41616 | 50579 | 78229 | 41518 |
| 20.06 | 85393 | 49312 | 36537 | 30263 | 41661 | 39972 | 52094 | 38771 | 54776 | 85225 | 43433 |
| 20.1 | 85280 | 49007 | 37083 | 31643 | 43929 | 39986 | 53318 | 35717 | 52818 | 88335 | 42318 |
| 20.14 | 86282 | 49182 | 36247 | 29300 | 49276 | 38932 | 53341 | 36312 | 52221 | 89093 | 42485 |
| 20.18 | 84864 | 49377 | 38305 | 30897 | 52744 | 38500 | 54637 | 32021 | 47678 | 86607 | 44951 |
| 20.22 | 88653 | 46800 | 36856 | 31776 | 57874 | 37827 | 55253 | 31505 | 47849 | 88769 | 44906 |
| 20.26 | 86585 | 45248 | 37452 | 30228 | 64247 | 38054 | 55472 | 29758 | 42417 | 84496 | 45118 |
| 20.3 | 89580 | 45066 | 36566 | 28889 | 70429 | 35740 | 56510 | 31141 | 40324 | 78486 | 44749 |
| 20.34 | 86010 | 42480 | 36758 | 29707 | 77670 | 35476 | 58351 | 32817 | 39332 | 73539 | 44534 |
| 20.38 | 86235 | 44127 | 36922 | 30471 | 82541 | 33887 | 59548 | 34377 | 34760 | 68790 | 45955 |
| 20.42 | 84907 | 43462 | 37622 | 29706 | 88414 | 34420 | 55993 | 37355 | 34193 | 63540 | 45854 |
| 20.46 | 87237 | 42079 | 38633 | 28776 | 90952 | 34214 | 56299 | 38397 | 31324 | 58084 | 46124 |
| 20.5 | 84877 | 40443 | 37575 | 29623 | 91922 | 34736 | 54814 | 40704 | 31500 | 57166 | 46770 |
| 20.54 | 82798 | 42991 | 38025 | 30250 | 90444 | 35689 | 55093 | 41667 | 31671 | 53049 | 44507 |
| 20.58 | 80387 | 41805 | 38055 | 30347 | 88472 | 35823 | 53990 | 39754 | 31849 | 50151 | 42976 |
| 20.62 | 79757 | 42614 | 38186 | 29513 | 84910 | 38859 | 52976 | 40512 | 30439 | 52185 | 45077 |
| 20.66 | 79144 | 42908 | 38863 | 29656 | 80997 | 38588 | 52704 | 39265 | 31715 | 48396 | 45801 |
| 20.7 | 77964 | 43162 | 37892 | 30485 | 72346 | 37458 | 51815 | 38032 | 30726 | 47278 | 45329 |
| 20.74 | 78335 | 43169 | 37753 | 30611 | 64558 | 40551 | 53733 | 37252 | 31219 | 45288 | 46174 |
| 20.78 | 78888 | 45325 | 38923 | 29081 | 61206 | 42283 | 55775 | 34198 | 31813 | 48001 | 44222 |
| 20.82 | 78674 | 43793 | 41023 | 29664 | 55313 | 43925 | 54262 | 33391 | 32050 | 49375 | 46798 |
| 20.86 | 76040 | 43540 | 37800 | 29960 | 51115 | 43849 | 54837 | 31162 | 29012 | 48086 | 44269 |
| 20.9 | 73387 | 42213 | 37548 | 28830 | 51586 | 47609 | 56536 | 29402 | 31139 | 50343 | 47181 |
| 20.94 | 81266 | 41478 | 38765 | 29808 | 53186 | 49738 | 56676 | 32194 | 33619 | 50676 | 50099 |
| 20.98 | 79072 | 38115 | 38525 | 28052 | 52135 | 45481 | 57202 | 28307 | 29074 | 52133 | 46551 |
| 21.02 | 82588 | 38829 | 39330 | 26736 | 52733 | 47855 | 55316 | 33029 | 30110 | 51648 | 44899 |
| 21.06 | 80732 | 41488 | 39526 | 28201 | 52860 | 47852 | 53231 | 31521 | 28439 | 49059 | 45942 |
| 21.1 | 80179 | 38808 | 42594 | 27327 | 54060 | 47814 | 55730 | 30958 | 30376 | 53622 | 44762 |
| 21.14 | 79143 | 39450 | 39742 | 29810 | 55143 | 48357 | 55871 | 29012 | 33823 | 50065 | 46928 |
| 21.18 | 75627 | 39693 | 41469 | 29955 | 52408 | 48607 | 56251 | 29703 | 32026 | 48355 | 42698 |
| 21.22 | 75883 | 41262 | 38518 | 28819 | 48402 | 45562 | 53376 | 30891 | 31145 | 48696 | 42892 |
| 21.26 | 72896 | 41682 | 34842 | 32968 | 51941 | 43565 | 50363 | 32038 | 30438 | 51329 | 42600 |
| 21.3 | 70171 | 48602 | 38737 | 30097 | 48092 | 41399 | 48818 | 31417 | 32293 | 48870 | 44447 |
| 21.34 | 68956 | 44856 | 38103 | 29104 | 50316 | 40528 | 51709 | 32937 | 34296 | 54490 | 41503 |
| 21.38 | 72147 | 45816 | 37826 | 28551 | 46699 | 40496 | 49061 | 35458 | 33257 | 49680 | 41596 |
| 21.42 | 64024 | 44289 | 41029 | 30030 | 39916 | 40087 | 51031 | 37433 | 32833 | 52415 | 41991 |
| 21.46 | 64305 | 44770 | 41074 | 29174 | 43540 | 38693 | 49563 | 38111 | 34903 | 48863 | 42491 |
| 21.5 | 68709 | 42587 | 40632 | 29200 | 41193 | 37772 | 53893 | 40693 | 32716 | 52130 | 38704 |
| 21.54 | 70075 | 44052 | 39781 | 29589 | 39655 | 37611 | 49006 | 41417 | 37247 | 54293 | 42147 |
| 21.58 | 68582 | 43698 | 41713 | 28433 | 39817 | 38359 | 50071 | 43128 | 34434 | 53360 | 40496 |
| 21.62 | 65180 | 40878 | 40952 | 27217 | 42715 | 37239 | 55361 | 50430 | 32503 | 55504 | 37017 |
| 21.66 | 64238 | 44758 | 42346 | 28313 | 44265 | 37545 | 49678 | 50210 | 36624 | 59524 | 36264 |
| 21.7 | 65693 | 40789 | 39429 | 28185 | 47620 | 36612 | 53039 | 50848 | 35956 | 60682 | 36833 |
| 21.74 | 59767 | 40782 | 39421 | 29725 | 52922 | 40002 | 52725 | 49940 | 38454 | 64950 | 38528 |
| 21.78 | 58829 | 41529 | 36061 | 27074 | 52960 | 38198 | 49928 | 48854 | 37254 | 57088 | 40718 |
| 21.82 | 60498 | 40777 | 39923 | 28168 | 55321 | 34292 | 52107 | 48113 | 40125 | 59729 | 37377 |
| 21.86 | 61683 | 41486 | 40955 | 29276 | 63521 | 35479 | 51201 | 43744 | 44574 | 60227 | 36423 |
| 21.9 | 65985 | 44166 | 40884 | 30582 | 67276 | 34151 | 52261 | 43599 | 48950 | 58127 | 35523 |
| 21.94 | 60072 | 45020 | 43590 | 28416 | 68722 | 35455 | 54864 | 44425 | 45685 | 54554 | 39472 |
| 21.98 | 60796 | 43042 | 39809 | 29224 | 68789 | 33960 | 54392 | 36719 | 47008 | 53308 | 36974 |
| 22.02 | 60337 | 41092 | 41113 | 31594 | 71213 | 33977 | 55746 | 38398 | 45159 | 52194 | 33885 |
| 22.06 | 61349 | 42916 | 38807 | 32328 | 72320 | 34899 | 56873 | 37633 | 43121 | 52258 | 34233 |
| 22.1 | 59029 | 39501 | 38784 | 29191 | 70591 | 34205 | 52545 | 39324 | 45353 | 53641 | 36948 |
| 22.14 | 59144 | 40871 | 39161 | 29961 | 73726 | 34319 | 56311 | 41641 | 44409 | 55410 | 37045 |
| 22.18 | 62367 | 42610 | 40474 | 32183 | 72695 | 34544 | 58309 | 42821 | 38844 | 53942 | 34362 |
| 22.22 | 62766 | 40504 | 44531 | 30612 | 71237 | 34802 | 52960 | 39854 | 39110 | 51573 | 35667 |
| 22.26 | 61742 | 41892 | 40061 | 30872 | 74292 | 32294 | 54722 | 42027 | 39142 | 55403 | 35221 |
| 22.3 | 61586 | 39995 | 41368 | 31906 | 68832 | 32780 | 54101 | 38610 | 35690 | 56075 | 33738 |
| 22.34 | 58653 | 43395 | 40771 | 27428 | 65891 | 30870 | 55823 | 39774 | 39729 | 57408 | 34580 |
| 22.38 | 59105 | 40565 | 37161 | 27916 | 63945 | 34121 | 55448 | 36579 | 39215 | 61146 | 33140 |
| 22.42 | 54629 | 45284 | 40873 | 28923 | 56309 | 31062 | 58419 | 36126 | 37267 | 65309 | 35028 |
| 22.46 | 58258 | 43250 | 38799 | 30386 | 56412 | 34212 | 55807 | 36234 | 39956 | 72932 | 33952 |
| 22.5 | 56787 | 47082 | 39088 | 29555 | 51257 | 31244 | 55812 | 35531 | 43028 | 72421 | 34956 |
| 22.54 | 62579 | 44518 | 38770 | 28425 | 45940 | 34474 | 55928 | 34359 | 43427 | 75251 | 34088 |
| 22.58 | 59955 | 42976 | 35824 | 28602 | 42642 | 33289 | 53537 | 36024 | 42244 | 76606 | 33789 |
| 22.62 | 56774 | 43181 | 37434 | 27810 | 42886 | 32625 | 55292 | 37914 | 45279 | 77145 | 32689 |
| 22.66 | 55144 | 40445 | 38797 | 29543 | 42237 | 34322 | 55478 | 36660 | 45702 | 76529 | 34730 |
| 22.7 | 57283 | 42122 | 39098 | 29514 | 39003 | 33611 | 55506 | 38223 | 46147 | 78418 | 36052 |
| 22.74 | 59868 | 42160 | 40421 | 26099 | 38693 | 33474 | 54657 | 36500 | 45428 | 78389 | 32798 |

-continued

| | | | | | | | | | | | |
|---|---|---|---|---|---|---|---|---|---|---|---|
| 22.78 | 60989 | 40603 | 39609 | 29175 | 39279 | 34172 | 58212 | 37572 | 43273 | 75745 | 32128 |
| 22.82 | 58454 | 39690 | 40486 | 25623 | 38192 | 34871 | 52041 | 37916 | 41273 | 71307 | 31535 |
| 22.86 | 57339 | 35721 | 37713 | 27939 | 42113 | 32741 | 55303 | 35354 | 39131 | 63146 | 34450 |
| 22.9 | 58002 | 35043 | 37292 | 26741 | 46996 | 35001 | 53330 | 36574 | 39409 | 63509 | 31424 |
| 22.94 | 57850 | 37529 | 38654 | 25783 | 56774 | 34727 | 53340 | 38294 | 37699 | 59904 | 33113 |
| 22.98 | 59731 | 36195 | 38381 | 27058 | 67020 | 34055 | 52706 | 40639 | 34864 | 55883 | 31474 |
| 23.02 | 57786 | 36984 | 37311 | 27625 | 83079 | 34044 | 53740 | 35794 | 33400 | 59307 | 34208 |
| 23.06 | 60115 | 36404 | 43640 | 26898 | 100179 | 32837 | 55248 | 37500 | 32770 | 55728 | 31957 |
| 23.1 | 60868 | 35221 | 40024 | 26382 | 109224 | 34140 | 56599 | 40906 | 34302 | 54435 | 34605 |
| 23.14 | 60672 | 35388 | 41840 | 27864 | 128673 | 34822 | 56990 | 40879 | 31833 | 53281 | 33372 |
| 23.18 | 64112 | 34599 | 40129 | 28602 | 140181 | 33762 | 61098 | 42938 | 31322 | 51587 | 36165 |
| 23.22 | 60451 | 36833 | 42689 | 29760 | 140031 | 35860 | 66155 | 48889 | 31752 | 51045 | 35783 |
| 23.26 | 61034 | 37510 | 44350 | 27700 | 140756 | 39288 | 64227 | 50548 | 32750 | 52348 | 34814 |
| 23.3 | 59388 | 38473 | 42384 | 25264 | 135858 | 41069 | 62586 | 56591 | 28407 | 53653 | 37151 |
| 23.34 | 59807 | 37283 | 40704 | 27258 | 128006 | 45279 | 65466 | 57333 | 29318 | 52031 | 38937 |
| 23.38 | 57905 | 37623 | 40404 | 25572 | 109238 | 45070 | 62986 | 58034 | 28777 | 50652 | 39458 |
| 23.42 | 59739 | 35699 | 42033 | 28353 | 96796 | 45858 | 62407 | 63675 | 30064 | 46802 | 40055 |
| 23.46 | 60691 | 35898 | 43574 | 28166 | 80947 | 51004 | 63029 | 68634 | 30784 | 50406 | 43483 |
| 23.5 | 62874 | 39849 | 41857 | 27361 | 71622 | 47291 | 61100 | 73688 | 29563 | 53422 | 38320 |
| 23.54 | 60197 | 43124 | 43998 | 26590 | 67003 | 47963 | 62047 | 78995 | 31527 | 50567 | 41353 |
| 23.58 | 62008 | 45972 | 44413 | 27949 | 63063 | 49322 | 64180 | 78900 | 31460 | 51640 | 40622 |
| 23.62 | 59905 | 45454 | 44329 | 26814 | 60717 | 47400 | 64163 | 79561 | 28016 | 52839 | 45248 |
| 23.66 | 57112 | 46312 | 42986 | 28794 | 67259 | 41432 | 66659 | 79437 | 32327 | 50385 | 48291 |
| 23.7 | 62266 | 49607 | 43748 | 27431 | 72095 | 41399 | 73091 | 74945 | 32377 | 54297 | 48234 |
| 23.74 | 63254 | 52569 | 44606 | 25603 | 72566 | 40882 | 82842 | 74954 | 31495 | 52790 | 48434 |
| 23.78 | 60779 | 52625 | 45436 | 27221 | 73284 | 37783 | 89017 | 67917 | 34856 | 53939 | 53996 |
| 23.82 | 66438 | 53839 | 44736 | 26443 | 74814 | 36914 | 99267 | 63308 | 34931 | 55151 | 55220 |
| 23.86 | 64266 | 52131 | 43037 | 26678 | 70161 | 39362 | 114165 | 56983 | 40687 | 57611 | 54457 |
| 23.9 | 63893 | 54347 | 44663 | 25413 | 67699 | 41505 | 123587 | 57307 | 43135 | 62536 | 55138 |
| 23.94 | 71130 | 54208 | 47910 | 28861 | 65228 | 42944 | 135244 | 60053 | 50299 | 67303 | 57642 |
| 23.98 | 69227 | 50798 | 49856 | 30006 | 59125 | 45602 | 136588 | 58932 | 52571 | 67621 | 55713 |
| 24.02 | 74699 | 48817 | 51093 | 28001 | 57470 | 46081 | 136188 | 58012 | 58678 | 78662 | 57538 |
| 24.06 | 75100 | 47686 | 48545 | 30025 | 51510 | 45588 | 140145 | 60561 | 60267 | 84146 | 57979 |
| 24.1 | 77074 | 47372 | 48055 | 28477 | 50472 | 45029 | 133555 | 61066 | 60540 | 93267 | 59080 |
| 24.14 | 86430 | 51065 | 50744 | 29205 | 51333 | 48033 | 125989 | 68203 | 67199 | 107932 | 61823 |
| 24.18 | 83003 | 50714 | 50534 | 28467 | 51366 | 49819 | 123048 | 71840 | 67034 | 129132 | 60758 |
| 24.22 | 88728 | 50248 | 51874 | 29494 | 55568 | 51677 | 119531 | 74882 | 83383 | 147641 | 61831 |
| 24.26 | 93821 | 51712 | 50573 | 29684 | 57364 | 56215 | 110853 | 77555 | 87536 | 152754 | 65658 |
| 24.3 | 93032 | 47004 | 47480 | 29585 | 58234 | 61468 | 110832 | 79125 | 102488 | 160763 | 66024 |
| 24.34 | 96594 | 46837 | 52242 | 30582 | 60221 | 63329 | 103564 | 86683 | 109946 | 162808 | 63918 |
| 24.38 | 100507 | 44796 | 50135 | 31200 | 60166 | 66107 | 103029 | 85018 | 122626 | 163348 | 64714 |
| 24.42 | 102244 | 46665 | 51134 | 27425 | 63893 | 66471 | 96816 | 85277 | 128845 | 159815 | 61869 |
| 24.46 | 106277 | 46681 | 51280 | 29345 | 62724 | 69287 | 104309 | 90206 | 136822 | 159843 | 64966 |
| 24.5 | 98930 | 47937 | 49341 | 31542 | 57409 | 67584 | 95404 | 86814 | 140080 | 148154 | 65102 |
| 24.54 | 105772 | 54246 | 51708 | 31934 | 57858 | 61531 | 99395 | 92265 | 135577 | 134937 | 66019 |
| 24.58 | 102323 | 60520 | 51424 | 33201 | 53721 | 58974 | 104078 | 86961 | 121048 | 125265 | 60750 |
| 24.62 | 106084 | 69523 | 48746 | 33464 | 57296 | 52675 | 110044 | 93189 | 104001 | 112107 | 61906 |
| 24.66 | 102393 | 65101 | 53381 | 31039 | 58518 | 48898 | 117028 | 89899 | 89549 | 106462 | 60776 |
| 24.7 | 100718 | 70489 | 54155 | 31686 | 66543 | 44118 | 127287 | 86392 | 77981 | 107447 | 60837 |
| 24.74 | 101001 | 70859 | 53231 | 32306 | 74502 | 40043 | 130822 | 87068 | 64010 | 106303 | 61097 |
| 24.78 | 93955 | 69339 | 52782 | 30524 | 81267 | 36961 | 143371 | 77633 | 52713 | 111109 | 61046 |
| 24.82 | 93813 | 65392 | 50644 | 31533 | 91968 | 37541 | 150208 | 71908 | 47448 | 113220 | 62448 |
| 24.86 | 91264 | 60972 | 49494 | 32365 | 99911 | 36631 | 158076 | 67495 | 43183 | 119065 | 59529 |
| 24.9 | 96179 | 61352 | 51189 | 32665 | 106900 | 35011 | 166485 | 59585 | 43320 | 126330 | 61406 |
| 24.94 | 90854 | 53197 | 49379 | 28888 | 108041 | 37957 | 173609 | 54587 | 46523 | 123004 | 62002 |
| 24.98 | 89442 | 51221 | 49796 | 30051 | 106228 | 38206 | 172772 | 52296 | 52452 | 126913 | 56700 |
| 25.02 | 87540 | 42586 | 46278 | 29068 | 100025 | 36993 | 170092 | 45244 | 53777 | 130318 | 57092 |
| 25.06 | 84135 | 42074 | 46308 | 30617 | 92332 | 35766 | 175866 | 45675 | 63031 | 131491 | 58408 |
| 25.1 | 83492 | 48601 | 46818 | 30247 | 81175 | 38192 | 168884 | 40289 | 65932 | 135813 | 61490 |
| 25.14 | 82449 | 44336 | 46790 | 28991 | 78260 | 37448 | 166309 | 40394 | 69600 | 132879 | 57386 |
| 25.18 | 79415 | 46099 | 49489 | 28036 | 65172 | 37089 | 162787 | 40522 | 64959 | 125793 | 58118 |
| 25.22 | 72122 | 46201 | 48314 | 30319 | 56122 | 36398 | 154162 | 43036 | 67629 | 131550 | 55637 |
| 25.26 | 71807 | 45130 | 44001 | 29464 | 47460 | 36118 | 144513 | 47123 | 70931 | 125104 | 55782 |
| 25.3 | 73708 | 48041 | 44892 | 29364 | 47564 | 38351 | 132487 | 47914 | 66993 | 127518 | 56372 |
| 25.34 | 70949 | 46361 | 46305 | 27870 | 42240 | 35119 | 123622 | 54949 | 58897 | 123731 | 53670 |
| 25.38 | 73489 | 45458 | 45039 | 29827 | 43057 | 35055 | 117327 | 57306 | 57336 | 121813 | 55313 |
| 25.42 | 73829 | 45344 | 45325 | 27250 | 40835 | 30735 | 104899 | 60637 | 54921 | 122105 | 55368 |
| 25.46 | 73405 | 43781 | 42528 | 27966 | 45398 | 32821 | 97865 | 64645 | 54060 | 118448 | 52221 |
| 25.5 | 70393 | 39497 | 42930 | 27380 | 44569 | 32351 | 97663 | 70625 | 50381 | 113043 | 52055 |
| 25.54 | 72581 | 37624 | 42581 | 30813 | 46063 | 33712 | 97005 | 75412 | 52983 | 110886 | 54236 |
| 25.58 | 73017 | 35160 | 42177 | 27410 | 47812 | 35542 | 101535 | 75417 | 54387 | 107405 | 52535 |
| 25.62 | 73688 | 37118 | 42318 | 28833 | 48605 | 37117 | 103392 | 76032 | 55175 | 100550 | 52687 |
| 25.66 | 73824 | 36584 | 45465 | 27754 | 44693 | 39461 | 110080 | 73559 | 56823 | 94850 | 52315 |
| 25.7 | 75640 | 38034 | 40954 | 27531 | 46948 | 40481 | 111007 | 68798 | 61127 | 91148 | 51806 |
| 25.74 | 76913 | 39327 | 40843 | 27075 | 44533 | 41660 | 114251 | 64031 | 60587 | 93284 | 48562 |
| 25.78 | 75932 | 43030 | 41467 | 28433 | 43321 | 41933 | 112853 | 59062 | 63183 | 93336 | 51352 |
| 25.82 | 73108 | 43868 | 41931 | 27804 | 42307 | 41889 | 111985 | 52145 | 67349 | 96242 | 48711 |
| 25.86 | 79451 | 44750 | 39836 | 26596 | 43550 | 42431 | 110428 | 48744 | 66396 | 102051 | 44511 |
| 25.9 | 80299 | 46526 | 39379 | 26070 | 43854 | 38783 | 108174 | 44464 | 73162 | 106282 | 48496 |

-continued

| | | | | | | | | | | | |
|---|---|---|---|---|---|---|---|---|---|---|---|
| 25.94 | 79872 | 47950 | 39388 | 28224 | 45732 | 40449 | 102277 | 39266 | 75785 | 113908 | 48864 |
| 25.98 | 84172 | 47254 | 39414 | 26024 | 47434 | 40305 | 91409 | 37335 | 79013 | 119274 | 48486 |
| 26.02 | 83029 | 47710 | 39735 | 25199 | 49910 | 39271 | 87440 | 34647 | 84928 | 120873 | 49009 |
| 26.06 | 84766 | 44831 | 37297 | 26493 | 48366 | 40161 | 78375 | 32736 | 90991 | 129017 | 47426 |
| 26.1 | 80384 | 43519 | 39756 | 24921 | 51023 | 37510 | 68711 | 33117 | 90752 | 127873 | 47091 |
| 26.14 | 80988 | 43295 | 39119 | 23779 | 54596 | 37055 | 66128 | 31460 | 93670 | 124196 | 46068 |
| 26.18 | 78710 | 44029 | 38530 | 26787 | 57855 | 34239 | 64830 | 33625 | 89778 | 122712 | 45077 |
| 26.22 | 77429 | 37086 | 36667 | 22376 | 58936 | 33895 | 61921 | 28750 | 84304 | 118832 | 43644 |
| 26.26 | 74676 | 38506 | 40530 | 23589 | 60450 | 33980 | 60521 | 28220 | 83507 | 116436 | 43478 |
| 26.3 | 75692 | 42990 | 38633 | 23580 | 65276 | 32468 | 60361 | 28273 | 77547 | 106015 | 43586 |
| 26.34 | 72804 | 40013 | 36412 | 24971 | 64376 | 33292 | 59708 | 28550 | 66285 | 98671 | 39419 |
| 26.38 | 67166 | 40628 | 34902 | 23340 | 65600 | 33119 | 62641 | 29066 | 59312 | 91315 | 38842 |
| 26.42 | 71723 | 39580 | 35582 | 24446 | 66800 | 31298 | 60497 | 29682 | 51363 | 84592 | 40891 |
| 26.46 | 68139 | 43222 | 36129 | 23165 | 69647 | 30015 | 63131 | 26991 | 44744 | 82112 | 38455 |
| 26.5 | 67440 | 43616 | 35965 | 22683 | 66431 | 26911 | 66351 | 29089 | 37192 | 73172 | 40775 |
| 26.54 | 69809 | 44332 | 34821 | 22602 | 63893 | 30124 | 69284 | 32798 | 32560 | 69873 | 39037 |
| 26.58 | 66502 | 43632 | 34816 | 23312 | 60393 | 30259 | 69235 | 32150 | 32939 | 65603 | 37980 |
| 26.62 | 66461 | 41251 | 37266 | 24580 | 63324 | 27212 | 69721 | 33881 | 28905 | 62571 | 37052 |
| 26.66 | 65880 | 44675 | 33626 | 25483 | 60148 | 25841 | 73207 | 35093 | 29164 | 60481 | 35416 |
| 26.7 | 60961 | 43198 | 34451 | 25757 | 61604 | 28482 | 75743 | 40696 | 30379 | 61295 | 36537 |
| 26.74 | 64182 | 41195 | 31079 | 24917 | 53828 | 26725 | 72585 | 39092 | 28729 | 57862 | 33462 |
| 26.78 | 61598 | 39307 | 34020 | 25347 | 51156 | 28779 | 75825 | 42149 | 26652 | 58256 | 37101 |
| 26.82 | 57505 | 40706 | 30752 | 22585 | 50593 | 30373 | 79382 | 43880 | 29747 | 61502 | 37168 |
| 26.86 | 58081 | 39005 | 33003 | 23727 | 48518 | 29829 | 79480 | 46651 | 26610 | 57140 | 35292 |
| 26.9 | 58975 | 38883 | 30876 | 25215 | 47716 | 31474 | 88268 | 49968 | 29525 | 60201 | 33303 |
| 26.94 | 57720 | 38620 | 30904 | 22148 | 49680 | 34114 | 92871 | 48095 | 29733 | 62438 | 34350 |
| 26.98 | 58597 | 33448 | 30859 | 24347 | 50692 | 36007 | 93231 | 48008 | 29758 | 66133 | 35122 |
| 27.02 | 57770 | 35931 | 32144 | 22839 | 48224 | 38065 | 92718 | 51319 | 34002 | 68999 | 33111 |
| 27.06 | 58574 | 36171 | 30721 | 23292 | 48313 | 36153 | 92756 | 48359 | 31290 | 70594 | 34725 |
| 27.1 | 57196 | 39229 | 31013 | 23522 | 42826 | 37599 | 94266 | 46937 | 37346 | 70958 | 33048 |
| 27.14 | 55030 | 38187 | 31166 | 22918 | 40994 | 37187 | 92183 | 46636 | 42600 | 71052 | 29736 |
| 27.18 | 55081 | 37053 | 31173 | 23468 | 41922 | 36211 | 92360 | 50953 | 42975 | 79772 | 33301 |
| 27.22 | 52019 | 37698 | 30500 | 21843 | 37809 | 36167 | 90295 | 53382 | 46801 | 78500 | 31794 |
| 27.26 | 53605 | 39361 | 29432 | 22107 | 36757 | 36519 | 87888 | 59340 | 53694 | 84027 | 33922 |
| 27.3 | 54301 | 39752 | 29736 | 21993 | 36800 | 34828 | 82901 | 64160 | 56995 | 78805 | 32406 |
| 27.34 | 50343 | 39735 | 31742 | 20933 | 36328 | 32978 | 80156 | 59996 | 58036 | 78608 | 32171 |
| 27.38 | 49771 | 35713 | 28001 | 21134 | 33812 | 34525 | 74056 | 63293 | 59315 | 76182 | 31549 |
| 27.42 | 52403 | 36378 | 29412 | 22253 | 34967 | 33378 | 72931 | 66108 | 55592 | 76198 | 29034 |
| 27.46 | 46420 | 35510 | 29002 | 19450 | 35551 | 32831 | 68263 | 68167 | 56079 | 74251 | 29894 |
| 27.5 | 50526 | 33031 | 29457 | 20891 | 36142 | 33169 | 69766 | 66643 | 51927 | 68698 | 29098 |
| 27.54 | 50570 | 36768 | 31231 | 20408 | 35012 | 31724 | 66018 | 66419 | 49200 | 66836 | 31629 |
| 27.58 | 47849 | 33389 | 32080 | 20934 | 37905 | 32180 | 64406 | 68435 | 45859 | 68213 | 31193 |
| 27.62 | 47496 | 34982 | 32367 | 22437 | 36694 | 31012 | 61317 | 66386 | 38590 | 65926 | 31031 |
| 27.66 | 50417 | 33797 | 29741 | 20307 | 36265 | 30790 | 58458 | 66768 | 39780 | 68235 | 31738 |
| 27.7 | 50751 | 30783 | 29429 | 19006 | 33503 | 28316 | 57738 | 62719 | 36990 | 66094 | 31363 |
| 27.74 | 50840 | 31460 | 30894 | 22582 | 34275 | 28360 | 57507 | 65396 | 37451 | 62665 | 29467 |
| 27.78 | 49686 | 30603 | 27965 | 21047 | 32476 | 28675 | 56167 | 63388 | 39533 | 64627 | 28904 |
| 27.82 | 48850 | 29509 | 29346 | 19039 | 33596 | 28113 | 56787 | 68932 | 42118 | 63374 | 28635 |
| 27.86 | 50501 | 29486 | 29019 | 20276 | 36806 | 27006 | 56219 | 64519 | 51227 | 63591 | 32764 |
| 27.9 | 54165 | 26467 | 26842 | 21884 | 35222 | 26874 | 56786 | 63877 | 51548 | 63943 | 31905 |
| 27.94 | 52113 | 24570 | 30854 | 18971 | 31911 | 25729 | 54227 | 64339 | 58049 | 65770 | 31238 |
| 27.98 | 52464 | 25318 | 30042 | 20409 | 32689 | 25476 | 54025 | 59587 | 62156 | 69119 | 33726 |
| 28.02 | 54359 | 25383 | 28539 | 20683 | 32319 | 23690 | 53353 | 54960 | 63822 | 69745 | 34774 |
| 28.06 | 54236 | 24765 | 31327 | 20376 | 35251 | 24770 | 53688 | 51554 | 70273 | 75974 | 31626 |
| 28.1 | 58059 | 25375 | 29963 | 18834 | 33374 | 23567 | 58958 | 47875 | 74179 | 74775 | 33648 |
| 28.14 | 56901 | 27317 | 27929 | 19950 | 31997 | 23341 | 55181 | 43841 | 73168 | 72562 | 32239 |
| 28.18 | 54147 | 27224 | 28069 | 20254 | 32862 | 22668 | 55559 | 42124 | 67590 | 68389 | 30451 |
| 28.22 | 57608 | 25183 | 27602 | 17800 | 29622 | 21621 | 58408 | 43816 | 65672 | 67879 | 32020 |
| 28.26 | 56704 | 24540 | 28295 | 18615 | 28428 | 22317 | 62122 | 40245 | 63222 | 63446 | 31460 |
| 28.3 | 60311 | 25495 | 26844 | 18049 | 29427 | 23803 | 70144 | 41829 | 59159 | 61440 | 30034 |
| 28.34 | 59444 | 26627 | 28355 | 19270 | 29823 | 23080 | 68171 | 38621 | 55563 | 59545 | 30953 |
| 28.38 | 57339 | 24062 | 26901 | 19601 | 29909 | 24324 | 72734 | 38546 | 47683 | 52412 | 29480 |
| 28.42 | 53877 | 23982 | 27717 | 18420 | 29886 | 22893 | 70910 | 36885 | 42067 | 51583 | 30097 |
| 28.46 | 52962 | 24597 | 25981 | 17827 | 28199 | 26568 | 70416 | 35177 | 39337 | 52272 | 30271 |
| 28.5 | 53926 | 26323 | 27349 | 18584 | 28619 | 23707 | 69194 | 37050 | 40983 | 50537 | 31114 |
| 28.54 | 51724 | 25420 | 26963 | 17882 | 29297 | 26500 | 66958 | 40485 | 39482 | 48491 | 32105 |
| 28.58 | 52955 | 26086 | 25882 | 19453 | 31801 | 24753 | 72656 | 36759 | 38602 | 49861 | 29946 |
| 28.62 | 51579 | 24807 | 27859 | 18936 | 30659 | 26871 | 65319 | 36327 | 36645 | 50246 | 29173 |
| 28.66 | 50408 | 25440 | 26360 | 19266 | 31805 | 26253 | 67546 | 31480 | 38056 | 47170 | 28149 |
| 28.7 | 49923 | 25466 | 25718 | 17940 | 30918 | 27756 | 63437 | 31306 | 37340 | 46911 | 27401 |
| 28.74 | 47693 | 25429 | 25111 | 16887 | 30302 | 23418 | 57619 | 35810 | 36899 | 45214 | 25997 |
| 28.78 | 48984 | 26595 | 27028 | 18278 | 31032 | 26048 | 63274 | 37105 | 37773 | 46908 | 28221 |
| 28.82 | 50484 | 26292 | 26560 | 17164 | 34580 | 25933 | 65419 | 38420 | 34335 | 48581 | 30518 |
| 28.86 | 45818 | 26590 | 27966 | 18140 | 33073 | 24113 | 64923 | 42116 | 30773 | 48202 | 29505 |
| 28.9 | 44002 | 21764 | 25593 | 15980 | 28694 | 22552 | 56390 | 40264 | 30645 | 47212 | 26833 |
| 28.94 | 44911 | 25912 | 24547 | 16315 | 31354 | 23161 | 59143 | 39469 | 29833 | 46578 | 28490 |
| 28.98 | 44417 | 25984 | 25186 | 18406 | 30502 | 21874 | 56084 | 43337 | 30854 | 51752 | 29762 |
| 29.02 | 43336 | 24101 | 25812 | 16495 | 29018 | 23245 | 56880 | 44489 | 29319 | 49706 | 28487 |
| 29.06 | 44829 | 24210 | 22417 | 16423 | 28828 | 21191 | 55759 | 43258 | 27414 | 49519 | 26839 |

-continued

| | | | | | | | | | | | |
|---|---|---|---|---|---|---|---|---|---|---|---|
| 29.1 | 42118 | 22573 | 23650 | 16499 | 29414 | 20591 | 55832 | 40402 | 28596 | 52224 | 28829 |
| 29.14 | 41831 | 23901 | 25156 | 18767 | 31277 | 22386 | 46904 | 40525 | 27517 | 49719 | 30419 |
| 29.18 | 44883 | 23903 | 27264 | 17900 | 33186 | 24847 | 54494 | 40554 | 27391 | 49989 | 31325 |
| 29.22 | 41891 | 21352 | 24460 | 17436 | 32286 | 23970 | 50311 | 35845 | 28450 | 49840 | 27988 |
| 29.26 | 42739 | 23124 | 23165 | 15748 | 34767 | 22729 | 46060 | 32931 | 25999 | 49704 | 27865 |
| 29.3 | 40710 | 23113 | 25371 | 16862 | 33255 | 23158 | 44658 | 31327 | 25353 | 49660 | 25391 |
| 29.34 | 41571 | 23233 | 23371 | 18111 | 32675 | 22949 | 43634 | 30810 | 24867 | 47852 | 26794 |
| 29.38 | 43071 | 24711 | 22798 | 17410 | 37121 | 22787 | 42899 | 29055 | 25020 | 48565 | 28220 |
| 29.42 | 43206 | 23757 | 23610 | 15904 | 34797 | 22031 | 43283 | 29300 | 24717 | 47800 | 28054 |
| 29.46 | 44411 | 23365 | 25483 | 15369 | 34687 | 23611 | 45548 | 29433 | 23853 | 48166 | 27292 |
| 29.5 | 42335 | 24290 | 22860 | 17087 | 35326 | 23629 | 43431 | 26388 | 22610 | 50564 | 26213 |
| 29.54 | 45840 | 25684 | 22598 | 16533 | 34471 | 21677 | 42035 | 27084 | 23505 | 49239 | 27520 |
| 29.58 | 40724 | 24020 | 24039 | 14645 | 33058 | 23035 | 40546 | 28973 | 21653 | 50018 | 28217 |
| 29.62 | 42366 | 25622 | 21741 | 15108 | 31580 | 22574 | 43998 | 30361 | 23337 | 49161 | 26620 |
| 29.66 | 39591 | 24204 | 22847 | 15072 | 32093 | 21852 | 39099 | 30081 | 21390 | 46080 | 26303 |
| 29.7 | 42996 | 23362 | 24286 | 16151 | 32323 | 22999 | 41828 | 33803 | 21849 | 46492 | 25804 |
| 29.74 | 43822 | 23166 | 24149 | 15440 | 32209 | 22978 | 39706 | 35934 | 21761 | 47130 | 26140 |
| 29.78 | 44646 | 23452 | 24932 | 15908 | 30565 | 19885 | 40324 | 36702 | 23592 | 45757 | 24846 |
| 29.82 | 46212 | 22846 | 24031 | 15071 | 30342 | 22162 | 41755 | 34607 | 23007 | 44626 | 24446 |
| 29.86 | 43735 | 22889 | 22902 | 15788 | 31279 | 21149 | 38665 | 33128 | 23617 | 42604 | 25683 |
| 29.9 | 45747 | 22180 | 21858 | 16105 | 31521 | 21200 | 40162 | 34847 | 23419 | 43005 | 23958 |
| 29.94 | 44643 | 23297 | 22178 | 15183 | 30018 | 21867 | 37632 | 33405 | 22870 | 42469 | 22902 |
| 29.98 | 44339 | 24178 | 22111 | 15515 | 30220 | 20931 | 42257 | 29654 | 24364 | 41128 | 24580 |
| 30.02 | 46552 | 24188 | 23968 | 16428 | 28610 | 19663 | 42268 | 30455 | 25078 | 42811 | 22599 |
| 30.06 | 47909 | 28048 | 21593 | 18182 | 30156 | 18120 | 43095 | 29009 | 25326 | 44015 | 22803 |
| 30.1 | 42231 | 28066 | 20894 | 17908 | 30367 | 19476 | 45627 | 30657 | 27339 | 42199 | 24120 |
| 30.14 | 43915 | 27358 | 20726 | 15316 | 29601 | 19731 | 42968 | 30159 | 26338 | 41045 | 21791 |
| 30.18 | 43637 | 30083 | 22425 | 16568 | 30438 | 19632 | 48847 | 28714 | 27609 | 42379 | 23332 |
| 30.22 | 42912 | 28667 | 21470 | 14837 | 26655 | 18377 | 48739 | 28828 | 28916 | 40010 | 23507 |
| 30.26 | 42128 | 27838 | 23593 | 16800 | 30980 | 19643 | 52007 | 30434 | 27566 | 40348 | 23971 |
| 30.3 | 42622 | 28335 | 21278 | 14845 | 28972 | 21490 | 53468 | 35322 | 28146 | 38587 | 23413 |
| 30.34 | 41680 | 27855 | 22289 | 14700 | 29885 | 19998 | 55798 | 30827 | 23184 | 39029 | 24552 |
| 30.38 | 41122 | 27046 | 19313 | 16592 | 27743 | 19260 | 53604 | 36710 | 24325 | 38155 | 22491 |
| 30.42 | 39915 | 25721 | 21299 | 16197 | 26658 | 18126 | 55701 | 36924 | 23176 | 37146 | 22262 |
| 30.46 | 39962 | 26742 | 20608 | 15938 | 27446 | 20323 | 58666 | 39922 | 22979 | 35549 | 24426 |
| 30.5 | 41180 | 25150 | 19502 | 15379 | 27443 | 19181 | 58130 | 38365 | 22094 | 34443 | 23987 |
| 30.54 | 40670 | 23784 | 20969 | 16375 | 24805 | 19208 | 55163 | 37683 | 22650 | 33294 | 23022 |
| 30.58 | 42314 | 23338 | 20246 | 16558 | 25460 | 18443 | 57263 | 37469 | 22109 | 34287 | 21746 |
| 30.62 | 40613 | 23825 | 18642 | 15071 | 26855 | 18322 | 54852 | 39369 | 21623 | 32050 | 22036 |
| 30.66 | 42482 | 25615 | 22418 | 15222 | 25582 | 18918 | 52119 | 38163 | 25115 | 33113 | 25448 |
| 30.7 | 40232 | 24157 | 20653 | 14442 | 25439 | 18376 | 51638 | 40060 | 23540 | 33800 | 25180 |
| 30.74 | 41544 | 24217 | 20801 | 15848 | 26570 | 20583 | 53217 | 38250 | 21929 | 32667 | 22574 |
| 30.78 | 38228 | 22842 | 20361 | 15970 | 26827 | 19724 | 53958 | 38466 | 21818 | 33840 | 23210 |
| 30.82 | 38901 | 21824 | 18621 | 15381 | 27541 | 20253 | 50724 | 37127 | 21134 | 34305 | 22627 |
| 30.86 | 42891 | 24059 | 19633 | 15106 | 28758 | 21572 | 48325 | 34240 | 24137 | 33427 | 23192 |
| 30.9 | 39841 | 21036 | 20493 | 14278 | 28269 | 19435 | 46533 | 32638 | 23243 | 33385 | 21751 |
| 30.94 | 40164 | 19220 | 17775 | 14615 | 27876 | 19851 | 46731 | 31504 | 24860 | 35124 | 22958 |
| 30.98 | 38966 | 22731 | 18445 | 13637 | 32051 | 21976 | 45989 | 30851 | 25965 | 34616 | 24892 |
| 31.02 | 38014 | 22668 | 19525 | 14708 | 31229 | 21876 | 44153 | 29458 | 27292 | 35411 | 24474 |
| 31.06 | 39581 | 21592 | 19851 | 14155 | 30704 | 23308 | 43648 | 29908 | 28453 | 37567 | 25149 |
| 31.1 | 39896 | 21633 | 19022 | 15201 | 30924 | 20376 | 45327 | 29490 | 31495 | 39832 | 24912 |
| 31.14 | 38779 | 22801 | 17786 | 13236 | 32709 | 22345 | 44620 | 29950 | 31191 | 40918 | 24057 |
| 31.18 | 39163 | 21099 | 18358 | 12336 | 32193 | 22508 | 42321 | 29059 | 30117 | 40583 | 22996 |
| 31.22 | 40725 | 19187 | 19521 | 14881 | 32386 | 20179 | 47199 | 29828 | 31406 | 39518 | 24272 |
| 31.26 | 38087 | 20703 | 18623 | 13166 | 31846 | 20654 | 43875 | 31143 | 30595 | 39245 | 22596 |
| 31.3 | 38990 | 21768 | 19715 | 14999 | 31293 | 19761 | 42889 | 27417 | 28891 | 38037 | 22142 |
| 31.34 | 38932 | 20015 | 18273 | 14153 | 29134 | 19195 | 43513 | 30329 | 29048 | 39210 | 22620 |
| 31.38 | 38297 | 19741 | 18341 | 14260 | 30258 | 19788 | 43068 | 30979 | 27298 | 41572 | 23661 |
| 31.42 | 40579 | 22851 | 18514 | 15797 | 30154 | 21101 | 45826 | 32097 | 27392 | 40585 | 23097 |
| 31.46 | 36099 | 24152 | 19522 | 15020 | 30217 | 22514 | 44137 | 30769 | 27451 | 40202 | 22257 |
| 31.5 | 35844 | 23531 | 19445 | 13463 | 27843 | 21356 | 42273 | 28679 | 24214 | 39597 | 21198 |
| 31.54 | 35689 | 26460 | 17919 | 14331 | 28034 | 20639 | 43659 | 30096 | 26725 | 36380 | 19757 |
| 31.58 | 35936 | 25020 | 18216 | 15181 | 27414 | 21232 | 39879 | 28661 | 28436 | 39943 | 23016 |
| 31.62 | 36303 | 23618 | 18497 | 14798 | 26075 | 19661 | 42994 | 26125 | 29277 | 40706 | 21518 |
| 31.66 | 39114 | 25787 | 18486 | 13835 | 29436 | 20026 | 42162 | 28937 | 30526 | 38440 | 22711 |
| 31.7 | 35163 | 26741 | 18631 | 14632 | 28709 | 20264 | 41944 | 26819 | 31789 | 37484 | 21749 |
| 31.74 | 36898 | 25016 | 16945 | 12699 | 28621 | 21195 | 41979 | 28555 | 34756 | 38886 | 20466 |
| 31.78 | 38592 | 24120 | 19358 | 14658 | 25702 | 21032 | 41634 | 26159 | 34190 | 41046 | 21476 |
| 31.82 | 38621 | 21680 | 18083 | 13907 | 25759 | 20244 | 38749 | 25340 | 36893 | 39641 | 23374 |
| 31.86 | 36598 | 22025 | 18170 | 14751 | 26551 | 21342 | 40326 | 25431 | 40031 | 40409 | 23425 |
| 31.9 | 38123 | 21489 | 18326 | 15205 | 25717 | 19458 | 38325 | 24288 | 42180 | 38324 | 21395 |
| 31.94 | 38773 | 21183 | 19253 | 13849 | 23989 | 17927 | 38609 | 21161 | 43323 | 37678 | 20830 |
| 31.98 | 36325 | 19700 | 17740 | 14698 | 24571 | 19956 | 38413 | 21684 | 44092 | 37903 | 19625 |
| 32.02 | 38876 | 20404 | 19185 | 13365 | 25158 | 19830 | 40981 | 22461 | 39187 | 39013 | 19383 |
| 32.06 | 37558 | 17437 | 19149 | 12332 | 23559 | 18216 | 37934 | 22255 | 36110 | 38613 | 19478 |
| 32.1 | 36352 | 20136 | 19631 | 14514 | 24355 | 18207 | 37710 | 21346 | 33818 | 36244 | 20079 |
| 32.14 | 35404 | 18371 | 19323 | 15162 | 24015 | 18929 | 38260 | 21665 | 33158 | 37614 | 21390 |
| 32.18 | 35711 | 19631 | 18641 | 15170 | 26069 | 17698 | 37611 | 20304 | 31428 | 38034 | 19276 |
| 32.22 | 34857 | 18748 | 19257 | 14284 | 26175 | 17745 | 38062 | 19994 | 28140 | 36393 | 20468 |

| | | | | | | | | | | | |
|---|---|---|---|---|---|---|---|---|---|---|---|
| 32.26 | 39473 | 20930 | 18711 | 15824 | 26305 | 19168 | 40056 | 20789 | 30088 | 35568 | 20184 |
| 32.3 | 36611 | 19588 | 17953 | 15415 | 25186 | 17295 | 36731 | 19117 | 27281 | 37534 | 19668 |
| 32.34 | 36584 | 18356 | 18938 | 14669 | 25969 | 17907 | 38201 | 18864 | 25212 | 37383 | 18582 |
| 32.38 | 35832 | 17044 | 17554 | 14722 | 26054 | 16545 | 38040 | 20086 | 24635 | 35009 | 19850 |
| 32.42 | 37831 | 18051 | 18381 | 14451 | 26301 | 18239 | 37373 | 21482 | 26660 | 36412 | 20403 |
| 32.46 | 41329 | 20459 | 18390 | 13740 | 25476 | 18326 | 38081 | 21257 | 25864 | 34075 | 22578 |
| 32.5 | 39558 | 19068 | 17373 | 15978 | 25727 | 17197 | 39311 | 23183 | 24131 | 33050 | 21972 |
| 32.54 | 38113 | 19114 | 17178 | 15427 | 23445 | 17080 | 40301 | 23606 | 24894 | 33364 | 20802 |
| 32.58 | 37555 | 20865 | 17971 | 14902 | 24974 | 18072 | 38266 | 25905 | 24182 | 33391 | 21552 |
| 32.62 | 35982 | 20680 | 17062 | 13024 | 27728 | 17577 | 39933 | 27132 | 23614 | 32878 | 20252 |
| 32.66 | 37605 | 20450 | 18465 | 14702 | 26568 | 17521 | 38485 | 29752 | 22716 | 33110 | 20413 |
| 32.7 | 39200 | 19730 | 19139 | 13491 | 24311 | 16714 | 37126 | 31915 | 23988 | 34203 | 21202 |
| 32.74 | 40518 | 21144 | 17700 | 13972 | 25378 | 18642 | 36334 | 33329 | 22708 | 33597 | 20698 |
| 32.78 | 37256 | 20532 | 18114 | 12848 | 24124 | 16679 | 35247 | 34083 | 23010 | 33906 | 19538 |
| 32.82 | 37162 | 20575 | 19137 | 15947 | 26115 | 16544 | 36244 | 34907 | 22100 | 35639 | 21054 |
| 32.86 | 37680 | 20026 | 18141 | 12735 | 23404 | 18213 | 35633 | 36335 | 21455 | 35248 | 21033 |
| 32.9 | 38927 | 19466 | 18243 | 14120 | 25921 | 16696 | 37848 | 36806 | 22610 | 37505 | 19899 |
| 32.94 | 39404 | 19887 | 19184 | 14122 | 25067 | 19177 | 35250 | 34571 | 24319 | 38233 | 18035 |
| 32.98 | 39080 | 19565 | 18005 | 13309 | 27613 | 17507 | 37265 | 35210 | 24312 | 34164 | 20931 |
| 33.02 | 38713 | 20601 | 19481 | 13494 | 29860 | 17765 | 35563 | 33506 | 26495 | 34303 | 20187 |
| 33.06 | 38295 | 19923 | 18548 | 15061 | 27309 | 18421 | 39092 | 33258 | 29045 | 35495 | 19632 |
| 33.1 | 37218 | 18865 | 18924 | 12830 | 28957 | 18872 | 36044 | 32840 | 28167 | 35022 | 18896 |
| 33.14 | 37636 | 19737 | 18302 | 13532 | 28178 | 17768 | 33854 | 29264 | 28351 | 36428 | 20440 |
| 33.18 | 37888 | 16762 | 17884 | 14084 | 30221 | 17924 | 36002 | 26254 | 28920 | 33109 | 21076 |
| 33.22 | 37408 | 17498 | 18581 | 13014 | 31629 | 17762 | 38728 | 25155 | 27292 | 32565 | 20587 |
| 33.26 | 36462 | 17792 | 17128 | 12587 | 32349 | 19178 | 36439 | 21788 | 29640 | 32785 | 20464 |
| 33.3 | 34599 | 19339 | 18273 | 13150 | 33070 | 16745 | 34200 | 23060 | 28183 | 31830 | 22328 |
| 33.34 | 36397 | 19162 | 16978 | 14060 | 30814 | 16831 | 36247 | 22531 | 27628 | 31443 | 19878 |
| 33.38 | 37518 | 17862 | 18534 | 12506 | 30310 | 16971 | 34314 | 20038 | 29047 | 29776 | 20701 |
| 33.42 | 35103 | 17344 | 17947 | 12262 | 27053 | 16471 | 33968 | 17707 | 27310 | 28856 | 20174 |
| 33.46 | 34025 | 17035 | 17990 | 13250 | 28629 | 16716 | 34468 | 17269 | 26883 | 29737 | 19275 |
| 33.5 | 37030 | 18694 | 17778 | 12959 | 27077 | 18545 | 35012 | 19133 | 22009 | 27497 | 18905 |
| 33.54 | 34510 | 18674 | 17494 | 12967 | 27005 | 16141 | 36306 | 17905 | 24720 | 28383 | 19881 |
| 33.58 | 33780 | 18194 | 17779 | 12459 | 23502 | 15931 | 32907 | 17092 | 23380 | 30917 | 19751 |
| 33.62 | 34869 | 19668 | 18330 | 11898 | 23484 | 17359 | 33523 | 16664 | 23765 | 28807 | 21678 |
| 33.66 | 34248 | 18772 | 17179 | 12364 | 22722 | 17443 | 35401 | 17300 | 25534 | 31078 | 19453 |
| 33.7 | 32128 | 19115 | 18340 | 13158 | 19812 | 14990 | 32721 | 18122 | 22384 | 28562 | 20160 |
| 33.74 | 35321 | 17866 | 17915 | 12880 | 21535 | 15682 | 34292 | 16977 | 21665 | 32824 | 20284 |
| 33.78 | 35448 | 20044 | 18413 | 13402 | 23223 | 15901 | 31389 | 16761 | 22507 | 32190 | 22579 |
| 33.82 | 31128 | 18889 | 16584 | 11994 | 21069 | 17236 | 32749 | 16164 | 22243 | 32799 | 20524 |
| 33.86 | 32827 | 20220 | 18344 | 11967 | 21797 | 17668 | 34411 | 17997 | 22078 | 32335 | 20591 |
| 33.9 | 32286 | 19807 | 16987 | 12412 | 22024 | 18530 | 36822 | 17387 | 19796 | 33533 | 21401 |
| 33.94 | 31616 | 19982 | 16818 | 13177 | 21267 | 18447 | 35324 | 18247 | 22107 | 34253 | 20042 |
| 33.98 | 33779 | 18927 | 17791 | 12891 | 21805 | 19179 | 35663 | 15544 | 21974 | 35391 | 21540 |
| 34.02 | 33063 | 18008 | 17541 | 12537 | 21338 | 18201 | 34000 | 16609 | 23041 | 34509 | 20392 |
| 34.06 | 35048 | 17016 | 17855 | 11805 | 20881 | 19500 | 36944 | 16434 | 23460 | 33147 | 20901 |
| 34.1 | 32177 | 19050 | 16763 | 11920 | 22068 | 21209 | 37125 | 17451 | 25527 | 34008 | 19984 |
| 34.14 | 33590 | 17204 | 17100 | 12728 | 19371 | 18957 | 34914 | 16399 | 25931 | 35337 | 18833 |
| 34.18 | 32115 | 18233 | 15456 | 13260 | 21263 | 19525 | 35146 | 16571 | 27663 | 32005 | 20441 |
| 34.22 | 33580 | 18016 | 16881 | 11237 | 20259 | 19155 | 34333 | 17619 | 24505 | 32146 | 22168 |
| 34.26 | 31389 | 17253 | 17191 | 11782 | 22227 | 19128 | 32723 | 18771 | 26286 | 30938 | 19836 |
| 34.3 | 31717 | 19018 | 16372 | 11928 | 22377 | 17504 | 33323 | 18353 | 27988 | 29280 | 19534 |
| 34.34 | 33328 | 19083 | 17721 | 12068 | 21164 | 19114 | 35054 | 16876 | 27554 | 27316 | 18464 |
| 34.38 | 32811 | 18257 | 17456 | 12079 | 22226 | 16524 | 34142 | 19131 | 24967 | 29841 | 19912 |
| 34.42 | 31866 | 17295 | 18225 | 13193 | 22541 | 17276 | 33120 | 18852 | 24854 | 29582 | 17908 |
| 34.46 | 32569 | 16704 | 18495 | 12518 | 21938 | 17494 | 32196 | 19140 | 24620 | 28857 | 19161 |
| 34.5 | 28971 | 16980 | 16437 | 12272 | 22990 | 17459 | 34590 | 20489 | 22791 | 30167 | 19981 |
| 34.54 | 30152 | 17687 | 17680 | 11119 | 24659 | 15995 | 34849 | 22092 | 22641 | 30244 | 17961 |
| 34.58 | 30947 | 18097 | 18242 | 12472 | 24281 | 17239 | 35639 | 24373 | 19992 | 31883 | 17942 |
| 34.62 | 32061 | 17627 | 18188 | 12255 | 23675 | 15585 | 36895 | 23514 | 21014 | 30449 | 19042 |
| 34.66 | 31291 | 16036 | 16552 | 12185 | 23403 | 17403 | 37111 | 23041 | 20066 | 33181 | 18197 |
| 34.7 | 32268 | 17361 | 16502 | 11062 | 23988 | 15890 | 34983 | 22509 | 19511 | 32857 | 19847 |
| 34.74 | 32738 | 18560 | 17355 | 12836 | 24035 | 15492 | 33861 | 23087 | 19820 | 32850 | 19057 |
| 34.78 | 33835 | 16681 | 17979 | 13317 | 22632 | 17100 | 33764 | 23017 | 18459 | 32080 | 18466 |
| 34.82 | 34686 | 17661 | 16653 | 11311 | 23970 | 15525 | 34844 | 24847 | 18143 | 29833 | 18843 |
| 34.86 | 32513 | 16645 | 16363 | 10396 | 21394 | 15727 | 34086 | 25051 | 19311 | 29029 | 18935 |
| 34.9 | 32831 | 16534 | 15788 | 12132 | 20857 | 17053 | 34007 | 24327 | 18733 | 30117 | 20358 |
| 34.94 | 33992 | 16161 | 16180 | 12152 | 21095 | 16598 | 31843 | 26096 | 17899 | 28755 | 21045 |
| 34.98 | 33156 | 17604 | 16378 | 11965 | 21806 | 16961 | 33260 | 25362 | 17703 | 28594 | 20337 |
| 35.02 | 33414 | 16435 | 16652 | 11660 | 21732 | 15023 | 31833 | 24296 | 19003 | 27765 | 18110 |
| 35.06 | 33218 | 17140 | 15460 | 10971 | 22210 | 15824 | 33181 | 23013 | 19920 | 29377 | 19142 |
| 35.1 | 31058 | 17197 | 15872 | 12125 | 20330 | 14448 | 32746 | 22859 | 20996 | 29119 | 19213 |
| 35.14 | 34196 | 18448 | 17140 | 12574 | 22406 | 15580 | 33991 | 22016 | 21631 | 29219 | 19333 |
| 35.18 | 32802 | 17140 | 16046 | 10878 | 24566 | 15422 | 31897 | 20790 | 22747 | 30328 | 16647 |
| 35.22 | 32731 | 17223 | 17879 | 10131 | 24024 | 15214 | 31192 | 20790 | 22853 | 30995 | 17092 |
| 35.26 | 33259 | 17209 | 14497 | 12332 | 24445 | 16184 | 33341 | 19336 | 26221 | 31094 | 17809 |
| 35.3 | 30925 | 17876 | 16829 | 11046 | 25692 | 14386 | 33425 | 19259 | 26424 | 30044 | 17385 |
| 35.34 | 29150 | 15977 | 17347 | 10494 | 26155 | 14946 | 33649 | 20512 | 24334 | 31867 | 17127 |
| 35.38 | 31463 | 17644 | 16969 | 11774 | 28816 | 14369 | 34542 | 18772 | 23554 | 30645 | 17681 |

| | | | | | | | | | | |
|---|---|---|---|---|---|---|---|---|---|---|
| 35.42 | 32708 | 18298 | 16820 | 12365 | 28797 | 15257 | 36131 | 20703 | 23320 | 30510 | 17513 |
| 35.46 | 31689 | 16785 | 14710 | 10848 | 27652 | 15040 | 34283 | 18719 | 22749 | 30824 | 18026 |
| 35.5 | 32000 | 16736 | 15842 | 12393 | 25667 | 14959 | 36250 | 18603 | 23143 | 30104 | 17370 |
| 35.54 | 31790 | 18035 | 16350 | 11229 | 28520 | 15675 | 37423 | 18036 | 21885 | 30397 | 18855 |
| 35.58 | 32774 | 19741 | 16716 | 11994 | 25441 | 15448 | 39401 | 17064 | 20317 | 31144 | 18454 |
| 35.62 | 31075 | 18120 | 15623 | 11601 | 27698 | 16281 | 38064 | 18770 | 19805 | 27487 | 18050 |
| 35.66 | 32615 | 17753 | 16023 | 11467 | 27195 | 15837 | 35901 | 19760 | 17540 | 28830 | 18351 |
| 35.7 | 31198 | 18773 | 16084 | 11660 | 26773 | 14516 | 36651 | 18519 | 18736 | 27245 | 19336 |
| 35.74 | 31540 | 18690 | 15828 | 10404 | 25987 | 16030 | 37484 | 20637 | 17919 | 28172 | 18553 |
| 35.78 | 31354 | 17372 | 15633 | 12307 | 27731 | 17330 | 35246 | 20868 | 17863 | 28385 | 17851 |
| 35.82 | 30489 | 19459 | 16193 | 11513 | 27182 | 16328 | 33672 | 22240 | 17887 | 26724 | 18141 |
| 35.86 | 30791 | 18939 | 15957 | 12901 | 26619 | 18190 | 34328 | 22781 | 18634 | 28032 | 19619 |
| 35.9 | 29807 | 17330 | 14461 | 9806 | 25359 | 16148 | 34852 | 22591 | 20195 | 27579 | 19971 |
| 35.94 | 30136 | 18281 | 15562 | 11365 | 25679 | 16874 | 31090 | 23858 | 17441 | 28607 | 18941 |
| 35.98 | 30467 | 17319 | 16923 | 10875 | 25649 | 17198 | 31519 | 23897 | 16423 | 27482 | 19527 |
| 36.02 | 30799 | 16813 | 15423 | 10274 | 23705 | 15340 | 30024 | 23752 | 17421 | 25805 | 19533 |
| 36.06 | 29935 | 16884 | 16655 | 10764 | 22592 | 16167 | 31810 | 22632 | 19569 | 28951 | 17788 |
| 36.1 | 28629 | 17776 | 14402 | 11579 | 21141 | 15843 | 31809 | 22938 | 16028 | 29208 | 20162 |
| 36.14 | 29801 | 18496 | 14919 | 10707 | 21965 | 17553 | 30131 | 22209 | 16024 | 29061 | 19451 |
| 36.18 | 27948 | 17991 | 13866 | 10320 | 20980 | 14691 | 30098 | 22306 | 18534 | 30975 | 21091 |
| 36.22 | 28654 | 17392 | 16879 | 10747 | 20632 | 15854 | 33314 | 24670 | 17795 | 31606 | 20489 |
| 36.26 | 30255 | 18073 | 15412 | 11236 | 21513 | 15089 | 31256 | 26327 | 18456 | 29581 | 20343 |
| 36.3 | 28885 | 18599 | 17186 | 11257 | 20519 | 16605 | 32416 | 23459 | 17717 | 27913 | 19154 |
| 36.34 | 29282 | 18178 | 14835 | 10018 | 21805 | 16496 | 32516 | 24477 | 21426 | 27139 | 20151 |
| 36.38 | 28134 | 17898 | 15727 | 11195 | 22437 | 16965 | 32561 | 24912 | 19783 | 29974 | 18693 |
| 36.42 | 30993 | 16944 | 14249 | 12065 | 23525 | 19443 | 34011 | 25720 | 19832 | 31237 | 18959 |
| 36.46 | 29997 | 17280 | 14182 | 10911 | 22350 | 19248 | 32657 | 24349 | 18922 | 26589 | 18186 |
| 36.5 | 30264 | 17762 | 15161 | 10873 | 21805 | 19586 | 35323 | 24567 | 19845 | 27371 | 19036 |
| 36.54 | 29469 | 17017 | 13886 | 11529 | 22614 | 17107 | 33022 | 26297 | 18515 | 26555 | 19050 |
| 36.58 | 31608 | 17988 | 15241 | 10776 | 22030 | 15722 | 33252 | 22939 | 17863 | 28810 | 17829 |
| 36.62 | 29844 | 18762 | 13967 | 10516 | 20695 | 16273 | 34339 | 24313 | 18443 | 29590 | 17631 |
| 36.66 | 27996 | 17991 | 14055 | 10655 | 20367 | 16584 | 33177 | 23502 | 17604 | 27926 | 17835 |
| 36.7 | 29492 | 18927 | 14190 | 10907 | 20401 | 17149 | 34352 | 23471 | 17363 | 27353 | 17306 |
| 36.74 | 29360 | 15639 | 15681 | 10138 | 22893 | 15361 | 32067 | 24697 | 17454 | 27120 | 18314 |
| 36.78 | 30694 | 16935 | 15270 | 10525 | 22372 | 14416 | 31444 | 22520 | 15602 | 27959 | 15981 |
| 36.82 | 31108 | 15032 | 14262 | 9385 | 21554 | 13994 | 31724 | 23157 | 19140 | 26994 | 17611 |
| 36.86 | 30347 | 16548 | 15380 | 11213 | 22184 | 14878 | 31369 | 23982 | 18370 | 29703 | 16154 |
| 36.9 | 29582 | 16079 | 15173 | 11349 | 22228 | 14568 | 32951 | 23863 | 19168 | 28315 | 18529 |
| 36.94 | 30416 | 14896 | 15037 | 11000 | 19032 | 15055 | 32264 | 20774 | 21102 | 28132 | 17416 |
| 36.98 | 28330 | 15823 | 15024 | 9892 | 22405 | 14003 | 33207 | 22125 | 21671 | 26964 | 18643 |
| 37.02 | 30756 | 16413 | 14750 | 11761 | 19595 | 14850 | 32132 | 24023 | 21779 | 28290 | 17158 |
| 37.06 | 31488 | 15822 | 15827 | 9908 | 22106 | 13374 | 31992 | 23841 | 22251 | 26586 | 17911 |
| 37.1 | 27877 | 15259 | 14894 | 10579 | 22259 | 13383 | 34085 | 22109 | 21054 | 29536 | 19359 |
| 37.14 | 29363 | 14888 | 15773 | 10917 | 23771 | 14628 | 29689 | 22078 | 22362 | 28553 | 17875 |
| 37.18 | 29111 | 14954 | 15212 | 10405 | 23632 | 13042 | 34511 | 21825 | 22814 | 28138 | 16818 |
| 37.22 | 29203 | 14139 | 15117 | 10707 | 24625 | 12831 | 35083 | 21284 | 23950 | 29238 | 18665 |
| 37.26 | 29433 | 14930 | 14718 | 9940 | 25559 | 13218 | 35026 | 22631 | 21844 | 30167 | 17640 |
| 37.3 | 29264 | 14679 | 13896 | 10178 | 24438 | 13487 | 34402 | 19758 | 23851 | 28587 | 19084 |
| 37.34 | 29077 | 15294 | 14623 | 11366 | 24653 | 14202 | 33704 | 21390 | 22659 | 31661 | 17673 |
| 37.38 | 28116 | 15022 | 14788 | 9699 | 24650 | 14093 | 34501 | 21098 | 22677 | 29443 | 17908 |
| 37.42 | 30277 | 15975 | 16173 | 10646 | 25161 | 14551 | 35531 | 19607 | 22618 | 28393 | 17484 |
| 37.46 | 29655 | 16079 | 15189 | 11604 | 26239 | 14518 | 36238 | 21229 | 23141 | 29810 | 18672 |
| 37.5 | 30808 | 17280 | 13151 | 9890 | 26887 | 15063 | 35467 | 21890 | 22082 | 30266 | 18534 |
| 37.54 | 29620 | 17697 | 15223 | 10363 | 25570 | 14917 | 34082 | 21837 | 23356 | 32209 | 18531 |
| 37.58 | 28942 | 16630 | 13266 | 11525 | 25064 | 15213 | 34162 | 22164 | 22092 | 31504 | 19423 |
| 37.62 | 30621 | 15802 | 14296 | 10118 | 21403 | 16425 | 35022 | 22450 | 22363 | 31645 | 17818 |
| 37.66 | 28849 | 17119 | 14236 | 9470 | 21828 | 13913 | 32637 | 22479 | 21893 | 30466 | 17589 |
| 37.7 | 29414 | 18007 | 15051 | 10852 | 22812 | 16233 | 34109 | 23462 | 23397 | 32285 | 17596 |
| 37.74 | 31603 | 16454 | 14238 | 9076 | 23821 | 15364 | 34282 | 22703 | 21757 | 30139 | 19454 |
| 37.78 | 29394 | 17549 | 14560 | 11155 | 22540 | 16987 | 32874 | 23722 | 22067 | 28337 | 17900 |
| 37.82 | 29235 | 15806 | 14301 | 10735 | 23640 | 16737 | 34731 | 24173 | 21990 | 27885 | 17609 |
| 37.86 | 30386 | 15607 | 15651 | 9662 | 21021 | 18595 | 32561 | 22699 | 21879 | 28900 | 17980 |
| 37.9 | 29818 | 16587 | 14285 | 9173 | 22524 | 16530 | 32831 | 22274 | 22500 | 27991 | 17565 |
| 37.94 | 30712 | 16669 | 13803 | 10417 | 23226 | 17517 | 34835 | 23526 | 21279 | 27326 | 18052 |
| 37.98 | 31771 | 15743 | 14689 | 10137 | 22330 | 16388 | 32474 | 22414 | 21956 | 27576 | 18348 |
| 38.02 | 30085 | 15545 | 13921 | 10375 | 21638 | 16172 | 31393 | 20524 | 21017 | 25949 | 18038 |
| 38.06 | 30498 | 17104 | 14937 | 9727 | 21610 | 17203 | 32549 | 22996 | 21494 | 25325 | 18657 |
| 38.1 | 30224 | 17352 | 13772 | 9989 | 19161 | 17172 | 32046 | 21055 | 21762 | 27130 | 18794 |
| 38.14 | 28300 | 18457 | 14109 | 9157 | 19704 | 16579 | 31803 | 21424 | 22043 | 25229 | 18220 |
| 38.18 | 29041 | 16695 | 14043 | 10886 | 20278 | 16858 | 31901 | 20430 | 21360 | 26711 | 18514 |
| 38.22 | 30526 | 17211 | 14482 | 8792 | 21013 | 15713 | 31301 | 20446 | 20728 | 27998 | 19896 |
| 38.26 | 29254 | 16899 | 14029 | 10009 | 20643 | 14784 | 31515 | 19797 | 20337 | 28351 | 19056 |
| 38.3 | 29405 | 17140 | 14715 | 10107 | 21158 | 14220 | 31518 | 20160 | 21648 | 26852 | 18579 |
| 38.34 | 30857 | 16678 | 14408 | 9987 | 21741 | 15745 | 32227 | 20965 | 21102 | 25009 | 19408 |
| 38.38 | 31170 | 16808 | 13900 | 11165 | 23603 | 15578 | 28987 | 20890 | 19241 | 28087 | 19123 |
| 38.42 | 29603 | 17157 | 15260 | 9646 | 19353 | 12986 | 31912 | 17903 | 18910 | 26703 | 19189 |
| 38.46 | 29821 | 16495 | 15970 | 11670 | 22814 | 13828 | 29182 | 19695 | 18022 | 25774 | 18614 |
| 38.5 | 29808 | 16980 | 14245 | 10837 | 22346 | 15650 | 27922 | 18395 | 20034 | 26278 | 18113 |
| 38.54 | 30371 | 15901 | 14425 | 10240 | 22582 | 14648 | 28286 | 19878 | 19078 | 26729 | 18059 |

| | | | | | | | | | | | |
|---|---|---|---|---|---|---|---|---|---|---|---|
| 38.58 | 30335 | 14613 | 14943 | 10367 | 24696 | 13898 | 29374 | 18535 | 20280 | 26670 | 19037 |
| 38.62 | 29884 | 14528 | 14343 | 9963 | 22441 | 15774 | 28646 | 19189 | 19795 | 26487 | 19577 |
| 38.66 | 28096 | 15933 | 14121 | 9610 | 22582 | 14759 | 28379 | 19799 | 17345 | 28131 | 20039 |
| 38.7 | 31019 | 14995 | 13807 | 10459 | 22632 | 12777 | 29575 | 19987 | 18221 | 26830 | 20000 |
| 38.74 | 30637 | 14673 | 14811 | 10750 | 22387 | 13417 | 28718 | 20162 | 19634 | 29903 | 20759 |
| 38.78 | 29071 | 16478 | 15798 | 9782 | 23323 | 14346 | 28892 | 18347 | 19909 | 28484 | 22480 |
| 38.82 | 30974 | 15796 | 14067 | 9252 | 23758 | 13734 | 28951 | 18671 | 19693 | 29986 | 19608 |
| 38.86 | 30293 | 15257 | 13666 | 10184 | 22115 | 13341 | 27806 | 18864 | 19256 | 31710 | 19278 |
| 38.9 | 29684 | 16487 | 16633 | 11148 | 20477 | 13424 | 28273 | 17567 | 19881 | 30960 | 19418 |
| 38.94 | 28208 | 15352 | 15543 | 9052 | 21869 | 13486 | 28957 | 17726 | 19096 | 30091 | 18268 |
| 38.98 | 28632 | 16943 | 13895 | 10122 | 22286 | 13114 | 28056 | 18756 | 18849 | 29256 | 19140 |
| 39.02 | 29366 | 15886 | 13847 | 9715 | 21763 | 14307 | 28341 | 18948 | 18151 | 28533 | 17205 |
| 39.06 | 29583 | 14943 | 15237 | 10161 | 22045 | 14610 | 30425 | 16968 | 17747 | 26438 | 19226 |
| 39.1 | 29291 | 15792 | 15031 | 9520 | 22025 | 12998 | 28594 | 16112 | 19621 | 29384 | 19669 |
| 39.14 | 27631 | 16894 | 13960 | 10708 | 23374 | 13814 | 29130 | 15769 | 20989 | 27076 | 17536 |
| 39.18 | 30390 | 17294 | 14330 | 9625 | 23342 | 14150 | 30034 | 16661 | 22559 | 27838 | 17726 |
| 39.22 | 28505 | 15863 | 14488 | 9914 | 23591 | 14158 | 27824 | 16412 | 22026 | 27218 | 17624 |
| 39.26 | 29864 | 16508 | 15159 | 9725 | 24770 | 14075 | 28573 | 16109 | 23255 | 26226 | 18611 |
| 39.3 | 28935 | 15963 | 15405 | 10143 | 22638 | 13602 | 28470 | 16808 | 23477 | 25710 | 18814 |
| 39.34 | 30792 | 17136 | 16355 | 10128 | 22833 | 15153 | 30328 | 15594 | 23154 | 26401 | 17911 |
| 39.38 | 28970 | 16985 | 13667 | 10690 | 22593 | 14798 | 31066 | 15928 | 25597 | 27025 | 16894 |
| 39.42 | 29823 | 18390 | 14576 | 9959 | 24511 | 13599 | 30351 | 16800 | 24442 | 25758 | 19502 |
| 39.46 | 29509 | 17727 | 14773 | 9839 | 22042 | 14364 | 28455 | 16002 | 24010 | 25585 | 17871 |
| 39.5 | 29164 | 18323 | 13416 | 10242 | 22311 | 14427 | 29501 | 14406 | 23776 | 27481 | 16609 |
| 39.54 | 28518 | 17963 | 14024 | 9812 | 20612 | 14501 | 30890 | 15455 | 21468 | 26567 | 16068 |
| 39.58 | 29628 | 17833 | 15014 | 9857 | 20985 | 14781 | 29711 | 13605 | 20136 | 26062 | 17094 |
| 39.62 | 30680 | 19293 | 13228 | 8750 | 21082 | 15289 | 28806 | 14050 | 19758 | 25890 | 16627 |
| 39.66 | 28467 | 18821 | 15314 | 9387 | 22189 | 14442 | 28738 | 16709 | 18893 | 25641 | 18135 |
| 39.7 | 30727 | 17068 | 12802 | 9356 | 19600 | 14607 | 28224 | 14626 | 17621 | 26154 | 17111 |
| 39.74 | 29365 | 18138 | 13933 | 10224 | 22315 | 14319 | 27302 | 14980 | 17965 | 25615 | 16676 |
| 39.78 | 27849 | 16672 | 14308 | 9808 | 20622 | 13637 | 27500 | 15359 | 16818 | 25753 | 16854 |
| 39.82 | 28747 | 17263 | 12721 | 9365 | 19542 | 12618 | 29552 | 16383 | 17880 | 25503 | 17026 |
| 39.86 | 28790 | 17884 | 15056 | 9881 | 18943 | 13953 | 27950 | 17695 | 20465 | 26966 | 17673 |
| 39.9 | 27769 | 16979 | 14987 | 9772 | 17681 | 13932 | 27835 | 17670 | 19287 | 27418 | 16535 |
| 39.94 | 29413 | 17504 | 14362 | 9076 | 19599 | 14634 | 28537 | 17224 | 20247 | 28067 | 17131 |
| 39.98 | 28038 | 17195 | 14795 | 10183 | 20252 | 13271 | 30174 | 17754 | 20592 | 27567 | 17381 |
| 40.02 | 29760 | 16377 | 14267 | 9324 | 19442 | 13399 | 30270 | 17772 | 23753 | 29807 | 16535 |
| 40.06 | 27988 | 17591 | 15014 | 8314 | 17621 | 14925 | 29066 | 19270 | 21040 | 28971 | 17667 |
| 40.1 | 28661 | 15381 | 13942 | 9495 | 18840 | 13747 | 32253 | 19569 | 22906 | 27946 | 16388 |
| 40.14 | 28742 | 16900 | 14288 | 10026 | 18296 | 15185 | 30021 | 18646 | 22587 | 26107 | 17617 |
| 40.18 | 27551 | 15703 | 14095 | 10089 | 19408 | 14481 | 30437 | 21350 | 22024 | 25857 | 16439 |
| 40.22 | 28424 | 15141 | 12851 | 10033 | 17448 | 15133 | 30817 | 20117 | 21109 | 28055 | 15849 |
| 40.26 | 27844 | 16258 | 13166 | 8855 | 18544 | 15209 | 31595 | 22909 | 21589 | 26410 | 18112 |
| 40.3 | 27940 | 15476 | 13015 | 9043 | 17027 | 13845 | 30004 | 20598 | 20349 | 25184 | 15281 |
| 40.34 | 26220 | 16305 | 13766 | 10073 | 16905 | 14313 | 30615 | 20842 | 20283 | 25155 | 17111 |
| 40.38 | 26803 | 16016 | 14150 | 9216 | 18072 | 14580 | 32175 | 22106 | 20049 | 25045 | 16217 |
| 40.42 | 27902 | 15650 | 14452 | 9486 | 17853 | 13870 | 30954 | 21550 | 17834 | 25842 | 17075 |
| 40.46 | 27847 | 15588 | 14105 | 10101 | 16348 | 14804 | 30304 | 23956 | 17258 | 26715 | 16604 |
| 40.5 | 28905 | 15561 | 12174 | 9288 | 16922 | 13138 | 31215 | 23988 | 18012 | 26408 | 14585 |
| 40.54 | 26040 | 15280 | 13534 | 10304 | 17246 | 12320 | 29385 | 22613 | 17892 | 27600 | 15237 |
| 40.58 | 27134 | 15281 | 13646 | 8791 | 16236 | 11036 | 29660 | 22437 | 17818 | 26414 | 16178 |
| 40.62 | 27472 | 16127 | 13298 | 9099 | 17276 | 12165 | 28025 | 22094 | 17276 | 26397 | 16833 |
| 40.66 | 26566 | 16257 | 13854 | 9055 | 16351 | 11968 | 28468 | 21897 | 17049 | 27074 | 14516 |
| 40.7 | 25445 | 14403 | 13296 | 8688 | 15133 | 12183 | 26060 | 22142 | 16525 | 25741 | 15361 |
| 40.74 | 28667 | 17143 | 12420 | 8361 | 16387 | 11732 | 27551 | 22170 | 16646 | 27957 | 15311 |
| 40.78 | 26348 | 14959 | 13867 | 8909 | 17438 | 11599 | 27980 | 20664 | 16684 | 24462 | 15735 |
| 40.82 | 25686 | 15912 | 12930 | 8765 | 17509 | 11906 | 25365 | 20757 | 16864 | 24941 | 16094 |
| 40.86 | 27823 | 14468 | 13743 | 9351 | 17383 | 11145 | 25231 | 20134 | 16092 | 25658 | 14035 |
| 40.9 | 27246 | 13098 | 14254 | 9263 | 19879 | 12374 | 25479 | 20896 | 16272 | 25925 | 15328 |
| 40.94 | 24652 | 14283 | 12747 | 9375 | 19214 | 11791 | 27998 | 16875 | 16183 | 26563 | 17074 |
| 40.98 | 25743 | 14401 | 11730 | 9098 | 19707 | 10836 | 26485 | 19650 | 16053 | 26931 | 14884 |
| 41.02 | 26401 | 12842 | 12501 | 8236 | 19628 | 11682 | 25922 | 18812 | 16615 | 27245 | 13845 |
| 41.06 | 24977 | 13113 | 12371 | 8953 | 19358 | 12173 | 24223 | 16456 | 15824 | 24404 | 15053 |
| 41.1 | 25117 | 12981 | 13223 | 8253 | 19886 | 11592 | 26972 | 16110 | 16438 | 23832 | 14196 |
| 41.14 | 26178 | 15035 | 12016 | 8478 | 21677 | 11814 | 26050 | 16962 | 15165 | 24547 | 15232 |
| 41.18 | 25402 | 14460 | 10476 | 6934 | 20477 | 11538 | 25468 | 17166 | 16569 | 24138 | 14269 |
| 41.22 | 24112 | 12561 | 12300 | 8745 | 20936 | 10716 | 24982 | 15523 | 15330 | 23752 | 14879 |
| 41.26 | 25256 | 12470 | 11668 | 8351 | 19539 | 11743 | 23203 | 15982 | 13353 | 21719 | 15270 |
| 41.3 | 23496 | 13331 | 12844 | 8040 | 20960 | 10720 | 27215 | 15827 | 14435 | 22833 | 16561 |
| 41.34 | 23870 | 12426 | 11315 | 9168 | 21245 | 11515 | 23574 | 14432 | 14293 | 23325 | 16132 |
| 41.38 | 25162 | 12983 | 10970 | 8618 | 21048 | 11223 | 23326 | 13260 | 13454 | 21144 | 14823 |
| 41.42 | 24673 | 13748 | 11836 | 8122 | 20684 | 12485 | 23599 | 14503 | 14635 | 21405 | 14893 |
| 41.46 | 24732 | 14253 | 12514 | 9476 | 21247 | 11063 | 24473 | 15591 | 12749 | 20837 | 14926 |
| 41.5 | 24586 | 15331 | 10901 | 8733 | 20701 | 11804 | 24163 | 14005 | 13272 | 19536 | 15924 |

-continued

| | Form | | | | | | | | |
|---|---|---|---|---|---|---|---|---|---|
| | Mao1 | Mao2_lc | Nds1a | Nds1b | Nds2 | Nds3_lc | Nds4_lc | Nds5 | Nsu1_lc |
| | | | | | ExperimentID | | | | |
| Counter ion | SSm53 Malonic acid | SSm20 Malonic acid | SSm35 1,5-Naphthalene-disulfonic acid | SSm68 1,5-Naphthalene-disulfonic acid | SSm69 1,5-Naphthalene-disulfonic acid | SSm2 1,5-Naphthalene-disulfonic acid | SSm3 1,5-Naphthalene-disulfonic acid | SSm68 1,5-Naphthalene-disulfonic acid | SSm9 Naphthalene-2-sulfonic acid |
| 1.5 | 2740 | 2337 | 1460 | 1547 | 2249 | 3891 | 1117 | 2095 | 3752 |
| 1.54 | 3097 | 4879 | 604 | 3681 | 4403 | 2884 | 2833 | 1895 | 5026 |
| 1.58 | 5605 | 3836 | 3420 | 1297 | 3562 | 3074 | 1410 | 1539 | 5270 |
| 1.62 | 5329 | 3118 | 2412 | 3249 | 3315 | 5030 | 3550 | 7037 | 8527 |
| 1.66 | 6811 | 4661 | 4153 | 3306 | 8259 | 7479 | 3771 | 2270 | 12707 |
| 1.7 | 8319 | 8338 | 3018 | 11452 | 6620 | 6139 | 6639 | 3775 | 12586 |
| 1.74 | 15217 | 5242 | 3004 | 8995 | 6312 | 7519 | 6918 | 5323 | 12796 |
| 1.78 | 14740 | 7928 | 4356 | 6616 | 4322 | 5188 | 6117 | 5408 | 12652 |
| 1.82 | 16482 | 9354 | 5649 | 5169 | 7424 | 8491 | 7706 | 5257 | 12024 |
| 1.86 | 17442 | 6938 | 10511 | 7269 | 6139 | 7022 | 8947 | 6425 | 17677 |
| 1.9 | 15096 | 6684 | 11973 | 8994 | 6711 | 6519 | 7891 | 6226 | 16590 |
| 1.94 | 18116 | 8915 | 10128 | 6977 | 10620 | 8269 | 9692 | 5301 | 24737 |
| 1.98 | 18052 | 9535 | 10412 | 9376 | 7949 | 11092 | 7563 | 7573 | 19293 |
| 2.02 | 23008 | 9739 | 10345 | 13486 | 7629 | 9736 | 8689 | 8075 | 23678 |
| 2.06 | 18930 | 10982 | 10412 | 12118 | 8421 | 8969 | 9900 | 6519 | 23535 |
| 2.1 | 19880 | 10490 | 10005 | 8628 | 6858 | 7656 | 6057 | 7573 | 17254 |
| 2.14 | 14375 | 10990 | 9956 | 11308 | 9218 | 10268 | 11449 | 9807 | 16059 |
| 2.18 | 20203 | 8087 | 10935 | 10027 | 9353 | 10200 | 8328 | 5129 | 21588 |
| 2.22 | 23841 | 10781 | 9321 | 9597 | 10844 | 8133 | 9091 | 7673 | 23345 |
| 2.26 | 15921 | 7864 | 11479 | 13226 | 11115 | 12921 | 10172 | 8491 | 18538 |
| 2.3 | 16259 | 8533 | 9485 | 9828 | 10409 | 10839 | 7517 | 7946 | 18060 |
| 2.34 | 18793 | 12691 | 9680 | 8311 | 9933 | 8940 | 11825 | 8874 | 21617 |
| 2.38 | 16452 | 9799 | 8678 | 12638 | 10569 | 8071 | 11961 | 6531 | 19958 |
| 2.42 | 17037 | 11286 | 9054 | 12122 | 12978 | 9711 | 10927 | 7605 | 22730 |
| 2.46 | 21307 | 8491 | 13863 | 11295 | 10400 | 7752 | 11516 | 9856 | 21752 |
| 2.5 | 20692 | 11623 | 13610 | 12634 | 7940 | 8463 | 12031 | 6913 | 20716 |
| 2.54 | 18588 | 10726 | 10076 | 12073 | 8939 | 10100 | 13383 | 7339 | 21944 |
| 2.58 | 20436 | 9401 | 10129 | 10622 | 11015 | 10361 | 12164 | 6619 | 21454 |
| 2.62 | 26119 | 12307 | 13555 | 11197 | 9576 | 8025 | 13584 | 7917 | 26033 |
| 2.66 | 21624 | 11961 | 14135 | 11210 | 7444 | 11178 | 7710 | 7950 | 24312 |
| 2.7 | 20582 | 13698 | 13799 | 10589 | 11658 | 13015 | 10680 | 6236 | 24215 |
| 2.74 | 23322 | 10571 | 14834 | 10943 | 11962 | 10122 | 13556 | 9147 | 23642 |
| 2.78 | 20357 | 12959 | 14807 | 12149 | 9777 | 9654 | 12979 | 8151 | 19381 |
| 2.82 | 23810 | 17833 | 10302 | 12326 | 12693 | 14350 | 11101 | 7306 | 24636 |
| 2.86 | 20621 | 13603 | 14271 | 13698 | 15783 | 9418 | 13391 | 8716 | 27095 |
| 2.9 | 21208 | 14818 | 12553 | 12525 | 12358 | 11630 | 16279 | 8271 | 27981 |
| 2.94 | 21585 | 12754 | 14948 | 12634 | 13716 | 13654 | 12960 | 7686 | 30508 |
| 2.98 | 25819 | 14955 | 11717 | 12123 | 14812 | 14442 | 16625 | 9442 | 28558 |
| 3.02 | 24989 | 15477 | 13503 | 11491 | 12870 | 14844 | 15637 | 10048 | 33244 |
| 3.06 | 28726 | 16158 | 15224 | 11245 | 12022 | 18448 | 13850 | 9994 | 36507 |
| 3.1 | 25291 | 17143 | 14320 | 14994 | 13277 | 16398 | 17253 | 12210 | 30662 |
| 3.14 | 25085 | 17249 | 11985 | 16299 | 12713 | 18705 | 16907 | 11381 | 34445 |
| 3.18 | 28690 | 21752 | 16429 | 18788 | 13885 | 21592 | 17254 | 10442 | 36692 |
| 3.22 | 27418 | 22570 | 17389 | 17232 | 14210 | 22938 | 15724 | 11094 | 38228 |
| 3.26 | 28906 | 22791 | 15166 | 16302 | 12560 | 25506 | 16896 | 12387 | 37976 |
| 3.3 | 29867 | 22575 | 14717 | 13135 | 12674 | 24335 | 17674 | 11345 | 36446 |
| 3.34 | 30228 | 20451 | 15431 | 17083 | 13526 | 21632 | 14122 | 12328 | 36102 |
| 3.38 | 30792 | 25464 | 14131 | 17502 | 13356 | 19994 | 15937 | 13691 | 38759 |
| 3.42 | 28243 | 26459 | 14655 | 15220 | 13627 | 17617 | 16610 | 15606 | 35698 |
| 3.46 | 32344 | 24802 | 15717 | 21533 | 14203 | 19637 | 15450 | 13458 | 41339 |
| 3.5 | 29117 | 23661 | 16037 | 19015 | 13013 | 17238 | 20476 | 11025 | 37060 |
| 3.54 | 32167 | 23622 | 17054 | 16393 | 15045 | 16470 | 17206 | 10681 | 38955 |
| 3.58 | 28286 | 24041 | 17367 | 18381 | 14760 | 12422 | 17082 | 14254 | 37850 |
| 3.62 | 29804 | 33310 | 18425 | 18719 | 15892 | 14795 | 19825 | 12652 | 40887 |
| 3.66 | 33461 | 26591 | 17428 | 18586 | 17094 | 13363 | 22342 | 14934 | 37928 |
| 3.7 | 29661 | 29658 | 16567 | 17458 | 15921 | 18224 | 17718 | 11003 | 36517 |
| 3.74 | 30664 | 32460 | 20669 | 13402 | 15688 | 15544 | 18543 | 13774 | 39225 |
| 3.78 | 31702 | 38241 | 15376 | 18022 | 15169 | 14464 | 20031 | 12876 | 34380 |
| 3.82 | 31369 | 34143 | 16784 | 16604 | 15540 | 20120 | 14917 | 9638 | 37564 |
| 3.86 | 31201 | 44227 | 14663 | 19186 | 15817 | 18904 | 16232 | 13506 | 34593 |
| 3.9 | 29060 | 49048 | 18754 | 18598 | 14653 | 18421 | 18189 | 13109 | 39247 |
| 3.94 | 33564 | 58535 | 19476 | 22487 | 13361 | 18866 | 17544 | 12982 | 42853 |
| 3.98 | 32471 | 62631 | 18549 | 21881 | 16485 | 17897 | 18325 | 13424 | 41742 |
| 4.02 | 28871 | 72244 | 16494 | 15634 | 17600 | 16378 | 20870 | 13246 | 35496 |
| 4.06 | 31954 | 60463 | 18502 | 17389 | 16530 | 17586 | 19026 | 13646 | 37139 |
| 4.1 | 34751 | 58546 | 16841 | 17129 | 16275 | 14239 | 16871 | 12949 | 43687 |
| 4.14 | 30691 | 65611 | 18522 | 17047 | 17404 | 20116 | 20325 | 13057 | 38711 |
| 4.18 | 30765 | 66518 | 17068 | 17102 | 16868 | 18835 | 17196 | 12736 | 46896 |

| | | | | | | | | | |
|---|---|---|---|---|---|---|---|---|---|
| 4.22 | 38166 | 64690 | 17443 | 20665 | 17727 | 17014 | 20651 | 18057 | 55730 |
| 4.26 | 35717 | 57763 | 19133 | 15762 | 15966 | 19188 | 19103 | 14841 | 48697 |
| 4.3 | 37066 | 48313 | 15709 | 17515 | 13692 | 17616 | 18976 | 17007 | 48481 |
| 4.34 | 40767 | 42943 | 18063 | 17909 | 14394 | 19672 | 19820 | 15331 | 51646 |
| 4.38 | 28899 | 36034 | 18603 | 20925 | 11887 | 19799 | 17947 | 14490 | 47139 |
| 4.42 | 36653 | 36958 | 18036 | 20932 | 16398 | 18561 | 20905 | 12124 | 46823 |
| 4.46 | 37207 | 29130 | 20446 | 20091 | 15157 | 16882 | 18320 | 14757 | 48097 |
| 4.5 | 39495 | 31757 | 15648 | 20056 | 19875 | 19832 | 17674 | 12870 | 48776 |
| 4.54 | 45303 | 28696 | 17182 | 21092 | 14936 | 21712 | 19651 | 12834 | 49655 |
| 4.58 | 41482 | 27205 | 20955 | 18456 | 17112 | 19930 | 20079 | 13393 | 47193 |
| 4.62 | 44207 | 23298 | 20061 | 20650 | 18743 | 20542 | 20347 | 13015 | 46202 |
| 4.66 | 42031 | 24756 | 20659 | 19260 | 15223 | 19634 | 17475 | 14554 | 46352 |
| 4.7 | 39246 | 22170 | 18298 | 18174 | 18433 | 19519 | 16992 | 14357 | 41995 |
| 4.74 | 49220 | 23167 | 20388 | 18201 | 16535 | 17213 | 18628 | 12788 | 47363 |
| 4.78 | 38574 | 23206 | 18760 | 16949 | 18498 | 19983 | 22844 | 14368 | 46033 |
| 4.82 | 37770 | 28931 | 17185 | 16936 | 18121 | 20932 | 18950 | 12195 | 43005 |
| 4.86 | 36581 | 24493 | 20789 | 18169 | 17361 | 19728 | 20518 | 14169 | 44806 |
| 4.9 | 34513 | 24989 | 16698 | 21137 | 17757 | 22827 | 19006 | 15702 | 49202 |
| 4.94 | 31128 | 18617 | 18586 | 20564 | 16961 | 19872 | 19371 | 13377 | 46487 |
| 4.98 | 32750 | 23069 | 19140 | 19980 | 13718 | 20762 | 17991 | 15437 | 48161 |
| 5.02 | 37692 | 22540 | 20538 | 22778 | 16747 | 19793 | 20836 | 15371 | 55129 |
| 5.06 | 38216 | 19884 | 19331 | 20409 | 15273 | 20713 | 20201 | 13780 | 55242 |
| 5.1 | 37967 | 21486 | 19963 | 23827 | 17993 | 22473 | 21310 | 15141 | 72780 |
| 5.14 | 38901 | 22397 | 24670 | 21279 | 17028 | 20641 | 20472 | 13802 | 76233 |
| 5.18 | 32985 | 20050 | 21038 | 20304 | 17150 | 19321 | 19320 | 14337 | 77120 |
| 5.22 | 36687 | 18387 | 19123 | 21165 | 15254 | 19297 | 18804 | 16276 | 78866 |
| 5.26 | 35944 | 21270 | 20396 | 23608 | 16445 | 19465 | 18681 | 16616 | 90894 |
| 5.3 | 33670 | 18215 | 20548 | 20973 | 18534 | 20533 | 18635 | 15546 | 84297 |
| 5.34 | 32769 | 20525 | 24098 | 21327 | 19822 | 20119 | 21327 | 14650 | 83442 |
| 5.38 | 37216 | 21332 | 23947 | 24890 | 20188 | 26232 | 23882 | 20569 | 84975 |
| 5.42 | 32565 | 19546 | 21584 | 19526 | 18394 | 23622 | 21269 | 17668 | 82363 |
| 5.46 | 32651 | 21095 | 22577 | 23454 | 18331 | 23187 | 21787 | 15110 | 73728 |
| 5.5 | 34444 | 21209 | 22650 | 19890 | 18488 | 23286 | 21531 | 14941 | 65053 |
| 5.54 | 34353 | 21429 | 18899 | 19089 | 18748 | 27265 | 20063 | 15541 | 67433 |
| 5.58 | 34584 | 19474 | 21774 | 20010 | 18720 | 25434 | 18313 | 19333 | 62428 |
| 5.62 | 33897 | 19135 | 21362 | 21466 | 18050 | 24660 | 18819 | 15734 | 66310 |
| 5.66 | 34849 | 17921 | 19451 | 20681 | 17888 | 27003 | 17281 | 16160 | 71535 |
| 5.7 | 34838 | 19328 | 19533 | 20772 | 20319 | 23728 | 22602 | 14552 | 77589 |
| 5.74 | 38513 | 21689 | 21216 | 20589 | 22651 | 25397 | 21634 | 19179 | 85659 |
| 5.78 | 37796 | 19053 | 21045 | 23203 | 17126 | 23593 | 18843 | 17157 | 94895 |
| 5.82 | 40541 | 18140 | 19938 | 18264 | 14888 | 20699 | 16795 | 16299 | 98980 |
| 5.86 | 39929 | 21001 | 19195 | 20741 | 15405 | 20552 | 17260 | 17137 | 98252 |
| 5.9 | 40968 | 17323 | 17554 | 19153 | 18096 | 19973 | 20166 | 15926 | 97648 |
| 5.94 | 39959 | 21374 | 18449 | 18708 | 18847 | 22448 | 19385 | 15554 | 94482 |
| 5.98 | 43045 | 21534 | 18736 | 18098 | 18714 | 20714 | 19997 | 16440 | 95653 |
| 6.02 | 43315 | 19944 | 18618 | 20693 | 14234 | 23047 | 20221 | 16599 | 89023 |
| 6.06 | 48667 | 19711 | 16816 | 22862 | 17195 | 24085 | 21963 | 15562 | 81748 |
| 6.1 | 45687 | 24585 | 22024 | 21843 | 19343 | 24734 | 20260 | 17204 | 70684 |
| 6.14 | 46273 | 19193 | 17989 | 18932 | 20267 | 25184 | 19300 | 15985 | 64137 |
| 6.18 | 52326 | 20972 | 22170 | 18221 | 17086 | 25788 | 22340 | 14487 | 60649 |
| 6.22 | 53657 | 20082 | 18534 | 19863 | 19078 | 27240 | 20330 | 16880 | 55676 |
| 6.26 | 53160 | 22165 | 18008 | 22581 | 14480 | 33376 | 21911 | 16081 | 55825 |
| 6.3 | 62021 | 19643 | 19342 | 23208 | 19283 | 33899 | 21874 | 17899 | 55164 |
| 6.34 | 58796 | 17396 | 17014 | 21726 | 18872 | 36777 | 22561 | 14565 | 60066 |
| 6.38 | 60055 | 20859 | 21479 | 19927 | 18457 | 37910 | 19829 | 16888 | 56782 |
| 6.42 | 54428 | 23469 | 19289 | 20981 | 16014 | 36141 | 20857 | 16739 | 59155 |
| 6.46 | 51289 | 22387 | 20687 | 23999 | 16233 | 34293 | 21632 | 16931 | 60555 |
| 6.5 | 48919 | 23742 | 20378 | 20954 | 14850 | 29884 | 18102 | 17271 | 59229 |
| 6.54 | 42123 | 19584 | 17930 | 18909 | 18754 | 30890 | 19035 | 14523 | 59274 |
| 6.58 | 40974 | 18752 | 20607 | 19736 | 18215 | 29796 | 20709 | 13876 | 57149 |
| 6.62 | 37207 | 21731 | 21629 | 23700 | 19318 | 27835 | 23556 | 17485 | 61747 |
| 6.66 | 36513 | 23546 | 22653 | 19723 | 15890 | 25482 | 21244 | 16948 | 56473 |
| 6.7 | 34908 | 23788 | 21632 | 19704 | 15796 | 24145 | 23395 | 17198 | 55744 |
| 6.74 | 36770 | 21768 | 19544 | 20620 | 20006 | 24203 | 20753 | 16440 | 50520 |
| 6.78 | 36227 | 23062 | 19014 | 18879 | 18389 | 21051 | 19116 | 17379 | 49544 |
| 6.82 | 34976 | 23756 | 19791 | 20412 | 14638 | 20754 | 20671 | 16702 | 46492 |
| 6.86 | 35056 | 21766 | 20587 | 21235 | 18024 | 21907 | 18791 | 16446 | 48153 |
| 6.9 | 34103 | 26220 | 19159 | 18997 | 19616 | 21675 | 22110 | 14675 | 46742 |
| 6.94 | 34371 | 26953 | 19816 | 19379 | 18903 | 21050 | 20483 | 16845 | 48739 |
| 6.98 | 39161 | 29514 | 21625 | 22251 | 16114 | 21892 | 21746 | 14644 | 50024 |
| 7.02 | 43011 | 31356 | 21035 | 20768 | 21131 | 20774 | 20903 | 15845 | 51997 |
| 7.06 | 48352 | 31085 | 19885 | 20018 | 19015 | 22638 | 19732 | 17223 | 53599 |
| 7.1 | 51838 | 31832 | 19782 | 18788 | 19197 | 19752 | 22230 | 15083 | 48807 |
| 7.14 | 52343 | 29869 | 20287 | 23136 | 18477 | 19941 | 19226 | 15166 | 50598 |
| 7.18 | 63807 | 31010 | 20864 | 20156 | 18631 | 20941 | 20229 | 15874 | 50157 |
| 7.22 | 68748 | 25960 | 22895 | 20900 | 16916 | 17833 | 19401 | 16603 | 54973 |
| 7.26 | 70014 | 28786 | 20772 | 21693 | 17681 | 18990 | 21349 | 13753 | 54935 |
| 7.3 | 75672 | 29681 | 21536 | 20502 | 18130 | 17236 | 21514 | 14097 | 55255 |
| 7.34 | 70168 | 29085 | 23376 | 23447 | 20510 | 21086 | 21505 | 16305 | 53999 |

-continued

| | | | | | | | | | |
|---|---|---|---|---|---|---|---|---|---|
| 7.38 | 65181 | 29140 | 19153 | 22812 | 18318 | 18361 | 21689 | 17272 | 46862 |
| 7.42 | 62765 | 24583 | 22075 | 21088 | 17747 | 20397 | 25091 | 17764 | 44306 |
| 7.46 | 55573 | 24729 | 18651 | 19414 | 16251 | 18094 | 21465 | 15645 | 48002 |
| 7.5 | 48185 | 28743 | 20804 | 19783 | 17335 | 21476 | 20204 | 16879 | 48268 |
| 7.54 | 46319 | 27869 | 22033 | 19298 | 19656 | 19621 | 22723 | 16863 | 49912 |
| 7.58 | 42198 | 26898 | 20973 | 22225 | 18481 | 20239 | 22705 | 18687 | 46667 |
| 7.62 | 42333 | 25234 | 22440 | 23246 | 21523 | 19462 | 21756 | 18122 | 45405 |
| 7.66 | 34638 | 26842 | 21821 | 23986 | 18556 | 23337 | 21365 | 17407 | 48104 |
| 7.7 | 34486 | 25038 | 18872 | 20800 | 18782 | 18059 | 21008 | 16826 | 46067 |
| 7.74 | 33741 | 26188 | 19277 | 19836 | 19020 | 19153 | 21186 | 14425 | 42761 |
| 7.78 | 32919 | 25585 | 21268 | 19683 | 20255 | 20524 | 19869 | 16340 | 41783 |
| 7.82 | 34388 | 25119 | 19984 | 22544 | 18527 | 17983 | 20962 | 15001 | 42345 |
| 7.86 | 36714 | 28586 | 20506 | 21576 | 18781 | 19159 | 21557 | 16677 | 46232 |
| 7.9 | 36769 | 26923 | 20825 | 21994 | 17271 | 20961 | 22295 | 15230 | 45037 |
| 7.94 | 35822 | 30425 | 20232 | 22475 | 18914 | 19375 | 21916 | 14801 | 49418 |
| 7.98 | 33096 | 30067 | 21738 | 21861 | 16719 | 18235 | 22636 | 15072 | 47255 |
| 8.02 | 37112 | 27778 | 21092 | 21649 | 20390 | 22060 | 20776 | 16045 | 43624 |
| 8.06 | 37907 | 30867 | 18101 | 20016 | 17715 | 20268 | 21393 | 17621 | 45646 |
| 8.1 | 36136 | 30348 | 19892 | 22155 | 19863 | 22957 | 21931 | 16380 | 41801 |
| 8.14 | 39086 | 31210 | 22761 | 21552 | 18435 | 24107 | 22420 | 19090 | 49893 |
| 8.18 | 36508 | 30430 | 22573 | 20121 | 19083 | 20846 | 23276 | 15547 | 46722 |
| 8.22 | 36644 | 31516 | 19062 | 18624 | 18624 | 23514 | 22708 | 16528 | 45956 |
| 8.26 | 33505 | 31834 | 20402 | 21852 | 18766 | 21472 | 21719 | 15991 | 45910 |
| 8.3 | 35340 | 30775 | 20804 | 21609 | 18203 | 20580 | 20966 | 20843 | 43563 |
| 8.34 | 36263 | 27843 | 21411 | 20902 | 18665 | 21551 | 21927 | 17248 | 43948 |
| 8.38 | 38396 | 29441 | 21215 | 25216 | 19603 | 25460 | 24273 | 19423 | 49154 |
| 8.42 | 38307 | 30970 | 21986 | 23178 | 17302 | 26127 | 22687 | 17471 | 49906 |
| 8.46 | 37545 | 28018 | 21286 | 20739 | 20955 | 24480 | 21766 | 16927 | 46446 |
| 8.5 | 35157 | 25100 | 23689 | 19950 | 20530 | 22082 | 20875 | 18263 | 44994 |
| 8.54 | 34414 | 26272 | 19135 | 18531 | 20402 | 23007 | 22363 | 18698 | 43391 |
| 8.58 | 33388 | 24779 | 22988 | 21648 | 20212 | 22785 | 26405 | 20463 | 45619 |
| 8.62 | 36486 | 26139 | 22182 | 23849 | 19989 | 22744 | 23045 | 18727 | 46198 |
| 8.66 | 40437 | 24942 | 21967 | 25984 | 22915 | 21828 | 21757 | 18229 | 49403 |
| 8.7 | 35199 | 24123 | 24459 | 25954 | 23385 | 23352 | 24213 | 19198 | 47173 |
| 8.74 | 38948 | 21772 | 24041 | 30092 | 21602 | 22049 | 23150 | 20049 | 45850 |
| 8.78 | 37721 | 23414 | 25182 | 27670 | 22074 | 23004 | 26319 | 22012 | 48973 |
| 8.82 | 41286 | 26198 | 27705 | 31192 | 22518 | 23533 | 27452 | 21270 | 52091 |
| 8.86 | 36673 | 25751 | 28712 | 35262 | 25673 | 21479 | 30250 | 22301 | 48948 |
| 8.9 | 37872 | 23891 | 29265 | 32086 | 22909 | 22871 | 30689 | 21507 | 48334 |
| 8.94 | 35938 | 25999 | 28582 | 34677 | 24421 | 19502 | 33395 | 21041 | 46473 |
| 8.98 | 38779 | 23528 | 31325 | 34172 | 21637 | 23581 | 31993 | 21629 | 48498 |
| 9.02 | 44501 | 25742 | 31664 | 31403 | 22403 | 21842 | 37997 | 19556 | 51355 |
| 9.06 | 45709 | 22627 | 32782 | 29994 | 22356 | 22583 | 37036 | 19588 | 48106 |
| 9.1 | 46395 | 23325 | 31443 | 26211 | 21145 | 19932 | 32848 | 19911 | 47750 |
| 9.14 | 44713 | 23215 | 28645 | 28017 | 20399 | 20569 | 32346 | 17534 | 45931 |
| 9.18 | 55829 | 24335 | 31206 | 24339 | 18658 | 21462 | 32097 | 18819 | 48166 |
| 9.22 | 51271 | 21699 | 24274 | 22093 | 20901 | 20665 | 31273 | 17990 | 45246 |
| 9.26 | 54991 | 23099 | 24229 | 20417 | 19007 | 21942 | 30721 | 18596 | 47098 |
| 9.3 | 55364 | 23344 | 25967 | 23871 | 19421 | 21526 | 29969 | 18758 | 46748 |
| 9.34 | 53531 | 25237 | 23365 | 23580 | 20700 | 20489 | 29889 | 20314 | 49996 |
| 9.38 | 53653 | 23689 | 25733 | 23386 | 20851 | 23148 | 32374 | 17437 | 47058 |
| 9.42 | 51260 | 24673 | 23124 | 22485 | 19616 | 21672 | 32566 | 16919 | 44864 |
| 9.46 | 44874 | 23562 | 20684 | 22070 | 19496 | 22116 | 30302 | 19468 | 48656 |
| 9.5 | 44175 | 24820 | 23047 | 23846 | 19435 | 21633 | 29780 | 18050 | 46118 |
| 9.54 | 43120 | 25281 | 24090 | 24508 | 17796 | 21603 | 31656 | 19018 | 44478 |
| 9.58 | 40163 | 23576 | 22939 | 24591 | 21188 | 22225 | 29553 | 19378 | 48748 |
| 9.62 | 37969 | 24548 | 23427 | 21725 | 19981 | 21088 | 28997 | 17810 | 46964 |
| 9.66 | 36955 | 24572 | 21497 | 23197 | 19690 | 21119 | 26597 | 18738 | 46367 |
| 9.7 | 39677 | 22724 | 25270 | 20003 | 20372 | 22215 | 28657 | 16783 | 48101 |
| 9.74 | 39880 | 25497 | 26635 | 23119 | 18817 | 22935 | 25618 | 19286 | 45967 |
| 9.78 | 44193 | 24292 | 23811 | 22792 | 17637 | 21209 | 26264 | 17466 | 46647 |
| 9.82 | 42289 | 25830 | 23532 | 23789 | 20590 | 23893 | 25674 | 16296 | 47106 |
| 9.86 | 48374 | 24979 | 26892 | 26028 | 19463 | 23664 | 26088 | 19202 | 46550 |
| 9.9 | 54547 | 23373 | 23932 | 23856 | 22171 | 23684 | 26310 | 18463 | 47859 |
| 9.94 | 54585 | 22712 | 24013 | 22659 | 21471 | 23336 | 25388 | 18080 | 48098 |
| 9.98 | 58172 | 26341 | 24639 | 25955 | 19065 | 23024 | 27833 | 18542 | 45214 |
| 10.02 | 57465 | 23889 | 28041 | 22694 | 19409 | 20801 | 26990 | 18594 | 46509 |
| 10.06 | 60311 | 24520 | 26020 | 25218 | 21186 | 23657 | 26011 | 18329 | 50720 |
| 10.1 | 58149 | 23873 | 25385 | 23421 | 20987 | 23048 | 27321 | 16723 | 47438 |
| 10.14 | 53034 | 25076 | 23740 | 24200 | 20275 | 21805 | 27369 | 16906 | 50169 |
| 10.18 | 52794 | 25296 | 24441 | 25001 | 21832 | 20254 | 33512 | 17942 | 49122 |
| 10.22 | 48064 | 24909 | 25742 | 26170 | 22259 | 20949 | 30624 | 18696 | 47397 |
| 10.26 | 41404 | 24436 | 26895 | 29814 | 22313 | 22550 | 30951 | 18535 | 51413 |
| 10.3 | 44358 | 27250 | 31129 | 31213 | 21737 | 22659 | 33081 | 18795 | 47612 |
| 10.34 | 42165 | 26562 | 32655 | 35355 | 21352 | 23350 | 31518 | 19849 | 49778 |
| 10.38 | 40324 | 24827 | 36551 | 32437 | 21395 | 24999 | 29825 | 18909 | 48888 |
| 10.42 | 37732 | 26130 | 36116 | 35062 | 23677 | 24693 | 33169 | 18683 | 48946 |
| 10.46 | 39341 | 28447 | 35527 | 34191 | 23564 | 22775 | 32324 | 19361 | 53217 |
| 10.5 | 38954 | 27022 | 36050 | 38884 | 23723 | 24206 | 34801 | 20548 | 55567 |

-continued

| | | | | | | | | | |
|---|---|---|---|---|---|---|---|---|---|
| 10.54 | 38193 | 26724 | 38914 | 35069 | 23451 | 24172 | 34567 | 22010 | 48876 |
| 10.58 | 39720 | 26960 | 34088 | 33620 | 26882 | 21376 | 35146 | 21811 | 49601 |
| 10.62 | 36699 | 25682 | 36265 | 33250 | 27778 | 24247 | 36799 | 21586 | 49491 |
| 10.66 | 41077 | 26125 | 35399 | 32749 | 25835 | 22068 | 35322 | 22638 | 52563 |
| 10.7 | 40137 | 27385 | 34140 | 29397 | 24392 | 22310 | 36156 | 22509 | 50347 |
| 10.74 | 38620 | 27116 | 31425 | 28594 | 23092 | 25869 | 32304 | 23191 | 56277 |
| 10.78 | 38627 | 27199 | 31844 | 29936 | 24152 | 24873 | 31352 | 21635 | 52668 |
| 10.82 | 39691 | 29047 | 29008 | 29940 | 24353 | 24821 | 34740 | 23033 | 53567 |
| 10.86 | 37504 | 26589 | 27235 | 29772 | 24399 | 24356 | 32630 | 21652 | 51077 |
| 10.9 | 39455 | 28695 | 30634 | 26249 | 25323 | 24676 | 32602 | 23132 | 52455 |
| 10.94 | 39118 | 26940 | 31040 | 28886 | 24329 | 24821 | 34319 | 19474 | 51703 |
| 10.98 | 41157 | 27517 | 31465 | 30852 | 24873 | 25024 | 37660 | 19729 | 49340 |
| 11.02 | 40449 | 29296 | 31541 | 26941 | 20790 | 25519 | 36040 | 20113 | 50539 |
| 11.06 | 42607 | 27876 | 31494 | 29787 | 25986 | 27637 | 35276 | 20461 | 52438 |
| 11.1 | 39882 | 28325 | 31634 | 28134 | 23446 | 25427 | 36089 | 20413 | 53079 |
| 11.14 | 41804 | 28817 | 31140 | 26800 | 26078 | 24740 | 36985 | 20932 | 54411 |
| 11.18 | 40734 | 27877 | 30109 | 27306 | 24545 | 28722 | 37096 | 21034 | 52966 |
| 11.22 | 42360 | 29465 | 30254 | 27206 | 24109 | 27694 | 35072 | 19655 | 54948 |
| 11.26 | 42080 | 27894 | 27772 | 29299 | 23229 | 26735 | 37168 | 19143 | 57752 |
| 11.3 | 39905 | 27800 | 30311 | 26799 | 25714 | 26401 | 36898 | 22146 | 55875 |
| 11.34 | 38324 | 28647 | 29098 | 24953 | 25519 | 26076 | 35211 | 21473 | 58075 |
| 11.38 | 42236 | 31212 | 28687 | 28825 | 23877 | 25421 | 35983 | 22396 | 57471 |
| 11.42 | 40095 | 28951 | 29332 | 27070 | 26905 | 28560 | 37902 | 22860 | 59871 |
| 11.46 | 42502 | 29348 | 27692 | 27356 | 24170 | 26277 | 37239 | 20858 | 60055 |
| 11.5 | 39200 | 31183 | 27771 | 24959 | 21115 | 29125 | 36868 | 21793 | 66340 |
| 11.54 | 40222 | 30716 | 27919 | 25498 | 23588 | 28511 | 39374 | 18356 | 65766 |
| 11.58 | 42319 | 29631 | 28229 | 26280 | 22599 | 27481 | 39086 | 22185 | 66573 |
| 11.62 | 39514 | 30088 | 29600 | 25113 | 22585 | 27500 | 39592 | 21917 | 64061 |
| 11.66 | 40947 | 33116 | 26838 | 26056 | 20603 | 29431 | 42679 | 21811 | 66659 |
| 11.7 | 44172 | 30966 | 27629 | 26598 | 23697 | 28944 | 45083 | 21054 | 69223 |
| 11.74 | 43953 | 30541 | 29613 | 26161 | 22291 | 29797 | 45132 | 21359 | 68023 |
| 11.78 | 42459 | 28738 | 27457 | 25493 | 22851 | 26540 | 43298 | 20739 | 71357 |
| 11.82 | 40406 | 29152 | 31134 | 25450 | 22585 | 27991 | 43246 | 20047 | 69535 |
| 11.86 | 42545 | 30847 | 27154 | 25125 | 23943 | 28611 | 43410 | 19716 | 71409 |
| 11.9 | 43756 | 28972 | 31942 | 27476 | 21521 | 25487 | 45648 | 19835 | 70287 |
| 11.94 | 43644 | 31581 | 29928 | 25773 | 23243 | 26286 | 44535 | 21554 | 71557 |
| 11.98 | 43551 | 29981 | 33075 | 28032 | 24768 | 27835 | 43803 | 20243 | 73542 |
| 12.02 | 46672 | 31157 | 34259 | 32128 | 26374 | 29194 | 47933 | 21147 | 73011 |
| 12.06 | 44536 | 30484 | 39044 | 35518 | 26656 | 30203 | 44169 | 24768 | 71661 |
| 12.1 | 42814 | 29009 | 42234 | 41335 | 29666 | 30413 | 45020 | 28044 | 74045 |
| 12.14 | 43116 | 29367 | 45306 | 47857 | 31698 | 30227 | 44279 | 28153 | 69352 |
| 12.18 | 45407 | 30583 | 49689 | 52070 | 30668 | 33007 | 45255 | 26887 | 69455 |
| 12.22 | 40798 | 29330 | 52881 | 58490 | 32116 | 35273 | 43059 | 32418 | 69069 |
| 12.26 | 40830 | 29114 | 57673 | 61040 | 30392 | 36239 | 44442 | 32184 | 68553 |
| 12.3 | 42700 | 29333 | 58387 | 61399 | 32339 | 35839 | 41539 | 28868 | 66486 |
| 12.34 | 45559 | 31852 | 54438 | 61435 | 29951 | 39183 | 41350 | 31451 | 65080 |
| 12.38 | 44937 | 31781 | 50708 | 58521 | 32178 | 36610 | 40562 | 30796 | 66415 |
| 12.42 | 41879 | 28580 | 46129 | 54886 | 30509 | 36626 | 37743 | 25880 | 66017 |
| 12.46 | 43432 | 31192 | 41130 | 51214 | 27826 | 35790 | 37905 | 24345 | 65343 |
| 12.5 | 47007 | 29660 | 37458 | 43464 | 26086 | 34437 | 35047 | 22779 | 61266 |
| 12.54 | 44018 | 31276 | 32915 | 40115 | 26882 | 32879 | 34329 | 23435 | 62991 |
| 12.58 | 44372 | 30562 | 32593 | 33663 | 24982 | 33843 | 35990 | 23144 | 62304 |
| 12.62 | 41749 | 28286 | 32719 | 30603 | 24430 | 29746 | 31884 | 21210 | 63135 |
| 12.66 | 45808 | 28949 | 31365 | 28169 | 26118 | 29079 | 35195 | 22065 | 64260 |
| 12.7 | 39414 | 31174 | 27878 | 28022 | 23687 | 28981 | 32252 | 22017 | 63744 |
| 12.74 | 43654 | 30064 | 32323 | 28779 | 23154 | 28214 | 31921 | 20659 | 59589 |
| 12.78 | 46185 | 30053 | 31373 | 27063 | 25535 | 29595 | 35881 | 22076 | 61892 |
| 12.82 | 43792 | 30529 | 32419 | 28647 | 24186 | 29072 | 33971 | 20582 | 61480 |
| 12.86 | 47330 | 30177 | 29455 | 28509 | 23461 | 30798 | 33633 | 19579 | 64168 |
| 12.9 | 45298 | 31237 | 32174 | 28052 | 23768 | 30300 | 33530 | 20549 | 63808 |
| 12.94 | 44009 | 30453 | 30069 | 27332 | 25686 | 33819 | 33211 | 23144 | 62218 |
| 12.98 | 46713 | 28122 | 28819 | 27087 | 23399 | 35552 | 33888 | 19626 | 64832 |
| 13.02 | 48524 | 30498 | 25574 | 29092 | 23752 | 33981 | 32587 | 20314 | 59803 |
| 13.06 | 48116 | 31518 | 27752 | 26906 | 22863 | 35777 | 29704 | 17949 | 61454 |
| 13.1 | 47097 | 29409 | 27709 | 25766 | 23945 | 36737 | 32714 | 21593 | 61494 |
| 13.14 | 48236 | 29941 | 27425 | 25234 | 22831 | 37473 | 33991 | 19654 | 57483 |
| 13.18 | 48415 | 29424 | 27379 | 24516 | 22158 | 37961 | 29696 | 20749 | 57852 |
| 13.22 | 47055 | 30959 | 28196 | 25304 | 22971 | 40574 | 32890 | 20375 | 57891 |
| 13.26 | 54019 | 32006 | 26185 | 24795 | 23087 | 35136 | 33766 | 19508 | 58560 |
| 13.3 | 55793 | 32234 | 27650 | 23782 | 25850 | 34913 | 32885 | 21036 | 59792 |
| 13.34 | 70276 | 32439 | 28294 | 24561 | 23402 | 33523 | 30776 | 20488 | 56965 |
| 13.38 | 86559 | 31479 | 27523 | 22838 | 22755 | 32962 | 30998 | 22491 | 56222 |
| 13.42 | 100882 | 31165 | 24906 | 24931 | 21573 | 34350 | 31497 | 20883 | 60828 |
| 13.46 | 112370 | 32178 | 27210 | 25367 | 23413 | 32869 | 31532 | 18852 | 62205 |
| 13.5 | 117118 | 32738 | 26416 | 25813 | 21573 | 33543 | 32218 | 20732 | 62534 |
| 13.54 | 124392 | 33189 | 28955 | 24851 | 21302 | 32975 | 32954 | 19459 | 64068 |
| 13.58 | 121269 | 31833 | 25171 | 23159 | 24332 | 33824 | 30306 | 19510 | 64565 |
| 13.62 | 118812 | 35240 | 25864 | 25541 | 21991 | 33940 | 28945 | 21407 | 65799 |
| 13.66 | 115336 | 32422 | 27150 | 25648 | 23496 | 33826 | 31431 | 22640 | 69816 |

-continued

| | | | | | | | | | |
|---|---|---|---|---|---|---|---|---|---|
| 13.7 | 106729 | 32474 | 28054 | 24628 | 24290 | 33754 | 32837 | 20353 | 71126 |
| 13.74 | 95138 | 32697 | 28036 | 25699 | 22389 | 29980 | 33608 | 21057 | 73130 |
| 13.78 | 84816 | 32814 | 30438 | 26603 | 23281 | 32705 | 34084 | 21228 | 70509 |
| 13.82 | 83418 | 33772 | 29383 | 24057 | 22392 | 32995 | 31466 | 20417 | 72111 |
| 13.86 | 88394 | 33385 | 28175 | 24814 | 22052 | 32304 | 31611 | 20377 | 72449 |
| 13.9 | 91341 | 32288 | 29362 | 24916 | 23669 | 33320 | 34770 | 21539 | 69063 |
| 13.94 | 100800 | 32409 | 29034 | 23663 | 23549 | 34761 | 30432 | 21923 | 69926 |
| 13.98 | 104573 | 31338 | 29701 | 24776 | 21467 | 36465 | 31998 | 20460 | 67465 |
| 14.02 | 107626 | 33046 | 28760 | 25408 | 23447 | 34827 | 32155 | 23021 | 69541 |
| 14.06 | 111210 | 33304 | 27818 | 25209 | 23060 | 35577 | 31724 | 21444 | 63487 |
| 14.1 | 103629 | 33675 | 25853 | 25682 | 24209 | 36677 | 34653 | 21665 | 63575 |
| 14.14 | 98693 | 32663 | 27790 | 25884 | 22187 | 36049 | 33073 | 21610 | 61863 |
| 14.18 | 90332 | 33841 | 25903 | 26416 | 23036 | 35506 | 30893 | 20870 | 63676 |
| 14.22 | 77750 | 32567 | 27695 | 27108 | 24626 | 34819 | 32507 | 20391 | 61925 |
| 14.26 | 66803 | 35370 | 27654 | 30106 | 21616 | 35407 | 31372 | 20499 | 64158 |
| 14.3 | 59427 | 35026 | 27767 | 28071 | 23323 | 32149 | 31880 | 21028 | 66382 |
| 14.34 | 51916 | 33962 | 26920 | 28410 | 23991 | 31273 | 33242 | 19426 | 65292 |
| 14.38 | 50324 | 35689 | 26077 | 32091 | 22435 | 31468 | 32429 | 18688 | 66934 |
| 14.42 | 50865 | 32956 | 26653 | 33733 | 23417 | 34913 | 34422 | 18908 | 68882 |
| 14.46 | 46857 | 34164 | 28936 | 33000 | 21693 | 33260 | 35820 | 19540 | 67005 |
| 14.5 | 47884 | 33991 | 30840 | 36984 | 20893 | 35967 | 36032 | 18975 | 67992 |
| 14.54 | 53435 | 33938 | 32266 | 35751 | 21319 | 35843 | 35956 | 19563 | 68167 |
| 14.58 | 50921 | 34186 | 35045 | 39777 | 23018 | 36714 | 35994 | 20542 | 65841 |
| 14.62 | 52335 | 33628 | 38862 | 39512 | 20017 | 36306 | 36445 | 20443 | 64416 |
| 14.66 | 53021 | 34836 | 42102 | 39451 | 23270 | 37037 | 39287 | 20594 | 66449 |
| 14.7 | 50323 | 33467 | 43037 | 39160 | 21656 | 37446 | 43764 | 21635 | 61464 |
| 14.74 | 52550 | 33440 | 42775 | 35863 | 20806 | 37390 | 43423 | 20531 | 65332 |
| 14.78 | 54566 | 35408 | 47326 | 33596 | 22709 | 37046 | 43176 | 20051 | 65010 |
| 14.82 | 57605 | 34942 | 44680 | 31487 | 21966 | 36663 | 43638 | 21031 | 60576 |
| 14.86 | 62319 | 33504 | 43348 | 30448 | 22849 | 36393 | 44660 | 20526 | 61077 |
| 14.9 | 78692 | 32000 | 42861 | 28584 | 20863 | 35318 | 47990 | 21356 | 59933 |
| 14.94 | 102497 | 34671 | 43144 | 28823 | 24012 | 35522 | 46520 | 20764 | 56914 |
| 14.98 | 133254 | 34170 | 41159 | 29553 | 23201 | 32027 | 48262 | 21862 | 60044 |
| 15.02 | 163036 | 31913 | 37737 | 33631 | 24060 | 34361 | 49931 | 22977 | 60400 |
| 15.06 | 183614 | 33178 | 40276 | 36653 | 25845 | 32841 | 45647 | 25767 | 58284 |
| 15.1 | 198743 | 36624 | 44055 | 42704 | 28267 | 34228 | 46334 | 24079 | 57555 |
| 15.14 | 212844 | 33093 | 48112 | 48587 | 27937 | 34645 | 46293 | 25640 | 60724 |
| 15.18 | 209073 | 34713 | 52850 | 52451 | 29731 | 37563 | 48793 | 28225 | 62031 |
| 15.22 | 211410 | 34050 | 53989 | 55687 | 32201 | 37638 | 44351 | 30606 | 61089 |
| 15.26 | 194267 | 35748 | 57752 | 60690 | 32871 | 37015 | 44176 | 30532 | 60426 |
| 15.3 | 177888 | 33471 | 59002 | 61723 | 35235 | 38734 | 48345 | 32051 | 60329 |
| 15.34 | 150669 | 32895 | 60928 | 60146 | 35691 | 40114 | 46477 | 31543 | 61698 |
| 15.38 | 134205 | 34915 | 56236 | 63382 | 36748 | 39637 | 42836 | 30549 | 63531 |
| 15.42 | 135971 | 34562 | 53439 | 60610 | 35391 | 40499 | 43040 | 32066 | 60179 |
| 15.46 | 129756 | 33820 | 49421 | 62974 | 35952 | 38010 | 39164 | 31211 | 62351 |
| 15.5 | 145689 | 33449 | 43184 | 61456 | 37314 | 38269 | 38180 | 33238 | 60510 |
| 15.54 | 166027 | 36674 | 40361 | 61683 | 39892 | 35816 | 38772 | 33721 | 65184 |
| 15.58 | 173319 | 34566 | 37712 | 63439 | 42426 | 39012 | 36699 | 33396 | 61588 |
| 15.62 | 181547 | 32846 | 38893 | 62748 | 51127 | 33819 | 32439 | 32463 | 67096 |
| 15.66 | 180487 | 33059 | 37244 | 63326 | 52918 | 36388 | 32918 | 36757 | 63445 |
| 15.7 | 168103 | 35239 | 37452 | 59993 | 57506 | 36124 | 36123 | 37676 | 64700 |
| 15.74 | 161405 | 33950 | 35754 | 57471 | 61042 | 34683 | 33922 | 38053 | 63607 |
| 15.78 | 143374 | 34131 | 39458 | 54167 | 59534 | 35404 | 36380 | 35939 | 62924 |
| 15.82 | 122923 | 36149 | 39024 | 54251 | 63224 | 34368 | 33966 | 37965 | 64180 |
| 15.86 | 97992 | 34354 | 39810 | 46517 | 65321 | 36659 | 35203 | 39158 | 67337 |
| 15.9 | 76581 | 35979 | 40195 | 44708 | 63235 | 36352 | 36946 | 39338 | 69186 |
| 15.94 | 60583 | 36435 | 42600 | 39021 | 62081 | 36052 | 34905 | 36289 | 71436 |
| 15.98 | 53543 | 34141 | 41497 | 37502 | 55410 | 36595 | 38675 | 33464 | 70033 |
| 16.02 | 51248 | 34985 | 37429 | 37282 | 54205 | 34606 | 35471 | 34034 | 68906 |
| 16.06 | 46491 | 36873 | 37887 | 34140 | 48607 | 34612 | 35632 | 32782 | 64212 |
| 16.1 | 46618 | 36378 | 35666 | 33597 | 44267 | 36089 | 32574 | 28384 | 68327 |
| 16.14 | 47933 | 36406 | 34241 | 31182 | 40521 | 38837 | 34136 | 28207 | 65494 |
| 16.18 | 50538 | 37269 | 33022 | 30038 | 39246 | 33450 | 34034 | 28109 | 66593 |
| 16.22 | 52674 | 37315 | 31848 | 30409 | 34951 | 34470 | 32656 | 25976 | 68655 |
| 16.26 | 51725 | 36261 | 28511 | 30848 | 31486 | 35856 | 31112 | 28185 | 67867 |
| 16.3 | 51889 | 37524 | 30281 | 29371 | 30141 | 34670 | 33865 | 24129 | 70159 |
| 16.34 | 49943 | 37526 | 29105 | 30483 | 29332 | 35321 | 30531 | 26204 | 68627 |
| 16.38 | 49987 | 38905 | 29056 | 31886 | 30260 | 32970 | 30228 | 24463 | 70703 |
| 16.42 | 50244 | 37202 | 27186 | 30795 | 31815 | 32486 | 29595 | 26881 | 70288 |
| 16.46 | 51374 | 38409 | 28018 | 32325 | 29560 | 33618 | 30432 | 24911 | 69664 |
| 16.5 | 47483 | 41109 | 28301 | 34983 | 30036 | 33969 | 29253 | 25447 | 69884 |
| 16.54 | 47765 | 41804 | 28896 | 32281 | 31478 | 37636 | 29582 | 28719 | 69950 |
| 16.58 | 47424 | 38027 | 29434 | 34108 | 30709 | 38884 | 30166 | 27441 | 64485 |
| 16.62 | 46807 | 38311 | 31379 | 34544 | 30526 | 33723 | 29604 | 26637 | 69222 |
| 16.66 | 46187 | 39988 | 28151 | 35516 | 29920 | 34388 | 29908 | 25283 | 66458 |
| 16.7 | 45337 | 37410 | 30428 | 33539 | 29523 | 36826 | 31045 | 24684 | 65565 |
| 16.74 | 45397 | 37369 | 31266 | 38577 | 28601 | 33823 | 32447 | 25039 | 65808 |
| 16.78 | 46444 | 38566 | 30624 | 39686 | 28206 | 35305 | 30181 | 22114 | 62762 |
| 16.82 | 44656 | 37826 | 33478 | 39304 | 27517 | 32661 | 33683 | 22729 | 61902 |

| | | | | | | | | | |
|---|---|---|---|---|---|---|---|---|---|
| 16.86 | 43803 | 35232 | 33594 | 43741 | 24267 | 34163 | 34178 | 21518 | 64090 |
| 16.9 | 45438 | 34144 | 35136 | 45512 | 22681 | 33867 | 35261 | 22414 | 61182 |
| 16.94 | 43845 | 35666 | 36458 | 46427 | 22791 | 34054 | 37784 | 20970 | 59441 |
| 16.98 | 45982 | 35714 | 38196 | 47124 | 22994 | 31522 | 40043 | 18757 | 60976 |
| 17.02 | 45326 | 35561 | 41098 | 50688 | 23155 | 34961 | 40767 | 19066 | 63803 |
| 17.06 | 47649 | 34011 | 43144 | 50587 | 23808 | 33205 | 43105 | 18695 | 62208 |
| 17.1 | 43977 | 33475 | 46297 | 49121 | 23951 | 31398 | 43551 | 21442 | 63402 |
| 17.14 | 47600 | 35015 | 47041 | 42620 | 23405 | 31562 | 46196 | 21542 | 63900 |
| 17.18 | 47849 | 34099 | 48862 | 39374 | 22366 | 30946 | 45709 | 22186 | 62707 |
| 17.22 | 50981 | 35261 | 49058 | 35146 | 21861 | 31981 | 48104 | 20710 | 61729 |
| 17.26 | 62005 | 34734 | 52387 | 33383 | 23219 | 31986 | 45425 | 20969 | 63895 |
| 17.3 | 71718 | 34759 | 49871 | 30647 | 23014 | 32328 | 43325 | 21590 | 64612 |
| 17.34 | 78077 | 33362 | 47685 | 29881 | 22797 | 33367 | 41277 | 22157 | 66288 |
| 17.38 | 85881 | 35293 | 47449 | 28575 | 23828 | 33060 | 39043 | 21534 | 65526 |
| 17.42 | 94267 | 35698 | 44378 | 29434 | 25743 | 35375 | 39002 | 23502 | 65948 |
| 17.46 | 93269 | 35612 | 39454 | 26851 | 24420 | 34384 | 36617 | 22890 | 65209 |
| 17.5 | 95517 | 35832 | 37881 | 27370 | 24794 | 35334 | 33060 | 20679 | 70145 |
| 17.54 | 95509 | 36171 | 33473 | 28117 | 23961 | 35841 | 32116 | 21759 | 69017 |
| 17.58 | 92378 | 34171 | 30784 | 26118 | 23984 | 36904 | 31146 | 22183 | 66779 |
| 17.62 | 82383 | 35763 | 27896 | 26066 | 24631 | 36834 | 29004 | 20102 | 65573 |
| 17.66 | 74098 | 36180 | 25801 | 26814 | 22478 | 35927 | 28476 | 21072 | 66640 |
| 17.7 | 64576 | 36755 | 24322 | 25287 | 23337 | 33974 | 28215 | 20667 | 64990 |
| 17.74 | 60203 | 37582 | 25073 | 26949 | 24082 | 33545 | 28947 | 20702 | 67440 |
| 17.78 | 52467 | 34234 | 26455 | 26619 | 24088 | 33017 | 28265 | 20834 | 65070 |
| 17.82 | 47654 | 35302 | 27320 | 26428 | 23355 | 33261 | 29053 | 20291 | 62969 |
| 17.86 | 45891 | 35941 | 28465 | 25937 | 24571 | 35590 | 29328 | 19088 | 63142 |
| 17.9 | 45752 | 34798 | 28201 | 28091 | 23216 | 30328 | 29166 | 18861 | 59554 |
| 17.94 | 45059 | 33028 | 26866 | 28253 | 22869 | 31203 | 31538 | 18427 | 62554 |
| 17.98 | 44301 | 34104 | 29492 | 28689 | 22142 | 31767 | 31121 | 19160 | 63435 |
| 18.02 | 42711 | 35681 | 27926 | 26500 | 24152 | 30643 | 32136 | 17600 | 61847 |
| 18.06 | 40933 | 33428 | 29168 | 29695 | 22886 | 29704 | 30889 | 18094 | 63652 |
| 18.1 | 44832 | 35489 | 28707 | 26997 | 21933 | 31499 | 31895 | 17119 | 64388 |
| 18.14 | 42374 | 35326 | 29321 | 27993 | 21945 | 30056 | 32609 | 17486 | 68073 |
| 18.18 | 42678 | 34594 | 26827 | 26196 | 19551 | 31342 | 30413 | 17674 | 64809 |
| 18.22 | 42965 | 33950 | 27898 | 27117 | 20455 | 30769 | 30675 | 17741 | 67833 |
| 18.26 | 47327 | 35392 | 27122 | 26314 | 20614 | 30819 | 31430 | 17350 | 66843 |
| 18.3 | 48285 | 33504 | 27157 | 27649 | 18365 | 31079 | 29423 | 17445 | 69131 |
| 18.34 | 51333 | 34538 | 26329 | 27294 | 20866 | 30095 | 28197 | 19298 | 67525 |
| 18.38 | 52769 | 35870 | 24281 | 26647 | 18874 | 31404 | 27446 | 19396 | 69229 |
| 18.42 | 56707 | 34729 | 24937 | 27191 | 19927 | 35492 | 27333 | 18290 | 66764 |
| 18.46 | 62663 | 34856 | 23712 | 28334 | 19005 | 32610 | 26488 | 17739 | 68660 |
| 18.5 | 66593 | 35255 | 24660 | 27951 | 18279 | 31479 | 27508 | 17926 | 66728 |
| 18.54 | 70830 | 34439 | 23678 | 25747 | 19874 | 31151 | 26963 | 18430 | 64975 |
| 18.58 | 76380 | 36430 | 23726 | 26644 | 19541 | 33848 | 26021 | 19090 | 64697 |
| 18.62 | 84011 | 37500 | 24449 | 24505 | 20330 | 31714 | 26671 | 18334 | 67458 |
| 18.66 | 98099 | 35752 | 25622 | 23487 | 21437 | 30608 | 28600 | 18841 | 63407 |
| 18.7 | 113993 | 35753 | 24509 | 23419 | 20972 | 31264 | 25594 | 19431 | 61967 |
| 18.74 | 135997 | 36219 | 26435 | 25560 | 20293 | 28495 | 27124 | 19566 | 62408 |
| 18.78 | 156239 | 38161 | 26237 | 25301 | 22277 | 29128 | 28250 | 21459 | 63519 |
| 18.82 | 172529 | 35066 | 27813 | 27846 | 23461 | 30185 | 28694 | 24363 | 63262 |
| 18.86 | 187207 | 36278 | 26346 | 29049 | 22795 | 28900 | 28510 | 30828 | 63804 |
| 18.9 | 197053 | 35527 | 26012 | 29600 | 22486 | 31096 | 27838 | 32954 | 65033 |
| 18.94 | 197463 | 36540 | 26168 | 27554 | 22859 | 30688 | 27940 | 41498 | 62145 |
| 18.98 | 190237 | 36517 | 26165 | 28968 | 23398 | 31926 | 27944 | 44241 | 61213 |
| 19.02 | 181984 | 33799 | 24334 | 30747 | 24861 | 30268 | 28410 | 46053 | 63155 |
| 19.06 | 172648 | 35322 | 27448 | 30988 | 22296 | 31145 | 27670 | 46894 | 59577 |
| 19.1 | 152774 | 34272 | 26969 | 31315 | 23396 | 32019 | 28289 | 45866 | 61345 |
| 19.14 | 141162 | 36939 | 26803 | 32499 | 22909 | 30941 | 26198 | 47176 | 61873 |
| 19.18 | 127906 | 38498 | 29621 | 35507 | 22646 | 33522 | 29554 | 45065 | 64104 |
| 19.22 | 120822 | 37074 | 28426 | 35436 | 23399 | 33770 | 30411 | 39800 | 62930 |
| 19.26 | 121301 | 37112 | 30422 | 33959 | 23582 | 33716 | 29347 | 35794 | 64835 |
| 19.3 | 118750 | 36063 | 31314 | 32950 | 23020 | 37695 | 32146 | 29263 | 61619 |
| 19.34 | 121124 | 35593 | 31663 | 35684 | 22689 | 37516 | 33277 | 26662 | 63001 |
| 19.38 | 130516 | 34281 | 33937 | 32939 | 23857 | 36366 | 32092 | 25806 | 63174 |
| 19.42 | 142911 | 32913 | 31614 | 33910 | 23009 | 38154 | 33859 | 22537 | 61420 |
| 19.46 | 149911 | 36514 | 30220 | 30996 | 23833 | 37239 | 33216 | 21808 | 61979 |
| 19.5 | 154033 | 36014 | 29381 | 29687 | 22720 | 35428 | 33715 | 20689 | 58709 |
| 19.54 | 155203 | 38852 | 28408 | 30608 | 21545 | 32981 | 34702 | 20486 | 58781 |
| 19.58 | 153016 | 36702 | 27266 | 30220 | 24942 | 33387 | 32875 | 20650 | 58496 |
| 19.62 | 152829 | 36076 | 26784 | 28715 | 24485 | 31810 | 30439 | 19648 | 56090 |
| 19.66 | 145413 | 33739 | 26682 | 28291 | 23581 | 29631 | 31348 | 19688 | 58036 |
| 19.7 | 137518 | 35507 | 26282 | 29913 | 23251 | 29186 | 28431 | 19148 | 59579 |
| 19.74 | 127931 | 36139 | 26191 | 29026 | 21748 | 32150 | 31780 | 20549 | 56368 |
| 19.78 | 118968 | 34151 | 24703 | 30319 | 23708 | 30926 | 28467 | 21193 | 59642 |
| 19.82 | 106833 | 35749 | 25430 | 32575 | 24061 | 29579 | 26800 | 21576 | 60049 |
| 19.86 | 92194 | 36573 | 24453 | 32911 | 26051 | 30138 | 29704 | 21546 | 60422 |
| 19.9 | 85045 | 35734 | 26203 | 33184 | 30800 | 30674 | 27675 | 22945 | 61931 |
| 19.94 | 76112 | 36738 | 28496 | 33369 | 29811 | 32178 | 26962 | 23034 | 59034 |
| 19.98 | 72179 | 35886 | 28263 | 33251 | 33521 | 32322 | 28855 | 25192 | 61090 |

-continued

| | | | | | | | | | |
|---|---|---|---|---|---|---|---|---|---|
| 20.02 | 71966 | 36940 | 30627 | 33604 | 35508 | 31034 | 29555 | 26384 | 61704 |
| 20.06 | 72498 | 34710 | 32048 | 33957 | 37033 | 33175 | 31018 | 24590 | 62917 |
| 20.1 | 73768 | 34653 | 31131 | 36251 | 41202 | 33759 | 28174 | 26756 | 63081 |
| 20.14 | 75415 | 35368 | 33345 | 39712 | 40875 | 35045 | 28837 | 23876 | 64485 |
| 20.18 | 75233 | 35555 | 31754 | 39293 | 42598 | 34232 | 31499 | 23186 | 64896 |
| 20.22 | 73379 | 34874 | 32548 | 43269 | 43134 | 35446 | 29040 | 22207 | 61833 |
| 20.26 | 75643 | 36722 | 32623 | 46489 | 40968 | 33165 | 29325 | 20948 | 64196 |
| 20.3 | 71876 | 37595 | 33588 | 46848 | 40901 | 33473 | 31080 | 21073 | 63151 |
| 20.34 | 66111 | 36726 | 33089 | 46969 | 36696 | 33000 | 30907 | 20239 | 61450 |
| 20.38 | 63219 | 36747 | 34748 | 48670 | 34602 | 33814 | 32954 | 21083 | 61432 |
| 20.42 | 64142 | 37049 | 37557 | 46526 | 33068 | 30778 | 36106 | 19806 | 61823 |
| 20.46 | 58950 | 36779 | 41118 | 43447 | 30633 | 30381 | 36471 | 21116 | 60845 |
| 20.5 | 56126 | 35789 | 43801 | 42679 | 27207 | 29908 | 38365 | 19506 | 59662 |
| 20.54 | 52457 | 37875 | 46247 | 40243 | 25162 | 29868 | 38729 | 20423 | 61359 |
| 20.58 | 47739 | 37117 | 47392 | 35033 | 25163 | 29336 | 40267 | 20705 | 60433 |
| 20.62 | 45263 | 36457 | 49794 | 32651 | 23500 | 30689 | 38796 | 22004 | 60166 |
| 20.66 | 44006 | 36752 | 48327 | 32071 | 23359 | 33330 | 40990 | 22072 | 59497 |
| 20.7 | 46647 | 37586 | 45750 | 28084 | 22688 | 29082 | 40020 | 20130 | 57888 |
| 20.74 | 47128 | 33220 | 44011 | 28917 | 21870 | 29697 | 37364 | 19768 | 56801 |
| 20.78 | 52403 | 35818 | 39858 | 25682 | 22384 | 29356 | 36824 | 20952 | 55968 |
| 20.82 | 53281 | 36160 | 37275 | 23744 | 22606 | 30940 | 35228 | 19173 | 58477 |
| 20.86 | 57516 | 34780 | 32746 | 25645 | 20313 | 31008 | 34508 | 18973 | 57299 |
| 20.9 | 58272 | 38003 | 29790 | 26440 | 19883 | 30530 | 30316 | 17667 | 55616 |
| 20.94 | 61064 | 40654 | 30055 | 27665 | 20435 | 30973 | 32636 | 18982 | 60900 |
| 20.98 | 60428 | 36466 | 26824 | 26609 | 20258 | 31057 | 33101 | 20135 | 58642 |
| 21.02 | 55896 | 37313 | 24462 | 28814 | 19263 | 29736 | 30196 | 18134 | 58966 |
| 21.06 | 53809 | 35089 | 21693 | 27018 | 20474 | 28866 | 32989 | 19438 | 58154 |
| 21.1 | 54407 | 36428 | 22682 | 26652 | 18555 | 29686 | 31382 | 17763 | 60758 |
| 21.14 | 47561 | 37105 | 22898 | 29118 | 19217 | 28136 | 27805 | 18185 | 62773 |
| 21.18 | 51000 | 38994 | 22843 | 28711 | 18860 | 29330 | 30043 | 19826 | 60521 |
| 21.22 | 43363 | 36376 | 20724 | 26525 | 19234 | 29521 | 28788 | 21350 | 63815 |
| 21.26 | 46577 | 36562 | 22031 | 26019 | 21259 | 29564 | 32122 | 24473 | 66731 |
| 21.3 | 44287 | 38569 | 24063 | 28021 | 22251 | 29952 | 31865 | 27428 | 64736 |
| 21.34 | 42810 | 41176 | 23642 | 28508 | 17253 | 29905 | 28551 | 33588 | 64310 |
| 21.38 | 44111 | 41230 | 22687 | 29897 | 19268 | 30959 | 28177 | 35218 | 61539 |
| 21.42 | 44036 | 35441 | 21825 | 27170 | 21344 | 32096 | 29997 | 41713 | 60962 |
| 21.46 | 44124 | 36859 | 26432 | 31420 | 21303 | 32474 | 30941 | 41858 | 63538 |
| 21.5 | 44614 | 35256 | 23513 | 28641 | 23581 | 30856 | 31378 | 44583 | 59655 |
| 21.54 | 42125 | 36168 | 28245 | 28834 | 22634 | 34653 | 32618 | 44660 | 59743 |
| 21.58 | 43702 | 38110 | 29481 | 30897 | 23158 | 31887 | 35145 | 44976 | 58627 |
| 21.62 | 43541 | 38395 | 30348 | 32407 | 24884 | 32367 | 34218 | 42094 | 57052 |
| 21.66 | 43053 | 36494 | 31218 | 30640 | 21635 | 32369 | 38962 | 35667 | 55722 |
| 21.7 | 44193 | 35319 | 32971 | 30355 | 24447 | 32412 | 35191 | 36147 | 60848 |
| 21.74 | 44364 | 39465 | 34900 | 32981 | 22474 | 30964 | 38743 | 28277 | 61057 |
| 21.78 | 40143 | 38143 | 35231 | 31336 | 21796 | 29215 | 39356 | 27595 | 57926 |
| 21.82 | 43221 | 38066 | 33897 | 33206 | 20033 | 29542 | 37330 | 21283 | 62585 |
| 21.86 | 47028 | 39214 | 34882 | 36216 | 22092 | 30681 | 43691 | 21192 | 58639 |
| 21.9 | 48672 | 37052 | 37104 | 37424 | 20651 | 29937 | 43169 | 18947 | 55573 |
| 21.94 | 54879 | 37784 | 36605 | 33666 | 22239 | 29638 | 43977 | 21349 | 57449 |
| 21.98 | 62629 | 37568 | 35613 | 36402 | 22218 | 29794 | 43614 | 19658 | 55760 |
| 22.02 | 64609 | 40275 | 41526 | 36087 | 21569 | 27941 | 46116 | 20986 | 57110 |
| 22.06 | 73911 | 38708 | 44459 | 39601 | 21070 | 29271 | 44170 | 22313 | 57643 |
| 22.1 | 75591 | 39170 | 46485 | 35145 | 20140 | 27646 | 45420 | 19986 | 59984 |
| 22.14 | 84842 | 42300 | 49608 | 36928 | 22126 | 29984 | 50139 | 20925 | 59105 |
| 22.18 | 81164 | 40352 | 52708 | 34946 | 20706 | 27818 | 47116 | 19153 | 57165 |
| 22.22 | 81704 | 37861 | 49113 | 41452 | 21434 | 30539 | 46633 | 19774 | 59864 |
| 22.26 | 81101 | 38841 | 48471 | 40529 | 20741 | 27097 | 50292 | 19947 | 60399 |
| 22.3 | 81327 | 41414 | 47576 | 41363 | 22458 | 29088 | 45339 | 19993 | 57653 |
| 22.34 | 73312 | 40905 | 46909 | 41898 | 21819 | 31217 | 46583 | 19642 | 58694 |
| 22.38 | 69187 | 43011 | 42481 | 44356 | 23138 | 31202 | 51816 | 19508 | 57872 |
| 22.42 | 63240 | 43343 | 40814 | 45844 | 21935 | 31103 | 44542 | 21314 | 62913 |
| 22.46 | 57099 | 42317 | 38832 | 44645 | 24498 | 29678 | 43474 | 21700 | 63012 |
| 22.5 | 54053 | 42259 | 34487 | 43492 | 23666 | 31689 | 44985 | 21853 | 62010 |
| 22.54 | 52618 | 41486 | 33116 | 43940 | 23130 | 31234 | 45404 | 25395 | 62286 |
| 22.58 | 49558 | 43972 | 33683 | 43588 | 25112 | 31682 | 44149 | 25678 | 66482 |
| 22.62 | 46466 | 42290 | 39427 | 41102 | 26751 | 33643 | 42280 | 27522 | 64251 |
| 22.66 | 48504 | 42026 | 45736 | 42124 | 28246 | 34927 | 42498 | 29000 | 66664 |
| 22.7 | 48630 | 43468 | 49261 | 44782 | 29282 | 33857 | 42490 | 30933 | 67875 |
| 22.74 | 48903 | 44212 | 52113 | 47126 | 29541 | 33964 | 42037 | 31542 | 61718 |
| 22.78 | 46479 | 43891 | 59498 | 48276 | 33750 | 34496 | 39622 | 32709 | 64190 |
| 22.82 | 47361 | 41841 | 62038 | 55042 | 32467 | 34395 | 39324 | 31301 | 64675 |
| 22.86 | 48810 | 45057 | 60277 | 56142 | 31699 | 32796 | 39460 | 31116 | 64431 |
| 22.9 | 51551 | 44209 | 60704 | 60523 | 31836 | 35069 | 36297 | 31621 | 65720 |
| 22.94 | 50425 | 42411 | 60413 | 68941 | 29583 | 32189 | 37268 | 30073 | 60251 |
| 22.98 | 56714 | 43838 | 56890 | 69817 | 31184 | 35386 | 36103 | 30928 | 65430 |
| 23.02 | 57446 | 44869 | 53100 | 70576 | 26254 | 31993 | 31992 | 27938 | 67545 |
| 23.06 | 67917 | 41930 | 45836 | 67926 | 27735 | 33667 | 32344 | 24875 | 61614 |
| 23.1 | 69625 | 44393 | 41296 | 67150 | 28753 | 32320 | 30537 | 22916 | 62959 |
| 23.14 | 81612 | 48418 | 35556 | 64060 | 26006 | 32771 | 31346 | 22275 | 61072 |

-continued

| | | | | | | | | | |
|---|---|---|---|---|---|---|---|---|---|
| 23.18 | 89457 | 50103 | 29656 | 56704 | 28051 | 32681 | 31646 | 22271 | 67531 |
| 23.22 | 90411 | 47715 | 25513 | 56013 | 23033 | 35694 | 30256 | 22926 | 62298 |
| 23.26 | 99552 | 48608 | 25363 | 48145 | 22678 | 32348 | 29387 | 22235 | 62632 |
| 23.3 | 103369 | 48151 | 26421 | 46754 | 21751 | 34163 | 28661 | 18620 | 60502 |
| 23.34 | 109595 | 50997 | 23928 | 38225 | 24251 | 30876 | 30132 | 17568 | 62415 |
| 23.38 | 108392 | 50716 | 21390 | 32259 | 20766 | 28463 | 26258 | 18544 | 61355 |
| 23.42 | 108824 | 52339 | 24414 | 34867 | 23634 | 34316 | 26089 | 16910 | 61323 |
| 23.46 | 107878 | 54624 | 22161 | 30949 | 23846 | 33647 | 29034 | 19725 | 61996 |
| 23.5 | 98495 | 52513 | 22264 | 29250 | 19702 | 36400 | 29524 | 17871 | 60050 |
| 23.54 | 99374 | 54526 | 24730 | 27054 | 19730 | 35042 | 26257 | 17652 | 60721 |
| 23.58 | 87985 | 55324 | 21803 | 27035 | 22461 | 33932 | 27517 | 17939 | 63523 |
| 23.62 | 82412 | 56103 | 23840 | 26945 | 20485 | 35322 | 28102 | 19165 | 61810 |
| 23.66 | 78545 | 52899 | 20777 | 26902 | 23266 | 32268 | 30558 | 17810 | 70900 |
| 23.7 | 78210 | 56808 | 24623 | 27535 | 22885 | 30738 | 30745 | 18377 | 72250 |
| 23.74 | 80379 | 59303 | 25477 | 29335 | 26228 | 31625 | 30306 | 19969 | 72647 |
| 23.78 | 89993 | 57789 | 23675 | 30346 | 24767 | 34502 | 30728 | 20891 | 75330 |
| 23.82 | 115868 | 56936 | 26400 | 31137 | 23950 | 33939 | 29592 | 19539 | 74576 |
| 23.86 | 145039 | 57309 | 27018 | 30219 | 25777 | 33401 | 30718 | 19794 | 81486 |
| 23.9 | 176331 | 59808 | 27962 | 32029 | 25293 | 39561 | 33624 | 22431 | 79376 |
| 23.94 | 224034 | 63059 | 28059 | 33176 | 24865 | 40524 | 35242 | 22649 | 86151 |
| 23.98 | 264295 | 59277 | 24531 | 30970 | 25524 | 45142 | 34035 | 23012 | 86035 |
| 24.02 | 283672 | 60296 | 29145 | 32717 | 22225 | 48065 | 34573 | 24899 | 82044 |
| 24.06 | 302003 | 55707 | 27524 | 35118 | 23623 | 46945 | 33865 | 27435 | 84726 |
| 24.1 | 301788 | 57620 | 30449 | 36110 | 23295 | 53050 | 34261 | 30939 | 79607 |
| 24.14 | 294834 | 62304 | 31462 | 37278 | 21572 | 55930 | 39758 | 49129 | 83749 |
| 24.18 | 277540 | 63368 | 32621 | 37590 | 22716 | 55584 | 37993 | 61286 | 80966 |
| 24.22 | 237735 | 61096 | 35409 | 38666 | 22744 | 54907 | 40582 | 82434 | 79966 |
| 24.26 | 201425 | 56857 | 39032 | 37437 | 21966 | 55436 | 38166 | 90465 | 75851 |
| 24.3 | 158323 | 65148 | 42114 | 37220 | 21612 | 52787 | 39578 | 98099 | 74473 |
| 24.34 | 124469 | 64322 | 46991 | 40429 | 22469 | 51333 | 42208 | 104690 | 76718 |
| 24.38 | 101326 | 61767 | 50274 | 40288 | 22541 | 49574 | 42618 | 102520 | 72798 |
| 24.42 | 81397 | 60603 | 54683 | 40190 | 24777 | 47889 | 42342 | 100253 | 78180 |
| 24.46 | 79970 | 62362 | 61683 | 41051 | 24299 | 46384 | 41787 | 100505 | 77206 |
| 24.5 | 71932 | 57247 | 64372 | 39340 | 24580 | 44005 | 39736 | 84374 | 76532 |
| 24.54 | 80947 | 61002 | 65683 | 40673 | 26403 | 41911 | 41766 | 80204 | 75933 |
| 24.58 | 81107 | 62805 | 69891 | 43475 | 25933 | 41813 | 40655 | 63936 | 76782 |
| 24.62 | 96262 | 60153 | 66106 | 45720 | 27576 | 39399 | 36609 | 48402 | 79789 |
| 24.66 | 113052 | 61025 | 62236 | 46897 | 28973 | 35433 | 39851 | 34221 | 78019 |
| 24.7 | 151612 | 60203 | 61760 | 47149 | 26300 | 37000 | 35815 | 31212 | 76120 |
| 24.74 | 193437 | 61208 | 61411 | 48981 | 29879 | 35413 | 36706 | 29202 | 81986 |
| 24.78 | 224220 | 57370 | 51069 | 46059 | 32208 | 32580 | 34093 | 28688 | 82399 |
| 24.82 | 261957 | 55054 | 45555 | 47821 | 28884 | 33923 | 31912 | 24399 | 76037 |
| 24.86 | 300112 | 60172 | 43650 | 49308 | 30114 | 32613 | 32316 | 26253 | 77637 |
| 24.9 | 317223 | 58258 | 37569 | 49824 | 32513 | 35415 | 31677 | 27398 | 78494 |
| 24.94 | 329796 | 56174 | 31873 | 49402 | 34854 | 34070 | 30704 | 25937 | 73098 |
| 24.98 | 336964 | 52657 | 31854 | 49786 | 29827 | 32574 | 28920 | 25979 | 75650 |
| 25.02 | 324394 | 56226 | 32008 | 49011 | 30962 | 34926 | 28595 | 23953 | 74409 |
| 25.06 | 290658 | 52438 | 27890 | 47852 | 35512 | 32321 | 27908 | 23115 | 68457 |
| 25.1 | 290658 | 55835 | 27480 | 47149 | 37079 | 35677 | 30109 | 22443 | 65641 |
| 25.14 | 264484 | 52369 | 27669 | 43954 | 37882 | 38385 | 29695 | 21961 | 66472 |
| 25.18 | 231624 | 52472 | 28817 | 40402 | 38364 | 34683 | 25522 | 23000 | 68348 |
| 25.22 | 198630 | 52527 | 25709 | 36166 | 36005 | 40046 | 26698 | 23767 | 63989 |
| 25.26 | 190496 | 54518 | 31851 | 33674 | 38003 | 41540 | 27082 | 23640 | 66787 |
| 25.3 | 172747 | 54514 | 28792 | 31107 | 36310 | 41248 | 25265 | 21759 | 65049 |
| 25.34 | 162875 | 51840 | 32134 | 31720 | 38106 | 44550 | 27289 | 24176 | 67598 |
| 25.38 | 164576 | 54499 | 33783 | 28438 | 36050 | 43740 | 26221 | 21609 | 70167 |
| 25.42 | 157120 | 54042 | 31422 | 26897 | 34650 | 44859 | 26232 | 20115 | 69221 |
| 25.46 | 148118 | 51958 | 29838 | 25150 | 24794 | 44389 | 27061 | 19672 | 71102 |
| 25.5 | 150845 | 49947 | 29952 | 26779 | 22923 | 41020 | 23700 | 17244 | 72534 |
| 25.54 | 145751 | 50305 | 30801 | 27689 | 22063 | 43665 | 23641 | 17314 | 74680 |
| 25.58 | 147965 | 50168 | 26704 | 27890 | 21144 | 43182 | 24784 | 16799 | 73818 |
| 25.62 | 153035 | 51124 | 28068 | 28635 | 20012 | 41703 | 24653 | 15813 | 74567 |
| 25.66 | 160041 | 49065 | 25060 | 29236 | 18508 | 38384 | 23874 | 17334 | 73788 |
| 25.7 | 166060 | 45644 | 26881 | 30392 | 18799 | 36133 | 25846 | 17345 | 69443 |
| 25.74 | 179343 | 47110 | 27905 | 32964 | 20618 | 36460 | 26766 | 16489 | 64693 |
| 25.78 | 191576 | 47708 | 28256 | 33923 | 20990 | 37482 | 25205 | 18047 | 68757 |
| 25.82 | 197873 | 43695 | 31003 | 36935 | 23086 | 32987 | 24770 | 19257 | 64267 |
| 25.86 | 197429 | 46463 | 29103 | 35786 | 24040 | 35250 | 24625 | 18964 | 61220 |
| 25.9 | 212258 | 49900 | 27904 | 34186 | 28470 | 35007 | 25454 | 19134 | 59883 |
| 25.94 | 212206 | 46184 | 30310 | 38579 | 28183 | 31415 | 25404 | 19508 | 57941 |
| 25.98 | 216055 | 42843 | 25544 | 33979 | 31247 | 32642 | 24053 | 20959 | 60076 |
| 26.02 | 211663 | 45120 | 25864 | 33633 | 30760 | 32980 | 23672 | 20422 | 58284 |
| 26.06 | 196848 | 46281 | 25392 | 29983 | 29502 | 31889 | 22144 | 20283 | 57501 |
| 26.1 | 175851 | 42836 | 23184 | 29917 | 29039 | 33245 | 22202 | 19029 | 60329 |
| 26.14 | 156713 | 41499 | 22007 | 28013 | 29307 | 30434 | 22192 | 20098 | 58162 |
| 26.18 | 150536 | 40975 | 21413 | 26268 | 26315 | 30475 | 21237 | 17637 | 56820 |
| 26.22 | 139352 | 42000 | 20825 | 23713 | 22615 | 31806 | 21197 | 16202 | 58981 |
| 26.26 | 128392 | 40496 | 22079 | 24574 | 21947 | 30615 | 19097 | 16304 | 63182 |
| 26.3 | 113870 | 39254 | 24062 | 24382 | 21482 | 32063 | 20887 | 17331 | 63919 |

-continued

| | | | | | | | | | |
|---|---|---|---|---|---|---|---|---|---|
| 26.34 | 99675 | 38989 | 21847 | 24633 | 18510 | 30170 | 21566 | 14463 | 62080 |
| 26.38 | 85435 | 39574 | 20278 | 21486 | 17434 | 29190 | 18941 | 15522 | 61005 |
| 26.42 | 71731 | 37966 | 19313 | 21980 | 17417 | 27928 | 19184 | 14442 | 61504 |
| 26.46 | 64645 | 38804 | 18574 | 20892 | 16290 | 28944 | 20797 | 13860 | 58078 |
| 26.5 | 56107 | 35307 | 19101 | 22937 | 15352 | 28893 | 19919 | 13315 | 54395 |
| 26.54 | 54823 | 37838 | 18384 | 21716 | 16172 | 30543 | 20656 | 14804 | 58599 |
| 26.58 | 51130 | 37858 | 19178 | 20753 | 14749 | 28947 | 22451 | 15836 | 51414 |
| 26.62 | 48168 | 37003 | 18978 | 23420 | 16025 | 27471 | 19234 | 12509 | 54650 |
| 26.66 | 47115 | 35438 | 19978 | 22000 | 15966 | 27788 | 19763 | 14774 | 51332 |
| 26.7 | 45049 | 35643 | 18770 | 21612 | 16197 | 30143 | 20470 | 15403 | 56160 |
| 26.74 | 47294 | 35667 | 19352 | 21920 | 14269 | 26633 | 19600 | 15246 | 52341 |
| 26.78 | 44172 | 35341 | 18894 | 21093 | 15891 | 25591 | 20780 | 15748 | 51890 |
| 26.82 | 46226 | 36704 | 18303 | 20384 | 17520 | 24948 | 21387 | 14280 | 50648 |
| 26.86 | 48927 | 32894 | 17702 | 21338 | 15307 | 24697 | 19223 | 13134 | 47084 |
| 26.9 | 53389 | 33774 | 19055 | 20360 | 14570 | 24843 | 21099 | 15047 | 46334 |
| 26.94 | 60778 | 34707 | 17809 | 20367 | 14644 | 25004 | 19944 | 14651 | 47353 |
| 26.98 | 72147 | 34898 | 19060 | 20253 | 16146 | 25500 | 19516 | 12811 | 47885 |
| 27.02 | 79157 | 33065 | 19598 | 19023 | 15579 | 23947 | 21507 | 14218 | 49417 |
| 27.06 | 87828 | 31469 | 20202 | 22002 | 15346 | 24106 | 21333 | 13565 | 51354 |
| 27.1 | 100287 | 31978 | 20369 | 21462 | 15840 | 24561 | 22978 | 14100 | 49486 |
| 27.14 | 112664 | 34088 | 21910 | 23884 | 15065 | 23320 | 22927 | 14112 | 48970 |
| 27.18 | 130139 | 31880 | 24086 | 25229 | 15874 | 24540 | 25787 | 15875 | 50600 |
| 27.22 | 133458 | 32853 | 26299 | 24563 | 16207 | 25194 | 23253 | 16119 | 52460 |
| 27.26 | 141011 | 32583 | 24809 | 26592 | 18276 | 26235 | 23192 | 16465 | 51981 |
| 27.3 | 143074 | 31692 | 27507 | 30383 | 18079 | 26579 | 22686 | 21766 | 49960 |
| 27.34 | 133277 | 31041 | 30179 | 30146 | 17929 | 24067 | 22994 | 21766 | 47449 |
| 27.38 | 122400 | 30236 | 30240 | 29221 | 16692 | 25430 | 22999 | 23906 | 51516 |
| 27.42 | 113705 | 29115 | 29586 | 31871 | 17482 | 21894 | 22437 | 24786 | 52865 |
| 27.46 | 98225 | 31050 | 27235 | 32184 | 18625 | 22876 | 22508 | 24302 | 52362 |
| 27.5 | 85234 | 31551 | 26581 | 30227 | 18175 | 24234 | 22482 | 25257 | 53887 |
| 27.54 | 73435 | 31493 | 26114 | 30196 | 19508 | 24481 | 21175 | 22171 | 50416 |
| 27.58 | 58201 | 31344 | 23774 | 29846 | 19057 | 25022 | 24493 | 22474 | 53125 |
| 27.62 | 52769 | 29908 | 22130 | 26724 | 17948 | 24427 | 22333 | 21872 | 52492 |
| 27.66 | 49013 | 31792 | 21617 | 25124 | 17142 | 25178 | 22847 | 19010 | 53846 |
| 27.7 | 44549 | 30670 | 21278 | 25661 | 15488 | 24689 | 21657 | 17224 | 52736 |
| 27.74 | 40946 | 30261 | 19812 | 23965 | 14257 | 23910 | 20323 | 14442 | 54202 |
| 27.78 | 39986 | 32126 | 17506 | 19622 | 15123 | 25964 | 22205 | 14428 | 52508 |
| 27.82 | 43859 | 30602 | 19942 | 18497 | 13880 | 24902 | 20591 | 14752 | 53755 |
| 27.86 | 43552 | 31572 | 22020 | 20774 | 13594 | 28212 | 21471 | 14762 | 53506 |
| 27.9 | 44771 | 28566 | 19032 | 18823 | 13810 | 25860 | 20646 | 14001 | 49737 |
| 27.94 | 46327 | 32425 | 19311 | 18732 | 14726 | 26405 | 20523 | 13182 | 49597 |
| 27.98 | 46862 | 30631 | 19579 | 19694 | 13902 | 26962 | 20042 | 12050 | 45907 |
| 28.02 | 53246 | 30854 | 20016 | 19148 | 14613 | 26225 | 20360 | 13429 | 49753 |
| 28.06 | 56092 | 28291 | 19190 | 19440 | 13818 | 27737 | 18464 | 12760 | 47264 |
| 28.1 | 61271 | 28999 | 18430 | 19477 | 16183 | 25777 | 17902 | 14641 | 49083 |
| 28.14 | 67658 | 31437 | 17203 | 18801 | 16051 | 27402 | 19006 | 14676 | 42667 |
| 28.18 | 68733 | 29230 | 17927 | 20981 | 15947 | 24740 | 19319 | 13368 | 40622 |
| 28.22 | 76381 | 29097 | 17324 | 20622 | 15134 | 23649 | 18925 | 14886 | 43383 |
| 28.26 | 83137 | 29651 | 18042 | 23258 | 14435 | 24995 | 18875 | 15032 | 38738 |
| 28.3 | 86533 | 29751 | 17525 | 23322 | 15017 | 24891 | 17955 | 13416 | 42802 |
| 28.34 | 92847 | 28094 | 17463 | 23136 | 14871 | 25179 | 19061 | 15516 | 41970 |
| 28.38 | 101970 | 27683 | 20361 | 24044 | 15830 | 23113 | 19384 | 14354 | 40201 |
| 28.42 | 100787 | 27505 | 19066 | 24764 | 15439 | 22906 | 20291 | 13610 | 40655 |
| 28.46 | 103600 | 28946 | 19398 | 25490 | 15629 | 21830 | 21423 | 14283 | 42366 |
| 28.5 | 105493 | 27585 | 20339 | 26419 | 14527 | 21488 | 22063 | 13403 | 40202 |
| 28.54 | 105280 | 27215 | 25013 | 25549 | 14158 | 22193 | 22570 | 15728 | 41598 |
| 28.58 | 101114 | 27251 | 26703 | 24782 | 16658 | 21663 | 24949 | 15104 | 38910 |
| 28.62 | 97732 | 27358 | 25112 | 24261 | 15360 | 21792 | 21640 | 14160 | 42987 |
| 28.66 | 91056 | 25251 | 24515 | 24106 | 14406 | 21197 | 20376 | 14211 | 42753 |
| 28.7 | 84531 | 26384 | 25951 | 23352 | 14251 | 21976 | 23220 | 12154 | 40404 |
| 28.74 | 76048 | 28391 | 23261 | 25577 | 14371 | 18048 | 20963 | 13776 | 39076 |
| 28.78 | 70481 | 27277 | 25232 | 22918 | 14542 | 19544 | 22575 | 13813 | 39765 |
| 28.82 | 64599 | 29283 | 24325 | 25074 | 15074 | 23630 | 22985 | 14460 | 42870 |
| 28.86 | 61027 | 27563 | 23296 | 24346 | 15807 | 21303 | 21902 | 13078 | 42368 |
| 28.9 | 56567 | 26270 | 22488 | 21903 | 15297 | 18412 | 21296 | 12748 | 40269 |
| 28.94 | 56369 | 26303 | 21214 | 20992 | 16019 | 18006 | 20018 | 14140 | 37725 |
| 28.98 | 56331 | 26100 | 21813 | 21588 | 16354 | 19710 | 20184 | 14771 | 35085 |
| 29.02 | 57289 | 26677 | 20564 | 21972 | 17636 | 21093 | 21769 | 15676 | 41371 |
| 29.06 | 54378 | 25747 | 19806 | 21224 | 16838 | 19437 | 21438 | 14736 | 42241 |
| 29.1 | 50736 | 23652 | 18095 | 21002 | 16568 | 18019 | 20985 | 12922 | 36787 |
| 29.14 | 49074 | 27407 | 16141 | 17115 | 16816 | 18520 | 19602 | 13220 | 38159 |
| 29.18 | 47831 | 27296 | 19929 | 20931 | 16243 | 22123 | 20058 | 13885 | 39266 |
| 29.22 | 42385 | 26367 | 20045 | 19974 | 15535 | 19223 | 20421 | 12997 | 36371 |
| 29.26 | 40351 | 25940 | 17239 | 18866 | 15323 | 21211 | 20735 | 12113 | 37831 |
| 29.3 | 38303 | 24118 | 16667 | 16868 | 17783 | 20480 | 21278 | 11173 | 36469 |
| 29.34 | 36416 | 25500 | 17307 | 18244 | 18097 | 19033 | 20007 | 11223 | 34666 |
| 29.38 | 36767 | 26871 | 18177 | 19624 | 18801 | 21374 | 20900 | 14154 | 38333 |
| 29.42 | 39233 | 23098 | 17915 | 20339 | 18561 | 22361 | 20311 | 12947 | 36054 |
| 29.46 | 35712 | 23639 | 17872 | 18430 | 19019 | 22862 | 20017 | 12895 | 34773 |

-continued

| | | | | | | | | | |
|---|---|---|---|---|---|---|---|---|---|
| 29.5 | 36666 | 25610 | 19414 | 19542 | 19501 | 22374 | 18630 | 12696 | 34445 |
| 29.54 | 36207 | 24345 | 19788 | 19358 | 19094 | 20003 | 17818 | 13603 | 33929 |
| 29.58 | 36082 | 24036 | 18174 | 19252 | 17433 | 21162 | 17443 | 12462 | 34903 |
| 29.62 | 36894 | 23608 | 21728 | 19167 | 17823 | 19864 | 19558 | 13138 | 34073 |
| 29.66 | 39246 | 23726 | 19721 | 18907 | 16647 | 18972 | 18363 | 12940 | 32952 |
| 29.7 | 36755 | 23602 | 20151 | 19690 | 16800 | 19460 | 17984 | 12082 | 34944 |
| 29.74 | 39972 | 24403 | 19951 | 18227 | 14662 | 17573 | 18789 | 11344 | 32578 |
| 29.78 | 39452 | 25884 | 20115 | 16706 | 13915 | 16611 | 18731 | 12170 | 32670 |
| 29.82 | 39464 | 23163 | 20126 | 19925 | 13298 | 18330 | 18868 | 12651 | 34902 |
| 29.86 | 39308 | 24057 | 18688 | 19795 | 12036 | 16778 | 17613 | 12202 | 33814 |
| 29.9 | 36756 | 22404 | 17817 | 17091 | 11084 | 16889 | 18164 | 11336 | 36278 |
| 29.94 | 37220 | 23980 | 17662 | 18534 | 13201 | 16008 | 15437 | 11541 | 31359 |
| 29.98 | 36171 | 23609 | 17358 | 18360 | 11968 | 16332 | 15222 | 12047 | 35699 |
| 30.02 | 33690 | 22867 | 15841 | 18737 | 12837 | 17122 | 17321 | 10574 | 34851 |
| 30.06 | 34214 | 24571 | 15126 | 17239 | 11722 | 16386 | 17016 | 12075 | 36283 |
| 30.1 | 34160 | 24744 | 15852 | 17101 | 12451 | 17718 | 15330 | 10660 | 34169 |
| 30.14 | 31999 | 23830 | 16550 | 15647 | 12266 | 16422 | 15796 | 10668 | 32926 |
| 30.18 | 35258 | 23591 | 14298 | 15587 | 10704 | 15486 | 15137 | 9700 | 33983 |
| 30.22 | 37183 | 22135 | 14428 | 15921 | 12071 | 16912 | 15851 | 10761 | 33253 |
| 30.26 | 40930 | 23906 | 14283 | 14670 | 12123 | 15195 | 15248 | 10061 | 31283 |
| 30.3 | 42213 | 22911 | 15187 | 12868 | 12776 | 15149 | 16068 | 11375 | 37045 |
| 30.34 | 49840 | 23892 | 14875 | 12938 | 13047 | 16932 | 16778 | 10656 | 34802 |
| 30.38 | 55387 | 23779 | 15496 | 14704 | 12484 | 14345 | 15327 | 9699 | 34084 |
| 30.42 | 58711 | 22848 | 12881 | 14022 | 11119 | 16374 | 15062 | 10959 | 32891 |
| 30.46 | 65432 | 22100 | 16037 | 13383 | 11559 | 14626 | 16004 | 10388 | 36094 |
| 30.5 | 71472 | 23114 | 16233 | 16682 | 12815 | 15058 | 17394 | 10252 | 35810 |
| 30.54 | 69300 | 22819 | 15300 | 15273 | 11430 | 14407 | 16850 | 11009 | 34130 |
| 30.58 | 76290 | 21539 | 16201 | 16116 | 11743 | 14301 | 16519 | 11643 | 35242 |
| 30.62 | 78790 | 23587 | 16793 | 16162 | 10712 | 14718 | 17109 | 10297 | 34018 |
| 30.66 | 78521 | 22838 | 18102 | 17714 | 13155 | 16470 | 17898 | 10439 | 35048 |
| 30.7 | 78489 | 22812 | 17078 | 16438 | 11115 | 15475 | 16341 | 11326 | 33239 |
| 30.74 | 78783 | 20369 | 16686 | 17257 | 12902 | 15332 | 17731 | 11710 | 35273 |
| 30.78 | 81017 | 22233 | 17385 | 17512 | 11916 | 15555 | 14458 | 11390 | 31946 |
| 30.82 | 79515 | 23338 | 18857 | 19386 | 11903 | 15499 | 16048 | 12542 | 34353 |
| 30.86 | 78055 | 22074 | 18845 | 18410 | 11545 | 16412 | 15542 | 11025 | 33004 |
| 30.9 | 72588 | 21599 | 17817 | 19982 | 11171 | 16167 | 16167 | 10910 | 34292 |
| 30.94 | 66752 | 21253 | 17270 | 18403 | 13118 | 15364 | 16818 | 11669 | 31908 |
| 30.98 | 69710 | 20676 | 16640 | 16553 | 11135 | 17275 | 16247 | 10716 | 32064 |
| 31.02 | 66383 | 21010 | 17121 | 19441 | 11770 | 15896 | 14328 | 11006 | 29399 |
| 31.06 | 60589 | 21247 | 16860 | 16002 | 12115 | 16026 | 15249 | 10604 | 31164 |
| 31.1 | 55576 | 20836 | 16584 | 15794 | 12056 | 16937 | 14335 | 9422 | 30724 |
| 31.14 | 51567 | 20771 | 14492 | 16202 | 11513 | 15216 | 14204 | 10448 | 32110 |
| 31.18 | 43108 | 19697 | 14690 | 14991 | 11597 | 16544 | 13941 | 10302 | 31631 |
| 31.22 | 43712 | 20022 | 13683 | 15732 | 10374 | 16201 | 14137 | 10121 | 29492 |
| 31.26 | 40571 | 20987 | 14706 | 14674 | 12651 | 16433 | 14689 | 10112 | 30103 |
| 31.3 | 41715 | 21689 | 13339 | 14833 | 12266 | 15000 | 14831 | 10369 | 27464 |
| 31.34 | 38488 | 20323 | 12828 | 15196 | 9424 | 17066 | 13482 | 9192 | 29510 |
| 31.38 | 37056 | 18951 | 14803 | 16438 | 10302 | 15220 | 13326 | 10813 | 28773 |
| 31.42 | 37090 | 21247 | 13720 | 16033 | 11455 | 14407 | 12944 | 8640 | 28962 |
| 31.46 | 37511 | 21483 | 12621 | 14929 | 11688 | 14560 | 12487 | 9542 | 29320 |
| 31.5 | 36426 | 19875 | 14864 | 15067 | 9773 | 15294 | 13543 | 9409 | 29149 |
| 31.54 | 34506 | 20417 | 14751 | 15336 | 10136 | 15865 | 14019 | 9931 | 29313 |
| 31.58 | 33959 | 18484 | 14957 | 14317 | 9955 | 15040 | 14346 | 9414 | 29315 |
| 31.62 | 34588 | 19295 | 12582 | 14022 | 11452 | 15333 | 12599 | 9311 | 30533 |
| 31.66 | 34434 | 22071 | 14956 | 15060 | 12312 | 16229 | 13311 | 10740 | 27434 |
| 31.7 | 35739 | 19696 | 15894 | 15241 | 12082 | 14068 | 13622 | 9635 | 27892 |
| 31.74 | 34481 | 21118 | 14984 | 15241 | 11637 | 13527 | 15284 | 11876 | 28046 |
| 31.78 | 34325 | 21128 | 13988 | 14806 | 11441 | 14319 | 14563 | 11004 | 29357 |
| 31.82 | 36592 | 18649 | 14396 | 15009 | 12826 | 14026 | 13528 | 11303 | 29627 |
| 31.86 | 38212 | 17989 | 14933 | 13425 | 12908 | 14367 | 14286 | 11072 | 30483 |
| 31.9 | 35578 | 18157 | 13508 | 13378 | 13288 | 13863 | 15781 | 12047 | 29273 |
| 31.94 | 39949 | 20119 | 13852 | 13520 | 13326 | 14897 | 12813 | 11420 | 30407 |
| 31.98 | 40664 | 20603 | 13399 | 13788 | 12447 | 15566 | 13147 | 11066 | 29795 |
| 32.02 | 40947 | 19534 | 14119 | 13333 | 11860 | 15792 | 14345 | 10832 | 31060 |
| 32.06 | 41286 | 19495 | 12798 | 11606 | 12363 | 16596 | 14417 | 10073 | 29798 |
| 32.1 | 40256 | 21017 | 12428 | 13918 | 12634 | 15151 | 13929 | 10171 | 28452 |
| 32.14 | 41884 | 19841 | 11324 | 12319 | 11255 | 15326 | 14174 | 10682 | 29700 |
| 32.18 | 40350 | 19941 | 12767 | 12522 | 12022 | 16037 | 13838 | 9029 | 28771 |
| 32.22 | 38077 | 17472 | 13069 | 10421 | 12457 | 13797 | 13261 | 10815 | 31234 |
| 32.26 | 38234 | 18897 | 13230 | 11471 | 14447 | 14630 | 13437 | 10583 | 28263 |
| 32.3 | 39259 | 18882 | 12510 | 12019 | 12365 | 14951 | 13645 | 9999 | 29627 |
| 32.34 | 37444 | 17178 | 13335 | 12846 | 12840 | 12801 | 13784 | 10305 | 29123 |
| 32.38 | 34871 | 18119 | 12270 | 11227 | 13876 | 14542 | 13493 | 9666 | 29130 |
| 32.42 | 38261 | 19166 | 12392 | 11283 | 13399 | 13797 | 14732 | 9093 | 28106 |
| 32.46 | 38333 | 20154 | 12275 | 11651 | 11588 | 14102 | 14318 | 9336 | 28600 |
| 32.5 | 40686 | 18273 | 13522 | 12000 | 11893 | 15968 | 12321 | 9479 | 30306 |
| 32.54 | 42244 | 19043 | 13047 | 11788 | 11736 | 14881 | 13472 | 9833 | 30773 |
| 32.58 | 45611 | 19947 | 11025 | 12220 | 11829 | 13783 | 12593 | 9741 | 28136 |
| 32.62 | 51223 | 18641 | 12179 | 12920 | 9948 | 13634 | 11755 | 9288 | 25242 |

| | | | | | | | | | |
|---|---|---|---|---|---|---|---|---|---|
| 32.66 | 59523 | 21617 | 12022 | 12621 | 9299 | 12926 | 12502 | 9307 | 26607 |
| 32.7 | 64785 | 17967 | 12414 | 12938 | 9557 | 14164 | 13492 | 8745 | 27439 |
| 32.74 | 66699 | 18759 | 11654 | 11706 | 9048 | 13016 | 12997 | 10307 | 28271 |
| 32.78 | 71940 | 19222 | 11254 | 11223 | 9708 | 12600 | 12180 | 9042 | 27758 |
| 32.82 | 76378 | 18843 | 10074 | 13044 | 9732 | 13187 | 12075 | 8750 | 27706 |
| 32.86 | 73042 | 18658 | 11954 | 12999 | 9864 | 14031 | 11887 | 9699 | 29191 |
| 32.9 | 71186 | 19060 | 10709 | 12970 | 9552 | 13168 | 12067 | 9291 | 26689 |
| 32.94 | 71435 | 18939 | 10874 | 10748 | 9455 | 13294 | 13332 | 9261 | 28116 |
| 32.98 | 68129 | 19708 | 11073 | 11621 | 8580 | 13901 | 11141 | 9987 | 27485 |
| 33.02 | 58425 | 18416 | 11399 | 11495 | 9245 | 14467 | 13214 | 8758 | 30299 |
| 33.06 | 60202 | 17752 | 11595 | 12061 | 10666 | 13087 | 12686 | 9210 | 27989 |
| 33.1 | 56231 | 19117 | 11872 | 11718 | 11194 | 15250 | 11982 | 8841 | 27195 |
| 33.14 | 48111 | 18921 | 11156 | 13306 | 10109 | 13597 | 13029 | 9434 | 27472 |
| 33.18 | 43141 | 19750 | 11154 | 12016 | 11835 | 14552 | 12735 | 9391 | 27674 |
| 33.22 | 41198 | 17807 | 11679 | 12284 | 11761 | 15237 | 14028 | 9909 | 27242 |
| 33.26 | 40535 | 18792 | 10970 | 12124 | 10651 | 15195 | 13604 | 10776 | 28723 |
| 33.3 | 39762 | 17032 | 10126 | 12534 | 11771 | 14136 | 13017 | 10436 | 26247 |
| 33.34 | 35048 | 19157 | 12708 | 12699 | 12591 | 14287 | 13772 | 11073 | 26393 |
| 33.38 | 36047 | 18027 | 12317 | 12090 | 10986 | 14741 | 13393 | 11913 | 26023 |
| 33.42 | 37844 | 17693 | 11868 | 13579 | 11500 | 16097 | 11965 | 10261 | 24181 |
| 33.46 | 36838 | 17098 | 14145 | 13141 | 10815 | 14313 | 13412 | 10855 | 25083 |
| 33.5 | 37582 | 18894 | 13177 | 11594 | 11900 | 12860 | 13286 | 11280 | 28326 |
| 33.54 | 44067 | 18576 | 13206 | 12727 | 10698 | 14018 | 13274 | 11634 | 25565 |
| 33.58 | 43307 | 17849 | 12477 | 11939 | 10928 | 14165 | 12543 | 10468 | 27068 |
| 33.62 | 42752 | 17390 | 15066 | 13188 | 9159 | 14737 | 14791 | 9617 | 26631 |
| 33.66 | 39985 | 18843 | 14264 | 12410 | 8926 | 13252 | 13792 | 10003 | 27110 |
| 33.7 | 43493 | 18316 | 13243 | 12271 | 8912 | 14442 | 11494 | 9774 | 26226 |
| 33.74 | 39628 | 16765 | 13548 | 12487 | 9326 | 13230 | 12367 | 8543 | 26322 |
| 33.78 | 39514 | 19133 | 13985 | 13489 | 9646 | 12114 | 14382 | 9836 | 25759 |
| 33.82 | 40298 | 18736 | 12339 | 12606 | 9015 | 14180 | 13851 | 10180 | 25738 |
| 33.86 | 37434 | 20316 | 12541 | 13648 | 8899 | 13547 | 14626 | 9289 | 27103 |
| 33.9 | 37177 | 17846 | 12399 | 12447 | 9612 | 13990 | 11960 | 9529 | 26173 |
| 33.94 | 32843 | 18832 | 13155 | 12061 | 9115 | 13251 | 13532 | 8655 | 25028 |
| 33.98 | 33015 | 20353 | 13027 | 13572 | 9002 | 13575 | 12691 | 9841 | 24128 |
| 34.02 | 33133 | 17676 | 13413 | 13367 | 9886 | 15209 | 13151 | 9480 | 25451 |
| 34.06 | 31588 | 18176 | 13450 | 13725 | 9692 | 13698 | 12695 | 9124 | 26386 |
| 34.1 | 35717 | 18012 | 12051 | 14923 | 11781 | 13102 | 11897 | 9814 | 25386 |
| 34.14 | 35174 | 17211 | 12806 | 14661 | 10476 | 12738 | 12260 | 10525 | 26236 |
| 34.18 | 38376 | 17732 | 12826 | 15045 | 10333 | 13997 | 12508 | 9894 | 26005 |
| 34.22 | 39891 | 18556 | 14687 | 16100 | 9627 | 12988 | 13123 | 8706 | 26410 |
| 34.26 | 38873 | 18231 | 12805 | 15792 | 9873 | 12385 | 13130 | 9694 | 26401 |
| 34.3 | 43381 | 17440 | 14374 | 17559 | 10734 | 13655 | 14455 | 10948 | 25724 |
| 34.34 | 43754 | 16409 | 13726 | 16443 | 11003 | 13305 | 11830 | 9803 | 24841 |
| 34.38 | 43156 | 18739 | 13085 | 16362 | 11062 | 14329 | 13675 | 8721 | 24526 |
| 34.42 | 40476 | 18334 | 14105 | 15582 | 12173 | 14010 | 13121 | 10430 | 25557 |
| 34.46 | 39455 | 18133 | 14100 | 16351 | 11951 | 12950 | 14277 | 11174 | 24267 |
| 34.5 | 39445 | 16700 | 14711 | 14390 | 11587 | 12096 | 13701 | 11278 | 24136 |
| 34.54 | 37475 | 16769 | 14349 | 14028 | 11941 | 12675 | 13938 | 11647 | 24180 |
| 34.58 | 35675 | 18253 | 14833 | 14346 | 11360 | 12739 | 15076 | 14310 | 25238 |
| 34.62 | 37264 | 16027 | 13652 | 13185 | 11866 | 12253 | 13791 | 17720 | 24438 |
| 34.66 | 35934 | 17431 | 13852 | 13413 | 13303 | 13407 | 14624 | 19619 | 24702 |
| 34.7 | 34890 | 17762 | 14626 | 13779 | 11557 | 12078 | 14075 | 21297 | 25134 |
| 34.74 | 35968 | 17145 | 14905 | 13127 | 12860 | 12733 | 13632 | 22101 | 24843 |
| 34.78 | 35125 | 15879 | 15281 | 14499 | 11904 | 12361 | 13634 | 22733 | 23860 |
| 34.82 | 37065 | 17844 | 14707 | 13640 | 11638 | 12834 | 13989 | 24128 | 22996 |
| 34.86 | 36277 | 16235 | 14850 | 14179 | 10349 | 11433 | 14010 | 22974 | 24350 |
| 34.9 | 38008 | 17440 | 13087 | 13392 | 11766 | 12839 | 14073 | 20812 | 23788 |
| 34.94 | 37626 | 16428 | 13736 | 13751 | 10449 | 11903 | 13081 | 18052 | 24940 |
| 34.98 | 35819 | 18210 | 13391 | 14708 | 9998 | 12452 | 13951 | 16284 | 23377 |
| 35.02 | 36543 | 15838 | 14024 | 13474 | 9096 | 11942 | 13931 | 12197 | 24727 |
| 35.06 | 37554 | 16335 | 13308 | 13340 | 9343 | 13354 | 12102 | 11955 | 23109 |
| 35.1 | 35970 | 16435 | 13403 | 13221 | 9509 | 14000 | 11875 | 10699 | 24295 |
| 35.14 | 37546 | 16837 | 12786 | 14254 | 9898 | 13287 | 12599 | 10824 | 23580 |
| 35.18 | 36444 | 17278 | 13229 | 12960 | 9133 | 12685 | 12206 | 10533 | 24677 |
| 35.22 | 33632 | 17068 | 12272 | 13185 | 8958 | 12517 | 13208 | 8226 | 23070 |
| 35.26 | 33502 | 16191 | 11876 | 13519 | 10304 | 11469 | 10974 | 9467 | 22742 |
| 35.3 | 34834 | 16817 | 11390 | 13671 | 9743 | 11952 | 12096 | 9279 | 23324 |
| 35.34 | 34128 | 16797 | 11454 | 13413 | 9240 | 12933 | 11197 | 9012 | 24463 |
| 35.38 | 35629 | 16664 | 13419 | 14384 | 9310 | 12257 | 12096 | 9266 | 23126 |
| 35.42 | 33525 | 17323 | 13254 | 14168 | 10305 | 11167 | 13104 | 9712 | 23819 |
| 35.46 | 34560 | 15755 | 11858 | 15673 | 8259 | 12596 | 11750 | 8598 | 23578 |
| 35.5 | 36557 | 16507 | 11863 | 13489 | 9439 | 10975 | 11502 | 9548 | 25324 |
| 35.54 | 37236 | 15583 | 12608 | 14004 | 9488 | 11595 | 11086 | 9080 | 24927 |
| 35.58 | 33023 | 15793 | 12980 | 13261 | 8766 | 10553 | 11660 | 9955 | 26129 |
| 35.62 | 36110 | 15707 | 11937 | 14084 | 8292 | 12607 | 12232 | 9417 | 22780 |
| 35.66 | 37006 | 15469 | 10553 | 13067 | 9237 | 10968 | 10320 | 8687 | 22287 |
| 35.7 | 36250 | 15848 | 12681 | 14995 | 9139 | 12358 | 12555 | 8303 | 24267 |
| 35.74 | 36432 | 15214 | 11953 | 14436 | 8823 | 11035 | 12237 | 9173 | 24754 |
| 35.78 | 37795 | 17246 | 12896 | 13931 | 8952 | 11994 | 11571 | 8710 | 23783 |

-continued

| | | | | | | | | | |
|---|---|---|---|---|---|---|---|---|---|
| 35.82 | 34684 | 15978 | 11188 | 13399 | 7325 | 12014 | 11454 | 9082 | 24809 |
| 35.86 | 37165 | 15985 | 12858 | 14350 | 9118 | 11586 | 11544 | 9085 | 24911 |
| 35.9 | 33250 | 15357 | 13425 | 14698 | 8279 | 11842 | 11799 | 7983 | 23076 |
| 35.94 | 31030 | 17090 | 12420 | 14578 | 9853 | 11708 | 12810 | 8836 | 24656 |
| 35.98 | 31922 | 15460 | 11459 | 14837 | 9212 | 12706 | 12840 | 9635 | 24444 |
| 36.02 | 28684 | 15501 | 11857 | 14429 | 9658 | 12854 | 12175 | 10626 | 22646 |
| 36.06 | 30748 | 16135 | 12630 | 15609 | 9930 | 12736 | 11731 | 11165 | 22610 |
| 36.1 | 27342 | 16335 | 12396 | 16482 | 9328 | 13155 | 13037 | 10969 | 24245 |
| 36.14 | 28206 | 15801 | 12778 | 15499 | 10595 | 11772 | 12431 | 10318 | 25397 |
| 36.18 | 30355 | 16012 | 12408 | 14401 | 10735 | 13154 | 12904 | 10568 | 24220 |
| 36.22 | 30424 | 14867 | 13980 | 15634 | 9765 | 11296 | 13824 | 11323 | 24022 |
| 36.26 | 29689 | 15723 | 13103 | 13997 | 11356 | 11833 | 13012 | 11054 | 25517 |
| 36.3 | 32249 | 15274 | 13167 | 13418 | 11630 | 12559 | 13980 | 12792 | 26418 |
| 36.34 | 31862 | 17381 | 12650 | 14368 | 10632 | 12696 | 14219 | 13446 | 26665 |
| 36.38 | 35533 | 16160 | 13989 | 14021 | 10590 | 13567 | 13753 | 15927 | 25961 |
| 36.42 | 36053 | 14533 | 14844 | 14774 | 12418 | 14420 | 14133 | 18545 | 24369 |
| 36.46 | 36383 | 15689 | 13489 | 12048 | 10143 | 14050 | 13581 | 19052 | 25607 |
| 36.5 | 36325 | 16728 | 14440 | 11473 | 10762 | 13848 | 12794 | 21569 | 25737 |
| 36.54 | 35703 | 15400 | 14607 | 11097 | 9472 | 14463 | 11144 | 22391 | 24916 |
| 36.58 | 36443 | 15870 | 14218 | 11192 | 8508 | 13620 | 12676 | 20533 | 24188 |
| 36.62 | 33256 | 16229 | 14521 | 10983 | 10868 | 14144 | 12888 | 21074 | 24887 |
| 36.66 | 32671 | 15775 | 14203 | 10420 | 8698 | 13641 | 12543 | 21069 | 24623 |
| 36.7 | 33886 | 15008 | 13309 | 11325 | 7869 | 12125 | 12602 | 18295 | 22864 |
| 36.74 | 32997 | 15808 | 12710 | 12008 | 7904 | 12543 | 11799 | 15028 | 24762 |
| 36.78 | 32424 | 15172 | 13518 | 12145 | 8263 | 12626 | 11943 | 13800 | 23792 |
| 36.82 | 35470 | 15585 | 11707 | 11630 | 8605 | 12446 | 12709 | 12652 | 23079 |
| 36.86 | 38732 | 15486 | 12584 | 12183 | 8731 | 12671 | 13148 | 9142 | 23308 |
| 36.9 | 39904 | 15274 | 12111 | 11842 | 8815 | 11657 | 11974 | 9913 | 23182 |
| 36.94 | 39776 | 15336 | 12914 | 11972 | 8570 | 14175 | 12511 | 9527 | 25021 |
| 36.98 | 43940 | 14557 | 11420 | 11044 | 8239 | 13047 | 11836 | 8626 | 24076 |
| 37.02 | 45518 | 16077 | 11411 | 11935 | 8653 | 11882 | 11933 | 7746 | 24628 |
| 37.06 | 46934 | 15183 | 12471 | 12078 | 9052 | 11817 | 12534 | 9027 | 23818 |
| 37.1 | 48040 | 15434 | 11357 | 12511 | 8543 | 11981 | 12519 | 8552 | 22610 |
| 37.14 | 49059 | 14474 | 11766 | 12086 | 9460 | 12121 | 12681 | 8539 | 23429 |
| 37.18 | 47106 | 15725 | 12326 | 12148 | 8010 | 11660 | 11535 | 9062 | 22786 |
| 37.22 | 46635 | 14339 | 12149 | 12485 | 7629 | 12790 | 11974 | 7478 | 23544 |
| 37.26 | 44841 | 16097 | 12947 | 11660 | 8538 | 12309 | 12033 | 8433 | 23193 |
| 37.3 | 43091 | 16521 | 13456 | 12770 | 8590 | 12989 | 11194 | 7662 | 22681 |
| 37.34 | 36507 | 14916 | 11967 | 11349 | 8401 | 11182 | 11797 | 8597 | 23736 |
| 37.38 | 37327 | 15624 | 11318 | 12090 | 9663 | 12944 | 11290 | 8105 | 24036 |
| 37.42 | 35053 | 15504 | 12802 | 11556 | 9423 | 13228 | 12337 | 9132 | 23399 |
| 37.46 | 34763 | 14459 | 11563 | 13159 | 9097 | 12416 | 11215 | 8702 | 23353 |
| 37.5 | 33149 | 15105 | 12114 | 12775 | 8760 | 11199 | 10059 | 8332 | 21608 |
| 37.54 | 35933 | 15877 | 10928 | 11392 | 9705 | 12759 | 10960 | 8597 | 21413 |
| 37.58 | 33631 | 14735 | 11727 | 13069 | 10510 | 12954 | 10942 | 9270 | 22106 |
| 37.62 | 32968 | 14836 | 11491 | 11839 | 8264 | 13129 | 11316 | 9412 | 22820 |
| 37.66 | 32049 | 15152 | 12426 | 12234 | 8513 | 12722 | 10739 | 8143 | 20898 |
| 37.7 | 33862 | 14168 | 11403 | 11172 | 8829 | 11455 | 12134 | 8822 | 22309 |
| 37.74 | 32327 | 15339 | 11537 | 11219 | 8241 | 11567 | 10874 | 9435 | 24071 |
| 37.78 | 37191 | 15485 | 12505 | 11175 | 8982 | 12687 | 11115 | 9406 | 22992 |
| 37.82 | 33619 | 14435 | 11502 | 11530 | 9294 | 11855 | 11556 | 8861 | 22496 |
| 37.86 | 31625 | 15108 | 11190 | 11254 | 8444 | 11023 | 10421 | 8138 | 24355 |
| 37.9 | 30407 | 14123 | 9952 | 11383 | 9054 | 13199 | 10949 | 7946 | 22394 |
| 37.94 | 29997 | 15803 | 9531 | 10925 | 9438 | 12562 | 11370 | 9739 | 23052 |
| 37.98 | 27268 | 14842 | 9900 | 10443 | 9247 | 12698 | 11333 | 9736 | 21437 |
| 38.02 | 29357 | 14356 | 10731 | 10838 | 9277 | 12310 | 10414 | 10360 | 20766 |
| 38.06 | 26238 | 14567 | 9990 | 11081 | 9168 | 11284 | 11397 | 10158 | 20637 |
| 38.1 | 25552 | 14502 | 11158 | 10180 | 9437 | 12612 | 9582 | 9399 | 23499 |
| 38.14 | 25797 | 14602 | 11341 | 11451 | 9799 | 12967 | 11724 | 10510 | 21979 |
| 38.18 | 27575 | 14912 | 11206 | 10515 | 8803 | 11944 | 11462 | 10408 | 22899 |
| 38.22 | 27802 | 14958 | 11912 | 10761 | 9669 | 11891 | 10522 | 11221 | 21896 |
| 38.26 | 28039 | 13747 | 11359 | 11454 | 10626 | 13249 | 9637 | 9794 | 20796 |
| 38.3 | 30970 | 13983 | 12081 | 12137 | 10683 | 12634 | 10865 | 10422 | 22249 |
| 38.34 | 30156 | 15835 | 10985 | 12252 | 10176 | 10711 | 10794 | 10706 | 22274 |
| 38.38 | 31421 | 15498 | 12075 | 12581 | 9567 | 12624 | 10531 | 10411 | 22843 |
| 38.42 | 31738 | 14452 | 10428 | 11845 | 9984 | 11870 | 10172 | 10444 | 20816 |
| 38.46 | 35229 | 14145 | 12037 | 11400 | 9424 | 12423 | 11573 | 11521 | 21132 |
| 38.5 | 37946 | 15486 | 10795 | 10389 | 9340 | 12938 | 10734 | 13894 | 22591 |
| 38.54 | 38881 | 15108 | 10499 | 11798 | 9668 | 11681 | 11338 | 13471 | 22758 |
| 38.58 | 42026 | 13684 | 10471 | 10672 | 8811 | 11795 | 11386 | 14533 | 23259 |
| 38.62 | 43217 | 14648 | 9884 | 11466 | 8479 | 11183 | 9736 | 17529 | 22932 |
| 38.66 | 41466 | 14685 | 10646 | 11919 | 9219 | 10885 | 10202 | 19124 | 21815 |
| 38.7 | 41393 | 13289 | 9505 | 10979 | 8999 | 11065 | 10027 | 19216 | 22097 |
| 38.74 | 40512 | 13427 | 9942 | 11419 | 8702 | 11616 | 10128 | 19648 | 21632 |
| 38.78 | 37266 | 13967 | 9248 | 11347 | 7831 | 10826 | 10339 | 22424 | 23188 |
| 38.82 | 37684 | 15398 | 10199 | 12052 | 8147 | 11036 | 10675 | 19686 | 23146 |
| 38.86 | 36255 | 15081 | 10364 | 11763 | 8239 | 11370 | 10293 | 17000 | 24092 |
| 38.9 | 34463 | 15760 | 8655 | 11382 | 7203 | 13207 | 10250 | 16816 | 21605 |
| 38.94 | 32810 | 15020 | 10512 | 11016 | 8108 | 11191 | 9645 | 12543 | 24460 |

| | | | | | | | | | |
|---|---|---|---|---|---|---|---|---|---|
| 38.98 | 31255 | 15467 | 10366 | 13545 | 8831 | 12619 | 10369 | 11126 | 23368 |
| 39.02 | 31082 | 14255 | 10090 | 12261 | 9850 | 11183 | 9871 | 9675 | 22748 |
| 39.06 | 30981 | 15244 | 11520 | 12204 | 9146 | 12755 | 9776 | 10683 | 22458 |
| 39.1 | 29842 | 15022 | 10646 | 12428 | 9936 | 12607 | 10186 | 9851 | 23681 |
| 39.14 | 29226 | 14976 | 11040 | 12443 | 9870 | 11101 | 10214 | 7874 | 22154 |
| 39.18 | 30890 | 14533 | 10050 | 11553 | 9571 | 13242 | 11386 | 8388 | 22801 |
| 39.22 | 32168 | 14961 | 11109 | 12861 | 10856 | 12445 | 10806 | 9361 | 21169 |
| 39.26 | 30423 | 15547 | 9909 | 12022 | 11605 | 11262 | 11576 | 8745 | 23261 |
| 39.3 | 32031 | 15364 | 9825 | 11658 | 10727 | 11940 | 9959 | 8239 | 22752 |
| 39.34 | 29739 | 14603 | 9719 | 12744 | 11145 | 12067 | 10809 | 9189 | 22016 |
| 39.38 | 30063 | 13860 | 10802 | 12955 | 12510 | 13638 | 10559 | 8807 | 23084 |
| 39.42 | 28821 | 14725 | 10469 | 13704 | 12607 | 13811 | 9845 | 7726 | 22040 |
| 39.46 | 30504 | 14294 | 10191 | 12213 | 12666 | 13203 | 9469 | 8463 | 23029 |
| 39.5 | 29869 | 14507 | 11123 | 12049 | 12689 | 12947 | 10351 | 7886 | 21960 |
| 39.54 | 27356 | 13968 | 10147 | 11378 | 13624 | 12205 | 9919 | 8690 | 21264 |
| 39.58 | 28983 | 14783 | 11497 | 11866 | 12507 | 13580 | 10138 | 7887 | 21543 |
| 39.62 | 29602 | 15551 | 10954 | 12157 | 12945 | 13871 | 10338 | 8358 | 21462 |
| 39.66 | 28784 | 12945 | 11118 | 10533 | 13080 | 13914 | 11167 | 8262 | 21024 |
| 39.7 | 33558 | 13969 | 10272 | 10827 | 12001 | 12827 | 9683 | 8150 | 20981 |
| 39.74 | 31841 | 15344 | 10708 | 11732 | 12904 | 12479 | 10442 | 8588 | 20589 |
| 39.78 | 33709 | 14163 | 11047 | 11493 | 10384 | 10893 | 10380 | 8325 | 20571 |
| 39.82 | 33421 | 14951 | 11531 | 9933 | 9661 | 12211 | 10009 | 7995 | 21874 |
| 39.86 | 32989 | 14210 | 10676 | 12239 | 9050 | 12571 | 10476 | 7485 | 20907 |
| 39.9 | 33243 | 13298 | 9699 | 11230 | 8490 | 12727 | 10698 | 8208 | 20969 |
| 39.94 | 32141 | 15331 | 10088 | 10446 | 7532 | 11769 | 9980 | 7503 | 20751 |
| 39.98 | 33438 | 15537 | 10987 | 11383 | 7343 | 11352 | 11026 | 6521 | 20977 |
| 40.02 | 32230 | 14495 | 9121 | 10532 | 8703 | 10949 | 10282 | 7251 | 21291 |
| 40.06 | 32321 | 14999 | 10791 | 10941 | 9172 | 10740 | 9763 | 7982 | 21477 |
| 40.1 | 30643 | 14436 | 11645 | 10199 | 8887 | 11778 | 9942 | 8519 | 21853 |
| 40.14 | 31571 | 14228 | 11203 | 10827 | 8797 | 10942 | 10195 | 7034 | 21962 |
| 40.18 | 30915 | 14589 | 10490 | 11322 | 7898 | 11587 | 9767 | 8137 | 21783 |
| 40.22 | 29071 | 14634 | 10417 | 10679 | 8886 | 10727 | 9774 | 8161 | 22215 |
| 40.26 | 29646 | 14395 | 11694 | 11277 | 7838 | 11399 | 10853 | 7802 | 21685 |
| 40.3 | 29195 | 14394 | 12228 | 10762 | 9010 | 11301 | 10813 | 8402 | 21745 |
| 40.34 | 27627 | 14301 | 11662 | 11137 | 8708 | 12015 | 10857 | 8255 | 23452 |
| 40.38 | 29288 | 14049 | 11838 | 12094 | 9480 | 11001 | 9703 | 7716 | 22486 |
| 40.42 | 28480 | 15023 | 11520 | 12232 | 9166 | 11547 | 10110 | 7804 | 19584 |
| 40.46 | 29818 | 13884 | 11765 | 11055 | 8766 | 11101 | 10148 | 7957 | 21808 |
| 40.5 | 29655 | 14059 | 12330 | 12303 | 8126 | 10383 | 10264 | 8391 | 22336 |
| 40.54 | 30635 | 14272 | 12423 | 12417 | 8486 | 10488 | 10451 | 7772 | 20625 |
| 40.58 | 33332 | 14164 | 11107 | 12005 | 8751 | 10205 | 10219 | 8068 | 22329 |
| 40.62 | 32166 | 13454 | 12144 | 13091 | 8126 | 10980 | 10660 | 7978 | 20856 |
| 40.66 | 33782 | 14673 | 11722 | 12159 | 7229 | 11264 | 10288 | 8625 | 21180 |
| 40.7 | 31605 | 14077 | 10879 | 11894 | 7945 | 10249 | 10365 | 7833 | 20959 |
| 40.74 | 30278 | 14520 | 11215 | 12141 | 8530 | 10065 | 10704 | 7537 | 20311 |
| 40.78 | 32247 | 13536 | 12118 | 13964 | 8775 | 10073 | 9188 | 7773 | 20784 |
| 40.82 | 32126 | 13755 | 11325 | 12464 | 8102 | 11695 | 9596 | 7879 | 20924 |
| 40.86 | 34204 | 13086 | 10845 | 12414 | 7721 | 9612 | 9753 | 8672 | 20990 |
| 40.9 | 32675 | 12691 | 9861 | 11756 | 7669 | 9597 | 10188 | 9928 | 22270 |
| 40.94 | 32028 | 14669 | 10627 | 11832 | 7818 | 11053 | 11189 | 11956 | 20888 |
| 40.98 | 29943 | 12379 | 10806 | 11211 | 7108 | 9572 | 9307 | 15628 | 20868 |
| 41.02 | 31103 | 11851 | 11302 | 11130 | 7257 | 10388 | 9372 | 17497 | 21146 |
| 41.06 | 30820 | 13100 | 9900 | 10365 | 8182 | 10611 | 10122 | 20981 | 19878 |
| 41.1 | 28893 | 13008 | 10983 | 9519 | 7651 | 8517 | 8465 | 24724 | 19923 |
| 41.14 | 28129 | 13131 | 9887 | 9814 | 7420 | 9768 | 9177 | 24776 | 20170 |
| 41.18 | 26745 | 12989 | 9439 | 9697 | 7203 | 9118 | 9206 | 23173 | 19550 |
| 41.22 | 27315 | 12076 | 10150 | 8804 | 6378 | 9538 | 8483 | 23888 | 19914 |
| 41.26 | 25972 | 12208 | 9668 | 10506 | 7305 | 8958 | 8641 | 20703 | 20058 |
| 41.3 | 27695 | 12971 | 8886 | 10475 | 7052 | 9203 | 9291 | 20748 | 18335 |
| 41.34 | 25417 | 12204 | 8427 | 10393 | 7188 | 8609 | 9498 | 17542 | 19724 |
| 41.38 | 25650 | 12186 | 8834 | 9570 | 6243 | 7763 | 9551 | 15259 | 21128 |
| 41.42 | 25198 | 12287 | 9101 | 9151 | 7044 | 8928 | 9795 | 12626 | 19612 |
| 41.46 | 25439 | 12922 | 9279 | 10006 | 5902 | 9555 | 9545 | 10839 | 19648 |
| 41.5 | 27542 | 12620 | 8633 | 8849 | 7129 | 8665 | 9436 | 9001 | 17872 |

| | Form | | | | | | | | | | |
|---|---|---|---|---|---|---|---|---|---|---|---|
| | Nsu2 | Nsu3_lc | Oxa1 | Pho1 | Pho2_lc | Suc1 | Suc2 | Suc1 + Suc3 | Sul1 | Sul2 | Sul3 |
| | | | | | ExperimentID | | | | | | |
| Counter ion | SSm42 Naphthalene-2-sulfonic acid | SSm75 Naphthalene-2-sulfonic acid | SSm12 Oxalic acid | SSm81 ortho-Phosphoric acid | SSm15 ortho-Phosphoric acid | SSm31 Succinic acid | SSm97 Succinic acid | SSm64 Succinic acid | SSm37 Sulphuric acid | SSm38 Sulphuric acid | SSm5 Sulphuric acid |
| 1.5 | 4385 | 1043 | 1016 | 1802 | 2000 | 2627 | 972 | 3091 | 847 | 1735 | 2023 |
| 1.54 | 2468 | 3924 | 538 | 4094 | 628 | 3463 | 1493 | 4426 | 2708 | 3588 | 3887 |
| 1.58 | 7064 | 3897 | 2853 | 2081 | 3834 | 4121 | 4753 | 3714 | 5608 | 2917 | 2073 |
| 1.62 | 6353 | 5452 | 4668 | 2581 | 1586 | 3048 | 3471 | 6608 | 3739 | 4648 | 5470 |
| 1.66 | 9559 | 2671 | 5827 | 4383 | 4968 | 3751 | 4548 | 7493 | 4001 | 2814 | 3371 |
| 1.7 | 8652 | 6661 | 5577 | 5963 | 5002 | 5046 | 7313 | 12350 | 2735 | 4289 | 6175 |
| 1.74 | 10979 | 8179 | 6272 | 6299 | 5683 | 8616 | 6195 | 13122 | 8358 | 3695 | 7547 |
| 1.78 | 13102 | 5783 | 10103 | 8306 | 8357 | 5828 | 5957 | 10599 | 4565 | 6224 | 5916 |
| 1.82 | 16082 | 9456 | 6204 | 6780 | 8126 | 6247 | 8194 | 9995 | 7453 | 9420 | 5969 |
| 1.86 | 19185 | 9564 | 7271 | 8547 | 6620 | 8596 | 8812 | 14095 | 7873 | 7583 | 8729 |
| 1.9 | 18495 | 9999 | 6327 | 10971 | 9967 | 9642 | 8520 | 19950 | 8986 | 9462 | 7820 |
| 1.94 | 20645 | 9274 | 9044 | 10051 | 5923 | 12607 | 11590 | 20314 | 8591 | 9156 | 9841 |
| 1.98 | 19256 | 6258 | 10545 | 11618 | 6347 | 9925 | 9940 | 16932 | 6488 | 8233 | 7401 |
| 2.02 | 23501 | 7147 | 6795 | 10962 | 10392 | 11034 | 13772 | 18164 | 7100 | 7120 | 9830 |
| 2.06 | 18829 | 10657 | 10548 | 8326 | 6497 | 8246 | 12246 | 20596 | 8865 | 10730 | 9014 |
| 2.1 | 20186 | 8961 | 10461 | 5643 | 8880 | 11118 | 9749 | 21161 | 8176 | 8605 | 9960 |
| 2.14 | 22400 | 7651 | 12755 | 8659 | 6808 | 10792 | 9998 | 17619 | 8781 | 7701 | 10836 |
| 2.18 | 24426 | 10271 | 8488 | 13061 | 8139 | 11155 | 10094 | 18179 | 8448 | 7950 | 7603 |
| 2.22 | 17884 | 9525 | 8546 | 9555 | 7530 | 8366 | 11201 | 20152 | 8402 | 9113 | 12616 |
| 2.26 | 16891 | 12043 | 8291 | 11264 | 7476 | 9080 | 12749 | 18453 | 9875 | 10517 | 6726 |
| 2.3 | 16584 | 14683 | 11369 | 8130 | 9130 | 10324 | 7478 | 18367 | 7577 | 7670 | 9544 |
| 2.34 | 18687 | 8807 | 10628 | 8931 | 6846 | 8972 | 11316 | 21802 | 8098 | 8887 | 12127 |
| 2.38 | 21681 | 10563 | 10991 | 8552 | 10920 | 8380 | 12935 | 18859 | 10908 | 10181 | 12931 |
| 2.42 | 19655 | 10456 | 10368 | 11309 | 11949 | 12440 | 14100 | 17042 | 10818 | 6924 | 12237 |
| 2.46 | 25037 | 11161 | 9696 | 10742 | 7068 | 11878 | 12928 | 19039 | 11101 | 8925 | 8494 |
| 2.5 | 25467 | 10787 | 8235 | 12128 | 7632 | 13486 | 13289 | 26034 | 8090 | 9805 | 8853 |
| 2.54 | 23846 | 10478 | 11744 | 11425 | 10875 | 14713 | 14031 | 25501 | 8311 | 10608 | 9098 |
| 2.58 | 23680 | 10571 | 10482 | 10985 | 12867 | 8771 | 15557 | 22460 | 6993 | 10420 | 11254 |
| 2.62 | 24156 | 11462 | 11075 | 9680 | 6827 | 9838 | 12868 | 26293 | 10257 | 12474 | 12830 |
| 2.66 | 25681 | 9787 | 12921 | 11449 | 8389 | 11220 | 14054 | 27726 | 10276 | 10817 | 11222 |
| 2.7 | 22735 | 11363 | 9841 | 11988 | 11623 | 12362 | 16413 | 27905 | 7037 | 11635 | 17007 |
| 2.74 | 22491 | 10972 | 13865 | 16285 | 11306 | 13311 | 12544 | 24889 | 8848 | 8451 | 11704 |
| 2.78 | 23200 | 10692 | 10538 | 13424 | 8507 | 14466 | 13058 | 24913 | 9744 | 11877 | 17625 |
| 2.82 | 25627 | 13385 | 13181 | 10657 | 11351 | 11586 | 14423 | 24115 | 8852 | 9881 | 18634 |
| 2.86 | 26138 | 10939 | 12328 | 16117 | 12766 | 10738 | 19088 | 23570 | 10344 | 13360 | 13777 |
| 2.9 | 24605 | 12980 | 13045 | 15947 | 11559 | 12644 | 19880 | 22743 | 12423 | 12498 | 15211 |
| 2.94 | 29336 | 9332 | 16787 | 14431 | 9678 | 12284 | 15498 | 26169 | 11237 | 9962 | 17783 |
| 2.98 | 24640 | 15995 | 14366 | 10233 | 13629 | 12456 | 18232 | 25058 | 9296 | 10137 | 13910 |
| 3.02 | 31167 | 15107 | 16108 | 13173 | 10803 | 17274 | 14639 | 26315 | 12361 | 13629 | 16084 |
| 3.06 | 24493 | 21851 | 14124 | 14336 | 13644 | 13755 | 14363 | 29346 | 13627 | 13028 | 17478 |
| 3.1 | 30892 | 21769 | 15718 | 12420 | 15170 | 17047 | 16386 | 32726 | 14425 | 11047 | 16070 |
| 3.14 | 31590 | 24190 | 17896 | 16597 | 14823 | 16962 | 13823 | 32338 | 10668 | 11735 | 13825 |
| 3.18 | 32392 | 20361 | 17422 | 13602 | 9527 | 21259 | 13438 | 32451 | 10299 | 14774 | 14532 |
| 3.22 | 29091 | 20065 | 15213 | 17716 | 13103 | 15263 | 15798 | 31714 | 11869 | 14320 | 14724 |
| 3.26 | 26779 | 27001 | 17788 | 16067 | 13514 | 19702 | 19966 | 27324 | 15028 | 15155 | 15811 |
| 3.3 | 33720 | 20432 | 15457 | 17791 | 12087 | 18371 | 16426 | 34188 | 15231 | 12879 | 19626 |
| 3.34 | 33363 | 24779 | 19066 | 17977 | 15988 | 20050 | 19728 | 34504 | 12084 | 12612 | 16800 |
| 3.38 | 29137 | 23318 | 19781 | 17137 | 16692 | 19109 | 15977 | 29773 | 10396 | 14082 | 16420 |
| 3.42 | 34322 | 25400 | 16712 | 16766 | 17468 | 22710 | 15726 | 31964 | 14315 | 15582 | 20635 |
| 3.46 | 34034 | 21671 | 17035 | 15734 | 15122 | 19810 | 18534 | 33756 | 13364 | 16240 | 13105 |
| 3.5 | 36070 | 22408 | 16705 | 18706 | 19179 | 19657 | 21004 | 30264 | 15288 | 14903 | 15623 |
| 3.54 | 34037 | 22384 | 15334 | 18468 | 14951 | 20156 | 18548 | 29946 | 14055 | 13446 | 16670 |
| 3.58 | 34779 | 24603 | 21088 | 20499 | 16462 | 19178 | 18436 | 33473 | 16329 | 12965 | 18273 |
| 3.62 | 40599 | 24460 | 20849 | 19821 | 18523 | 21111 | 23206 | 36683 | 17843 | 12959 | 23347 |
| 3.66 | 44968 | 22468 | 18675 | 19599 | 13123 | 22936 | 20383 | 36733 | 17704 | 13454 | 18888 |
| 3.7 | 48142 | 20812 | 18455 | 22252 | 16375 | 23035 | 17475 | 36483 | 15709 | 16245 | 20062 |
| 3.74 | 49919 | 20112 | 19856 | 20154 | 17441 | 25144 | 21974 | 34697 | 13117 | 15760 | 19458 |
| 3.78 | 63470 | 19549 | 15691 | 18642 | 18830 | 23230 | 21807 | 29614 | 14708 | 13411 | 16465 |
| 3.82 | 68962 | 21303 | 15618 | 21748 | 18099 | 21929 | 18878 | 35915 | 13165 | 15593 | 19870 |
| 3.86 | 66251 | 17605 | 18937 | 18971 | 16242 | 22412 | 19415 | 37315 | 17257 | 14984 | 20938 |
| 3.9 | 65998 | 19785 | 18516 | 19618 | 21203 | 22042 | 20305 | 37119 | 15785 | 17795 | 23381 |
| 3.94 | 57279 | 21034 | 19040 | 22793 | 20082 | 24293 | 21702 | 34742 | 16944 | 18315 | 25217 |
| 3.98 | 65982 | 20899 | 16855 | 22937 | 25066 | 25242 | 19468 | 37283 | 13545 | 18278 | 21159 |
| 4.02 | 57261 | 20236 | 20709 | 21699 | 22482 | 24464 | 20597 | 38885 | 12275 | 15487 | 20431 |
| 4.06 | 58540 | 19379 | 17891 | 18460 | 24045 | 20356 | 20443 | 37560 | 12664 | 14911 | 17649 |
| 4.1 | 50624 | 18568 | 19053 | 23746 | 24930 | 22436 | 18085 | 33621 | 10772 | 18049 | 16830 |
| 4.14 | 46287 | 19310 | 20465 | 22038 | 24733 | 21716 | 21191 | 40452 | 13202 | 20069 | 16112 |
| 4.18 | 36095 | 19084 | 17887 | 21420 | 23032 | 22262 | 18514 | 40213 | 17342 | 21217 | 19604 |
| 4.22 | 45932 | 21357 | 21467 | 22185 | 30797 | 25678 | 21003 | 34688 | 17063 | 24687 | 19889 |
| 4.26 | 41066 | 22316 | 20842 | 23604 | 24427 | 22842 | 20030 | 36941 | 14077 | 22610 | 21593 |

-continued

| | | | | | | | | | | | |
|---|---|---|---|---|---|---|---|---|---|---|---|
| 4.3 | 40393 | 25018 | 21363 | 23348 | 25640 | 23349 | 19695 | 35615 | 14726 | 20366 | 19559 |
| 4.34 | 38811 | 23534 | 19007 | 21737 | 21811 | 24498 | 19786 | 36995 | 11616 | 21347 | 20408 |
| 4.38 | 39747 | 28420 | 17978 | 22282 | 21528 | 21659 | 20435 | 37562 | 13396 | 18007 | 19660 |
| 4.42 | 37137 | 25147 | 19893 | 22504 | 18556 | 18684 | 20566 | 38689 | 14126 | 22679 | 19813 |
| 4.46 | 40042 | 28499 | 22554 | 21242 | 19368 | 21201 | 23420 | 39684 | 14344 | 21179 | 18604 |
| 4.5 | 38859 | 31059 | 22465 | 23723 | 17172 | 20685 | 20114 | 39865 | 16296 | 17902 | 23321 |
| 4.54 | 40117 | 28570 | 21248 | 20848 | 22270 | 20588 | 22163 | 38705 | 13253 | 16448 | 20594 |
| 4.58 | 38422 | 29030 | 20370 | 23958 | 19443 | 22574 | 26978 | 38522 | 13000 | 16758 | 21665 |
| 4.62 | 40375 | 30553 | 19881 | 21710 | 20451 | 25374 | 19161 | 38198 | 15865 | 17757 | 22254 |
| 4.66 | 38557 | 28013 | 21625 | 22151 | 21342 | 25585 | 23633 | 43026 | 15080 | 14025 | 20843 |
| 4.7 | 39805 | 26220 | 15675 | 25820 | 16878 | 26752 | 23829 | 39256 | 15444 | 14114 | 21886 |
| 4.74 | 40412 | 30112 | 19662 | 28963 | 19664 | 26222 | 26933 | 41928 | 13356 | 13647 | 21208 |
| 4.78 | 45280 | 24547 | 21213 | 31766 | 18454 | 24764 | 30197 | 44063 | 16856 | 16390 | 19390 |
| 4.82 | 37634 | 22481 | 19699 | 40178 | 17098 | 28819 | 38842 | 45836 | 13925 | 16791 | 22558 |
| 4.86 | 38695 | 19262 | 19652 | 41247 | 15781 | 30781 | 47440 | 50851 | 14453 | 18045 | 18777 |
| 4.9 | 42045 | 20638 | 21727 | 42477 | 18197 | 34885 | 54160 | 63728 | 14388 | 16344 | 21030 |
| 4.94 | 44284 | 17591 | 19695 | 35069 | 18818 | 37184 | 64720 | 74257 | 16105 | 18754 | 20720 |
| 4.98 | 43742 | 19715 | 20582 | 39430 | 18413 | 42038 | 71208 | 86786 | 15055 | 14099 | 18401 |
| 5.02 | 41215 | 22764 | 22804 | 44219 | 20078 | 55054 | 76439 | 104465 | 18059 | 17124 | 20013 |
| 5.06 | 38873 | 19970 | 22154 | 38120 | 19868 | 58010 | 79935 | 118768 | 17092 | 14921 | 21278 |
| 5.1 | 39195 | 17084 | 20045 | 37525 | 20315 | 58264 | 79320 | 127807 | 17003 | 18708 | 22122 |
| 5.14 | 42905 | 17239 | 20601 | 32056 | 17782 | 60391 | 73466 | 129088 | 13228 | 18627 | 18837 |
| 5.18 | 40991 | 20539 | 18499 | 26889 | 15961 | 50339 | 62650 | 124391 | 17247 | 17427 | 19914 |
| 5.22 | 42744 | 18658 | 22579 | 23003 | 15935 | 58075 | 54321 | 113980 | 16110 | 17621 | 17552 |
| 5.26 | 42394 | 18724 | 17569 | 22293 | 18245 | 51366 | 47767 | 115558 | 14607 | 14215 | 25677 |
| 5.3 | 43200 | 18964 | 20140 | 21456 | 15110 | 47062 | 33297 | 86075 | 16837 | 17309 | 24929 |
| 5.34 | 42184 | 19497 | 22384 | 20673 | 14436 | 41861 | 30572 | 86265 | 15426 | 16105 | 27571 |
| 5.38 | 45103 | 21118 | 21577 | 21483 | 17581 | 33845 | 30259 | 67862 | 17588 | 16673 | 31077 |
| 5.42 | 47276 | 23237 | 20432 | 20041 | 18784 | 33432 | 24390 | 56851 | 17223 | 17994 | 38360 |
| 5.46 | 44230 | 21112 | 21071 | 24436 | 19873 | 26174 | 23564 | 51008 | 14153 | 16051 | 39219 |
| 5.5 | 47288 | 25314 | 19721 | 22780 | 18764 | 23070 | 23167 | 47637 | 17130 | 18635 | 42199 |
| 5.54 | 39353 | 23821 | 22314 | 21939 | 18313 | 23281 | 20200 | 45580 | 14043 | 15405 | 38442 |
| 5.58 | 45905 | 20615 | 19591 | 20288 | 17333 | 24409 | 22253 | 50498 | 14907 | 16484 | 37613 |
| 5.62 | 44179 | 26672 | 19118 | 17657 | 17367 | 22446 | 22030 | 40885 | 17369 | 18013 | 39427 |
| 5.66 | 48010 | 26505 | 18823 | 21118 | 17913 | 24926 | 22294 | 40664 | 15171 | 18054 | 41178 |
| 5.7 | 46120 | 28081 | 18958 | 21806 | 18202 | 24216 | 23684 | 43941 | 16736 | 19356 | 42270 |
| 5.74 | 56120 | 27180 | 20000 | 20941 | 19130 | 26752 | 24496 | 41596 | 19319 | 20007 | 43024 |
| 5.78 | 63275 | 27950 | 24463 | 24033 | 15845 | 21501 | 24110 | 42098 | 19824 | 16048 | 44773 |
| 5.82 | 75961 | 30977 | 20263 | 21896 | 19452 | 26153 | 23801 | 44620 | 17806 | 17751 | 43943 |
| 5.86 | 85544 | 25111 | 21744 | 19887 | 23688 | 23188 | 22357 | 44307 | 14665 | 18896 | 48535 |
| 5.9 | 106568 | 30442 | 17555 | 22948 | 18115 | 22481 | 23165 | 41891 | 14841 | 18744 | 39531 |
| 5.94 | 119798 | 25237 | 22789 | 22097 | 20240 | 22433 | 20872 | 46935 | 16104 | 17792 | 38630 |
| 5.98 | 142779 | 29190 | 21756 | 21072 | 18485 | 18660 | 24391 | 42199 | 17202 | 16181 | 39213 |
| 6.02 | 155121 | 26977 | 21066 | 21869 | 16026 | 20917 | 23754 | 40642 | 17432 | 16103 | 38670 |
| 6.06 | 160476 | 26752 | 21098 | 24394 | 18527 | 22706 | 24448 | 43790 | 19027 | 16075 | 33110 |
| 6.1 | 171766 | 35251 | 22670 | 23362 | 19143 | 21155 | 26456 | 43598 | 17530 | 18398 | 33160 |
| 6.14 | 157836 | 37044 | 21258 | 26050 | 19988 | 24020 | 23447 | 47767 | 20076 | 17188 | 28524 |
| 6.18 | 136617 | 44172 | 23069 | 25175 | 17241 | 24379 | 24875 | 47124 | 16410 | 16407 | 27232 |
| 6.22 | 133195 | 44490 | 20305 | 19926 | 22174 | 24660 | 26437 | 43124 | 17832 | 20072 | 25704 |
| 6.26 | 108789 | 53311 | 20766 | 22726 | 18965 | 23031 | 28599 | 46776 | 18871 | 17979 | 25877 |
| 6.3 | 87450 | 59790 | 21408 | 23587 | 16255 | 21005 | 31746 | 49925 | 17013 | 17260 | 23759 |
| 6.34 | 76900 | 60086 | 24779 | 21600 | 17263 | 22788 | 35422 | 47368 | 16895 | 22685 | 26807 |
| 6.38 | 59877 | 66857 | 21861 | 22335 | 19616 | 23077 | 37491 | 52667 | 17461 | 20405 | 24301 |
| 6.42 | 52808 | 65662 | 23380 | 25061 | 19944 | 24148 | 41771 | 57386 | 20567 | 20304 | 23941 |
| 6.46 | 48830 | 62646 | 27128 | 25383 | 20529 | 27039 | 40910 | 70605 | 23840 | 19551 | 26202 |
| 6.5 | 48617 | 59935 | 24854 | 25329 | 19876 | 23070 | 39194 | 79332 | 29493 | 22725 | 28798 |
| 6.54 | 48288 | 51623 | 26506 | 30546 | 20131 | 23716 | 40460 | 87100 | 37088 | 27642 | 28795 |
| 6.58 | 45046 | 51827 | 35484 | 31847 | 19215 | 24045 | 40683 | 93508 | 53886 | 38759 | 34155 |
| 6.62 | 49984 | 45891 | 58961 | 37425 | 21213 | 27029 | 37040 | 97109 | 66816 | 47190 | 36611 |
| 6.66 | 46778 | 38569 | 94643 | 46172 | 18424 | 26479 | 32057 | 101425 | 76151 | 56285 | 36077 |
| 6.7 | 42679 | 33023 | 142045 | 48867 | 19396 | 23771 | 28600 | 99367 | 85171 | 70136 | 35073 |
| 6.74 | 43966 | 33068 | 176635 | 56300 | 21758 | 23934 | 26601 | 94540 | 88758 | 77835 | 39423 |
| 6.78 | 46283 | 28026 | 211510 | 54801 | 19272 | 20571 | 24737 | 86455 | 87080 | 78513 | 41132 |
| 6.82 | 46846 | 27107 | 222245 | 56343 | 20073 | 25608 | 24406 | 78513 | 82040 | 76725 | 40289 |
| 6.86 | 50639 | 24957 | 234362 | 50492 | 19075 | 22567 | 23973 | 73372 | 74593 | 69509 | 41786 |
| 6.9 | 57412 | 23992 | 230930 | 49176 | 21130 | 22785 | 25247 | 68671 | 64443 | 68580 | 40231 |
| 6.94 | 58524 | 23116 | 222517 | 47085 | 20772 | 26747 | 24939 | 58289 | 52447 | 58707 | 32706 |
| 6.98 | 64322 | 25043 | 206921 | 39588 | 18496 | 23978 | 22918 | 59824 | 43649 | 48027 | 35708 |
| 7.02 | 65885 | 25397 | 183223 | 33458 | 20053 | 23444 | 23923 | 61066 | 33743 | 42164 | 35553 |
| 7.06 | 72311 | 23847 | 136523 | 29962 | 20988 | 25673 | 24204 | 67780 | 22084 | 29744 | 36471 |
| 7.1 | 74457 | 21326 | 92818 | 24956 | 20202 | 23440 | 24253 | 65504 | 19845 | 24530 | 33429 |
| 7.14 | 68678 | 22512 | 63762 | 23711 | 20143 | 23035 | 23751 | 68121 | 19483 | 19682 | 30678 |
| 7.18 | 68399 | 23579 | 41634 | 22733 | 21007 | 23917 | 19938 | 67113 | 18723 | 22330 | 31073 |
| 7.22 | 59664 | 22087 | 30134 | 20887 | 21769 | 21680 | 21391 | 67569 | 18294 | 18322 | 29094 |
| 7.26 | 66715 | 20692 | 26004 | 21538 | 21866 | 23298 | 22712 | 67100 | 17348 | 21238 | 31140 |
| 7.3 | 56072 | 21781 | 24892 | 22481 | 22257 | 24891 | 24270 | 64510 | 17988 | 21068 | 30667 |
| 7.34 | 50436 | 23053 | 24597 | 26181 | 23201 | 26167 | 23808 | 65096 | 16880 | 19317 | 32709 |
| 7.38 | 47111 | 19403 | 22820 | 19966 | 19575 | 23171 | 21744 | 55952 | 18019 | 19916 | 33472 |
| 7.42 | 46245 | 22525 | 21702 | 23214 | 20438 | 23185 | 24000 | 56900 | 18412 | 20069 | 29730 |

| | | | | | | | | | | | |
|---|---|---|---|---|---|---|---|---|---|---|---|
| 7.46 | 45638 | 20659 | 21480 | 20916 | 21466 | 22067 | 23130 | 53097 | 18208 | 20496 | 30440 |
| 7.5 | 48127 | 19905 | 22015 | 21713 | 22376 | 21036 | 22445 | 50994 | 18656 | 20636 | 27375 |
| 7.54 | 49565 | 22237 | 21546 | 22231 | 21574 | 26646 | 24400 | 53285 | 18483 | 17075 | 30501 |
| 7.58 | 51895 | 21666 | 24594 | 20713 | 20604 | 23445 | 24309 | 56347 | 18699 | 20435 | 29719 |
| 7.62 | 53279 | 21821 | 21859 | 21660 | 24546 | 24188 | 28250 | 50732 | 17756 | 18008 | 29523 |
| 7.66 | 52474 | 24254 | 21875 | 21805 | 20286 | 26105 | 24817 | 49400 | 17476 | 17485 | 28112 |
| 7.7 | 51588 | 21988 | 21412 | 22896 | 18987 | 25285 | 22337 | 49366 | 21586 | 19131 | 25635 |
| 7.74 | 53922 | 19356 | 22771 | 24238 | 23506 | 26360 | 22013 | 48378 | 18841 | 17201 | 29581 |
| 7.78 | 51196 | 18426 | 22282 | 20189 | 19293 | 23518 | 24135 | 46247 | 19101 | 20060 | 24244 |
| 7.82 | 50596 | 20699 | 22984 | 19701 | 23093 | 24682 | 25906 | 46290 | 18324 | 19338 | 26279 |
| 7.86 | 55147 | 23225 | 22800 | 22493 | 23183 | 27893 | 23601 | 53284 | 19092 | 20987 | 31033 |
| 7.9 | 48818 | 22620 | 21412 | 22144 | 24265 | 29096 | 25678 | 46862 | 19191 | 20881 | 31853 |
| 7.94 | 49035 | 20946 | 24408 | 20839 | 24804 | 27773 | 26629 | 50458 | 18713 | 21494 | 30631 |
| 7.98 | 49611 | 19001 | 23419 | 24568 | 23044 | 27684 | 23352 | 52068 | 16823 | 18297 | 31183 |
| 8.02 | 49251 | 21054 | 20962 | 22248 | 22472 | 27183 | 27355 | 51990 | 18089 | 19699 | 29997 |
| 8.06 | 48597 | 21710 | 20473 | 25391 | 22886 | 31060 | 28873 | 54918 | 19404 | 22542 | 28824 |
| 8.1 | 48504 | 21263 | 22548 | 23274 | 23575 | 31241 | 35298 | 57779 | 19267 | 20918 | 30549 |
| 8.14 | 45769 | 21214 | 22000 | 25101 | 22517 | 28994 | 41244 | 63802 | 23471 | 18631 | 32588 |
| 8.18 | 43760 | 21164 | 21628 | 24114 | 25873 | 32656 | 43122 | 61615 | 20025 | 21825 | 32328 |
| 8.22 | 43326 | 19503 | 20403 | 24436 | 24313 | 32543 | 47235 | 65736 | 20789 | 20182 | 26898 |
| 8.26 | 40519 | 20582 | 19911 | 23349 | 24033 | 33069 | 49494 | 73023 | 20732 | 18281 | 26759 |
| 8.3 | 39719 | 20275 | 22913 | 24024 | 24904 | 35448 | 56890 | 77144 | 22612 | 18387 | 24361 |
| 8.34 | 45480 | 22286 | 23880 | 23799 | 28206 | 37443 | 53731 | 86896 | 20931 | 19024 | 23892 |
| 8.38 | 42970 | 22268 | 24169 | 22361 | 25833 | 40988 | 60761 | 85346 | 22528 | 20039 | 25146 |
| 8.42 | 46614 | 23042 | 21287 | 24010 | 25147 | 42844 | 56362 | 91035 | 25738 | 19567 | 25307 |
| 8.46 | 43723 | 28065 | 22395 | 22265 | 26318 | 40252 | 49409 | 84832 | 23084 | 19451 | 21602 |
| 8.5 | 43045 | 22562 | 21569 | 22582 | 23417 | 40741 | 42023 | 75933 | 22558 | 19868 | 22286 |
| 8.54 | 44624 | 23928 | 20582 | 22494 | 23014 | 38740 | 38070 | 77091 | 19540 | 18684 | 22893 |
| 8.58 | 48783 | 24059 | 20312 | 24466 | 23371 | 39207 | 33997 | 71625 | 20639 | 22298 | 24300 |
| 8.62 | 49671 | 23685 | 21859 | 24460 | 23281 | 34041 | 29543 | 62049 | 18850 | 20670 | 22718 |
| 8.66 | 46286 | 23220 | 21237 | 25016 | 21705 | 34349 | 27794 | 52563 | 18722 | 18529 | 24474 |
| 8.7 | 46509 | 22991 | 21364 | 26090 | 24359 | 31437 | 25192 | 52217 | 18838 | 19373 | 21315 |
| 8.74 | 47361 | 24240 | 20720 | 25071 | 25094 | 25195 | 24000 | 50503 | 19806 | 20219 | 19615 |
| 8.78 | 47378 | 26712 | 22261 | 24338 | 22382 | 26819 | 22853 | 47899 | 19984 | 21377 | 21753 |
| 8.82 | 49396 | 23550 | 22078 | 25789 | 20684 | 26358 | 29360 | 45886 | 18617 | 23039 | 21455 |
| 8.86 | 43643 | 23227 | 23859 | 24499 | 23561 | 26839 | 24348 | 46259 | 20156 | 22335 | 23035 |
| 8.9 | 44964 | 23029 | 21416 | 25528 | 23831 | 25646 | 25651 | 42656 | 18681 | 20574 | 22552 |
| 8.94 | 43167 | 23332 | 23369 | 22979 | 23658 | 27229 | 26607 | 46006 | 19160 | 20138 | 21669 |
| 8.98 | 46209 | 24282 | 23965 | 23421 | 21453 | 23956 | 25978 | 46377 | 20359 | 19905 | 23919 |
| 9.02 | 46312 | 25979 | 21932 | 25464 | 24163 | 27349 | 26219 | 48063 | 20621 | 22296 | 22485 |
| 9.06 | 44241 | 22734 | 22589 | 26579 | 22083 | 28083 | 25558 | 45564 | 20535 | 21570 | 27412 |
| 9.1 | 42516 | 25237 | 23742 | 24466 | 20664 | 24904 | 25935 | 45656 | 22316 | 18148 | 21048 |
| 9.14 | 43986 | 25419 | 23627 | 25603 | 24158 | 27719 | 23745 | 46177 | 18623 | 19776 | 22663 |
| 9.18 | 44074 | 24743 | 24204 | 27757 | 22248 | 28458 | 27689 | 48266 | 18734 | 20924 | 24472 |
| 9.22 | 43089 | 26513 | 22130 | 28219 | 23182 | 26157 | 30840 | 50141 | 19025 | 21628 | 23927 |
| 9.26 | 43741 | 24122 | 25577 | 30288 | 23998 | 28321 | 29987 | 49018 | 22593 | 21986 | 24878 |
| 9.3 | 44358 | 24429 | 26190 | 32061 | 23462 | 28021 | 30882 | 47732 | 22484 | 22467 | 23196 |
| 9.34 | 43061 | 25319 | 23105 | 33142 | 22874 | 31385 | 31628 | 50596 | 21530 | 22350 | 24627 |
| 9.38 | 43343 | 27808 | 25813 | 32275 | 23466 | 32747 | 33896 | 52155 | 23962 | 20804 | 21046 |
| 9.42 | 42504 | 25490 | 24013 | 30431 | 23724 | 26542 | 33489 | 51541 | 21037 | 21245 | 20666 |
| 9.46 | 42604 | 24021 | 25153 | 30815 | 23057 | 28419 | 31112 | 46488 | 19055 | 19735 | 21883 |
| 9.5 | 44650 | 25254 | 24954 | 29596 | 21356 | 24089 | 27739 | 43174 | 21292 | 21481 | 22758 |
| 9.54 | 43972 | 24638 | 25000 | 28979 | 25091 | 26002 | 27307 | 48210 | 22210 | 22050 | 22895 |
| 9.58 | 46263 | 24280 | 26854 | 29616 | 25076 | 26103 | 27464 | 44688 | 20019 | 23832 | 22509 |
| 9.62 | 44863 | 25022 | 28250 | 26604 | 26375 | 26285 | 25765 | 42518 | 20834 | 24172 | 22329 |
| 9.66 | 44544 | 26003 | 25599 | 25158 | 21093 | 27877 | 25013 | 46417 | 21036 | 23555 | 24525 |
| 9.7 | 41233 | 26127 | 27164 | 25597 | 22843 | 25990 | 25406 | 47017 | 21873 | 23498 | 23684 |
| 9.74 | 42605 | 25936 | 30141 | 26752 | 22996 | 24485 | 24835 | 42680 | 21599 | 20668 | 22839 |
| 9.78 | 44111 | 23679 | 30002 | 25551 | 24684 | 26603 | 24105 | 43151 | 24648 | 20506 | 20834 |
| 9.82 | 44431 | 25929 | 31010 | 23906 | 23812 | 28426 | 26442 | 41124 | 24487 | 23414 | 23504 |
| 9.86 | 46038 | 25542 | 31647 | 23898 | 23466 | 26733 | 27615 | 41756 | 24154 | 25851 | 23718 |
| 9.9 | 49756 | 27288 | 29688 | 26311 | 25426 | 28123 | 24012 | 44036 | 24091 | 25168 | 21498 |
| 9.94 | 46952 | 26277 | 30083 | 28439 | 23723 | 28213 | 26732 | 47006 | 24950 | 25912 | 23740 |
| 9.98 | 50946 | 25193 | 29784 | 29129 | 26247 | 26878 | 27081 | 46257 | 23229 | 25538 | 23115 |
| 10.02 | 53501 | 24468 | 27869 | 27513 | 24536 | 25976 | 28167 | 45223 | 24222 | 26140 | 24299 |
| 10.06 | 58012 | 25241 | 28225 | 27860 | 25322 | 28630 | 26563 | 45576 | 22902 | 26000 | 21782 |
| 10.1 | 56234 | 26894 | 24430 | 25861 | 23661 | 26984 | 28996 | 43426 | 23725 | 24452 | 22015 |
| 10.14 | 59986 | 30322 | 28800 | 25927 | 23311 | 27766 | 28011 | 45345 | 23860 | 25622 | 21421 |
| 10.18 | 52493 | 30073 | 27237 | 27319 | 26674 | 26114 | 28858 | 47501 | 23584 | 26250 | 22478 |
| 10.22 | 56274 | 25623 | 24943 | 25952 | 25021 | 29448 | 27201 | 47510 | 23113 | 24651 | 21638 |
| 10.26 | 54657 | 27202 | 27357 | 27325 | 23844 | 29950 | 29410 | 46606 | 24291 | 26821 | 23444 |
| 10.3 | 52040 | 29151 | 26818 | 27613 | 26890 | 31155 | 32363 | 45143 | 24370 | 24421 | 25233 |
| 10.34 | 51455 | 26488 | 25744 | 27438 | 29147 | 29730 | 33705 | 50436 | 24930 | 26113 | 23937 |
| 10.38 | 52144 | 25581 | 26095 | 30005 | 24777 | 28615 | 31657 | 49158 | 24174 | 26434 | 24613 |
| 10.42 | 50986 | 24920 | 27481 | 27437 | 28726 | 28824 | 30458 | 49289 | 23126 | 23370 | 22083 |
| 10.46 | 49208 | 27531 | 27037 | 30503 | 27658 | 29513 | 29726 | 49466 | 25475 | 24398 | 24082 |
| 10.5 | 54155 | 30637 | 29007 | 32614 | 28987 | 30330 | 31415 | 48894 | 24052 | 24842 | 24315 |
| 10.54 | 55684 | 31318 | 27442 | 33672 | 29527 | 28629 | 31087 | 46940 | 24563 | 24260 | 21307 |
| 10.58 | 62725 | 28780 | 29819 | 31225 | 27746 | 28500 | 27770 | 43067 | 24543 | 24198 | 24641 |

-continued

| | | | | | | | | | | | |
|---|---|---|---|---|---|---|---|---|---|---|---|
| 10.62 | 66622 | 29670 | 29338 | 32111 | 27592 | 29437 | 28086 | 47112 | 24050 | 23538 | 24307 |
| 10.66 | 68758 | 32016 | 33543 | 33588 | 30162 | 31480 | 26751 | 48575 | 27661 | 25669 | 25757 |
| 10.7 | 70094 | 31297 | 37473 | 36991 | 28147 | 32211 | 29615 | 49974 | 27436 | 26104 | 27664 |
| 10.74 | 69924 | 30797 | 43375 | 40429 | 27615 | 31806 | 28975 | 49324 | 26210 | 25441 | 25955 |
| 10.78 | 66834 | 34144 | 43230 | 39907 | 31686 | 28014 | 28007 | 46224 | 27200 | 24589 | 26932 |
| 10.82 | 64061 | 34549 | 44432 | 49590 | 30013 | 32639 | 30979 | 49564 | 27717 | 28109 | 26504 |
| 10.86 | 67612 | 34472 | 46770 | 50974 | 31341 | 31010 | 27948 | 47130 | 28241 | 29937 | 27632 |
| 10.9 | 63001 | 33226 | 48392 | 49629 | 32319 | 29310 | 26733 | 49337 | 27919 | 28393 | 28778 |
| 10.94 | 58608 | 34099 | 49410 | 50362 | 31923 | 30809 | 27941 | 50093 | 27400 | 27051 | 28062 |
| 10.98 | 57066 | 31320 | 45417 | 50388 | 32282 | 30293 | 26566 | 49563 | 27996 | 25849 | 31446 |
| 11.02 | 52506 | 33622 | 48588 | 50140 | 30677 | 33276 | 28197 | 52435 | 27000 | 27587 | 29666 |
| 11.06 | 54113 | 29439 | 42830 | 49479 | 30481 | 31809 | 29565 | 55120 | 27129 | 29246 | 29427 |
| 11.1 | 51306 | 32572 | 41406 | 44620 | 29906 | 33986 | 29852 | 58063 | 26945 | 28731 | 30106 |
| 11.14 | 45655 | 33311 | 36897 | 39920 | 31918 | 36045 | 29668 | 65199 | 26659 | 30638 | 28373 |
| 11.18 | 46491 | 35150 | 33940 | 35350 | 31580 | 38266 | 33392 | 68880 | 26539 | 29288 | 29288 |
| 11.22 | 49990 | 36615 | 32017 | 32784 | 32929 | 41924 | 36303 | 74673 | 27181 | 33662 | 28884 |
| 11.26 | 47956 | 37260 | 31764 | 32919 | 32696 | 46815 | 41144 | 78861 | 31033 | 33750 | 28890 |
| 11.3 | 47594 | 39242 | 31626 | 31825 | 29269 | 51621 | 44537 | 85500 | 30331 | 34373 | 27535 |
| 11.34 | 49547 | 40408 | 31878 | 32940 | 29644 | 51632 | 44457 | 87602 | 33246 | 33408 | 29067 |
| 11.38 | 47660 | 40914 | 31911 | 33006 | 30393 | 54826 | 47530 | 94301 | 33660 | 37291 | 27718 |
| 11.42 | 46298 | 40253 | 31672 | 29388 | 29923 | 56762 | 45884 | 97379 | 33214 | 38341 | 28770 |
| 11.46 | 49051 | 44643 | 32923 | 30614 | 31086 | 56278 | 48061 | 97666 | 36524 | 34937 | 28019 |
| 11.5 | 48114 | 40884 | 31027 | 28898 | 30318 | 57067 | 45910 | 95587 | 34289 | 34636 | 28532 |
| 11.54 | 49068 | 41367 | 33546 | 29252 | 29599 | 58132 | 47526 | 100184 | 31382 | 32677 | 28714 |
| 11.58 | 51925 | 43280 | 32283 | 27956 | 30820 | 55966 | 44072 | 102516 | 34261 | 31799 | 29376 |
| 11.62 | 48917 | 48341 | 31865 | 29294 | 29973 | 55734 | 43540 | 101949 | 33500 | 31404 | 29781 |
| 11.66 | 51969 | 46813 | 32887 | 29753 | 29848 | 52147 | 42633 | 99219 | 31708 | 30752 | 29786 |
| 11.7 | 50789 | 46432 | 33479 | 30878 | 31656 | 53204 | 44652 | 102346 | 33858 | 30353 | 28584 |
| 11.74 | 56751 | 47257 | 31323 | 31938 | 32439 | 51207 | 50142 | 96918 | 31500 | 33290 | 28988 |
| 11.78 | 57660 | 44241 | 32917 | 30681 | 30997 | 47829 | 53989 | 91794 | 32354 | 30174 | 28261 |
| 11.82 | 54926 | 42549 | 30914 | 26546 | 30784 | 47100 | 57285 | 93187 | 33568 | 29458 | 28446 |
| 11.86 | 57687 | 43000 | 33117 | 32244 | 30031 | 44311 | 59219 | 87132 | 30680 | 29724 | 30650 |
| 11.9 | 60178 | 41679 | 33204 | 30260 | 31805 | 44366 | 67145 | 77154 | 33021 | 29904 | 29353 |
| 11.94 | 62251 | 41452 | 30689 | 30787 | 32303 | 44838 | 71287 | 71990 | 33366 | 28259 | 28035 |
| 11.98 | 63309 | 41803 | 33151 | 29100 | 32266 | 40094 | 71247 | 71077 | 32359 | 30557 | 26162 |
| 12.02 | 63889 | 39411 | 33725 | 28637 | 32080 | 40356 | 70880 | 69860 | 34533 | 30929 | 27584 |
| 12.06 | 62476 | 40219 | 32401 | 30209 | 29692 | 38744 | 74606 | 69297 | 30815 | 29699 | 26518 |
| 12.1 | 65635 | 42948 | 34311 | 30095 | 32412 | 41866 | 74808 | 70017 | 31348 | 30018 | 27364 |
| 12.14 | 65137 | 42521 | 35385 | 33342 | 32389 | 39978 | 69543 | 76589 | 32849 | 34287 | 28890 |
| 12.18 | 64411 | 44778 | 30626 | 30921 | 31081 | 40876 | 66984 | 85458 | 29438 | 29388 | 25078 |
| 12.22 | 64964 | 43545 | 32983 | 29206 | 29592 | 40966 | 65909 | 89406 | 28346 | 29456 | 28846 |
| 12.26 | 69012 | 46195 | 32733 | 30525 | 29505 | 38047 | 61571 | 91930 | 29703 | 30333 | 27790 |
| 12.3 | 69705 | 43742 | 33829 | 30292 | 31272 | 37537 | 56221 | 91515 | 30205 | 29366 | 28124 |
| 12.34 | 63871 | 46126 | 33307 | 35577 | 30906 | 38957 | 53032 | 95870 | 31007 | 32348 | 29130 |
| 12.38 | 66300 | 45990 | 35263 | 36339 | 31705 | 40984 | 49428 | 91680 | 32261 | 31032 | 28322 |
| 12.42 | 67830 | 44889 | 41210 | 37268 | 30730 | 40288 | 47202 | 94247 | 35843 | 30167 | 31064 |
| 12.46 | 63752 | 43023 | 44721 | 42735 | 32411 | 38000 | 49208 | 87412 | 35217 | 31681 | 31127 |
| 12.5 | 66289 | 43853 | 49055 | 42667 | 31178 | 39206 | 52582 | 87194 | 37948 | 28332 | 27697 |
| 12.54 | 63137 | 41440 | 54727 | 45227 | 30528 | 39125 | 54806 | 82278 | 41255 | 31062 | 29341 |
| 12.58 | 60285 | 45867 | 58010 | 47522 | 32110 | 43848 | 55985 | 82331 | 42726 | 29363 | 32522 |
| 12.62 | 64403 | 49739 | 58364 | 49304 | 30442 | 38632 | 57887 | 77475 | 43263 | 28318 | 27353 |
| 12.66 | 63140 | 48886 | 57399 | 50599 | 30846 | 40547 | 59382 | 76888 | 42314 | 30388 | 30656 |
| 12.7 | 61657 | 47749 | 55275 | 52694 | 33067 | 39436 | 58380 | 73409 | 41231 | 31059 | 27227 |
| 12.74 | 63527 | 49926 | 57827 | 52486 | 29837 | 40786 | 58228 | 72959 | 41589 | 32383 | 29013 |
| 12.78 | 61376 | 50402 | 51693 | 48444 | 32847 | 39938 | 56173 | 70807 | 39068 | 31422 | 30767 |
| 12.82 | 62050 | 50304 | 46602 | 43853 | 30953 | 40885 | 54005 | 70674 | 36476 | 30373 | 27141 |
| 12.86 | 64084 | 48604 | 38245 | 43163 | 29905 | 40318 | 51942 | 76739 | 35034 | 33289 | 29119 |
| 12.9 | 62715 | 49669 | 37075 | 38601 | 30612 | 40597 | 47172 | 71779 | 33060 | 34461 | 28810 |
| 12.94 | 63445 | 44546 | 34590 | 37980 | 31481 | 39705 | 48130 | 78647 | 30067 | 34577 | 33267 |
| 12.98 | 63316 | 46075 | 28994 | 35219 | 31311 | 42354 | 41927 | 83135 | 29902 | 37471 | 34626 |
| 13.02 | 67018 | 41398 | 30855 | 35087 | 28895 | 45007 | 40377 | 87120 | 32257 | 36790 | 34643 |
| 13.06 | 65302 | 39622 | 31339 | 36230 | 31250 | 47261 | 35823 | 93404 | 32387 | 40874 | 33291 |
| 13.1 | 65361 | 42316 | 30989 | 36016 | 29532 | 46963 | 34573 | 95310 | 33536 | 40358 | 36750 |
| 13.14 | 61446 | 39602 | 30529 | 39069 | 29287 | 45238 | 30736 | 102227 | 33214 | 42165 | 34965 |
| 13.18 | 62996 | 37263 | 34869 | 41574 | 29634 | 48561 | 30633 | 100957 | 35109 | 43502 | 36796 |
| 13.22 | 68874 | 37183 | 33612 | 43509 | 30506 | 48967 | 30738 | 102644 | 32993 | 44143 | 34665 |
| 13.26 | 67864 | 38612 | 39712 | 43127 | 31388 | 48302 | 30997 | 99155 | 34420 | 44202 | 38406 |
| 13.3 | 72279 | 36800 | 45152 | 47209 | 31184 | 44852 | 29970 | 100028 | 34947 | 45787 | 36425 |
| 13.34 | 74120 | 36133 | 58155 | 46502 | 28576 | 41714 | 29300 | 96052 | 34971 | 49248 | 36790 |
| 13.38 | 78371 | 38617 | 71871 | 47729 | 29329 | 41915 | 29211 | 90607 | 36958 | 48575 | 37987 |
| 13.42 | 91432 | 39189 | 84683 | 49106 | 30566 | 40800 | 32635 | 82753 | 39167 | 46384 | 34024 |
| 13.46 | 98084 | 36128 | 93529 | 46712 | 30634 | 40474 | 30608 | 75003 | 39655 | 44035 | 37513 |
| 13.5 | 104949 | 39684 | 106307 | 44958 | 27781 | 35594 | 28316 | 74673 | 42633 | 42242 | 39469 |
| 13.54 | 111788 | 39015 | 109400 | 43916 | 28011 | 36775 | 29367 | 73875 | 45706 | 40904 | 42006 |
| 13.58 | 115438 | 41365 | 104402 | 41399 | 28794 | 37577 | 29620 | 69965 | 45999 | 39314 | 43545 |
| 13.62 | 114646 | 41139 | 105148 | 41524 | 30196 | 36066 | 29695 | 74929 | 46617 | 39723 | 42212 |
| 13.66 | 116000 | 44185 | 102172 | 37787 | 30897 | 35550 | 30933 | 78910 | 45227 | 39588 | 44615 |
| 13.7 | 114135 | 43143 | 84620 | 38364 | 30034 | 35324 | 33050 | 80926 | 41113 | 38574 | 46363 |
| 13.74 | 104216 | 47167 | 72823 | 38181 | 30399 | 37790 | 31307 | 77183 | 38574 | 43142 | 46878 |

-continued

| | | | | | | | | | | | |
|---|---|---|---|---|---|---|---|---|---|---|---|
| 13.78 | 102003 | 45223 | 59483 | 36229 | 30193 | 38351 | 29667 | 81515 | 36381 | 45013 | 49007 |
| 13.82 | 93034 | 47059 | 48110 | 32044 | 27557 | 39350 | 29019 | 83606 | 34023 | 52129 | 51816 |
| 13.86 | 87676 | 43989 | 39341 | 32335 | 30746 | 36280 | 28960 | 80497 | 30712 | 54264 | 52025 |
| 13.9 | 82478 | 43562 | 37089 | 34547 | 28977 | 35757 | 30816 | 78839 | 29720 | 60146 | 54498 |
| 13.94 | 73263 | 44873 | 30668 | 32662 | 28431 | 37730 | 29327 | 78744 | 28612 | 61786 | 58538 |
| 13.98 | 70618 | 43588 | 29793 | 31983 | 30893 | 34752 | 32201 | 75810 | 26933 | 63903 | 66410 |
| 14.02 | 71390 | 41853 | 29177 | 34312 | 31723 | 37660 | 29134 | 74462 | 26912 | 64719 | 66218 |
| 14.06 | 71839 | 44466 | 28711 | 34446 | 32337 | 37416 | 29459 | 69386 | 27593 | 64190 | 68367 |
| 14.1 | 71593 | 42368 | 28876 | 33667 | 32223 | 36625 | 28833 | 66482 | 23445 | 59519 | 68867 |
| 14.14 | 68383 | 41613 | 31108 | 32666 | 31208 | 37712 | 29397 | 62264 | 24871 | 53591 | 67983 |
| 14.18 | 70202 | 41383 | 28744 | 33884 | 29178 | 36898 | 29106 | 59965 | 23753 | 47803 | 68178 |
| 14.22 | 68350 | 41296 | 29624 | 31990 | 31958 | 32542 | 27651 | 60483 | 25291 | 43808 | 70138 |
| 14.26 | 67842 | 38842 | 30845 | 34170 | 29425 | 35763 | 27830 | 61910 | 24576 | 38697 | 62086 |
| 14.3 | 64499 | 41576 | 29212 | 32581 | 32501 | 37378 | 30679 | 64302 | 23974 | 34364 | 58395 |
| 14.34 | 70707 | 42007 | 29787 | 35096 | 28687 | 35955 | 28309 | 57473 | 25920 | 32335 | 53383 |
| 14.38 | 68749 | 41000 | 29242 | 37637 | 29067 | 35473 | 27681 | 58528 | 25951 | 29567 | 47465 |
| 14.42 | 67077 | 40957 | 34077 | 36233 | 31823 | 38715 | 28056 | 60040 | 27897 | 28955 | 47399 |
| 14.46 | 66563 | 41471 | 39367 | 35129 | 30840 | 36191 | 29579 | 59864 | 27139 | 29848 | 39779 |
| 14.5 | 69290 | 42604 | 49252 | 36420 | 31799 | 35748 | 29451 | 56919 | 27690 | 25027 | 39324 |
| 14.54 | 67030 | 42845 | 62681 | 38542 | 32530 | 38129 | 31650 | 58641 | 25552 | 24574 | 39007 |
| 14.58 | 65294 | 38120 | 71820 | 40929 | 31777 | 38015 | 31617 | 58017 | 30009 | 27133 | 33547 |
| 14.62 | 67161 | 38254 | 85649 | 44851 | 31913 | 37269 | 31715 | 61570 | 30182 | 28899 | 32897 |
| 14.66 | 67338 | 37995 | 89436 | 49337 | 30905 | 36183 | 31271 | 62908 | 29958 | 25972 | 32506 |
| 14.7 | 64786 | 36110 | 92007 | 56407 | 30187 | 37056 | 31842 | 60140 | 26571 | 26864 | 31018 |
| 14.74 | 64238 | 37056 | 95663 | 57932 | 32911 | 37059 | 31289 | 62734 | 25025 | 30145 | 30585 |
| 14.78 | 62196 | 36742 | 93257 | 66361 | 32485 | 37711 | 32899 | 66360 | 24717 | 28953 | 33193 |
| 14.82 | 63798 | 35418 | 92222 | 71623 | 30012 | 34198 | 34911 | 61478 | 25939 | 26708 | 30444 |
| 14.86 | 67708 | 34150 | 80228 | 75400 | 31484 | 36886 | 33095 | 62725 | 22384 | 27910 | 32908 |
| 14.9 | 64340 | 35381 | 70286 | 77148 | 29911 | 37126 | 32496 | 65140 | 23537 | 28034 | 31823 |
| 14.94 | 62853 | 34420 | 59628 | 76261 | 31610 | 34005 | 33360 | 63732 | 21502 | 27614 | 30230 |
| 14.98 | 64324 | 34653 | 50815 | 69795 | 30652 | 38417 | 33004 | 65244 | 25029 | 27716 | 29784 |
| 15.02 | 59274 | 35002 | 40326 | 64355 | 31744 | 34545 | 34284 | 67511 | 25945 | 29792 | 30904 |
| 15.06 | 60014 | 34998 | 39527 | 63096 | 28984 | 37258 | 33258 | 70041 | 23962 | 28903 | 30247 |
| 15.1 | 63693 | 33799 | 41133 | 54996 | 30907 | 37411 | 33227 | 74002 | 22337 | 28147 | 29616 |
| 15.14 | 63864 | 35013 | 40874 | 48251 | 30810 | 35189 | 31946 | 70795 | 22860 | 29236 | 29486 |
| 15.18 | 59653 | 32862 | 46880 | 38680 | 30824 | 34210 | 32316 | 68821 | 22427 | 27482 | 29702 |
| 15.22 | 57822 | 33340 | 46527 | 39337 | 30695 | 33147 | 32696 | 75078 | 21737 | 25864 | 28664 |
| 15.26 | 61589 | 35970 | 52983 | 38055 | 31659 | 33493 | 30621 | 72391 | 23542 | 28162 | 27788 |
| 15.3 | 61874 | 37345 | 50995 | 36821 | 31202 | 34324 | 29397 | 76264 | 24014 | 27252 | 29183 |
| 15.34 | 63248 | 35585 | 53433 | 40471 | 32664 | 36425 | 30497 | 77525 | 23827 | 28065 | 28941 |
| 15.38 | 61430 | 37672 | 52942 | 41657 | 30303 | 37560 | 29684 | 80065 | 22666 | 26645 | 28267 |
| 15.42 | 67013 | 36757 | 51511 | 43483 | 30927 | 37464 | 30088 | 79021 | 26832 | 27373 | 30323 |
| 15.46 | 65971 | 38670 | 49296 | 45091 | 31560 | 39370 | 29161 | 81843 | 25866 | 27141 | 28015 |
| 15.5 | 66959 | 35841 | 45878 | 49109 | 32063 | 37369 | 30414 | 82860 | 26781 | 27349 | 29067 |
| 15.54 | 69593 | 37046 | 44631 | 53048 | 31189 | 36012 | 28653 | 83244 | 25364 | 31451 | 29417 |
| 15.58 | 73847 | 36668 | 40469 | 52796 | 30869 | 35885 | 32382 | 80742 | 26637 | 32045 | 28992 |
| 15.62 | 75184 | 36468 | 37336 | 53731 | 31579 | 37198 | 31891 | 78024 | 28091 | 34421 | 30886 |
| 15.66 | 80447 | 38145 | 39722 | 52707 | 29627 | 38497 | 33712 | 76997 | 26827 | 36990 | 31886 |
| 15.7 | 86628 | 38795 | 40715 | 53564 | 30065 | 37059 | 34927 | 79751 | 27897 | 38504 | 32366 |
| 15.74 | 92226 | 35967 | 43280 | 50294 | 30889 | 37536 | 37510 | 73203 | 30357 | 38926 | 32300 |
| 15.78 | 96086 | 37155 | 45378 | 50485 | 32598 | 37560 | 37262 | 72492 | 30267 | 42001 | 32517 |
| 15.82 | 101312 | 34976 | 51899 | 45996 | 31717 | 38057 | 38738 | 69942 | 30457 | 42260 | 34359 |
| 15.86 | 96733 | 35167 | 52185 | 43580 | 30078 | 36825 | 40432 | 72116 | 29530 | 41431 | 32971 |
| 15.9 | 98926 | 38512 | 56342 | 42831 | 31405 | 39270 | 39654 | 72532 | 31142 | 42084 | 33718 |
| 15.94 | 105194 | 37937 | 61204 | 39824 | 32115 | 39504 | 39309 | 73324 | 27682 | 41265 | 33687 |
| 15.98 | 101162 | 36930 | 62945 | 36837 | 32657 | 39019 | 40461 | 70169 | 29794 | 38748 | 33413 |
| 16.02 | 102916 | 36352 | 60160 | 35976 | 31470 | 41233 | 35693 | 69334 | 27723 | 39672 | 32446 |
| 16.06 | 97729 | 35560 | 56251 | 35279 | 32724 | 40220 | 33177 | 70134 | 26364 | 38128 | 34881 |
| 16.1 | 93741 | 36713 | 49018 | 33996 | 31664 | 40995 | 33381 | 70517 | 26808 | 36372 | 31112 |
| 16.14 | 90687 | 37711 | 44205 | 34835 | 30333 | 40391 | 32965 | 68053 | 28382 | 32219 | 32318 |
| 16.18 | 86144 | 39288 | 42051 | 32019 | 30238 | 41044 | 31545 | 69932 | 32243 | 31551 | 30837 |
| 16.22 | 82784 | 36274 | 35760 | 35995 | 31695 | 40133 | 30577 | 68396 | 36036 | 31169 | 32442 |
| 16.26 | 80624 | 37673 | 29154 | 32948 | 30948 | 39401 | 30435 | 74888 | 37271 | 31221 | 33164 |
| 16.3 | 79894 | 37228 | 28768 | 34988 | 31721 | 41844 | 29712 | 74702 | 41011 | 31064 | 34187 |
| 16.34 | 74691 | 36723 | 28832 | 33965 | 30611 | 42014 | 31126 | 73272 | 49258 | 28869 | 33913 |
| 16.38 | 70176 | 38350 | 26930 | 34570 | 31369 | 39296 | 31167 | 76047 | 56845 | 29105 | 34144 |
| 16.42 | 72651 | 39016 | 26414 | 34248 | 35174 | 42779 | 30168 | 77629 | 62255 | 27803 | 36292 |
| 16.46 | 76456 | 37788 | 27382 | 33270 | 35093 | 41191 | 30451 | 82020 | 68282 | 28644 | 41157 |
| 16.5 | 72495 | 38151 | 26243 | 33524 | 35079 | 40987 | 32936 | 80072 | 74767 | 29511 | 44264 |
| 16.54 | 75563 | 38561 | 25532 | 30403 | 33935 | 42532 | 32839 | 83548 | 75641 | 32464 | 42285 |
| 16.58 | 77068 | 38443 | 28174 | 32544 | 35705 | 38937 | 32768 | 81612 | 76606 | 32746 | 41797 |
| 16.62 | 76143 | 37858 | 25330 | 33364 | 34422 | 38409 | 32196 | 86788 | 74026 | 32095 | 41451 |
| 16.66 | 76986 | 39269 | 24312 | 35394 | 33645 | 38886 | 35132 | 91155 | 70712 | 34280 | 42142 |
| 16.7 | 74352 | 35696 | 24900 | 31469 | 35746 | 41140 | 33125 | 87846 | 65954 | 34902 | 41655 |
| 16.74 | 79848 | 36398 | 24714 | 33739 | 33565 | 41602 | 34577 | 85513 | 56112 | 35323 | 43013 |
| 16.78 | 78098 | 32455 | 26069 | 33605 | 34070 | 39657 | 36703 | 84050 | 53356 | 35324 | 40664 |
| 16.82 | 78326 | 31909 | 24088 | 32406 | 33646 | 41555 | 34650 | 81259 | 45224 | 36726 | 37281 |
| 16.86 | 77872 | 35452 | 24467 | 33255 | 31601 | 41967 | 38101 | 79074 | 38062 | 32074 | 36989 |
| 16.9 | 78023 | 31864 | 26297 | 32475 | 31982 | 43639 | 35204 | 76492 | 32829 | 30131 | 37883 |

-continued

| | | | | | | | | | | | |
|---|---|---|---|---|---|---|---|---|---|---|---|
| 16.94 | 79957 | 34575 | 23592 | 34264 | 33041 | 45668 | 36757 | 76578 | 28122 | 28096 | 35571 |
| 16.98 | 79210 | 32167 | 25002 | 35628 | 33686 | 43599 | 33318 | 72801 | 27074 | 28290 | 34034 |
| 17.02 | 86564 | 34241 | 24414 | 32909 | 30603 | 45954 | 35004 | 77682 | 24085 | 26716 | 36761 |
| 17.06 | 85309 | 33032 | 25899 | 35533 | 29225 | 46470 | 36771 | 76728 | 25256 | 25243 | 38171 |
| 17.1 | 87917 | 33269 | 24163 | 34422 | 31620 | 49444 | 36366 | 75758 | 24534 | 26093 | 36686 |
| 17.14 | 89539 | 33299 | 24324 | 35181 | 31733 | 47842 | 37069 | 77851 | 25384 | 25825 | 37026 |
| 17.18 | 85923 | 36603 | 24664 | 36438 | 31350 | 49467 | 34069 | 76453 | 26748 | 25584 | 35630 |
| 17.22 | 86630 | 34260 | 25315 | 39515 | 29378 | 50041 | 34002 | 74234 | 25914 | 26121 | 35058 |
| 17.26 | 86752 | 35772 | 23993 | 36302 | 29172 | 49108 | 34730 | 75939 | 27037 | 24571 | 35463 |
| 17.3 | 80216 | 37629 | 25277 | 38723 | 29343 | 45145 | 31419 | 73437 | 25729 | 26074 | 35711 |
| 17.34 | 81360 | 36691 | 25081 | 35202 | 29949 | 46914 | 34952 | 75290 | 25629 | 27617 | 36000 |
| 17.38 | 77048 | 36668 | 24394 | 36640 | 29401 | 49882 | 32831 | 72857 | 25970 | 26646 | 34923 |
| 17.42 | 81258 | 37040 | 23941 | 40059 | 31359 | 48364 | 32282 | 70093 | 25450 | 26482 | 37331 |
| 17.46 | 76840 | 33284 | 25730 | 38337 | 29401 | 47643 | 30665 | 70083 | 26091 | 27297 | 34723 |
| 17.5 | 72174 | 36145 | 27285 | 39640 | 29646 | 48241 | 30771 | 68229 | 24327 | 25168 | 36324 |
| 17.54 | 74265 | 34915 | 26160 | 37825 | 28363 | 43069 | 31525 | 66302 | 23926 | 25072 | 33873 |
| 17.58 | 75240 | 36032 | 27633 | 40151 | 29998 | 45466 | 30933 | 67854 | 21854 | 25072 | 35618 |
| 17.62 | 71582 | 35806 | 27160 | 38447 | 29597 | 48315 | 31654 | 66101 | 22640 | 24318 | 34427 |
| 17.66 | 66223 | 36294 | 27032 | 40181 | 29203 | 45726 | 29852 | 64819 | 21845 | 23734 | 36492 |
| 17.7 | 66805 | 35944 | 27553 | 36746 | 30722 | 45546 | 32339 | 63661 | 21320 | 24708 | 37340 |
| 17.74 | 67979 | 36890 | 25734 | 36173 | 29622 | 46083 | 31542 | 61959 | 24617 | 24319 | 35436 |
| 17.78 | 67928 | 35697 | 26527 | 35956 | 29918 | 46276 | 31656 | 62686 | 27086 | 24671 | 37543 |
| 17.82 | 66082 | 35964 | 27070 | 34645 | 31843 | 45053 | 34143 | 63833 | 26928 | 25393 | 38372 |
| 17.86 | 64788 | 38624 | 26523 | 36027 | 31010 | 45745 | 33678 | 63429 | 27311 | 26600 | 36370 |
| 17.9 | 64630 | 35962 | 27166 | 34984 | 29516 | 45998 | 35036 | 66759 | 27969 | 27318 | 34258 |
| 17.94 | 64852 | 36522 | 29109 | 34538 | 28518 | 45109 | 35547 | 63872 | 29357 | 26160 | 34717 |
| 17.98 | 63389 | 38020 | 27222 | 34300 | 28777 | 47642 | 33273 | 65248 | 30275 | 27730 | 36430 |
| 18.02 | 65722 | 38652 | 28972 | 33769 | 29813 | 44553 | 33178 | 68336 | 27243 | 28818 | 35344 |
| 18.06 | 63141 | 39499 | 27760 | 35335 | 30031 | 46796 | 33822 | 69706 | 27295 | 27463 | 36517 |
| 18.1 | 64470 | 37061 | 27456 | 34450 | 28778 | 46133 | 31220 | 70667 | 30052 | 29548 | 35461 |
| 18.14 | 67959 | 38304 | 27282 | 37281 | 29741 | 47901 | 33278 | 71667 | 29073 | 30900 | 33998 |
| 18.18 | 65660 | 39100 | 27440 | 36286 | 29796 | 49009 | 31511 | 73667 | 33161 | 35754 | 34006 |
| 18.22 | 67549 | 37985 | 26721 | 38312 | 29996 | 48707 | 31443 | 75184 | 34666 | 37336 | 35116 |
| 18.26 | 66365 | 36227 | 25342 | 36574 | 29071 | 49833 | 32588 | 73031 | 32758 | 36385 | 35930 |
| 18.3 | 65969 | 34367 | 25993 | 39627 | 28418 | 50831 | 32285 | 71403 | 32263 | 39739 | 33833 |
| 18.34 | 68854 | 33796 | 25446 | 39276 | 29191 | 52159 | 31517 | 72723 | 35024 | 38960 | 34069 |
| 18.38 | 67899 | 31707 | 26944 | 39075 | 29001 | 53452 | 33855 | 78841 | 33712 | 35970 | 32880 |
| 18.42 | 65052 | 33690 | 27606 | 40053 | 30667 | 51411 | 35928 | 75728 | 30343 | 36637 | 32496 |
| 18.46 | 64254 | 32168 | 26943 | 40577 | 29470 | 51306 | 38045 | 78910 | 26535 | 35810 | 31715 |
| 18.5 | 65896 | 33072 | 29168 | 39393 | 28956 | 52161 | 40008 | 79495 | 25346 | 32480 | 32128 |
| 18.54 | 62656 | 32726 | 32074 | 41061 | 27915 | 49911 | 41170 | 76948 | 24780 | 31497 | 33107 |
| 18.58 | 61819 | 29558 | 30985 | 42269 | 30668 | 51397 | 41596 | 77931 | 24216 | 27123 | 34820 |
| 18.62 | 64023 | 32698 | 32374 | 41588 | 29992 | 52517 | 44513 | 74054 | 20460 | 28847 | 33866 |
| 18.66 | 65103 | 30581 | 33835 | 42232 | 29163 | 52562 | 45194 | 75031 | 20611 | 24369 | 32735 |
| 18.7 | 66301 | 31957 | 32184 | 42170 | 28654 | 50850 | 44692 | 76742 | 20510 | 24856 | 33718 |
| 18.74 | 63738 | 32612 | 32589 | 48342 | 27880 | 50569 | 46175 | 76253 | 20675 | 24515 | 34003 |
| 18.78 | 62972 | 34099 | 30907 | 46861 | 29668 | 54031 | 43837 | 78117 | 19532 | 22964 | 36205 |
| 18.82 | 68262 | 34483 | 29514 | 46719 | 31237 | 51882 | 43022 | 76804 | 18775 | 23977 | 36704 |
| 18.86 | 69087 | 35067 | 31157 | 44682 | 29600 | 53026 | 40370 | 77071 | 18195 | 23701 | 38707 |
| 18.9 | 65902 | 33954 | 30262 | 42617 | 30402 | 49887 | 36297 | 73383 | 18864 | 23495 | 41248 |
| 18.94 | 67532 | 33415 | 27467 | 42076 | 29783 | 49830 | 37181 | 75557 | 19262 | 22054 | 39245 |
| 18.98 | 68828 | 31308 | 28160 | 42161 | 29511 | 51166 | 36441 | 73861 | 19394 | 22328 | 38528 |
| 19.02 | 64673 | 35666 | 30012 | 40118 | 30113 | 49321 | 35611 | 77537 | 17787 | 21539 | 40186 |
| 19.06 | 63513 | 34594 | 35764 | 36254 | 31035 | 48464 | 30852 | 79946 | 18035 | 22334 | 42536 |
| 19.1 | 63619 | 33610 | 45630 | 36155 | 33291 | 49632 | 31594 | 75765 | 17175 | 21545 | 43461 |
| 19.14 | 63345 | 31013 | 51055 | 37812 | 31478 | 49672 | 30460 | 76068 | 19573 | 23355 | 45104 |
| 19.18 | 60362 | 31512 | 63490 | 37048 | 30695 | 49039 | 26974 | 82004 | 20222 | 21766 | 46935 |
| 19.22 | 62175 | 34307 | 70499 | 37645 | 30871 | 49691 | 29003 | 79732 | 18494 | 19986 | 46808 |
| 19.26 | 59014 | 34330 | 77359 | 35869 | 31590 | 50303 | 29827 | 78054 | 18633 | 22027 | 45890 |
| 19.3 | 56450 | 30868 | 81579 | 37505 | 30569 | 50290 | 31506 | 79251 | 17617 | 22551 | 47071 |
| 19.34 | 59341 | 30952 | 86635 | 37126 | 30118 | 53568 | 28348 | 80492 | 18651 | 20049 | 48364 |
| 19.38 | 59351 | 32305 | 88844 | 36792 | 31212 | 51157 | 30119 | 79875 | 19424 | 21504 | 45466 |
| 19.42 | 56588 | 31774 | 85792 | 38481 | 31246 | 52151 | 33889 | 79049 | 17804 | 22057 | 44217 |
| 19.46 | 56302 | 33344 | 84039 | 39797 | 30287 | 53720 | 31186 | 80751 | 17427 | 21288 | 43197 |
| 19.5 | 55956 | 31720 | 75016 | 40681 | 30278 | 52484 | 32507 | 80401 | 18317 | 22250 | 39906 |
| 19.54 | 55648 | 34480 | 71979 | 40177 | 29921 | 52661 | 34453 | 80669 | 19245 | 20157 | 39283 |
| 19.58 | 60172 | 31441 | 64082 | 40124 | 29887 | 53466 | 31518 | 82226 | 19756 | 23175 | 36737 |
| 19.62 | 60397 | 31545 | 53717 | 41651 | 28271 | 53251 | 35483 | 79646 | 18018 | 20227 | 37792 |
| 19.66 | 57065 | 31346 | 47161 | 40533 | 29733 | 52684 | 37684 | 83386 | 19928 | 20489 | 35551 |
| 19.7 | 55580 | 30796 | 42415 | 42145 | 29617 | 50012 | 38479 | 84867 | 19983 | 21943 | 34777 |
| 19.74 | 58911 | 29745 | 39136 | 42105 | 30644 | 50143 | 41839 | 84960 | 20749 | 21410 | 36407 |
| 19.78 | 57220 | 30751 | 34214 | 40104 | 29819 | 51093 | 37744 | 83902 | 19667 | 20815 | 36495 |
| 19.82 | 57360 | 35619 | 31325 | 41822 | 29774 | 55223 | 40357 | 87617 | 19587 | 23082 | 35204 |
| 19.86 | 57531 | 33517 | 30677 | 41481 | 30381 | 53289 | 39756 | 88835 | 19806 | 22851 | 35564 |
| 19.9 | 56388 | 32837 | 28604 | 39493 | 30193 | 51222 | 40606 | 90389 | 20849 | 23256 | 35089 |
| 19.94 | 55204 | 33898 | 27525 | 40370 | 29845 | 52855 | 40984 | 88272 | 23102 | 24616 | 35423 |
| 19.98 | 55738 | 32969 | 25853 | 40332 | 29890 | 53888 | 39933 | 89346 | 24691 | 26516 | 37146 |
| 20.02 | 57435 | 36076 | 24108 | 37744 | 29140 | 51174 | 38956 | 91387 | 26131 | 25965 | 38804 |
| 20.06 | 59045 | 34645 | 22270 | 38692 | 30048 | 52413 | 38554 | 92208 | 27199 | 28620 | 37401 |

-continued

| | | | | | | | | | | | |
|---|---|---|---|---|---|---|---|---|---|---|---|
| 20.1 | 58573 | 36272 | 24562 | 36416 | 30447 | 53098 | 36527 | 91703 | 30418 | 29613 | 37731 |
| 20.14 | 60629 | 35416 | 24917 | 35512 | 30473 | 53297 | 37551 | 90925 | 34404 | 31898 | 36260 |
| 20.18 | 62622 | 34651 | 25724 | 34242 | 29656 | 52347 | 37935 | 94182 | 36769 | 34097 | 36064 |
| 20.22 | 61388 | 34620 | 26969 | 32500 | 29990 | 52965 | 36109 | 89926 | 38196 | 36426 | 34088 |
| 20.26 | 63836 | 35485 | 27608 | 34352 | 31516 | 54935 | 35075 | 88580 | 37418 | 37655 | 36607 |
| 20.3 | 66853 | 35410 | 25780 | 32816 | 28520 | 58908 | 34467 | 86797 | 36133 | 38987 | 34979 |
| 20.34 | 67290 | 34715 | 24971 | 33665 | 27786 | 60581 | 36090 | 84619 | 35661 | 39143 | 37186 |
| 20.38 | 68781 | 33325 | 25009 | 36363 | 29235 | 62846 | 33928 | 86129 | 34967 | 38390 | 37598 |
| 20.42 | 66018 | 33973 | 25620 | 34500 | 30695 | 64406 | 33944 | 83700 | 32578 | 37094 | 37060 |
| 20.46 | 65796 | 34111 | 25266 | 34391 | 29342 | 65517 | 33612 | 86650 | 30088 | 37663 | 40841 |
| 20.5 | 67739 | 34409 | 24584 | 35974 | 29797 | 70240 | 32549 | 89779 | 29425 | 37351 | 43007 |
| 20.54 | 66461 | 32307 | 22770 | 34242 | 29029 | 66653 | 31438 | 87694 | 26306 | 34729 | 43198 |
| 20.58 | 65442 | 34384 | 23441 | 34128 | 29999 | 69579 | 29556 | 91986 | 26469 | 30637 | 42045 |
| 20.62 | 67060 | 32133 | 24947 | 32662 | 30746 | 67592 | 30046 | 95853 | 24923 | 33470 | 44049 |
| 20.66 | 64759 | 32794 | 23396 | 34740 | 29046 | 65828 | 30584 | 98150 | 24997 | 31125 | 43762 |
| 20.7 | 64053 | 32541 | 23064 | 32161 | 30207 | 65446 | 29581 | 105751 | 23808 | 30812 | 39018 |
| 20.74 | 65201 | 31920 | 22521 | 31953 | 30889 | 64875 | 30746 | 106808 | 23420 | 27327 | 40366 |
| 20.78 | 64510 | 31835 | 24132 | 33917 | 30708 | 65315 | 33516 | 111859 | 24001 | 29800 | 40593 |
| 20.82 | 63633 | 34248 | 22400 | 32124 | 33123 | 69907 | 31566 | 111351 | 22041 | 27595 | 40459 |
| 20.86 | 62602 | 33446 | 22868 | 32977 | 31013 | 74586 | 34661 | 112952 | 22499 | 26283 | 38450 |
| 20.9 | 64807 | 33423 | 24090 | 33156 | 30816 | 76059 | 34896 | 114969 | 23251 | 28284 | 37475 |
| 20.94 | 68548 | 34514 | 27517 | 33734 | 32042 | 87105 | 36456 | 122898 | 25767 | 28728 | 38210 |
| 20.98 | 60514 | 32569 | 26760 | 32603 | 31598 | 84689 | 38448 | 122260 | 26611 | 26168 | 36312 |
| 21.02 | 62953 | 32936 | 31352 | 31876 | 29850 | 84519 | 38036 | 118444 | 28076 | 27630 | 36744 |
| 21.06 | 59134 | 32962 | 32542 | 32575 | 29810 | 87949 | 41078 | 118187 | 30758 | 29092 | 34811 |
| 21.1 | 60026 | 35375 | 34546 | 34936 | 29331 | 89643 | 40508 | 122690 | 32845 | 29686 | 35376 |
| 21.14 | 60148 | 30949 | 32760 | 33982 | 29615 | 88479 | 42338 | 113512 | 31419 | 27600 | 34905 |
| 21.18 | 65975 | 33964 | 31946 | 33865 | 30858 | 89047 | 39316 | 114328 | 33753 | 26321 | 36947 |
| 21.22 | 64299 | 32967 | 35716 | 30930 | 32012 | 81168 | 45123 | 114435 | 35490 | 26805 | 34472 |
| 21.26 | 64984 | 34772 | 31434 | 32068 | 32167 | 73353 | 40507 | 111728 | 34240 | 26495 | 32626 |
| 21.3 | 64828 | 32498 | 31172 | 32962 | 32725 | 73340 | 43030 | 107756 | 35767 | 26892 | 33397 |
| 21.34 | 67165 | 33441 | 30377 | 32280 | 31305 | 73834 | 40735 | 109095 | 35341 | 25056 | 33805 |
| 21.38 | 61927 | 31062 | 27148 | 30993 | 30261 | 68316 | 41812 | 106961 | 36467 | 25247 | 31942 |
| 21.42 | 65858 | 32239 | 26287 | 32185 | 29135 | 65800 | 40755 | 111384 | 34182 | 25223 | 33520 |
| 21.46 | 60544 | 30476 | 24875 | 30218 | 31950 | 63196 | 43407 | 109967 | 30275 | 24818 | 35438 |
| 21.5 | 63965 | 32240 | 25235 | 32473 | 34092 | 67656 | 46138 | 106424 | 31218 | 26463 | 32596 |
| 21.54 | 63069 | 31749 | 24550 | 31394 | 29640 | 63697 | 49415 | 109459 | 27573 | 25175 | 36711 |
| 21.58 | 65272 | 31172 | 24744 | 34333 | 32267 | 64774 | 51410 | 113741 | 28989 | 26953 | 36846 |
| 21.62 | 62948 | 33208 | 23122 | 31925 | 30720 | 58650 | 54031 | 116336 | 23616 | 22988 | 37453 |
| 21.66 | 58886 | 30841 | 22726 | 32119 | 31129 | 58121 | 56569 | 112318 | 20761 | 24067 | 36651 |
| 21.7 | 61369 | 27796 | 26474 | 32239 | 29595 | 58480 | 56263 | 112647 | 20929 | 27370 | 36158 |
| 21.74 | 62956 | 29985 | 27601 | 34829 | 31203 | 61178 | 55704 | 117615 | 21884 | 28964 | 35227 |
| 21.78 | 60682 | 32124 | 26331 | 38517 | 33939 | 54895 | 57317 | 114482 | 21994 | 27595 | 35263 |
| 21.82 | 61401 | 32507 | 29236 | 39834 | 31889 | 55999 | 52689 | 114024 | 20875 | 26469 | 35680 |
| 21.86 | 61568 | 31108 | 29680 | 44029 | 30457 | 56440 | 50422 | 116076 | 20764 | 26172 | 34311 |
| 21.9 | 62936 | 32921 | 29692 | 47127 | 31873 | 56622 | 48531 | 111689 | 21232 | 29322 | 33453 |
| 21.94 | 62572 | 31111 | 31301 | 48341 | 31288 | 57449 | 49920 | 109707 | 21752 | 27904 | 34929 |
| 21.98 | 55340 | 31438 | 28986 | 45454 | 30839 | 54383 | 50923 | 112709 | 20344 | 28371 | 32981 |
| 22.02 | 63281 | 29548 | 29167 | 52468 | 30822 | 55525 | 53178 | 111854 | 16410 | 27137 | 36621 |
| 22.06 | 57757 | 30138 | 30458 | 50396 | 32538 | 58826 | 51421 | 110589 | 20455 | 26252 | 34582 |
| 22.1 | 57888 | 29596 | 26656 | 48591 | 30076 | 58514 | 47036 | 101007 | 18877 | 24388 | 31456 |
| 22.14 | 58879 | 31445 | 25626 | 43985 | 31885 | 57355 | 50055 | 100264 | 16949 | 23595 | 33681 |
| 22.18 | 59820 | 30854 | 26243 | 41772 | 30754 | 56427 | 50610 | 102092 | 16713 | 25963 | 30678 |
| 22.22 | 58760 | 29785 | 22703 | 42313 | 31291 | 58535 | 52854 | 96208 | 19647 | 24552 | 30476 |
| 22.26 | 61677 | 29791 | 23809 | 40213 | 32211 | 53801 | 48155 | 91484 | 18475 | 25779 | 30555 |
| 22.3 | 58552 | 28274 | 23166 | 36734 | 31039 | 54510 | 49709 | 87436 | 16801 | 23585 | 34059 |
| 22.34 | 59604 | 29119 | 23270 | 35433 | 32627 | 54812 | 49764 | 83410 | 18675 | 23262 | 31543 |
| 22.38 | 57828 | 28804 | 24959 | 34560 | 33064 | 54088 | 51348 | 82326 | 18338 | 22747 | 30688 |
| 22.42 | 57227 | 28680 | 30021 | 33387 | 31967 | 52400 | 50868 | 80486 | 18553 | 21835 | 32006 |
| 22.46 | 61346 | 27311 | 30923 | 37046 | 31622 | 52315 | 53443 | 75974 | 18950 | 23632 | 27162 |
| 22.5 | 58641 | 31390 | 35229 | 35159 | 32670 | 51937 | 51529 | 74203 | 14886 | 23018 | 32358 |
| 22.54 | 58307 | 29457 | 38377 | 34191 | 33779 | 48671 | 51564 | 72646 | 16914 | 23166 | 30061 |
| 22.58 | 58497 | 29894 | 41020 | 34830 | 29454 | 51992 | 55465 | 73940 | 18733 | 22789 | 30319 |
| 22.62 | 57078 | 29797 | 42722 | 32659 | 32441 | 54463 | 55909 | 73160 | 19043 | 21088 | 30173 |
| 22.66 | 60161 | 34058 | 42485 | 35458 | 33006 | 50901 | 49819 | 78481 | 17407 | 21229 | 29649 |
| 22.7 | 63590 | 30681 | 41149 | 35417 | 31199 | 51383 | 54138 | 78112 | 17947 | 20155 | 30753 |
| 22.74 | 59137 | 32119 | 42415 | 34188 | 30800 | 46876 | 52993 | 74050 | 18360 | 19487 | 29661 |
| 22.78 | 60035 | 33147 | 40738 | 35975 | 31849 | 50198 | 53416 | 77769 | 17606 | 23350 | 35489 |
| 22.82 | 62555 | 34167 | 37296 | 35209 | 33352 | 46218 | 53206 | 77984 | 17722 | 19128 | 28406 |
| 22.86 | 59951 | 32182 | 36144 | 35511 | 34122 | 51342 | 51739 | 78818 | 17907 | 18709 | 28597 |
| 22.9 | 59436 | 34641 | 30180 | 34089 | 31796 | 50237 | 49094 | 84590 | 19067 | 18789 | 28433 |
| 22.94 | 58501 | 34864 | 31992 | 34062 | 33777 | 46699 | 47741 | 91379 | 21002 | 21050 | 26902 |
| 22.98 | 60345 | 33641 | 33374 | 35996 | 34503 | 50328 | 46352 | 88167 | 18725 | 19696 | 30361 |
| 23.02 | 59702 | 33868 | 33517 | 37185 | 31905 | 49078 | 47157 | 89003 | 22015 | 21226 | 27895 |
| 23.06 | 62134 | 31597 | 38329 | 40228 | 33672 | 45373 | 45922 | 94570 | 19532 | 21457 | 25654 |
| 23.1 | 59349 | 33340 | 38267 | 40857 | 34231 | 44399 | 44634 | 94506 | 22872 | 19254 | 27138 |
| 23.14 | 62485 | 32153 | 40262 | 40207 | 34070 | 43822 | 43960 | 89752 | 22999 | 20561 | 27756 |
| 23.18 | 65709 | 30866 | 42155 | 42788 | 34239 | 45410 | 43904 | 96796 | 22848 | 18825 | 29123 |
| 23.22 | 63649 | 33362 | 45837 | 43525 | 38552 | 43408 | 41143 | 94999 | 24351 | 19450 | 31622 |

-continued

| | | | | | | | | | | | |
|---|---|---|---|---|---|---|---|---|---|---|---|
| 23.26 | 63832 | 30767 | 42651 | 41540 | 34893 | 42075 | 40326 | 90795 | 23628 | 20394 | 27202 |
| 23.3 | 65636 | 31300 | 42626 | 43222 | 35971 | 39768 | 37485 | 93055 | 25450 | 19891 | 24926 |
| 23.34 | 68732 | 31054 | 44647 | 40820 | 34538 | 40736 | 35644 | 94149 | 25723 | 20615 | 24667 |
| 23.38 | 67782 | 29830 | 43289 | 41119 | 34934 | 40377 | 34888 | 92817 | 26561 | 21469 | 22503 |
| 23.42 | 68961 | 28148 | 40516 | 41998 | 36107 | 39047 | 34320 | 94474 | 25520 | 20602 | 25339 |
| 23.46 | 79503 | 31620 | 40566 | 46422 | 36441 | 43984 | 32852 | 97426 | 24283 | 21649 | 25566 |
| 23.5 | 79117 | 34447 | 39682 | 48438 | 38426 | 42056 | 34148 | 97704 | 24500 | 23496 | 29713 |
| 23.54 | 80953 | 36964 | 38561 | 50251 | 33055 | 39989 | 36110 | 92019 | 23508 | 20776 | 26702 |
| 23.58 | 86002 | 33759 | 37482 | 51556 | 37666 | 38936 | 35844 | 95125 | 24341 | 22683 | 29512 |
| 23.62 | 83668 | 36960 | 38545 | 53487 | 35398 | 40420 | 34887 | 88331 | 20896 | 23193 | 25829 |
| 23.66 | 91635 | 34591 | 38368 | 58657 | 36054 | 39664 | 34107 | 87792 | 20088 | 20959 | 26396 |
| 23.7 | 94894 | 38048 | 40570 | 54565 | 39240 | 36689 | 37574 | 93379 | 18893 | 21913 | 26921 |
| 23.74 | 96655 | 36491 | 46094 | 56016 | 37573 | 39070 | 40283 | 86920 | 20147 | 22955 | 26588 |
| 23.78 | 97838 | 36978 | 60540 | 55768 | 34149 | 39418 | 38047 | 82638 | 20145 | 23507 | 28305 |
| 23.82 | 103391 | 37270 | 68978 | 55542 | 39057 | 38290 | 39458 | 82801 | 20178 | 20796 | 26811 |
| 23.86 | 96760 | 42260 | 73166 | 57323 | 39717 | 37773 | 43864 | 83297 | 20248 | 22924 | 28097 |
| 23.9 | 104132 | 37513 | 79061 | 62212 | 38096 | 37614 | 41650 | 88790 | 21620 | 23357 | 27136 |
| 23.94 | 96560 | 38392 | 86024 | 60560 | 38874 | 40508 | 47535 | 90771 | 23545 | 24366 | 30743 |
| 23.98 | 96360 | 38294 | 80848 | 62031 | 40657 | 43516 | 40618 | 88599 | 24271 | 24697 | 27594 |
| 24.02 | 97032 | 38501 | 80181 | 60718 | 36158 | 40877 | 40136 | 89846 | 25220 | 23597 | 27147 |
| 24.06 | 91683 | 39234 | 79131 | 57700 | 36467 | 42099 | 42414 | 86840 | 23543 | 23563 | 29620 |
| 24.1 | 89876 | 37310 | 67514 | 57421 | 38222 | 39762 | 38062 | 94440 | 22753 | 23100 | 29506 |
| 24.14 | 91840 | 37355 | 60889 | 55229 | 36642 | 44796 | 40152 | 96734 | 25582 | 28430 | 28150 |
| 24.18 | 80761 | 40679 | 52585 | 56006 | 38608 | 42906 | 38312 | 98254 | 24439 | 26808 | 27741 |
| 24.22 | 84030 | 40609 | 46174 | 53564 | 41578 | 47710 | 39334 | 97643 | 28109 | 28088 | 28720 |
| 24.26 | 81486 | 39428 | 36709 | 48759 | 37635 | 45057 | 38165 | 96994 | 27373 | 28135 | 27050 |
| 24.3 | 83271 | 40502 | 33728 | 50457 | 39372 | 44936 | 34576 | 97312 | 29775 | 29643 | 27435 |
| 24.34 | 80548 | 39577 | 34189 | 45412 | 38794 | 47040 | 32634 | 98084 | 28971 | 26012 | 26940 |
| 24.38 | 77555 | 41165 | 35135 | 44832 | 39305 | 43862 | 34210 | 96476 | 27895 | 27539 | 28975 |
| 24.42 | 81283 | 41189 | 34844 | 47873 | 40232 | 45597 | 33202 | 97031 | 26890 | 27072 | 25947 |
| 24.46 | 82343 | 41259 | 38514 | 46055 | 37675 | 43523 | 32197 | 101875 | 29267 | 29119 | 27716 |
| 24.5 | 84364 | 44608 | 41026 | 44216 | 38786 | 44769 | 29283 | 103143 | 29171 | 26701 | 30275 |
| 24.54 | 88975 | 48664 | 44363 | 51477 | 40021 | 43973 | 31380 | 107009 | 33568 | 28590 | 27978 |
| 24.58 | 91005 | 48733 | 47159 | 48119 | 40997 | 46342 | 31132 | 103424 | 33274 | 28647 | 28323 |
| 24.62 | 91400 | 46529 | 52706 | 48754 | 38276 | 46481 | 29684 | 105012 | 35963 | 24278 | 29158 |
| 24.66 | 90909 | 46936 | 54562 | 50512 | 40107 | 49173 | 26581 | 108530 | 41117 | 25223 | 29431 |
| 24.7 | 90665 | 50298 | 60731 | 55878 | 39946 | 47558 | 27310 | 111283 | 48601 | 26601 | 32495 |
| 24.74 | 90173 | 52731 | 61861 | 53710 | 39459 | 49457 | 27777 | 116486 | 49418 | 27013 | 32461 |
| 24.78 | 96999 | 46448 | 62416 | 54960 | 36786 | 50245 | 26158 | 108316 | 50725 | 25664 | 31187 |
| 24.82 | 93979 | 48748 | 65603 | 52600 | 39929 | 47777 | 25354 | 106517 | 54144 | 25596 | 32731 |
| 24.86 | 96919 | 46363 | 59963 | 49964 | 38988 | 48988 | 26168 | 108365 | 57366 | 27254 | 32392 |
| 24.9 | 94581 | 41636 | 57967 | 51721 | 41736 | 51884 | 25955 | 114078 | 58395 | 26275 | 35905 |
| 24.94 | 99823 | 40202 | 55776 | 46943 | 39210 | 50566 | 26881 | 113156 | 56157 | 28590 | 34841 |
| 24.98 | 97610 | 41315 | 45660 | 49400 | 40877 | 46409 | 26836 | 109727 | 57950 | 26190 | 37028 |
| 25.02 | 102043 | 40767 | 37932 | 46253 | 38029 | 48979 | 25089 | 106362 | 59374 | 26711 | 37252 |
| 25.06 | 102978 | 36152 | 36270 | 45267 | 38653 | 46548 | 25962 | 105438 | 52279 | 26394 | 37504 |
| 25.1 | 106287 | 37336 | 31315 | 45132 | 39056 | 50260 | 26871 | 108553 | 52505 | 28112 | 41035 |
| 25.14 | 103006 | 40973 | 30848 | 45611 | 40753 | 48025 | 26151 | 113758 | 52204 | 29537 | 41012 |
| 25.18 | 99346 | 39261 | 28657 | 46213 | 37559 | 44728 | 28894 | 113663 | 49179 | 33090 | 40348 |
| 25.22 | 102302 | 37109 | 29698 | 46756 | 37298 | 48476 | 27456 | 114883 | 48117 | 34582 | 44319 |
| 25.26 | 101016 | 34884 | 31832 | 47282 | 36337 | 48692 | 32194 | 117610 | 45280 | 34609 | 42640 |
| 25.3 | 94852 | 35873 | 33626 | 46727 | 35748 | 45254 | 31750 | 117869 | 40828 | 33624 | 41259 |
| 25.34 | 94418 | 34409 | 33990 | 46333 | 36914 | 45229 | 32381 | 120829 | 36017 | 33456 | 40232 |
| 25.38 | 93764 | 36928 | 37416 | 46821 | 37981 | 46680 | 32167 | 121950 | 33978 | 35077 | 43056 |
| 25.42 | 89887 | 34470 | 41287 | 45926 | 37089 | 44250 | 31541 | 121629 | 27329 | 35614 | 43222 |
| 25.46 | 91957 | 34717 | 44347 | 46145 | 38292 | 46865 | 33614 | 122120 | 25408 | 34713 | 41312 |
| 25.5 | 84861 | 34170 | 41388 | 41771 | 37863 | 42902 | 35743 | 118266 | 20153 | 33731 | 44531 |
| 25.54 | 81780 | 36796 | 43612 | 42561 | 36864 | 42936 | 33480 | 111421 | 19289 | 31929 | 44103 |
| 25.58 | 82083 | 34271 | 42993 | 41827 | 37016 | 44668 | 32634 | 108422 | 18628 | 33530 | 44588 |
| 25.62 | 79687 | 32821 | 41170 | 38985 | 34854 | 44542 | 34792 | 103486 | 19463 | 30831 | 44762 |
| 25.66 | 81065 | 32044 | 44709 | 38325 | 36123 | 41692 | 32874 | 99049 | 19783 | 30358 | 47275 |
| 25.7 | 78745 | 33956 | 48715 | 37965 | 34129 | 42804 | 31526 | 94664 | 18032 | 28186 | 51083 |
| 25.74 | 76641 | 33145 | 50915 | 34890 | 35070 | 42911 | 32377 | 91373 | 18780 | 26592 | 52798 |
| 25.78 | 74355 | 33175 | 58801 | 33772 | 37085 | 41383 | 29313 | 83921 | 18175 | 30748 | 51944 |
| 25.82 | 71177 | 30109 | 61135 | 33431 | 37154 | 41611 | 28545 | 80425 | 20907 | 26450 | 52417 |
| 25.86 | 69882 | 30560 | 68359 | 32617 | 35563 | 38591 | 29685 | 79925 | 21626 | 25964 | 55177 |
| 25.9 | 65617 | 29883 | 72916 | 33784 | 35275 | 39923 | 29673 | 80468 | 23940 | 29494 | 55737 |
| 25.94 | 66330 | 29976 | 73511 | 33458 | 34954 | 39633 | 30976 | 72186 | 23225 | 28436 | 57663 |
| 25.98 | 65370 | 30482 | 73102 | 34970 | 37673 | 40404 | 28152 | 75659 | 28850 | 26631 | 55620 |
| 26.02 | 62460 | 31414 | 70084 | 31204 | 33305 | 39957 | 29895 | 72666 | 28165 | 25737 | 55316 |
| 26.06 | 62638 | 32159 | 63542 | 31303 | 34273 | 39244 | 34461 | 72931 | 30831 | 28063 | 53550 |
| 26.1 | 61089 | 30023 | 56864 | 33750 | 33397 | 41557 | 32669 | 69221 | 30872 | 25413 | 53659 |
| 26.14 | 60733 | 32180 | 52625 | 32259 | 31742 | 38617 | 32543 | 69463 | 32970 | 24133 | 50871 |
| 26.18 | 56105 | 31953 | 43409 | 32128 | 33173 | 37460 | 33122 | 66398 | 34507 | 23011 | 48531 |
| 26.22 | 57419 | 28908 | 36013 | 34707 | 32952 | 37927 | 34147 | 66266 | 33331 | 24395 | 47167 |
| 26.26 | 58806 | 30469 | 32705 | 33762 | 31779 | 41321 | 34100 | 65974 | 34339 | 22461 | 44004 |
| 26.3 | 54457 | 32950 | 33870 | 32609 | 30955 | 38470 | 32315 | 67114 | 32992 | 22636 | 39573 |
| 26.34 | 59534 | 30796 | 36114 | 34322 | 30164 | 38196 | 32212 | 69800 | 29519 | 20517 | 36718 |
| 26.38 | 58984 | 31597 | 37674 | 33674 | 32185 | 39515 | 30784 | 69443 | 30344 | 21914 | 37218 |

-continued

| | | | | | | | | | | | |
|---|---|---|---|---|---|---|---|---|---|---|---|
| 26.42 | 56844 | 31585 | 42800 | 33103 | 29335 | 35458 | 34235 | 72705 | 26605 | 22767 | 36274 |
| 26.46 | 57494 | 29801 | 44338 | 34121 | 31172 | 38497 | 32739 | 73928 | 27318 | 21737 | 33263 |
| 26.5 | 57341 | 32142 | 40542 | 38176 | 28235 | 35902 | 31102 | 73456 | 28228 | 22796 | 31845 |
| 26.54 | 59759 | 30467 | 46318 | 36293 | 29810 | 38813 | 28779 | 72571 | 28321 | 23182 | 31542 |
| 26.58 | 61360 | 30203 | 44587 | 38111 | 31179 | 36180 | 27826 | 72977 | 29857 | 23118 | 30372 |
| 26.62 | 57289 | 28860 | 41657 | 35990 | 29349 | 36536 | 26984 | 73917 | 29054 | 25287 | 29486 |
| 26.66 | 60161 | 28580 | 39203 | 38916 | 29277 | 35886 | 28648 | 73172 | 25670 | 23368 | 30539 |
| 26.7 | 63052 | 27825 | 35299 | 40781 | 31380 | 36225 | 26687 | 70868 | 24938 | 24775 | 31230 |
| 26.74 | 64916 | 27661 | 30996 | 37892 | 29862 | 32883 | 24676 | 69604 | 24883 | 23946 | 31028 |
| 26.78 | 60179 | 26659 | 28014 | 38287 | 26137 | 33941 | 23790 | 67590 | 24925 | 26457 | 30206 |
| 26.82 | 60463 | 26647 | 24515 | 36915 | 28303 | 32365 | 23542 | 67971 | 24047 | 24881 | 30226 |
| 26.86 | 62941 | 30317 | 22376 | 35185 | 29944 | 33108 | 25187 | 69076 | 21665 | 25506 | 30544 |
| 26.9 | 67114 | 28436 | 19886 | 34762 | 26795 | 31005 | 23404 | 62997 | 22242 | 24209 | 29601 |
| 26.94 | 69355 | 29024 | 23220 | 32672 | 26461 | 33036 | 23072 | 60517 | 23382 | 24012 | 29732 |
| 26.98 | 69801 | 27851 | 22576 | 30718 | 28173 | 31083 | 23347 | 63832 | 22995 | 23134 | 32797 |
| 27.02 | 73303 | 28923 | 23494 | 31654 | 27989 | 31160 | 22593 | 63227 | 22427 | 23511 | 32368 |
| 27.06 | 69061 | 26919 | 23574 | 31929 | 24180 | 31545 | 23770 | 62032 | 22848 | 24089 | 29230 |
| 27.1 | 68588 | 26892 | 24208 | 34972 | 26943 | 31919 | 21778 | 60365 | 22108 | 22934 | 32298 |
| 27.14 | 73156 | 27528 | 26455 | 31882 | 26524 | 31286 | 23976 | 60886 | 21816 | 24055 | 34426 |
| 27.18 | 76592 | 27184 | 28793 | 33351 | 24593 | 28244 | 24321 | 61533 | 22419 | 23370 | 34303 |
| 27.22 | 72013 | 28176 | 27960 | 32868 | 26688 | 29324 | 22972 | 60105 | 21817 | 24635 | 39083 |
| 27.26 | 71642 | 25487 | 27140 | 33430 | 27284 | 32198 | 24619 | 63331 | 21816 | 26071 | 35331 |
| 27.3 | 76841 | 27431 | 26165 | 33115 | 25656 | 32723 | 23508 | 61969 | 23951 | 25239 | 34810 |
| 27.34 | 76187 | 26724 | 25324 | 35469 | 25568 | 29453 | 20807 | 62179 | 22943 | 26587 | 36326 |
| 27.38 | 73231 | 27406 | 24345 | 31422 | 25397 | 28238 | 22431 | 63898 | 21923 | 23864 | 33491 |
| 27.42 | 73335 | 27103 | 24988 | 33641 | 25793 | 30385 | 24341 | 59725 | 20552 | 27455 | 34400 |
| 27.46 | 72790 | 25164 | 24202 | 32299 | 21923 | 27540 | 22733 | 63354 | 23014 | 28023 | 29965 |
| 27.5 | 68178 | 27749 | 23936 | 31473 | 25074 | 28342 | 24017 | 62158 | 21997 | 27291 | 30777 |
| 27.54 | 69541 | 26139 | 27316 | 31326 | 24737 | 30046 | 23915 | 61940 | 20371 | 29959 | 30692 |
| 27.58 | 70186 | 25821 | 27688 | 29808 | 24304 | 32246 | 25044 | 60946 | 19732 | 28850 | 29486 |
| 27.62 | 62003 | 27466 | 28192 | 28380 | 23818 | 30211 | 23943 | 57828 | 18811 | 24699 | 28737 |
| 27.66 | 63805 | 25847 | 30507 | 27798 | 23236 | 28253 | 22290 | 58169 | 18317 | 24709 | 26897 |
| 27.7 | 63157 | 25310 | 30554 | 28176 | 24065 | 26950 | 23396 | 61014 | 18158 | 24725 | 25354 |
| 27.74 | 60780 | 27295 | 31759 | 29828 | 23019 | 26524 | 24488 | 56927 | 17554 | 24931 | 26666 |
| 27.78 | 62066 | 27035 | 33104 | 28657 | 25021 | 28701 | 23932 | 60395 | 19043 | 23981 | 25440 |
| 27.82 | 58614 | 23983 | 33757 | 29610 | 24199 | 30184 | 23265 | 61588 | 21807 | 24032 | 26764 |
| 27.86 | 61427 | 25629 | 35795 | 31017 | 25185 | 29635 | 23716 | 64751 | 20584 | 22966 | 28478 |
| 27.9 | 59748 | 26241 | 31544 | 29167 | 23397 | 28817 | 21298 | 61720 | 19913 | 24833 | 25868 |
| 27.94 | 58746 | 25270 | 34727 | 29724 | 23505 | 29080 | 20575 | 62470 | 20464 | 22913 | 23839 |
| 27.98 | 56827 | 28037 | 31221 | 28369 | 22222 | 28347 | 22315 | 60423 | 22163 | 23388 | 24440 |
| 28.02 | 53958 | 25029 | 31157 | 30203 | 23702 | 27199 | 22713 | 67521 | 20001 | 21219 | 25188 |
| 28.06 | 51951 | 26378 | 29088 | 33156 | 24378 | 28683 | 20774 | 66221 | 20883 | 24742 | 26425 |
| 28.1 | 54154 | 26002 | 32646 | 31392 | 22439 | 29961 | 19425 | 67210 | 18668 | 24192 | 23847 |
| 28.14 | 53079 | 25155 | 29866 | 27618 | 23597 | 27687 | 21661 | 59960 | 19128 | 24056 | 23558 |
| 28.18 | 52468 | 25113 | 34265 | 30736 | 24975 | 25512 | 20227 | 59432 | 17974 | 22409 | 23465 |
| 28.22 | 53841 | 22386 | 33051 | 27827 | 23401 | 27114 | 17688 | 58456 | 17326 | 24247 | 21860 |
| 28.26 | 53626 | 23868 | 30591 | 26189 | 23684 | 22295 | 18703 | 56831 | 18902 | 23733 | 22242 |
| 28.3 | 53325 | 23125 | 27540 | 26468 | 23795 | 27734 | 18833 | 54295 | 16487 | 22995 | 24935 |
| 28.34 | 52872 | 22290 | 28342 | 27693 | 24580 | 28329 | 19198 | 54940 | 16731 | 23504 | 24034 |
| 28.38 | 50552 | 22403 | 28664 | 24457 | 21631 | 24935 | 18811 | 50303 | 18374 | 22221 | 23482 |
| 28.42 | 50481 | 22290 | 25659 | 24116 | 21519 | 25077 | 18220 | 49261 | 19483 | 21330 | 22099 |
| 28.46 | 49567 | 23813 | 21729 | 23133 | 23749 | 24939 | 17599 | 52628 | 18587 | 20391 | 24137 |
| 28.5 | 45673 | 22875 | 22119 | 22208 | 22266 | 24257 | 17945 | 54095 | 17075 | 19343 | 24102 |
| 28.54 | 49400 | 25117 | 21888 | 23701 | 22532 | 24254 | 19090 | 52426 | 18078 | 19409 | 23536 |
| 28.58 | 53787 | 24174 | 20408 | 24423 | 22516 | 26116 | 20850 | 47794 | 17050 | 19092 | 25039 |
| 28.62 | 51744 | 24397 | 19903 | 22694 | 20456 | 22500 | 17985 | 46478 | 15123 | 17481 | 22132 |
| 28.66 | 47078 | 25026 | 20747 | 23088 | 20648 | 24097 | 17808 | 49230 | 15601 | 16629 | 23397 |
| 28.7 | 47001 | 25861 | 21756 | 23127 | 22399 | 23971 | 19115 | 47631 | 16778 | 16664 | 21667 |
| 28.74 | 48641 | 23978 | 21262 | 21660 | 21490 | 24590 | 17794 | 48196 | 16586 | 17148 | 22164 |
| 28.78 | 49430 | 23545 | 20955 | 22401 | 21794 | 24348 | 17392 | 49220 | 19578 | 16627 | 22870 |
| 28.82 | 48899 | 24827 | 20064 | 26124 | 22829 | 24625 | 19817 | 47024 | 18603 | 17088 | 23556 |
| 28.86 | 44928 | 23505 | 21918 | 25333 | 21001 | 23909 | 18972 | 46554 | 18059 | 17575 | 25012 |
| 28.9 | 45311 | 22020 | 21155 | 21423 | 19422 | 22953 | 19776 | 44298 | 19119 | 15037 | 22154 |
| 28.94 | 46812 | 23118 | 19527 | 22782 | 22115 | 25829 | 20405 | 45614 | 19585 | 15874 | 23193 |
| 28.98 | 42678 | 23481 | 22355 | 23014 | 19317 | 23643 | 20251 | 48358 | 20060 | 16481 | 24876 |
| 29.02 | 43811 | 22121 | 21754 | 24212 | 21338 | 24766 | 20301 | 48245 | 19562 | 16170 | 24883 |
| 29.06 | 43167 | 22494 | 20769 | 24145 | 18949 | 22142 | 19309 | 44107 | 19199 | 16279 | 21822 |
| 29.1 | 38865 | 21162 | 18986 | 23554 | 17983 | 23781 | 19139 | 44000 | 17083 | 16770 | 21387 |
| 29.14 | 39850 | 21121 | 19105 | 22435 | 19406 | 22180 | 18283 | 44279 | 16044 | 15226 | 20517 |
| 29.18 | 40962 | 21835 | 22533 | 23252 | 20992 | 26545 | 22912 | 48747 | 17128 | 16585 | 23235 |
| 29.22 | 41177 | 22110 | 23768 | 24534 | 19251 | 23129 | 20337 | 45568 | 16680 | 16233 | 21115 |
| 29.26 | 38850 | 22589 | 23713 | 22928 | 19972 | 24024 | 21045 | 44187 | 16368 | 16687 | 19743 |
| 29.3 | 38179 | 20381 | 24755 | 23847 | 18672 | 21451 | 19652 | 42045 | 16534 | 17770 | 18249 |
| 29.34 | 40245 | 20793 | 25490 | 22712 | 19111 | 24709 | 19989 | 42316 | 15519 | 17650 | 20197 |
| 29.38 | 41635 | 20823 | 28859 | 21811 | 18558 | 23470 | 23006 | 44319 | 17126 | 18581 | 19901 |
| 29.42 | 41653 | 20519 | 26553 | 23570 | 20293 | 23410 | 21948 | 44051 | 18322 | 16366 | 21792 |
| 29.46 | 39260 | 20429 | 28113 | 22433 | 19651 | 24165 | 23415 | 41450 | 19862 | 18352 | 19155 |
| 29.5 | 40776 | 18729 | 27182 | 21324 | 18303 | 25116 | 21609 | 42348 | 17543 | 19572 | 18853 |
| 29.54 | 40821 | 18813 | 28984 | 23658 | 20719 | 23301 | 22894 | 43378 | 19621 | 20848 | 19283 |

-continued

| | | | | | | | | | | | |
|---|---|---|---|---|---|---|---|---|---|---|---|
| 29.58 | 41061 | 18488 | 27073 | 21055 | 19927 | 22278 | 22026 | 41180 | 19578 | 21777 | 19300 |
| 29.62 | 37499 | 19492 | 25167 | 23290 | 18915 | 24074 | 20903 | 43081 | 18427 | 21046 | 19798 |
| 29.66 | 38396 | 18533 | 23219 | 23098 | 19276 | 24280 | 23366 | 43539 | 19970 | 19451 | 17614 |
| 29.7 | 38075 | 20224 | 20993 | 26188 | 18027 | 24522 | 21089 | 43066 | 20575 | 19547 | 18771 |
| 29.74 | 40124 | 19616 | 20333 | 26312 | 19069 | 21978 | 21860 | 39412 | 21460 | 20612 | 20644 |
| 29.78 | 39381 | 18854 | 19548 | 26321 | 19419 | 22672 | 20169 | 39304 | 21641 | 21155 | 18754 |
| 29.82 | 40986 | 19326 | 18408 | 28088 | 20583 | 23093 | 20908 | 44423 | 19863 | 20196 | 19644 |
| 29.86 | 37797 | 20326 | 18148 | 29176 | 18760 | 21607 | 20537 | 42399 | 20345 | 19052 | 19546 |
| 29.9 | 37275 | 18234 | 16317 | 29262 | 17900 | 24310 | 18815 | 38600 | 19456 | 19461 | 20109 |
| 29.94 | 37009 | 18098 | 15869 | 31374 | 17827 | 21644 | 18680 | 40058 | 19617 | 19923 | 19479 |
| 29.98 | 38589 | 18718 | 17772 | 30553 | 20059 | 20929 | 17382 | 39400 | 19279 | 17579 | 20828 |
| 30.02 | 36661 | 18747 | 16563 | 32904 | 17916 | 21201 | 17552 | 42157 | 17714 | 18253 | 19189 |
| 30.06 | 37815 | 19044 | 16242 | 30809 | 19124 | 23635 | 18010 | 41350 | 16565 | 18086 | 19615 |
| 30.1 | 33936 | 18961 | 16818 | 30835 | 18299 | 23824 | 17514 | 43667 | 16427 | 16735 | 20761 |
| 30.14 | 37279 | 17109 | 16953 | 24880 | 16786 | 23189 | 16915 | 40937 | 16556 | 15217 | 22339 |
| 30.18 | 34150 | 17212 | 19036 | 26053 | 15772 | 22741 | 17373 | 40361 | 15751 | 16843 | 19889 |
| 30.22 | 34973 | 17961 | 18138 | 23952 | 16914 | 23207 | 17030 | 38783 | 14376 | 16380 | 20308 |
| 30.26 | 36064 | 18729 | 15910 | 24787 | 17864 | 21804 | 15151 | 39693 | 13081 | 17528 | 20523 |
| 30.3 | 35282 | 17535 | 17666 | 23568 | 17904 | 21093 | 16821 | 41165 | 13168 | 15799 | 20634 |
| 30.34 | 34149 | 18872 | 18990 | 23835 | 17817 | 22893 | 17202 | 40418 | 13701 | 15526 | 19033 |
| 30.38 | 34451 | 16236 | 17125 | 21141 | 18605 | 21575 | 16992 | 39920 | 12296 | 16840 | 18761 |
| 30.42 | 34489 | 16813 | 16836 | 22653 | 17788 | 21691 | 15842 | 40913 | 12834 | 15085 | 17459 |
| 30.46 | 35823 | 14328 | 15678 | 21714 | 15260 | 20834 | 16101 | 42359 | 11722 | 15210 | 18356 |
| 30.5 | 36135 | 16598 | 16279 | 21735 | 16942 | 22238 | 15006 | 42185 | 12756 | 14323 | 18548 |
| 30.54 | 33783 | 16644 | 16519 | 20483 | 17246 | 22709 | 15014 | 38945 | 10833 | 16483 | 17253 |
| 30.58 | 36609 | 16376 | 17166 | 19927 | 17156 | 22561 | 16547 | 40195 | 12016 | 14529 | 18085 |
| 30.62 | 33882 | 16982 | 18124 | 19880 | 16405 | 19539 | 14990 | 39182 | 11666 | 14544 | 16464 |
| 30.66 | 34123 | 15891 | 20467 | 20670 | 14212 | 21909 | 15228 | 42784 | 10592 | 17038 | 17624 |
| 30.7 | 35864 | 16057 | 19361 | 19561 | 15507 | 22904 | 14772 | 39477 | 10574 | 14711 | 18792 |
| 30.74 | 32651 | 16443 | 25230 | 19152 | 15970 | 21383 | 15667 | 39207 | 12477 | 15010 | 16878 |
| 30.78 | 34538 | 18354 | 26939 | 19820 | 15307 | 21961 | 15715 | 39353 | 12009 | 13635 | 16443 |
| 30.82 | 35327 | 16790 | 31426 | 20630 | 17750 | 19748 | 15815 | 38941 | 11395 | 13427 | 17888 |
| 30.86 | 35329 | 16329 | 29780 | 21680 | 15704 | 21287 | 15575 | 39998 | 10038 | 14136 | 16877 |
| 30.9 | 36058 | 16170 | 35463 | 20132 | 16855 | 20519 | 16187 | 40915 | 10723 | 12138 | 17254 |
| 30.94 | 33400 | 15826 | 38925 | 20659 | 16997 | 20600 | 14857 | 40713 | 11982 | 13354 | 16050 |
| 30.98 | 34682 | 15183 | 39610 | 21591 | 16276 | 21471 | 15270 | 41282 | 10818 | 13383 | 17046 |
| 31.02 | 36454 | 16614 | 41757 | 20933 | 14714 | 22702 | 15683 | 43067 | 10013 | 13257 | 17444 |
| 31.06 | 33238 | 15711 | 39435 | 22225 | 16236 | 21992 | 14655 | 42046 | 11880 | 13719 | 16645 |
| 31.1 | 34606 | 15367 | 38378 | 18982 | 15194 | 22815 | 15374 | 41134 | 12192 | 13540 | 15445 |
| 31.14 | 34719 | 16240 | 36627 | 18991 | 16823 | 21423 | 16852 | 41393 | 11680 | 12020 | 18077 |
| 31.18 | 34756 | 14805 | 30861 | 18534 | 16490 | 22209 | 16633 | 39939 | 10311 | 13910 | 14746 |
| 31.22 | 35899 | 17466 | 28103 | 19822 | 15478 | 22751 | 15402 | 41314 | 10529 | 13861 | 16934 |
| 31.26 | 37680 | 16573 | 26345 | 18127 | 15170 | 21831 | 15092 | 43336 | 12026 | 14027 | 17673 |
| 31.3 | 35851 | 15464 | 24915 | 20124 | 14886 | 24723 | 15970 | 41694 | 11319 | 13417 | 17732 |
| 31.34 | 35747 | 16309 | 21652 | 17594 | 16130 | 22602 | 15307 | 42558 | 11351 | 13648 | 16555 |
| 31.38 | 37154 | 16073 | 21160 | 18149 | 16465 | 22536 | 16024 | 41737 | 11590 | 12068 | 17369 |
| 31.42 | 36016 | 16870 | 20130 | 19541 | 17834 | 23601 | 16863 | 41888 | 10694 | 12608 | 17455 |
| 31.46 | 38670 | 16650 | 20141 | 17383 | 16339 | 24533 | 16132 | 43428 | 10859 | 11525 | 15887 |
| 31.5 | 36710 | 16269 | 18818 | 16890 | 14688 | 23187 | 17177 | 42514 | 11522 | 13901 | 16062 |
| 31.54 | 37027 | 16527 | 17961 | 19594 | 14631 | 21330 | 16567 | 42496 | 10796 | 11728 | 15725 |
| 31.58 | 38278 | 15379 | 17741 | 19189 | 15341 | 23612 | 15920 | 43853 | 10824 | 13804 | 16508 |
| 31.62 | 35235 | 15509 | 18729 | 15816 | 15885 | 22909 | 17767 | 43747 | 10377 | 13120 | 14521 |
| 31.66 | 34278 | 15411 | 17270 | 17658 | 14469 | 23528 | 17741 | 42095 | 10789 | 12362 | 16266 |
| 31.7 | 35711 | 16968 | 16432 | 17693 | 14704 | 21316 | 17840 | 45381 | 11496 | 13249 | 16515 |
| 31.74 | 35249 | 15277 | 15987 | 16129 | 14262 | 22757 | 17866 | 43321 | 12016 | 13445 | 15137 |
| 31.78 | 34116 | 15126 | 15898 | 17601 | 14192 | 21077 | 18626 | 43343 | 11225 | 13209 | 15293 |
| 31.82 | 33319 | 15668 | 14792 | 16481 | 14697 | 22040 | 19576 | 42315 | 12282 | 12347 | 13333 |
| 31.86 | 34359 | 15343 | 15577 | 16789 | 14198 | 23048 | 20562 | 42282 | 11932 | 13406 | 15343 |
| 31.9 | 33028 | 16122 | 15875 | 15700 | 15864 | 20825 | 19944 | 41474 | 11147 | 14240 | 14922 |
| 31.94 | 33755 | 15903 | 15478 | 17718 | 15660 | 20994 | 21237 | 40709 | 11984 | 13221 | 14559 |
| 31.98 | 33563 | 14991 | 16259 | 17721 | 15537 | 21745 | 19915 | 38816 | 11867 | 14314 | 14867 |
| 32.02 | 32913 | 16141 | 17401 | 15507 | 15383 | 21503 | 19642 | 40697 | 13608 | 13754 | 15454 |
| 32.06 | 32820 | 15561 | 20004 | 14366 | 14090 | 21506 | 19386 | 41827 | 12862 | 12968 | 15238 |
| 32.1 | 31479 | 15550 | 19888 | 17055 | 13781 | 22707 | 18693 | 43291 | 12587 | 12618 | 15236 |
| 32.14 | 32858 | 17186 | 18549 | 17332 | 14197 | 20371 | 20477 | 42939 | 12745 | 12094 | 13460 |
| 32.18 | 30645 | 15302 | 20922 | 16075 | 13912 | 19996 | 18752 | 37787 | 13563 | 11848 | 13880 |
| 32.22 | 32563 | 15317 | 19493 | 16733 | 13803 | 21337 | 17114 | 38950 | 11944 | 12214 | 14855 |
| 32.26 | 31810 | 16777 | 21234 | 17051 | 14580 | 23353 | 16944 | 42446 | 12496 | 13572 | 14666 |
| 32.3 | 30330 | 15394 | 21040 | 18198 | 14426 | 20239 | 15599 | 40595 | 12466 | 13687 | 13969 |
| 32.34 | 30787 | 14365 | 19748 | 16157 | 14151 | 20546 | 16357 | 41546 | 11751 | 12726 | 14312 |
| 32.38 | 32150 | 15580 | 20969 | 18191 | 14738 | 21317 | 16446 | 42529 | 12625 | 12051 | 13710 |
| 32.42 | 29932 | 14690 | 20113 | 16911 | 13791 | 21953 | 15960 | 42382 | 13023 | 11633 | 14261 |
| 32.46 | 29288 | 14091 | 18687 | 17126 | 14790 | 19570 | 15243 | 40274 | 11914 | 11784 | 13498 |
| 32.5 | 32934 | 14522 | 19828 | 17565 | 15534 | 21221 | 15469 | 40710 | 12705 | 12058 | 15891 |
| 32.54 | 31618 | 14546 | 17112 | 16486 | 16288 | 21288 | 14954 | 40217 | 12759 | 13278 | 14370 |
| 32.58 | 32107 | 16280 | 16667 | 18617 | 15912 | 21859 | 15747 | 39477 | 12959 | 12683 | 14240 |
| 32.62 | 29503 | 14719 | 15507 | 16601 | 13708 | 22145 | 15994 | 36816 | 12962 | 12917 | 13775 |
| 32.66 | 28357 | 14129 | 14933 | 17598 | 15089 | 19915 | 15600 | 39984 | 13379 | 12928 | 14714 |
| 32.7 | 30262 | 13062 | 13327 | 16712 | 15475 | 19137 | 15911 | 37486 | 12771 | 12435 | 15305 |

-continued

| | | | | | | | | | | | |
|---|---|---|---|---|---|---|---|---|---|---|---|
| 32.74 | 28519 | 14301 | 14091 | 17689 | 11886 | 19737 | 13345 | 38065 | 11247 | 10770 | 15716 |
| 32.78 | 27918 | 14950 | 14518 | 16769 | 15044 | 20533 | 14804 | 36567 | 11784 | 13381 | 16126 |
| 32.82 | 32039 | 15200 | 15118 | 16213 | 14318 | 19526 | 15445 | 37124 | 11384 | 14412 | 15251 |
| 32.86 | 29678 | 13781 | 14484 | 17437 | 12397 | 20394 | 15313 | 36463 | 11159 | 12701 | 15559 |
| 32.9 | 28380 | 14914 | 13251 | 16351 | 14152 | 18556 | 14967 | 36306 | 11450 | 12741 | 15331 |
| 32.94 | 29083 | 14297 | 14793 | 17508 | 14571 | 19645 | 16553 | 36182 | 11931 | 13692 | 13927 |
| 32.98 | 31519 | 13156 | 13951 | 15630 | 15128 | 21355 | 14001 | 38000 | 11009 | 13953 | 14630 |
| 33.02 | 30258 | 15185 | 15713 | 17646 | 14069 | 19393 | 13872 | 36254 | 13153 | 13615 | 15316 |
| 33.06 | 31340 | 16426 | 14540 | 15775 | 14407 | 18231 | 13889 | 36667 | 11931 | 12589 | 16009 |
| 33.1 | 28539 | 13902 | 16538 | 16297 | 14740 | 19955 | 14512 | 34968 | 10050 | 12640 | 15321 |
| 33.14 | 28062 | 14512 | 14129 | 16925 | 14693 | 17027 | 13366 | 35352 | 11613 | 12264 | 14863 |
| 33.18 | 29270 | 14755 | 14984 | 16029 | 14094 | 17781 | 14235 | 34913 | 12487 | 12979 | 18124 |
| 33.22 | 28252 | 14894 | 16212 | 16478 | 14750 | 18505 | 14634 | 36314 | 13535 | 12967 | 16103 |
| 33.26 | 29260 | 13277 | 14901 | 17082 | 12641 | 19544 | 15943 | 34605 | 13423 | 12184 | 15281 |
| 33.3 | 29272 | 13558 | 15267 | 17150 | 13457 | 18793 | 14699 | 35895 | 14072 | 12990 | 16789 |
| 33.34 | 27881 | 14056 | 15757 | 16863 | 13880 | 19182 | 12332 | 35947 | 13507 | 12616 | 16061 |
| 33.38 | 28086 | 15925 | 16024 | 17378 | 13450 | 18859 | 15280 | 35903 | 14633 | 11718 | 17099 |
| 33.42 | 28507 | 14872 | 15315 | 17076 | 14204 | 19553 | 13860 | 35971 | 13236 | 11381 | 17623 |
| 33.46 | 28512 | 14236 | 17252 | 17541 | 15313 | 19556 | 15377 | 38151 | 11632 | 10472 | 16952 |
| 33.5 | 29474 | 13769 | 18250 | 16745 | 13503 | 20890 | 15289 | 33087 | 13004 | 11552 | 15779 |
| 33.54 | 28491 | 14502 | 17468 | 16672 | 12731 | 19066 | 15131 | 35027 | 11056 | 11450 | 17332 |
| 33.58 | 28102 | 14252 | 17571 | 18541 | 11872 | 20530 | 14873 | 32322 | 12199 | 10315 | 14947 |
| 33.62 | 27603 | 14190 | 17482 | 17560 | 12766 | 20655 | 15956 | 34159 | 12066 | 11028 | 15526 |
| 33.66 | 28880 | 14246 | 17094 | 17021 | 13554 | 18742 | 14340 | 35690 | 11338 | 11064 | 15832 |
| 33.7 | 26969 | 13251 | 18962 | 17050 | 12565 | 21780 | 16604 | 36695 | 11030 | 10785 | 14500 |
| 33.74 | 29367 | 14475 | 17502 | 17061 | 13964 | 20089 | 16105 | 35468 | 9683 | 11576 | 15819 |
| 33.78 | 27417 | 13910 | 17050 | 16978 | 14409 | 19766 | 16551 | 35653 | 10963 | 11465 | 15583 |
| 33.82 | 26783 | 13341 | 16764 | 16969 | 13486 | 20408 | 14358 | 35425 | 10676 | 11382 | 14931 |
| 33.86 | 27155 | 13925 | 16074 | 17308 | 12548 | 18662 | 16336 | 34621 | 10822 | 11159 | 15048 |
| 33.9 | 27808 | 14828 | 15503 | 17125 | 12560 | 19451 | 16016 | 33519 | 11260 | 11503 | 13240 |
| 33.94 | 28562 | 12373 | 15385 | 17098 | 13706 | 18799 | 14799 | 34180 | 12754 | 10505 | 14084 |
| 33.98 | 29585 | 13848 | 15745 | 17761 | 12911 | 19092 | 12814 | 33639 | 10151 | 12484 | 12575 |
| 34.02 | 29116 | 12196 | 15322 | 17300 | 12234 | 18362 | 14825 | 33949 | 12202 | 10586 | 13184 |
| 34.06 | 27933 | 14752 | 14577 | 16899 | 12921 | 20587 | 14222 | 35355 | 11978 | 10998 | 14037 |
| 34.1 | 29448 | 14326 | 14783 | 16720 | 14613 | 19048 | 13658 | 33429 | 13359 | 10564 | 13088 |
| 34.14 | 29818 | 13184 | 15363 | 16027 | 13993 | 19470 | 14351 | 31216 | 13724 | 12749 | 13122 |
| 34.18 | 29976 | 14151 | 15071 | 16386 | 13920 | 19108 | 13468 | 36286 | 12913 | 11569 | 13024 |
| 34.22 | 30022 | 13994 | 15718 | 17206 | 12803 | 19683 | 15388 | 33856 | 13611 | 12470 | 13458 |
| 34.26 | 28232 | 12400 | 14310 | 16777 | 12513 | 19136 | 13938 | 33475 | 13504 | 12769 | 12351 |
| 34.3 | 28148 | 14368 | 15061 | 17209 | 12317 | 18622 | 14197 | 33609 | 15384 | 13209 | 13263 |
| 34.34 | 28517 | 13832 | 14911 | 17791 | 12675 | 19721 | 14600 | 33021 | 15437 | 11484 | 12495 |
| 34.38 | 27467 | 12791 | 14392 | 16192 | 12566 | 18256 | 13573 | 35866 | 13685 | 12350 | 13715 |
| 34.42 | 29855 | 13066 | 13979 | 16645 | 13990 | 18166 | 14473 | 32617 | 12621 | 13813 | 13558 |
| 34.46 | 30120 | 13322 | 14278 | 17269 | 13631 | 19159 | 15520 | 32510 | 11558 | 12237 | 13367 |
| 34.5 | 28530 | 13357 | 13960 | 16317 | 13456 | 18028 | 14277 | 32625 | 11187 | 12820 | 13352 |
| 34.54 | 30708 | 14436 | 12447 | 17290 | 13225 | 19908 | 15026 | 34870 | 12027 | 11699 | 12466 |
| 34.58 | 27885 | 13882 | 14092 | 16342 | 13150 | 19713 | 15984 | 31939 | 11958 | 12169 | 15271 |
| 34.62 | 29076 | 13396 | 12756 | 15855 | 12169 | 18916 | 14757 | 33554 | 10159 | 12250 | 12895 |
| 34.66 | 28933 | 13472 | 13526 | 15813 | 12651 | 18768 | 13440 | 34718 | 10945 | 12032 | 12765 |
| 34.7 | 26838 | 12579 | 13163 | 17403 | 13716 | 17984 | 14589 | 34431 | 9030 | 11547 | 11434 |
| 34.74 | 27878 | 12337 | 14462 | 17741 | 11095 | 17704 | 13941 | 33420 | 9698 | 10180 | 12964 |
| 34.78 | 27758 | 13193 | 14405 | 17796 | 11712 | 19889 | 14308 | 34483 | 11163 | 10170 | 12336 |
| 34.82 | 27502 | 12046 | 14288 | 16131 | 12092 | 16950 | 15896 | 33245 | 10945 | 10398 | 13876 |
| 34.86 | 27515 | 12685 | 17268 | 17134 | 12563 | 18974 | 14142 | 33912 | 9182 | 10726 | 13012 |
| 34.9 | 27481 | 12330 | 16303 | 16724 | 13242 | 18502 | 13595 | 33998 | 10718 | 10153 | 12839 |
| 34.94 | 27166 | 12685 | 16867 | 15896 | 12685 | 19538 | 16128 | 34112 | 11000 | 10381 | 12485 |
| 34.98 | 27850 | 12233 | 16214 | 16067 | 12273 | 18921 | 13798 | 34122 | 10799 | 11264 | 13885 |
| 35.02 | 28098 | 13716 | 16296 | 15307 | 12864 | 18952 | 15174 | 33427 | 9793 | 10782 | 13023 |
| 35.06 | 27715 | 13600 | 18645 | 15792 | 13084 | 18566 | 15289 | 33861 | 10868 | 10020 | 12038 |
| 35.1 | 27811 | 13782 | 18813 | 15594 | 12473 | 17381 | 15076 | 36476 | 9802 | 10130 | 14709 |
| 35.14 | 25875 | 12390 | 16080 | 14895 | 11877 | 17668 | 13316 | 35322 | 11650 | 10855 | 12769 |
| 35.18 | 27523 | 12570 | 16682 | 15303 | 13282 | 18952 | 14130 | 35741 | 11171 | 10427 | 14449 |
| 35.22 | 27158 | 12929 | 17262 | 15248 | 12686 | 17558 | 14173 | 33230 | 13397 | 10317 | 13911 |
| 35.26 | 26411 | 11962 | 16224 | 17006 | 12998 | 19070 | 14778 | 33442 | 13261 | 10490 | 11508 |
| 35.3 | 26742 | 14210 | 16219 | 16869 | 12302 | 19950 | 13686 | 33578 | 12372 | 10229 | 13863 |
| 35.34 | 26289 | 13348 | 17218 | 17174 | 11782 | 17624 | 14558 | 32358 | 13619 | 11009 | 13866 |
| 35.38 | 28172 | 12438 | 16808 | 16369 | 12900 | 17716 | 13535 | 33933 | 11656 | 10801 | 13069 |
| 35.42 | 27871 | 13185 | 17731 | 17406 | 12035 | 18544 | 14539 | 33329 | 13262 | 9610 | 14491 |
| 35.46 | 26928 | 12620 | 18930 | 16797 | 12268 | 18761 | 15302 | 33177 | 12616 | 9452 | 12733 |
| 35.5 | 26267 | 12946 | 18939 | 16504 | 12022 | 17623 | 15039 | 31419 | 11699 | 10120 | 12923 |
| 35.54 | 27897 | 12447 | 19490 | 16993 | 12647 | 17417 | 14289 | 32609 | 12754 | 10403 | 13078 |
| 35.58 | 26563 | 11947 | 20890 | 15089 | 12637 | 16605 | 14435 | 32872 | 10904 | 10028 | 12668 |
| 35.62 | 26206 | 12064 | 21478 | 15692 | 12849 | 17503 | 13396 | 33937 | 11403 | 10005 | 11728 |
| 35.66 | 27400 | 13130 | 21138 | 17015 | 12621 | 18251 | 15823 | 31389 | 10809 | 10671 | 12894 |
| 35.7 | 27068 | 13929 | 20472 | 15051 | 12126 | 17555 | 16461 | 29349 | 11025 | 9670 | 13047 |
| 35.74 | 25126 | 13047 | 22449 | 15238 | 11091 | 15231 | 14673 | 30999 | 10626 | 10097 | 13392 |
| 35.78 | 28281 | 13573 | 19868 | 15388 | 10721 | 15594 | 14699 | 30981 | 11231 | 8982 | 13681 |
| 35.82 | 29113 | 12224 | 18995 | 14677 | 11798 | 17298 | 14888 | 29722 | 10663 | 9658 | 13521 |
| 35.86 | 27178 | 14254 | 17526 | 15058 | 12914 | 17803 | 13699 | 32285 | 10141 | 10437 | 13751 |

-continued

| | | | | | | | | | | | |
|---|---|---|---|---|---|---|---|---|---|---|---|
| 35.9 | 28224 | 14362 | 14713 | 15272 | 12672 | 17708 | 14162 | 31948 | 10668 | 8841 | 12216 |
| 35.94 | 28844 | 11485 | 15863 | 14719 | 13143 | 16746 | 13677 | 30265 | 10850 | 9302 | 13588 |
| 35.98 | 27939 | 12961 | 16375 | 13473 | 11151 | 17182 | 13804 | 32047 | 10762 | 9908 | 11287 |
| 36.02 | 27830 | 12608 | 16294 | 14777 | 10356 | 16002 | 14086 | 32709 | 11296 | 9681 | 13943 |
| 36.06 | 27312 | 12511 | 14388 | 13249 | 10753 | 18495 | 14185 | 31096 | 11624 | 9938 | 12651 |
| 36.1 | 27022 | 12021 | 14205 | 15411 | 10826 | 15820 | 14032 | 31956 | 11203 | 11103 | 12356 |
| 36.14 | 29057 | 11395 | 15388 | 15268 | 12743 | 17982 | 13660 | 29773 | 10346 | 10419 | 11642 |
| 36.18 | 27688 | 13230 | 15055 | 14357 | 12146 | 16944 | 13723 | 31163 | 10238 | 10044 | 11539 |
| 36.22 | 28459 | 13149 | 15330 | 16418 | 12677 | 16017 | 13664 | 32470 | 11442 | 10899 | 11103 |
| 36.26 | 29667 | 12627 | 16317 | 15304 | 12082 | 17495 | 13942 | 30477 | 11996 | 11137 | 12094 |
| 36.3 | 30183 | 12229 | 15434 | 14418 | 11333 | 18163 | 15337 | 31212 | 12113 | 10594 | 12366 |
| 36.34 | 28212 | 12971 | 16275 | 16029 | 12151 | 18044 | 15378 | 31492 | 12494 | 10223 | 11687 |
| 36.38 | 28891 | 12747 | 16861 | 15888 | 12164 | 17731 | 16228 | 30113 | 11544 | 11695 | 13226 |
| 36.42 | 28897 | 13927 | 16818 | 17964 | 13101 | 18079 | 14813 | 31653 | 10428 | 10467 | 11663 |
| 36.46 | 28802 | 12672 | 14573 | 16216 | 10576 | 16285 | 15705 | 30303 | 12146 | 10323 | 11805 |
| 36.5 | 29719 | 12437 | 15434 | 15477 | 11797 | 16760 | 15011 | 29634 | 11355 | 9505 | 12388 |
| 36.54 | 30114 | 13311 | 14858 | 15564 | 11441 | 17318 | 15251 | 29123 | 11803 | 10397 | 12316 |
| 36.58 | 27303 | 11962 | 16459 | 15685 | 12604 | 17766 | 14751 | 31670 | 10770 | 11301 | 12756 |
| 36.62 | 27525 | 12078 | 14617 | 16793 | 12038 | 16282 | 14127 | 31005 | 10486 | 10495 | 12320 |
| 36.66 | 27731 | 11774 | 15452 | 17216 | 12301 | 17579 | 13180 | 30366 | 11581 | 10813 | 12163 |
| 36.7 | 25887 | 12091 | 15947 | 14723 | 10749 | 16651 | 14817 | 32956 | 10177 | 10931 | 11532 |
| 36.74 | 26600 | 12924 | 15260 | 14794 | 11205 | 17434 | 14262 | 31475 | 10122 | 11900 | 12014 |
| 36.78 | 25459 | 12987 | 15254 | 14090 | 10825 | 17206 | 13700 | 30924 | 10061 | 10697 | 12226 |
| 36.82 | 25110 | 13012 | 15539 | 14034 | 10958 | 15830 | 13672 | 32859 | 10301 | 10616 | 12440 |
| 36.86 | 25102 | 12580 | 14553 | 14400 | 10277 | 16038 | 12027 | 30631 | 9844 | 11439 | 11672 |
| 36.9 | 26053 | 12653 | 15277 | 15285 | 11735 | 16146 | 12888 | 30527 | 10515 | 10128 | 11911 |
| 36.94 | 26713 | 11519 | 14328 | 14670 | 12030 | 16889 | 12964 | 31367 | 10604 | 10884 | 11133 |
| 36.98 | 27481 | 12189 | 15238 | 14216 | 10390 | 16259 | 13196 | 30410 | 10686 | 10968 | 12021 |
| 37.02 | 26255 | 13486 | 14943 | 12311 | 11063 | 15372 | 13535 | 29841 | 10267 | 10335 | 11137 |
| 37.06 | 24901 | 12425 | 15034 | 14390 | 10770 | 16461 | 12989 | 30462 | 10588 | 9843 | 11569 |
| 37.1 | 27190 | 12349 | 15234 | 12969 | 10262 | 16182 | 13003 | 31863 | 9490 | 9752 | 11045 |
| 37.14 | 25351 | 13330 | 15238 | 14341 | 11013 | 16199 | 12356 | 29830 | 9353 | 8765 | 11316 |
| 37.18 | 25154 | 12993 | 16046 | 13336 | 10973 | 15275 | 13081 | 30385 | 9702 | 9962 | 11437 |
| 37.22 | 25937 | 11234 | 15488 | 13842 | 11019 | 14687 | 12807 | 28326 | 8808 | 10211 | 12671 |
| 37.26 | 24792 | 13169 | 14994 | 13396 | 12153 | 15197 | 12451 | 27389 | 9027 | 9127 | 12809 |
| 37.3 | 25179 | 12698 | 13861 | 14947 | 10844 | 13852 | 12699 | 28526 | 8808 | 9132 | 11972 |
| 37.34 | 25376 | 12796 | 15584 | 14193 | 10854 | 15375 | 12065 | 28059 | 9742 | 9488 | 11115 |
| 37.38 | 24279 | 12329 | 15437 | 14543 | 10302 | 15506 | 11757 | 29652 | 8834 | 9292 | 11110 |
| 37.42 | 24737 | 10643 | 16439 | 13535 | 10590 | 15839 | 12535 | 29068 | 9352 | 9606 | 10889 |
| 37.46 | 22887 | 12290 | 15167 | 14801 | 11720 | 15108 | 12314 | 29385 | 8557 | 10240 | 11755 |
| 37.5 | 25474 | 12242 | 15344 | 13996 | 10642 | 16219 | 12454 | 30453 | 9197 | 9224 | 10750 |
| 37.54 | 25462 | 13211 | 16599 | 16491 | 11982 | 15143 | 13430 | 29546 | 9582 | 10058 | 12066 |
| 37.58 | 26453 | 12024 | 16002 | 14040 | 10851 | 15784 | 13518 | 31281 | 9996 | 9241 | 11177 |
| 37.62 | 24707 | 12561 | 15023 | 14197 | 10423 | 15022 | 14196 | 29690 | 10746 | 10243 | 12081 |
| 37.66 | 26064 | 12386 | 14455 | 13206 | 10605 | 14226 | 13640 | 31663 | 9090 | 9516 | 11550 |
| 37.7 | 26531 | 11618 | 15600 | 14791 | 11018 | 15624 | 12532 | 32414 | 9580 | 10578 | 10799 |
| 37.74 | 26028 | 11998 | 15092 | 14599 | 11104 | 15783 | 14276 | 31056 | 10533 | 9674 | 10685 |
| 37.78 | 25965 | 12208 | 15913 | 13354 | 10912 | 15897 | 14019 | 29511 | 9632 | 9786 | 11640 |
| 37.82 | 27170 | 12677 | 16113 | 14116 | 9771 | 15524 | 13607 | 32397 | 8676 | 11030 | 11856 |
| 37.86 | 25593 | 11773 | 15018 | 13368 | 10669 | 15160 | 13769 | 28997 | 9303 | 10438 | 11868 |
| 37.9 | 25382 | 13740 | 15865 | 13272 | 11676 | 15930 | 15028 | 30046 | 8822 | 10491 | 11593 |
| 37.94 | 25934 | 11801 | 14574 | 13338 | 11084 | 15377 | 14112 | 31930 | 9674 | 9747 | 11967 |
| 37.98 | 25997 | 10685 | 14710 | 12589 | 10400 | 15989 | 14301 | 29193 | 9386 | 10141 | 11047 |
| 38.02 | 25088 | 11329 | 16252 | 12763 | 11244 | 14756 | 13671 | 29419 | 8896 | 10939 | 13029 |
| 38.06 | 27159 | 13452 | 14721 | 14204 | 11271 | 16168 | 13323 | 32453 | 8221 | 9910 | 13296 |
| 38.1 | 26114 | 13154 | 16023 | 13889 | 11104 | 16169 | 13298 | 30837 | 8688 | 10273 | 12127 |
| 38.14 | 26751 | 13030 | 16425 | 14901 | 10169 | 15534 | 13291 | 29115 | 9013 | 9547 | 11176 |
| 38.18 | 27635 | 14261 | 15252 | 13467 | 11091 | 15451 | 13883 | 30212 | 9348 | 9587 | 10993 |
| 38.22 | 25320 | 11224 | 16351 | 13690 | 10827 | 15044 | 13481 | 31215 | 9125 | 9808 | 13718 |
| 38.26 | 26107 | 11939 | 17143 | 12190 | 10274 | 16614 | 13162 | 29061 | 8520 | 10873 | 11707 |
| 38.3 | 25598 | 12339 | 16402 | 12733 | 10443 | 16075 | 13852 | 28214 | 9072 | 10485 | 12216 |
| 38.34 | 25146 | 13204 | 17146 | 12948 | 10607 | 16016 | 13644 | 31232 | 8572 | 10152 | 12919 |
| 38.38 | 26202 | 12513 | 15021 | 13419 | 10752 | 17697 | 12865 | 29811 | 9281 | 10424 | 12170 |
| 38.42 | 26891 | 11208 | 15967 | 14298 | 12065 | 16974 | 13134 | 28047 | 9847 | 9874 | 12936 |
| 38.46 | 24171 | 12971 | 15392 | 12712 | 10689 | 16137 | 12754 | 28767 | 8851 | 10475 | 11522 |
| 38.5 | 24946 | 11559 | 16222 | 13646 | 10015 | 17296 | 12636 | 31670 | 9988 | 9986 | 13666 |
| 38.54 | 27024 | 12239 | 14896 | 12465 | 11173 | 14702 | 12737 | 28350 | 9430 | 8937 | 13468 |
| 38.58 | 24487 | 12291 | 14769 | 12732 | 10469 | 15510 | 12180 | 29789 | 9876 | 9623 | 13367 |
| 38.62 | 24253 | 12563 | 13265 | 13170 | 10183 | 15584 | 12767 | 29939 | 11162 | 11026 | 12636 |
| 38.66 | 25134 | 12151 | 12859 | 13378 | 9650 | 15412 | 13229 | 29965 | 10043 | 10247 | 12285 |
| 38.7 | 25843 | 12645 | 13450 | 13228 | 10124 | 14430 | 12142 | 31142 | 9716 | 10294 | 11774 |
| 38.74 | 25394 | 13253 | 13919 | 13659 | 9587 | 16420 | 12920 | 32526 | 10417 | 10925 | 11774 |
| 38.78 | 28144 | 12951 | 13176 | 12632 | 9220 | 16266 | 12174 | 33108 | 9460 | 11050 | 12453 |
| 38.82 | 25776 | 12249 | 14097 | 13042 | 9740 | 15851 | 13593 | 30428 | 9908 | 9835 | 12449 |
| 38.86 | 24215 | 12397 | 12368 | 12149 | 9876 | 15875 | 12352 | 30344 | 9985 | 10034 | 12273 |
| 38.9 | 26954 | 13203 | 13232 | 12948 | 10005 | 16331 | 12797 | 30242 | 11864 | 10972 | 12414 |
| 38.94 | 26228 | 12246 | 12456 | 13641 | 9848 | 16483 | 11762 | 29626 | 12200 | 10899 | 12329 |
| 38.98 | 25598 | 12828 | 12669 | 13696 | 9765 | 17018 | 12841 | 30779 | 11911 | 9124 | 12547 |
| 39.02 | 26389 | 11928 | 11701 | 12773 | 10465 | 16284 | 11197 | 30077 | 11421 | 9307 | 11674 |

| | | | | | | | | | | |
|---|---|---|---|---|---|---|---|---|---|---|
| 39.06 | 27322 | 12791 | 12630 | 12288 | 11581 | 14752 | 12579 | 30766 | 11434 | 10870 | 12403 |
| 39.1 | 27664 | 11273 | 12946 | 12217 | 11636 | 14466 | 11521 | 29714 | 10446 | 9608 | 11363 |
| 39.14 | 26348 | 12810 | 11811 | 11974 | 9867 | 15699 | 11649 | 29937 | 10353 | 9272 | 11844 |
| 39.18 | 26941 | 11773 | 12600 | 13247 | 11026 | 14396 | 11416 | 30590 | 11305 | 10191 | 11602 |
| 39.22 | 27275 | 11844 | 13140 | 12811 | 10350 | 14855 | 12041 | 29045 | 9236 | 9747 | 11696 |
| 39.26 | 25960 | 12723 | 13584 | 12540 | 10662 | 15121 | 10967 | 28837 | 9431 | 9692 | 12166 |
| 39.3 | 27202 | 13237 | 14083 | 12944 | 10643 | 15786 | 11843 | 29961 | 9681 | 8352 | 11032 |
| 39.34 | 27308 | 11854 | 12603 | 11917 | 10784 | 15570 | 11752 | 31687 | 9253 | 9913 | 11574 |
| 39.38 | 27698 | 12031 | 13133 | 12661 | 10036 | 15443 | 12136 | 31894 | 9469 | 10602 | 12874 |
| 39.42 | 26126 | 12191 | 12694 | 10954 | 8974 | 15889 | 12194 | 30575 | 8601 | 10980 | 11893 |
| 39.46 | 26754 | 12312 | 13819 | 12752 | 9173 | 16798 | 12972 | 29779 | 10110 | 10154 | 12100 |
| 39.5 | 27116 | 12291 | 14577 | 12580 | 9607 | 15614 | 11423 | 30150 | 9306 | 10645 | 11396 |
| 39.54 | 24534 | 12044 | 13541 | 12181 | 11545 | 14328 | 12297 | 28673 | 9927 | 10582 | 11695 |
| 39.58 | 26254 | 12727 | 13770 | 13145 | 11418 | 13560 | 10533 | 30252 | 8632 | 10263 | 11954 |
| 39.62 | 26671 | 12500 | 13660 | 13618 | 9321 | 14631 | 10135 | 29715 | 8805 | 10752 | 11178 |
| 39.66 | 24064 | 13067 | 14745 | 12692 | 10837 | 14497 | 10998 | 31063 | 9234 | 10784 | 11805 |
| 39.7 | 24098 | 13261 | 16373 | 13416 | 11133 | 15248 | 11638 | 31476 | 9230 | 10695 | 10472 |
| 39.74 | 24928 | 11735 | 17660 | 13633 | 10387 | 15791 | 11109 | 30860 | 8822 | 9740 | 11025 |
| 39.78 | 24378 | 11187 | 15049 | 12934 | 10647 | 16300 | 11351 | 29031 | 8158 | 10264 | 10960 |
| 39.82 | 24023 | 12620 | 15941 | 13316 | 10180 | 14165 | 11849 | 30808 | 8438 | 10105 | 10551 |
| 39.86 | 24447 | 12263 | 17612 | 12921 | 11717 | 15857 | 11988 | 30280 | 9441 | 10397 | 11664 |
| 39.9 | 24364 | 12127 | 14993 | 14050 | 10794 | 16777 | 10757 | 30883 | 8719 | 9951 | 11882 |
| 39.94 | 25432 | 11519 | 15528 | 13635 | 11086 | 15299 | 11901 | 31144 | 9188 | 11083 | 12663 |
| 39.98 | 25788 | 12092 | 15635 | 14067 | 10726 | 15851 | 12358 | 31415 | 8805 | 10679 | 11973 |
| 40.02 | 24761 | 12306 | 14983 | 13571 | 11117 | 15311 | 10910 | 29121 | 9242 | 11116 | 12093 |
| 40.06 | 25214 | 12750 | 14197 | 13268 | 10176 | 14885 | 12173 | 29312 | 9643 | 9606 | 10431 |
| 40.1 | 23951 | 11899 | 14565 | 13171 | 10542 | 15710 | 10512 | 29754 | 9944 | 9559 | 12861 |
| 40.14 | 23252 | 12084 | 13207 | 13488 | 9985 | 15338 | 11143 | 29453 | 9928 | 9959 | 11061 |
| 40.18 | 24133 | 11788 | 11895 | 14818 | 9687 | 16121 | 10495 | 29215 | 7954 | 9381 | 11850 |
| 40.22 | 25508 | 12688 | 12465 | 12517 | 10332 | 16450 | 12245 | 30722 | 10380 | 9689 | 11064 |
| 40.26 | 23767 | 12708 | 12108 | 15018 | 10331 | 15702 | 11568 | 30406 | 9177 | 10286 | 11451 |
| 40.3 | 25504 | 12284 | 12913 | 12494 | 10378 | 15164 | 11506 | 28581 | 9708 | 10067 | 10486 |
| 40.34 | 24742 | 11872 | 11845 | 12954 | 11142 | 16714 | 11849 | 28610 | 9283 | 10081 | 9290 |
| 40.38 | 26068 | 11749 | 11020 | 13859 | 10811 | 16355 | 11195 | 28598 | 9648 | 9815 | 10710 |
| 40.42 | 24769 | 11890 | 11494 | 13516 | 9623 | 13411 | 11378 | 29066 | 9355 | 10416 | 10626 |
| 40.46 | 24280 | 12946 | 11714 | 13988 | 9257 | 14988 | 10366 | 29136 | 8487 | 10007 | 10078 |
| 40.5 | 24154 | 12061 | 11484 | 11470 | 9616 | 14713 | 10651 | 29845 | 10081 | 10182 | 12125 |
| 40.54 | 25008 | 12434 | 11774 | 13133 | 10552 | 15015 | 11376 | 29458 | 9994 | 11634 | 10978 |
| 40.58 | 25159 | 11443 | 11541 | 12724 | 10484 | 14956 | 10986 | 28512 | 8072 | 11488 | 10381 |
| 40.62 | 25753 | 11252 | 12159 | 13266 | 10971 | 15320 | 11770 | 28903 | 8853 | 11122 | 10549 |
| 40.66 | 25614 | 11954 | 11898 | 13209 | 10788 | 14107 | 9999 | 27574 | 8863 | 10975 | 12266 |
| 40.7 | 23843 | 11009 | 11117 | 11227 | 9959 | 14146 | 9024 | 28253 | 7815 | 10291 | 10207 |
| 40.74 | 24973 | 11871 | 12119 | 10868 | 9644 | 13977 | 10804 | 27976 | 6867 | 11544 | 11555 |
| 40.78 | 24695 | 12224 | 12212 | 11906 | 9712 | 13418 | 10868 | 26581 | 7790 | 10462 | 10903 |
| 40.82 | 21759 | 12131 | 10704 | 12333 | 9413 | 14709 | 10631 | 27423 | 8254 | 10621 | 12700 |
| 40.86 | 24148 | 11170 | 11323 | 13478 | 10177 | 14675 | 10114 | 28140 | 6792 | 10511 | 10015 |
| 40.9 | 25538 | 10609 | 10957 | 11044 | 9683 | 14933 | 10579 | 29300 | 7527 | 10840 | 12516 |
| 40.94 | 24361 | 11450 | 11560 | 11471 | 9834 | 13126 | 9443 | 26758 | 7982 | 10020 | 11736 |
| 40.98 | 22811 | 10911 | 10520 | 11213 | 10161 | 13854 | 9674 | 26708 | 6869 | 9662 | 10561 |
| 41.02 | 23514 | 11345 | 11531 | 11895 | 9388 | 13859 | 10004 | 28450 | 6923 | 10471 | 11025 |
| 41.06 | 24487 | 10742 | 11298 | 11408 | 10127 | 14101 | 10805 | 27086 | 6937 | 10539 | 11317 |
| 41.1 | 23081 | 12453 | 12966 | 11774 | 9399 | 13710 | 10514 | 28567 | 6943 | 9403 | 10117 |
| 41.14 | 22832 | 11473 | 12598 | 11069 | 9658 | 13602 | 10731 | 27832 | 6061 | 9863 | 10756 |
| 41.18 | 22613 | 10475 | 11755 | 11181 | 9353 | 13856 | 10023 | 25591 | 6688 | 9545 | 11404 |
| 41.22 | 23045 | 11798 | 11258 | 10627 | 9431 | 13664 | 9954 | 26825 | 7178 | 8256 | 11026 |
| 41.26 | 23855 | 10391 | 12413 | 9076 | 8711 | 13284 | 9277 | 25545 | 7587 | 9681 | 10635 |
| 41.3 | 21809 | 10728 | 12039 | 9887 | 10191 | 12913 | 9998 | 25855 | 7385 | 8278 | 11032 |
| 41.34 | 22613 | 11021 | 11471 | 11735 | 8659 | 13244 | 10051 | 26416 | 6387 | 9197 | 10719 |
| 41.38 | 23349 | 10353 | 11157 | 10355 | 8529 | 13568 | 9809 | 26153 | 7451 | 10039 | 10572 |
| 41.42 | 23745 | 9754 | 11445 | 11273 | 9847 | 13899 | 10815 | 25984 | 7525 | 7681 | 10684 |
| 41.46 | 23361 | 10380 | 10975 | 11054 | 9567 | 13265 | 10311 | 26726 | 8061 | 8887 | 11947 |
| 41.5 | 21132 | 10775 | 11098 | 11225 | 9046 | 14054 | 9974 | 26712 | 8358 | 8704 | 10751 |

| | | Form | | | | | | |
|---|---|---|---|---|---|---|---|---|
| | Sul4_lc | Tar1 + Tar2_lc | Tar2_lc | Tar3 | Tos1 | Tos2 | Tos1 + Tos3 | Xin1 |
| | | | | ExperimentID | | | | |
| Counter ion | SSm4 Sulphuric acid | SSn56 L(+)-Tartaric acid | SSm88 L(+)-Tartaric acid | SSm22 L(+)-Tartaric acid | SSm8 p-Toluenesulfonic acid | SSm41 p-Toluenesulfonic acid | SSm8 p-Toluenesulfonic acid | SSm19 1-Hydroxy-2-napthoic acid |
| 1.5 | 766 | 1454 | 1451 | 2164 | 2661 | 2020 | 1965 | 2047 |
| 1.54 | 2324 | 1520 | 2965 | 4518 | 4014 | 5343 | 3457 | 3570 |
| 1.58 | 4241 | 1935 | 2696 | 5757 | 4099 | 6496 | 1954 | 5272 |
| 1.62 | 3882 | 6835 | 2910 | 4305 | 3287 | 9131 | 1092 | 3742 |
| 1.66 | 6820 | 6053 | 5956 | 2247 | 5513 | 10191 | 4426 | 2789 |

-continued

| | | | | | | | | |
|---|---|---|---|---|---|---|---|---|
| 1.7 | 6259 | 3384 | 3455 | 5772 | 6517 | 11195 | 4788 | 7836 |
| 1.74 | 5220 | 6292 | 5128 | 6057 | 6347 | 12699 | 7404 | 6630 |
| 1.78 | 6899 | 7482 | 4282 | 4479 | 9706 | 12760 | 6000 | 8682 |
| 1.82 | 5738 | 9732 | 9013 | 9806 | 7208 | 11279 | 6019 | 7010 |
| 1.86 | 5493 | 7045 | 9790 | 14518 | 6970 | 15115 | 4392 | 8915 |
| 1.9 | 7848 | 10058 | 8113 | 12110 | 6894 | 16431 | 8570 | 9908 |
| 1.94 | 9830 | 11607 | 8745 | 9023 | 11457 | 15802 | 7187 | 7975 |
| 1.98 | 12144 | 12005 | 7112 | 11193 | 9312 | 22961 | 8941 | 8267 |
| 2.02 | 10817 | 11054 | 8384 | 7660 | 11034 | 21017 | 7653 | 8851 |
| 2.06 | 8547 | 10111 | 8144 | 9699 | 8617 | 20681 | 8055 | 8084 |
| 2.1 | 11014 | 11045 | 8232 | 11315 | 9417 | 14490 | 8337 | 8993 |
| 2.14 | 7213 | 12897 | 9399 | 10760 | 9527 | 18995 | 7492 | 11111 |
| 2.18 | 11917 | 13798 | 8633 | 9016 | 13377 | 19784 | 7173 | 8362 |
| 2.22 | 12397 | 7768 | 10295 | 8393 | 11919 | 21854 | 7636 | 8855 |
| 2.26 | 12411 | 8559 | 8193 | 10248 | 9952 | 17678 | 8841 | 10942 |
| 2.3 | 9125 | 9649 | 11534 | 10852 | 13084 | 22821 | 10785 | 10794 |
| 2.34 | 11895 | 10374 | 7517 | 11728 | 13698 | 19966 | 8745 | 11205 |
| 2.38 | 11955 | 8857 | 7444 | 9110 | 13374 | 24155 | 9094 | 10897 |
| 2.42 | 9419 | 12089 | 9679 | 8332 | 10036 | 20479 | 8077 | 12932 |
| 2.46 | 9617 | 13134 | 8869 | 10522 | 11201 | 23452 | 9234 | 13074 |
| 2.5 | 14182 | 9708 | 10812 | 11677 | 12104 | 25140 | 7392 | 10780 |
| 2.54 | 11634 | 11592 | 9140 | 11834 | 14232 | 20668 | 10207 | 11509 |
| 2.58 | 7196 | 14219 | 10956 | 12209 | 11181 | 21370 | 10325 | 10372 |
| 2.62 | 10628 | 12742 | 6892 | 10933 | 10718 | 19547 | 6764 | 10664 |
| 2.66 | 13261 | 14363 | 10669 | 12180 | 12903 | 23535 | 12199 | 11369 |
| 2.7 | 12043 | 11359 | 9579 | 12030 | 10946 | 26420 | 9770 | 12264 |
| 2.74 | 13862 | 14942 | 10341 | 10147 | 11355 | 22700 | 8433 | 11988 |
| 2.78 | 10474 | 13170 | 12958 | 7656 | 14955 | 28745 | 7462 | 13227 |
| 2.82 | 10463 | 15737 | 10002 | 11515 | 14073 | 26059 | 10158 | 12803 |
| 2.86 | 10659 | 14446 | 9271 | 11028 | 13089 | 25752 | 11378 | 15439 |
| 2.9 | 13173 | 15822 | 11131 | 13072 | 15185 | 26781 | 11680 | 15376 |
| 2.94 | 12699 | 17864 | 11651 | 15171 | 15890 | 25710 | 10032 | 13496 |
| 2.98 | 11381 | 15963 | 8991 | 10427 | 16678 | 29564 | 11531 | 13154 |
| 3.02 | 16404 | 15848 | 11134 | 11467 | 15199 | 26666 | 12085 | 16973 |
| 3.06 | 16069 | 17861 | 10800 | 15246 | 17582 | 30204 | 12915 | 14501 |
| 3.1 | 18107 | 21369 | 11774 | 14710 | 17349 | 30902 | 11614 | 16064 |
| 3.14 | 13590 | 17387 | 12576 | 17430 | 17679 | 28608 | 14593 | 13092 |
| 3.18 | 13918 | 19762 | 11158 | 17090 | 15197 | 31801 | 12890 | 14396 |
| 3.22 | 16403 | 20905 | 11530 | 13630 | 19488 | 32105 | 15661 | 14857 |
| 3.26 | 15800 | 26866 | 13444 | 21777 | 18573 | 34074 | 16112 | 19526 |
| 3.3 | 15823 | 20221 | 15314 | 18655 | 24370 | 38103 | 16677 | 17049 |
| 3.34 | 13749 | 25989 | 14642 | 16315 | 25688 | 37778 | 13788 | 15085 |
| 3.38 | 12151 | 20826 | 13680 | 16475 | 20273 | 36240 | 14916 | 15411 |
| 3.42 | 16806 | 19671 | 12421 | 20685 | 24853 | 39056 | 15745 | 18458 |
| 3.46 | 18058 | 21670 | 14401 | 24127 | 21899 | 36447 | 18047 | 18628 |
| 3.5 | 16242 | 19964 | 19138 | 22136 | 23313 | 39775 | 13723 | 14780 |
| 3.54 | 14780 | 19565 | 16239 | 23301 | 20469 | 38423 | 14401 | 17707 |
| 3.58 | 19282 | 20459 | 17890 | 28510 | 21370 | 36269 | 17468 | 20306 |
| 3.62 | 18656 | 20012 | 18546 | 32328 | 25241 | 35470 | 15098 | 20798 |
| 3.66 | 15069 | 21056 | 20065 | 34452 | 21007 | 39477 | 19559 | 25672 |
| 3.7 | 20224 | 20372 | 17526 | 34094 | 21514 | 41341 | 16848 | 22796 |
| 3.74 | 16707 | 20928 | 20393 | 32347 | 22701 | 41551 | 16620 | 19705 |
| 3.78 | 19231 | 21248 | 19365 | 34024 | 21028 | 39914 | 17215 | 20820 |
| 3.82 | 21388 | 21965 | 24545 | 31376 | 23413 | 45325 | 17691 | 20141 |
| 3.86 | 21793 | 21170 | 25499 | 32347 | 22152 | 38460 | 16142 | 24522 |
| 3.9 | 28703 | 20487 | 29533 | 28976 | 20226 | 41017 | 17563 | 21031 |
| 3.94 | 34434 | 21093 | 26617 | 25613 | 27978 | 42674 | 19093 | 26101 |
| 3.98 | 36013 | 17871 | 30254 | 21433 | 25100 | 43628 | 20996 | 29479 |
| 4.02 | 42570 | 18024 | 32094 | 21494 | 28225 | 45910 | 20591 | 32830 |
| 4.06 | 47661 | 22651 | 27588 | 20091 | 25170 | 41087 | 18609 | 36474 |
| 4.1 | 49562 | 20489 | 29793 | 22698 | 26957 | 42549 | 17533 | 48521 |
| 4.14 | 50550 | 28069 | 26493 | 20040 | 23326 | 45579 | 16374 | 63414 |
| 4.18 | 55001 | 28385 | 25540 | 17280 | 23671 | 41249 | 18973 | 76302 |
| 4.22 | 52726 | 33608 | 27666 | 16874 | 27279 | 44922 | 19223 | 102111 |
| 4.26 | 44958 | 43204 | 28656 | 22175 | 29990 | 47694 | 19733 | 104767 |
| 4.3 | 37694 | 46805 | 22326 | 17923 | 24518 | 45278 | 15608 | 111050 |
| 4.34 | 32664 | 49709 | 20730 | 18071 | 24565 | 41308 | 19741 | 120033 |
| 4.38 | 30780 | 52249 | 20828 | 17282 | 25006 | 35095 | 16301 | 115993 |
| 4.42 | 26124 | 54237 | 19166 | 20954 | 26074 | 41371 | 17993 | 103851 |
| 4.46 | 24944 | 54378 | 18600 | 20361 | 23832 | 39051 | 17467 | 110699 |
| 4.5 | 23071 | 54996 | 16130 | 17432 | 25603 | 42854 | 17863 | 88192 |
| 4.54 | 23069 | 47604 | 18293 | 18799 | 23321 | 42856 | 19461 | 69665 |
| 4.58 | 22021 | 42871 | 13466 | 23092 | 32396 | 41132 | 19321 | 52340 |
| 4.62 | 21822 | 40294 | 16746 | 18646 | 26304 | 51614 | 19209 | 41575 |
| 4.66 | 17315 | 33487 | 17618 | 20997 | 26986 | 44147 | 19604 | 31237 |
| 4.7 | 18347 | 24580 | 17047 | 17067 | 28405 | 48518 | 18689 | 25311 |
| 4.74 | 18094 | 23718 | 16909 | 16506 | 23501 | 47103 | 19938 | 24529 |
| 4.78 | 18374 | 24103 | 20460 | 15307 | 27837 | 49552 | 19422 | 24262 |
| 4.82 | 19912 | 24079 | 16525 | 16623 | 26433 | 49076 | 19346 | 22367 |

-continued

| | | | | | | | | |
|---|---|---|---|---|---|---|---|---|
| 4.86 | 20723 | 21226 | 17462 | 20873 | 29128 | 48151 | 20528 | 24001 |
| 4.9 | 20007 | 22218 | 18219 | 18459 | 30103 | 49461 | 20075 | 21048 |
| 4.94 | 14371 | 24261 | 14971 | 18236 | 30350 | 43939 | 18445 | 23222 |
| 4.98 | 19957 | 23012 | 17522 | 18989 | 35384 | 48940 | 20345 | 22591 |
| 5.02 | 17339 | 18845 | 16899 | 19055 | 37846 | 53122 | 19100 | 18925 |
| 5.06 | 19823 | 23194 | 21509 | 20447 | 39208 | 48061 | 23885 | 24958 |
| 5.1 | 19268 | 24310 | 21749 | 22156 | 39721 | 50254 | 22499 | 21939 |
| 5.14 | 18104 | 24980 | 19039 | 19336 | 34394 | 51397 | 20167 | 24359 |
| 5.18 | 19147 | 18867 | 19978 | 18472 | 39185 | 50396 | 19852 | 20946 |
| 5.22 | 20354 | 21339 | 20490 | 19503 | 41855 | 52375 | 18089 | 22826 |
| 5.26 | 20234 | 24284 | 16786 | 19902 | 46983 | 54154 | 20591 | 18314 |
| 5.3 | 20137 | 26313 | 15413 | 20457 | 46216 | 54214 | 21334 | 21535 |
| 5.34 | 17845 | 26355 | 18885 | 21846 | 45067 | 54651 | 22880 | 20221 |
| 5.38 | 19518 | 34256 | 16670 | 26514 | 48130 | 57280 | 22100 | 21490 |
| 5.42 | 18592 | 35884 | 16006 | 26650 | 51640 | 53659 | 21629 | 23992 |
| 5.46 | 21704 | 36641 | 18526 | 23846 | 48779 | 57365 | 23196 | 23342 |
| 5.5 | 19434 | 46422 | 18839 | 32895 | 53736 | 54813 | 23642 | 22255 |
| 5.54 | 18044 | 46426 | 16911 | 34974 | 52045 | 59707 | 21914 | 23167 |
| 5.58 | 19324 | 50298 | 17885 | 35715 | 49231 | 53363 | 19392 | 19737 |
| 5.62 | 22538 | 51451 | 17091 | 37296 | 50016 | 59480 | 22933 | 18948 |
| 5.66 | 21963 | 49861 | 17580 | 39615 | 49986 | 57654 | 24925 | 22590 |
| 5.7 | 23200 | 47017 | 18546 | 39182 | 41916 | 58194 | 23923 | 23335 |
| 5.74 | 22586 | 45235 | 18198 | 34780 | 47546 | 59281 | 23427 | 20671 |
| 5.78 | 22438 | 39393 | 17298 | 37298 | 49600 | 61997 | 27491 | 22100 |
| 5.82 | 20536 | 37839 | 20463 | 34106 | 43004 | 61411 | 26236 | 20542 |
| 5.86 | 20095 | 33782 | 19519 | 28043 | 40304 | 53423 | 25106 | 21716 |
| 5.9 | 21637 | 27794 | 18047 | 30051 | 40517 | 53393 | 27012 | 18292 |
| 5.94 | 20594 | 24762 | 18299 | 24083 | 39387 | 56831 | 24904 | 20899 |
| 5.98 | 23655 | 22181 | 18445 | 21546 | 38103 | 54375 | 24730 | 18753 |
| 6.02 | 20836 | 20689 | 15829 | 21104 | 42303 | 61279 | 26271 | 21786 |
| 6.06 | 23541 | 21543 | 18179 | 20019 | 38721 | 61297 | 28458 | 18047 |
| 6.1 | 23861 | 24268 | 19781 | 20279 | 39978 | 62461 | 37367 | 21036 |
| 6.14 | 22308 | 21763 | 18578 | 17916 | 35587 | 69383 | 44064 | 23398 |
| 6.18 | 20696 | 21192 | 20647 | 18780 | 40388 | 64780 | 61850 | 22915 |
| 6.22 | 20070 | 21902 | 17618 | 21114 | 44265 | 72883 | 87472 | 22579 |
| 6.26 | 21580 | 23924 | 19948 | 19987 | 57814 | 77533 | 114113 | 21565 |
| 6.3 | 23900 | 21034 | 20139 | 20143 | 65288 | 82322 | 140231 | 21394 |
| 6.34 | 22115 | 23841 | 19242 | 20744 | 77944 | 81824 | 170967 | 20268 |
| 6.38 | 21482 | 21224 | 21038 | 17105 | 79243 | 85139 | 188658 | 17742 |
| 6.42 | 22034 | 21244 | 22632 | 18371 | 91626 | 81275 | 192062 | 18611 |
| 6.46 | 20392 | 24370 | 27391 | 21772 | 95067 | 85742 | 191636 | 19935 |
| 6.5 | 21381 | 23470 | 31128 | 22535 | 97234 | 85730 | 183087 | 18037 |
| 6.54 | 23867 | 26167 | 36708 | 19744 | 94066 | 85340 | 167722 | 20561 |
| 6.58 | 22110 | 24879 | 39060 | 23226 | 91198 | 92416 | 151636 | 19726 |
| 6.62 | 23728 | 27469 | 35816 | 20281 | 81870 | 97694 | 119803 | 20280 |
| 6.66 | 20740 | 28971 | 39570 | 25063 | 67353 | 117023 | 85119 | 20399 |
| 6.7 | 22394 | 28414 | 38656 | 22044 | 55831 | 136806 | 62307 | 23747 |
| 6.74 | 21382 | 29978 | 38908 | 23890 | 49361 | 157566 | 46628 | 20889 |
| 6.78 | 23740 | 27443 | 38850 | 22647 | 37011 | 170511 | 34051 | 22072 |
| 6.82 | 21034 | 24975 | 32262 | 26899 | 34805 | 175773 | 31171 | 21848 |
| 6.86 | 19975 | 24250 | 27174 | 26719 | 29571 | 175927 | 26978 | 17823 |
| 6.9 | 21340 | 23435 | 27030 | 27102 | 28636 | 177557 | 23171 | 21276 |
| 6.94 | 25265 | 24496 | 23802 | 29431 | 28519 | 172481 | 20370 | 23129 |
| 6.98 | 23266 | 23706 | 20473 | 33135 | 30802 | 151814 | 25502 | 20277 |
| 7.02 | 25605 | 21733 | 19997 | 39832 | 30343 | 130280 | 24579 | 19165 |
| 7.06 | 25762 | 18115 | 22092 | 46592 | 29615 | 104311 | 24086 | 18694 |
| 7.1 | 25581 | 18066 | 20441 | 44256 | 29157 | 85718 | 21691 | 20439 |
| 7.14 | 26235 | 19200 | 20489 | 46002 | 27465 | 64086 | 24466 | 20701 |
| 7.18 | 28108 | 20151 | 22180 | 51560 | 27820 | 54396 | 25659 | 20122 |
| 7.22 | 25968 | 20920 | 20841 | 54264 | 27003 | 52417 | 25785 | 21654 |
| 7.26 | 28099 | 19730 | 19252 | 47445 | 27313 | 52703 | 25031 | 20557 |
| 7.3 | 29585 | 22609 | 22098 | 47116 | 28283 | 48916 | 20856 | 23623 |
| 7.34 | 29450 | 23146 | 19413 | 49705 | 31191 | 53942 | 23718 | 22332 |
| 7.38 | 26071 | 21726 | 18952 | 40872 | 28560 | 47557 | 22663 | 20455 |
| 7.42 | 24618 | 20668 | 21557 | 40396 | 28572 | 50741 | 21526 | 19370 |
| 7.46 | 23061 | 20861 | 20471 | 38753 | 23241 | 45691 | 20884 | 20263 |
| 7.5 | 22855 | 21361 | 19654 | 38666 | 27890 | 42951 | 21291 | 20561 |
| 7.54 | 24983 | 20492 | 21147 | 44523 | 29287 | 47748 | 20704 | 22299 |
| 7.58 | 24558 | 21587 | 20603 | 45467 | 31902 | 48624 | 20879 | 22588 |
| 7.62 | 26896 | 23637 | 20205 | 49137 | 29520 | 49483 | 19452 | 23255 |
| 7.66 | 24905 | 21111 | 20935 | 47853 | 28468 | 45245 | 20045 | 22799 |
| 7.7 | 24076 | 21754 | 20113 | 47332 | 28519 | 47957 | 21954 | 20601 |
| 7.74 | 24725 | 21809 | 17802 | 42139 | 28176 | 45133 | 19920 | 21677 |
| 7.78 | 22911 | 22896 | 20492 | 43004 | 26184 | 45861 | 17425 | 21323 |
| 7.82 | 22342 | 21691 | 19823 | 38301 | 25566 | 42940 | 19918 | 22366 |
| 7.86 | 27242 | 22946 | 22407 | 34961 | 25868 | 45391 | 18927 | 26496 |
| 7.9 | 23071 | 22969 | 23369 | 28252 | 25749 | 46980 | 19916 | 24722 |
| 7.94 | 26265 | 26102 | 22789 | 26134 | 26743 | 47632 | 19753 | 23918 |
| 7.98 | 24359 | 26219 | 27591 | 23015 | 27787 | 46935 | 21193 | 19957 |

-continued

| | | | | | | | | |
|---|---|---|---|---|---|---|---|---|
| 8.02 | 28032 | 28093 | 29463 | 21043 | 25450 | 42005 | 20206 | 22988 |
| 8.06 | 27531 | 30089 | 25071 | 23658 | 23839 | 47143 | 18519 | 24769 |
| 8.1 | 27717 | 34553 | 28937 | 21642 | 26414 | 48441 | 20519 | 29524 |
| 8.14 | 27683 | 37715 | 30218 | 21727 | 27151 | 48622 | 22616 | 34736 |
| 8.18 | 28415 | 38955 | 26738 | 24275 | 24558 | 45285 | 20520 | 42474 |
| 8.22 | 29741 | 40680 | 29274 | 23380 | 24911 | 45496 | 19471 | 51984 |
| 8.26 | 30390 | 41212 | 21276 | 22122 | 24604 | 47069 | 21280 | 53294 |
| 8.3 | 30287 | 43383 | 24294 | 22562 | 24210 | 48508 | 20738 | 65200 |
| 8.34 | 30354 | 49429 | 26027 | 22797 | 24792 | 45285 | 20588 | 66938 |
| 8.38 | 29245 | 51135 | 27244 | 24236 | 27270 | 45660 | 22019 | 73870 |
| 8.42 | 34919 | 55371 | 19430 | 22250 | 28366 | 47622 | 20974 | 69815 |
| 8.46 | 29116 | 54439 | 23468 | 21089 | 27955 | 43256 | 22892 | 73179 |
| 8.5 | 27765 | 55405 | 19463 | 20130 | 28390 | 43564 | 20450 | 66565 |
| 8.54 | 25928 | 50083 | 18805 | 20422 | 29766 | 46984 | 18978 | 62062 |
| 8.58 | 25765 | 46359 | 19749 | 23068 | 32541 | 46925 | 21362 | 54912 |
| 8.62 | 27689 | 44876 | 20833 | 22733 | 28066 | 49259 | 21668 | 48657 |
| 8.66 | 26633 | 44658 | 19129 | 24050 | 28991 | 46726 | 24550 | 44875 |
| 8.7 | 24203 | 40485 | 20615 | 20301 | 30554 | 45146 | 24474 | 38634 |
| 8.74 | 25065 | 35427 | 22875 | 24369 | 32654 | 46913 | 24703 | 32660 |
| 8.78 | 22200 | 34683 | 21087 | 21398 | 29251 | 46589 | 24606 | 32734 |
| 8.82 | 26094 | 33698 | 21589 | 23825 | 30663 | 50504 | 27214 | 31614 |
| 8.86 | 24443 | 28103 | 20952 | 24012 | 27489 | 48980 | 27133 | 28664 |
| 8.9 | 23294 | 28225 | 20154 | 20914 | 27208 | 46636 | 27419 | 26141 |
| 8.94 | 23965 | 29179 | 20789 | 22465 | 23509 | 44484 | 25121 | 25600 |
| 8.98 | 23980 | 26648 | 20155 | 25646 | 28539 | 44555 | 25107 | 24034 |
| 9.02 | 22188 | 27561 | 19619 | 25100 | 28905 | 47887 | 24764 | 24566 |
| 9.06 | 23303 | 26311 | 20422 | 22342 | 26111 | 47162 | 22772 | 25058 |
| 9.1 | 24646 | 23700 | 19743 | 24708 | 25567 | 45980 | 24176 | 22083 |
| 9.14 | 21326 | 21275 | 19377 | 23190 | 23721 | 46413 | 24502 | 24183 |
| 9.18 | 23158 | 24114 | 20014 | 22554 | 25774 | 49783 | 26705 | 23459 |
| 9.22 | 23639 | 22712 | 20242 | 23662 | 27937 | 49202 | 29146 | 22868 |
| 9.26 | 23417 | 21738 | 21913 | 25078 | 27029 | 45020 | 29420 | 22876 |
| 9.3 | 24778 | 23782 | 19996 | 23174 | 25282 | 47199 | 32847 | 24490 |
| 9.34 | 23071 | 25363 | 20761 | 23733 | 27788 | 45563 | 32340 | 23682 |
| 9.38 | 24371 | 23646 | 18078 | 23305 | 27232 | 49306 | 31515 | 24338 |
| 9.42 | 20776 | 24360 | 18502 | 22477 | 25266 | 47726 | 32390 | 22697 |
| 9.46 | 23734 | 25389 | 19300 | 25572 | 24893 | 45105 | 29101 | 23123 |
| 9.5 | 25086 | 21226 | 18817 | 25034 | 26424 | 46964 | 29305 | 20584 |
| 9.54 | 24300 | 21018 | 21452 | 26295 | 28545 | 47478 | 25732 | 23319 |
| 9.58 | 23614 | 23867 | 22487 | 28037 | 27862 | 51392 | 24884 | 20476 |
| 9.62 | 23801 | 22744 | 21979 | 28603 | 30621 | 50888 | 25401 | 22286 |
| 9.66 | 24161 | 24874 | 20408 | 26894 | 32649 | 47197 | 21677 | 22155 |
| 9.7 | 26682 | 25524 | 20414 | 28101 | 29647 | 48800 | 21590 | 22197 |
| 9.74 | 26569 | 22936 | 22038 | 29974 | 31043 | 51042 | 19507 | 22694 |
| 9.78 | 24757 | 23045 | 22855 | 27791 | 27573 | 60515 | 20070 | 22835 |
| 9.82 | 23913 | 21573 | 19651 | 28298 | 25604 | 65309 | 19259 | 22907 |
| 9.86 | 23045 | 23428 | 19566 | 29458 | 29082 | 75515 | 22073 | 23065 |
| 9.9 | 26464 | 25417 | 20866 | 31560 | 28578 | 79921 | 19963 | 25688 |
| 9.94 | 24676 | 24520 | 21834 | 28803 | 27537 | 82185 | 22219 | 25239 |
| 9.98 | 24114 | 25532 | 22085 | 30006 | 27966 | 87313 | 21293 | 22239 |
| 10.02 | 25716 | 23606 | 19502 | 27263 | 28547 | 87184 | 20424 | 26667 |
| 10.06 | 26504 | 24557 | 23553 | 28557 | 24868 | 85335 | 20356 | 22305 |
| 10.1 | 23531 | 24659 | 21317 | 27357 | 24337 | 82007 | 20762 | 24764 |
| 10.14 | 24839 | 23555 | 21000 | 31879 | 23605 | 77504 | 21863 | 22924 |
| 10.18 | 23729 | 25043 | 22715 | 30077 | 25400 | 70489 | 20736 | 29202 |
| 10.22 | 24601 | 26037 | 19924 | 29835 | 24994 | 62143 | 20497 | 26666 |
| 10.26 | 25375 | 25377 | 21483 | 30190 | 25052 | 54179 | 21513 | 27272 |
| 10.3 | 26379 | 25137 | 21454 | 31674 | 26003 | 50444 | 19274 | 26042 |
| 10.34 | 23746 | 27399 | 23005 | 31160 | 26596 | 51943 | 21503 | 27847 |
| 10.38 | 27285 | 24476 | 21458 | 30669 | 27785 | 48812 | 19701 | 25767 |
| 10.42 | 26168 | 27671 | 20889 | 27842 | 27443 | 46227 | 19619 | 25660 |
| 10.46 | 26639 | 26354 | 21933 | 27087 | 26250 | 48986 | 21204 | 26291 |
| 10.5 | 24804 | 26326 | 26349 | 29551 | 27860 | 49022 | 23391 | 29039 |
| 10.54 | 25173 | 26448 | 23282 | 29265 | 25163 | 49848 | 20119 | 28569 |
| 10.58 | 26684 | 26458 | 22782 | 28184 | 26345 | 49903 | 19519 | 32094 |
| 10.62 | 27232 | 25664 | 24086 | 29628 | 26162 | 48237 | 21344 | 34035 |
| 10.66 | 29711 | 24759 | 23626 | 27551 | 26513 | 54641 | 21386 | 38326 |
| 10.7 | 29808 | 24417 | 25786 | 27066 | 28985 | 57321 | 23185 | 37193 |
| 10.74 | 29081 | 26721 | 25040 | 26455 | 26541 | 60957 | 21539 | 36302 |
| 10.78 | 30257 | 23245 | 23384 | 26940 | 23662 | 62096 | 21130 | 35751 |
| 10.82 | 32087 | 23748 | 27448 | 25723 | 28063 | 66573 | 21536 | 38963 |
| 10.86 | 33792 | 26827 | 30074 | 25440 | 25929 | 64475 | 22720 | 34930 |
| 10.9 | 35473 | 23916 | 25096 | 25546 | 27752 | 62090 | 22580 | 32965 |
| 10.94 | 37710 | 25120 | 27701 | 25759 | 25232 | 64273 | 22342 | 33607 |
| 10.98 | 36399 | 25788 | 24904 | 27776 | 26077 | 58299 | 23562 | 30523 |
| 11.02 | 34866 | 25766 | 26082 | 25370 | 25703 | 55948 | 22218 | 31211 |
| 11.06 | 33897 | 25246 | 24637 | 25025 | 26328 | 57846 | 22454 | 27510 |
| 11.1 | 34641 | 27748 | 24480 | 27319 | 27164 | 54778 | 21837 | 25417 |
| 11.14 | 33442 | 26905 | 26416 | 28386 | 27727 | 50375 | 21355 | 24282 |

-continued

| | | | | | | | | |
|---|---|---|---|---|---|---|---|---|
| 11.18 | 35156 | 26259 | 26751 | 29130 | 27504 | 50493 | 23199 | 23841 |
| 11.22 | 34145 | 26269 | 27109 | 30204 | 28292 | 48577 | 22010 | 23006 |
| 11.26 | 32477 | 28019 | 27373 | 27310 | 27236 | 50562 | 20845 | 25831 |
| 11.3 | 32599 | 27777 | 23214 | 31502 | 28466 | 52835 | 21765 | 26360 |
| 11.34 | 30198 | 27796 | 25364 | 28272 | 26005 | 50563 | 23665 | 25885 |
| 11.38 | 31228 | 27253 | 26981 | 32225 | 26395 | 50607 | 21906 | 24085 |
| 11.42 | 31433 | 28585 | 25196 | 30509 | 28504 | 55428 | 23227 | 26745 |
| 11.46 | 29390 | 29154 | 24090 | 33755 | 30045 | 60376 | 21470 | 25930 |
| 11.5 | 28074 | 27868 | 22322 | 31987 | 24808 | 62115 | 21096 | 26257 |
| 11.54 | 28110 | 24772 | 25889 | 31504 | 27272 | 63595 | 23454 | 22572 |
| 11.58 | 28830 | 26073 | 23695 | 32217 | 27043 | 68976 | 21818 | 24582 |
| 11.62 | 26464 | 26183 | 24175 | 30273 | 27567 | 68359 | 22733 | 24828 |
| 11.66 | 28910 | 28510 | 22945 | 30068 | 28505 | 67943 | 17989 | 25559 |
| 11.7 | 30407 | 28966 | 27250 | 29378 | 30382 | 69671 | 22778 | 26675 |
| 11.74 | 30228 | 29178 | 28484 | 27228 | 29498 | 65628 | 23774 | 26886 |
| 11.78 | 31185 | 28285 | 25914 | 27823 | 29883 | 69393 | 24534 | 25269 |
| 11.82 | 28863 | 29612 | 27444 | 26371 | 30752 | 64303 | 22515 | 26120 |
| 11.86 | 31685 | 33226 | 27128 | 26099 | 31544 | 59850 | 23972 | 25377 |
| 11.9 | 29715 | 35089 | 24387 | 27860 | 30066 | 54099 | 22655 | 27289 |
| 11.94 | 30627 | 41081 | 28252 | 28837 | 30833 | 56161 | 22684 | 25104 |
| 11.98 | 31581 | 42411 | 26944 | 29554 | 29457 | 53208 | 22668 | 28091 |
| 12.02 | 31600 | 44975 | 25423 | 31103 | 30046 | 54988 | 22789 | 28021 |
| 12.06 | 30416 | 46497 | 24619 | 29973 | 30510 | 53182 | 22683 | 25769 |
| 12.1 | 31776 | 49030 | 26316 | 29930 | 30550 | 52456 | 23431 | 28737 |
| 12.14 | 31475 | 49418 | 28349 | 30308 | 30539 | 55554 | 24631 | 29998 |
| 12.18 | 32092 | 50740 | 27133 | 31134 | 29093 | 52594 | 24217 | 30833 |
| 12.22 | 30357 | 49375 | 25711 | 31773 | 31476 | 53595 | 24906 | 28631 |
| 12.26 | 33349 | 48036 | 28838 | 31535 | 31830 | 53238 | 23933 | 30421 |
| 12.3 | 32059 | 44439 | 27406 | 34894 | 30660 | 54044 | 26664 | 29924 |
| 12.34 | 33650 | 41836 | 27192 | 32673 | 31442 | 55414 | 25665 | 29736 |
| 12.38 | 32949 | 41949 | 29390 | 33082 | 32698 | 56659 | 25327 | 31377 |
| 12.42 | 33066 | 39868 | 29451 | 34099 | 35497 | 55114 | 27460 | 31708 |
| 12.46 | 30927 | 38833 | 27674 | 34188 | 31720 | 57338 | 25353 | 33395 |
| 12.5 | 31230 | 33755 | 28996 | 32767 | 33962 | 58085 | 26566 | 33846 |
| 12.54 | 30105 | 34765 | 29351 | 35977 | 33429 | 62618 | 24500 | 30864 |
| 12.58 | 31086 | 33069 | 29710 | 33743 | 32607 | 62523 | 26735 | 33558 |
| 12.62 | 32406 | 29648 | 27740 | 35944 | 31473 | 63572 | 28255 | 33642 |
| 12.66 | 30761 | 29913 | 29837 | 33237 | 33331 | 68192 | 31282 | 32444 |
| 12.7 | 31776 | 30238 | 28545 | 33332 | 32988 | 61071 | 34807 | 29923 |
| 12.74 | 30575 | 26712 | 27880 | 33911 | 37065 | 63488 | 38812 | 32651 |
| 12.78 | 30134 | 27656 | 26780 | 34442 | 34143 | 66243 | 44908 | 32543 |
| 12.82 | 33827 | 25220 | 29375 | 35851 | 37307 | 64582 | 45724 | 32996 |
| 12.86 | 31169 | 26960 | 27211 | 34987 | 40198 | 64241 | 49442 | 29535 |
| 12.9 | 31462 | 26915 | 28480 | 35045 | 38877 | 64184 | 48553 | 29179 |
| 12.94 | 33130 | 29297 | 27935 | 35077 | 40705 | 59476 | 46042 | 34543 |
| 12.98 | 30461 | 25830 | 28404 | 34524 | 41794 | 61661 | 46061 | 30203 |
| 13.02 | 31280 | 26926 | 27204 | 35371 | 49765 | 60142 | 47011 | 28914 |
| 13.06 | 30462 | 25428 | 25270 | 29615 | 50567 | 58877 | 45269 | 30085 |
| 13.1 | 30131 | 25053 | 27803 | 33133 | 49626 | 57211 | 43613 | 30993 |
| 13.14 | 30615 | 29215 | 27268 | 30976 | 51174 | 61047 | 42427 | 35339 |
| 13.18 | 31002 | 27151 | 30345 | 31625 | 54888 | 58857 | 41917 | 34282 |
| 13.22 | 29433 | 28185 | 32708 | 33444 | 49495 | 60495 | 45318 | 36964 |
| 13.26 | 30000 | 26519 | 31322 | 35227 | 48191 | 61859 | 47295 | 38829 |
| 13.3 | 31552 | 28732 | 32903 | 37761 | 50990 | 61142 | 53956 | 39916 |
| 13.34 | 31332 | 30416 | 30640 | 37681 | 46778 | 61806 | 49457 | 41989 |
| 13.38 | 30549 | 31447 | 34164 | 43523 | 47050 | 62129 | 51335 | 40914 |
| 13.42 | 28853 | 32371 | 34286 | 43058 | 41321 | 62973 | 50773 | 43320 |
| 13.46 | 30880 | 36262 | 37541 | 43770 | 39173 | 66544 | 51484 | 43948 |
| 13.5 | 31617 | 39202 | 35020 | 49542 | 38911 | 66825 | 47924 | 41957 |
| 13.54 | 29759 | 43245 | 32469 | 48988 | 36272 | 73723 | 43699 | 46517 |
| 13.58 | 32027 | 52554 | 32520 | 53713 | 37407 | 85660 | 38539 | 47396 |
| 13.62 | 31465 | 55900 | 30213 | 52900 | 35804 | 96038 | 34641 | 48687 |
| 13.66 | 30949 | 60812 | 31711 | 59452 | 34904 | 111305 | 31501 | 46215 |
| 13.7 | 31114 | 60557 | 29531 | 58740 | 36650 | 122309 | 31393 | 53630 |
| 13.74 | 30543 | 56987 | 27534 | 59623 | 37806 | 130380 | 27646 | 52883 |
| 13.78 | 29845 | 56741 | 26830 | 64427 | 38400 | 135884 | 27676 | 55259 |
| 13.82 | 32616 | 54273 | 26420 | 60153 | 39903 | 132502 | 27722 | 56463 |
| 13.86 | 30723 | 48700 | 26098 | 61098 | 34200 | 132061 | 26374 | 59883 |
| 13.9 | 31586 | 44818 | 24520 | 57640 | 36941 | 128449 | 28557 | 59855 |
| 13.94 | 31787 | 39959 | 29101 | 54423 | 36660 | 113340 | 27959 | 58637 |
| 13.98 | 29082 | 34325 | 24986 | 48058 | 36163 | 99146 | 29630 | 60923 |
| 14.02 | 31491 | 33211 | 27541 | 45194 | 35092 | 87793 | 30662 | 59430 |
| 14.06 | 32121 | 28111 | 29165 | 39665 | 33266 | 74972 | 27530 | 60375 |
| 14.1 | 30446 | 26167 | 27052 | 37659 | 34852 | 68498 | 31484 | 57952 |
| 14.14 | 32955 | 25975 | 27635 | 35366 | 33093 | 64719 | 33152 | 57972 |
| 14.18 | 30981 | 28687 | 28495 | 33124 | 33915 | 58911 | 32827 | 58572 |
| 14.22 | 30648 | 29617 | 31319 | 30761 | 34037 | 57226 | 31703 | 55247 |
| 14.26 | 32825 | 26238 | 29309 | 34424 | 35628 | 56447 | 31324 | 52903 |
| 14.3 | 32650 | 26637 | 31341 | 34234 | 36173 | 60287 | 33104 | 50818 |

-continued

| | | | | | | | | |
|---|---|---|---|---|---|---|---|---|
| 14.34 | 31377 | 29449 | 30986 | 35586 | 36482 | 57933 | 33815 | 47841 |
| 14.38 | 31499 | 27329 | 30247 | 39270 | 39490 | 58815 | 33359 | 47661 |
| 14.42 | 32975 | 26882 | 30476 | 41889 | 41994 | 60101 | 34502 | 47452 |
| 14.46 | 32974 | 27373 | 32088 | 42207 | 39957 | 58445 | 34191 | 46204 |
| 14.5 | 31307 | 25822 | 33040 | 40970 | 39952 | 62696 | 35596 | 41437 |
| 14.54 | 32016 | 24940 | 31375 | 39308 | 39800 | 63548 | 36392 | 39858 |
| 14.58 | 30910 | 27424 | 33185 | 41567 | 38798 | 60702 | 38936 | 39399 |
| 14.62 | 33805 | 27771 | 30459 | 39129 | 40915 | 61910 | 39414 | 35881 |
| 14.66 | 33319 | 26215 | 30031 | 35924 | 38763 | 60769 | 44254 | 35747 |
| 14.7 | 32145 | 27079 | 31953 | 37669 | 38105 | 59098 | 44666 | 31955 |
| 14.74 | 33675 | 26873 | 30824 | 34928 | 37364 | 57214 | 41034 | 30250 |
| 14.78 | 33469 | 26926 | 30222 | 34098 | 38200 | 59484 | 44530 | 30406 |
| 14.82 | 33675 | 28507 | 30219 | 34927 | 37327 | 61747 | 43480 | 28792 |
| 14.86 | 35558 | 27536 | 28543 | 31950 | 39646 | 58892 | 43722 | 31120 |
| 14.9 | 32140 | 26201 | 29706 | 31331 | 41330 | 61831 | 41970 | 27880 |
| 14.94 | 33639 | 26779 | 28196 | 32174 | 35792 | 59453 | 35098 | 30074 |
| 14.98 | 34003 | 26958 | 30342 | 34821 | 36128 | 57944 | 36342 | 29134 |
| 15.02 | 34719 | 25979 | 28657 | 32656 | 38849 | 59751 | 29929 | 29206 |
| 15.06 | 34473 | 25604 | 27428 | 32794 | 41004 | 60091 | 29012 | 28230 |
| 15.1 | 39088 | 26102 | 30005 | 32632 | 40325 | 58283 | 27766 | 26628 |
| 15.14 | 35881 | 24245 | 29151 | 32788 | 42171 | 59015 | 27183 | 27460 |
| 15.18 | 37963 | 24527 | 27668 | 35692 | 39362 | 58923 | 26883 | 27605 |
| 15.22 | 37928 | 26270 | 28111 | 34291 | 38672 | 57846 | 26913 | 29326 |
| 15.26 | 36664 | 26424 | 28378 | 37058 | 40531 | 58284 | 25866 | 28958 |
| 15.3 | 37297 | 27680 | 27262 | 36895 | 38135 | 58909 | 25969 | 30018 |
| 15.34 | 39096 | 27433 | 25843 | 36252 | 39098 | 59083 | 23841 | 30564 |
| 15.38 | 38375 | 27837 | 25761 | 37682 | 36980 | 61688 | 25806 | 31051 |
| 15.42 | 37701 | 28960 | 25616 | 36908 | 39188 | 60935 | 26758 | 32891 |
| 15.46 | 37725 | 29667 | 26860 | 38190 | 39266 | 61529 | 27864 | 35279 |
| 15.5 | 38488 | 33371 | 25227 | 33169 | 36813 | 62024 | 25654 | 36423 |
| 15.54 | 38993 | 37525 | 27289 | 34046 | 37858 | 62891 | 25996 | 36353 |
| 15.58 | 40829 | 41842 | 27264 | 34920 | 33361 | 65434 | 26242 | 39751 |
| 15.62 | 37832 | 47259 | 26848 | 34503 | 37014 | 63123 | 25524 | 40586 |
| 15.66 | 35428 | 53309 | 28132 | 36130 | 35622 | 65620 | 24951 | 43203 |
| 15.7 | 34754 | 55326 | 30615 | 34521 | 33493 | 62162 | 24193 | 43705 |
| 15.74 | 35700 | 59185 | 27685 | 36156 | 33958 | 65143 | 24281 | 45871 |
| 15.78 | 37587 | 58771 | 32302 | 37693 | 33819 | 62036 | 24477 | 48061 |
| 15.82 | 37268 | 59779 | 34014 | 41094 | 35634 | 64069 | 25801 | 46551 |
| 15.86 | 36337 | 58708 | 36824 | 41985 | 35066 | 60903 | 25653 | 50832 |
| 15.9 | 37846 | 58850 | 36673 | 43841 | 36166 | 60849 | 26871 | 53101 |
| 15.94 | 36951 | 57385 | 37255 | 44967 | 37272 | 60144 | 27143 | 54890 |
| 15.98 | 38522 | 53924 | 41019 | 46822 | 37078 | 58995 | 24069 | 55847 |
| 16.02 | 37939 | 48899 | 42982 | 47065 | 34167 | 61479 | 24742 | 56951 |
| 16.06 | 36473 | 46120 | 41205 | 51594 | 34176 | 62553 | 25942 | 60290 |
| 16.1 | 38240 | 41299 | 44654 | 48115 | 35772 | 61849 | 25804 | 59609 |
| 16.14 | 37209 | 43109 | 44594 | 51078 | 36605 | 63307 | 27205 | 59782 |
| 16.18 | 35683 | 42647 | 44537 | 48545 | 38766 | 62409 | 26185 | 59161 |
| 16.22 | 37972 | 37131 | 44973 | 50396 | 37974 | 62216 | 28228 | 53307 |
| 16.26 | 37329 | 40032 | 46377 | 49902 | 35398 | 64140 | 27976 | 52704 |
| 16.3 | 38166 | 43128 | 47600 | 47376 | 37764 | 65300 | 27047 | 47497 |
| 16.34 | 37621 | 39297 | 49631 | 42586 | 38333 | 64647 | 28181 | 44837 |
| 16.38 | 37655 | 39971 | 49293 | 46152 | 38034 | 65183 | 26358 | 43710 |
| 16.42 | 39994 | 38567 | 49181 | 45611 | 36752 | 66226 | 24284 | 40160 |
| 16.46 | 40942 | 38242 | 48741 | 46671 | 37588 | 68598 | 28094 | 39600 |
| 16.5 | 41697 | 35860 | 49331 | 44599 | 36198 | 72763 | 25068 | 34649 |
| 16.54 | 40218 | 36728 | 47298 | 47878 | 35406 | 74393 | 24945 | 34768 |
| 16.58 | 39284 | 37246 | 46647 | 47120 | 37636 | 79742 | 24681 | 34285 |
| 16.62 | 41205 | 33307 | 43776 | 46168 | 38004 | 86145 | 25502 | 35585 |
| 16.66 | 38896 | 32637 | 42208 | 46176 | 39554 | 95103 | 25714 | 33927 |
| 16.7 | 39019 | 31781 | 37636 | 43596 | 38610 | 101744 | 26329 | 33498 |
| 16.74 | 39148 | 30832 | 37117 | 45187 | 39561 | 110422 | 26045 | 33604 |
| 16.78 | 37040 | 30950 | 34466 | 41766 | 38318 | 110553 | 26546 | 32373 |
| 16.82 | 36604 | 29258 | 34149 | 42795 | 36125 | 109790 | 27008 | 33379 |
| 16.86 | 35983 | 27458 | 30953 | 44931 | 37370 | 107721 | 29594 | 33448 |
| 16.9 | 34265 | 29696 | 30719 | 41361 | 37368 | 102145 | 30460 | 33109 |
| 16.94 | 35481 | 30937 | 28996 | 42836 | 36187 | 102613 | 32093 | 33985 |
| 16.98 | 35103 | 31313 | 27747 | 42586 | 35979 | 92987 | 30217 | 35054 |
| 17.02 | 35118 | 32866 | 27985 | 42940 | 37449 | 84494 | 31617 | 33560 |
| 17.06 | 35457 | 31681 | 26262 | 43079 | 36142 | 81467 | 31801 | 35506 |
| 17.1 | 34337 | 31826 | 24858 | 43011 | 36684 | 73313 | 31810 | 33220 |
| 17.14 | 35414 | 31080 | 26478 | 43240 | 38261 | 65661 | 28440 | 32198 |
| 17.18 | 34539 | 33511 | 26588 | 43781 | 37535 | 65017 | 30581 | 33308 |
| 17.22 | 31068 | 31426 | 24959 | 41725 | 35627 | 65087 | 30467 | 32212 |
| 17.26 | 33607 | 31699 | 24945 | 40427 | 36129 | 62101 | 28563 | 33718 |
| 17.3 | 34750 | 28592 | 26696 | 40925 | 38287 | 60624 | 30130 | 32810 |
| 17.34 | 32932 | 29028 | 24051 | 36544 | 36739 | 62454 | 28229 | 30184 |
| 17.38 | 34276 | 25573 | 25400 | 37703 | 34605 | 60662 | 26407 | 31176 |
| 17.42 | 32814 | 25729 | 24648 | 37179 | 35291 | 64040 | 25319 | 31114 |
| 17.46 | 34912 | 25344 | 26635 | 36157 | 35314 | 62051 | 27506 | 29822 |

| | | | | | | | | |
|---|---|---|---|---|---|---|---|---|
| 17.5 | 33982 | 25350 | 26079 | 36538 | 35445 | 63759 | 27208 | 30479 |
| 17.54 | 31809 | 25565 | 27069 | 38535 | 35504 | 65708 | 27243 | 31557 |
| 17.58 | 34269 | 25901 | 26530 | 35654 | 35588 | 66609 | 28305 | 29732 |
| 17.62 | 34329 | 28141 | 28853 | 38085 | 36013 | 69502 | 30007 | 29471 |
| 17.66 | 32675 | 27999 | 28081 | 32626 | 35278 | 68945 | 31858 | 30100 |
| 17.7 | 34311 | 27879 | 29612 | 34863 | 34963 | 68464 | 29925 | 28785 |
| 17.74 | 33091 | 28764 | 29355 | 38654 | 36192 | 67006 | 30309 | 31309 |
| 17.78 | 34239 | 29226 | 31847 | 40923 | 35754 | 67677 | 31755 | 28666 |
| 17.82 | 33831 | 29079 | 33503 | 46627 | 36278 | 69274 | 33284 | 29864 |
| 17.86 | 31766 | 26972 | 32485 | 49956 | 35968 | 66229 | 32866 | 28628 |
| 17.9 | 32785 | 29494 | 32439 | 53503 | 38841 | 69737 | 32989 | 26979 |
| 17.94 | 31178 | 28453 | 32628 | 56213 | 38631 | 71705 | 32899 | 27743 |
| 17.98 | 31006 | 27055 | 32854 | 59202 | 38191 | 72435 | 33538 | 25981 |
| 18.02 | 33385 | 24527 | 32754 | 57407 | 41584 | 79059 | 33231 | 28021 |
| 18.06 | 33215 | 26406 | 32222 | 58334 | 38696 | 86826 | 36514 | 27835 |
| 18.1 | 31822 | 26037 | 30237 | 59771 | 38221 | 97964 | 34915 | 26520 |
| 18.14 | 32970 | 24658 | 27242 | 58302 | 40037 | 115271 | 33733 | 27142 |
| 18.18 | 32374 | 24349 | 25945 | 56786 | 37446 | 122601 | 35054 | 27399 |
| 18.22 | 33185 | 22893 | 28326 | 49211 | 37881 | 123715 | 36352 | 28236 |
| 18.26 | 32660 | 24736 | 28079 | 49293 | 39129 | 131752 | 34109 | 29610 |
| 18.3 | 33080 | 25864 | 25226 | 47073 | 37002 | 129959 | 38176 | 29959 |
| 18.34 | 34493 | 25732 | 23945 | 44714 | 37533 | 128860 | 38669 | 31055 |
| 18.38 | 31661 | 26866 | 24988 | 42931 | 35353 | 114248 | 38930 | 33228 |
| 18.42 | 33283 | 25187 | 25301 | 41318 | 34975 | 107564 | 38846 | 33141 |
| 18.46 | 33860 | 28117 | 23798 | 45028 | 35846 | 100150 | 41980 | 34178 |
| 18.5 | 32243 | 29055 | 27403 | 42561 | 35264 | 83834 | 43145 | 38239 |
| 18.54 | 34002 | 28419 | 23511 | 41920 | 35147 | 77108 | 46490 | 38972 |
| 18.58 | 33442 | 31844 | 24898 | 42741 | 37353 | 72744 | 47662 | 39791 |
| 18.62 | 31886 | 32563 | 26694 | 40306 | 36562 | 64247 | 49201 | 39196 |
| 18.66 | 33967 | 32723 | 25902 | 40262 | 39029 | 62092 | 46885 | 40067 |
| 18.7 | 33770 | 32012 | 25930 | 38874 | 41116 | 64809 | 46937 | 36934 |
| 18.74 | 34381 | 30857 | 25419 | 40046 | 40843 | 60543 | 45042 | 40893 |
| 18.78 | 35975 | 29861 | 28099 | 40240 | 43512 | 63110 | 46471 | 39664 |
| 18.82 | 35279 | 31852 | 29926 | 38584 | 46500 | 62258 | 41120 | 37448 |
| 18.86 | 36834 | 29794 | 27820 | 38372 | 51062 | 61098 | 39468 | 35417 |
| 18.9 | 36419 | 28353 | 29336 | 36740 | 50542 | 60839 | 36868 | 33386 |
| 18.94 | 34824 | 27575 | 27379 | 34673 | 52271 | 59488 | 35830 | 32922 |
| 18.98 | 34264 | 27158 | 25390 | 37073 | 51140 | 62238 | 37699 | 31718 |
| 19.02 | 36442 | 28599 | 26798 | 34597 | 51426 | 62660 | 35031 | 31031 |
| 19.06 | 36137 | 28169 | 26213 | 35237 | 52943 | 61511 | 36140 | 29178 |
| 19.1 | 35828 | 26056 | 29605 | 36756 | 49146 | 61878 | 37107 | 30040 |
| 19.14 | 33495 | 27683 | 24572 | 36903 | 46164 | 61654 | 34272 | 30723 |
| 19.18 | 35573 | 27142 | 26417 | 36846 | 44799 | 62192 | 35237 | 30292 |
| 19.22 | 33474 | 30077 | 26588 | 36736 | 44653 | 58045 | 35023 | 29228 |
| 19.26 | 35268 | 30078 | 24946 | 38266 | 42657 | 57737 | 30591 | 28132 |
| 19.3 | 35439 | 33741 | 26204 | 37710 | 39343 | 58732 | 31221 | 29575 |
| 19.34 | 35854 | 36406 | 27057 | 38989 | 37313 | 58028 | 31290 | 28464 |
| 19.38 | 35968 | 36224 | 24691 | 40336 | 39285 | 60344 | 28549 | 29784 |
| 19.42 | 34219 | 41073 | 25931 | 42263 | 36914 | 60427 | 28557 | 30349 |
| 19.46 | 34373 | 44696 | 25014 | 43755 | 38267 | 56974 | 28597 | 31051 |
| 19.5 | 33766 | 42661 | 24196 | 45523 | 35633 | 58012 | 27624 | 28428 |
| 19.54 | 33678 | 45402 | 24442 | 46815 | 37930 | 58292 | 26488 | 28018 |
| 19.58 | 31989 | 41872 | 25422 | 52873 | 37164 | 56652 | 26341 | 29420 |
| 19.62 | 32574 | 43256 | 24411 | 55121 | 38266 | 57358 | 26609 | 29837 |
| 19.66 | 32061 | 40842 | 23259 | 57877 | 40600 | 56318 | 24803 | 30276 |
| 19.7 | 32299 | 37578 | 25248 | 60325 | 35956 | 55213 | 24405 | 29903 |
| 19.74 | 32563 | 33436 | 25812 | 64203 | 38392 | 58980 | 25408 | 28820 |
| 19.78 | 32417 | 32385 | 25769 | 57195 | 39120 | 58836 | 27246 | 29991 |
| 19.82 | 33828 | 30483 | 25214 | 63008 | 37773 | 56652 | 27642 | 27837 |
| 19.86 | 34906 | 28079 | 26683 | 57036 | 40493 | 58259 | 29997 | 27772 |
| 19.9 | 33877 | 24656 | 26621 | 51570 | 40805 | 61106 | 30853 | 27031 |
| 19.94 | 33097 | 23944 | 26233 | 50518 | 39780 | 60345 | 32290 | 28125 |
| 19.98 | 33739 | 24829 | 27550 | 49358 | 41262 | 58898 | 35046 | 25665 |
| 20.02 | 32244 | 23699 | 27940 | 47351 | 42830 | 64390 | 38373 | 27233 |
| 20.06 | 33222 | 25625 | 27862 | 42426 | 37875 | 62186 | 38985 | 24989 |
| 20.1 | 34659 | 28288 | 27145 | 41183 | 38727 | 64574 | 42960 | 24769 |
| 20.14 | 33665 | 27959 | 26156 | 40548 | 38213 | 66773 | 41712 | 27466 |
| 20.18 | 32684 | 28612 | 26245 | 41771 | 37786 | 67021 | 42495 | 26382 |
| 20.22 | 32589 | 31154 | 26639 | 39815 | 37229 | 66205 | 41428 | 27437 |
| 20.26 | 33163 | 29710 | 27784 | 40381 | 36573 | 65649 | 39163 | 28826 |
| 20.3 | 33561 | 29496 | 28557 | 38562 | 35087 | 66070 | 36176 | 29045 |
| 20.34 | 33010 | 30747 | 28482 | 37155 | 35894 | 67309 | 33766 | 31120 |
| 20.38 | 35053 | 30015 | 29041 | 37310 | 35967 | 68075 | 31049 | 31667 |
| 20.42 | 34165 | 30916 | 29921 | 38427 | 35746 | 68907 | 28368 | 32149 |
| 20.46 | 34555 | 28792 | 28494 | 39813 | 36713 | 69659 | 27600 | 30995 |
| 20.5 | 35667 | 27333 | 28881 | 37712 | 37873 | 71832 | 26933 | 32764 |
| 20.54 | 34877 | 24129 | 28649 | 39540 | 36811 | 74877 | 25375 | 31524 |
| 20.58 | 33072 | 25553 | 28552 | 38015 | 35081 | 79204 | 25701 | 30888 |
| 20.62 | 35035 | 23207 | 28180 | 38547 | 35458 | 81708 | 26031 | 29650 |

-continued

| | | | | | | | | |
|---|---|---|---|---|---|---|---|---|
| 20.66 | 35303 | 23566 | 26499 | 40835 | 36204 | 83956 | 24193 | 31297 |
| 20.7 | 35724 | 22094 | 27114 | 41865 | 34315 | 81209 | 22823 | 31833 |
| 20.74 | 34911 | 23187 | 27174 | 42501 | 35534 | 80428 | 24097 | 29172 |
| 20.78 | 36049 | 23305 | 27195 | 43309 | 34622 | 81444 | 25150 | 31272 |
| 20.82 | 34854 | 24562 | 27509 | 43754 | 34510 | 78755 | 26711 | 31995 |
| 20.86 | 32944 | 24022 | 25164 | 43357 | 32324 | 74718 | 24825 | 33109 |
| 20.9 | 35228 | 25061 | 25624 | 45644 | 35805 | 65732 | 22631 | 31912 |
| 20.94 | 36974 | 25594 | 28500 | 47848 | 35489 | 66021 | 24211 | 31231 |
| 20.98 | 35358 | 23758 | 23616 | 45338 | 34562 | 63732 | 24524 | 32589 |
| 21.02 | 37214 | 23634 | 25264 | 41653 | 31264 | 57887 | 24261 | 30552 |
| 21.06 | 36204 | 21501 | 25285 | 42396 | 32767 | 60591 | 23518 | 33181 |
| 21.1 | 36917 | 23991 | 24633 | 42692 | 37438 | 57842 | 24263 | 31127 |
| 21.14 | 35544 | 22726 | 25520 | 38813 | 34769 | 60446 | 24338 | 33584 |
| 21.18 | 36235 | 25432 | 28065 | 42007 | 36068 | 65475 | 23686 | 30909 |
| 21.22 | 36252 | 23925 | 27793 | 40245 | 34763 | 66663 | 23205 | 33933 |
| 21.26 | 35115 | 28551 | 26973 | 39148 | 37534 | 72274 | 25428 | 33704 |
| 21.3 | 35442 | 29419 | 27061 | 39588 | 35284 | 70095 | 25355 | 33438 |
| 21.34 | 36947 | 28496 | 26700 | 35256 | 36487 | 76938 | 26219 | 34158 |
| 21.38 | 36684 | 28203 | 27922 | 39928 | 37003 | 76901 | 26130 | 37482 |
| 21.42 | 34700 | 31608 | 27977 | 38277 | 35605 | 78700 | 24975 | 37995 |
| 21.46 | 35318 | 29539 | 28304 | 38634 | 35223 | 76025 | 21783 | 38133 |
| 21.5 | 38768 | 29951 | 28404 | 40624 | 33787 | 76846 | 24585 | 41535 |
| 21.54 | 37141 | 32159 | 27564 | 39661 | 35666 | 74834 | 23695 | 41967 |
| 21.58 | 35317 | 31716 | 29697 | 40620 | 36919 | 74947 | 24079 | 44466 |
| 21.62 | 36382 | 29955 | 28170 | 41647 | 41531 | 67484 | 25047 | 44741 |
| 21.66 | 33537 | 28636 | 25266 | 44562 | 35201 | 71671 | 23342 | 42445 |
| 21.7 | 35752 | 27275 | 23831 | 38900 | 37227 | 71106 | 24205 | 42475 |
| 21.74 | 33469 | 29180 | 26616 | 37079 | 40807 | 73565 | 24956 | 40885 |
| 21.78 | 33170 | 30743 | 26842 | 41111 | 37398 | 68065 | 22863 | 38339 |
| 21.82 | 31254 | 31793 | 25138 | 40207 | 36900 | 68056 | 26908 | 37344 |
| 21.86 | 32696 | 29825 | 24906 | 40816 | 38251 | 73690 | 29057 | 34867 |
| 21.9 | 36632 | 32446 | 26594 | 39459 | 41074 | 73103 | 28066 | 35020 |
| 21.94 | 34029 | 31468 | 26426 | 37907 | 40244 | 70266 | 28306 | 34047 |
| 21.98 | 33661 | 30019 | 24971 | 39917 | 39925 | 69322 | 31194 | 33418 |
| 22.02 | 37029 | 29438 | 27434 | 40658 | 40671 | 70415 | 31115 | 34634 |
| 22.06 | 34535 | 32200 | 25026 | 41604 | 38724 | 63832 | 32024 | 31930 |
| 22.1 | 33604 | 28675 | 23443 | 43029 | 36889 | 63373 | 35349 | 33520 |
| 22.14 | 35934 | 30113 | 24240 | 36871 | 37944 | 62734 | 34000 | 33261 |
| 22.18 | 34746 | 28522 | 22169 | 39105 | 37022 | 66135 | 29810 | 34177 |
| 22.22 | 37650 | 26509 | 24944 | 42456 | 34068 | 60514 | 33192 | 33865 |
| 22.26 | 38543 | 28894 | 24936 | 43171 | 34283 | 61498 | 32991 | 35264 |
| 22.3 | 36222 | 24275 | 25365 | 42681 | 35404 | 60897 | 29151 | 40396 |
| 22.34 | 37647 | 25073 | 25644 | 40831 | 35577 | 59468 | 28957 | 38850 |
| 22.38 | 36943 | 25287 | 25271 | 40622 | 33924 | 63998 | 28757 | 38548 |
| 22.42 | 39233 | 24878 | 26796 | 41110 | 35322 | 60794 | 27077 | 38390 |
| 22.46 | 37447 | 24474 | 26261 | 40908 | 35922 | 57773 | 24605 | 36164 |
| 22.5 | 35922 | 24634 | 24659 | 42322 | 38229 | 57540 | 26982 | 33222 |
| 22.54 | 35577 | 24416 | 26368 | 37887 | 34756 | 58438 | 26532 | 35578 |
| 22.58 | 38665 | 24110 | 25527 | 38340 | 35890 | 59473 | 27103 | 32415 |
| 22.62 | 35480 | 23907 | 25770 | 38766 | 34816 | 56371 | 28131 | 32791 |
| 22.66 | 36917 | 21058 | 26184 | 33931 | 36351 | 57489 | 26266 | 32604 |
| 22.7 | 36322 | 20782 | 27163 | 32114 | 38314 | 61593 | 25616 | 32338 |
| 22.74 | 34948 | 21021 | 26027 | 36882 | 36663 | 59050 | 26499 | 31165 |
| 22.78 | 36204 | 20955 | 25739 | 36355 | 33362 | 56634 | 26534 | 30759 |
| 22.82 | 35888 | 19133 | 26005 | 36262 | 35512 | 61345 | 27038 | 32185 |
| 22.86 | 35375 | 22455 | 26245 | 34508 | 32677 | 57689 | 29451 | 30770 |
| 22.9 | 35929 | 24520 | 28162 | 37097 | 35107 | 61592 | 28640 | 30664 |
| 22.94 | 37011 | 21900 | 29549 | 34812 | 35519 | 58217 | 28388 | 30305 |
| 22.98 | 38150 | 22372 | 25124 | 36618 | 33398 | 55392 | 26950 | 30534 |
| 23.02 | 37684 | 20291 | 26730 | 37692 | 33894 | 61410 | 26834 | 28540 |
| 23.06 | 36988 | 18823 | 26259 | 37397 | 33034 | 58991 | 30059 | 27591 |
| 23.1 | 34543 | 19437 | 26377 | 37902 | 34122 | 58711 | 29059 | 27573 |
| 23.14 | 37600 | 20486 | 28586 | 37963 | 35171 | 57961 | 28972 | 27573 |
| 23.18 | 38307 | 20293 | 27568 | 38676 | 35698 | 61374 | 27048 | 29146 |
| 23.22 | 41646 | 20713 | 28890 | 39677 | 35366 | 66537 | 28536 | 29673 |
| 23.26 | 41244 | 21924 | 28187 | 38301 | 33637 | 72688 | 26426 | 26420 |
| 23.3 | 42675 | 22288 | 24514 | 39617 | 32990 | 77582 | 22467 | 26718 |
| 23.34 | 43833 | 21015 | 28707 | 35701 | 35132 | 80893 | 25736 | 25796 |
| 23.38 | 41143 | 18940 | 26154 | 36037 | 32922 | 80007 | 25883 | 24543 |
| 23.42 | 41710 | 24243 | 28684 | 35833 | 33490 | 82725 | 26583 | 26693 |
| 23.46 | 41804 | 24160 | 28886 | 38301 | 31344 | 81614 | 23937 | 27470 |
| 23.5 | 44361 | 22083 | 28179 | 37622 | 32854 | 82625 | 26303 | 27037 |
| 23.54 | 41198 | 23339 | 30799 | 37257 | 35058 | 80891 | 26090 | 28906 |
| 23.58 | 40537 | 21663 | 33536 | 39635 | 34394 | 78775 | 27616 | 28960 |
| 23.62 | 44432 | 24605 | 33012 | 37791 | 35127 | 75492 | 26468 | 27121 |
| 23.66 | 43481 | 26142 | 34023 | 37582 | 37384 | 67763 | 26809 | 29140 |
| 23.7 | 39064 | 25611 | 36329 | 38927 | 36100 | 68864 | 29959 | 29313 |
| 23.74 | 41537 | 25793 | 39057 | 41104 | 35354 | 65658 | 32031 | 29190 |
| 23.78 | 44955 | 22830 | 37651 | 39966 | 39417 | 66652 | 35008 | 29468 |

-continued

| | | | | | | | | |
|---|---|---|---|---|---|---|---|---|
| 23.82 | 43988 | 24814 | 38703 | 40042 | 39737 | 67984 | 35676 | 32053 |
| 23.86 | 41398 | 26012 | 39830 | 43714 | 41545 | 75376 | 37009 | 33887 |
| 23.9 | 41695 | 26652 | 40725 | 41357 | 39948 | 75796 | 38100 | 37638 |
| 23.94 | 41969 | 33168 | 43725 | 42747 | 45310 | 82573 | 41721 | 38040 |
| 23.98 | 40691 | 30825 | 41934 | 43875 | 42873 | 84847 | 41943 | 37041 |
| 24.02 | 42504 | 34901 | 43620 | 44583 | 42706 | 83733 | 42799 | 38562 |
| 24.06 | 41860 | 35828 | 40840 | 49304 | 42163 | 87329 | 44764 | 42119 |
| 24.1 | 43320 | 38352 | 43128 | 46714 | 42676 | 88415 | 39851 | 39974 |
| 24.14 | 43854 | 42912 | 44737 | 46680 | 43098 | 87721 | 43053 | 42307 |
| 24.18 | 41370 | 44226 | 43776 | 47616 | 42120 | 89494 | 41726 | 42741 |
| 24.22 | 43007 | 43601 | 46374 | 49703 | 47149 | 90016 | 45206 | 48114 |
| 24.26 | 43083 | 45009 | 44003 | 49487 | 46589 | 85080 | 40282 | 47909 |
| 24.3 | 40839 | 45727 | 45562 | 49245 | 50112 | 84360 | 40176 | 45999 |
| 24.34 | 42585 | 50099 | 46882 | 48918 | 48439 | 84155 | 41584 | 43571 |
| 24.38 | 40758 | 51343 | 47627 | 50586 | 50250 | 82427 | 43256 | 43416 |
| 24.42 | 43770 | 51776 | 48523 | 48560 | 53014 | 83354 | 47358 | 43020 |
| 24.46 | 42796 | 52663 | 49338 | 52029 | 54824 | 85625 | 54351 | 43271 |
| 24.5 | 41104 | 48482 | 50523 | 47478 | 59945 | 87308 | 65072 | 41651 |
| 24.54 | 42146 | 49410 | 49707 | 49097 | 60949 | 93656 | 77079 | 42267 |
| 24.58 | 40650 | 51807 | 50941 | 50612 | 67625 | 98247 | 89397 | 40472 |
| 24.62 | 42439 | 46698 | 50036 | 46461 | 68469 | 98496 | 93577 | 36988 |
| 24.66 | 41856 | 43122 | 47864 | 48554 | 69558 | 94218 | 93802 | 39393 |
| 24.7 | 44426 | 40161 | 46727 | 48738 | 77288 | 96723 | 99901 | 39262 |
| 24.74 | 43785 | 39280 | 43515 | 45578 | 78684 | 100925 | 105477 | 42296 |
| 24.78 | 41449 | 32994 | 40937 | 45787 | 76734 | 99146 | 105684 | 40475 |
| 24.82 | 44709 | 32983 | 39963 | 46172 | 78010 | 102063 | 105515 | 40923 |
| 24.86 | 44719 | 33794 | 40093 | 44646 | 75254 | 109153 | 100329 | 37802 |
| 24.9 | 46634 | 32621 | 40964 | 45923 | 77315 | 112446 | 86888 | 41400 |
| 24.94 | 40480 | 29875 | 37985 | 46183 | 72269 | 116479 | 81454 | 41032 |
| 24.98 | 43293 | 29081 | 39096 | 41762 | 69513 | 124825 | 77333 | 41573 |
| 25.02 | 45899 | 30210 | 37610 | 43367 | 68037 | 128166 | 71639 | 42832 |
| 25.06 | 43417 | 34101 | 34357 | 43779 | 64058 | 127007 | 68027 | 44131 |
| 25.1 | 43697 | 34566 | 36332 | 43314 | 66343 | 135277 | 69048 | 45098 |
| 25.14 | 42425 | 36758 | 35395 | 51746 | 66285 | 133726 | 62523 | 50604 |
| 25.18 | 44860 | 38323 | 33511 | 45475 | 59187 | 139966 | 57126 | 52004 |
| 25.22 | 44562 | 44391 | 32812 | 48317 | 56235 | 131734 | 54216 | 54356 |
| 25.26 | 45547 | 48599 | 36839 | 53936 | 59897 | 135554 | 54312 | 61641 |
| 25.3 | 43010 | 50089 | 33480 | 50935 | 56679 | 123378 | 56129 | 59954 |
| 25.34 | 43356 | 51717 | 33624 | 52456 | 53242 | 115465 | 59776 | 64385 |
| 25.38 | 43448 | 54694 | 35857 | 53899 | 51237 | 113199 | 57513 | 64545 |
| 25.42 | 42381 | 53910 | 34585 | 50467 | 49700 | 108182 | 57615 | 62457 |
| 25.46 | 41762 | 53378 | 34430 | 52045 | 46206 | 95026 | 52646 | 62567 |
| 25.5 | 43302 | 49317 | 33560 | 53338 | 44569 | 88061 | 52933 | 67274 |
| 25.54 | 43980 | 47398 | 33932 | 53298 | 45471 | 82216 | 49060 | 62899 |
| 25.58 | 39335 | 39820 | 33252 | 52507 | 44403 | 78615 | 44877 | 64930 |
| 25.62 | 39304 | 37535 | 34679 | 49944 | 42892 | 71178 | 40614 | 60593 |
| 25.66 | 40632 | 32593 | 30714 | 49548 | 40287 | 69637 | 38827 | 57814 |
| 25.7 | 39897 | 30291 | 29705 | 49163 | 43656 | 62923 | 37827 | 56917 |
| 25.74 | 37963 | 27737 | 32940 | 48611 | 46072 | 62870 | 36204 | 54264 |
| 25.78 | 39626 | 27736 | 33307 | 48155 | 46771 | 63002 | 38328 | 56493 |
| 25.82 | 37994 | 28322 | 33660 | 48510 | 43884 | 63831 | 41314 | 49346 |
| 25.86 | 40092 | 28004 | 30626 | 48221 | 46233 | 62424 | 42173 | 49092 |
| 25.9 | 36678 | 30403 | 31114 | 52336 | 45309 | 64314 | 42509 | 45453 |
| 25.94 | 35996 | 29321 | 33449 | 50772 | 43778 | 68505 | 50367 | 43493 |
| 25.98 | 36746 | 29698 | 36137 | 52742 | 47195 | 66146 | 58922 | 41436 |
| 26.02 | 37279 | 28735 | 33677 | 52994 | 46819 | 61387 | 59350 | 39396 |
| 26.06 | 36783 | 30802 | 32485 | 55797 | 49089 | 67047 | 57410 | 38799 |
| 26.1 | 36659 | 30616 | 32581 | 55230 | 51138 | 68488 | 58908 | 35649 |
| 26.14 | 35891 | 31127 | 32151 | 54597 | 49832 | 64125 | 57299 | 33736 |
| 26.18 | 36053 | 31446 | 30185 | 53730 | 50547 | 68585 | 62154 | 33692 |
| 26.22 | 34446 | 28422 | 31311 | 51742 | 50619 | 69767 | 59211 | 33093 |
| 26.26 | 34741 | 33496 | 31055 | 50596 | 49834 | 71159 | 54518 | 31531 |
| 26.3 | 32452 | 34111 | 30221 | 50627 | 52197 | 79715 | 51357 | 33758 |
| 26.34 | 34519 | 35139 | 28060 | 48545 | 48333 | 82154 | 42545 | 31309 |
| 26.38 | 33903 | 35354 | 28946 | 50607 | 47424 | 83912 | 38910 | 29211 |
| 26.42 | 34781 | 37253 | 28213 | 45751 | 50245 | 89046 | 37683 | 28020 |
| 26.46 | 34735 | 38304 | 27375 | 48767 | 46830 | 90939 | 35519 | 27747 |
| 26.5 | 32432 | 34162 | 25838 | 47039 | 43834 | 89274 | 33754 | 26919 |
| 26.54 | 34920 | 33992 | 26332 | 46754 | 41666 | 89976 | 35283 | 29554 |
| 26.58 | 33450 | 33686 | 26720 | 47675 | 40284 | 92860 | 36936 | 26977 |
| 26.62 | 32957 | 33406 | 27597 | 47721 | 39203 | 90688 | 35124 | 30478 |
| 26.66 | 33891 | 34422 | 27871 | 48296 | 39237 | 94552 | 36181 | 29748 |
| 26.7 | 32640 | 35162 | 25946 | 47633 | 38596 | 89617 | 39864 | 30506 |
| 26.74 | 32921 | 33236 | 26668 | 47928 | 36774 | 90252 | 38759 | 30900 |
| 26.78 | 32582 | 36760 | 27978 | 47438 | 39495 | 87660 | 37985 | 29038 |
| 26.82 | 32159 | 37243 | 30971 | 46564 | 37588 | 85288 | 40724 | 29087 |
| 26.86 | 32786 | 38314 | 27851 | 48897 | 37965 | 81712 | 38467 | 28979 |
| 26.9 | 31276 | 37426 | 26409 | 44966 | 37479 | 80618 | 36874 | 31408 |
| 26.94 | 31174 | 35650 | 27421 | 41231 | 39278 | 74288 | 37865 | 31051 |

-continued

| | | | | | | | | |
|---|---|---|---|---|---|---|---|---|
| 26.98 | 31459 | 37977 | 28538 | 41787 | 38715 | 71708 | 37319 | 30386 |
| 27.02 | 32266 | 33451 | 28700 | 43098 | 38555 | 67927 | 37163 | 30870 |
| 27.06 | 31701 | 31854 | 29448 | 40587 | 35785 | 63036 | 31822 | 29244 |
| 27.1 | 26750 | 30904 | 30357 | 41155 | 36682 | 56477 | 32863 | 25662 |
| 27.14 | 26095 | 27921 | 31359 | 39506 | 37964 | 54204 | 32363 | 28121 |
| 27.18 | 27144 | 26393 | 30577 | 40292 | 33444 | 49692 | 34457 | 26217 |
| 27.22 | 29137 | 25445 | 31309 | 41262 | 35663 | 53773 | 33289 | 26440 |
| 27.26 | 27662 | 26786 | 31584 | 39157 | 35115 | 53556 | 38396 | 27059 |
| 27.3 | 27162 | 26514 | 28947 | 39871 | 33738 | 53071 | 40082 | 28083 |
| 27.34 | 28813 | 25267 | 28395 | 38106 | 30998 | 49803 | 42986 | 25446 |
| 27.38 | 27658 | 24196 | 28181 | 39030 | 32377 | 48437 | 42689 | 26039 |
| 27.42 | 29272 | 25896 | 28959 | 38030 | 29129 | 52229 | 45068 | 28237 |
| 27.46 | 26063 | 25249 | 25633 | 34716 | 30341 | 50320 | 45652 | 25839 |
| 27.5 | 26084 | 21748 | 26281 | 34966 | 29497 | 49775 | 47852 | 27135 |
| 27.54 | 27546 | 21111 | 22783 | 33591 | 30426 | 51370 | 44242 | 29478 |
| 27.58 | 28878 | 22189 | 23970 | 34073 | 31203 | 55754 | 42193 | 29796 |
| 27.62 | 27412 | 21728 | 22495 | 33486 | 30705 | 59036 | 39506 | 28098 |
| 27.66 | 26673 | 19813 | 24743 | 32638 | 30412 | 59823 | 36091 | 26119 |
| 27.7 | 26476 | 19093 | 22931 | 32251 | 30933 | 62867 | 34485 | 29014 |
| 27.74 | 27709 | 19012 | 21348 | 32016 | 32067 | 60646 | 31259 | 28573 |
| 27.78 | 28496 | 19968 | 21965 | 32872 | 30170 | 61640 | 28231 | 29798 |
| 27.82 | 28676 | 20020 | 21532 | 32700 | 33940 | 62087 | 26486 | 25293 |
| 27.86 | 29410 | 19060 | 22076 | 35320 | 33865 | 60158 | 28954 | 27553 |
| 27.9 | 25808 | 16297 | 21200 | 34999 | 32152 | 59798 | 23972 | 25850 |
| 27.94 | 27355 | 17390 | 20705 | 34424 | 31764 | 55715 | 25629 | 23080 |
| 27.98 | 25819 | 18765 | 21953 | 34373 | 33207 | 55271 | 27029 | 24884 |
| 28.02 | 26762 | 19404 | 21594 | 36740 | 30585 | 53263 | 25176 | 21741 |
| 28.06 | 25660 | 19037 | 21360 | 36400 | 28814 | 50372 | 25276 | 22973 |
| 28.1 | 27459 | 17309 | 23390 | 36442 | 30265 | 51253 | 23647 | 21027 |
| 28.14 | 26350 | 18130 | 20287 | 34092 | 31913 | 49284 | 25290 | 21536 |
| 28.18 | 26327 | 17237 | 22626 | 32837 | 28984 | 45209 | 23324 | 19848 |
| 28.22 | 25522 | 19118 | 19782 | 28862 | 26552 | 44573 | 24586 | 20097 |
| 28.26 | 24480 | 18536 | 21115 | 29381 | 24847 | 43558 | 24329 | 20260 |
| 28.3 | 24119 | 19788 | 20336 | 28556 | 25187 | 42128 | 24038 | 19938 |
| 28.34 | 24243 | 19484 | 20102 | 30460 | 25613 | 42883 | 24449 | 19824 |
| 28.38 | 25078 | 20679 | 21612 | 28651 | 24637 | 43494 | 24826 | 18725 |
| 28.42 | 25818 | 19682 | 22981 | 28280 | 23423 | 40443 | 24458 | 20030 |
| 28.46 | 24302 | 21362 | 20162 | 27163 | 23860 | 41411 | 24113 | 21187 |
| 28.5 | 26403 | 22796 | 20833 | 26583 | 21844 | 42165 | 21926 | 21171 |
| 28.54 | 24715 | 21975 | 20902 | 30246 | 24909 | 45901 | 22974 | 22184 |
| 28.58 | 25634 | 24125 | 21351 | 30512 | 25262 | 43119 | 23397 | 20163 |
| 28.62 | 24146 | 25946 | 20702 | 27248 | 23281 | 40922 | 22686 | 20439 |
| 28.66 | 23656 | 27399 | 19740 | 28596 | 21915 | 41899 | 23671 | 22882 |
| 28.7 | 23222 | 26619 | 19690 | 28196 | 26169 | 41320 | 23545 | 23074 |
| 28.74 | 23560 | 29868 | 21266 | 29427 | 23786 | 44183 | 23749 | 23165 |
| 28.78 | 22659 | 33742 | 21197 | 29107 | 24220 | 45077 | 25820 | 24856 |
| 28.82 | 22634 | 36025 | 22317 | 31006 | 25706 | 44909 | 27112 | 24995 |
| 28.86 | 21923 | 34513 | 21813 | 31283 | 24334 | 44415 | 26636 | 24823 |
| 28.9 | 23156 | 34429 | 23556 | 30817 | 24235 | 40442 | 23695 | 22330 |
| 28.94 | 22455 | 32588 | 21538 | 29955 | 24736 | 39695 | 26263 | 22680 |
| 28.98 | 21365 | 34974 | 23692 | 29878 | 25750 | 41591 | 26781 | 24207 |
| 29.02 | 22459 | 33520 | 24592 | 30982 | 26892 | 44880 | 26748 | 23184 |
| 29.06 | 19532 | 32860 | 23717 | 30605 | 28666 | 42783 | 24018 | 20913 |
| 29.1 | 21488 | 30143 | 22651 | 29483 | 25403 | 44029 | 25738 | 21079 |
| 29.14 | 22423 | 27771 | 22301 | 29230 | 26357 | 43644 | 23001 | 21601 |
| 29.18 | 23293 | 29662 | 20997 | 31121 | 28708 | 51060 | 23032 | 21985 |
| 29.22 | 23101 | 28408 | 24806 | 27307 | 26374 | 47193 | 21618 | 19634 |
| 29.26 | 22086 | 27312 | 19904 | 27293 | 25632 | 48161 | 18345 | 19483 |
| 29.3 | 22011 | 28287 | 21846 | 28066 | 25364 | 52093 | 19494 | 20007 |
| 29.34 | 22594 | 28050 | 21825 | 27881 | 27476 | 52099 | 19489 | 18806 |
| 29.38 | 22191 | 27842 | 18445 | 28384 | 27786 | 55137 | 18917 | 20598 |
| 29.42 | 21367 | 27097 | 17319 | 26800 | 26921 | 55796 | 19418 | 18786 |
| 29.46 | 23121 | 27299 | 18771 | 28169 | 26051 | 55930 | 18856 | 17433 |
| 29.5 | 22107 | 26831 | 17241 | 28128 | 25464 | 54588 | 18540 | 18943 |
| 29.54 | 22719 | 27958 | 17358 | 28028 | 24654 | 53997 | 18405 | 18029 |
| 29.58 | 20433 | 24777 | 18784 | 28603 | 23596 | 47988 | 18728 | 18470 |
| 29.62 | 20868 | 27068 | 17942 | 24014 | 26043 | 47797 | 18745 | 20126 |
| 29.66 | 21094 | 24993 | 19473 | 25963 | 23550 | 44315 | 17808 | 17045 |
| 29.7 | 21957 | 21422 | 17845 | 26715 | 23487 | 40455 | 16678 | 18841 |
| 29.74 | 21558 | 20881 | 17292 | 26112 | 22692 | 38417 | 18066 | 18852 |
| 29.78 | 21395 | 21600 | 17306 | 26534 | 23971 | 39158 | 17841 | 20857 |
| 29.82 | 20958 | 19623 | 18624 | 26250 | 22581 | 38643 | 17949 | 20232 |
| 29.86 | 19230 | 18671 | 18106 | 27378 | 22330 | 36273 | 18504 | 18401 |
| 29.9 | 18284 | 19932 | 19126 | 25732 | 21846 | 38431 | 16284 | 19256 |
| 29.94 | 19516 | 19548 | 19015 | 24934 | 20779 | 37442 | 16394 | 20296 |
| 29.98 | 19742 | 17324 | 18303 | 25186 | 24327 | 37906 | 15010 | 20072 |
| 30.02 | 20974 | 15850 | 17388 | 23502 | 22692 | 41003 | 16792 | 18944 |
| 30.06 | 20193 | 19058 | 17595 | 23509 | 23947 | 42343 | 18363 | 19493 |
| 30.1 | 21943 | 17319 | 16644 | 25988 | 21698 | 42971 | 16641 | 21079 |

-continued

| | | | | | | | | |
|---|---|---|---|---|---|---|---|---|
| 30.14 | 21365 | 16157 | 17978 | 22764 | 21747 | 43304 | 18734 | 20250 |
| 30.18 | 20217 | 16128 | 19850 | 22161 | 22073 | 46754 | 18427 | 19008 |
| 30.22 | 20503 | 15027 | 16593 | 24825 | 21435 | 51671 | 20763 | 20755 |
| 30.26 | 19398 | 14230 | 16236 | 26013 | 20830 | 47489 | 20099 | 22571 |
| 30.3 | 20248 | 14551 | 16816 | 25185 | 22754 | 49673 | 18991 | 23510 |
| 30.34 | 18209 | 14765 | 15759 | 24042 | 23773 | 47597 | 19429 | 21794 |
| 30.38 | 18282 | 14481 | 16541 | 26108 | 23231 | 47135 | 20084 | 22137 |
| 30.42 | 19887 | 15834 | 16749 | 27676 | 21262 | 48161 | 18309 | 22448 |
| 30.46 | 18715 | 15313 | 15429 | 27211 | 21361 | 44683 | 18324 | 22357 |
| 30.5 | 19069 | 15276 | 17125 | 28791 | 21457 | 45678 | 18966 | 20853 |
| 30.54 | 18456 | 15784 | 16819 | 27469 | 22527 | 42776 | 18633 | 20801 |
| 30.58 | 19770 | 14456 | 15059 | 27490 | 18901 | 41255 | 17645 | 19097 |
| 30.62 | 17759 | 12853 | 16457 | 26881 | 22309 | 36944 | 19775 | 19657 |
| 30.66 | 15550 | 14814 | 17056 | 26794 | 21225 | 41099 | 21813 | 21830 |
| 30.7 | 19558 | 14720 | 14544 | 26908 | 20030 | 37447 | 20848 | 21164 |
| 30.74 | 17613 | 14432 | 16269 | 26684 | 21511 | 33611 | 20967 | 19945 |
| 30.78 | 17460 | 12847 | 15357 | 25059 | 20882 | 34615 | 20066 | 18891 |
| 30.82 | 16831 | 14271 | 16573 | 26350 | 22073 | 35403 | 18609 | 20261 |
| 30.86 | 18352 | 13982 | 17429 | 25777 | 22628 | 34628 | 18975 | 20082 |
| 30.9 | 19676 | 14662 | 16438 | 25376 | 19680 | 34485 | 20638 | 19543 |
| 30.94 | 16397 | 15297 | 15216 | 24928 | 20432 | 33312 | 17937 | 17057 |
| 30.98 | 18176 | 13579 | 14471 | 26625 | 20287 | 33149 | 16487 | 17807 |
| 31.02 | 16790 | 13915 | 16932 | 26402 | 18579 | 34089 | 16412 | 18698 |
| 31.06 | 17221 | 14613 | 15480 | 26021 | 19238 | 32928 | 15148 | 17581 |
| 31.1 | 19155 | 14930 | 15784 | 25090 | 20677 | 34822 | 17435 | 16249 |
| 31.14 | 16404 | 15341 | 15503 | 26539 | 20227 | 34095 | 15788 | 16034 |
| 31.18 | 17200 | 15015 | 16207 | 25305 | 21237 | 32281 | 14693 | 16158 |
| 31.22 | 17861 | 15038 | 15169 | 25592 | 19259 | 34061 | 15739 | 16373 |
| 31.26 | 16908 | 15128 | 16687 | 24306 | 18746 | 33790 | 15082 | 18375 |
| 31.3 | 17499 | 14457 | 16268 | 23149 | 19280 | 34782 | 15182 | 16642 |
| 31.34 | 17388 | 15265 | 14915 | 23510 | 20017 | 34519 | 14828 | 16007 |
| 31.38 | 18631 | 16826 | 15054 | 22317 | 18942 | 35061 | 15196 | 17051 |
| 31.42 | 16415 | 17967 | 15976 | 24398 | 19297 | 34438 | 16861 | 17267 |
| 31.46 | 17301 | 17460 | 16840 | 24241 | 19473 | 33205 | 15046 | 17293 |
| 31.5 | 18113 | 16618 | 16320 | 23363 | 19351 | 34067 | 16211 | 16061 |
| 31.54 | 19243 | 18348 | 14668 | 24264 | 19541 | 32700 | 15930 | 15276 |
| 31.58 | 17298 | 18875 | 14542 | 22883 | 18889 | 33444 | 16642 | 14690 |
| 31.62 | 16615 | 17072 | 15669 | 22351 | 17403 | 33572 | 15811 | 16631 |
| 31.66 | 16753 | 18344 | 16027 | 23887 | 19829 | 31850 | 15926 | 17120 |
| 31.7 | 16050 | 19290 | 15478 | 23744 | 18879 | 33885 | 16767 | 17650 |
| 31.74 | 18200 | 18105 | 15090 | 22586 | 17666 | 32863 | 15767 | 16907 |
| 31.78 | 15933 | 19696 | 15799 | 20278 | 17905 | 32521 | 14922 | 16411 |
| 31.82 | 15875 | 17732 | 15764 | 22533 | 17599 | 33100 | 15536 | 17121 |
| 31.86 | 16892 | 17970 | 15191 | 22624 | 17182 | 34773 | 15405 | 16596 |
| 31.9 | 17300 | 17064 | 15442 | 21174 | 17743 | 34424 | 14209 | 15237 |
| 31.94 | 15663 | 19848 | 16054 | 22907 | 17020 | 34956 | 15496 | 16052 |
| 31.98 | 15586 | 15830 | 16665 | 20023 | 18057 | 35408 | 15143 | 17070 |
| 32.02 | 15250 | 15619 | 15549 | 20960 | 19257 | 34311 | 15068 | 14682 |
| 32.06 | 15709 | 18398 | 16697 | 19660 | 17882 | 34073 | 14232 | 15108 |
| 32.1 | 16355 | 15955 | 15570 | 19462 | 18004 | 33378 | 12975 | 14483 |
| 32.14 | 16056 | 16836 | 15463 | 20463 | 19694 | 32889 | 13724 | 14939 |
| 32.18 | 15579 | 16069 | 15526 | 22362 | 16608 | 31189 | 14020 | 14878 |
| 32.22 | 16041 | 14754 | 15728 | 22913 | 16932 | 30731 | 12452 | 13560 |
| 32.26 | 16232 | 15005 | 16165 | 21048 | 17355 | 31020 | 15946 | 14147 |
| 32.3 | 15808 | 15105 | 15815 | 21872 | 18465 | 29965 | 15516 | 14345 |
| 32.34 | 16158 | 14746 | 15975 | 24357 | 18269 | 32052 | 15149 | 13161 |
| 32.38 | 15732 | 14318 | 14860 | 22771 | 17634 | 32038 | 14796 | 12707 |
| 32.42 | 17122 | 17881 | 15177 | 25477 | 17534 | 33847 | 15123 | 13885 |
| 32.46 | 16328 | 15853 | 16259 | 21722 | 18008 | 32984 | 16291 | 14548 |
| 32.5 | 15003 | 14699 | 14919 | 22596 | 16781 | 36818 | 17176 | 13656 |
| 32.54 | 15875 | 14486 | 15477 | 24261 | 19064 | 36887 | 17891 | 15280 |
| 32.58 | 16231 | 17120 | 14514 | 25082 | 19551 | 37894 | 20663 | 14547 |
| 32.62 | 16188 | 15332 | 16629 | 23307 | 19051 | 37768 | 18717 | 15163 |
| 32.66 | 16600 | 17101 | 14427 | 25165 | 19836 | 38733 | 19877 | 15793 |
| 32.7 | 15230 | 15623 | 14524 | 23078 | 19361 | 39139 | 18759 | 14108 |
| 32.74 | 15462 | 15066 | 14723 | 21426 | 18435 | 38288 | 17571 | 13129 |
| 32.78 | 16175 | 16036 | 15370 | 21927 | 17734 | 39764 | 17880 | 15766 |
| 32.82 | 15867 | 15210 | 15510 | 22317 | 17944 | 38756 | 18033 | 14450 |
| 32.86 | 16015 | 13883 | 14114 | 21789 | 19066 | 38039 | 16807 | 14648 |
| 32.9 | 16566 | 14516 | 15451 | 22233 | 20255 | 37171 | 18467 | 13808 |
| 32.94 | 15382 | 14938 | 15224 | 19972 | 18975 | 35540 | 18309 | 14836 |
| 32.98 | 16040 | 13768 | 15274 | 22118 | 20249 | 35265 | 17573 | 14002 |
| 33.02 | 15216 | 15235 | 13812 | 21995 | 19924 | 37172 | 16255 | 14532 |
| 33.06 | 16468 | 15172 | 13831 | 19833 | 20085 | 33537 | 14407 | 13366 |
| 33.1 | 15634 | 13712 | 14632 | 22058 | 19962 | 32781 | 14925 | 14509 |
| 33.14 | 14798 | 14297 | 16081 | 22491 | 19036 | 32058 | 14064 | 14412 |
| 33.18 | 15863 | 13996 | 13490 | 21232 | 19565 | 31005 | 14606 | 14298 |
| 33.22 | 14813 | 13786 | 14457 | 20079 | 18789 | 30191 | 14430 | 13204 |
| 33.26 | 15275 | 14316 | 15490 | 20767 | 20058 | 30933 | 13029 | 14221 |

-continued

| | | | | | | | | |
|---|---|---|---|---|---|---|---|---|
| 33.3 | 14658 | 13815 | 13816 | 22215 | 19771 | 29240 | 15399 | 15196 |
| 33.34 | 15644 | 15008 | 15138 | 22442 | 20300 | 30010 | 15577 | 13858 |
| 33.38 | 15642 | 12996 | 14013 | 20090 | 17371 | 30224 | 15409 | 15455 |
| 33.42 | 15841 | 12480 | 12273 | 20475 | 18566 | 29495 | 15811 | 15345 |
| 33.46 | 16212 | 13397 | 14637 | 20853 | 18423 | 28399 | 16183 | 14298 |
| 33.5 | 15625 | 12866 | 11487 | 20462 | 16392 | 30155 | 14775 | 15317 |
| 33.54 | 15473 | 13973 | 12751 | 22278 | 18121 | 31875 | 16041 | 14564 |
| 33.58 | 15874 | 13083 | 14117 | 20891 | 18127 | 32508 | 14443 | 14807 |
| 33.62 | 15555 | 14200 | 13158 | 20233 | 18537 | 33002 | 15918 | 14443 |
| 33.66 | 15053 | 14962 | 14058 | 19769 | 16552 | 32229 | 15936 | 15595 |
| 33.7 | 15357 | 15485 | 12904 | 20966 | 18720 | 34256 | 16254 | 14242 |
| 33.74 | 14061 | 13316 | 14129 | 21983 | 16827 | 34255 | 16286 | 14595 |
| 33.78 | 15163 | 14532 | 12900 | 20482 | 16727 | 35127 | 19101 | 14219 |
| 33.82 | 15760 | 13834 | 14280 | 21162 | 15960 | 35097 | 16914 | 13680 |
| 33.86 | 14872 | 15952 | 15432 | 21204 | 16888 | 37175 | 18123 | 12541 |
| 33.9 | 15032 | 15916 | 13596 | 20802 | 17477 | 38510 | 17616 | 15087 |
| 33.94 | 16059 | 14542 | 13435 | 21876 | 17711 | 34839 | 16574 | 13618 |
| 33.98 | 14264 | 16127 | 13027 | 21833 | 16750 | 36363 | 15804 | 13383 |
| 34.02 | 16530 | 14899 | 13637 | 22037 | 15981 | 36532 | 15741 | 11250 |
| 34.06 | 14732 | 15721 | 12466 | 22009 | 17356 | 33124 | 14359 | 11654 |
| 34.1 | 14099 | 15512 | 12344 | 21369 | 16919 | 32962 | 15029 | 14003 |
| 34.14 | 16094 | 16188 | 12495 | 22628 | 17040 | 32628 | 15458 | 13285 |
| 34.18 | 13925 | 15212 | 12283 | 22723 | 18845 | 30153 | 14494 | 12833 |
| 34.22 | 14737 | 15787 | 13284 | 21821 | 17617 | 30604 | 14280 | 12756 |
| 34.26 | 13213 | 14141 | 12448 | 22854 | 17448 | 33181 | 15050 | 13458 |
| 34.3 | 13278 | 14158 | 12448 | 22655 | 17668 | 33000 | 14202 | 12411 |
| 34.34 | 14490 | 14359 | 12950 | 21293 | 16277 | 34488 | 13818 | 12336 |
| 34.38 | 16106 | 14302 | 12972 | 21762 | 16491 | 34731 | 14456 | 11321 |
| 34.42 | 15762 | 12973 | 14472 | 19935 | 16403 | 34397 | 13700 | 12413 |
| 34.46 | 14529 | 12994 | 13088 | 20326 | 16453 | 36011 | 12975 | 12605 |
| 34.5 | 16054 | 13035 | 13849 | 21336 | 16737 | 36379 | 12962 | 11085 |
| 34.54 | 14357 | 12458 | 12546 | 20332 | 14735 | 37649 | 13523 | 12199 |
| 34.58 | 14709 | 13267 | 13301 | 20040 | 15780 | 35588 | 14027 | 12986 |
| 34.62 | 15242 | 12550 | 13405 | 18866 | 16369 | 35048 | 13877 | 12287 |
| 34.66 | 14238 | 12517 | 12973 | 21250 | 14995 | 33460 | 12906 | 14773 |
| 34.7 | 14196 | 13261 | 13544 | 22227 | 15336 | 33595 | 13438 | 13206 |
| 34.74 | 14284 | 13500 | 13452 | 20757 | 15130 | 31406 | 11426 | 12388 |
| 34.78 | 13917 | 13529 | 13793 | 20822 | 16223 | 30209 | 13073 | 12222 |
| 34.82 | 16781 | 12978 | 12689 | 19824 | 15608 | 29388 | 13739 | 12164 |
| 34.86 | 14738 | 13976 | 13063 | 21656 | 15424 | 27484 | 12251 | 12059 |
| 34.9 | 14417 | 13287 | 13456 | 21213 | 15494 | 27879 | 12539 | 12683 |
| 34.94 | 15038 | 15663 | 13951 | 20390 | 14896 | 30146 | 11880 | 12406 |
| 34.98 | 14236 | 14569 | 12718 | 20343 | 15423 | 29103 | 12114 | 13234 |
| 35.02 | 14568 | 13748 | 13285 | 20928 | 16306 | 29241 | 13454 | 12983 |
| 35.06 | 15117 | 13417 | 12861 | 21214 | 15096 | 27422 | 13238 | 12591 |
| 35.1 | 14816 | 13449 | 11415 | 20246 | 14629 | 27554 | 12112 | 11748 |
| 35.14 | 14915 | 11937 | 12177 | 20325 | 16102 | 29271 | 11574 | 14266 |
| 35.18 | 14858 | 13041 | 11646 | 19422 | 15401 | 30671 | 10976 | 13243 |
| 35.22 | 13093 | 13546 | 13211 | 20087 | 15936 | 30401 | 11211 | 12754 |
| 35.26 | 13485 | 12518 | 12414 | 19543 | 15097 | 31160 | 12067 | 12484 |
| 35.3 | 13772 | 12271 | 12741 | 19953 | 14650 | 30926 | 11933 | 12138 |
| 35.34 | 14118 | 10193 | 13254 | 18900 | 14300 | 31889 | 12022 | 11914 |
| 35.38 | 14072 | 12515 | 12733 | 19323 | 15508 | 31723 | 12532 | 13225 |
| 35.42 | 13473 | 13194 | 12732 | 20086 | 14312 | 30480 | 12569 | 11971 |
| 35.46 | 13201 | 13142 | 11176 | 20041 | 14822 | 31306 | 11920 | 12797 |
| 35.5 | 13121 | 13873 | 11852 | 20570 | 16411 | 30787 | 13309 | 12672 |
| 35.54 | 13449 | 13380 | 12998 | 20627 | 15352 | 29549 | 12805 | 12454 |
| 35.58 | 14069 | 11258 | 12667 | 18924 | 15580 | 28182 | 11480 | 11918 |
| 35.62 | 14704 | 13077 | 13491 | 22037 | 14547 | 30758 | 11958 | 12702 |
| 35.66 | 13177 | 13491 | 11910 | 19781 | 14630 | 30267 | 11280 | 12467 |
| 35.7 | 13924 | 12519 | 12170 | 21236 | 15353 | 29288 | 13783 | 12368 |
| 35.74 | 12867 | 13008 | 12699 | 20454 | 15768 | 28120 | 12394 | 12023 |
| 35.78 | 14516 | 12863 | 13015 | 21131 | 15226 | 29633 | 14134 | 12483 |
| 35.82 | 13118 | 13651 | 12585 | 18871 | 13797 | 29164 | 13515 | 13709 |
| 35.86 | 13997 | 14500 | 12606 | 21191 | 15642 | 28505 | 13887 | 13688 |
| 35.9 | 13336 | 12830 | 13932 | 20716 | 13202 | 27609 | 13576 | 13149 |
| 35.94 | 13614 | 12922 | 13707 | 20333 | 14589 | 27776 | 15047 | 14182 |
| 35.98 | 12431 | 13729 | 14633 | 20283 | 14032 | 27859 | 14404 | 13393 |
| 36.02 | 12777 | 14070 | 15020 | 19995 | 14979 | 29563 | 14285 | 13202 |
| 36.06 | 13449 | 11523 | 14500 | 19277 | 15335 | 29791 | 14709 | 13705 |
| 36.1 | 12900 | 12176 | 13251 | 21233 | 14563 | 29949 | 15142 | 14369 |
| 36.14 | 13005 | 13610 | 13858 | 22297 | 14355 | 29377 | 15136 | 13819 |
| 36.18 | 12608 | 14283 | 15102 | 21770 | 14495 | 30528 | 14024 | 13283 |
| 36.22 | 13976 | 12436 | 13640 | 21480 | 16941 | 29841 | 14661 | 14637 |
| 36.26 | 13037 | 12771 | 15939 | 19403 | 15515 | 30177 | 15185 | 12761 |
| 36.3 | 12541 | 13676 | 14535 | 21035 | 14790 | 32432 | 14126 | 13159 |
| 36.34 | 12160 | 13283 | 15178 | 21571 | 14821 | 31148 | 14610 | 13109 |
| 36.38 | 14021 | 14441 | 13993 | 23901 | 14992 | 31145 | 13141 | 14208 |
| 36.42 | 12583 | 13816 | 15955 | 21035 | 15111 | 30013 | 12474 | 13530 |

-continued

| | | | | | | | | |
|---|---|---|---|---|---|---|---|---|
| 36.46 | 13430 | 13445 | 14322 | 21351 | 15092 | 29879 | 11626 | 13469 |
| 36.5 | 13864 | 14160 | 13794 | 20019 | 14453 | 28764 | 10806 | 12572 |
| 36.54 | 14556 | 13457 | 13236 | 21563 | 14799 | 30393 | 12464 | 12968 |
| 36.58 | 12552 | 12664 | 13068 | 20123 | 15039 | 29863 | 12639 | 13844 |
| 36.62 | 11364 | 13099 | 13506 | 19558 | 14840 | 29918 | 12677 | 12084 |
| 36.66 | 12481 | 13250 | 14030 | 20859 | 15357 | 25996 | 12298 | 12021 |
| 36.7 | 12427 | 13174 | 13784 | 19848 | 13690 | 28385 | 12822 | 11534 |
| 36.74 | 12524 | 14601 | 12449 | 19613 | 14081 | 28810 | 12533 | 12394 |
| 36.78 | 12236 | 13723 | 12797 | 19399 | 15225 | 28366 | 12947 | 12197 |
| 36.82 | 13534 | 13067 | 13647 | 18631 | 14780 | 29558 | 12019 | 12014 |
| 36.86 | 12342 | 12581 | 14246 | 17996 | 13515 | 29375 | 13103 | 12732 |
| 36.9 | 12323 | 14106 | 12556 | 18553 | 14405 | 29389 | 11981 | 11718 |
| 36.94 | 12256 | 12974 | 12873 | 18653 | 14342 | 31990 | 12345 | 13442 |
| 36.98 | 12883 | 13486 | 12843 | 17726 | 15015 | 29402 | 11924 | 12442 |
| 37.02 | 12976 | 13679 | 13701 | 19253 | 15030 | 29049 | 11312 | 12749 |
| 37.06 | 14628 | 14967 | 13347 | 18443 | 16048 | 31258 | 13057 | 13980 |
| 37.1 | 11999 | 13154 | 13239 | 18179 | 15418 | 27339 | 13753 | 13353 |
| 37.14 | 12271 | 13440 | 12072 | 17665 | 15276 | 29526 | 14031 | 13956 |
| 37.18 | 13119 | 12193 | 12123 | 19486 | 16107 | 28348 | 13791 | 12525 |
| 37.22 | 12668 | 12276 | 13127 | 18211 | 14840 | 26918 | 13014 | 14001 |
| 37.26 | 12741 | 11816 | 14036 | 18532 | 14595 | 27719 | 14201 | 15026 |
| 37.3 | 12090 | 12934 | 13124 | 16436 | 15054 | 25584 | 16618 | 12812 |
| 37.34 | 12563 | 14518 | 12720 | 18135 | 14341 | 26462 | 15790 | 13068 |
| 37.38 | 12233 | 14075 | 11926 | 19251 | 15297 | 25332 | 15651 | 13573 |
| 37.42 | 13015 | 13506 | 13772 | 19203 | 14223 | 26592 | 15532 | 12774 |
| 37.46 | 11991 | 13841 | 13174 | 20202 | 15319 | 26728 | 14433 | 13532 |
| 37.5 | 11990 | 13753 | 13344 | 18937 | 15356 | 25416 | 13685 | 13466 |
| 37.54 | 12700 | 15087 | 11654 | 18942 | 15718 | 26743 | 15159 | 13275 |
| 37.58 | 12405 | 13953 | 12840 | 19927 | 14487 | 26429 | 15860 | 13578 |
| 37.62 | 12639 | 14670 | 12526 | 19065 | 16287 | 26297 | 14125 | 11977 |
| 37.66 | 12169 | 16614 | 14236 | 19386 | 16348 | 28382 | 13378 | 12230 |
| 37.7 | 12296 | 15053 | 12425 | 20423 | 15354 | 27615 | 12681 | 12765 |
| 37.74 | 12251 | 15926 | 11906 | 18052 | 15793 | 27821 | 12649 | 14114 |
| 37.78 | 12038 | 16383 | 11880 | 19040 | 14550 | 27049 | 11757 | 12770 |
| 37.82 | 13884 | 14849 | 12032 | 20779 | 14622 | 27566 | 11910 | 13743 |
| 37.86 | 11734 | 14636 | 13612 | 19770 | 14277 | 29235 | 12266 | 13060 |
| 37.9 | 13090 | 14337 | 13305 | 18483 | 13619 | 29887 | 11913 | 12887 |
| 37.94 | 13164 | 14498 | 12713 | 19940 | 15618 | 30879 | 11725 | 13471 |
| 37.98 | 12507 | 12907 | 12220 | 21270 | 16108 | 28094 | 11469 | 14029 |
| 38.02 | 11360 | 12743 | 12239 | 19793 | 15747 | 28611 | 11322 | 13372 |
| 38.06 | 10722 | 13236 | 12403 | 18985 | 14845 | 28852 | 11658 | 13148 |
| 38.1 | 11418 | 13496 | 12664 | 19642 | 15169 | 26601 | 11812 | 13384 |
| 38.14 | 12676 | 12277 | 11662 | 20170 | 13706 | 26627 | 11964 | 12449 |
| 38.18 | 11905 | 12099 | 12326 | 19681 | 15664 | 26318 | 12053 | 12424 |
| 38.22 | 11822 | 12566 | 12497 | 21527 | 15500 | 25624 | 11802 | 13813 |
| 38.26 | 12179 | 13014 | 13459 | 19897 | 15080 | 26132 | 10495 | 12727 |
| 38.3 | 12606 | 12187 | 11892 | 20254 | 16179 | 25813 | 12117 | 12537 |
| 38.34 | 11826 | 12135 | 14203 | 20119 | 14888 | 27514 | 12945 | 13899 |
| 38.38 | 12292 | 12932 | 14211 | 20034 | 14319 | 27443 | 11523 | 14473 |
| 38.42 | 11160 | 12825 | 13346 | 19158 | 12977 | 28386 | 12526 | 13370 |
| 38.46 | 12017 | 11091 | 13666 | 20580 | 14898 | 26693 | 13405 | 12353 |
| 38.5 | 12400 | 11757 | 13288 | 18684 | 13958 | 28561 | 11822 | 12162 |
| 38.54 | 13665 | 12062 | 13000 | 19375 | 14637 | 26555 | 11812 | 12704 |
| 38.58 | 12250 | 11828 | 12764 | 19948 | 13398 | 28562 | 12947 | 12002 |
| 38.62 | 12870 | 12191 | 12320 | 20607 | 14101 | 27401 | 13679 | 13300 |
| 38.66 | 12396 | 11188 | 12223 | 20198 | 13895 | 26763 | 14963 | 13006 |
| 38.7 | 11203 | 11641 | 11972 | 21248 | 15133 | 27418 | 13076 | 13077 |
| 38.74 | 12617 | 11124 | 12599 | 21139 | 14190 | 27308 | 13246 | 13361 |
| 38.78 | 12446 | 10715 | 10890 | 19628 | 14172 | 26915 | 15291 | 13164 |
| 38.82 | 11756 | 10519 | 11816 | 20727 | 15358 | 28396 | 14316 | 13660 |
| 38.86 | 12237 | 11764 | 11787 | 21141 | 14772 | 25692 | 13309 | 13814 |
| 38.9 | 11486 | 11029 | 11502 | 20390 | 13313 | 28819 | 14665 | 14003 |
| 38.94 | 11080 | 10738 | 11411 | 20383 | 14308 | 25772 | 14376 | 12797 |
| 38.98 | 11687 | 10726 | 12350 | 19785 | 14486 | 26582 | 13714 | 12488 |
| 39.02 | 12471 | 11168 | 12074 | 19454 | 14071 | 28383 | 11701 | 11507 |
| 39.06 | 11946 | 12210 | 12195 | 18876 | 14190 | 28095 | 12790 | 13235 |
| 39.1 | 12756 | 13128 | 10390 | 19161 | 14065 | 28584 | 13160 | 13563 |
| 39.14 | 11854 | 12149 | 11255 | 18747 | 14551 | 29371 | 12947 | 13450 |
| 39.18 | 12561 | 12061 | 11684 | 18257 | 15622 | 30831 | 11776 | 12481 |
| 39.22 | 12032 | 13220 | 11583 | 18007 | 13515 | 30445 | 10707 | 13466 |
| 39.26 | 12388 | 13747 | 11955 | 18978 | 14578 | 28982 | 12185 | 12441 |
| 39.3 | 12034 | 13164 | 11622 | 20138 | 16330 | 29584 | 12391 | 12809 |
| 39.34 | 12510 | 13670 | 12845 | 19124 | 15585 | 30624 | 12585 | 11802 |
| 39.38 | 13370 | 13511 | 10700 | 18389 | 15059 | 30292 | 12438 | 12780 |
| 39.42 | 11859 | 14243 | 11710 | 17020 | 15881 | 28944 | 12799 | 11559 |
| 39.46 | 11642 | 13223 | 11961 | 17353 | 14804 | 31191 | 13366 | 13594 |
| 39.5 | 12782 | 12296 | 11537 | 17541 | 14936 | 29847 | 13669 | 12292 |
| 39.54 | 10527 | 12667 | 11715 | 17990 | 14276 | 28797 | 14500 | 12210 |
| 39.58 | 11437 | 13290 | 10703 | 18123 | 14375 | 27328 | 14441 | 12422 |

-continued

| | | | | | | | |
|---|---|---|---|---|---|---|---|
| 39.62 | 12617 | 11953 | 11825 | 18500 | 15020 | 27831 | 14937 | 12515 |
| 39.66 | 11377 | 13553 | 11027 | 17279 | 14461 | 27486 | 15549 | 12776 |
| 39.7 | 12308 | 11736 | 11002 | 18751 | 13715 | 26441 | 15572 | 11880 |
| 39.74 | 11597 | 12271 | 11214 | 17485 | 14303 | 25324 | 15549 | 13226 |
| 39.78 | 10770 | 11363 | 12147 | 18388 | 14583 | 25562 | 15842 | 12621 |
| 39.82 | 11759 | 12024 | 11949 | 18417 | 14652 | 25608 | 15415 | 10831 |
| 39.86 | 12502 | 12015 | 11002 | 18803 | 13841 | 25507 | 14193 | 12963 |
| 39.9 | 12576 | 13584 | 10998 | 18190 | 14628 | 26501 | 13914 | 13646 |
| 39.94 | 12047 | 13179 | 12233 | 16985 | 14446 | 26508 | 13129 | 12274 |
| 39.98 | 12977 | 13079 | 10159 | 18511 | 13786 | 25717 | 14675 | 14802 |
| 40.02 | 12049 | 13503 | 11560 | 18580 | 14799 | 25021 | 13399 | 13086 |
| 40.06 | 11943 | 12740 | 10368 | 16708 | 13429 | 24736 | 13002 | 12708 |
| 40.1 | 11644 | 13146 | 9871 | 17802 | 13486 | 27528 | 13521 | 13808 |
| 40.14 | 12665 | 14147 | 10022 | 17759 | 15013 | 27666 | 12278 | 13239 |
| 40.18 | 10718 | 14689 | 10082 | 18439 | 14313 | 28263 | 12448 | 13094 |
| 40.22 | 12156 | 15867 | 11128 | 18178 | 13662 | 28514 | 12013 | 13649 |
| 40.26 | 10875 | 13782 | 10577 | 17486 | 14606 | 28258 | 12446 | 14089 |
| 40.3 | 11690 | 14155 | 11218 | 17586 | 14800 | 29584 | 11317 | 13193 |
| 40.34 | 12450 | 12054 | 12117 | 15774 | 14890 | 28769 | 11251 | 11869 |
| 40.38 | 12353 | 14416 | 11192 | 15589 | 14972 | 29036 | 12558 | 13474 |
| 40.42 | 11085 | 12173 | 12692 | 16841 | 14327 | 28922 | 12597 | 13203 |
| 40.46 | 11102 | 11302 | 10518 | 17474 | 14636 | 28047 | 11597 | 12067 |
| 40.5 | 11303 | 12342 | 11501 | 16940 | 13007 | 27889 | 12043 | 12241 |
| 40.54 | 12671 | 11064 | 11339 | 16809 | 14065 | 27055 | 12920 | 12454 |
| 40.58 | 11065 | 12438 | 11600 | 17876 | 14853 | 29238 | 12227 | 11277 |
| 40.62 | 11387 | 10975 | 11060 | 16537 | 14485 | 26558 | 12811 | 11004 |
| 40.66 | 10695 | 9722 | 10926 | 17327 | 13589 | 28244 | 12018 | 12458 |
| 40.7 | 11291 | 10290 | 10172 | 15188 | 14111 | 26737 | 12173 | 11638 |
| 40.74 | 10465 | 10484 | 10239 | 15168 | 13137 | 27606 | 12193 | 12320 |
| 40.78 | 11021 | 11973 | 10559 | 14875 | 13840 | 26990 | 11858 | 11987 |
| 40.82 | 11381 | 11533 | 10598 | 15043 | 12087 | 26676 | 14178 | 11706 |
| 40.86 | 10577 | 10801 | 10933 | 15582 | 13209 | 27997 | 13875 | 10966 |
| 40.9 | 11037 | 11632 | 11674 | 16647 | 13551 | 26095 | 13071 | 11023 |
| 40.94 | 11307 | 10900 | 11692 | 15902 | 12969 | 25845 | 13275 | 11292 |
| 40.98 | 10045 | 10063 | 10525 | 14191 | 12319 | 22429 | 12870 | 11048 |
| 41.02 | 10127 | 10908 | 10664 | 14585 | 12966 | 24932 | 12472 | 11384 |
| 41.06 | 9516 | 10874 | 9953 | 16004 | 11848 | 23330 | 12894 | 11908 |
| 41.1 | 9872 | 10431 | 9897 | 16032 | 13101 | 22619 | 11168 | 12051 |
| 41.14 | 11811 | 11598 | 10987 | 16264 | 13471 | 21844 | 12369 | 12201 |
| 41.18 | 10211 | 11032 | 9515 | 15541 | 12457 | 22060 | 11644 | 11326 |
| 41.22 | 9329 | 11953 | 10242 | 15975 | 11398 | 19805 | 11883 | 10729 |
| 41.26 | 10598 | 10528 | 11225 | 14255 | 10850 | 21142 | 10483 | 10911 |
| 41.3 | 9735 | 10801 | 9516 | 15183 | 12921 | 20894 | 11728 | 10835 |
| 41.34 | 10551 | 9963 | 9965 | 14704 | 12354 | 22191 | 10854 | 11469 |
| 41.38 | 8791 | 10558 | 8864 | 13349 | 12269 | 20915 | 9736 | 12139 |
| 41.42 | 10753 | 11554 | 9083 | 14654 | 12817 | 20408 | 9535 | 11296 |
| 41.46 | 10640 | 10183 | 9536 | 13274 | 12965 | 21437 | 10701 | 10807 |
| 41.5 | 9730 | 10822 | 9762 | 14233 | 11472 | 20010 | 10310 | 10769 |

The invention claimed is:

1. A crystal form of voruciclib, selected from:
voruciclib malonate characterized by an X-ray powder diffraction pattern comprising one or more peaks selected from 7.30°±0.2°, 13.58°±0.2°, 14.06°±0.2°, 15.18°±0.2°, 15.66°±0.2°, 17.50°±0.2°, 18.94°±0.2°, 19.54°±0.2°, 22.22°±0.2°, 23.38°±0.2°, 24.10°±0.2°, 24.98°±0.2°, 25.94°±0.2°, 27.26°±0.2°, 28.50°±0.2°, and 32.82°±0.2° 2θ,
voruciclib dibenzoyl-tartrate characterized by an X-ray powder diffraction pattern comprising one or more peaks selected from 5.06°±0.2°, 6.42°±0.2°, 9.34°±0.2°, 10.14°±0.2°, 12.30°±0.2°, 13.66°±0.2°, 14.14°±0.2°, 15.82°±0.2°, 17.02°±0.2°, 19.74°±0.2°, 20.38°±0.2°, 21.82°±0.2°, 22.66°±0.2°, 24.62°±0.2°, 25.78°±0.2°, 26.58°±0.2°, 28.66°±0.2°, and 29.98°±0.2° 2θ,
voruciclib phosphate characterized by an X-ray powder diffraction pattern comprising one or more peaks selected from 4.94°±0.2°, 6.78°±0.2°, 9.34°±0.2°, 10.94°±0.2°, 12.70°±0.2°, 13.38°±0.2°, 14.90°±0.2°, 15.66°±0.2°, 17.54°±0.2°, 18.82°±0.2°, 22.02°±0.2°, 23.98°±0.2°, 24.78°±0.2°, 25.30°±0.2°, 26.66°±0.2°, and 29.98°±0.2° 2θ,
voruciclib oxalate characterized by an X-ray powder diffraction pattern comprising one or more peaks selected from 6.86°±0.2°, 12.66°±0.2°, 13.58°±0.2°, 14.74°±0.2°, 15.98°±0.2°, 19.38°±0.2°, 23.94°±0.2°, 24.78°±0.2°, and 25.94°±0.2° 2θ, and
voruciclib napadisylate, characterized by an X-ray powder diffraction pattern comprising one or more peaks selected from 9.02°±0.2°, 10.50°±0.2°, 11.06°±0.2°, 12.30°±0.2°, 12.82°±0.2°, 13.90°±0.2°, 14.82°±0.2°, 15.30°±0.2°, 15.94°±0.2°, 17.26°±0.2°, 19.34°±0.2°, 20.62°±0.2°, 22.18°±0.2°, 22.86°±0.2°, 24.58°±0.2°, 25.42°±0.2°, 25.86°±0.2°, 27.38° ±0.2°, and 28.66°±0.2° 2θ.

2. The voruciclib malonate crystal form of claim 1, characterized by an X-ray powder diffraction pattern comprising one or more peaks selected from 7.30°±0.2°, 13.58°±0.2°, 14.06°±0.2°, 15.18°±0.2°, 15.66°±0.2°, 17.50°±0.2°, 18.94°±0.2°, 19.54°±0.2°, 22.22°±0.2°, 23.38°±0.2°, 24.10°±0.2°, 24.98°±0.2°, 25.94°±0.2°, 27.26°±0.2°, 28.50°±0.2°, and 32.82°±0.2° 2θ.

3. The voruciclib dibenzoyl-tartrate crystal form of claim 1, characterized by an X-ray powder diffraction pattern comprising one or more peaks selected from 5.06°±0.2°, 6.42°±0.2°, 9.34°±0.2°, 10.14°±0.2°, 12.30°±0.2°, 13.66°

±0.2°, 14.14°±0.2°, 15.82°±0.2°, 17.02°±0.2°, 19.74°±0.2°, 20.38°±0.2°, 21.82°±0.2°, 22.66°±0.2°, 24.62°±0.2°, 25.78°±0.2°, 26.58°±0.2°, 28.66°±0.2°, and 29.98°±0.2° 2θ.

4. The voruciclib phosphate crystal form of claim 1, characterized by an X-ray powder diffraction pattern comprising one or more peaks selected from 4.94°±0.2°, 6.78°±0.2°, 9.34°±0.2°, 10.94°±0.2°, 12.70°±0.2°, 13.38°±0.2°, 14.90°±0.2°, 15.66°±0.2°, 17.54°±0.2°, 18.82°±0.2°, 22.02°±0.2°, 23.98°±0.2°, 24.78°±0.2°, 25.30°±0.2°, 26.66°±0.2°, and 29.98°±0.2° 2θ.

5. The voruciclib oxalate crystal form of claim 1, characterized by an X-ray powder diffraction pattern comprising one or more peaks selected from 6.86°±0.2°, 12.66°±0.2°, 13.58°±0.2°, 14.74°±0.2°, 15.98°±0.2°, 19.38°±0.2°, 23.94°±0.2°, 24.78°±0.2°, and 25.94°±0.2° 2θ.

6. The voruciclib napadisylate crystal form of claim 1, characterized by an X-ray powder diffraction pattern comprising one or more peaks selected from 9.02°±0.2°, 10.50°±0.2°, 11.06°±0.2°, 12.30°±0.2°, 12.82°±0.2°, 13.90°±0.2°, 14.82°±0.2°, 15.30°±0.2°, 15.94°±0.2°, 17.26°±0.2°, 19.34°±0.2°, 20.62°±0.2°, 22.18°±0.2°, 22.86°±0.2°, 24.58°±0.2°, 25.42°±0.2°, 25.86°±0.2°, 27.38°±0.2°, and 28.66°±0.2° 2θ.

7. The crystal form of claim 1, wherein the crystal form is a crystalline anhydrate.

8. The crystal form of claim 1, wherein the crystal form is a crystalline hydrate.

9. A crystal form malonate characterized by an X-ray powder diffraction pattern comprising one or more peaks selected from 6.36°±0.2° 2θ, 7.31°±0.2° 2θ, 9.34°±0.2° 2θ, 10.05°±0.2° 2θ, 13.59°±0.2° 2θ, 14.08°±0.2° 2θ, 15.21°±0.2° 2θ, 15.67°±0.2° 2θ, 17.53°±0.2° 2θ, 18.70°±0.2° 2θ, 18.98°±0.2° 2θ, 19.38°±0.2° 2θ, 19.67°±0.2° 2θ, 20.16°±0.2° 2θ, 20.39°±0.2° 2θ, 21.01°±0.2° 2θ, 22.27°±0.2° 2θ, 23.35°±0.2° 2θ, 24.15°±0.2° 2θ, 24.67°±0.2° 2θ, 25.00°±0.2° 2θ, 25.18°±0.2° 2θ, 25.57°±0.2° 2θ, 25.93°±0.2° 2θ, 26.21°±0.2° 2θ, 27.19°±0.2° 2θ, and 27.38°±0.2° 2θ.

10. A crystal form oxalate characterized by an X-ray powder diffraction pattern comprising one or more peaks selected from 6.86°±0.2° 2θ, 9.70°±0.2° 2θ, 10.84°±0.2° 2θ, 12.50°±0.2° 2θ, 12.66°±0.2° 2θ, 12.81°±0.2° 2θ, 13.41°±0.2° 2θ, 13.71°±0.2° 2θ, 14.54°±0.2° 2θ, 15.35°±0.2° 2θ, 15.83°±0.2° 2θ, 18.70°±0.2° 2θ, 19.00°±0.2° 2θ, 19.43°±0.2° 2θ, 19.62°±0.2° 2θ, 21.75°±0.2° 2θ, 22.75°±0.2° 2θ, 23.35°±0.2° 2θ, 23.47°±0.2° 2θ, 23.81°±0.2° 2θ, 23.98°±0.2° 2θ, 24.36°±0.2° 2θ, 24.60°±0.2° 2θ, 24.86°±0.2° 2θ, 25.11°±0.2° 2θ, 25.60°±0.2° 2θ, 25.75°±0.2° 2θ, and 26.25°±0.2° 2θ.

11. A crystal form phosphate characterized by an X-ray powder diffraction pattern comprising one or more peaks selected from 4.93°±0.2° 2θ, 6.79°±0.2° 2θ, 9.35°±0.2° 2θ, 10.58°±0.2° 2θ, 10.91°±0.2° 2θ, 12.64°±0.2° 2θ, 13.35°±0.2° 2θ, 13.58°±0.2° 2θ, 14.81°±0.2° 2θ, 15.60°±0.2° 2θ, 17.18°±0.2° 2θ, 17.52°±0.2° 2θ, 18.32°±0.2° 2θ, 18.78°±0.2° 2θ, 19.34°±0.2° 2θ, 19.64°±0.2° 2θ, 19.78°±0.2° 2θ, 22.02°±0.2° 2θ, 23.20°±0.2° 2θ, 23.67°±0.2° 2θ, 24.00°±0.2° 2θ, 24.71°±0.2° 2θ, 25.21°±0.2° 2θ, 25.39°±0.2° 2θ, 26.55°±0.2° 2θ, 27.22°±0.2° 2θ, 28.07°±0.2° 2θ, and 29.90°±0.2° 2θ.

12. The crystal form of claim 9, wherein the crystal form is a crystalline anhydrate.

13. The crystal form of claim 9, wherein the crystal form is a crystalline hydrate.

14. The crystal form of claim 10, wherein the crystal form is a crystalline anhydrate.

15. The crystal form of claim 10, wherein the crystal form is a crystalline hydrate.

16. The crystal form of claim 11, wherein the crystal form is a crystalline anhydrate.

17. The crystal form of claim 11, wherein the crystal form is a crystalline hydrate.

\* \* \* \* \*

UNITED STATES PATENT AND TRADEMARK OFFICE
CERTIFICATE OF CORRECTION

PATENT NO. : 12,421,216 B2
APPLICATION NO. : 17/602935
DATED : September 23, 2025
INVENTOR(S) : David Frank Duncan Page 1 of 1

It is certified that error appears in the above-identified patent and that said Letters Patent is hereby corrected as shown below:

In the Claims

Column 337, Line 28, in Claim 9, insert the words --of voruciclib-- between "form" and "malonate";

Column 338, Line 1, in Claim 10, insert the words --of voruciclib-- between "form" and "oxalate";

Column 338, Line 13, in Claim 11, insert the words --of voruciclib-- between "form" and "phosphate".

Signed and Sealed this
Sixteenth Day of December, 2025

John A. Squires
*Director of the United States Patent and Trademark Office*